(12) United States Patent
Byun et al.

(10) Patent No.: US 12,240,862 B2
(45) Date of Patent: *Mar. 4, 2025

(54) INHIBITORS OF PEPTIDYLARGININE DEIMINASES

(71) Applicant: Gilead Sciences, Inc., Foster City, CA (US)

(72) Inventors: Daniel H. Byun, Foster City, CA (US); Eda Y. Canales, San Mateo, CA (US); Laurent P. Debien, San Francisco, CA (US); Petr Jansa, Foster City, CA (US); Rick A. Lee, Livermore, CA (US); Jennifer A. Loyer-Drew, Seattle, WA (US); Stephane Perreault, Brier, WA (US); Hyung-Jung Pyun, Fremont, CA (US); Roland D. Saito, San Mateo, CA (US); Michael S. Sangi, San Mateo, CA (US); Adam J. Schrier, Redwood City, CA (US); Marina E. Shatskikh, Irvine, CA (US); James G. Taylor, Burlingame, CA (US); Jennifer A. Treiberg, Redmond, WA (US); Joshua J. Van Veldhuizen, Seattle, WA (US); Lianhong Xu, Palo Alto, CA (US)

(73) Assignee: Gilead Sciences, Inc., Foster City, CA (US)

(*) Notice: Subject to any disclaimer, the term of this patent is extended or adjusted under 35 U.S.C. 154(b) by 87 days.

This patent is subject to a terminal disclaimer.

(21) Appl. No.: 17/558,130

(22) Filed: Dec. 21, 2021

(65) Prior Publication Data

US 2022/0227787 A1 Jul. 21, 2022

Related U.S. Application Data

(60) Provisional application No. 63/129,421, filed on Dec. 22, 2020.

(51) Int. Cl.
*A61P 35/02* (2006.01)
*C07D 519/00* (2006.01)

(52) U.S. Cl.
CPC .................. *C07D 519/00* (2013.01)

(58) Field of Classification Search
CPC .................. C07D 519/00; A61P 35/02
See application file for complete search history.

(56) References Cited

U.S. PATENT DOCUMENTS 11,878,965 B2 * 1/2024 Byun .................. A61P 35/02
11,976,083 B2   5/2024 Canales et al.

FOREIGN PATENT DOCUMENTS

| WO | WO-2014015905 A1 | 1/2014 |
| WO | WO-2016185279 A1 | 11/2016 |
| WO | WO-2017100594 A1 | 6/2017 |
| WO | WO-2017100601 A1 | 6/2017 |
| WO | WO-2017147102 A1 | 8/2017 |
| WO | WO-2018022897 A1 | 2/2018 |
| WO | WO-2018049296 A1 | 3/2018 |
| WO | WO-2019058393 A1 | 3/2019 |
| WO | WO-2019077631 A1 | 4/2019 |
| WO | WO-2019152883 A1 | 8/2019 |
| WO | WO-2019161803 A1 | 8/2019 |
| WO | WO-2020033488 A1 | 2/2020 |
| WO | WO-2020033490 A1 | 2/2020 |
| WO | WO-2020033514 A1 | 2/2020 |
| WO | WO-2020033520 A1 | 2/2020 |
| WO | WO-2021057910 A1 | 4/2021 |
| WO | WO-2021158840 A1 | 8/2021 |
| WO | WO-2021163254 A1 | 8/2021 |
| WO | WO-2021222353 A1 | 11/2021 |
| WO | WO-2022034616 A1 | 2/2022 |

OTHER PUBLICATIONS

Peterson, E.A., "Discovery and optimization of potent and selective imidazopyridine and imidazopyridazine mTOR inhibitors." Bioorganic & medicinal chemistry letters 22.15 (2012): 4967-4974.*
International Search Report and Written Opinion of the International Searching Authority, dated Jun. 24, 2022, for Intl. Appl. No. PCT/US2021/064669.
Wermuth, C. G. (1998) "The Practice of Medicinal Chemistry" First Volume, Technomics, Inc., p. 273-296, Chapter 14, conversion of ring structure.

* cited by examiner

*Primary Examiner* — John M Mauro

(57) ABSTRACT

The present disclosure relates to novel compounds for use in therapeutic treatment of a disease associated with peptidylarginine deiminases (PADs), such as peptidylarginine deiminase type 4 (PAD4). The present disclosure also relates to processes and intermediates for the preparation of such compounds, methods of using such compounds and pharmaceutical compositions comprising the compounds described herein.

12 Claims, No Drawings
Specification includes a Sequence Listing.

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
gcccagggga cattgatccg t        21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
tcagggcacc atgttccacc a        21

INHIBITORS OF PEPTIDYLARGININE DEIMINASES

CROSS REFERENCE TO RELATED APPLICATIONS

This application claims priority to U.S. Provisional Application No. 63/129,421, filed Dec. 22, 2020, which is incorporated herein in its entireties for all purposes.

SEQUENCE LISTING

The instant application contains a Sequence Listing which has been submitted electronically in ASCII format and is hereby incorporated by reference in its entirety. Said ASCII copy, created on Dec. 2, 2021, is named 1249-US-NP_SL and is 702 bytes in size.

FIELD

The present disclosure relates to novel compounds for use in therapeutic treatment of a disease associated with peptidylarginine deiminases (PADs). The present disclosure also relates to processes and intermediates for the preparation of such compounds, methods of using such compounds and pharmaceutical compositions comprising the compounds described herein.

BACKGROUND

Peptidylarginine deiminases catalyze the posttranslational modification of peptidyl arginine to peptidyl citrulline. There are five known PAD isozymes with 45% to 58% amino acid sequence identity between human isozymes and at least 70% identity across each vertebrate orthologue. PADs have diverse tissue distribution, different putative physiological functions, and reported associations with various disease states. PAD6 is thought to be the only catalytically inactive PAD and is expressed mainly in oocyte, ovary and early embryo; it is proposed to be involved in oocyte cytoskeletal sheet formation and female fertility. PAD1 and PAD3 are expressed in epidermis and hair follicles and are proposed to be involved in cornification of epidermal tissues, hair growth and maintenance of the stratum corneum. PAD2 is expressed more broadly and can be found in multiple tissues and cell types including brain, spinal cord, skeletal muscles, pituitary glands, spleen, neutrophils and macrophages. It is proposed to be involved in plasticity of CNS, transcription regulation, chemokine signaling, and female reproduction. Expression of PAD4 is restricted to cells of the myeloid lineage, in particular: neutrophils, eosinophils and monocyte/macrophages. PAD4 is hypothesized to be involved in an array of functions, including regulation of transcription, cell cycle, apoptosis, formation of neutrophil extracellular traps (NETs), and tumorgenesis. Accordingly, there is a need for inhibitors of PADs that have therapeutic potential in treatment of disease linked to pathological consequences of citrullination and NETosis including, for example, rheumatoid arthritis, systemic lupus erythematous, antiphospholipid antibody syndrome, small vessels vasculitis, colitis, thrombosis, atherosclerosis, sepsis, diabetes and certain types of cancer.

SUMMARY

Provided herein are compounds for inhibiting peptidylarginine deiminase type 4 (PAD4). The present disclosure provides a compound of Formula I:

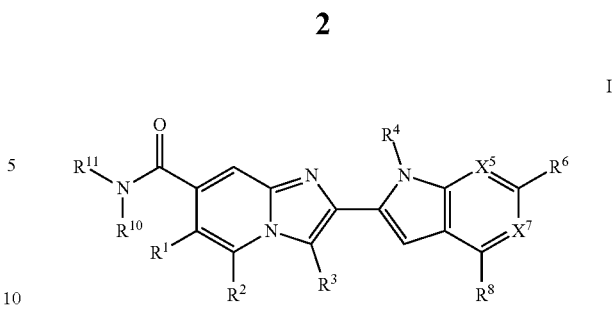

or a pharmaceutically acceptable salt thereof, wherein:

$X^5$ is N or C—$R^5$;

$X^7$ is N or C—$R^7$;

$R^1$ is hydrogen, halo, —CN, —$OR^{12}$, —$N(R^{12})_2$, —$SR^{12}$, $C_{1-8}$ alkyl optionally substituted with 1 to 5 $Z^1$, $C_{3-6}$ cycloalkyl optionally substituted with 1 to 5 $Z^1$, or 4-6 membered heterocyclyl optionally substituted with 1 to 5 $Z^1$;

$R^2$ is hydrogen, halo, —CN, —$OR^{12}$, —$N(R^{12})_2$, —$SR^{12}$, —$S(O)R^{20}$, $C_{1-8}$ alkyl optionally substituted with 1 to 5 $Z^1$, $C_{3-6}$ cycloalkyl optionally substituted with 1 to 5 $Z^1$, or 4-6 membered heterocyclyl optionally substituted with 1 to 5 $Z^1$;

$R^3$ is hydrogen, —$N(R^{12})_2$, $C_{1-8}$ alkyl optionally substituted with 1 to 5 $Z^1$, $C_{2-8}$ alkenyl optionally substituted with 1 to 5 $Z^1$, $C_{2-8}$ alkynyl optionally substituted with 1 to 5 $Z^1$, $C_{3-10}$ cycloalkyl optionally substituted with 1 to 5 $Z^1$, or 4-10 membered heterocyclyl optionally substituted with 1 to 5 $Z^1$; or $R^2$ and $R^3$ are taken together with the atoms to which they are attached to form an optionally substituted 6 to 8 membered heterocyclyl ring;

$R^4$ is hydrogen, $C_{1-8}$ alkyl optionally substituted with 1 to 5 $Z^1$, $C_{3-10}$ alkenyl optionally substituted with 1 to 5 $Z^1$, $C_{3-10}$ alkynyl optionally substituted with 1 to 5 $Z^1$, $C_{3-10}$ cycloalkyl optionally substituted with 1 to 5 $Z^1$, 4-10 membered heterocyclyl optionally substituted with 1 to 5 $Z^1$, $C_{6-10}$ aryl optionally substituted with 1 to 5 $Z^1$, or 5-10 membered heteroaryl optionally substituted with 1 to 5 $Z^1$;

$R^5$ is hydrogen, halo, —CN, —$OR^{12}$, —$C_{1-8}$ alkyl optionally substituted with 1 to 3 $Z^1$, $C_{3-6}$ cycloalkyl optionally substituted with 1 to 3 $Z^1$, or 4-6 membered heterocyclyl optionally substituted with 1 to 3 $Z^1$;

$R^6$ is —$N(R^{14})S(O)_2R^9$, —$N(R^{14})C(O)OR^9$, —$OC(O)R^9$, —$OC(O)OR^9$, -L-$R^{13}$, —$OR^{15}$, $C_{2-8}$ alkenyl optionally substituted with 1 to 5 $Z^1$, $C_{2-8}$ alkynyl optionally substituted with 1 to 5 $Z^1$, $C_{3-10}$ cycloalkyl substituted with 1 to 5 $Z^1$, $C_{6-10}$ aryl substituted with 1 to 5 $Z^1$, 4-10 membered heterocyclyl substituted with 1 to 5 $Z^1$,

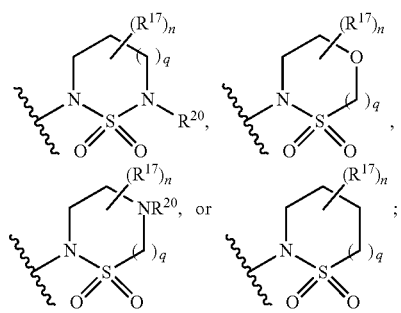

where q is 0, 1 or 2; and n is 0, 1, 2, 3, 4, 5, or 6;

$R^7$ is hydrogen, halo, —CN, —OR$^{12}$, —C$_{1-8}$ alkyl optionally substituted with 1 to 3 $Z^1$, C$_{3-6}$ cycloalkyl optionally substituted with 1 to 3 $Z^1$, or 4-6 membered heterocyclyl optionally substituted with 1 to 3 $Z^1$;

$R^8$ is hydrogen, halo, —CN, —OR$^{12}$, —C$_{1-8}$ alkyl optionally substituted with 1 to 3 $Z^1$, C$_{3-6}$ cycloalkyl optionally substituted with 1 to 3 $Z^1$, or 4-6 membered heterocyclyl optionally substituted with 1 to 3 $Z^1$;

each $R^9$ is independently C$_{1-8}$ alkyl optionally substituted with 1 to 5 $Z^1$, C$_{2-8}$ alkenyl optionally substituted with 1 to 5 $Z^1$, C$_{2-8}$ alkynyl optionally substituted with 1 to 5 $Z^1$, C$_{3-10}$ cycloalkyl optionally substituted with 1 to 5 $Z^1$, 4-10 membered heterocyclyl optionally substituted with 1 to 5 $Z^1$, C$_{6-10}$ aryl optionally substituted with 1 to 5 $Z^1$, or 5-10 membered heteroaryl optionally substituted with 1 to 5 $Z^1$;

$R^{10}$ is hydrogen, C$_{1-8}$ alkyl optionally substituted with 1 to 5 $Z^1$, C$_{2-8}$ alkenyl optionally substituted with 1 to 5 $Z^1$, C$_{2-8}$ alkynyl optionally substituted with 1 to 5 $Z^1$, C$_{3-10}$ cycloalkyl optionally substituted with 1 to 5 $Z^1$;

$R^{11}$ is hydrogen, C$_{1-8}$ alkyl optionally substituted with 1 to 5 $Z^1$, C$_{2-8}$ alkenyl optionally substituted with 1 to 5 $Z^1$, C$_{2-8}$ alkynyl optionally substituted with 1 to 5 $Z^1$, C$_{3-10}$ cycloalkyl optionally substituted with 1 to 5 $Z^1$, 4-10 membered heterocyclyl optionally substituted with 1 to 5 $Z^1$, C$_{6-10}$ aryl optionally substituted with 1 to 5 $Z^1$, or 5-10 membered heteroaryl optionally substituted with 1 to 5 $Z^1$; or $R^{10}$ and $R^{11}$ are taken together with the nitrogen to which they are attached to form a 4-12-membered heterocyclyl optionally substituted with 1 to 4 $Z^1$;

each $R^{12}$ is independently hydrogen, C$_{1-8}$ alkyl optionally substituted with 1 to 5 $Z^{1b}$, C$_{3-8}$ alkenyl optionally substituted with 1 to 5 $Z^{1b}$, C$_{3-8}$ alkynyl optionally substituted with 1 to 5 $Z^{1b}$, C$_{3-10}$ cycloalkyl optionally substituted with 1 to 5 $Z^{1b}$, 4-10 membered heterocyclyl optionally substituted with 1 to 5 $Z^{th}$, C$_{6-10}$ aryl optionally substituted with 1 to 5 $Z^{1b}$, or 5-10 membered heteroaryl optionally substituted with 1 to 5 $Z^1b$;

L is C$_{1-8}$ alkylene, —O—C$_{1-8}$ alkylene, C$_{1-8}$ haloalkylene, —O—C$_{1-8}$ haloalkylene, or 5-10 membered heteroarylene; and each C$_{1-8}$ alkylene, C$_{1-8}$ haloalkylene, or 5-10 membered heteroarylene of L is optionally substituted with 1 to 5 $Z^1$;

$R^{13}$ is —OR$^{15}$, —N(R$^{15}$)(R$^{14}$), —C(O)N(R$^{14}$)$_2$, —OC(O)N(R$^{14}$)$_2$, —N(R$^{14}$)C(O)R$^9$, —N(R$^{14}$)C(O)OR$^9$, —N(R$^{14}$)C(O)N(R$^{14}$)$_2$, —N(R$^{14}$)S(O)$_2$R$^9$, —NR$^{14}$S(O)$_2$N(R$^{14}$)$_2$, —NR$^{14}$S(O)$_2$O R$^9$, —NS(O)(R$^9$)$_2$, —Si(R$^{14}$)$_2$R$^9$, —SR$^9$, —S(O)R$^9$, —S(O)$_2$R$^9$, —SF$_5$, —S(O)(NR$^{14}$)R$^9$, —S(NR$^{14}$)(NR$^{14}$)R$^9$, —S(O)(NR$^{14}$)N(R$^{14}$)$_2$, —S(O)(NCN)R$^9$, —S(O)$_2$N(R$^{14}$)$_2$, —C(O)N(R$^{14}$)S(O)$_2$R$^9$, —S(O)$_2$N(R$^{14}$)C(O)R$^9$, or C$_{3-10}$ cycloalkyl substituted with 1 to 5 $Z^1$;

each $R^{14}$ is independently hydrogen, C$_{1-8}$ alkyl optionally substituted with 1 to 5 $Z^1$, C$_{2-8}$ alkenyl optionally substituted with 1 to 5 $Z^1$, C$_{2-8}$ alkynyl optionally substituted with 1 to 5 $Z^1$, C$_{3-10}$ cycloalkyl optionally substituted with 1 to 5 $Z^1$, 4-10 membered heterocyclyl optionally substituted with 1 to 5 $Z^1$, C$_{6-10}$ aryl optionally substituted with 1 to 5 $Z^1$, or 5-10 membered heteroaryl optionally substituted with 1 to 5 $Z^1$;

$R^{15}$ is cycloalkyl optionally substituted with 1 to 5 $Z^1$, 4-10 membered heterocyclyl optionally substituted with 1 to 5 $Z^1$, C$_{6-10}$ aryl optionally substituted with 1 to 5 $Z^1$, 5-10 membered heteroaryl optionally substituted with 1 to 5 $Z^1$;

each $R^{17}$ is independently hydrogen, halo, —NO$_2$, —N$_3$, —CN, C$_{1-8}$ alkyl optionally substituted by 1 to 3 $Z^{1a}$, C$_{2-8}$ alkenyl optionally substituted by 1 to 3 $Z^{1a}$, C$_{2-8}$ alkynyl optionally substituted by 1 to 3 $Z^{1a}$, C$_{3-8}$ cycloalkyl optionally substituted by 1 to 3 $Z^{1a}$, 6-10 membered aryl optionally substituted by 1 to 3 $Z^{1a}$, 4-10 membered heterocyclyl optionally substituted by 1 to 3 $Z^{1a}$, 5-10 membered heteroaryl optionally substituted with 1 to 3 $Z^{1a}$, —OR$^{20}$, —C(O)R$^{20}$, —C(O)OR$^{20}$, —C(O)N(R$^{20}$)$_2$, —N(R$^{20}$)$_2$, —N(R$^{20}$)$_3^+$, —N(R$^{20}$)C(O)R$^{20}$, —N(R$^{20}$)C(O)OR$^{20}$, —N(R$^{20}$)C(O)N(R$^{20}$)$_2$, —N(R$^{20}$)S(O)$_2$(R$^{20}$), —NR$^{20}$S(O)$_2$N(R$^{20}$)$_2$, —NR$^{20}$S(O)$_2$O(R$^{20}$), —NS(O)(R$^{20}$)$_2$, —OC(O)R$^{20}$, —OC(O)OR$^{20}$, —OC(O)N(R$^{20}$)$_2$, —Si(R$^{20}$)$_3$, —S(O)R$^{20}$, —SF$_5$, —S(O)(NR$^{20}$)R$^{20}$, —S(NR$^{20}$)(NR$^{20}$)R$^{20}$, —S(O)(NR$^{20}$)N(R$^{20}$)$_2$, —S(O)(NCN)R$^{20}$, —S(O)$_2$R$^{20}$, —S(O)$_2$N(R$^{20}$)$_2$, —C(O)N(R$^{20}$)S(O)$_2$R$^{20}$, or —S(O)$_2$N(R$^{20}$)C(O)R$^{20}$; or two $R^{17}$ on the same or different carbon atoms are taken together to form a 3-8-membered ring optionally substituted with 1 to 4 $Z^1$;

each $Z^1$ is independently halo, —NO$_2$, —N$_3$, —CN, C$_{1-8}$ alkyl optionally substituted by 1 to 5 $Z^{1a}$, C$_{2-8}$ alkenyl optionally substituted by 1 to 5 $Z^{1a}$, C$_{2-8}$ alkynyl optionally substituted by 1 to 5 $Z^{1a}$, C$_{3-10}$ cycloalkyl optionally substituted by 1 to 5 $Z^{1a}$, 6-10 membered C$_{6-10}$ aryl optionally substituted by 1 to 5 $Z^{1a}$, 4-10 membered heterocyclyl optionally substituted by 1 to 5 $Z^{1a}$, 5-10 membered heteroaryl optionally substituted with 1 to 5 $Z^{1a}$, —OR$^{20}$, —C(O)R$^{20}$, —C(O)OR$^{20}$, —C(O)N(R$^{20}$)$_2$, —N(R$^{20}$)$_2$, —N(R$^{20}$)$^+$, —N(R$^{20}$)C(O)R$^{20}$, —N(R$^{20}$)C(O)OR$^{20}$, —N(R$^{20}$)C(O)N(R$^{20}$)$_2$, —N(R$^{20}$)S(O)$_2$(R$^{20}$), —NR$^{20}$S(O)$_2$N(R$^{20}$)$_2$, —NR$^{20}$S(O)$_2$O(R$^{20}$), —NS(O)(R$^{20}$)$_2$, —OC(O)R$^{20}$, —OC(O)OR$^{20}$, —OC(O)N(R$^{20}$)$_2$, —Si(R$^{20}$)$_3$, —S(O)R$^{20}$, —SF$_5$, —S(O)(NR$^{20}$)R$^{20}$, —S(NR$^{20}$)(NR$^{20}$)R$^{20}$, —S(O)(NR$^{20}$)N(R$^{20}$)$_2$, —S(O)(NCN)R$^{20}$, —S(O)$_2$R$^{20}$, —S(O)$_2$N(R$^{20}$)$_2$, —C(O)N(R$^{20}$)S(O)$_2$R$^{20}$, or —S(O)$_2$N(R$^{20}$)C(O)R$^{20}$;

each $Z^{1a}$ is independently oxo, halo, —NO$_2$, —N$_3$, —CN, C$_{1-8}$ alkyl optionally substituted by 1 to 5 $Z^{1b}$, C$_{2-8}$ alkenyl optionally substituted by 1 to 5 $Z^{1b}$, C$_{2-8}$ alkynyl optionally substituted by 1 to 5 $Z^{1b}$, C$_{3-10}$ cycloalkyl optionally substituted by 1 to 5 $Z^{1b}$, 6-10 membered aryl optionally substituted by 1 to 5 $Z^{1b}$, 4-10 membered heterocyclyl optionally substituted by 1 to 5 $Z^{1b}$, 5-10 membered heteroaryl optionally substituted with 1 to 5 $Z^{1b}$, —OR$^{21}$, —C(O)R$^{21}$, —C(O)OR$^{21}$, —C(O)N(R$^{21}$)$_2$, —N(R$^{21}$)$_2$, —N(R$^{21}$)$_3^+$, —N(R$^{21}$)C(O)R$^{21}$, —N(R$^{21}$)C(O)OR$^{21}$, —N(R$^{21}$)C(O)N(R$^{21}$)$_2$, —N(R$^{21}$)S(O)$_2$(R$^{21}$), —NR$^{21}$S(O)$_2$N(R$^{21}$)$_2$, —NR$^{21}$S(O)$_2$O(R$^{21}$), —NS(O)(R$^{21}$)$_2$, —OC(O)R$^{21}$, —OC(O)OR$^{21}$, —OC(O)N(R$^{21}$)$_2$, —Si(R$^{21}$)$_3$, —SR$^{21}$, —S(O)R$^{21}$, —SF$_5$, —S(O)(NR$^{21}$)R$^{21}$, —S(NR$^{21}$)(NR$^{21}$)R$^{21}$, —S(O)(NR$^{21}$)N(R$^{21}$)$_2$, —S(O)(NCN)R$^{21}$, —S(O)$_2$R$^{21}$, —S(O)$_2$N(R$^{21}$)$_2$, —C(O)N(R$^{21}$)S(O)$_2$R$^{21}$, or —S(O)$_2$N(R$^{21}$)C(O)R$^{21}$;

each $R^{20}$, $R^{21}$ and $R^{22}$ is independently hydrogen, C$_{1-8}$ alkyl optionally substituted with 1 to 5 $Z^{1b}$, C$_{2-8}$ alkenyl optionally substituted with 1 to 5 $Z^{1b}$, C$_{2-8}$ alkynyl optionally substituted with 1 to 5 $Z^{1b}$, C$_{3-10}$ cycloalkyl optionally substituted with 1 to 5 $Z^{1b}$, 4-10 membered heterocyclyl optionally substituted with 1 to 5 $Z^{1b}$, $C_{6-10}$ aryl optionally substituted with 1 to 5 $Z^{1b}$, or 5-10 membered heteroaryl optionally substituted with 1 to 5 $Z^{1b}$; and each $Z^1b$ is independently oxo, hydroxy, halo, —NO$_2$, —N$_3$, —CN, $C_{1-9}$ alkyl, $C_{2-6}$ alkenyl, $C_{2-6}$ alkynyl, $C_{3-10}$ cycloalkyl, $C_{1-8}$ haloalkyl, $C_{6-10}$ aryl, 5-10 membered heteroaryl, 4-10 membered heterocyclyl, —O($C_{1-9}$ alkyl), —O($C_{2-6}$ alkenyl), —O($C_{2-6}$ alkynyl), —O($C_{3-10}$ cycloalkyl), —O($C_{1-8}$ haloalkyl), —O(aryl), —O(heteroaryl), —O(heterocyclyl), —OC(O) ($C_{1-9}$ alkyl), —OC(O)($C_{2-6}$ alkenyl), —OC(O)($C_{2-6}$ alkenyl), —OC(O)($C_{2-6}$ alkynyl), —OC(O)($C_{3-10}$ cycloalkyl), —OC(O)($C_{1-8}$ haloalkyl), —OC(O)(aryl), —OC(O)(heteroaryl), —OC(O)(heterocyclyl), —NH$_2$, —NH($C_{1-9}$ alkyl), —NH($C_{2-6}$ alkenyl), —NH($C_{2-6}$ alkynyl), —NH($C_{3-10}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-10}$ cycloalkyl)$_2$, —N($C_{2-6}$ alkenyl)$_2$, —N($C_{2-6}$ alkynyl)$_2$, —N($C_{3-10}$ cycloalkyl)$_2$, —N($C_{1-8}$ haloalkyl)$_2$, —N(aryl)$_2$, —N(heteroaryl)$_2$, —N(heterocyclyl)$_2$, —N($C_{1-9}$ alkyl)($C_{3-10}$ cycloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-10}$ cycloalkyl), —N($C_{1-9}$ alkyl)($C_{1-8}$ haloalkyl), —N($C_{1-9}$ alkyl)(aryl), —N($C_{1-9}$ alkyl)(heteroaryl), —N($C_{1-9}$ alkyl)(heterocyclyl), —C(O)($C_{1-9}$ alkyl), —C(O)($C_{2-6}$ alkenyl), —C(O)($C_{2-6}$ alkynyl), —C(O)($C_{3-10}$ cycloalkyl), —C(O)($C_{1-8}$ haloalkyl), —C(O)(aryl), —C(O)(heteroaryl), —C(O)(heterocyclyl), —C(O)O($C_{1-9}$ alkyl), —C(O)O($C_{2-6}$ alkenyl), —C(O)O($C_{2-6}$ alkynyl), —C(O)O($C_{3-10}$ cycloalkyl), —C(O)O($C_{1-8}$ haloalkyl), —C(O)O(aryl), —C(O)O(heteroaryl), —C(O)O(heterocyclyl), —C(O)NH$_2$, —C(O)NH($C_{1-9}$ alkyl), —C(O)NH($C_{2-6}$ alkenyl), —C(O)NH($C_{2-6}$ alkynyl), —C(O)NH($C_{3-10}$ cycloalkyl), —C(O)NH($C_{1-8}$ haloalkyl), —C(O)NH(aryl), —C(O)NH(heteroaryl), —C(O)NH(heterocyclyl), —C(O)N($C_{1-9}$ alkyl)$_2$, —C(O)N($C_{3-10}$ cycloalkyl)$_2$, —C(O)N($C_{2-6}$ alkenyl)$_2$, —C(O)N($C_{2-6}$ alkynyl)$_2$, —C(O)N($C_{1-8}$ haloalkyl)$_2$, —C(O)N(aryl)$_2$, —C(O)N(heteroaryl)$_2$, —C(O)N(heterocyclyl)$_2$, —NHC(O)($C_{1-9}$ alkyl), —NHC(O)($C_{2-6}$ alkenyl), —NHC(O)($C_{2-6}$ alkynyl), —NHC(O)($C_{3-10}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkenyl), —NHC(O)O($C_{2-6}$ alkynyl), —NHC(O)O($C_{3-10}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —NHC(O)NH($C_{2-6}$ alkenyl), —NHC(O)NH($C_{2-6}$ alkynyl), —NHC(O)NH($C_{3-10}$ cycloalkyl), —NHC(O)NH($C_{1-8}$ haloalkyl), —NHC(O)NH(aryl), —NHC(O)NH(heteroaryl), —NHC(O)NH(heterocyclyl), —SH, —S($C_{1-9}$ alkyl), —S($C_{2-6}$ alkenyl), —S($C_{2-6}$ alkynyl), —S($C_{3-10}$ cycloalkyl), —S($C_{1-8}$ haloalkyl), —S(aryl), —S(heteroaryl), —S(heterocyclyl), —NHS(O)($C_{1-9}$ alkyl), —N($C_{1-9}$ alkyl)(S(O)($C_{1-9}$ alkyl), —S(O)N($C_{1-9}$ alkyl)$_2$, —S(O)($C_{1-9}$ alkyl), —S(O)(NH)($C_{1-9}$ alkyl), —S(O)($C_{2-6}$ alkenyl), —S(O)($C_{2-6}$ alkynyl), —S(O)($C_{3-10}$ cycloalkyl), —S(O)($C_{1-8}$ haloalkyl), —S(O)(aryl), —S(O)(heteroaryl), —S(O)(heterocyclyl), —S(O)$_2$($C_{1-9}$ alkyl), —S(O)$_2$($C_{2-6}$ alkenyl), —S(O)$_2$($C_{2-6}$ alkynyl), —S(O)$_2$($C_{3-10}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), or —S(O)$_2$N($C_{1-9}$ alkyl)$_2$;

wherein any alkyl, cycloalkyl, aryl, heteroaryl, or heterocyclyl of $Z^{1b}$ is optionally substituted with one or more halo, $C_{1-9}$ alkyl, $C_{1-8}$ haloalkyl, —OH, —NH$_2$, —NH($C_{1-9}$ alkyl), —NH($C_{3-10}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-10}$ cycloalkyl)$_2$, —NHC(O)($C_{3-10}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkynyl), —NHC(O)O($C_{3-10}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —S(O)(NH)($C_{1-9}$ alkyl), —S(O)$_2$ ($C_{1-9}$ alkyl), —S(O)$_2$($C_{3-10}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), —S(O)$_2$N($C_{1-9}$ alkyl)$_2$, —O($C_{3-10}$ cycloalkyl), —O($C_{1-8}$ haloalkyl), —O(aryl), —O(heteroaryl), —O(heterocyclyl), or —O($C_{1-9}$ alkyl).

Also provided herein are compounds of Table 1, or a pharmaceutically acceptable salt thereof.

The present disclosure provides a method of inhibiting peptidylarginine deiminase type 4 (PAD4) comprising contacting an effective amount of a compound of Formula I, or any formula described herein, or a pharmaceutically acceptable salt thereof, with a cell.

The present disclosure provides a method of inhibiting peptidylarginine deiminase type 4 (PAD4) comprising administering an effective amount of a compound of Formula I, or any formula described herein, or a pharmaceutically acceptable salt thereof, to a patient in need thereof.

The present disclosure provides a method for treating a disease or disorder mediated by peptidylarginine deiminase type 4 (PAD4), comprising administering an effective amount of a compound of Formula I, or any formula described herein, or a pharmaceutically acceptable salt thereof, to a patient in need thereof.

The present disclosure provides a method for treating acute lymphocytic leukemia, ankylosing spondylitis, cancer, chronic lymphocytic leukemia, colitis, lupus, systemic lupus erythematosus, cutaneous lupus erythematosus, rheumatoid arthritis, multiple sclerosis, or ulcerative colitis, comprising administering an effective amount of a compound of Formula I, or any formula described herein, or a pharmaceutically acceptable salt thereof, to a patient in need thereof.

In one embodiment, the present disclosure provides a pharmaceutical composition comprising a compound of Formula I, or any formula described herein, or a pharmaceutically acceptable salt thereof, and a pharmaceutically acceptable carrier or excipient.

In one embodiment, the present disclosure provides a pharmaceutical composition comprising a compound of Formula I, or any formula described herein, or a pharmaceutically acceptable salt thereof, and at least one additional therapeutic agent and at least one pharmaceutically acceptable carrier or excipient.

In one embodiment, the present disclosure provides a pharmaceutical composition comprising a compound of Formula I, or any formula described herein, or a pharmaceutically acceptable salt thereof, at least one additional therapeutic agent suitable for treating rheumatoid arthritis, and at least one pharmaceutically acceptable carrier or excipient.

In one embodiment, the present disclosure provides a kit that includes a compound of Formula I, or any formula described herein, or a pharmaceutically acceptable salt thereof, a label and/or instructions for use of the compound in the treatment of rheumatoid arthritis or a disease or condition mediated by peptidylarginine deiminase type 4 (PAD4).

In one embodiment, the present disclosure provides a compound of Formula I, or any formula described herein, or a pharmaceutically acceptable salt thereof, for use in therapy.

In another embodiment, the present disclosure provides a compound of Formula I, or any formula described herein, or a pharmaceutically acceptable salt thereof, for use in the manufacture of a medicament for treating rheumatoid arthritis or a disease or condition mediated by peptidylarginine deiminase type 4 (PAD4).

DETAILED DESCRIPTION

Unless defined otherwise, all technical and scientific terms used herein have the same meaning as commonly understood by one of ordinary skill in the art. It must be noted that as used herein and in the appended claims, the singular forms "a", "and", and "the" include plural referents unless the context clearly dictates otherwise. Thus, e.g., reference to "the compound" includes a plurality of such compounds and reference to "the assay" includes reference to one or more assays and equivalents thereof known to those skilled in the art, and so forth.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. Unless chemically or structurally required, no directionality is indicated or implied by the order in which a chemical group is written or named.

A wavy line on a chemical group as shown below, for example,

indicates a point of attachment, i.e., it shows the broken bond by which the group is connected to another described group.

The prefix "C$_{u-v}$" indicates that the following group has from u to v carbon atoms. For example, "C$_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., C$_{1-20}$ alkyl), 1 to 12 carbon atoms (i.e., C$_{1-12}$ alkyl), 1 to 10 carbon atoms (i.e., CH$_{1-10}$ alkyl), 1 to 8 carbon atoms (i.e., C$_{1-8}$ alkyl), 1 to 6 carbon atoms (i.e., C$_{1-6}$ alkyl), or 1 to 4 carbon atoms (i.e., C$_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e., —(CH$_2$)$_3$CH$_3$), sec-butyl (i.e., —CH(CH$_3$)CH$_2$CH$_3$), isobutyl (i.e., —CH$_2$CH(CH$_3$)$_2$) and tert-butyl (i.e., —C(CH$_3$)$_3$); and "propyl" includes n-propyl (i.e., —(CH$_2$)$_2$CH$_3$) and isopropyl (i.e., —CH(CH$_3$)$_2$).

"Alkenyl" refers to any group derived from a straight or branched hydrocarbon with at least one carbon-carbon double bond. Unless otherwise specified, alkenyl groups have from 2 to 20 carbon atoms (i.e., C$_{2-20}$ alkenyl), 2 to 12 carbon atoms (i.e., C$_{2-12}$ alkenyl), 2 to 10 carbon atoms (i.e., C$_{2-10}$ alkenyl), 2 to 8 carbon atoms (i.e., C$_{2-8}$ alkenyl), 2 to 6 carbon atoms (i.e., C$_{2-6}$ alkenyl), or 2 to 4 carbon atoms (i.e., C$_{2-4}$ alkenyl). Examples of alkenyl groups include ethenyl, propenyl, butadienyl (including 1,2-butadienyl, and 1,3-butadienyl).

"Alkynyl" refers to any group derived from a straight or branched hydrocarbon with at least one carbon-carbon triple bond. Unless otherwise specified, alkynyl groups have from 2 to 20 carbon atoms (i.e., C$_{2-20}$ alkynyl), 2 to 12 carbon atoms (i.e., C$_{2-12}$ alkynyl), 2 to 10 carbon atoms (i.e., C$_{2-10}$ alkynyl), 2 to 8 carbon atoms (i.e., C$_{2-8}$ alkynyl), 2 to 6 carbon atoms (i.e., C$_{2-6}$ alkynyl), or 2 to 4 carbon atoms (i.e., C$_{2-4}$ alkynyl). The term "alkynyl" also includes those groups having one triple bond and one double bond. Examples of alkynyl groups include, but are not limited to, ethynyl propargyl (—CH$_2$C≡C—), (E)-pent-3-en-1-ynyl, and the like.

The term "aryl" as used herein refers to a single all carbon aromatic ring or a multiple condensed all carbon ring system wherein at least one of the rings is aromatic. For example, in certain embodiments, an aryl group 6 to 20 ring carbon atoms (i.e., C$_{6-20}$ aryl), 6 to 14 carbon ring atoms (i.e., C$_{6-14}$ aryl), 6 to 12 carbon ring atoms (i.e., C$_{6-12}$ aryl), or 6 to 10 carbon ring atoms (i.e., C$_{6-10}$ aryl). Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. Aryl, however, does not encompass or overlap in any way with heteroaryl defined below. If one or more aryl groups are fused with a heteroaryl ring, the resulting ring system is heteroaryl. It is also to be understood that when reference is made to a certain atom-range membered aryl (e.g., C$_{6-10}$ aryl), the atom range is for the total ring atoms of the aryl. For example, a 6-membered aryl would include phenyl and a 10-membered aryl would include naphthyl and 1,2,3,4-tetrahydronaphthyl. Aryl groups include, but are not limited to, those groups derived from acenaphthylene, anthracene, azulene, benzene, chrysene, a cyclopentadienyl anion, naphthalene, fluoranthene, fluorene, indane, perylene, phenalene, phenanthrene, pyrene, and the like. Non-limiting examples of aryl groups include, but are not limited to, phenyl, indenyl, naphthyl, 1,2,3,4-tetrahydronaphthyl, anthracenyl, and the like.

The term "cycloalkyl" refers to a single saturated or partially unsaturated all carbon ring having 3 to 20 annular carbon atoms (i.e., $C_{3-20}$ cycloalkyl), 3 to 14 ring carbon atoms (i.e., $C_{3-14}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). As used herein the term "cycloalkenyl" refers to the non-aromatic carbocyclic (partially saturated cyclic alkyl) group having at least one double bond. Accordingly, cycloalkyl includes multicyclic carbocycles such as a bicyclic carbocycles (e.g., bicyclic carbocycles having about 6 to 12 annular carbon atoms such as bicyclo[3.1.0]hexane, bicyclo[2.1.1]hexane), bicyclo[1.1.1]pentane, and polycyclic carbocycles (e.g., tricyclic and tetracyclic carbocycles with up to about 20 annular carbon atoms). The rings of a multiple condensed ring system can be connected to each other via fused, spiro and bridged bonds when allowed by valency requirements. Non-limiting examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, spiro[3.3]heptane, and 1-cyclohex-3-enyl.

"Halo" and "halogen" refer to fluoro, chloro, bromo and iodo.

"Haloalkyl" refers to an alkyl group as defined herein, wherein one or more hydrogen atoms (e.g., 1-5, or 1-3) are replaced by a halogen. Examples include, but are not limited to, —CH$_2$Cl, CH$_2$F, —CH$_2$Br, —CFClBr, —CH$_2$CH$_2$Cl, —CH$_2$CH$_2$F, —CF$_3$, —CH$_2$CF$_3$, —CH$_2$CCl3, and the like, as well as alkyl groups such as perfluoroalkyl in which all hydrogen atoms are replaced by fluorine atoms.

"Heteroalkyl" refers to an alkyl in which one or more of the carbon atoms (and any associated hydrogen atoms) are each independently replaced with the same or different heteroatom or heteroatomic group. Heteroatoms include, but are not limited to, N, P, O, S, etc. Heteroatomic groups include, but are not limited to, —NR—, —O—, —S—, —PH—, —P(O)$_2$—, —S(O)—, —S(O)$_2$—, and the like, where R is H, alkyl, aryl, cycloalkyl, heteroalkyl, heteroaryl or cycloheteroalkyl. Heteroalkyl groups include, but are not limited to, —OCH$_3$, —CH$_2$OCH$_3$, —SCH$_3$, —CH$_2$SCH$_3$, —NRCH$_3$, —CH$_2$NRCH$_3$, —CH$_2$OH and the like, where R is hydrogen, alkyl, aryl, arylalkyl, heteroalkyl, or heteroaryl. As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to a monoradical or diradical aromatic group having a single ring, multiple rings, or multiple fused rings, with one or more ring heteroatoms independently selected from nitrogen, oxygen, and sulfur. The term includes fused ring systems wherein one or more (e.g., one, two, or three) fused rings is/are fully or partially unsaturated. As used herein, heteroaryl include 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Non-limiting examples of heteroaryl groups include, but are not limited to, groups derived from acridine, benzimidazole, benzothiophene, benzofuran, benzoxazole, benzothiazole, carbazole, carboline, cinnoline, furan, imidazole, imidazopyridine, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyridone, pyrimidine, pyrrole, pyrrolizine, quinazoline, quinoline, quinolizine, quinoxaline, tetrazole, thiadiazole, thiazole, thiophene, triazole, xanthene, and the like.

"Heterocyclyl" refers to a saturated or unsaturated cyclic alkyl group, with one or more ring heteroatoms independently selected from nitrogen, oxygen and sulfur. The term "heterocyclyl" includes heterocycloalkenyl groups (i.e. the heterocyclyl group having at least one double bond), bridged-groups, fused-heterocyclyl groups, and spiro-heterocyclyl groups. A heterocyclyl may be a single ring or multiple rings wherein the multiple rings may be fused, bridged, or spiro. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms, 2 to 12 ring carbon atoms, 2 to 10 ring carbon atoms, 2 to 8 ring carbon atoms, 3 to 12 ring carbon atoms, 3 to 8 ring carbon atoms, or 3 to 6 ring carbon atoms; and having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. A heterocyclyl may contain one or more oxo and/or thioxo groups. Examples of heterocyclyl groups include, but are not limited to, groups derived from azetidine, aziridine, imidazolidine, morpholine, oxirane (epoxide), oxetane, piperazine, piperidine, pyrazolidine, piperidine, pyrrolidine, pyrrolidinone, tetrahydrofuran, tetrahydrothiophene, dihydropyridine, tetrahydropyridine, tetrahydro-2H-thiopyran 1,1-dioxide, quinuclidine, N-bromopyrrolidine, N-chloropiperidine, and the like. Heterocycles include spirocycles, such as, for example, aza or oxo-spiroheptanes. As used herein, the term "bridged-heterocyclyl" refers to a four- to ten-membered cyclic moiety connected at two non-adjacent atoms of the heterocyclyl with one or more (e.g., 1 or 2) four- to ten-membered cyclic moiety having at least one heteroatom where each heteroatom is independently selected from nitrogen, oxygen, and sulfur. As used herein, bridged-heterocyclyl includes bicyclic and tricyclic ring systems. Non-limiting examples of bridged-heterocyclyl include 8-azabicyclo[3.2.1]octan-8-yl, 2-azabicyclo[3.2.1] octan-2-yl, 2-azabicyclo[2.2.1]heptan-2-yl, and 7-azabicyclo[2.2.1]heptan-7-yl. Also used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl rings include bicyclic and tricyclic ring systems, such as 2-oxa-7-azaspiro[3.5] nonanyl, 2-oxa-6-azaspiro[3.4]octanyl, 5-azaspiro[2.4]heptanyl, and 6-oxa-1-azaspiro[3.3]heptanyl. Examples of the fused-heterocyclyl rings include, but are not limited to, 3-azabicyclo[3.1.0]hexanyl, 1,2,3,4-tetrahydroisoquinolinyl, 1-oxo-1,2,3,4-tetrahydroisoquinolinyl, 1-oxo-1,2-dihydroisoquinolinyl, 4,5,6,7-tetrahydrothieno[2,3-c]pyridinyl, indolinyl, and isoindolinyl, where the heterocyclyl can be bound via either ring of the fused system. Additional examples, but are not limited to, groups derived from include dihydroquinolines, e.g., 3,4-dihydroquinoline, dihydroisoquinolines, e.g., 1,2-dihydroisoquinoline, dihydroimidazole, tetrahydroimidazole, etc., indoline, isoindoline, isoindolones (e.g., isoindolin-1-one), isatin, dihydrophthalazine, quinolinone, spiro[cyclopropane-1,1'-isoindolin]-3'-one, and the like. Additional examples of heterocycles include, but are not limited to, groups derived from 2-azabicyclo[2.2.1]heptane, 8-azabicyclo[3.2.1]octane, 3-azabicyclo[4.1.0]heptane, octahydro-2H-pyrido[4,3-b][1,4]oxazine, hexahydropyridazine, 3,8-diazabicyclo[3.2.1]octane, 2,5-diazabicyclo[2.2.1]heptane, 3,6-diazabicyclo[3.1.1]heptane, 3-oxa-7,9-diazabicyclo[3.3.1]nonane, 7azabicyclo[2.2.1]heptane, 2-azabicyclo[2.2.2]octane, 6-oxa-2-azabicyclo[3.2.1]octane, and hexahydropyrazino[2,1-c][1,4]oxazine, for example, where the heterocycle can be bound via either ring of the fused system.

"Bridged" refers to a ring fusion wherein non-adjacent atoms on a ring are joined by a divalent substituent, such as an alkylene or heteroalkylene group or a single heteroatom. Quinuclidinyl and adamantyl are examples of bridged ring systems.

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents. When substituents bound to the same atom join together (e.g., two $Z^8$ groups join together) they may be taken from the same point of attachment to form a spiro ring.

The term "fused" refers to a ring which is bound to an adjacent ring.

"Oxo" refers to =O or —O⁻. "Hydroxyl" and "hydroxy" are used interchangeably and refer to OH. Where tautomeric forms of the compound exist, hydroxyl and oxo groups are interchangeable.

It is understood that combinations of chemical groups may be used and will be recognized by persons of ordinary skill in the art. For instance, the group "hydroxyalkyl" would refer to a hydroxyl group attached to an alkyl group. A great number of such combinations may be readily envisaged. Additional examples of substituent combinations used herein include: $C_{1-6}$ alkylamiocarbonyl (e.g., $CH_3CH_2NHC(O)$—), $C_{1-6}$ alkoxycarbonyl (e.g., $CH_3O$—C(O)—), 5-7 membered heterocyclyl-$C_{1-6}$ alkyl (e.g., piperazinyl-$CH_2$—), $C_{1-6}$alkylsulfonyl-5-7 membered heterocyclyl (e.g., $CH_3S(O)_2$-morpholinyl-), 5-7 membered heterocyclyl $C_{1-6}$ alkoxy, 5-7 membered heterocyclyloxy, (4-7 membered heterocyclyl)-4-7 membered heterocyclyl (e.g., oxetanyl-pyrrolidinyl-), $C_{3-6}$ cycloalkylaminocarbonyl (e.g., cyclopropyl-NH—C(O)—), 5-7 membered heterocyclyl-$C_{2-6}$ alkynyl (e.g., N-piperazinyl-$CH_2C\equiv CCH_2$-), and $C_{6-10}$ arylaminocarbonyl (e.g., phenyl-NH—C(O)—).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. The suffix "ene" is often used to refer to a group that has two single bond points of attachments to other groups. For example, methylene refers to —$CH_2$—. Similarly, alkylene, alkenylene, alkynylene, cycloalkylene, heterocyclene, arylene, and heteroarylene refer to respective alkyl, alkenyl, alkynyl, cycloalkyl, heterocyclyl, aryl, and heteroaryl groups as defined herein having two single bond points of attachments to other groups. Also, unless indicated explicitly otherwise, where combinations of groups are referred to herein as one moiety, e.g., arylalkyl, the last-mentioned group contains the atom by which the moiety is attached to the rest of the molecule.

The compounds described herein include isomers, stereoisomers and the like. As used herein, the term "isomers" refers to different compounds that have the same molecular formula but differ in arrangement and configuration of the atoms. Also as used herein, the term "a stereoisomer" refers to any of the various stereo isomeric configurations which may exist for a given compound disclosed herein and includes geometric isomers. It is understood that a substituent may be attached at a chiral center of a carbon atom. Therefore, the compound disclosed herein includes enantiomers, diastereomers or racemates of the compound.

"Enantiomers" are a pair of stereoisomers that are non-superimposable mirror images of each other. A 1:1 mixture of a pair of enantiomers is a "racemic" mixture.

The term is used to designate a racemic mixture where appropriate. "Diastereoisomers" are stereoisomers that have at least two stereocenters, but which are not mirror-images of each other.

The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S)-. The present disclosure is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included. To the extent that compounds depicted herein are represented as having a particular stereochemistry, it is understood by one of skill in the art that such compounds may contain some detectable or undetectable levels of compounds sharing the same structure, but having different stereochemistry.

"$IC_{95}$" or "$EC_{95}$" refers to the inhibitory concentration required to achieve 95% of the maximum desired effect, which in many cases herein is the inhibition of the PAD4 enzyme.

"$IC_{50}$" or "$EC_{50}$" refers to the inhibitory concentration required to achieve 50% of the maximum desired effect, which in many cases herein is the inhibition of the PAD4 enzyme.

"Pharmaceutically acceptable" refers to compounds, salts, compositions, dosage forms and other materials which are useful in preparing a pharmaceutical composition that is suitable for veterinary or human pharmaceutical use.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" refers to a salt of a compound that is pharmaceutically acceptable and that possesses (or can be converted to a form that possesses) the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, lactic acid, maleic acid, malonic acid, mandelic acid, methanesulfonic acid, 2-naphthalenesulfonic acid, oleic acid, palmitic acid, propionic acid, stearic acid, succinic acid, tartaric acid, p-toluenesulfonic acid, trimethylacetic acid, and the like, and salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott, Williams & Wilkins, Philadelphia, PA, (2005), at p. 732, Table 38-5, both of which are hereby incorporated by reference herein.

Compounds disclosed herein include isotopically labeled, solvates, hydrates, tautomers, stereoisomers and salt forms thereof.

Provided are also compounds in which from 1 to n hydrogen atoms attached to a carbon atom may be replaced by deuterium atom or D, in which n is the number of hydrogen atoms in the molecule. As known in the art, the deuterium atom is a non-radioactive isotope of the hydrogen atom. Such compounds exhibit may increase resistance to metabolism, and thus may be useful for increasing the half-life of the compounds when administered to a mammal. See, e.g., Foster, "Deuterium Isotope Effects in Studies of Drug Metabolism," Trends Pharmacol. Sci., 5(12):524-527 (1984). Such compounds are synthesized by means well known in the art, for example by employing starting materials in which one or more hydrogen atoms have been replaced by deuterium.

Any formula or structure given herein, including Formula I, or any formula disclosed herein, is intended to represent unlabeled forms as well as isotopically labeled forms of the compounds. Isotopically labeled compounds have structures depicted by the formulas given herein except that one or more (e.g., one to three, or one to five) atoms are replaced by an isotope having a selected atomic mass or mass number. Examples of isotopes that can be incorporated into compounds of the disclosure include isotopes of hydrogen, carbon, nitrogen, oxygen, phosphorus, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl, and $^{125}$I. Various isotopically labeled compounds of the present disclosure, for example those into which radioactive isotopes such as $^3$H and $^{14}$C are incorporated, are within the ambit of the present disclosure. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in treatment of patients. Such isotopically labeled analogs of compounds of the present disclosure may also be useful for treatment of diseases disclosed herein because they may provide improved pharmacokinetic and/or pharmacodynamic properties over the unlabeled forms of the same compounds. Such isotopically leveled forms of or analogs of compounds herein are within the ambit of the present disclosure. One of skill in the art is able to prepare and use such isotopically labeled forms following procedures for isotopically labeling compounds or aspects of compounds to arrive at isotopic or radiolabeled analogs of compounds disclosed herein.

The present disclosure also provides for prodrugs of the compounds disclosed herein. A "prodrug" is defined in the pharmaceutical field as a biologically inactive derivative of a drug that upon administration to the human body is converted to the biologically active parent drug according to some chemical or enzymatic pathway.

Compounds

Provided herein are compounds that function as inhibitors of peptidylarginine deiminase type 4 (PAD4), methods of using such compounds and compositions comprising such compounds optionally in combination with one or more additional agents or therapies. In all embodiments discussed herein where there is more than one occurrence of a group or variable, it is intended that the group or variable is independently selected the list that follows. All embodiments directed to compounds also include any salt, stereoisomer, mixture of stereoisomers, prodrug, isotopically labeled, solvate, hydrate, or tautomer thereof.

Provided is a compound of Formula I:

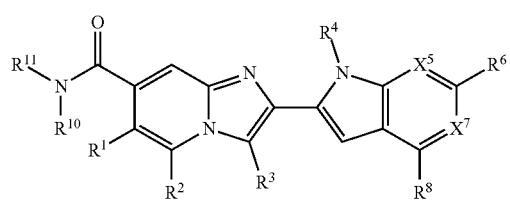

or a pharmaceutically acceptable salt thereof, wherein:

$X^5$ is N or C—$R^5$;

$X^7$ is N or C—$R^7$;

$R^1$ is hydrogen, halo, —CN, —O$R^{12}$, —N($R^{12}$)$_2$, —S$R^{12}$, $C_{1-8}$ alkyl optionally substituted with 1 to 5 $Z^1$, $C_{3-6}$ cycloalkyl optionally substituted with 1 to 5 $Z^1$, or 4-6 membered heterocyclyl optionally substituted with 1 to 5 $Z^1$;

$R^2$ is hydrogen, halo, —CN, —O$R^{12}$, —N($R^{12}$)$_2$, —S$R^{12}$, —S(O)$R^{20}$, $C_{1-8}$ alkyl optionally substituted with 1 to 5 $Z^1$, $C_{3-6}$ cycloalkyl optionally substituted with 1 to 5 $Z^1$, or 4-6 membered heterocyclyl optionally substituted with 1 to 5 $Z^1$;

$R^3$ is hydrogen, —N($R^{12}$)$_2$, $C_{1-8}$ alkyl optionally substituted with 1 to 5 $Z^1$, $C_{2-8}$ alkenyl optionally substituted with 1 to 5 $Z^1$, $C_{2-8}$ alkynyl optionally substituted with 1 to 5 $Z^1$, $C_{3-10}$ cycloalkyl optionally substituted with 1 to 5 $Z^1$, or 4-10 membered heterocyclyl optionally substituted with 1 to 5 $Z^1$; or $R^2$ and $R^3$ are taken together with the atoms to which they are attached to form an optionally substituted 6 to 8 membered heterocyclyl ring;

$R^4$ is hydrogen, $C_{1-8}$ alkyl optionally substituted with 1 to 5 $Z^1$, $C_{3-10}$ alkenyl optionally substituted with 1 to 5 $Z^1$, $C_{3-10}$ alkynyl optionally substituted with 1 to 5 $Z^1$, $C_{3-10}$ cycloalkyl optionally substituted with 1 to 5 $Z^1$, 4-10 membered heterocyclyl optionally substituted with 1 to 5 $Z^1$, $C_{6-10}$ aryl optionally substituted with 1 to 5 $Z^1$, or 5-10 membered heteroaryl optionally substituted with 1 to 5 $Z^1$;

$R^5$ is hydrogen, halo, —CN, —$OR^{12}$, —$C_{1-8}$ alkyl optionally substituted with 1 to 3 $Z^1$, $C_{3-6}$ cycloalkyl optionally substituted with 1 to 3 $Z^1$, or 4-6 membered heterocyclyl optionally substituted with 1 to 3 $Z^1$;

$R^6$ is —$N(R^{14})S(O)_2R^9$, —$N(R^{14})C(O)OR^9$, —$OC(O)R^9$, —$OC(O)OR^9$, -L-$R^{13}$, —$OR^{15}$, $C_{2-8}$ alkenyl optionally substituted with 1 to 5 $Z^1$, $C_{2-8}$ alkynyl optionally substituted with 1 to 5 $Z^1$, $C_{3-10}$ cycloalkyl substituted with 1 to 5 $Z^1$, $C_{6-10}$ aryl substituted with 1 to 5 $Z^1$, 4-10 membered heterocyclyl substituted with 1 to 5 $Z^1$,

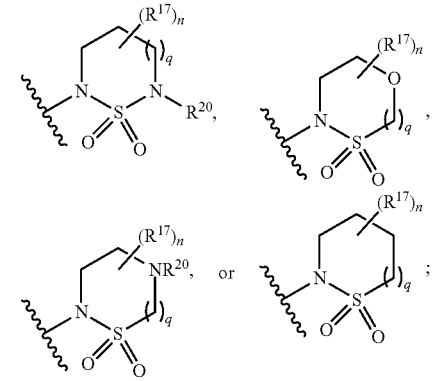

where q is 0, 1 or 2; and n is 0, 1, 2, 3, 4, 5, or 6;

$R^7$ is hydrogen, halo, —CN, —$OR^{12}$, —$C_{1-8}$ alkyl optionally substituted with 1 to 3 $Z^1$, $C_{3-6}$ cycloalkyl optionally substituted with 1 to 3 $Z^1$, or 4-6 membered heterocyclyl optionally substituted with 1 to 3 $Z^1$;

$R^8$ is hydrogen, halo, —CN, —$OR^{12}$, —$C_{1-8}$ alkyl optionally substituted with 1 to 3 $Z^1$, $C_{3-6}$ cycloalkyl optionally substituted with 1 to 3 $Z^1$, or 4-6 membered heterocyclyl optionally substituted with 1 to 3 $Z^1$;

each $R^9$ is independently $C_{1-8}$ alkyl optionally substituted with 1 to 5 $Z^1$, $C_{2-8}$ alkenyl optionally substituted with 1 to 5 $Z^1$, $C_{2-8}$ alkynyl optionally substituted with 1 to 5 $Z^1$, $C_{3-10}$ cycloalkyl optionally substituted with 1 to 5 $Z^1$, 4-10 membered heterocyclyl optionally substituted with 1 to 5 $Z^1$, $C_{6-10}$ aryl optionally substituted with 1 to 5 $Z^1$, or 5-10 membered heteroaryl optionally substituted with 1 to 5 $Z^1$;

$R^{10}$ is hydrogen, $C_{1-8}$ alkyl optionally substituted with 1 to 5 $Z^1$, $C_{2-8}$ alkenyl optionally substituted with 1 to 5 $Z^1$, $C_{2-8}$ alkynyl optionally substituted with 1 to 5 $Z^1$, $C_{3-10}$ cycloalkyl optionally substituted with 1 to 5 $Z^1$;

$R^{11}$ is hydrogen, $C_{1-8}$ alkyl optionally substituted with 1 to 5 $Z^1$, $C_{2-8}$ alkenyl optionally substituted with 1 to 5 $Z^1$, $C_{2-8}$ alkynyl optionally substituted with 1 to 5 $Z^1$, $C_{3-10}$ cycloalkyl optionally substituted with 1 to 5 $Z^1$, 4-10 membered heterocyclyl optionally substituted with 1 to 5 $Z^1$, $C_{6-10}$ aryl optionally substituted with 1 to 5 $Z^1$, or 5-10 membered heteroaryl optionally substituted with 1 to 5 $Z^1$; or $R^{10}$ and $R^{11}$ are taken together with the nitrogen to which they are attached to form a 4-12-membered heterocyclyl optionally substituted with 1 to 4 $Z^1$;

each $R^{12}$ is independently hydrogen, $C_{1-8}$ alkyl optionally substituted with 1 to 5 $Z^{1b}$, $C_{3-8}$ alkenyl optionally substituted with 1 to 5 $Z^{1b}$, $C_{3-8}$ alkynyl optionally substituted with 1 to 5 $Z^{1b}$, $C_{3-10}$ cycloalkyl optionally substituted with 1 to 5 $Z^{1b}$, 4-10 membered heterocyclyl optionally substituted with 1 to 5 $Z^{1b}$, $C_{6-10}$ aryl optionally substituted with 1 to 5 $Z^{1b}$, or 5-10 membered heteroaryl optionally substituted with 1 to 5 $Z^1b$;

L is $C_{1-8}$ alkylene, —O—$C_{1-8}$ alkylene, $C_{1-8}$ haloalkylene, —O—$C_{1-8}$ haloalkylene, or 5-10 membered heteroarylene; and each $C_{1-8}$ alkylene, $C_{1-8}$ haloalkylene, or 5-10 membered heteroarylene of L is optionally substituted with 1 to 5 $Z^1$;

$R^{13}$ is —$OR^{15}$, —$N(R^{15})(R^{14})$, —$C(O)N(R^{14})_2$, —$OC(O)N(R^{14})_2$, —$N(R^{14})C(O)R^9$, —$N(R^{14})C(O)OR^9$, —$N(R^{14})C(O)N(R^{14})_2$, —$N(R^{14})S(O)_2R^9$, —$NR^{14}S(O)_2N(R^{14})_2$, —$NR^{14}S(O)_2OR^9$, —$NS(O)(R^9)_2$, —$Si(R^{14})_2R^9$, —$SR^9$, —$S(O)R^9$, —$S(O)_2R^9$, —$SF_5$, —$S(O)(NR^{14})R^9$, —$S(NR^{14})(NR^{14})R^9$, —$S(O)(NR^{14})N(R^{14})_2$, —$S(O)(NCN)R^9$, —$S(O)_2N(R^{14})_2$, —$C(O)N(R^{14})S(O)_2R^9$, —$S(O)_2N(R^{14})C(O)R^9$, or $C_{3-10}$ cycloalkyl substituted with 1 to 5 $Z^1$;

each $R^{14}$ is independently hydrogen, $C_{1-8}$ alkyl optionally substituted with 1 to 5 $Z^1$, $C_{2-8}$ alkenyl optionally substituted with 1 to 5 $Z^1$, $C_{2-8}$ alkynyl optionally substituted with 1 to 5 $Z^1$, $C_{3-10}$ cycloalkyl optionally substituted with 1 to 5 $Z^1$, 4-10 membered heterocyclyl optionally substituted with 1 to 5 $Z^1$, $C_{6-10}$ aryl optionally substituted with 1 to 5 $Z^1$, or 5-10 membered heteroaryl optionally substituted with 1 to 5 $Z^1$;

$R^{15}$ is cycloalkyl optionally substituted with 1 to 5 $Z^1$, 4-10 membered heterocyclyl optionally substituted with 1 to 5 $Z^1$, $C_{6-10}$ aryl optionally substituted with 1 to 5 $Z^1$, 5-10 membered heteroaryl optionally substituted with 1 to 5 $Z^1$;

each $R^{17}$ is independently hydrogen, halo, —$NO_2$, —$N_3$, —CN, $C_{1-8}$ alkyl optionally substituted by 1 to 3 $Z^{1a}$, $C_{2-8}$ alkenyl optionally substituted by 1 to 3 $Z^{1a}$, $C_{2-8}$ alkynyl optionally substituted by 1 to 3 $Z^{1a}$, $C_{3-8}$ cycloalkyl optionally substituted by 1 to 3 $Z^{1a}$, 6-10 membered aryl optionally substituted by 1 to 3 $Z^{1a}$, 4-10 membered heterocyclyl optionally substituted by 1 to 3 $Z^{1a}$, 5-10 membered heteroaryl optionally substituted with 1 to 3 $Z^{1a}$, —$OR^{20}$, —$C(O)R^{20}$, —$C(O)OR^{20}$, —$C(O)N(R^{20})_2$, —$N(R^{20})_2$, —$N(R^{20})_3^+$, —$N(R^{20})C(O)R^{20}$, —$N(R^{20})C(O)OR^{20}$, —$N(R^{20})C(O)N(R^{20})_2$, —$N(R^{20})S(O)_2(R^{20})$, —$NR^{20}S(O)_2N(R^{20})_2$, —$NR^{20}S(O)_2O(R^{20})$, —$NS(O)(R^{20})_2$, —$OC(O)R^{20}$, —$OC(O)OR^{20}$, —$OC(O)N(R^{20})_2$, —$Si(R^{20})_3$, —$S(O)R^{20}$, —$SF_5$, —$S(O)(NR^{20})R^{20}$, —$S(NR^{20})(NR^{20})R^{20}$, —$S(O)(NR^{20})N(R^{20})_2$, —$S(O)(NCN)R^{20}$, —$S(O)_2R^{20}$, —$S(O)_2N(R^{20})_2$, —$C(O)N(R^{20})S(O)_2R^{20}$, or —$S(O)_2N(R^{20})C(O)R^{20}$; or two $R^{17}$ on the same or different carbon atoms are taken together to form a 3-8-membered ring optionally substituted with 1 to 4 $Z^1$;

each $Z^1$ is independently halo, —$NO_2$, —$N_3$, —CN, $C_{1-8}$ alkyl optionally substituted by 1 to 5 $Z^{1a}$, $C_{2-8}$ alkenyl optionally substituted by 1 to 5 $Z^{1a}$, $C_{2-8}$ alkynyl optionally substituted by 1 to 5 $Z^{1a}$, $C_{3-10}$ cycloalkyl optionally substituted by 1 to 5 $Z^{1a}$, 6-10 membered $C_{6-10}$ aryl optionally substituted by 1 to 5 $Z^{1a}$, 4-10 membered heterocyclyl optionally substituted by 1 to 5

$Z^{1a}$, 5-10 membered heteroaryl optionally substituted with 1 to 5 $Z^{1a}$, —C(O)R$^{20}$, —C(O)OR$^{20}$, —C(O)N(R$^{20}$)$_2$, —N(R$^{20}$)$_2$, —N(R$^{20}$)$_3$$^+$, —N(R$^{20}$)C(O)R$^{20}$, —N(R$^{20}$)C(O)OR$^{20}$,
—N(R$^{20}$)C(O)N(R$^{20}$)$_2$, —N(R$^{20}$)S(O)$_2$(R$^{20}$), —NR$^{20}$S(O)$_2$N(R$^{20}$)$_2$, —NR$^{20}$S(O)$_2$O(R$^{20}$), —NS(O)(R$^{20}$)$_2$, —OC(O)R$^{20}$,
—OC(O)OR$^{20}$, —OC(O)N(R$^{20}$)$_2$, —Si(R$^{20}$)$_3$, —S(O)R$^{20}$, —SF$_5$, —S(O)(NR$^{20}$)R$^{20}$, —S(NR$^{20}$)(NR$^{20}$)R$^{20}$,
—S(O)(NR$^{20}$)N(R$^{20}$)$_2$, —S(O)(NCN)R$^{20}$, —S(O)$_2$R$^{20}$, —S(O)$_2$N(R$^{20}$)$_2$, —C(O)N(R$^{20}$)S(O)$_2$R$^{20}$, or —S(O)$_2$N(R$^{20}$)C(O)R$^{20}$, each $Z^{1a}$ is independently oxo, halo, —NO$_2$, —N$_3$, —CN, C$_{1-8}$ alkyl optionally substituted by 1 to 5 $Z^{1b}$, C$_{2-8}$ alkenyl optionally substituted by 1 to 5 $Z^{1b}$, C$_{2-8}$ alkynyl optionally substituted by 1 to 5 $Z^{1b}$, C$_{3-10}$ cycloalkyl optionally substituted by 1 to 5 $Z^{1b}$, 6-10 membered aryl optionally substituted by 1 to 5 $Z^{1b}$, 4-10 membered heterocyclyl optionally substituted by 1 to 5 $Z^{1b}$, 5-10 membered heteroaryl optionally substituted with 1 to 5 $Z^{1b}$, —OR$^{21}$, —C(O)R$^{21}$, —C(O)OR$^{21}$, —C(O)N(R$^{21}$)$_2$, —N(R$^{21}$)$_2$, —N(R$^{21}$)$_3$$^+$, —N(R$^{21}$)C(O)R$^{21}$, —N(R$^{21}$)C(O)OR$^{21}$,
—N(R$^{21}$)C(O)N(R$^{21}$)$_2$, —N(R$^{21}$)S(O)$_2$(R$^{21}$), —NR$^{21}$S(O)$_2$N(R$^{21}$)$_2$, —NR$^{21}$S(O)$_2$O(R$^{21}$), —NS(O)(R$^{21}$)$_2$, —OC(O)R$^{21}$,
—OC(O)OR$^{21}$, —OC(O)N(R$^{21}$)$_2$, —Si(R$^{21}$)$_3$, —SR$^{21}$, —S(O)R$^{21}$, —SF$_5$, —S(O)(NR$^{21}$)R$^{21}$, —S(NR$^{21}$)(NR$^{21}$)R$^{21}$,
—S(O)(NR$^{21}$)N(R$^{21}$)$_2$, —S(O)(NCN)R$^{21}$, —S(O)$_2$R$^{21}$, —S(O)$_2$N(R$^{21}$)$_2$, —C(O)N(R$^{21}$)S(O)$_2$R$^{21}$, or —S(O)$_2$N(R$^{21}$)C(O)R$^{21}$;

each R$^{20}$, R$^{21}$ and R$^{22}$ is independently hydrogen, C$_{1-8}$ alkyl optionally substituted with 1 to 5 $Z^{1b}$, C$_{2-8}$ alkenyl optionally substituted with 1 to 5 $Z^{1b}$, C$_{2-8}$ alkynyl optionally substituted with 1 to 5 $Z^{1b}$, C$_{3-10}$ cycloalkyl optionally substituted with 1 to 5 $Z^{1b}$, 4-10 membered heterocyclyl optionally substituted with 1 to 5 $Z^{1b}$, C$_{6-10}$ aryl optionally substituted with 1 to 5 $Z^{1b}$, or 5-10 membered heteroaryl optionally substituted with 1 to 5 $Z^{1}$b; and each $Z^{1b}$ is independently oxo, hydroxy, halo, —NO$_2$, —N$_3$, —CN, C$_{1-9}$ alkyl, C$_{2-6}$ alkenyl, C$_{2-6}$ alkynyl, C$_{3-10}$ cycloalkyl, C$_{1-8}$ haloalkyl, C$_{6-10}$ aryl, 5-10 membered heteroaryl, 4-10 membered heterocyclyl,
—O(C$_{1-9}$ alkyl), —O(C$_{2-6}$ alkenyl), —O(C$_{2-6}$ alkynyl), —O(C$_{3-10}$ cycloalkyl), —O(C$_{1-8}$ haloalkyl), —O(aryl), —O(heteroaryl), —O(heterocyclyl), —OC(O) (C$_{1-9}$ alkyl), —OC(O)(C$_{2-6}$ alkenyl), —OC(O)(C$_{2-6}$ alkenyl),
—OC(O)(C$_{2-6}$ alkynyl), —OC(O)(C$_{3-10}$ cycloalkyl), —OC(O)(C$_{1-8}$ haloalkyl), —OC(O)(aryl), —OC(O)(heteroaryl), —OC(O)(heterocyclyl), —NH$_2$, —NH(C$_{1-9}$ alkyl), —NH(C$_{2-6}$ alkenyl), —NH(C$_{2-6}$ alkynyl), —NH(C$_{3-10}$ cycloalkyl),
—NH(C$_{1-8}$ haloalkyl), —NH(aryl), —NH(heteroaryl), —NH(heterocyclyl), —N(C$_{1-9}$ alkyl)$_2$, —N(C$_{3-10}$ cycloalkyl)$_2$,
—N(C$_{2-6}$ alkenyl)$_2$, —N(C$_{2-6}$ alkynyl)$_2$, —N(C$_{3-10}$ cycloalkyl)$_2$, —N(C$_{1-8}$ haloalkyl)$_2$, —N(aryl)$_2$, —N(heteroaryl)$_2$, —N(heterocyclyl)$_2$, —N(C$_{1-9}$ alkyl)(C$_{3-10}$ cycloalkyl), —N(C$_{1-9}$ alkyl)(C$_{2-6}$ alkenyl), —N(C$_{1-9}$ alkyl)(C$_{2-6}$ alkynyl),
—N(C$_{1-9}$ alkyl)(C$_{3-10}$ cycloalkyl), —N(C$_{1-9}$ alkyl)(C$_{1-8}$ haloalkyl), —N(C$_{1-9}$ alkyl)(aryl), —N(C$_{1-9}$ alkyl)(heteroaryl),
—N(C$_{1-9}$ alkyl)(heterocyclyl), —C(O)(C$_{1-9}$ alkyl), —C(O)(C$_{2-6}$ alkenyl), —C(O)(C$_{2-6}$ alkynyl),
—C(O)(C$_{3-10}$ cycloalkyl), —C(O)(C$_{1-8}$ haloalkyl), —C(O)(aryl), —C(O)(heteroaryl), —C(O)(heterocyclyl),
—C(O)O(C$_{1-9}$ alkyl), —C(O)O(C$_{2-6}$ alkenyl), —C(O)O(C$_{2-6}$ alkynyl), —C(O)O(C$_{3-10}$ cycloalkyl),
—C(O)O(C$_{1-8}$ haloalkyl), —C(O)O(aryl), —C(O)O(heteroaryl), —C(O)O(heterocyclyl), —C(O)NH$_2$,
—C(O)NH(C$_{1-9}$ alkyl), —C(O)NH(C$_{2-6}$ alkenyl), —C(O)NH(C$_{2-6}$ alkynyl), —C(O)NH(C$_{3-10}$ cycloalkyl),
—C(O)NH(C$_{1-8}$haloalkyl), —C(O)NH(aryl), —C(O)NH(heteroaryl), —C(O)NH(heterocyclyl),
—C(O)N(C$_{1-9}$ alkyl)$_2$, —C(O)N(C$_{3-10}$ cycloalkyl)$_2$, —C(O)N(C$_{2-6}$ alkenyl)$_2$, —C(O)N(C$_{2-6}$ alkynyl)$_2$,
—C(O)N(C$_{1-8}$ haloalkyl)$_2$, —C(O)N(aryl)$_2$, —C(O)N(heteroaryl)$_2$, —C(O)N(heterocyclyl)$_2$, —NHC(O)(C$_{1-9}$ alkyl), —NHC(O)(C$_{2-6}$ alkenyl), —NHC(O)(C$_{2-6}$ alkynyl), —NHC(O)(C$_{3-10}$ cycloalkyl), —NHC(O)(C$_{1-8}$haloalkyl),
—NHC(O)(aryl), —NHC(O)(heteroaryl), —NHC(O)(heterocyclyl), —NHC(O)O(C$_{1-9}$ alkyl),
—NHC(O)O(C$_{2-6}$ alkenyl), —NHC(O)O(C$_{2-6}$ alkynyl), —NHC(O)O(C$_{3-10}$ cycloalkyl), —NHC(O)O(C$_{1-8}$ haloalkyl),
—NHC(O)O(aryl), —NHC(O)O(heteroaryl), —NHC(O)O(heterocyclyl), —NHC(O)NH(C$_{1-9}$ alkyl),
—NHC(O)NH(C$_{2-6}$ alkenyl), —NHC(O)NH(C$_{2-6}$ alkynyl), —NHC(O)NH(C$_{3-10}$ cycloalkyl),
—NHC(O)NH(C$_{1-8}$ haloalkyl), —NHC(O)NH(aryl), —NHC(O)NH(heteroaryl), —NHC(O)NH(heterocyclyl),
—SH,
—S(C$_{1-9}$ alkyl), —S(C$_{2-6}$ alkenyl), —S(C$_{2-6}$ alkynyl), —S(C$_{3-10}$ cycloalkyl), —S(C$_{1-8}$ haloalkyl), —S(aryl),
—S(heteroaryl), —S(heterocyclyl), —NHS(O)(C$_{1-9}$ alkyl), —N(C$_{1-9}$ alkyl)(S(O)(C$_{1-9}$ alkyl), —S(O)N(C$_{1-9}$ alkyl)$_2$,
—S(O)(C$_{1-9}$ alkyl), —S(O)(NH)(C$_{1-9}$ alkyl), —S(O)(C$_{2-6}$ alkenyl), —S(O)(C$_{2-6}$ alkynyl), —S(O)(C$_{3-10}$ cycloalkyl),
—S(O)(C$_{1-8}$ haloalkyl), —S(O)(aryl), —S(O)(heteroaryl), —S(O)(heterocyclyl), —S(O)$_2$(C$_{1-9}$ alkyl),
—S(O)$_2$(C$_{2-6}$ alkenyl), —S(O)$_2$(C$_{2-6}$ alkynyl), —S(O)$_2$(C$_{3-10}$ cycloalkyl), —S(O)$_2$(C$_{1-8}$ haloalkyl), —S(O)$_2$(aryl),
—S(O)$_2$(heteroaryl), —S(O)$_2$(heterocyclyl), —S(O)$_2$NH(C$_{1-9}$ alkyl), or —S(O)$_2$N(C$_{1-9}$ alkyl)$_2$;

wherein any alkyl, cycloalkyl, aryl, heteroaryl, or heterocyclyl of $Z^{1b}$ is optionally substituted with one or more halo, C$_{1-9}$ alkyl, C$_{1-8}$ haloalkyl, —OH, —NH$_2$, —NH(C$_{1-9}$ alkyl), —NH(C$_{3-10}$ cycloalkyl), —NH(C$_{1-8}$ haloalkyl),
—NH(aryl), —NH(heteroaryl), —NH(heterocyclyl), —N(C$_{1-9}$ alkyl)$_2$, —N(C$_{3-10}$ cycloalkyl)$_2$,
—NHC(O)(C$_{3-10}$ cycloalkyl), —NHC(O)(C$_{1-8}$ haloalkyl), —NHC(O)(aryl), —NHC(O)(heteroaryl),
—NHC(O)(heterocyclyl), —NHC(O)O(C$_{1-9}$ alkyl), —NHC(O)O(C$_{2-6}$ alkynyl), —NHC(O)O(C$_{3-10}$ cycloalkyl),
—NHC(O)O(C$_{1-8}$ haloalkyl), —NHC(O)O(aryl), —NHC(O)O(heteroaryl), —NHC(O)O(heterocyclyl),
—NHC(O)NH(C$_{1-9}$ alkyl), —S(O)(NH)(C$_{1-9}$ alkyl), —S(O)$_2$ (C$_{1-9}$ alkyl), —S(O)$_2$(C$_{3-10}$ cycloalkyl),
—S(O)$_2$(C$_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl),
—S(O)$_2$N(C$_{1-9}$ alkyl)$_2$, —O(C$_{3-10}$ cycloalkyl), —O(C$_{1-8}$ haloalkyl), —O(aryl), —O(heteroaryl), —O(heterocyclyl), or
—O(C$_{1-9}$ alkyl).

In certain embodiments, $X^5$ is N. In certain embodiments, $X^5$ is C—R$^5$. In certain embodiments, $X^5$ is C—H or C—F.

In certain embodiments, $X^7$ is N. In certain embodiments, $X^7$ is C—R$^7$. In certain embodiments, $X^7$ is C—H or C—F.

In certain embodiments, R$^8$ is hydrogen.

Also provided is a compound of Formula IB:

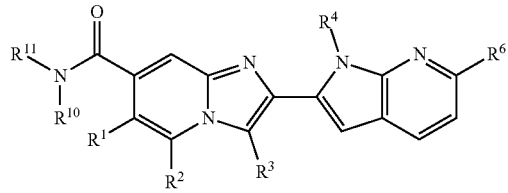

wherein each of $R^1$, $R^2$, $R^3$, $R^4$, $R^6$, $R^{10}$, and $R^{11}$ are independently as defined herein.

In certain embodiments, $R^1$ is hydrogen, halo or —$C_{1-8}$ alkyl optionally substituted with 1 to 3 $Z^1$. In certain embodiments, $R^1$ is hydrogen, halo or —$C_{1-8}$ alkyl. In certain embodiments, $R^1$ is hydrogen or halo. In certain embodiments, $R^1$ is hydrogen, fluoro or methyl. In certain embodiments, $R^1$ is hydrogen or fluoro. In certain embodiments, $R^1$ is hydrogen.

In certain embodiments, $R^2$ is hydrogen, halo, —$OR^{12}$, —$N(R^{12})_2$, —$SR^{20}$, —$S(O)R^{20}$, $C_{1-8}$ alkyl optionally substituted with 1 to 5 $Z^1$, $C_{3-6}$ cycloalkyl optionally substituted with 1 to 5 $Z^1$. In certain embodiments, $R^2$ is hydrogen, halo, or —O—$C_{1-8}$ alkyl. In certain embodiments, $R^2$ is hydrogen, fluoro, methyl, ethyl, —$CHF_2$, —OH, —$OCH_3$, —SH, —$SCH_3$, —$S(O)CH_3$, cyclopropyl, —$NHCH_3$, —$N(CH_3)_2$, or 2-cyanopyrimidin-5-oxy. In certain embodiments, $R^2$ is hydrogen, methyl, ethyl, —OH, —$OCH_3$, —SH, —$SCH_3$, —$S(O)CH_3$, cyclopropyl, —$NHCH_3$, —$N(CH_3)_2$, or 2-cyanopyrimidin-5-oxy. In certain embodiments, $R^2$ is hydrogen, fluoro, chloro, or methoxy. In certain embodiments, $R^2$ is fluoro, chloro, or methoxy. In certain embodiments, $R^2$ is hydrogen, fluoro, or —$OCH_3$. In certain embodiments, $R^2$ is hydrogen or —$OCH_3$. In certain embodiments, $R^2$ is —O—$C_{1-8}$ alkyl. In certain embodiments, $R^2$ is methoxy. In certain embodiments, $R^2$ is halo. In certain embodiments, $R^2$ is halo. In certain embodiments, $R^2$ is fluoro and chloro. In certain embodiments, $R^2$ is fluoro. In certain embodiments, $R^2$ is hydrogen or fluoro. In certain embodiments, $R^2$ is hydrogen.

In certain embodiments, $R^3$ is hydrogen, $C_{1-8}$ alkyl optionally substituted with 1 to 5 $Z^1$, or $C_{3-10}$ cycloalkyl optionally substituted with 1 to 5 $Z^1$. In certain embodiments, $R^3$ is $C_{1-8}$ alkyl optionally substituted with 1 to 5 $Z^1$ or $C_{3-10}$ cycloalkyl optionally substituted with 1 to 5 $Z^1$. In certain embodiments, $R^3$ is $C_{1-8}$ alkyl optionally substituted with 1 to 5 $Z^1$. In certain embodiments, $R^3$ is $C_{3-10}$ cycloalkyl optionally substituted with 1 to 5 $Z^1$.

In certain embodiments, $R^3$ is methyl, ethyl, isopropyl, $CHF_2$, —$NH_2$,

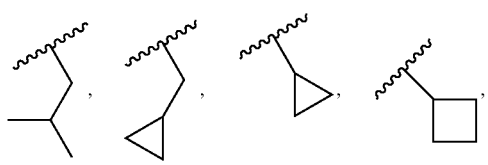

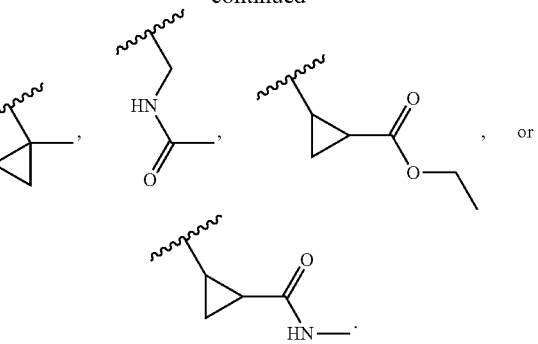

In certain embodiments, $R^3$ is methyl or cyclopropyl.

In certain embodiments, $R^2$ is hydrogen, halo, —CN, —$OR^{12}$, —$N(R^{12})_2$, —$SR^{12}$, —$C_{1-8}$ alkyl optionally substituted with 1 to 5 $Z^1$, $C_{3-6}$ cycloalkyl optionally substituted with 1 to 5 $Z^1$, or 4-6 membered heterocyclyl optionally substituted with 1 to 5 $Z^1$; and $R^3$ is hydrogen, $C_{1-8}$ alkyl optionally substituted with 1 to 5 $Z^1$, $C_{3-10}$ alkenyl optionally substituted with 1 to 5 $Z^1$, $C_{3-10}$ alkynyl optionally substituted with 1 to 5 $Z^1$, $C_{3-10}$ cycloalkyl optionally substituted with 1 to 5 $Z^1$, or 4-10 membered heterocyclyl optionally substituted with 1 to 5 $Z^1$.

In certain embodiments, $R^2$ and $R^3$ are taken together with the atoms to which they are attached to form an optionally substituted 6 to 8 membered heterocyclyl ring.

In certain embodiments, $R^4$ is hydrogen, $C_{1-8}$ alkyl optionally substituted with 1 to 5 $Z^1$, $C_{6-10}$ aryl optionally substituted with 1 to 5 $Z^1$, or 5-10 membered heteroaryl optionally substituted with 1 to 5 $Z^1$. In certain embodiments, $R^4$ is $C_{1-8}$ alkyl optionally substituted with 1 to 5 $Z^1$ or $C_{3-10}$ cycloalkyl optionally substituted with 1 to 5 $Z^1$. In certain embodiments, $R^4$ is $C_{1-8}$ alkyl optionally substituted with 1 to 5 $Z^1$. In certain embodiments, $R^4$ is $C_{3-10}$ cycloalkyl optionally substituted with 1 to 5 $Z^1$. In certain embodiments, $R^4$ is hydrogen, methyl, ethyl,

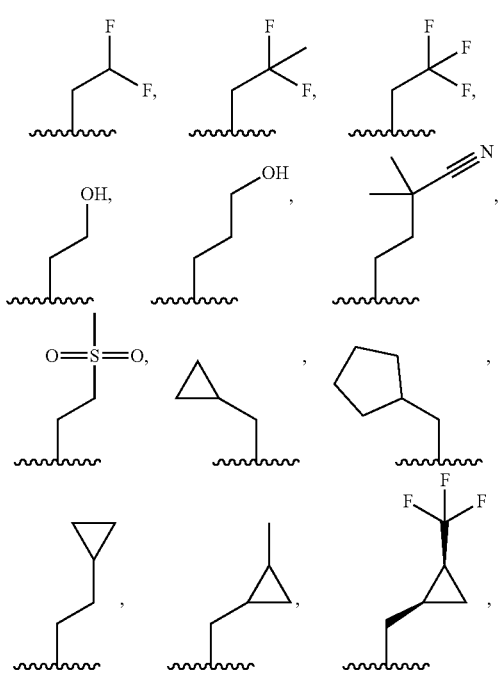

-continued

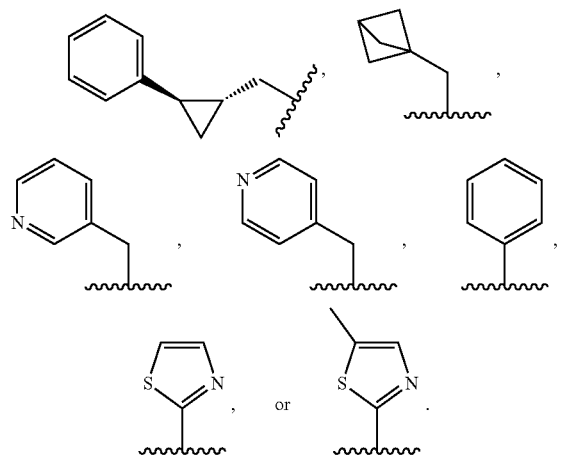

In certain embodiments, R⁴ is hydrogen, methyl, ethyl,

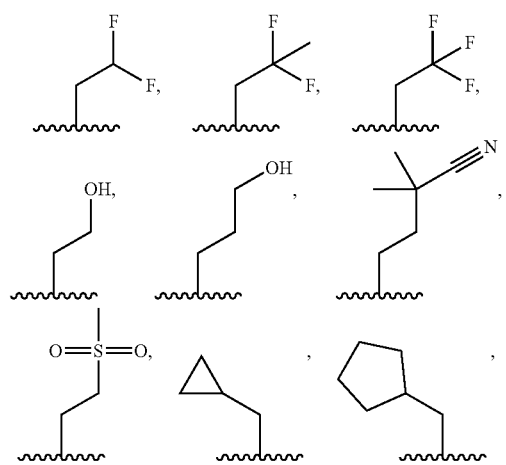

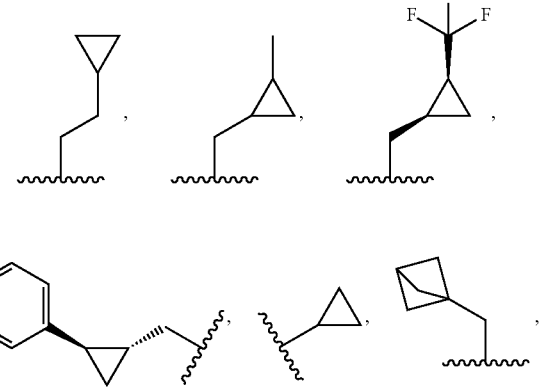

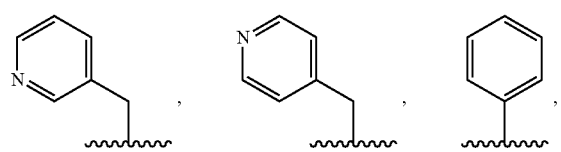

-continued

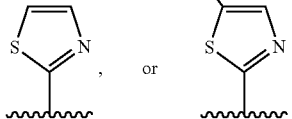

In certain embodiments, R⁴ is ethyl,

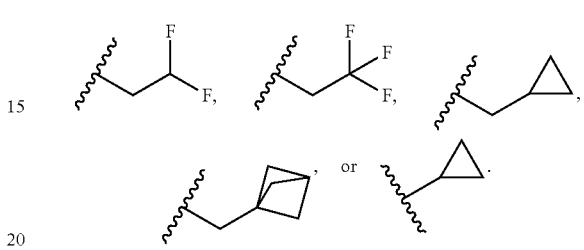

In certain embodiments, R⁴ is

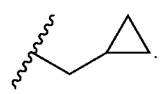

In certain embodiments, R⁶ is —N(R¹⁴)S(O)₂R⁹, —N(R¹⁴)C(O)OR⁹, —OC(O)R⁹, or —OC(O)OR⁹. In certain embodiments, R⁶ is —N(R¹⁴)S(O)₂R⁹. In certain embodiments, R⁶ is —N(R¹⁴)C(O)OR⁹. In certain embodiments, R⁶ is —OC(O)R⁹. In certain embodiments, R⁶ is —OC(O)OR⁹. In certain embodiments, R⁶ is —N(R¹⁴)C(O)OR⁹, —OC(O)R⁹, or —OC(O)OR⁹.

L is $C_{1-8}$ alkylene, —O—$C_{1-8}$ alkylene, $C_{1-8}$ haloalkylene, —O—$C_{1-8}$ haloalkylene, or 5-10 membered heteroarylene; and each $C_{1-8}$ alkylene, $C_{1-8}$ haloalkylene, or 5-10 membered heteroarylene of L is optionally substituted with 1 to 5 Z¹; In certain embodiments, R⁶ is -L-R¹³; wherein L is $C_{1-8}$ alkylene, —O—$C_{1-8}$ alkylene, $C_{1-8}$ haloalkylene, —O—$C_{1-8}$ haloalkylene, or 5-10 membered heteroarylene; and each $C_{1-8}$ alkylene, $C_{1-8}$ haloalkylene, or 5-10 membered heteroarylene of L is optionally substituted with 1 to 5 Z¹; and R¹³ is —OR¹⁵), —N(R¹⁵)(R¹⁴), —C(O)N(R¹⁴)₂, —OC(O)N(R¹⁴)C(O)R⁹, —N(R¹⁴)C(O)OR⁹, —N(R¹⁴)C(O)N(R¹⁴)₂, —N(R¹⁴)S(O)₂R⁹, —NR¹⁴S(O)₂N(R¹⁴)₂, —NR¹⁴S(O)₂OR⁹, —NS(O)(R⁹)₂, —Si(R¹⁴)₂R⁹, —SR⁹, —S(O)R⁹, —S(O)₂R⁹, —SF₅, —S(O)(NR¹⁴)R⁹, —S(NR¹⁴)(NR¹⁴)R⁹, —S(O)(NR¹⁴)N(R¹⁴)₂, —S(O)(NCN)R⁹, —S(O)₂N(R¹⁴)₂, —C(O)N(R¹⁴)S(O)₂R⁹, —S(O)₂N(R¹⁴)C(O)R⁹, or $C_{3-10}$ cycloalkyl substituted with 1 to 5 Z¹.

In certain embodiments, R⁶ is -L-R¹³; wherein L is $C_{1-8}$ alkylene, $C_{1-8}$ haloalkylene, or 5-10 membered heteroarylene; and each $C_{1-8}$ alkylene, $C_{1-8}$ haloalkylene, or 5-10 membered heteroarylene of L is optionally substituted with 1 to 5 Z¹; and R¹³ is —N(R¹⁵)(R¹⁴), —C(O)N(R¹⁴)₂, —N(R¹⁴)C(O)R⁹, —N(R¹⁴)C(O)OR⁹, —N(R¹⁴)C(O)N(R¹⁴)₂, or —N(R¹⁴)S(O)₂R⁹.

In certain embodiments, R⁶ is —OR¹⁵, $C_{2-8}$ alkenyl optionally substituted with 1 to 5 Z¹, $C_{2-8}$ alkynyl optionally substituted with 1 to 5 Z¹, $C_{3-10}$ cycloalkyl substituted with 1 to 5 Z¹, $C_{6-10}$ aryl substituted with 1 to 5 Z¹, or 4-10 membered heterocyclyl substituted with 1 to 5 $Z^1$; and $R^{15}$ is cycloalkyl optionally substituted with 1 to 5 $Z^1$, 4-10 membered heterocyclyl optionally substituted with 1 to 5 $Z^1$, $C_{6-10}$ aryl optionally substituted with 1 to 5 $Z^1$, or 5-10 membered heteroaryl optionally substituted with 1 to 5 $Z^1$.

In certain embodiments, $R^6$ is —$OR^{15}$; and $R^{15}$ is cycloalkyl optionally substituted with 1 to 5 $Z^1$, 4-10 membered heterocyclyl optionally substituted with 1 to 5 $Z^1$, $C_{6-10}$ aryl optionally substituted with 1 to 5 $Z^1$, or 5-10 membered heteroaryl optionally substituted with 1 to 5 $Z^1$. In certain embodiments, $R^6$ is $C_{2-8}$ alkenyl optionally substituted with 1 to 5 $Z^1$. In certain embodiments, $R^6$ is $C_{2-8}$ alkynyl optionally substituted with 1 to 5 $Z^1$. In certain embodiments, $R^6$ is $C_{3-10}$ cycloalkyl substituted with 1 to 5 $Z^1$. In certain embodiments, $R^6$ is $C_{6-10}$ aryl substituted with 1 to 5 $Z^1$. In certain embodiments, $R^6$ is 4-10 membered heterocyclyl substituted with 1 to 5 $Z^1$.

In certain embodiments, $R^6$ is

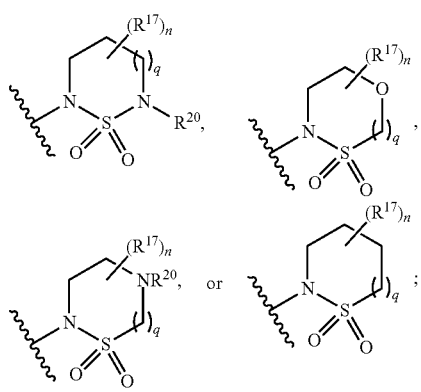

wherein q is 0, 1 or 2; and n is 0, 1, 2, 3, 4, 5, or 6. In certain embodiments, q is 0. In certain embodiments, q is 1. In certain embodiments, q is 2.

In certain embodiments, $R^6$ is

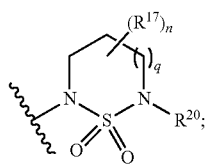

wherein q is 0, 1 or 2; and n is 0, 1, 2, 3, 4, 5, or 6. In certain embodiments, q is 0. In certain embodiments, q is 1. In certain embodiments, q is 2.

In certain embodiments, $R^6$ is

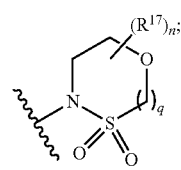

wherein q is 0, 1 or 2; and n is 0, 1, 2, 3, 4, 5, or 6. In certain embodiments, q is 0. In certain embodiments, q is 1. In certain embodiments, q is 2.

In certain embodiments, $R^6$ is

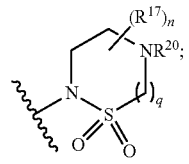

wherein q is 0, 1 or 2; and n is 0, 1, 2, 3, 4, 5, or 6. In certain embodiments, q is 0. In certain embodiments, q is 1. In certain embodiments, q is 2.

In certain embodiments, $R^6$ is

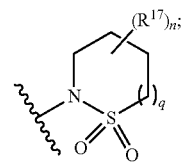

wherein q is 0, 1 or 2; and n is 0, 1, 2, 3, 4, 5, or 6. In certain embodiments, q is 0. In certain embodiments, q is 1. In certain embodiments, q is 2.

In certain embodiments, n is 0. In certain embodiments, n is 1. In certain embodiments, n is 2. In certain embodiments, n is 3. In certain embodiments, n is 4. In certain embodiments, n is 5. In certain embodiments, n is 6. In certain embodiments, n is 0, 1, 2, 3, or 4. In certain embodiments, n is 0, 1, or 2.

In certain embodiments, $R^6$ is —Cl, —CN,

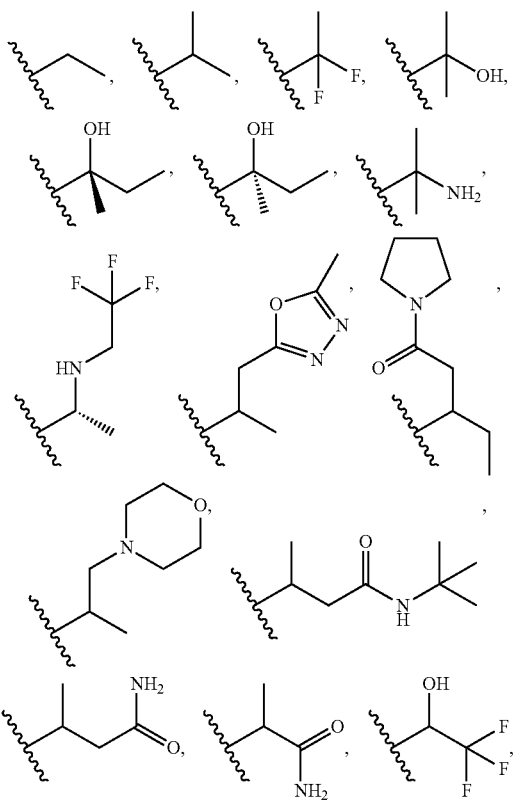

25
-continued
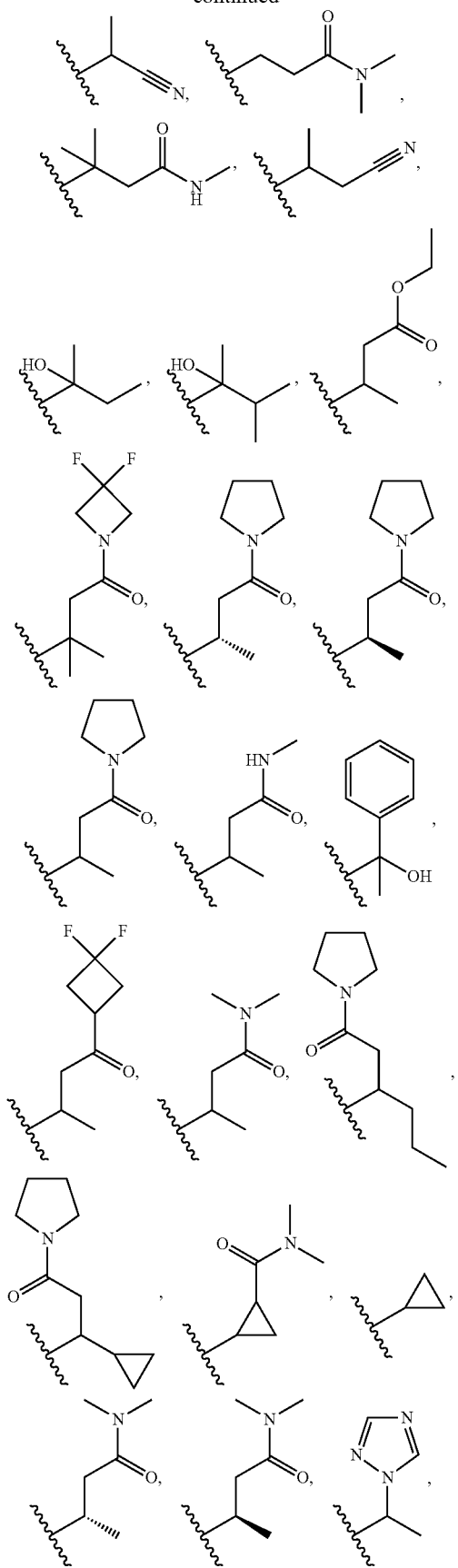
26
-continued
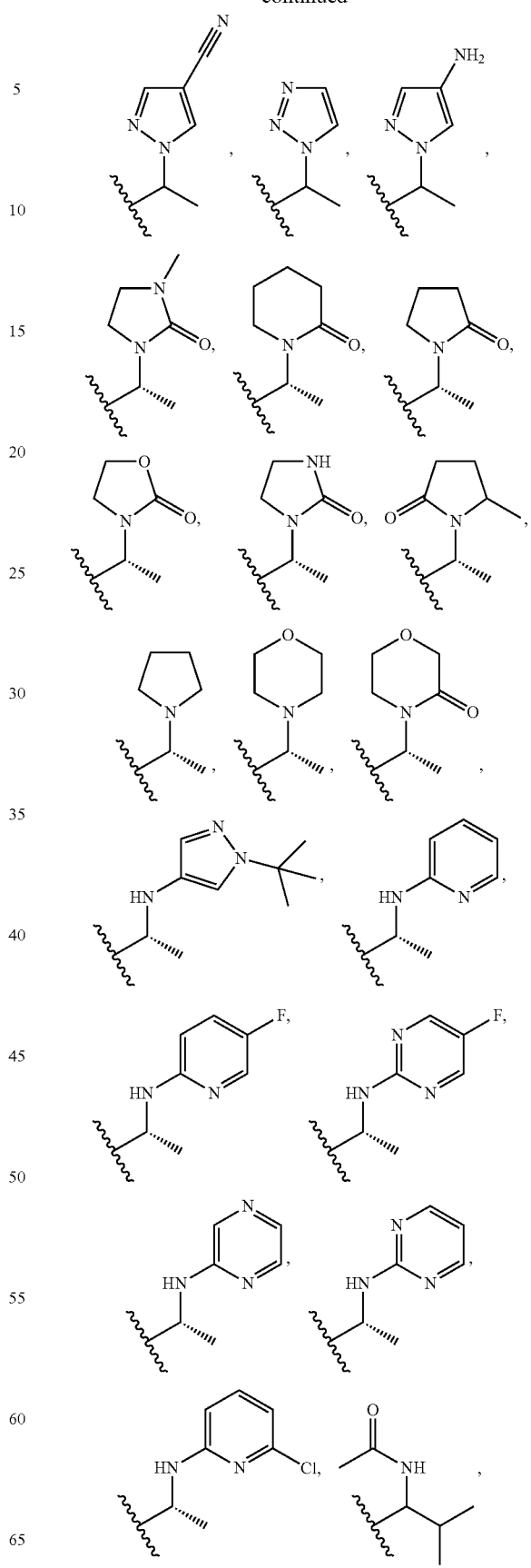

-continued
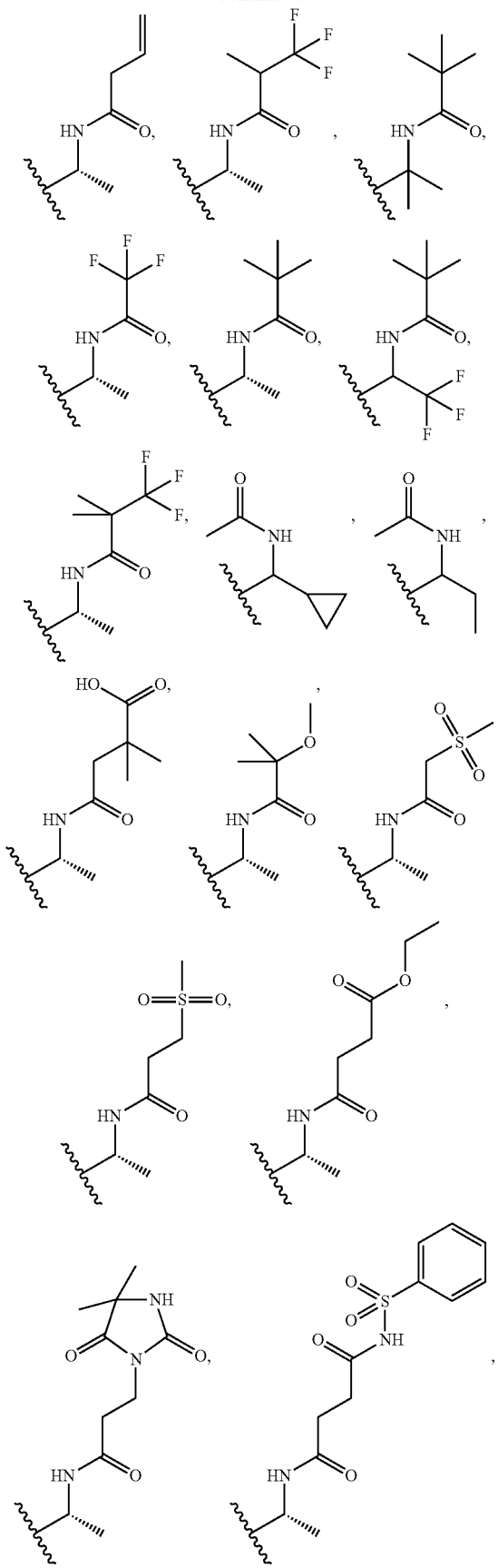
-continued
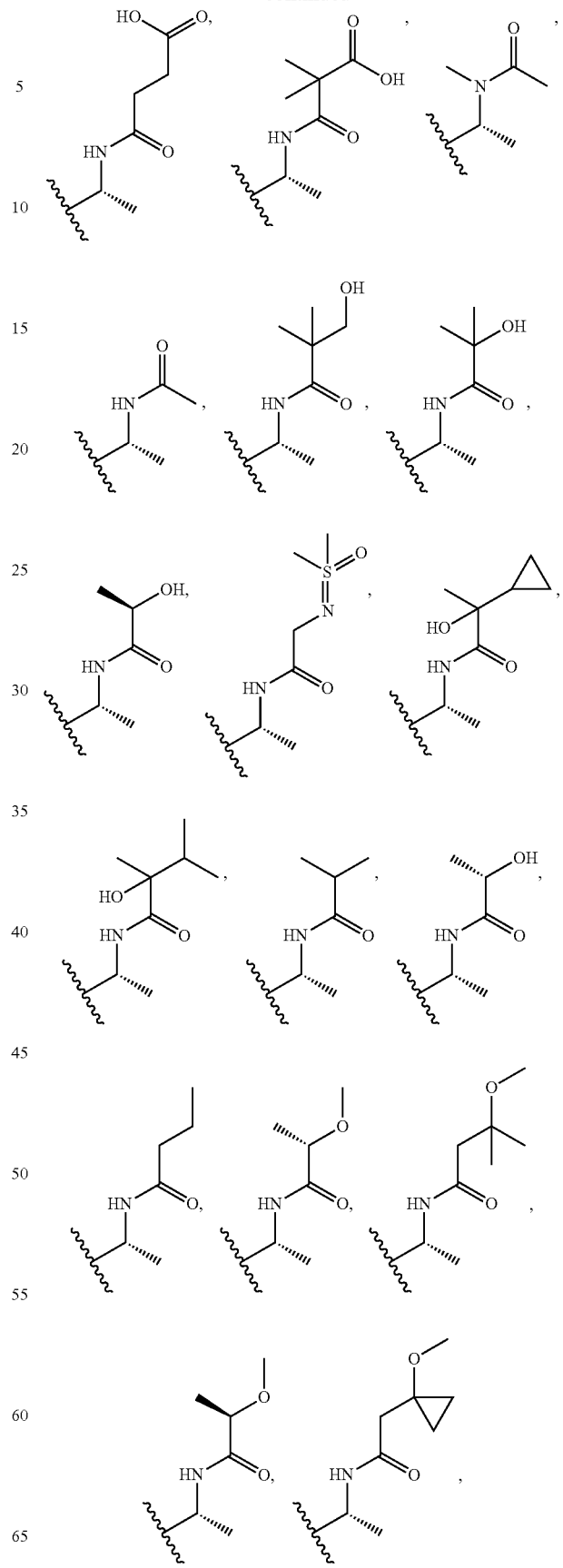

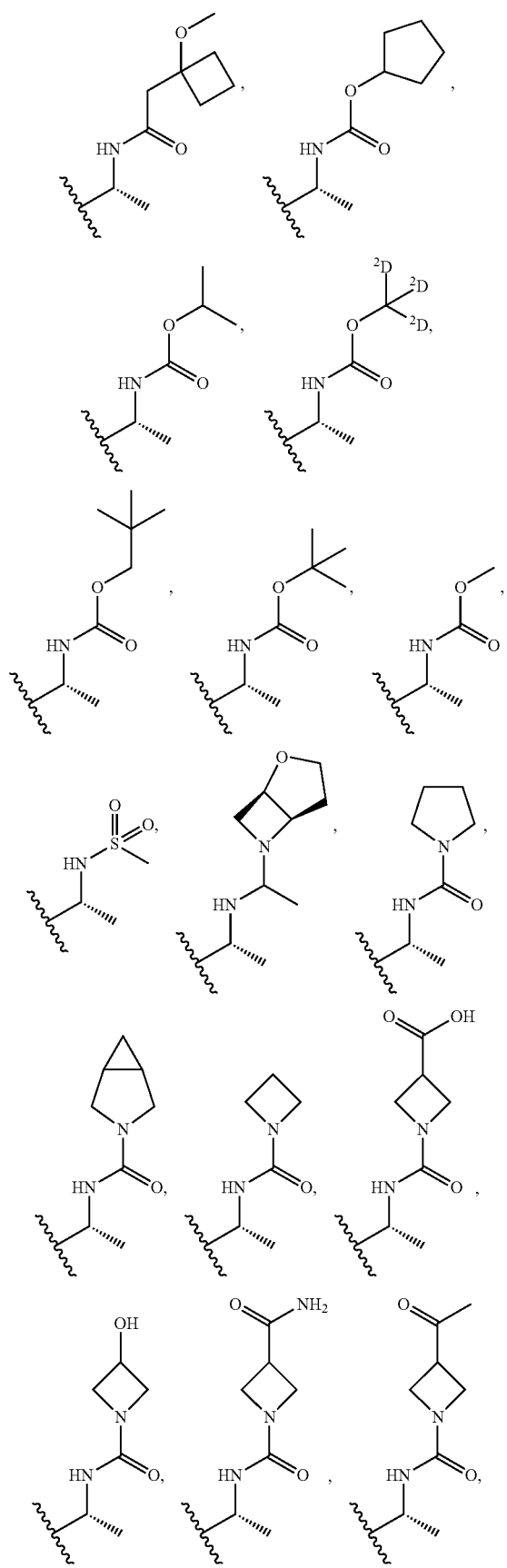
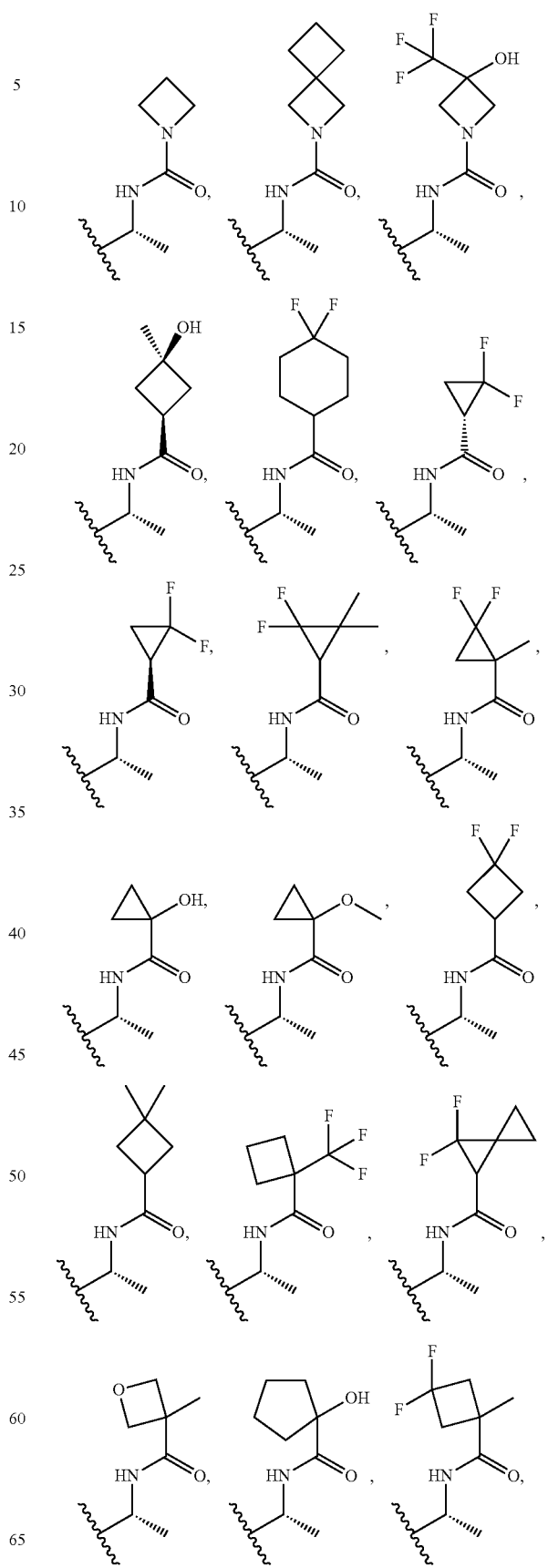

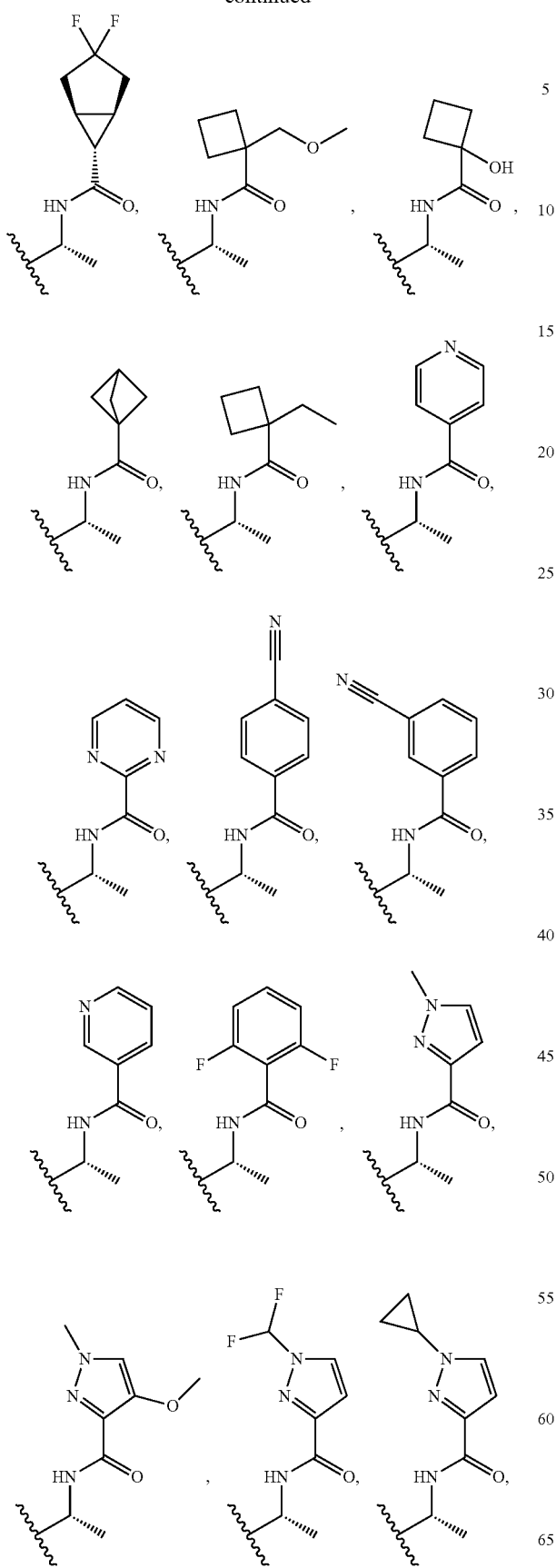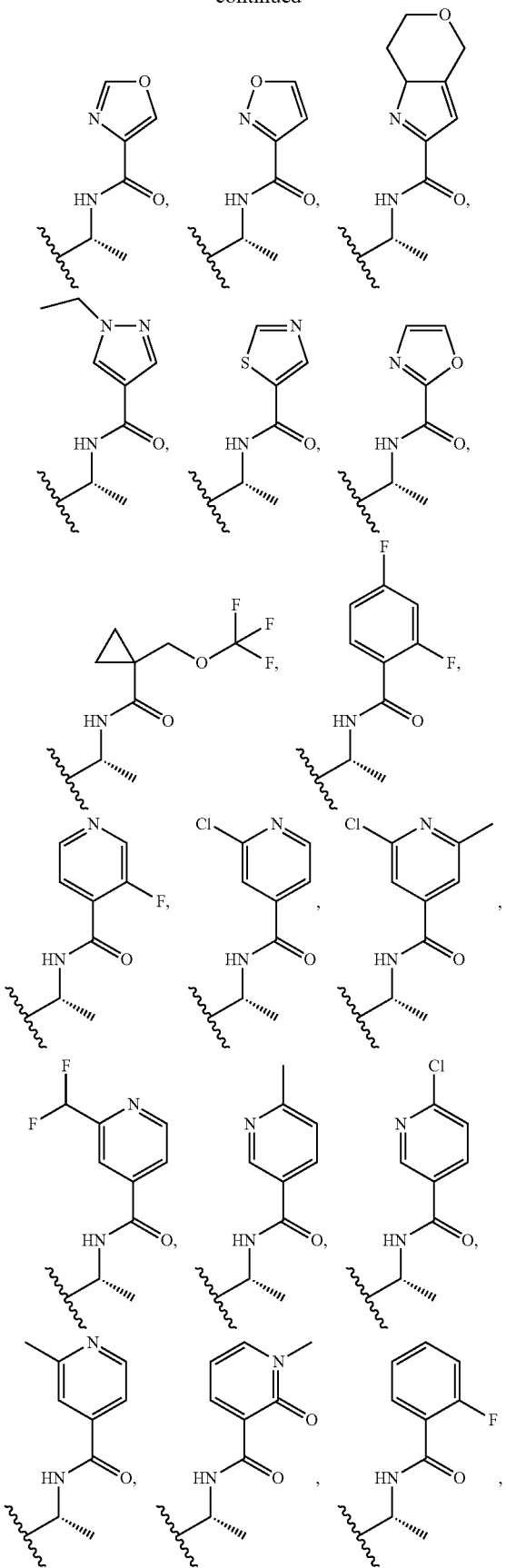

33
-continued
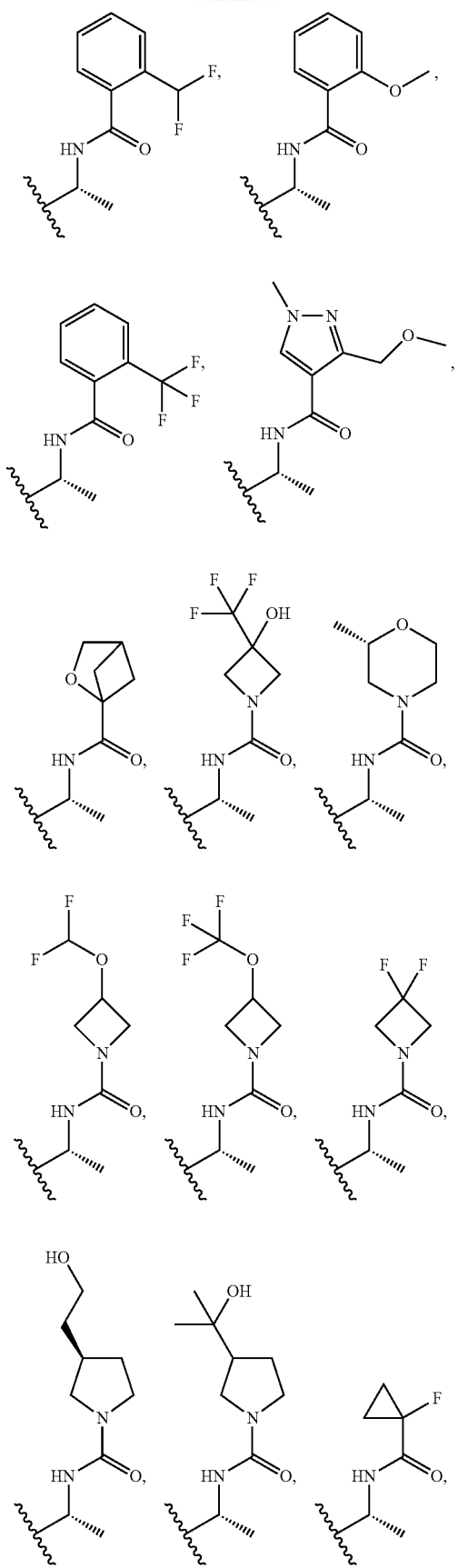
34
-continued
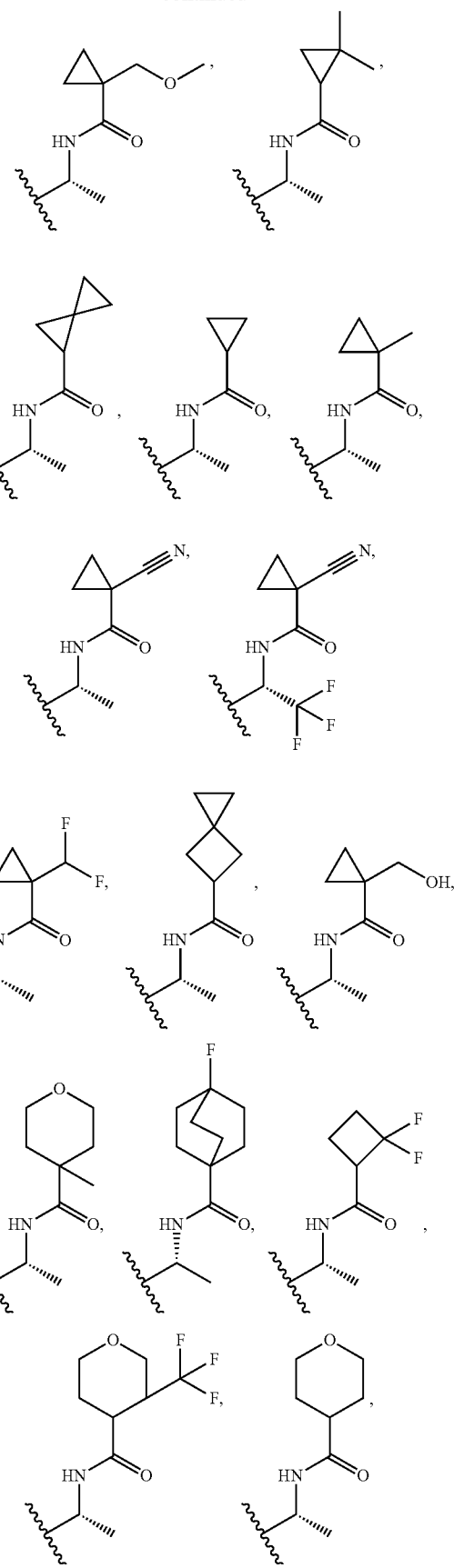

35
-continued
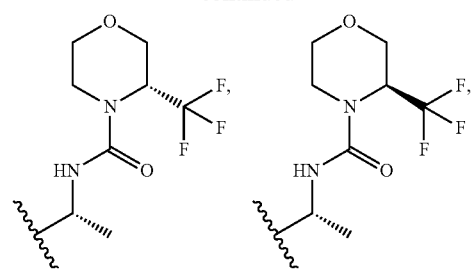
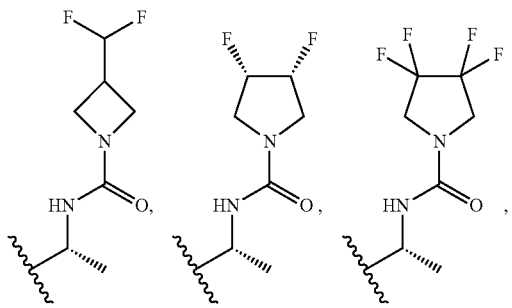
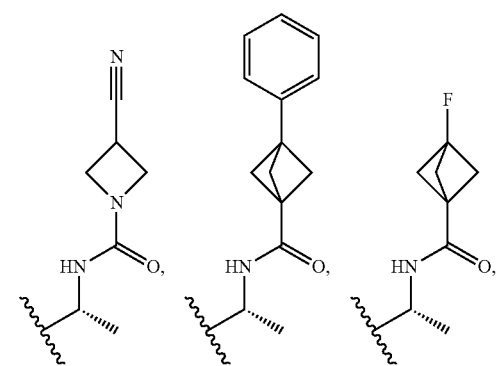
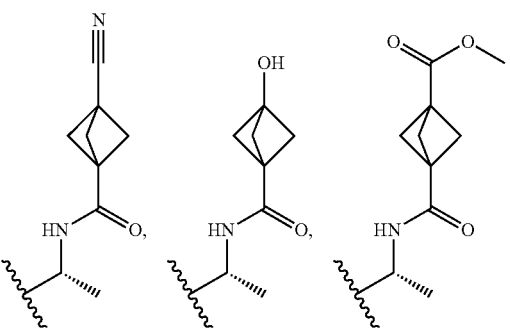
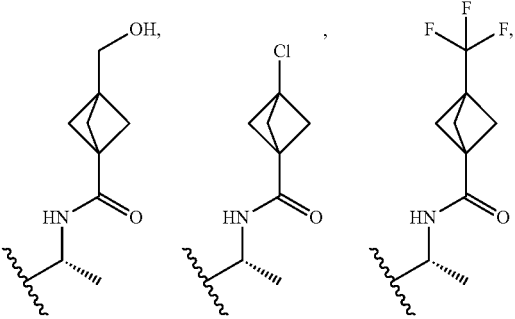
36
-continued
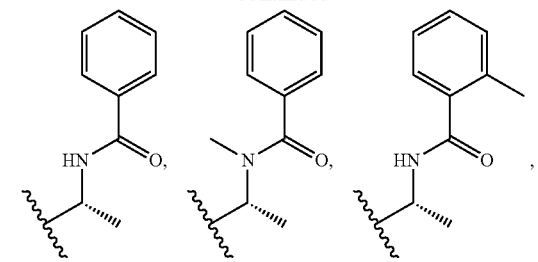
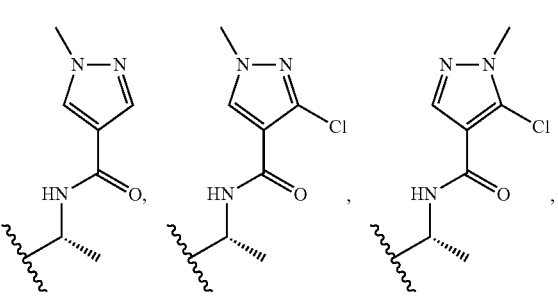
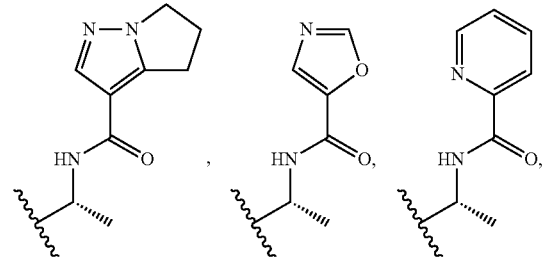
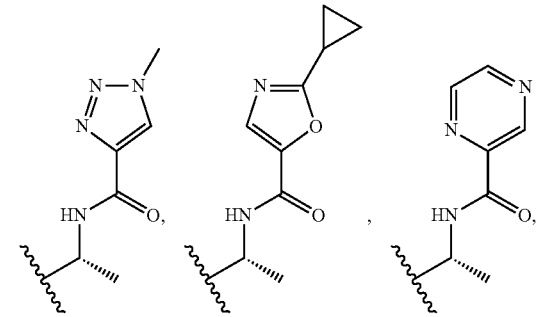
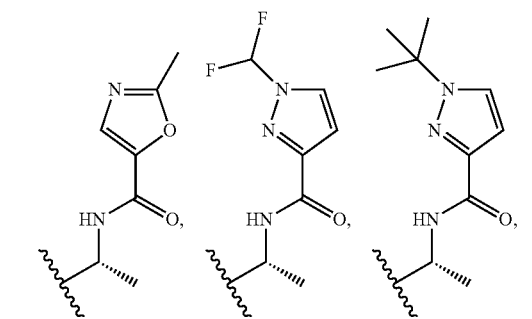

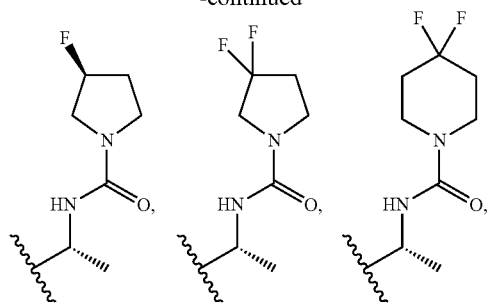
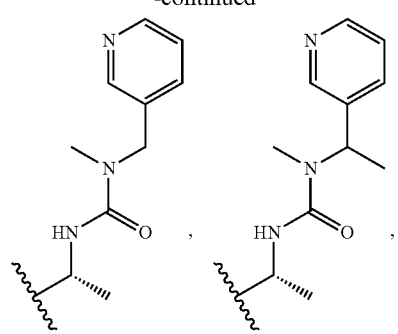
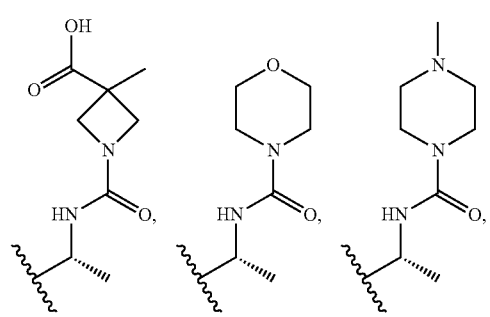
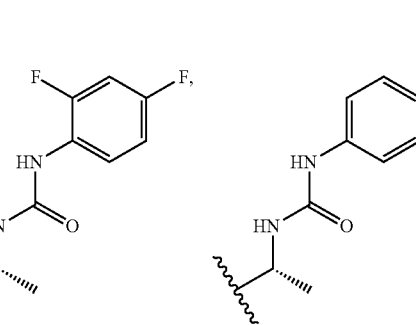
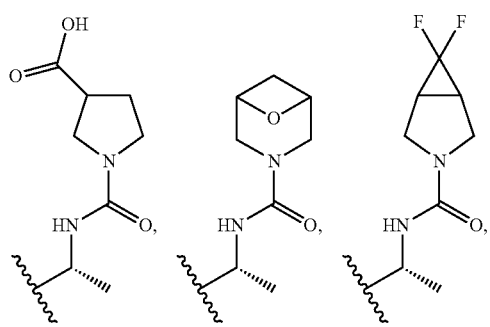
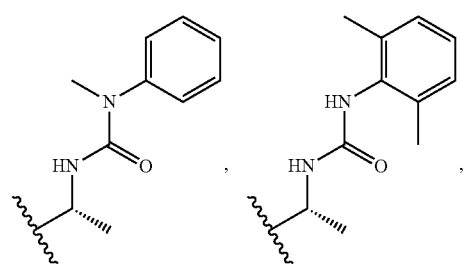
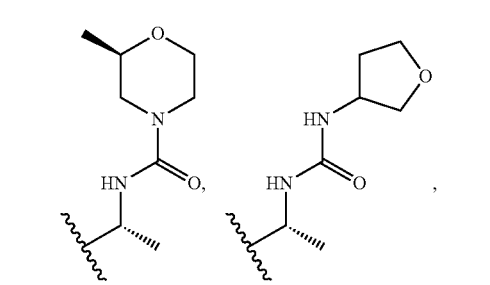
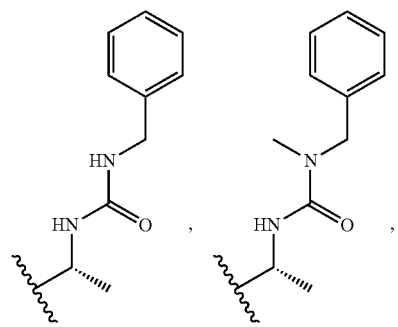
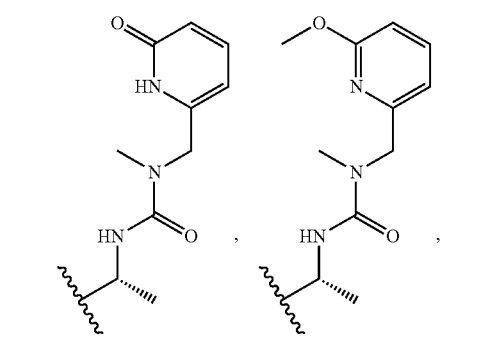
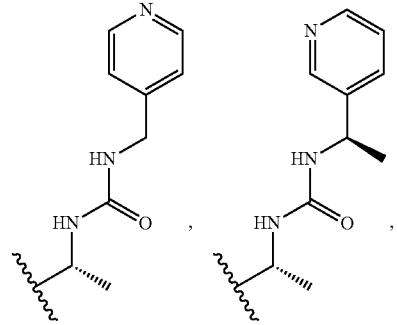

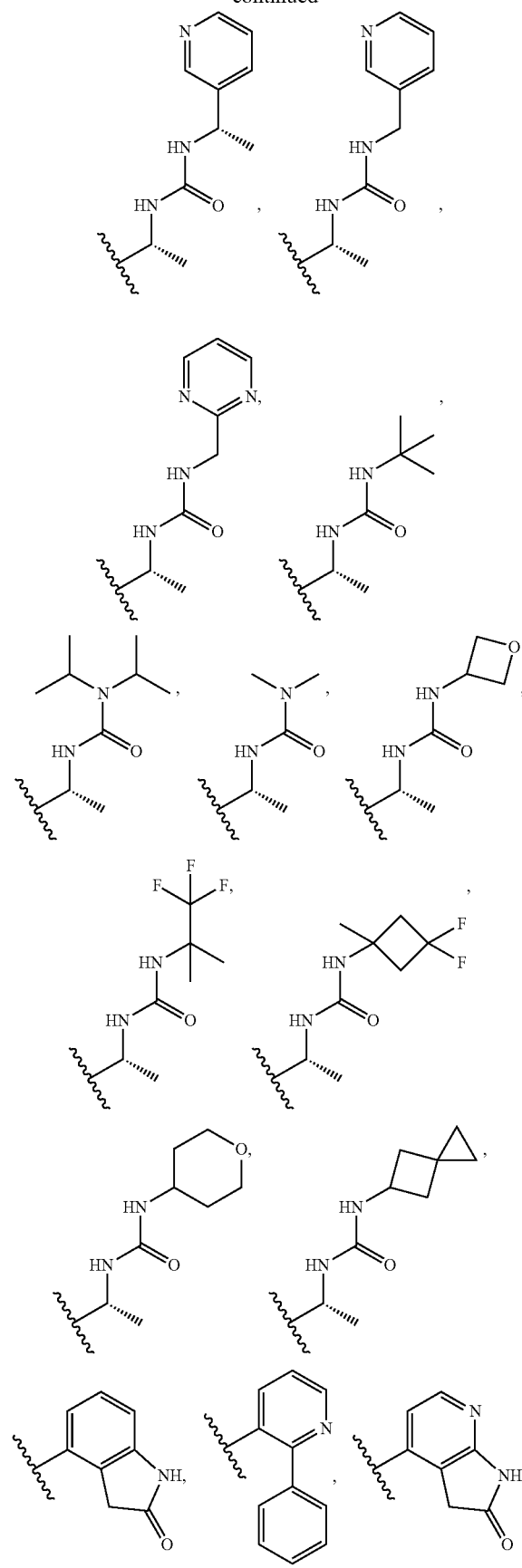
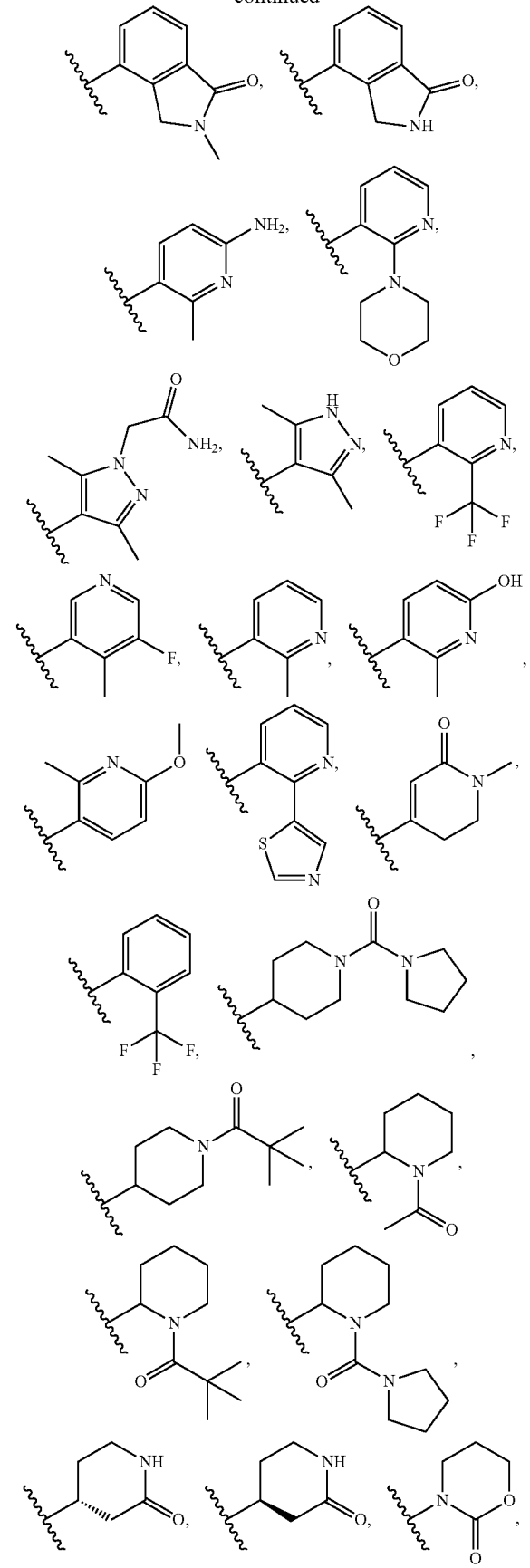

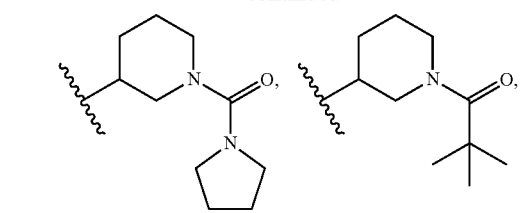
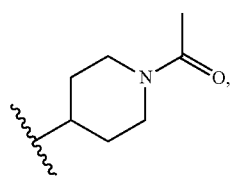
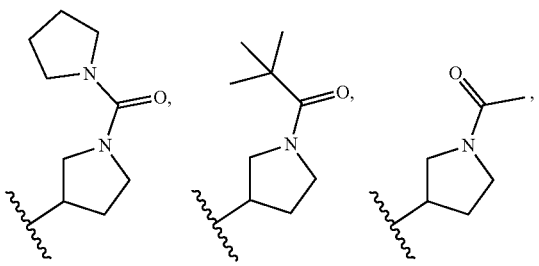
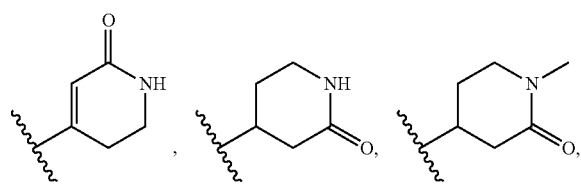
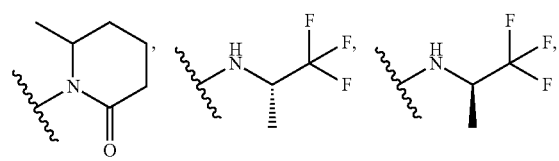
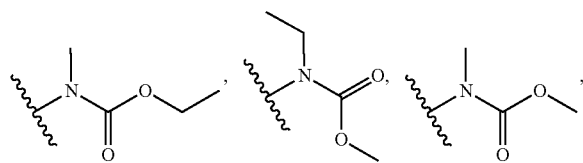
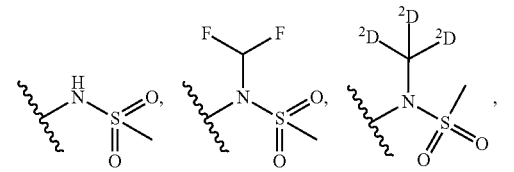
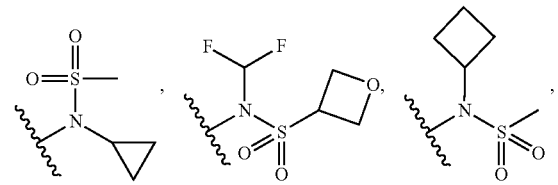
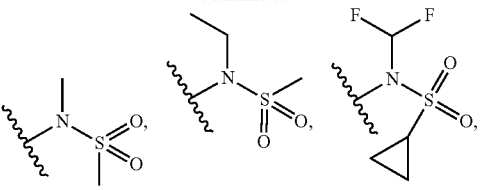
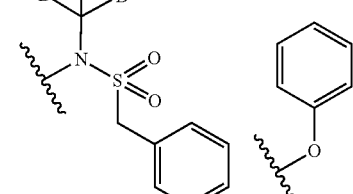
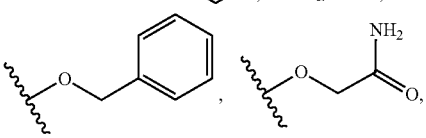
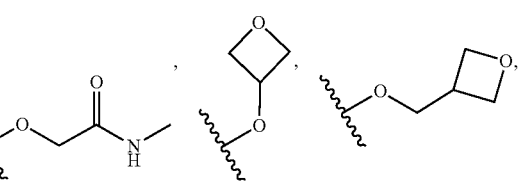
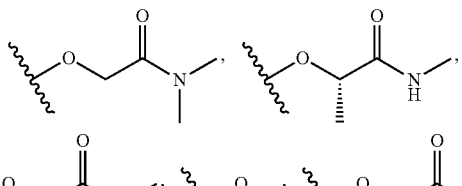
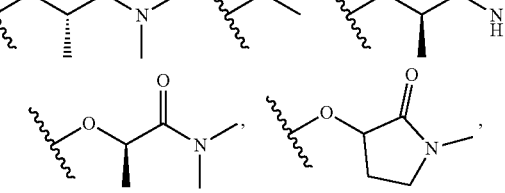
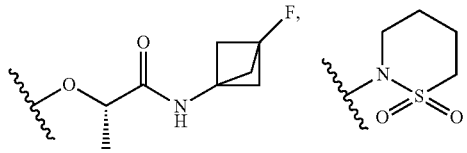
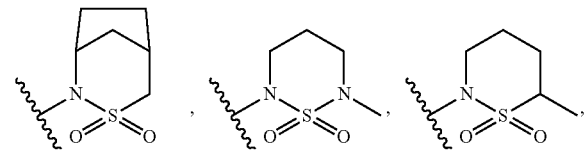
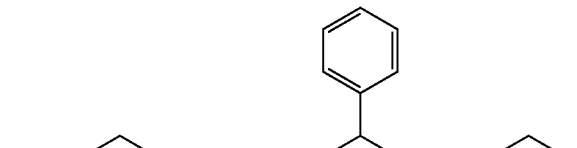
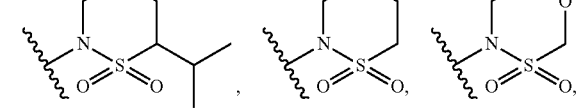

-continued
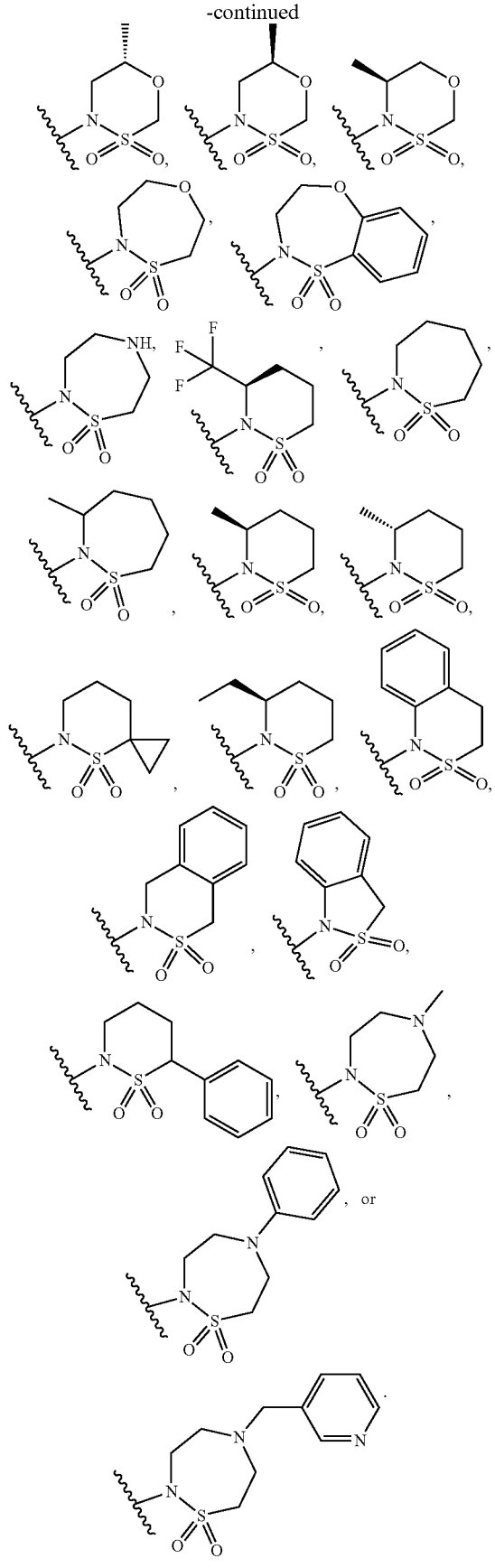
In certain embodiments, $R^6$ is
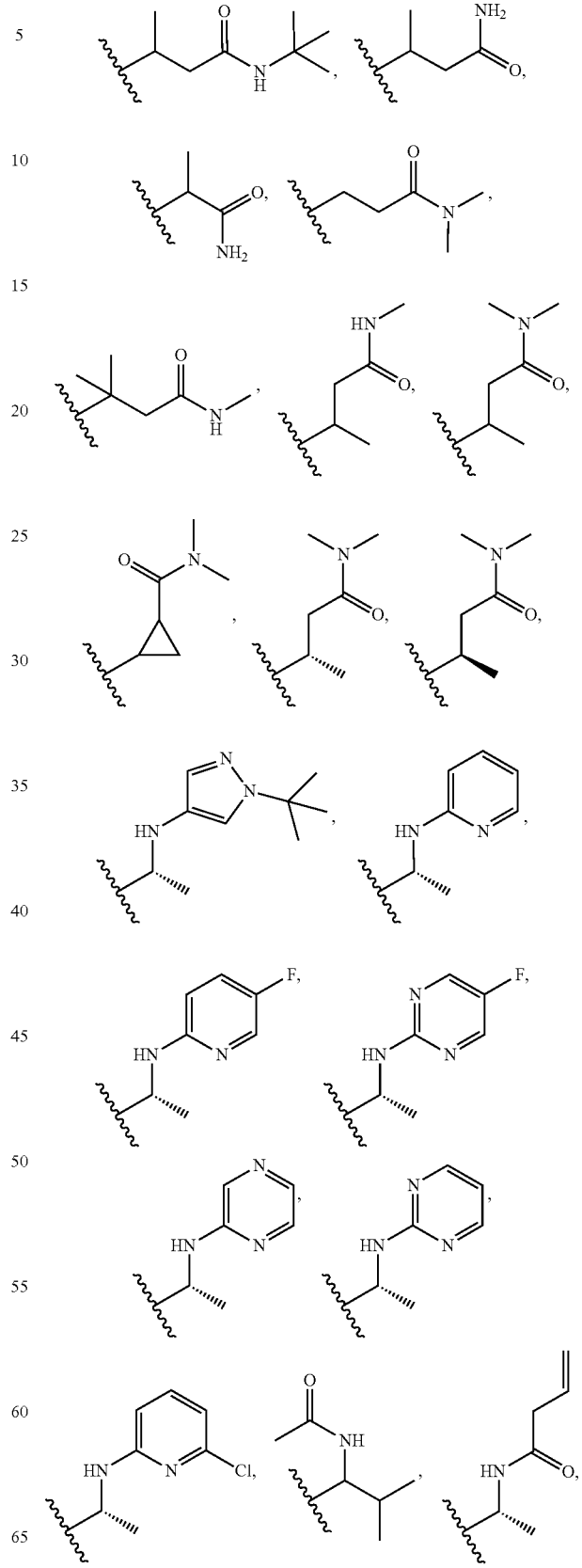

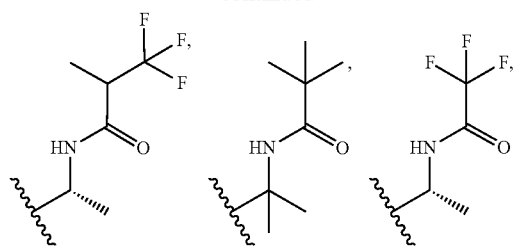
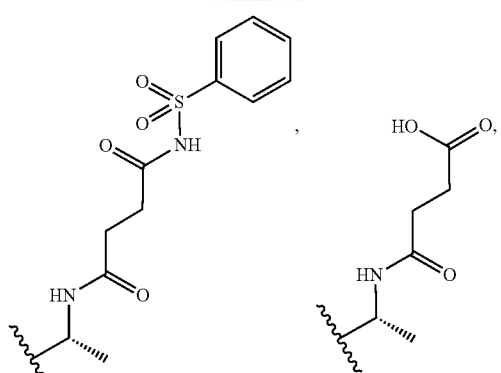
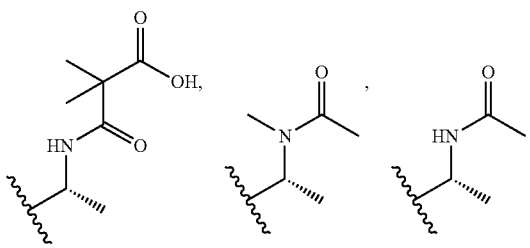
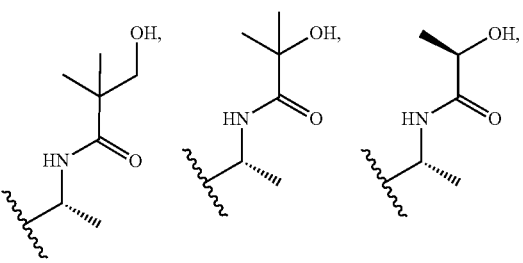
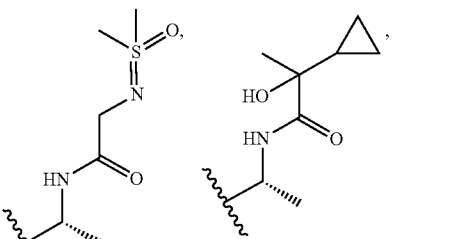
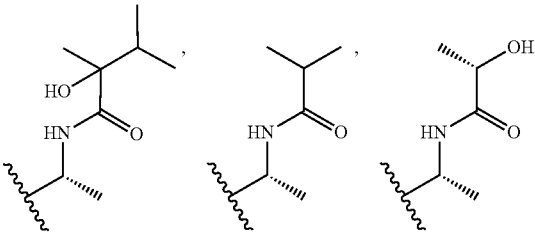
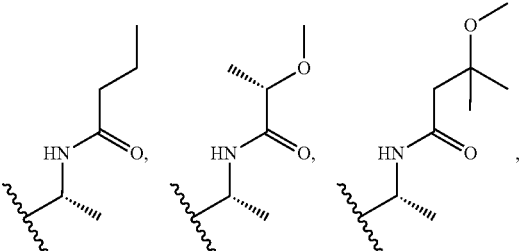

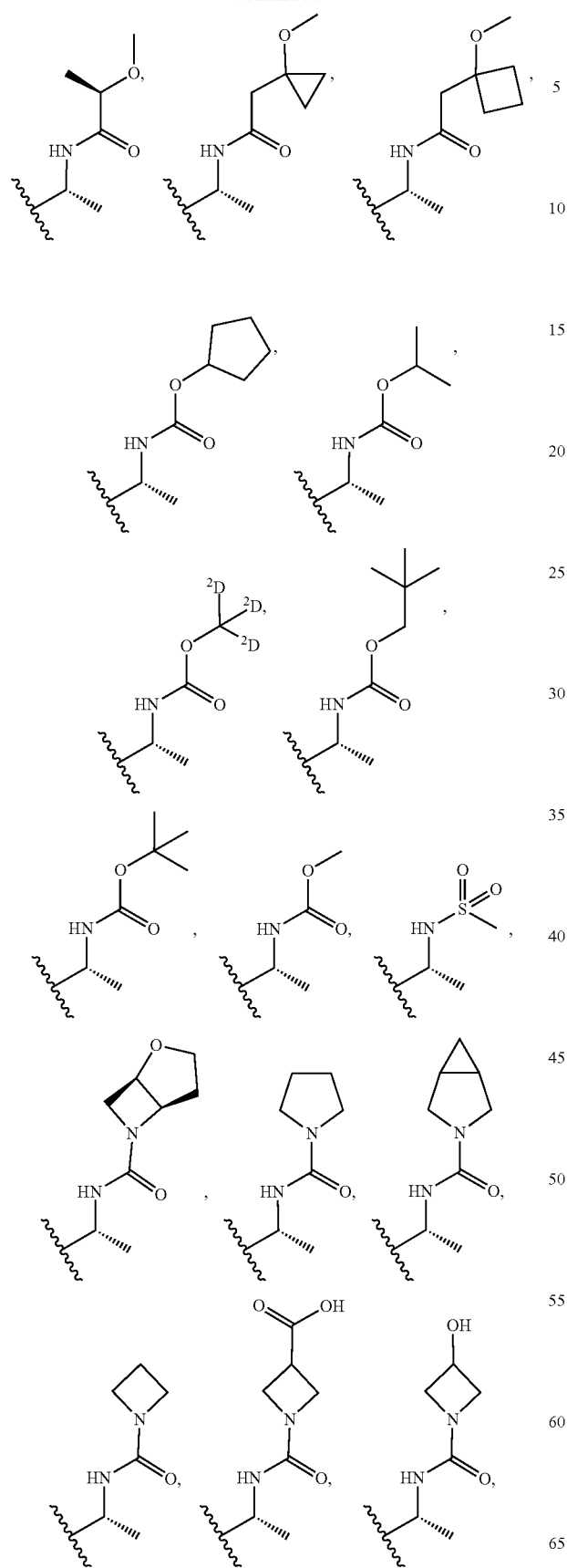
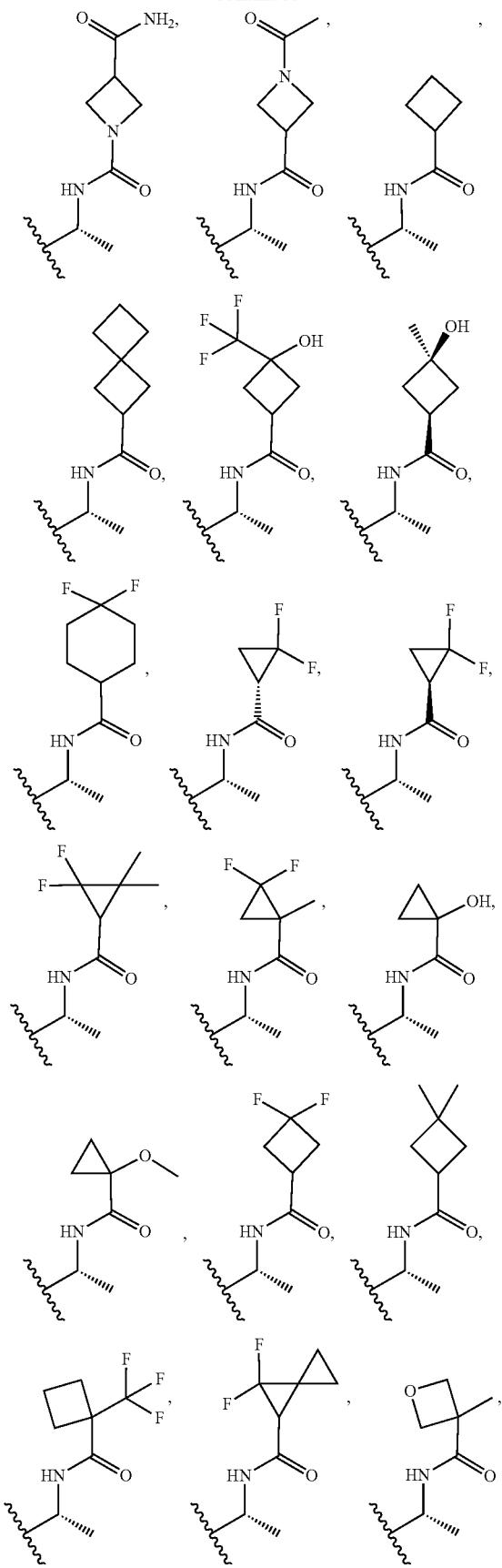

-continued
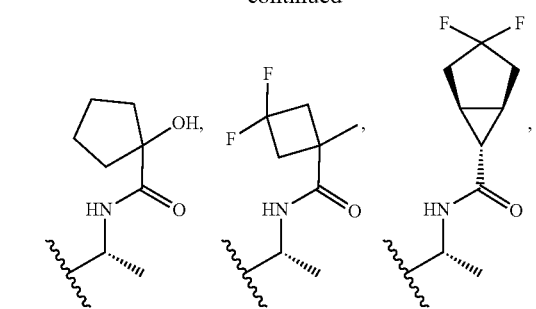
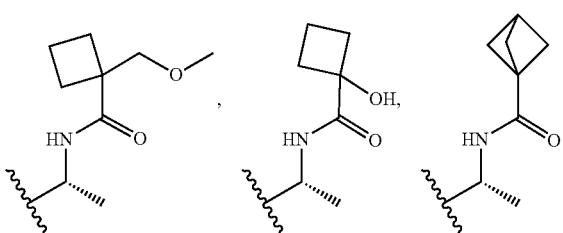
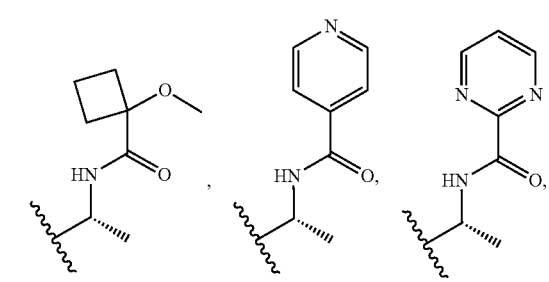
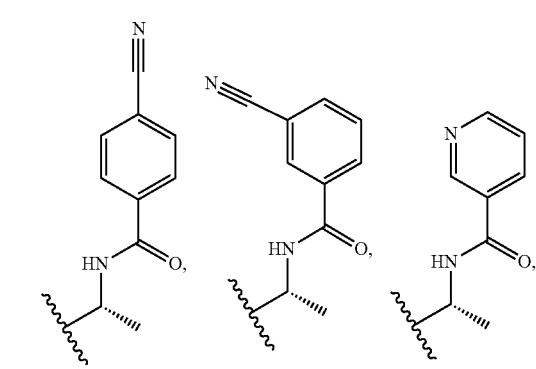
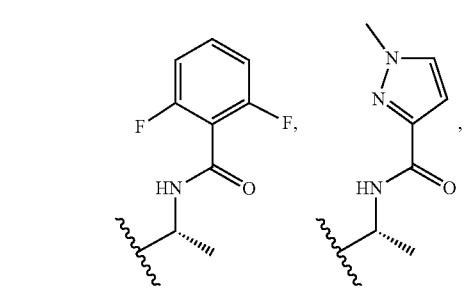
-continued
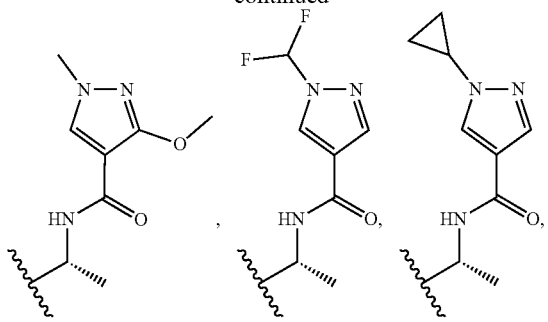
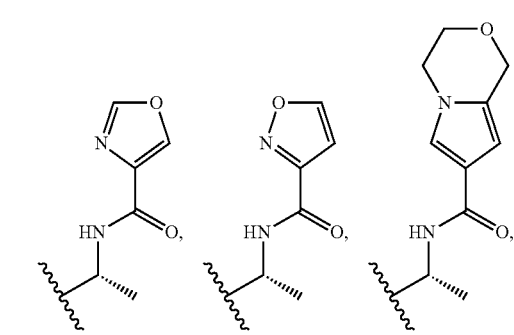
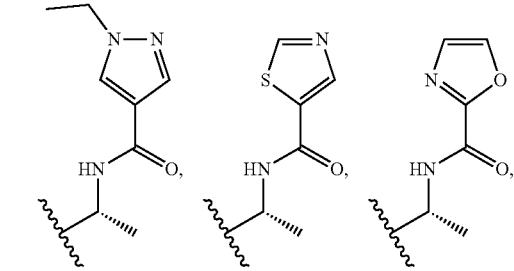
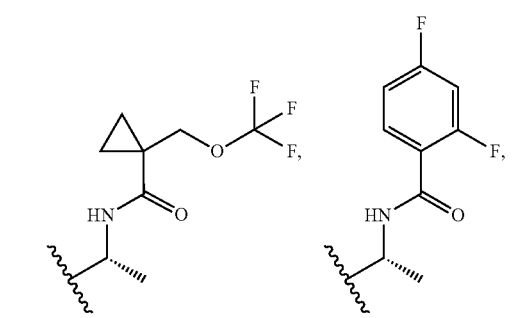
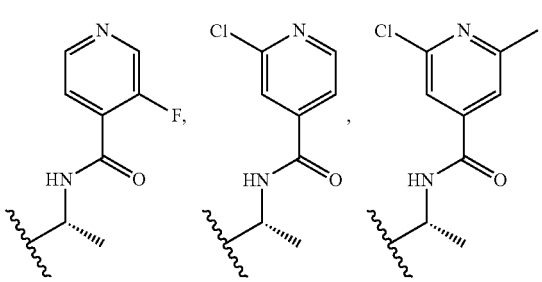

-continued
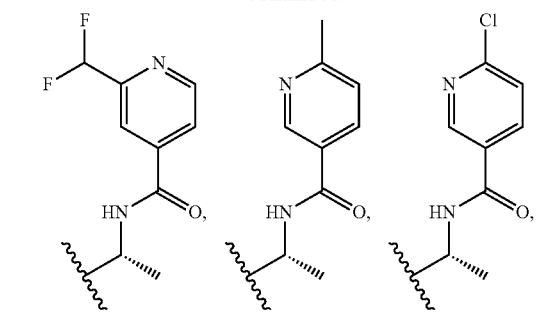
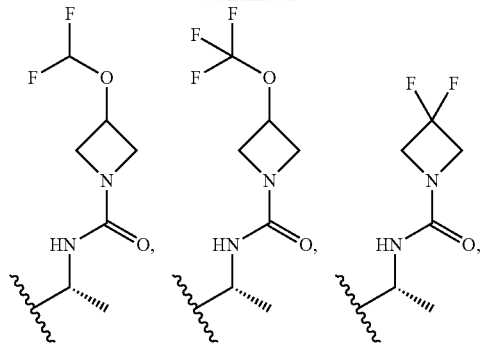
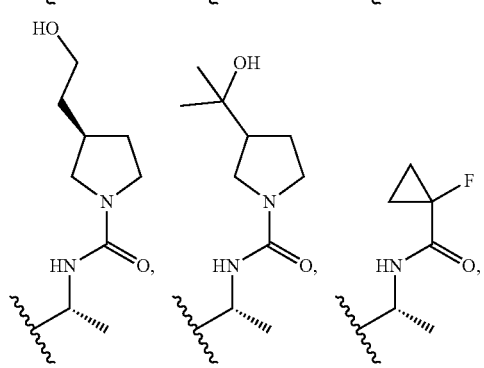
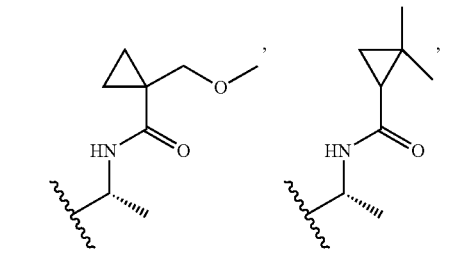
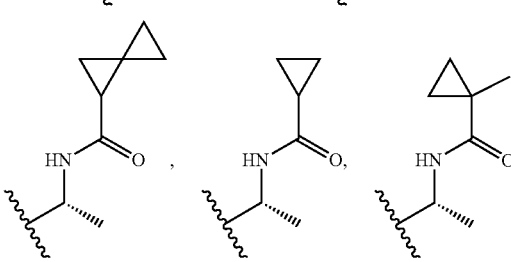
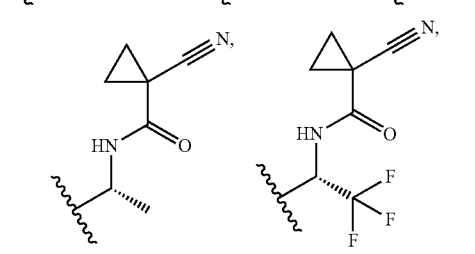
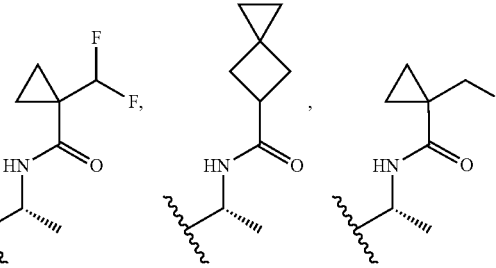

-continued
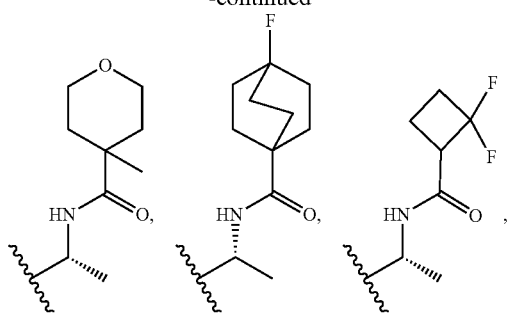
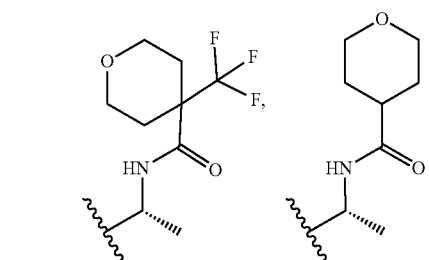
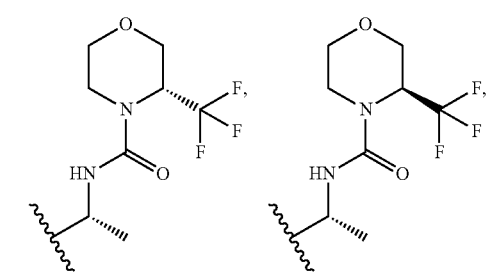
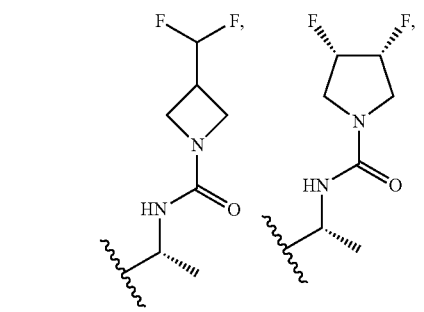
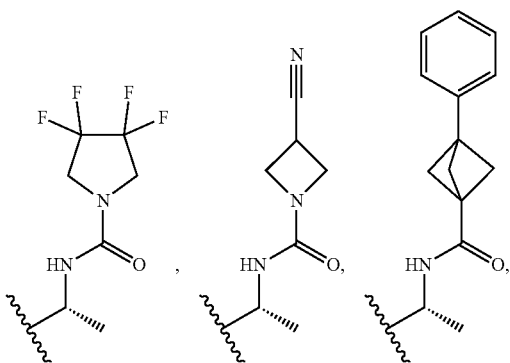
-continued
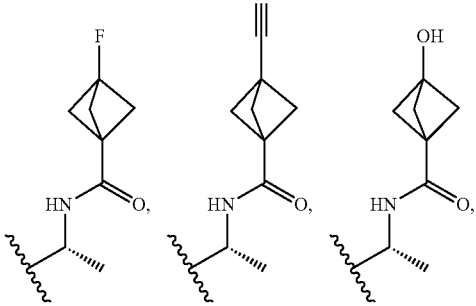
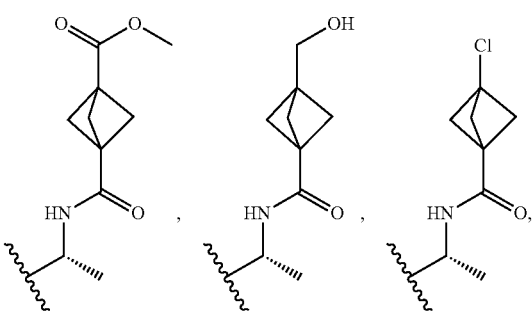
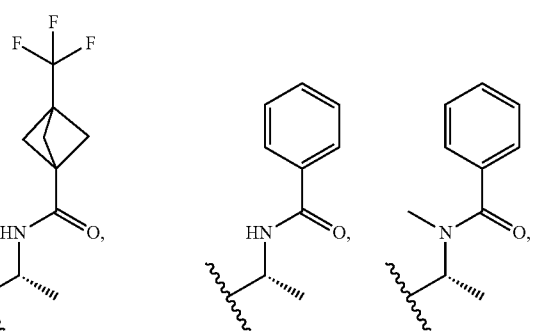
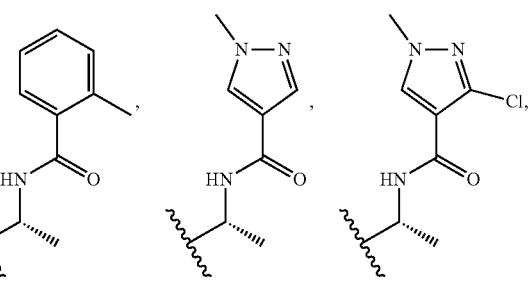
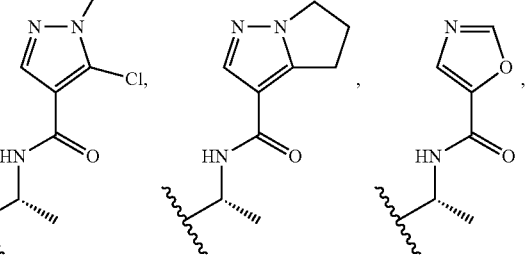

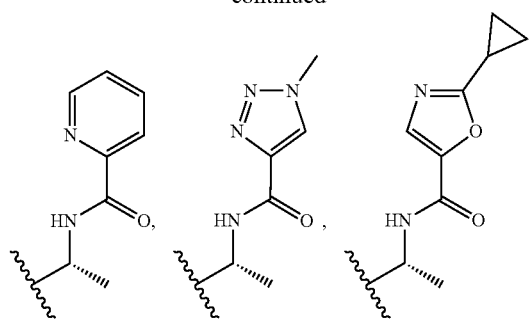
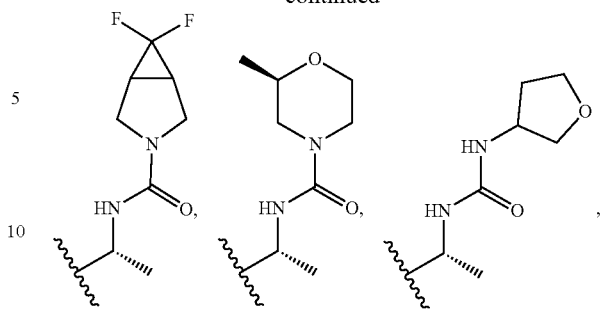
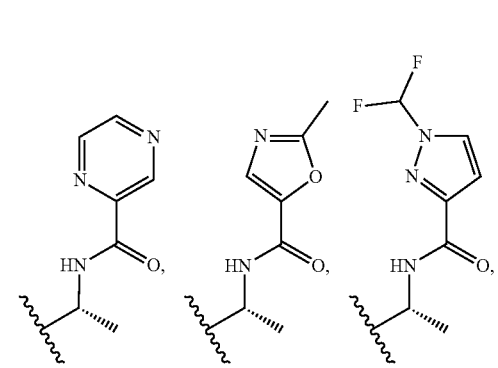
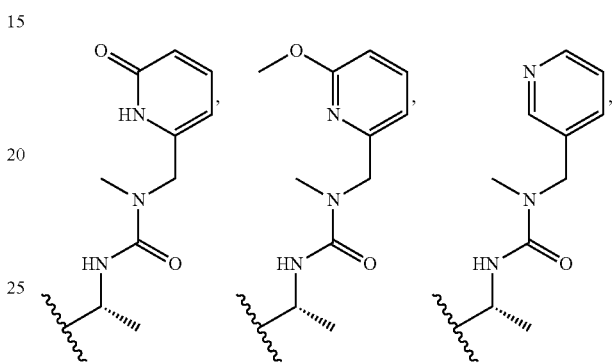
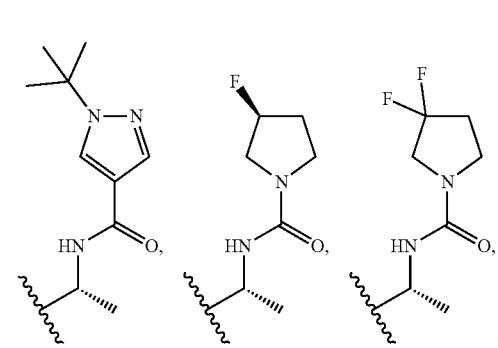
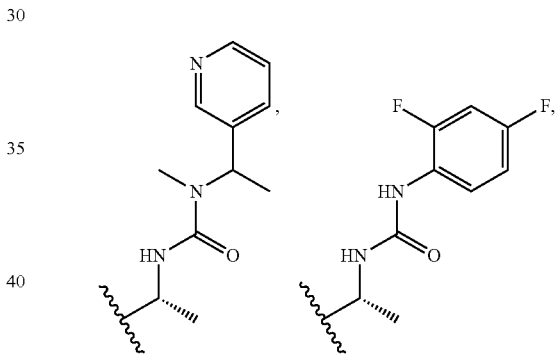
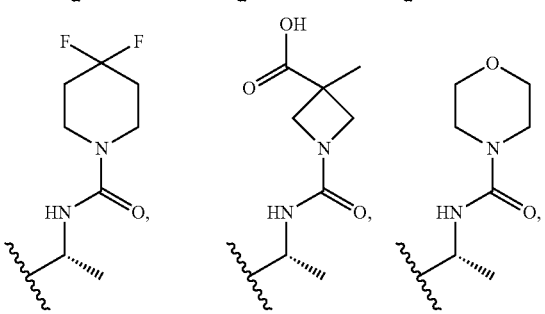
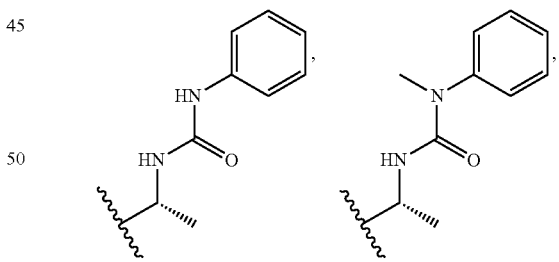
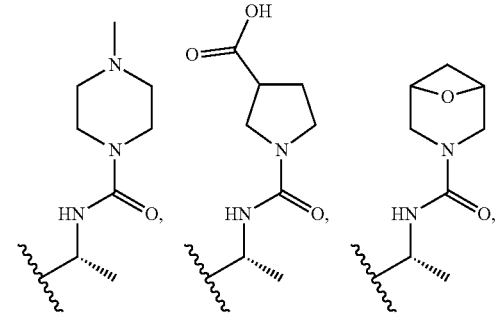
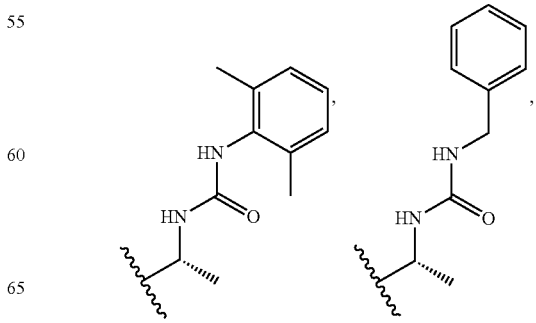

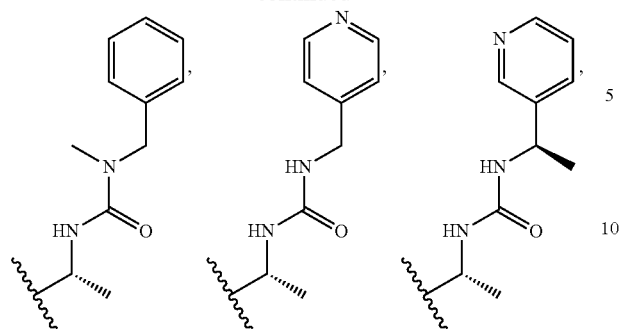
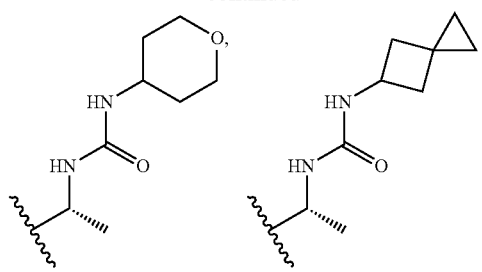
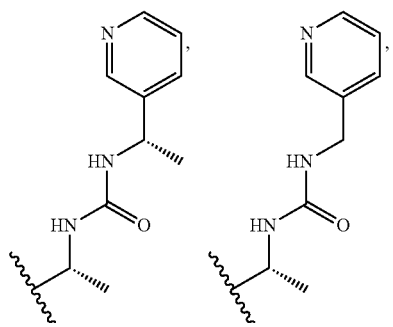
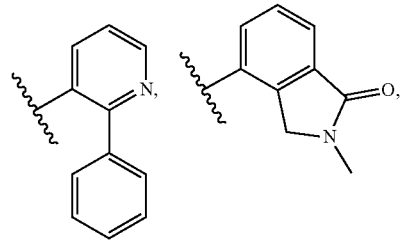
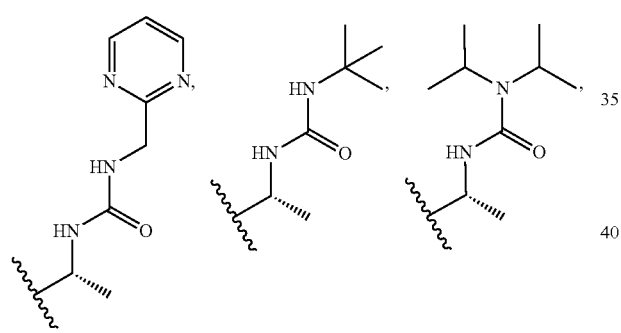
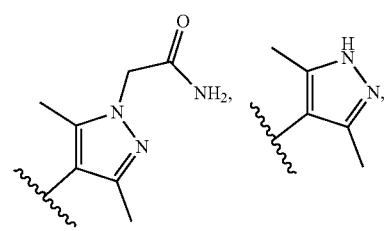
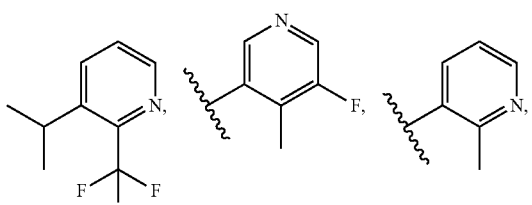
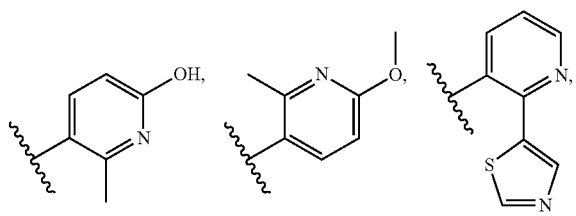
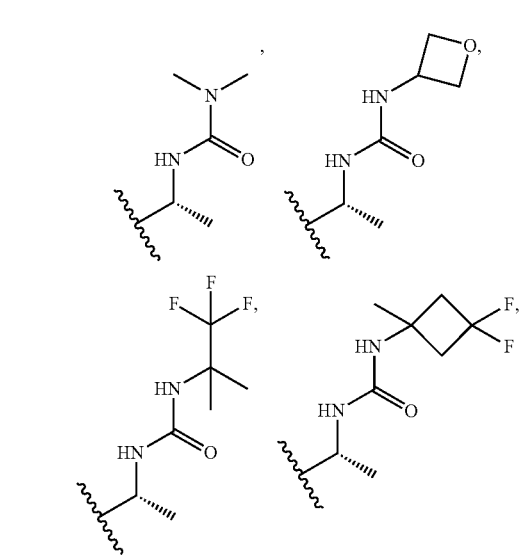
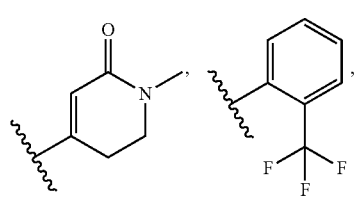

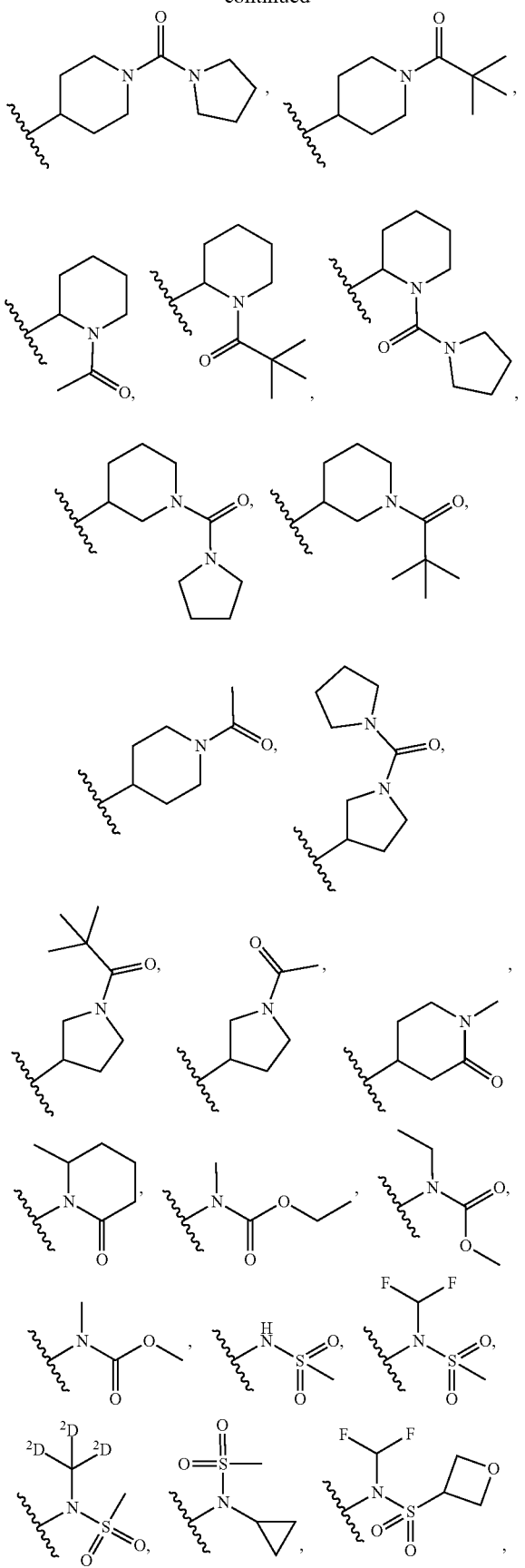
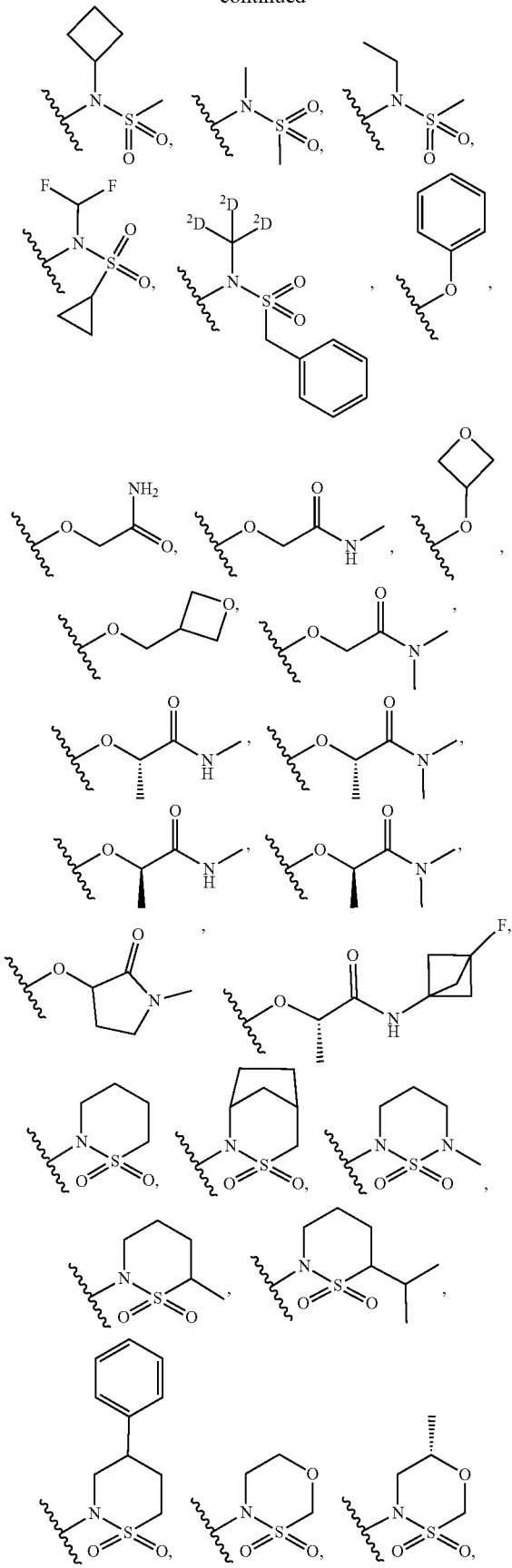

-continued
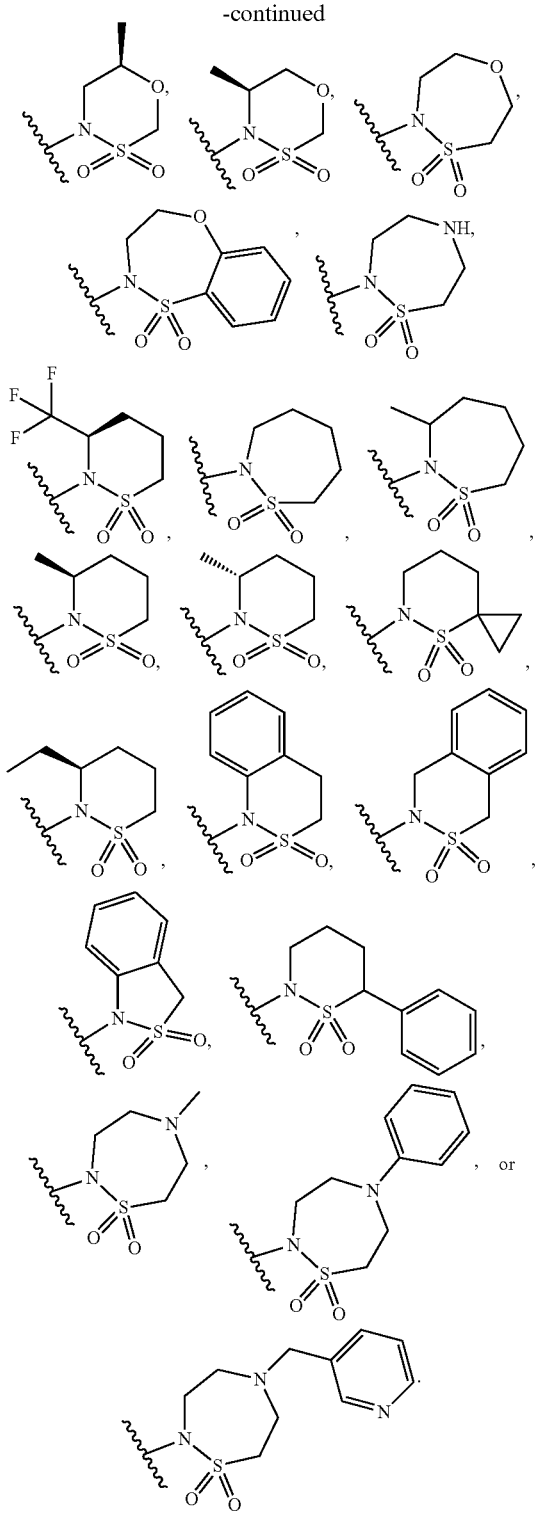
In certain embodiments, $R^6$ is —Cl, —CN,
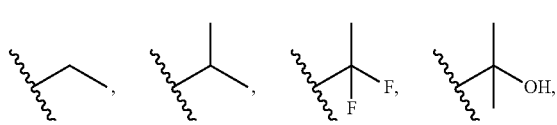
-continued

In certain embodiments, $R^6$ is

In certain embodiments, $R^6$ is
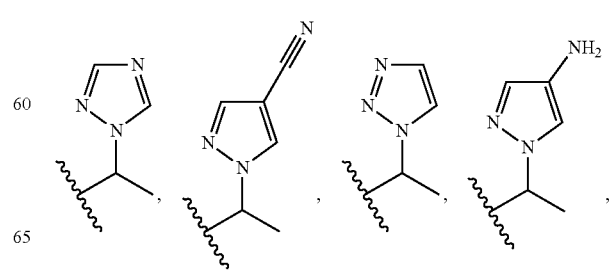

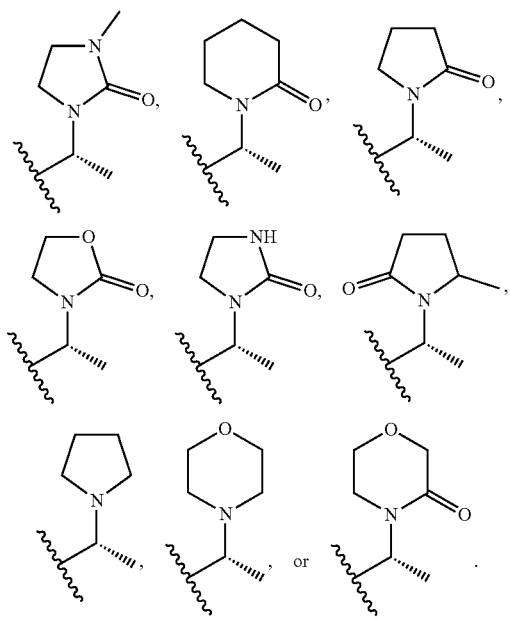
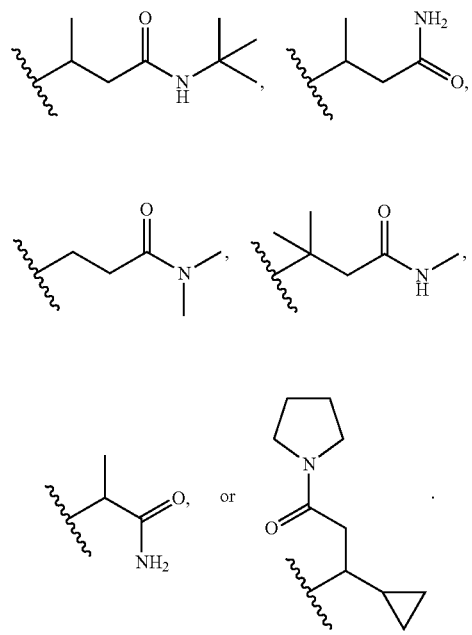
In certain embodiments, $R^6$ is
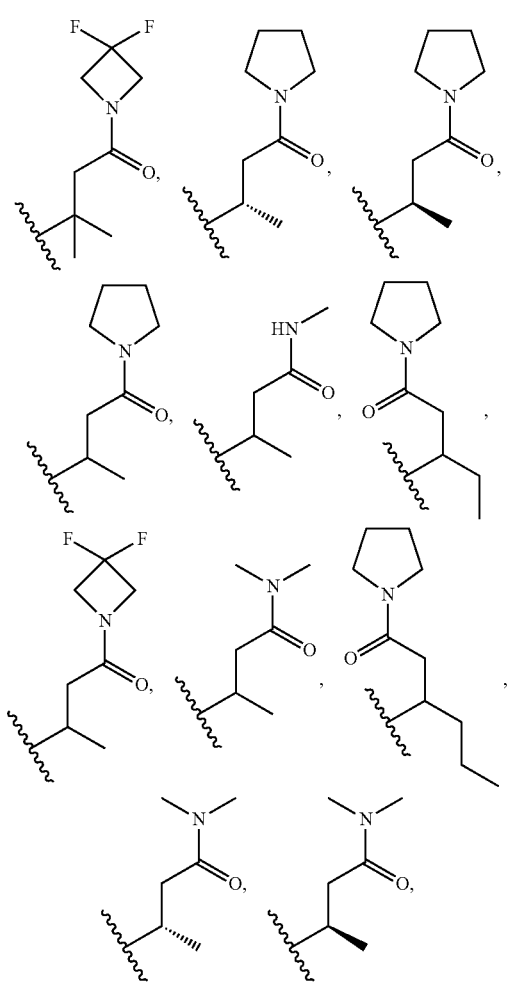
In certain embodiments, $R^6$ is
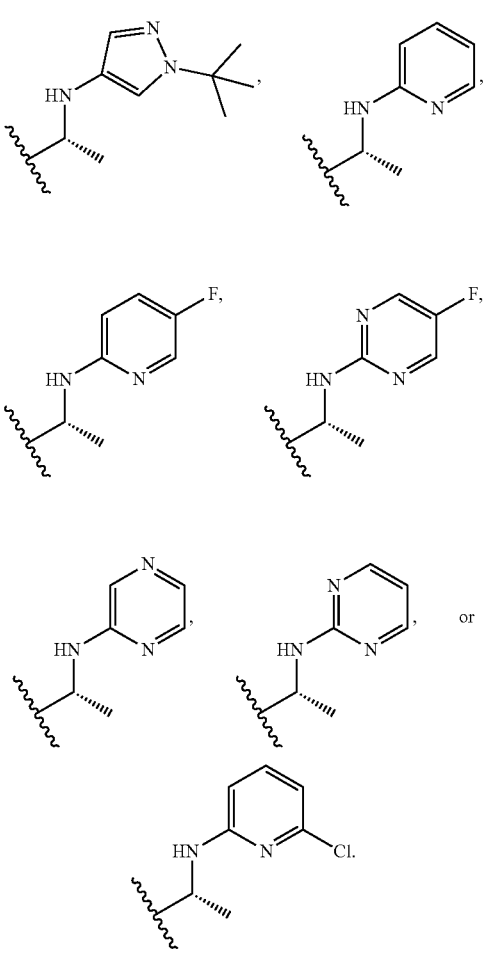

In certain embodiments, R⁶ is
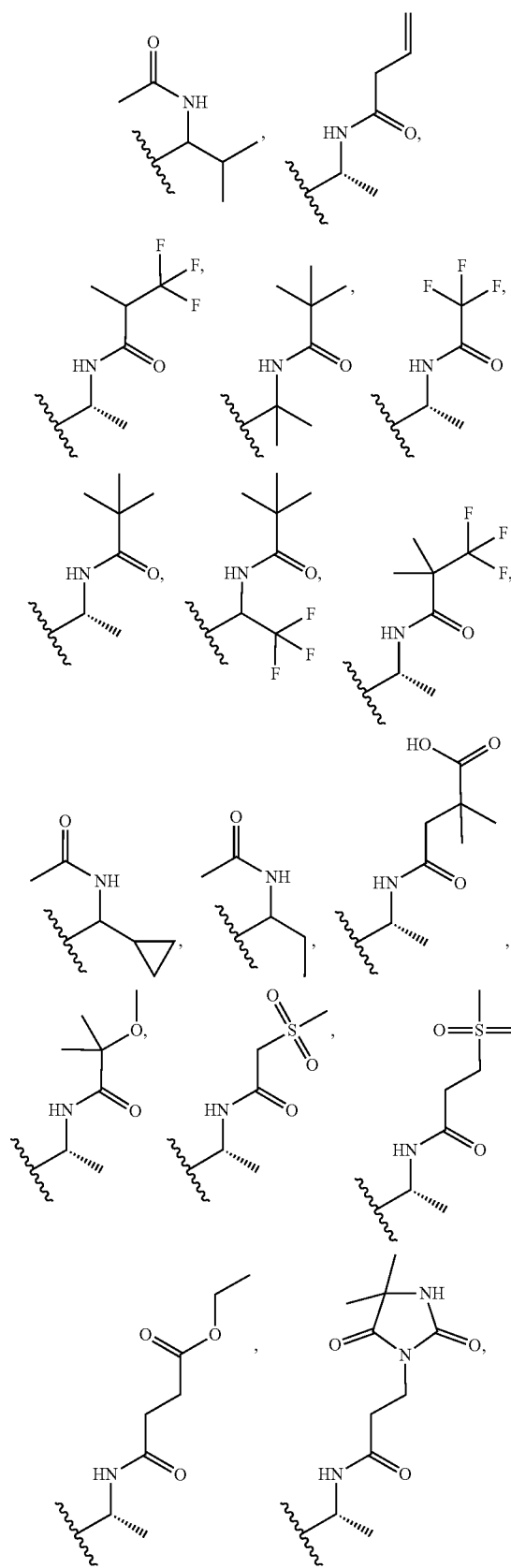
-continued
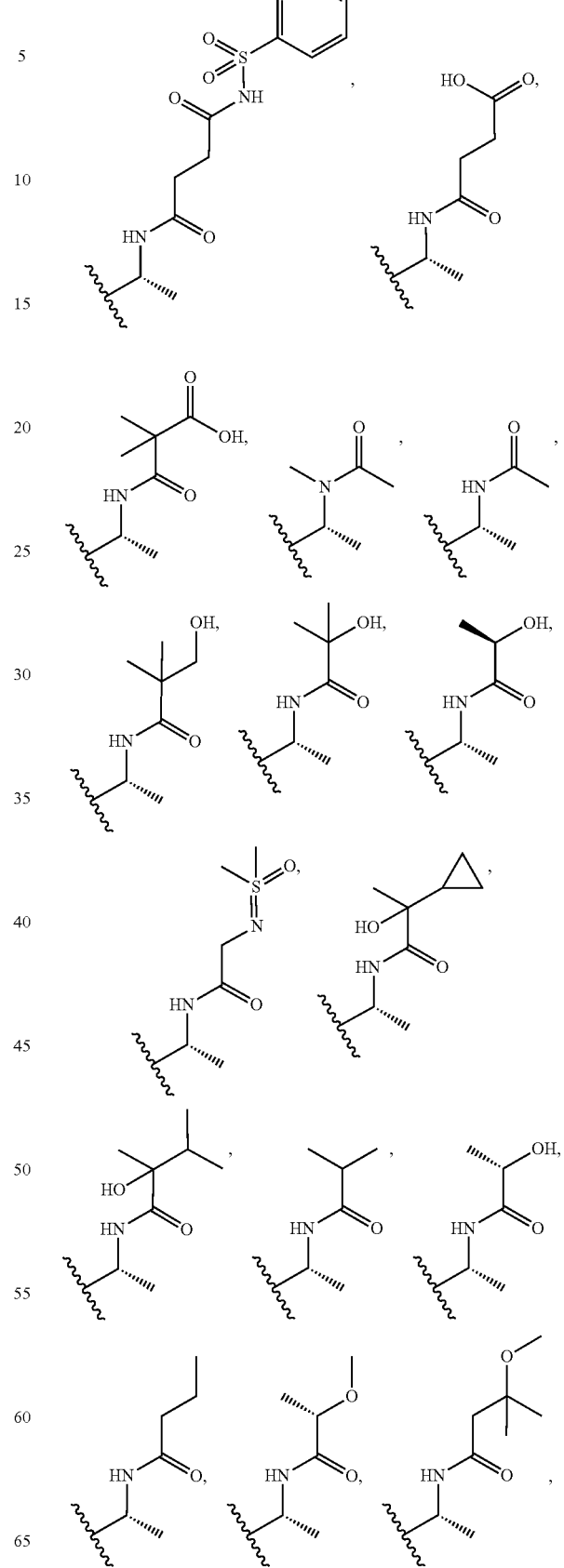

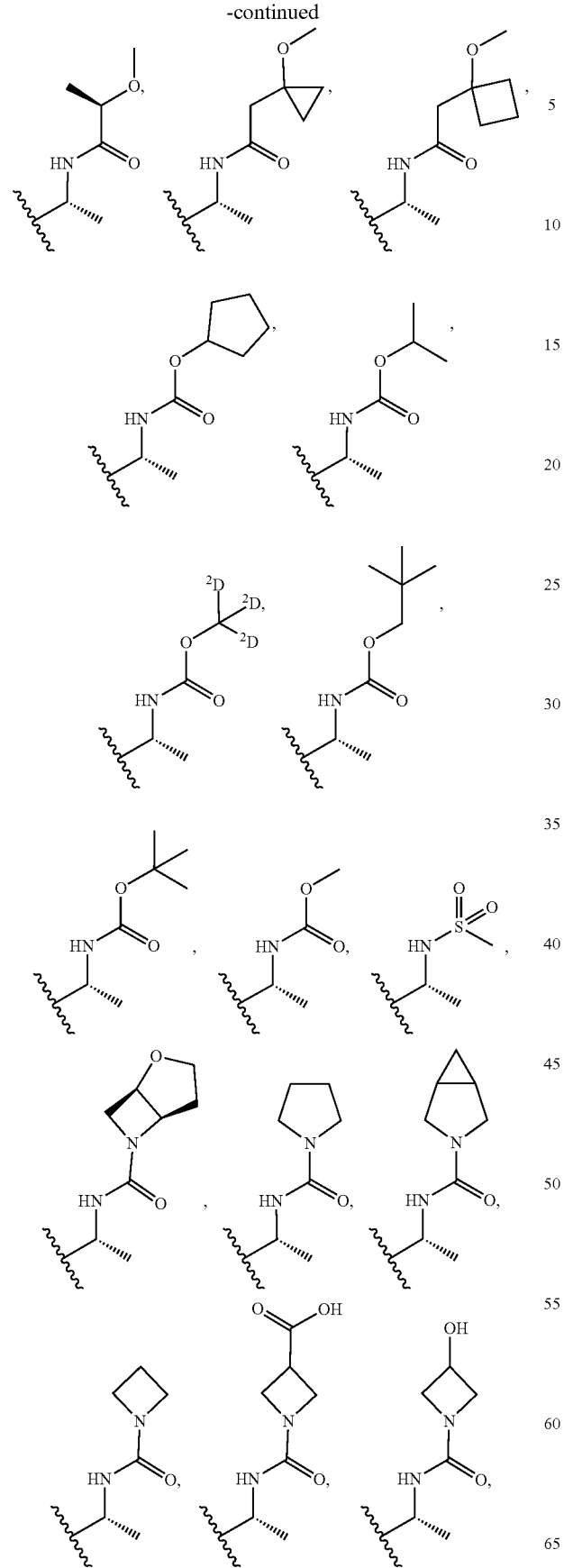
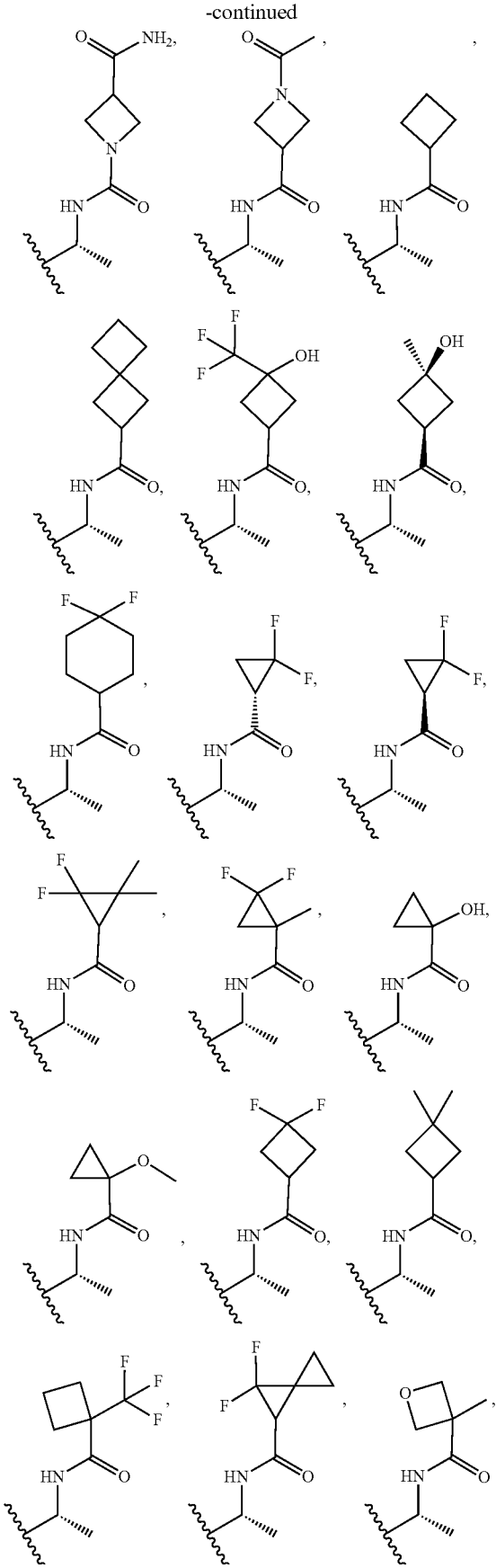

-continued
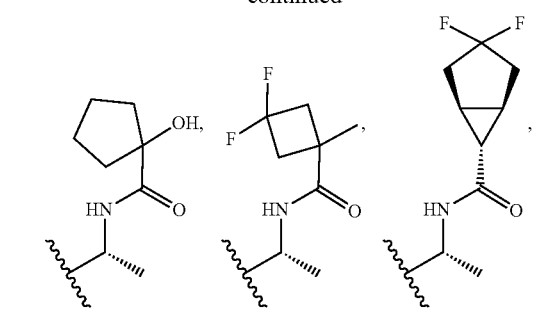
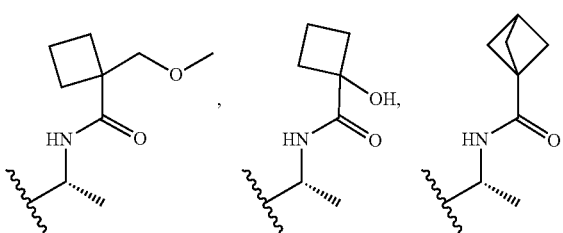
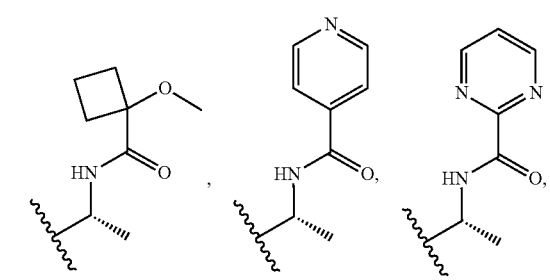
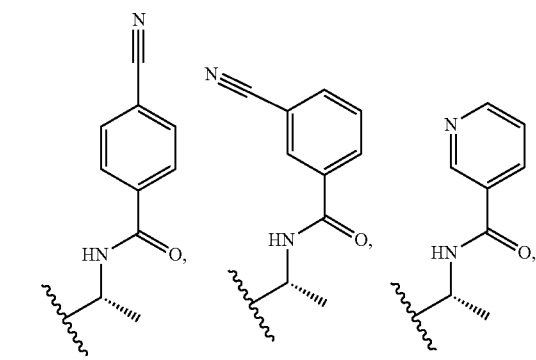
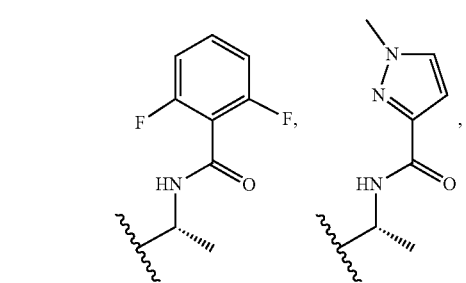
-continued
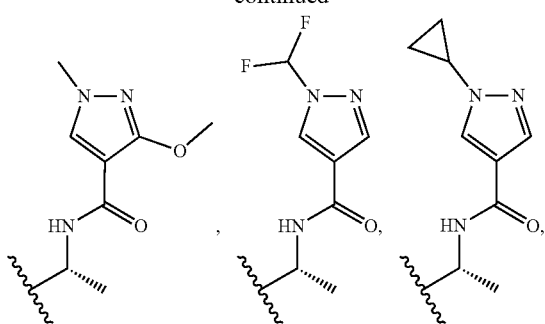
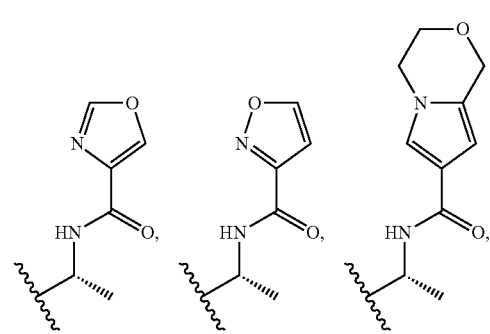
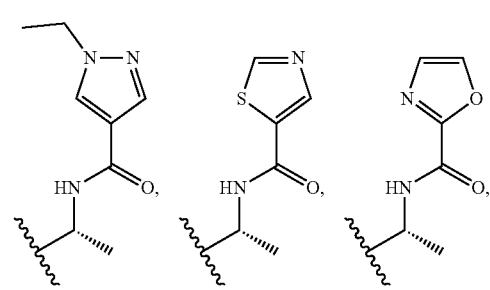
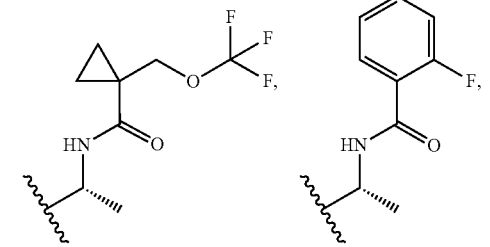

-continued
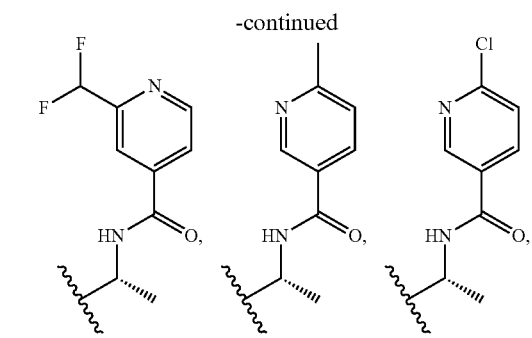
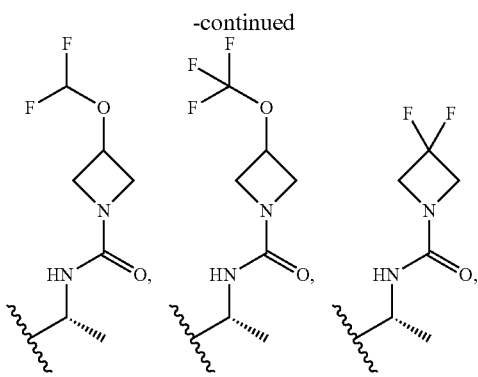
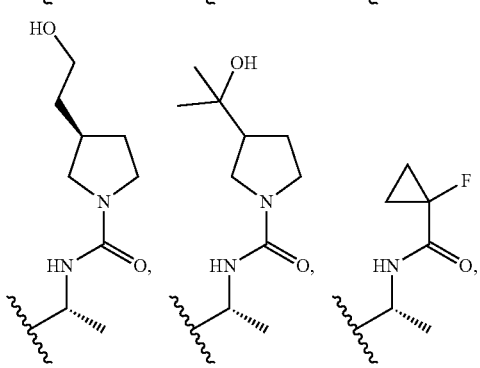
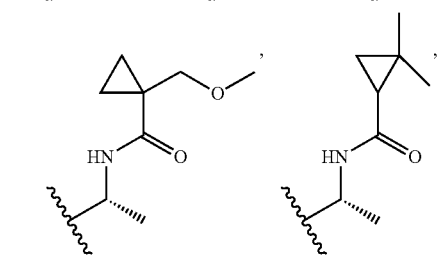
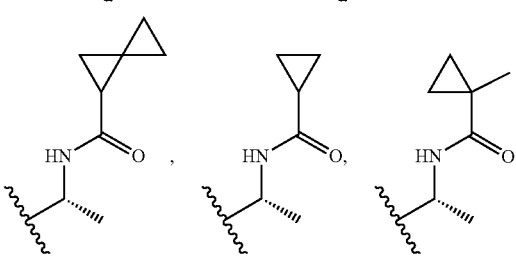
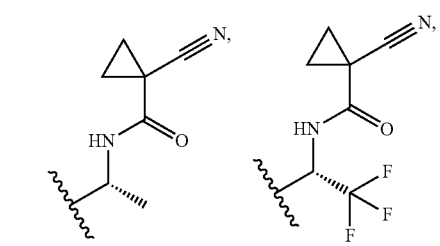
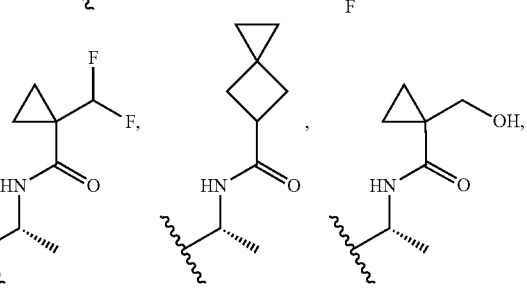

-continued
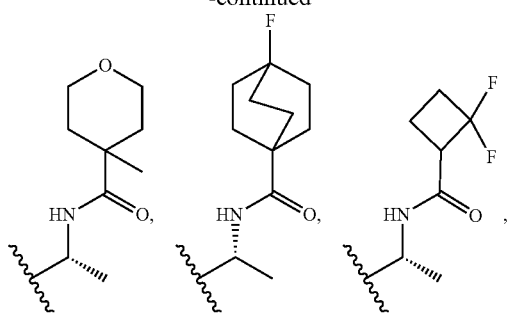
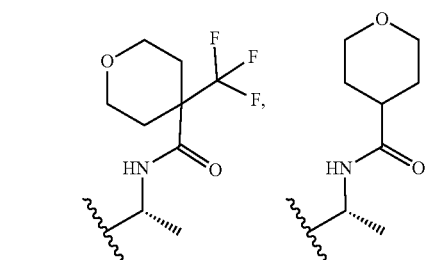
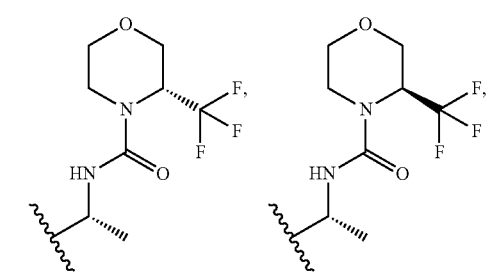
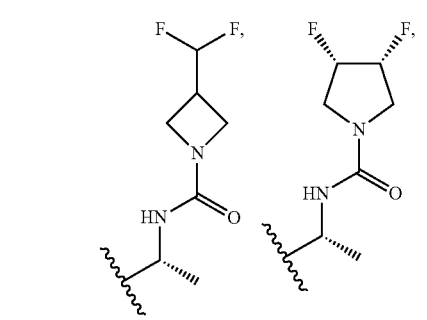
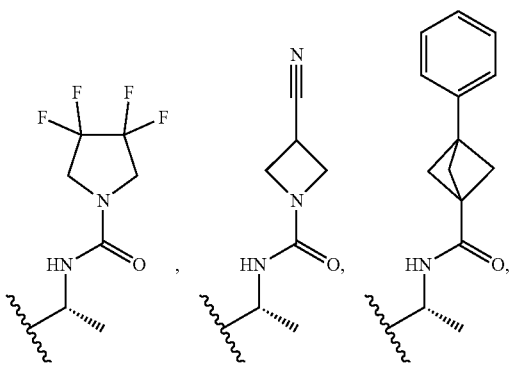
-continued
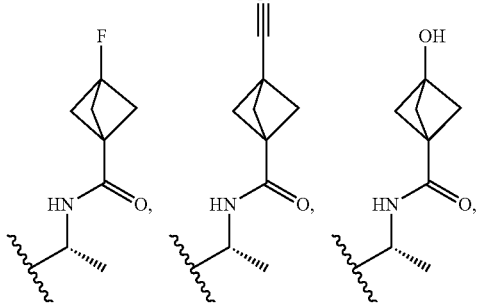
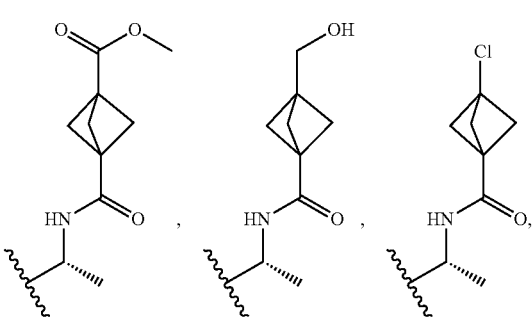
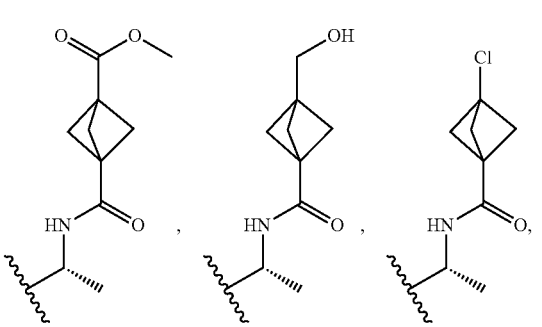
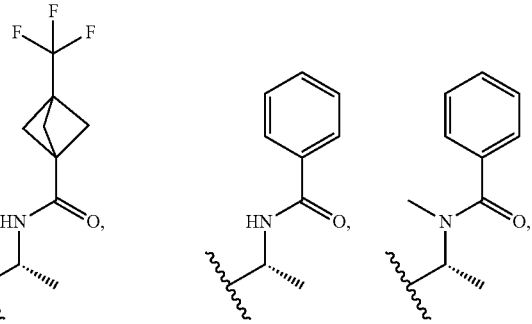
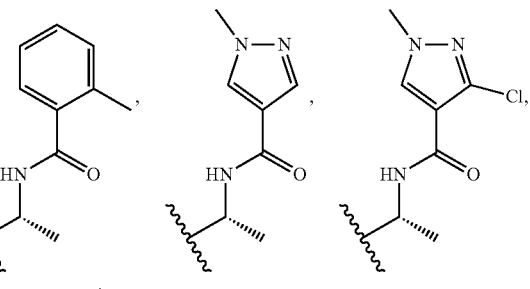
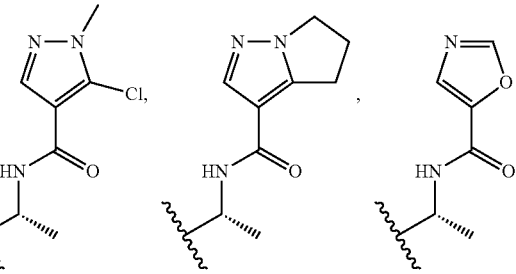

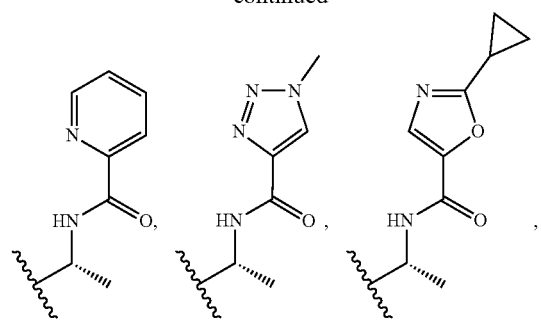
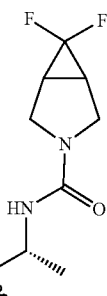
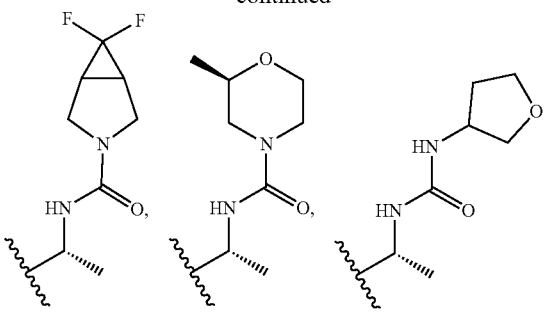
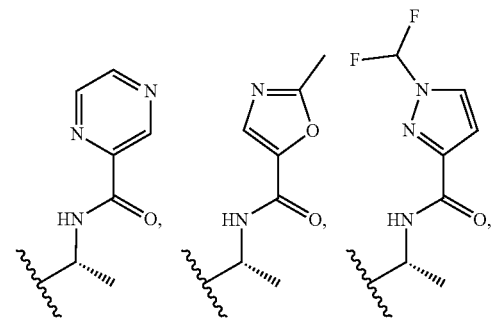
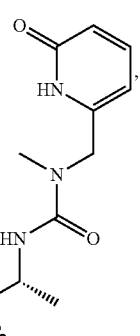
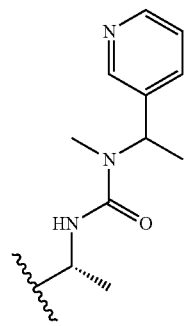
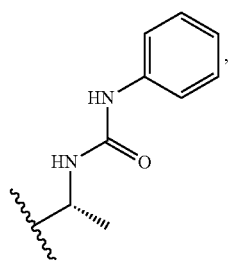
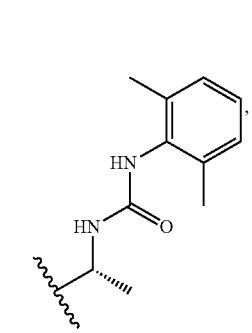

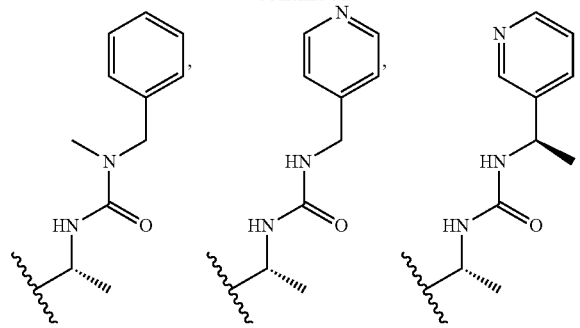
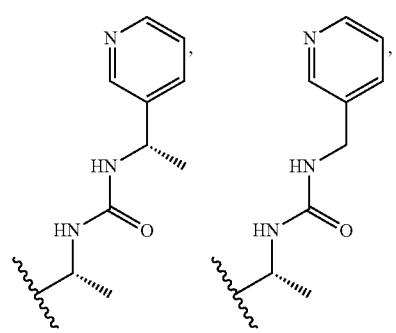
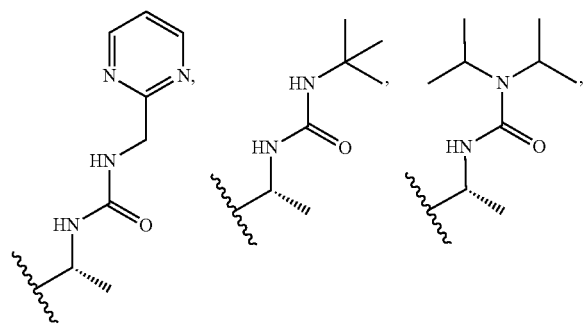
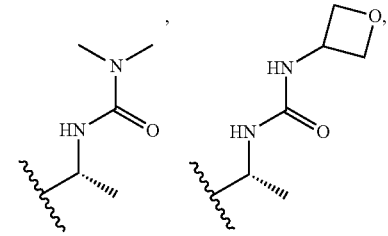
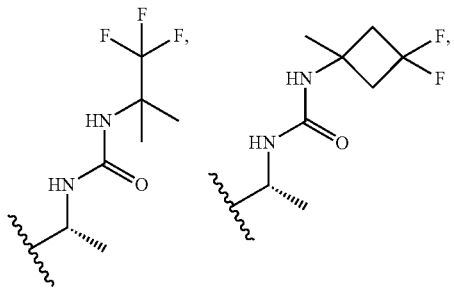
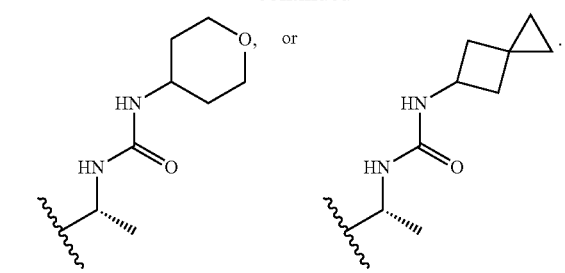
In certain embodiments, $R^6$ is
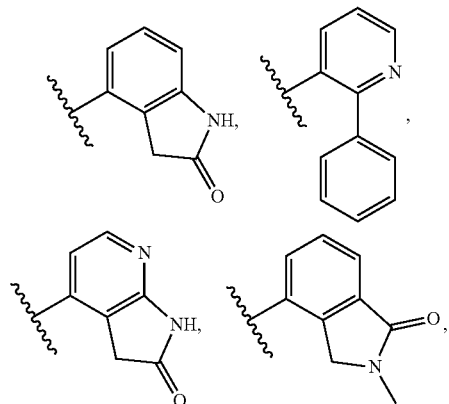
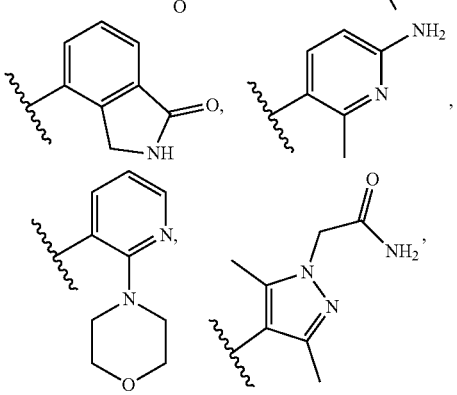
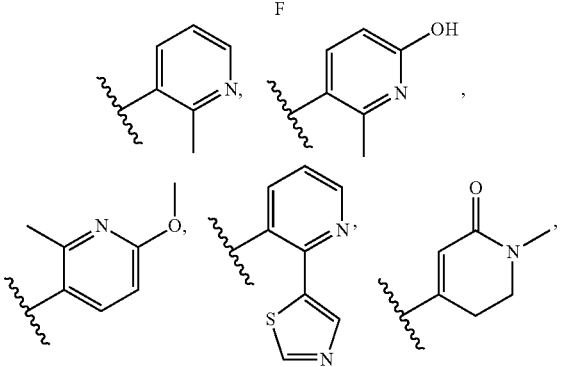

-continued
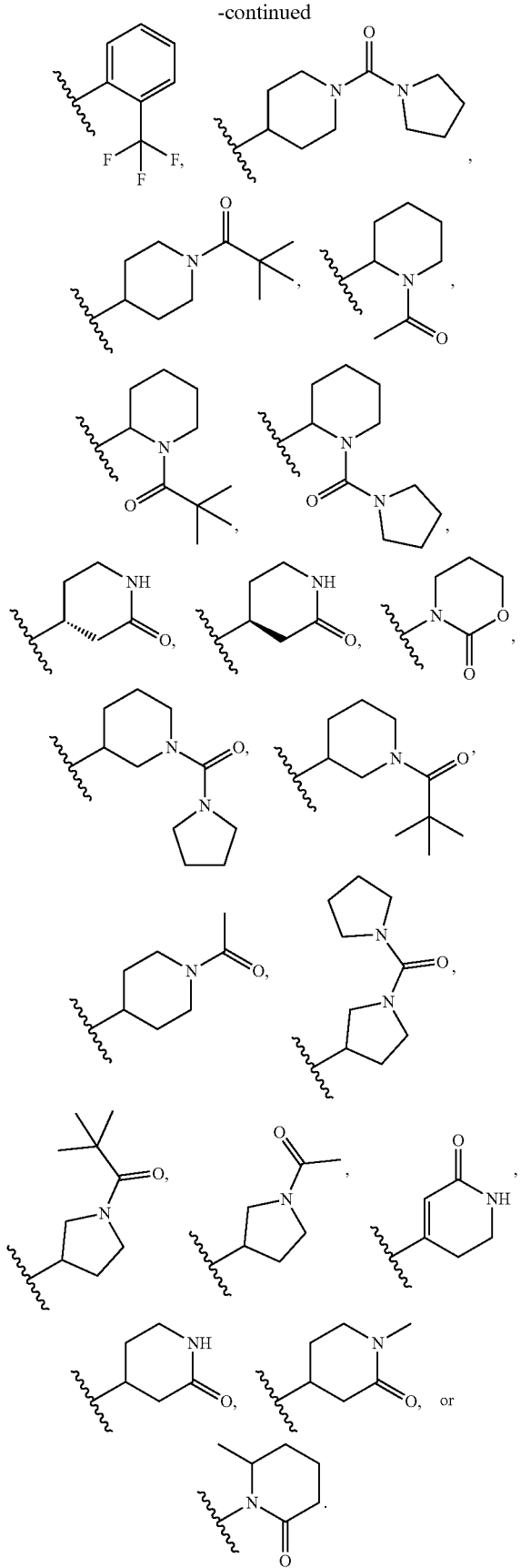
In certain embodiments, $R^6$ is
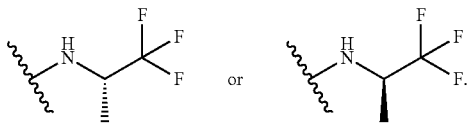
In certain embodiments, $R^6$ is
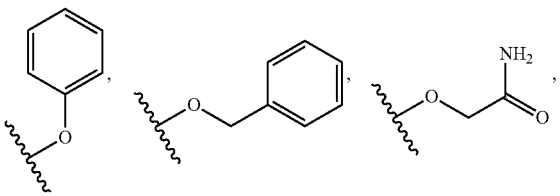
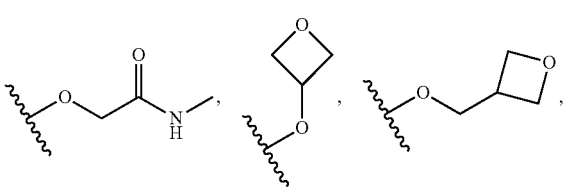
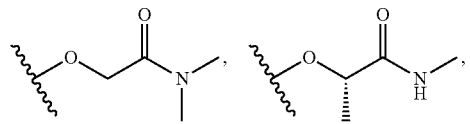
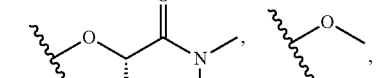
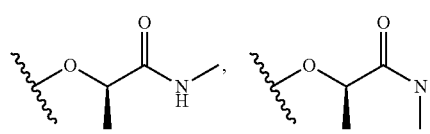
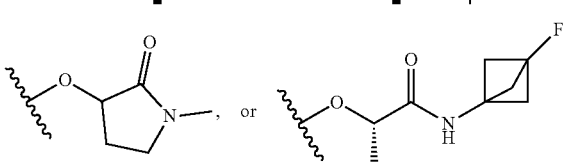
In certain embodiments, $R^6$ is
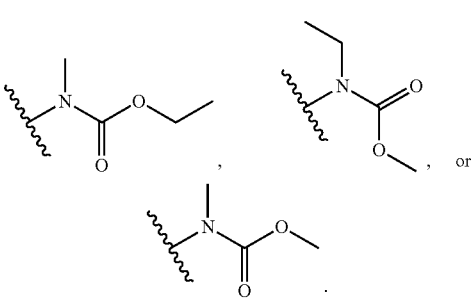

In certain embodiments, $R^6$ is

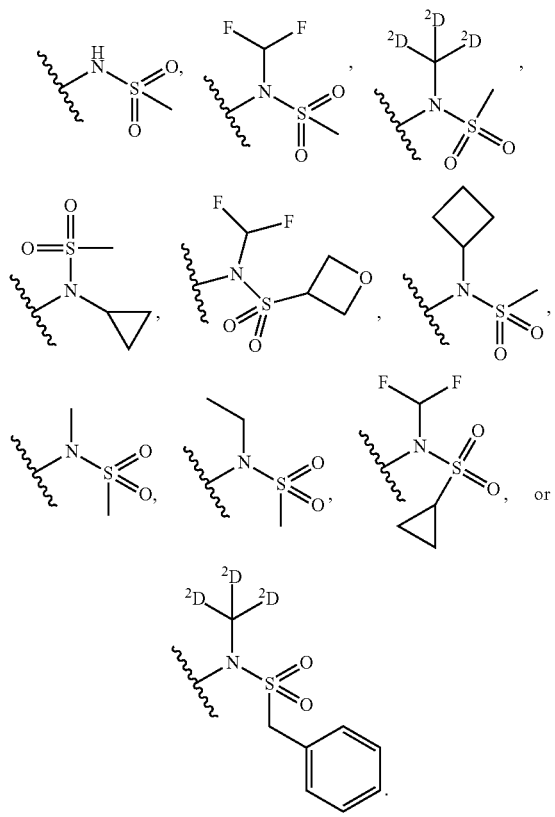

In certain embodiments, $R^6$ is

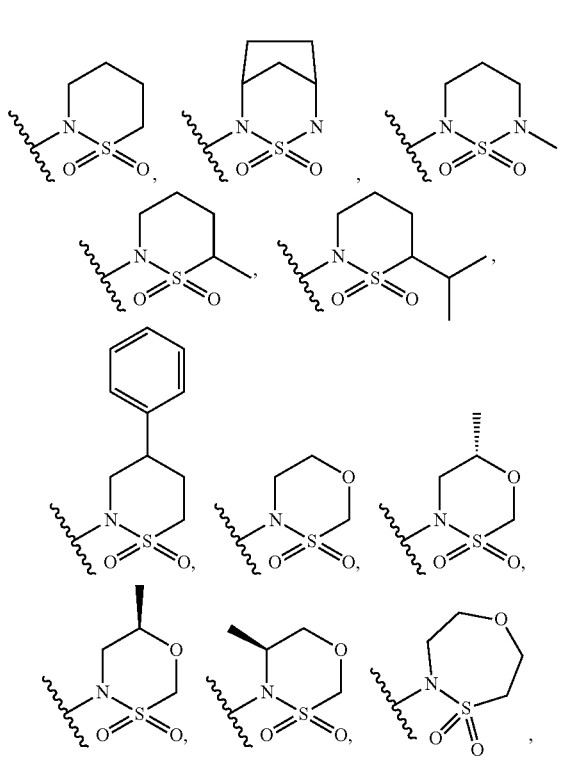

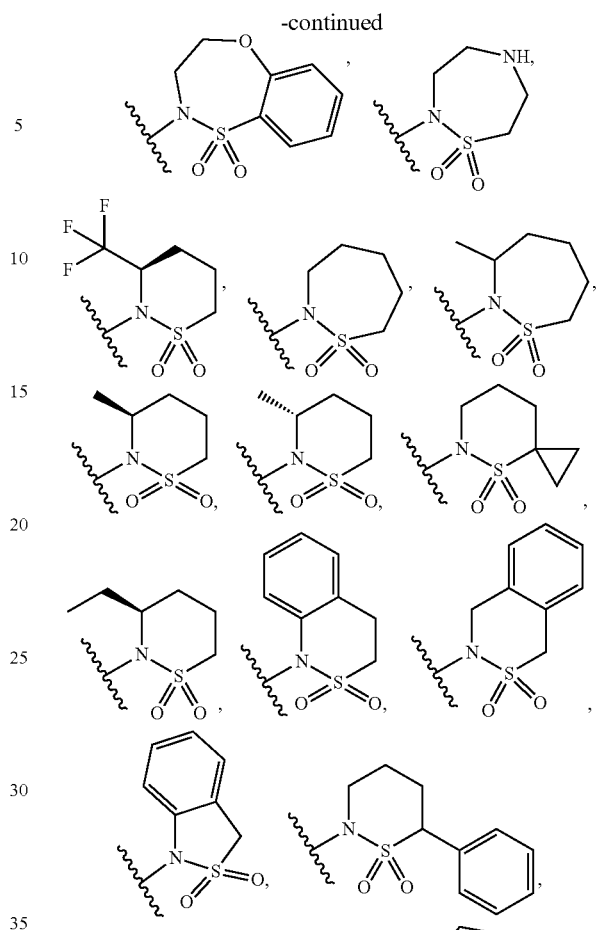

In certain embodiments, $R^7$ is hydrogen.
In certain embodiments, $R^8$ is hydrogen.
In certain embodiments, $R^{10}$ is hydrogen, $C_{1-8}$ alkyl optionally substituted with 1 to 3 $Z^{10}$, or $C_{3-6}$ cycloalkyl optionally substituted with 1 to 3 $Z^{10}$;
$R^{11}$ is $C_{1-8}$ alkyl optionally substituted with 1 to 4 $Z^{10}$, $C_{3-8}$ cycloalkyl optionally substituted with 1 to 4 $Z^{10}$, or 4-12-membered heterocyclyl optionally substituted with 1 to 4 $Z^{10}$; or
$R^{10}$ and $R^{11}$ are taken together with the nitrogen to which they are attached to form a 4-12-membered heterocyclyl optionally substituted with 1 to 4 $Z^{10}$.
In certain embodiments, $R^{10}$ is hydrogen or —$CH_3$, and $R^{11}$ is $C_{1-6}$ alkyl optionally substituted with 1 to 3 $Z^{10}$, $C_{3-6}$ cycloalkyl optionally substituted with 1 to 3 $Z^{10}$, or 4-12-membered heterocyclyl optionally substituted with 1 to 3 $Z^{10}$; or $R^{10}$ and $R^{11}$ taken together form a 4-10-membered heterocyclyl optionally substituted with 1 to 3 $Z^{10}$.

In certain embodiments, $R^{10}$ is hydrogen or —$CH_3$, and $R^{11}$ is 4-12 membered heterocyclyl optionally substituted with 1 to 3 $Z^{10}$.

In certain embodiments, $R^{10}$ and $R^{11}$ taken together with the nitrogen to which they are attached form a 4-10 membered heterocyclyl optionally substituted with 1 to 3 $Z^{11}$.

In certain embodiments, the moiety

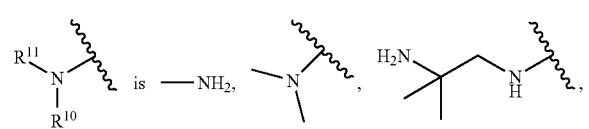

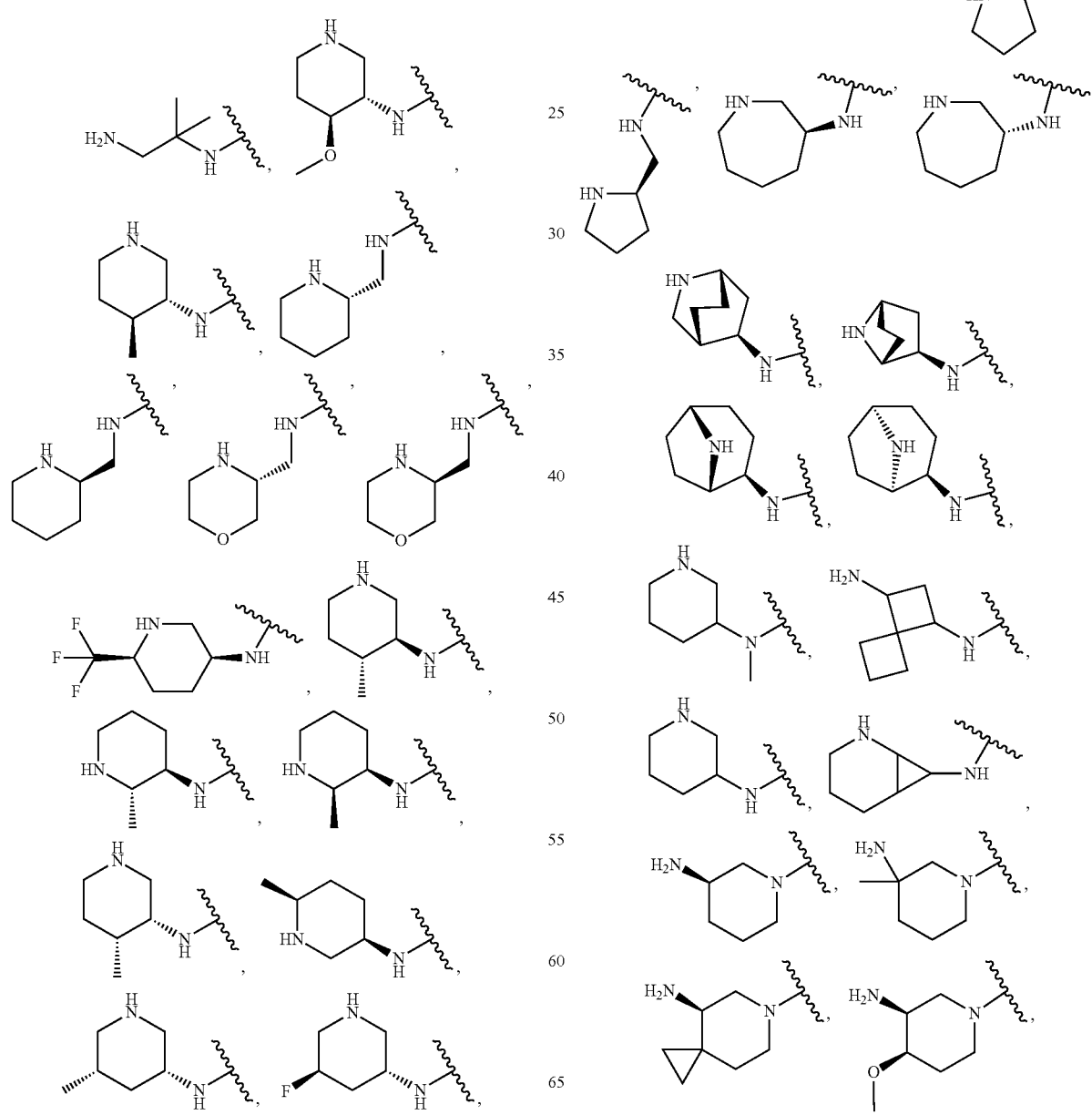

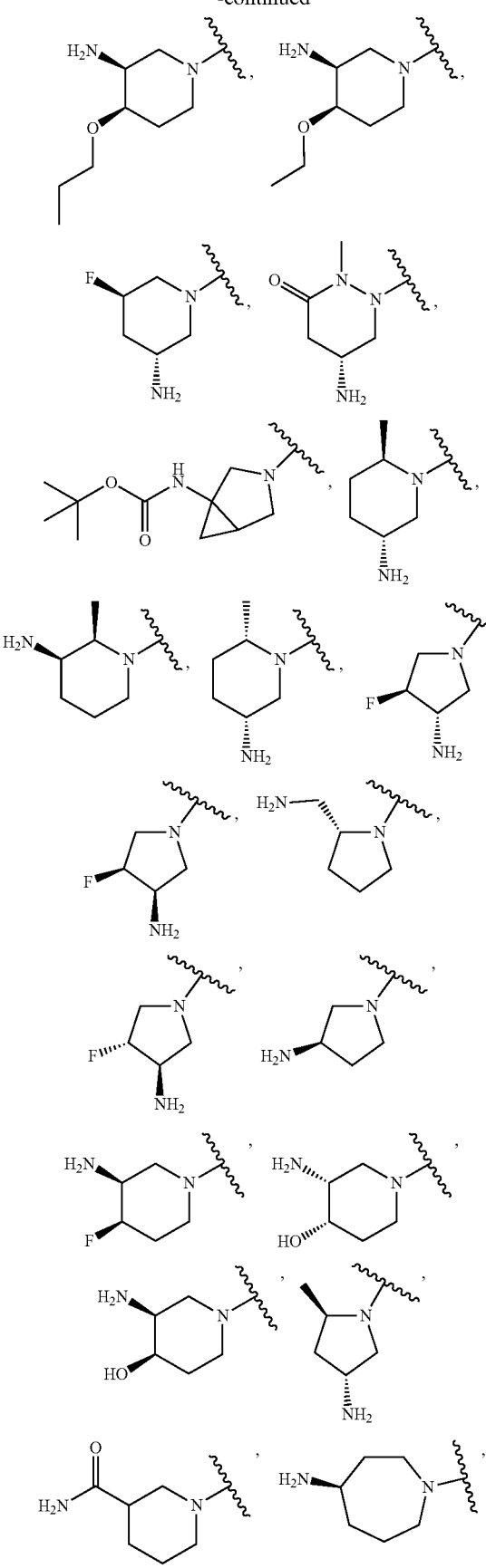
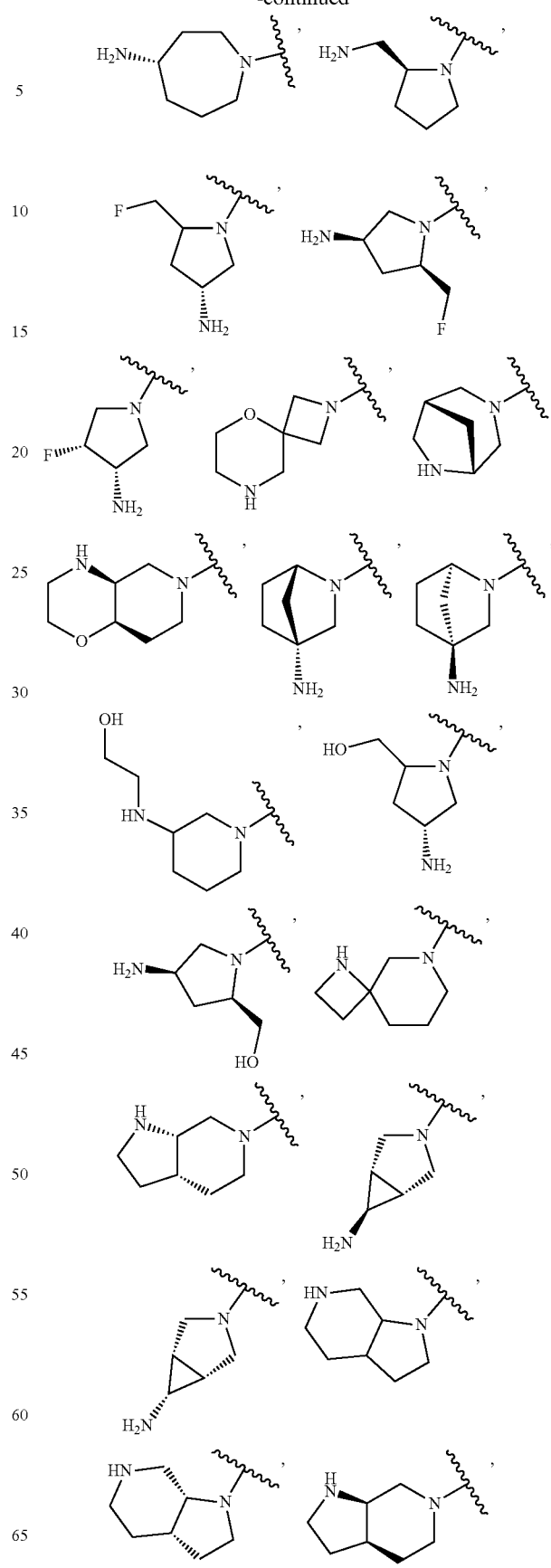

87
-continued
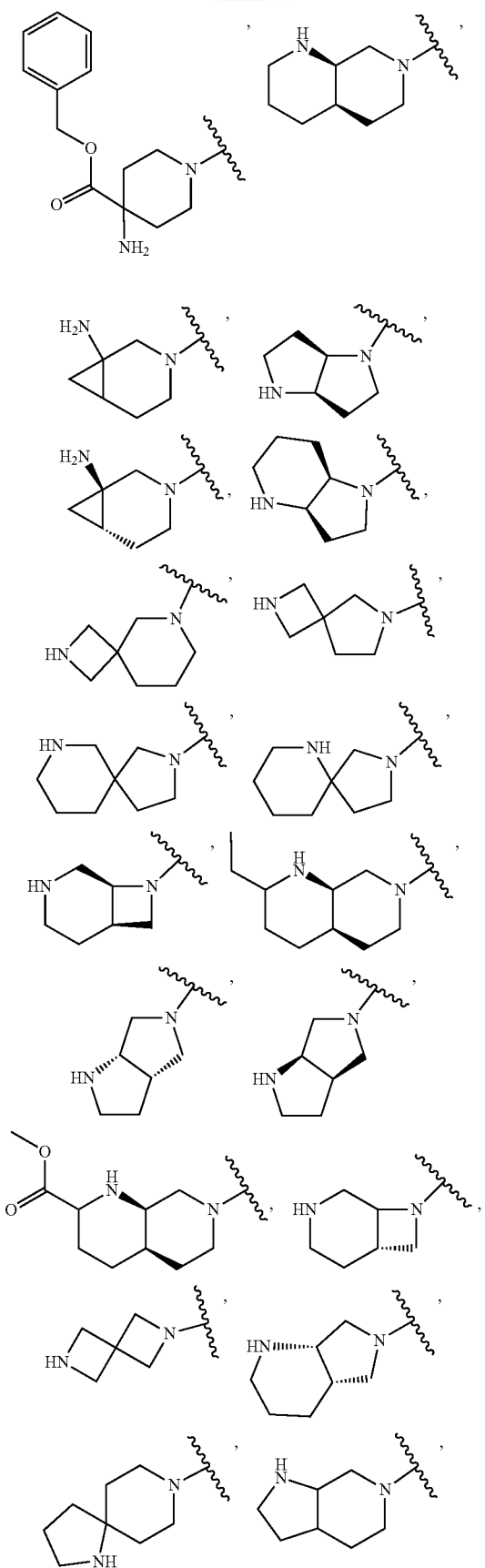
88
-continued
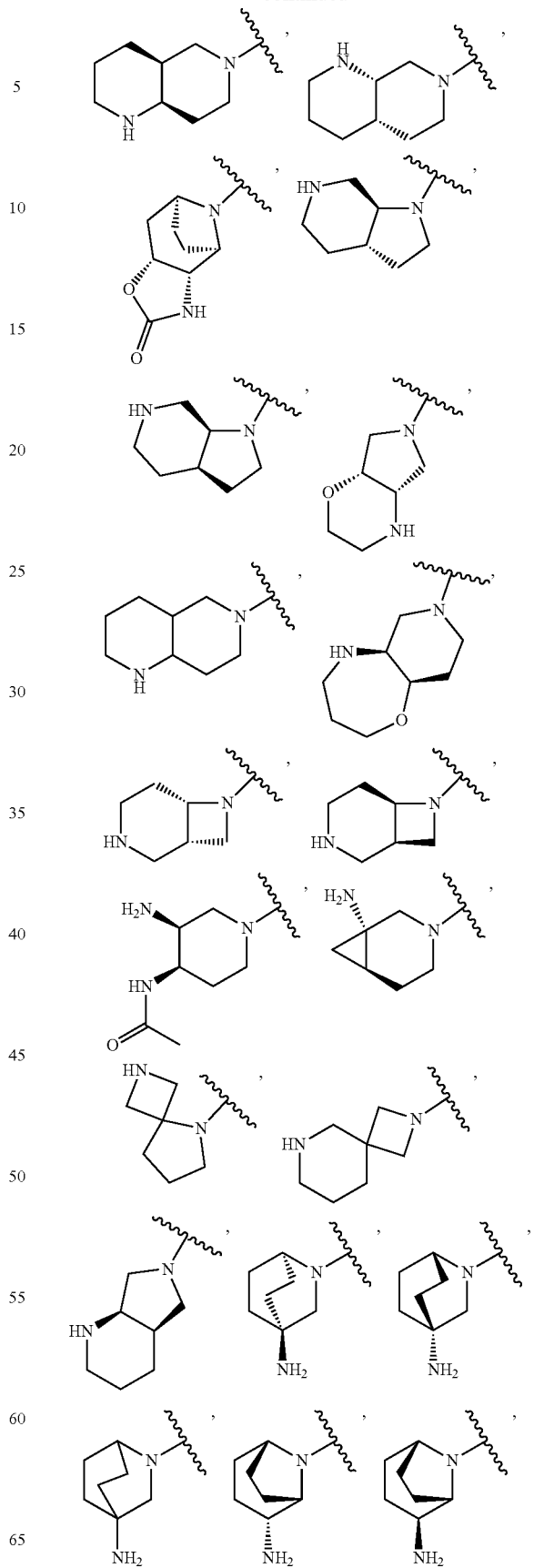

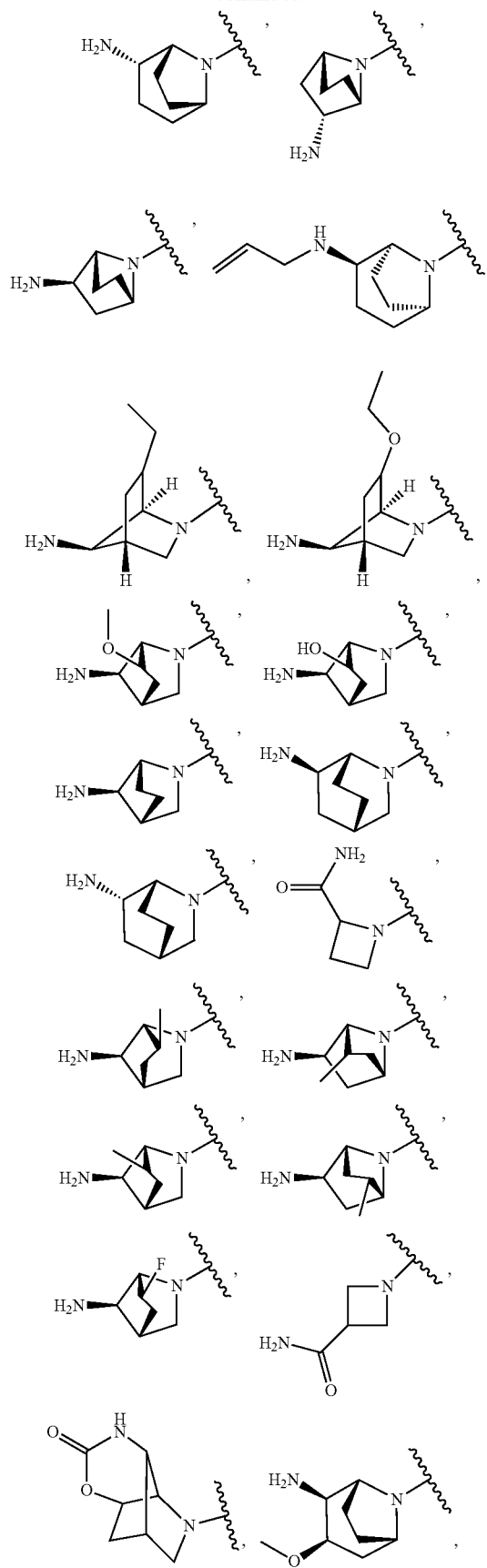
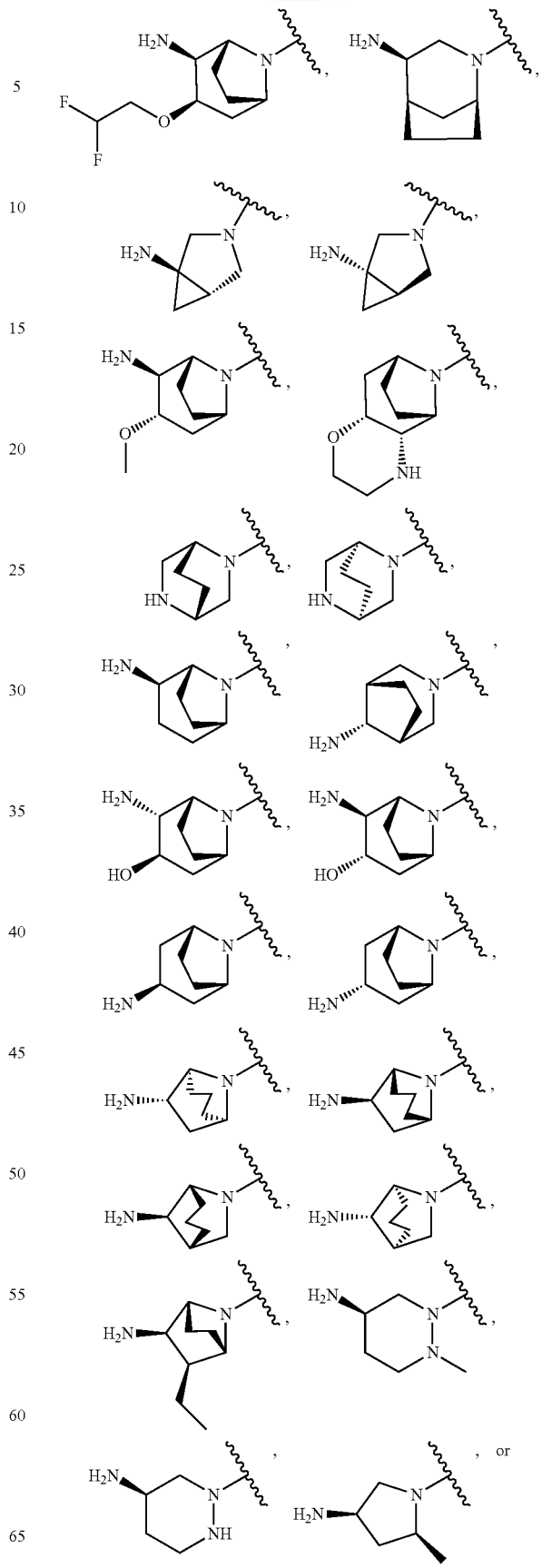

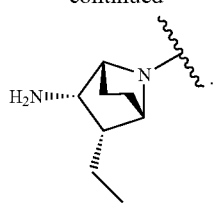
In certain embodiments, the moiety
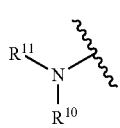
is —NH$_2$,
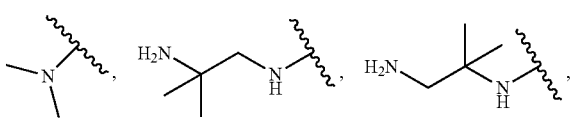
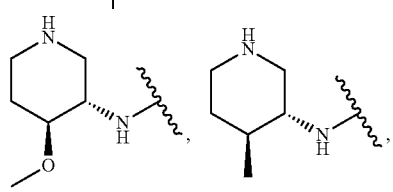
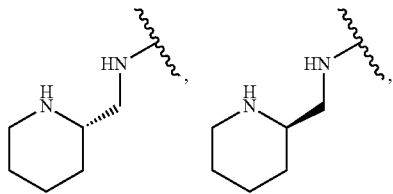
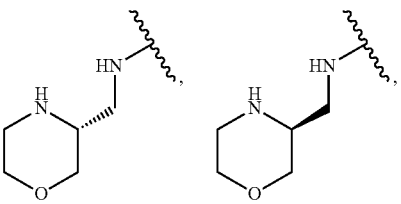
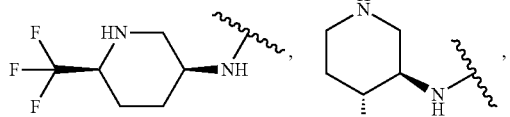
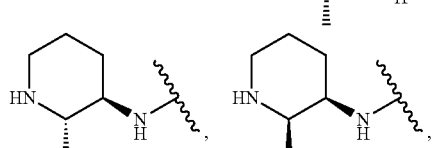
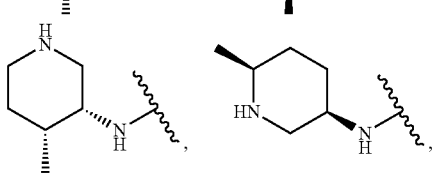
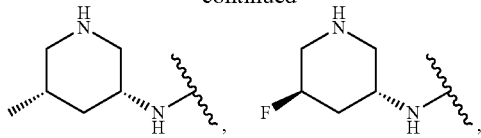
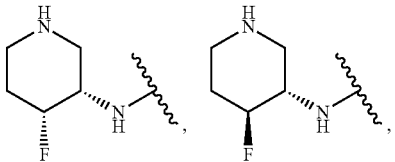
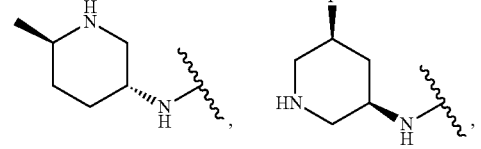
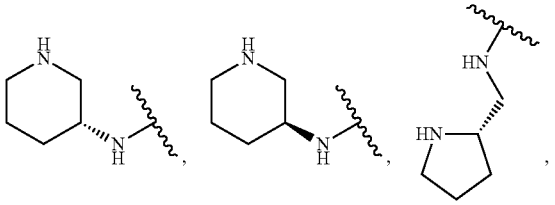
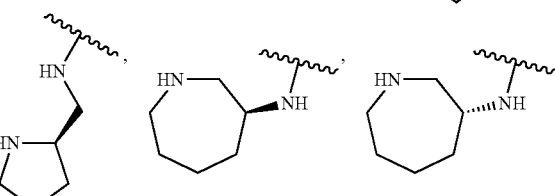
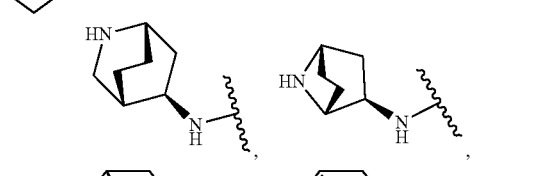
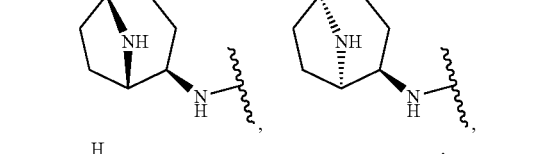
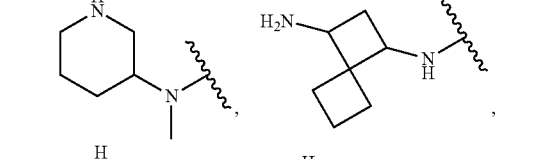
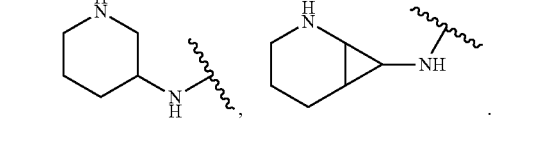
In certain embodiments, the moiety
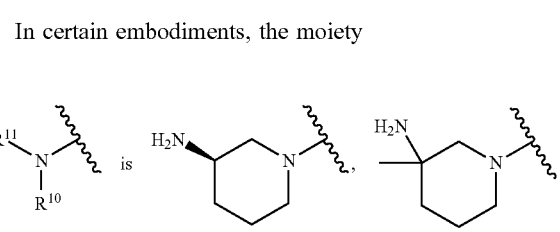
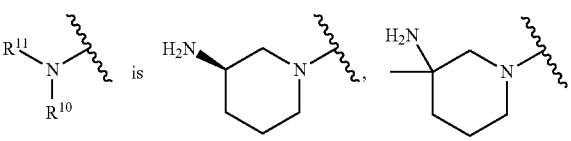

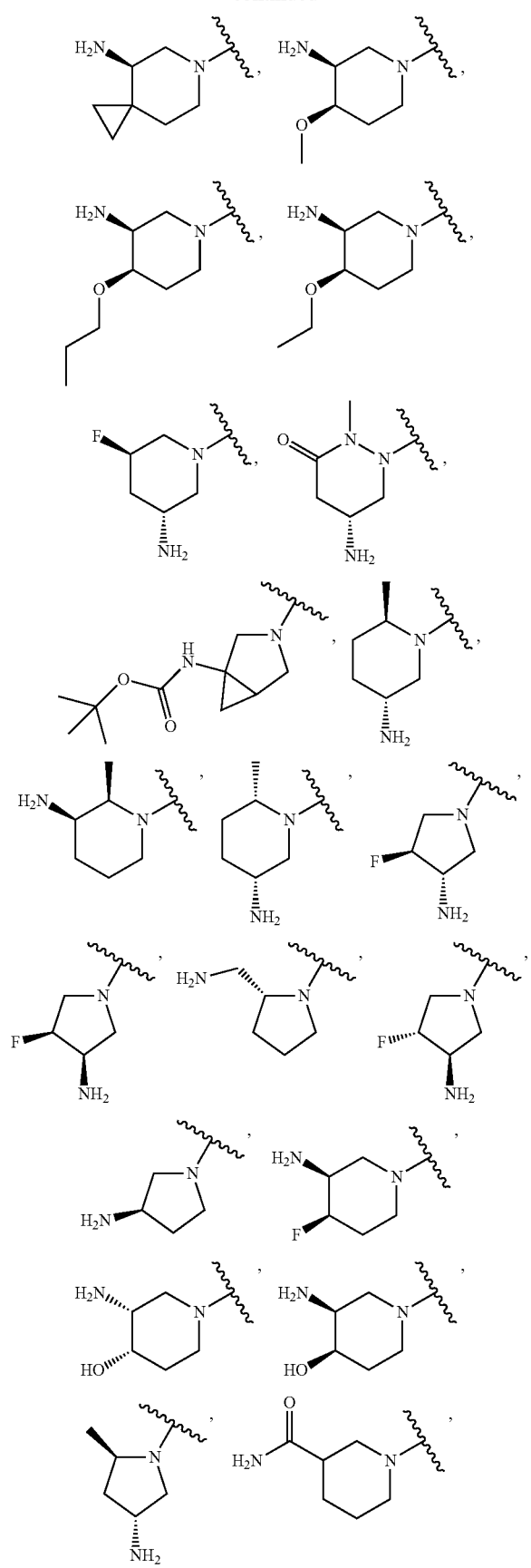
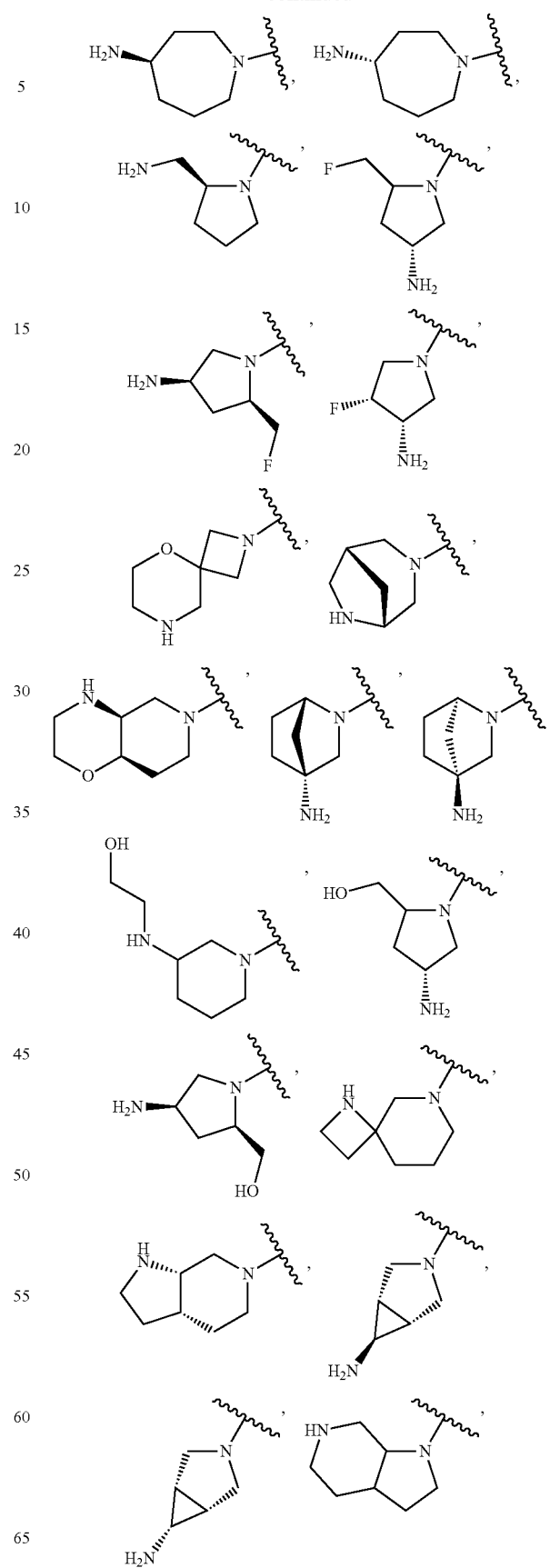

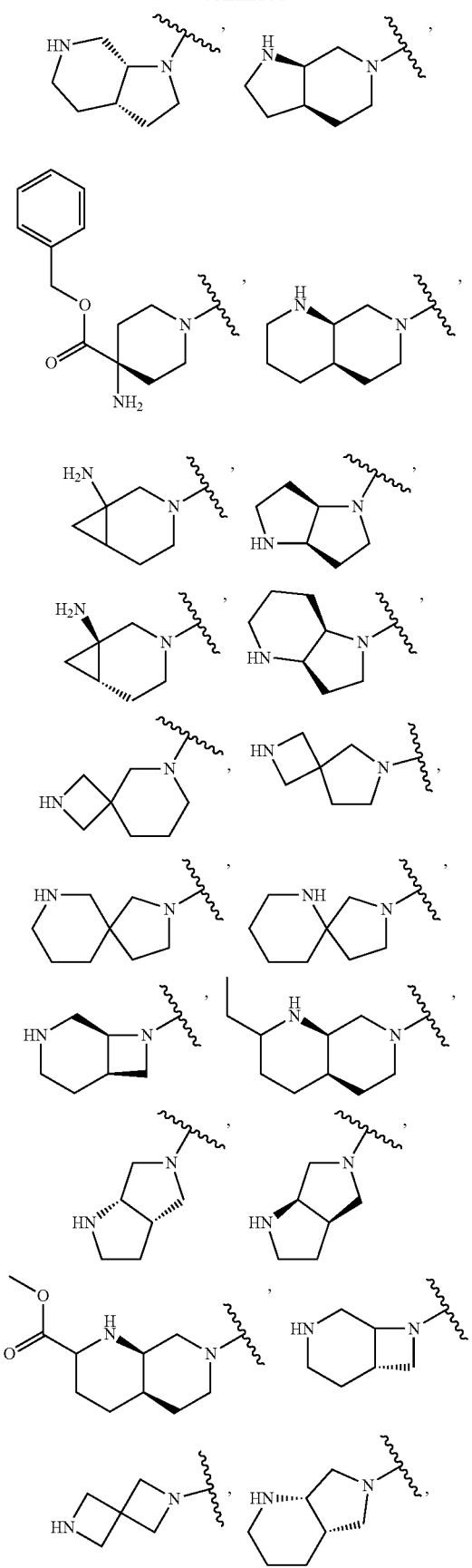
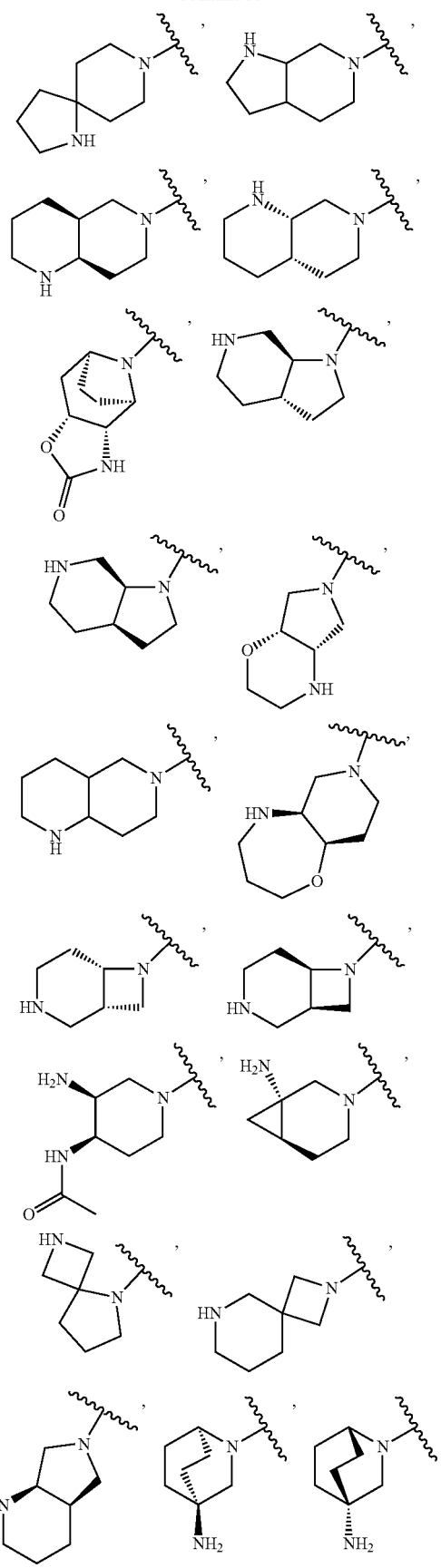

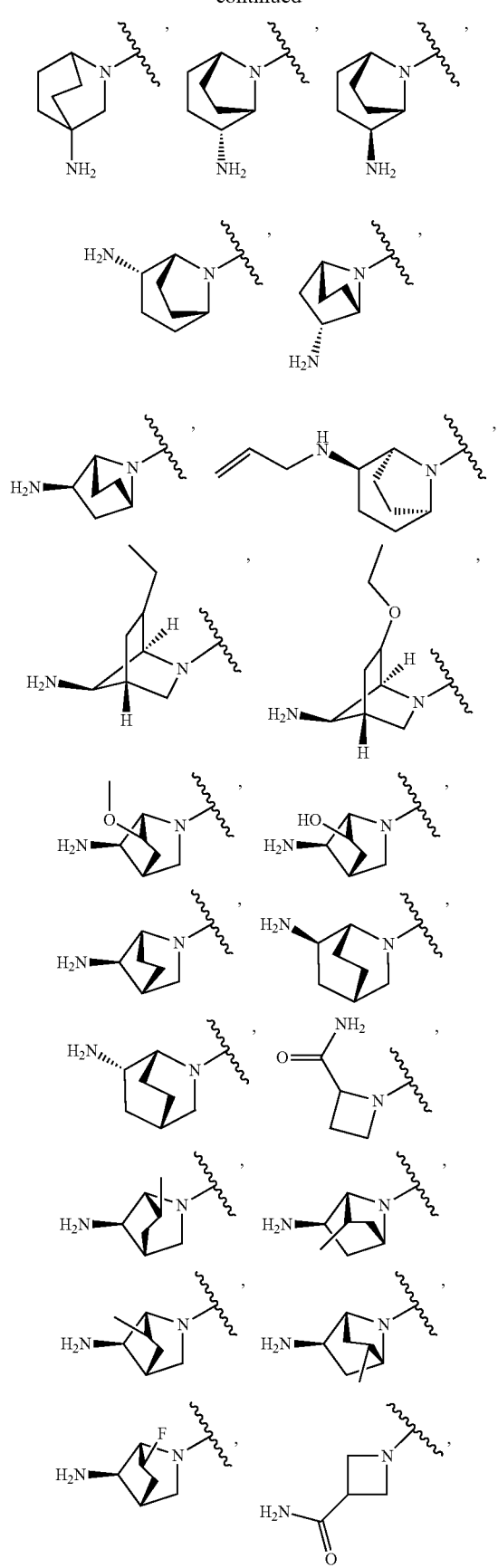
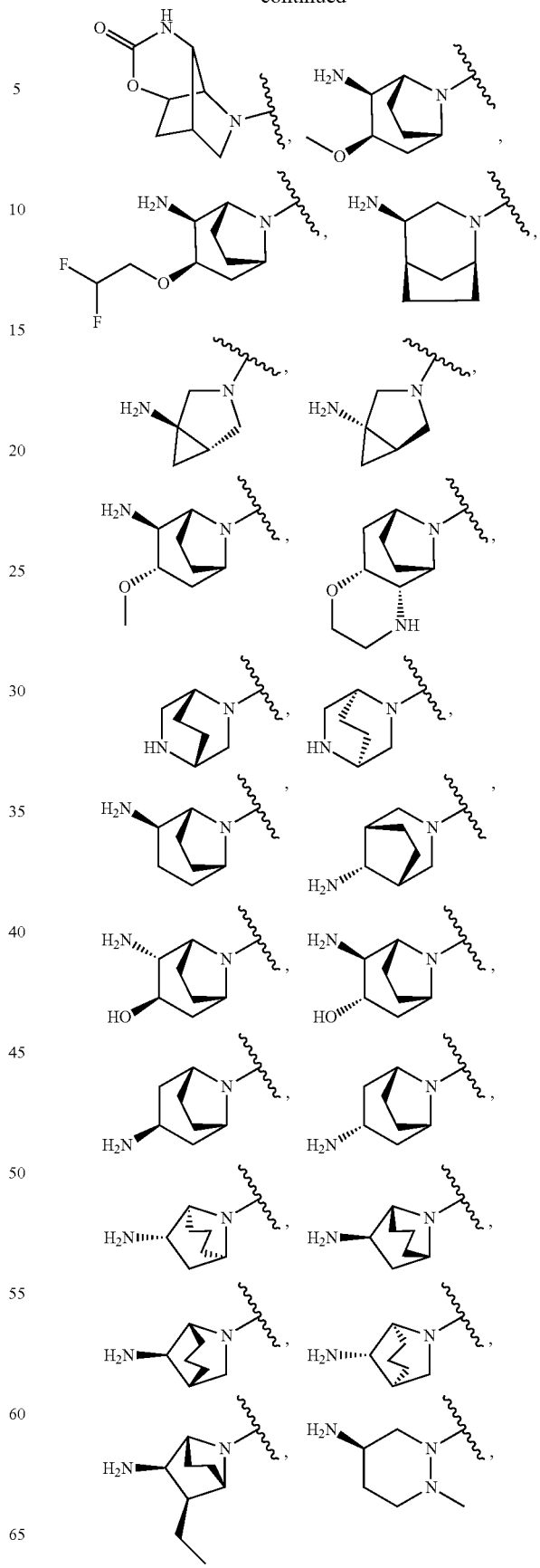

-continued

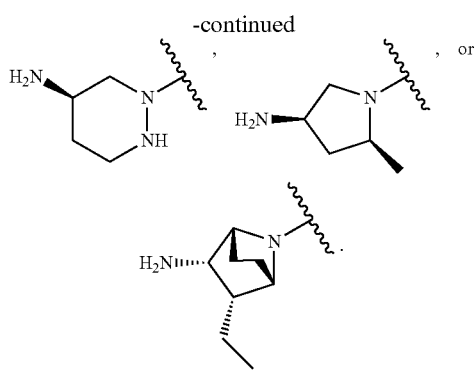

In certain embodiments, provided is compound is represented by Formula IC:

IC

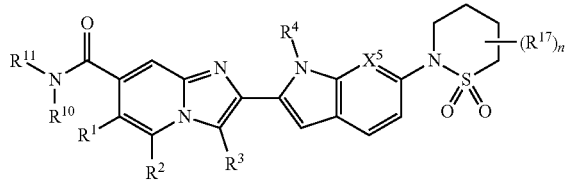

wherein each of n, $R^1$, $R^2$, $R^3$, $R^4$, $X^5$, $R^{10}$, $R^{11}$, and $R^{17}$ are independently as defined herein.

In certain embodiments, provided is compound is represented by Formula ID:

ID

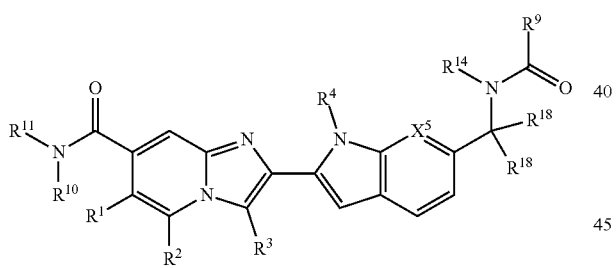

wherein each $R^{18}$ is independently hydrogen or $Z^1$; and each of $R^1$, $R^2$, $R^3$, $R^4$, $X^5$, $R^9$, $R^{10}$, $R^{11}$, and $R^{14}$ are independently as defined herein.

In certain embodiments, provided is compound is represented by Formula IE:

IE

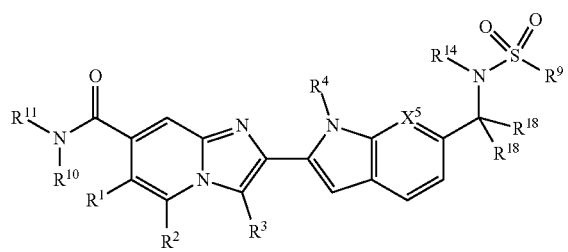

wherein each $R^{18}$ is independently hydrogen or $Z^1$; and each of $R^1$, $R^2$, $R^3$, $R^4$, $X^5$, $R^9$, $R^{10}$, $R^{11}$, and $R^{14}$ are independently as defined herein.

In certain embodiments, provided is compound is represented by Formula IF:

IF

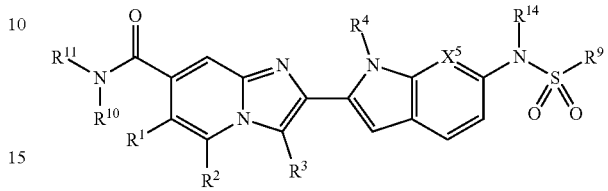

wherein each of $R^1$, $R^2$, $R^3$, $R^4$, $X^5$, $R^9$, $R^{10}$, $R^{11}$, and $R^{14}$ are independently as defined herein.

In certain embodiments, provided is compound is represented by Formula IG:

IG

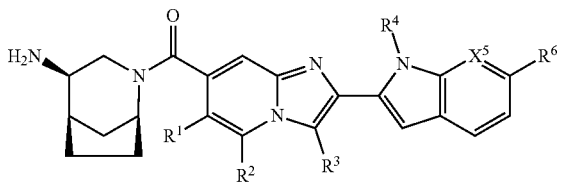

wherein each of $R^1$, $R^2$, $R^3$, $R^4$, $X^5$, and $R^6$ are independently as defined herein.

In certain embodiments, provided is compound is represented by Formula IH:

IH

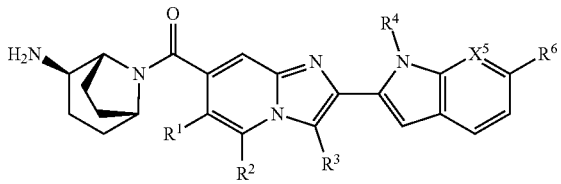

wherein each of $R^1$, $R^2$, $R^3$, $R^4$, $X^5$, and $R^6$ are independently as defined herein.

In certain embodiments, provided is compound is represented by Formula IJ:

IJ

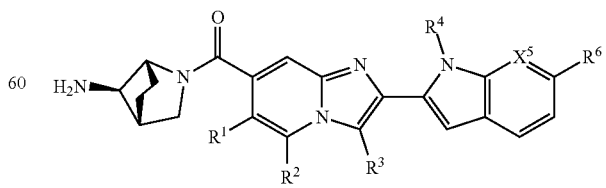

wherein each of $R^1$, $R^2$, $R^3$, $R^4$, $X^5$, and $R^6$ are independently as defined herein.

In certain embodiments, provided is compound is represented by Formula IK:

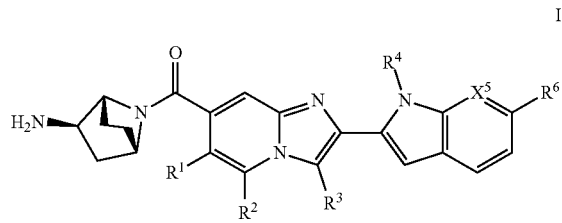

wherein each of $R^1$, $R^2$, $R^3$, $R^4$, $X^5$, and $R^6$ are independently as defined herein.

In certain embodiments, provided is compound is represented by Formula IL:

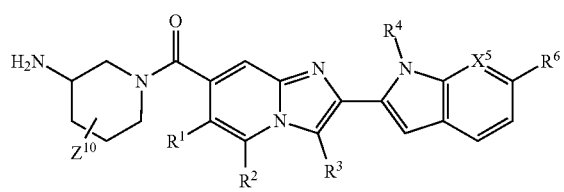

wherein each of $Z^{10}$, $R^1$, $R^2$, $R^3$, $R^4$, $X^5$, and $R^6$ are independently as defined herein.

In certain embodiments, provided is compound is represented by Formula IM:

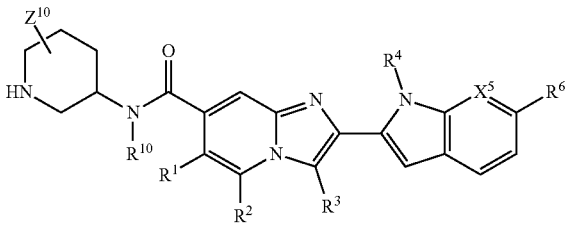

wherein each of $Z^{10}$, $R^{10}$, $R^1$, $R^2$, $R^3$, $R^4$, $X^5$, and $R^6$ are independently as defined herein.

In certain embodiments, provided is compound is represented by Formula IN:

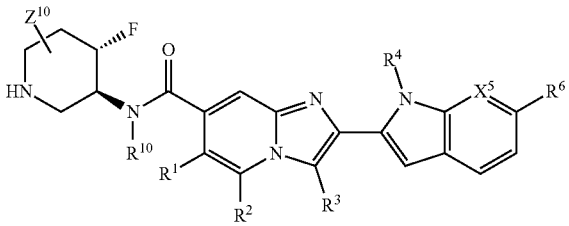

wherein each of $Z^{10}$, $R^{10}$, $R^1$, $R^2$, $R^3$, $R^4$, $X^5$, and $R^6$ are independently as defined herein.

In certain embodiments, provided is compound is represented by Formula IO:

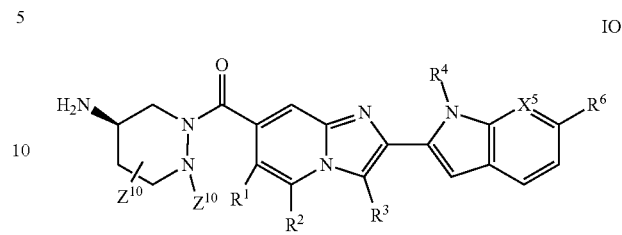

wherein each of $Z^{10}$, $R^{10}$, $R^1$, $R^2$, $R^3$, $R^4$, $X^5$, and $R^6$ are independently as defined herein.

In certain embodiments, $R^4$ is $C_{1-8}$ alkyl optionally substituted with 1 to 3 $Z^1$ or $C_{3-10}$ cycloalkyl optionally substituted with 1 to 3 $Z^1$. In certain embodiments, $R^4$ is $C_{1-8}$ alkyl optionally substituted with 1 to 3 $Z^1$. In certain embodiments, $R^4$ is $C_{3-10}$ cycloalkyl optionally substituted with 1 to 3 $Z^1$. In certain embodiments, $R^4$ is ethyl,

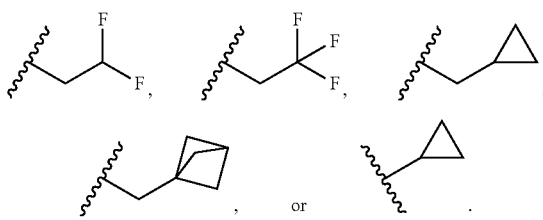

In certain embodiments, $R^4$ is

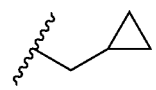

In certain embodiments, the moiety

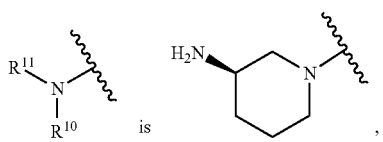

is

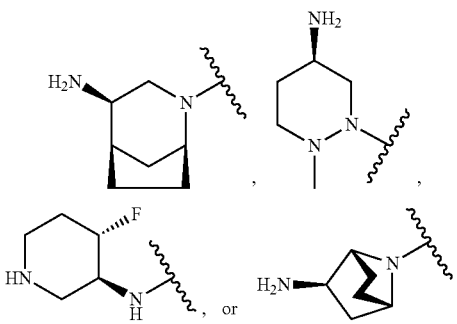

In certain embodiments, the moiety

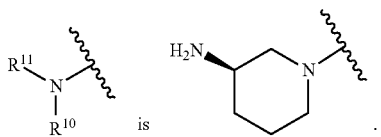 is .

In certain embodiments, the moiety

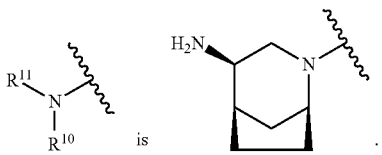 is .

In certain embodiments, the moiety

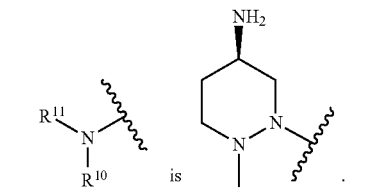 is .

In certain embodiments, the moiety

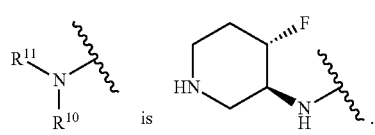 is .

In certain embodiments, the moiety

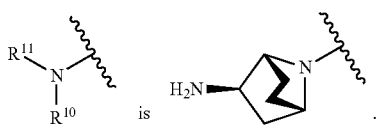 is .

In certain embodiments, provided is compound is represented by Formula IP:

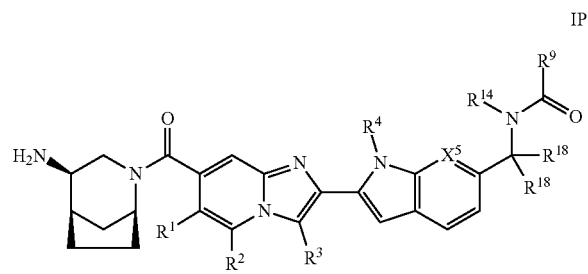

wherein each of $R^1$, $R^2$, $R^3$, $R^4$, $X^5$, $R^9$, $R^{14}$ and $R^{18}$ are independently as defined herein.

In certain embodiments, provided is compound is represented by Formula IQ:

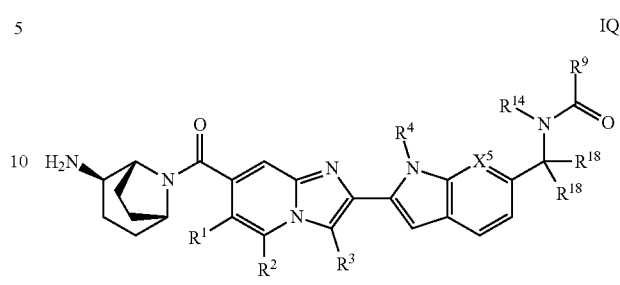

wherein each of $R^1$, $R^2$, $R^3$, $R^4$, $X^5$, $R^9$, $R^{14}$ and $R^{18}$ are independently as defined herein.

In certain embodiments, provided is compound is represented by Formula IR:

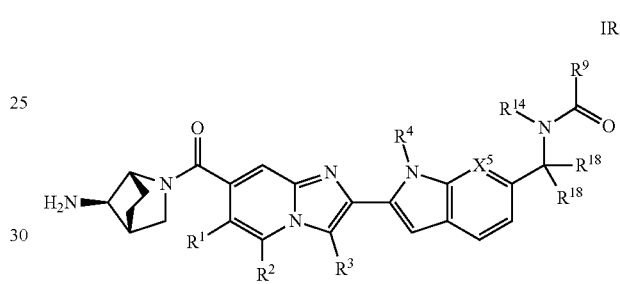

wherein each of $R^1$, $R^2$, $R^3$, $R^4$, $X^5$, $R^9$, $R^{14}$ and $R^{18}$ are each of R are independently as defined herein.

In certain embodiments, provided is compound is represented by Formula IS:

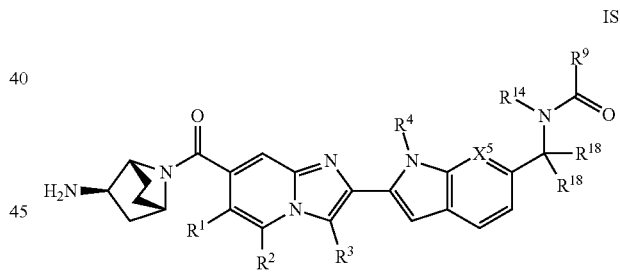

wherein each of $R^1$, $R^2$, $R^3$, $R^4$, $X^5$, $R^9$, $R^{14}$ and $R^{18}$ are independently as defined herein.

In certain embodiments, provided is compound is represented by Formula IT:

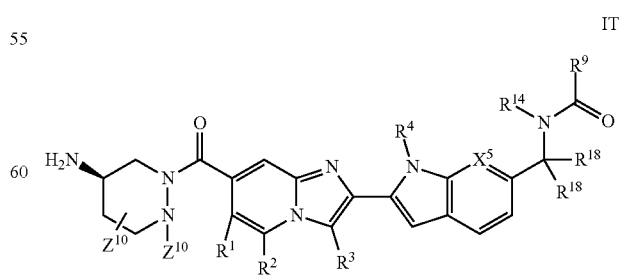

wherein each of $Z^{10}$, $R^1$, $R^2$, $R^3$, $R^4$, $X^5$, $R^9$, $R^{14}$ and $R^{18}$ are independently as defined herein.

In certain embodiments, provided is compound is represented by Formula IU:

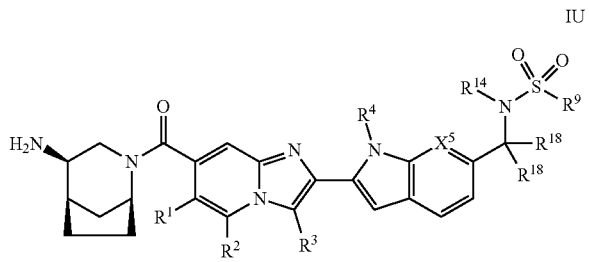

IU wherein each of $R^1$, $R^2$, $R^3$, $R^4$, $X^5$, $R^9$, $R^{14}$ and $R^{18}$ are independently as defined herein.

In certain embodiments, provided is compound is represented by Formula IV:

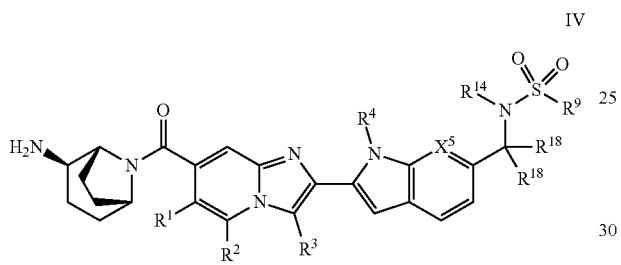

IV wherein each of $R^1$, $R^2$, $R^3$, $R^4$, $X^5$, $R^9$, $R^{14}$ and $R^{18}$ are independently as defined herein.

In certain embodiments, each $R^{18}$ is independently hydrogen, or $Z^1$. In certain embodiments, each $R^{18}$ is independently hydrogen, $C_{1-8}$ alkyl optionally substituted with 1 to 5 $Z^{1a}$, $C_{2-8}$ alkenyl optionally substituted with 1 to 5 $Z^{1a}$, $C_{2-8}$ alkynyl optionally substituted with 1 to 5 $Z^{1a}$, $C_{3-10}$ cycloalkyl optionally substituted with 1 to 5 $Z^{1a}$, 4-10 membered heterocyclyl optionally substituted with 1 to 5 $Z^{1a}$, $C_{6-10}$ aryl optionally substituted with 1 to 5 $Z^{1a}$, or 5-10 membered heteroaryl optionally substituted with 1 to 5 Zia. In certain embodiments, each $R^{18}$ is independently hydrogen or $C_{1-8}$ alkyl optionally substituted with 1 to 5 $Z^1$. In certain embodiments, each $R^{18}$ is independently hydrogen or $C_{1-8}$ alkyl optionally substituted with 1 to 5 halo. In certain embodiments, each $R^{18}$ is independently hydrogen or $C_{1-8}$ alkyl. In certain embodiments, each $R^{18}$ is independently hydrogen or methyl. In certain embodiments, one $R^{18}$ is hydrogen and the other is methyl. In certain embodiments, each $R^{18}$ is methyl. In certain embodiments, each $R^{18}$ is hydrogen.

In certain embodiments, provided is compound is represented by Formula IW:

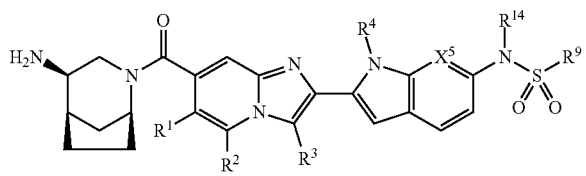

IW wherein each of $R^1$, $R^2$, $R^3$, $R^4$, $X^5$, $R^9$, and $R^{14}$ are independently as defined herein.

In certain embodiments, provided is compound is represented by Formula IX:

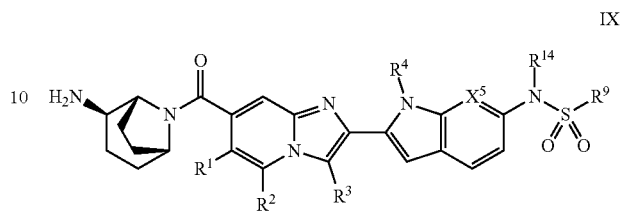

IX wherein each of $R^1$, $R^2$, $R^3$, $R^4$, $X^5$, $R^9$, and $R^{14}$ are independently as defined herein.

In certain embodiments, provided is compound is represented by Formula IY:

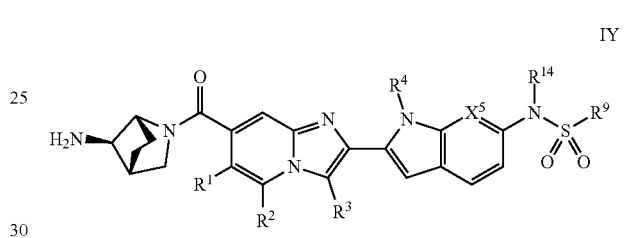

IY wherein each of $R^1$, $R^2$, $R^3$, $R^4$, $X^5$, $R^9$, and $R^{14}$ are independently as defined herein.

In certain embodiments, provided is compound is represented by Formula IZ:

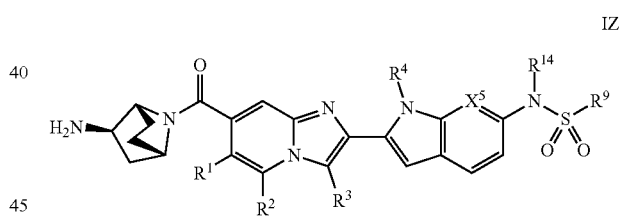

IZ wherein each of $R^1$, $R^2$, $R^3$, $R^4$, $X^5$, $R^9$, and $R^{14}$ are independently as defined herein.

In certain embodiments, provided is compound is represented by Formula IAA:

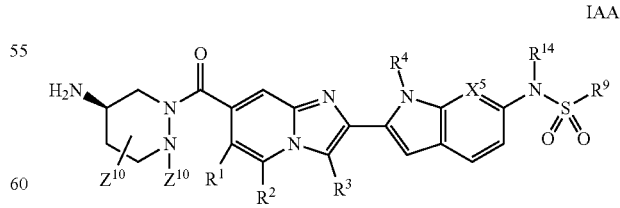

IAA wherein each of $R^1$, $R^2$, $R^3$, $R^4$, $X^5$, $R^9$, and $R^{14}$ are independently as defined herein.

In certain embodiments, $R^{14}$ is hydrogen or $C_{1-8}$ alkyl optionally substituted with 1 to 5 $Z^1$. In certain embodiments, $R^{14}$ is hydrogen.

In certain embodiments, $R^{20}$ is hydrogen or $C_{1-8}$ alkyl optionally substituted by 1 to 3 $Z^{1a}$. In certain embodiments, $R^{20}$ is hydrogen or $C_{1-8}$ alkyl. In certain embodiments, $R^{20}$ is hydrogen or methyl. In certain embodiments, $R^{20}$ is methyl. In certain embodiments, $R^{20}$ is hydrogen.

In certain embodiments, each $Z^1$ is independently halo, —$NO_2$, —$N_3$, —CN, $C_{1-8}$ alkyl optionally substituted by 1 to 5 $Z^{1b}$, $C_{2-8}$ alkenyl optionally substituted by 1 to 5 $Z^{1b}$, $C_{2-8}$ alkynyl optionally substituted by 1 to 5 $Z^{1b}$, $C_{3-10}$ cycloalkyl optionally substituted by 1 to 5 $Z^{1b}$, 6-10 membered aryl optionally substituted by 1 to 5 $Z^{1b}$, 4-10 membered heterocyclyl optionally substituted by 1 to 5 $Z^{1b}$, 5-10 membered heteroaryl optionally substituted with 1 to 5 $Z^{1b}$, —$OR^{21}$, —$C(O)R^{21}$, —$C(O)OR^{21}$, —$C(O)N(R^{21})_2$, —$N(R^{21})_2$, —$N(R^{21})_3^+$, —$N(R^{21})C(O)R^{21}$, —$N(R^{21})C(O)OR^{21}$,
—$N(R^{21})C(O)N(R^{21})_2$, —$N(R^{21})S(O)_2(R^{21})$, —$NR^{21}S(O)_2N(R^{21})_2$, —$NR^{21}S(O)_2O(R^{21})$, —$NS(O)(R^{21})_2$, —$OC(O)R^{21}$,
—$OC(O)R^{21}$, —$OC(O)OR^{21}$, —$OC(O)N(R^{21})_2$, —$Si(R^{21})_3$, —$SR^{21}$, —$S(O)R^{21}$, —$SF_5$, —$S(O)(NR^{21})R^{21}$, —$S(NR^{21})(NR^{21})R^{21}$,
—$S(O)(NR^{21})N(R^{21})_2$, —$S(O)(NCN)R^{21}$, —$S(O)_2R^{21}$, —$S(O)_2N(R^{21})_2$, —$C(O)N(R^{21})S(O)_2R^{21}$, or —$S(O)_2N(R^{21})C(O)R^{21}$;

each $R^{20}$, $R^{21}$ and $R^{22}$ is independently hydrogen, $C_{1-8}$ alkyl optionally substituted with 1 to 5 $Z^{1b}$, $C_{2-8}$ alkenyl optionally substituted with 1 to 5 $Z^{1b}$, $C_{2-8}$ alkynyl optionally substituted with 1 to 5 $Z^{1b}$, $C_{3-10}$ cycloalkyl optionally substituted with 1 to 5 $Z^{1b}$, 4-10 membered heterocyclyl optionally substituted with 1 to 5 $Z^{1b}$, $C_{6-10}$ aryl optionally substituted with 1 to 5 $Z^{1b}$, or 5-10 membered heteroaryl optionally substituted with 1 to 5 $Z^{1b}$; and each $Z^1b$ is independently oxo, hydroxy, halo, —$NO_2$, —$N_3$, —CN, $C_{1-9}$ alkyl, $C_{2-6}$ alkenyl, $C_{2-6}$ alkynyl, $C_{3-10}$ cycloalkyl, $C_{1-8}$ haloalkyl, $C_{6-10}$ aryl, 5-10 membered heteroaryl, 4-10 membered heterocyclyl,
—O($C_{1-9}$ alkyl), —O($C_{2-6}$ alkenyl), —O($C_{2-6}$ alkynyl), —O($C_{3-10}$ cycloalkyl), —O($C_{1-8}$ haloalkyl), —O(aryl), —O(heteroaryl), —O(heterocyclyl), —OC(O) ($C_{1-9}$ alkyl), —OC(O)($C_{2-6}$ alkenyl), —OC(O)($C_{2-6}$ alkenyl),
—OC(O)($C_{2-6}$ alkynyl), —OC(O)($C_{3-10}$ cycloalkyl), —OC(O)($C_{1-8}$ haloalkyl), —OC(O)(aryl), —OC(O)(heteroaryl), —OC(O)(heterocyclyl), —$NH_2$, —NH($C_{1-9}$ alkyl), —NH ($C_{2-6}$ alkenyl), —NH($C_{2-6}$ alkynyl), —NH($C_{3-10}$ cycloalkyl),
—NH($C_{1-8}$ haloalkyl), —NH(aryl), —NH(heteroaryl), —NH(heterocyclyl), —N($C_{1-9}$ alkyl)$_2$, —N($C_{3-10}$ cycloalkyl)$_2$,
—N($C_{2-6}$ alkenyl)$_2$, —N($C_{2-6}$ alkynyl)$_2$, —N($C_{3-10}$ cycloalkyl)$_2$, —N($C_{1-8}$ haloalkyl)$_2$, —N(aryl)$_2$, —N(heteroaryl)$_2$, —N(heterocyclyl)$_2$, —N($C_{1-9}$ alkyl)($C_{3-10}$ cycloalkyl), —N($C_{1-9}$ alkyl)($C_{2-6}$ alkenyl), —N($C_{1-9}$ alkyl)($C_{2-6}$ alkynyl),
—N($C_{1-9}$ alkyl)($C_{3-10}$ cycloalkyl), —N($C_{1-9}$ alkyl)($C_{1-8}$ haloalkyl), —N($C_{1-9}$ alkyl)(aryl), —N($C_{1-9}$ alkyl)(heteroaryl),
—N($C_{1-9}$ alkyl)(heterocyclyl), —C(O)($C_{1-9}$ alkyl), —C(O) ($C_{2-6}$ alkenyl), —C(O)($C_{2-6}$ alkynyl),
—C(O)($C_{3-10}$ cycloalkyl), —C(O)($C_{1-8}$ haloalkyl), —C(O) (aryl), —C(O)(heteroaryl), —C(O)(heterocyclyl),
—C(O)O($C_{1-9}$ alkyl), —C(O)O($C_{2-6}$ alkenyl), —C(O)O ($C_{2-6}$ alkynyl), —C(O)O($C_{3-10}$ cycloalkyl),
—C(O)O($C_{1-8}$ haloalkyl), —C(O)O(aryl), —C(O)O(heteroaryl), —C(O)O(heterocyclyl), —C(O)$NH_2$,
—C(O)NH($C_{1-9}$ alkyl), —C(O)NH($C_{2-6}$ alkenyl), —C(O) NH($C_{2-6}$ alkynyl), —C(O)NH($C_{3-10}$ cycloalkyl),
—C(O)NH($C_{1-8}$ haloalkyl), —C(O)NH(aryl), —C(O)NH (heteroaryl), —C(O)NH(heterocyclyl),
—C(O)N($C_{1-9}$ alkyl)$_2$, —C(O)N($C_{3-10}$ cycloalkyl)$_2$, —C(O) N($C_{2-6}$ alkenyl)$_2$, —C(O)N($C_{2-6}$ alkynyl)$_2$,
—C(O)N($C_{1-8}$ haloalkyl)$_2$, —C(O)N(aryl)$_2$, —C(O)N(heteroaryl)$_2$, —C(O)N(heterocyclyl)$_2$, —NHC(O)($C_{1-9}$ alkyl),
—NHC(O)($C_{2-6}$ alkenyl), —NHC(O)($C_{2-6}$ alkynyl), —NHC(O)($C_{3-10}$ cycloalkyl), —NHC(O)($C_{1-8}$ haloalkyl),
—NHC(O)(aryl), —NHC(O)(heteroaryl), —NHC(O)(heterocyclyl), —NHC(O)O($C_{1-9}$ alkyl),
—NHC(O)O($C_{2-6}$ alkenyl), —NHC(O)O($C_{2-6}$ alkynyl), —NHC(O)O($C_{3-10}$ cycloalkyl), —NHC(O)O($C_{1-8}$ haloalkyl),
—NHC(O)O(aryl), —NHC(O)O(heteroaryl), —NHC(O)O (heterocyclyl), —NHC(O)NH($C_{1-9}$ alkyl),
—NHC(O)NH($C_{2-6}$ alkenyl), —NHC(O)NH($C_{2-6}$ alkynyl), —NHC(O)NH($C_{3-10}$ cycloalkyl),
—NHC(O)NH($C_{1-8}$ haloalkyl), —NHC(O)NH(aryl), —NHC(O)NH(heteroaryl), —NHC(O)NH(heterocyclyl),
—SH,
—S($C_{1-9}$ alkyl), —S($C_{2-6}$ alkenyl), —S($C_{2-6}$ alkynyl), —S($C_{3-10}$ cycloalkyl), —S($C_{1-8}$ haloalkyl), —S(aryl),
—S(heteroaryl), —S(heterocyclyl), —NHS(O)($C_{1-9}$ alkyl), —N($C_{1-9}$ alkyl)(S(O)($C_{1-9}$ alkyl), —S(O)N($C_{1-9}$ alkyl)$_2$,
—S(O)($C_{1-9}$ alkyl), —S(O)(NH)($C_{1-9}$ alkyl), —S(O)($C_{2-6}$ alkenyl), —S(O)($C_{2-6}$ alkynyl), —S(O)($C_{3-10}$ cycloalkyl),
—S(O)($C_{1-8}$haloalkyl), —S(O)(aryl), —S(O)(heteroaryl), —S(O)(heterocyclyl), —S(O)$_2$($C_{1-9}$ alkyl),
—S(O)$_2$($C_{2-6}$ alkenyl), —S(O)$_2$($C_{2-6}$ alkynyl), —S(O)$_2$($C_{3-10}$ cycloalkyl), —S(O)$_2$($C_{1-8}$ haloalkyl), —S(O)$_2$(aryl),
—S(O)$_2$(heteroaryl), —S(O)$_2$(heterocyclyl), —S(O)$_2$NH ($C_{1-9}$ alkyl), or —S(O)$_2$N($C_{1-9}$ alkyl)$_2$;

wherein any alkyl, cycloalkyl, aryl, heteroaryl, or heterocyclyl of $Z^{1b}$ is optionally substituted with one or more halo, $C_{1-9}$ alkyl, $C_{1-8}$ haloalkyl, —OH, —$NH_2$, —NH ($C_{1-9}$ alkyl), —NH($C_{3-10}$ cycloalkyl), —NH($C_{1-8}$haloalkyl),
—NH(aryl), —NH(heteroaryl), —NH(heterocyclyl), —N($C_{1-9}$ alkyl)$_2$, —N($C_{3-10}$ cycloalkyl)$_2$,
—NHC(O)($C_{3-10}$ cycloalkyl), —NHC(O)($C_{1-8}$ haloalkyl), —NHC(O)(aryl), —NHC(O)(heteroaryl),
—NHC(O)(heterocyclyl), —NHC(O)O($C_{1-9}$ alkyl), —NHC(O)O($C_{2-6}$ alkynyl), —NHC(O)O($C_{3-10}$ cycloalkyl),
—NHC(O)O($C_{1-8}$ haloalkyl), —NHC(O)O(aryl), —NHC(O)O(heteroaryl), —NHC(O)O(heterocyclyl),
—NHC(O)NH($C_{1-9}$ alkyl), —S(O)(NH)($C_{1-9}$ alkyl), —S(O)$_2$ ($C_{1-9}$ alkyl), —S(O)$_2$($C_{3-10}$ cycloalkyl),
—S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl),
—S(O)$_2$N($C_{1-9}$ alkyl)$_2$, —O($C_{3-10}$ cycloalkyl), —O($C_{1-8}$ haloalkyl), —O(aryl), —O(heteroaryl), —O(heterocyclyl), or
—O($C_{1-9}$ alkyl).

In certain embodiments, each $Z^1$ is independently oxo, hydroxy, fluoro, chloro, —CN, —$CH_3$, ethyl, isopropyl, tert-butyl, —$CF_3$, —$CHF_2$, cyclopropyl, cyclobutyl, —$OCH_3$, —O-ethyl, —O-isopropyl, —O-cyclopropyl, —$OCF_3$, —$OCF_2H$, —C(O)-alkyl, —C(O)-cycloalkyl, —C(O)-aryl, —C(O)-heteroaryl, or —$NH_2$.

In certain embodiments, each $Z^1$ is independently halo, oxo, —CN, $C_{1-6}$ alkyl optionally substituted by 1 to 3 $Z^{1a}$, $C_{3-6}$ cycloalkyl optionally substituted with 1 to 3 $Z^{1b}$, 4-6 membered heterocyclyl having 1 to 2 heteroatoms selected from O and N that is optionally substituted by 1 to 3 $Z^{1a}$, 5-6 membered heteroaryl having 1 to 4 heteroatoms selected from O and N and optionally substituted with 1 to 3 $Z^{1a}$, —$OR^{12}$, —$N(R^{12})_2$, —$C(O)R^{12}$, $N(R^{12})C(O)R^{12}$, —$N(R^{12})C(O)OR^{12}$, —$N(R^{12})S(O)_2R^{12}$, —$OC(O)R^{12}$, —$OC(O)OR^{12}$, —$OC(O)N(R^{12})_2$, or —$S(O)_2R^{12}$.

In certain embodiments, each $Z^1$ is independently fluoro, chloro, —CN, $C_{1-6}$ alkyl optionally substituted with 1 to 3 $Z^{1b}$, $C_{3-6}$ cycloalkyl optionally substituted by 1 to 3 $Z^{1b}$, —$OR^{12}$, —$N(R^{12})_2$, —$C(O)R^{12}$, $N(R^{12})C(O)R^{12}$, —$N(R^{12})C(O)OR^{12}$, —$N(R^{12})S(O)_2R^{12}$, —$OC(O)R^{12}$, —$OC(O)OR^{12}$, —$OC(O)N(R^{12})_2$, or —$S(O)_2R^{12}$.

In certain embodiments, each $Z^1$ is independently oxo, hydroxy, fluoro, chloro, —CN, —CH$_3$, ethyl, isopropyl, tert-butyl, —CF$_3$, —CHF$_2$, cyclopropyl, cyclobutyl, —OCH$_3$, —O-ethyl, —O-isopropyl, —O-cyclopropyl, —OCF$_3$, —OCF$_2$H, —C(O)-alkyl, —C(O)-cycloalkyl, —C(O)-aryl, —C(O)-heteroaryl, or —NH$_2$.

In certain embodiments, each $Z^1$ is independently fluoro, chloro, —CN, —OH, —OCH$_3$, —OCHF$_2$, —OCF$_3$, —CH$_3$, —CHF$_2$, —CF$_3$, —CH$_2$OH, —CH$_2$OCH$_3$, or —NH$_2$.

In certain embodiments, each $Z^1$ is independently halo, oxo, —CN, C$_{1-6}$ alkyl optionally substituted by 1 to 3 $Z^{1a}$, C$_{3-6}$ cycloalkyl optionally substituted with 1 to 3 $Z^{1b}$, 4-6 membered heterocyclyl having 1 to 2 heteroatoms selected from O and N that is optionally substituted by 1 to 3 $Z^{1a}$, 5-6 membered heteroaryl having 1 to 4 heteroatoms selected from O and N and optionally substituted with 1 to 3 $Z^{1a}$, —OR$^{12}$, —N(R$^{12}$)$_2$, —C(O)R$^{12}$, N(R$^{12}$)C(O)R$^{12}$, —N(R$^{12}$)C(O)OR$^{12}$, —N(R$^{12}$)S(O)$_2$R$^{12}$, —OC(O)R$^{12}$, —OC(O)OR$^{12}$, —OC(O)N(R$^{12}$)$_2$, or —S(O)$_2$R$^{12}$.

In certain embodiments, each $Z^1$ is independently oxo, hydroxy, fluoro, chloro, —CN, —CH$_3$, ethyl, isopropyl, tert-butyl, —CF$_3$, —CHF$_2$, cyclopropyl, cyclobutyl, —OCH$_3$, —O-ethyl, —O-isopropyl, —O-cyclopropyl, —OCF$_3$, —OCF$_2$H, —C(O)-alkyl, —C(O)-cycloalkyl, —C(O)-aryl, —C(O)-heteroaryl, or —NH$_2$.

In certain embodiments, each $Z^1$ is independently halo, oxo, —CN, C$_{1-6}$ alkyl optionally substituted by 1 to 3 $Z^{1a}$, C$_{3-6}$ cycloalkyl optionally substituted with 1 to 3 $Z^{1b}$, 4-6 membered heterocyclyl having 1 to 2 heteroatoms selected from O and N that is optionally substituted by 1 to 3 $Z^{1a}$, 5-6 membered heteroaryl having 1 to 4 heteroatoms selected from O and N and optionally substituted with 1 to 3 $Z^{1a}$, —OR$^{12}$, —N(R$^{12}$)$_2$, —C(O)R$^{12}$, N(R$^{12}$)C(O)R$^{12}$, —N(R$^{12}$)C(O)OR$^{12}$, —N(R$^{12}$)S(O)$_2$R$^{12}$, —OC(O)R$^{12}$, —OC(O)OR$^{12}$, —OC(O)N(R$^{12}$)$_2$, or —S(O)$_2$R$^{12}$.

In certain embodiments, each $Z^1$ is independently oxo, hydroxy, fluoro, chloro, —CN, —CH$_3$, ethyl, isopropyl, tert-butyl, —CF$_3$, —CHF$_2$, cyclopropyl, cyclobutyl, —OCH$_3$, —O-ethyl, —O-isopropyl, —O-cyclopropyl, —OCF$_3$, —OCF$_2$H, —C(O)-alkyl, —C(O)-cycloalkyl, —C(O)-aryl, —C(O)-heteroaryl, or —NH$_2$.

In certain embodiments, each $Z^1$ is independently halo, oxo, —CN, C$_{1-6}$ alkyl optionally substituted by 1 to 3 $Z^{1a}$, C$_{3-6}$ cycloalkyl optionally substituted with 1 to 3 $Z^{1b}$, 4-6 membered heterocyclyl having 1 to 2 heteroatoms selected from O and N that is optionally substituted by 1 to 3 $Z^{1a}$, 5-6 membered heteroaryl having 1 to 4 heteroatoms selected from O and N and optionally substituted with 1 to 3 $Z^{1a}$, —OR$^{12}$, —N(R$^{12}$)$_2$, —C(O)R$^{12}$, N(R$^{12}$)C(O)R$^{12}$, —N(R$^{12}$)C(O)OR$^{12}$, —N(R$^{12}$)S(O)$_2$R$^{12}$, —OC(O)R$^{12}$, —OC(O)OR$^{12}$, —OC(O)N(R$^{12}$)$_2$, or —S(O)$_2$R$^{12}$.

In certain embodiments, each $Z^1$ is independently oxo, hydroxy, fluoro, chloro, —CN, —CH$_3$, ethyl, isopropyl, tert-butyl, —CF$_3$, —CHF$_2$, cyclopropyl, cyclobutyl, —OCH$_3$, —O-ethyl, —O-isopropyl, —O-cyclopropyl, —OCF$_3$, —OCF$_2$H, —C(O)-alkyl, —C(O)-cycloalkyl, —C(O)-aryl, —C(O)-heteroaryl, or —NH$_2$.

In certain embodiments, each $Z^1$ is independently halo, oxo, —CN, C$_{1-6}$ alkyl optionally substituted by 1 to 3 $Z^{1a}$, C$_{3-6}$ cycloalkyl optionally substituted with 1 to 3 $Z^{1b}$, 4-6 membered heterocyclyl having 1 to 2 heteroatoms selected from O and N that is optionally substituted by 1 to 3 $Z^{1a}$, 5-6 membered heteroaryl having 1 to 4 heteroatoms selected from O and N and optionally substituted with 1 to 3 $Z^{1a}$, —OR$^{12}$, —N(R$^{12}$)$_2$, —C(O)R$^{12}$, N(R$^{12}$)C(O)R$^{12}$, —N(R$^{12}$)C(O)OR$^{12}$, —N(R$^{12}$)S(O)$_2$R$^{12}$, —OC(O)R$^{12}$, —OC(O)OR$^{12}$, —OC(O)N(R$^{12}$)$_2$, or —S(O)$_2$R$^{12}$.

In certain embodiments, each $Z^1$ is independently oxo, hydroxy, fluoro, chloro, —CN, —CH$_3$, ethyl, isopropyl, tert-butyl, —CF$_3$, —CHF$_2$, cyclopropyl, cyclobutyl, —OCH$_3$, —O-ethyl, —O-isopropyl, —O-cyclopropyl, —OCF$_3$, —OCF$_2$H, —C(O)-alkyl, —C(O)-cycloalkyl, —C(O)-aryl, —C(O)-heteroaryl, or —NH$_2$.

In certain embodiments, each $Z^1$ is independently halo, C$_{1-8}$ alkyl optionally substituted by 1 to 3 $Z^{1a}$, or —OR$^9$. In certain embodiments, each $Z^1$ is independently halo, C$_{1-8}$ alkyl, C$_{1-8}$ haloalkyl, or —O—C$_{1-8}$ alkyl. In certain embodiments, each $Z^1$ is independently fluoro, methyl, —CF$_3$, or —O—CH$_3$.

In certain embodiments, each $Z^{1a}$ is independently halo, —CN, C$_{1-6}$ alkyl optionally substituted by 1 to 3 $Z^{1b}$, C$_{3-6}$ cycloalkyl optionally substituted by 1 to 3 $Z^{1b}$, 6 membered aryl optionally substituted by 1 to 3 $Z^{1b}$, 4-6 membered heterocyclyl having 1 to 2 heteroatoms selected from 0 or N that is optionally substituted by 1 to 3 $Z^{1b}$, 5-6 membered heteroaryl having 1 to 2 heteroatoms selected from O and N and optionally substituted with 1 to 3 $Z^{1b}$, —OR$^{12}$, —N(R$^{12}$)$_2$, —C(O)R$^{12}$, N(R$^{12}$)C(O)R$^{12}$, —N(R$^{12}$)C(O)OR$^{12}$, —N(R$^{12}$)S(O)$_2$R$^{12}$, —OC(O)R$^{12}$, —OC(O)OR$^{12}$, —OC(O)N(R$^{12}$)$_2$, or —S(O)$_2$R$^{12}$.

In certain embodiments, each $Z^{1a}$ is independently halo, —CH$_3$, cyclopropyl, or —OCH$_3$.

In certain embodiments, each $Z^{1b}$ is independently hydroxy, halo, —CN, C$_{1-6}$ alkyl, C$_{2-6}$ alkenyl, C$_{2-6}$ alkynyl, C$_{3-6}$ cycloalkyl, C$_{1-6}$ haloalkyl, C$_{6-10}$ aryl, 5-10 membered heteroaryl, 4-10 membered heterocyclyl or —O(C$_{1-6}$ alkyl).

In certain embodiments, provided is a compound as shown in Table 1, or a pharmaceutically acceptable salt thereof:

| Ex | Structure | Name |
|---|---|---|
| 1 | 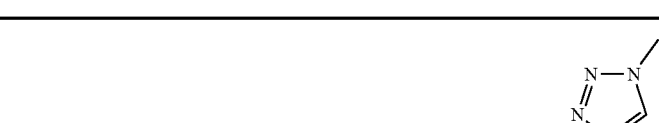 | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1-methyltriazole-4-carboxamide |

-continued

| Ex | Structure | Name |
|---|---|---|
| 2 | 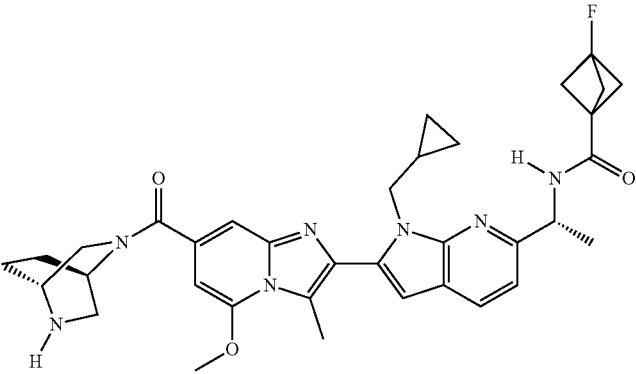 [SMILES: COc1cc(C(=O)N2C[C@H]3CC[C@@H]2CN3)cc2nc(-c3cc4ccc([C@@H](C)NC(=O)C56CC(F)(C5)C6)nc4n3CC3CC3)c(C)n12] | ~{N}-[(1~{R})-1-[1-(cyclopropylmethyl)-2-[7-[(1~{R},4~{R})-2,5-diazabicyclo[2.2.2]octane-2-carbonyl]-5-methoxy-3-methylimidazo[1,2-a]pyridin-2-yl]pyrrolo[2,3-b]pyridin-6-yl]ethyl]-3-fluorobicyclo[1.1.1]pentane-1-carboxamide |
| 3 | 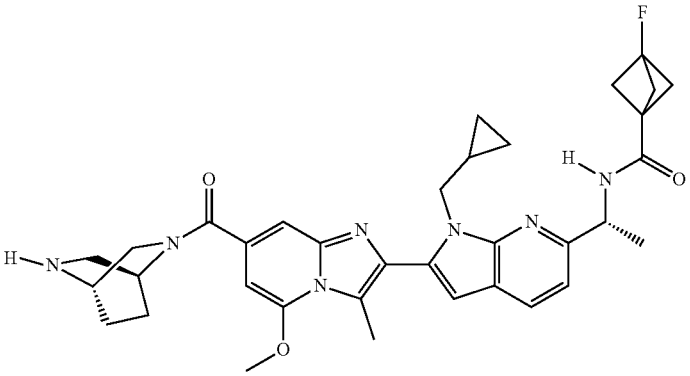 [SMILES: COc1cc(C(=O)N2C[C@@H]3CC[C@H]2CN3)cc2nc(-c3cc4ccc([C@@H](C)NC(=O)C56CC(F)(C5)C6)nc4n3CC3CC3)c(C)n12] | ~{N}-[(1~{R})-1-[1-(cyclopropylmethyl)-2-[7-[(1~{S},4~{S})-2,5-diazabicyclo[2.2.2]octane-2-carbonyl]-5-methoxy-3-methylimidazo[1,2-a]pyridin-2-yl]pyrrolo[2,3-b]pyridin-6-yl]ethyl]-3-fluorobicyclo[1.1.1]pentane-1-carboxamide |
| 4 | 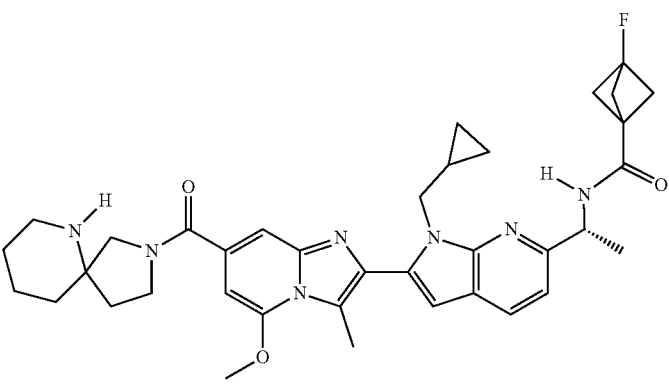 [SMILES: COc1cc(C(=O)N2CCC3(CCCCN3)C2)cc2nc(-c3cc4ccc([C@@H](C)NC(=O)C56CC(F)(C5)C6)nc4n3CC3CC3)c(C)n12] | ~{N}-[(1~{R})-1-[1-(cyclopropylmethyl)-2-[7-(2,6-diazaspiro[4.5]decane-2-carbonyl)-5-methoxy-3-methylimidazo[1,2-a]pyridin-2-yl]pyrrolo[2,3-b]pyridin-6-yl]ethyl]-3-fluorobicyclo[1.1.1]pentane-1-carboxamide |
| 5 | 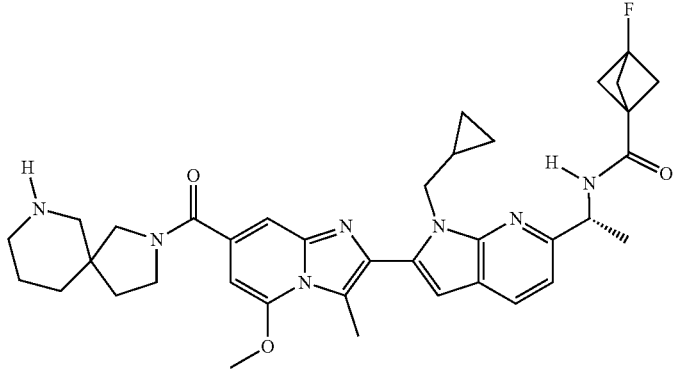 [SMILES: COc1cc(C(=O)N2CCC3(CCCNC3)C2)cc2nc(-c3cc4ccc([C@@H](C)NC(=O)C56CC(F)(C5)C6)nc4n3CC3CC3)c(C)n12] | ~{N}-[(1~{R})-1-[1-(cyclopropylmethyl)-2-[7-(2,9-diazaspiro[4.5]decane-2-carbonyl)-5-methoxy-3-methylimidazo[1,2-a]pyridin-2-yl]pyrrolo[2,3-b]pyridin-6-yl]ethyl]-3-fluorobicyclo[1.1.1]pentane-1-carboxamide |

| Ex | Structure | Name |
|---|---|---|
| 6 | 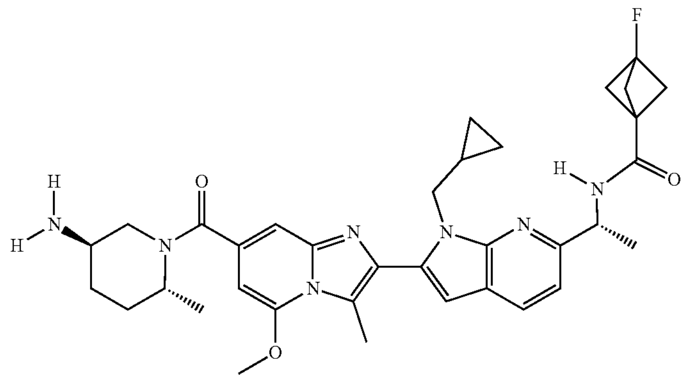 [SMILES: COc1cc(C(=O)N2C[C@H](N)CC[C@H]2C)cc2nc(-c3cc4ccc([C@@H](C)NC(=O)C56CC(F)(C5)C6)nc4n3CC3CC3)c(C)n12] | ~{N}-[(1~{R})-1-[2-[7-[(2~{R},5~{R})-5-amino-2-methylpiperidine-1-carbonyl]-5-methoxy-3-methylimidazo[1,2-a]pyridin-2-yl]-1-(cyclopropylmethyl)pyrrolo[2,3-b]pyridin-6-yl]ethyl]-3-fluorobicyclo[1.1.1]pentane-1-carboxamide |
| 7 | 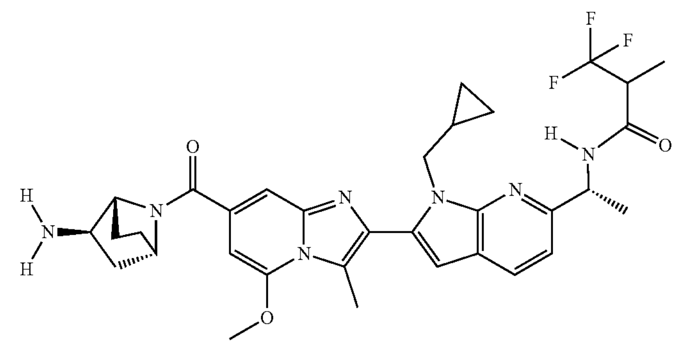 [SMILES: COc1cc(C(=O)N2[C@H]3CC[C@@H]2[C@H](N)C3)cc2nc(-c3cc4ccc([C@@H](C)NC(=O)C(C)C(F)(F)F)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3,3,3-trifluoro-2-methylpropanamide |
| 8 | 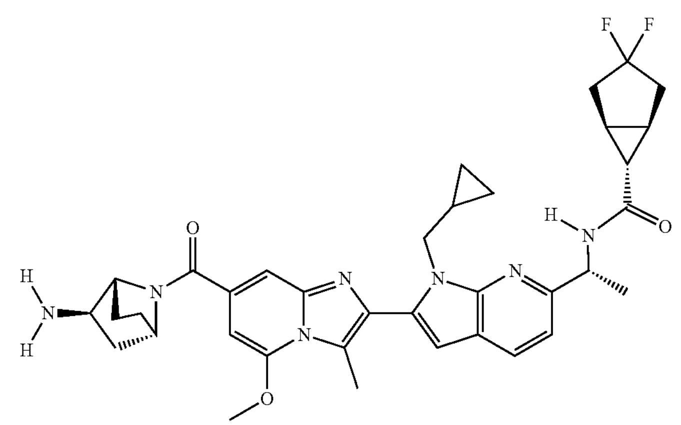 [SMILES: COc1cc(C(=O)N2[C@H]3CC[C@@H]2[C@H](N)C3)cc2nc(-c3cc4ccc([C@@H](C)NC(=O)[C@H]5[C@@H]6CC(F)(F)C[C@@H]65)nc4n3CC3CC3)c(C)n12] | (1~{R},5~{S})-~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3,3-difluorobicyclo[3.1.0]hexane-6-carboxamide |
| 9 | 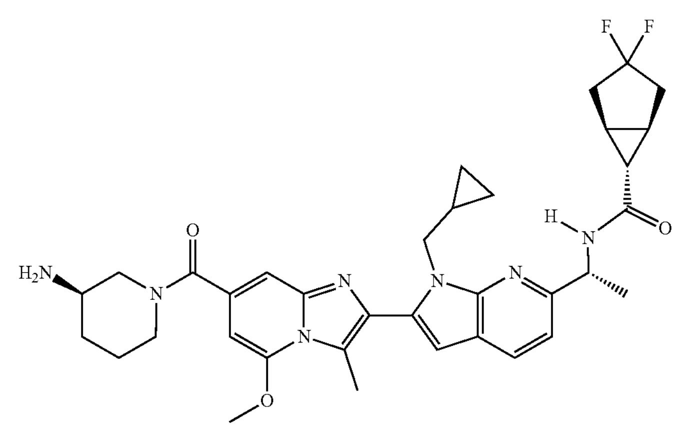 [SMILES: COc1cc(C(=O)N2CCC[C@@H](N)C2)cc2nc(-c3cc4ccc([C@@H](C)NC(=O)[C@H]5[C@@H]6CC(F)(F)C[C@@H]65)nc4n3CC3CC3)c(C)n12] | (1~{R},5~{S})-~{N}-[(1~{R})-1-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]ethyl]-3,3-difluorobicyclo[3.1.0]hexane-6-carboxamide |

-continued

| Ex | Structure | Name |
|---|---|---|
| 10 | 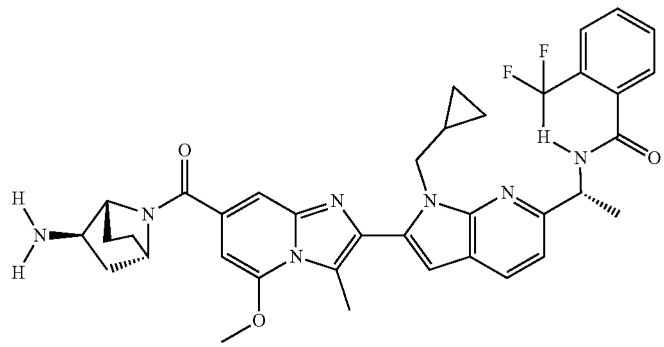 | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2-(trifluoromethyl)benzamide |
| 11 | 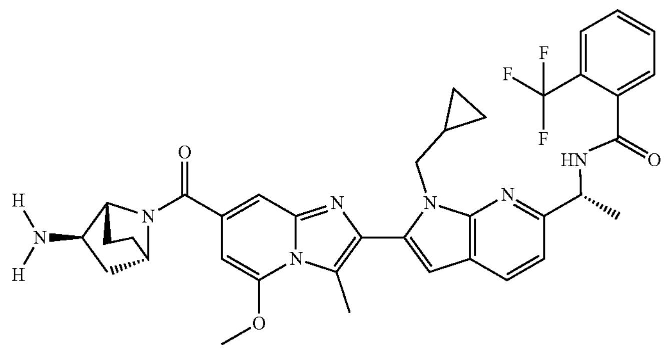 [SMILES: COc1cc(C(=O)N2[C@H]3CC[C@@H]2[C@H](N)C3)cc2nc(-c3cc4ccc([C@@H](C)NC(=O)c5ccccc5C(F)(F)F)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2-(difluoromethyl)benzamide |
| 12 | 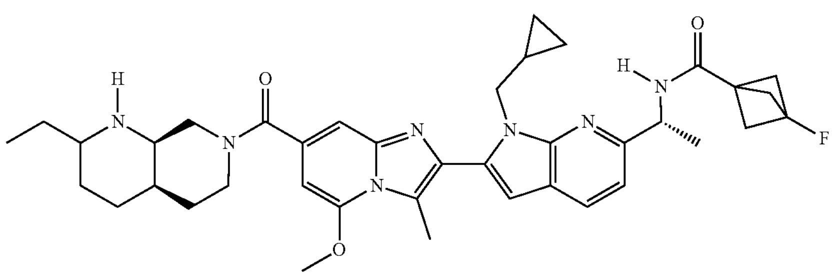 [SMILES: CCC1CC[C@@H]2CCN(C(=O)c3cc(OC)n4c(C)c(-c5cc6ccc([C@@H](C)NC(=O)C78CC(F)(C7)C8)nc6n5CC5CC5)nc4c3)C[C@@H]2N1] | ~{N}-[(1~{R})-1-[2-[7-[(4~{a}~{R},8~{a}~{R})-2-ethyl-2,3,4,4~{a},5,6,8,8~{a}-octahydro-1~{H}-1,7-naphthyridine-7-carbonyl]-5-methoxy-3-methylimidazo[1,2-a]pyridin-2-yl]-1-(cyclopropylmethyl)pyrrolo[2,3-b]pyridin-6-yl]ethyl]-3-fluorobicyclo[1.1.1]pentane-1-carboxamide |
| 13 | 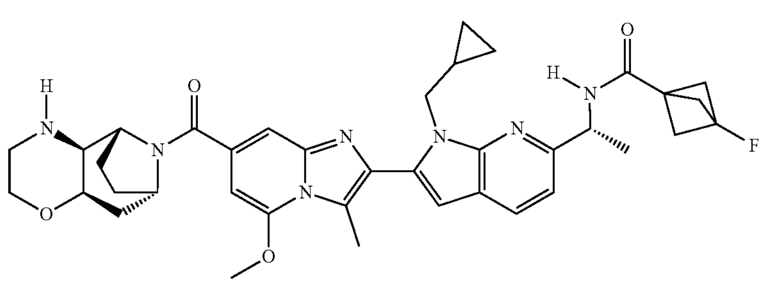 [SMILES: COc1cc(C(=O)N2[C@H]3CC[C@@H]2[C@@H]2NCCO[C@@H]2C3)cc2nc(-c3cc4ccc([C@@H](C)NC(=O)C56CC(F)(C5)C6)nc4n3CC3CC3)c(C)n12] | ~{N}-[(1~{R})-1-[1-(cyclopropylmethyl)-2-[5-methoxy-3-methyl-7-[(1~{R},2~{S},7~{R},9~{S})-6-oxa-3,12-diazatricyclo[7.2.1.0~{2,7}]dodecane-12-carbonyl]imidazo[1,2-a]pyridin-2-yl]pyrrolo[2,3-b]pyridin-6-yl]ethyl]-3-fluorobicyclo[1.1.1]pentane-1-carboxamide |

| Ex | Structure | Name |
|---|---|---|
| 14 | 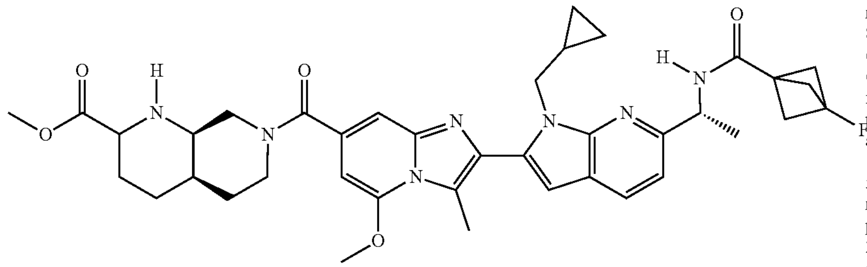 [SMILES: COC(=O)C1CC[C@@H]2CCN(C(=O)c3cc(OC)n4c(C)c(-c5cc6ccc([C@@H](C)NC(=O)C78CC(F)(C7)C8)nc6n5CC5CC5)nc4c3)C[C@@H]2N1] | methyl (4~{a}~{R}, 8~{a}~{R})-7-[2-[1-(cyclopropylmethyl)-6-[(1~{R})-1-[(3-fluorobicyclo[1.1.1]pentane-1-carbonyl)amino]ethyl]pyrrolo[2,3-b]pyridin-2-yl]-5-methoxy-3-methylimidazo[1,2-a]pyridine-7-carbonyl]-2,3,4,4~{a},5,6,8,8~{a}-octahydro-1~{H}-1,7-naphthyridine-2-carboxylate |
| 15 | 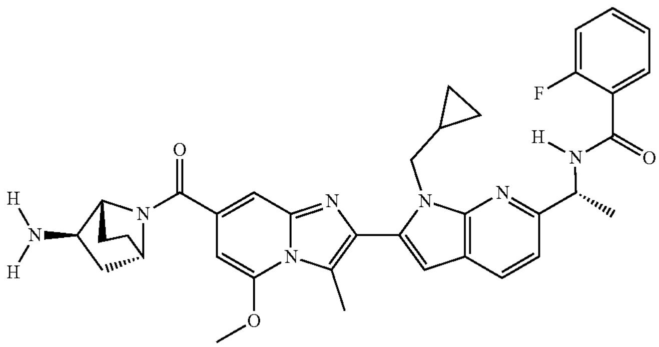 [SMILES: COc1cc(C(=O)N2[C@H]3CC[C@@H]2[C@H](N)C3)cc2nc(-c3cc4ccc([C@@H](C)NC(=O)c5ccccc5F)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2-fluorobenzamide |
| 16 | 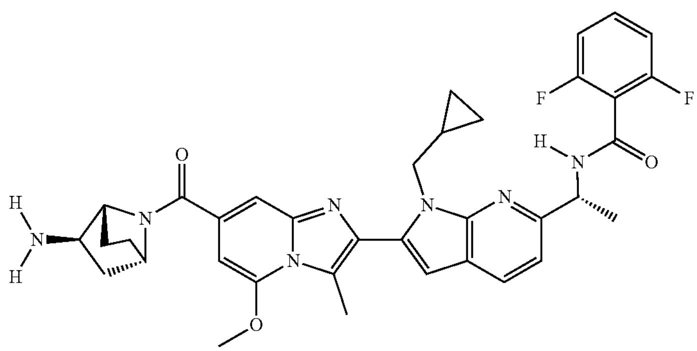 [SMILES: COc1cc(C(=O)N2[C@H]3CC[C@@H]2[C@H](N)C3)cc2nc(-c3cc4ccc([C@@H](C)NC(=O)c5c(F)cccc5F)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2,6-difluorobenzamide |
| 17 | 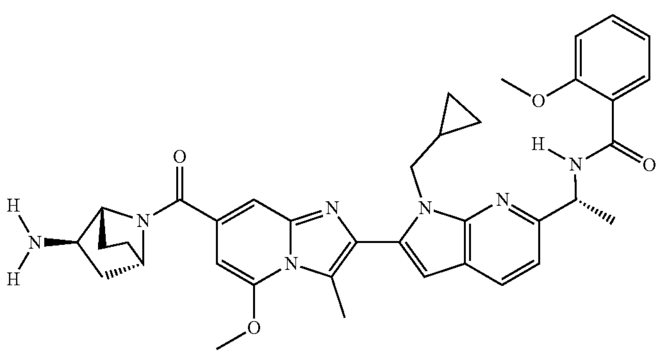 [SMILES: COc1ccccc1C(=O)N[C@H](C)c1ccc2cc(-c3nc4cc(C(=O)N5[C@H]6CC[C@@H]5[C@H](N)C6)cc(OC)n4c3C)n(CC3CC3)c2n1] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2-methoxybenzamide |

| Ex | Structure | Name |
|---|---|---|
| 18 | 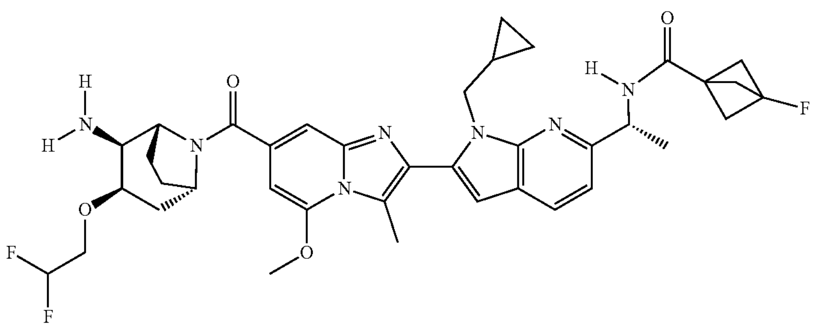 [SMILES: COc1cc(C(=O)N2[C@H]3CC[C@@H]2[C@H](N)[C@H](OCC(F)F)C3)cc2nc(-c3cc4ccc([C@@H](C)NC(=O)C56CC(F)(C5)C6)nc4n3CC3CC3)c(C)n12] | ~{N}-[(1~{R})-1-[2-[7-amino-3-(2,2-difluoroethoxy)-8-azabicyclo[3.2.1]octane-8-carbonyl]-5-methoxy-3-methylimidazo[1,2-a]pyridin-2-yl]-1-(cyclopropylmethyl)pyrrolo[2,3-b]pyridin-6-yl]ethyl]-3-fluorobicyclo[1.1.1]pentane-1-carboxamide |
| 19 | 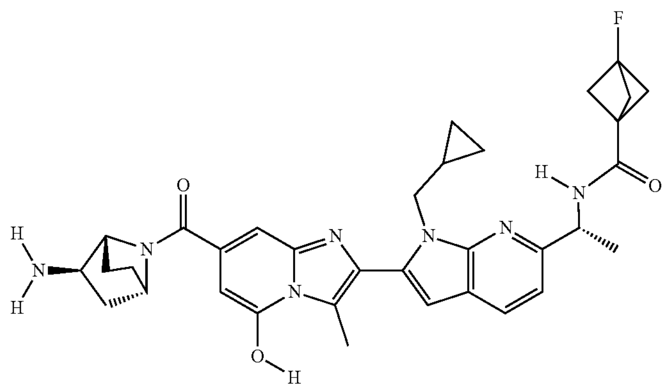 [SMILES: Cc1c(-c2cc3ccc([C@@H](C)NC(=O)C45CC(F)(C4)C5)nc3n2CC2CC2)nc2cc(C(=O)N3[C@H]4CC[C@@H]3[C@H](N)C4)cc(O)n12] | ~{N}-[(1~{R})-1-[2-[7-[(1~{R},2~{R},4~{S})-2-amino-7-azabicyclo[2.2.1]heptane-7-carbonyl]-5-hydroxy-3-methylimidazo[1,2-a]pyridin-2-yl]-1-(cyclopropylmethyl)pyrrolo[2,3-b]pyridin-6-yl]ethyl]-3-fluorobicyclo[1.1.1]pentane-1-carboxamide |
| 20 | 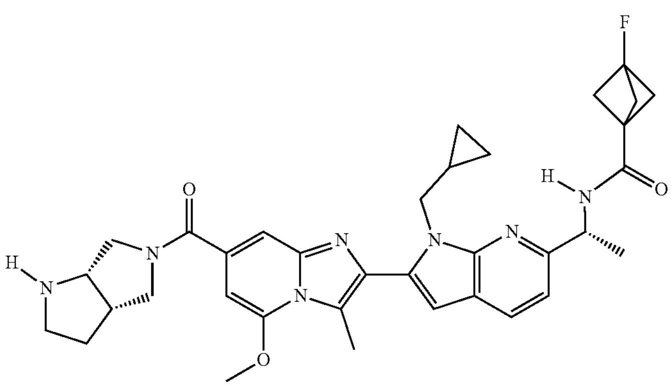 [SMILES: COc1cc(C(=O)N2C[C@@H]3CCN[C@@H]3C2)cc2nc(-c3cc4ccc([C@@H](C)NC(=O)C56CC(F)(C5)C6)nc4n3CC3CC3)c(C)n12] | ~{N}-[(1~{R})-1-[2-[7-[(3~{a}~{S},6~{a}~{S})-2,3,3~{a},4,6,6~{a}-hexahydro-1~{H}-pyrrolo[3,4-b]pyrrole-5-carbonyl]-5-methoxy-3-methylimidazo[1,2-a]pyridin-2-yl]-1-(cyclopropylmethyl)pyrrolo[2,3-b]pyridin-6-yl]ethyl]-3-fluorobicyclo[1.1.1]pentane-1-carboxamide |
| 21 | 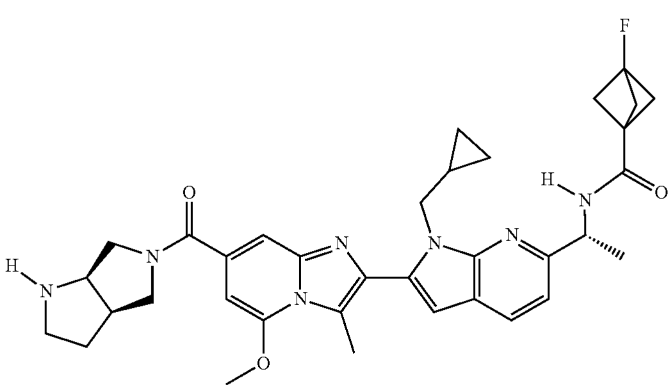 [SMILES: COc1cc(C(=O)N2C[C@H]3CCN[C@H]3C2)cc2nc(-c3cc4ccc([C@@H](C)NC(=O)C56CC(F)(C5)C6)nc4n3CC3CC3)c(C)n12] | ~{N}-[(1~{R})-1-[2-[7-2,3,3~{a},4,6,6~{a}-hexahydro-1~{H}-pyrrolo[3,4-b]pyrrole-5-carbonyl]-5-methoxy-3-methylimidazo[1,2-a]pyridin-2-yl]-1-(cyclopropylmethyl)pyrrolo[2,3-b]pyridin-6-yl]ethyl]-3-fluorobicyclo[1.1.1]pentane-1-carboxamide |

| Ex | Structure | Name |
| --- | --- | --- |
| 22 | 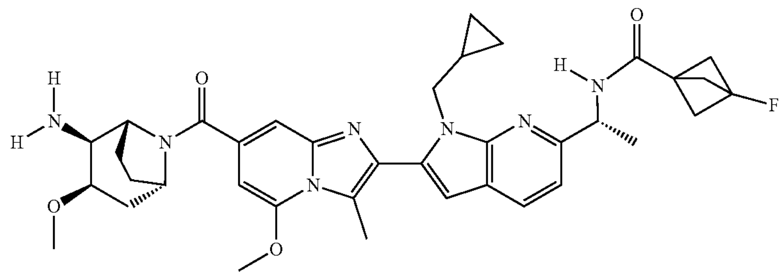 [SMILES: COc1cc(C(=O)N2[C@H]3CC[C@@H]2[C@H](N)[C@H](OC)C3)cc2nc(-c3cc4ccc([C@@H](C)NC(=O)C56CC(F)(C5)C6)nc4n3CC3CC3)c(C)n12] | ~{N}-[(1~{R})-1-[2-[7-[(1~{R},2~{S},3~{R},5~{S})-2-amino-3-methoxy-8-azabicyclo[3.2.1]octane-8-carbonyl]-5-methoxy-3-methylimidazo[1,2-a]pyridin-2-yl]-1-(cyclopropylmethyl)pyrrolo[2,3-b]pyridin-6-yl]ethyl]-3-fluorobicyclo[1.1.1]pentane-1-carboxamide |
| 23 | 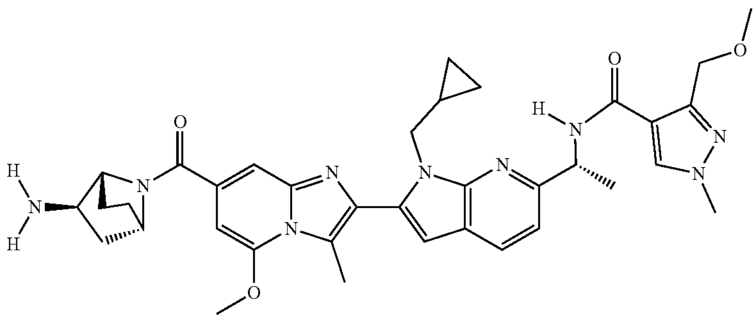 [SMILES: COCc1nn(C)cc1C(=O)N[C@H](C)c1ccc2cc(-c3nc4cc(C(=O)N5[C@H]6CC[C@@H]5[C@H](N)C6)cc(OC)n4c3C)n(CC3CC3)c2n1] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-(methoxymethyl)-1-methylpyrazole-4-carboxamide |
| 24 | 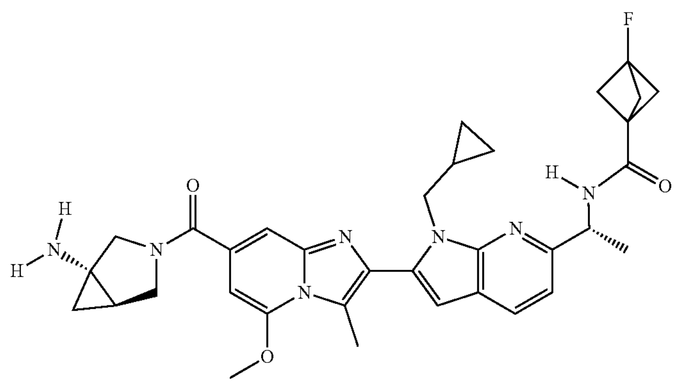 [SMILES: COc1cc(C(=O)N2C[C@H]3C[C@@]3(N)C2)cc2nc(-c3cc4ccc([C@@H](C)NC(=O)C56CC(F)(C5)C6)nc4n3CC3CC3)c(C)n12] | ~{N}-[(1~{R})-1-[2-[7-[(1~{S},5~{R})-1-amino-3-azabicyclo[3.1.0]hexane-3-carbonyl]-5-methoxy-3-methylimidazo[1,2-a]pyridin-2-yl]-1-(cyclopropylmethyl)pyrrolo[2,3-b]pyridin-6-yl]ethyl]-3-fluorobicyclo[1.1.1]pentane-1-carboxamide |
| 25 | 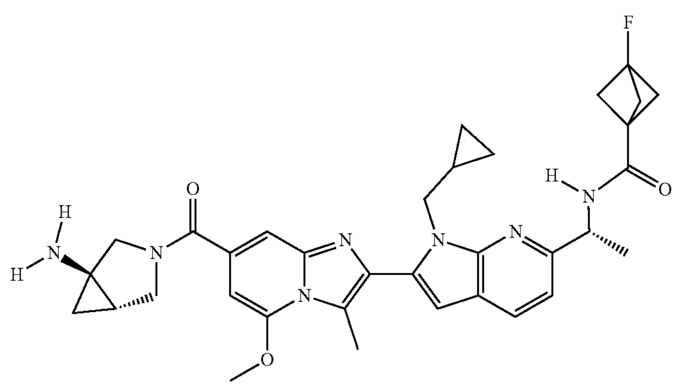 [SMILES: COc1cc(C(=O)N2C[C@@H]3C[C@]3(N)C2)cc2nc(-c3cc4ccc([C@@H](C)NC(=O)C56CC(F)(C5)C6)nc4n3CC3CC3)c(C)n12] | ~{N}-[(1~{R})-1-[2-[7-[(1~{R},5~{S})-1-amino-3-azabicyclo[3.1.0]hexane-3-carbonyl]-5-methoxy-3-methylimidazo[1,2-a]pyridin-2-yl]-1-(cyclopropylmethyl)pyrrolo[2,3-b]pyridin-6-yl]ethyl]-3-fluorobicyclo[1.1.1]pentane-1-carboxamide |

| Ex | Structure | Name |
|---|---|---|
| 26 | 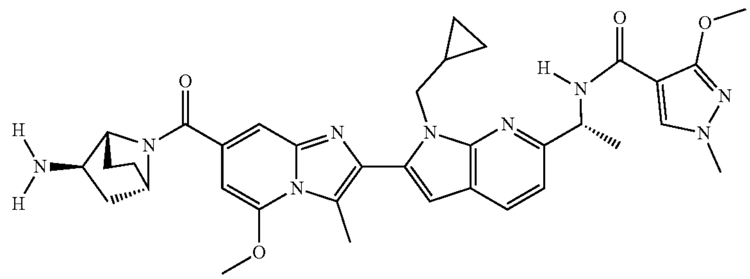 [SMILES: COc1nn(C)cc1C(=O)N[C@H](C)c1ccc2cc(-c3nc4cc(C(=O)N5[C@H]6CC[C@@H]5[C@H](N)C6)cc(OC)n4c3C)n(CC3CC3)c2n1] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-methoxy-1-methylpyrazole-4-carboxamide |
| 27 | 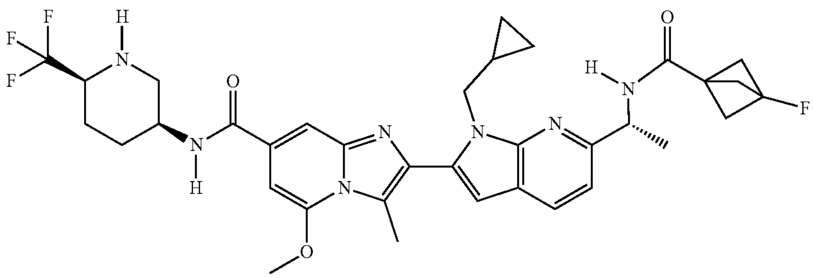 [SMILES: COc1cc(C(=O)N[C@H]2CC[C@@H](C(F)(F)F)NC2)cc2nc(-c3cc4ccc([C@@H](C)NC(=O)C56CC(F)(C5)C6)nc4n3CC3CC3)c(C)n12] | 2-[1-(cyclopropylmethyl)-6-[(1~{R})-1-[(3-fluorobicyclo[1.1.1]pentane-1-carbonyl)amino]ethyl]pyrrolo[2,3-b]pyridin-2-yl]-5-methoxy-3-methyl-~{N}-[(3~{S},6~{S})-6-(trifluoromethyl)piperidin-3-yl]imidazo[1,2-a]pyridine-7-carboxamide |
| 28 | 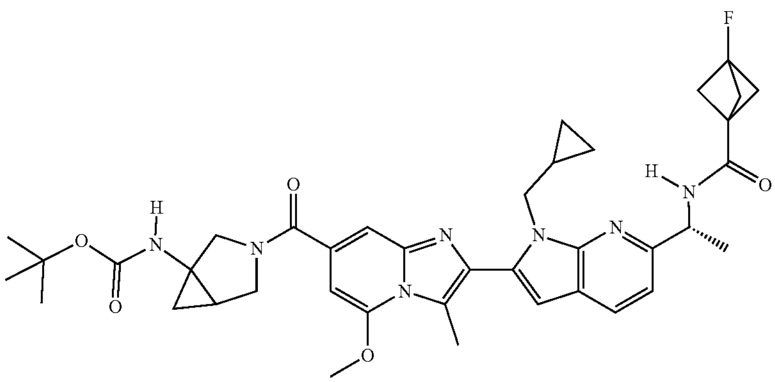 [SMILES: COc1cc(C(=O)N2CC3CC3(NC(=O)OC(C)(C)C)C2)cc2nc(-c3cc4ccc([C@@H](C)NC(=O)C56CC(F)(C5)C6)nc4n3CC3CC3)c(C)n12] | ~{tert}-butyl~{N}-[3-[2-[1-(cyclopropylmethyl)-6-[(1~{R})-1-[(3-fluorobicyclo[1.1.1]pentane-1-carbonyl)amino]ethyl]pyrrolo[2,3-b]pyridin-2-yl]-5-methoxy-3-methylimidazo[1,2-a]pyridine-7-carbonyl]-3-azabicyclo[3.1.0]hexan-1-yl]carbamate |
| 29 | 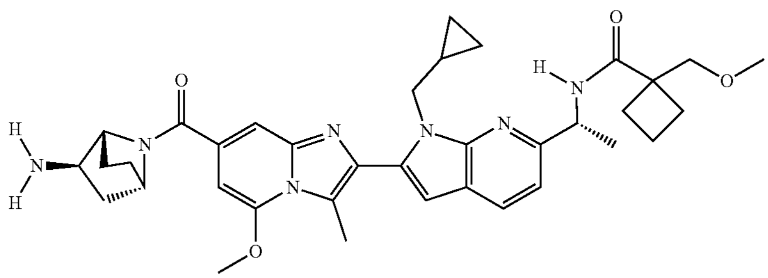 [SMILES: COCC1(C(=O)N[C@H](C)c2ccc3cc(-c4nc5cc(C(=O)N6[C@H]7CC[C@@H]6[C@H](N)C7)cc(OC)n5c4C)n(CC4CC4)c3n2)CCC1] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1-(methoxymethyl)cyclobutane-1-carboxamide |
| 30 | 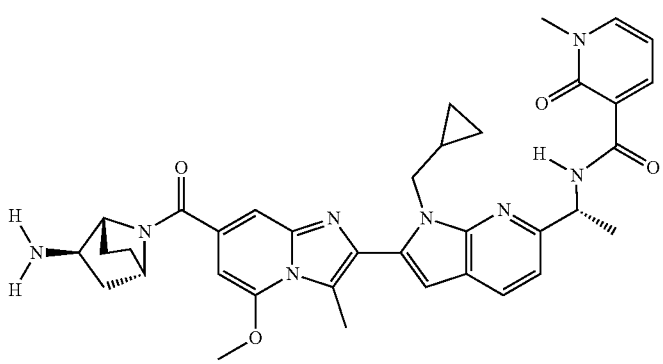 [SMILES: COc1cc(C(=O)N2[C@H]3CC[C@@H]2[C@H](N)C3)cc2nc(-c3cc4ccc([C@@H](C)NC(=O)c5cccn(C)c5=O)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1-methyl-2-oxopyridine-3-carboxamide |

-continued

| Ex | Structure | Name |
|---|---|---|
| 31 | 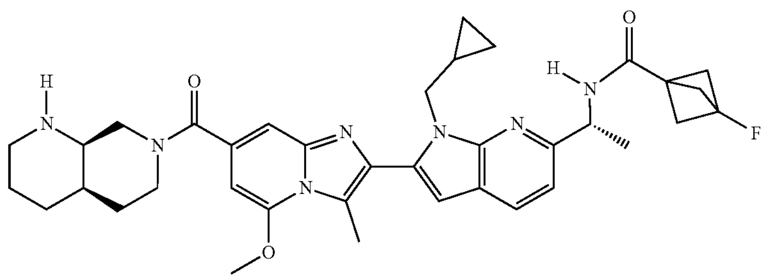 [SMILES: COc1cc(C(=O)N2CC[C@H]3CCCN[C@H]3C2)cc2nc(-c3cc4ccc([C@@H](C)NC(=O)C56CC(F)(C5)C6)nc4n3CC3CC3)c(C)n12] | ~{N}-[(1~{R})-1-[2-[7-[(4~{a}~{R},8~{a}~{R})-2,3,4,4~{a},5,6,8,8~{a}-octahydro-1~{H}-1,7-naphthyridine-7-carbonyl]-5-methoxy-3-methylimidazo[1,2-a]pyridin-2-yl]-1-(cyclopropylmethyl)pyrrolo[2,3-b]pyridin-6-yl]ethyl]-3-fluorobicyclo[1.1.1]pentane-1-carboxamide |
| 32 | 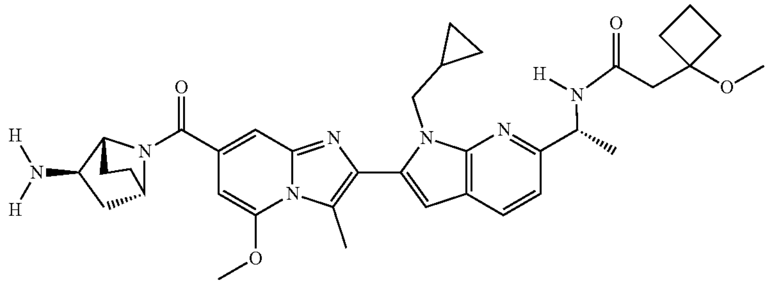 [SMILES: COc1cc(C(=O)N2[C@H]3CC[C@@H]2[C@H](N)C3)cc2nc(-c3cc4ccc([C@@H](C)NC(=O)CC5(OC)CCC5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2-(1-methoxycyclobutyl)acetamide |
| 33 | 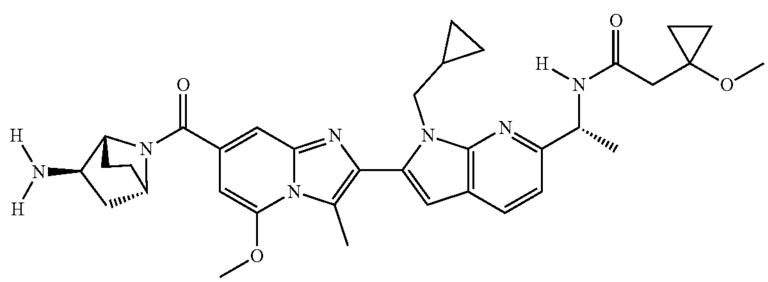 [SMILES: COc1cc(C(=O)N2[C@H]3CC[C@@H]2[C@H](N)C3)cc2nc(-c3cc4ccc([C@@H](C)NC(=O)CC5(OC)CC5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2-(1-methoxycyclopropyl)acetamide |
| 34 | 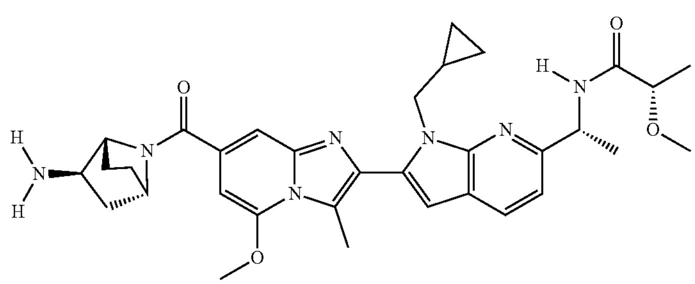 [SMILES: COc1cc(C(=O)N2[C@H]3CC[C@@H]2[C@H](N)C3)cc2nc(-c3cc4ccc([C@@H](C)NC(=O)[C@H](C)OC)nc4n3CC3CC3)c(C)n12] | (2~{S})-~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2-methoxypropanamide |
| 35 | 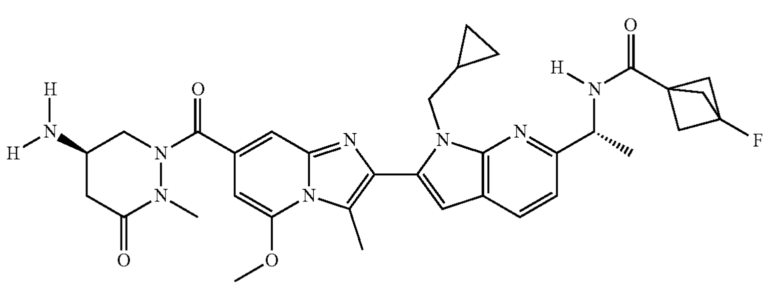 [SMILES: COc1cc(C(=O)N2C[C@H](N)CC(=O)N2C)cc2nc(-c3cc4ccc([C@@H](C)NC(=O)C56CC(F)(C5)C6)nc4n3CC3CC3)c(C)n12] | ~{N}-[(1~{R})-1-[2-[7-[(5~{R})-5-amino-2-methyl-3-oxodiazinane-1-carbonyl]-5-methoxy-3-methylimidazo[1,2-a]pyridin-2-yl]-1-(cyclopropylmethyl)pyrrolo[2,3-b]pyridin-6-yl]ethyl]-3-fluorobicyclo[1.1.1]pentane-1-carboxamide |

-continued

| Ex | Structure | Name |
|---|---|---|
| 36 | 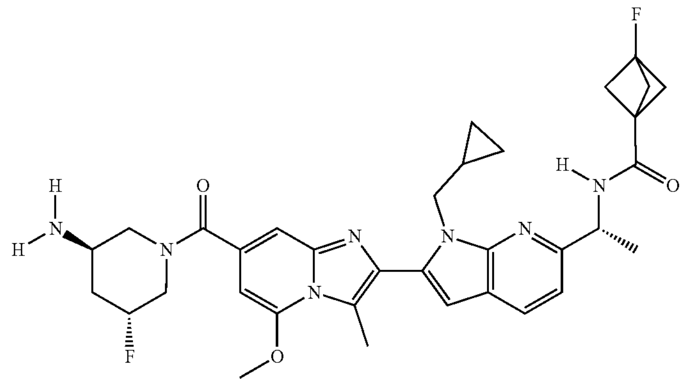 [SMILES: COc1cc(C(=O)N2C[C@H](N)C[C@@H](F)C2)cc2nc(-c3cc4ccc([C@@H](C)NC(=O)C56CC(F)(C5)C6)nc4n3CC3CC3)c(C)n12] | ~{N}-[(1~{R})-1-[2-[7-[(3~{R},5~{R})-3-amino-5-fluoropiperidine-1-carbonyl]-5-methoxy-3-methylimidazo[1,2-a]pyridin-2-yl]-1-(cyclopropylmethyl)pyrrolo[2,3-b]pyridin-6-yl]ethyl]-3-fluorobicyclo[1.1.1]pentane-1-carboxamide |
| 37 | 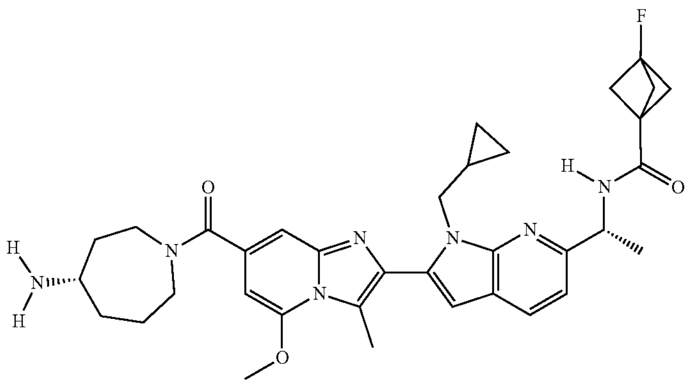 [SMILES: COc1cc(C(=O)N2CCC[C@H](N)CC2)cc2nc(-c3cc4ccc([C@@H](C)NC(=O)C56CC(F)(C5)C6)nc4n3CC3CC3)c(C)n12] | ~{N}-[(1~{R})-1-[2-[7-[(4~{S})-4-aminoazepane-1-carbonyl]-5-methoxy-3-methylimidazo[1,2-a]pyridin-2-yl]-1-(cyclopropylmethyl)pyrrolo[2,3-b]pyridin-6-yl]ethyl]-3-fluorobicyclo[1.1.1]pentane-1-carboxamide |
| 38 | 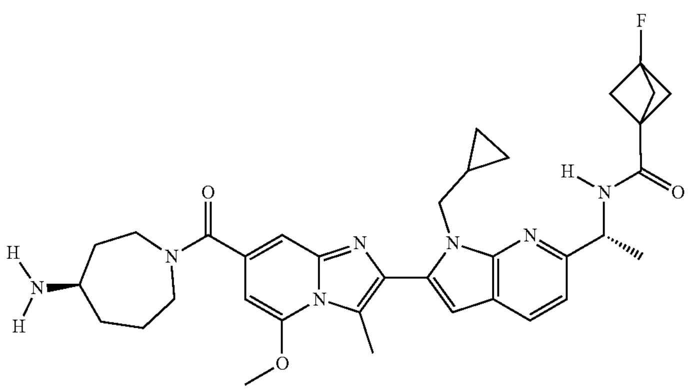 [SMILES: COc1cc(C(=O)N2CCC[C@@H](N)CC2)cc2nc(-c3cc4ccc([C@@H](C)NC(=O)C56CC(F)(C5)C6)nc4n3CC3CC3)c(C)n12] | ~{N}-[(1~{R})-1-[2-[7-[(4~{R})-4-aminoazepane-1-carbonyl]-5-methoxy-3-methylimidazo[1,2-a]pyridin-2-yl]-1-(cyclopropylmethyl)pyrrolo[2,3-b]pyridin-6-yl]ethyl]-3-fluorobicyclo[1.1.1]pentane-1-carboxamide |
| 39 | 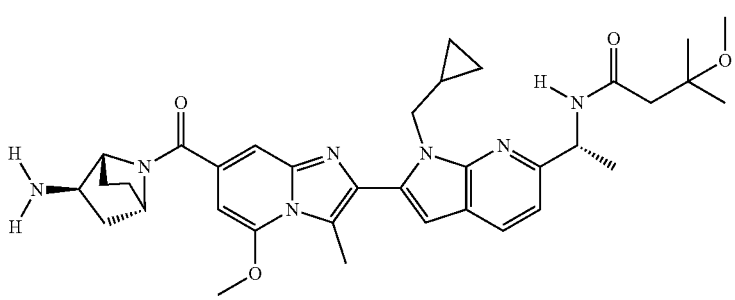 [SMILES: COc1cc(C(=O)N2[C@H]3CC[C@@H]2[C@H](N)C3)cc2nc(-c3cc4ccc([C@@H](C)NC(=O)CC(C)(C)OC)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-methoxy-3-methylbutanamide |

| Ex | Structure | Name |
|---|---|---|
| 40 | 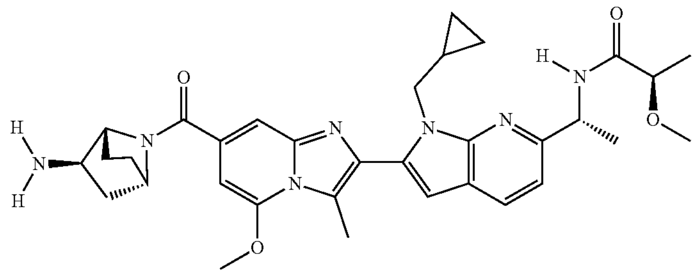 [SMILES: COc1cc(C(=O)N2[C@H]3CC[C@@H]2[C@H](N)C3)cc2nc(-c3cc4ccc([C@@H](C)NC(=O)[C@@H](C)OC)nc4n3CC3CC3)c(C)n12] | (2~{R})-~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2-methoxypropanamide |
| 41 | 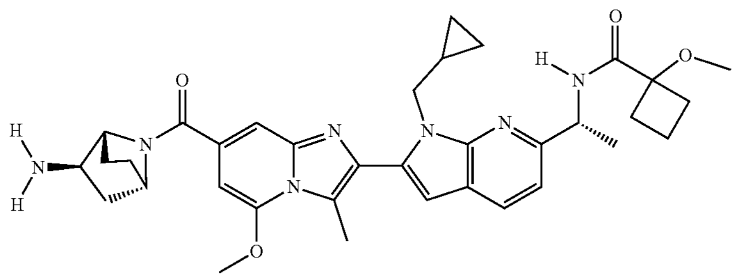 [SMILES: COc1cc(C(=O)N2[C@H]3CC[C@@H]2[C@H](N)C3)cc2nc(-c3cc4ccc([C@@H](C)NC(=O)C5(OC)CCC5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1-methoxycyclobutane-1-carboxamide |
| 42 | 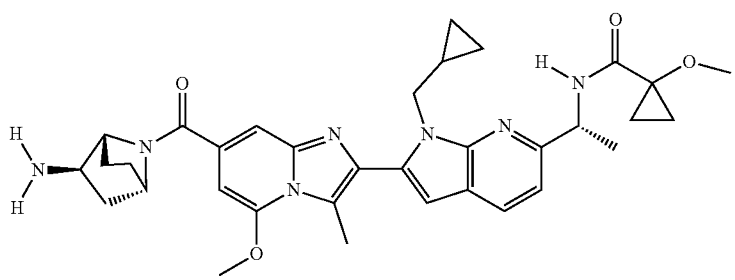 [SMILES: COc1cc(C(=O)N2[C@H]3CC[C@@H]2[C@H](N)C3)cc2nc(-c3cc4ccc([C@@H](C)NC(=O)C5(OC)CC5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1-methoxycyclopropane-1-carboxamide |
| 43 | 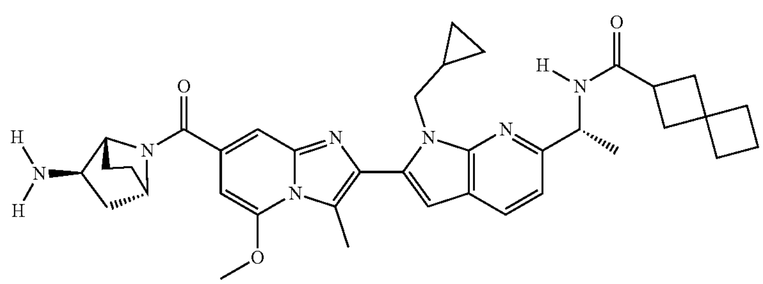 [SMILES: COc1cc(C(=O)N2[C@H]3CC[C@@H]2[C@H](N)C3)cc2nc(-c3cc4ccc([C@@H](C)NC(=O)C5CC6(CCC6)C5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]spiro[3.3]heptane-2-carboxamide |
| 44 | 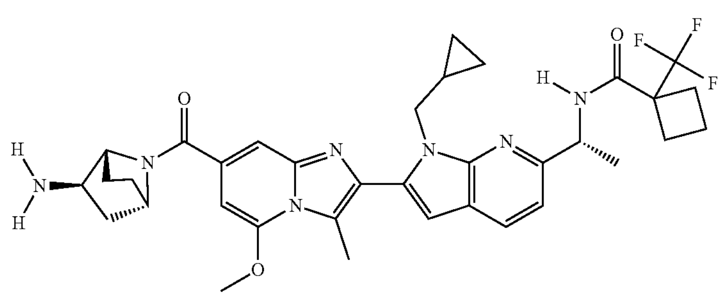 [SMILES: COc1cc(C(=O)N2[C@H]3CC[C@@H]2[C@H](N)C3)cc2nc(-c3cc4ccc([C@@H](C)NC(=O)C5(C(F)(F)F)CCC5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1-(trifluoromethyl)cyclobutane-1-carboxamide |

-continued

| Ex | Structure | Name |
|---|---|---|
| 45 | 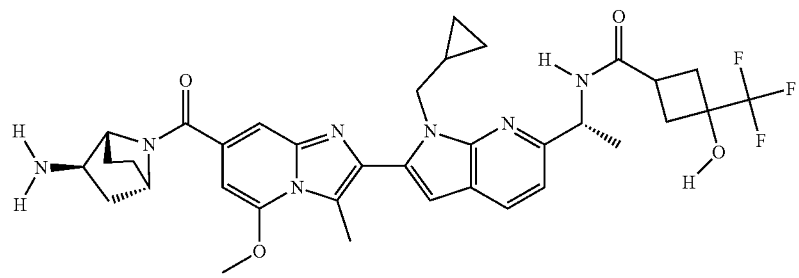 [SMILES: COc1cc(C(=O)N2[C@H]3CC[C@@H]2[C@H](N)C3)cc2nc(-c3cc4ccc([C@@H](C)NC(=O)C5CC(O)(C(F)(F)F)C5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-hydroxy-3-(trifluoromethyl)cyclobutane-1-carboxamide |
| 46 | 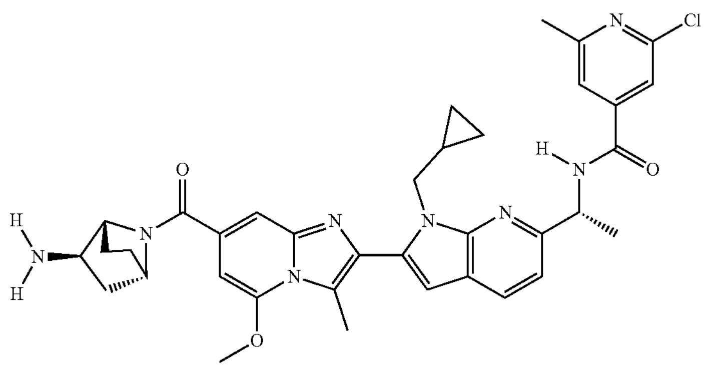 [SMILES: COc1cc(C(=O)N2[C@H]3CC[C@@H]2[C@H](N)C3)cc2nc(-c3cc4ccc([C@@H](C)NC(=O)c5cc(C)nc(Cl)c5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2-chloro-6-methylpyridine-4-carboxamide |
| 47 | 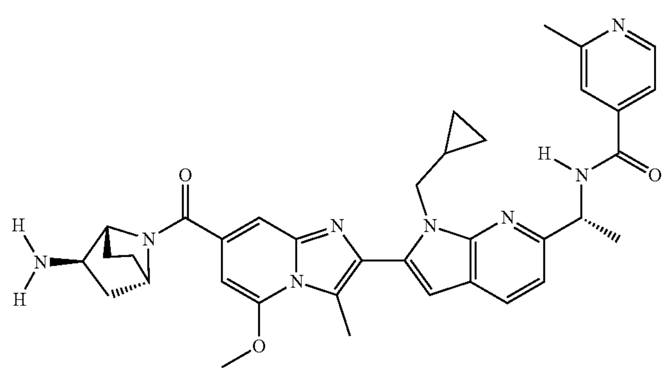 [SMILES: COc1cc(C(=O)N2[C@H]3CC[C@@H]2[C@H](N)C3)cc2nc(-c3cc4ccc([C@@H](C)NC(=O)c5ccnc(C)c5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2-methylpyridine-4-carboxamide |
| 48 | 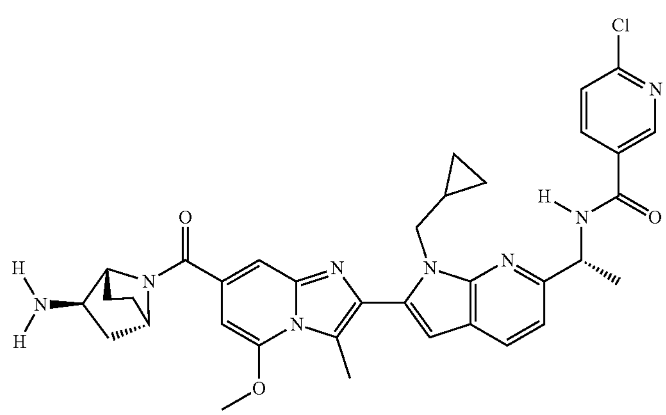 [SMILES: COc1cc(C(=O)N2[C@H]3CC[C@@H]2[C@H](N)C3)cc2nc(-c3cc4ccc([C@@H](C)NC(=O)c5ccc(Cl)nc5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-6-chloropyridine-3-carboxamide |

-continued

| Ex | Structure | Name |
|---|---|---|
| 49 | 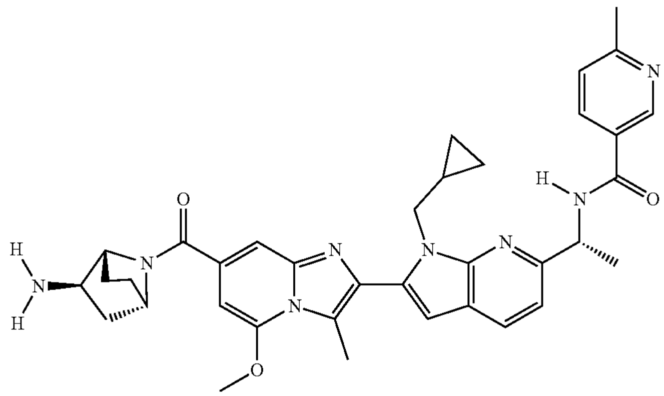 [SMILES: COc1cc(C(=O)N2[C@H]3CC[C@@H]2[C@H](N)C3)cc2nc(-c3cc4ccc([C@@H](C)NC(=O)c5ccc(C)nc5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-6-methylpyridine-3-carboxamide |
| 50 | 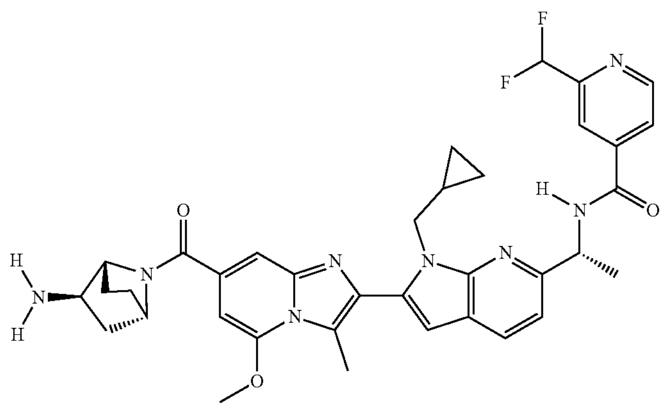 [SMILES: COc1cc(C(=O)N2[C@H]3CC[C@@H]2[C@H](N)C3)cc2nc(-c3cc4ccc([C@@H](C)NC(=O)c5ccnc(C(F)F)c5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2-(difluoromethyl)pyridine-4-carboxamide |
| 51 | 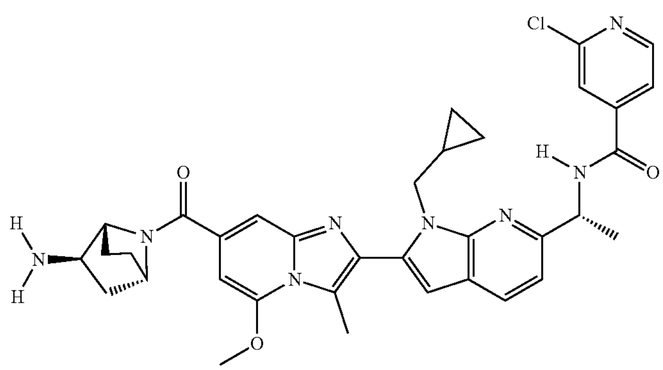 [SMILES: COc1cc(C(=O)N2[C@H]3CC[C@@H]2[C@H](N)C3)cc2nc(-c3cc4ccc([C@@H](C)NC(=O)c5ccnc(Cl)c5)nc4n3CC3CC3)c(C)n12] | [(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2-chloropyridine-4-carboxamide |
| 52 | 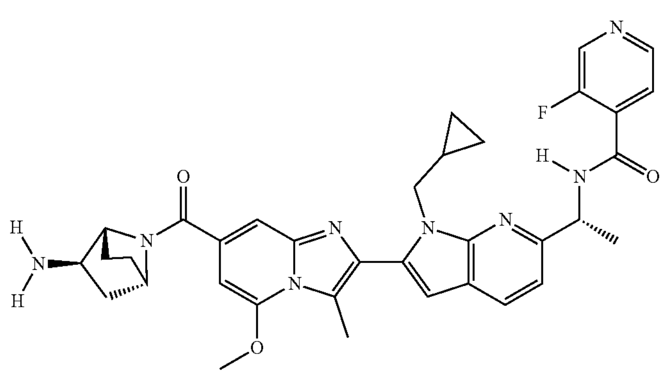 [SMILES: COc1cc(C(=O)N2[C@H]3CC[C@@H]2[C@H](N)C3)cc2nc(-c3cc4ccc([C@@H](C)NC(=O)c5ccncc5F)nc4n3CC3CC3)c(C)n12] | [(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-fluoropyridine-4-carboxamide |

| Ex | Structure | Name |
|---|---|---|
| 53 | 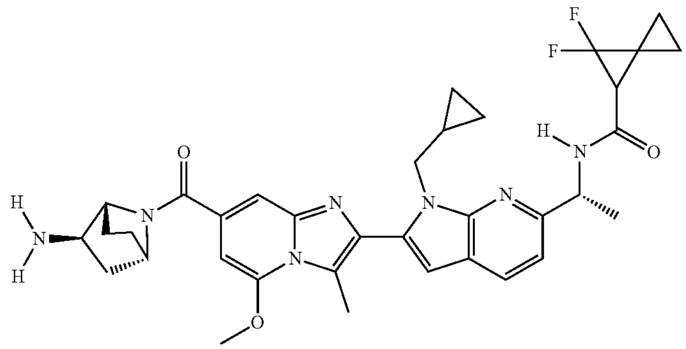 [SMILES: COc1cc(C(=O)N2[C@H]3CC[C@@H]2[C@H](N)C3)cc2nc(-c3cc4ccc([C@@H](C)NC(=O)C5C(F)(F)C56CC6)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2,2-difluorospiro[2.2]pentane-1-carboxamide |
| 54 | 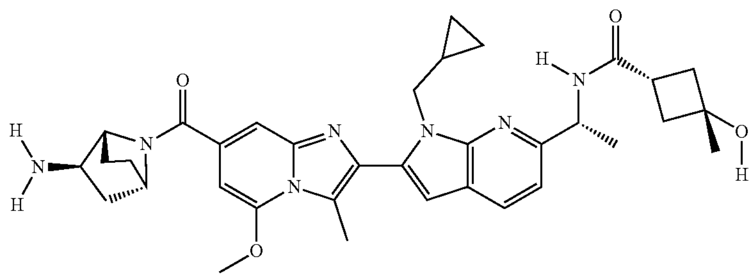 [SMILES: COc1cc(C(=O)N2[C@H]3CC[C@@H]2[C@H](N)C3)cc2nc(-c3cc4ccc([C@@H](C)NC(=O)[C@H]5C[C@@](C)(O)C5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-hydroxy-3-methylcyclobutane-1-carboxamide |
| 55 | 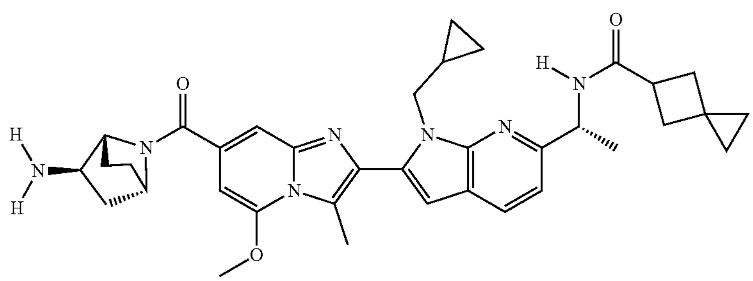 [SMILES: COc1cc(C(=O)N2[C@H]3CC[C@@H]2[C@H](N)C3)cc2nc(-c3cc4ccc([C@@H](C)NC(=O)C5CC6(CC6)C5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]spiro[2.3]hexane-5-carboxamide |
| 56 | 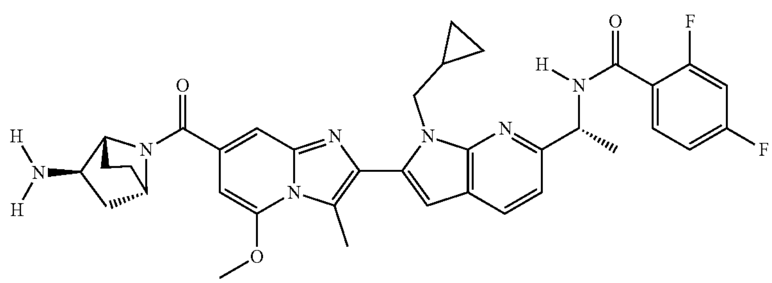 [SMILES: COc1cc(C(=O)N2[C@H]3CC[C@@H]2[C@H](N)C3)cc2nc(-c3cc4ccc([C@@H](C)NC(=O)c5ccc(F)cc5F)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2,4-difluorobenzamide |
| 57 | 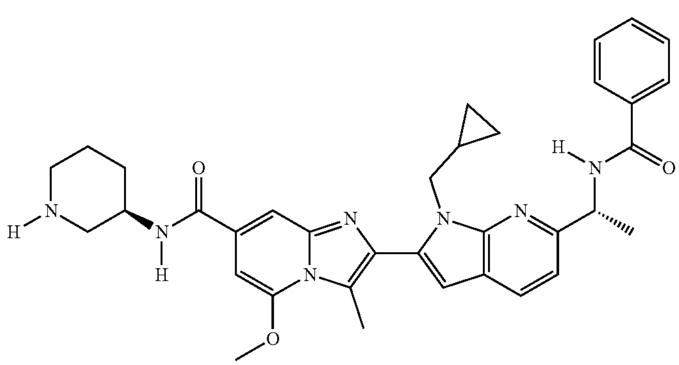 [SMILES: COc1cc(C(=O)N[C@@H]2CCCNC2)cc2nc(-c3cc4ccc([C@@H](C)NC(=O)c5ccccc5)nc4n3CC3CC3)c(C)n12] | 2-[6-[(1~{R})-1-benzamidoethyl]-1-(cyclopropylmethyl)pyrrolo[2,3-b]pyridin-2-yl]-5-methoxy-3-methyl-~{N}-[(3~{R})-piperidin-3-yl]imidazo[1,2-a]pyridine-7-carboxamide |

| Ex | Structure | Name |
|---|---|---|
| 58 | 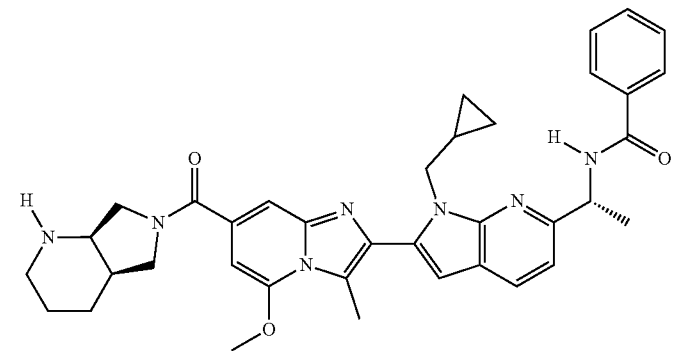 [SMILES: COc1cc(C(=O)N2C[C@H]3CCCN[C@H]3C2)cc2nc(-c3cc4ccc([C@@H](C)NC(=O)c5ccccc5)nc4n3CC3CC3)c(C)n12] | ~{N}-[(1~{R})-1-[2-[7-[(4~{a}~{R},7~{a}~{R})-1,2,3,4,4~{a},5,7,7~{a}-octahydropyrrolo[3,4-b]pyridine-6-carbonyl]-5-methoxy-3-methylimidazo[1,2-a]pyridin-2-yl]-1-(cyclopropylmethyl)pyrrolo[2,3-b]pyridin-6-yl]ethyl]benzamide |
| 59 | 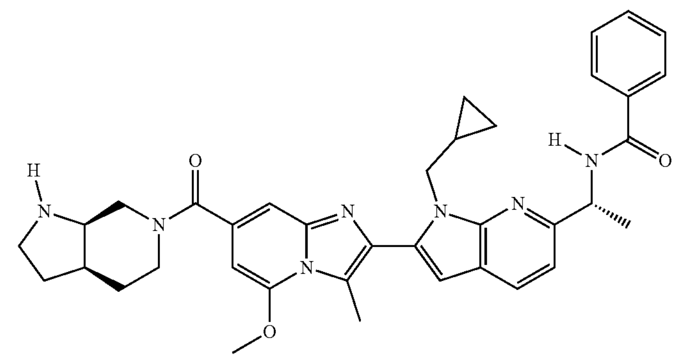 [SMILES: COc1cc(C(=O)N2CC[C@H]3CCN[C@H]3C2)cc2nc(-c3cc4ccc([C@@H](C)NC(=O)c5ccccc5)nc4n3CC3CC3)c(C)n12] | ~{N}-[(1~{R})-1-[2-[7-[(3~{a}~{R},7~{a}~{R})-1,2,3,3~{a},4,5,7,7~{a}-octahydropyrrolo[2,3-c]pyridine-6-carbonyl]-5-methoxy-3-methylimidazo[1,2-a]pyridin-2-yl]-1-(cyclopropylmethyl)pyrrolo[2,3-b]pyridin-6-yl]ethyl]benzamide |
| 60 | 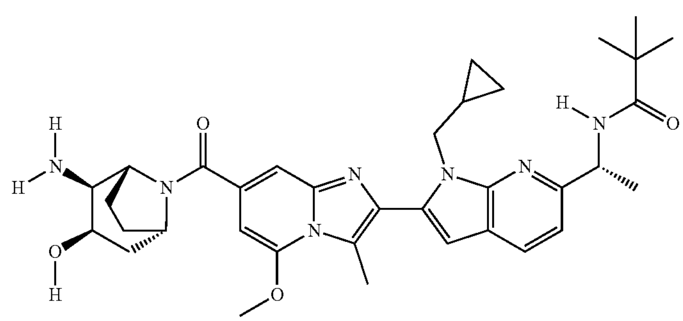 [SMILES: COc1cc(C(=O)N2[C@H]3CC[C@@H]2[C@H](N)[C@H](O)C3)cc2nc(-c3cc4ccc([C@@H](C)NC(=O)C(C)(C)C)nc4n3CC3CC3)c(C)n12] | ~{N}-[(1~{R})-1-[2-[7-[(1~{R},2~{S},3~{R},5~{S})-2-amino-3-hydroxy-8-azabicyclo[3.2.1]octane-8-carbonyl]-5-methoxy-3-methylimidazo[1,2-a]pyridin-2-yl]-1-(cyclopropylmethyl)pyrrolo[2,3-b]pyridin-6-yl]ethyl]-2,2-dimethylpropanamide |
| 61 | 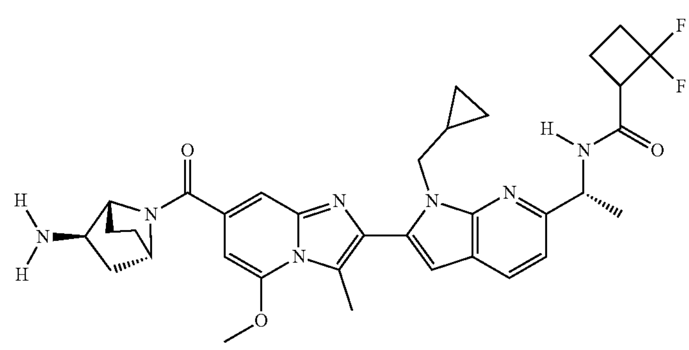 [SMILES: COc1cc(C(=O)N2[C@H]3CC[C@@H]2[C@H](N)C3)cc2nc(-c3cc4ccc([C@@H](C)NC(=O)C5CCC5(F)F)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2,2-difluorocyclobutane-1-carboxamide |

-continued

| Ex | Structure | Name |
|---|---|---|
| 62 | 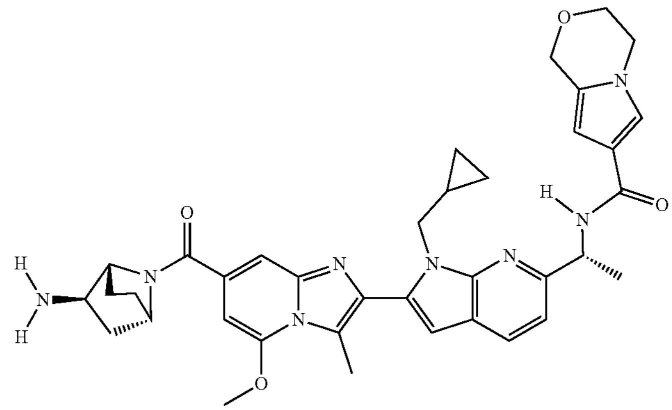 [SMILES: COc1cc(C(=O)N2[C@H]3CC[C@@H]2[C@H](N)C3)cc2nc(-c3cc4ccc([C@@H](C)NC(=O)c5cc6n(c5)CCOC6)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3,4-dihydro-1~{H}-pyrrolo[2,1-c][1,4]oxazine-7-carboxamide |
| 63 | 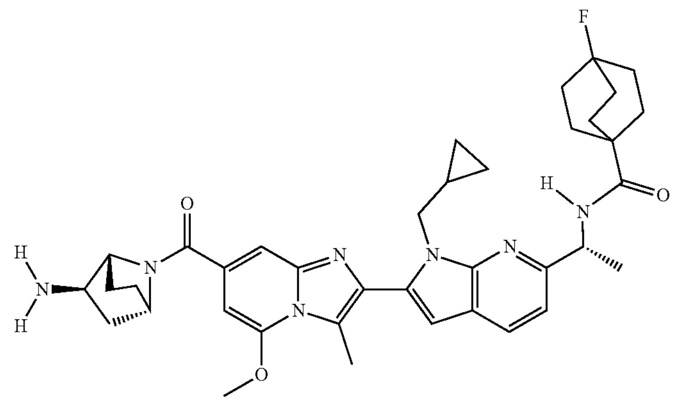 [SMILES: COc1cc(C(=O)N2[C@H]3CC[C@@H]2[C@H](N)C3)cc2nc(-c3cc4ccc([C@@H](C)NC(=O)C56CCC(F)(CC5)CC6)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-4-fluorobicyclo[2.2.2]octane-1-carboxamide |
| 64 | 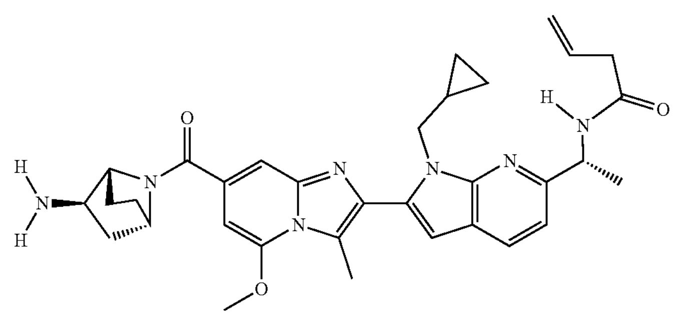 [SMILES: C=CCC(=O)N[C@H](C)c1ccc2cc(-c3nc4cc(C(=O)N5[C@H]6CC[C@@H]5[C@H](N)C6)cc(OC)n4c3C)n(CC3CC3)c2n1] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]but-3-enamide |
| 65 | 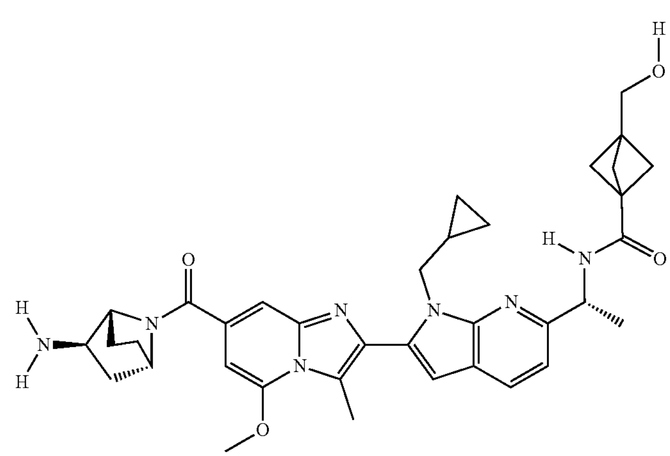 [SMILES: COc1cc(C(=O)N2[C@H]3CC[C@@H]2[C@H](N)C3)cc2nc(-c3cc4ccc([C@@H](C)NC(=O)C56CC(CO)(C5)C6)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-(hydroxymethyl)bicyclo[1.1.1]pentane-1-carboxamide |

| Ex | Structure | Name |
|---|---|---|
| 66 | 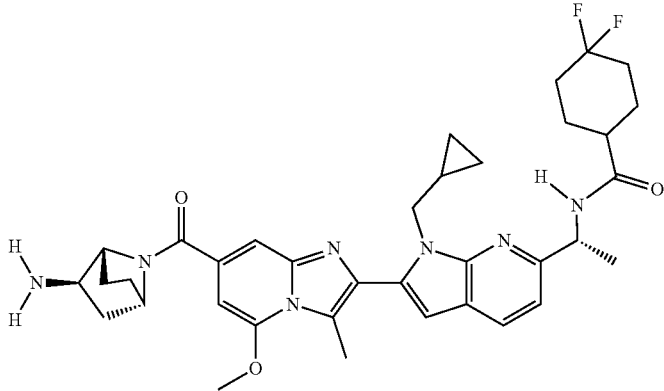 [SMILES: COc1cc(C(=O)N2[C@H]3CC[C@@H]2[C@H](N)C3)cc2nc(-c3cc4ccc([C@@H](C)NC(=O)C5CCC(F)(F)CC5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-4,4-difluorocyclohexane-1-carboxamide |
| 67 | 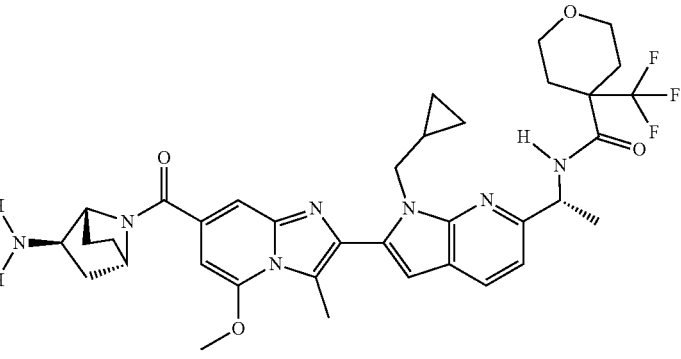 | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-4-(trifluoromethyl)oxane-4-carboxamide |
| 68 | 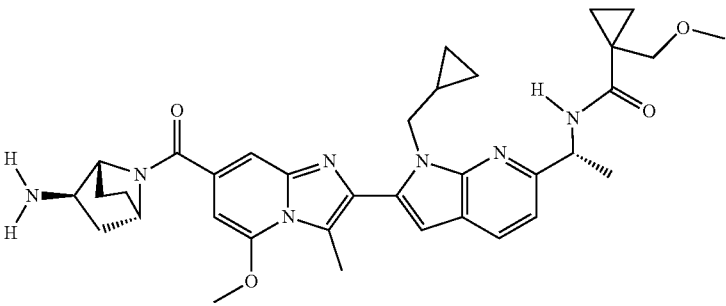 [SMILES: COCC1(C(=O)N[C@H](C)c2ccc3cc(-c4nc5cc(C(=O)N6[C@H]7CC[C@@H]6[C@H](N)C7)cc(OC)n5c4C)n(CC4CC4)c3n2)CC1] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1-(methoxymethyl)cyclopropane-1-carboxamide |
| 69 | 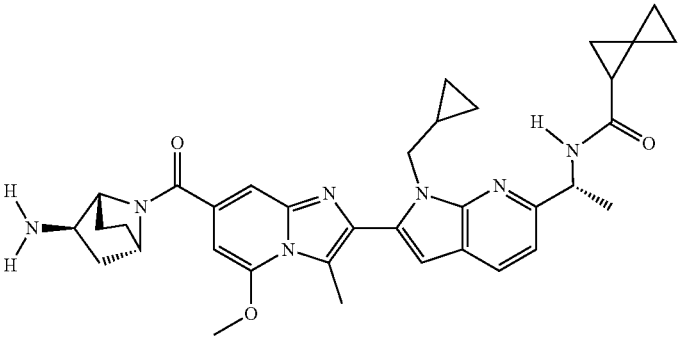 [SMILES: COc1cc(C(=O)N2[C@H]3CC[C@@H]2[C@H](N)C3)cc2nc(-c3cc4ccc([C@@H](C)NC(=O)C5CC56CC6)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]spiro[2.2]pentane-2-carboxamide |

-continued

| Ex | Structure | Name |
|---|---|---|
| 70 | 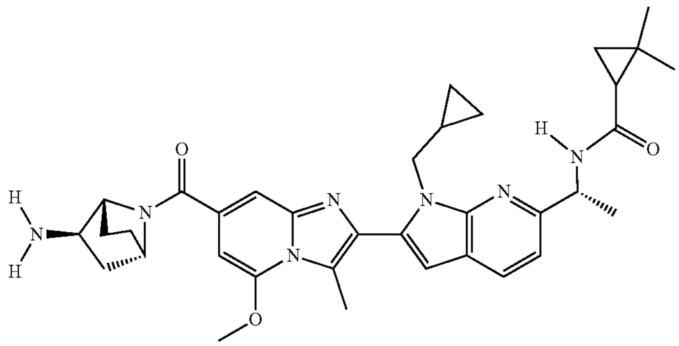 [SMILES: COc1cc(C(=O)N2[C@H]3CC[C@@H]2[C@H](N)C3)cc2nc(-c3cc4ccc([C@@H](C)NC(=O)C5CC5(C)C)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-ylethyl]-2,2-dimethylcyclopropane-1-carboxamide |
| 71 | 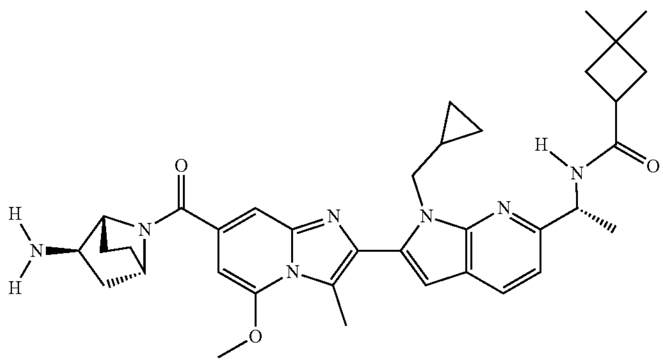 [SMILES: COc1cc(C(=O)N2[C@H]3CC[C@@H]2[C@H](N)C3)cc2nc(-c3cc4ccc([C@@H](C)NC(=O)C5CC(C)(C)C5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3,3-dimethylcyclobutane-1-carboxamide |
| 72 | 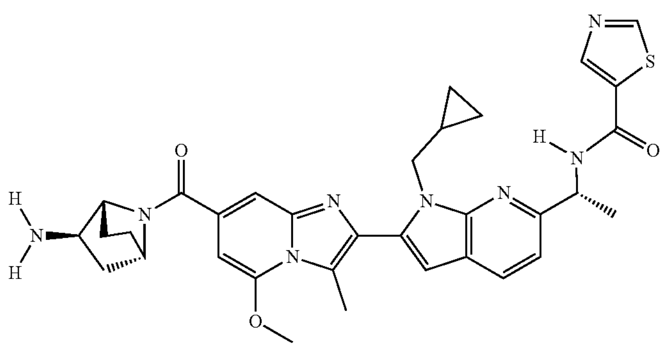 [SMILES: COc1cc(C(=O)N2[C@H]3CC[C@@H]2[C@H](N)C3)cc2nc(-c3cc4ccc([C@@H](C)NC(=O)c5cncs5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1,3-thiazole-5-carboxamide |
| 73 | 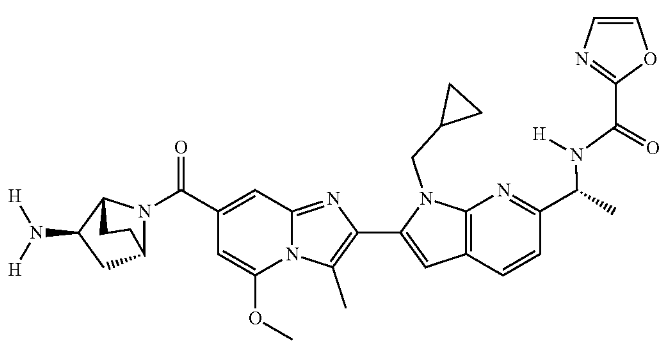 [SMILES: COc1cc(C(=O)N2[C@H]3CC[C@@H]2[C@H](N)C3)cc2nc(-c3cc4ccc([C@@H](C)NC(=O)c5ncco5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1,3-oxazole-2-carboxamide |

| Ex | Structure | Name |
|---|---|---|
| 74 | 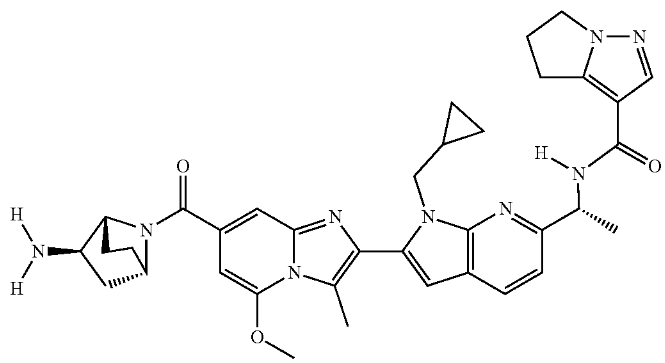 [SMILES: COc1cc(C(=O)N2[C@H]3CC[C@@H]2[C@H](N)C3)cc2nc(-c3cc4ccc([C@@H](C)NC(=O)c5cnn6c5CCC6)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-5,6-dihydro-4~{H}-pyrrolo[1,2-b]pyrazole-3-carboxamide |
| 75 | 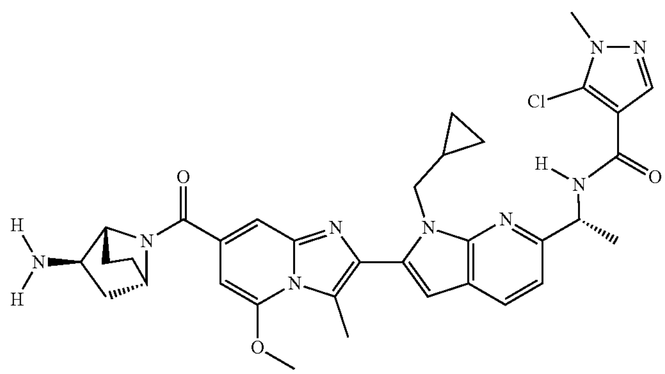 [SMILES: COc1cc(C(=O)N2[C@H]3CC[C@@H]2[C@H](N)C3)cc2nc(-c3cc4ccc([C@@H](C)NC(=O)c5cnn(C)c5Cl)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-5-chloro-1-methylpyrazole-4-carboxamide |
| 76 | 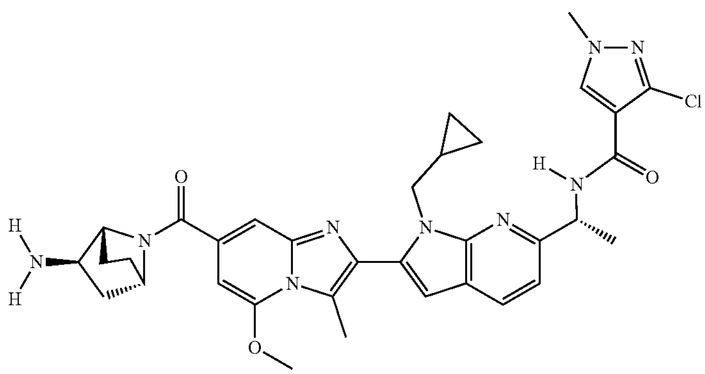 [SMILES: COc1cc(C(=O)N2[C@H]3CC[C@@H]2[C@H](N)C3)cc2nc(-c3cc4ccc([C@@H](C)NC(=O)c5cn(C)nc5Cl)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-chloro-1-methylpyrazole-4-carboxamide |
| 77 | 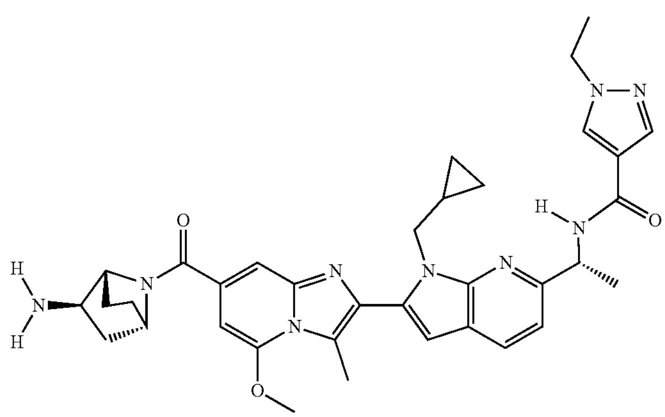 [SMILES: CCn1cc(C(=O)N[C@H](C)c2ccc3cc(-c4nc5cc(C(=O)N6[C@H]7CC[C@@H]6[C@H](N)C7)cc(OC)n5c4C)n(CC4CC4)c3n2)cn1] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1-ethylpyrazole-4-carboxamide |

-continued

| Ex | Structure | Name |
|---|---|---|
| 78 | 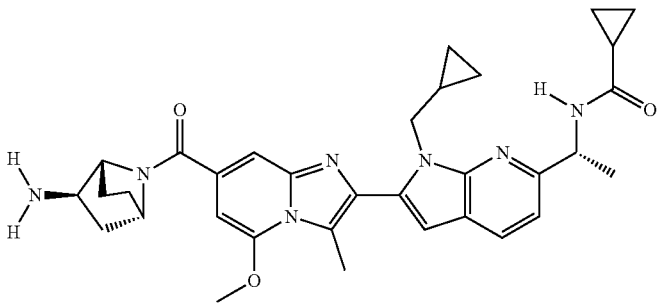 [SMILES: COc1cc(C(=O)N2[C@H]3CC[C@@H]2[C@H](N)C3)cc2nc(-c3cc4ccc([C@@H](C)NC(=O)C5CC5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]cyclopropanecarboxamide |
| 79 | 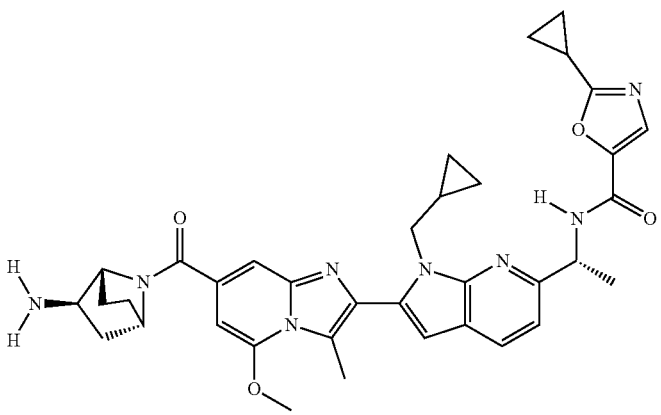 [SMILES: COc1cc(C(=O)N2[C@H]3CC[C@@H]2[C@H](N)C3)cc2nc(-c3cc4ccc([C@@H](C)NC(=O)c5cnc(C6CC6)o5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2-cyclopropyl-1,3-oxazole-5-carboxamide |
| 80 | 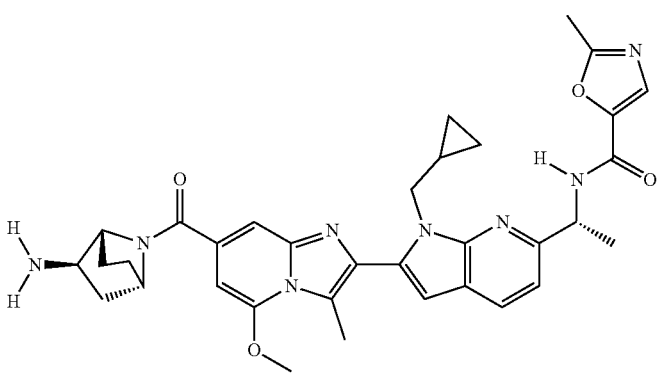 [SMILES: COc1cc(C(=O)N2[C@H]3CC[C@@H]2[C@H](N)C3)cc2nc(-c3cc4ccc([C@@H](C)NC(=O)c5cnc(C)o5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2-methyl-1,3-oxazole-5-carboxamide |
| 81 | 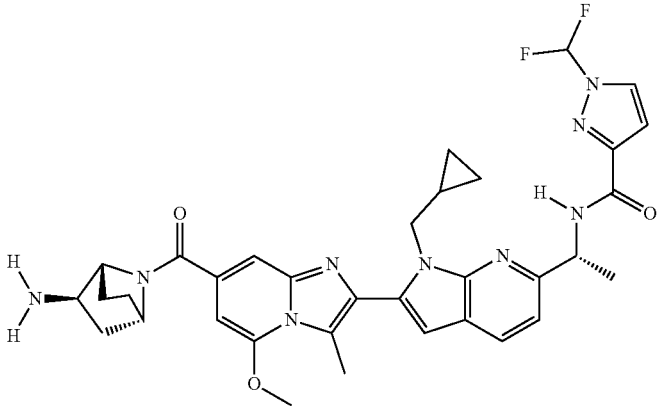 [SMILES: COc1cc(C(=O)N2[C@H]3CC[C@@H]2[C@H](N)C3)cc2nc(-c3cc4ccc([C@@H](C)NC(=O)c5ccn(C(F)F)n5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1-(difluoromethyl)pyrazole-3-carboxamide |

-continued

| Ex | Structure | Name |
|---|---|---|
| 82 | 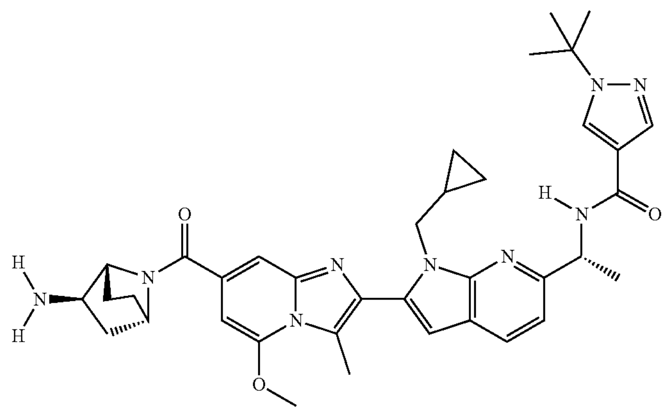 [SMILES: COc1cc(C(=O)N2[C@H]3CC[C@@H]2[C@H](N)C3)cc2nc(-c3cc4ccc([C@@H](C)NC(=O)c5cnn(C(C)(C)C)c5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1-~{tert}-butylpyrazole-4-carboxamide |
| 83 | 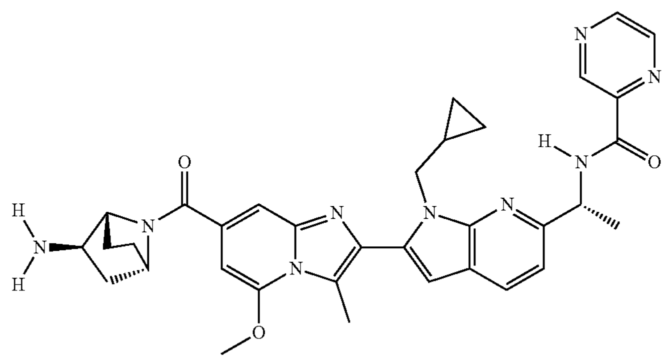 [SMILES: COc1cc(C(=O)N2[C@H]3CC[C@@H]2[C@H](N)C3)cc2nc(-c3cc4ccc([C@@H](C)NC(=O)c5cnccn5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-ylethyl]pyrazine-2-carboxamide |
| 84 | 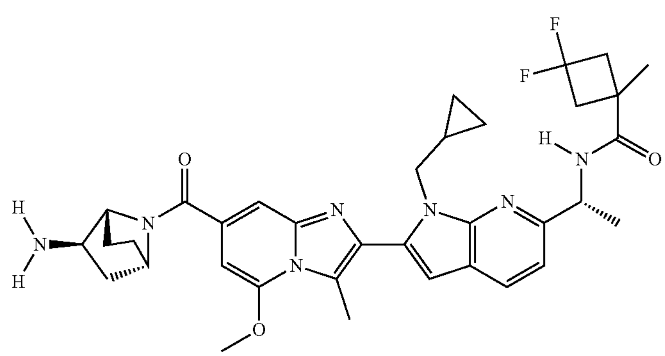 [SMILES: COc1cc(C(=O)N2[C@H]3CC[C@@H]2[C@H](N)C3)cc2nc(-c3cc4ccc([C@@H](C)NC(=O)C5(C)CC(F)(F)C5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3,3-difluoro-1-methylcyclobutane-1-carboxamide |
| 85 | 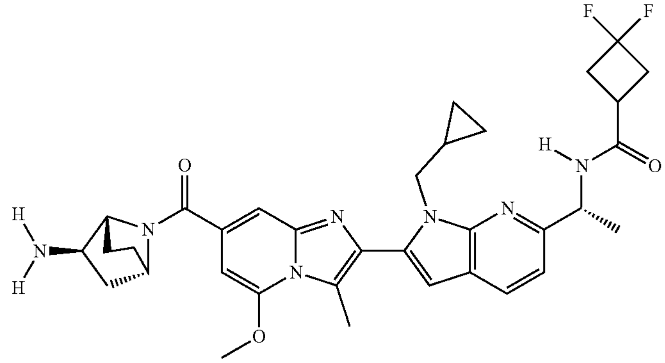 [SMILES: COc1cc(C(=O)N2[C@H]3CC[C@@H]2[C@H](N)C3)cc2nc(-c3cc4ccc([C@@H](C)NC(=O)C5CC(F)(F)C5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3,3-difluorocyclobutane-1-carboxamide |

| Ex | Structure | Name |
|---|---|---|
| 86 | 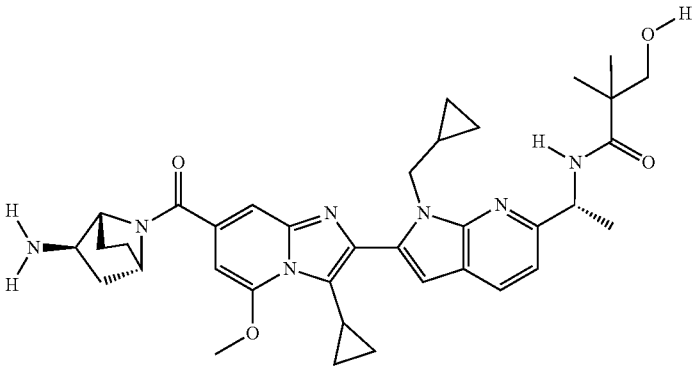 [SMILES: COc1cc(C(=O)N2[C@H]3CC[C@@H]2[C@H](N)C3)cc2nc(-c3cc4ccc([C@@H](C)NC(=O)C(C)(C)CO)nc4n3CC3CC3)c(C3CC3)n12] | ~{N}-[(1~{R})-1-[2-[7-[(1~{R},2~{R},4~{S})-2-amino-7-azabicyclo[2.2.1]heptane-7-carbonyl]-3-cyclopropyl-5-methoxyimidazo[1,2-a]pyridin-2-yl]-1-(cyclopropylmethyl)pyrrolo[2,3-b]pyridin-6-yl]ethyl]-3-hydroxy-2,2-dimethylpropanamide |
| 87 | 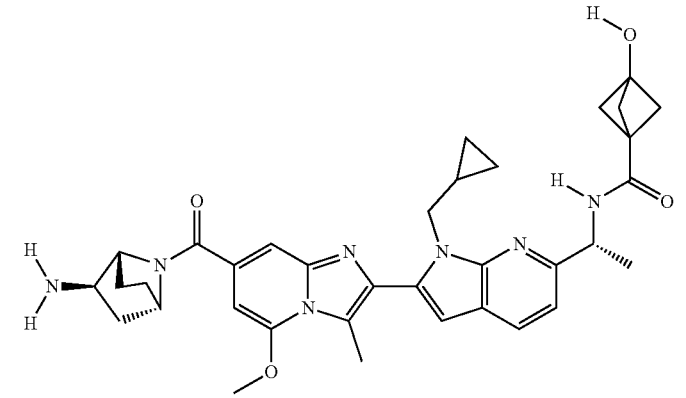 [SMILES: COc1cc(C(=O)N2[C@H]3CC[C@@H]2[C@H](N)C3)cc2nc(-c3cc4ccc([C@@H](C)NC(=O)C56CC(O)(C5)C6)nc4n3CC3CC3)c(C)n12] | [(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-hydroxybicyclo[1.1.1]pentane-1-carboxamide |
| 88 | 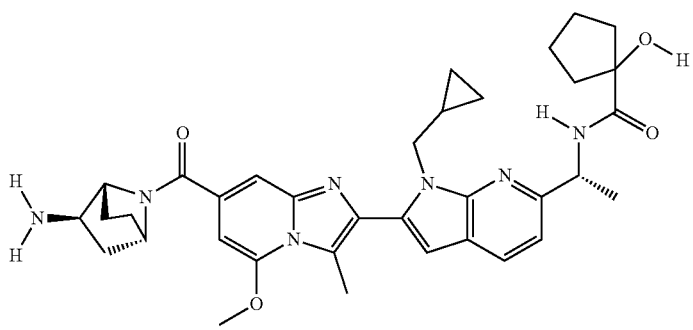 [SMILES: COc1cc(C(=O)N2[C@H]3CC[C@@H]2[C@H](N)C3)cc2nc(-c3cc4ccc([C@@H](C)NC(=O)C5(O)CCCC5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1-hydroxycyclopentane-1-carboxamide |
| 89 | 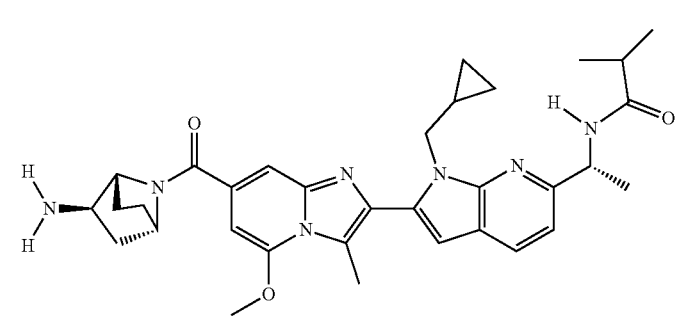 [SMILES: COc1cc(C(=O)N2[C@H]3CC[C@@H]2[C@H](N)C3)cc2nc(-c3cc4ccc([C@@H](C)NC(=O)C(C)C)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2-methylpropanamide |

| Ex | Structure | Name |
|---|---|---|
| 90 | 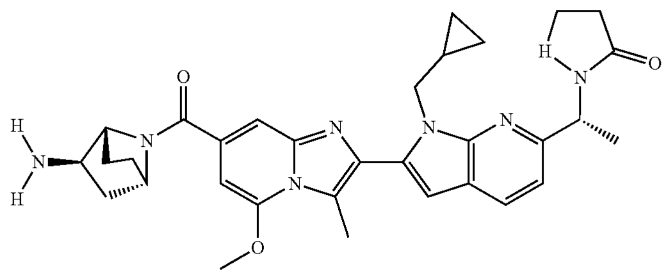 | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]butanamide |
| 91 | 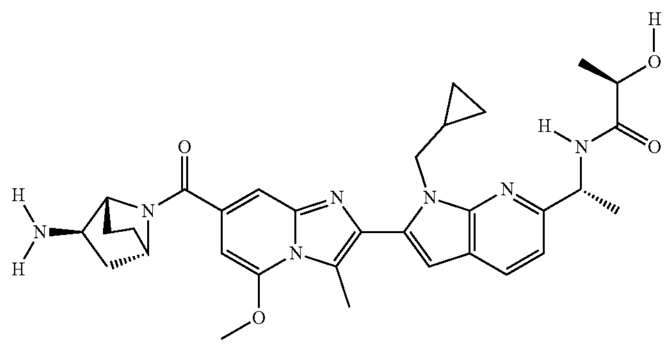 [SMILES: COc1cc(C(=O)N2[C@H]3CC[C@@H]2[C@H](N)C3)cc2nc(-c3cc4ccc([C@@H](C)NC(=O)[C@@H](C)O)nc4n3CC3CC3)c(C)n12] | (2~{R})-~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2-hydroxypropanamide |
| 92 | 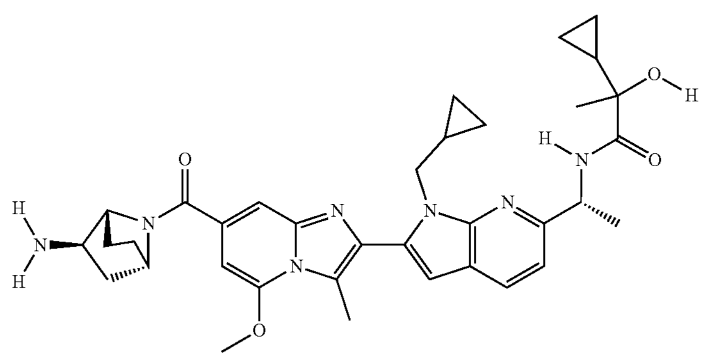 [SMILES: COc1cc(C(=O)N2[C@H]3CC[C@@H]2[C@H](N)C3)cc2nc(-c3cc4ccc([C@@H](C)NC(=O)C(C)(O)C5CC5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2-cyclopropyl-2-hydroxypropanamide |
| 93 | 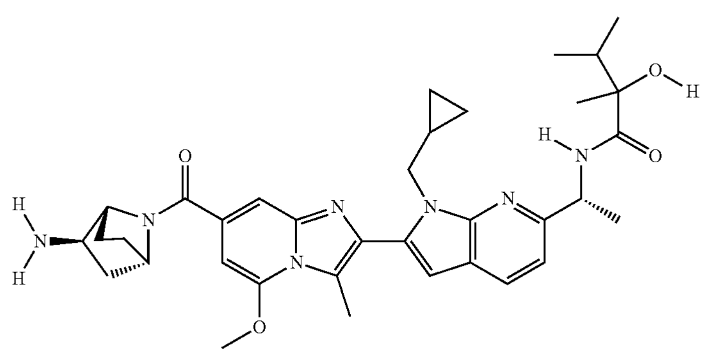 [SMILES: COc1cc(C(=O)N2[C@H]3CC[C@@H]2[C@H](N)C3)cc2nc(-c3cc4ccc([C@@H](C)NC(=O)C(C)(O)C(C)C)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2-hydroxy-2,3-dimethylbutanamide |

-continued

| Ex | Structure | Name |
|---|---|---|
| 94 | 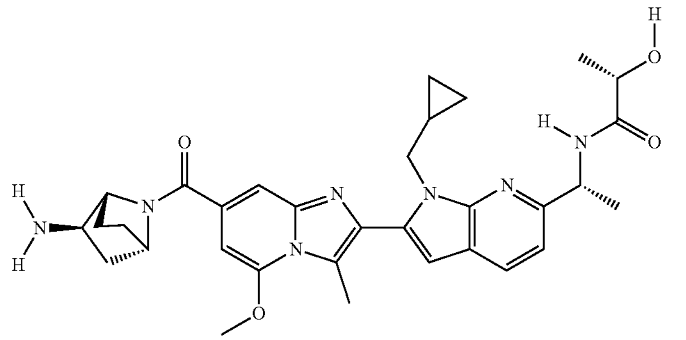 [SMILES: COc1cc(C(=O)N2[C@H]3CC[C@@H]2[C@H](N)C3)cc2nc(-c3cc4ccc([C@@H](C)NC(=O)[C@H](C)O)nc4n3CC3CC3)c(C)n12] | (2~{S})-~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2-hydroxypropanamide |
| 95 | 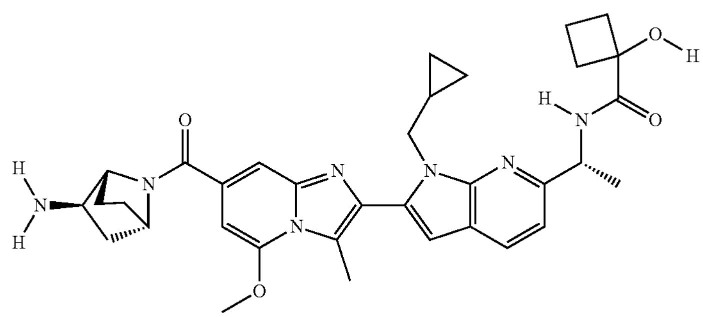 [SMILES: COc1cc(C(=O)N2[C@H]3CC[C@@H]2[C@H](N)C3)cc2nc(-c3cc4ccc([C@@H](C)NC(=O)C5(O)CCC5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1-hydroxycyclobutane-1-carboxamide |
| 96 | 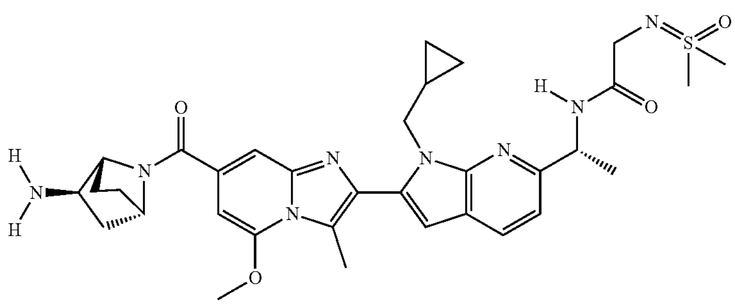 [SMILES: COc1cc(C(=O)N2[C@H]3CC[C@@H]2[C@H](N)C3)cc2nc(-c3cc4ccc([C@@H](C)NC(=O)CN=S(C)(C)=O)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2-[dimethyl(oxo)-$l^{6}$-sulfanylidene]amino]acetamide |
| 97 | 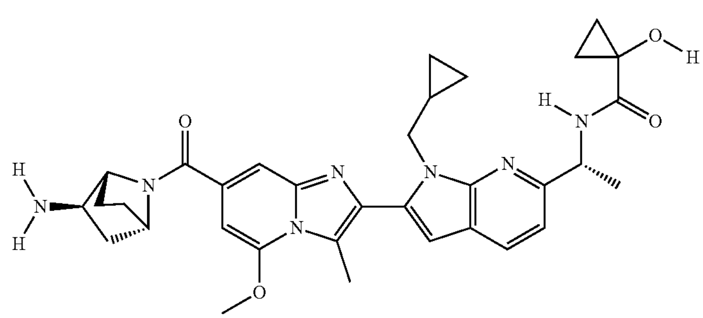 [SMILES: COc1cc(C(=O)N2[C@H]3CC[C@@H]2[C@H](N)C3)cc2nc(-c3cc4ccc([C@@H](C)NC(=O)C5(O)CC5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1-hydroxycyclopropane-1-carboxamide |

| Ex | Structure | Name |
|---|---|---|
| 98 | 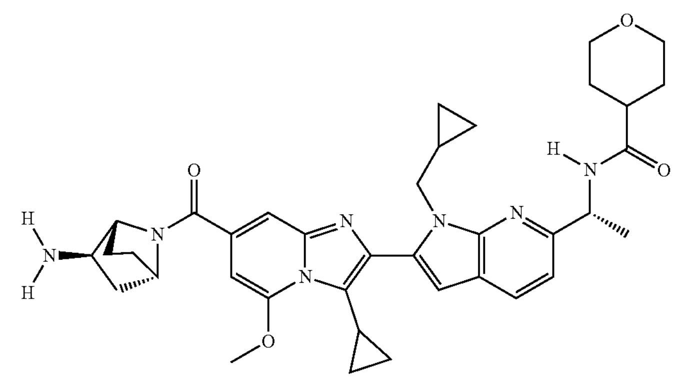 [SMILES: COc1cc(C(=O)N2[C@H]3CC[C@@H]2[C@H](N)C3)cc2nc(-c3cc4ccc([C@@H](C)NC(=O)C5CCOCC5)nc4n3CC3CC3)c(C3CC3)n12] | [(1~{R},2~{R},4~{S})-2-amino-7-azabicyclo[2.2.1]heptane-7-carbonyl]-3-cyclopropyl-5-methoxyimidazo[1,2-a]pyridin-2-yl]-1-(cyclopropylmethyl)pyrrolo[2,3-b]pyridin-6-yl]ethyl]oxane-4-carboxamide |
| 99 | 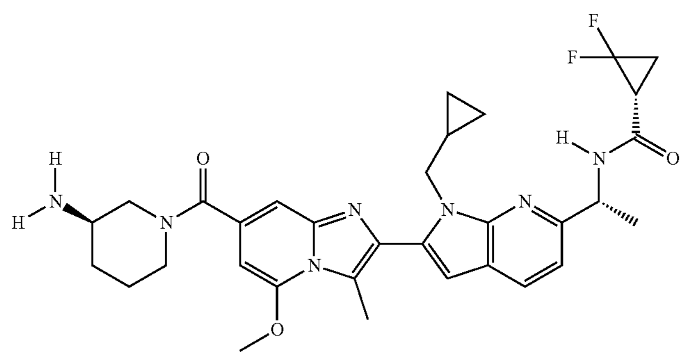 [SMILES: COc1cc(C(=O)N2CCC[C@@H](N)C2)cc2nc(-c3cc4ccc([C@@H](C)NC(=O)[C@H]5CC5(F)F)nc4n3CC3CC3)c(C)n12] | (1~{R})-~{N}-[(1~{R})-1-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]ethyl]-2,2-difluorocyclopropane-1-carboxamide |
| 100 | 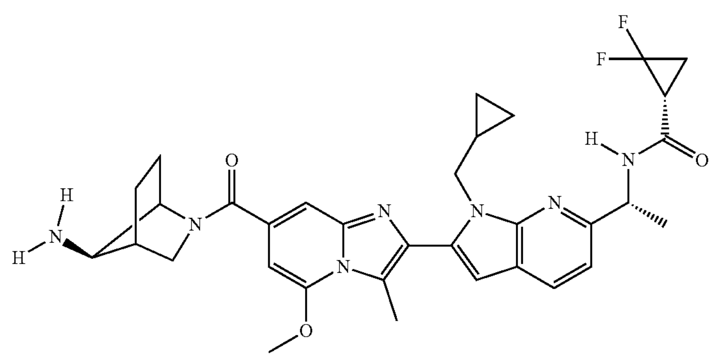 [SMILES: COc1cc(C(=O)N2CC3CCC2[C@@H]3N)cc2nc(-c3cc4ccc([C@@H](C)NC(=O)[C@H]5CC5(F)F)nc4n3CC3CC3)c(C)n12] | (R)-N-((R)-1-(2-(7-((1R,4R,7R)-7-amino-2-azabicyclo[2.2.1]heptane-2-carbonyl)-5-methoxy-3-methylimidazo[1,2-a]pyridin-2-yl)-1-(cyclopropylmethyl)-1H-pyrrolo[2,3-b]pyridin-6-yl)ethyl)-2,2-difluorocyclopropane-1-carboxamide |
| 101 | 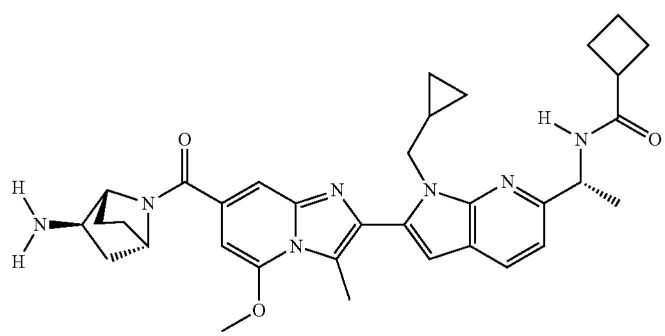 [SMILES: COc1cc(C(=O)N2[C@H]3CC[C@@H]2[C@H](N)C3)cc2nc(-c3cc4ccc([C@@H](C)NC(=O)C5CCC5)nc4n3CC3CC3)c(C)n12] | [(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]cyclobutanecarboxamide |

| Ex | Structure | Name |
|---|---|---|
| 102 | 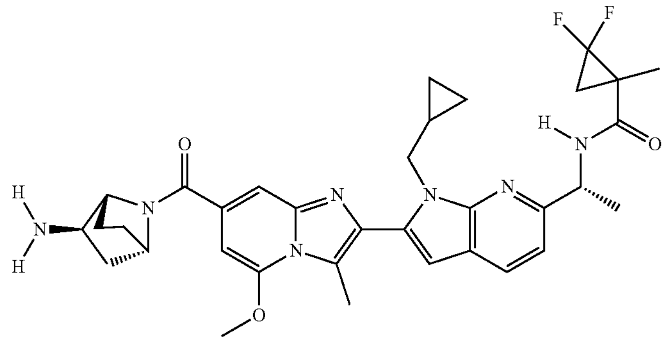 [SMILES: COc1cc(C(=O)N2[C@H]3CC[C@@H]2[C@H](N)C3)cc2nc(-c3cc4ccc([C@@H](C)NC(=O)C5(C)CC5(F)F)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2,2-difluoro-1-methylcyclopropane-1-carboxamide |
| 103 | 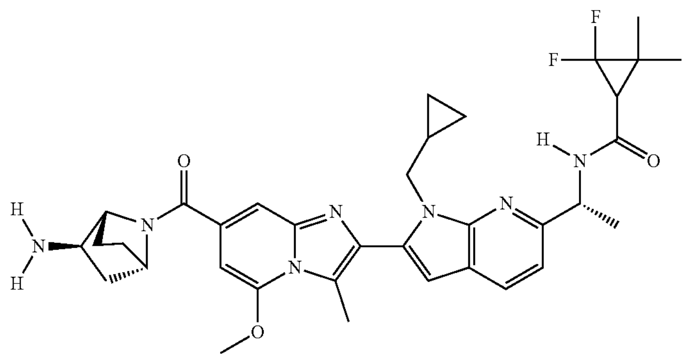 [SMILES: COc1cc(C(=O)N2[C@H]3CC[C@@H]2[C@H](N)C3)cc2nc(-c3cc4ccc([C@@H](C)NC(=O)C5C(C)(C)C5(F)F)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2,2-difluoro-3,3-dimethylcyclopropane-1-carboxamide |
| 104 | 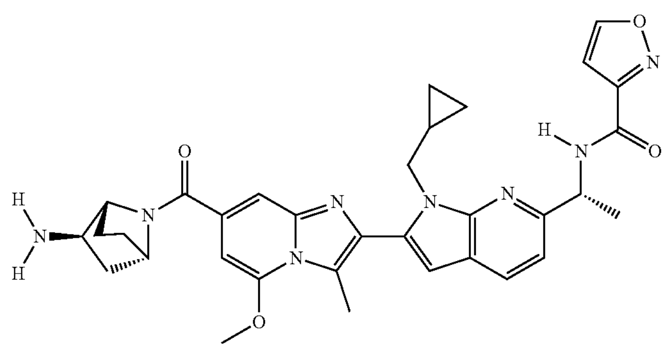 [SMILES: COc1cc(C(=O)N2[C@H]3CC[C@@H]2[C@H](N)C3)cc2nc(-c3cc4ccc([C@@H](C)NC(=O)c5ccon5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1,2-oxazole-3-carboxamide |
| 105 | 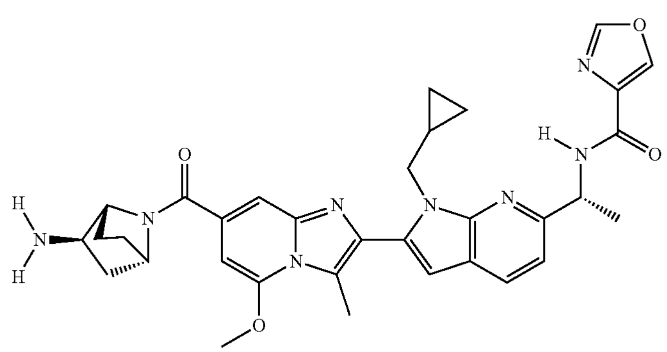 [SMILES: COc1cc(C(=O)N2[C@H]3CC[C@@H]2[C@H](N)C3)cc2nc(-c3cc4ccc([C@@H](C)NC(=O)c5cocn5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1,3-oxazole-4-carboxamide |

-continued

| Ex | Structure | Name |
|---|---|---|
| 106 | 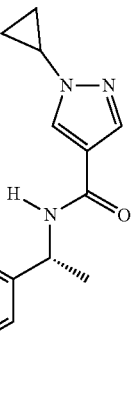 | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1-cyclopropylpyrazole-4-carboxamide |
| 107 | 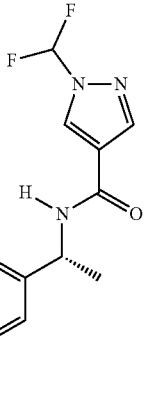 | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-ylethyl]-1-(difluoromethyl)pyrazole-4-carboxamide |
| 108 | 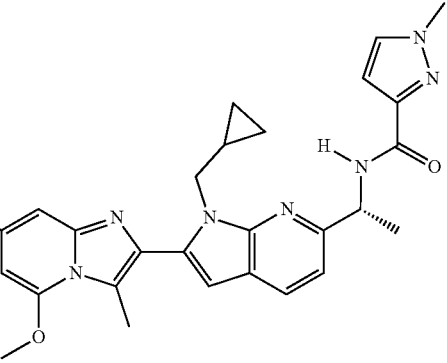 | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1-methylpyrazole-3-carboxamide |
| 109 | 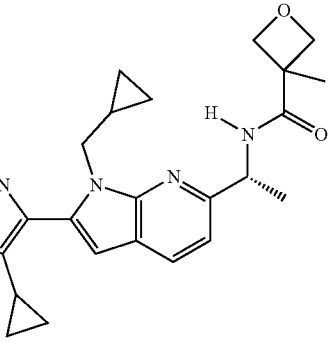 | ~{N}-[(1~{R})-1-[2-[7-[(1~{R},2~{R},4~{S})-2-amino-7-azabicyclo[2.2.1]heptane-7-carbonyl]-3-cyclopropyl-5-methoxyimidazo[1,2-a]pyridin-2-yl]-1-(cyclopropylmethyl)pyrrolo[2,3-b]pyridin-6-yl]ethyl]-3-methyloxetane-3-carboxamide |

-continued

| Ex | Structure | Name |
|---|---|---|
| 110 | 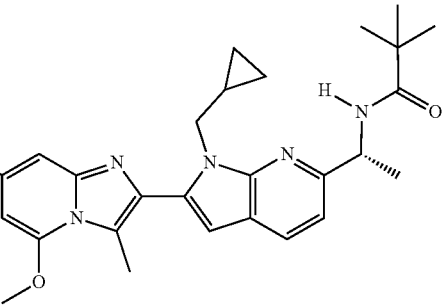 | ~{N}-[(1~{R})-1-[1-(cyclopropylmethyl)-2-[5-methoxy-3-methyl-7-5-oxa-3,11-diazatricyclo[6.2.1.0^{2,6}]undecane-11-carbonyl]imidazo[1,2-a]pyridin-2-yl]pyrrolo[2,3-b]pyridin-6-yl]ethyl]-2,2-dimethylpropanamide |
| 111 | 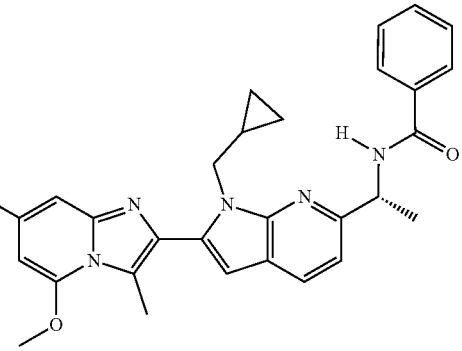 | ~{N}-[(1~{R})-1-[2-[7-[(3~{S},4~{R})-3-amino-4-propoxypiperidine-1-carbonyl]-5-methoxy-3-methylimidazo[1,2-a]pyridin-2-yl]-1-(cyclopropylmethyl)pyrrolo[2,3-b]pyridin-6-yl]ethyl]benzamide |
| 112 | 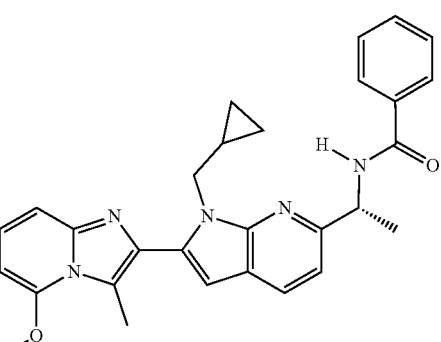 | ~{N}-[(1~{R})-1-[2-[7-[(3~{S},4~{R})-3-amino-4-ethoxypiperidine-1-carbonyl]-5-methoxy-3-methylimidazo[1,2-a]pyridin-2-yl]-1-(cyclopropylmethyl)pyrrolo[2,3-b]pyridin-6-yl]ethyl]benzamide |
| 113 | 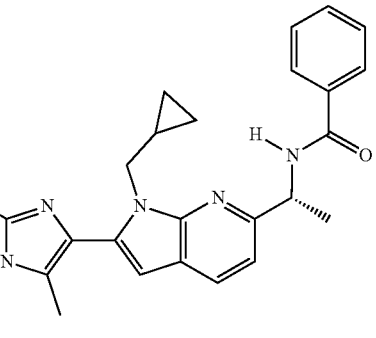 | 2-[6-[(1~{R})-1-benzamidoethyl]-1-(cyclopropylmethyl)pyrrolo[2,3-b]pyridin-2-yl]-5-methoxy-3-methylimidazo[1,2-a]pyridine-7-carboxamide |

| Ex | Structure | Name |
|---|---|---|
| 114 | 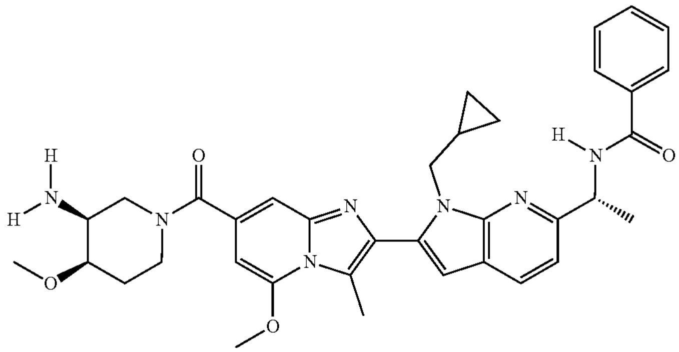 [SMILES: COc1cc(C(=O)N2CC[C@@H](OC)[C@@H](N)C2)cc2nc(-c3cc4ccc([C@@H](C)NC(=O)c5ccccc5)nc4n3CC3CC3)c(C)n12] | ~{N}-[(1~{R})-1-[2-[7-[(3~{S},4~{R})-3-amino-4-methoxypiperidine-1-carbonyl]-5-methoxy-3-methylimidazo[1,2-a]pyridin-2-yl]-1-(cyclopropylmethyl)pyrrolo[2,3-b]pyridin-6-yl]ethyl]benzamide |
| 115 | 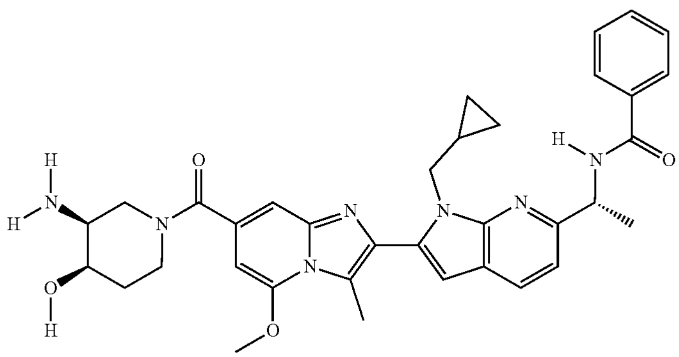 [SMILES: COc1cc(C(=O)N2CC[C@@H](O)[C@@H](N)C2)cc2nc(-c3cc4ccc([C@@H](C)NC(=O)c5ccccc5)nc4n3CC3CC3)c(C)n12] | ~{N}-[(1~{R})-1-[2-[7-[(3~{S},4~{R})-3-amino-4-hydroxypiperidine-1-carbonyl]-5-methoxy-3-methylimidazo[1,2-a]pyridin-2-yl]-1-(cyclopropylmethyl)pyrrolo[2,3-b]pyridin-6-yl]ethyl]benzamide |
| 116 | 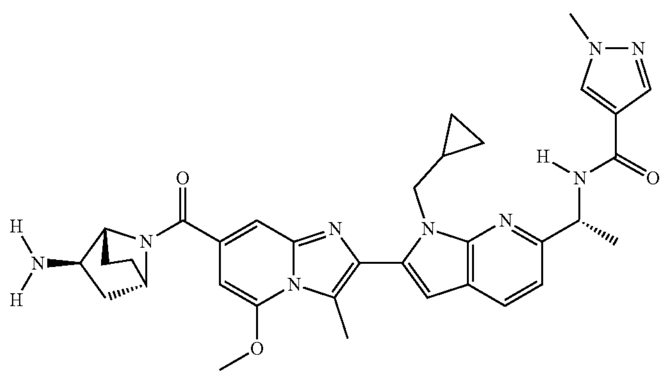 [SMILES: COc1cc(C(=O)N2[C@H]3CC[C@@H]2[C@H](N)C3)cc2nc(-c3cc4ccc([C@@H](C)NC(=O)c5cnn(C)c5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1-methylpyrazole-4-carboxamide |
| 117 | 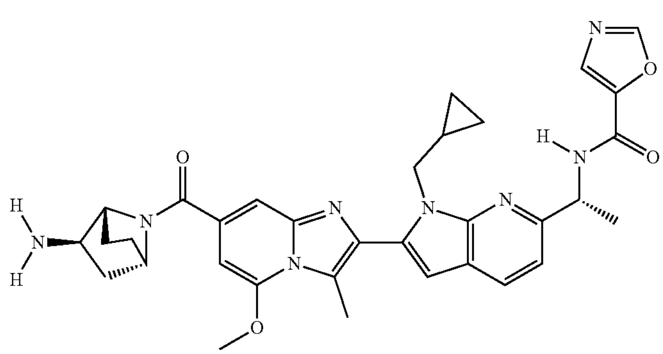 [SMILES: COc1cc(C(=O)N2[C@H]3CC[C@@H]2[C@H](N)C3)cc2nc(-c3cc4ccc([C@@H](C)NC(=O)c5cnco5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1,3-oxazole-5-carboxamide |

-continued

| Ex | Structure | Name |
|---|---|---|
| 118 | 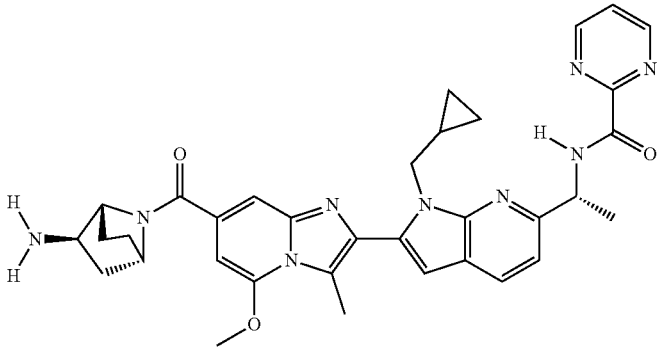 [SMILES: COc1cc(C(=O)N2[C@H]3CC[C@@H]2[C@H](N)C3)cc2nc(-c3cc4ccc([C@@H](C)NC(=O)c5ncccn5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]pyrimidine-2-carboxamide |
| 119 | 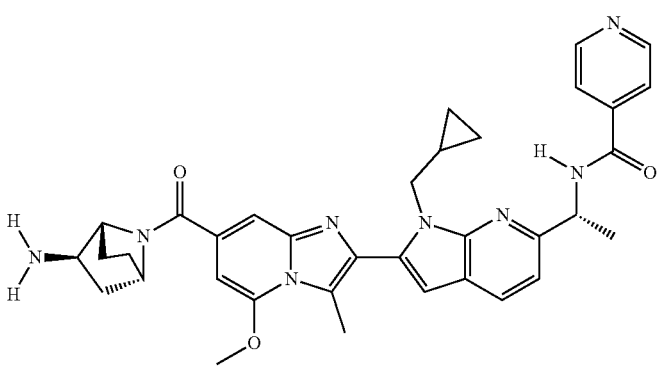 [SMILES: COc1cc(C(=O)N2[C@H]3CC[C@@H]2[C@H](N)C3)cc2nc(-c3cc4ccc([C@@H](C)NC(=O)c5ccncc5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]pyridine-4-carboxamide |
| 120 | 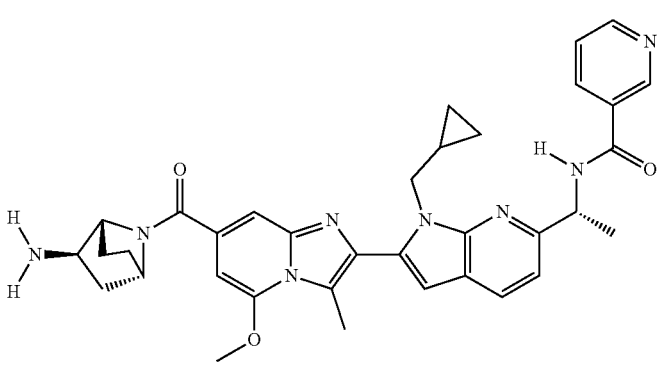 [SMILES: COc1cc(C(=O)N2[C@H]3CC[C@@H]2[C@H](N)C3)cc2nc(-c3cc4ccc([C@@H](C)NC(=O)c5cccnc5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]pyridine-3-carboxamide |
| 121 | 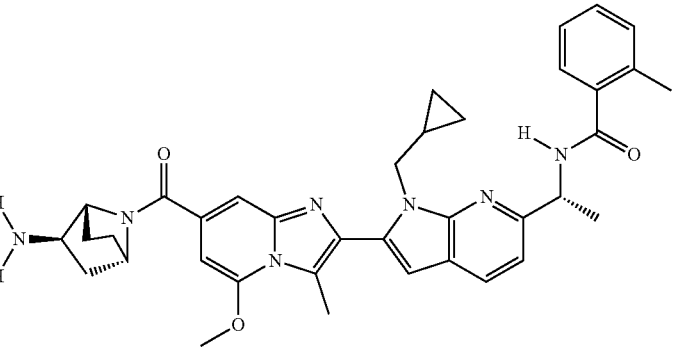 | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2-methylbenzamide |

-continued

| Ex | Structure | Name |
|---|---|---|
| 122 | 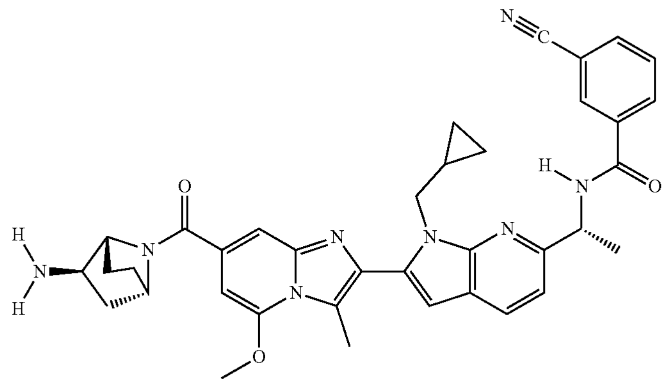 [SMILES: COc1cc(C(=O)N2[C@H]3CC[C@@H]2[C@H](N)C3)cc2nc(-c3cc4ccc([C@@H](C)NC(=O)c5cccc(C#N)c5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-cyanobenzamide |
| 123 | 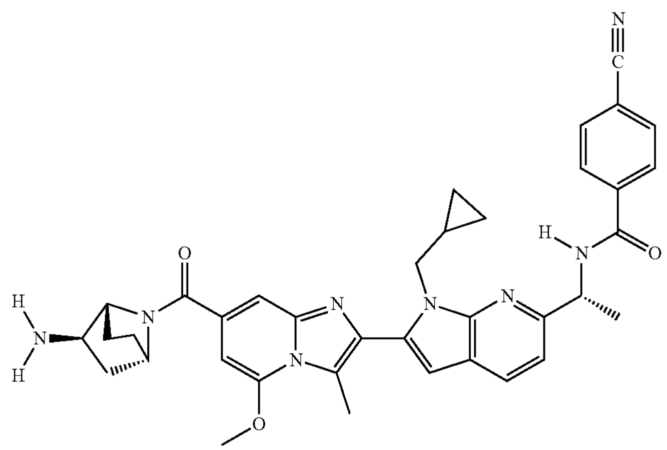 [SMILES: COc1cc(C(=O)N2[C@H]3CC[C@@H]2[C@H](N)C3)cc2nc(-c3cc4ccc([C@@H](C)NC(=O)c5ccc(C#N)cc5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-4-cyanobenzamide |
| 124 | 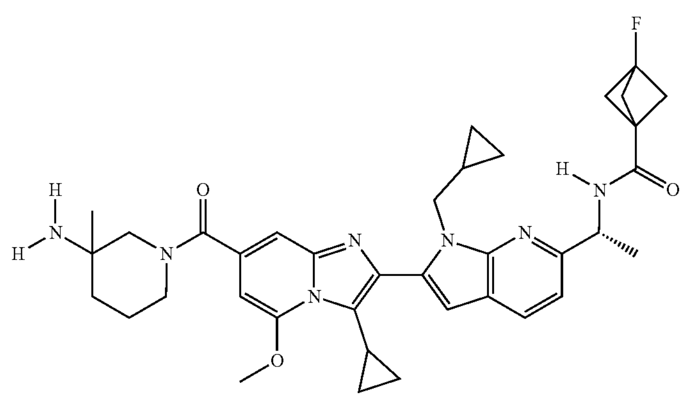 [SMILES: COc1cc(C(=O)N2CCCC(C)(N)C2)cc2nc(-c3cc4ccc([C@@H](C)NC(=O)C56CC(F)(C5)C6)nc4n3CC3CC3)c(C3CC3)n12] | ~{N}-[(1~{R})-1-[2-[7-(3-amino-3-methylpiperidine-1-carbonyl)-3-cyclopropyl-5-methoxyimidazo[1,2-a]pyridin-2-yl]-1-(cyclopropylmethyl)pyrrolo[2,3-b]pyridin-6-yl]ethyl]-3-fluorobicyclo[1.1.1]pentane-1-carboxamide |
| 125 | 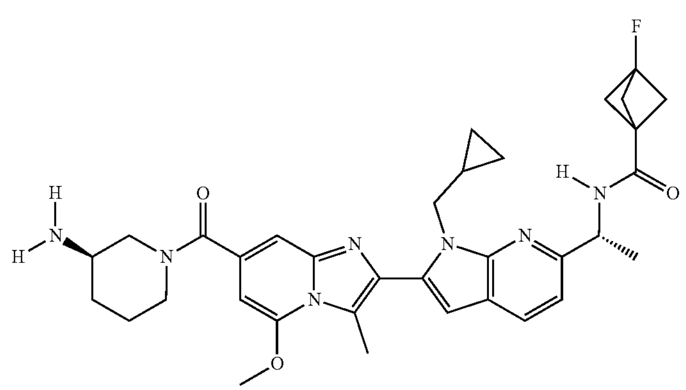 [SMILES: COc1cc(C(=O)N2CCC[C@@H](N)C2)cc2nc(-c3cc4ccc([C@@H](C)NC(=O)C56CC(F)(C5)C6)nc4n3CC3CC3)c(C)n12] | ~{N}-[(1~{R})-1-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]ethyl]-3-fluorobicyclo[1.1.1]pentane-1-carboxamide |

-continued

| Ex | Structure | Name |
|---|---|---|
| 126 | 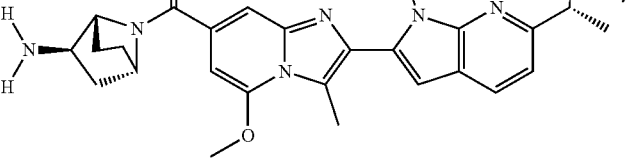 | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2-hydroxy-2-methylpropanamide |
| 127 | 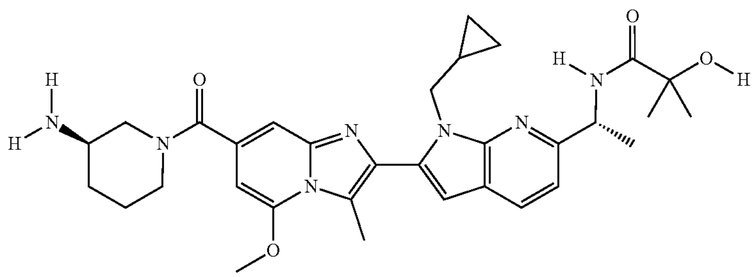 [SMILES: COc1cc(C(=O)N2CCC[C@@H](N)C2)cc2nc(-c3cc4ccc([C@@H](C)NC(=O)C(C)(C)O)nc4n3CC3CC3)c(C)n12] | ~{N}-[(1~{R})-1-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]ethyl]-2-hydroxy-2-methylpropanamide |
| 128 | 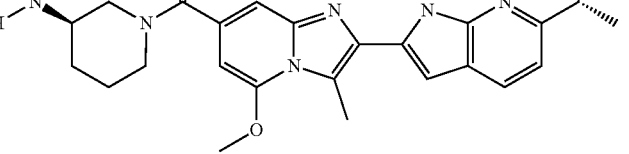 | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1-(hydroxymethyl)cyclopropane-1-carboxamide |
| 129 | 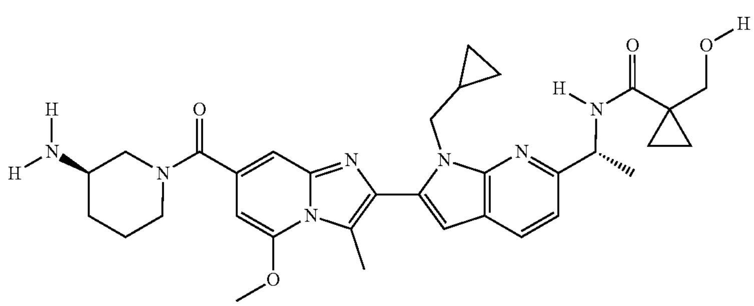 [SMILES: COc1cc(C(=O)N2CCC[C@@H](N)C2)cc2nc(-c3cc4ccc([C@@H](C)NC(=O)C5(CO)CC5)nc4n3CC3CC3)c(C)n12] | ~{N}-[(1~{R})-1-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]ethyl]-1-(hydroxymethyl)cyclopropane-1-carboxamide |
| 130 | 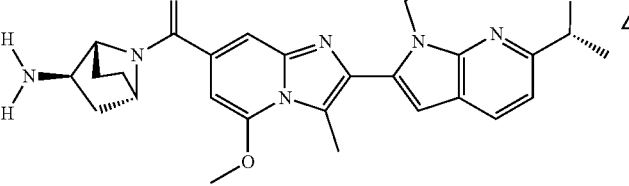 | (1~{S})-~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2,2-difluorocyclopropane-1-carboxamide |

| Ex | Structure | Name |
|---|---|---|
| 131 | 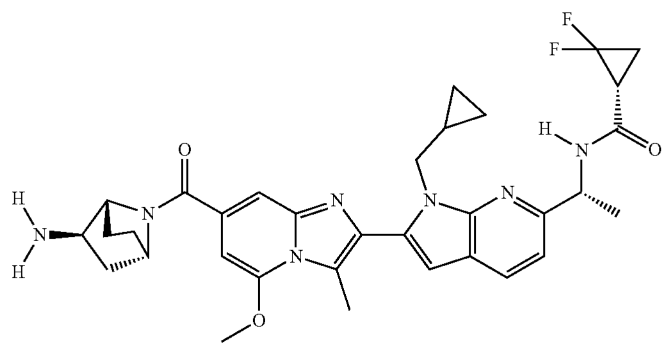 [SMILES: COc1cc(C(=O)N2[C@H]3CC[C@@H]2[C@H](N)C3)cc2nc(-c3cc4ccc([C@@H](C)NC(=O)[C@H]5CC5(F)F)nc4n3CC3CC3)c(C)n12] | (1~{R})-~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2,2-difluorocyclopropane-1-carboxamide |
| 132 | 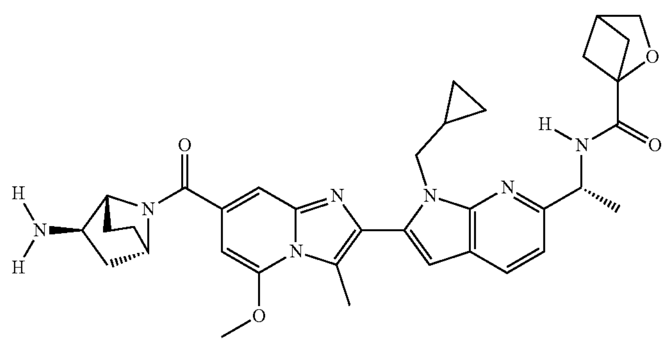 [SMILES: COc1cc(C(=O)N2[C@H]3CC[C@@H]2[C@H](N)C3)cc2nc(-c3cc4ccc([C@@H](C)NC(=O)C56CC(CO5)C6)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2-oxabicyclo[2.1.1]hexane-1-carboxamide |
| 133 | 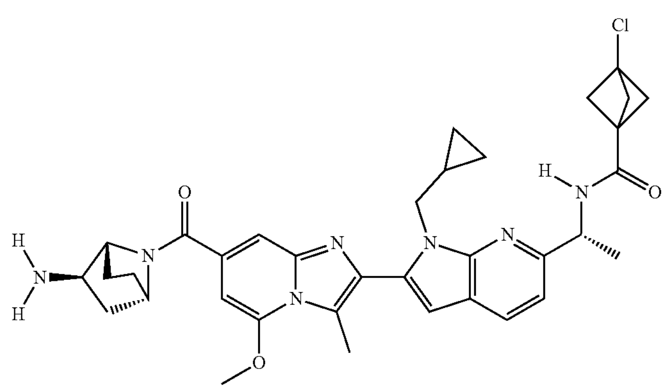 [SMILES: COc1cc(C(=O)N2[C@H]3CC[C@@H]2[C@H](N)C3)cc2nc(-c3cc4ccc([C@@H](C)NC(=O)C56CC(Cl)(C5)C6)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-chlorobicyclo[1.1.1]pentane-1-carboxamide |
| 134 | 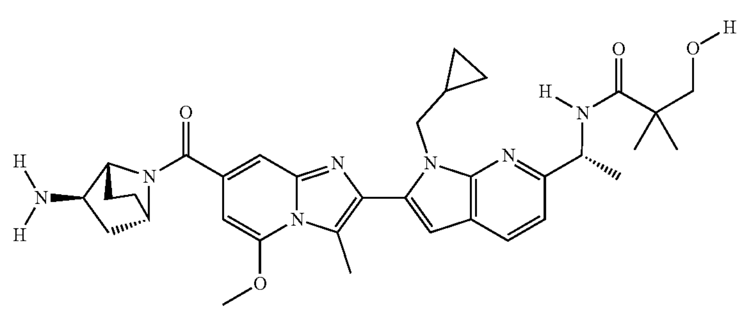 [SMILES: COc1cc(C(=O)N2[C@H]3CC[C@@H]2[C@H](N)C3)cc2nc(-c3cc4ccc([C@@H](C)NC(=O)C(C)(C)CO)nc4n3CC3CC3)c(C)n12] | [(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-hydroxy-2,2-dimethylpropanamide |

| Ex | Structure | Name |
|---|---|---|
| 135 | 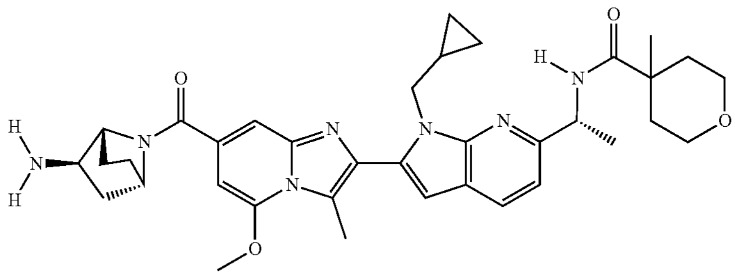 [SMILES: COc1cc(C(=O)N2[C@H]3CC[C@@H]2[C@H](N)C3)cc2nc(-c3cc4ccc([C@@H](C)NC(=O)C5(C)CCOCC5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-4-methyloxane-4-carboxamide |
| 136 | 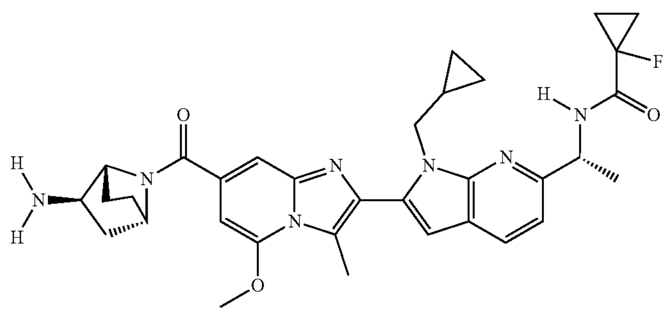 [SMILES: COc1cc(C(=O)N2[C@H]3CC[C@@H]2[C@H](N)C3)cc2nc(-c3cc4ccc([C@@H](C)NC(=O)C5(F)CC5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1-fluorocyclopropane-1-carboxamide |
| 137 | 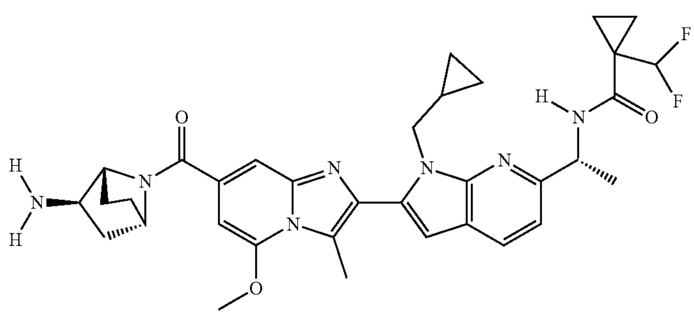 [SMILES: COc1cc(C(=O)N2[C@H]3CC[C@@H]2[C@H](N)C3)cc2nc(-c3cc4ccc([C@@H](C)NC(=O)C5(C(F)F)CC5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1-(difluoromethyl)cyclopropane-1-carboxamide |
| 138 | 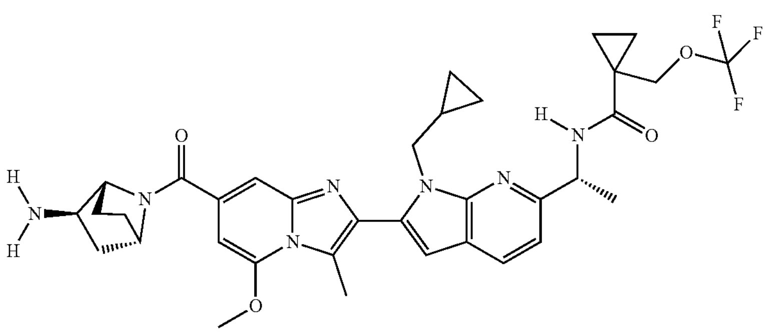 [SMILES: COc1cc(C(=O)N2[C@H]3CC[C@@H]2[C@H](N)C3)cc2nc(-c3cc4ccc([C@@H](C)NC(=O)C5(COC(F)(F)F)CC5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1-(trifluoromethoxymethyl)cyclopropane-1-carboxamide |

| Ex | Structure | Name |
|---|---|---|
| 139 | 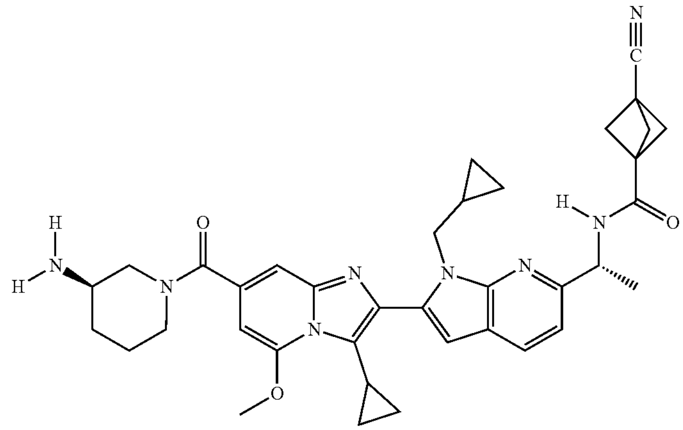 [SMILES: COc1cc(C(=O)N2CCC[C@@H](N)C2)cc2nc(-c3cc4ccc([C@@H](C)NC(=O)C56CC(C#N)(C5)C6)nc4n3CC3CC3)c(C3CC3)n12] | ~{N}-[(1~{R})-1-[2-[7-[(3~{R})-3-aminopiperidine-1-carbonyl]-3-cyclopropyl-5-methoxyimidazo[1,2-a]pyridin-2-yl]-1-(cyclopropylmethyl)pyrrolo[2,3-b]pyridin-6-yl]ethyl]-3-cyanobicyclo[1.1.1]pentane-1-carboxamide |
| 140 | 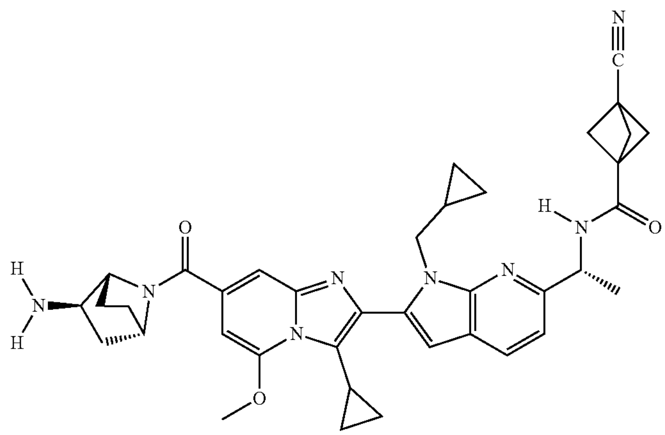 [SMILES: COc1cc(C(=O)N2[C@H]3CC[C@@H]2[C@H](N)C3)cc2nc(-c3cc4ccc([C@@H](C)NC(=O)C56CC(C#N)(C5)C6)nc4n3CC3CC3)c(C3CC3)n12] | ~{N}-[(1~{R})-1-[2-[7-[(1~{R},2~{R},4~{S})-2-amino-7-azabicyclo[2.2.1]heptane-7-carbonyl]-3-cyclopropyl-5-methoxyimidazo[1,2-a]pyridin-2-yl]-1-(cyclopropylmethyl)pyrrolo[2,3-b]pyridin-6-yl]ethyl]-3-cyanobicyclo[1.1.1]pentane-1-carboxamide |
| 141 | 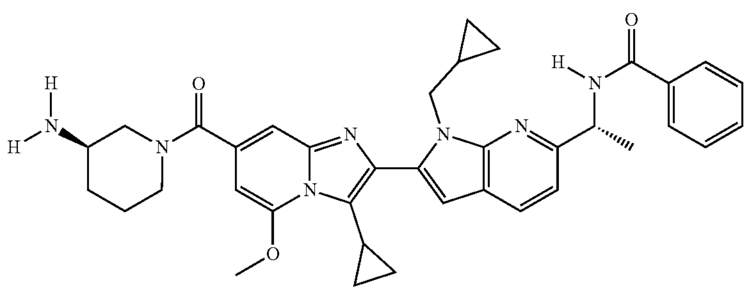 [SMILES: COc1cc(C(=O)N2CCC[C@@H](N)C2)cc2nc(-c3cc4ccc([C@@H](C)NC(=O)c5ccccc5)nc4n3CC3CC3)c(C3CC3)n12] | ~{N}-[(1~{R})-1-[2-[7-[(3~{R})-3-aminopiperidine-1-carbonyl]-3-cyclopropyl-5-methoxyimidazo[1,2-a]pyridin-2-yl]-1-(cyclopropylmethyl)pyrrolo[2,3-b]pyridin-6-yl]ethyl]benzamide |
| 142 | 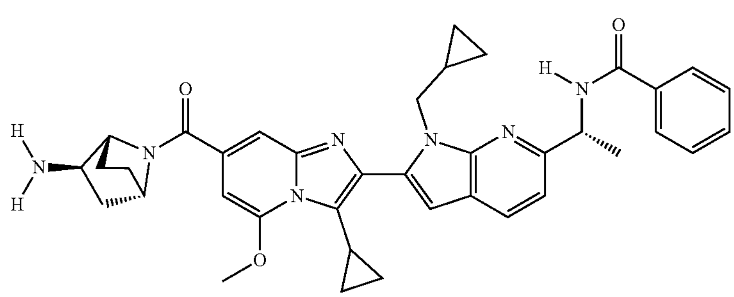 [SMILES: COc1cc(C(=O)N2[C@H]3CC[C@@H]2[C@H](N)C3)cc2nc(-c3cc4ccc([C@@H](C)NC(=O)c5ccccc5)nc4n3CC3CC3)c(C3CC3)n12] | ~{N}-[(1~{R})-1-[2-[7-[(1~{R},2~{R},4~{S})-2-amino-7-azabicyclo[2.2.1]heptane-7-carbonyl]-3-cyclopropyl-5-methoxyimidazo[1,2-a]pyridin-2-yl]-1-(cyclopropylmethyl)pyrrolo[2,3-b]pyridin-6-yl]ethyl]benzamide |

-continued

| Ex | Structure | Name |
|---|---|---|
| 143 | 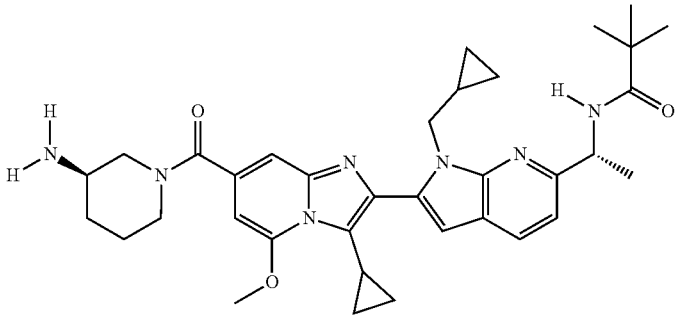 [SMILES: COc1cc(C(=O)N2CCC[C@@H](N)C2)cc2nc(-c3cc4ccc([C@@H](C)NC(=O)C(C)(C)C)nc4n3CC3CC3)c(C3CC3)n12] | ~{N}-[(1~{R})-1-[2-[7-[(3~{R})-3-aminopiperidine-1-carbonyl]-3-cyclopropyl-5-methoxyimidazo[1,2-a]pyridin-2-yl]-1-(cyclopropylmethyl)pyrrolo[2,3-b]pyridin-6-yl]ethyl]-2,2-dimethylpropanamide |
| 144 | 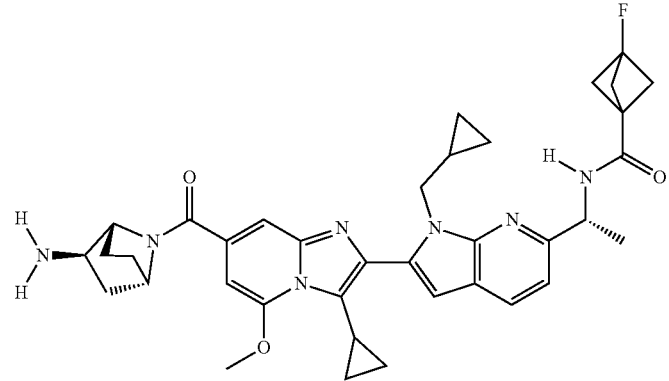 [SMILES: COc1cc(C(=O)N2[C@H]3CC[C@@H]2[C@H](N)C3)cc2nc(-c3cc4ccc([C@@H](C)NC(=O)C56CC(F)(C5)C6)nc4n3CC3CC3)c(C3CC3)n12] | ~{N}-[(1~{R})-1-[2-[7-[(1~{R},2~{R},4~{S})-2-amino-7-azabicyclo[2.2.1]heptane-7-carbonyl]-3-cyclopropyl-5-methoxyimidazo[1,2-a]pyridin-2-yl]-1-(cyclopropylmethyl)pyrrolo[2,3-b]pyridin-6-yl]ethyl]-3-fluorobicyclo[1.1.1]pentane-1-carboxamide |
| 145 | 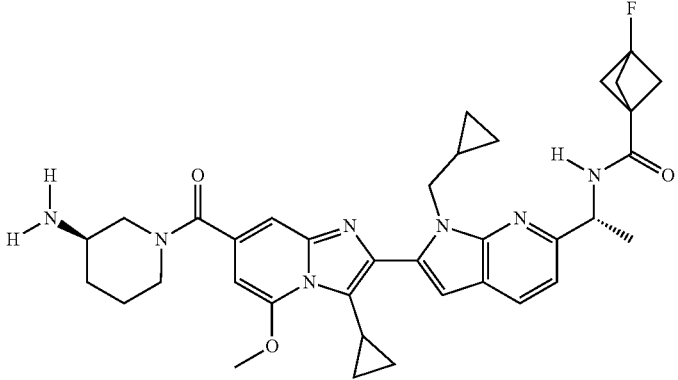 [SMILES: COc1cc(C(=O)N2CCC[C@@H](N)C2)cc2nc(-c3cc4ccc([C@@H](C)NC(=O)C56CC(F)(C5)C6)nc4n3CC3CC3)c(C3CC3)n12] | ~{N}-[(1~{R})-1-[2-[7-[(3~{R})-3-aminopiperidine-1-carbonyl]-3-cyclopropyl-5-methoxyimidazo[1,2-a]pyridin-2-yl]-1-(cyclopropylmethyl)pyrrolo[2,3-b]pyridin-6-yl]ethyl]-3-fluorobicyclo[1.1.1]pentane-1-carboxamide |
| 146 | 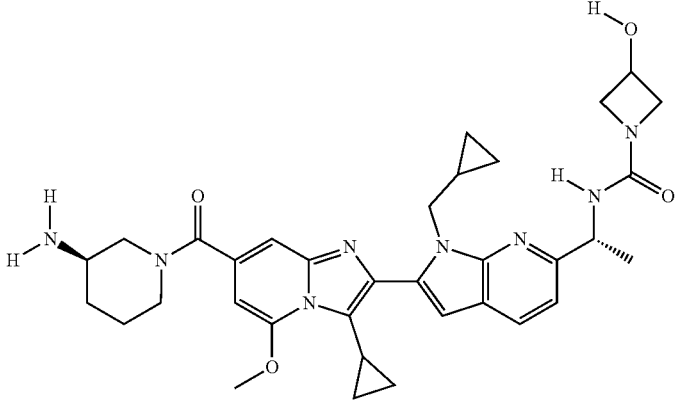 [SMILES: COc1cc(C(=O)N2CCC[C@@H](N)C2)cc2nc(-c3cc4ccc([C@@H](C)NC(=O)N5CC(O)C5)nc4n3CC3CC3)c(C3CC3)n12] | ~{N}-[(1~{R})-1-[2-[7-[(3~{R})-3-aminopiperidine-1-carbonyl]-3-cyclopropyl-5-methoxyimidazo[1,2-a]pyridin-2-yl]-1-(cyclopropylmethyl)pyrrolo[2,3-b]pyridin-6-yl]ethyl]-3-hydroxyazetidine-1-carboxamide |

-continued

| Ex | Structure | Name |
|---|---|---|
| 147 | 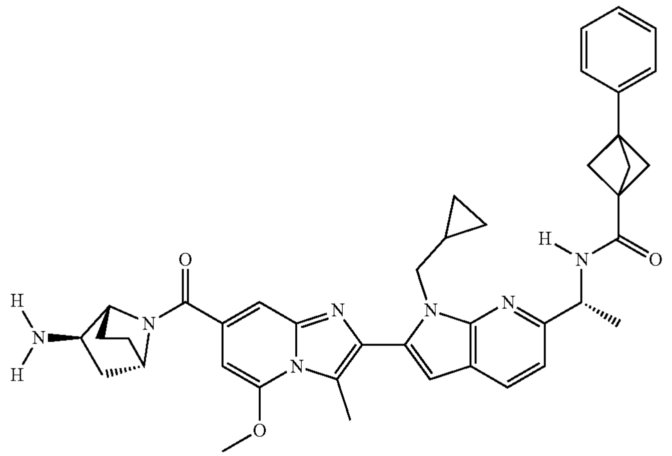 [SMILES: COc1cc(C(=O)N2[C@H]3CC[C@@H]2[C@H](N)C3)cc2nc(-c3cc4ccc([C@@H](C)NC(=O)C56CC(c7ccccc7)(C5)C6)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-phenylbicyclo[1.1.1]pentane-1-carboxamide |
| 148 | 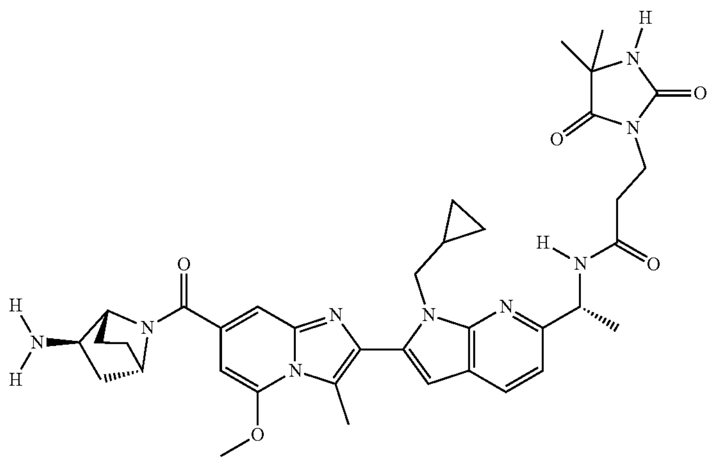 [SMILES: COc1cc(C(=O)N2[C@H]3CC[C@@H]2[C@H](N)C3)cc2nc(-c3cc4ccc([C@@H](C)NC(=O)CCN5C(=O)NC(C)(C)C5=O)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-(4,4-dimethyl-2,5-dioxoimidazolidin-1-yl)propenamide |
| 149 | 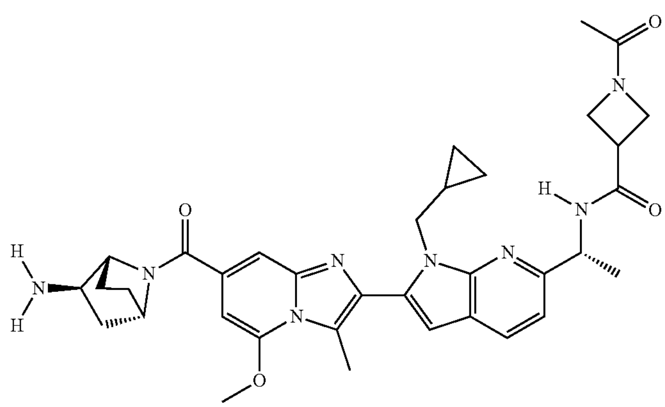 [SMILES: COc1cc(C(=O)N2[C@H]3CC[C@@H]2[C@H](N)C3)cc2nc(-c3cc4ccc([C@@H](C)NC(=O)C5CN(C(C)=O)C5)nc4n3CC3CC3)c(C)n12] | 1-acetyl-~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]azetidine-3-carboxamide |
| 150 | 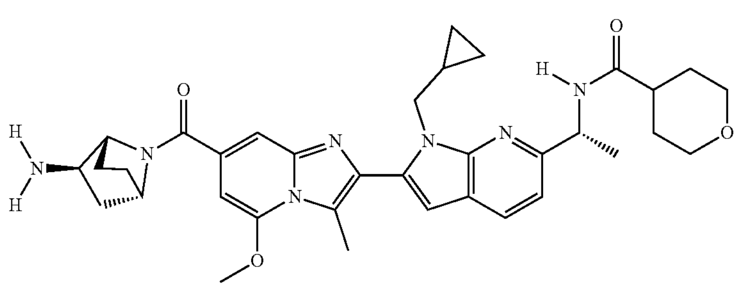 [SMILES: COc1cc(C(=O)N2[C@H]3CC[C@@H]2[C@H](N)C3)cc2nc(-c3cc4ccc([C@@H](C)NC(=O)C5CCOCC5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]oxane-4-carboxamide |

-continued

| Ex | Structure | Name |
|---|---|---|
| 151 | 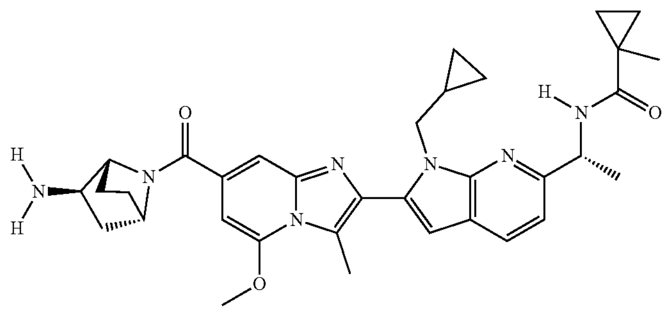 [SMILES: COc1cc(C(=O)N2[C@H]3CC[C@@H]2[C@H](N)C3)cc2nc(-c3cc4ccc([C@@H](C)NC(=O)C5(C)CC5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1-methylcyclopropane-1-carboxamide |
| 152 | 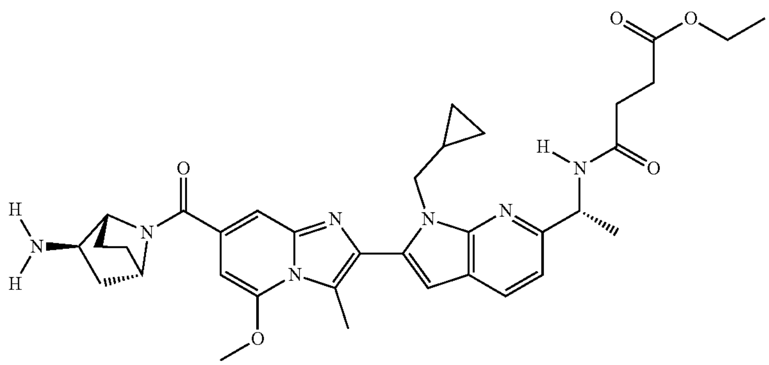 [SMILES: CCOC(=O)CCC(=O)N[C@H](C)c1ccc2cc(-c3nc4cc(C(=O)N5[C@H]6CC[C@@H]5[C@H](N)C6)cc(OC)n4c3C)n(CC3CC3)c2n1] | ethyl 4-[[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]amino]-4-oxobutanoate |
| 153 | 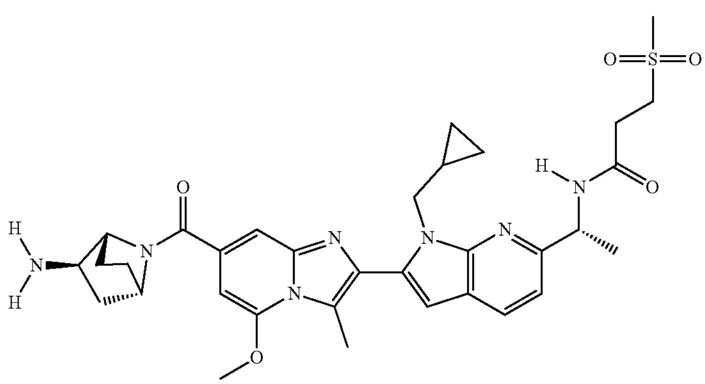 [SMILES: COc1cc(C(=O)N2[C@H]3CC[C@@H]2[C@H](N)C3)cc2nc(-c3cc4ccc([C@@H](C)NC(=O)CCS(C)(=O)=O)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-methylsulfonylpropanamide |
| 154 | 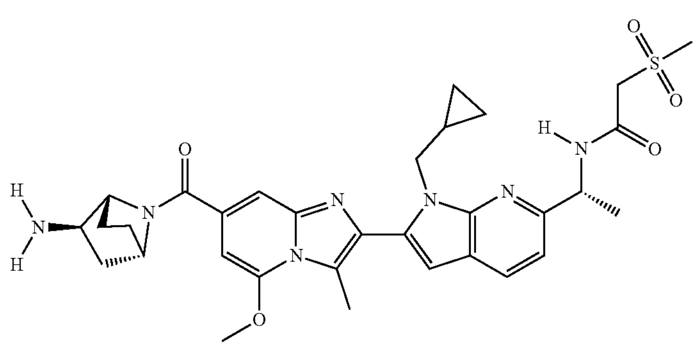 [SMILES: COc1cc(C(=O)N2[C@H]3CC[C@@H]2[C@H](N)C3)cc2nc(-c3cc4ccc([C@@H](C)NC(=O)CS(C)(=O)=O)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2-methylsulfonylacetamide |

-continued

| Ex | Structure | Name |
|---|---|---|
| 155 | 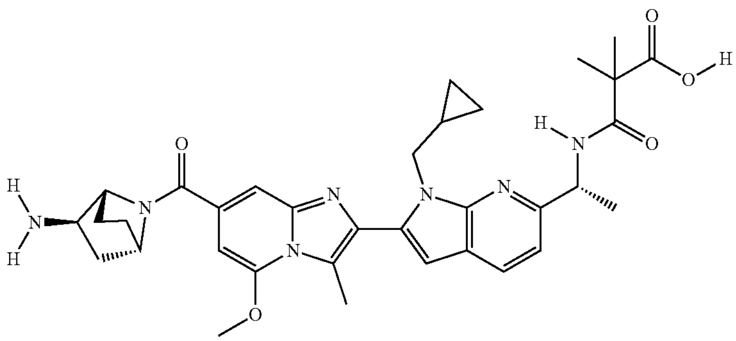 [SMILES: COc1cc(C(=O)N2[C@H]3CC[C@@H]2[C@H](N)C3)cc2nc(-c3cc4ccc([C@@H](C)NC(=O)C(C)(C)C(=O)O)nc4n3CC3CC3)c(C)n12] | 3-[[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]amino]-2,2-dimethyl-3-oxopropanoic acid |
| 156 | 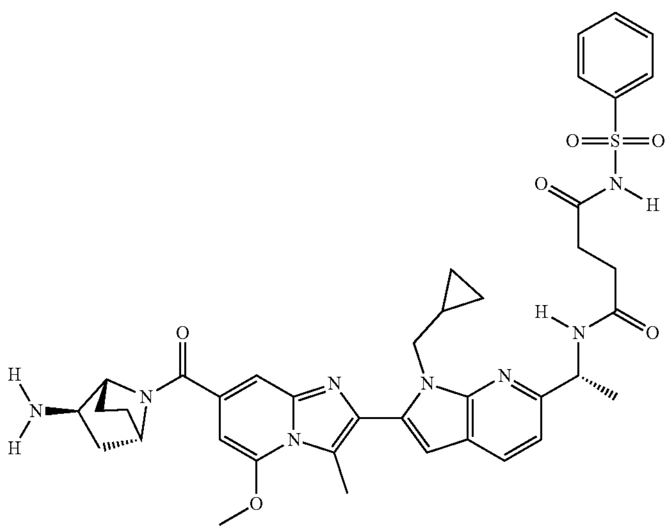 [SMILES: COc1cc(C(=O)N2[C@H]3CC[C@@H]2[C@H](N)C3)cc2nc(-c3cc4ccc([C@@H](C)NC(=O)CCC(=O)NS(=O)(=O)c5ccccc5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-~{N}'-(benzenesulfonyl)butanediamide |
| 157 | 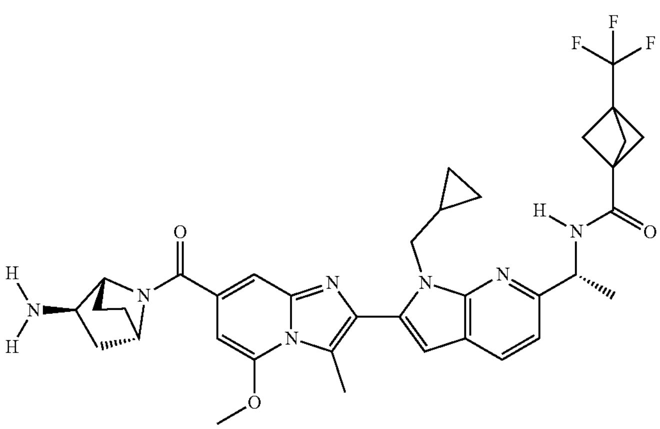 [SMILES: COc1cc(C(=O)N2[C@H]3CC[C@@H]2[C@H](N)C3)cc2nc(-c3cc4ccc([C@@H](C)NC(=O)C56CC(C(F)(F)F)(C5)C6)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-(trifluoromethyl)bicyclo[1.1.1]pentane-1-carboxamide |

-continued

| Ex | Structure | Name |
|---|---|---|
| 158 | 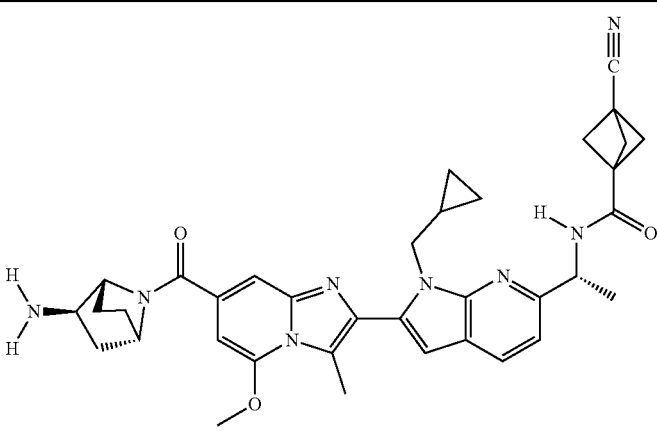 | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-cyanobicyclo[1.1.1]pentane-1-carboxamide |
| 159 | 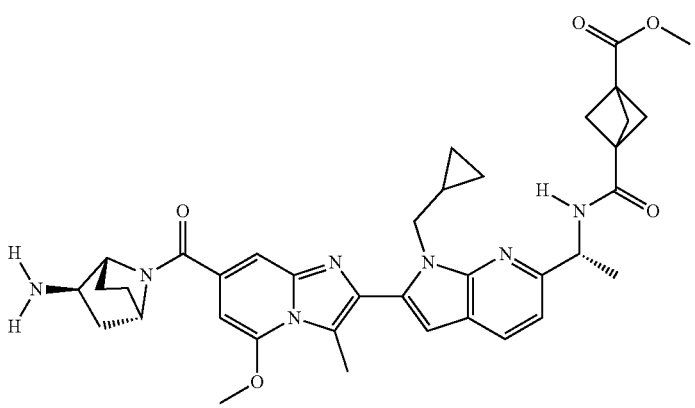 [SMILES: COC(=O)C12CC(C(=O)N[C@H](C)c3ccc4cc(-c5nc6cc(C(=O)N7[C@H]8CC[C@@H]7[C@H](N)C8)cc(OC)n6c5C)n(CC5CC5)c4n3)(C1)C2] | methyl 3-[[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]carbamoyl]bicyclo[1.1.1]pentane-1-carboxylate |
| 160 | 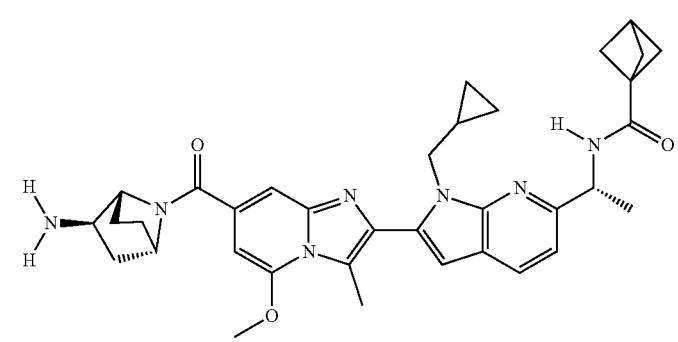 [SMILES: COc1cc(C(=O)N2[C@H]3CC[C@@H]2[C@H](N)C3)cc2nc(-c3cc4ccc([C@@H](C)NC(=O)C56CC(C5)C6)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]bicyclo[1.1.1]pentane-1-carboxamide |
| 161 | 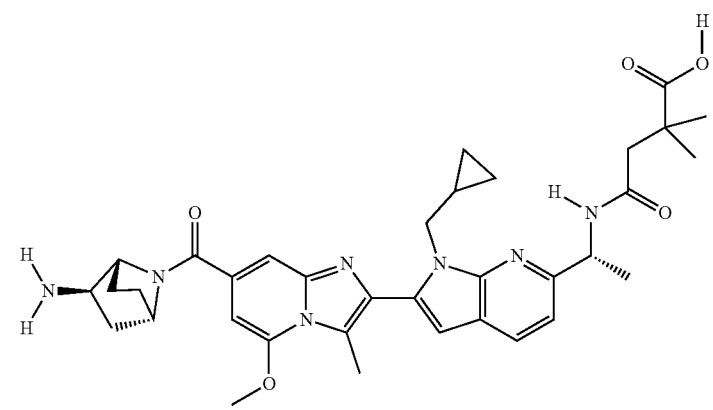 [SMILES: COc1cc(C(=O)N2[C@H]3CC[C@@H]2[C@H](N)C3)cc2nc(-c3cc4ccc([C@@H](C)NC(=O)CC(C)(C)C(=O)O)nc4n3CC3CC3)c(C)n12] | 4-[[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]amino]-2,2-dimethyl-4-oxobutanoic acid |

| Ex | Structure | Name |
|---|---|---|
| 162 | 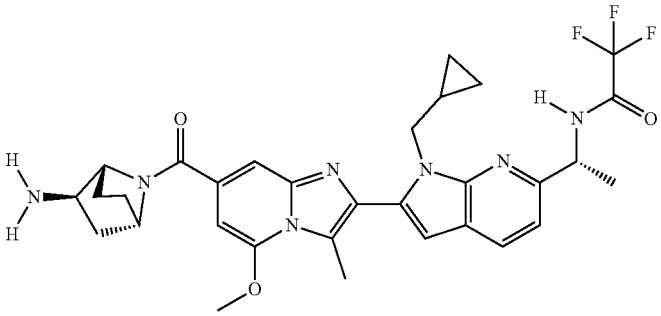 [SMILES: COc1cc(C(=O)N2[C@H]3CC[C@@H]2[C@H](N)C3)cc2nc(-c3cc4ccc([C@@H](C)NC(=O)C(F)(F)F)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2,2,2-trifluoroacetamide |
| 163 | 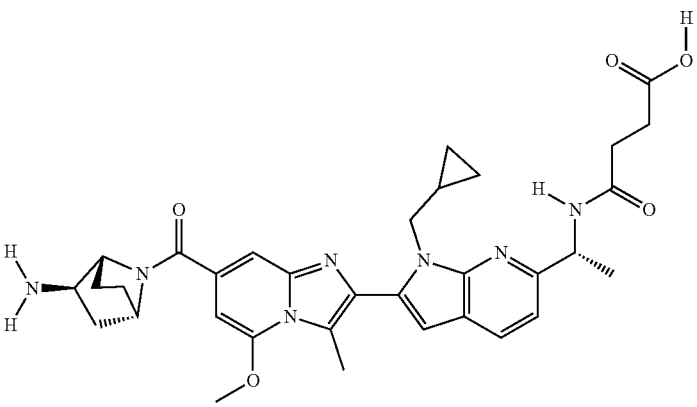 [SMILES: COc1cc(C(=O)N2[C@H]3CC[C@@H]2[C@H](N)C3)cc2nc(-c3cc4ccc([C@@H](C)NC(=O)CCC(=O)O)nc4n3CC3CC3)c(C)n12] | 4-[[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]amino]-4-oxobutanoic acid |
| 164 | 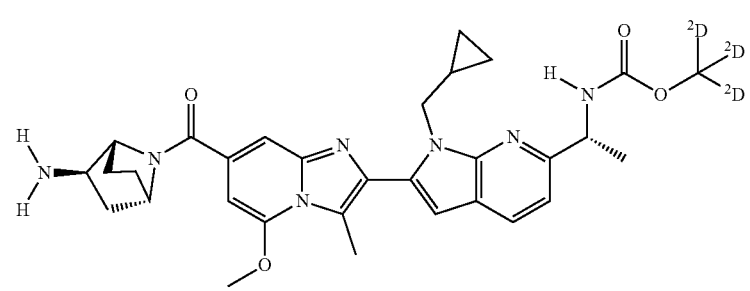 [SMILES: [2H]C([2H])([2H])OC(=O)N[C@H](C)c1ccc2cc(-c3nc4cc(C(=O)N5[C@H]6CC[C@@H]5[C@H](N)C6)cc(OC)n4c3C)n(CC3CC3)c2n1] | trideuteriomethyl~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl] carbamate |
| 165 | 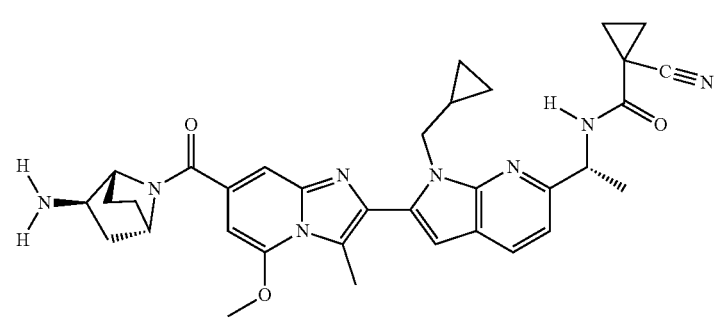 [SMILES: COc1cc(C(=O)N2[C@H]3CC[C@@H]2[C@H](N)C3)cc2nc(-c3cc4ccc([C@@H](C)NC(=O)C5(C#N)CC5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1-cyanocyclopropane-1-carboxamide |

-continued

| Ex | Structure | Name |
|---|---|---|
| 166 | 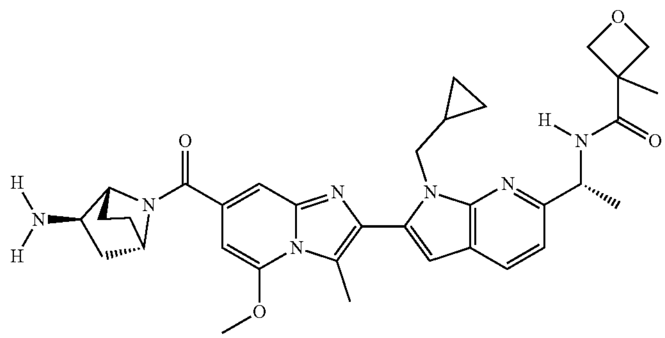 [SMILES: COc1cc(C(=O)N2[C@H]3CC[C@@H]2[C@H](N)C3)cc2nc(-c3cc4ccc([C@@H](C)NC(=O)C5(C)COC5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-methyloxetane-3-carboxamide |
| 167 | 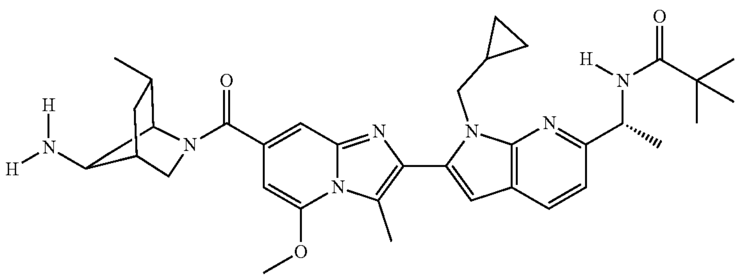 [SMILES: COc1cc(C(=O)N2CC3CC(C)C2CC3N)cc2nc(-c3cc4ccc([C@@H](C)NC(=O)C(C)(C)C)nc4n3CC3CC3)c(C)n12] | N-((R)-1-(2-(7-((1R,4R,6S,7R)-7-amino-6-methyl-2-azabicyclo[2.2.1]heptane-2-carbonyl)-5-methoxy-3-methylimidazo[1,2-a]pyridin-2-yl)-1-(cyclopropylmethyl)-1H-pyrrolo[2,3-b]pyridin-6-yl)ethyl)pivalamide |
| 168 | 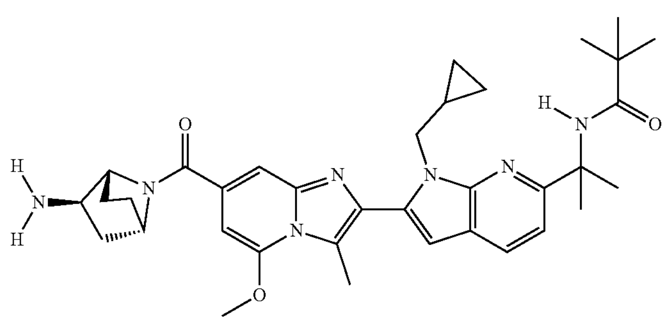 [SMILES: COc1cc(C(=O)N2[C@H]3CC[C@@H]2[C@H](N)C3)cc2nc(-c3cc4ccc(C(C)(C)NC(=O)C(C)(C)C)nc4n3CC3CC3)c(C)n12] | ~{N}-[2-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]propan-2-yl]-2,2-dimethylpropanamide |
| 169 | 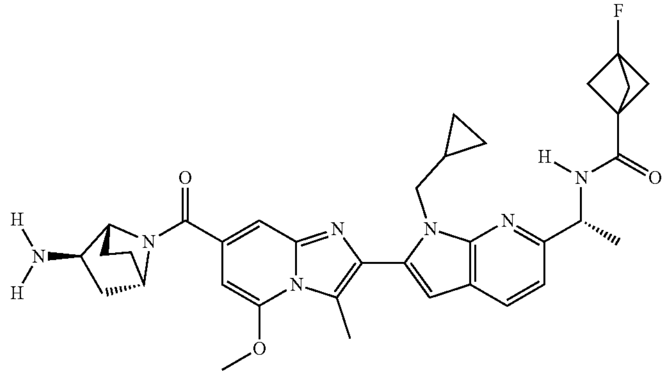 [SMILES: COc1cc(C(=O)N2[C@H]3CC[C@@H]2[C@H](N)C3)cc2nc(-c3cc4ccc([C@@H](C)NC(=O)C56CC(F)(C5)C6)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-fluorobicyclo[1.1.1]pentane-1-carboxamide |

-continued

| Ex | Structure | Name |
|---|---|---|
| 170 | 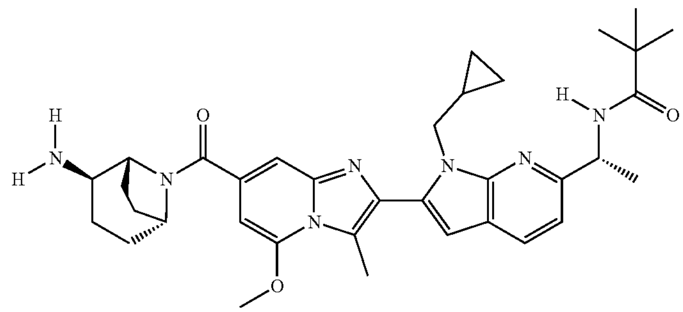 [SMILES: COc1cc(C(=O)N2[C@@H]3CC[C@@H](N)[C@H]2CC3)cc2nc(-c3cc4ccc([C@@H](C)NC(=O)C(C)(C)C)nc4n3CC3CC3)c(C)n12] | ~{N}-[(1~{R})-1-[2-[7-[(1~{R},2~{R},5~{R})-2-amino-8-azabicyclo[3.2.1]octane-8-carbonyl]-5-methoxy-3-methylimidazo[1,2-a]pyridin-2-yl]-1-(cyclopropylmethyl)pyrrolo[2,3-b]pyridin-6-yl]ethyl]-2,2-dimethylpropanamide |
| 171 | 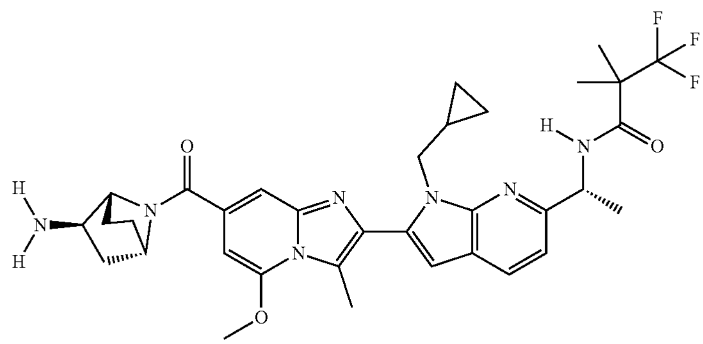 [SMILES: COc1cc(C(=O)N2[C@H]3CC[C@@H]2[C@H](N)C3)cc2nc(-c3cc4ccc([C@@H](C)NC(=O)C(C)(C)C(F)(F)F)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3,3,3-trifluoro-2,2-dimethylpropanamide |
| 172 | 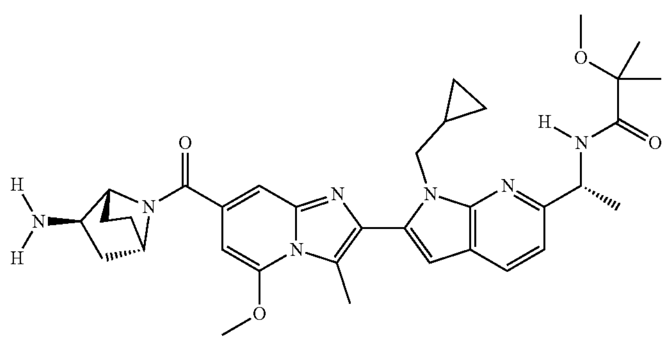 [SMILES: COc1cc(C(=O)N2[C@H]3CC[C@@H]2[C@H](N)C3)cc2nc(-c3cc4ccc([C@@H](C)NC(=O)C(C)(C)OC)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2-methoxy-2-methylpropanamide |
| 173 | 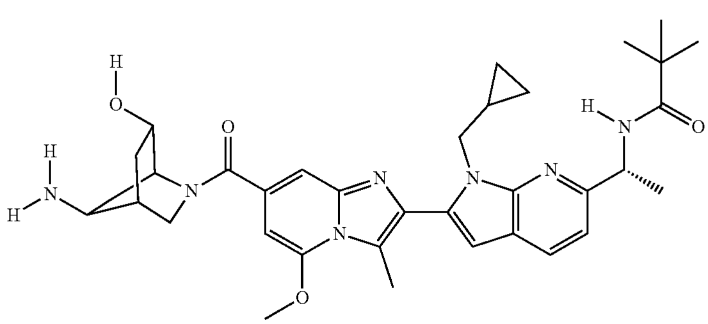 [SMILES: COc1cc(C(=O)N2CC3CC(O)C2CC3N)cc2nc(-c3cc4ccc([C@@H](C)NC(=O)C(C)(C)C)nc4n3CC3CC3)c(C)n12] | N-((R)-1-(2-(7-((1S,4R,6S,7R)-7-amino-6-hydroxy-2-azabicyclo[2.2.1]heptane-2-carbonyl)-5-methoxy-3-methylimidazo[1,2-a]pyridin-2-yl)-1-(cyclopropylmethyl)-1H-pyrrolo[2,3-b]pyridin-6-yl)ethyl)pivalamide |

| Ex | Structure | Name |
|---|---|---|
| 174 | 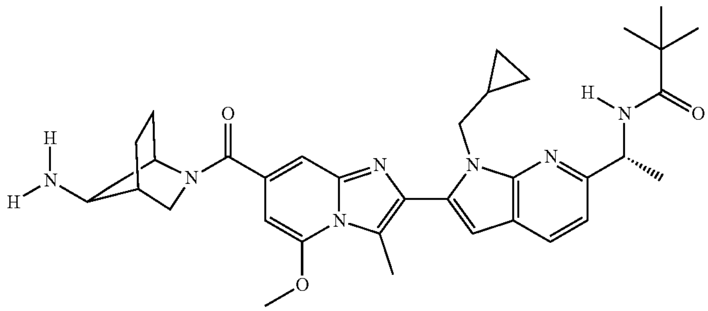 [SMILES: COc1cc(C(=O)N2CC3CCC2CC3N)cc2nc(-c3cc4ccc([C@@H](C)NC(=O)C(C)(C)C)nc4n3CC3CC3)c(C)n12] | N-((R)-1-(2-(7-((1R,4R,7R)-7-amino-2-azabicyclo[2.2.1]heptane-2-carbonyl)-5-methoxy-3-methylimidazo[1,2-a]pyridin-2-yl)-1-(cyclopropylmethyl)-1H-pyrrolo[2,3-b]pyridin-6-yl)ethyl)pivalamide |
| 175 | 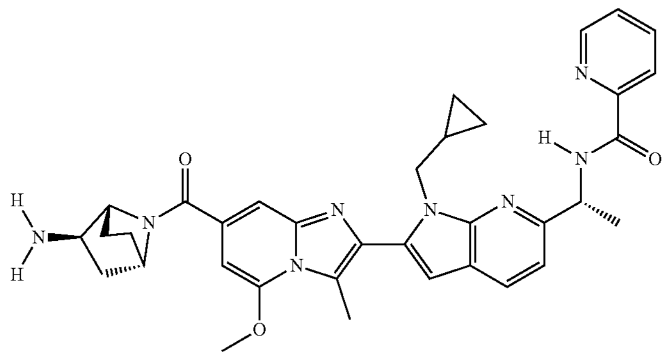 | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]pyridine-2-carboxamide |
| 176 | 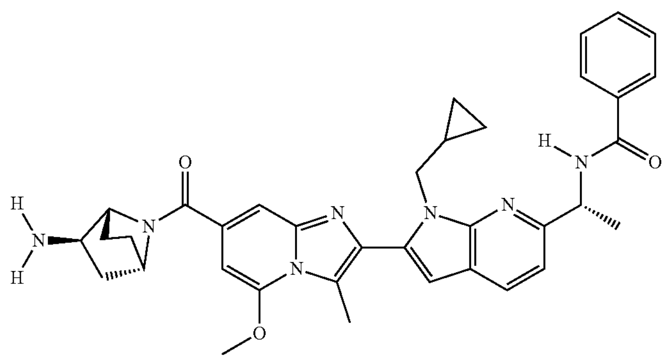 [SMILES: COc1cc(C(=O)N2[C@H]3CC[C@@H]2[C@H](N)C3)cc2nc(-c3cc4ccc([C@@H](C)NC(=O)c5ccccc5)nc4n3CC3CC3)c(C)n12] | [(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]benzamide |
| 177 | 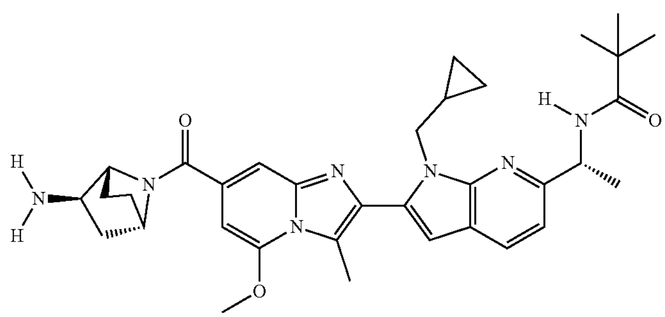 [SMILES: COc1cc(C(=O)N2[C@H]3CC[C@@H]2[C@H](N)C3)cc2nc(-c3cc4ccc([C@@H](C)NC(=O)C(C)(C)C)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2,2-dimethylpropanamide |

| Ex | Structure | Name |
|---|---|---|
| 178 | 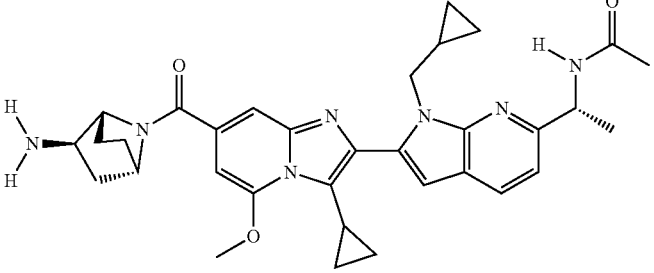 | ~{N}-[(1~{R})-1-[2-[7-[(1~{R},2~{R},4~{S})-2-amino-7-azabicyclo[2.2.1]heptane-7-carbonyl]-3-cyclopropyl-5-methoxyimidazo[1,2-a]pyridin-2-yl]-1-(cyclopropylmethyl)pyrrolo[2,3-b]pyridin-6-yl]ethyl]acetamide |
| 179 | 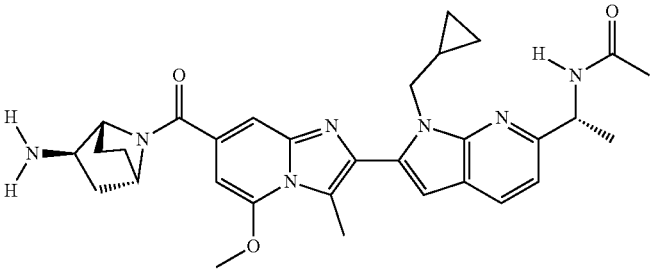 [SMILES: COc1cc(C(=O)N2[C@H]3CC[C@@H]2[C@H](N)C3)cc2nc(-c3cc4ccc([C@@H](C)NC(C)=O)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]acetamide |
| 180 | 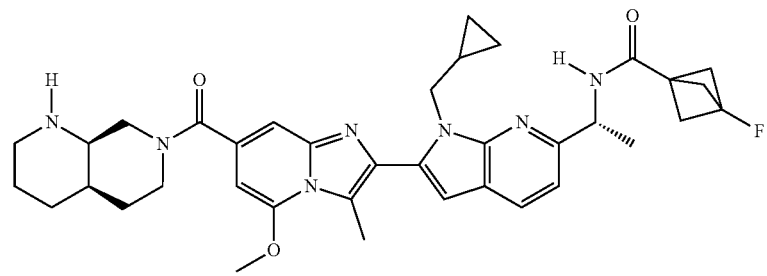 [SMILES: COc1cc(C(=O)N2CC[C@H]3CCCN[C@H]3C2)cc2nc(-c3cc4ccc([C@@H](C)NC(=O)C56CC(F)(C5)C6)nc4n3CC3CC3)c(C)n12] | ~{N}-[(1~{R})-1-[2-[7-[(4~{a}~{R},8~{a}~{R})-2,3,4,4~{a},5,6,8,8~{a}-octahydro-1~{H}-1,7-naphthyridine-7-carbonyl]-5-methoxy-3-methylimidazo[1,2-a]pyridin-2-yl]-1-(cyclopropylmethyl)pyrrolo[2,3-b]pyridin-6-yl]ethyl]-3-fluorobicyclo[1.1.1]pentane-1-carboxamide |
| 181 | 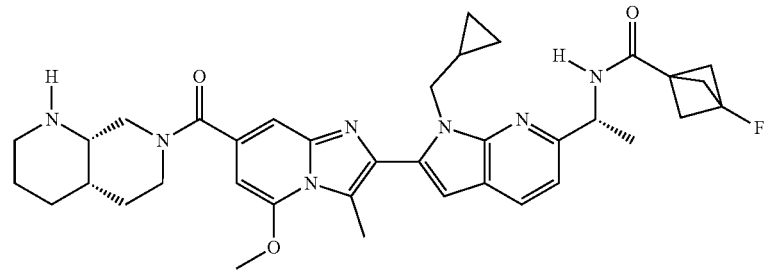 [SMILES: COc1cc(C(=O)N2CC[C@@H]3CCCN[C@@H]3C2)cc2nc(-c3cc4ccc([C@@H](C)NC(=O)C56CC(F)(C5)C6)nc4n3CC3CC3)c(C)n12] | ~{N}-[(1~{R})-1-[2-[7-[(4~{a}~{S},8~{a}~{S})-2,3,4,4~{a},5,6,8,8~{a}-octahydro-1~{H}-1,7-naphthyridine-7-carbonyl]-5-methoxy-3-methylimidazo[1,2-a]pyridin-2-yl]-1-(cyclopropylmethyl)pyrrolo[2,3-b]pyridin-6-yl]ethyl]-3-fluorobicyclo[1.1.1]pentane-1-carboxamide |
| 182 | 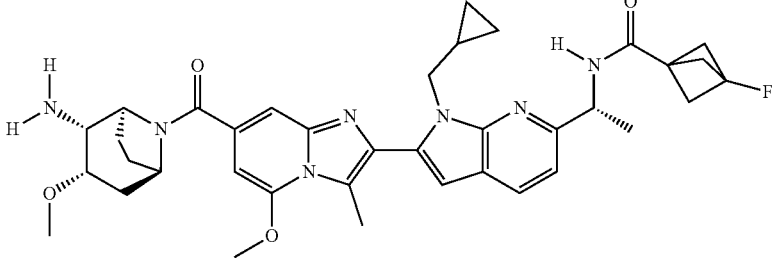 | ~{N}-[(1~{R})-1-[2-[7-amino-3-methoxy-8-azabicyclo[3.2.1]octane-8-carbonyl]-5-methoxy-3-methylimidazo[1,2-a]pyridin-2-yl]-1-(cyclopropylmethyl)pyrrolo[2,3-b]pyridin-6-yl]ethyl]-3-fluorobicyclo[1.1.1]pentane-1-carboxamide |

| Ex | Structure | Name |
|---|---|---|
| 183 | 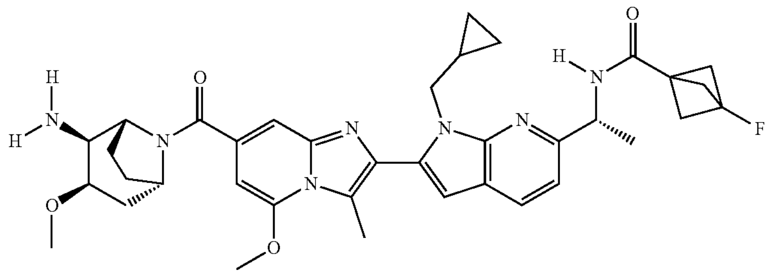 [SMILES: COc1cc(C(=O)N2[C@H]3CC[C@@H]2[C@H](N)[C@H](OC)C3)cc2nc(-c3cc4ccc([C@@H](C)NC(=O)C56CC(F)(C5)C6)nc4n3CC3CC3)c(C)n12] | ~{N}-[(1~{R})-1-[2-[7-[(1~{R},2~{S},3~{R},5~{S})-2-amino-3-methoxy-8-azabicyclo[3.2.1]octane-8-carbonyl]-5-methoxy-3-methylimidazo[1,2-a]pyridin-2-yl]-1-(cyclopropylmethyl)pyrrolo[2,3-b]pyridin-6-yl]ethyl]-3-fluorobicyclo[1.1.1]pentane-1-carboxamide |
| 184 | 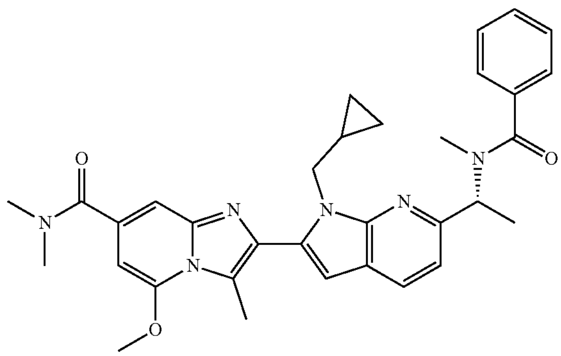 [SMILES: COc1cc(C(=O)N(C)C)cc2nc(-c3cc4ccc([C@@H](C)N(C)C(=O)c5ccccc5)nc4n3CC3CC3)c(C)n12] | 2-[6-[(1~{R})-1-[benzoyl(methyl)amino]ethyl]-1-(cyclopropylmethyl)pyrrolo[2,3-b]pyridin-2-yl]-5-methoxy-~{N},~{N},3-trimethylimidazo[1,2-a]pyridine-7-carboxamide |
| 185 | 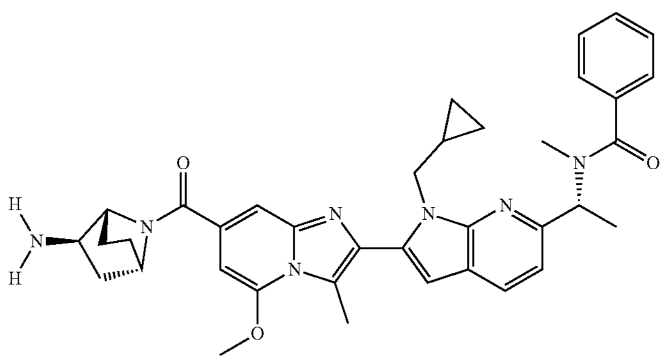 [SMILES: COc1cc(C(=O)N2[C@H]3CC[C@@H]2[C@H](N)C3)cc2nc(-c3cc4ccc([C@@H](C)N(C)C(=O)c5ccccc5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-~{N}-methylbenzamide |
| 186 | 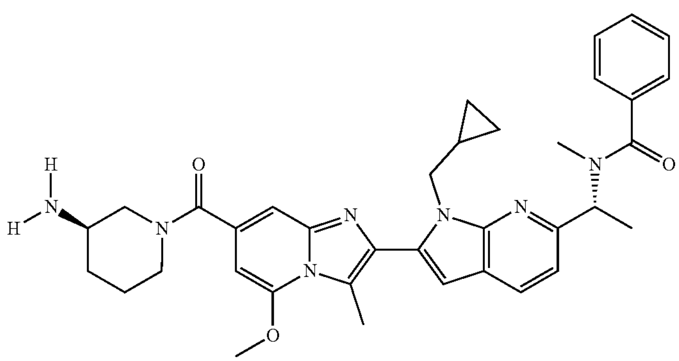 [SMILES: COc1cc(C(=O)N2CCC[C@@H](N)C2)cc2nc(-c3cc4ccc([C@@H](C)N(C)C(=O)c5ccccc5)nc4n3CC3CC3)c(C)n12] | ~{N}-[(1~{R})-1-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]ethyl]-~{N}-methylbenzamide |

-continued

| Ex | Structure | Name |
|---|---|---|
| 187 | 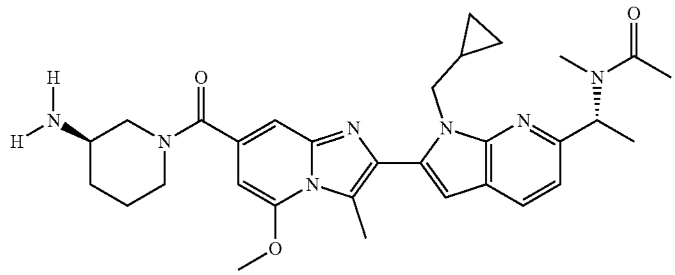 [SMILES: COc1cc(C(=O)N2CCC[C@@H](N)C2)cc2nc(-c3cc4ccc([C@@H](C)N(C)C(C)=O)nc4n3CC3CC3)c(C)n12] | ~{N}-[(1~{R})-1-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]ethyl]-~{N}-methylacetamide |
| 188 | 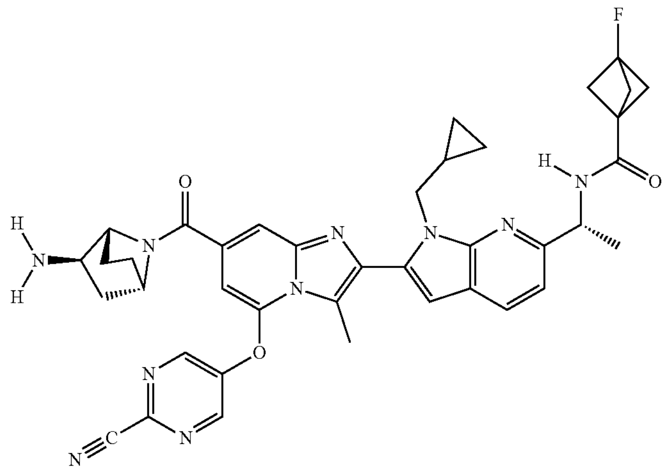 [SMILES: Cc1c(-c2cc3ccc([C@@H](C)NC(=O)C45CC(F)(C4)C5)nc3n2CC2CC2)nc2cc(C(=O)N3[C@H]4CC[C@@H]3[C@H](N)C4)cc(Oc3cnc(C#N)nc3)n12] | ~{N}-[(1~{R})-1-[2-[7-[(1~{R},2~{R},4~{S})-2-amino-7-azabicyclo[2.2.1]heptane-7-carbonyl]-5-(2-cyanopyrimidin-5-yl)oxy-3-methylimidazo[1,2-a]pyridin-2-yl]-1-(cyclopropylmethyl)pyrrolo[2,3-b]pyridin-6-yl]ethyl]-3-fluorobicyclo[1.1.1]pentane-1-carboxamide |
| 189 | 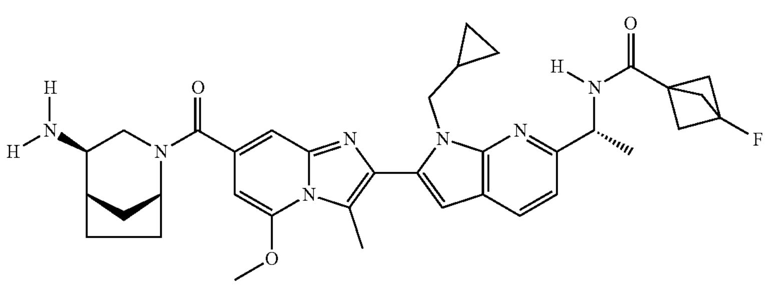 [SMILES: COc1cc(C(=O)N2C[C@H](N)[C@H]3CC[C@@H]2C3)cc2nc(-c3cc4ccc([C@@H](C)NC(=O)C56CC(F)(C5)C6)nc4n3CC3CC3)c(C)n12] | ~{N}-[(1~{R})-1-[2-[7-[(1~{S},4~{R},5~{R})-4-amino-2-azabicyclo[3.2.1]octane-2-carbonyl]-5-methoxy-3-methylimidazo[1,2-a]pyridin-2-yl]-1-(cyclopropylmethyl)pyrrolo[2,3-b]pyridin-6-yl]ethyl]-3-fluorobicyclo[1.1.1]pentane-1-carboxamide |
| 190 | 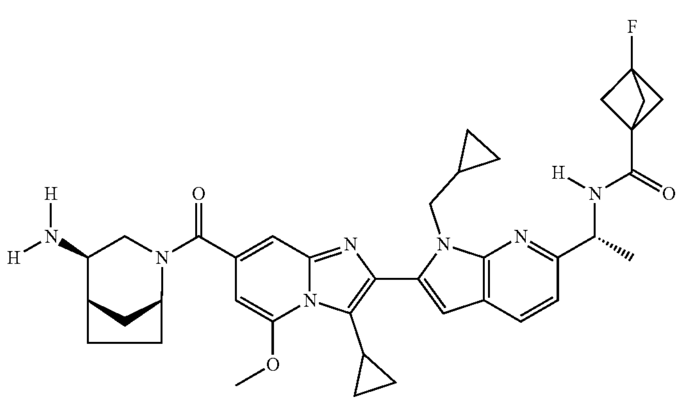 [SMILES: COc1cc(C(=O)N2C[C@H](N)[C@H]3CC[C@@H]2C3)cc2nc(-c3cc4ccc([C@@H](C)NC(=O)C56CC(F)(C5)C6)nc4n3CC3CC3)c(C3CC3)n12] | ~{N}-[(1~{R})-1-[2-[7-[(1~{S},4~{R},5~{R})-4-amino-2-azabicyclo[3.2.1]octane-2-carbonyl]-3-cyclopropyl-5-methoxyimidazo[1,2-a]pyridin-2-yl]-1-(cyclopropylmethyl)pyrrolo[2,3-b]pyridin-6-yl]ethyl]-3-fluorobicyclo[1.1.1]pentane-1-carboxamide |

-continued

| Ex | Structure | Name |
|---|---|---|
| 191 | 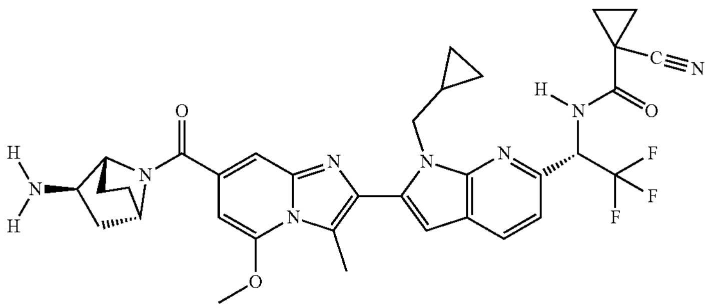 [SMILES: COc1cc(C(=O)N2[C@H]3CC[C@@H]2[C@H](N)C3)cc2nc(-c3cc4ccc([C@H](NC(=O)C5(C#N)CC5)C(F)(F)F)nc4n3CC3CC3)c(C)n12] | ~{N}-[(1~{S})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]-2,2,2-trifluoroethyl]-1-cyanocyclopropane-1-carboxamide |
| 192 | 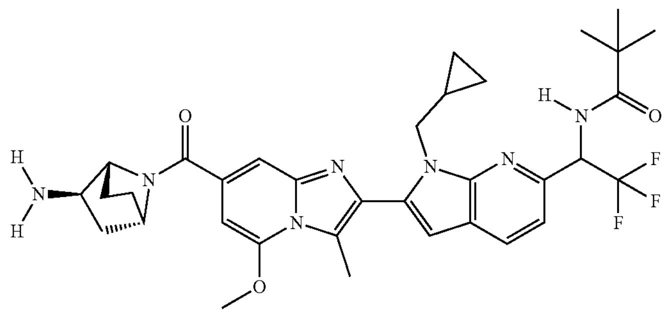 [SMILES: COc1cc(C(=O)N2[C@H]3CC[C@@H]2[C@H](N)C3)cc2nc(-c3cc4ccc(C(NC(=O)C(C)(C)C)C(F)(F)F)nc4n3CC3CC3)c(C)n12] | ~{N}-[1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]-2,2,2-trifluoroethyl]-2,2-dimethylpropanamide |
| 193 | 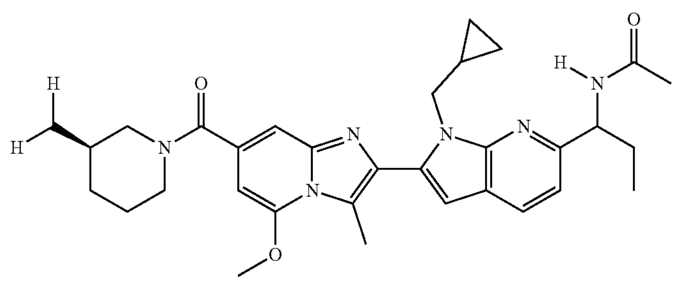 [SMILES: CCC(NC(C)=O)c1ccc2cc(-c3nc4cc(C(=O)N5CCC[C@@H](C)C5)cc(OC)n4c3C)n(CC3CC3)c2n1] | ~{N}-[1-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]propyl]acetamide |
| 194 | 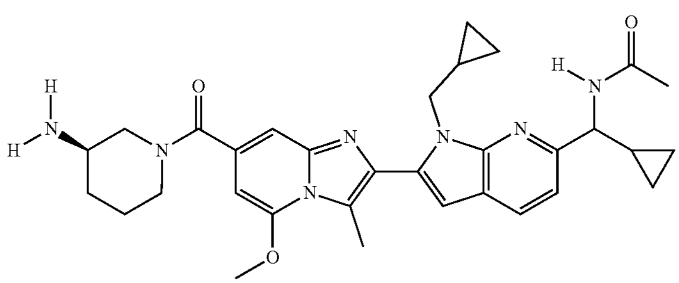 [SMILES: COc1cc(C(=O)N2CCC[C@@H](N)C2)cc2nc(-c3cc4ccc(C(NC(C)=O)C5CC5)nc4n3CC3CC3)c(C)n12] | ~{N}-[[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]-cyclopropylmethyl]acetamide |
| 195 | 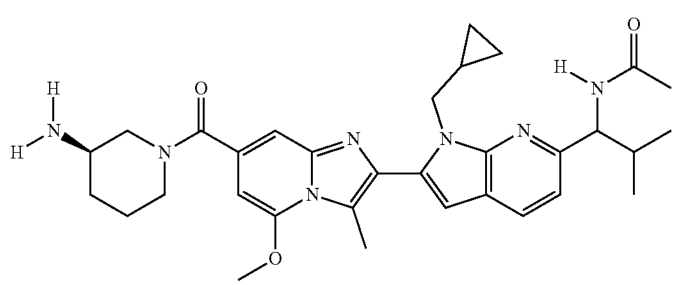 [SMILES: COc1cc(C(=O)N2CCC[C@@H](N)C2)cc2nc(-c3cc4ccc(C(NC(C)=O)C(C)C)nc4n3CC3CC3)c(C)n12] | ~{N}-[1-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]-2-methylpropyl]acetamide |

| Ex | Structure | Name |
|---|---|---|
| 196 | 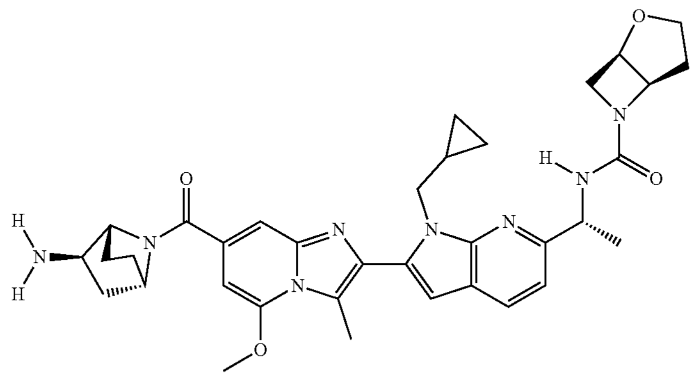 [SMILES: COc1cc(C(=O)N2[C@H]3CC[C@@H]2[C@H](N)C3)cc2nc(-c3cc4ccc([C@@H](C)NC(=O)N5C[C@H]6OCC[C@H]65)nc4n3CC3CC3)c(C)n12] | (1~{R},5~{R})-~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2-oxa-6-azabicyclo[3.2.0]heptane-6-carboxamide |
| 197 | 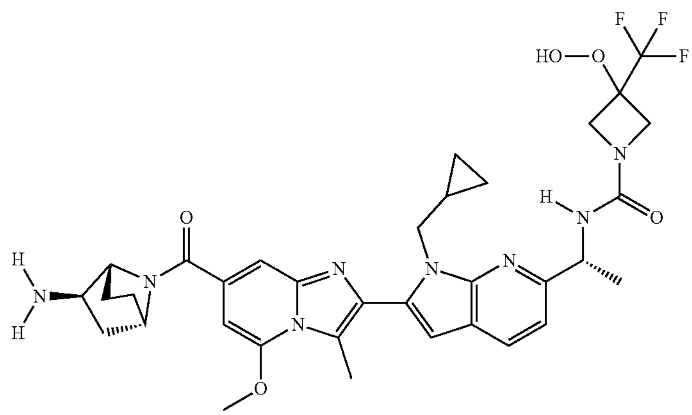 [SMILES: COc1cc(C(=O)N2[C@H]3CC[C@@H]2[C@H](N)C3)cc2nc(-c3cc4ccc([C@@H](C)NC(=O)N5CC(OO)(C(F)(F)F)C5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-hydroxy-3-(trifluoromethyl)azetidine-1-carboxamide |
| 198 | 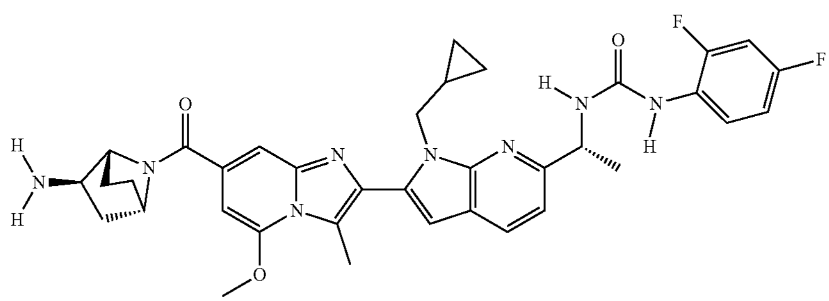 [SMILES: COc1cc(C(=O)N2[C@H]3CC[C@@H]2[C@H](N)C3)cc2nc(-c3cc4ccc([C@@H](C)NC(=O)Nc5ccc(F)cc5F)nc4n3CC3CC3)c(C)n12] | 1-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-(2,4-difluorophenyl)urea |
| 199 | 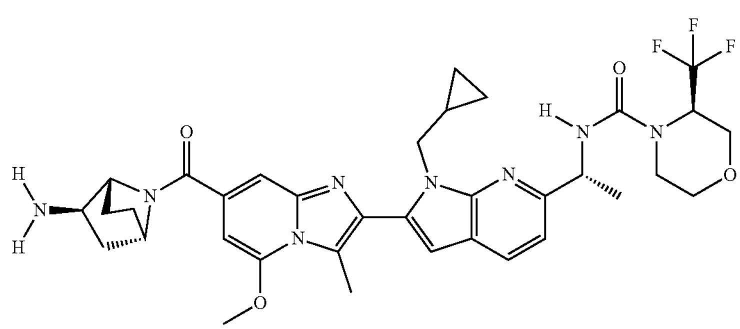 [SMILES: COc1cc(C(=O)N2[C@H]3CC[C@@H]2[C@H](N)C3)cc2nc(-c3cc4ccc([C@@H](C)NC(=O)N5CCOC[C@@H]5C(F)(F)F)nc4n3CC3CC3)c(C)n12] | (3~{R})-~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-(trifluoromethyl)morpholine-4-carboxamide |

| Ex | Structure | Name |
|---|---|---|
| 200 | 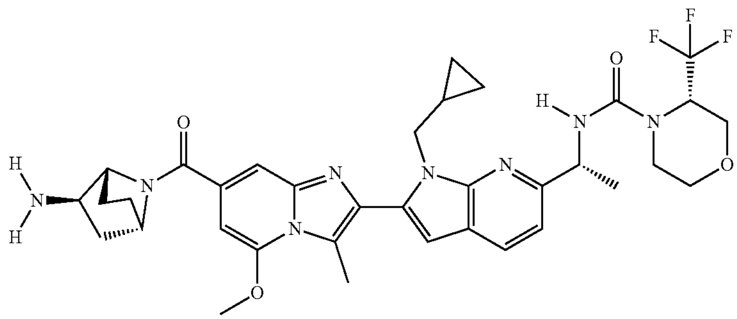 [SMILES: COc1cc(C(=O)N2[C@H]3CC[C@@H]2[C@H](N)C3)cc2nc(-c3cc4ccc([C@@H](C)NC(=O)N5CCOC[C@H]5C(F)(F)F)nc4n3CC3CC3)c(C)n12] | (3~{S})-~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-(trifluoromethyl)morpholine-4-carboxamide |
| 201 | 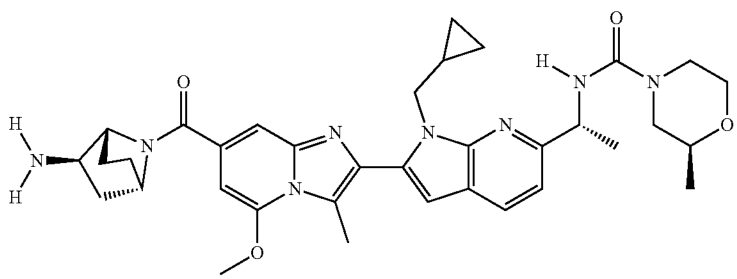 [SMILES: COc1cc(C(=O)N2[C@H]3CC[C@@H]2[C@H](N)C3)cc2nc(-c3cc4ccc([C@@H](C)NC(=O)N5CCO[C@@H](C)C5)nc4n3CC3CC3)c(C)n12] | (2~{S})-~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2-methylmorpholine-4-carboxamide |
| 202 | 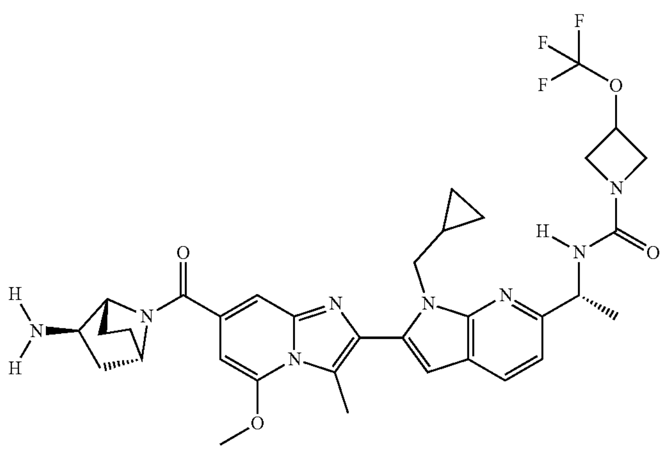 [SMILES: COc1cc(C(=O)N2[C@H]3CC[C@@H]2[C@H](N)C3)cc2nc(-c3cc4ccc([C@@H](C)NC(=O)N5CC(OC(F)(F)F)C5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-(trifluoromethoxy)azetidine-1-carboxamide |
| 203 | 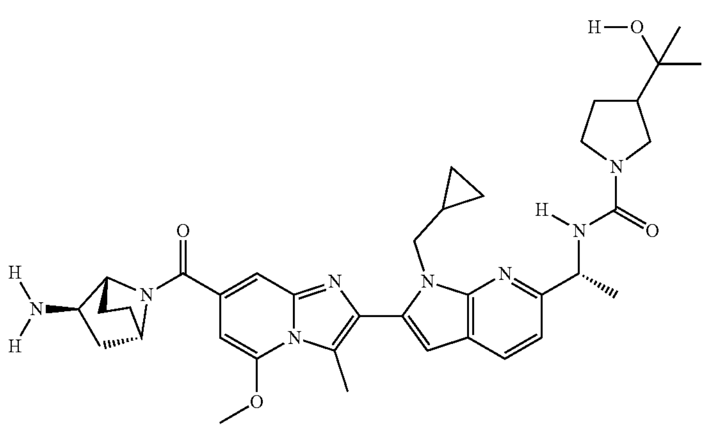 [SMILES: COc1cc(C(=O)N2[C@H]3CC[C@@H]2[C@H](N)C3)cc2nc(-c3cc4ccc([C@@H](C)NC(=O)N5CCC(C(C)(C)O)C5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-(2-hydroxypropan-2-yl)pyrrolidine-1-carboxamide |

-continued

| Ex | Structure | Name |
|---|---|---|
| 204 | 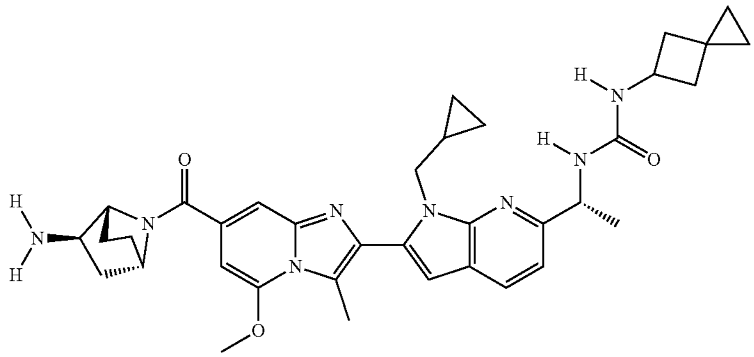 [SMILES: COc1cc(C(=O)N2[C@H]3CC[C@@H]2[C@H](N)C3)cc2nc(-c3cc4ccc([C@@H](C)NC(=O)NC5CC6(CC6)C5)nc4n3CC3CC3)c(C)n12] | 1-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-spiro[2.3]hexan-5-ylurea |
| 205 | 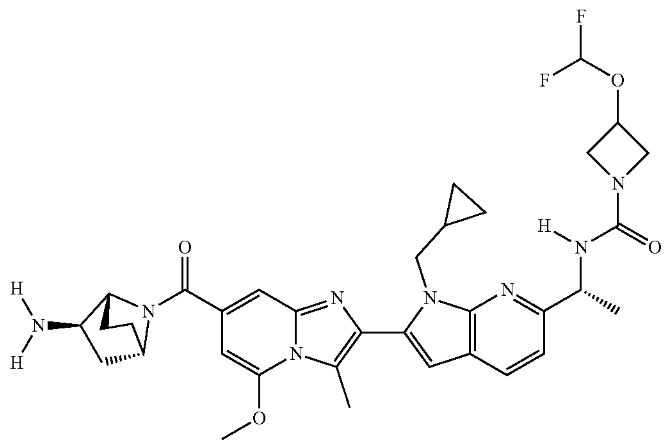 [SMILES: COc1cc(C(=O)N2[C@H]3CC[C@@H]2[C@H](N)C3)cc2nc(-c3cc4ccc([C@@H](C)NC(=O)N5CC(OC(F)F)C5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-(difluoromethoxy)azetidine-1-carboxamide |
| 206 | 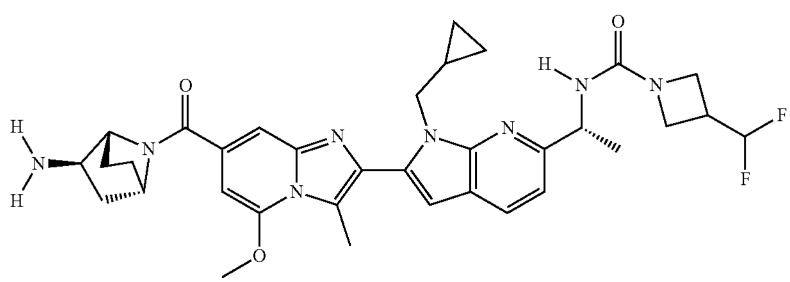 [SMILES: COc1cc(C(=O)N2[C@H]3CC[C@@H]2[C@H](N)C3)cc2nc(-c3cc4ccc([C@@H](C)NC(=O)N5CC(C(F)F)C5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-(difluoromethyl)azetidine-1-carboxamide |
| 207 | 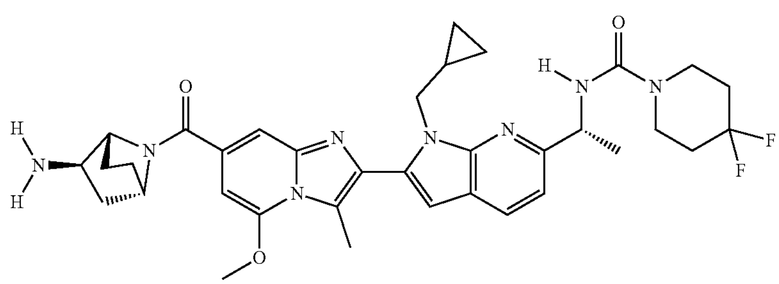 [SMILES: COc1cc(C(=O)N2[C@H]3CC[C@@H]2[C@H](N)C3)cc2nc(-c3cc4ccc([C@@H](C)NC(=O)N5CCC(F)(F)CC5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-4,4-difluoropiperidine-1-carboxamide |

-continued

| Ex | Structure | Name |
|---|---|---|
| 208 | 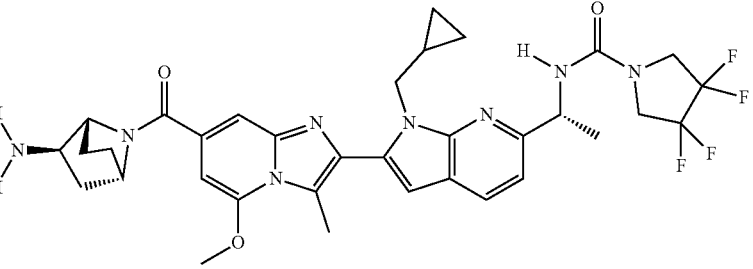 | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3,3,4,4-tetrafluoropyrrolidine-1-carboxamide |
| 209 | 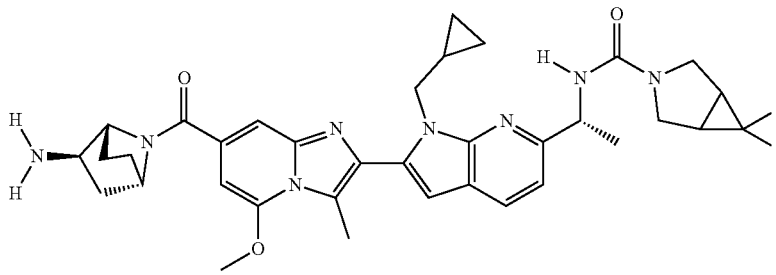 | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-6,6-difluoro-3-azabicyclo[3.1.0]hexane-3-carboxamide |
| 210 | 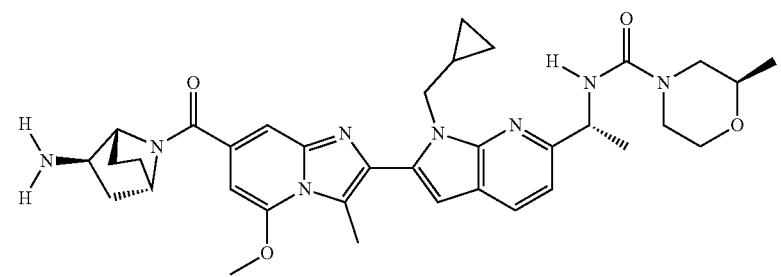 [SMILES: COc1cc(C(=O)N2[C@H]3CC[C@@H]2[C@H](N)C3)cc2nc(-c3cc4ccc([C@@H](C)NC(=O)N5CCO[C@H](C)C5)nc4n3CC3CC3)c(C)n12] | (2~{R})-~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-2-methylmorpholine-4-carboxamide |
| 211 | 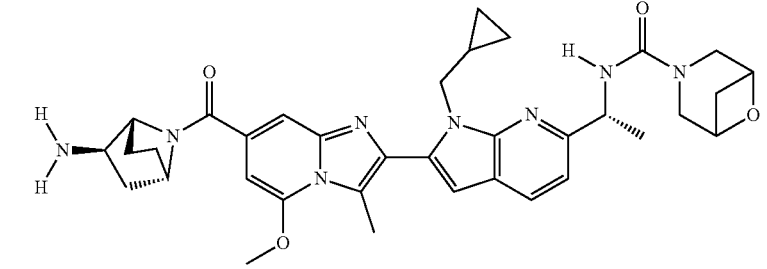 [SMILES: COc1cc(C(=O)N2[C@H]3CC[C@@H]2[C@H](N)C3)cc2nc(-c3cc4ccc([C@@H](C)NC(=O)N5CC6CC(C5)O6)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-6-oxa-3-azabicyclo[3.1.1]heptane-3-carboxamide |
| 212 | 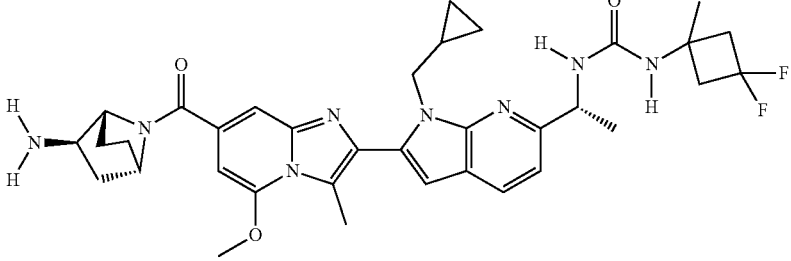 | 1-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-(3,3-difluoro-1-methylcyclobutyl)urea |

-continued

| Ex | Structure | Name |
|---|---|---|
| 213 | 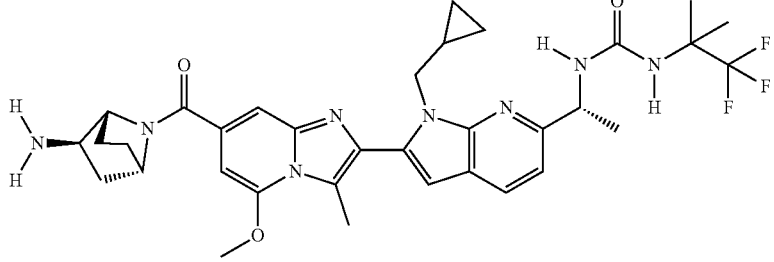 | 1-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-(1,1,1-trifluoro-2-methylpropan-2-yl)urea |
| 214 | 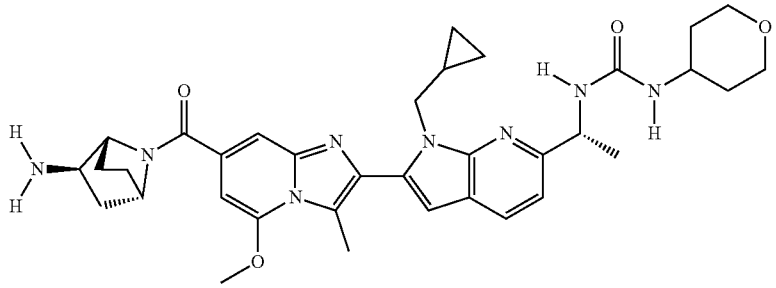 [SMILES: COc1cc(C(=O)N2[C@H]3CC[C@@H]2[C@H](N)C3)cc2nc(-c3cc4ccc([C@@H](C)NC(=O)NC5CCOCC5)nc4n3CC3CC3)c(C)n12] | 1-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-(oxan-4-yl)urea |
| 215 | 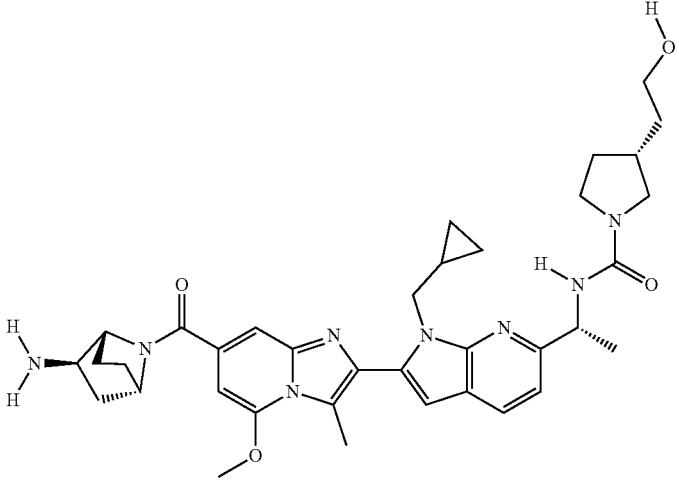 [SMILES: COc1cc(C(=O)N2[C@H]3CC[C@@H]2[C@H](N)C3)cc2nc(-c3cc4ccc([C@@H](C)NC(=O)N5CC[C@H](CCO)C5)nc4n3CC3CC3)c(C)n12] | (3~{R})-~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-(2-hydroxyethyl)pyrrolidine-1-carboxamide |
| 216 | 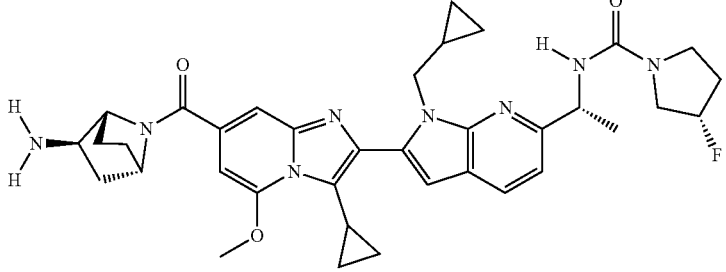 | (3~{S})-~{N}-[(1~{R})-1-[2-[7-[(1~{R},2~{R},4~{S})-2-amino-7-azabicyclo[2.2.1]heptane-7-carbonyl]-3-cyclopropyl-5-methoxyimidazo[1,2-a]pyridin-2-yl]-1-(cyclopropylmethyl)pyrrolo[2,3-b]pyridin-6-yl]ethyl]-3-fluoropyrrolidine-1-carboxamide |

| Ex | Structure | Name |
|---|---|---|
| 217 | 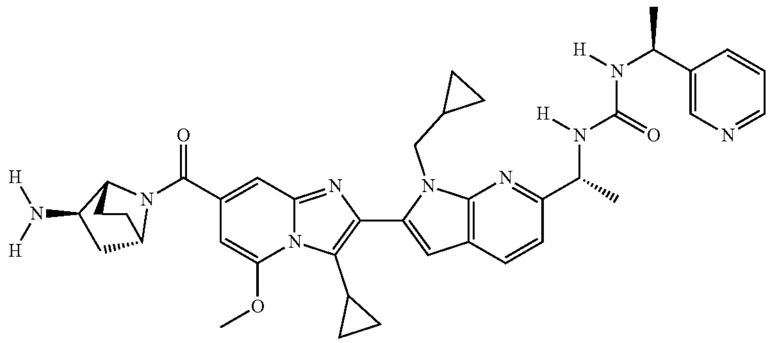 [SMILES: COc1cc(C(=O)N2[C@H]3CC[C@@H]2[C@H](N)C3)cc2nc(-c3cc4ccc([C@@H](C)NC(=O)N[C@@H](C)c5cccnc5)nc4n3CC3CC3)c(C3CC3)n12] | 1-[(1~{R})-1-[2-[7-[(1~{R},2~{R},4~{S})-2-amino-7-azabicyclo[2.2.1]heptane-7-carbonyl]-3-cyclopropyl-5-methoxyimidazo[1,2-a]pyridin-2-yl]-1-(cyclopropylmethyl)pyrrolo[2,3-b]pyridin-6-yl]ethyl]-3-[(1~{S})-1-pyridin-3-ylethyl]urea |
| 218 | 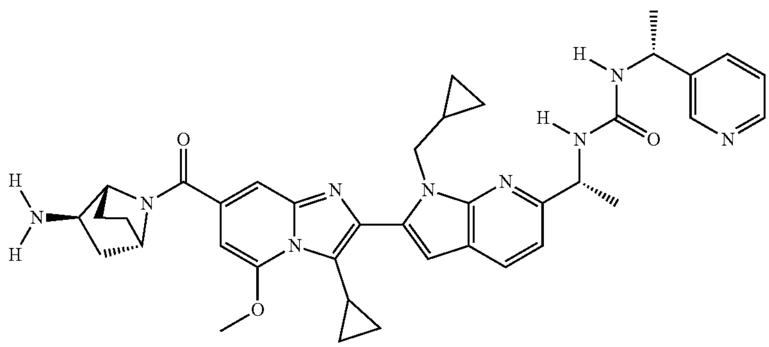 [SMILES: COc1cc(C(=O)N2[C@H]3CC[C@@H]2[C@H](N)C3)cc2nc(-c3cc4ccc([C@@H](C)NC(=O)N[C@H](C)c5cccnc5)nc4n3CC3CC3)c(C3CC3)n12] | 1-[(1~{R})-1-[2-[7-[(1~{R},2~{R},4~{S})-2-amino-7-azabicyclo[2.2.1]heptane-7-carbonyl]-3-cyclopropyl-5-methoxyimidazo[1,2-a]pyridin-2-yl]-1-(cyclopropylmethyl)pyrrolo[2,3-b]pyridin-6-yl]ethyl]-3-[(1~{R})-1-pyridin-3-ylethyl]urea |
| 219 | 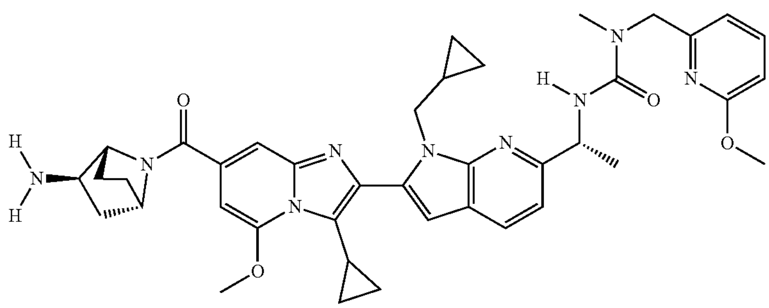 [SMILES: COc1cccc(CN(C)C(=O)N[C@H](C)c2ccc3cc(-c4nc5cc(C(=O)N6[C@H]7CC[C@@H]6[C@H](N)C7)cc(OC)n5c4C4CC4)n(CC4CC4)c3n2)n1] | 3-[(1~{R})-1-[2-[7-[(1~{R},2~{R},4~{S})-2-amino-7-azabicyclo[2.2.1]heptane-7-carbonyl]-3-cyclopropyl-5-methoxyimidazo[1,2-a]pyridin-2-yl]-1-(cyclopropylmethyl)pyrrolo[2,3-b]pyridin-6-yl]ethyl]-1-[(6-methoxypyridin-2-yl)methyl]-1-methylurea |
| 220 | 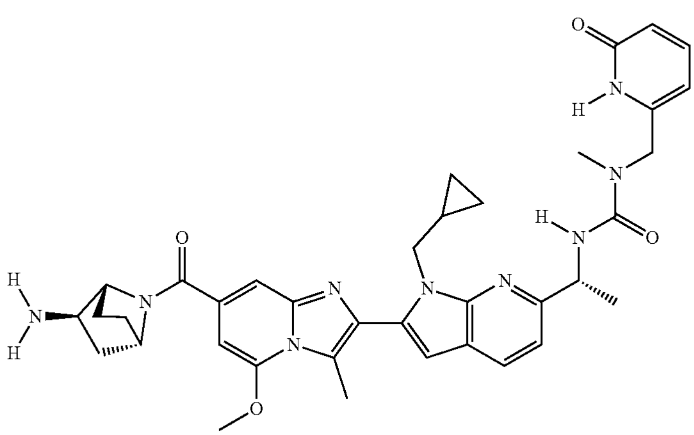 [SMILES: COc1cc(C(=O)N2[C@H]3CC[C@@H]2[C@H](N)C3)cc2nc(-c3cc4ccc([C@@H](C)NC(=O)N(C)Cc5cccc(=O)[nH]5)nc4n3CC3CC3)c(C)n12] | 3-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1-methyl-1-[(6-oxo-1~{H}-pyridin-2-yl)methyl]urea |

| Ex | Structure | Name |
|---|---|---|
| 221 | 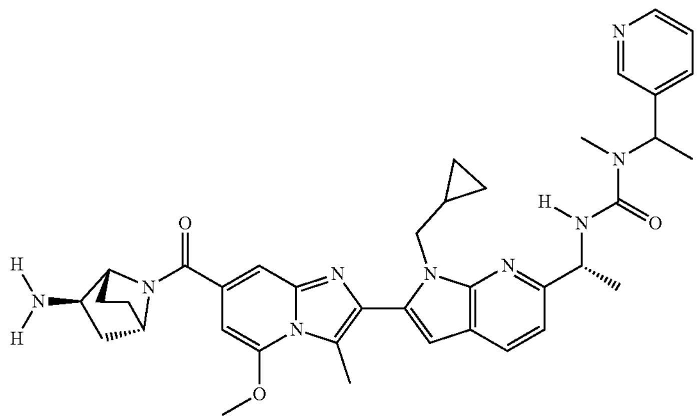 [SMILES: COc1cc(C(=O)N2[C@H]3CC[C@@H]2[C@H](N)C3)cc2nc(-c3cc4ccc([C@@H](C)NC(=O)N(C)C(C)c5cccnc5)nc4n3CC3CC3)c(C)n12] | 3-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1-methyl-1-(1-pyridin-3-ylethyl)urea |
| 222 | 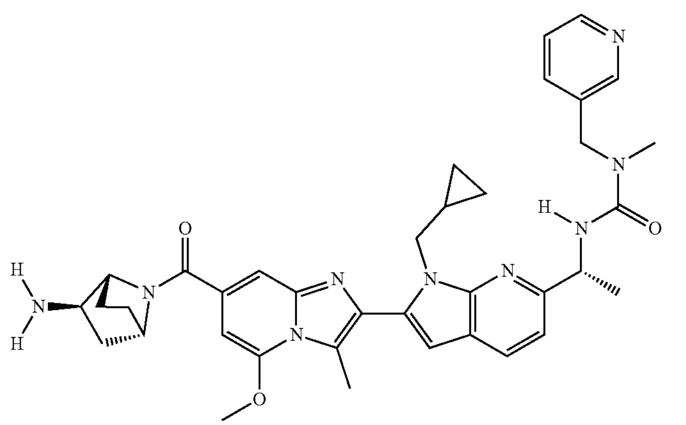 | 3-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1-methyl-1-(pyridin-3-ylmethyl)urea |
| 223 | 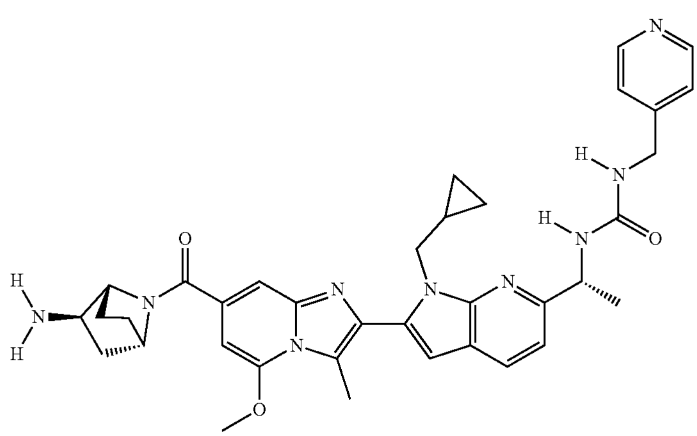 [SMILES: COc1cc(C(=O)N2[C@H]3CC[C@@H]2[C@H](N)C3)cc2nc(-c3cc4ccc([C@@H](C)NC(=O)NCc5ccncc5)nc4n3CC3CC3)c(C)n12] | 1-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-(pyridin-4-ylmethyl)urea |

| Ex | Structure | Name |
| --- | --- | --- |
| 224 | 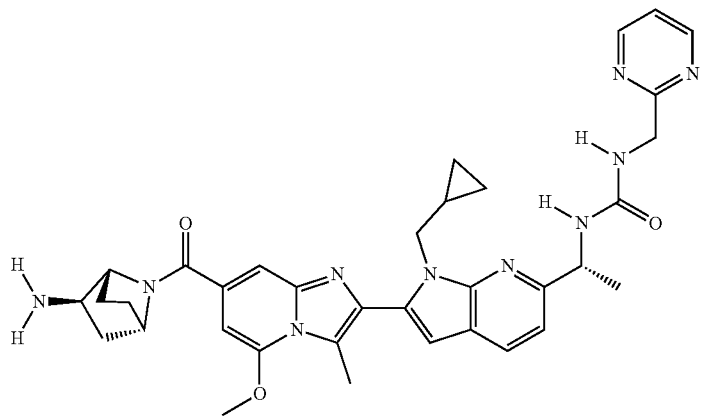 [SMILES: COc1cc(C(=O)N2[C@H]3CC[C@@H]2[C@H](N)C3)cc2nc(-c3cc4ccc([C@@H](C)NC(=O)NCc5ncccn5)nc4n3CC3CC3)c(C)n12] | 1-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-(pyrimidin-2-ylmethyl)urea |
| 225 | 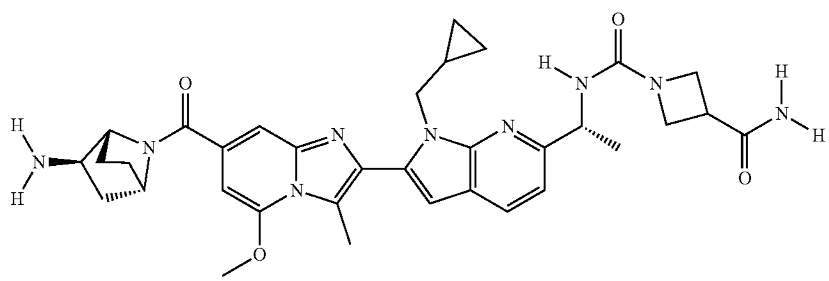 [SMILES: COc1cc(C(=O)N2[C@H]3CC[C@@H]2[C@H](N)C3)cc2nc(-c3cc4ccc([C@@H](C)NC(=O)N5CC(C(N)=O)C5)nc4n3CC3CC3)c(C)n12] | 1-~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]azetidine-1,3-dicarboxamide |
| 226 | 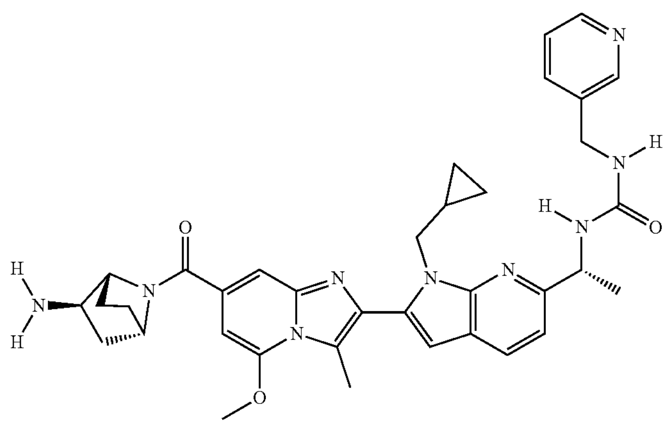 [SMILES: COc1cc(C(=O)N2[C@H]3CC[C@@H]2[C@H](N)C3)cc2nc(-c3cc4ccc([C@@H](C)NC(=O)NCc5cccnc5)nc4n3CC3CC3)c(C)n12] | 1-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-(pyridin-3-ylmethyl)urea |
| 227 | 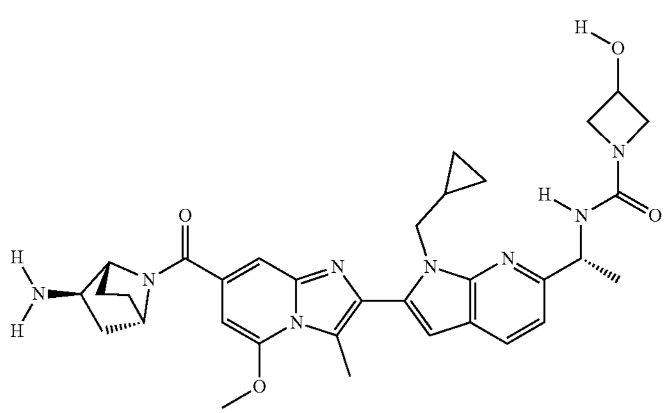 [SMILES: COc1cc(C(=O)N2[C@H]3CC[C@@H]2[C@H](N)C3)cc2nc(-c3cc4ccc([C@@H](C)NC(=O)N5CC(O)C5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-hydroxyazetidine-1-carboxamide |

| Ex | Structure | Name |
|---|---|---|
| 228 | 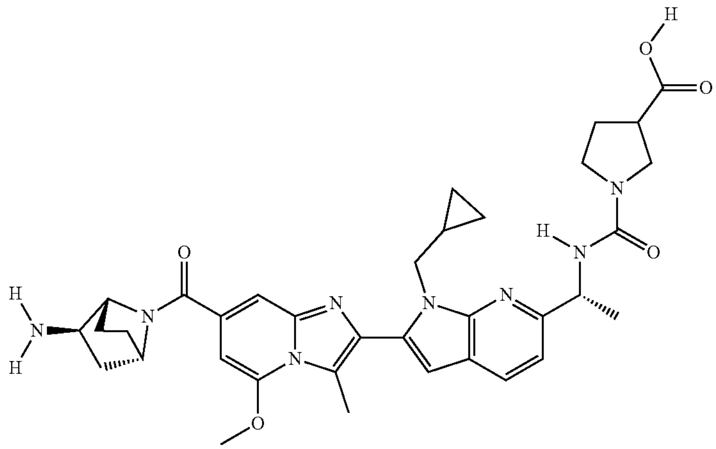 [SMILES: COc1cc(C(=O)N2[C@H]3CC[C@@H]2[C@H](N)C3)cc2nc(-c3cc4ccc([C@@H](C)NC(=O)N5CCC(C(=O)O)C5)nc4n3CC3CC3)c(C)n12] | 1-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]carbamoyl]pyrrolidine-3-carboxylic acid |
| 229 | 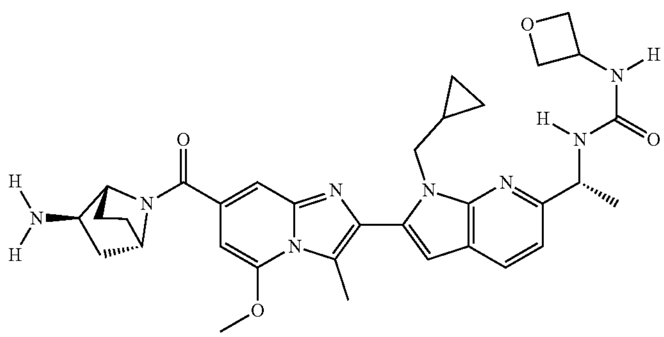 [SMILES: COc1cc(C(=O)N2[C@H]3CC[C@@H]2[C@H](N)C3)cc2nc(-c3cc4ccc([C@@H](C)NC(=O)NC5COC5)nc4n3CC3CC3)c(C)n12] | 1-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-(oxetan-3-yl)urea |
| 230 | 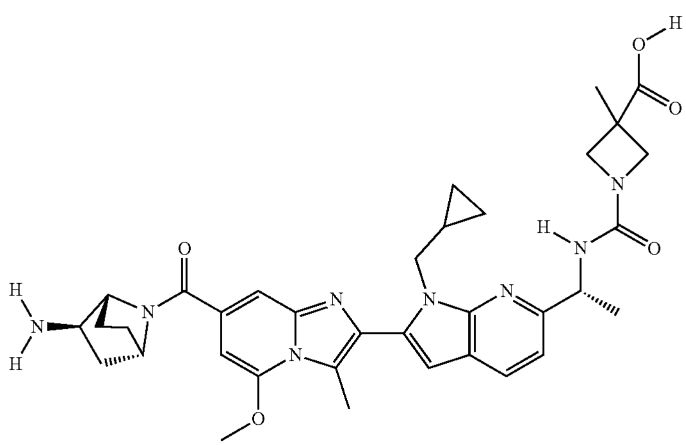 [SMILES: COc1cc(C(=O)N2[C@H]3CC[C@@H]2[C@H](N)C3)cc2nc(-c3cc4ccc([C@@H](C)NC(=O)N5CC(C)(C(=O)O)C5)nc4n3CC3CC3)c(C)n12] | 1-[[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]carbamoyl]-3-methylazetidine-3-carboxylic acid |
| 231 | 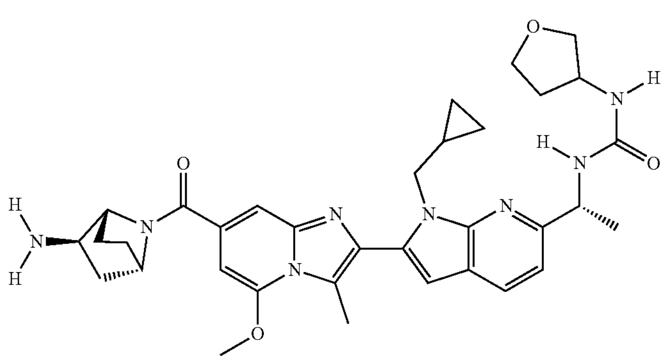 [SMILES: COc1cc(C(=O)N2[C@H]3CC[C@@H]2[C@H](N)C3)cc2nc(-c3cc4ccc([C@@H](C)NC(=O)NC5CCOC5)nc4n3CC3CC3)c(C)n12] | 1-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-(oxolan-3-yl)urea |

-continued

| Ex | Structure | Name |
|---|---|---|
| 232 | 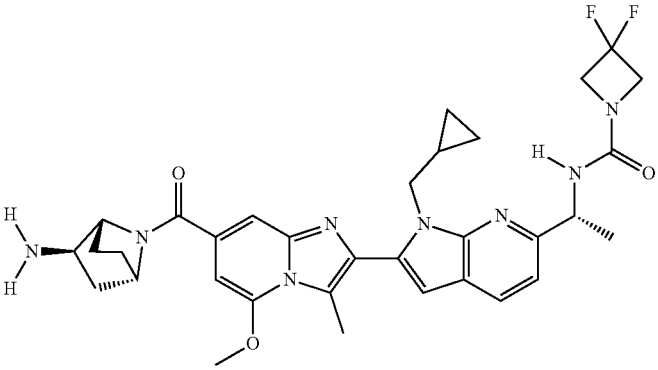 [SMILES: COc1cc(C(=O)N2[C@H]3CC[C@@H]2[C@H](N)C3)cc2nc(-c3cc4ccc([C@@H](C)NC(=O)N5CC(F)(F)C5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3,3-difluoroazetidine-1-carboxamide |
| 233 | 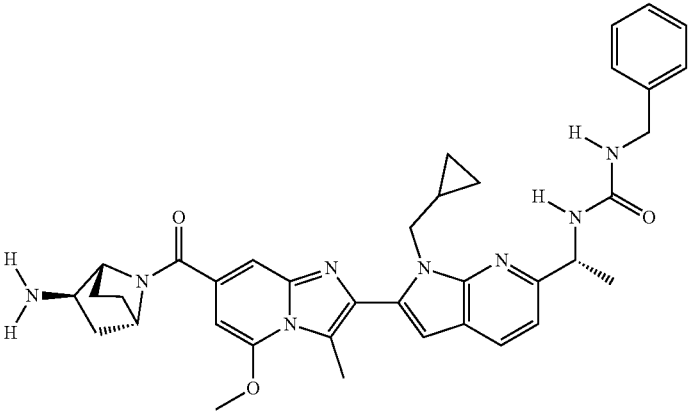 [SMILES: COc1cc(C(=O)N2[C@H]3CC[C@@H]2[C@H](N)C3)cc2nc(-c3cc4ccc([C@@H](C)NC(=O)NCc5ccccc5)nc4n3CC3CC3)c(C)n12] | 1-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-benzylurea |
| 234 | 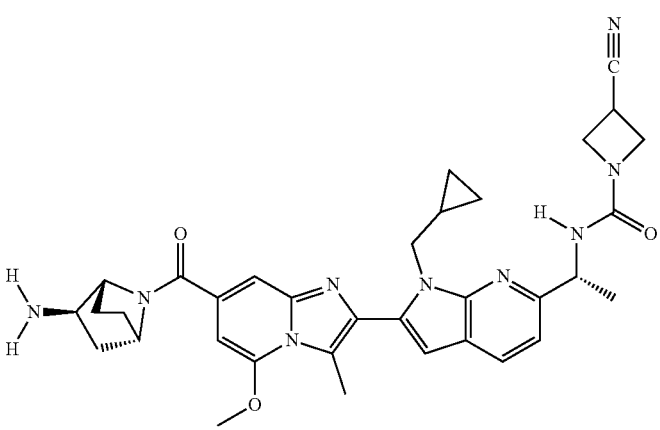 [SMILES: COc1cc(C(=O)N2[C@H]3CC[C@@H]2[C@H](N)C3)cc2nc(-c3cc4ccc([C@@H](C)NC(=O)N5CC(C#N)C5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-cyanoazetidine-1-carboxamide |
| 235 | 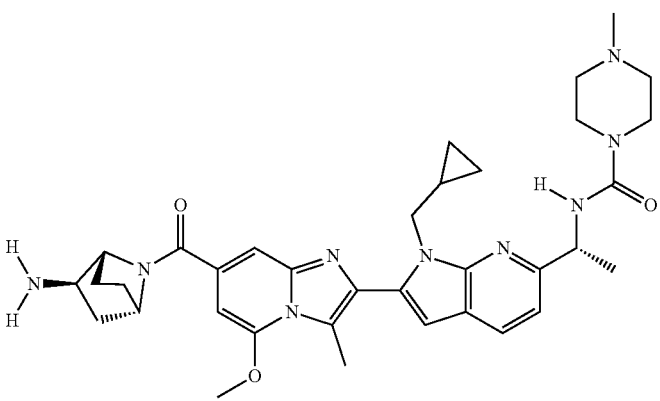 [SMILES: COc1cc(C(=O)N2[C@H]3CC[C@@H]2[C@H](N)C3)cc2nc(-c3cc4ccc([C@@H](C)NC(=O)N5CCN(C)CC5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-4-methylpiperazine-1-carboxamide |

| Ex | Structure | Name |
| --- | --- | --- |
| 236 | 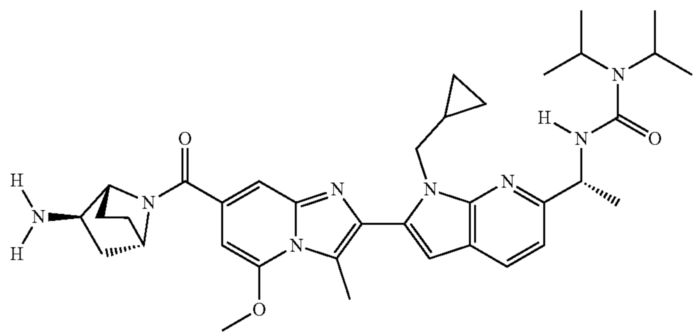 [SMILES: COc1cc(C(=O)N2[C@H]3CC[C@@H]2[C@H](N)C3)cc2nc(-c3cc4ccc([C@@H](C)NC(=O)N(C(C)C)C(C)C)nc4n3CC3CC3)c(C)n12] | 3-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1,1-di(propan-2-yl)urea |
| 237 | 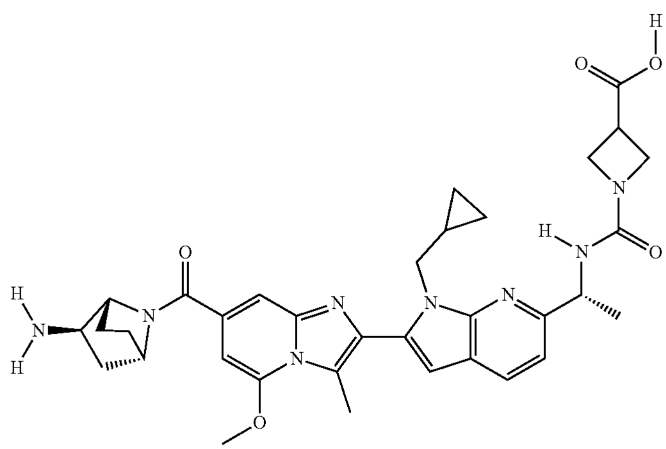 [SMILES: COc1cc(C(=O)N2[C@H]3CC[C@@H]2[C@H](N)C3)cc2nc(-c3cc4ccc([C@@H](C)NC(=O)N5CC(C(=O)O)C5)nc4n3CC3CC3)c(C)n12] | 1-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]carbamoyl]azetidine-3-carboxylic acid |
| 238 | 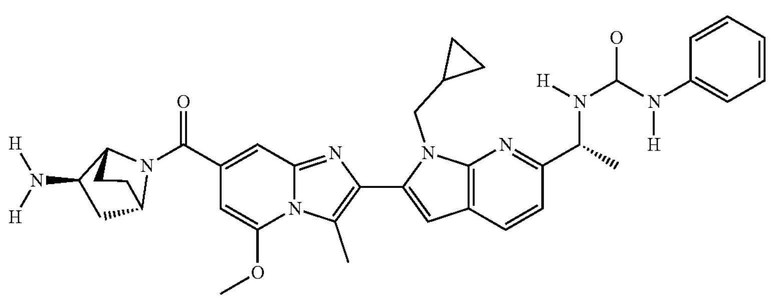 [SMILES: COc1cc(C(=O)N2[C@H]3CC[C@@H]2[C@H](N)C3)cc2nc(-c3cc4ccc([C@@H](C)NC(O)Nc5ccccc5)nc4n3CC3CC3)c(C)n12] | 1-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-(2,6-dimethylphenyl)urea |
| 239 | 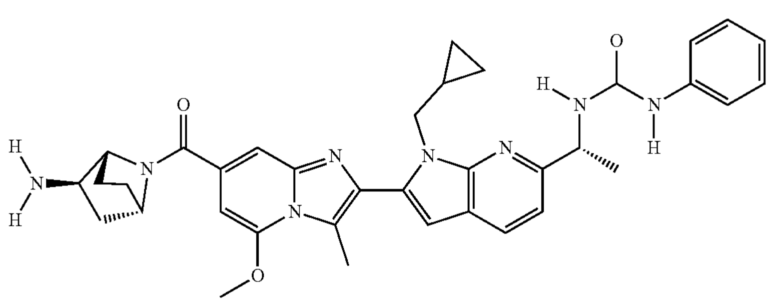 [SMILES: COc1cc(C(=O)N2[C@H]3CC[C@@H]2[C@H](N)C3)cc2nc(-c3cc4ccc([C@@H](C)NC(O)Nc5ccccc5)nc4n3CC3CC3)c(C)n12] | 1-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-phenylurea |

| Ex | Structure | Name |
|---|---|---|
| 240 | 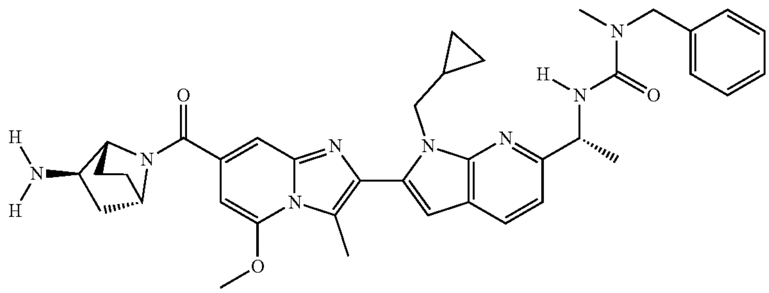 [SMILES: COc1cc(C(=O)N2[C@H]3CC[C@@H]2[C@H](N)C3)cc2nc(-c3cc4ccc([C@@H](C)NC(=O)N(C)Cc5ccccc5)nc4n3CC3CC3)c(C)n12] | 3-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1-benzyl-1-methylurea |
| 241 | 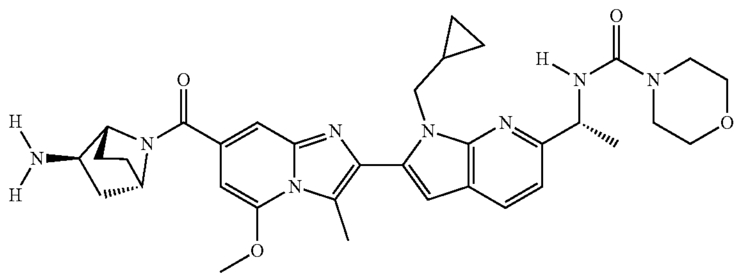 [SMILES: COc1cc(C(=O)N2[C@H]3CC[C@@H]2[C@H](N)C3)cc2nc(-c3cc4ccc([C@@H](C)NC(=O)N5CCOCC5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]morpholine-4-carboxamide |
| 242 | 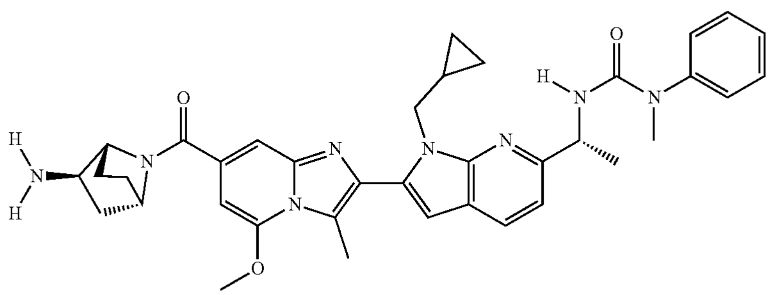 [SMILES: COc1cc(C(=O)N2[C@H]3CC[C@@H]2[C@H](N)C3)cc2nc(-c3cc4ccc([C@@H](C)NC(=O)N(C)c5ccccc5)nc4n3CC3CC3)c(C)n12] | 3-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1-methyl-1-phenylurea |
| 243 | 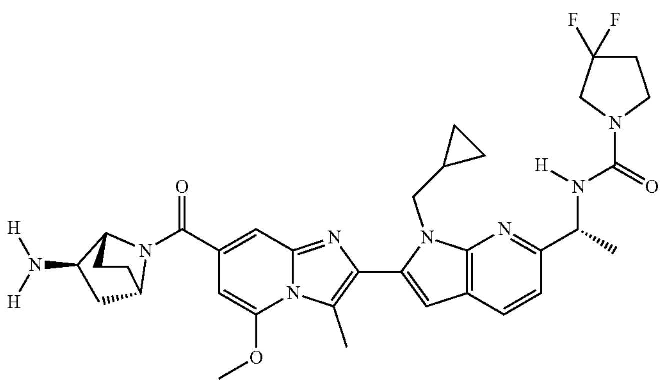 [SMILES: COc1cc(C(=O)N2[C@H]3CC[C@@H]2[C@H](N)C3)cc2nc(-c3cc4ccc([C@@H](C)NC(=O)N5CCC(F)(F)C5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3,3-difluoropyrrolidine-1-carboxamide |
| 244 | 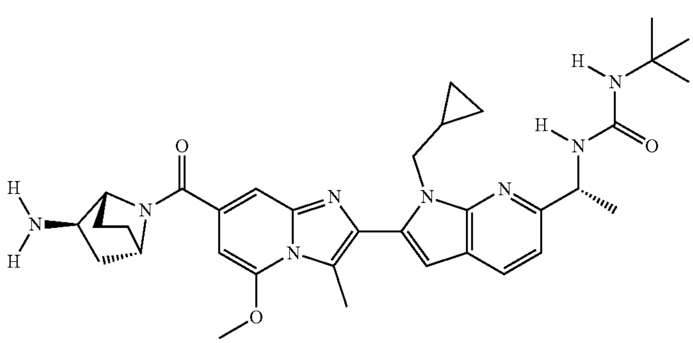 [SMILES: COc1cc(C(=O)N2[C@H]3CC[C@@H]2[C@H](N)C3)cc2nc(-c3cc4ccc([C@@H](C)NC(=O)NC(C)(C)C)nc4n3CC3CC3)c(C)n12] | 1-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-~{tert}-butylurea |

-continued

| Ex | Structure | Name |
|---|---|---|
| 245 | 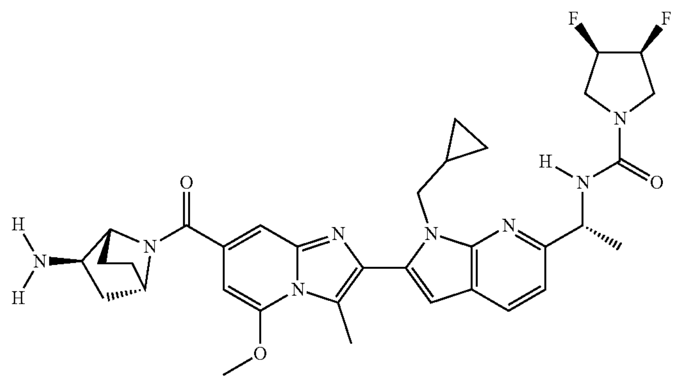 [SMILES: COc1cc(C(=O)N2[C@H]3CC[C@@H]2[C@H](N)C3)cc2nc(-c3cc4ccc([C@@H](C)NC(=O)N5C[C@@H](F)[C@@H](F)C5)nc4n3CC3CC3)c(C)n12] | (3~{R},4~{S})-~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3,4-difluoropyrrolidine-1-carboxamide |
| 246 | 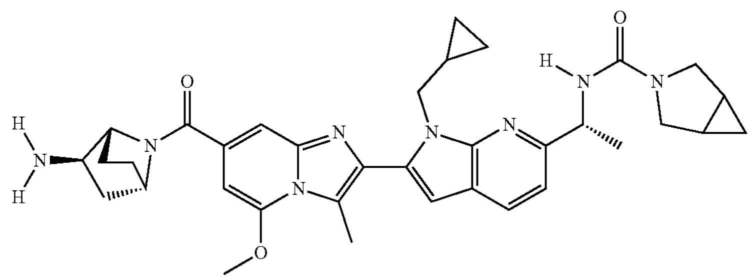 [SMILES: COc1cc(C(=O)N2[C@H]3CC[C@@H]2[C@H](N)C3)cc2nc(-c3cc4ccc([C@@H](C)NC(=O)N5CC6CC6C5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-azabicyclo[3.1.0]hexane-3-carboxamide |
| 247 | 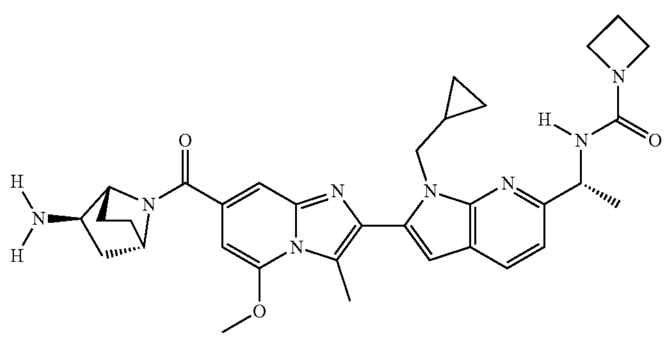 [SMILES: COc1cc(C(=O)N2[C@H]3CC[C@@H]2[C@H](N)C3)cc2nc(-c3cc4ccc([C@@H](C)NC(=O)N5CCC5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-ylethyl]azetidine-1-carboxamide |
| 248 | 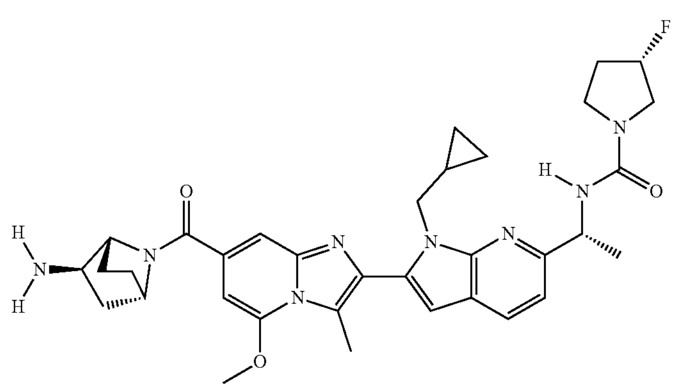 [SMILES: COc1cc(C(=O)N2[C@H]3CC[C@@H]2[C@H](N)C3)cc2nc(-c3cc4ccc([C@@H](C)NC(=O)N5CC[C@H](F)C5)nc4n3CC3CC3)c(C)n12] | (3~{S})-~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-fluoropyrrolidine-1-carboxamide |

-continued

| Ex | Structure | Name |
|---|---|---|
| 249 | 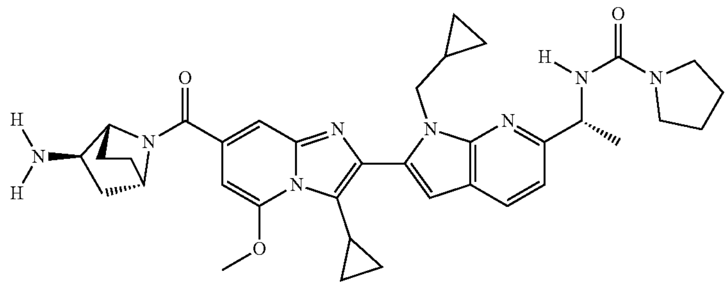 [SMILES: COc1cc(C(=O)N2[C@H]3CC[C@@H]2[C@H](N)C3)cc2nc(-c3cc4ccc([C@@H](C)NC(=O)N5CCCC5)nc4n3CC3CC3)c(C3CC3)n12] | ~{N}-[(1~{R})-1-[2-[7-[(1~{R},2~{R},4~{S})-2-amino-7-azabicyclo[2.2.1]heptane-7-carbonyl]-3-cyclopropyl-5-methoxyimidazo[1,2-a]pyridin-2-yl]-1-(cyclopropylmethyl)pyrrolo[2,3-b]pyridin-6-yl]ethyl]pyrrolidine-1-carboxamide |
| 250 | 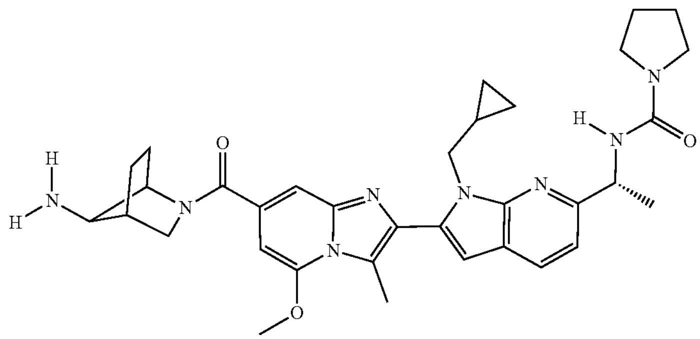 [SMILES: COc1cc(C(=O)N2CC3CCC2C3N)cc2nc(-c3cc4ccc([C@@H](C)NC(=O)N5CCCC5)nc4n3CC3CC3)c(C)n12] | N-((R)-1-(2-(7-((1R,4R,7R)-7-amino-2-azabicyclo[2.2.1]heptane-2-carbonyl)-5-methoxy-3-methylimidazo[1,2-a]pyridin-2-yl)-1-(cyclopropylmethyl)-1H-pyrrolo[2,3-b]pyridin-6-yl)ethyl)pyrrolidine-1-carboxamide |
| 251 | 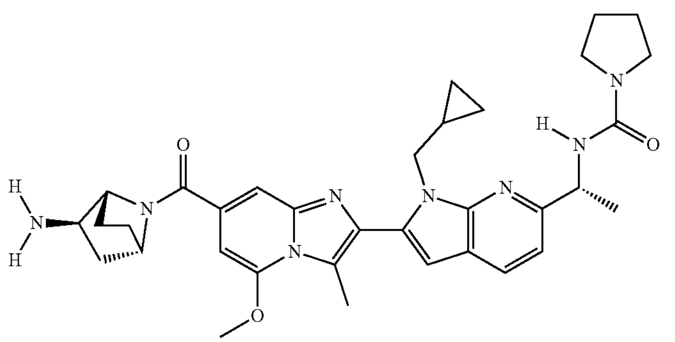 [SMILES: COc1cc(C(=O)N2[C@H]3CC[C@@H]2[C@H](N)C3)cc2nc(-c3cc4ccc([C@@H](C)NC(=O)N5CCCC5)nc4n3CC3CC3)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]pyrrolidine-1-carboxamide |
| 252 | 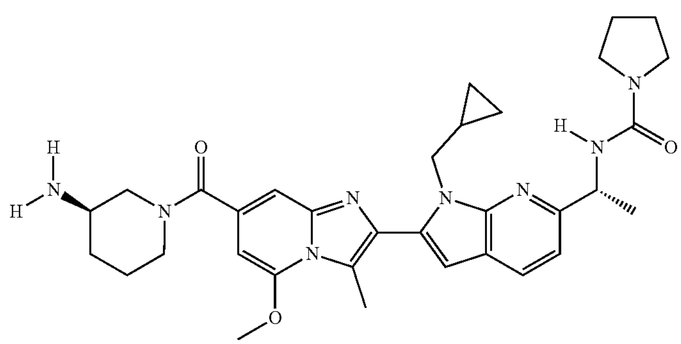 [SMILES: COc1cc(C(=O)N2CCC[C@@H](N)C2)cc2nc(-c3cc4ccc([C@@H](C)NC(=O)N5CCCC5)nc4n3CC3CC3)c(C)n12] | ~{N}-[(1~{R})-1-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]ethyl]pyrrolidine-1-carboxamide |
| 253 | 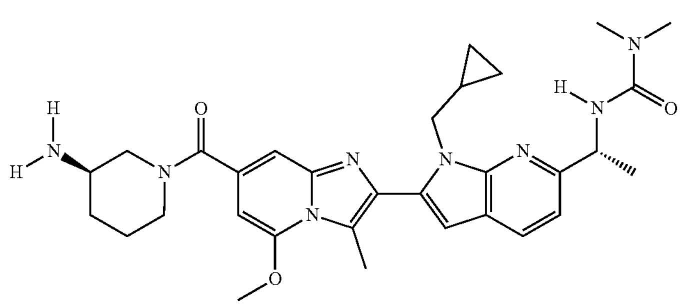 [SMILES: COc1cc(C(=O)N2CCC[C@@H](N)C2)cc2nc(-c3cc4ccc([C@@H](C)NC(=O)N(C)C)nc4n3CC3CC3)c(C)n12] | 3-[(1~{R})-1-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]ethyl]-1,1-dimethylurea |

-continued

| Ex | Structure | Name |
|---|---|---|
| 254 | 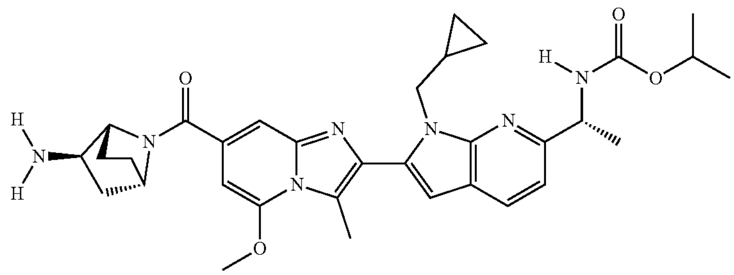 [SMILES: COc1cc(C(=O)N2[C@H]3CC[C@@H]2[C@H](N)C3)cc2nc(-c3cc4ccc([C@@H](C)NC(=O)OC(C)C)nc4n3CC3CC3)c(C)n12] | propan-2-yl~{N}-[(1~{R})-1-[2-[7-[(1~{R}, 2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]carbamate |
| 255 | 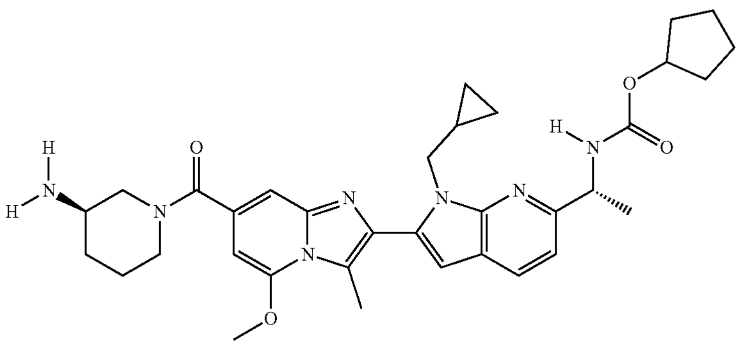 [SMILES: COc1cc(C(=O)N2CCC[C@@H](N)C2)cc2nc(-c3cc4ccc([C@@H](C)NC(=O)OC5CCCC5)nc4n3CC3CC3)c(C)n12] | cyclopentyl~{N}-[(1~{R})-1-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]ethyl]carbamate |
| 256 | 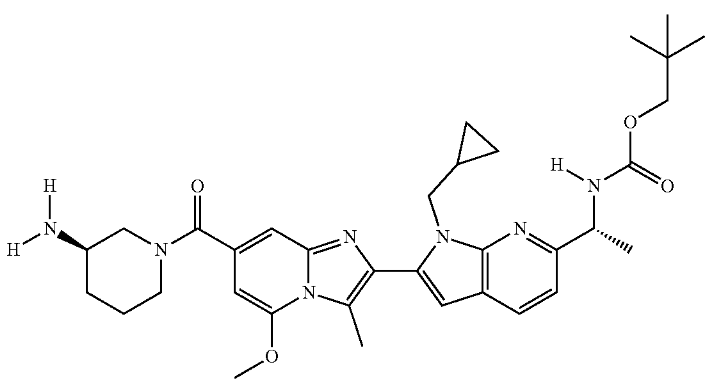 [SMILES: COc1cc(C(=O)N2CCC[C@@H](N)C2)cc2nc(-c3cc4ccc([C@@H](C)NC(=O)OCC(C)(C)C)nc4n3CC3CC3)c(C)n12] | 2,2-dimethylpropyl~{N}-[(1~{R})-1-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]ethyl]carbamate |
| 257 | 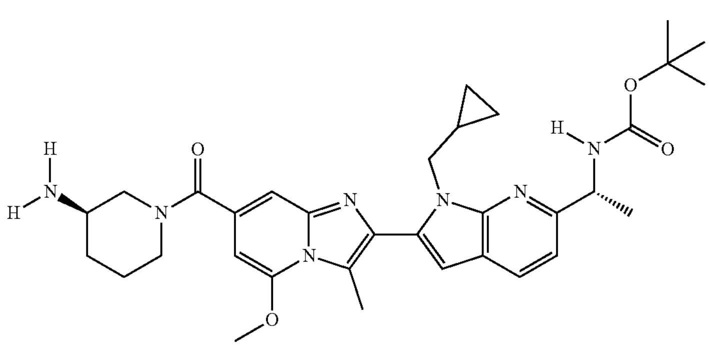 [SMILES: COc1cc(C(=O)N2CCC[C@@H](N)C2)cc2nc(-c3cc4ccc([C@@H](C)NC(=O)OC(C)(C)C)nc4n3CC3CC3)c(C)n12] | ~{tert}-butyl~{N}-[(1~{R})-1-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]ethyl]carbamate |

| Ex | Structure | Name |
|---|---|---|
| 258 | 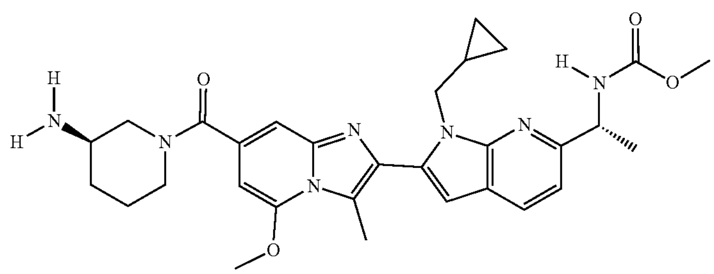 [SMILES: COC(=O)N[C@H](C)c1ccc2cc(-c3nc4cc(C(=O)N5CCC[C@@H](N)C5)cc(OC)n4c3C)n(CC3CC3)c2n1] | methyl~{N}-[(1~{R})-1-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-ylethyl]carbamate |
| 259 | 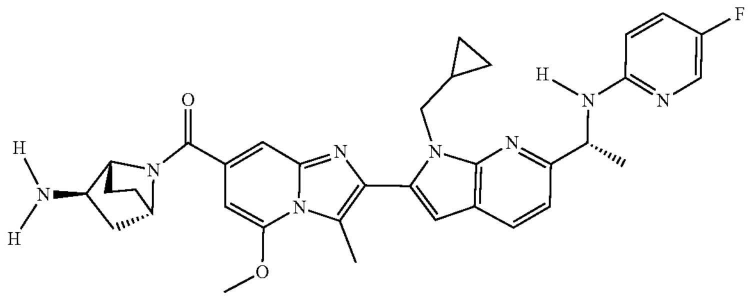 [SMILES: COc1cc(C(=O)N2[C@H]3CC[C@@H]2[C@H](N)C3)cc2nc(-c3cc4ccc([C@@H](C)Nc5ccc(F)cn5)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-[(1~{R})-1-[(5-fluoropyridin-2-yl)amino]ethyl]pyrrolo[2,3-b]pyridin-2-yl]-5-methoxy-3-methylimidazo[1,2-a]pyridin-7-yl]methanone |
| 260 | 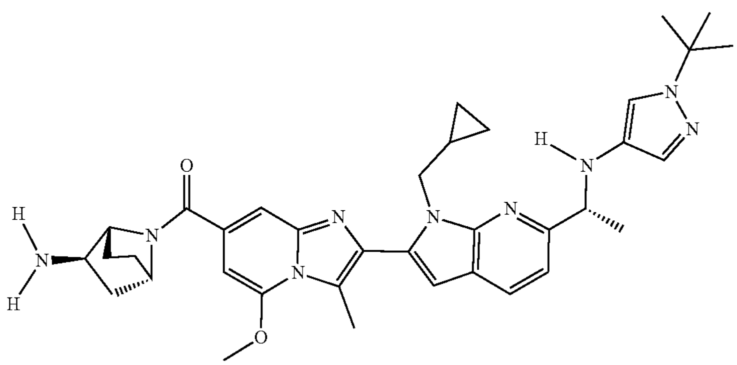 [SMILES: COc1cc(C(=O)N2[C@H]3CC[C@@H]2[C@H](N)C3)cc2nc(-c3cc4ccc([C@@H](C)Nc5cnn(C(C)(C)C)c5)nc4n3CC3CC3)c(C)n12] | [(1~{R},2~{R},4~{S})-2-amino-7-azabicyclo[2.2.1]heptan-7-yl]-[2-[6-[(1~{R})-1-[(1-~{tert}-butylpyrazol-4-yl)amino]ethyl]-1-(cyclopropylmethyl)pyrrolo[2,3-b]pyridin-2-yl]-5-methoxy-3-methylimidazo[1,2-a]pyridin-7-yl]methanone |
| 261 | 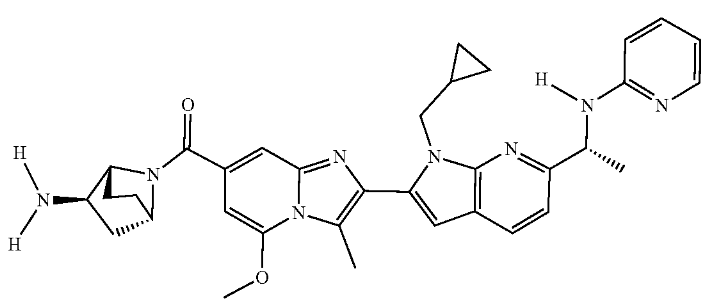 [SMILES: COc1cc(C(=O)N2[C@H]3CC[C@@H]2[C@H](N)C3)cc2nc(-c3cc4ccc([C@@H](C)Nc5ccccn5)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-[(1~{R})-1-(pyridin-2-ylamino)ethyl]pyrrolo[2,3-b]pyridin-2-yl]-5-methoxy-3-methylimidazo[1,2-a]pyridin-7-yl]methanone |
| 262 | 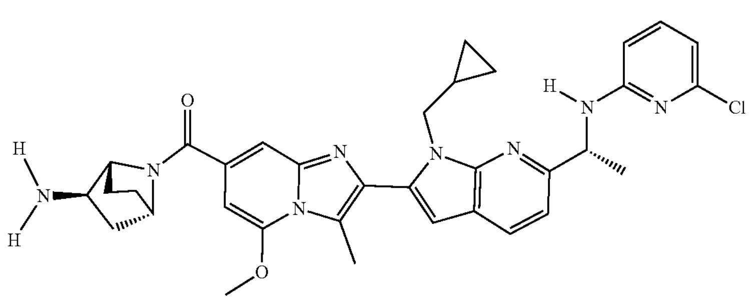 [SMILES: COc1cc(C(=O)N2[C@H]3CC[C@@H]2[C@H](N)C3)cc2nc(-c3cc4ccc([C@@H](C)Nc5cccc(Cl)n5)nc4n3CC3CC3)c(C)n12] | [(1~{R},2~{R},4~{S})-2-amino-7-azabicyclo[2.2.1]heptan-7-yl]-[2-[6-[(1~{R})-1-[(6-chloropyridin-2-yl)amino]ethyl]-1-(cyclopropylmethyl)pyrrolo[2,3-b]pyridin-2-yl]-5-methoxy-3-methylimidazo[1,2-a]pyridin-7-yl]methanone |

| Ex | Structure | Name |
|---|---|---|
| 263 | 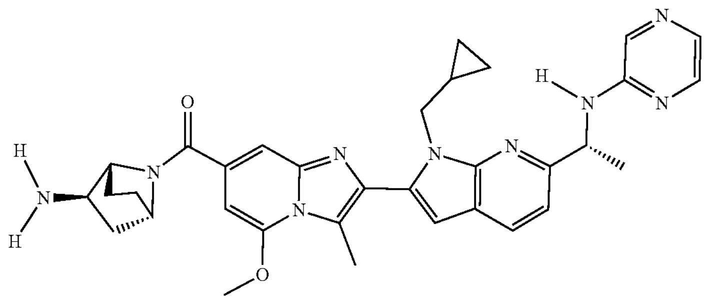 [SMILES: COc1cc(C(=O)N2[C@H]3CC[C@@H]2[C@H](N)C3)cc2nc(-c3cc4ccc([C@@H](C)Nc5cnccn5)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-[(1~{R})-1-(pyrazin-2-ylamino)ethyl]pyrrolo[2,3-b]pyridin-2-yl]-5-methoxy-3-methylimidazo[1,2-a]pyridin-7-yl]methanone |
| 264 | 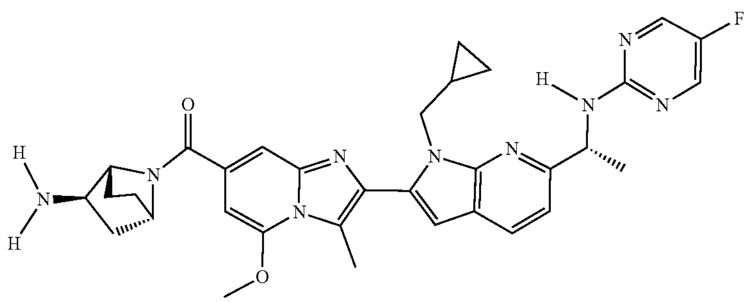 | [(1~{R},2~{R},4~{S})-2-amino-7-azabicyclo[2.2.1]heptan-7-yl]-[2-[1-(cyclopropylmethyl)-6-[(1~{R})-1-[(5-fluoropyrimidin-2-yl)amino]ethyl]pyrrolo[2,3-b]pyridin-2-yl]-5-methoxy-3-methylimidazo[1,2-a]pyridin-7-yl]methanone |
| 265 | 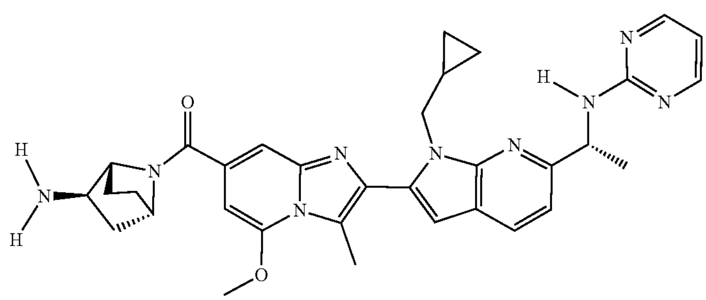 [SMILES: COc1cc(C(=O)N2[C@H]3CC[C@@H]2[C@H](N)C3)cc2nc(-c3cc4ccc([C@@H](C)Nc5ncccn5)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-[(1~{R})-1-(pyrimidin-2-ylamino)ethyl]pyrrolo[2,3-b]pyridin-2-yl]-5-methoxy-3-methylimidazo[1,2-a]pyridin-7-yl]methanone |
| 266 | 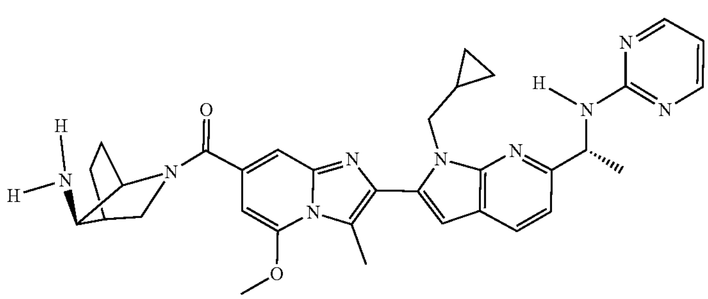 [SMILES: COc1cc(C(=O)N2CC3CCC2[C@@H]3N)cc2nc(-c3cc4ccc([C@@H](C)Nc5ncccn5)nc4n3CC3CC3)c(C)n12] | ((1R,4R,7R)-7-amino-2-azabicyclo[2.2.1]heptan-2-yl)(2-(1-(cyclopropylmethyl)-6-((R)-1-(pyrimidin-2-ylamino)ethyl)-1H-pyrrolo[2,3-b]pyridin-2-yl)-5-methoxy-3-methylimidazo[1,2-a]pyridin-7-yl)methanone |
| 267 | 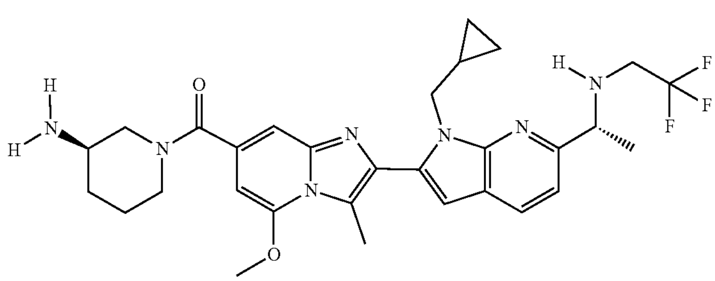 [SMILES: COc1cc(C(=O)N2CCC[C@@H](N)C2)cc2nc(-c3cc4ccc([C@@H](C)NCC(F)(F)F)nc4n3CC3CC3)c(C)n12] | [(3~{R})-3-aminopiperidin-1-yl]-[2-[1-(cyclopropylmethyl)-6-[(1~{R})-1-(2,2,2-trifluoroethylamino)ethyl]pyrrolo[2,3-b]pyridin-2-yl]-5-methoxy-3-methylimidazo[1,2-a]pyridin-7-yl]methanone |

| Ex | Structure | Name |
|---|---|---|
| 268 | 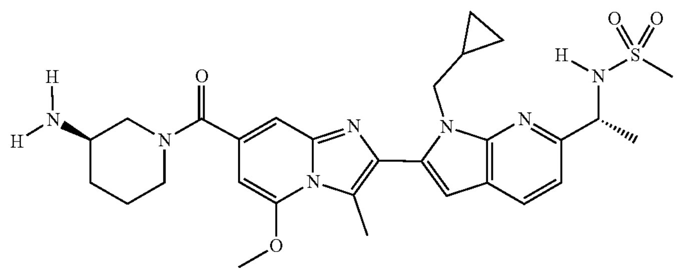 [SMILES: COc1cc(C(=O)N2CCC[C@@H](N)C2)cc2nc(-c3cc4ccc([C@@H](C)NS(C)(=O)=O)nc4n3CC3CC3)c(C)n12] | ~{N}-[(1~{R})-1-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]ethyl]methanesulfonamide |
| 269 | 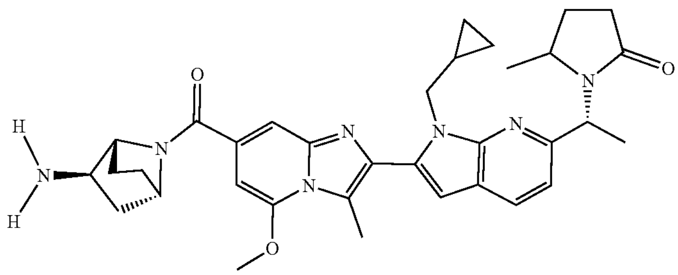 [SMILES: COc1cc(C(=O)N2[C@H]3CC[C@@H]2[C@H](N)C3)cc2nc(-c3cc4ccc([C@@H](C)N5C(=O)CCC5C)nc4n3CC3CC3)c(C)n12] | 1-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-5-methylpyrrolidin-2-one |
| 270 | 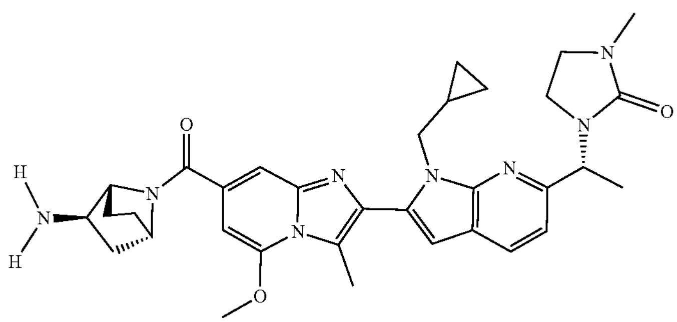 [SMILES: COc1cc(C(=O)N2[C@H]3CC[C@@H]2[C@H](N)C3)cc2nc(-c3cc4ccc([C@@H](C)N5CCN(C)C5=O)nc4n3CC3CC3)c(C)n12] | 1-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-3-methylimidazolidin-2-one |
| 271 | 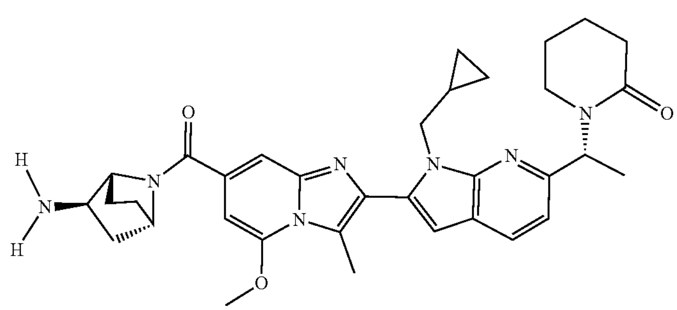 [SMILES: COc1cc(C(=O)N2[C@H]3CC[C@@H]2[C@H](N)C3)cc2nc(-c3cc4ccc([C@@H](C)N5CCCCC5=O)nc4n3CC3CC3)c(C)n12] | 1-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-ylethyl]piperidin-2-one |
| 272 | 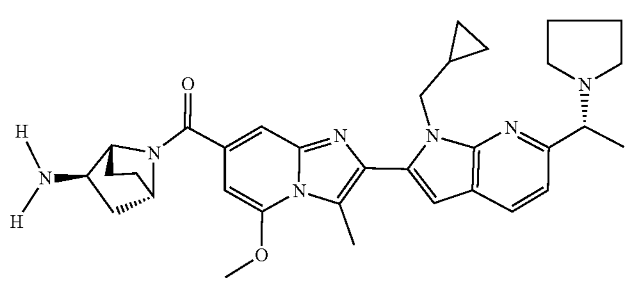 [SMILES: COc1cc(C(=O)N2[C@H]3CC[C@@H]2[C@H](N)C3)cc2nc(-c3cc4ccc([C@@H](C)N5CCCC5)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-[(1~{R})-1-pyrrolidin-1-ylethyl]pyrrolo[2,3-b]pyridin-2-yl]-5-methoxy-3-methylimidazo[1,2-a]pyridin-7-yl]methanone |

-continued

| Ex | Structure | Name |
|---|---|---|
| 273 | 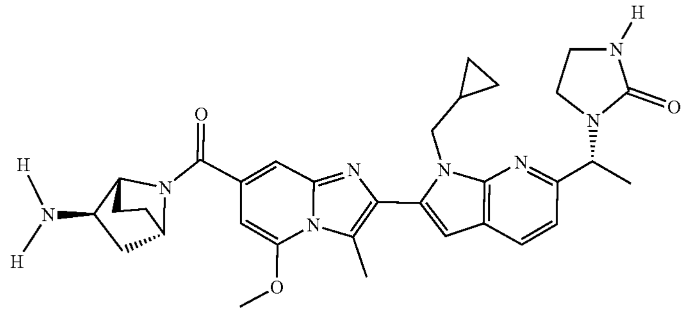 [SMILES: COc1cc(C(=O)N2[C@H]3CC[C@@H]2[C@H](N)C3)cc2nc(-c3cc4ccc([C@@H](C)N5CCNC5=O)nc4n3CC3CC3)c(C)n12] | 1-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]imidazolidin-2-one |
| 274 | 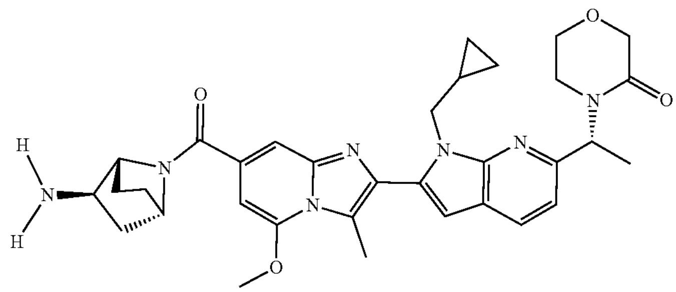 [SMILES: COc1cc(C(=O)N2[C@H]3CC[C@@H]2[C@H](N)C3)cc2nc(-c3cc4ccc([C@@H](C)N5CCOCC5=O)nc4n3CC3CC3)c(C)n12] | 4-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]morpholin-3-one |
| 275 | 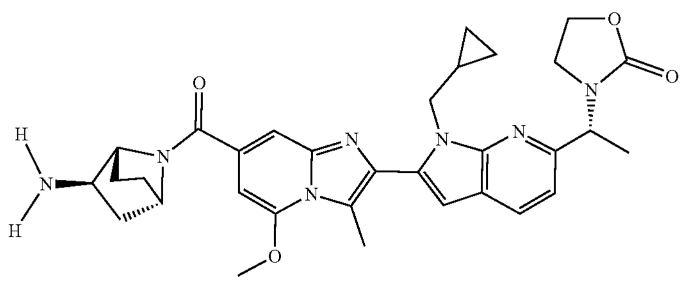 [SMILES: COc1cc(C(=O)N2[C@H]3CC[C@@H]2[C@H](N)C3)cc2nc(-c3cc4ccc([C@@H](C)N5CCOC5=O)nc4n3CC3CC3)c(C)n12] | 3-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]-1,3-oxazolidin-2-one |
| 276 | 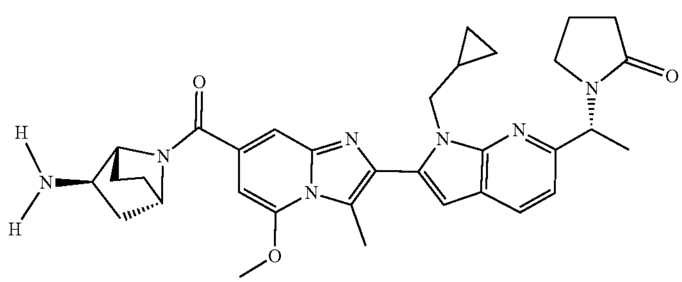 [SMILES: COc1cc(C(=O)N2[C@H]3CC[C@@H]2[C@H](N)C3)cc2nc(-c3cc4ccc([C@@H](C)N5CCCC5=O)nc4n3CC3CC3)c(C)n12] | 1-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]pyrrolidin-2-one |
| 277 | 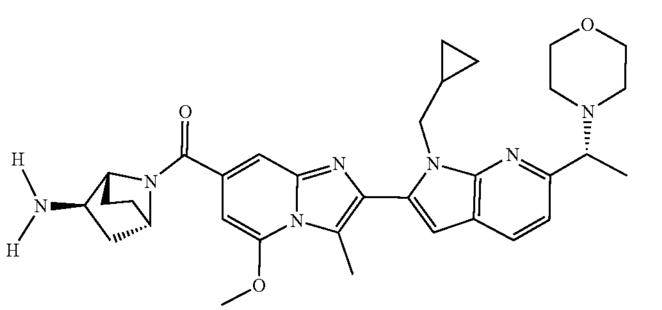 [SMILES: COc1cc(C(=O)N2[C@H]3CC[C@@H]2[C@H](N)C3)cc2nc(-c3cc4ccc([C@@H](C)N5CCOCC5)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-[(1~{R})-1-morpholin-4-ylethyl]pyrrolo[2,3-b]pyridin-2-yl]-5-methoxy-3-methylimidazo[1,2-a]pyridin-7-yl]methanone |

-continued

| Ex | Structure | Name |
|---|---|---|
| 278 | 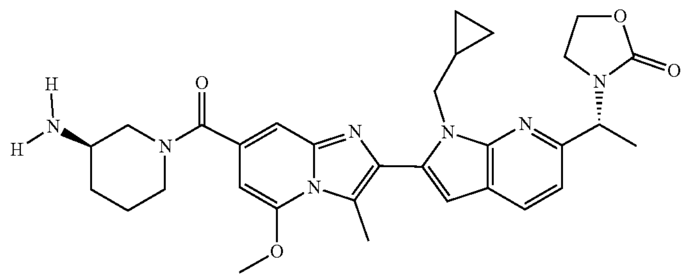 [SMILES: COc1cc(C(=O)N2CCC[C@@H](N)C2)cc2nc(-c3cc4ccc([C@@H](C)N5CCOC5=O)nc4n3CC3CC3)c(C)n12] | 3-[(1~{R})-1-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]ethyl]-1,3-oxazolidin-2-one |
| 279 | 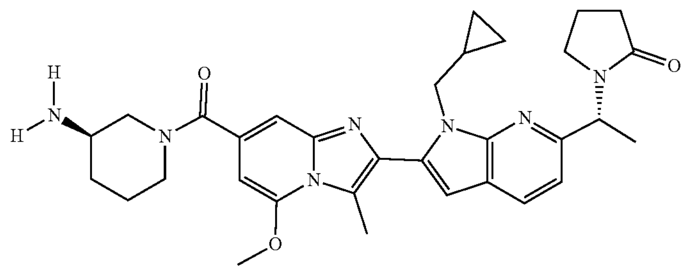 [SMILES: COc1cc(C(=O)N2CCC[C@@H](N)C2)cc2nc(-c3cc4ccc([C@@H](C)N5CCCC5=O)nc4n3CC3CC3)c(C)n12] | 1-[(1~{R})-1-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]ethyl]pyrrolidin-2-one |
| 280 | 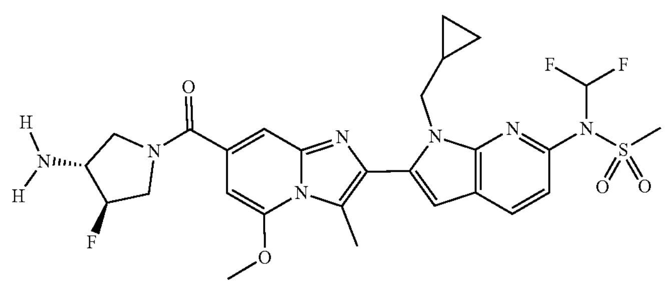 [SMILES: COc1cc(C(=O)N2C[C@@H](N)[C@H](F)C2)cc2nc(-c3cc4ccc(N(C(F)F)S(C)(=O)=O)nc4n3CC3CC3)c(C)n12] | ~{N}-[2-[7-[(3~{R},4~{R})-3-amino-4-fluoropyrrolidine-1-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 281 | 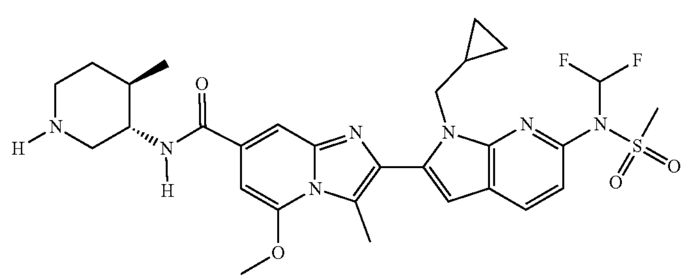 [SMILES: COc1cc(C(=O)N[C@@H]2CNCC[C@H]2C)cc2nc(-c3cc4ccc(N(C(F)F)S(C)(=O)=O)nc4n3CC3CC3)c(C)n12] | 2-[1-(cyclopropylmethyl)-6-[difluoromethyl(methylsulfonyl)amino]pyrrolo[2,3-b]pyridin-2-yl]-5-methoxy-3-methyl-~{N}-[(3~{S},4~{R})-4-methylpiperidin-3-yl]imidazo[1,2-a]pyridine-7-carboxamide |
| 282 | 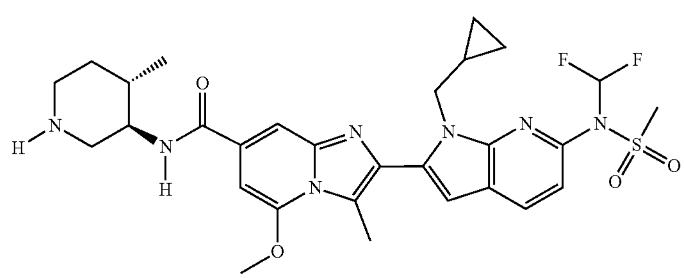 [SMILES: COc1cc(C(=O)N[C@H]2CNCC[C@@H]2C)cc2nc(-c3cc4ccc(N(C(F)F)S(C)(=O)=O)nc4n3CC3CC3)c(C)n12] | 2-[1-(cyclopropylmethyl)-6-[difluoromethyl(methylsulfonyl)amino]pyrrolo[2,3-b]pyridin-2-yl]-5-methoxy-3-methyl-~{N}-[(3~{R},4~{S})-4-methylpiperidin-3-yl]imidazo[1,2-a]pyridine-7-carboxamide |

US 12,240,862 B2

245                                                                                              246
-continued

| Ex | Structure | Name |
|---|---|---|
| 283 | 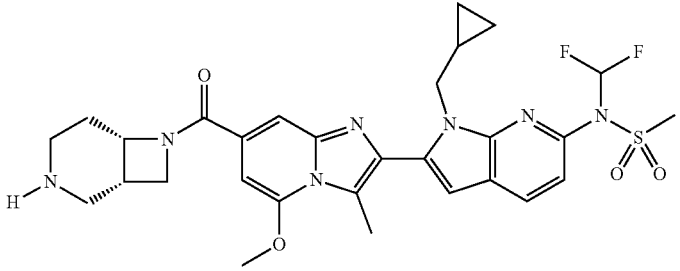 [SMILES: COc1cc(C(=O)N2C[C@@H]3CNCC[C@@H]32)cc2nc(-c3cc4ccc(N(C(F)F)S(C)(=O)=O)nc4n3CC3CC3)c(C)n12] | ~{N}-[1-(cyclopropylmethyl)-2-[7-[(1~{S},6~{S})-3,7-diazabicyclo[4.2.0]octane-7-carbonyl]-5-methoxy-3-methylimidazo[1,2-a]pyridin-2-yl]pyrrolo[2,3-b]pyridin-6-yl]-~{N}-(difluoromethyl)methanesulfonamide |
| 284 | 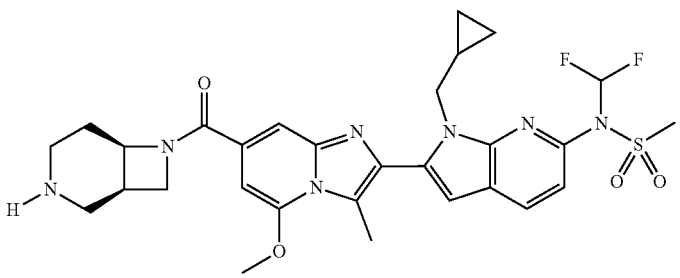 [SMILES: COc1cc(C(=O)N2C[C@H]3CNCC[C@H]32)cc2nc(-c3cc4ccc(N(C(F)F)S(C)(=O)=O)nc4n3CC3CC3)c(C)n12] | ~{N}-[1-(cyclopropylmethyl)-2-[7-[(1~{R},6~{R})-3,7-diazabicyclo[4.2.0]octane-7-carbonyl]-5-methoxy-3-methylimidazo[1,2-a]pyridin-2-yl]pyrrolo[2,3-b]pyridin-6-yl]-~{N}-(difluoromethyl)methanesulfonamide |
| 285 | 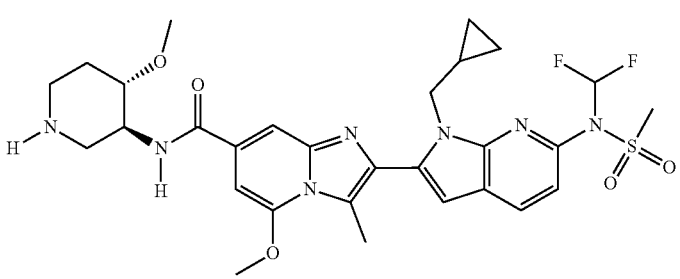 [SMILES: COc1cc(C(=O)N[C@H]2CNCC[C@@H]2OC)cc2nc(-c3cc4ccc(N(C(F)F)S(C)(=O)=O)nc4n3CC3CC3)c(C)n12] | 2-[1-(cyclopropylmethyl)-6-[difluoromethyl(methylsulfonyl)amino]pyrrolo[2,3-b]pyridin-2-yl]-5-methoxy-~{N}-[(3~{S},4~{S})-4-methoxypiperidin-3-yl]-3-methylimidazo[1,2-a]pyridine-7-carboxamide |
| 286 | 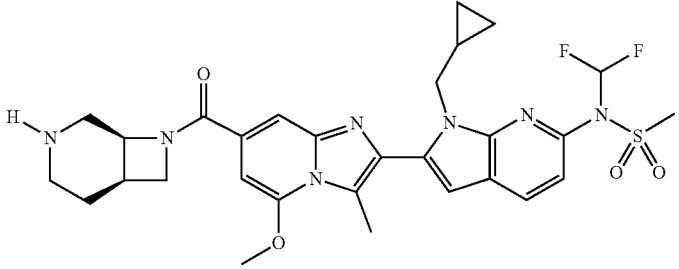 [SMILES: COc1cc(C(=O)N2C[C@H]3CCNC[C@H]32)cc2nc(-c3cc4ccc(N(C(F)F)S(C)(=O)=O)nc4n3CC3CC3)c(C)n12] | ~{N}-[1-(cyclopropylmethyl)-2-[7-[(1~{S},6~{R})-3,8-diazabicyclo[4.2.0]octane-8-carbonyl]-5-methoxy-3-methylimidazo[1,2-a]pyridin-2-yl]pyrrolo[2,3-b]pyridin-6-yl]-~{N}-(difluoromethyl)methanesulfonamide |
| 287 | 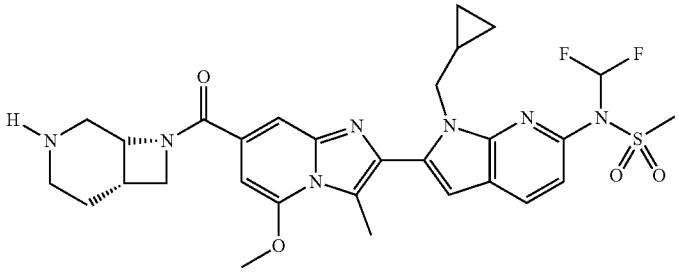 | ~{N}-[1-(cyclopropylmethyl)-2-[7-[(6~{S},8~{R})-3,8-diazabicyclo[4.2.0]octane-8-carbonyl]-5-methoxy-3-methylimidazo[1,2-a]pyridin-2-yl]pyrrolo[2,3-b]pyridin-6-yl]-~{N}-(difluoromethyl)methanesulfonamide |

-continued

| Ex | Structure | Name |
|---|---|---|
| 288 | 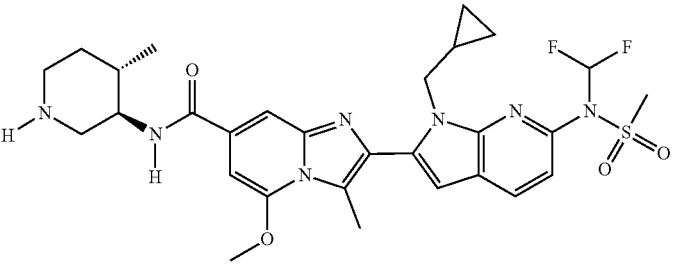 [SMILES: COc1cc(C(=O)N[C@H]2CNCC[C@@H]2C)cc2nc(-c3cc4ccc(N(C(F)F)S(C)(=O)=O)nc4n3CC3CC3)c(C)n12] | 2-[1-(cyclopropylmethyl)-6-[difluoromethyl(methylsulfonyl)amino]pyrrolo[2,3-b]pyridin-2-yl]-5-methoxy-3-methyl-~{N}-[(3~{R},4~{S})-4-methylpiperidin-3-yl]imidazo[1,2-a]pyridine-7-carboxamide |
| 289 | 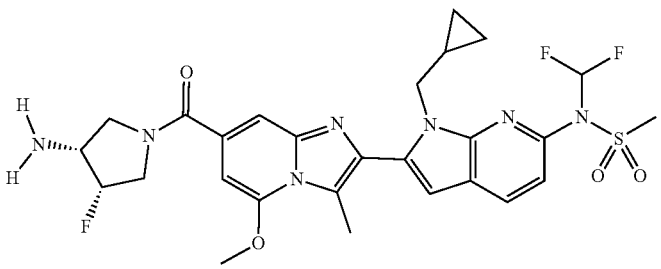 [SMILES: COc1cc(C(=O)N2C[C@@H](N)[C@@H](F)C2)cc2nc(-c3cc4ccc(N(C(F)F)S(C)(=O)=O)nc4n3CC3CC3)c(C)n12] | ~{N}-[2-[7-[(3~{R},4~{S})-3-amino-4-fluoropyrrolidine-1-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 290 | 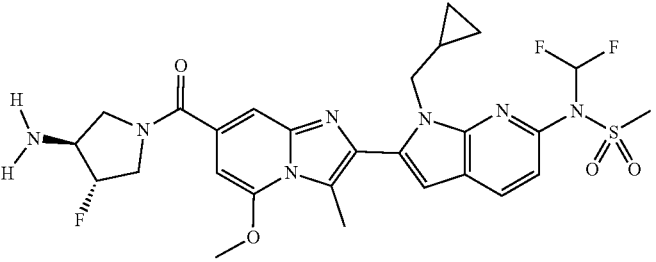 [SMILES: COc1cc(C(=O)N2C[C@H](N)[C@@H](F)C2)cc2nc(-c3cc4ccc(N(C(F)F)S(C)(=O)=O)nc4n3CC3CC3)c(C)n12] | ~{N}-[2-[7-[(3~{S},4~{S})-3-amino-4-fluoropyrrolidine-1-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 291 | 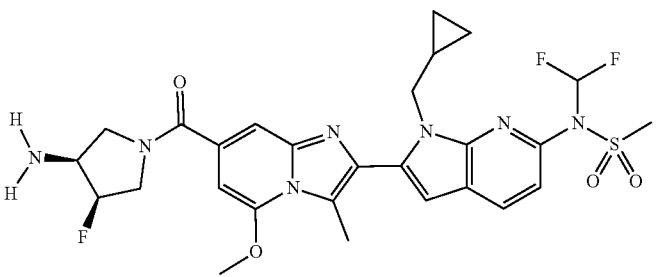 [SMILES: COc1cc(C(=O)N2C[C@@H](F)[C@@H](N)C2)cc2nc(-c3cc4ccc(N(C(F)F)S(C)(=O)=O)nc4n3CC3CC3)c(C)n12] | ~{N}-[2-[7-[(3~{S},4~{R})-3-amino-4-fluoropyrrolidine-1-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 292 | 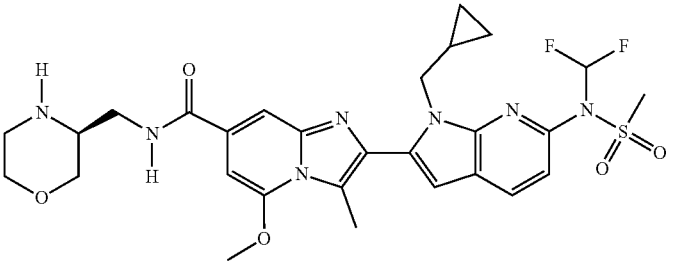 [SMILES: COc1cc(C(=O)NC[C@H]2COCCN2)cc2nc(-c3cc4ccc(N(C(F)F)S(C)(=O)=O)nc4n3CC3CC3)c(C)n12] | 2-[1-(cyclopropylmethyl)-6-[difluoromethyl(methylsulfonyl)amino]pyrrolo[2,3-b]pyridin-2-yl]-5-methoxy-3-methyl-~{N}-[[(3~{S})-morpholin-3-yl]methyl]imidazo[1,2-a]pyridine-7-carboxamide |

| Ex | Structure | Name |
|---|---|---|
| 293 | 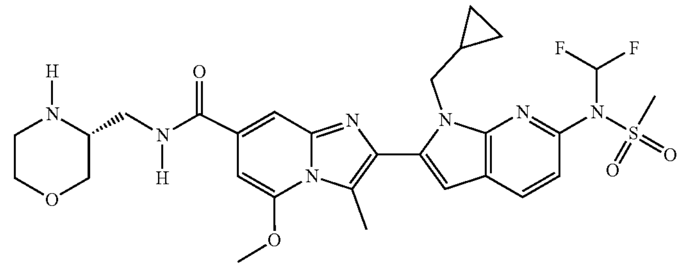 [SMILES: COc1cc(C(=O)NC[C@@H]2COCCN2)cc2nc(-c3cc4ccc(N(C(F)F)S(C)(=O)=O)nc4n3CC3CC3)c(C)n12] | 2-[1-(cyclopropylmethyl)-6-[difluoromethyl(methylsulfonyl)amino]pyrrolo[2,3-b]pyridin-2-yl]-5-methoxy-3-methyl-~{N}-[[(3~{R})-morpholin-3-yl]methyl]imidazo[1,2-a]pyridine-7-carboxamide |
| 294 | 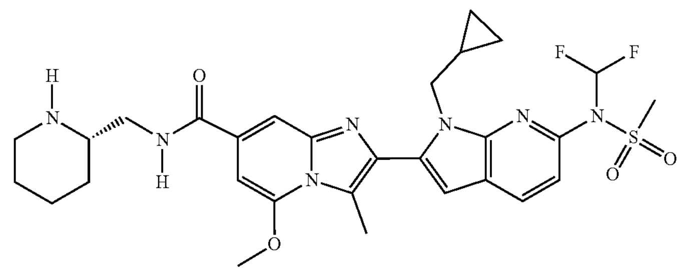 [SMILES: COc1cc(C(=O)NC[C@@H]2CCCCN2)cc2nc(-c3cc4ccc(N(C(F)F)S(C)(=O)=O)nc4n3CC3CC3)c(C)n12] | 2-[1-(cyclopropylmethyl)-6-[difluoromethyl(methylsulfonyl)amino]pyrrolo[2,3-b]pyridin-2-yl]-5-methoxy-3-methyl-~{N}-[[(2~{S})-piperidin-2-yl]methyl]imidazo[1,2-a]pyridine-7-carboxamide |
| 295 | 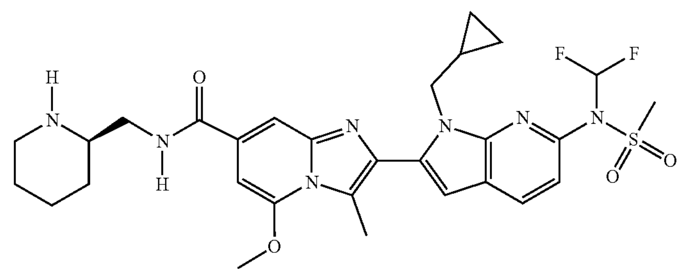 [SMILES: COc1cc(C(=O)NC[C@H]2CCCCN2)cc2nc(-c3cc4ccc(N(C(F)F)S(C)(=O)=O)nc4n3CC3CC3)c(C)n12] | 2-[1-(cyclopropylmethyl)-6-[difluoromethyl(methylsulfonyl)amino]pyrrolo[2,3-b]pyridin-2-yl]-5-methoxy-3-methyl-~{N}-[[(2~{R})-piperidin-2-yl]methyl]imidazo[1,2-a]pyridine-7-carboxamide |
| 296 | 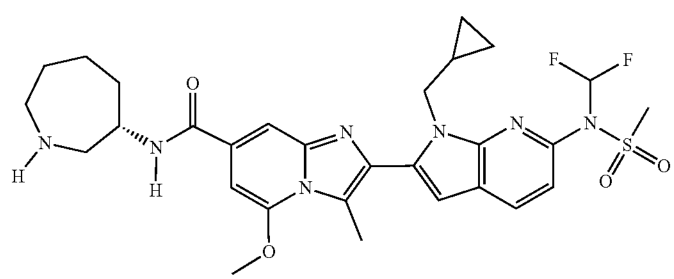 [SMILES: COc1cc(C(=O)N[C@H]2CCCCNC2)cc2nc(-c3cc4ccc(N(C(F)F)S(C)(=O)=O)nc4n3CC3CC3)c(C)n12] | ~{N}-[(3~{S})-azepan-3-yl]-2-[1-(cyclopropylmethyl)-6-[difluoromethyl(methylsulfonyl)amino]pyrrolo[2,3-b]pyridin-2-yl]-5-methoxy-3-methylimidazo[1,2-a]pyridine-7-carboxamide |
| 297 | 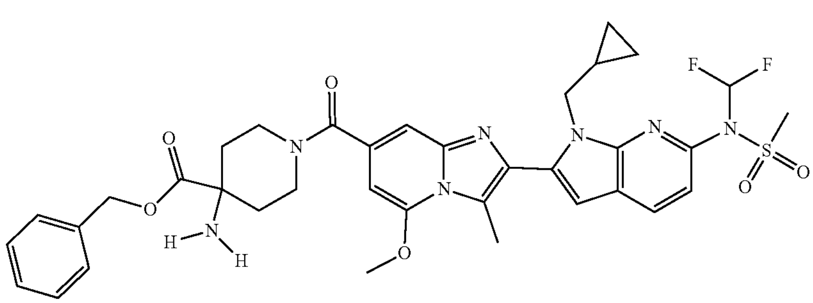 [SMILES: COc1cc(C(=O)N2CCC(N)(C(=O)OCc3ccccc3)CC2)cc2nc(-c3cc4ccc(N(C(F)F)S(C)(=O)=O)nc4n3CC3CC3)c(C)n12] | benzyl 4-amino-1-[2-[1-(cyclopropylmethyl)-6-[difluoromethyl(methylsulfonyl)amino]pyrrolo[2,3-b]pyridin-2-yl]-5-methoxy-3-methylimidazo[1,2-a]pyridine-7-carbonyl]piperidine-4-carboxylate |

-continued

| Ex | Structure | Name |
|---|---|---|
| 298 | 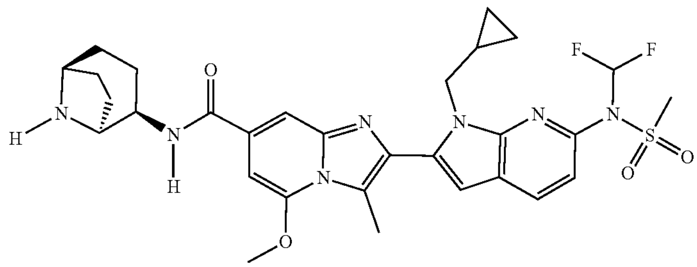 [SMILES: COc1cc(C(=O)N[C@@H]2CC[C@H]3CC[C@@H]2N3)cc2nc(-c3cc4ccc(N(C(F)F)S(C)(=O)=O)nc4n3CC3CC3)c(C)n12] | ~{N}-[(1~{S},2~{R}, 5~{R})-8-azabicyclo [3.2.1]octan-2-yl]-2- [1-(cyclopropylmethyl)-6- [difluoromethyl (methylsulfonyl)amino] pyrrolo[2,3-b]pyridin-2- yl]-5-methoxy-3- methylimidazo[1,2- a]pyridine-7-carboxamide |
| 299 | 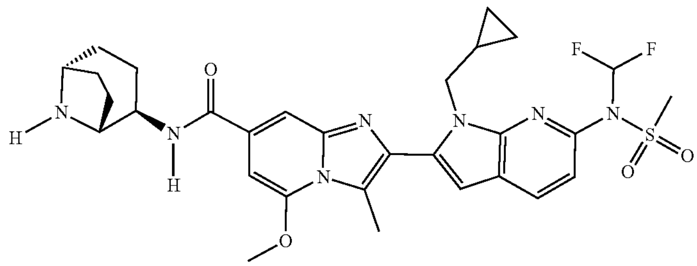 [SMILES: COc1cc(C(=O)N[C@@H]2CC[C@@H]3CC[C@H]2N3)cc2nc(-c3cc4ccc(N(C(F)F)S(C)(=O)=O)nc4n3CC3CC3)c(C)n12] | ~{N}-[(1~{R},2~{R}, 5~{S})-8-azabicyclo [3.2.1]octan-2-yl]-2- [1-(cyclopropylmethyl)-6- [difluoromethyl (methylsulfonyl)amino] pyrrolo[2,3-b]pyridin-2- yl]-5-methoxy-3- methylimidazo[1,2- a]pyridine-7-carboxamide |
| 300 | 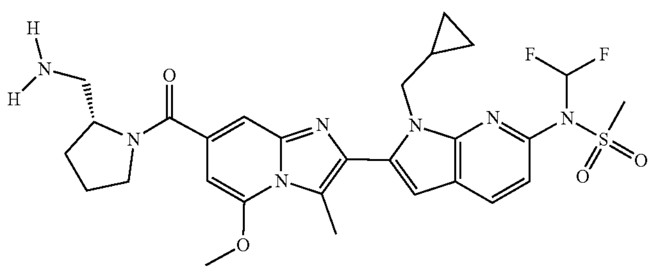 [SMILES: COc1cc(C(=O)N2CCC[C@@H]2CN)cc2nc(-c3cc4ccc(N(C(F)F)S(C)(=O)=O)nc4n3CC3CC3)c(C)n12] | ~{N}-[2-[7-[(2~{R})-2- (aminomethyl)pyrrolidine-1- carbonyl]-5-methoxy-3- methylimidazo[1,2-a]pyridin- 2-yl]-1- (cyclopropylmethyl)pyrrolo [2,3-b]pyridin-6-yl]-~{N}- (difluoromethyl) methanesulfonamide |
| 301 | 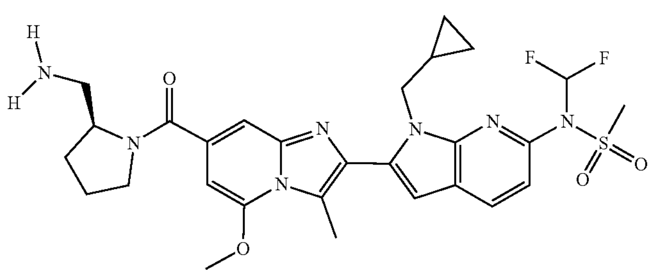 [SMILES: COc1cc(C(=O)N2CCC[C@H]2CN)cc2nc(-c3cc4ccc(N(C(F)F)S(C)(=O)=O)nc4n3CC3CC3)c(C)n12] | ~{N}-[2-[7-[(2~{S})-2- (aminomethyl)pyrrolidine-1- carbonyl]-5-methoxy-3- methylimidazo[1,2-a]pyridin- 2-yl]-1- (cyclopropylmethyl)pyrrolo [2,3-b]pyridin-6-yl]-~{N}- (difluoromethyl) methanesulfonamide |
| 302 | 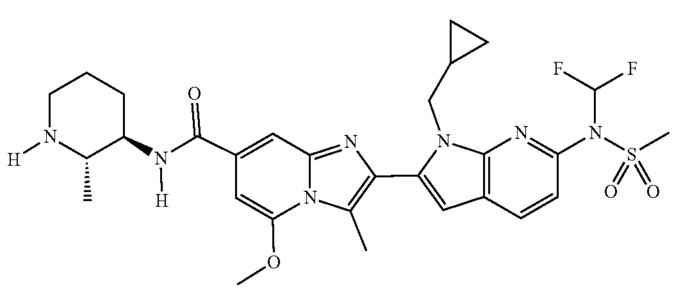 [SMILES: COc1cc(C(=O)N[C@@H]2CCCN[C@H]2C)cc2nc(-c3cc4ccc(N(C(F)F)S(C)(=O)=O)nc4n3CC3CC3)c(C)n12] | 2-[1-(cyclopropylmethyl)- 6-[difluoromethyl (methylsulfonyl) amino]pyrrolo[2,3-b] pyridin-2-yl]-5- methoxy-3-methyl-~{N}- [(2~{S},3~{R})-2- methylpiperidin- 3-yl]imidazo[1,2-a] pyridine-7-carboxamide |

-continued

| Ex | Structure | Name |
|---|---|---|
| 303 | 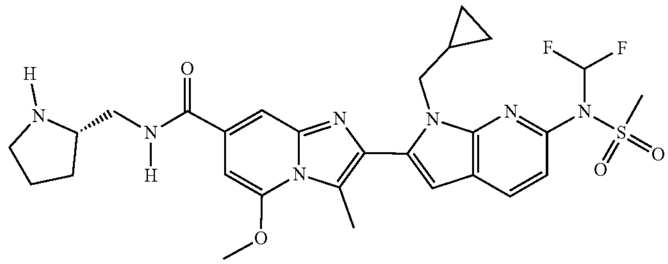 [SMILES: COc1cc(C(=O)NC[C@@H]2CCCN2)cc2nc(-c3cc4ccc(N(C(F)F)S(C)(=O)=O)nc4n3CC3CC3)c(C)n12] | 2-[1-(cyclopropylmethyl)-6-[difluoromethyl (methylsulfonyl)amino] pyrrolo[2,3-b]pyridin-2-yl]-5-methoxy-3-methyl-~{N}-[[(2~{S})-pyrrolidin-2-yl]methyl] imidazo[1,2-a] pyridine-7-carboxamide |
| 304 | 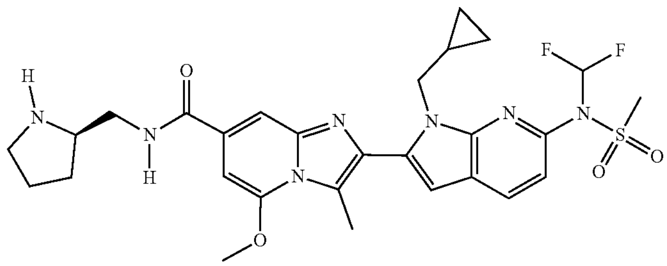 [SMILES: COc1cc(C(=O)NC[C@H]2CCCN2)cc2nc(-c3cc4ccc(N(C(F)F)S(C)(=O)=O)nc4n3CC3CC3)c(C)n12] | 2-[1-(cyclopropylmethyl)-6-[difluoromethyl (methylsulfonyl)amino] pyrrolo[2,3-b]pyridin-2-yl]-5-methoxy-3-methyl-~{N}-[[(2~{R})-pyrrolidin-2-yl]methyl] imidazo[1,2-a]pyridine-7-carboxamide |
| 305 | 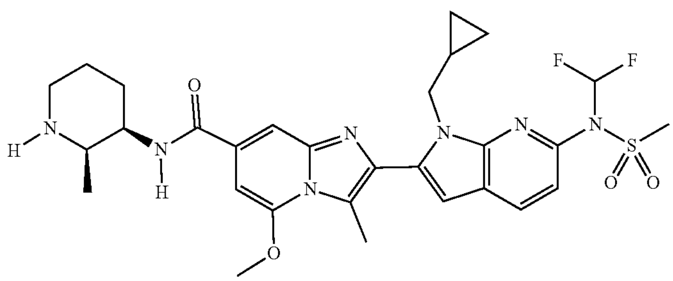 [SMILES: COc1cc(C(=O)N[C@@H]2CCCN[C@@H]2C)cc2nc(-c3cc4ccc(N(C(F)F)S(C)(=O)=O)nc4n3CC3CC3)c(C)n12] | 2-[1-(cyclopropylmethyl)-6-[difluoromethyl (methylsulfonyl)amino] pyrrolo[2,3-b]pyridin-2-yl]-5-methoxy-3-methyl-~{N}-[(2~{R},3~{R})-2-methylpiperidin-3-yl]imidazo[1,2-a] pyridine-7-carboxamide |
| 306 | 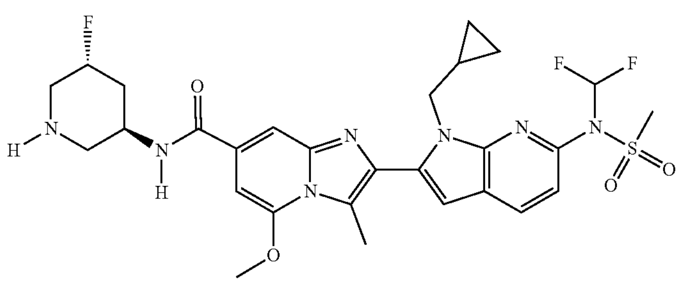 [SMILES: COc1cc(C(=O)N[C@H]2CNC[C@H](F)C2)cc2nc(-c3cc4ccc(N(C(F)F)S(C)(=O)=O)nc4n3CC3CC3)c(C)n12] | 2-[1-(cyclopropylmethyl)-6-[difluoromethyl (methylsulfonyl) amino]pyrrolo[2,3-b] pyridin-2-yl]-~{N}-[(3~{R},5~{R})-5-fluoropiperidin-3-yl]-5-methoxy-3-methylimidazo [1,2-a]pyridine-7-carboxamide |
| 307 | 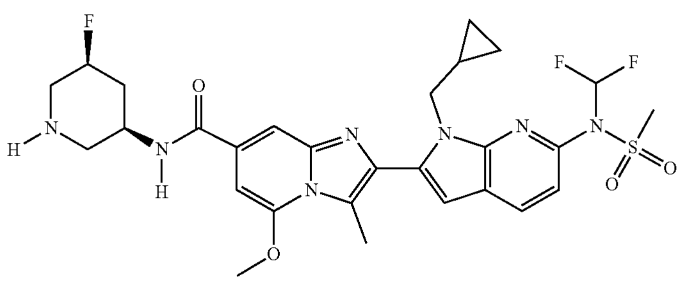 [SMILES: COc1cc(C(=O)N[C@H]2CNC[C@@H](F)C2)cc2nc(-c3cc4ccc(N(C(F)F)S(C)(=O)=O)nc4n3CC3CC3)c(C)n12] | 2-[1-(cyclopropylmethyl)-6-[difluoromethyl (methylsulfonyl) amino]pyrrolo[2,3-b] pyridin-2-yl]-~{N}-[(3~{R},5~{S})-5-fluoropiperidin-3-yl]-5-methoxy-3-methylimidazo [1,2-a]pyridine-7-carboxamide |

| Ex | Structure | Name |
|---|---|---|
| 308 | 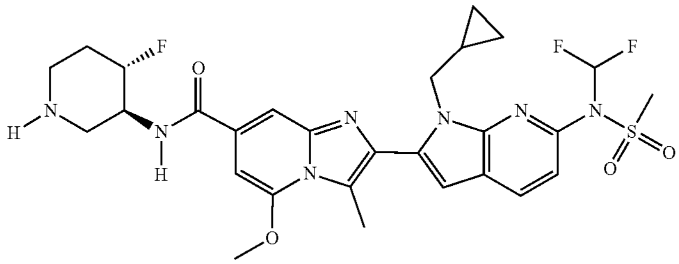 [SMILES: COc1cc(C(=O)N[C@H]2CNCC[C@@H]2F)cc2nc(-c3cc4ccc(N(C(F)F)S(C)(=O)=O)nc4n3CC3CC3)c(C)n12] | 2-[1-(cyclopropylmethyl)-6-[difluoromethyl(methylsulfonyl)amino]pyrrolo[2,3-b]pyridin-2-yl]-~{N}-[(3~{S},4~{S})-4-fluoropiperidin-3-yl]-5-methoxy-3-methylimidazo[1,2-a]pyridine-7-carboxamide |
| 309 | 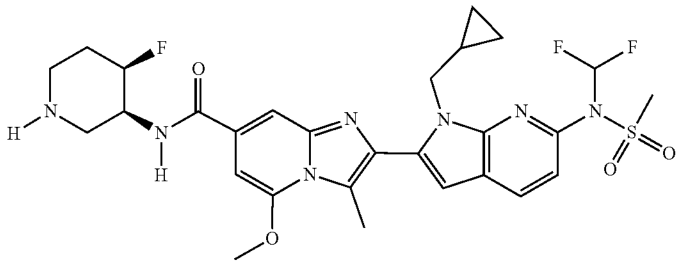 [SMILES: COc1cc(C(=O)N[C@H]2CNCC[C@H]2F)cc2nc(-c3cc4ccc(N(C(F)F)S(C)(=O)=O)nc4n3CC3CC3)c(C)n12] | 2-[1-(cyclopropylmethyl)-6-[difluoromethyl(methylsulfonyl)amino]pyrrolo[2,3-b]pyridin-2-yl]-~{N}-[(3~{S},4~{R})-4-fluoropiperidin-3-yl]-5-methoxy-3-methylimidazo[1,2-a]pyridine-7-carboxamide |
| 310 | 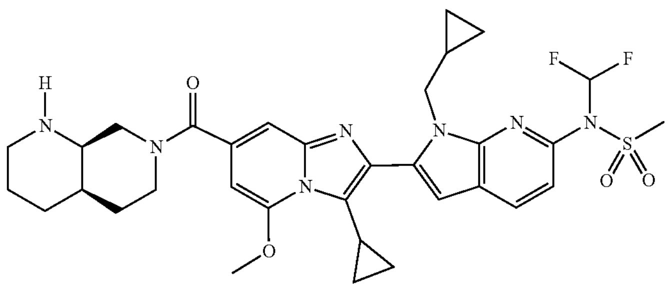 [SMILES: COc1cc(C(=O)N2CC[C@H]3CCCN[C@H]3C2)cc2nc(-c3cc4ccc(N(C(F)F)S(C)(=O)=O)nc4n3CC3CC3)c(C3CC3)n12] | ~{N}-[2-[7-[(4~{a}~{R},8~{a}~{R})-2,3,4,4~{a},5,6,8,8~{a}-octahydro-1~{H}-1,7-naphthyridine-7-carbonyl]-3-cyclopropyl-5-methoxyimidazo[1,2-a]pyridin-2-yl]-1-(cyclopropylmethyl)pyrrolo[2,3-b]pyridin-6-yl]-~{N}-(difluoromethyl)methanesulfonamide |
| 311 | 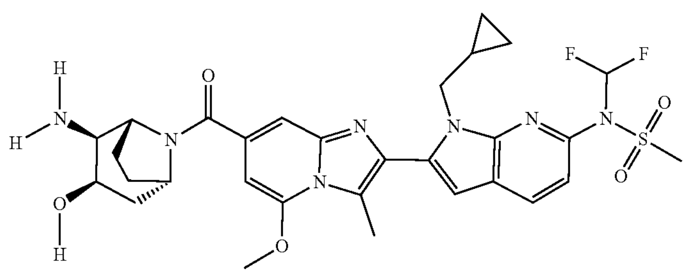 [SMILES: COc1cc(C(=O)N2[C@H]3CC[C@@H]2[C@H](N)[C@H](O)C3)cc2nc(-c3cc4ccc(N(C(F)F)S(C)(=O)=O)nc4n3CC3CC3)c(C)n12] | ~{N}-[2-[7-[(1~{R},2~{S},3~{R},5~{S})-2-amino-3-hydroxy-8-azabicyclo[3.2.1]octane-8-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 312 | 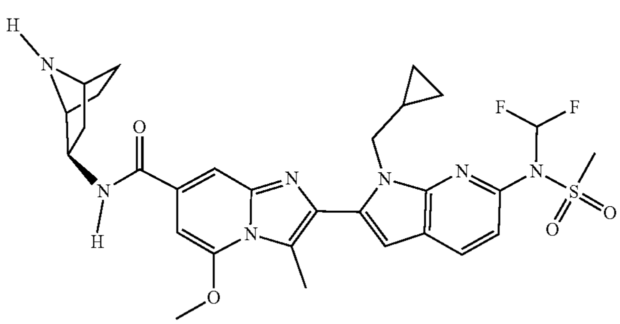 [SMILES: COc1cc(C(=O)N[C@@H]2CC3CCC2N3)cc2nc(-c3cc4ccc(N(C(F)F)S(C)(=O)=O)nc4n3CC3CC3)c(C)n12] | N-[(1R,2R,4S)-7-azabicyclo[2.2.1]heptan-2-yl]-2-[1-(cyclopropylmethyl)-6-[difluoromethyl(methylsulfonyl)amino]pyrrolo[2,3-b]pyridin-2-yl]-5-methoxy-3-methyl-imidazo[1,2-a]pyridine-7-carboxamide |

| Ex | Structure | Name |
| --- | --- | --- |
| 313 | 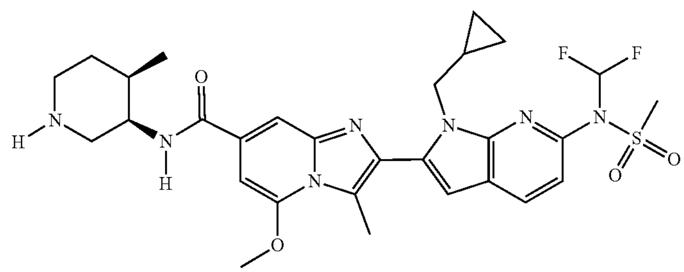 [SMILES: COc1cc(C(=O)N[C@H]2CNCC[C@H]2C)cc2nc(-c3cc4ccc(N(C(F)F)S(C)(=O)=O)nc4n3CC3CC3)c(C)n12] | 2-[1-(cyclopropylmethyl)-6-[difluoromethyl(methylsulfonyl)amino]pyrrolo[2,3-b]pyridin-2-yl]-5-methoxy-3-methyl-~{N}-[(3~{R},4~{R})-4-methylpiperidin-3-yl]imidazo[1,2-a]pyridine-7-carboxamide |
| 314 | 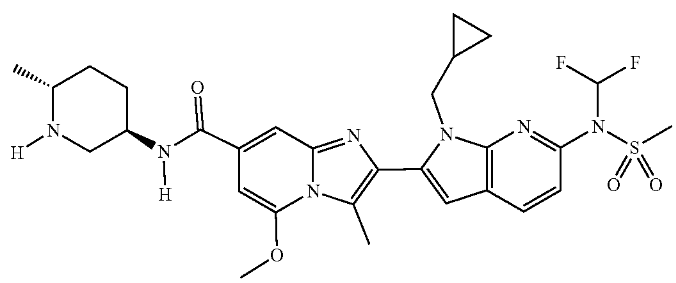 | 2-[1-(cyclopropylmethyl)-6-[difluoromethyl(methylsulfonyl)amino]pyrrolo[2,3-b]pyridin-2-yl]-5-methoxy-3-methyl-~{N}-[(3~{R},6~{R})-6-methylpiperidin-3-yl]imidazo[1,2-a]pyridine-7-carboxamide |
| 315 | 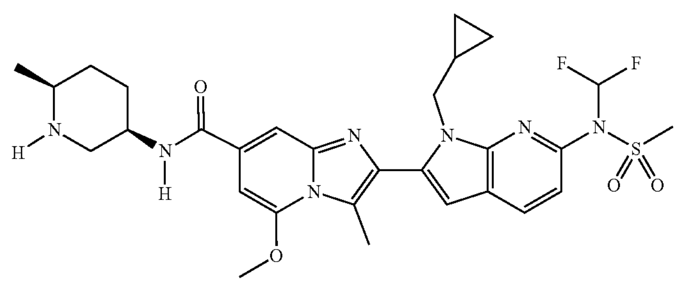 | 2-[1-(cyclopropylmethyl)-6-[difluoromethyl(methylsulfonyl)amino]pyrrolo[2,3-b]pyridin-2-yl]-5-methoxy-3-methyl-~{N}-[(3~{R},6~{S})-6-methylpiperidin-3-yl]imidazo[1,2-a]pyridine-7-carboxamide |
| 316 | 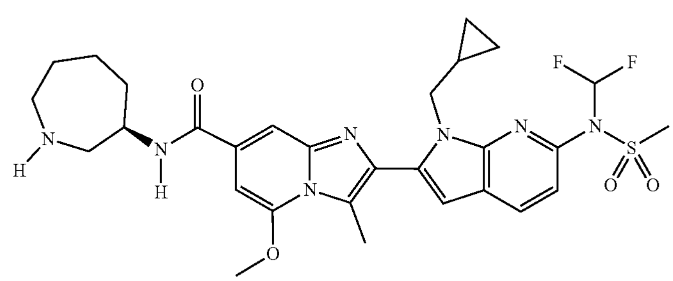 [SMILES: COc1cc(C(=O)N[C@@H]2CCCCNC2)cc2nc(-c3cc4ccc(N(C(F)F)S(C)(=O)=O)nc4n3CC3CC3)c(C)n12] | ~{N}-[(3~{R})-azepan-3-yl]-2-[1-(cyclopropylmethyl)-6-[difluoromethyl(methylsulfonyl)amino]pyrrolo[2,3-b]pyridin-2-yl]-5-methoxy-3-methylimidazo[1,2-a]pyridine-7-carboxamide |
| 317 | 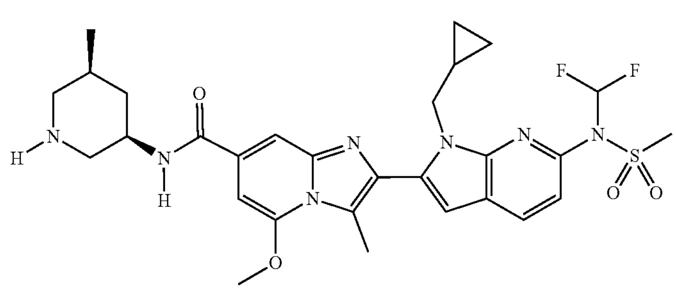 [SMILES: COc1cc(C(=O)N[C@H]2CNC[C@@H](C)C2)cc2nc(-c3cc4ccc(N(C(F)F)S(C)(=O)=O)nc4n3CC3CC3)c(C)n12] | 2-[1-(cyclopropylmethyl)-6-[difluoromethyl(methylsulfonyl)amino]pyrrolo[2,3-b]pyridin-2-yl]-5-methoxy-3-methyl-~{N}-[(3~{R},5~{S})-5-methylpiperidin-3-yl]imidazo[1,2-a]pyridine-7-carboxamide |

| Ex | Structure | Name |
|---|---|---|
| 318 | 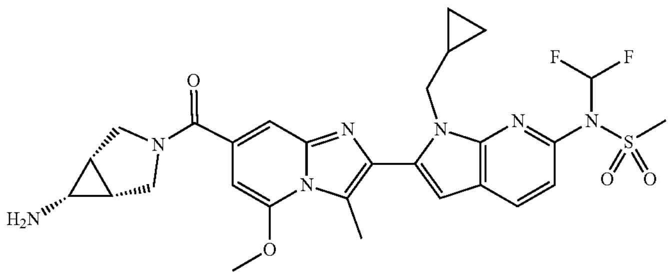 [SMILES: COc1cc(C(=O)N2C[C@@H]3[C@H](N)[C@@H]3C2)cc2nc(-c3cc4ccc(N(C(F)F)S(C)(=O)=O)nc4n3CC3CC3)c(C)n12] | ~{N}-[2-[7-[(1~{S}, 5~{R})-6-amino-3-azabicyclo[3.1.0]hexane-3-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 319 | 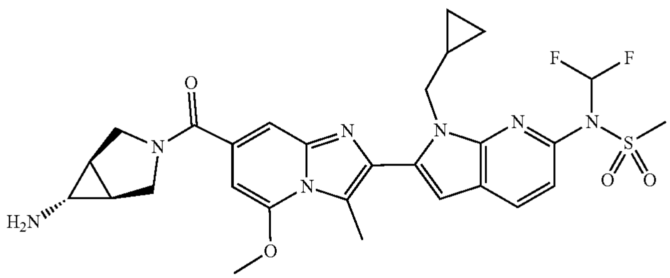 [SMILES: COc1cc(C(=O)N2C[C@@H]3[C@@H](N)[C@@H]3C2)cc2nc(-c3cc4ccc(N(C(F)F)S(C)(=O)=O)nc4n3CC3CC3)c(C)n12] | ~{N}-[2-[7-[(1~{R}, 5~{S})-6-amino-3-azabicyclo[3.1.0]hexane-3-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 320 | 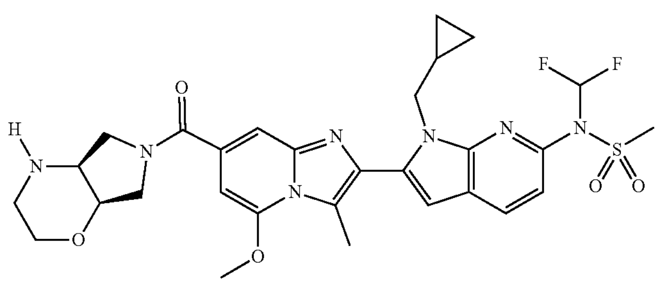 [SMILES: COc1cc(C(=O)N2C[C@@H]3NCCO[C@@H]3C2)cc2nc(-c3cc4ccc(N(C(F)F)S(C)(=O)=O)nc4n3CC3CC3)c(C)n12] | ~{N}-[2-[7-[(4~{a}~{S},7~{a}~{R})-3,4,4~{a},5,7,7~{a}-hexahydro-2~{H}-pyrrolo[3,4-b][1,4]oxazine-6-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 321 | 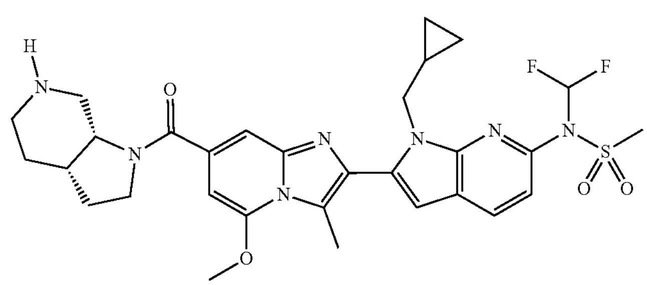 [SMILES: COc1cc(C(=O)N2CC[C@@H]3CCNC[C@@H]32)cc2nc(-c3cc4ccc(N(C(F)F)S(C)(=O)=O)nc4n3CC3CC3)c(C)n12] | ~{N}-[2-[7-[(3~{a}~{S},7~{a}~{R})-2,3,3~{a},4,5,6,7,7~{a}-octahydropyrrolo[2,3-c]pyridine-1-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 322 | 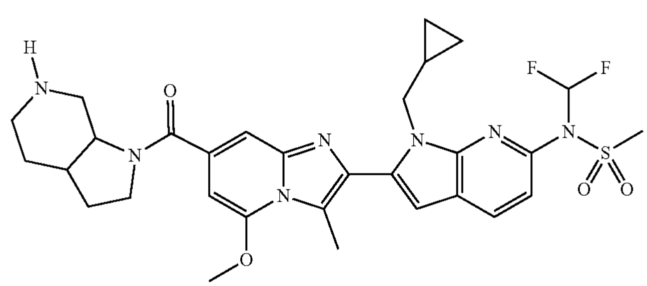 [SMILES: COc1cc(C(=O)N2CCC3CCNCC32)cc2nc(-c3cc4ccc(N(C(F)F)S(C)(=O)=O)nc4n3CC3CC3)c(C)n12] | ~{N}-[2-[7-(2,3,3~{a},4,5,6,7,7~{a}-octahydropyrrolo[2,3-c]pyridine-1-carbonyl)-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |

| Ex | Structure | Name |
|---|---|---|
| 323 | 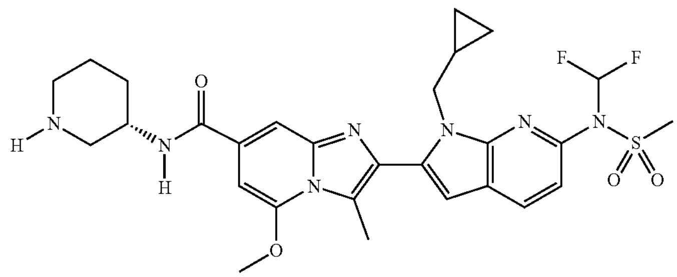 | 2-[1-(cyclopropylmethyl)-6-[difluoromethyl (methylsulfonyl)amino] pyrrolo[2,3-b]pyridin-2-yl]-5-methoxy-3-methyl-~{N}-[(3~{S})-piperidin-3-yl] imidazo[1,2-a]pyridine-7-carboxamide |
| 324 | 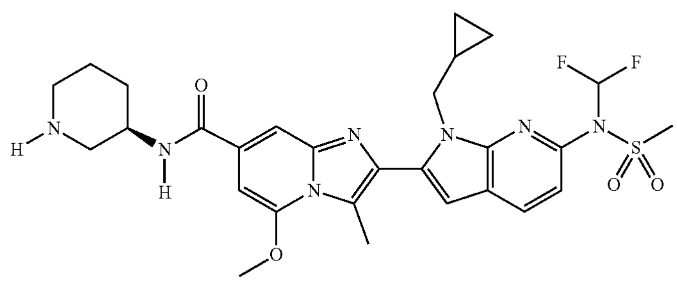 [SMILES: COc1cc(C(=O)N[C@@H]2CCCNC2)cc2nc(-c3cc4ccc(N(C(F)F)S(C)(=O)=O)nc4n3CC3CC3)c(C)n12] | 2-[1-(cyclopropylmethyl)-6-[difluoromethyl (methylsulfonyl)amino] pyrrolo[2,3-b]pyridin-2-yl]-5-methoxy-3-methyl-~{N}-[(3~{R})-piperidin-3-yl]imidazo [1,2-a]pyridine-7-carboxamide |
| 325 | 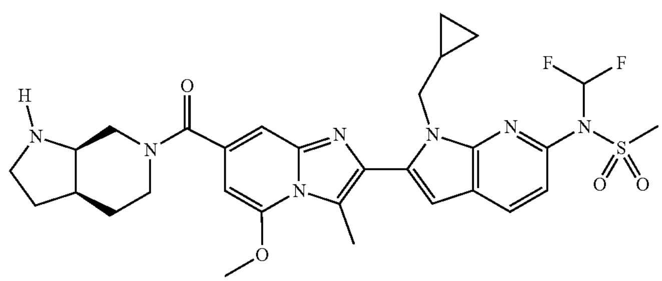 [SMILES: COc1cc(C(=O)N2CC[C@H]3CCN[C@H]3C2)cc2nc(-c3cc4ccc(N(C(F)F)S(C)(=O)=O)nc4n3CC3CC3)c(C)n12] | ~{N}-[2-[7-[(4~{a}~{S},7~{a}~{R})-3,4,4~{a},5,7,7~{a}-hexahydro-2~{H}-pyrrolo[3,4-b][1,4] oxazine-6-carbonyl]-5-methoxy-3-methylimidazo [1,2-a]pyridin-2-yl]-1-(cyclopropylmethyl)pyrrolo [2,3-b]pyridin-6-yl]-~{N}-(difluoromethyl) methanesulfonamide |
| 326 | 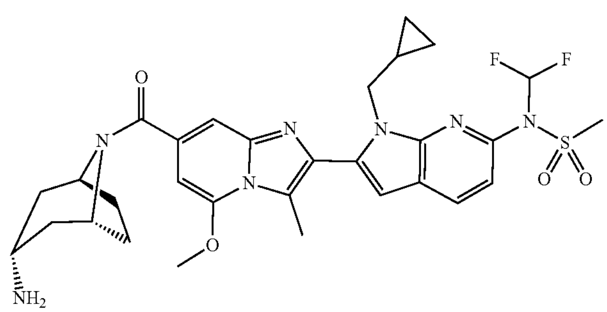 [SMILES: COc1cc(C(=O)N2[C@@H]3CC[C@H]2C[C@@H](N)C3)cc2nc(-c3cc4ccc(N(C(F)F)S(C)(=O)=O)nc4n3CC3CC3)c(C)n12] | ~{N}-[2-[7-[(1~{R},5~{S})-3-amino-8-azabicyclo[3.2.1] octane-8-carbonyl]-5-methoxy-3-methylimidazo[1,2-a] pyridin-2-yl]-1-(cyclopropylmethyl) pyrrolo[2,3-b]pyridin-6-yl]-~{N}-(difluoromethyl) methanesulfonamide |
| 327 | 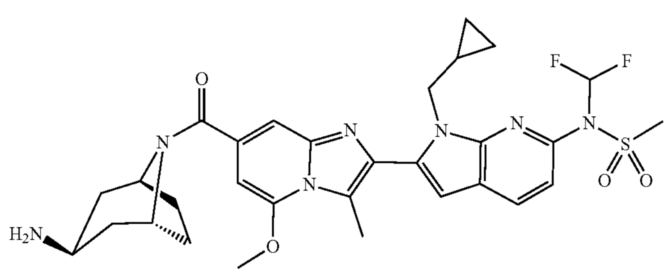 [SMILES: COc1cc(C(=O)N2[C@@H]3CC[C@H]2C[C@H](N)C3)cc2nc(-c3cc4ccc(N(C(F)F)S(C)(=O)=O)nc4n3CC3CC3)c(C)n12] | ~{N}-[2-[7-[(1~{R},5~{S})-3-amino-8-azabicyclo[3.2.1] octane-8-carbonyl]-5-methoxy-3-methylimidazo[1,2-a] pyridin-2-yl]-1-(cyclopropylmethyl) pyrrolo[2,3-b]pyridin-6-yl]-~{N}-(difluoromethyl) methanesulfonamide |

-continued

| Ex | Structure | Name |
|---|---|---|
| 328 | 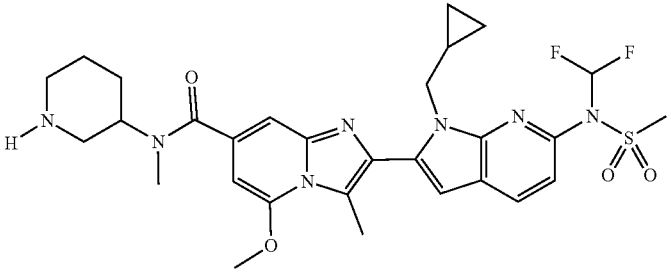 [SMILES: COc1cc(C(=O)N(C)C2CCCNC2)cc2nc(-c3cc4ccc(N(C(F)F)S(C)(=O)=O)nc4n3CC3CC3)c(C)n12] | 2-[1-(cyclopropylmethyl)-6-[difluoromethyl(methylsulfonyl)amino]pyrrolo[2,3-b]pyridin-2-yl]-5-methoxy-~{N},3-dimethyl-~{N}-piperidin-3-ylimidazo[1,2-a]pyridine-7-carboxamide |
| 329 | 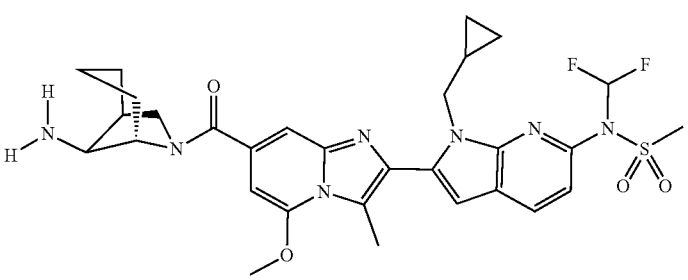 [SMILES: COc1cc(C(=O)N2C[C@@H]3CCC[C@H]2C3N)cc2nc(-c3cc4ccc(N(C(F)F)S(C)(=O)=O)nc4n3CC3CC3)c(C)n12] | N-[2-[7-[(1S,5S,8S)-8-amino-6-azabicyclo[3.2.1]octane-6-carbonyl]-5-methoxy-3-methyl-imidazo[1,2-a]pyridin-2-yl]-1-(cyclopropylmethyl)pyrrolo[2,3-b]pyridin-6-yl]-N-(difluoromethyl)methanesulfonamide |
| 330 | 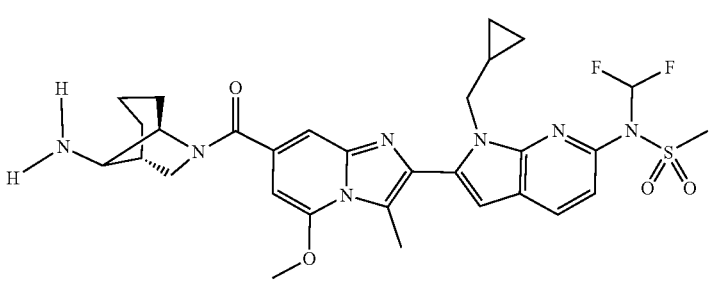 [SMILES: COc1cc(C(=O)N2C[C@H]3CCC[C@@H]2C3N)cc2nc(-c3cc4ccc(N(C(F)F)S(C)(=O)=O)nc4n3CC3CC3)c(C)n12] | N-[2-[7-[(1R,5R,8R)-8-amino-6-azabicyclo[3.2.1]octane-6-carbonyl]-5-methoxy-3-methyl-imidazo[1,2-a]pyridin-2-yl]-1-(cyclopropylmethyl)pyrrolo[2,3-b]pyridin-6-yl]-N-(difluoromethyl)methanesulfonamide |
| 331 | 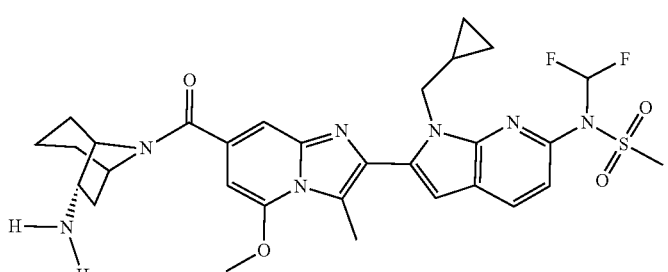 | N-[2-[7-[(1R,5S,6S)-6-amino-8-azabicyclo[3.2.1]octane-8-carbonyl]-5-methoxy-3-methyl-imidazo[1,2-a]pyridin-2-yl]-1-(cyclopropylmethyl)pyrrolo[2,3-b]pyridin-6-yl]-N-(difluoromethyl)methanesulfonamide |
| 332 | 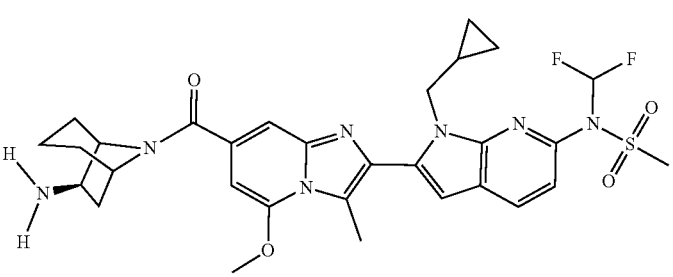 [SMILES: COc1cc(C(=O)N2C3CCCC2[C@H](N)C3)cc2nc(-c3cc4ccc(N(C(F)F)S(C)(=O)=O)nc4n3CC3CC3)c(C)n12] | N-[2-[7-[(1S,5R,6R)-6-amino-8-azabicyclo[3.2.1]octane-8-carbonyl]-5-methoxy-3-methyl-imidazo[1,2-a]pyridin-2-yl]-1-(cyclopropylmethyl)pyrrolo[2,3-b]pyridin-6-yl]-N-(difluoromethyl)methanesulfonamide |

| Ex | Structure | Name |
|---|---|---|
| 333 | 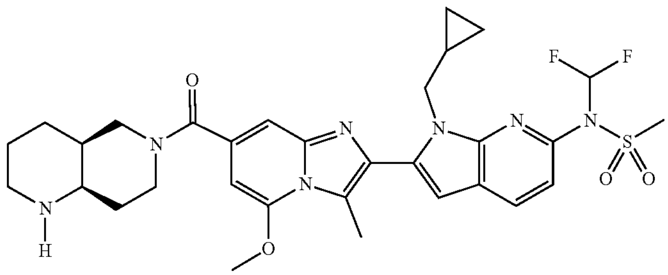 [SMILES: COc1cc(C(=O)N2CC[C@H]3NCCC[C@H]3C2)cc2nc(-c3cc4ccc(N(C(F)F)S(C)(=O)=O)nc4n3CC3CC3)c(C)n12] | ~{N}-[2-[7-[(4~{a}~{S},8~{a}~{R})-2,3,4,4~{a},5,7,8,8~{a}-octahydro-1~{H}-1,6-naphthyridine-6-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 334 | 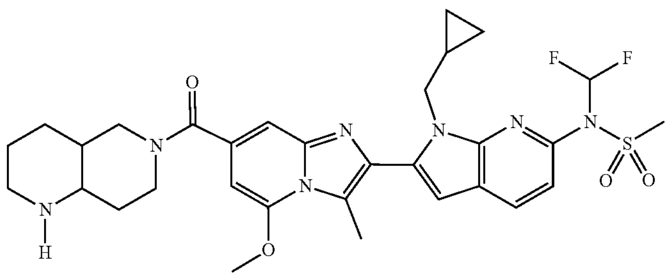 [SMILES: COc1cc(C(=O)N2CCC3NCCCC3C2)cc2nc(-c3cc4ccc(N(C(F)F)S(C)(=O)=O)nc4n3CC3CC3)c(C)n12] | ~{N}-[2-[7-(2,3,4,4~{a},5,7,8,8~{a}-octahydro-1~{H}-1,6-naphthyridine-6-carbonyl)-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 335 | 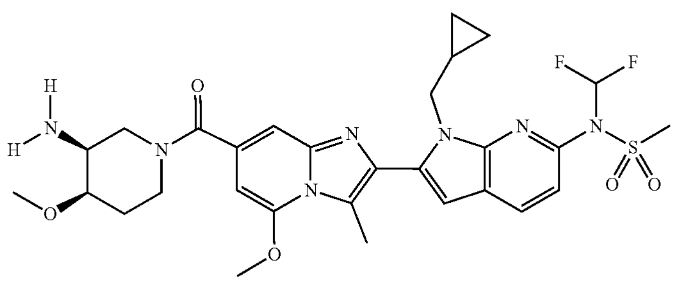 [SMILES: COc1cc(C(=O)N2CC[C@@H](OC)[C@@H](N)C2)cc2nc(-c3cc4ccc(N(C(F)F)S(C)(=O)=O)nc4n3CC3CC3)c(C)n12] | ~{N}-[2-[7-[(3~{S},4~{R})-3-amino-4-methoxypiperidine-1-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 336 | 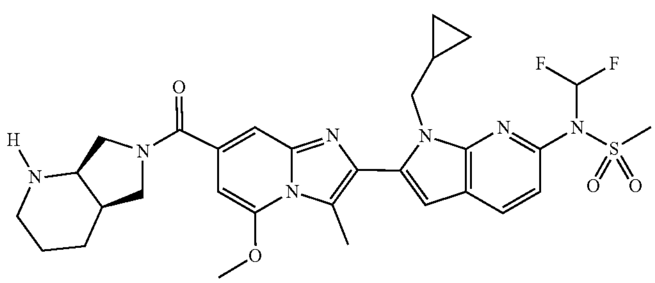 [SMILES: COc1cc(C(=O)N2C[C@H]3CCCN[C@H]3C2)cc2nc(-c3cc4ccc(N(C(F)F)S(C)(=O)=O)nc4n3CC3CC3)c(C)n12] | ~{N}-[2-[7-[(4~{a}~{R},7~{a}~{R})-1,2,3,4,4~{a},5,7,7~{a}-octahydropyrrolo[3,4-b]pyridine-6-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 337 | 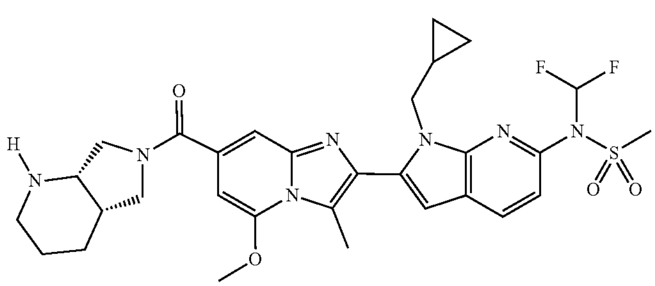 [SMILES: COc1cc(C(=O)N2C[C@@H]3CCCN[C@@H]3C2)cc2nc(-c3cc4ccc(N(C(F)F)S(C)(=O)=O)nc4n3CC3CC3)c(C)n12] | ~{N}-[2-[7-[(4~{a}~{S},7~{a}~{S})-1,2,3,4,4~{a},5,7,7~{a}-octahydropyrrolo[3,4-b]pyridine-6-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |

| Ex | Structure | Name |
|---|---|---|
| 338 | 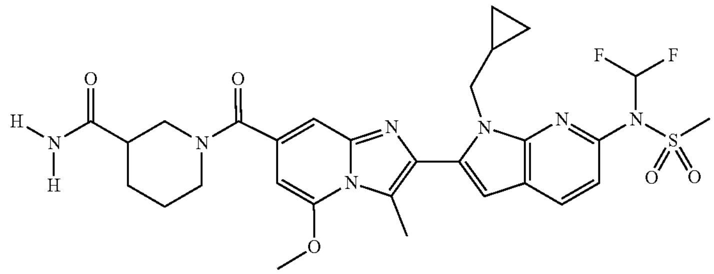 [SMILES: COc1cc(C(=O)N2CCCC(C(N)=O)C2)cc2nc(-c3cc4ccc(N(C(F)F)S(C)(=O)=O)nc4n3CC3CC3)c(C)n12] | 1-[2-[1-(cyclopropylmethyl)-6-[difluoromethyl(methylsulfonyl)amino]pyrrolo[2,3-b]pyridin-2-yl]-5-methoxy-3-methylimidazo[1,2-a]pyridine-7-carbonyl]piperidine-3-carboxamide |
| 339 | 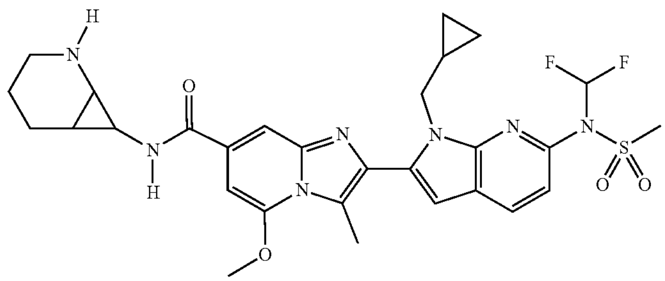 [SMILES: COc1cc(C(=O)NC2C3CCCNC32)cc2nc(-c3cc4ccc(N(C(F)F)S(C)(=O)=O)nc4n3CC3CC3)c(C)n12] | ~{N}-(2-azabicyclo[4.1.0]heptan-7-yl)-2-[1-(cyclopropylmethyl)-6-[difluoromethyl(methylsulfonyl)amino]pyrrolo[2,3-b]pyridin-2-yl]-5-methoxy-3-methylimidazo[1,2-a]pyridine-7-carboxamide |
| 340 | 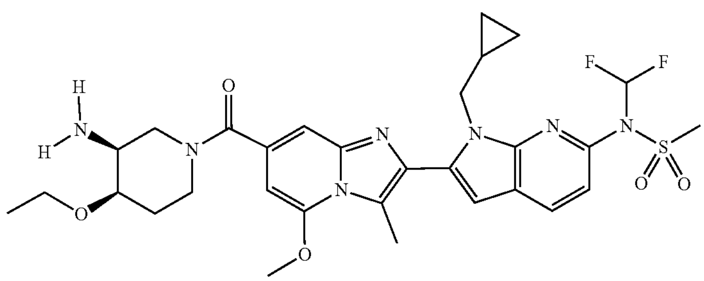 [SMILES: CCO[C@@H]1CCN(C(=O)c2cc(OC)n3c(C)c(-c4cc5ccc(N(C(F)F)S(C)(=O)=O)nc5n4CC4CC4)nc3c2)C[C@@H]1N] | ~{N}-[2-[7-[(3~{S},4~{R})-3-amino-4-ethoxypiperidine-1-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 341 | 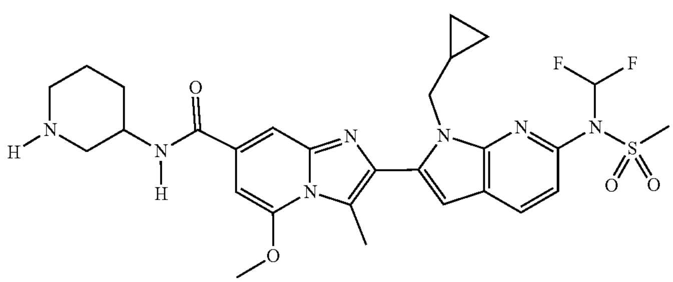 [SMILES: COc1cc(C(=O)NC2CCCNC2)cc2nc(-c3cc4ccc(N(C(F)F)S(C)(=O)=O)nc4n3CC3CC3)c(C)n12] | 2-[1-(cyclopropylmethyl)-6-[difluoromethyl(methylsulfonyl)amino]pyrrolo[2,3-b]pyridin-2-yl]-5-methoxy-3-methyl-~{N}-piperidin-3-ylimidazo[1,2-a]pyridine-7-carboxamide |
| 342 | 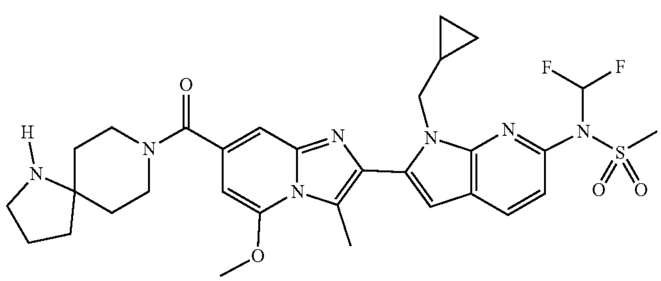 [SMILES: COc1cc(C(=O)N2CCC3(CCCN3)CC2)cc2nc(-c3cc4ccc(N(C(F)F)S(C)(=O)=O)nc4n3CC3CC3)c(C)n12] | ~{N}-[1-(cyclopropylmethyl)-2-[7-(1,8-diazaspiro[4.5]decane-8-carbonyl)-5-methoxy-3-methylimidazo[1,2-a]pyridin-2-yl]pyrrolo[2,3-b]pyridin-6-yl]-~{N}-(difluoromethyl)methanesulfonamide |

-continued

| Ex | Structure | Name |
|---|---|---|
| 343 | 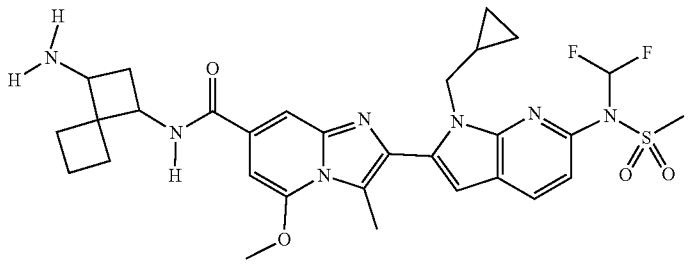 [SMILES: COc1cc(C(=O)NC2CC(N)C23CCC3)cc2nc(-c3cc4ccc(N(C(F)F)S(C)(=O)=O)nc4n3CC3CC3)c(C)n12] | ~{N}-(1-aminospiro[3.3]heptan-3-yl)-2-[1-(cyclopropylmethyl)-6-[difluoromethyl(methylsulfonyl)amino]pyrrolo[2,3-b]pyridin-2-yl]-5-methoxy-3-methylimidazo[1,2-a]pyridine-7-carboxamide |
| 344 | 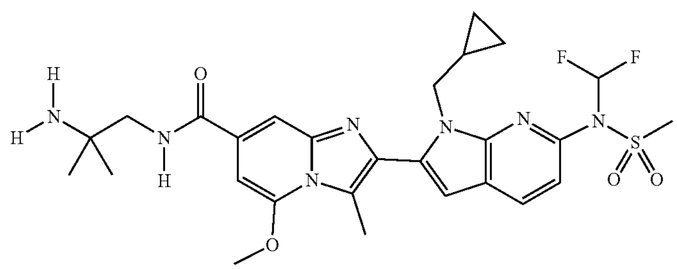 [SMILES: COc1cc(C(=O)NCC(C)(C)N)cc2nc(-c3cc4ccc(N(C(F)F)S(C)(=O)=O)nc4n3CC3CC3)c(C)n12] | ~{N}-(2-amino-2-methylpropyl)-2-[1-(cyclopropylmethyl)-6-[difluoromethyl(methylsulfonyl)amino]pyrrolo[2,3-b]pyridin-2-yl]-5-methoxy-3-methylimidazo[1,2-a]pyridine-7-carboxamide |
| 345 | 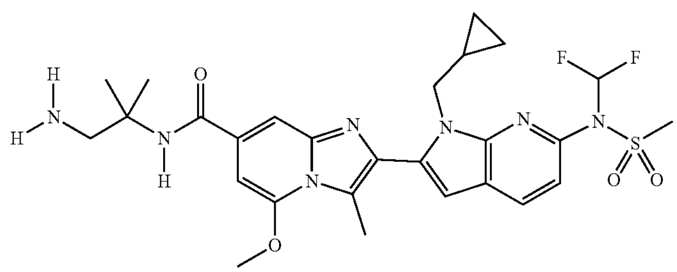 [SMILES: COc1cc(C(=O)NC(C)(C)CN)cc2nc(-c3cc4ccc(N(C(F)F)S(C)(=O)=O)nc4n3CC3CC3)c(C)n12] | ~{N}-(1-amino-2-methylpropan-2-yl)-2-[1-(cyclopropylmethyl)-6-[difluoromethyl(methylsulfonyl)amino]pyrrolo[2,3-b]pyridin-2-yl]-5-methoxy-3-methylimidazo[1,2-a]pyridine-7-carboxamide |
| 346 | 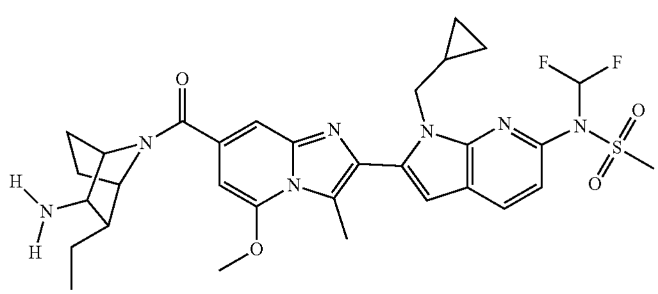 [SMILES: CCC1C(N)C2CCC1N2C(=O)c1cc(OC)n2c(C)c(-c3cc4ccc(N(C(F)F)S(C)(=O)=O)nc4n3CC3CC3)nc2c1] | N-[2-[7-[(1R,2R,3S,4S)-2-amino-3-ethyl-7-azabicyclo[2.2.1]heptane-7-carbonyl]-5-methoxy-3-methyl-imidazo[1,2-a]pyridin-2-yl]-1-(cyclopropylmethyl)pyrrolo[2,3-b]pyridin-6-yl]-N-(difluoromethyl)methanesulfonamide |
| 347 | 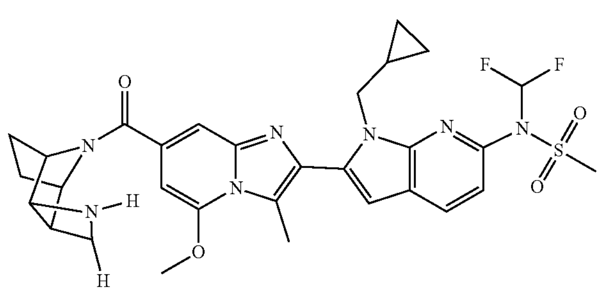 [SMILES: COc1cc(C(=O)N2C3CCC2C2NCC23)cc2nc(-c3cc4ccc(N(C(F)F)S(C)(=O)=O)nc4n3CC3CC3)c(C)n12] | N-[2-[7-[(1R,2S,3R,4S)-2-amino-3-ethyl-7-azabicyclo[2.2.1]heptane-7-carbonyl]-5-methoxy-3-methyl-imidazo[1,2-a]pyridin-2-yl]-1-(cyclopropylmethyl)pyrrolo[2,3-b]pyridin-6-yl]-N-(difluoromethyl)methanesulfonamide |

| Ex | Structure | Name |
|---|---|---|
| 348 | 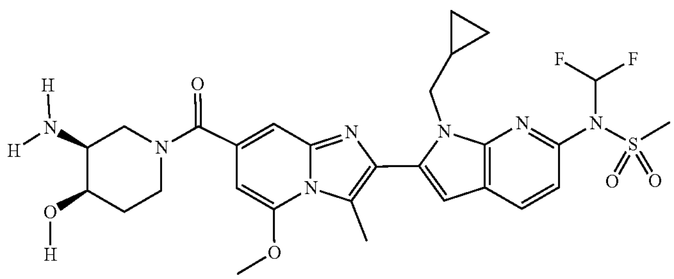 [SMILES: COc1cc(C(=O)N2CC[C@@H](O)[C@@H](N)C2)cc2nc(-c3cc4ccc(N(C(F)F)S(C)(=O)=O)nc4n3CC3CC3)c(C)n12] | ~{N}-[2-[7-[(3~{S},4~{R})-3-amino-4-hydroxypiperidine-1-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 349 | 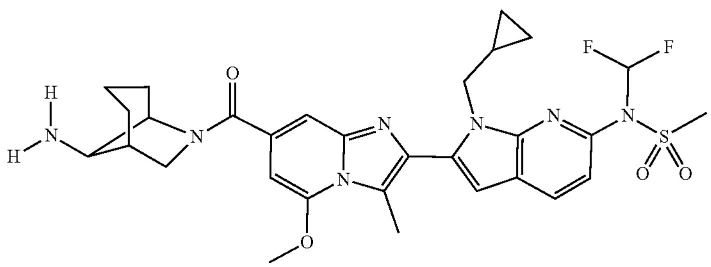 [SMILES: COc1cc(C(=O)N2CC3CCCC2C3N)cc2nc(-c3cc4ccc(N(C(F)F)S(C)(=O)=O)nc4n3CC3CC3)c(C)n12] | N-(2-(7-((1R,5R,8R)-8-amino-6-azabicyclo[3.2.1]octane-6-carbonyl)-5-methoxy-3-methylimidazo[1,2-a]pyridin-2-yl)-1-(cyclopropylmethyl)-1H-pyrrolo[2,3-b]pyridin-6-yl)-N-(difluoromethyl)methanesulfonamide |
| 350 | 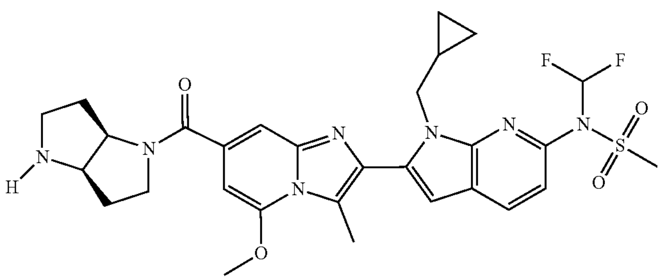 [SMILES: COc1cc(C(=O)N2CC[C@H]3NCC[C@H]32)cc2nc(-c3cc4ccc(N(C(F)F)S(C)(=O)=O)nc4n3CC3CC3)c(C)n12] | ~{N}-[2-[7-[(3~{a}~{R},6~{a}~{R})-2,3,3~{a},5,6,6~{a}-hexahydro-1~{H}-pyrrolo[3,2-b]pyrrole-4-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 351 | 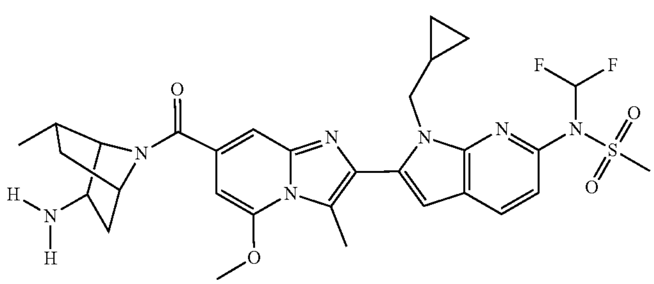 [SMILES: COc1cc(C(=O)N2C3CC(C)C2C(N)C3)cc2nc(-c3cc4ccc(N(C(F)F)S(C)(=O)=O)nc4n3CC3CC3)c(C)n12] | N-[2-[7-[(1R,2R,4S)-2-amino-6-methyl-7-azabicyclo[2.2.1]heptane-7-carbonyl]-5-methoxy-3-methyl-imidazo[1,2-a]pyridin-2-yl]-1-(cyclopropylmethyl)pyrrolo[2,3-b]pyridin-6-yl]-N-(difluoromethyl)methanesulfonamide |
| 352 | 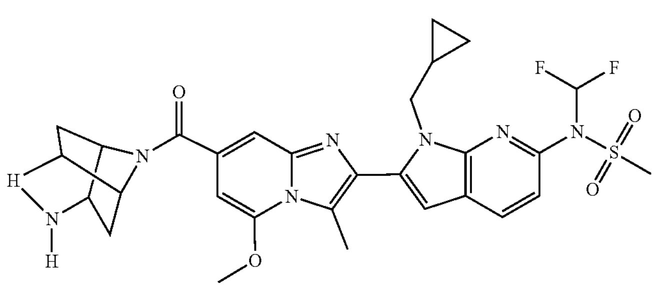 | N-[2-[7-[(1R,2R,4R)-2-amino-5-methyl-7-azabicyclo[2.2.1]heptane-7-carbonyl]-5-methoxy-3-methyl-imidazo[1,2-a]pyridin-2-yl]-1-(cyclopropylmethyl)pyrrolo[2,3-b]pyridin-6-yl]-N-(difluoromethyl)methanesulfonamide |

| Ex | Structure | Name |
|---|---|---|
| 353 | 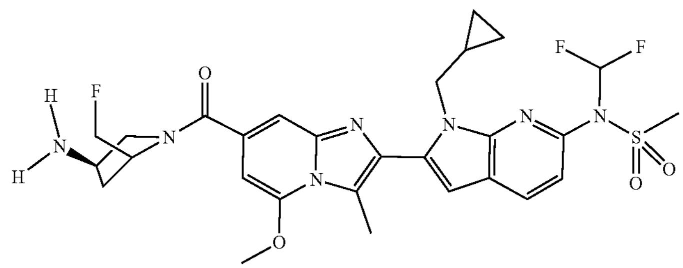 | N-[2-[7-[(2R,4R)-4-amino-2-(fluoromethyl)pyrrolidine-1-carbonyl]-5-methoxy-3-methyl-imidazo[1,2-a]pyridin-2-yl]-1-(cyclopropylmethyl)pyrrolo[2,3-b]pyridin-6-yl]-N-(difluoromethyl)methanesulfonamide |
| 354 | 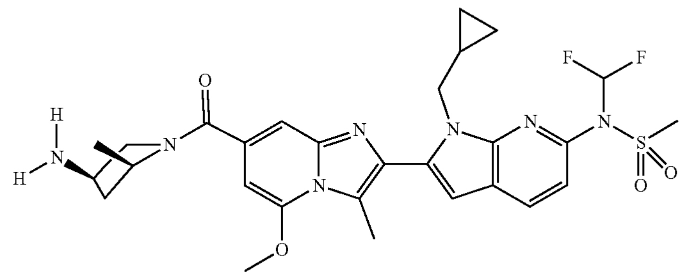 | N-[2-[7-[(2S,4R)-4-amino-2-methyl-pyrrolidine-1-carbonyl]-5-methoxy-3-methyl-imidazo[1,2-a]pyridin-2-yl]-1-(cyclopropylmethyl)pyrrolo[2,3-b]pyridin-6-yl]-N-(difluoromethyl)methanesulfonamide |
| 355 | 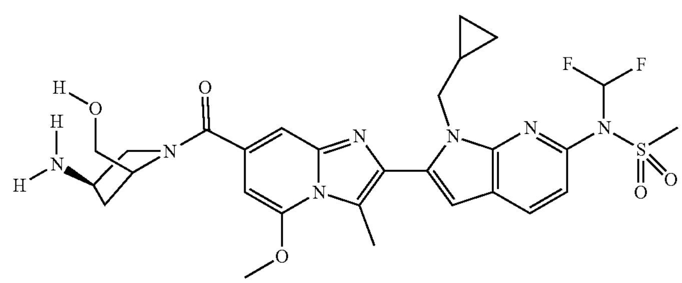 | N-[2-[7-[(2R,4R)-4-amino-2-(hydroxymethyl)pyrrolidine-1-carbonyl]-5-methoxy-3-methyl-imidazo[1,2-a]pyridin-2-yl]-1-(cyclopropylmethyl)pyrrolo[2,3-b]pyridin-6-yl]-N-(difluoromethyl)methanesulfonamide |
| 356 | 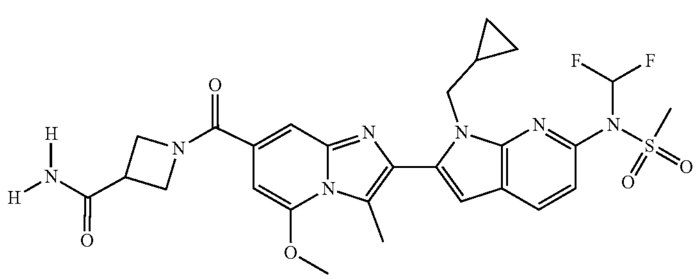 [SMILES: COc1cc(C(=O)N2CC(C(N)=O)C2)cc2nc(-c3cc4ccc(N(C(F)F)S(C)(=O)=O)nc4n3CC3CC3)c(C)n12] | 1-[2-[1-(cyclopropylmethyl)-6-[difluoromethyl(methylsulfonyl)amino]pyrrolo[2,3-b]pyridin-2-yl]-5-methoxy-3-methylimidazo[1,2-a]pyridine-7-carbonyl]azetidine-3-carboxamide |
| 357 | 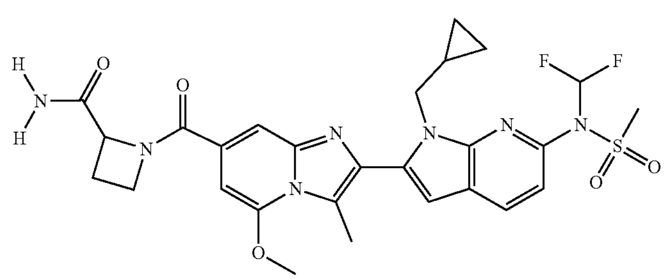 [SMILES: COc1cc(C(=O)N2CCC2C(N)=O)cc2nc(-c3cc4ccc(N(C(F)F)S(C)(=O)=O)nc4n3CC3CC3)c(C)n12] | 1-[2-[1-(cyclopropylmethyl)-6-[difluoromethyl(methylsulfonyl)amino]pyrrolo[2,3-b]pyridin-2-yl]-5-methoxy-3-methylimidazo[1,2-a]pyridine-7-carbonyl]azetidine-2-carboxamide |

| Ex | Structure | Name |
| --- | --- | --- |
| 358 | 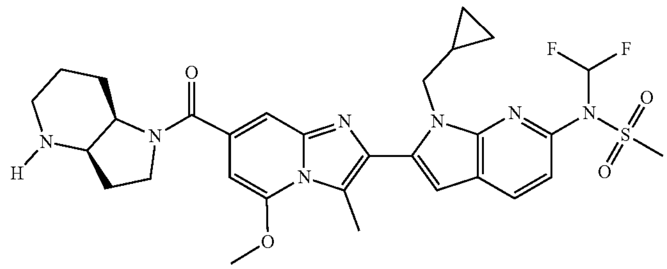 [SMILES: COc1cc(C(=O)N2CC[C@H]3NCCC[C@H]32)cc2nc(-c3cc4ccc(N(C(F)F)S(C)(=O)=O)nc4n3CC3CC3)c(C)n12] | ~{N}-[2-[7-[(3~{a}~{R},7~{a}~{R})-2,3,3~{a},4,5,6,7,7~{a}-octahydropyrrolo[3,2-b]pyridine-1-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 359 | 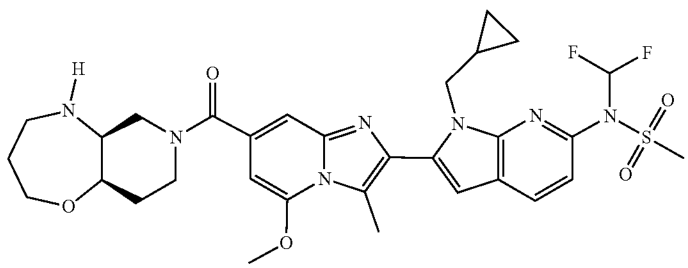 [SMILES: COc1cc(C(=O)N2CC[C@H]3OCCCN[C@H]3C2)cc2nc(-c3cc4ccc(N(C(F)F)S(C)(=O)=O)nc4n3CC3CC3)c(C)n12] | ~{N}-[2-[7-3,4,5,5~{a},6,8,9,9~{a}-octahydro-2~{H}-pyrido[4,3-b][1,4]oxazepine-7-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 360 | 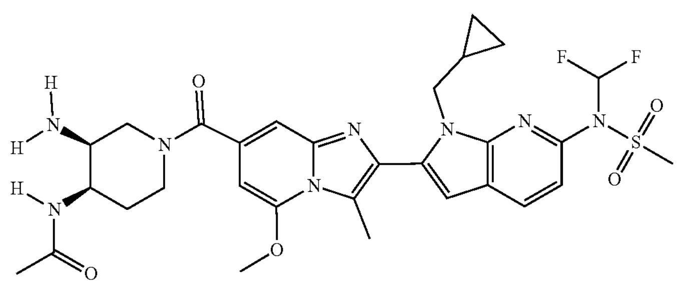 [SMILES: COc1cc(C(=O)N2CC[C@@H](NC(C)=O)[C@@H](N)C2)cc2nc(-c3cc4ccc(N(C(F)F)S(C)(=O)=O)nc4n3CC3CC3)c(C)n12] | ~{N}-[(3~{S},4~{R})-3-amino-1-[2-[1-(cyclopropylmethyl)-6-[difluoromethyl(methylsulfonyl)amino]pyrrolo[2,3-b]pyridin-2-yl]-5-methoxy-3-methylimidazo[1,2-a]pyridine-7-carbonyl]piperidin-4-yl]acetamide |
| 361 | 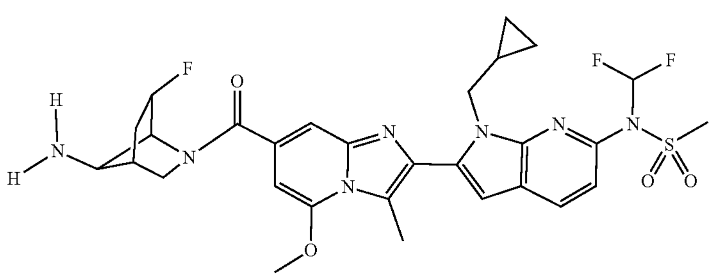 [SMILES: COc1cc(C(=O)N2CC3CC(F)C2C3N)cc2nc(-c3cc4ccc(N(C(F)F)S(C)(=O)=O)nc4n3CC3CC3)c(C)n12] | N-[2-[7-[(1S,4R,7R)-7-amino-6-fluoro-2-azabicyclo[2.2.1]heptane-2-carbonyl]-5-methoxy-3-methyl-imidazo[1,2-a]pyridin-2-yl]-1-(cyclopropylmethyl)pyrrolo[2,3-b]pyridin-6-yl]-N-(difluoromethyl)methanesulfonamide |
| 362 | 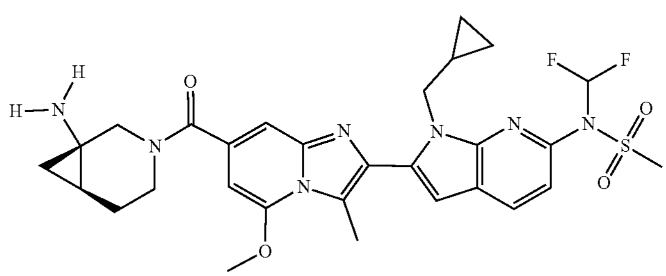 [SMILES: COc1cc(C(=O)N2CC[C@H]3C[C@@]3(N)C2)cc2nc(-c3cc4ccc(N(C(F)F)S(C)(=O)=O)nc4n3CC3CC3)c(C)n12] | ~{N}-[2-[7-[(1~{S},6~{S})-1-amino-3-azabicyclo[4.1.0]heptane-3-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |

-continued

| Ex | Structure | Name |
|---|---|---|
| 363 | 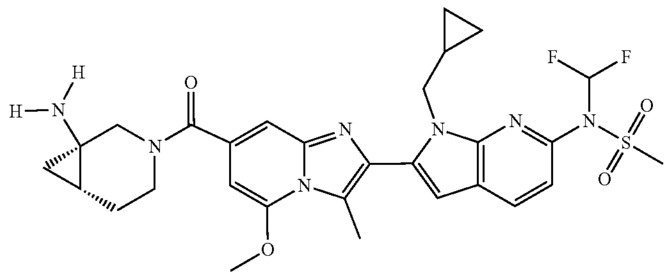 [SMILES: COc1cc(C(=O)N2CC[C@@H]3C[C@]3(N)C2)cc2nc(-c3cc4ccc(N(C(F)F)S(C)(=O)=O)nc4n3CC3CC3)c(C)n12] | ~{N}-[2-[7-[(1~{R},6~{R})-1-amino-3-azabicyclo[4.1.0]heptane-3-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 364 | 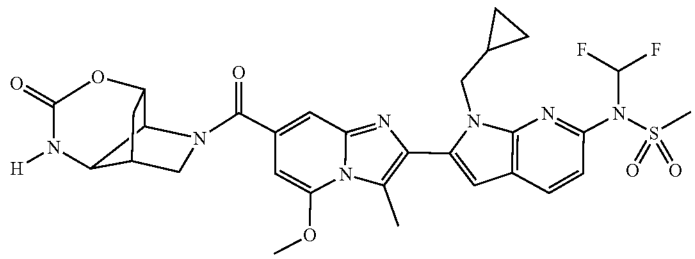 [SMILES: COc1cc(C(=O)N2CC3CC4OC(=O)NC3C42)cc2nc(-c3cc4ccc(N(C(F)F)S(C)(=O)=O)nc4n3CC3CC3)c(C)n12] | ~{N}-[1-(cyclopropylmethyl)-2-[5-methoxy-3-methyl-7-(4-oxo-5-oxa-3,10-diazatricyclo[4.4.0.0^{2,8}]decane-10-carbonyl)imidazo[1,2-a]pyridin-2-yl]pyrrolo[2,3-b]pyridin-6-yl]-~{N}-(difluoromethyl)methanesulfonamide |
| 365 | 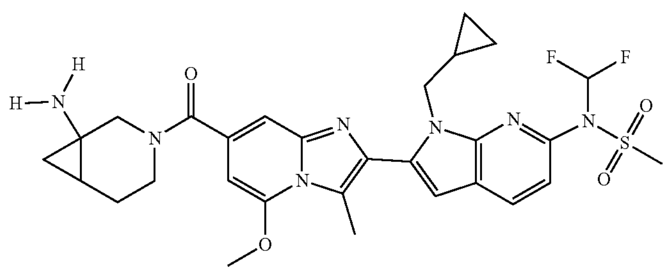 [SMILES: COc1cc(C(=O)N2CCC3CC3(N)C2)cc2nc(-c3cc4ccc(N(C(F)F)S(C)(=O)=O)nc4n3CC3CC3)c(C)n12] | ~{N}-[2-[7-(1-amino-3-azabicyclo[4.1.0]heptane-3-carbonyl)-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 366 | 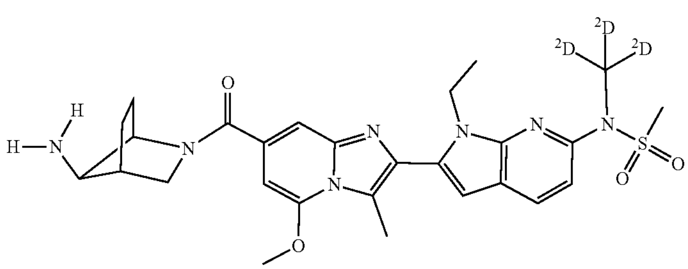 [SMILES: [2H]C([2H])([2H])N(c1ccc2cc(-c3nc4cc(C(=O)N5CC6CCC5C6N)cc(OC)n4c3C)n(CC)c2n1)S(C)(=O)=O] | N-[2-[7-[(1R,4R,7R)-7-amino-2-azabicyclo[2.2.1]heptane-2-carbonyl]-5-methoxy-3-methyl-imidazo[1,2-a]pyridin-2-yl]-1-ethyl-pyrrolo[2,3-b]pyridin-6-yl]-N-(trideuteriomethyl)methanesulfonamide |
| 367 | 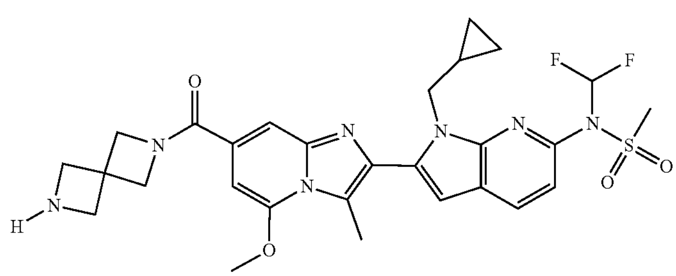 [SMILES: COc1cc(C(=O)N2CC3(CNC3)C2)cc2nc(-c3cc4ccc(N(C(F)F)S(C)(=O)=O)nc4n3CC3CC3)c(C)n12] | ~{N}-[1-(cyclopropylmethyl)-2-[7-(2,6-diazaspiro[3.3]heptane-2-carbonyl)-5-methoxy-3-methylimidazo[1,2-a]pyridin-2-yl]pyrrolo[2,3-b]pyridin-6-yl]-~{N}-(difluoromethyl)methanesulfonamide |

| Ex | Structure | Name |
|---|---|---|
| 368 | 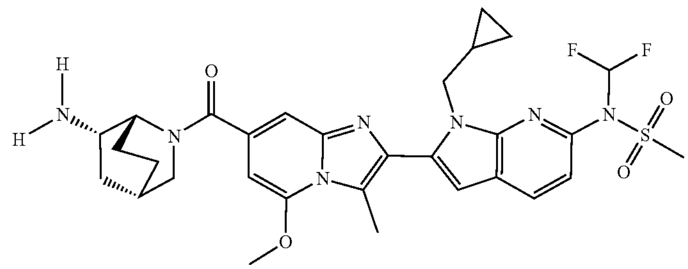 [SMILES: COc1cc(C(=O)N2C[C@H]3CC[C@@H]2[C@@H](N)C3)cc2nc(-c3cc4ccc(N(C(F)F)S(C)(=O)=O)nc4n3CC3CC3)c(C)n12] | ~{N}-[2-[7-[(1~{R},4~{S},6~{S})-6-amino-2-azabicyclo[2.2.2]octane-2-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 369 | 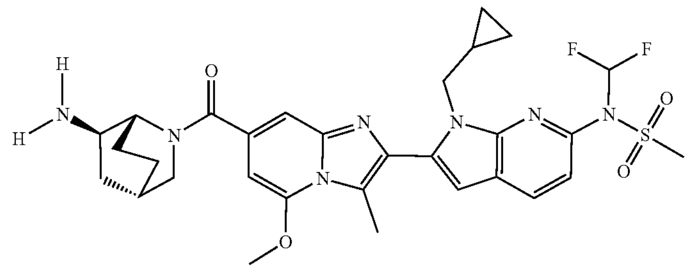 [SMILES: COc1cc(C(=O)N2C[C@H]3CC[C@@H]2[C@H](N)C3)cc2nc(-c3cc4ccc(N(C(F)F)S(C)(=O)=O)nc4n3CC3CC3)c(C)n12] | ~{N}-[2-[7-[(1~{S},4~{R},6~{R})-6-amino-2-azabicyclo[2.2.2]octane-2-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 370 | 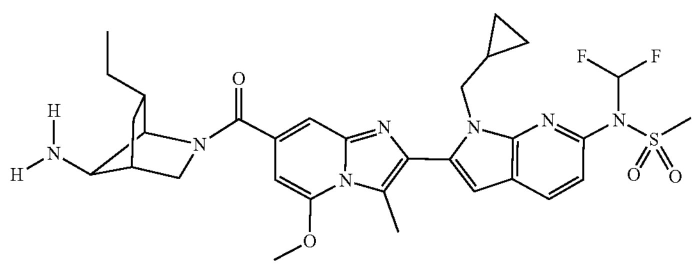 [SMILES: CCC1CC2CN(C(=O)c3cc(OC)n4c(C)c(-c5cc6ccc(N(C(F)F)S(C)(=O)=O)nc6n5CC5CC5)nc4c3)C1C2N] | N-[2-[7-[(1R,4R,6S,7R)-7-amino-6-methyl-2-azabicyclo[2.2.1]heptane-2-carbonyl]-5-methoxy-3-methyl-imidazo[1,2-a]pyridin-2-yl]-1-(cyclopropylmethyl)pyrrolo[2,3-b]pyridin-6-yl]-N-(difluoromethyl)methanesulfonamide |
| 371 | 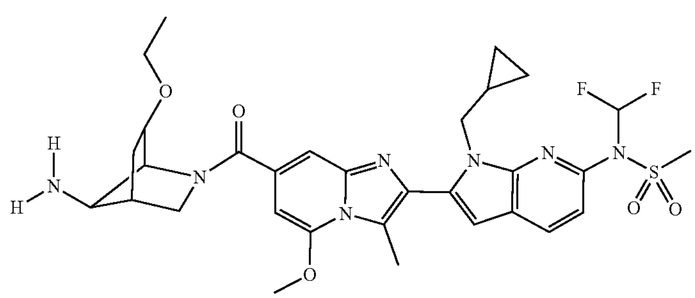 [SMILES: CCOC1CC2CN(C(=O)c3cc(OC)n4c(C)c(-c5cc6ccc(N(C(F)F)S(C)(=O)=O)nc6n5CC5CC5)nc4c3)C1C2N] | N-[2-[7-[(1S,4R,7R)-7-amino-6-ethoxy-2-azabicyclo[2.2.1]heptane-2-carbonyl]-5-methoxy-3-methyl-imidazo[1,2-a]pyridin-2-yl]-1-(cyclopropylmethyl)pyrrolo[2,3-b]pyridin-6-yl]-N-(difluoromethyl)methanesulfonamide |
| 372 | 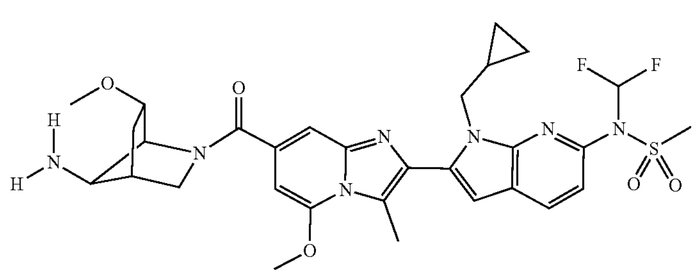 [SMILES: COc1cc(C(=O)N2CC3CC(OC)C2C3N)cc2nc(-c3cc4ccc(N(C(F)F)S(C)(=O)=O)nc4n3CC3CC3)c(C)n12] | N-[2-[7-[(1S,4R,6S,7R)-7-amino-6-methoxy-2-azabicyclo[2.2.1]heptane-2-carbonyl]-5-methoxy-3-methyl-imidazo[1,2-a]pyridin-2-yl]-1-(cyclopropylmethyl)pyrrolo[2,3-b]pyridin-6-yl]-N-(difluoromethyl)methanesulfonamide |

-continued

| Ex | Structure | Name |
|---|---|---|
| 373 | 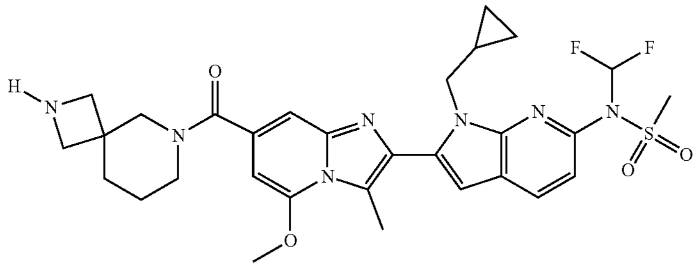 [SMILES: COc1cc(C(=O)N2CCCC3(CNC3)C2)cc2nc(-c3cc4ccc(N(C(F)F)S(C)(=O)=O)nc4n3CC3CC3)c(C)n12] | ~{N}-[1-(cyclopropylmethyl)-2-[7-(2,6-diazaspiro[3.5]nonane-6-carbonyl)-5-methoxy-3-methylimidazo[1,2-a]pyridin-2-yl]pyrrolo[2,3-b]pyridin-6-yl]-~{N}-(difluoromethyl)methanesulfonamide |
| 374 | 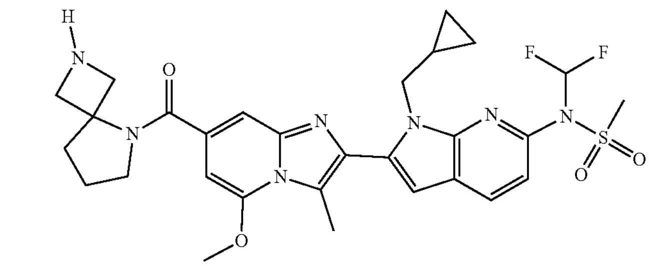 [SMILES: COc1cc(C(=O)N2CCCC23CNC3)cc2nc(-c3cc4ccc(N(C(F)F)S(C)(=O)=O)nc4n3CC3CC3)c(C)n12] | ~{N}-[1-(cyclopropylmethyl)-2-[7-(2,5-diazaspiro[3.4]octane-5-carbonyl)-5-methoxy-3-methylimidazo[1,2-a]pyridin-2-yl]pyrrolo[2,3-b]pyridin-6-yl]-~{N}-(difluoromethyl)methanesulfonamide |
| 375 | 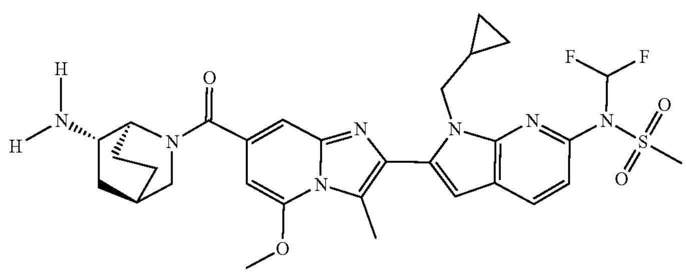 [SMILES: COc1cc(C(=O)N2C[C@@H]3CC[C@H]2[C@@H](N)C3)cc2nc(-c3cc4ccc(N(C(F)F)S(C)(=O)=O)nc4n3CC3CC3)c(C)n12] | ~{N}-[2-[7-[(1~{S},4~{R},6~{S})-6-amino-2-azabicyclo[2.2.2]octane-2-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 376 | 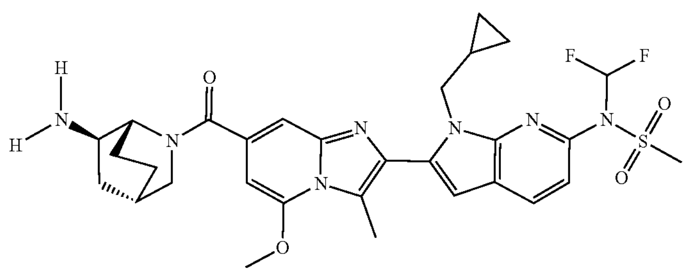 [SMILES: COc1cc(C(=O)N2C[C@H]3CC[C@@H]2[C@H](N)C3)cc2nc(-c3cc4ccc(N(C(F)F)S(C)(=O)=O)nc4n3CC3CC3)c(C)n12] | ~{N}-[2-[7-[(1~{R},4~{S},6~{R})-6-amino-2-azabicyclo[2.2.2]octane-2-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 377 | 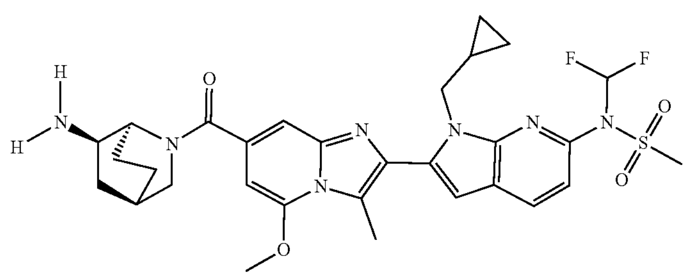 [SMILES: COc1cc(C(=O)N2C[C@@H]3CC[C@H]2[C@H](N)C3)cc2nc(-c3cc4ccc(N(C(F)F)S(C)(=O)=O)nc4n3CC3CC3)c(C)n12] | ~{N}-[2-[7-[(1~{R},4~{S},6~{R})-6-amino-2-azabicyclo[2.2.2]octane-2-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |

-continued

| Ex | Structure | Name |
|---|---|---|
| 378 | 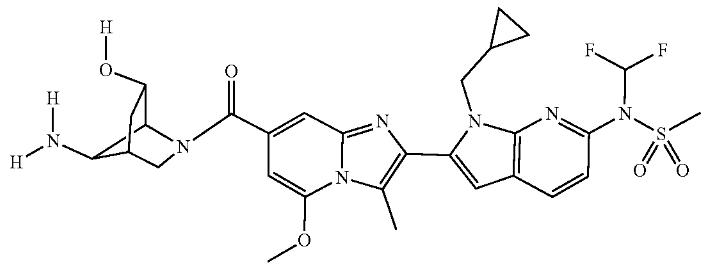 [SMILES: COc1cc(C(=O)N2CC3CC(O)C2C3N)cc2nc(-c3cc4ccc(N(C(F)F)S(C)(=O)=O)nc4n3CC3CC3)c(C)n12] | N-[2-[7-[(1S,4R,6S,7R)-7-amino-6-hydroxy-2-azabicyclo[2.2.1]heptane-2-carbonyl]-5-methoxy-3-methyl-imidazo[1,2-a]pyridin-2-yl]-1-(cyclopropylmethyl)pyrrolo[2,3-b]pyridin-6-yl]-N-(difluoromethyl)methanesulfonamide |
| 379 | 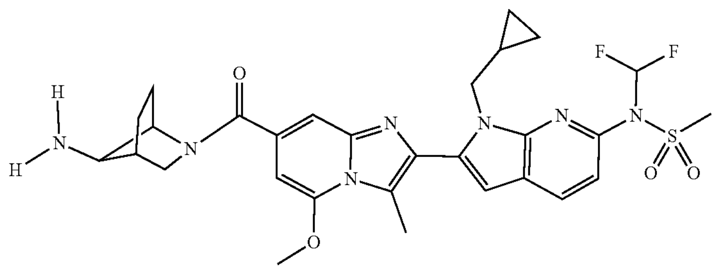 [SMILES: COc1cc(C(=O)N2CC3CCC2C3N)cc2nc(-c3cc4ccc(N(C(F)F)S(C)(=O)=O)nc4n3CC3CC3)c(C)n12] | N-[2-[7-[(1R,4R,7R)-7-amino-2-azabicyclo[2.2.1]heptane-2-carbonyl]-5-methoxy-3-methyl-imidazo[1,2-a]pyridin-2-yl]-1-(cyclopropylmethyl)pyrrolo[2,3-b]pyridin-6-yl]-N-(difluoromethyl)methanesulfonamide |
| 380 | 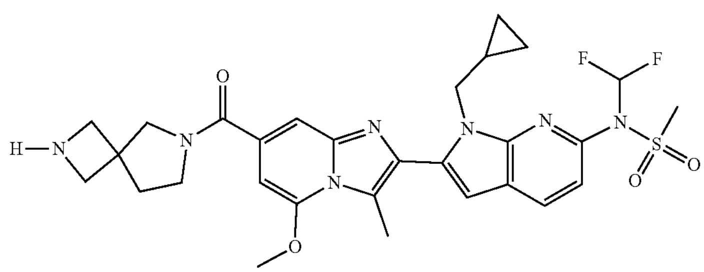 [SMILES: COc1cc(C(=O)N2CCC3(CNC3)C2)cc2nc(-c3cc4ccc(N(C(F)F)S(C)(=O)=O)nc4n3CC3CC3)c(C)n12] | ~{N}-[1-(cyclopropylmethyl)-2-[7-(2,6-diazaspiro[3.4]octane-6-carbonyl)-5-methoxy-3-methylimidazo[1,2-a]pyridin-2-yl]pyrrolo[2,3-b]pyridin-6-yl]-~{N}-(difluoromethyl)methanesulfonamide |
| 381 | 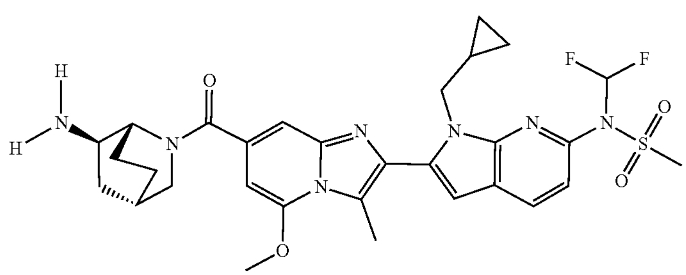 [SMILES: COc1cc(C(=O)N2C[C@H]3CC[C@@H]2[C@H](N)C3)cc2nc(-c3cc4ccc(N(C(F)F)S(C)(=O)=O)nc4n3CC3CC3)c(C)n12] | ~{N}-[2-[7-[(1~{R},4~{S},6~{R})-6-amino-2-azabicyclo[2.2.2]octane-2-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 382 | 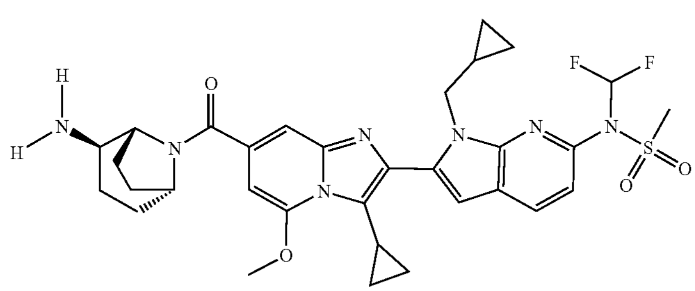 [SMILES: COc1cc(C(=O)N2[C@@H]3CC[C@@H](N)[C@H]2CC3)cc2nc(-c3cc4ccc(N(C(F)F)S(C)(=O)=O)nc4n3CC3CC3)c(C3CC3)n12] | ~{N}-[2-[7-[(1~{R},2~{R},5~{R})-2-amino-8-azabicyclo[3.2.1]octane-8-carbonyl]-3-cyclopropyl-5-methoxyimidazo[1,2-a]pyridin-2-yl]-1-(cyclopropylmethyl)pyrrolo[2,3-b]pyridin-6-yl]-~{N}-(difluoromethyl)methanesulfonamide |

-continued

| Ex | Structure | Name |
|---|---|---|
| 383 | 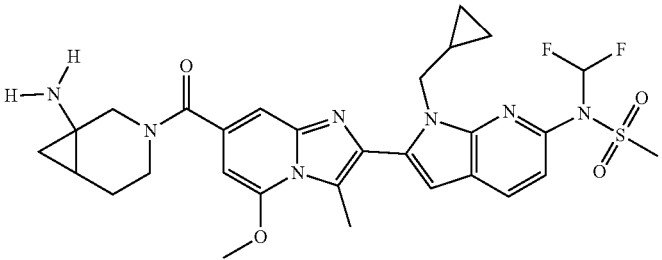 [SMILES: COc1cc(C(=O)N2CCC3CC3(N)C2)cc2nc(-c3cc4ccc(N(C(F)F)S(C)(=O)=O)nc4n3CC3CC3)c(C)n12] | ~{N}-[2-[7-[(4~{a}~{S},8~{a}~{R})-2,3,4,4~{a},5,7,8,8~{a}-octahydropyrido[4,3-b][1,4]oxazine-6-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 384 | 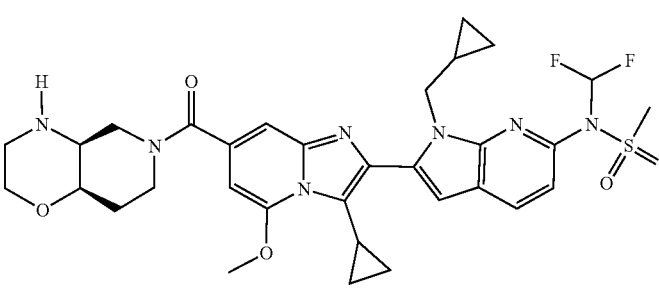 | ~{N}-[2-[7-[(4~{a}~{S},8~{a}~{R})-2,3,4,4~{a},5,7,8,8~{a}-octahydropyrido[4,3-b][1,4]oxazine-6-carbonyl]-3-cyclopropyl-5-methoxyimidazo[1,2-a]pyridin-2-yl]-1-(cyclopropylmethyl)pyrrolo[2,3-b]pyridin-6-yl]-~{N}-(difluoromethyl)methanesulfonamide |
| 385 | 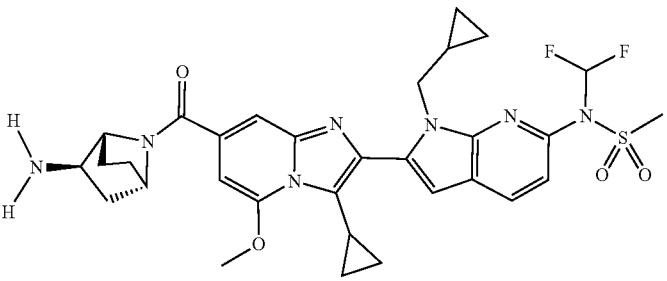 [SMILES: COc1cc(C(=O)N2[C@H]3CC[C@@H]2[C@H](N)C3)cc2nc(-c3cc4ccc(N(C(F)F)S(C)(=O)=O)nc4n3CC3CC3)c(C3CC3)n12] | ~{N}-[2-[7-[(1~{R},2~{R},4~{S})-2-amino-7-azabicyclo[2.2.1]heptane-7-carbonyl]-3-cyclopropyl-5-methoxyimidazo[1,2-a]pyridin-2-yl]-1-(cyclopropylmethyl)pyrrolo[2,3-b]pyridin-6-yl]-~{N}-(difluoromethyl)methanesulfonamide |
| 386 | 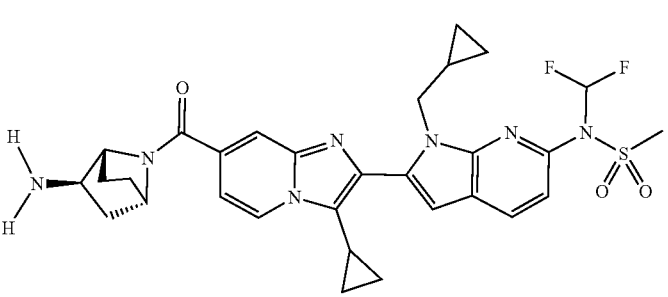 [SMILES: CS(=O)(=O)N(c1ccc2cc(-c3nc4cc(C(=O)N5[C@H]6CC[C@@H]5[C@H](N)C6)ccn4c3C3CC3)n(CC3CC3)c2n1)C(F)F] | ~{N}-[2-[7-[(1~{R},2~{R},4~{S})-2-amino-7-azabicyclo[2.2.1]heptane-7-carbonyl]-3-cyclopropylimidazo[1,2-a]pyridin-2-yl]-1-(cyclopropylmethyl)pyrrolo[2,3-b]pyridin-6-yl]-~{N}-(difluoromethyl)methanesulfonamide |
| 387 | 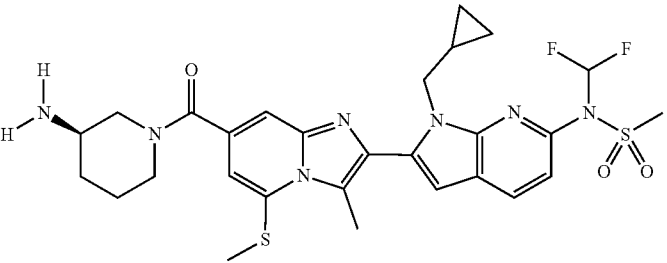 [SMILES: CSc1cc(C(=O)N2CCC[C@@H](N)C2)cc2nc(-c3cc4ccc(N(C(F)F)S(C)(=O)=O)nc4n3CC3CC3)c(C)n12] | ~{N}-[2-[7-[(3~{R})-3-aminopiperidine-1-carbonyl]-3-methyl-5-methylsulfanylimidazo[1,2-a]pyridin-2-yl]-1-(cyclopropylmethyl)pyrrolo[2,3-b]pyridin-6-yl]-~{N}-(difluoromethyl)methanesulfonamide |

| Ex | Structure | Name |
|---|---|---|
| 388 | 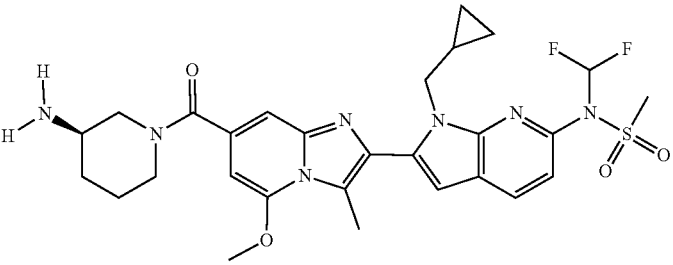 [SMILES: COc1cc(C(=O)N2CCC[C@@H](N)C2)cc2nc(-c3cc4ccc(N(C(F)F)S(C)(=O)=O)nc4n3CC3CC3)c(C)n12] | ~{N}-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 389 | 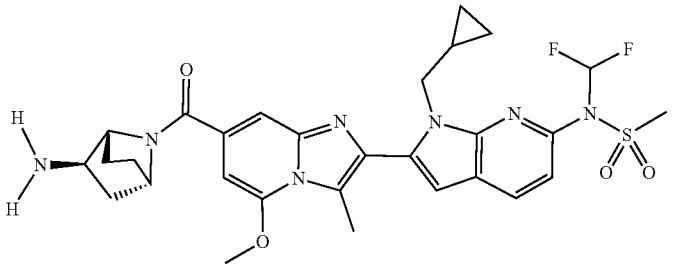 [SMILES: COc1cc(C(=O)N2[C@H]3CC[C@@H]2[C@H](N)C3)cc2nc(-c3cc4ccc(N(C(F)F)S(C)(=O)=O)nc4n3CC3CC3)c(C)n12] | ~{N}-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 390 | 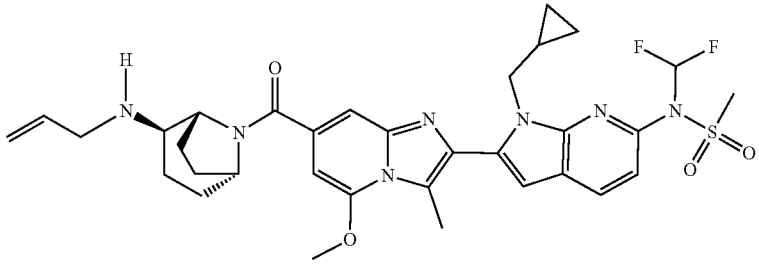 [SMILES: C=CCN[C@@H]1CC[C@@H]2CC[C@H]1N2C(=O)c1cc(OC)n2c(C)c(-c3cc4ccc(N(C(F)F)S(C)(=O)=O)nc4n3CC3CC3)nc2c1] | ~{N}-[1-(cyclopropylmethyl)-2-[5-methoxy-3-methyl-7-[(1~{R},2~{R},5~{R})-2-(prop-2-enylamino)-8-azabicyclo[3.2.1]octane-8-carbonyl]imidazo[1,2-a]pyridin-2-yl]pyrrolo[2,3-b]pyridin-6-yl]-~{N}-(difluoromethyl)methanesulfonamide |
| 391 | 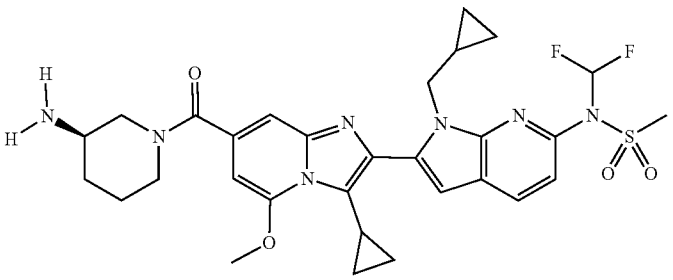 [SMILES: COc1cc(C(=O)N2CCC[C@@H](N)C2)cc2nc(-c3cc4ccc(N(C(F)F)S(C)(=O)=O)nc4n3CC3CC3)c(C3CC3)n12] | ~{N}-[2-[7-[(3~{R})-3-aminopiperidine-1-carbonyl]-3-cyclopropyl-5-methoxyimidazo[1,2-a]pyridin-2-yl]-1-(cyclopropylmethyl)pyrrolo[2,3-b]pyridin-6-yl]-~{N}-(difluoromethyl)methanesulfonamide |
| 392 | 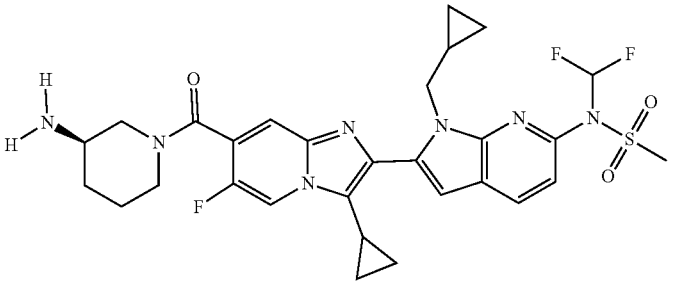 [SMILES: CS(=O)(=O)N(c1ccc2cc(-c3nc4cc(C(=O)N5CCC[C@@H](N)C5)c(F)cn4c3C3CC3)n(CC3CC3)c2n1)C(F)F] | ~{N}-[2-[7-[(3~{R})-3-aminopiperidine-1-carbonyl]-3-cyclopropyl-6-fluoroimidazo[1,2-a]pyridin-2-yl]-1-(cyclopropylmethyl)pyrrolo[2,3-b]pyridin-6-yl]-~{N}-(difluoromethyl)methanesulfonamide |

| Ex | Structure | Name |
| --- | --- | --- |
| 393 | 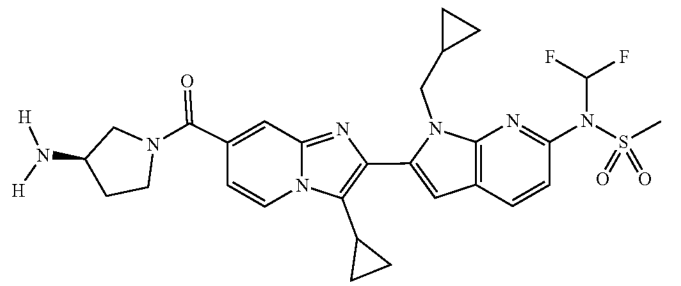 [SMILES: CS(=O)(=O)N(c1ccc2cc(-c3nc4cc(C(=O)N5CC[C@@H](N)C5)ccn4c3C3CC3)n(CC3CC3)c2n1)C(F)F] | ~{N}-[2-[7-[(3~{R})-3-aminopyrrolidine-1-carbonyl]-3-cyclopropylimidazo[1,2-a]pyridin-2-yl]-1-(cyclopropylmethyl)pyrrolo[2,3-b]pyridin-6-yl]-~{N}-(difluoromethyl)methanesulfonamide |
| 394 | 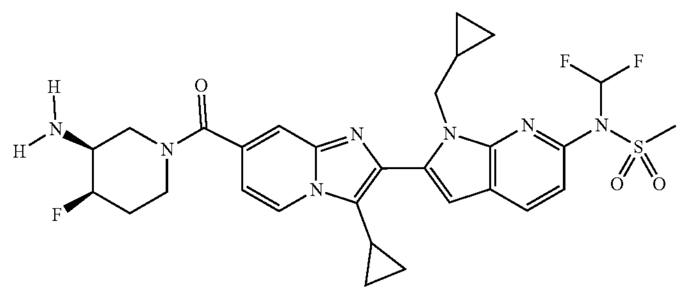 [SMILES: CS(=O)(=O)N(c1ccc2cc(-c3nc4cc(C(=O)N5CC[C@@H](F)[C@@H](N)C5)ccn4c3C3CC3)n(CC3CC3)c2n1)C(F)F] | ~{N}-[2-[7-[(3~{S},4~{R})-3-amino-4-fluoropiperidine-1-carbonyl]-3-cyclopropylimidazo[1,2-a]pyridin-2-yl]-1-(cyclopropylmethyl)pyrrolo[2,3-b]pyridin-6-yl]-~{N}-(difluoromethyl)methanesulfonamide |
| 395 | 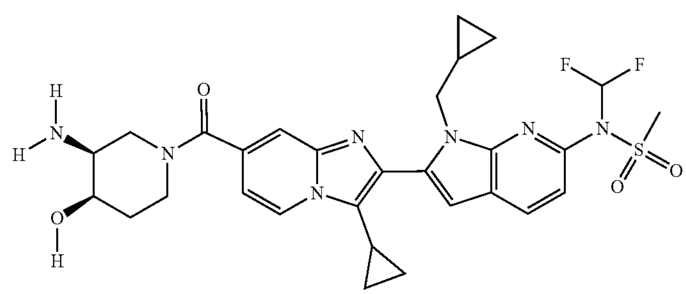 [SMILES: CS(=O)(=O)N(c1ccc2cc(-c3nc4cc(C(=O)N5CC[C@@H](O)[C@@H](N)C5)ccn4c3C3CC3)n(CC3CC3)c2n1)C(F)F] | ~{N}-[2-[7-[(3~{S},4~{R})-3-amino-4-hydroxypiperidine-1-carbonyl]-3-cyclopropylimidazo[1,2-a]pyridin-2-yl]-1-(cyclopropylmethyl)pyrrolo[2,3-b]pyridin-6-yl]-~{N}-(difluoromethyl)methanesulfonamide |
| 396 | 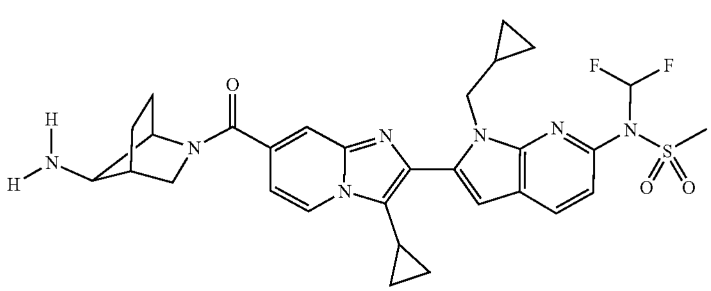 [SMILES: CS(=O)(=O)N(c1ccc2cc(-c3nc4cc(C(=O)N5CC6CCC5C6N)ccn4c3C3CC3)n(CC3CC3)c2n1)C(F)F] | N-[2-[7-[(1R,4R,7R)-7-amino-2-azabicyclo[2.2.1]heptane-2-carbonyl]-3-cyclopropyl-imidazo[1,2-a]pyridin-2-yl]-1-(cyclopropylmethyl)pyrrolo[2,3-b]pyridin-6-yl]-N-(difluoromethyl)methanesulfonamide |
| 397 | 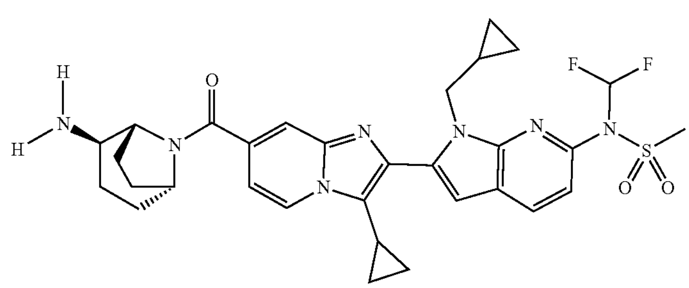 [SMILES: CS(=O)(=O)N(c1ccc2cc(-c3nc4cc(C(=O)N5[C@@H]6CC[C@@H](N)[C@H]5CC6)ccn4c3C3CC3)n(CC3CC3)c2n1)C(F)F] | 2-amino-8-azabicyclo[3.2.1]octane-8-carbonyl]-3-cyclopropylimidazo[1,2-a]pyridin-2-yl]-1-(cyclopropylmethyl)pyrrolo[2,3-b]pyridin-6-yl]-~{N}-(difluoromethyl)methanesulfonamide |

| Ex | Structure | Name |
|---|---|---|
| 398 | 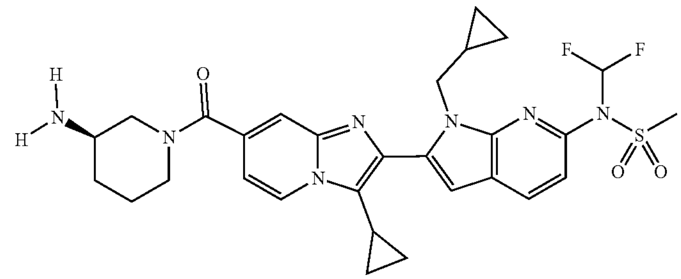 [SMILES: CS(=O)(=O)N(c1ccc2cc(-c3nc4cc(C(=O)N5CCC[C@@H](N)C5)ccn4c3C3CC3)n(CC3CC3)c2n1)C(F)F] | ~{N}-[2-[7-[(3~{R})-3-aminopiperidine-1-carbonyl]-3-cyclopropylimidazo[1,2-a]pyridin-2-yl]-1-(cyclopropylmethyl)pyrrolo[2,3-b]pyridin-6-yl]-~{N}-(difluoromethyl)methanesulfonamide |
| 399 | 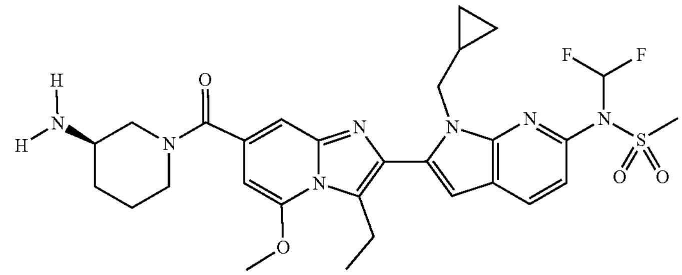 [SMILES: CCc1c(-c2cc3ccc(N(C(F)F)S(C)(=O)=O)nc3n2CC2CC2)nc2cc(C(=O)N3CCC[C@@H](N)C3)cc(OC)n12] | ~{N}-[2-[7-[(3~{R})-3-aminopiperidine-1-carbonyl]-3-ethyl-5-methoxyimidazo[1,2-a]pyridin-2-yl]-1-(cyclopropylmethyl)pyrrolo[2,3-b]pyridin-6-yl]-~{N}-(difluoromethyl)methanesulfonamide |
| 400 | 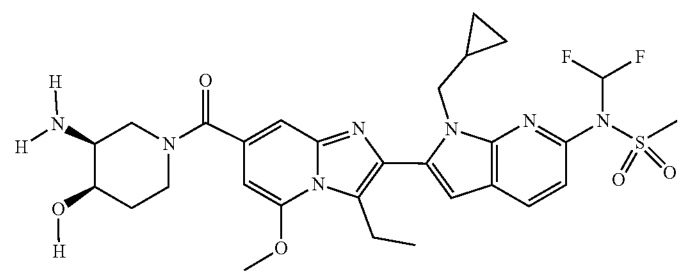 [SMILES: CCc1c(-c2cc3ccc(N(C(F)F)S(C)(=O)=O)nc3n2CC2CC2)nc2cc(C(=O)N3CC[C@@H](O)[C@@H](N)C3)cc(OC)n12] | ~{N}-[2-[7-[(3~{S},4~{R})-3-amino-4-hydroxypiperidine-1-carbonyl]-3-ethyl-5-methoxyimidazo[1,2-a]pyridin-2-yl]-1-(cyclopropylmethyl)pyrrolo[2,3-b]pyridin-6-yl]-~{N}-(difluoromethyl)methanesulfonamide |
| 401 | 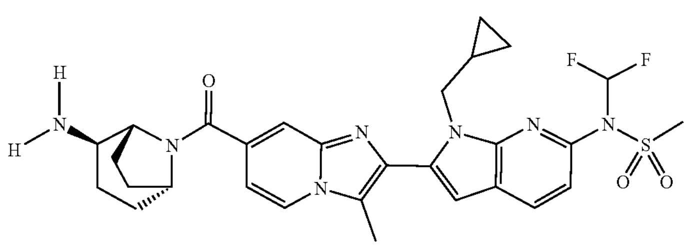 [SMILES: Cc1c(-c2cc3ccc(N(C(F)F)S(C)(=O)=O)nc3n2CC2CC2)nc2cc(C(=O)N3[C@@H]4CC[C@@H](N)[C@H]3CC4)ccn12] | ~{N}-[2-[7-[(1~{R},2~{R},5~{R})-2-amino-8-azabicyclo[3.2.1]octane-8-carbonyl]-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 402 | 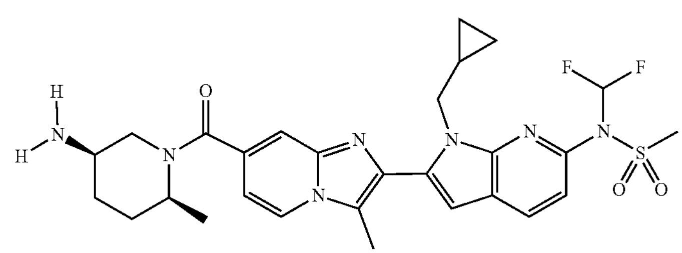 [SMILES: Cc1c(-c2cc3ccc(N(C(F)F)S(C)(=O)=O)nc3n2CC2CC2)nc2cc(C(=O)N3C[C@H](N)CC[C@@H]3C)ccn12] | ~{N}-[2-[7-[(2~{S},5~{R})-5-amino-2-methylpiperidine-1-carbonyl]-3-methylimidazo[1,2-a]pyridin-2-yl]-1-(cyclopropylmethyl)pyrrolo[2,3-b]pyridin-6-yl]-~{N}-(difluoromethyl)methanesulfonamide |

| Ex | Structure | Name |
|---|---|---|
| 403 | 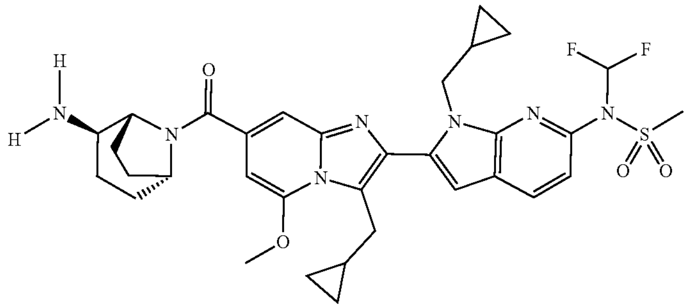 [SMILES: COc1cc(C(=O)N2[C@@H]3CC[C@@H](N)[C@H]2CC3)cc2nc(-c3cc4ccc(N(C(F)F)S(C)(=O)=O)nc4n3CC3CC3)c(CC3CC3)n12] | ~{N}-[2-[7-[(1~{R},2~{R},5~{R})-2-amino-8-azabicyclo[3.2.1]octane-8-carbonyl]-3-(cyclopropylmethyl)-5-methoxyimidazo[1,2-a]pyridin-2-yl]-1-(cyclopropylmethyl)pyrrolo[2,3-b]pyridin-6-yl]-~{N}-(difluoromethyl)methanesulfonamide |
| 404 | 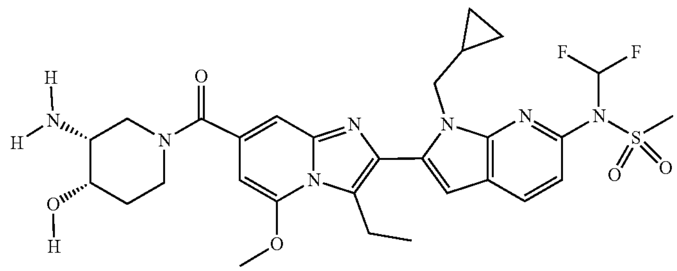 [SMILES: CCc1c(-c2cc3ccc(N(C(F)F)S(C)(=O)=O)nc3n2CC2CC2)nc2cc(C(=O)N3CC[C@H](O)[C@H](N)C3)cc(OC)n12] | ~{N}-[2-[7-[(3~{R},4~{S})-3-amino-4-hydroxypiperidine-1-carbonyl]-3-ethyl-5-methoxyimidazo[1,2-a]pyridin-2-yl]-1-(cyclopropylmethyl)pyrrolo[2,3-b]pyridin-6-yl]-~{N}-(difluoromethyl)methanesulfonamide |
| 405 | 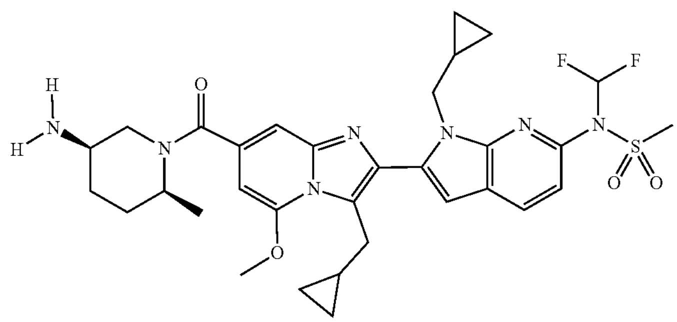 [SMILES: COc1cc(C(=O)N2C[C@H](N)CC[C@@H]2C)cc2nc(-c3cc4ccc(N(C(F)F)S(C)(=O)=O)nc4n3CC3CC3)c(CC3CC3)n12] | ~{N}-[2-[7-[(2~{S},5~{R})-5-amino-2-methylpiperidine-1-carbonyl]-3-(cyclopropylmethyl)-5-methoxyimidazo[1,2-a]pyridin-2-yl]-1-(cyclopropylmethyl)pyrrolo[2,3-b]pyridin-6-yl]-~{N}-(difluoromethyl)methanesulfonamide |
| 406 | 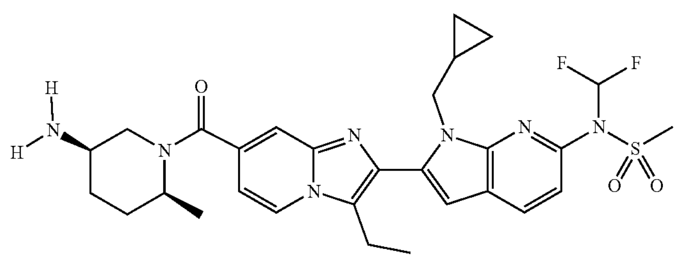 [SMILES: CCc1c(-c2cc3ccc(N(C(F)F)S(C)(=O)=O)nc3n2CC2CC2)nc2cc(C(=O)N3C[C@H](N)CC[C@@H]3C)ccn12] | ~{N}-[2-[7-[(2~{S},5~{R})-5-amino-2-methylpiperidine-1-carbonyl]-3-ethylimidazo[1,2-a]pyridin-2-yl]-1-(cyclopropylmethyl)pyrrolo[2,3-b]pyridin-6-yl]-~{N}-(difluoromethyl)methanesulfonamide |
| 407 | 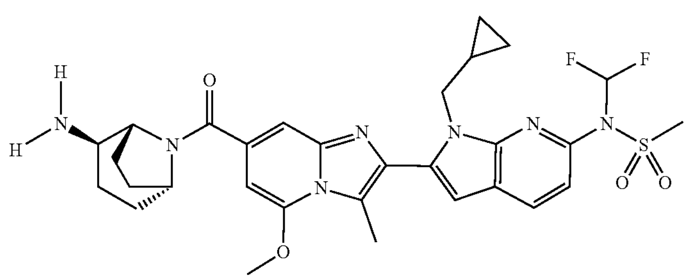 [SMILES: COc1cc(C(=O)N2[C@@H]3CC[C@@H](N)[C@H]2CC3)cc2nc(-c3cc4ccc(N(C(F)F)S(C)(=O)=O)nc4n3CC3CC3)c(C)n12] | ~{N}-[2-[7-[(1~{R},2~{R},5~{R})-2-amino-8-azabicyclo[3.2.1]octane-8-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |

| Ex | Structure | Name |
|---|---|---|
| 408 | 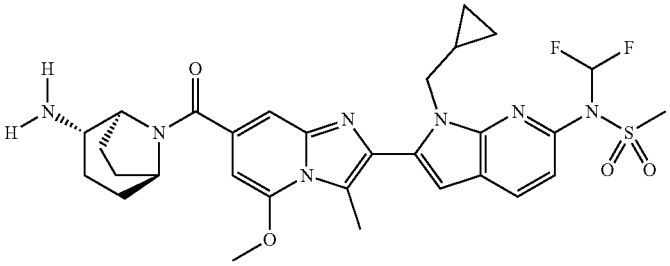 [SMILES: COc1cc(C(=O)N2[C@H]3CC[C@H](N)[C@@H]2CC3)cc2nc(-c3cc4ccc(N(C(F)F)S(C)(=O)=O)nc4n3CC3CC3)c(C)n12] | ~{N}-[2-[7-[(1~{S},2~{S},5~{S})-2-amino-8-azabicyclo[3.2.1]octane-8-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 409 | 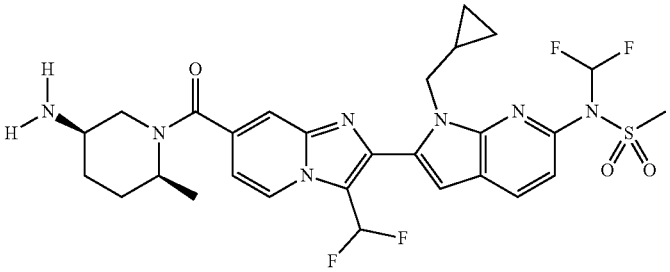 [SMILES: C[C@H]1CC[C@@H](N)CN1C(=O)c1ccn2c(C(F)F)c(-c3cc4ccc(N(C(F)F)S(C)(=O)=O)nc4n3CC3CC3)nc2c1] | ~{N}-[2-[7-[(2~{S},5~{R})-5-amino-2-methylpiperidine-1-carbonyl]-3-(difluoromethyl)imidazo[1,2-a]pyridin-2-yl]-1-(cyclopropylmethyl)pyrrolo[2,3-b]pyridin-6-yl]-~{N}-(difluoromethyl)methanesulfonamide |
| 410 | 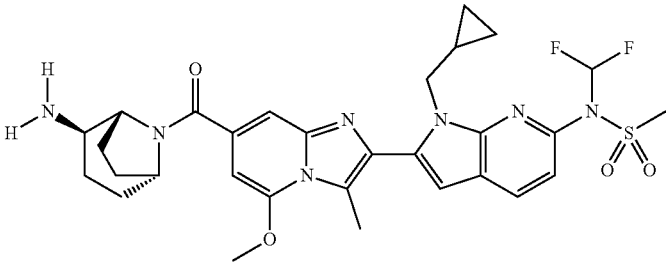 [SMILES: COc1cc(C(=O)N2[C@@H]3CC[C@@H](N)[C@H]2CC3)cc2nc(-c3cc4ccc(N(C(F)F)S(C)(=O)=O)nc4n3CC3CC3)c(C)n12] | ~{N}-[2-[7-[(1~{R},2~{R},5~{R})-2-amino-8-azabicyclo[3.2.1]octane-8-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 411 | 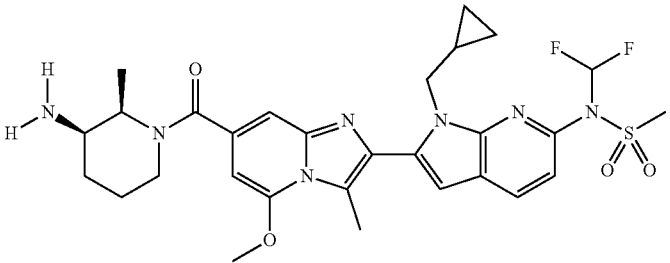 [SMILES: COc1cc(C(=O)N2CCC[C@@H](N)[C@H]2C)cc2nc(-c3cc4ccc(N(C(F)F)S(C)(=O)=O)nc4n3CC3CC3)c(C)n12] | ~{N}-[2-[7-[(2~{R},3~{R})-3-amino-2-methylpiperidine-1-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 412 | 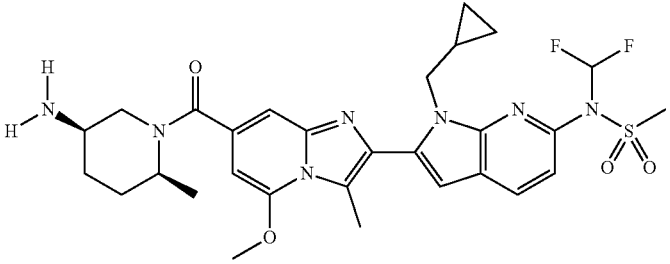 [SMILES: COc1cc(C(=O)N2C[C@H](N)CC[C@@H]2C)cc2nc(-c3cc4ccc(N(C(F)F)S(C)(=O)=O)nc4n3CC3CC3)c(C)n12] | ~{N}-[2-[7-[(2~{S},5~{R})-5-amino-2-methylpiperidine-1-carbonyl]-5-methoxy-3-methylimidazo[1,2-a]pyridin-2-yl]-1-(cyclopropylmethyl)pyrrolo-[2,3b]pyridin-6-yl]-~{N}-(difluoromethyl)methanesulfonamide |

| Ex | Structure | Name |
|---|---|---|
| 413 | 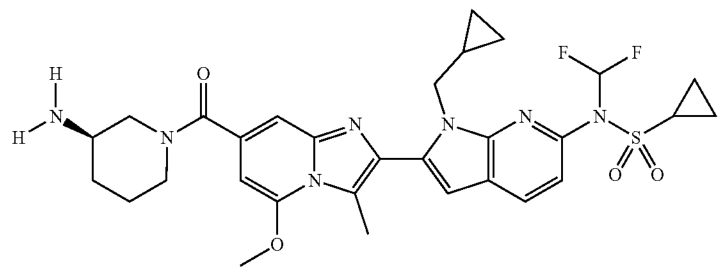 [SMILES: COc1cc(C(=O)N2CCC[C@@H](N)C2)cc2nc(-c3cc4ccc(N(C(F)F)S(=O)(=O)C5CC5)nc4n3CC3CC3)c(C)n12] | ~{N}-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)cyclopropanesulfonamide |
| 414 | 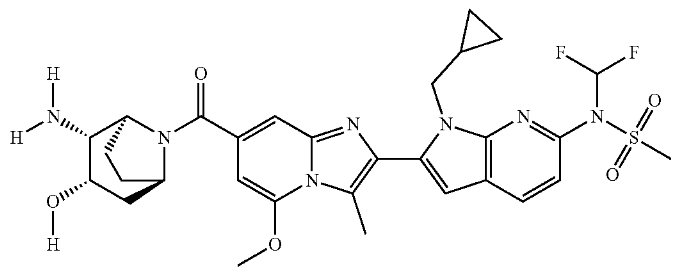 [SMILES: COc1cc(C(=O)N2[C@@H]3CC[C@H]2[C@@H](N)[C@@H](O)C3)cc2nc(-c3cc4ccc(N(C(F)F)S(C)(=O)=O)nc4n3CC3CC3)c(C)n12] | ~{N}-[2-[7-[(1~{S},2~{R},3~{S},5~{R})-2-amino-3-hydroxy-8-azabicyclo[3.2.1]octane-8-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 415 | 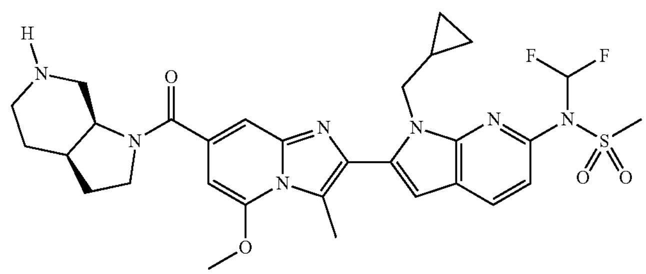 [SMILES: COc1cc(C(=O)N2CC[C@H]3CCNC[C@H]32)cc2nc(-c3cc4ccc(N(C(F)F)S(C)(=O)=O)nc4n3CC3CC3)c(C)n12] | ~{N}-[2-[7-[(3~{a}~{R},7~{a}~{S})-2,3,3~{a},4,5,6,7,7~{a}-octahydropyrrolo[2,3-c]pyridine-1-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 416 | 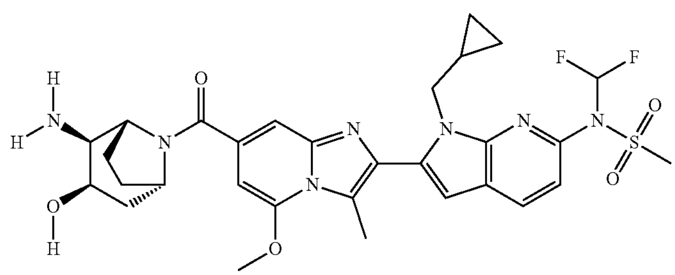 [SMILES: COc1cc(C(=O)N2[C@H]3CC[C@@H]2[C@H](N)[C@H](O)C3)cc2nc(-c3cc4ccc(N(C(F)F)S(C)(=O)=O)nc4n3CC3CC3)c(C)n12] | ~{N}-[2-[7-[(1~{R},2~{S},3~{R},5~{S})-2-amino-3-hydroxy-8-azabicyclo[3.2.1]octane-8-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 417 | 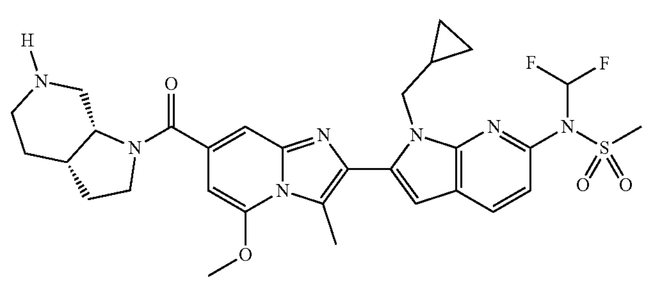 [SMILES: COc1cc(C(=O)N2CC[C@@H]3CCNC[C@@H]32)cc2nc(-c3cc4ccc(N(C(F)F)S(C)(=O)=O)nc4n3CC3CC3)c(C)n12] | ~{N}-[2-[7-2,3,3~{a},4,5,6,7,7~{a}-octahydropyrrolo[2,3-c]pyridine-1-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |

-continued

| Ex | Structure | Name |
|---|---|---|
| 418 | 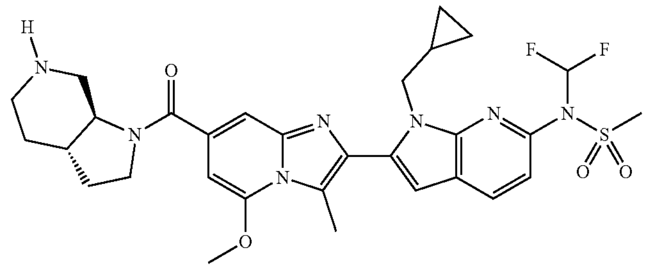 [SMILES: COc1cc(C(=O)N2CC[C@@H]3CCNC[C@H]32)cc2nc(-c3cc4ccc(N(C(F)F)S(C)(=O)=O)nc4n3CC3CC3)c(C)n12] | ~{N}-[2-[7-[(3~{a}~{S},7~{a}~{S})-2,3,3~{a},4,5,6,7,7~{a}-octahydropyrrolo[2,3-c]pyridine-1-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 419 | 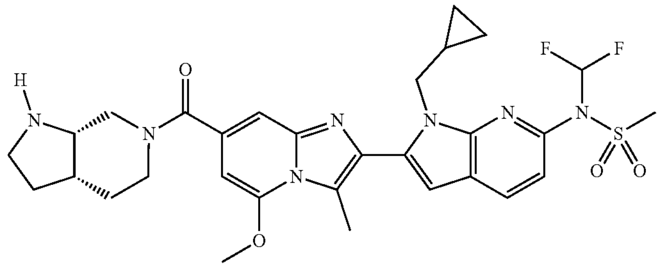 [SMILES: COc1cc(C(=O)N2CC[C@@H]3CCN[C@@H]3C2)cc2nc(-c3cc4ccc(N(C(F)F)S(C)(=O)=O)nc4n3CC3CC3)c(C)n12] | 1,2,3,3~{a},4,5,7,7~{a}-octahydropyrrolo[2,3-c]pyridine-6-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 420 | 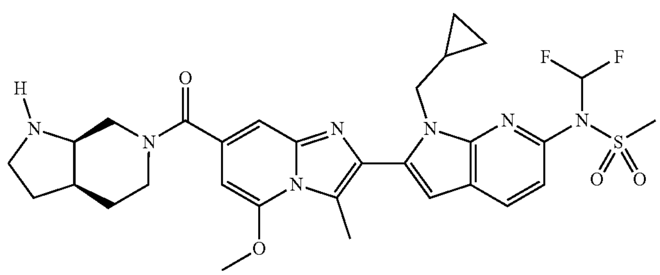 [SMILES: COc1cc(C(=O)N2CC[C@H]3CCN[C@H]3C2)cc2nc(-c3cc4ccc(N(C(F)F)S(C)(=O)=O)nc4n3CC3CC3)c(C)n12] | ~{N}-[2-[7-[(3~{a}~{R},7~{a}~{R})-1,2,3,3~{a},4,5,7,7~{a}-octahydropyrrolo[2,3-c]pyridine-6-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 421 | 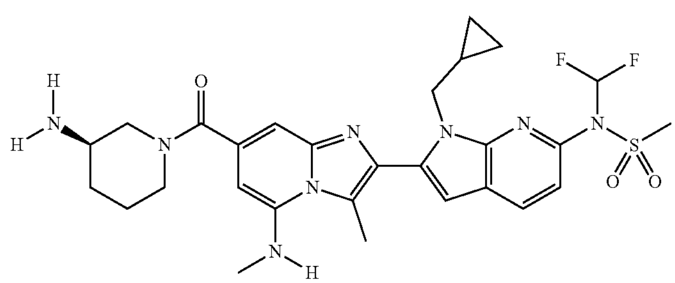 [SMILES: CNc1cc(C(=O)N2CCC[C@@H](N)C2)cc2nc(-c3cc4ccc(N(C(F)F)S(C)(=O)=O)nc4n3CC3CC3)c(C)n12] | ~{N}-[2-[7-[(3~{R})-3-aminopiperidine-1-carbonyl]-3-methyl-5-(methylamino)imidazo[1,2-a]pyridin-2-yl]-1-(cyclopropylmethyl)pyrrolo[2,3-b]pyridin-6-yl]-~{N}-(difluoromethyl)methanesulfonamide |
| 422 | 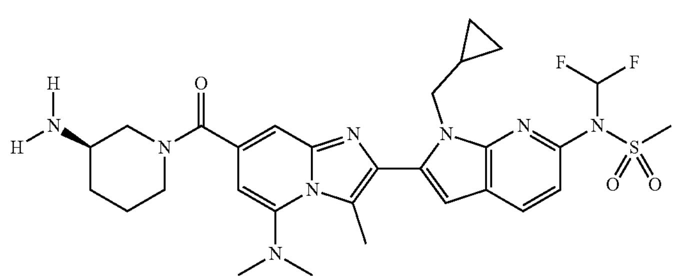 [SMILES: Cc1c(-c2cc3ccc(N(C(F)F)S(C)(=O)=O)nc3n2CC2CC2)nc2cc(C(=O)N3CCC[C@@H](N)C3)cc(N(C)C)n12] | ~{N}-[2-[7-[(3~{R})-3-aminopiperidine-1-carbonyl]-5-(dimethylamino)-3-methylimidazo[1,2-a]pyridin-2-yl]-1-(cyclopropylmethyl)pyrrolo[2,3-b]pyridin-6-yl]-~{N}-(difluoromethyl)methanesulfonamide |

-continued

| Ex | Structure | Name |
|---|---|---|
| 423 | 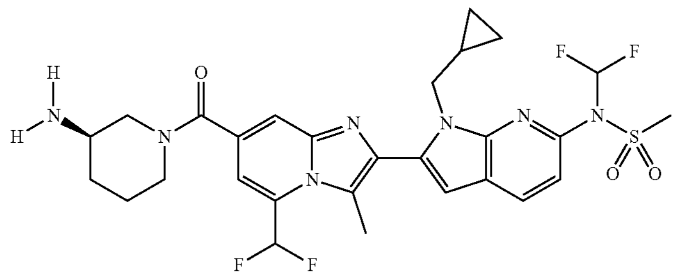 [SMILES: Cc1c(-c2cc3ccc(N(C(F)F)S(C)(=O)=O)nc3n2CC2CC2)nc2cc(C(=O)N3CCC[C@@H](N)C3)cc(C(F)F)n12] | ~{N}-[2-[7-[(3~{R})-3-aminopiperidine-1-carbonyl]-5-(difluoromethyl)-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 424 | 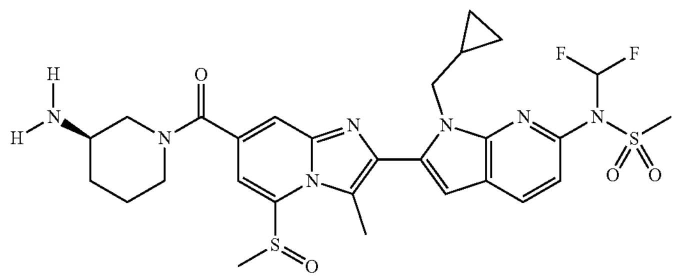 | ~{N}-[2-[7-[(3~{R})-3-aminopiperidine-1-carbonyl]-3-methyl-5-methylsulfinylimidazo[1,2-a]pyridin-2-yl]-1-(cyclopropylmethyl)pyrrolo[2,3-b]pyridin-6-yl]-~{N}-(difluoromethyl)methanesulfonamide |
| 425 | 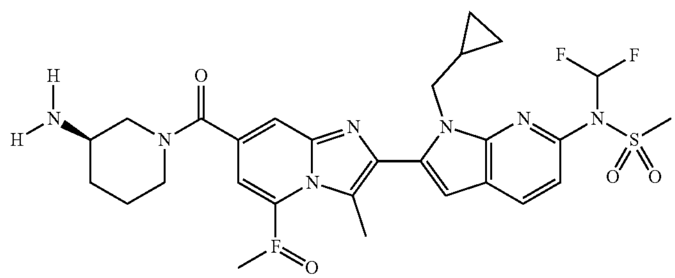 [SMILES: Cc1c(-c2cc3ccc(N(C(F)F)S(C)(=O)=O)nc3n2CC2CC2)nc2cc(C(=O)N3CCC[C@@H](N)C3)cc(S(C)=O)n12] | ~{N}-[2-[7-[(3~{R})-3-aminopiperidine-1-carbonyl]-3-methyl-5-methylsulfinylimidazo[1,2-a]pyridin-2-yl]-1-(cyclopropylmethyl)pyrrolo[2,3-b]pyridin-6-yl]-~{N}-(difluoromethyl)methanesulfonamide |
| 426 | 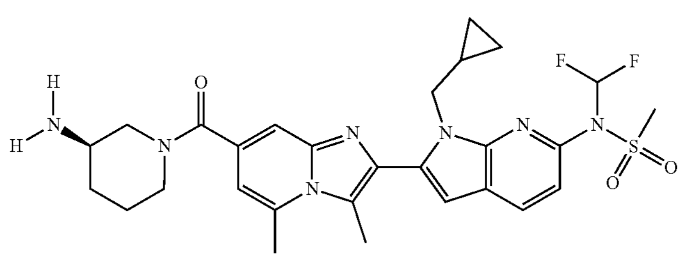 [SMILES: Cc1cc(C(=O)N2CCC[C@@H](N)C2)cc2nc(-c3cc4ccc(N(C(F)F)S(C)(=O)=O)nc4n3CC3CC3)c(C)n12] | ~{N}-[2-[7-[(3~{R})-3-aminopiperidine-1-carbonyl]-3,5-dimethylimidazo[1,2-a]pyridin-2-yl]-1-(cyclopropylmethyl)pyrrolo[2,3-b]pyridin-6-yl]-~{N}-(difluoromethyl)methanesulfonamide |
| 427 | 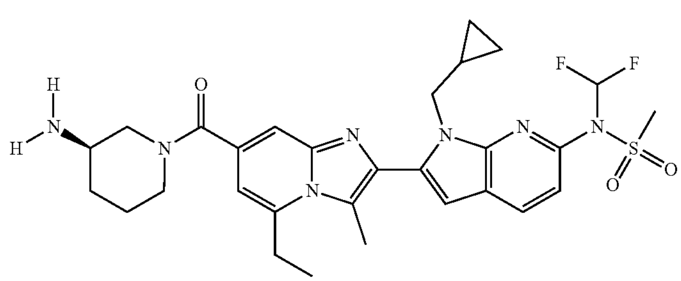 [SMILES: CCc1cc(C(=O)N2CCC[C@@H](N)C2)cc2nc(-c3cc4ccc(N(C(F)F)S(C)(=O)=O)nc4n3CC3CC3)c(C)n12] | ~{N}-[2-[7-[(3~{R})-3-aminopiperidine-1-carbonyl]-5-ethyl-3-methylimidazo[1,2-a]pyridin-2-yl]-1-(cyclopropylmethyl)pyrrolo[2,3-b]pyridin-6-yl]-~{N}-(difluoromethyl)methanesulfonamide |

| Ex | Structure | Name |
| --- | --- | --- |
| 428 | 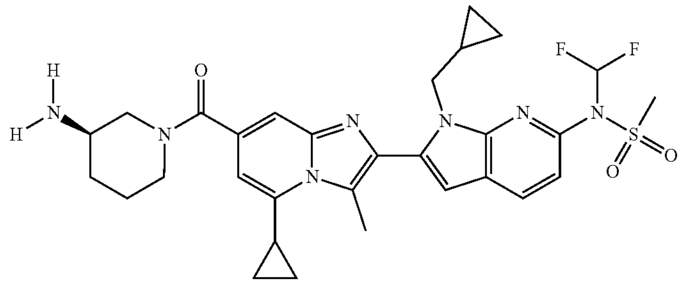 [SMILES: Cc1c(-c2cc3ccc(N(C(F)F)S(C)(=O)=O)nc3n2CC2CC2)nc2cc(C(=O)N3CCC[C@@H](N)C3)cc(C3CC3)n12] | ~{N}-[2-[7-[(3~{R})-3-aminopiperidine-1-carbonyl]-5-cyclopropyl-3-methylimidazo[1,2-a]pyridin-2-yl]-1-(cyclopropylmethyl)pyrrolo[2,3-b]pyridin-6-yl]-~{N}-(difluoromethyl)methanesulfonamide |
| 429 | 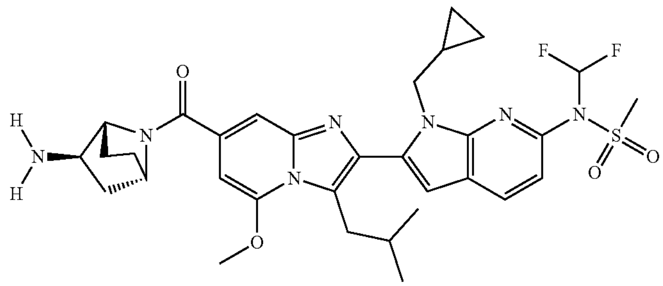 [SMILES: COc1cc(C(=O)N2[C@H]3CC[C@@H]2[C@H](N)C3)cc2nc(-c3cc4ccc(N(C(F)F)S(C)(=O)=O)nc4n3CC3CC3)c(CC(C)C)n12] | ~{N}-[2-[7-[(1~{R},2~{R},4~{S})-2-amino-7-azabicyclo[2.2.1]heptane-7-carbonyl]-5-methoxy-3-(2-methylpropyl)imidazo[1,2-a]pyridin-2-yl]-1-(cyclopropylmethyl)pyrrolo[2,3-b]pyridin-6-yl]-~{N}-(difluoromethyl)methanesulfonamide |
| 430 | 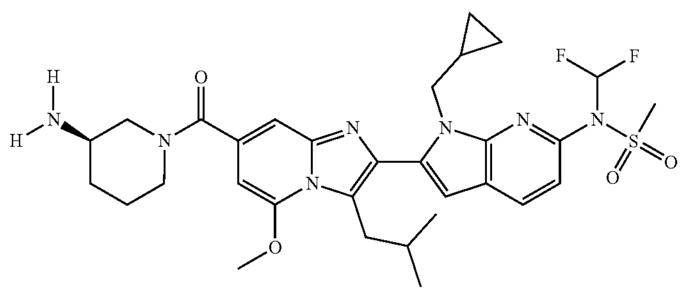 [SMILES: COc1cc(C(=O)N2CCC[C@@H](N)C2)cc2nc(-c3cc4ccc(N(C(F)F)S(C)(=O)=O)nc4n3CC3CC3)c(CC(C)C)n12] | ~{N}-[2-[7-[(3~{R})-3-aminopiperidine-1-carbonyl]-5-methoxy-3-(2-methylpropyl)imidazo[1,2-a]pyridin-2-yl]-1-(cyclopropylmethyl)pyrrolo[2,3-b]pyridin-6-yl]-~{N}-(difluoromethyl)methanesulfonamide |
| 431 | 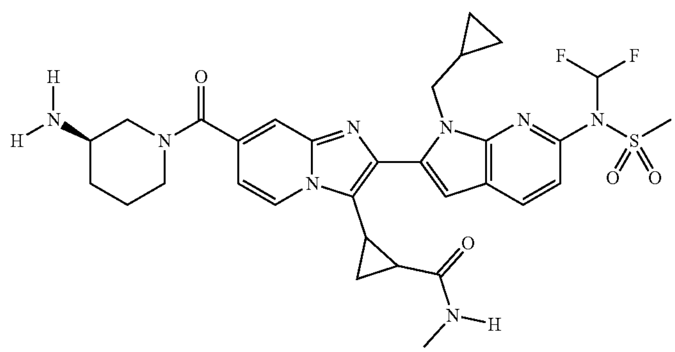 [SMILES: CNC(=O)C1CC1c1c(-c2cc3ccc(N(C(F)F)S(C)(=O)=O)nc3n2CC2CC2)nc2cc(C(=O)N3CCC[C@@H](N)C3)ccn12] | 2-[7-[(3~{R})-3-aminopiperidine-1-carbonyl]-2-[1-(cyclopropylmethyl)-6-[difluoromethyl(methylsulfonyl)amino]pyrrolo[2,3-b]pyridin-2-yl]imidazo[1,2-a]pyridin-3-yl]-~{N}-methylcyclopropane-1-carboxamide |
| 432 | 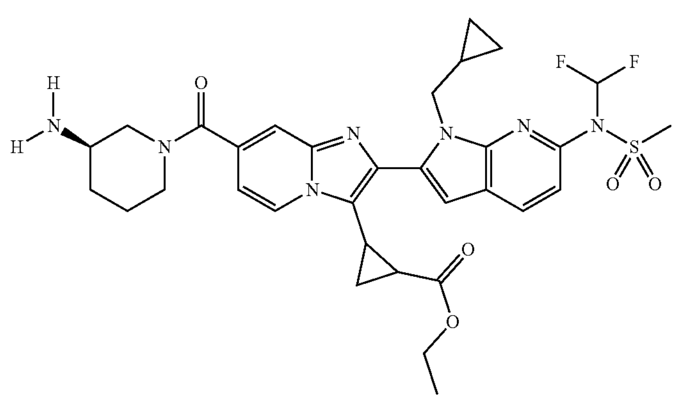 [SMILES: CCOC(=O)C1CC1c1c(-c2cc3ccc(N(C(F)F)S(C)(=O)=O)nc3n2CC2CC2)nc2cc(C(=O)N3CCC[C@@H](N)C3)ccn12] | ethyl 2-[7-[(3~{R})-3-aminopiperidine-1-carbonyl]-2-[1-(cyclopropylmethyl)-6-[difluoromethyl(methylsulfonyl)amino]pyrrolo[2,3-b]pyridin-2-yl]imidazo[1,2-a]pyridin-3-yl]cyclopropane-1-carboxylate |

| Ex | Structure | Name |
|---|---|---|
| 433 | 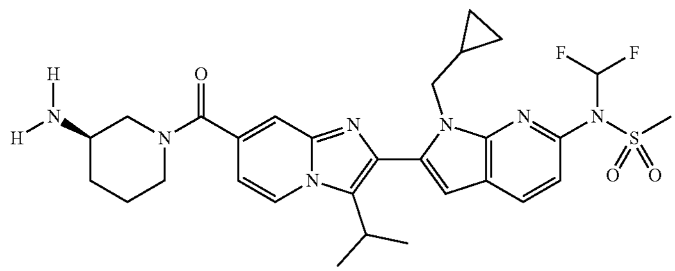 [SMILES: CC(C)c1c(-c2cc3ccc(N(C(F)F)S(C)(=O)=O)nc3n2CC2CC2)nc2cc(C(=O)N3CCC[C@@H](N)C3)ccn12] | ~{N}-[2-[7-[(3~{R})-3-aminopiperidine-1-carbonyl]-3-propan-2-ylimidazo[1,2-a]pyridin-2-yl]-1-(cyclopropylmethyl)pyrrolo[2,3-b]pyridin-6-yl]-~{N}-(difluoromethyl)methanesulfonamide |
| 434 | 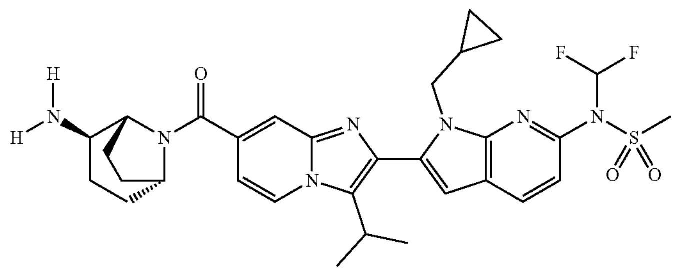 [SMILES: CC(C)c1c(-c2cc3ccc(N(C(F)F)S(C)(=O)=O)nc3n2CC2CC2)nc2cc(C(=O)N3[C@@H]4CC[C@@H](N)[C@H]3CC4)ccn12] | 2-amino-8-azabicyclo[3.2.1]octane-8-carbonyl]-3-propan-2-ylimidazo[1,2-a]pyridin-2-yl]-1-(cyclopropylmethyl)pyrrolo[2,3-b]pyridin-6-yl]-~{N}-(difluoromethyl)methanesulfonamide |
| 435 | 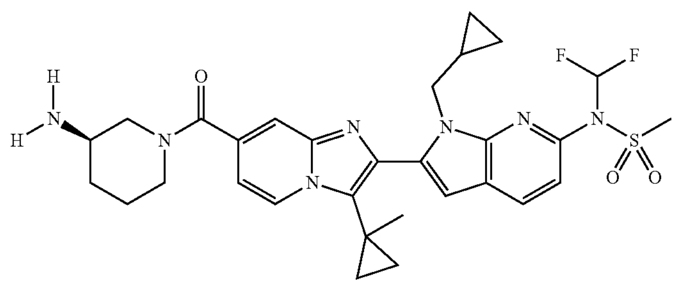 [SMILES: CC1(c2c(-c3cc4ccc(N(C(F)F)S(C)(=O)=O)nc4n3CC3CC3)nc3cc(C(=O)N4CCC[C@@H](N)C4)ccn23)CC1] | ~{N}-[2-[7-[(3~{R})-3-aminopiperidine-1-carbonyl]-3-(1-methylcyclopropyl)imidazo[1,2-a]pyridin-2-yl]-1-(cyclopropylmethyl)pyrrolo[2,3-b]pyridin-6-yl]-~{N}-(difluoromethyl)methanesulfonamide |
| 436 | 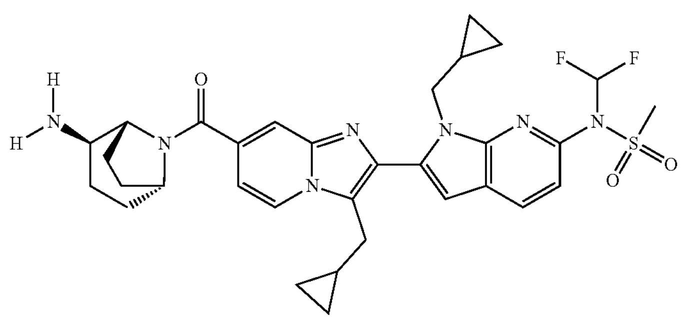 [SMILES: CS(=O)(=O)N(c1ccc2cc(-c3nc4cc(C(=O)N5[C@@H]6CC[C@@H](N)[C@H]5CC6)ccn4c3CC3CC3)n(CC3CC3)c2n1)C(F)F] | ~{N}-[2-[7-[(1~{R},2~{R},5~{R})-2-amino-8-azabicyclo[3.2.1]octane-8-carbonyl]-3-(cyclopropylmethyl)imidazo[1,2-a]pyridin-2-yl]-1-(cyclopropylmethyl)pyrrolo[2,3-b]pyridin-6-yl]-~{N}-(difluoromethyl)methanesulfonamide |
| 437 | 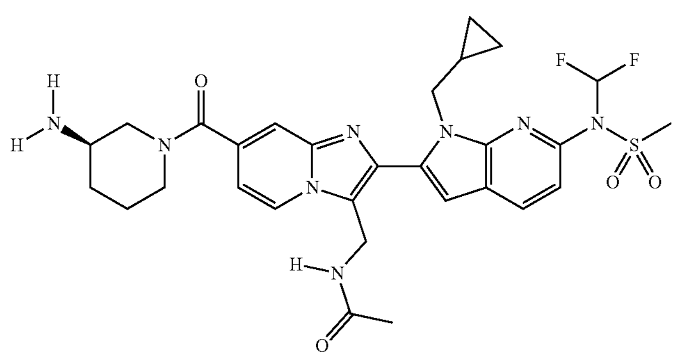 [SMILES: CC(=O)NCc1c(-c2cc3ccc(N(C(F)F)S(C)(=O)=O)nc3n2CC2CC2)nc2cc(C(=O)N3CCC[C@@H](N)C3)ccn12] | ~{N}-[[7-[(3~{R})-3-aminopiperidine-1-carbonyl]-2-[1-(cyclopropylmethyl)-6-[difluoromethyl(methylsulfonyl)amino]pyrrolo[2,3-b]pyridin-2-yl]imidazo[1,2-a]pyridin-3-yl]methyl]acetamide |

| Ex | Structure | Name |
|---|---|---|
| 438 | 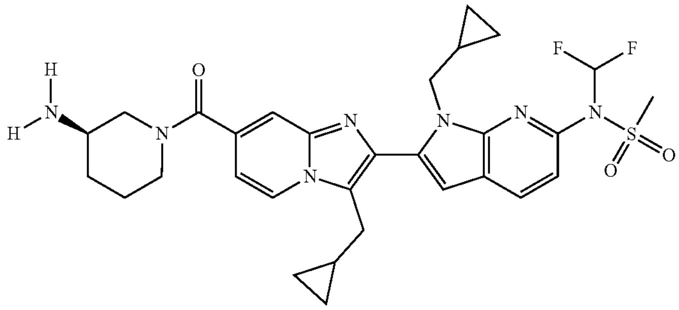 [SMILES: CS(=O)(=O)N(c1ccc2cc(-c3nc4cc(C(=O)N5CCC[C@@H](N)C5)ccn4c3CC3CC3)n(CC3CC3)c2n1)C(F)F] | ~{N}-[2-[7-[(3~{R})-3-aminopiperidine-1-carbonyl]-3-(cyclopropylmethyl) imidazo[1,2-a]pyridin-2-yl]-1-(cyclopropylmethyl)pyrrolo[2,3-b]pyridin-6-yl]-~{N}-(difluoromethyl) methanesulfonamide |
| 439 | 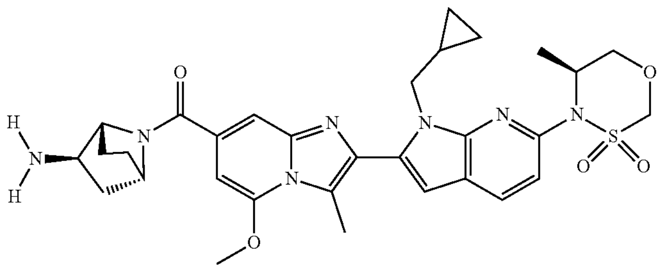 [SMILES: COc1cc(C(=O)N2[C@H]3CC[C@@H]2[C@H](N)C3)cc2nc(-c3cc4ccc(N5[C@@H](C)COCS5(=O)=O)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-[(5~{S})-5-methyl-3,3-dioxo-1,3,4-oxathiazinan-4-yl]pyrrolo[2,3-b]pyridin-2-yl]-5-methoxy-3-methylimidazo[1,2-a]pyridin-7-yl] methanone |
| 440 | 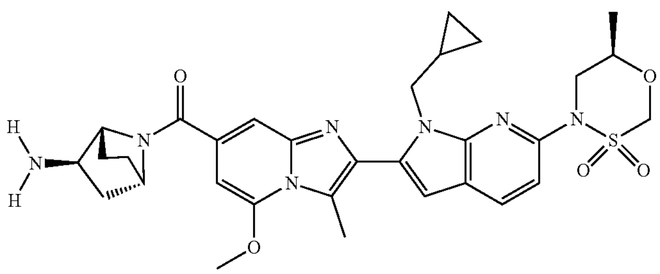 [SMILES: COc1cc(C(=O)N2[C@H]3CC[C@@H]2[C@H](N)C3)cc2nc(-c3cc4ccc(N5C[C@@H](C)OCS5(=O)=O)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-[(6~{R})-6-methyl-3,3-dioxo-1,3,4-oxathiazinan-4-yl]pyrrolo[2,3-b]pyridin-2-yl]-5-methoxy-3-methylimidazo[1,2-a]pyridin-7-yl] methanone |
| 441 | 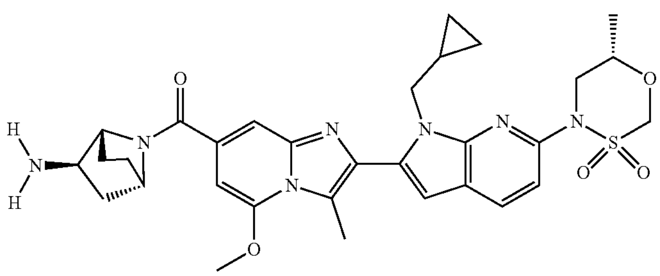 [SMILES: COc1cc(C(=O)N2[C@H]3CC[C@@H]2[C@H](N)C3)cc2nc(-c3cc4ccc(N5C[C@H](C)OCS5(=O)=O)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-[(6~{S})-6-methyl-3,3-dioxo-1,3,4-oxathiazinan-4-yl]pyrrolo[2,3-b]pyridin-2-yl]-5-methoxy-3-methylimidazo[1,2-a]pyridin-7-yl]methanone |
| 442 | 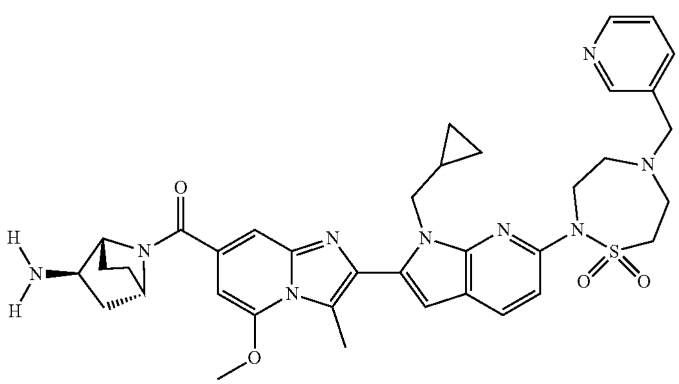 [SMILES: COc1cc(C(=O)N2[C@H]3CC[C@@H]2[C@H](N)C3)cc2nc(-c3cc4ccc(N5CCN(Cc6cccnc6)CCS5(=O)=O)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-[1,1-dioxo-5-(pyridin-3-ylmethyl)-1,2,5-thiadiazepan-2-yl]pyrrolo[2,3-b]pyridin-2-yl]-5-methoxy-3-methylimidazo[1,2-a]pyridin-7-yl] methanone |

| Ex | Structure | Name |
|---|---|---|
| 443 | 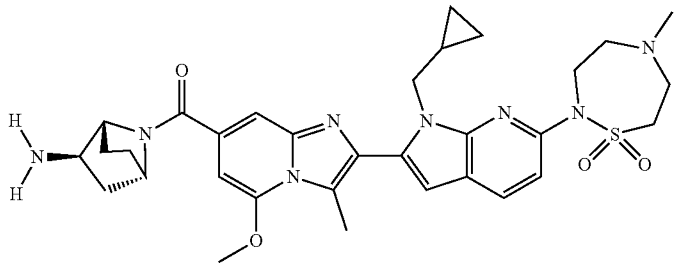 [SMILES: COc1cc(C(=O)N2[C@H]3CC[C@@H]2[C@H](N)C3)cc2nc(-c3cc4ccc(N5CCN(C)CCS5(=O)=O)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-(5-methyl-1,1-dioxo-1,2,5-thiadiazepan-2-yl)pyrrolo[2,3-b]pyridin-2-yl]-5-methoxy-3-methylimidazo[1,2-a]pyridin-7-yl]methanone |
| 444 | 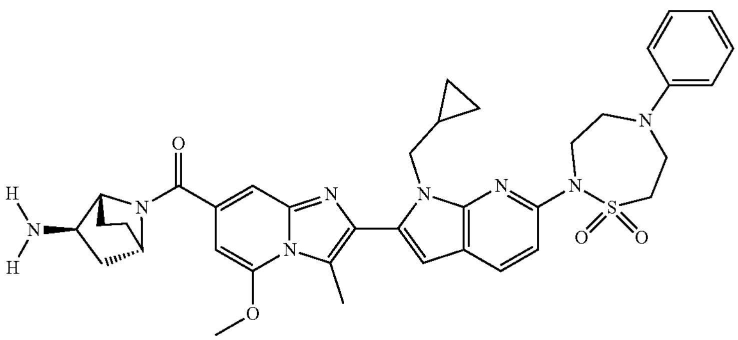 [SMILES: COc1cc(C(=O)N2[C@H]3CC[C@@H]2[C@H](N)C3)cc2nc(-c3cc4ccc(N5CCN(c6ccccc6)CCS5(=O)=O)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-(1,1-dioxo-5-phenyl-1,2,5-thiadiazepan-2-yl)pyrrolo[2,3-b]pyridin-2-yl]-5-methoxy-3-methylimidazo[1,2-a]pyridin-7-yl]methanone |
| 445 | 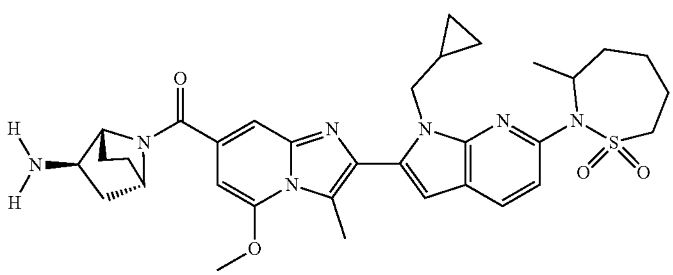 [SMILES: COc1cc(C(=O)N2[C@H]3CC[C@@H]2[C@H](N)C3)cc2nc(-c3cc4ccc(N5C(C)CCCCS5(=O)=O)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-(3-methyl-1,1-dioxothiazepan-2-yl)pyrrolo[2,3-b]pyridin-2-yl]-5-methoxy-3-methylimidazo[1,2-a]pyridin-7-yl]methanone |
| 446 | 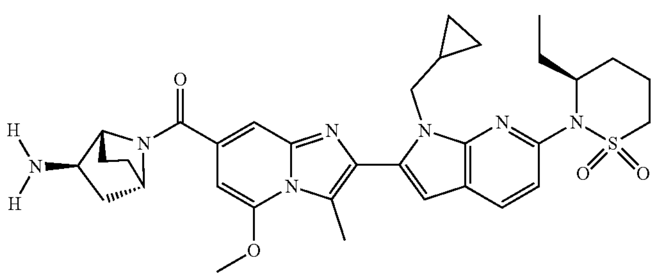 [SMILES: CC[C@H]1CCCS(=O)(=O)N1c1ccc2cc(-c3nc4cc(C(=O)N5[C@H]6CC[C@@H]5[C@H](N)C6)cc(OC)n4c3C)n(CC3CC3)c2n1] | [(1~{R},2~{R},4~{S})-2-amino-7-azabicyclo[2.2.1]heptan-7-yl]-[2-[1-(cyclopropylmethyl)-6-[(3~{S})-3-ethyl-1,1-dioxothiazinan-2-yl]pyrrolo[2,3-b]pyridin-2-yl]-5-methoxy-3-methylimidazo[1,2-a]pyridin-7-yl]methanone |
| 447 | 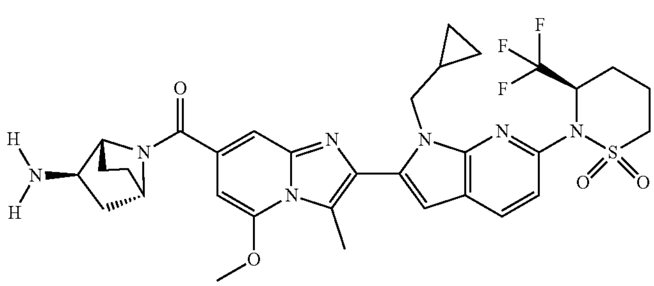 [SMILES: COc1cc(C(=O)N2[C@H]3CC[C@@H]2[C@H](N)C3)cc2nc(-c3cc4ccc(N5[C@@H](C(F)(F)F)CCCS5(=O)=O)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-[(3~{R})-1,1-dioxo-3-(trifluoromethyl)thiazinan-2-yl]pyrrolo[2,3-b]pyridin-2-yl]-5-methoxy-3-methylimidazo[1,2-a]pyridin-7-yl]methanone |

| Ex | Structure | Name |
|---|---|---|
| 448 | 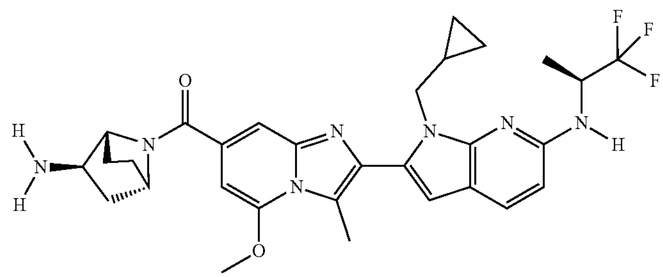 [SMILES: COc1cc(C(=O)N2[C@H]3CC[C@@H]2[C@H](N)C3)cc2nc(-c3cc4ccc(N[C@@H](C)C(F)(F)F)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-[[(2~{S})-1,1,1-trifluoropropan-2-yl]amino]pyrrolo[2,3-b]pyridin-2-yl]-5-methoxy-3-methylimidazo[1,2-a]pyridin-7-yl]methanone |
| 449 | 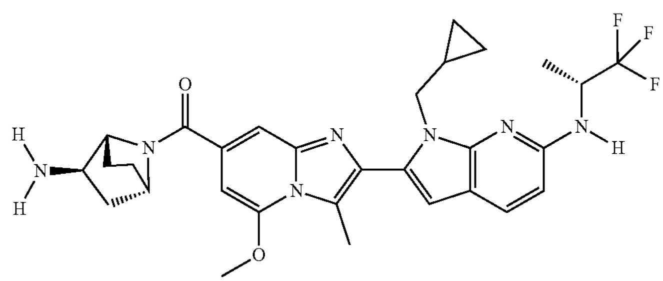 [SMILES: COc1cc(C(=O)N2[C@H]3CC[C@@H]2[C@H](N)C3)cc2nc(-c3cc4ccc(N[C@H](C)C(F)(F)F)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-[(2~{R})-1,1,1-trifluoropropan-2-yl]amino]pyrrolo[2,3-b]pyridin-2-yl]-5-methoxy-3-methylimidazo[1,2-a]pyridin-7-yl]methanone |
| 450 | 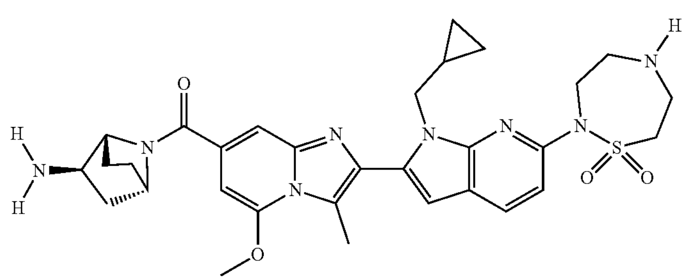 [SMILES: COc1cc(C(=O)N2[C@H]3CC[C@@H]2[C@H](N)C3)cc2nc(-c3cc4ccc(N5CCNCCS5(=O)=O)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-(1,1-dioxo-1,2,5-thiadiazepan-2-yl)pyrrolo[2,3-b]pyridin-2-yl]-5-methoxy-3-methylimidazo[1,2-a]pyridin-7-yl]methanone |
| 451 | 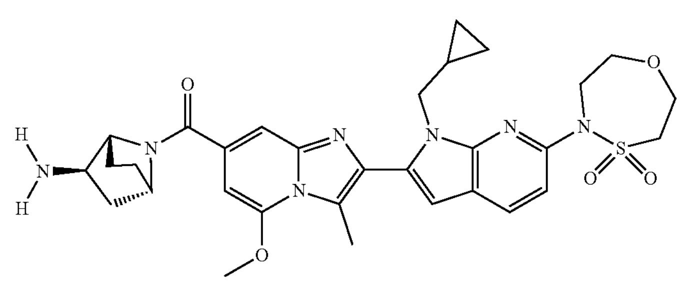 [SMILES: COc1cc(C(=O)N2[C@H]3CC[C@@H]2[C@H](N)C3)cc2nc(-c3cc4ccc(N5CCOCCS5(=O)=O)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-(4,4-dioxo-1,4,5-oxathiazepan-5-yl)pyrrolo[2,3-b]pyridin-2-yl]-5-methoxy-3-methylimidazo[1,2-a]pyridin-7-yl]methanone |
| 452 | 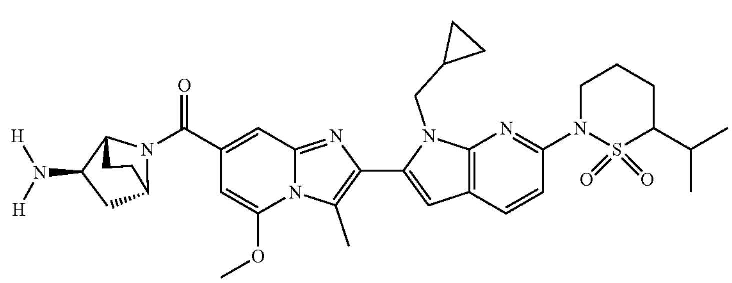 [SMILES: COc1cc(C(=O)N2[C@H]3CC[C@@H]2[C@H](N)C3)cc2nc(-c3cc4ccc(N5CCCC(C(C)C)S5(=O)=O)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-(1,1-dioxo-6-propan-2-ylthiazinan-2-yl)pyrrolo[2,3-b]pyridin-2-yl]-5-methoxy-3-methylimidazo[1,2-a]pyridin-7-yl]methanone |

-continued

| Ex | Structure | Name |
|---|---|---|
| 453 | 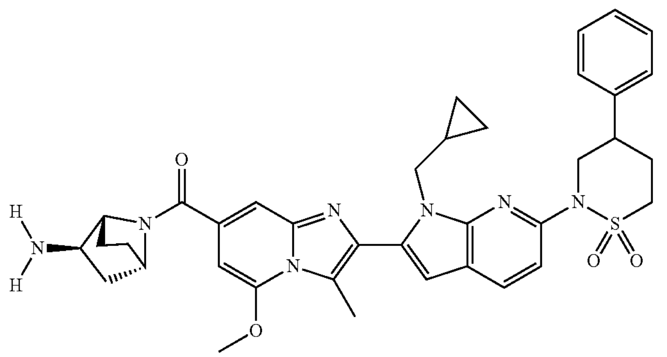 [SMILES: COc1cc(C(=O)N2[C@H]3CC[C@@H]2[C@H](N)C3)cc2nc(-c3cc4ccc(N5CC(c6ccccc6)CCS5(=O)=O)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-(1,1-dioxo-4-phenylthiazinan-2-yl)pyrrolo[2,3-b]pyridin-2-yl]-5-methoxy-3-methylimidazo[1,2-a]pyridin-7-yl]methanone |
| 454 | 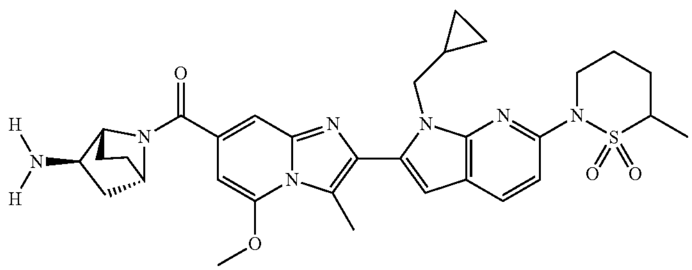 [SMILES: COc1cc(C(=O)N2[C@H]3CC[C@@H]2[C@H](N)C3)cc2nc(-c3cc4ccc(N5CCCN(C)S5(=O)=O)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-(6-methyl-1,1-dioxothiazinan-2-yl)pyrrolo[2,3-b]pyridin-2-yl]-5-methoxy-3-methylimidazo[1,2-a]pyridin-7-yl]methanone |
| 455 | 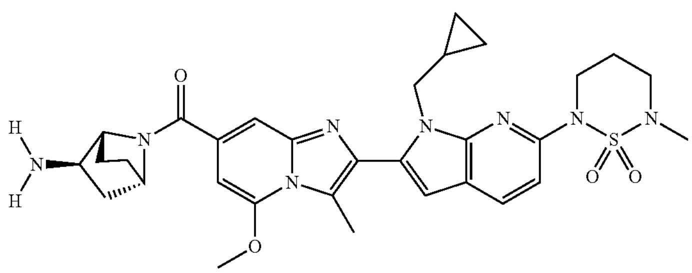 | [(1~{R},2~{R},4~{S})-2-amino-7-azabicyclo[2.2.1]heptan-7-yl]-[2-[1-(cyclopropylmethyl)-6-(6-methyl-1,1-dioxo-1,2,6-thiadiazinan-2-yl)pyrrolo[2,3-b]pyridin-2-yl]-5-methoxy-3-methylimidazo[1,2-a]pyridin-7-yl]methanone |
| 456 | 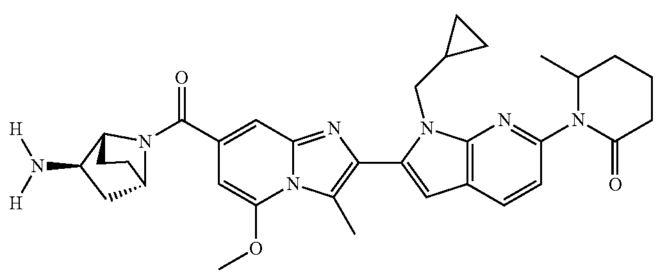 [SMILES: COc1cc(C(=O)N2[C@H]3CC[C@@H]2[C@H](N)C3)cc2nc(-c3cc4ccc(N5C(=O)CCCC5C)nc4n3CC3CC3)c(C)n12] | 1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]-6-methylpiperidin-2-one |
| 457 | 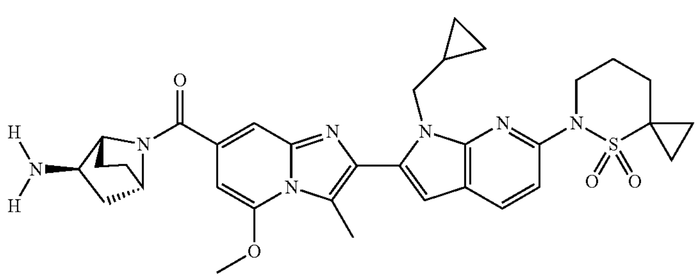 [SMILES: COc1cc(C(=O)N2[C@H]3CC[C@@H]2[C@H](N)C3)cc2nc(-c3cc4ccc(N5CCCC6(CC6)S5(=O)=O)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-(4,4-dioxo-4$l^{6}-thia-5-azaspiro[2.5]octan-5-yl)pyrrolo[2,3-b]pyridin-2-yl]-5-methoxy-3-methylimidazo[1,2-a]pyridin-7-yl]methanone |

-continued

| Ex | Structure | Name |
|---|---|---|
| 458 | 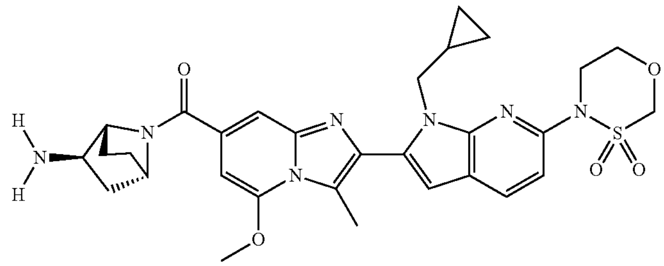 [SMILES: COc1cc(C(=O)N2[C@H]3CC[C@@H]2[C@H](N)C3)cc2nc(-c3cc4ccc(N5CCOCS5(=O)=O)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-(3,3-dioxo-1,3,4-oxathiazinan-4-yl)pyrrolo[2,3-b]pyridin-2-yl]-5-methoxy-3-methylimidazo[1,2-a]pyridin-7-yl]methanone |
| 459 | 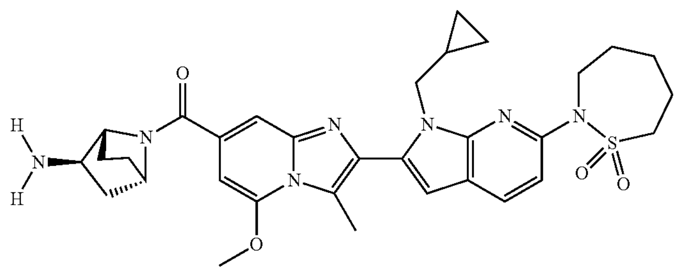 [SMILES: COc1cc(C(=O)N2[C@H]3CC[C@@H]2[C@H](N)C3)cc2nc(-c3cc4ccc(N5CCCCCS5(=O)=O)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-(1,1-dioxothiazepan-2-yl)pyrrolo[2,3-b]pyridin-2-yl]-5-methoxy-3-methylimidazo[1,2-a]pyridin-7-yl]methanone |
| 460 | 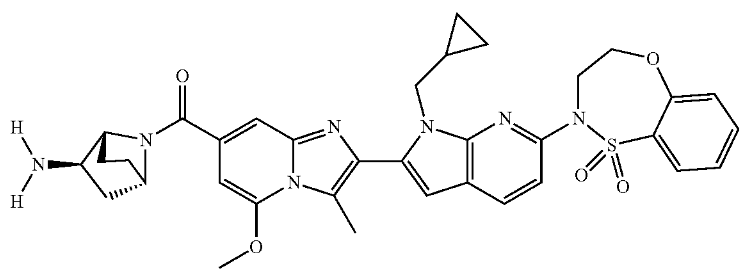 [SMILES: COc1cc(C(=O)N2[C@H]3CC[C@@H]2[C@H](N)C3)cc2nc(-c3cc4ccc(N5CCOc6ccccc6S5(=O)=O)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-(1,1-dioxo-3,4-dihydro-5,1$l^{6}$,2-benzoxathiazepin-2-yl)pyrrolo[2,3-b]pyridin-2-yl]-5-methoxy-3-methylimidazo[1,2-a]pyridin-7-yl]methanone |
| 461 | 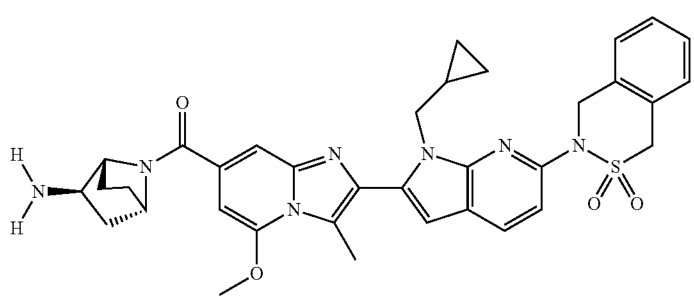 [SMILES: COc1cc(C(=O)N2[C@H]3CC[C@@H]2[C@H](N)C3)cc2nc(-c3cc4ccc(N5Cc6ccccc6CS5(=O)=O)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-(2,2-dioxo-1,4-dihydro-2$l^{6}$,3-benzothiazin-3-yl)pyrrolo[2,3-b]pyridin-2-yl]-5-methoxy-3-methylimidazo[1,2-a]pyridin-7-yl]methanone |
| 462 | 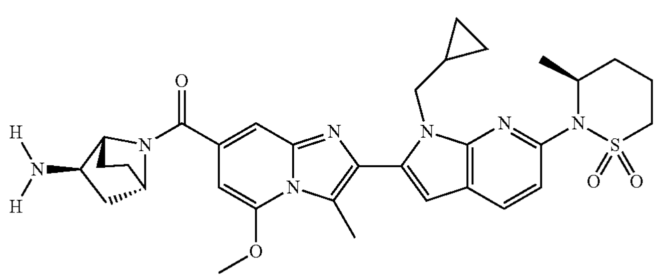 [SMILES: COc1cc(C(=O)N2[C@H]3CC[C@@H]2[C@H](N)C3)cc2nc(-c3cc4ccc(N5[C@@H](C)CCCS5(=O)=O)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-[(3~{S})-3-methyl-1,1-dioxothiazinan-2-yl]pyrrolo[2,3-b]pyridin-2-yl]-5-methoxy-3-methylimidazo[1,2-a]pyridin-7-yl]methanone |

-continued

| Ex | Structure | Name |
|---|---|---|
| 463 | 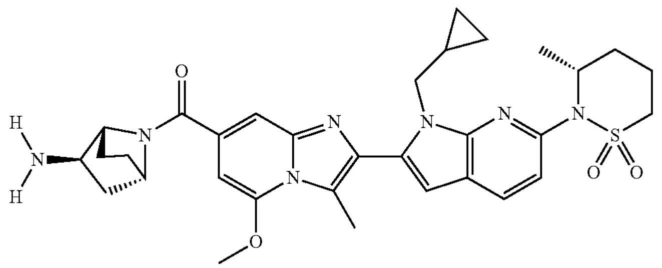 [SMILES: COc1cc(C(=O)N2[C@H]3CC[C@@H]2[C@H](N)C3)cc2nc(-c3cc4ccc(N5[C@H](C)CCCS5(=O)=O)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-[(3~{R})-3-methyl-1,1-dioxothiazinan-2-yl]pyrrolo[2,3-b]pyridin-2-yl]-5-methoxy-3-methylimidazo[1,2-a]pyridin-7-yl]methanone |
| 464 | 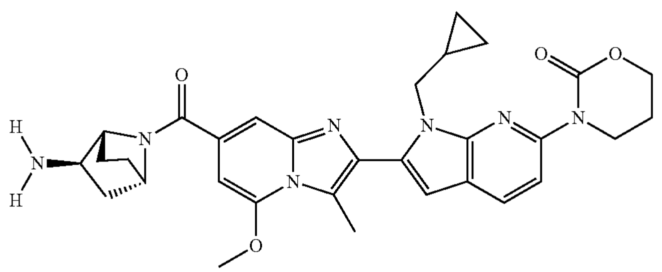 [SMILES: COc1cc(C(=O)N2[C@H]3CC[C@@H]2[C@H](N)C3)cc2nc(-c3cc4ccc(N5CCCOC5=O)nc4n3CC3CC3)c(C)n12] | 3-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]-1,3-oxazinan-2-one |
| 465 | 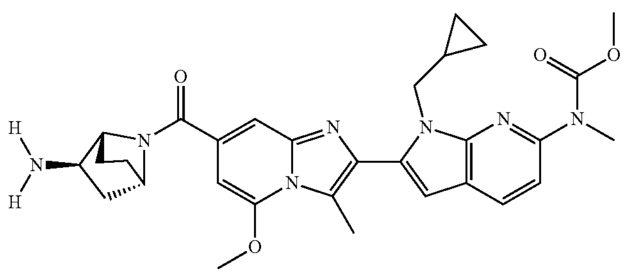 [SMILES: COC(=O)N(C)c1ccc2cc(-c3nc4cc(C(=O)N5[C@H]6CC[C@@H]5[C@H](N)C6)cc(OC)n4c3C)n(CC3CC3)c2n1] | methyl~{N}-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]-~{N}-methylcarbamate |
| 466 | 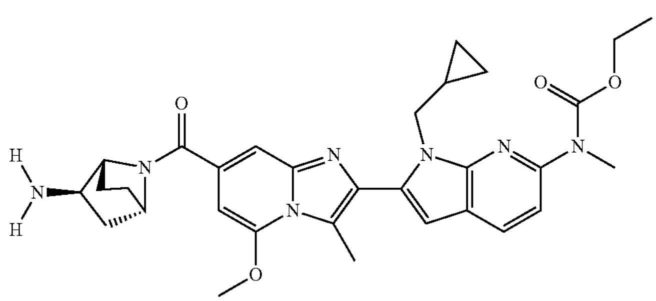 [SMILES: CCOC(=O)N(C)c1ccc2cc(-c3nc4cc(C(=O)N5[C@H]6CC[C@@H]5[C@H](N)C6)cc(OC)n4c3C)n(CC3CC3)c2n1] | ethyl~{N}-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]-~{N}-methylcarbamate |
| 467 | 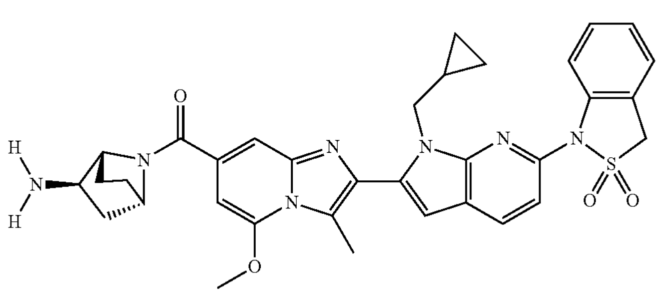 [SMILES: COc1cc(C(=O)N2[C@H]3CC[C@@H]2[C@H](N)C3)cc2nc(-c3cc4ccc(N5c6ccccc6CS5(=O)=O)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-(2,2-dioxo-3~{H}-2,1-benzothiazol-1-yl)pyrrolo[2,3-b]pyridin-2-yl]-5-methoxy-3-methylimidazo[1,2-a]pyridin-7-yl]methanone |

| Ex | Structure | Name |
|---|---|---|
| 468 | 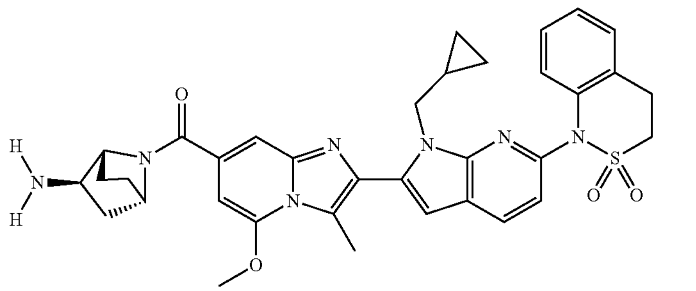 [SMILES: COc1cc(C(=O)N2[C@H]3CC[C@@H]2[C@H](N)C3)cc2nc(-c3cc4ccc(N5c6ccccc6CCS5(=O)=O)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-(2,2-dioxo-3,4-dihydro-2$I^{6}$,1-benzothiazin-1-yl)pyrrolo[2,3-b]pyridin-2-yl]-5-methoxy-3-methylimidazo[1,2-a]pyridin-7-yl]methanone |
| 469 | 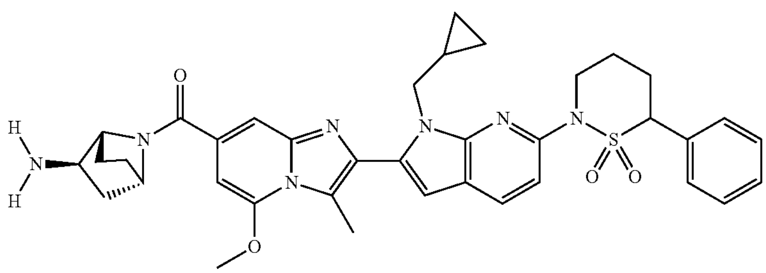 [SMILES: COc1cc(C(=O)N2[C@H]3CC[C@@H]2[C@H](N)C3)cc2nc(-c3cc4ccc(N5CCCC(c6ccccc6)S5(=O)=O)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-(1,1-dioxo-6-phenylthiazinan-2-yl)pyrrolo[2,3-b]pyridin-2-yl]-5-methoxy-3-methylimidazo[1,2-a]pyridin-7-yl]methanone |
| 470 | 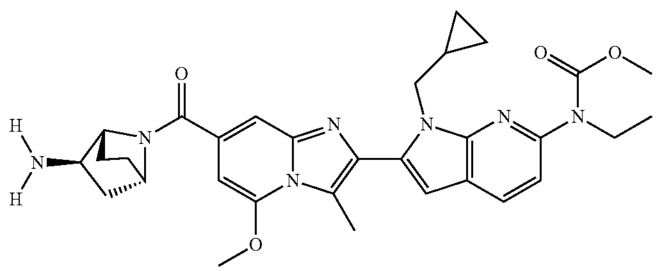 [SMILES: CCN(C(=O)OC)c1ccc2cc(-c3nc4cc(C(=O)N5[C@H]6CC[C@@H]5[C@H](N)C6)cc(OC)n4c3C)n(CC3CC3)c2n1] | methyl~{N}-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]-~{N}-ethylcarbamate |
| 471 | 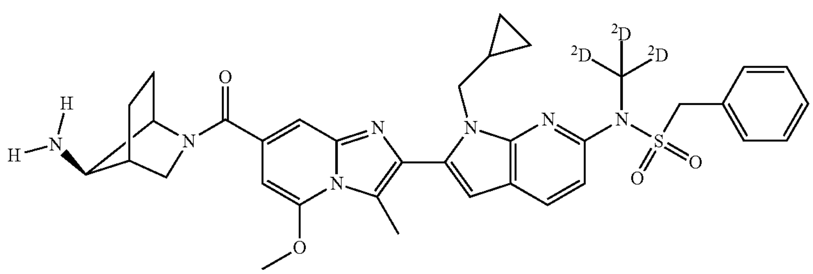 [SMILES: [2H]C([2H])([2H])N(c1ccc2cc(-c3nc4cc(C(=O)N5CC6CCC5[C@@H]6N)cc(OC)n4c3C)n(CC3CC3)c2n1)S(=O)(=O)Cc1ccccc1] | N-[2-[7-[(1R,4R,7R)-7-amino-2-azabicyclo[2.2.1]heptane-2-carbonyl]-5-methoxy-3-methyl-imidazo[1,2-a]pyridin-2-yl]-1-(cyclopropylmethyl)pyrrolo[2,3-b]pyridin-6-yl]-1-phenyl-N-(trideuteriomethyl)methanesulfonamide |
| 472 | 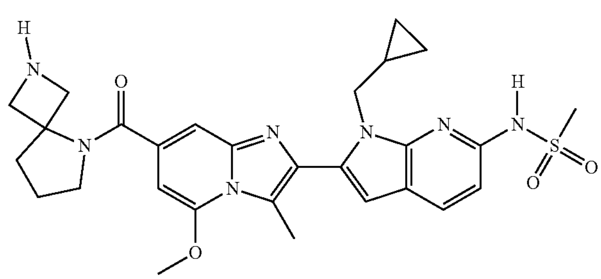 [SMILES: COc1cc(C(=O)N2CCCC23CNC3)cc2nc(-c3cc4ccc(NS(C)(=O)=O)nc4n3CC3CC3)c(C)n12] | ~{N}-[1-(cyclopropylmethyl)-2-[7-(2,5-diazaspiro[3.4]octane-5-carbonyl)-5-methoxy-3-methylimidazo[1,2-a]pyridin-2-yl]pyrrolo[2,3-b]pyridin-6-yl]methanesulfonamide |

-continued

| Ex | Structure | Name |
|---|---|---|
| 473 | 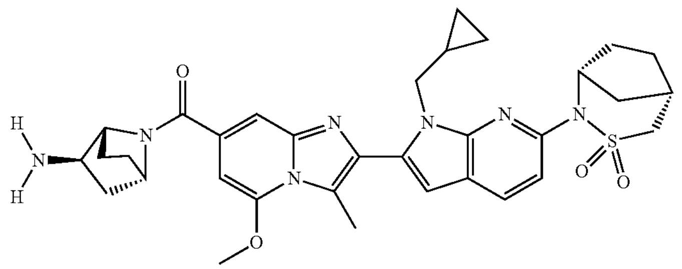 [SMILES: COc1cc(C(=O)N2[C@H]3CC[C@@H]2[C@H](N)C3)cc2nc(-c3cc4ccc(N5[C@@H]6CC[C@@H](C6)CS5(=O)=O)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-[(1~{R},5~{S})-3,3-dioxo-3$l^{6}-thia-2-azabicyclo[3.2.1]octan-2-yl]pyrrolo[2,3-b]pyridin-2-yl]-5-methoxy-3-methylimidazo[1,2-a]pyridin-7-yl]methanone |
| 474 | 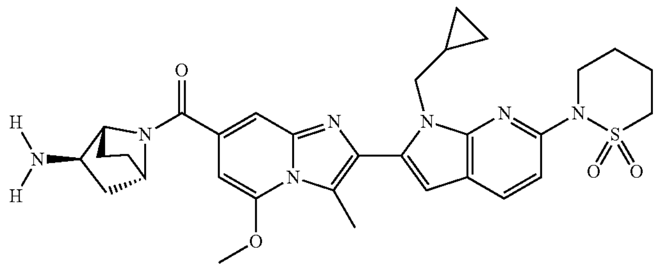 [SMILES: COc1cc(C(=O)N2[C@H]3CC[C@@H]2[C@H](N)C3)cc2nc(-c3cc4ccc(N5CCCCS5(=O)=O)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-(1,1-dioxothiazinan-2-yl)pyrrolo[2,3-b]pyridin-2-yl]-5-methoxy-3-methylimidazo[1,2-a]pyridin-7-yl]methanone |
| 475 | 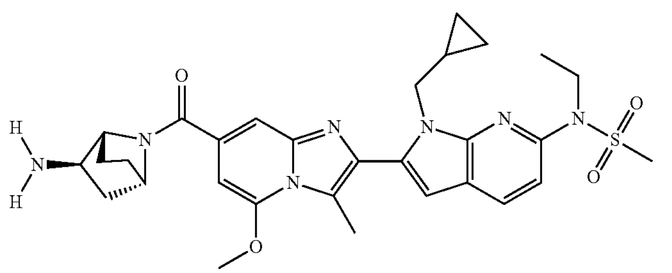 [SMILES: CCN(c1ccc2cc(-c3nc4cc(C(=O)N5[C@H]6CC[C@@H]5[C@H](N)C6)cc(OC)n4c3C)n(CC3CC3)c2n1)S(C)(=O)=O] | ~{N}-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]-~{N}-ethylmethanesulfonamide |
| 476 | 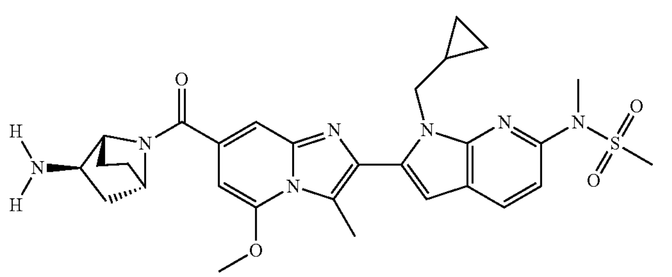 [SMILES: COc1cc(C(=O)N2[C@H]3CC[C@@H]2[C@H](N)C3)cc2nc(-c3cc4ccc(N(C)S(C)(=O)=O)nc4n3CC3CC3)c(C)n12] | ~{N}-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]-~{N}-methylmethanesulfonamide |
| 477 | 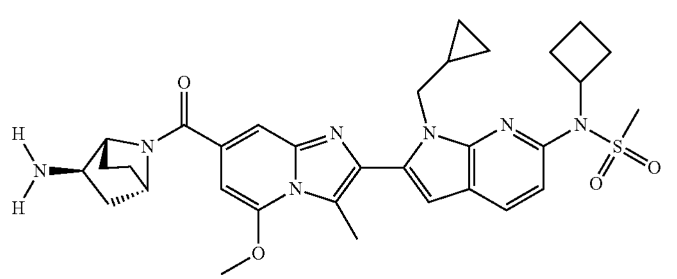 [SMILES: COc1cc(C(=O)N2[C@H]3CC[C@@H]2[C@H](N)C3)cc2nc(-c3cc4ccc(N(C5CCC5)S(C)(=O)=O)nc4n3CC3CC3)c(C)n12] | ~{N}-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]-~{N}-cyclobutylmethanesulfonamide |

-continued

| Ex | Structure | Name |
|---|---|---|
| 478 | 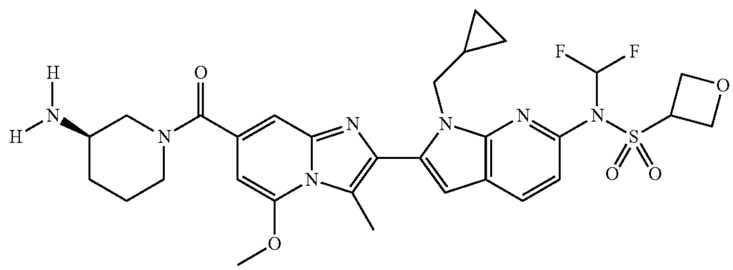 [SMILES: COc1cc(C(=O)N2CCC[C@@H](N)C2)cc2nc(-c3cc4ccc(N(C(F)F)S(=O)(=O)C5COC5)nc4n3CC3CC3)c(C)n12] | ~{N}-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]-~{N}-(difluoromethyl)oxetane-3-sulfonamide |
| 479 | 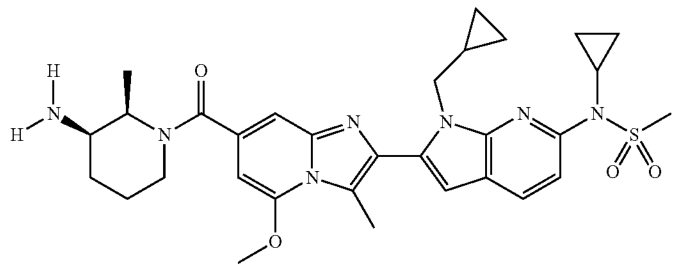 [SMILES: COc1cc(C(=O)N2CCC[C@@H](N)[C@H]2C)cc2nc(-c3cc4ccc(N(C5CC5)S(C)(=O)=O)nc4n3CC3CC3)c(C)n12] | ~{N}-[2-[7-[(2~{R},3~{R})-3-amino-2-methylpiperidine-1-carbonyl]-5-methoxy-3-methylimidazo[1,2-a]pyridin-2-yl]-1-(cyclopropylmethyl)pyrrolo[2,3-b]pyridin-6-yl]-~{N}-cyclopropylmethane-sulfonamide |
| 480 | 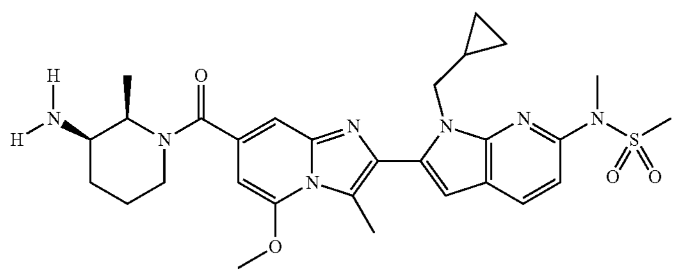 [SMILES: COc1cc(C(=O)N2CCC[C@@H](N)[C@H]2C)cc2nc(-c3cc4ccc(N(C)S(C)(=O)=O)nc4n3CC3CC3)c(C)n12] | ~{N}-[2-[7-[(2~{R},3~{R})-3-amino-2-methylpiperidine-1-carbonyl]-5-methoxy-3-methylimidazo[1,2-a]pyridin-2-yl]-1-(cyclopropylmethyl)pyrrolo[2,3-b]pyridin-6-yl]-~{N}-methylmethanesulfonamide |
| 481 | 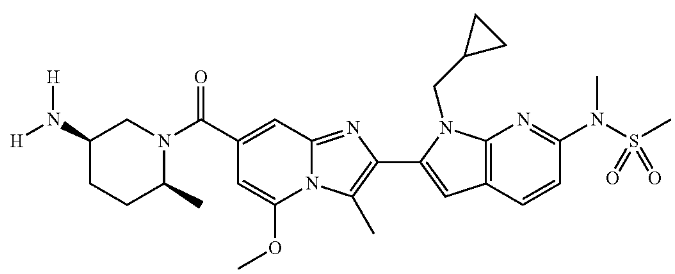 [SMILES: COc1cc(C(=O)N2C[C@H](N)CC[C@@H]2C)cc2nc(-c3cc4ccc(N(C)S(C)(=O)=O)nc4n3CC3CC3)c(C)n12] | ~{N}-[2-[7-[(2~{S},5~{R})-5-amino-2-methylpiperidine-1-carbonyl]-5-methoxy-3-methylimidazo[1,2-a]pyridin-2-yl]-1-(cyclopropylmethyl)pyrrolo[2,3-b]pyridin-6-yl]-~{N}-methylmethanesulfonamide |
| 482 | 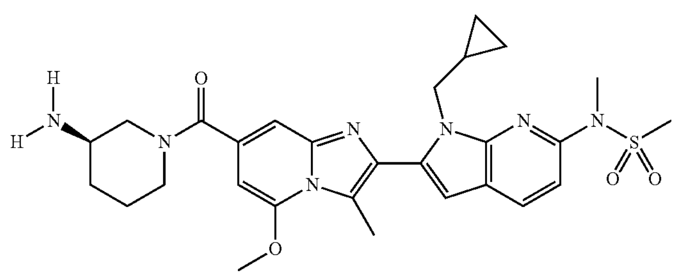 [SMILES: COc1cc(C(=O)N2CCC[C@@H](N)C2)cc2nc(-c3cc4ccc(N(C)S(C)(=O)=O)nc4n3CC3CC3)c(C)n12] | ~{N}-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]-~{N}-methylmethanesulfonamide |

-continued

| Ex | Structure | Name |
|---|---|---|
| 483 | 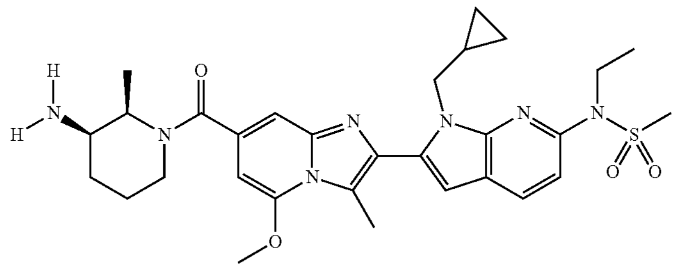 [SMILES: CCN(c1ccc2cc(-c3nc4cc(C(=O)N5CCC[C@@H](N)[C@H]5C)cc(OC)n4c3C)n(CC3CC3)c2n1)S(C)(=O)=O] | ~{N}-[2-[7-[(2~{R},3~{R})-3-amino-2-methylpiperidine-1-carbonyl]-5-methoxy-3-methylimidazo[1,2-a]pyridin-2-yl]-1-(cyclopropylmethyl)pyrrolo[2,3-b]pyridin-6-yl]-~{N}-ethylmethanesulfonamide |
| 484 | 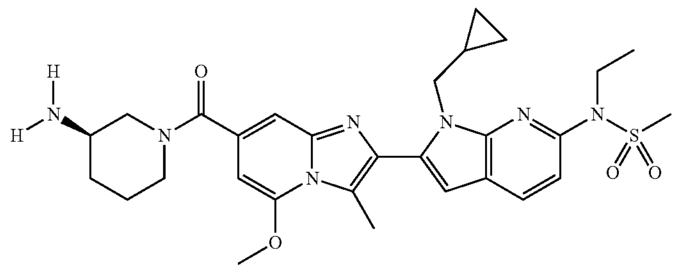 [SMILES: CCN(c1ccc2cc(-c3nc4cc(C(=O)N5CCC[C@@H](N)C5)cc(OC)n4c3C)n(CC3CC3)c2n1)S(C)(=O)=O] | ~{N}-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]-~{N}-ethylmethanesulfonamide |
| 485 | 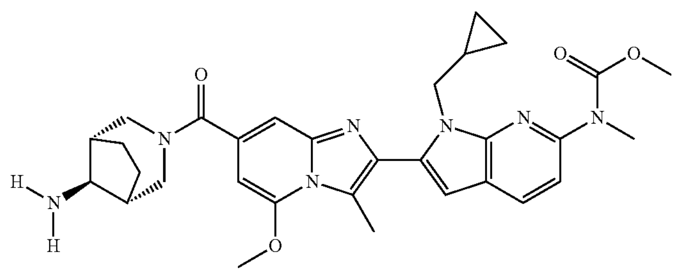 [SMILES: COC(=O)N(C)c1ccc2cc(-c3nc4cc(C(=O)N5C[C@H]6CC[C@@H](C5)[C@@H]6N)cc(OC)n4c3C)n(CC3CC3)c2n1] | methyl~{N}-[2-[7-[(1~{S},5~{R})-8-amino-3-azabicyclo[3.2.1]octane-3-carbonyl]-5-methoxy-3-methylimidazo[1,2-a]pyridin-2-yl]-1-(cyclopropylmethyl)pyrrolo[2,3-b]pyridin-6-yl]-~{N}-methylcarbamate |
| 486 | 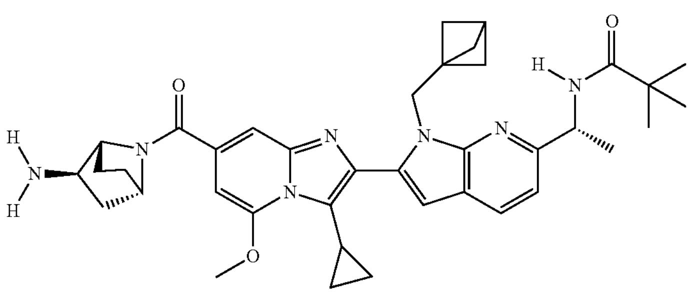 [SMILES: COc1cc(C(=O)N2[C@H]3CC[C@@H]2[C@H](N)C3)cc2nc(-c3cc4ccc([C@@H](C)NC(=O)C(C)(C)C)nc4n3CC34CC(C3)C4)c(C3CC3)n12] | ~{N}-[(1~{R})-1-[2-[7-[(1~{R},2~{R},4~{S})-2-amino-7-azabicyclo[2.2.1]heptane-7-carbonyl]-3-cyclopropyl-5-methoxyimidazo[1,2-a]pyridin-2-yl]-1-(1-bicyclo[1.1.1]pentanylmethyl)pyrrolo[2,3-b]pyridin-6-yl]ethyl]-2,2-dimethylpropanamide |
| 487 | 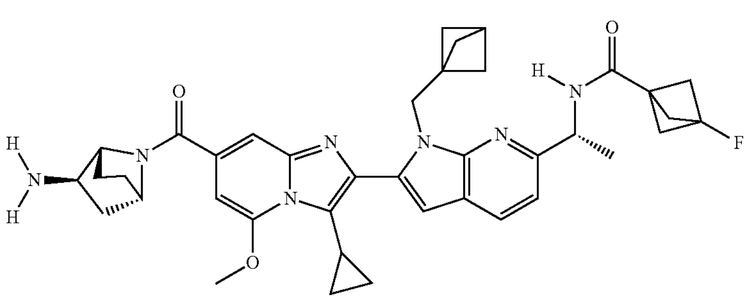 [SMILES: COc1cc(C(=O)N2[C@H]3CC[C@@H]2[C@H](N)C3)cc2nc(-c3cc4ccc([C@@H](C)NC(=O)C56CC(F)(C5)C6)nc4n3CC34CC(C3)C4)c(C3CC3)n12] | ~{N}-[(1~{R})-1-[2-[7-[(1~{R},2~{R},4~{S})-2-amino-7-azabicyclo[2.2.1]heptane-7-carbonyl]-3-cyclopropyl-5-methoxyimidazo[1,2-a]pyridin-2-yl]-1-(1-bicyclo[1.1.1]pentanylmethyl)pyrrolo[2,3-b]pyridin-6-yl]ethyl]-3-fluorobicyclo[1.1.1]pentane-1-carboxamide |

-continued

| Ex | Structure | Name |
|---|---|---|
| 488 | 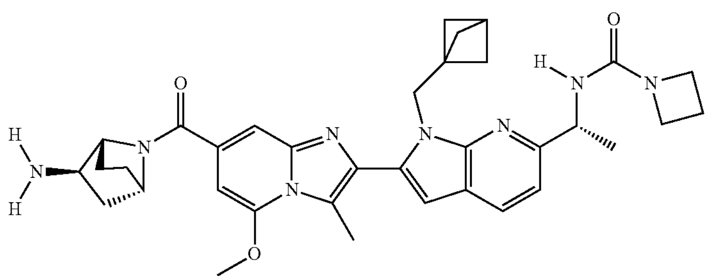 [SMILES: COc1cc(C(=O)N2[C@H]3CC[C@@H]2[C@H](N)C3)cc2nc(-c3cc4ccc([C@@H](C)NC(=O)N5CCC5)nc4n3CC34CC(C3)C4)c(C)n12] | [(1~{R},2~{R},4~{S})-2-amino-7-azabicyclo[2.2.1]heptane-7-carbonyl]-5-methoxy-3-methylimidazo[1,2-a]pyridin-2-yl]-1-(1-bicyclo[1.1.1]pentanylmethyl)pyrrolo[2,3-b]pyridin-6-yl]ethyl]azetidine-1-carboxamide |
| 489 | 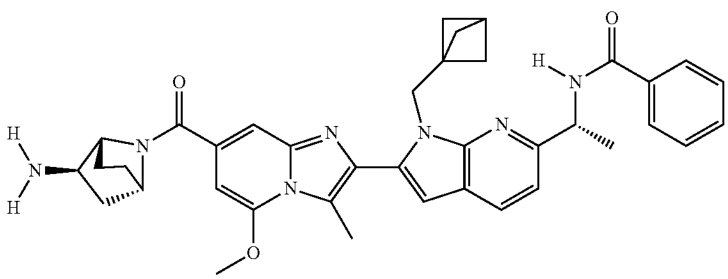 [SMILES: COc1cc(C(=O)N2[C@H]3CC[C@@H]2[C@H](N)C3)cc2nc(-c3cc4ccc([C@@H](C)NC(=O)c5ccccc5)nc4n3CC34CC(C3)C4)c(C)n12] | ~{N}-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(1-bicyclo[1.1.1]pentanylmethyl)pyrrolo[2,3-b]pyridin-6-yl]ethyl]benzamide |
| 490 | 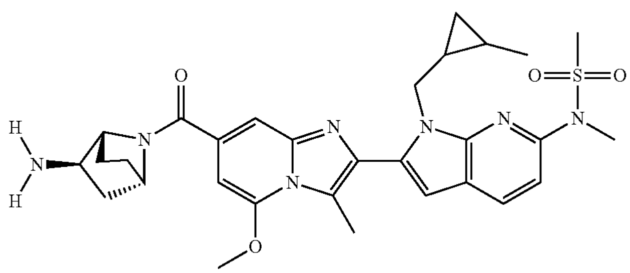 [SMILES: COc1cc(C(=O)N2[C@H]3CC[C@@H]2[C@H](N)C3)cc2nc(-c3cc4ccc(N(C)S(C)(=O)=O)nc4n3CC3CC3C)c(C)n12] | ~{N}-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-[(2-methylcyclopropyl)methyl]pyrrolo[2,3-b]pyridin-6-yl]-~{N}-methylmethanesulfonamide |
| 491 | 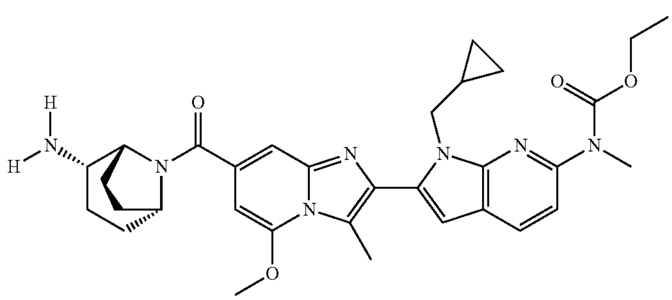 | ethyl~{N}-[2-[7-[(1~{R},2~{S},5~{R})-2-amino-8-azabicyclo[3.2.1]octane-8-carbonyl]-5-methoxy-3-methylimidazo[1,2-a]pyridin-2-yl]-1-(cyclopropylmethyl)pyrrolo[2,3-b]pyridin-6-yl]-~{N}-methylcarbamate |
| 492 | 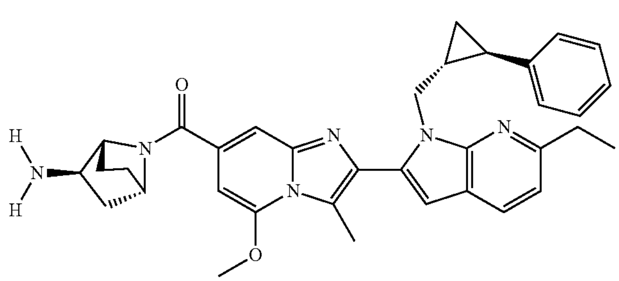 [SMILES: CCc1ccc2cc(-c3nc4cc(C(=O)N5[C@H]6CC[C@@H]5[C@H](N)C6)cc(OC)n4c3C)n(C[C@@H]3C[C@H]3c3ccccc3)c2n1] | [(1~{R},2~{R},4~{S})-2-amino-7-azabicyclo[2.2.1]heptan-7-yl]-[2-[6-ethyl-1-[(1~{R},2~{R})-2-phenylcyclopropyl]methyl]pyrrolo[2,3-b]pyridin-2-yl]-5-methoxy-3-methylimidazo[1,2-a]pyridin-7-yl]methanone |

-continued

| Ex | Structure | Name |
|---|---|---|
| 493 | 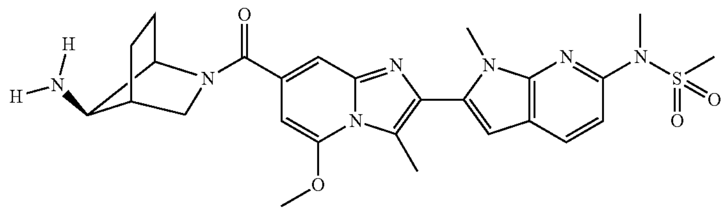 [SMILES: COc1cc(C(=O)N2CC3CCC2[C@@H]3N)cc2nc(-c3cc4ccc(N(C)S(C)(=O)=O)nc4n3C)c(C)n12] | N-[2-[7-[(1R,4R, 7R)-7-amino-2-azabicyclo[2.2.1]heptane-2-carbonyl]-5-methoxy-3-methyl-imidazo[1,2-a]pyridin-2-yl]-1-methyl-pyrrolo[2,3-b]pyridin-6-yl]-N-methyl-methanesulfonamide |
| 494 | 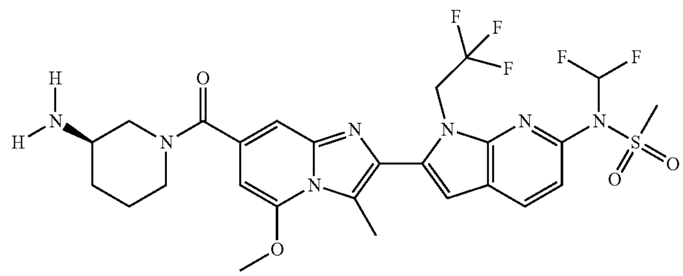 [SMILES: COc1cc(C(=O)N2CCC[C@@H](N)C2)cc2nc(-c3cc4ccc(N(C(F)F)S(C)(=O)=O)nc4n3CC(F)(F)F)c(C)n12] | ~{N}-[2-[7-[(3~{R})-3-aminopiperidine-1-carbonyl]-5-methoxy-3-methylimidazo[1,2-a]pyridin-2-yl]-1-(2,2,2-trifluoroethyl)pyrrolo[2,3-b]pyridin-6-yl]-~{N}-(difluoromethyl)methanesulfonamide |
| 495 | 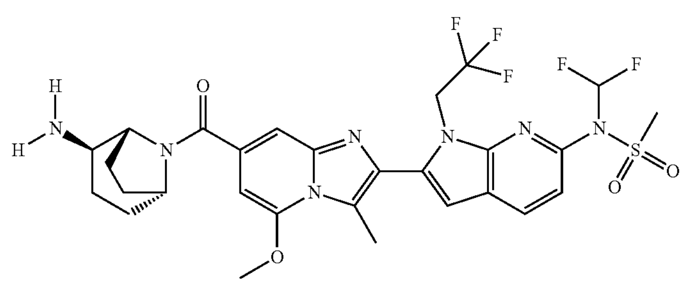 [SMILES: COc1cc(C(=O)N2[C@@H]3CC[C@@H](N)[C@H]2CC3)cc2nc(-c3cc4ccc(N(C(F)F)S(C)(=O)=O)nc4n3CC(F)(F)F)c(C)n12] | ~{N}-[2-[7-[(1~{R},2~{R},5~{R})-2-amino-8-azabicyclo[3.2.1]octane-8-carbonyl]-5-methoxy-3-methylimidazo[1,2-a]pyridin-2-yl]-1-(2,2,2-trifluoroethyl)pyrrolo[2,3-b]pyridin-6-yl]-~{N}-(difluoromethyl)methanesulfonamide |
| 496 | 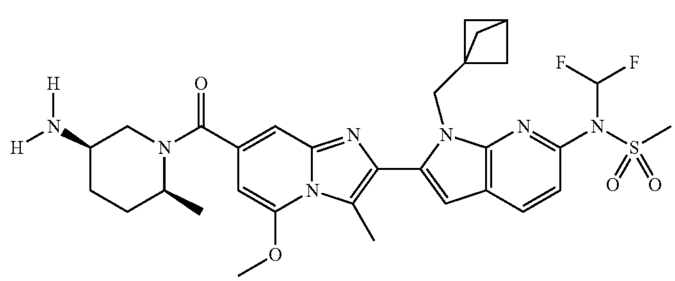 [SMILES: COc1cc(C(=O)N2C[C@H](N)CC[C@@H]2C)cc2nc(-c3cc4ccc(N(C(F)F)S(C)(=O)=O)nc4n3CC34CC(C3)C4)c(C)n12] | ~{N}-[2-[7-[(2~{S},5~{R})-5-amino-2-methylpiperidine-1-carbonyl]-5-methoxy-3-methylimidazo[1,2-a]pyridin-2-yl]-1-(1-bicyclo[1.1.1]pentanylmethyl)pyrrolo[2,3-b]pyridin-6-yl]-~{N}-(difluoromethyl)methanesulfonamide |
| 497 | 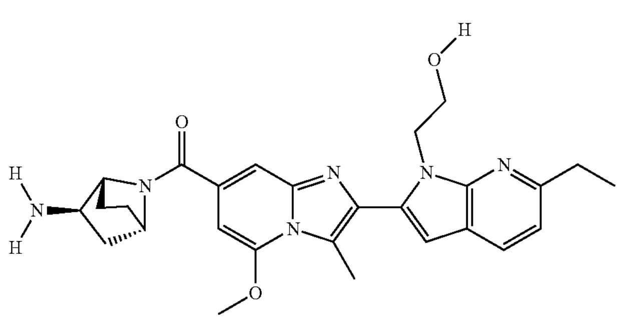 [SMILES: CCc1ccc2cc(-c3nc4cc(C(=O)N5[C@H]6CC[C@@H]5[C@H](N)C6)cc(OC)n4c3C)n(CCO)c2n1] | [(1~{R},2~{R},4~{S})-2-amino-7-azabicyclo[2.2.1]heptan-7-yl]-[2-[6-ethyl-1-(2-hydroxyethyl)pyrrolo[2,3-b]pyridin-2-yl]-5-methoxy-3-methylimidazo[1,2-a]pyridin-7-yl]methanone |

| Ex | Structure | Name |
|---|---|---|
| 498 | 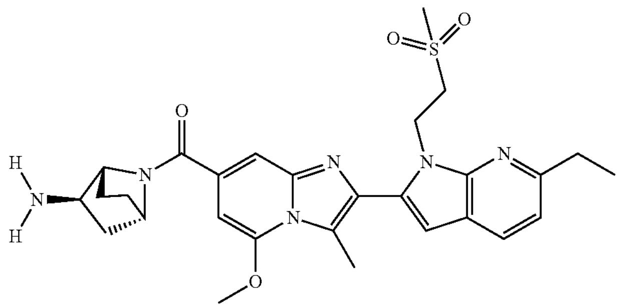 [SMILES: CCc1ccc2cc(-c3nc4cc(C(=O)N5[C@H]6CC[C@@H]5[C@H](N)C6)cc(OC)n4c3C)n(CCS(C)(=O)=O)c2n1] | [(1~{R},2~{R},4~{S})-2-amino-7-azabicyclo[2.2.1]heptan-7-yl]-[2-[6-ethyl-1-(2-methylsulfonylethyl)pyrrolo[2,3-b]pyridin-2-yl]-5-methoxy-3-methylimidazo[1,2-a]pyridin-7-yl]methanone |
| 499 | 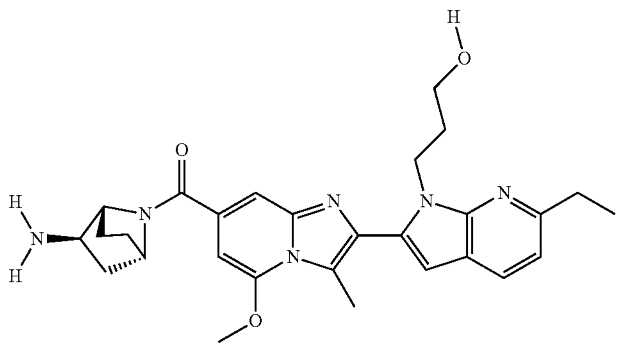 [SMILES: CCc1ccc2cc(-c3nc4cc(C(=O)N5[C@H]6CC[C@@H]5[C@H](N)C6)cc(OC)n4c3C)n(CCCO)c2n1] | [(1~{R},2~{R},4~{S})-2-amino-7-azabicyclo[2.2.1]heptan-7-yl]-[2-[6-ethyl-1-(3-hydroxypropyl)pyrrolo[2,3-b]pyridin-2-yl]-5-methoxy-3-methylimidazo[1,2-a]pyridin-7-yl]methanone |
| 500 | 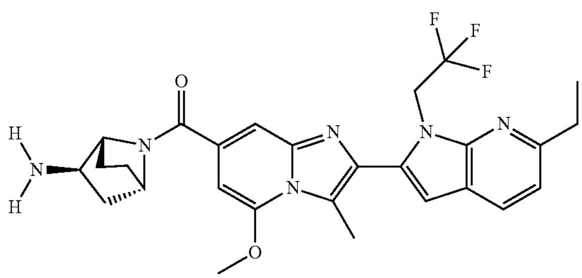 [SMILES: CCc1ccc2cc(-c3nc4cc(C(=O)N5[C@H]6CC[C@@H]5[C@H](N)C6)cc(OC)n4c3C)n(CC(F)(F)F)c2n1] | [(1~{R},2~{R},4~{S})-2-amino-7-azabicyclo[2.2.1]heptan-7-yl]-[2-[1-(2,2-difluoropropyl)-6-ethylpyrrolo[2,3-b]pyridin-2-yl]-5-methoxy-3-methylimidazo[1,2-a]pyridin-7-yl]methanone |
| 501 | 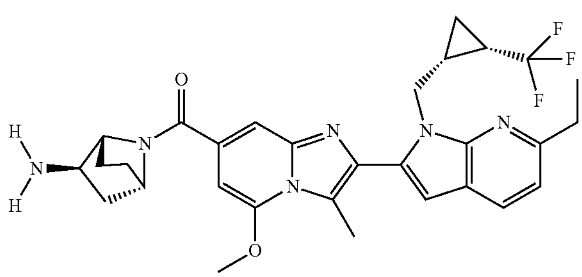 [SMILES: CCc1ccc2cc(-c3nc4cc(C(=O)N5[C@H]6CC[C@@H]5[C@H](N)C6)cc(OC)n4c3C)n(C[C@@H]3C[C@@H]3C(F)(F)F)c2n1] | [(1~{R},2~{R},4~{S})-2-amino-7-azabicyclo[2.2.1]heptan-7-yl]-[2-[6-ethyl-1-[[(1~{R},2~{S})-2-(trifluoromethyl)cyclopropyl]methyl]pyrrolo[2,3-b]pyridin-2-yl]-5-methoxy-3-methylimidazo[1,2-a]pyridin-7-yl]methanone |
| 502 | 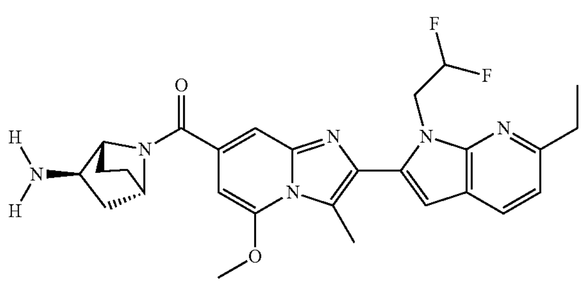 [SMILES: CCc1ccc2cc(-c3nc4cc(C(=O)N5[C@H]6CC[C@@H]5[C@H](N)C6)cc(OC)n4c3C)n(CC(F)F)c2n1] | [(1~{R},2~{R},4~{S})-2-amino-7-azabicyclo[2.2.1]heptan-7-yl]-[2-[1-(2,2-difluoroethyl)-6-ethylpyrrolo[2,3-b]pyridin-2-yl]-5-methoxy-3-methylimidazo[1,2-a]pyridin-7-yl]methanone |

| Ex | Structure | Name |
|---|---|---|
| 503 | 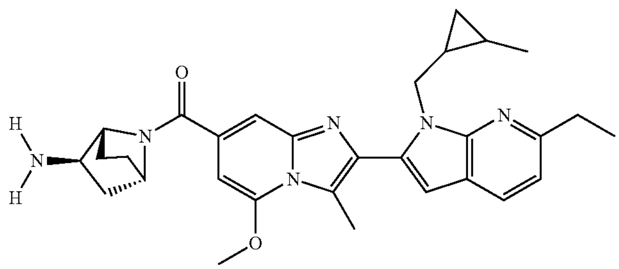 [SMILES: CCc1ccc2cc(-c3nc4cc(C(=O)N5[C@H]6CC[C@@H]5[C@H](N)C6)cc(OC)n4c3C)n(CC3CC3C)c2n1] | [(1~{R},2~{R},4~{S})-2-amino-7-azabicyclo[2.2.1]heptan-7-yl]-[2-[6-ethyl-1-[(2-methylcyclopropyl)methyl]pyrrolo[2,3-b]pyridin-2-yl]-5-methoxy-3-methylimidazo[1,2-a]pyridin-7-yl]methanone |
| 504 | 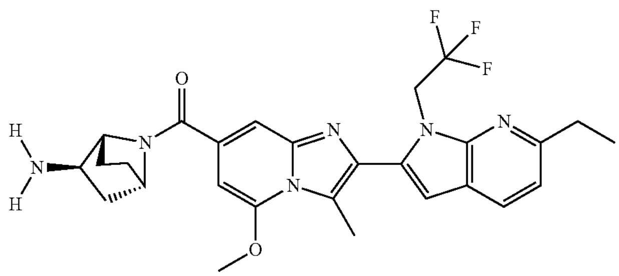 [SMILES: CCc1ccc2cc(-c3nc4cc(C(=O)N5[C@H]6CC[C@@H]5[C@H](N)C6)cc(OC)n4c3C)n(CC(F)(F)F)c2n1] | [(1~{R},2~{R},4~{S})-2-amino-7-azabicyclo[2.2.1]heptan-7-yl]-[2-[6-ethyl-1-(2,2,2-trifluoroethyl)pyrrolo[2,3-b]pyridin-2-yl]-5-methoxy-3-methylimidazo[1,2-a]pyridin-7-yl]methanone |
| 505 | 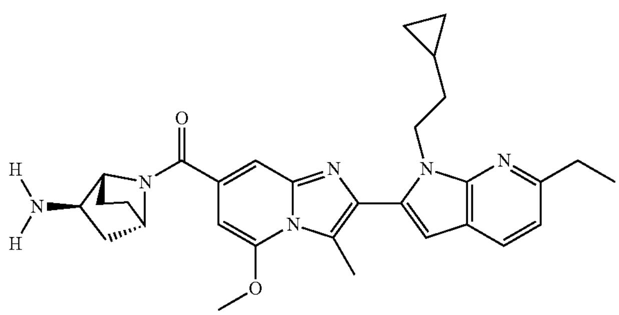 [SMILES: CCc1ccc2cc(-c3nc4cc(C(=O)N5[C@H]6CC[C@@H]5[C@H](N)C6)cc(OC)n4c3C)n(CCC3CC3)c2n1] | [(1~{R},2~{R},4~{S})-2-amino-7-azabicyclo[2.2.1]heptan-7-yl]-[2-[1-(2-cyclopropylethyl)-6-ethylpyrrolo[2,3-b]pyridin-2-yl]-5-methoxy-3-methylimidazo[1,2-a]pyridin-7-yl]methanone |
| 506 | 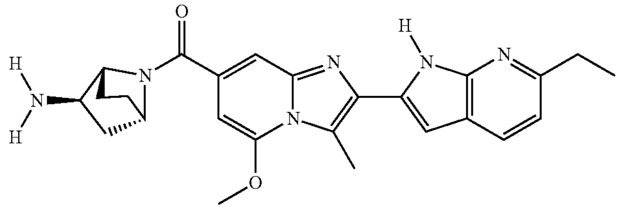 [SMILES: CCc1ccc2cc(-c3nc4cc(C(=O)N5[C@H]6CC[C@@H]5[C@H](N)C6)cc(OC)n4c3C)[nH]c2n1] | [(1~{R},2~{R},4~{S})-2-amino-7-azabicyclo[2.2.1]heptan-7-yl]-[2-(6-ethyl-1-{H}-pyrrolo[2,3-b]pyridin-2-yl)-5-methoxy-3-methylimidazo[1,2-a]pyridin-7-yl]methanone |
| 507 | 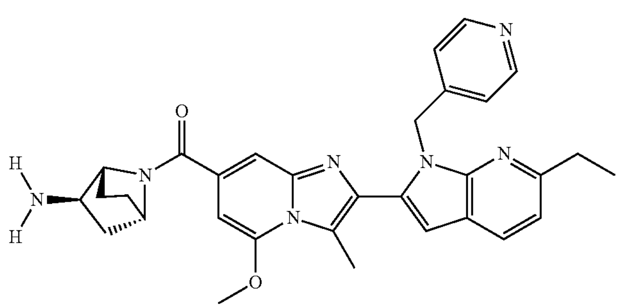 [SMILES: CCc1ccc2cc(-c3nc4cc(C(=O)N5[C@H]6CC[C@@H]5[C@H](N)C6)cc(OC)n4c3C)n(Cc3ccncc3)c2n1] | [(1~{R},2~{R},4~{S})-2-amino-7-azabicyclo[2.2.1]heptan-7-yl]-[2-[6-ethyl-1-(pyridin-4-ylmethyl)pyrrolo[2,3-b]pyridin-2-yl]-5-methoxy-3-methylimidazo[1,2-a]pyridin-7-yl]methanone |

-continued

| Ex | Structure | Name |
|---|---|---|
| 508 | 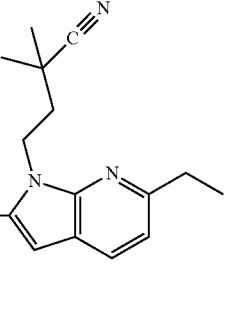 | 4-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-6-ethylpyrrolo[2,3-b]pyridin-1-yl]-2,2-dimethylbutanenitrile |
| 509 | 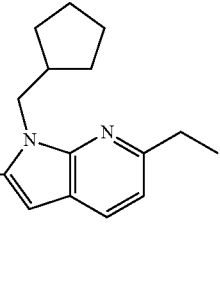 | [(1~{R},2~{R},4~{S})-2-amino-7-azabicyclo[2.2.1]heptan-7-yl]-[2-[1-(cyclopentylmethyl)-6-ethylpyrrolo[2,3-b]pyridin-2-yl]-5-methoxy-3-methylimidazo[1,2-a]pyridin-7-yl]methanone |
| 510 | 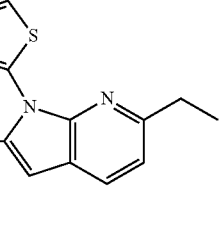 | [(1~{R},2~{R},4~{S})-2-amino-7-azabicyclo[2.2.1]heptan-7-yl]-[2-[6-ethyl-1-(1,3-thiazol-2-yl)pyrrolo[2,3-b]pyridin-2-yl]-5-methoxy-3-methylimidazo[1,2-a]pyridin-7-yl]methanone |
| 511 | 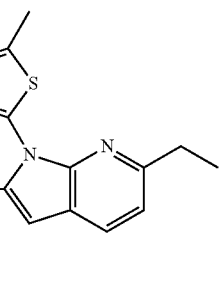 | [(1~{R},2~{R},4~{S})-2-amino-7-azabicyclo[2.2.1]heptan-7-yl]-[2-[6-ethyl-1-(2-methyl-1,3-thiazol-5-yl)pyrrolo[2,3-b]pyridin-2-yl]-5-methoxy-3-methylimidazo[1,2-a]pyridin-7-yl]methanone |
| 512 | 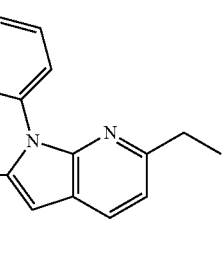 | [(1~{R},2~{R},4~{S})-2-amino-7-azabicyclo[2.2.1]heptan-7-yl]-[2-(6-ethyl-1-phenylpyrrolo[2,3-b]pyridin-2-yl)-5-methoxy-3-methylimidazo[1,2-a]pyridin-7-yl]methanone |

| Ex | Structure | Name |
|---|---|---|
| 513 | 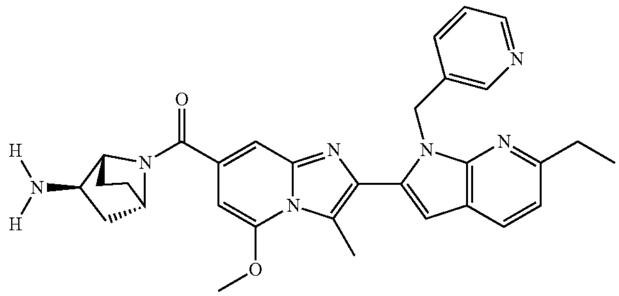 [SMILES: CCc1ccc2cc(-c3nc4cc(C(=O)N5[C@H]6CC[C@@H]5[C@H](N)C6)cc(OC)n4c3C)n(Cc3cccnc3)c2n1] | [(1~{R},2~{R},4~{S})-2-amino-7-azabicyclo[2.2.1]heptan-7-yl]-[2-[6-ethyl-1-(pyridin-3-ylmethyl)pyrrolo[2,3-b]pyridin-2-yl]-5-methoxy-3-methylimidazo[1,2-a]pyridin-7-yl]methanone |
| 514 | 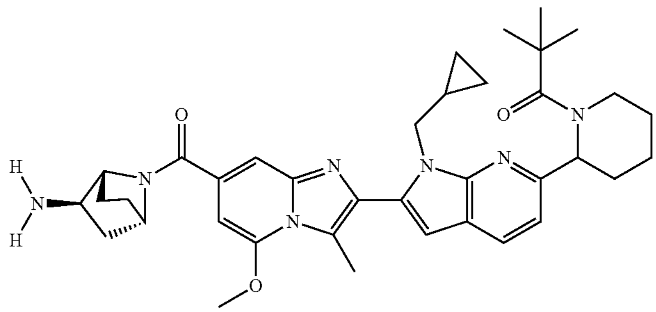 [SMILES: COc1cc(C(=O)N2[C@H]3CC[C@@H]2[C@H](N)C3)cc2nc(-c3cc4ccc(C5CCCCN5C(=O)C(C)(C)C)nc4n3CC3CC3)c(C)n12] | 1-[2-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]piperidin-1-yl]-2,2-dimethylpropan-1-one |
| 515 | 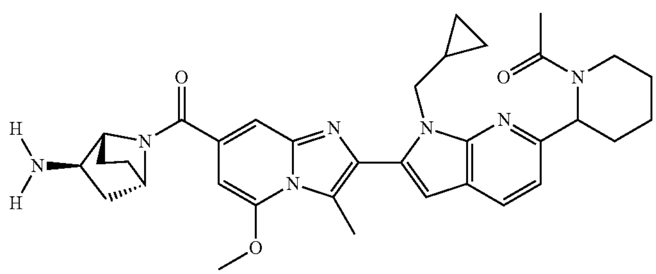 [SMILES: COc1cc(C(=O)N2[C@H]3CC[C@@H]2[C@H](N)C3)cc2nc(-c3cc4ccc(C5CCCCN5C(C)=O)nc4n3CC3CC3)c(C)n12] | 1-[2-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]piperidin-1-yl]ethenone |
| 516 | 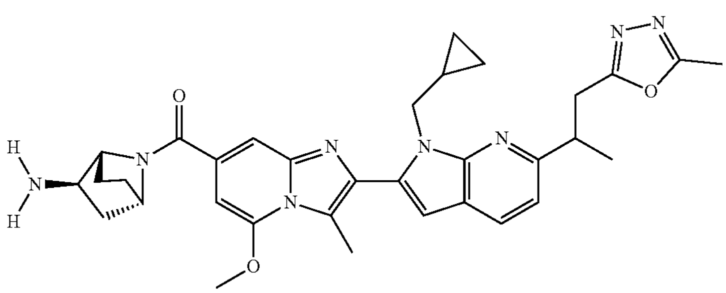 [SMILES: COc1cc(C(=O)N2[C@H]3CC[C@@H]2[C@H](N)C3)cc2nc(-c3cc4ccc(C(C)Cc5nnc(C)o5)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-[1-(5-methyl-1,3,4-oxadiazol-2-yl)propan-2-yl]pyrrolo[2,3-b]pyridin-2-yl]-5-methoxy-3-methylimidazo[1,2-a]pyridin-7-yl]methanone |
| 517 | 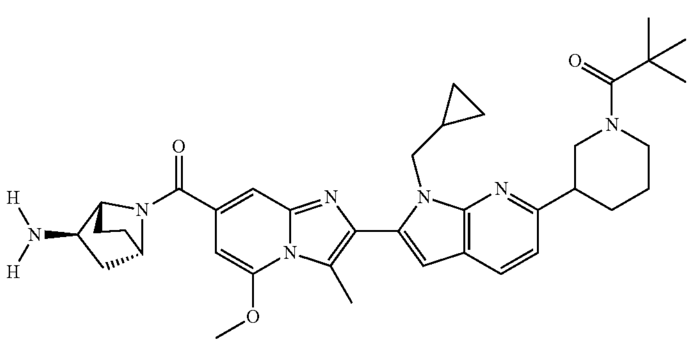 [SMILES: COc1cc(C(=O)N2[C@H]3CC[C@@H]2[C@H](N)C3)cc2nc(-c3cc4ccc(C5CCCN(C(=O)C(C)(C)C)C5)nc4n3CC3CC3)c(C)n12] | 1-[3-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]piperidin-1-yl]-2,2-dimethylpropan-1-one |

| Ex | Structure | Name |
|---|---|---|
| 518 | 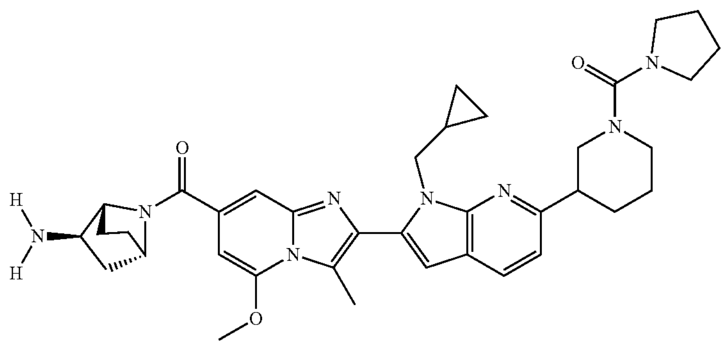 [SMILES: COc1cc(C(=O)N2[C@H]3CC[C@@H]2[C@H](N)C3)cc2nc(-c3cc4ccc(C5CCCN(C(=O)N6CCCC6)C5)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-[1-(pyrrolidine-1-carbonyl)piperidin-3-yl]pyrrolo[2,3-b]pyridin-2-yl]-5-methoxy-3-methylimidazo[1,2-a]pyridin-7-yl]methanone |
| 519 | 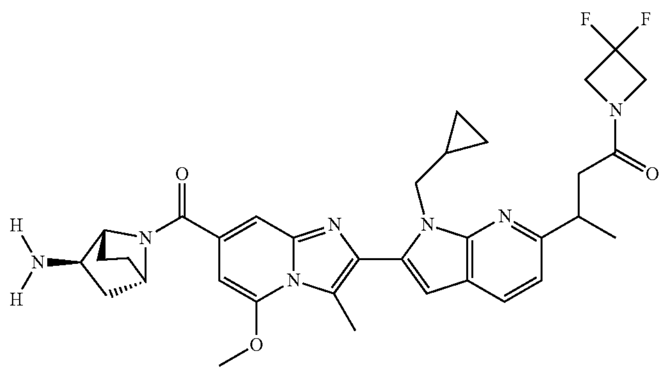 [SMILES: COc1cc(C(=O)N2[C@H]3CC[C@@H]2[C@H](N)C3)cc2nc(-c3cc4ccc(C(C)CC(=O)N5CC(F)(F)C5)nc4n3CC3CC3)c(C)n12] | 3-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]-1-(3,3-difluoroazetidin-1-yl)butan-1-one |
| 520 | 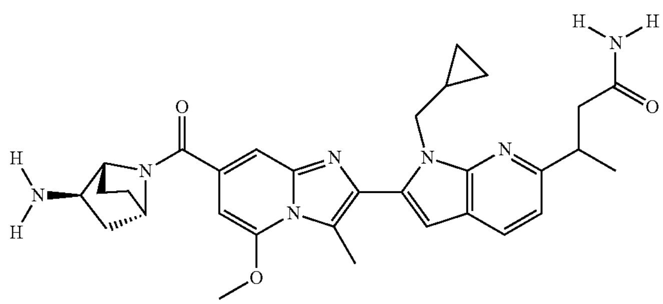 [SMILES: COc1cc(C(=O)N2[C@H]3CC[C@@H]2[C@H](N)C3)cc2nc(-c3cc4ccc(C(C)CC(N)=O)nc4n3CC3CC3)c(C)n12] | 3-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]butanamide |
| 521 | 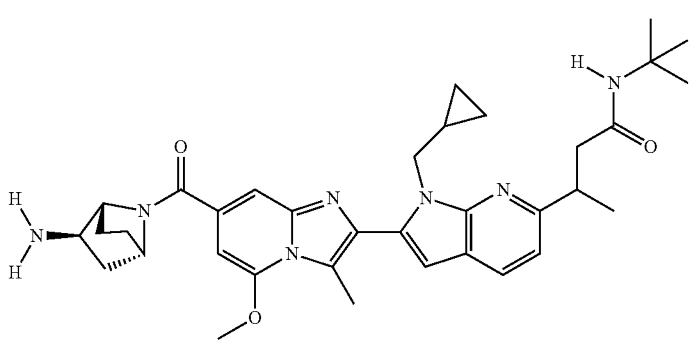 [SMILES: COc1cc(C(=O)N2[C@H]3CC[C@@H]2[C@H](N)C3)cc2nc(-c3cc4ccc(C(C)CC(=O)NC(C)(C)C)nc4n3CC3CC3)c(C)n12] | 3-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]-~{N}-~{tert}-butylbutanamide |

| Ex | Structure | Name |
|---|---|---|
| 522 | 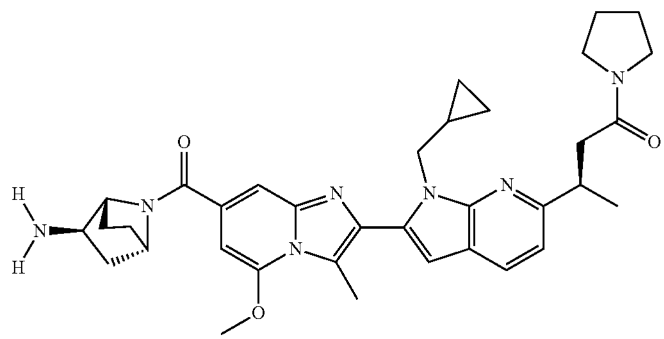 [SMILES: COc1cc(C(=O)N2[C@H]3CC[C@@H]2[C@H](N)C3)cc2nc(-c3cc4ccc([C@H](C)CC(=O)N5CCCC5)nc4n3CC3CC3)c(C)n12] | (3~{R})-3-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]-1-pyrrolidin-1-ylbutan-1-one |
| 523 | 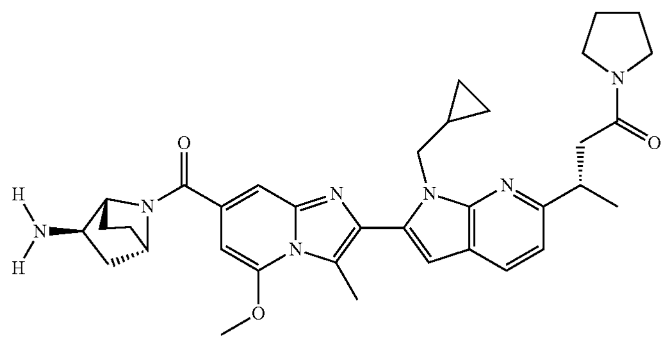 [SMILES: COc1cc(C(=O)N2[C@H]3CC[C@@H]2[C@H](N)C3)cc2nc(-c3cc4ccc([C@@H](C)CC(=O)N5CCCC5)nc4n3CC3CC3)c(C)n12] | (3~{S})-3-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]-1-pyrrolidin-1-ylbutan-1-one |
| 524 | 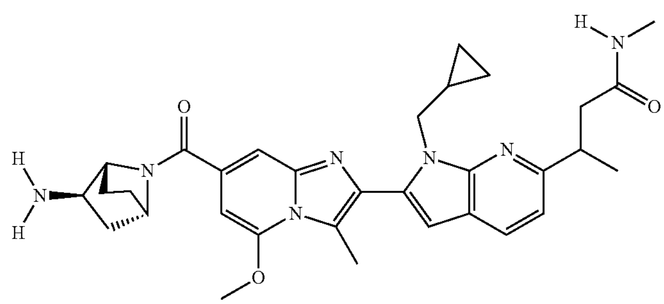 [SMILES: CNC(=O)CC(C)c1ccc2cc(-c3nc4cc(C(=O)N5[C@H]6CC[C@@H]5[C@H](N)C6)cc(OC)n4c3C)n(CC3CC3)c2n1] | 3-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]-~{N}-methylbutanamide |
| 525 | 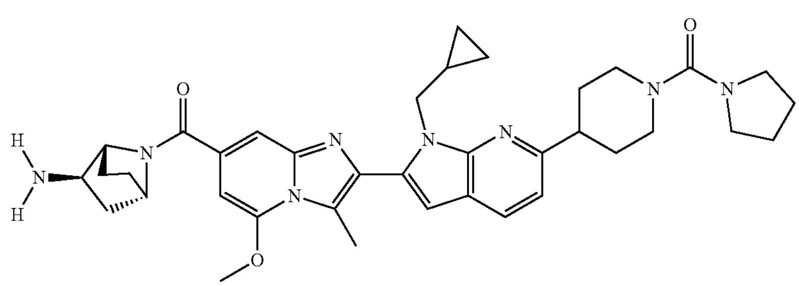 [SMILES: COc1cc(C(=O)N2[C@H]3CC[C@@H]2[C@H](N)C3)cc2nc(-c3cc4ccc(C5CCN(C(=O)N6CCCC6)CC5)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-[1-(pyrrolidine-1-carbonyl)piperidin-4-yl]pyrrolo[2,3-b]pyridin-2-yl]-5-methoxy-3-methylimidazo[1,2-a]pyridin-7-yl]methanone |
| 526 | 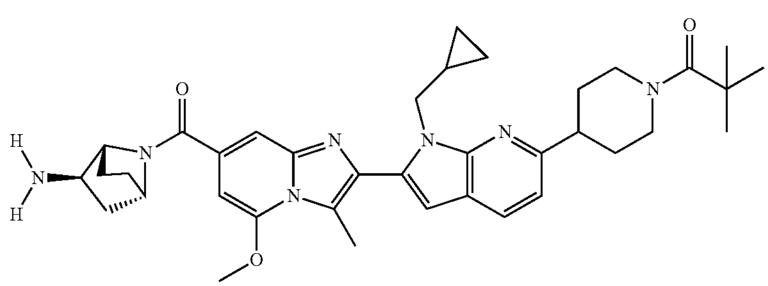 [SMILES: COc1cc(C(=O)N2[C@H]3CC[C@@H]2[C@H](N)C3)cc2nc(-c3cc4ccc(C5CCN(C(=O)C(C)(C)C)CC5)nc4n3CC3CC3)c(C)n12] | 1-[4-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]piperidin-1-yl]-2,2-dimethylpropan-1-one |

-continued

| Ex | Structure | Name |
|---|---|---|
| 527 | 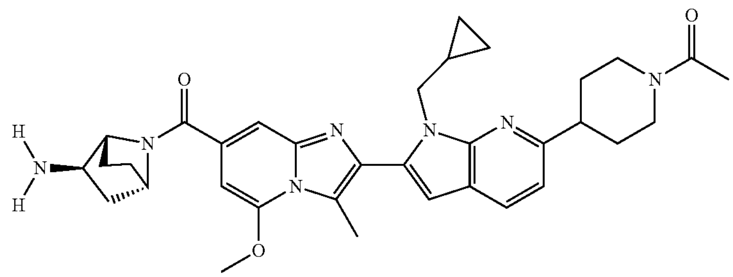 [SMILES: COc1cc(C(=O)N2[C@H]3CC[C@@H]2[C@H](N)C3)cc2nc(-c3cc4ccc(C5CCN(C(C)=O)CC5)nc4n3CC3CC3)c(C)n12] | 1-[4-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]piperidin-1-yl]ethenone |
| 528 | 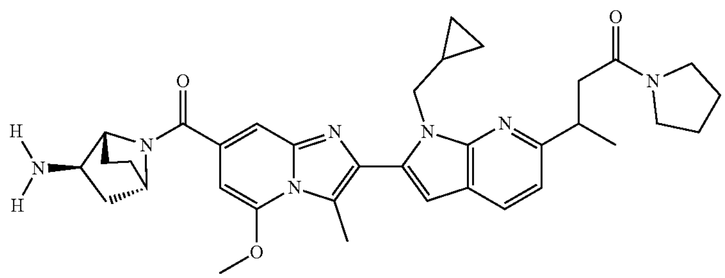 [SMILES: COc1cc(C(=O)N2[C@H]3CC[C@@H]2[C@H](N)C3)cc2nc(-c3cc4ccc(C(C)CC(=O)N5CCCC5)nc4n3CC3CC3)c(C)n12] | 3-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]-1-pyrrolidin-1-ylbutan-1-one |
| 529 | 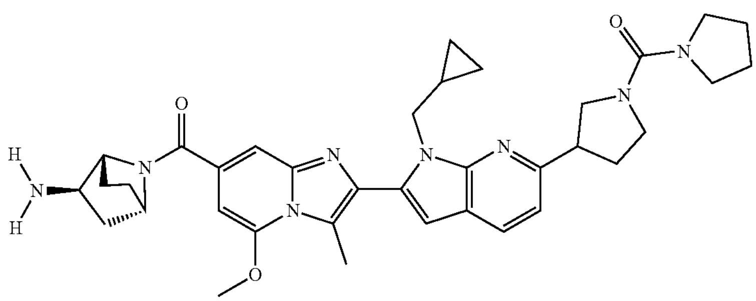 [SMILES: COc1cc(C(=O)N2[C@H]3CC[C@@H]2[C@H](N)C3)cc2nc(-c3cc4ccc(C5CCN(C(=O)N6CCCC6)C5)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-[1-(pyrrolidine-1-carbonyl)pyrrolidin-3-yl]pyrrolo[2,3-b]pyridin-2-yl]-5-methoxy-3-methylimidazo[1,2-a]pyridin-7-yl]methanone |
| 530 | 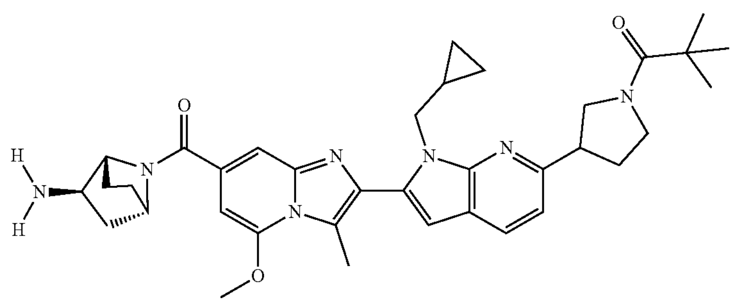 [SMILES: COc1cc(C(=O)N2[C@H]3CC[C@@H]2[C@H](N)C3)cc2nc(-c3cc4ccc(C5CCN(C(=O)C(C)(C)C)C5)nc4n3CC3CC3)c(C)n12] | 1-[3-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]pyrrolidin-1-yl]-2,2-dimethylpropan-1-one |
| 531 | 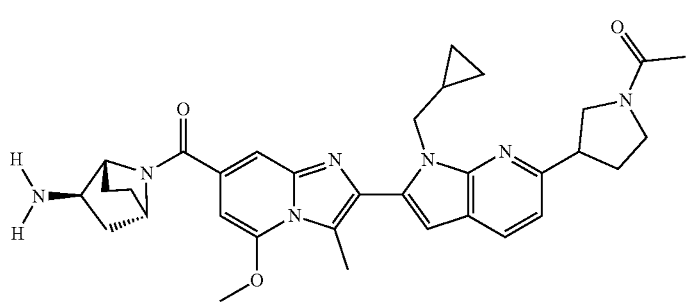 [SMILES: COc1cc(C(=O)N2[C@H]3CC[C@@H]2[C@H](N)C3)cc2nc(-c3cc4ccc(C5CCN(C(C)=O)C5)nc4n3CC3CC3)c(C)n12] | 1-[3-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]pyrrolidin-1-yl]ethanone |

| Ex | Structure | Name |
|---|---|---|
| 532 | 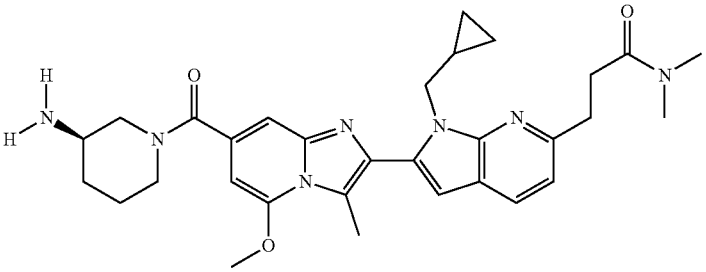 [SMILES: COc1cc(C(=O)N2CCC[C@@H](N)C2)cc2nc(-c3cc4ccc(CCC(=O)N(C)C)nc4n3CC3CC3)c(C)n12] | 3-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]-~{N},~{N}-dimethylpropanamide |
| 533 | 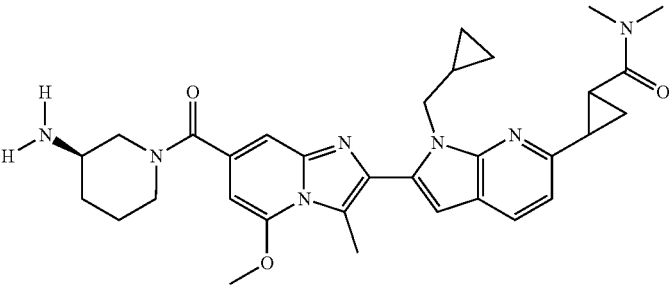 [SMILES: COc1cc(C(=O)N2CCC[C@@H](N)C2)cc2nc(-c3cc4ccc(C5CC5C(=O)N(C)C)nc4n3CC3CC3)c(C)n12] | 2-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]-~{N},~{N}-dimethylcyclopropane-1-carboxamide |
| 534 | 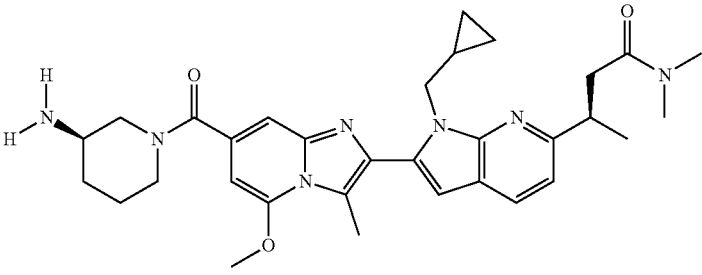 [SMILES: COc1cc(C(=O)N2CCC[C@@H](N)C2)cc2nc(-c3cc4ccc([C@H](C)CC(=O)N(C)C)nc4n3CC3CC3)c(C)n12] | (3~{R})-3-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]-~{N},~{N}-dimethylbutanamide |
| 535 | 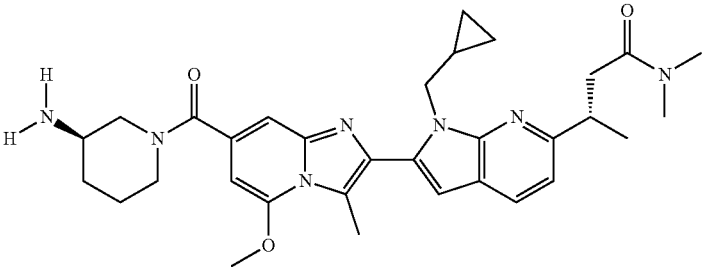 [SMILES: COc1cc(C(=O)N2CCC[C@@H](N)C2)cc2nc(-c3cc4ccc(C(C)CC(=O)N(C)C)nc4n3CC3CC3)c(C)n12] | (3~{S})-3-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]-~{N},~{N}-dimethylbutanamide |
| 536 | 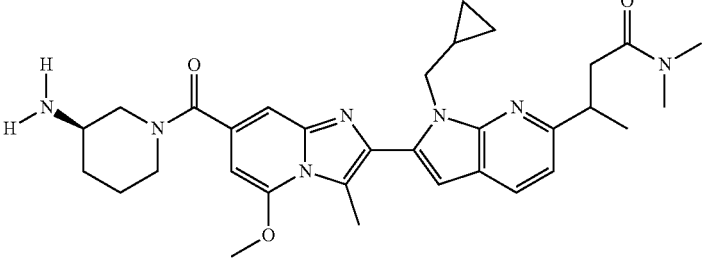 | 3-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]-~{N},~{N}-dimethylbutanamide |

-continued

| Ex | Structure | Name |
|---|---|---|
| 537 | 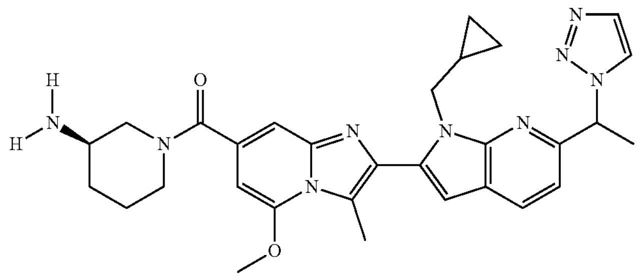 [SMILES: COc1cc(C(=O)N2CCC[C@@H](N)C2)cc2nc(-c3cc4ccc(C(C)n5ccnn5)nc4n3CC3CC3)c(C)n12] | [(3~{R})-3-aminopiperidin-1-yl]-[2-[1-(cyclopropylmethyl)-6-[1-(triazol-1-yl)ethyl] pyrrolo[2,3-b]pyridin-2-yl]-5-methoxy-3-methylimidazo[1,2-a] pyridin-7-yl]methanone |
| 538 | 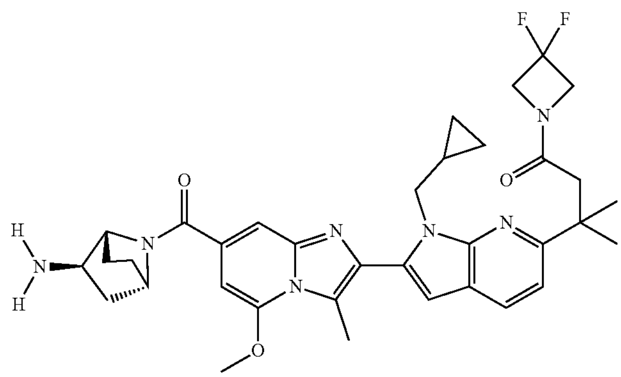 [SMILES: COc1cc(C(=O)N2[C@H]3CC[C@@H]2[C@H](N)C3)cc2nc(-c3cc4ccc(C(C)(C)CC(=O)N5CC(F)(F)C5)nc4n3CC3CC3)c(C)n12] | 3-[2-[7-[(1~{R},2~{R},4~{S})-2-amino-7-azabicyclo[2.2.1]heptane-7-carbonyl]-5-methoxy-3-methylimidazo[1,2-a] pyridin-2-yl]-1-(cyclopropylmethyl)pyrrolo [2,3-b]pyridin-6-yl]-1-(3,3-difluoroazetidin-1-yl)-3-methylbutan-1-one |
| 539 | 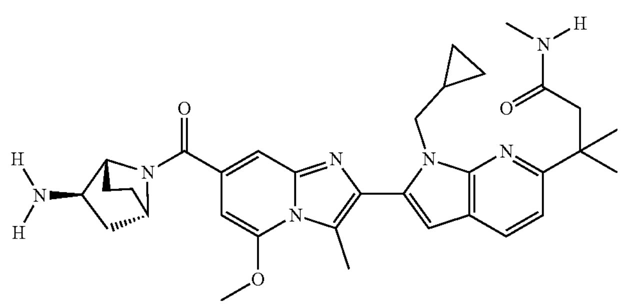 [SMILES: CNC(=O)CC(C)(C)c1ccc2cc(-c3nc4cc(C(=O)N5[C@H]6CC[C@@H]5[C@H](N)C6)cc(OC)n4c3C)n(CC3CC3)c2n1] | 3-[2-[7-[(1~{R},2~{R},4~{S})-2-amino-7-azabicyclo[2.2.1]heptane-7-carbonyl]-5-methoxy-3-methylimidazo[1,2-a] pyridin-2-yl]-1-(cyclopropylmethyl) pyrrolo[2,3-b] pyridin-6-yl]-~{N},3-dimethylbutanamide |
| 540 | 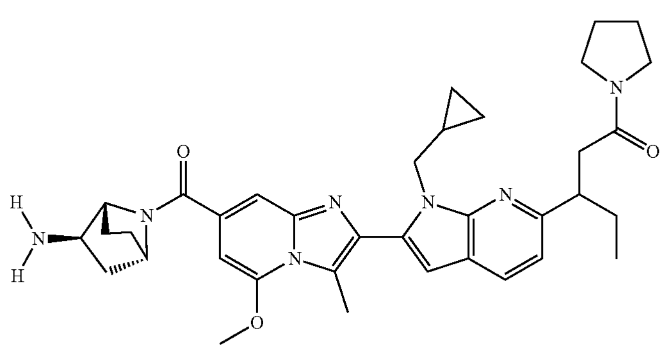 [SMILES: CCC(CC(=O)N1CCCC1)c1ccc2cc(-c3nc4cc(C(=O)N5[C@H]6CC[C@@H]5[C@H](N)C6)cc(OC)n4c3C)n(CC3CC3)c2n1] | 3-[2-[7-[(1~{R},2~{R},4~{S})-2-amino-7-azabicyclo[2.2.1]heptane-7-carbonyl]-5-methoxy-3-methylimidazo[1,2-a] pyridin-2-yl]-1-(cyclopropylmethyl) pyrrolo[2,3-b] pyridin-6-yl]-1-pyrrolidin-1-ylpentan-1-one |

-continued

| Ex | Structure | Name |
|---|---|---|
| 541 | 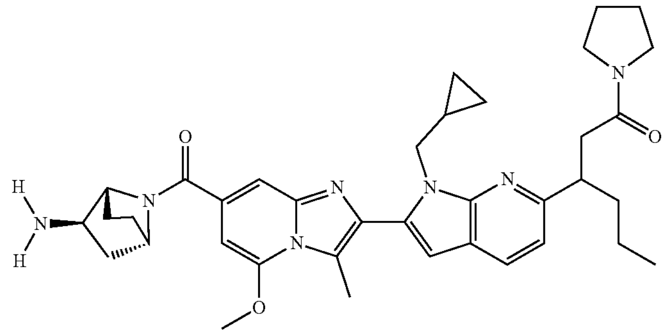 [SMILES: CCCC(CC(=O)N1CCCC1)c1ccc2cc(-c3nc4cc(C(=O)N5[C@H]6CC[C@@H]5[C@H](N)C6)cc(OC)n4c3C)n(CC3CC3)c2n1] | 3-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]-1-pyrrolidin-1-ylhexan-1-one |
| 542 | 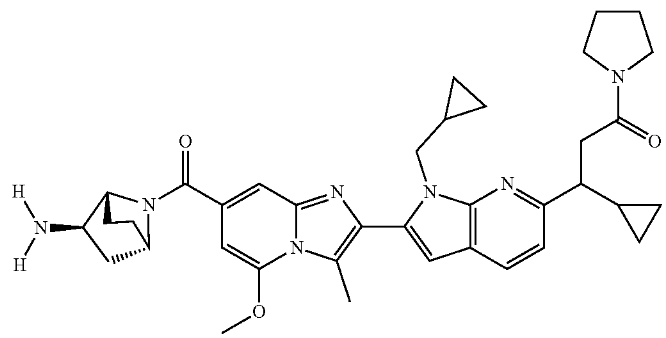 [SMILES: COc1cc(C(=O)N2[C@H]3CC[C@@H]2[C@H](N)C3)cc2nc(-c3cc4ccc(C(CC(=O)N5CCCC5)C5CC5)nc4n3CC3CC3)c(C)n12] | 3-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]-3-cyclopropyl-1-pyrrolidin-1-ylpropan-1-one |
| 543 | 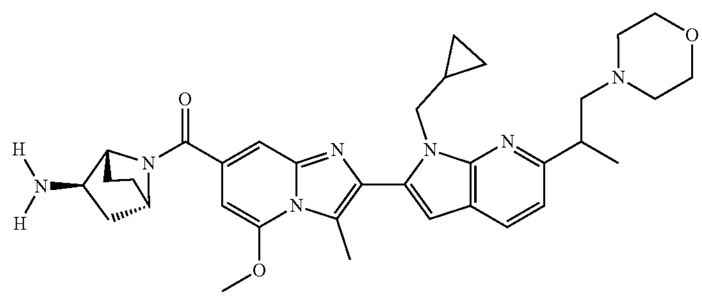 [SMILES: COc1cc(C(=O)N2[C@H]3CC[C@@H]2[C@H](N)C3)cc2nc(-c3cc4ccc(C(C)CN5CCOCC5)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-(1-morpholin-4-ylpropan-2-yl)pyrrolo[2,3-b]pyridin-2-yl]-5-methoxy-3-methylimidazo[1,2-a]pyridin-7-yl]methanone |
| 544 | 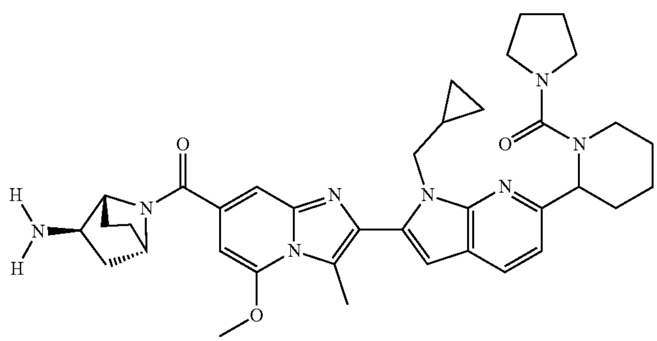 [SMILES: COc1cc(C(=O)N2[C@H]3CC[C@@H]2[C@H](N)C3)cc2nc(-c3cc4ccc(C5CCCCN5C(=O)N5CCCC5)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-[1-(pyrrolidine-1-carbonyl)piperidin-2-yl]pyrrolo[2,3-b]pyridin-2-yl]-5-methoxy-3-methylimidazo[1,2-a]pyridin-7-yl]methanone |
| 545 | 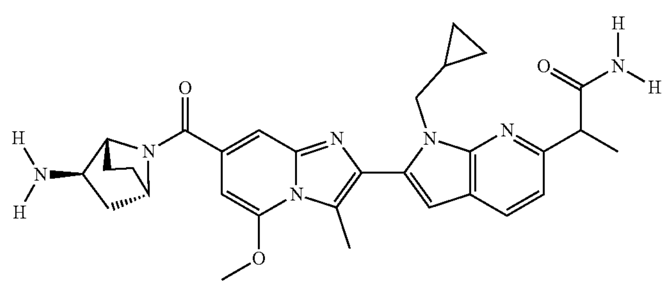 [SMILES: COc1cc(C(=O)N2[C@H]3CC[C@@H]2[C@H](N)C3)cc2nc(-c3cc4ccc(C(C)C(N)=O)nc4n3CC3CC3)c(C)n12] | 2-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]propenamide |

-continued

| Ex | Structure | Name |
|---|---|---|
| 546 | 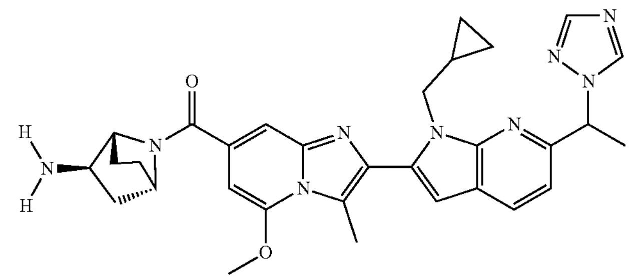 [SMILES: COc1cc(C(=O)N2[C@H]3CC[C@@H]2[C@H](N)C3)cc2nc(-c3cc4ccc(C(C)n5cncn5)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-[1-(1,2,4-triazol-1-yl)ethyl]pyrrolo[2,3-b]pyridin-2-yl]-5-methoxy-3-methylimidazo[1,2-a]pyridin-7-yl]methanone |
| 547 | 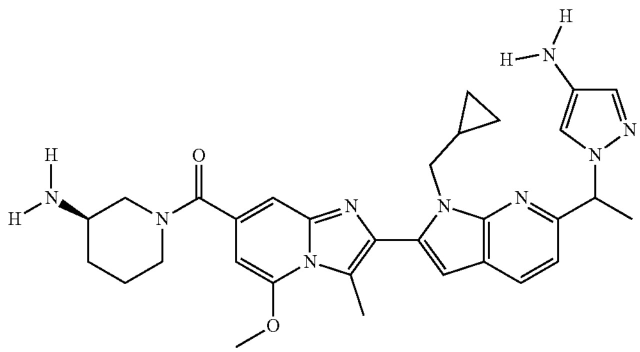 [SMILES: COc1cc(C(=O)N2CCC[C@@H](N)C2)cc2nc(-c3cc4ccc(C(C)n5cc(N)cn5)nc4n3CC3CC3)c(C)n12] | [(3~{R})-3-aminopiperidin-1-yl]-[2-[6-[1-(4-aminopyrazol-1-yl)ethyl]-1-(cyclopropylmethyl)pyrrolo[2,3-b]pyridin-2-yl]-5-methoxy-3-methylimidazo[1,2-a]pyridin-7-yl]methanone |
| 548 | 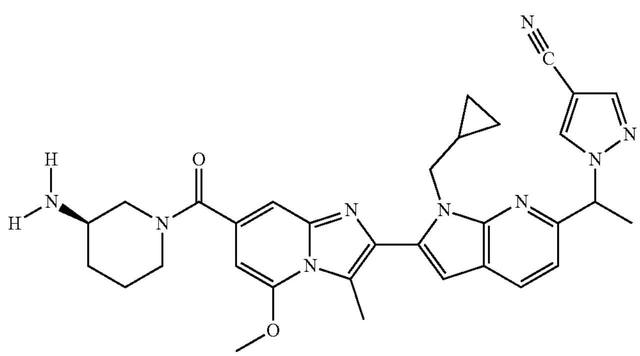 [SMILES: COc1cc(C(=O)N2CCC[C@@H](N)C2)cc2nc(-c3cc4ccc(C(C)n5cc(C#N)cn5)nc4n3CC3CC3)c(C)n12] | 1-[1-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]ethyl]pyrazole-4-carbonitrile |
| 549 | 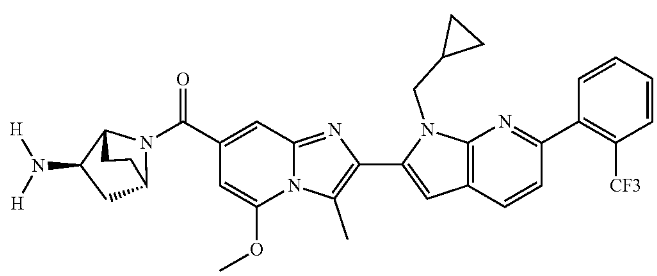 [SMILES: COc1cc(C(=O)N2[C@H]3CC[C@@H]2[C@H](N)C3)cc2nc(-c3cc4ccc(-c5ccccc5C(F)(F)F)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-[2-(trifluoromethyl)phenyl]pyrrolo[2,3-b]pyridin-2-yl]-5-methoxy-3-methylimidazo[1,2-a]pyridin-7-yl]methanone |
| 550 | 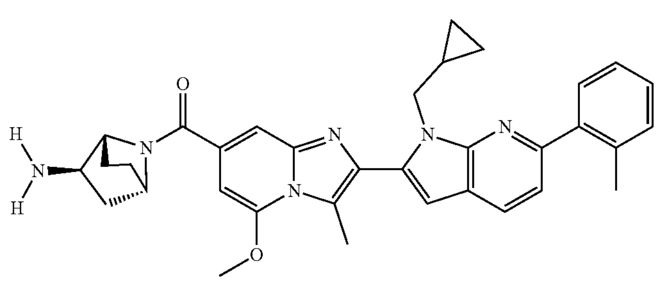 [SMILES: COc1cc(C(=O)N2[C@H]3CC[C@@H]2[C@H](N)C3)cc2nc(-c3cc4ccc(-c5ccccc5C)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-(2-methylphenyl)pyrrolo[2,3-b]pyridin-2-yl]-5-methoxy-3-methylimidazo[1,2-a]pyridin-7-yl]methanone |

| Ex | Structure | Name |
|---|---|---|
| 551 | 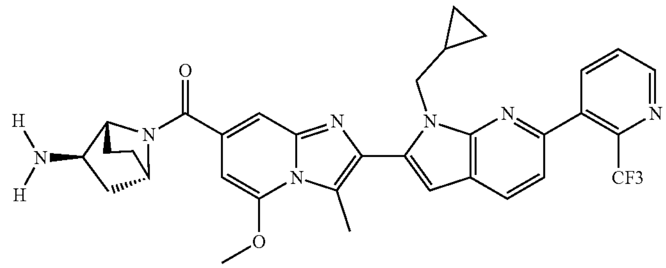 [SMILES: COc1cc(C(=O)N2[C@H]3CC[C@@H]2[C@H](N)C3)cc2nc(-c3cc4ccc(-c5cccnc5C(F)(F)F)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-[2-(trifluoromethyl)pyridin-3-yl]pyrrolo[2,3-b]pyridin-2-yl]-5-methoxy-3-methylimidazo[1,2-a]pyridin-7-yl]methanone |
| 552 | 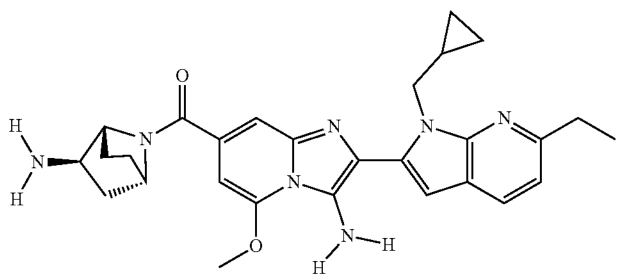 [SMILES: CCc1ccc2cc(-c3nc4cc(C(=O)N5[C@H]6CC[C@@H]5[C@H](N)C6)cc(OC)n4c3N)n(CC3CC3)c2n1] | [(1~{R},2~{R},4~{S})-2-amino-7-azabicyclo[2.2.1]heptan-7-yl]-[3-amino-2-[1-(cyclopropylmethyl)-6-ethylpyrrolo[2,3-b]pyridin-2-yl]-5-methoxyimidazo[1,2-a]pyridin-7-yl]methanone |
| 553 | 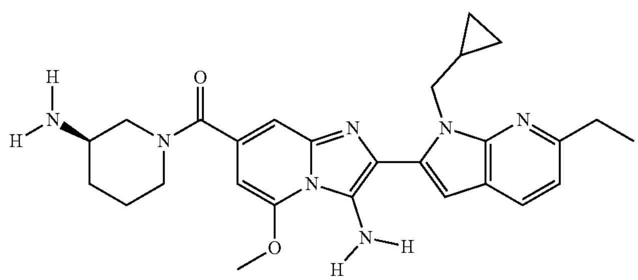 [SMILES: CCc1ccc2cc(-c3nc4cc(C(=O)N5CCC[C@@H](N)C5)cc(OC)n4c3N)n(CC3CC3)c2n1] | [3-amino-2-[1-(cyclopropylmethyl)-6-ethylpyrrolo[2,3-b]pyridin-2-yl]-5-methoxyimidazo[1,2-a]pyridin-7-yl]-[(3~{R})-3-aminopiperidin-1-yl]methanone |
| 554 | 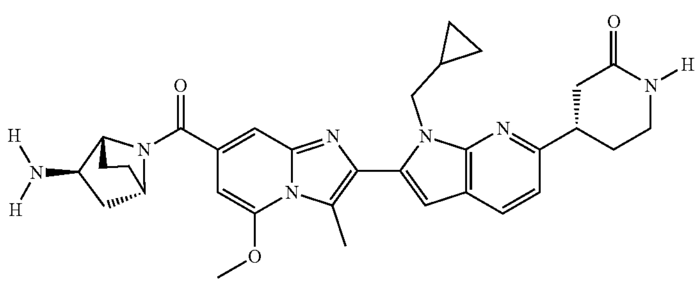 [SMILES: COc1cc(C(=O)N2[C@H]3CC[C@@H]2[C@H](N)C3)cc2nc(-c3cc4ccc([C@H]5CCNC(=O)C5)nc4n3CC3CC3)c(C)n12] | (4~{S})-4-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]piperidin-2-one |
| 555 | 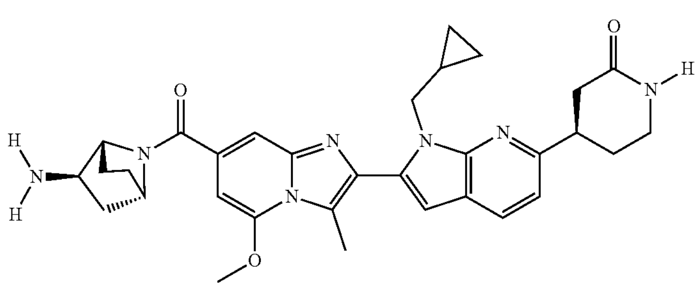 [SMILES: COc1cc(C(=O)N2[C@H]3CC[C@@H]2[C@H](N)C3)cc2nc(-c3cc4ccc([C@@H]5CCNC(=O)C5)nc4n3CC3CC3)c(C)n12] | (4~{R})-4-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]piperidin-2-one |

-continued

| Ex | Structure | Name |
|---|---|---|
| 556 | 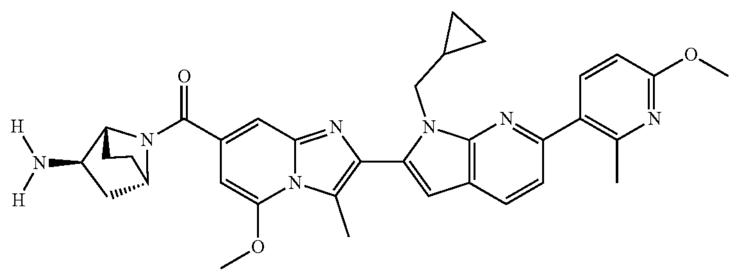 [SMILES: COc1ccc(-c2ccc3cc(-c4nc5cc(C(=O)N6[C@H]7CC[C@@H]6[C@H](N)C7)cc(OC)n5c4C)n(CC4CC4)c3n2)c(C)n1] | [(1~{R},2~{R},4~{S})-2-amino-7-azabicyclo[2.2.1]heptan-7-yl]-[2-[1-(cyclopropylmethyl)-6-(6-methoxy-2-methylpyridin-3-yl)pyrrolo[2,3-b]pyridin-2-yl]-5-methoxy-3-methylimidazo[1,2-a]pyridin-7-yl]methanone |
| 557 | 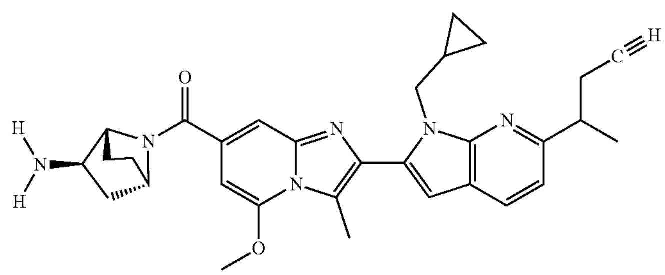 | 3-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]butanenitrile |
| 558 | 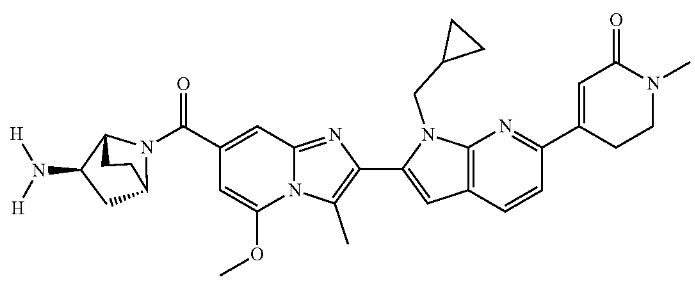 [SMILES: COc1cc(C(=O)N2[C@H]3CC[C@@H]2[C@H](N)C3)cc2nc(-c3cc4ccc(C5=CC(=O)N(C)CC5)nc4n3CC3CC3)c(C)n12] | 4-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]-1-methyl-2,3-dihydropyridin-6-one |
| 559 | 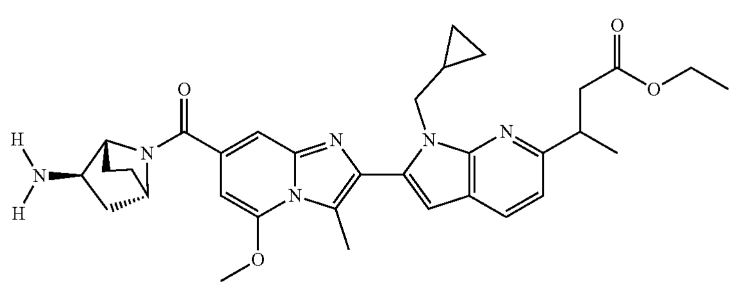 [SMILES: CCOC(=O)CC(C)c1ccc2cc(-c3nc4cc(C(=O)N5[C@H]6CC[C@@H]5[C@H](N)C6)cc(OC)n4c3C)n(CC3CC3)c2n1] | ethyl 3-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]butanoate |
| 560 | 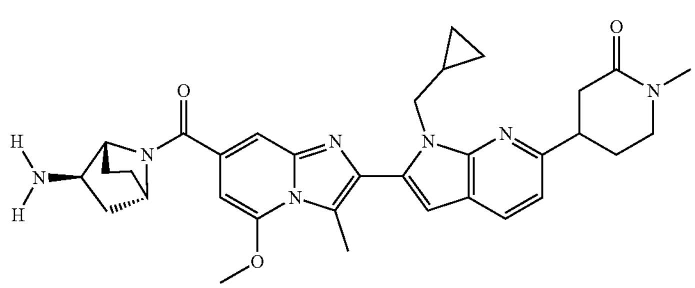 [SMILES: COc1cc(C(=O)N2[C@H]3CC[C@@H]2[C@H](N)C3)cc2nc(-c3cc4ccc(C5CCN(C)C(=O)C5)nc4n3CC3CC3)c(C)n12] | 4-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]-1-methylpiperidin-2-one |

| Ex | Structure | Name |
|---|---|---|
| 561 | 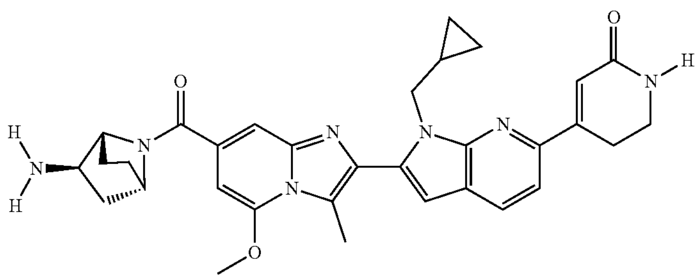 [SMILES: COc1cc(C(=O)N2[C@H]3CC[C@@H]2[C@H](N)C3)cc2nc(-c3cc4ccc(C5=CC(=O)NCC5)nc4n3CC3CC3)c(C)n12] | 4-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]-2,3-dihydro-1~{H}-pyridin-6-one |
| 562 | 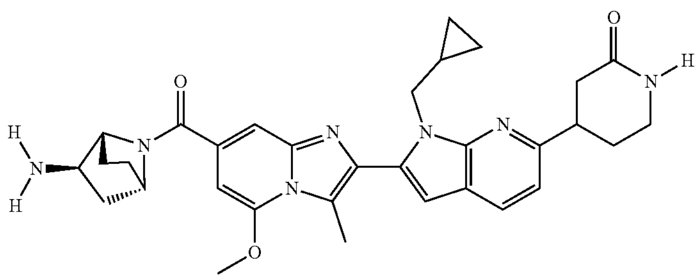 [SMILES: COc1cc(C(=O)N2[C@H]3CC[C@@H]2[C@H](N)C3)cc2nc(-c3cc4ccc(C5CCNC(=O)C5)nc4n3CC3CC3)c(C)n12] | 4-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]piperidin-2-one |
| 563 | 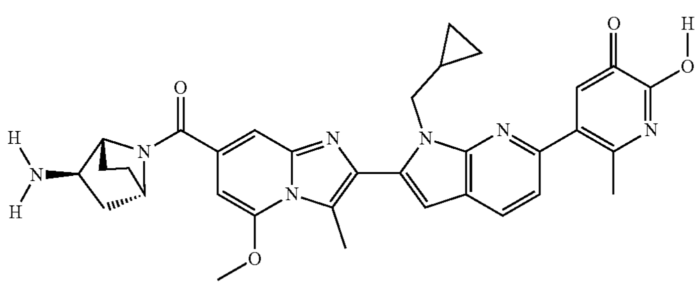 | [(1~{R},2~{R},4~{S})-2-amino-7-azabicyclo[2.2.1]heptan-7-yl]-[2-[1-(cyclopropylmethyl)-6-(6-hydroxy-2-methylpyridin-3-yl)pyrrolo[2,3-b]pyridin-2-yl]-5-methoxy-3-methylimidazo[1,2-a]pyridin-7-yl]methanone |
| 564 | 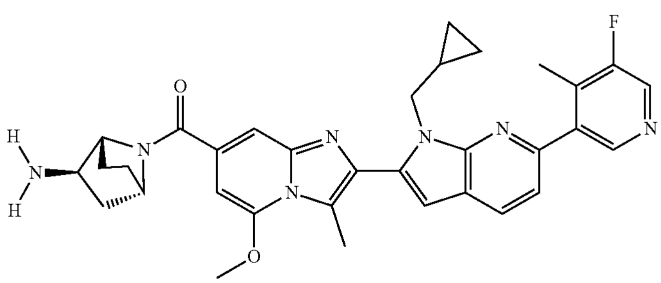 [SMILES: COc1cc(C(=O)N2[C@H]3CC[C@@H]2[C@H](N)C3)cc2nc(-c3cc4ccc(-c5cncc(F)c5C)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-(5-fluoro-4-methylpyridin-3-yl)pyrrolo[2,3-b]pyridin-2-yl]-5-methoxy-3-methylimidazo[1,2-a]pyridin-7-yl]methanone |
| 565 | 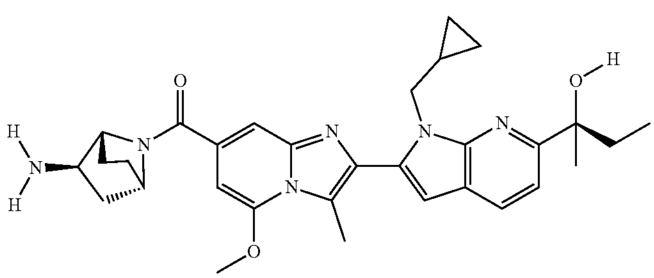 [SMILES: CC[C@](C)(O)c1ccc2cc(-c3nc4cc(C(=O)N5[C@H]6CC[C@@H]5[C@H](N)C6)cc(OC)n4c3C)n(CC3CC3)c2n1] | [(1~{R},2~{R},4~{S})-2-amino-7-azabicyclo[2.2.1]heptan-7-yl]-[2-[1-(cyclopropylmethyl)-6-[(2~{S})-2-hydroxybutan-2-yl]pyrrolo[2,3-b]pyridin-2-yl]-5-methoxy-3-methylimidazo[1,2-a]pyridin-7-yl]methanone |

| Ex | Structure | Name |
| --- | --- | --- |
| 566 | 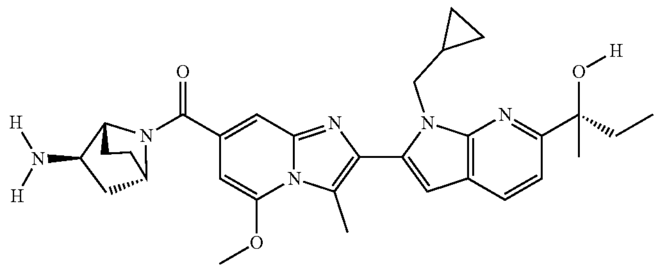 [SMILES: CC[C@@](C)(O)c1ccc2cc(-c3nc4cc(C(=O)N5[C@H]6CC[C@@H]5[C@H](N)C6)cc(OC)n4c3C)n(CC3CC3)c2n1] | [(1~{R},2~{R},4~{S})-2-amino-7-azabicyclo[2.2.1]heptan-7-yl]-[2-[1-(cyclopropylmethyl)-6-[(2~{R})-2-hydroxybutan-2-yl]pyrrolo[2,3-b]pyridin-2-yl]-5-methoxy-3-methylimidazo[1,2-a]pyridin-7-yl]methanone |
| 567 | 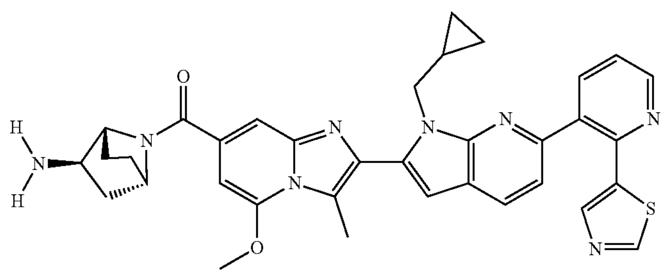 [SMILES: COc1cc(C(=O)N2[C@H]3CC[C@@H]2[C@H](N)C3)cc2nc(-c3cc4ccc(-c5cccnc5-c5cncs5)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-[2-(1,3-thiazol-5-yl)pyridin-3-yl]pyrrolo[2,3-b]pyridin-2-yl]-5-methoxy-3-methylimidazo[1,2-a]pyridin-7-yl]methanone |
| 568 | 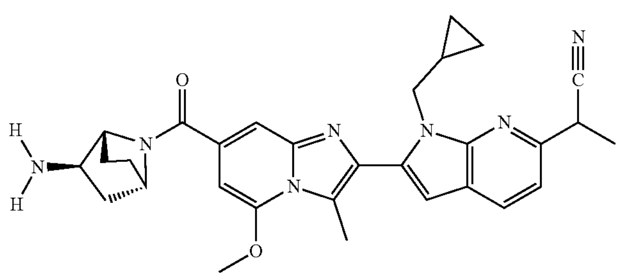 [SMILES: COc1cc(C(=O)N2[C@H]3CC[C@@H]2[C@H](N)C3)cc2nc(-c3cc4ccc(C(C)C#N)nc4n3CC3CC3)c(C)n12] | 2-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]propanenitrile |
| 569 | 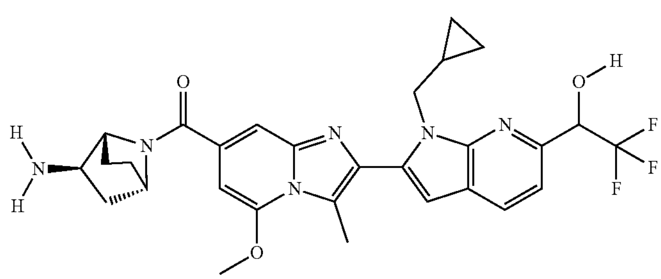 [SMILES: COc1cc(C(=O)N2[C@H]3CC[C@@H]2[C@H](N)C3)cc2nc(-c3cc4ccc(C(O)C(F)(F)F)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-(2,2,2-trifluoro-1-hydroxyethyl)pyrrolo[2,3-b]pyridin-2-yl]-5-methoxy-3-methylimidazo[1,2-a]pyridin-7-yl]methanone |
| 570 | 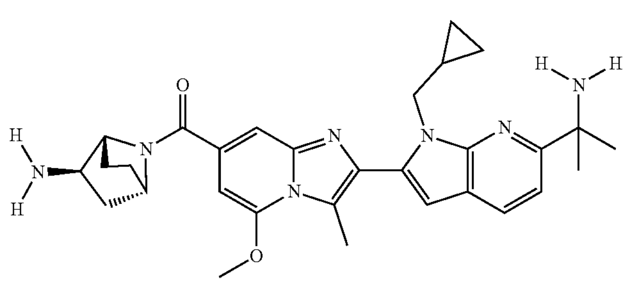 [SMILES: COc1cc(C(=O)N2[C@H]3CC[C@@H]2[C@H](N)C3)cc2nc(-c3cc4ccc(C(C)(C)N)nc4n3CC3CC3)c(C)n12] | [(1~{R},2~{R},4~{S})-2-amino-7-azabicyclo[2.2.1]heptan-7-yl]-[2-[6-(2-aminopropan-2-yl)-1-(cyclopropylmethyl)pyrrolo[2,3-b]pyridin-2-yl]-5-methoxy-3-methylimidazo[1,2-a]pyridin-7-yl]methanone |

| Ex | Structure | Name |
|---|---|---|
| 571 | 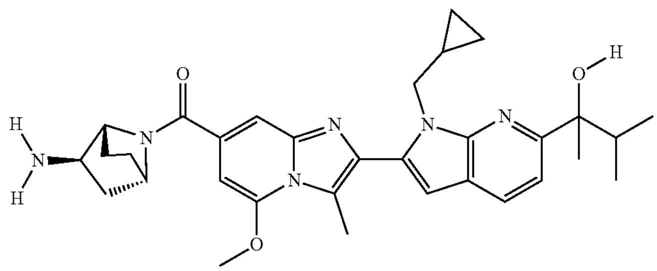 [SMILES: COc1cc(C(=O)N2[C@H]3CC[C@@H]2[C@H](N)C3)cc2nc(-c3cc4ccc(C(C)(O)C(C)C)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-(2-hydroxy-3-methylbutan-2-yl)pyrrolo[2,3-b]pyridin-2-yl]-5-methoxy-3-methylimidazo[1,2-a]pyridin-7-yl]methanone |
| 572 | 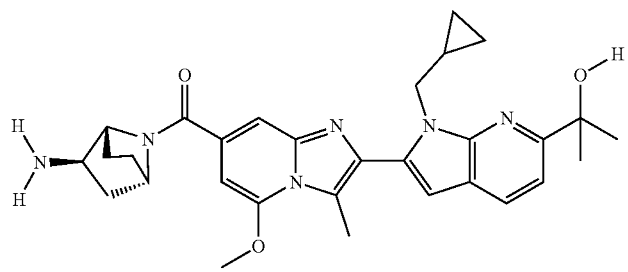 [SMILES: COc1cc(C(=O)N2[C@H]3CC[C@@H]2[C@H](N)C3)cc2nc(-c3cc4ccc(C(C)(C)O)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-(2-hydroxybutan-2-yl)pyrrolo[2,3-b]pyridin-2-yl]-5-methoxy-3-methylimidazo[1,2-a]pyridin-7-yl]methanone |
| 573 | 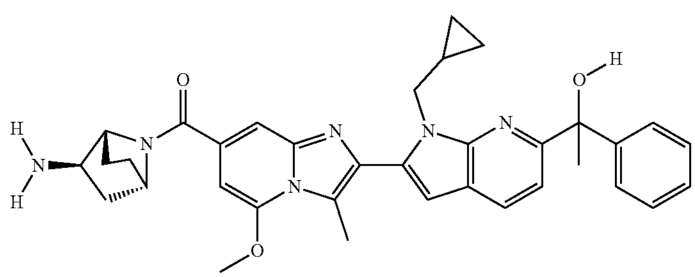 [SMILES: COc1cc(C(=O)N2[C@H]3CC[C@@H]2[C@H](N)C3)cc2nc(-c3cc4ccc(C(C)(O)c5ccccc5)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-(1-hydroxy-1-phenylethyl)pyrrolo[2,3-b]pyridin-2-yl]-5-methoxy-3-methylimidazo[1,2-a]pyridin-7-yl]methanone |
| 574 | 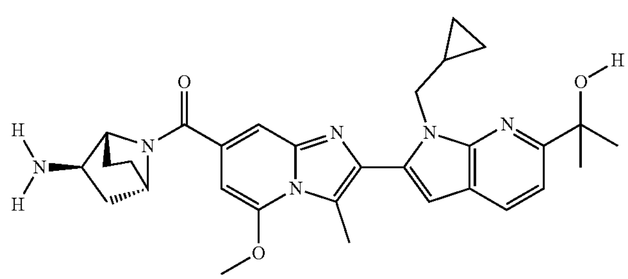 [SMILES: COc1cc(C(=O)N2[C@H]3CC[C@@H]2[C@H](N)C3)cc2nc(-c3cc4ccc(C(C)(C)O)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-(2-hydroxypropan-2-yl)pyrrolo[2,3-b]pyridin-2-yl]-5-methoxy-3-methylimidazo[1,2-a]pyridin-7-yl]methanone |
| 575 | 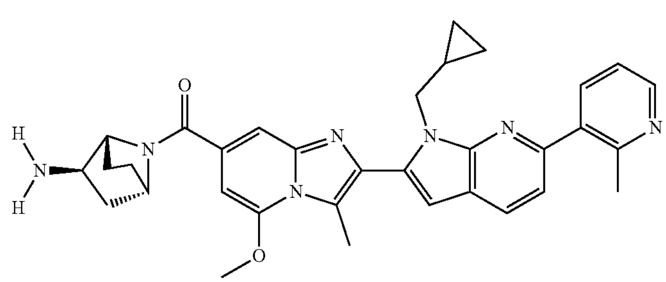 [SMILES: COc1cc(C(=O)N2[C@H]3CC[C@@H]2[C@H](N)C3)cc2nc(-c3cc4ccc(-c5cccnc5C)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-(2-methylpyridin-3-yl)pyrrolo[2,3-b]pyridin-2-yl]-5-methoxy-3-methylimidazo[1,2-a]pyridin-7-yl]methanone |

-continued

| Ex | Structure | Name |
|---|---|---|
| 576 | 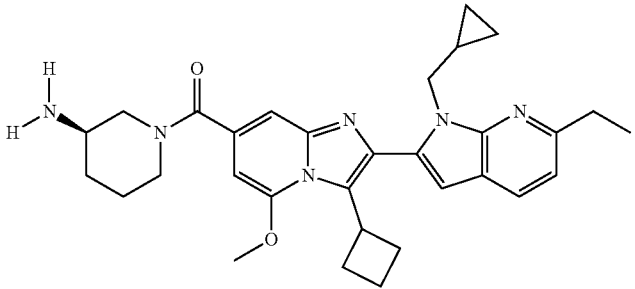 [SMILES: CCc1ccc2cc(-c3nc4cc(C(=O)N5CCC[C@@H](N)C5)cc(OC)n4c3C3CCC3)n(CC3CC3)c2n1] | [(3~{R})-3-aminopiperidin-1-yl]-[3-cyclobutyl-2-[1-(cyclopropylmethyl)-6-ethylpyrrolo[2,3-b]pyridin-2-yl]-5-methoxyimidazo[1,2-a]pyridin-7-yl]methanone |
| 577 | 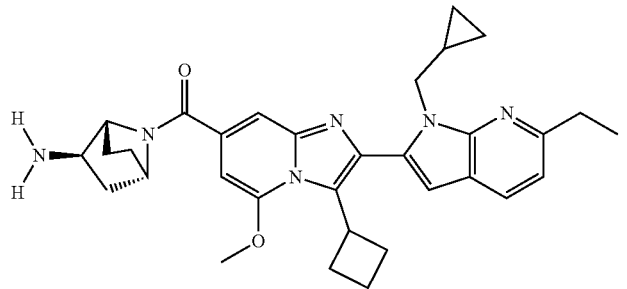 [SMILES: CCc1ccc2cc(-c3nc4cc(C(=O)N5[C@H]6CC[C@@H]5[C@H](N)C6)cc(OC)n4c3C3CCC3)n(CC3CC3)c2n1] | [(1~{R},2~{R},4~{S})-2-amino-7-azabicyclo[2.2.1]heptan-7-yl]-[3-cyclobutyl-2-[1-(cyclopropylmethyl)-6-ethylpyrrolo[2,3-b]pyridin-2-yl]-5-methoxyimidazo[1,2-a]pyridin-7-yl]methanone |
| 578 | 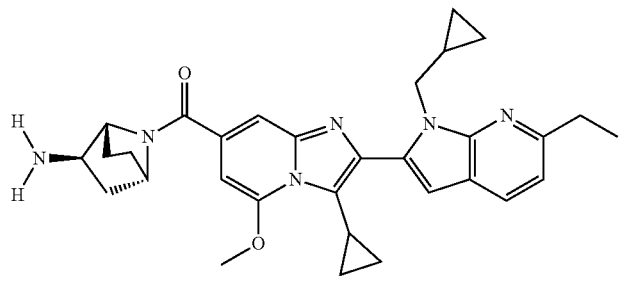 [SMILES: CCc1ccc2cc(-c3nc4cc(C(=O)N5[C@H]6CC[C@@H]5[C@H](N)C6)cc(OC)n4c3C3CC3)n(CC3CC3)c2n1] | [(1~{R},2~{R},4~{S})-2-amino-7-azabicyclo[2.2.1]heptan-7-yl]-[3-cyclopropyl-2-[1-(cyclopropylmethyl)-6-ethylpyrrolo[2,3-b]pyridin-2-yl]-5-methoxyimidazo[1,2-a]pyridin-7-yl]methanone |
| 579 | 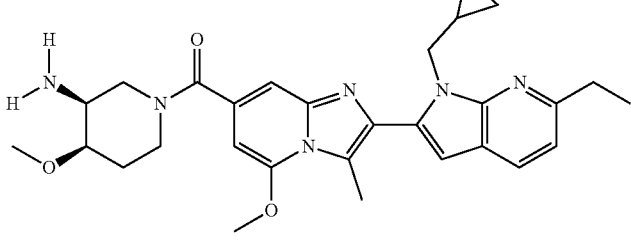 | [(3~{S},4~{R})-3-amino-4-methoxypiperidin-1-yl]-[2-[1-(cyclopropylmethyl)-6-ethylpyrrolo[2,3-b]pyridin-2-yl]-5-methoxy-3-methylimidazo[1,2-a]pyridin-7-yl]methanone |
| 580 | 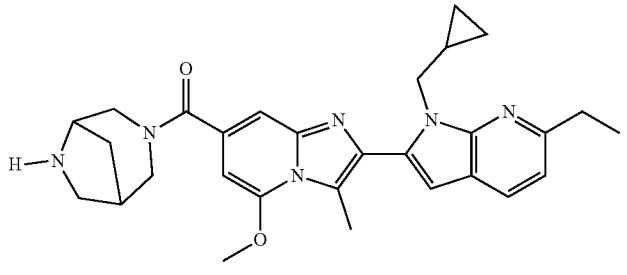 [SMILES: CCc1ccc2cc(-c3nc4cc(C(=O)N5CC6CNC(C6)C5)cc(OC)n4c3C)n(CC3CC3)c2n1] | [2-[1-(cyclopropylmethyl)-6-ethylpyrrolo[2,3-b]pyridin-2-yl]-5-methoxy-3-methylimidazo[1,2-a]pyridin-7-yl]-(3,6-diazabicyclo[3.2.1]octan-3-yl)methanone |

| Ex | Structure | Name |
|---|---|---|
| 581 | 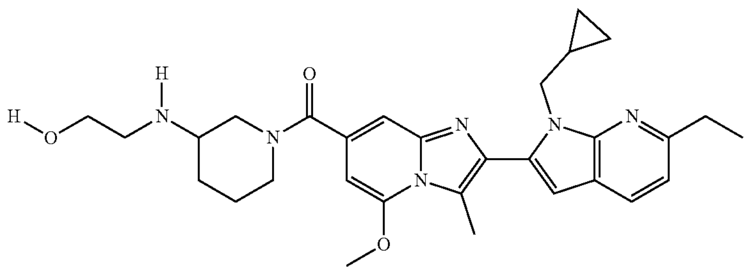 [SMILES: CCc1ccc2cc(-c3nc4cc(C(=O)N5CCCC(NCCO)C5)cc(OC)n4c3C)n(CC3CC3)c2n1] | [2-[1-(cyclopropylmethyl)-6-ethylpyrrolo[2,3-b]pyridin-2-yl]-5-methoxy-3-methylimidazo[1,2-a]pyridin-7-yl]-[3-(2-hydroxyethylamino)piperidin-1-yl]methanone |
| 582 | 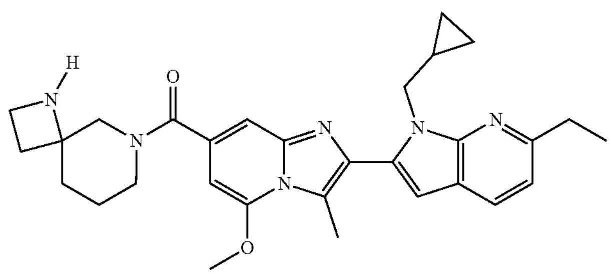 [SMILES: CCc1ccc2cc(-c3nc4cc(C(=O)N5CCCC6(CCN6)C5)cc(OC)n4c3C)n(CC3CC3)c2n1] | [2-[1-(cyclopropylmethyl)-6-ethylpyrrolo[2,3-b]pyridin-2-yl]-5-methoxy-3-methylimidazo[1,2-a]pyridin-7-yl]-(1,8-diazaspiro[3.5]nonan-8-yl)methanone |
| 583 | 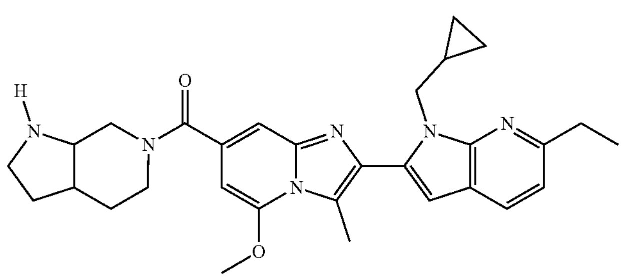 [SMILES: CCc1ccc2cc(-c3nc4cc(C(=O)N5CCC6CCNC6C5)cc(OC)n4c3C)n(CC3CC3)c2n1] | 1,2,3,3~{a},4,5,7,7~{a}-octahydropyrrolo[2,3-c]pyridin-6-yl-[2-[1-(cyclopropylmethyl)-6-ethylpyrrolo[2,3-b]pyridin-2-yl]-5-methoxy-3-methylimidazo[1,2-a]pyridin-7-yl]methanone |
| 584 | 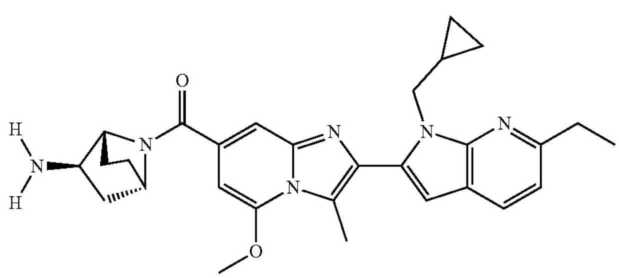 [SMILES: CCc1ccc2cc(-c3nc4cc(C(=O)N5[C@H]6CC[C@@H]5[C@H](N)C6)cc(OC)n4c3C)n(CC3CC3)c2n1] | [(1~{R},2~{R},4~{S})-2-amino-7-azabicyclo[2.2.1]heptan-7-yl]-[2-[1-(cyclopropylmethyl)-6-ethylpyrrolo[2,3-b]pyridin-2-yl]-5-methoxy-3-methylimidazo[1,2-a]pyridin-7-yl]methanone |
| 585 | 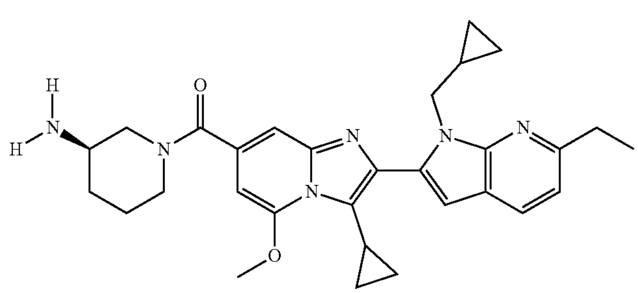 [SMILES: CCc1ccc2cc(-c3nc4cc(C(=O)N5CCC[C@@H](N)C5)cc(OC)n4c3C3CC3)n(CC3CC3)c2n1] | [(3~{R})-3-aminopiperidin-1-yl]-[3-cyclopropyl-2-[1-(cyclopropylmethyl)-6-ethylpyrrolo[2,3-b]pyridin-2-yl]-5-methoxyimidazo[1,2-a]pyridin-7-yl]methanone |

| Ex | Structure | Name |
|---|---|---|
| 586 | 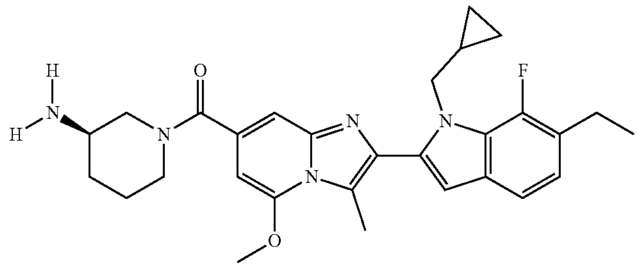 [SMILES: CCc1ccc2cc(-c3nc4cc(C(=O)N5CCC[C@@H](N)C5)cc(OC)n4c3C)n(CC3CC3)c2c1F] | [(3~{R})-3-aminopiperidin-1-yl]-[2-[1-(cyclopropylmethyl)-6-ethyl-7-fluoroindol-2-yl]-5-methoxy-3-methylimidazo[1,2-a]pyridin-7-yl]methanone |
| 587 | 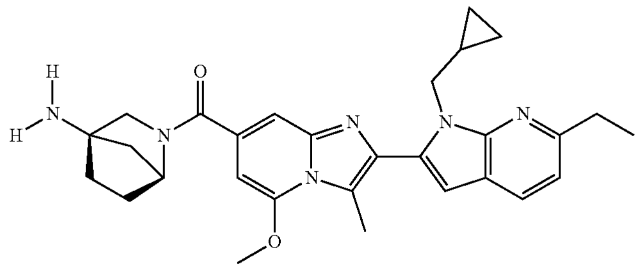 [SMILES: CCc1ccc2cc(-c3nc4cc(C(=O)N5C[C@]6(N)CC[C@H]5C6)cc(OC)n4c3C)n(CC3CC3)c2n1] | [(1~{S},4~{S})-4-amino-2-azabicyclo[2.2.1]heptan-2-yl]-[2-[1-(cyclopropylmethyl)-6-ethylpyrrolo[2,3-b]pyridin-2-yl]-5-methoxy-3-methylimidazo[1,2-a]pyridin-7-yl]methanone |
| 588 | 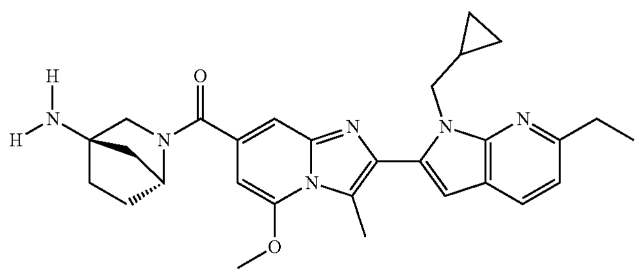 [SMILES: CCc1ccc2cc(-c3nc4cc(C(=O)N5C[C@@]6(N)CC[C@@H]5C6)cc(OC)n4c3C)n(CC3CC3)c2n1] | [(1~{R},4~{R})-4-amino-2-azabicyclo[2.2.1]heptan-2-yl]-[2-[1-(cyclopropylmethyl)-6-ethylpyrrolo[2,3-b]pyridin-2-yl]-5-methoxy-3-methylimidazo[1,2-a]pyridin-7-yl]methanone |
| 589 | 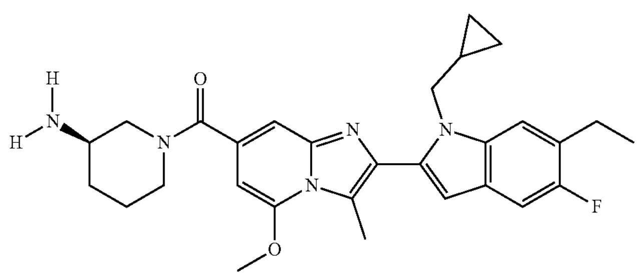 [SMILES: CCc1cc2c(cc1F)cc(-c1nc3cc(C(=O)N4CCC[C@@H](N)C4)cc(OC)n3c1C)n2CC1CC1] | [(3~{R})-3-aminopiperidin-1-yl]-[2-[1-(cyclopropylmethyl)-6-ethyl-5-fluoroindol-2-yl]-5-methoxy-3-methylimidazo[1,2-a]pyridin-7-yl]methanone |
| 590 | 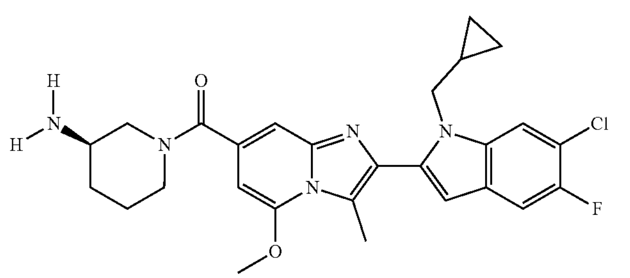 [SMILES: COc1cc(C(=O)N2CCC[C@@H](N)C2)cc2nc(-c3cc4cc(F)c(Cl)cc4n3CC3CC3)c(C)n12] | [(3~{R})-3-aminopiperidin-1-yl]-[2-[6-chloro-1-(cyclopropylmethyl)-5-fluoroindol-2-yl]-5-methoxy-3-methylimidazo[1,2-a]pyridin-7-yl]methanone |

-continued

| Ex | Structure | Name |
| --- | --- | --- |
| 591 | 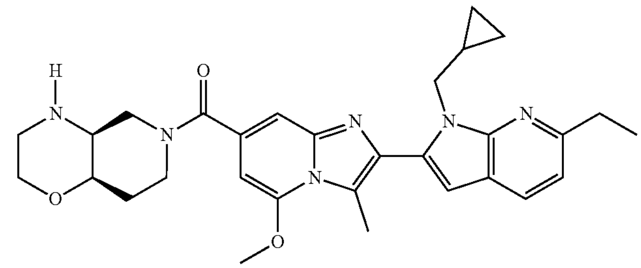 [SMILES: CCc1ccc2cc(-c3nc4cc(C(=O)N5CC[C@H]6OCCN[C@H]6C5)cc(OC)n4c3C)n(CC3CC3)c2n1] | [(4~{a}~{S},8~{a}~{R})-2,3,4,4~{a},5,7,8,8~{a}-octahydropyrido[4,3-b][1,4]oxazin-6-yl]-[2-[1-(cyclopropylmethyl)-6-ethylpyrrolo[2,3-b]pyridin-2-yl]-5-methoxy-3-methylimidazo[1,2-a]pyridin-7-yl]methanone |
| 592 | 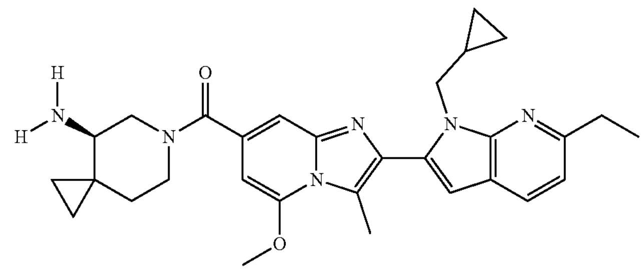 [SMILES: CCc1ccc2cc(-c3nc4cc(C(=O)N5CCC6(CC6)[C@@H](N)C5)cc(OC)n4c3C)n(CC3CC3)c2n1] | [(8~{R})-8-amino-6-azaspiro[2.5]octan-6-yl]-[2-[1-(cyclopropylmethyl)-6-ethylpyrrolo[2,3-b]pyridin-2-yl]-5-methoxy-3-methylimidazo[1,2-a]pyridin-7-yl]methanone |
| 593 | 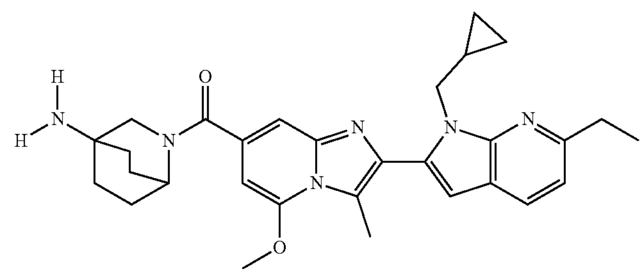 [SMILES: CCc1ccc2cc(-c3nc4cc(C(=O)N5CC6(N)CCC5CC6)cc(OC)n4c3C)n(CC3CC3)c2n1] | (4-amino-2-azabicyclo[2.2.2]octan-2-yl)-[2-[1-(cyclopropylmethyl)-6-ethylpyrrolo[2,3-b]pyridin-2-yl]-5-methoxy-3-methylimidazo[1,2-a]pyridin-7-yl]methanone |
| 594 | 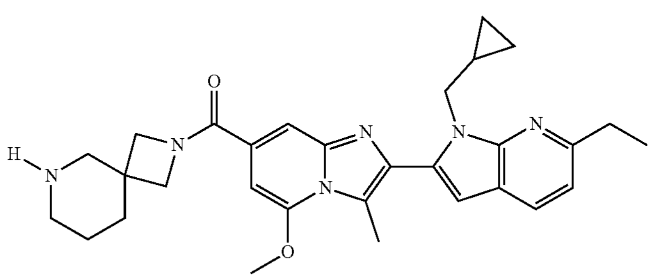 | [2-[1-(cyclopropylmethyl)-6-ethylpyrrolo[2,3-b]pyridin-2-yl]-5-methoxy-3-methylimidazo[1,2-a]pyridin-7-yl]-(2,8-diazaspiro[3.5]nonan-2-yl)methanone |
| 595 | 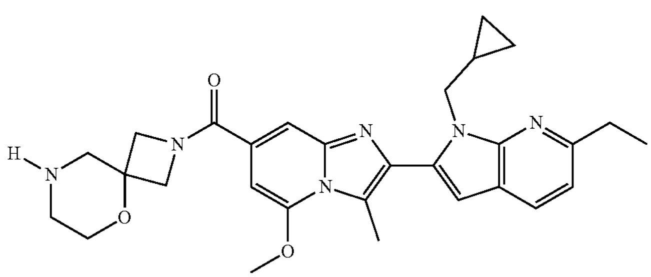 [SMILES: CCc1ccc2cc(-c3nc4cc(C(=O)N5CC6(CNCCO6)C5)cc(OC)n4c3C)n(CC3CC3)c2n1] | [2-[1-(cyclopropylmethyl)-6-ethylpyrrolo[2,3-b]pyridin-2-yl]-5-methoxy-3-methylimidazo[1,2-a]pyridin-7-yl]-(5-oxa-2,8-diazaspiro[3.5]nonan-2-yl)methanone |

-continued

| Ex | Structure | Name |
|---|---|---|
| 596 | 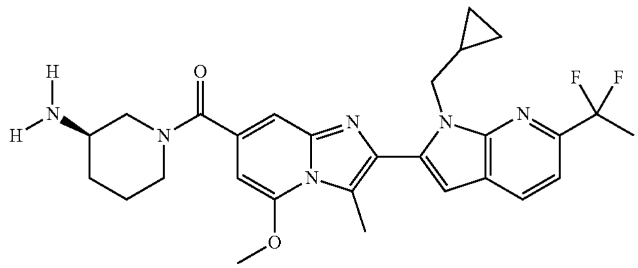 [SMILES: COc1cc(C(=O)N2CCC[C@@H](N)C2)cc2nc(-c3cc4ccc(C(C)(F)F)nc4n3CC3CC3)c(C)n12] | [(3~{R})-3-aminopiperidin-1-yl]-[2-[1-(cyclopropylmethyl)-6-(1,1-difluoroethyl)pyrrolo[2,3-b]pyridin-2-yl]-5-methoxy-3-methylimidazo[1,2-a]pyridin-7-yl]methanone |
| 597 | 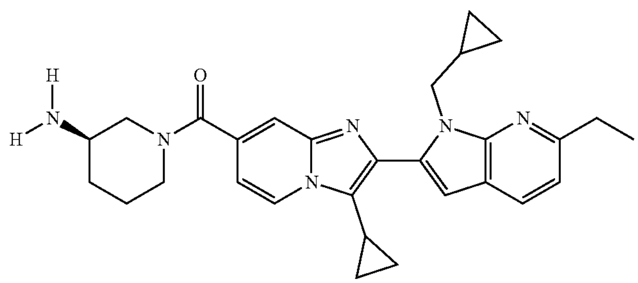 [SMILES: CCc1ccc2cc(-c3nc4cc(C(=O)N5CCC[C@@H](N)C5)ccn4c3C3CC3)n(CC3CC3)c2n1] | [(3~{R})-3-aminopiperidin-1-yl]-[3-cyclopropyl-2-[1-(cyclopropylmethyl)-6-ethylpyrrolo[2,3-b]pyridin-2-yl]imidazo[1,2-a]pyridin-7-yl]methanone |
| 598 | 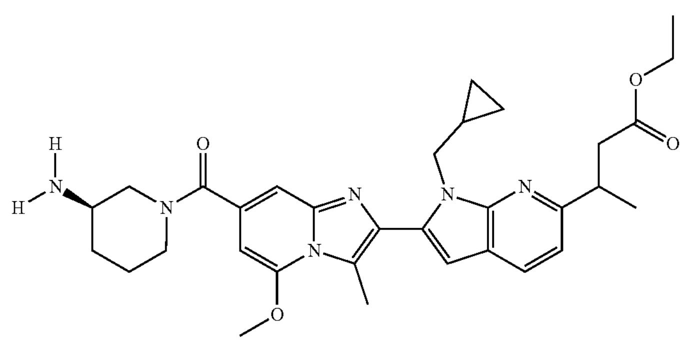 [SMILES: CCOC(=O)CC(C)c1ccc2cc(-c3nc4cc(C(=O)N5CCC[C@@H](N)C5)cc(OC)n4c3C)n(CC3CC3)c2n1] | ethyl 3-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]butanoate |
| 599 | 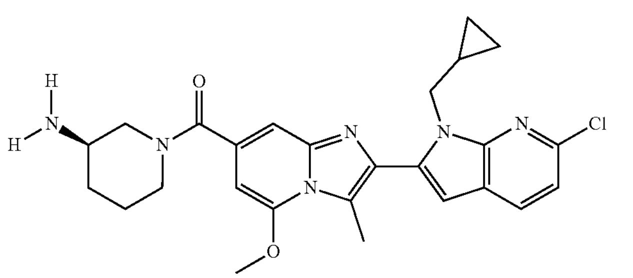 [SMILES: COc1cc(C(=O)N2CCC[C@@H](N)C2)cc2nc(-c3cc4ccc(Cl)nc4n3CC3CC3)c(C)n12] | [(3~{R})-3-aminopiperidin-1-yl]-[2-[6-chloro-1-(cyclopropylmethyl)pyrrolo[2,3-b]pyridin-2-yl]-5-methoxy-3-methylimidazo[1,2-a]pyridin-7-yl]methanone |
| 600 | 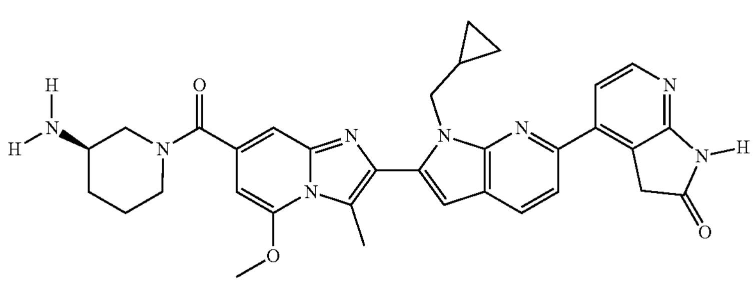 [SMILES: COc1cc(C(=O)N2CCC[C@@H](N)C2)cc2nc(-c3cc4ccc(-c5ccnc6c5CC(=O)N6)nc4n3CC3CC3)c(C)n12] | 4-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]-1,3-dihydropyrrolo[2,3-b]pyridin-2-one |

-continued

| Ex | Structure | Name |
|---|---|---|
| 601 | 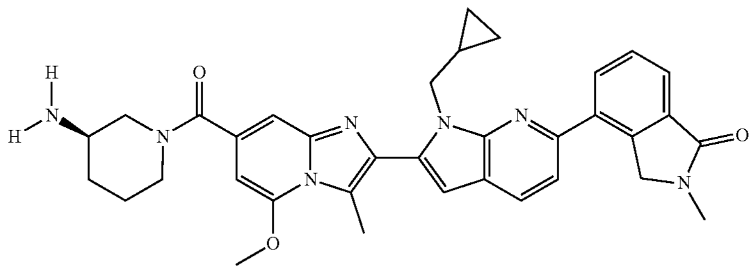 [SMILES: COc1cc(C(=O)N2CCC[C@@H](N)C2)cc2nc(-c3cc4ccc(-c5cccc6c5CN(C)C6=O)nc4n3CC3CC3)c(C)n12] | 4-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]-2-methyl-3~{H}-isoindol-1-one |
| 602 | 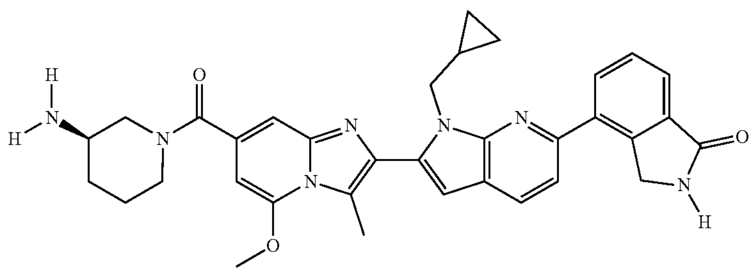 [SMILES: COc1cc(C(=O)N2CCC[C@@H](N)C2)cc2nc(-c3cc4ccc(-c5cccc6c5CNC6=O)nc4n3CC3CC3)c(C)n12] | 4-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]-2,3-dihydroisoindol-1-one |
| 603 | 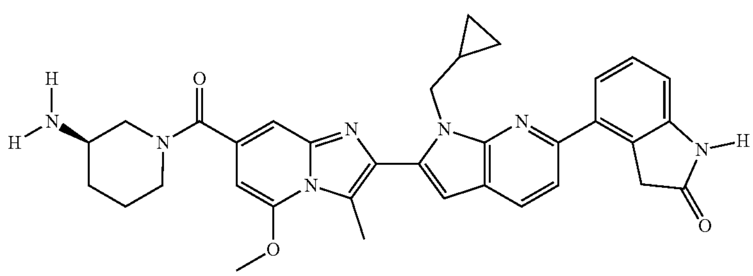 | 4-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]-1,3-dihydroindol-2-one |
| 604 | 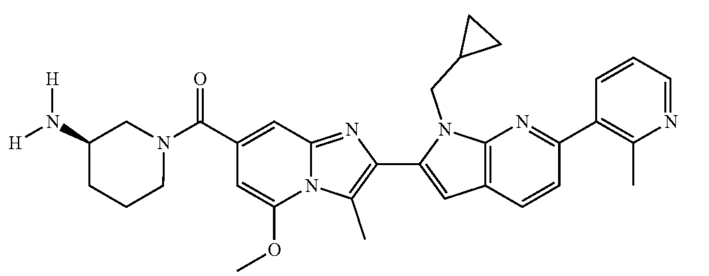 [SMILES: COc1cc(C(=O)N2CCC[C@@H](N)C2)cc2nc(-c3cc4ccc(-c5cccnc5C)nc4n3CC3CC3)c(C)n12] | [(3~{R})-3-aminopiperidin-1-yl]-[2-[1-(cyclopropylmethyl)-6-(2-methylpyridin-3-yl)pyrrolo[2,3-b]pyridin-2-yl]-5-methoxy-3-methylimidazo[1,2-a]pyridin-7-yl]methanone |
| 605 | 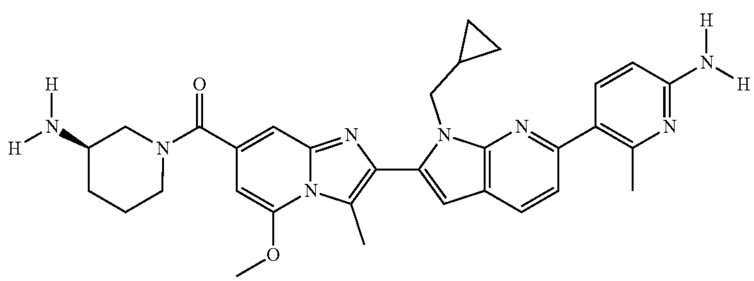 [SMILES: COc1cc(C(=O)N2CCC[C@@H](N)C2)cc2nc(-c3cc4ccc(-c5ccc(N)nc5C)nc4n3CC3CC3)c(C)n12] | [2-[6-(6-amino-2-methylpyridin-3-yl)-1-(cyclopropylmethyl)pyrrolo[2,3-b]pyridin-2-yl]-5-methoxy-3-methylimidazo[1,2-a]pyridin-7-yl]-[(3~{R})-3-aminopiperidin-1-yl]methanone |

| Ex | Structure | Name |
|---|---|---|
| 606 | 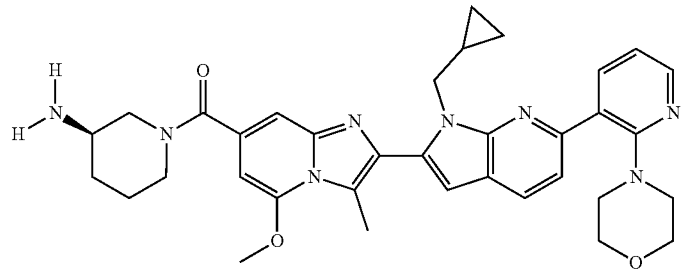 [SMILES: COc1cc(C(=O)N2CCC[C@@H](N)C2)cc2nc(-c3cc4ccc(-c5cccnc5N5CCOCC5)nc4n3CC3CC3)c(C)n12] | [(3~{R})-3-aminopiperidin-1-yl]-[2-[1-(cyclopropylmethyl)-6-(2-morpholin-4-ylpyridin-3-yl)pyrrolo[2,3-b]pyridin-2-yl]-5-methoxy-3-methylimidazo[1,2-a]pyridin-7-yl]methanone |
| 607 | 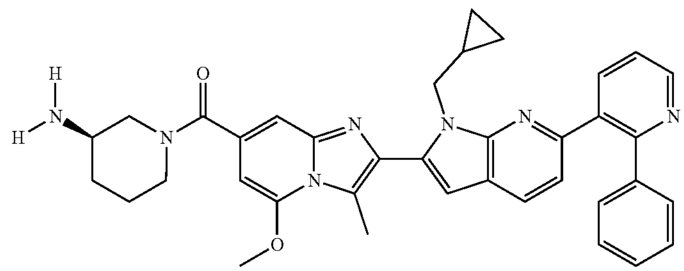 [SMILES: COc1cc(C(=O)N2CCC[C@@H](N)C2)cc2nc(-c3cc4ccc(-c5cccnc5-c5ccccc5)nc4n3CC3CC3)c(C)n12] | [(3~{R})-3-aminopiperidin-1-yl]-[2-[1-(cyclopropylmethyl)-6-(2-phenylpyridin-3-yl)pyrrolo[2,3-b]pyridin-2-yl]-5-methoxy-3-methylimidazo[1,2-a]pyridin-7-yl]methanone |
| 608 | 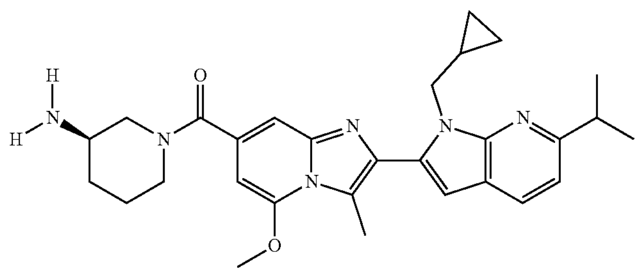 [SMILES: COc1cc(C(=O)N2CCC[C@@H](N)C2)cc2nc(-c3cc4ccc(C(C)C)nc4n3CC3CC3)c(C)n12] | [(3~{R})-3-aminopiperidin-1-yl]-[2-[1-(cyclopropylmethyl)-6-propan-2-ylpyrrolo[2,3-b]pyridin-2-yl]-5-methoxy-3-methylimidazo[1,2-a]pyridin-7-yl]methanone |
| 609 | 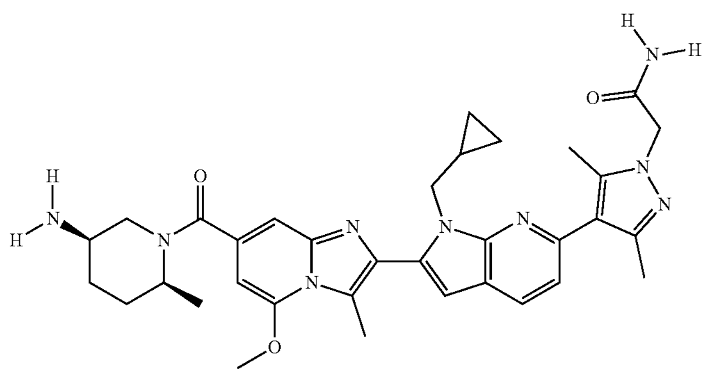 [SMILES: COc1cc(C(=O)N2C[C@H](N)CC[C@@H]2C)cc2nc(-c3cc4ccc(-c5c(C)nn(CC(N)=O)c5C)nc4n3CC3CC3)c(C)n12] | 2-[4-[2-[7-[(2~{S},5~{R})-5-amino-2-methylpiperidine-1-carbonyl]-5-methoxy-3-methylimidazo[1,2-a]pyridin-2-yl]-1-(cyclopropylmethyl)pyrrolo[2,3-b]pyridin-6-yl]-3,5-dimethylpyrazol-1-yl]acetamide |
| 610 | 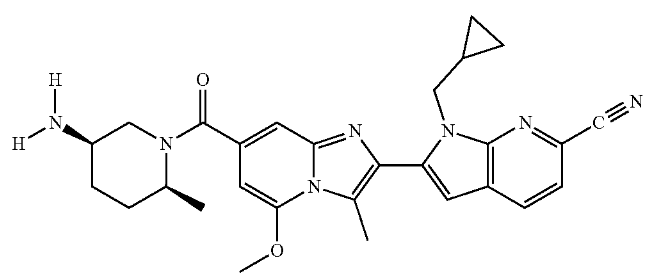 [SMILES: COc1cc(C(=O)N2C[C@H](N)CC[C@@H]2C)cc2nc(-c3cc4ccc(C#N)nc4n3CC3CC3)c(C)n12] | 2-[7-[(2~{S},5~{R})-5-amino-2-methylpiperidine-1-carbonyl]-5-methoxy-3-methylimidazo[1,2-a]pyridin-2-yl]-1-(cyclopropylmethyl)pyrrolo[2,3-b]pyridine-6-carbonitrile |

| Ex | Structure | Name |
|---|---|---|
| 611 | 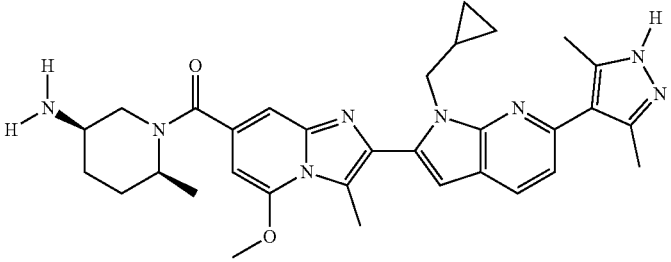 [SMILES: COc1cc(C(=O)N2C[C@H](N)CC[C@@H]2C)cc2nc(-c3cc4ccc(-c5c(C)n[nH]c5C)nc4n3CC3CC3)c(C)n12] | [(2~{S},5~{R})-5-amino-2-methylpiperidin-1-yl]-[2-[1-(cyclopropylmethyl)-6-(3,5-dimethyl-1~{H}-pyrazol-4-yl)pyrrolo[2,3-b]pyridin-2-yl]-5-methoxy-3-methylimidazo[1,2-a]pyridin-7-yl]methanone |
| 612 | 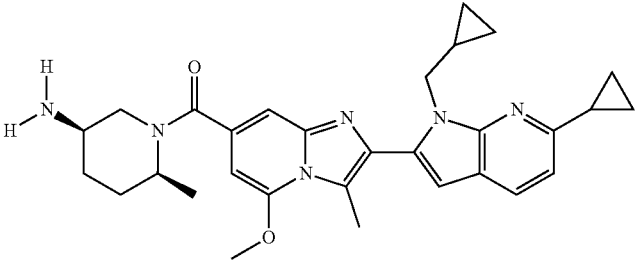 [SMILES: COc1cc(C(=O)N2C[C@H](N)CC[C@@H]2C)cc2nc(-c3cc4ccc(C5CC5)nc4n3CC3CC3)c(C)n12] | [(2~{S},5~{R})-5-amino-2-methylpiperidin-1-yl]-[2-[6-cyclopropyl-1-(cyclopropylmethyl)pyrrolo[2,3-b]pyridin-2-yl]-5-methoxy-3-methylimidazo[1,2-a]pyridin-7-yl]methanone |
| 613 | 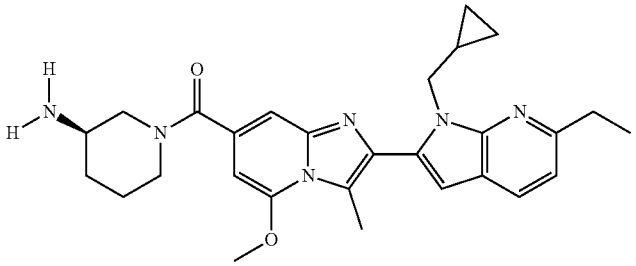 | [(3~{R})-3-aminopiperidin-1-yl]-[2-[1-(cyclopropylmethyl)-6-ethylpyrrolo[2,3-b]pyridin-2-yl]-5-methoxy-3-methylimidazo[1,2-a]pyridin-7-yl]methanone |
| 614 | 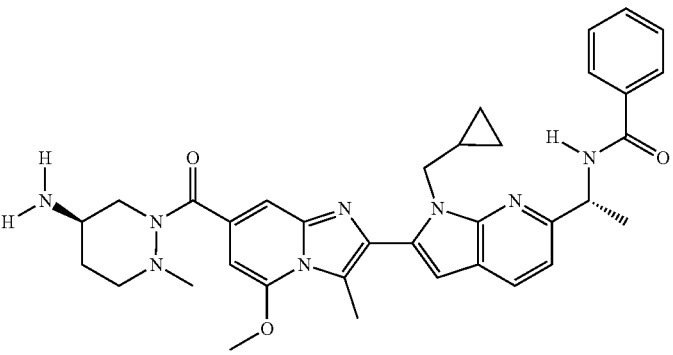 [SMILES: COc1cc(C(=O)N2C[C@H](N)CCN2C)cc2nc(-c3cc4ccc([C@@H](C)NC(=O)c5ccccc5)nc4n3CC3CC3)c(C)n12] | N-((R)-1-(2-(7-((R)-5-amino-2-methylhexahydropyridazine-1-carbonyl)-5-methoxy-3-methylimidazo[1,2-a]pyridin-2-yl)-1-(cyclopropylmethyl)-1H-pyrrolo[2,3-b]pyridin-6-yl)ethyl)benzamide |
| 615 | 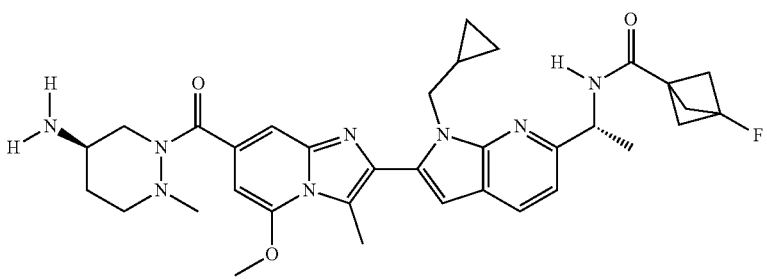 [SMILES: COc1cc(C(=O)N2C[C@H](N)CCN2C)cc2nc(-c3cc4ccc([C@@H](C)NC(=O)C56CC(F)(C5)C6)nc4n3CC3CC3)c(C)n12] | N-((R)-1-(2-(7-((R)-5-amino-2-methylhexahydropyridazine-1-carbonyl)-5-methoxy-3-methylimidazo[1,2-a]pyridin-2-yl)-1-(cyclopropylmethyl)-1H-pyrrolo[2,3-b]pyridin-6-yl)ethyl)-3-fluorobicyclo[1.1.1]pentane-1-carboxamide |

| Ex | Structure | Name |
|---|---|---|
| 616 | 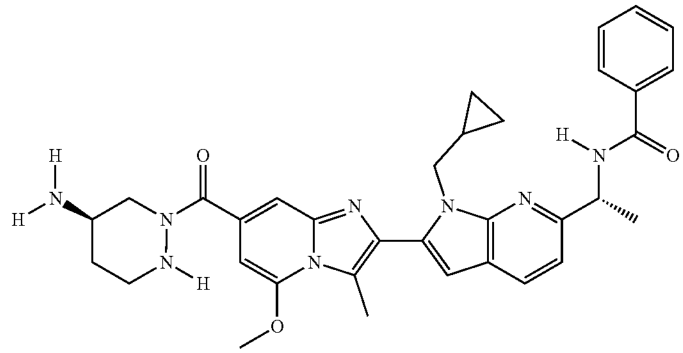 [SMILES: COc1cc(C(=O)N2C[C@H](N)CCN2)cc2nc(-c3cc4ccc([C@@H](C)NC(=O)c5ccccc5)nc4n3CC3CC3)c(C)n12] | tert-butyl N-[(4R)-2-[2-[6-[(1R)-1-benzamidoethyl]-1-(cyclopropylmethyl)pyrrolo[2,3-b]pyridin-2-yl]-5-methoxy-3-methyl-imidazo[1,2-a]pyridine-7-carbonyl]hexahydropyridazin-4-yl]carbamate |
| 617 | 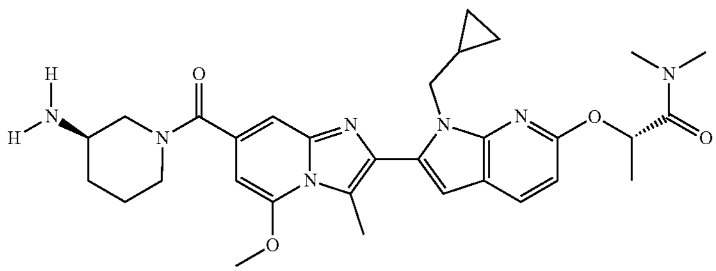 [SMILES: COc1cc(C(=O)N2CCC[C@@H](N)C2)cc2nc(-c3cc4ccc(O[C@@H](C)C(=O)N(C)C)nc4n3CC3CC3)c(C)n12] | (2~{S})-2-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]oxy-~{N},~{N}-dimethylpropanamide |
| 618 | 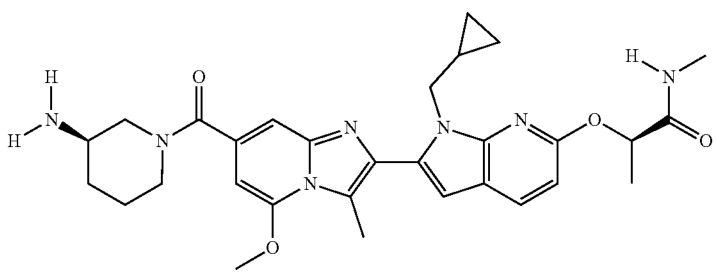 | ethyl 4-[(1~{R})-1-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]ethyl]amino]-4-oxobutanoate |
| 619 | 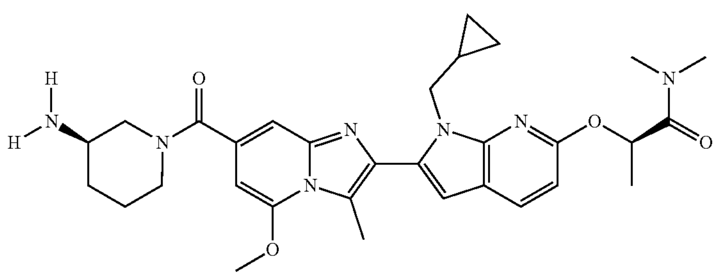 [SMILES: COc1cc(C(=O)N2CCC[C@@H](N)C2)cc2nc(-c3cc4ccc(O[C@H](C)C(=O)N(C)C)nc4n3CC3CC3)c(C)n12] | (2~{R})-2-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]oxy-~{N},~{N}-dimethylpropanamide |
| 620 | 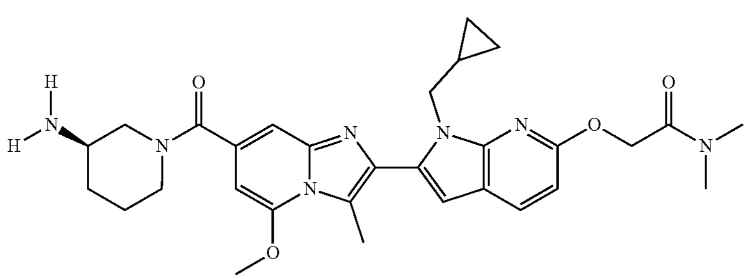 [SMILES: COc1cc(C(=O)N2CCC[C@@H](N)C2)cc2nc(-c3cc4ccc(OCC(=O)N(C)C)nc4n3CC3CC3)c(C)n12] | 2-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]oxy-~{N},~{N}-dimethylacetamide |

-continued

| Ex | Structure | Name |
|---|---|---|
| 621 | 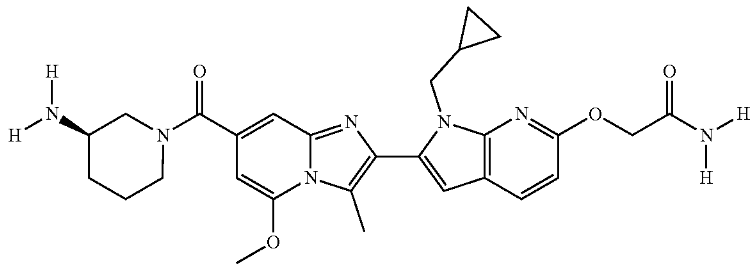 [SMILES: COc1cc(C(=O)N2CCC[C@@H](N)C2)cc2nc(-c3cc4ccc(OCC(N)=O)nc4n3CC3CC3)c(C)n12] | 2-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]oxyacetamide |
| 622 | 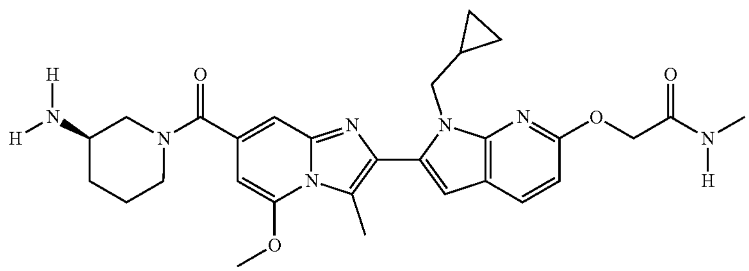 | 2-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]oxy-~{N}-methylacetamide |
| 623 | 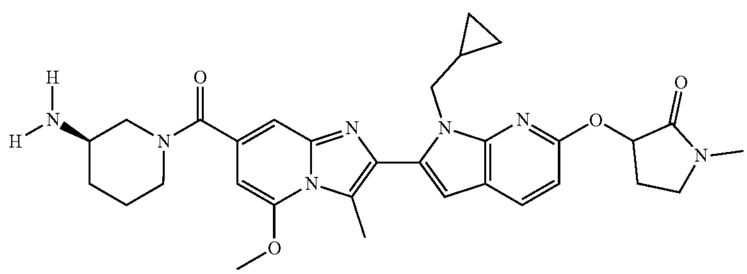 [SMILES: COc1cc(C(=O)N2CCC[C@@H](N)C2)cc2nc(-c3cc4ccc(OC5CCN(C)C5=O)nc4n3CC3CC3)c(C)n12] | 3-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]oxy-1-methylpyrrolidin-2-one |
| 624 | 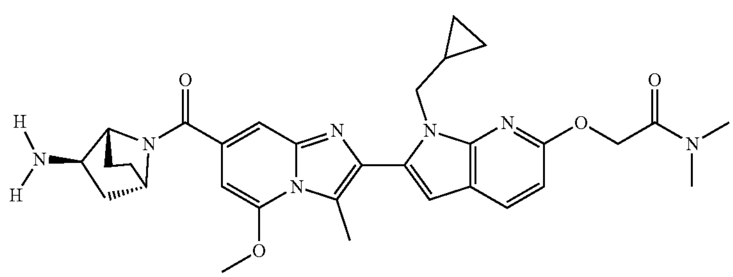 [SMILES: COc1cc(C(=O)N2[C@H]3CC[C@@H]2[C@H](N)C3)cc2nc(-c3cc4ccc(OCC(=O)N(C)C)nc4n3CC3CC3)c(C)n12] | 2-[2-[7-[(1~{R},2~{R},4~{S})-2-amino-7-azabicyclo[2.2.1]heptane-7-carbonyl]-5-methoxy-3-methylimidazo[1,2-a]pyridin-2-yl]-1-(cyclopropylmethyl)pyrrolo[2,3-b]pyridin-6-yl]oxy-~{N},~{N}-dimethylacetamide |
| 625 | 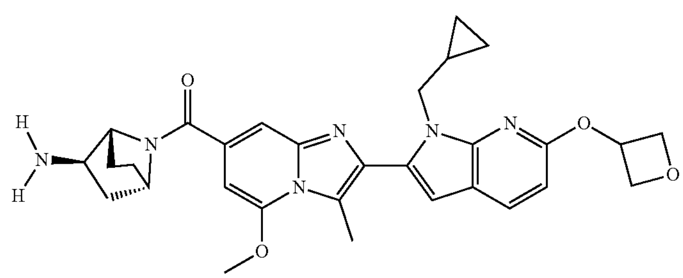 [SMILES: COc1cc(C(=O)N2[C@H]3CC[C@@H]2[C@H](N)C3)cc2nc(-c3cc4ccc(OC5COC5)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-(oxetan-3-yloxy)pyrrolo[2,3-b]pyridin-2-yl]-5-methoxy-3-methylimidazo[1,2-a]pyridin-7-yl]methanone |

| Ex | Structure | Name |
|---|---|---|
| 626 | 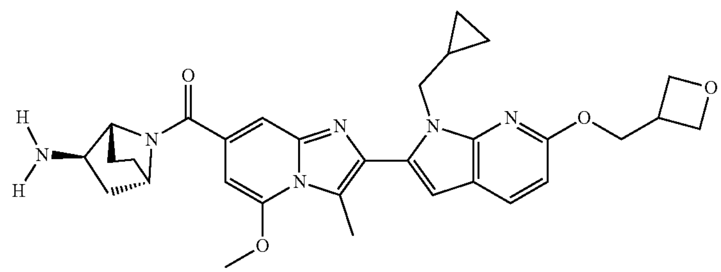 [SMILES: COc1cc(C(=O)N2[C@H]3CC[C@@H]2[C@H](N)C3)cc2nc(-c3cc4ccc(OCC5COC5)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-(oxetan-3-ylmethoxy)pyrrolo[2,3-b]pyridin-2-yl]-5-methoxy-3-methylimidazo[1,2-a]pyridin-7-yl]methanone |
| 627 | 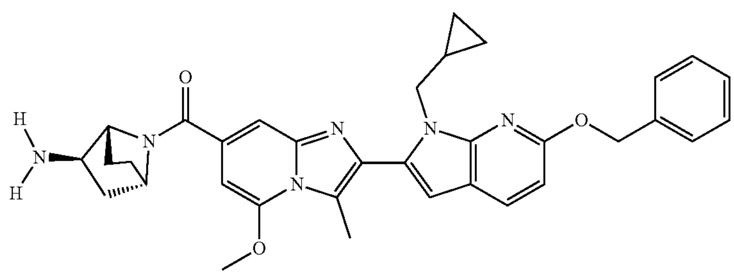 [SMILES: COc1cc(C(=O)N2[C@H]3CC[C@@H]2[C@H](N)C3)cc2nc(-c3cc4ccc(OCc5ccccc5)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-phenylmethoxypyrrolo[2,3-b]pyridin-2-yl]-5-methoxy-3-methylimidazo[1,2-a]pyridin-7-yl]methanone |
| 628 | 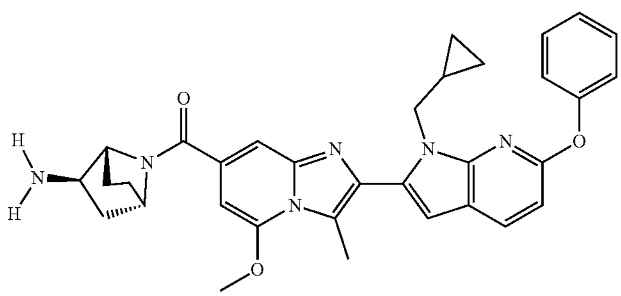 [SMILES: COc1cc(C(=O)N2[C@H]3CC[C@@H]2[C@H](N)C3)cc2nc(-c3cc4ccc(Oc5ccccc5)nc4n3CC3CC3)c(C)n12] | [(1~{R},2~{R},4~{S})-2-amino-7-azabicyclo[2.2.1]heptan-7-yl]-[2-[1-(cyclopropylmethyl)-6-phenoxypyrrolo[2,3-b]pyridin-2-yl]-5-methoxy-3-methylimidazo[1,2-a]pyridin-7-yl]methanone |
| 629 | 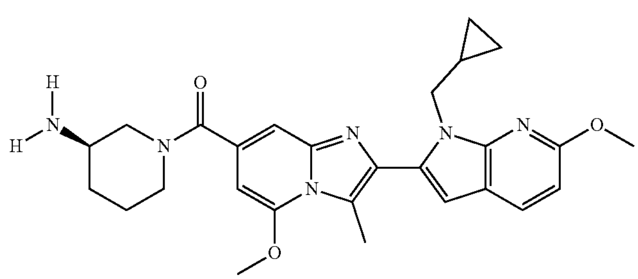 [SMILES: COc1ccc2cc(-c3nc4cc(C(=O)N5CCC[C@@H](N)C5)cc(OC)n4c3C)n(CC3CC3)c2n1] | [(3~{R})-3-aminopiperidin-1-yl]-[2-[1-(cyclopropylmethyl)-6-methoxypyrrolo[2,3-b]pyridin-2-yl]-5-methoxy-3-methylimidazo[1,2-a]pyridin-7-yl]methanone |
| 630 | 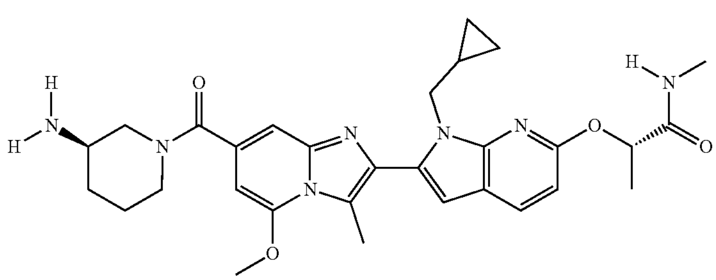 | (2~{S})-2-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]oxy-~{N}-methylpropanamide |

| Ex | Structure | Name |
|---|---|---|
| 631 | 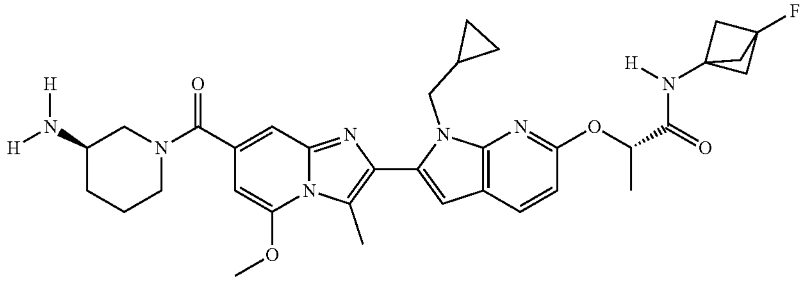 [SMILES: COc1cc(C(=O)N2CCC[C@@H](N)C2)cc2nc(-c3cc4ccc(O[C@@H](C)C(=O)NC56CC(F)(C5)C6)nc4n3CC3CC3)c(C)n12] | (2~{S})-2-[2-[7-[(3~{R})-3-aminopiperidine-1-carbonyl]-5-methoxy-3-methylimidazo[1,2-a]pyridin-2-yl]-1-(cyclopropylmethyl)pyrrolo[2,3-b]pyridin-6-yl]oxy-~{N}-(3-fluoro-1-bicyclo[1.1.1]pentanyl)propanamide |
| 632 | 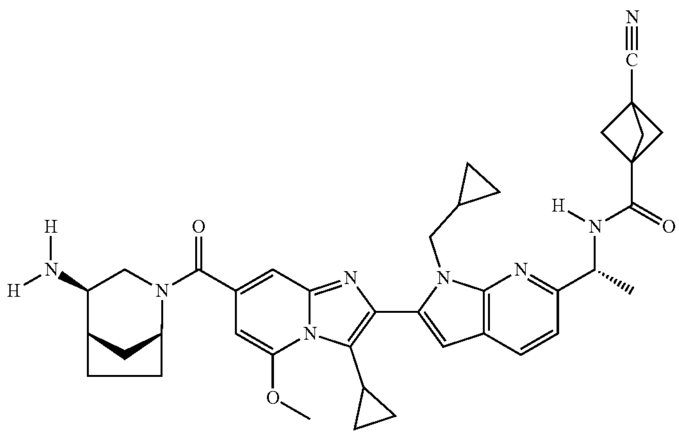 [SMILES: COc1cc(C(=O)N2C[C@H](N)[C@H]3CC[C@@H]2C3)cc2nc(-c3cc4ccc([C@@H](C)NC(=O)C56CC(C#N)(C5)C6)nc4n3CC3CC3)c(C3CC3)n12] | N-((R)-1-(2-(7-((1S,4R,5R)-4-amino-2-azabicyclo[3.2.1]octane-2-carbonyl)-3-cyclopropyl-5-methoxyimidazo[1,2-a]pyridin-2-yl)-1-(cyclopropylmethyl)-1H-pyrrolo[2,3-b]pyridin-6-yl)ethyl)-3-cyanobicyclo[1.1.1]pentane-1-carboxamide |

One of skill in the art is aware that each and every embodiment of a group (e.g., $R^1$) disclosed herein may be combined with any other embodiment of each of the remaining groups (e.g., $R^{10}$, $R^{11}$, $Z^1$, etc.) to generate a complete compound of Formula I, or any Formula described herein or a pharmaceutically acceptable salt thereof, each of which is deemed within the ambit of the present disclosure.

Methods and Compositions

Peptidylarginine deiminase type 4 (PAD4) is hypothesized to be involved in an array of functions, including regulation of transcription, cell cycle, apoptosis, formation of neutrophil extracellular traps (NETs), and tumorgenesis. Expression of PAD4 is restricted to cells of the myeloid lineage, such as neutrophils, eosinophils and monocyte/macrophages.

The present disclosure provides compounds and compositions capable of inhibiting peptidylarginine deiminase type 4 (PAD4), and thus, the present disclosure provides a method for treating a disease or disorder mediated by peptidylarginine deiminase type 4 (PAD4), comprising administering an effective amount of a compound of Formula I, or any formula described herein, or a pharmaceutically acceptable salt thereof, to a patient in need thereof.

As used herein, "treatment" or "treating" is an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and/or c) relieving the disease or condition, e.g., causing the regression of clinical symptoms, ameliorating the disease state, delaying the progression of the disease, increasing the quality of life, and/or prolonging survival.

As used herein, "delaying" development of a disease or condition means to defer, hinder, slow, retard, stabilize and/or postpone development of the disease or condition. This delay can be of varying lengths of time, depending on the history of the disease and/or subject being treated.

As used herein, "prevention" or "preventing" refers to a regimen that protects against the onset of the disease or disorder such that the clinical symptoms of the disease do not develop. Thus, "prevention" relates to administration of a therapy (e.g., administration of a therapeutic substance) to a subject before signs of disease are detectable in the subject.

As used herein, the term "therapeutically effective amount" or "effective amount" refers to an amount that is effective to elicit the desired biological or medical response, including the amount of a compound that, when administered to a subject for treating a disease, is sufficient to effect such treatment for the disease or to an amount that is effective to protect against the contracting or onset of a disease. The effective amount will vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment outcome. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

"Patient" and "subject" refer to humans, domestic animals (e.g., dogs and cats), farm animals (e.g., cattle, horses, sheep, goats and pigs), laboratory animals (e.g., mice, rats, hamsters, guinea pigs, pigs, pocket pets, rabbits, dogs, and monkeys), and the like. In certain embodiments, the patient is a human.

Protein arginine deiminases (PADs) have been contemplated to display some level of substrate specificity possibly related to their tissue specific expression pattern. For example, keratins are physiological substrates of PAD1 and PAD3, myelin basic protein, enolase are citrullinated by PAD2, whereas histones and transcription factors are citrullinated by PAD4. In vitro, PADs are capable of citrullinating various substrates including intracellular and extracellular arginine containing proteins, peptides and peptide mimetics such as benzoyl arginine ethyl ester, used frequently in biochemical assays. Hydrolysis of peptidyl arginine to citrulline removes positive charge, and therefore may affect protein folding, stability, activity, and ability to form hydrogen bonds. Moreover, citrullinated proteins in susceptible individuals such as rheumatoid arthritis (RA) patients become neo-antigens and elicit an autoimmune response leading to the production of anti-citrullinated protein antibodies known as ACPA. The immunogenic property of citrullinated epitopes appears to be specific to RA, with ACPA detectable in 75% of RA patients and displaying 98% specificity for the disease. RA is a disabling autoimmune disease characterized by chronic inflammation of the joints and synovial tissues, pain and progressive bone destruction. ACPA may appear years prior to the onset of clinical RA and their presence correlates with disease prognosis. ACPA are regarded not only as a useful biomarker for RA diagnosis and for predicting a severe disease course, but they have also been postulated to contribute to a disease pathogenesis. Although the antigens recognized by ACPA are diverse and differ between RA patients, a number of common autoantigens have been reported: citrullinated forms of vimentin, enolase, fibrinogen, collagen II, and histones. PAD4 and also PAD2 are contemplated to be responsible for the generation of citrullinated neo-epitopes in RA as their expression is elevated in the inflamed synovium. Neutrophils and macrophages are the main source of these enzymes. Neutrophils are the most abundant white blood cells in circulation. As critical players in the early innate immune response, they hone quickly to sites of inflammation, are abundant in RA synovial fluid and have been shown to be involved in disease pathology. Neutrophils are also short-lived and may undergo inflammatory forms of cell death, including NETosis and necroptosis, which have been implicated in driving inflammation in the RA synovium. Several lines of evidence point to a putative role for citrullination and ACPAs in driving RA. Genetic (HLA-DR-SE risk allele) and environmental (smoking, periodontitis) factors linked to RA are intimately associated with citrullination and ACPAs. Multiple intracellular and extracellular citrullinated proteins (for example enolase, vimentin, fibrinogen, histones, actin, and collagen) are present in RA synovial tissues but absent in healthy or non-RA synovial tissue. Moreover, PADI4 polymorphisms are linked to RA susceptibility and have been identified in large GWAS studies. PAD4 itself is a target of an autoimmune response and 13-18% of RA patients develop anti-PAD4 antibodies; these auto-antibodies have been shown to activate PAD4 by modulating the enzyme's requirement for calcium and are associated with increased risk of progressive joint damage, interstitial lung disease, and poorer response to SOC.

Currently, it is not fully understood what drives excessive citrullination in RA, or even RA "at risk" individuals. It is contemplated that stimulation of synovial protein citrullination might be linked to the neutrophil cell death/lysis that can occur via one of several proinflammatory mechanisms. Moreover, it is hypothesized that citrullinated proteins are not only acting as neo-epitopes, but are involved directly in disease pathology. PAD4 is postulated to contribute to inflammatory processes in RA via the generation of ACPA neo-epitopes and formation of ACPA-immune complexes which could promote further citrullination, inflammation and pathology through engagement of Fc receptors. Aberrant protein citrullination might also modify the function of critical processes in the RA synovium, either independently or upon association of with cognate ACPAs. For example, it was demonstrated that osteoclast differentiation is linked to the citrullination of proteins and that some ACPAs were able to bind to osteoclast precursor cells promoting differentiation and activation in vitro and stimulation of IL-8 production. Moreover, infusion of some ACPAs into mice causes IL-8 dependent bone loss and IL-8 mediated pain behavior and exaggerate bone erosion in a methylate bovine serum albumin induced arthritis.

Therefore, PAD4 inhibitors should be explored as novel therapeutics for treatment of ACPA positive RA (over 75% of all RA patients) where disease could be exaggerated by citrullination and ACPA immune complexes and other types of RA. Animal studies with the use of knockout (KO) animals or PAD inhibitors provided additional rationale for the use of PAD4 inhibitors in treatment of RA. For example, in a chronic joint inflammation models such as collagen induced arthritis (CIA) or glucose-6 phosphate isomerase induced arthritis, PAD4 KO (DBA/1J) mice display improved clinical (around 60% reduction), histological scores, reduced antibody titer, and reduction of some pro inflammatory cytokines. Similarly, prophylactic treatment with pan-PAD covalent inhibitors such as chloroamidine and BB-chloroamidine or reversible PAD4-specific inhibitor GSK199 in a murine CIA model led to improvement of clinical and histological scores, reduction of antibodies titer and epitope spreading, reduction of citrullinated proteins in joints and shift from pro-inflammatory to pro-resolution immunological responses.

Beyond RA, activated PAD4 was also shown to be necessary and sufficient for citrullination of a histone H3 on neutrophil extracellular traps (NETs). Therefore, it is thought that PAD4 might be involved in a formation of NETs and citrullination of additional proteins associated with these structures. NETs are composed of chromatin and nuclear, cytoplasmic and granules proteins extruded from neutrophils during programmed cell death known as NETosis. NETosis is often regarded as a doubled-edged sword, because although it is a part of a normal antimicrobial defense, excessive NETs formation and/or defective NETs clearance induce inflammatory responses. NETosis results in a release of citrullinated proteins, granules' enzymes, antimicrobial proteins and DNA-protein complexes that can become neo-antigens and fuel autoimmunity in susceptible individuals. Moreover, active PADs are released during NETosis and can citrullinate cellular proteins associated with NETs and extracellular proteins in synovium or vasculature. NETs were also contemplated to serve as scaffolds for thrombosis. For that reason, NETosis has been postulated to exacerbate autoimmune and other inflammatory diseases with neutrophil infiltration. Thus, it was contemplated that targeting PAD4 may have therapeutic potential in diseases associated with sterile inflammation. PAD4 KO mice show improved outcome, protection from tissue and organs injury, deceased disease parameters and attenuation of NETosis markers in several murine models of acute or chronic injury such as stenosis model of deep vein thrombosis, myocardial ischemia/reperfusion, LPS endotoxemic shock and cecal ligation puncture (CLP) sepsis. Moreover, pan-PAD covalent inhibitors such as BB-chloroamidine, chloroamidine, or YW3-56 resulted in reduction of clinical, inflammatory, histopathological and mechanical end points, attenuation of NETosis and improved outcome in various models of chronic and acute inflammatory diseases including MRL/lpr mouse model of lupus, hemorrhagic shock in rats, mouse CLP sepsis model, mouse DSS-colitis, mouse ApoE$^{-/-}$ and high fat diet arteriosclerosis model, mouse streptozotocin induced diabetic wound healing model. Therefore, PAD4 inhibitors may have therapeutic potential in treatment of disease linked to pathological consequences of NETosis beyond RA, such as systemic lupus erythematous, antiphospholipid antibody syndrome, small vessels vasculitis, colitis, thrombosis, atherosclerosis, sepsis, diabetes, among others.

In certain embodiments, the disease or disorder mediated by peptidylarginine deiminase type 4 (PAD4) is acute lymphocytic leukemia, ankylosing spondylitis, cancer, chronic lymphocytic leukemia, colitis, lupus, systemic lupus erythematosus, cutaneous lupus erythematosus, rheumatoid arthritis, multiple sclerosis, or ulcerative colitis. Accordingly, provided is a method for treating acute lymphocytic leukemia, ankylosing spondylitis, cancer, chronic lymphocytic leukemia, colitis, lupus, systemic lupus erythematosus, cutaneous lupus erythematosus, rheumatoid arthritis, multiple sclerosis, or ulcerative colitis, comprising administering an effective amount of a compound of Formula I, or any formula described herein, or a pharmaceutically acceptable salt thereof, to a patient in need thereof.

As PAD4 may contribute to the initiation and propagation of RA, PAD4 inhibitors can be envisioned as a prophylactic treatment for individuals that are at risk of developing clinical RA, as identified by ACPA positivity, family history of RA, exposure to environmental factors, genetic predisposition and presence of arthralgia.

In certain embodiments, the disease or disorder is inflammatory arthritis. In certain embodiments, the disease or disorder is rheumatoid arthritis. Accordingly, provided is a method for treating rheumatoid arthritis, comprising administering an effective amount of a compound of Formula I, or any formula described herein, or a pharmaceutically acceptable salt thereof, to a patient in need thereof provided is a method for treating rheumatoid arthritis, comprising administering an effective amount of a compound of Table 1, or a pharmaceutically acceptable salt thereof, to a patient in need thereof. In certain embodiments, the disease or disorder is systemic lupus. In certain embodiments, the disease or disorder is vasculitis. In certain embodiments, the disease or disorder is cutaneous lupus erythematosus. In certain embodiments, the disease or disorder is psoriasis. In certain embodiments, the disease or disorder is a fibrotic lung disease, such as idiopathic pulmonary fibrosis (IPF). In certain embodiments, the disease or disorder is fibroproliferative lung disease. In certain embodiments, the disease or disorder is rheumatoid arthritis with joint and/or lung disease. In certain embodiments, the disease or disorder is inflammatory bowel disease.

In certain embodiments, the disease or disorder is acid-induced lung injury, acne (PAPA), acute lymphocytic leukemia, acute, respiratory distress syndrome, Addison's disease, adrenal hyperplasia, adrenocortical insufficiency, ageing, AIDS, alcoholic hepatitis, alcoholic hepatitis, alcoholic liver disease, allergen induced asthma, allergic bronchopulmonary, aspergillosis, allergic conjunctivitis, alopecia, Alzheimer's disease, amyloidosis, amyotrophic lateral sclerosis, and weight loss, angina pectoris, angioedema, anhidrotic ecodermal dysplasia-ID, ankylosing spondylitis, anterior segment, inflammation, antiphospholipid syndrome, aphthous stomatitis, appendicitis, arthritis, asthma, atherosclerosis, atopic dermatitis, autoimmune diseases, autoimmune hepatitis, bee sting-induced inflammation, Behcet's disease, Behcet's syndrome, Bells Palsy, berylliosis, Blau syndrome, bone pain, bronchiolitis, burns, bursitis, cancer, cardiac hypertrophy, carpal tunnel syndrome, catabolic disorders, cataracts, cerebral aneurysm, chemical irritant-induced inflammation, chorioretinitis, chronic heart failure, chronic lung disease of prematurity, chronic lymphocytic leukemia, chronic obstructive pulmonary disease, colitis, complex regional pain syndrome, connective tissue disease, corneal ulcer, Crohn's disease, cryopyrin-associated periodic syndromes, cyrptococcosis, cystic fibrosis, deficiency of the interleukin-1receptor antagonist (DIRA), dermatitis, dermatitis endotoxemia, dermatomyositis, diffuse intrinsic pontine glioma, endometriosis, endotoxemia, epicondylitis, erythroblastopenia, familial amyloidotic polyneuropathy, familial cold urticarial, familial Mediterranean fever, fetal growth retardation, glaucoma, glomerular disease, glomerular nephritis, gout, gouty arthritis, graft-versus-host disease, gut diseases, head injury, headache, hearing loss, heart disease, hemolytic anemia, Henoch-Scholein purpura, hepatitis, hereditary periodic fever syndrome, herpes zoster and simplex, HIV-1, hypercalcemia, hypercholesterolemia, hyperimmunoglobulinemia D with recurrent fever (HIDS), hypoplastic and other anemias, hypoplastic anemia, idiopathic thrombocytopenic purpura, incontinentia pigmenti, infectious mononucleosis, inflammatory bowel disease, inflammatory lung disease, inflammatory neuropathy, inflammatory pain, insect bite-induced inflammation, iritis, irritant-induced inflammation, ischemia/reperfusion, juvenile rheumatoid arthritis, keratitis, kidney disease, kidney injury caused by parasitic infections, kidney injury caused by parasitic infections, kidney transplant rejection prophylaxis, leptospiriosis, leukemia, Loeffler's syndrome, lung injury, fibrotic lung disease, lupus, lupus nephritis, lymphoma, meningitis, mesothelioma, mixed connective tissue disease, Muckle-Wells syndrome (urticaria deafness amyloidosis), multiple sclerosis, muscle wasting, muscular dystrophy, myasthenia gravis, myocarditis, mycosis fungoides, mycosis fungoides, myelodysplastic syndrome, myositis, nasal sinusitis, necrotizing enterocolitis, neonatal onset multisystem inflammatory disease (NOMID), nephrotic syndrome, neuritis, neuropathological diseases, non-allergen induced asthma, obesity, ocular allergy, optic neuritis, organ transplant, osteoarthritis, otitis media, Paget's disease, pain, pancreatitis, Parkinson's disease, pemphigus, pericarditis, periodic fever, periodontitis, peritoneal endometriosis, pertussis, pharyngitis and adenitis (PFAPA syndrome), plant irritant-induced inflammation, pneumonia, pneumonitis, pneumosysts infection, poison ivy/urushiol oil-induced inflammation, polyarteritis nodosa, polychondritis, polycystic kidney disease, polymyositis, psoriasis, psoriasis, psoriasis, psoriasis, psychosocial stress diseases, pulmonary disease, pulmonary hypertension, pulmonary fibrosis, pyoderma gangrenosum, pyogenic sterile arthritis, renal disease, retinal disease, rheumatic carditis, rheumatic disease, rheumatoid arthritis, sarcoidosis, seborrhea, sepsis, severe pain, sickle cell, sickle cell anemia, silica-induced disease, Sjogren's syndrome, skin diseases, sleep apnea, solid tumors, spinal cord injury, Stevens-Johnson syndrome, stroke, subarachnoid haemorrhage, sunburn, temporal arteritis, tenosynovitis, thrombocytopenia, thyroiditis, tissue transplant, TNF receptor associated periodic syndrome (TRAPS), toxoplasmosis, transplant, traumatic brain injury, tuberculosis, type 1 diabetes, type 2 diabetes, ulcerative colitis, urticarial, uveitis, Wegener's granulomatosis, interstitial lung disease, psoriatic arthritis, juvenile idiopathic arthritis, Sjogren's syndrome, antineutrophil cytoplasmic antibody (ANCA)-associated Alzheimer's, scleroderma or CREST syndrome.

In certain embodiments, the disease or disorder is one or more of rheumatoid arthritis, systemic lupus erythematosus, multiple sclerosis, or cancer.

In certain embodiments, the present disclosure provides a method for treating anti-neutrophil cytoplasm antibodies (ANCA) vasculitis, antiphospholipid syndrome, psoriasis, lung inflammatory diseases, interstitial lung disease (ILD), idiopathic pulmonary fibrosis (IPF), acute lung injury (ALI), acute respiratory distress syndrome (ARDS), chronic obstructive pulmonary disease (COPD), cystic fibrosis (CF), or COVID 19 ARDS, comprising administering an effective amount of a compound of Formula I, or any formula described herein, or a pharmaceutically acceptable salt thereof, to a patient in need thereof.

Also provided is a pharmaceutical composition comprising a compound of Formula I, or any formula described herein, or a pharmaceutically acceptable salt thereof, and a pharmaceutically acceptable carrier or excipient. Also provided is a pharmaceutical composition comprising a compound of Table 1, or a pharmaceutically acceptable salt thereof, and a pharmaceutically acceptable carrier or excipient.

The pharmaceutical compositions of compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

In one aspect, the compounds described herein may be administered orally. Oral administration may be via, for example, capsule or enteric coated tablets. In making the pharmaceutical compositions that include at least one compound of Formula I, or a pharmaceutically acceptable salt, is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions may, in some embodiments, be formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. In some embodiments, for oral administration, each dosage unit contains from about 10 mg to about 1000 mg of a compound described herein, for example from about 50 mg to about 500 mg, for example about 50 mg, about 75 mg, about 100 mg, about 150 mg, about 200 mg, about 225 mg, about 250 mg, about 275 mg, about 300 mg, about 325 mg, about 350 mg, about 375 mg, about 400 mg, about 425 mg, about 450 mg, about 475 mg, or about 500 mg. In other embodiments, for parenteral administration, each dosage unit contains from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual subject, and the severity of the subject's symptoms.

In certain embodiments, dosage levels of the compound of Formula I may be from 0.1 mg to 100 mg per kilogram of body weight per day, for example from about 1 mg to about 50 mg per kilogram, for example from about 5 mg to about 30 mg per kilogram. Such dosage levels may, in certain instances, be useful in the treatment of the above-indicated conditions. In other embodiments, dosage levels may be from about 10 mg to about 2000 mg per subject per day. The amount of active ingredient that may be combined with the vehicle to produce a single dosage form will vary depending upon the host treated and the particular mode of administration. Dosage unit forms may contain from 1 mg to 1000 mg of an active ingredient.

The compounds disclosed herein, or a pharmaceutically acceptable salt thereof, may be administered to a subject in accordance with an effective dosing regimen for a desired period of time or duration, such as at least about one day, at least about one week, at least about one month, at least about 2 months, at least about 3 months, at least about 4 months, at least about 6 months, or at least about 12 months or longer. In one variation, the compound is administered on a daily or intermittent schedule. In one variation, the compound is administered on a monthly schedule. In one variation, the compound is administered every two months. In one variation, the compound is administered every three months. In one variation, the compound is administered every four months. In one variation, the compound is administered every five months. In one variation, the compound is administered every 6 months.

The dosage or dosing frequency of a compound disclosed herein, or a pharmaceutically acceptable salt thereof, may be adjusted over the course of the treatment, based on the judgment of the administering physician. The compound may be administered to a subject (e.g., a human) in an effective amount. In certain embodiments, the compound is administered once daily.

For preparing solid compositions such as tablets, the principal active ingredient may be mixed with a pharmaceutical excipient to form a solid preformulation composition containing a homogeneous mixture of a compound of Formula I, or a pharmaceutically acceptable salt, thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

In certain embodiments, a method of treating or preventing rheumatoid arthritis (RA) comprising administering a therapeutically effective amount of a compound disclosed herein, or a pharmaceutically acceptable salt thereof, to a subject in need thereof, is provided. In certain embodiments, a method of treating RA comprising administering a therapeutically effective amount of a compound disclosed herein, or a pharmaceutically acceptable salt thereof, to a subject in need thereof, is provided. In certain embodiments, the method comprises administering a compound disclosed herein, or a pharmaceutically acceptable salt thereof, in combination with one, two, three, or four additional therapeutic agents. In certain embodiments, the subject may have not previously received prior treatment (treatment nave) for RA. In certain embodiments, the subject may have previously received treatment (treatment experienced) for RA.

In certain embodiments, a compound disclosed herein, or a pharmaceutically acceptable salt thereof for use in the manufacture of a medicament for treating RA in a subject (e.g., a human) is disclosed.

Also disclosed herein is a compound disclosed herein, or a pharmaceutically acceptable salt thereof, for use in the therapeutic treatment or delaying the onset of RA.

Also disclosed herein is a compound disclosed herein, or a pharmaceutically acceptable salt thereof, for use in the therapeutic treatment of RA.

In certain embodiments, a compound disclosed herein, or a pharmaceutically acceptable salt thereof can be used as a research tool (e.g., to study the inhibition of PAD4 in a subject or in vitro).

Kits that include a compound of Formula I, or a pharmaceutically acceptable salt, thereof, and suitable packaging are provided. In one embodiment, a kit further includes instructions for use. In one aspect, a kit includes a compound of Formula I, or a pharmaceutically acceptable salt thereof, and instructions for use of the compounds in the treatment of the diseases or conditions described herein.

Articles of manufacture that include a compound of Formula I, or a pharmaceutically acceptable salt thereof, in a suitable container are provided. The container may be a vial, jar, ampoule, preloaded syringe, and intravenous bag.

Combination Therapy

In certain embodiments, a compound disclosed herein is administered with one or more additional therapeutic agents. In one embodiment, the present disclosure provides a pharmaceutical composition comprising a compound of Formula I, or any formula described herein, or a pharmaceutically acceptable salt thereof, and at least one additional therapeutic agent and at least one pharmaceutically acceptable carrier or excipient.

In one embodiment, the present disclosure provides a pharmaceutical composition comprising a compound of Formula I, or any formula described herein, or a pharmaceutically acceptable salt thereof, at least one additional therapeutic agent suitable for treating rheumatoid arthritis, and at least one pharmaceutically acceptable carrier or excipient.

Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and the one or more additional therapeutic agents are both present in the body of the patient. When administered sequentially, the combination may be administered in two or more administrations.

Co-administration includes administration of unit dosages of the compounds disclosed herein before or after administration of unit dosages of one or more additional therapeutic agents. For example, the compound disclosed herein may be administered within seconds, minutes, or hours of the administration of the one or more additional therapeutic agents. In some embodiments, a unit dose of a compound disclosed herein is administered first, followed within seconds or minutes by administration of a unit dose of one or more additional therapeutic agents. Alternatively, a unit dose of one or more additional therapeutic agents is administered first, followed by administration of a unit dose of a compound disclosed herein within seconds or minutes. In other embodiments, a unit dose of a compound disclosed herein is administered first, followed, after a period of hours (e.g., 1-12 hours), by administration of a unit dose of one or more additional therapeutic agents. In yet other embodiments, a unit dose of one or more additional therapeutic agents is administered first, followed, after a period of hours (e.g., 1-12 hours), by administration of a unit dose of a compound disclosed herein.

In certain embodiments, a compound disclosed herein is combined with one or more additional therapeutic agents in a unitary dosage form for simultaneous administration to a patient, for example as a solid dosage form for oral administration.

In certain embodiments, a compound of Formula I is formulated as a tablet, which may optionally contain one or more other compounds useful for treating the target indication. In certain embodiments, such tablets are suitable for once daily dosing. In other embodiments, the tablets are suitable for twice a day dosing.

Combination Drugs

In one embodiment, a compound as disclosed herein, such as a compound of Formula I, or Table 1, may be combined with one or more other active agents.

For example, in certain embodiments, a compound as disclosed herein, such as a compound of Formula I, or Table 1, may be used in combination with conventional synthetic and targeted synthetic disease-modifying antirheumatic drugs (DMARDs) or biological DMARDs due to orthogonal or complementary mechanisms of action.

The one or more active agents may be chosen from 14-3-3 protein eta inhibitors, 5-Lipoxygenase inhibitors, Abl tyrosine kinase inhibitors, ACTH receptor agonists, Adenosine A3 receptor agonists, adenosine deaminase inhibitors, ADP ribosyl cyclase-1 inhibitors, ADP ribosyl cyclase-1 modulators, ADP ribosylation factor 6 inhibitors, Adrenocorticotrophic hormone ligands, Aggrecanase-2 inhibitors, Albumin modulators, AP1 transcription factor inhibitors, Basigin inhibitors, Bcr protein inhibitors, B-lymphocyte antigen CD19 inhibitors, B-lymphocyte antigen CD20 inhibitors, B-lymphocyte antigen CD20 modulators, B-lymphocyte stimulator ligand inhibitors, Bradykinin receptor modulators, BRAF gene inhibitors, branched amino acid aminotransferase 1 inhibitors, Bromodomain containing protein inhibitors, BTK tyrosine kinase inhibitors, Cadherin-11 antagonists, Calcineurin inhibitors, Calcium channel inhibitors, Carbonic anhydrase inhibitors, Cathepsin K inhibitors, Cathepsin S inhibitors, CCR1 chemokine antagonists, CCR2 chemokine antagonists, CCR3 gene modulators, CCR5 chemokine antagonists, CD126 antagonists, CD29 modulators, CD3 modulators, CD39 agonists, CD4 agonists, CD4 antagonists, CD40 ligand inhibitors, CD40 ligand receptor antagonists, CD40 ligand receptor modulators, CD52 antagonists, CD73 agonists, CD79b modulators, CD80 antagonists, CD86 antagonists, CD95 antagonists, Cell adhesion molecule inhibitors, Choline kinase inhibitors, Clusterin stimulators, Complement $C_5$ factor inhibitors, Complement Factor stimulators, C-reactive protein inhibitors, CSF-1 antagonists, CXC10 chemokine ligand inhibitors, CXCR4 chemokine antagonists, Cyclin-dependent kinase inhibitor 1 inhibitors, Cyclin-dependent kinase-2 inhibitors, Cyclin-dependent kinase-4 inhibitors, Cyclin-dependent kinase-5 inhibitors, Cyclin-dependent kinase-6 inhibitors, Cyclin-dependent kinase-7 inhibitors, Cyclin-dependent kinase-9 inhibitors, Cyclooxygenase 2 inhibitors, Cyclooxygenase 2 modulators, Cyclooxygenase inhibitors, Cytosolic phospholipase A2 inhibitors, Cytotoxic T-lymphocyte protein-4 modulators, Cytotoxic T-lymphocyte protein-4 stimulators, DHFR inhibitors, Diamine acetyltransferase inhibitors, Dihydroorotate dehydrogenase inhibitors, Elongation factor 2 inhibitors, Eotaxin 2 ligand inhibitors, EP4 prostanoid receptor antagonists, Erythropoietin receptor agonists, Fas ligands, FGF-2 ligand inhibitors, FK506 binding protein-12 modulators, Folate antagonists, Folate receptor agonists, Folate receptor beta antagonists, Folate receptor modulators, Fractalkine ligand inhibitors, Fyn tyrosine kinase inhibitors, G protein coupled receptor 15 antagonists, GABAA receptor modulators, glucocorticoid agonists, Glucocorticoid antagonists, Glucocorticoid induced leucine zipper stimulators, GM-CSF ligand inhibitors, GM-CSF receptor antagonists, GM-CSF receptor modulators, growth regulated protein alpha ligand inhibitors, H+ K+ ATPase inhibitors, histamine H4 receptor antagonists, histone deacetylase inhibitors, histone deacetylase-6 inhibitors, HIV-1 gp120 protein inhibitors, HLA class II antigen DQ-2 alpha modulators, HLA class II antigen inhibitors, HLA class II antigen modulators, Hsp 70 family inhibitors, Hypoxia inducible factor-1 inhibitors, IFNB gene stimulators, I-kappa B kinase beta inhibitors, I-kappa B kinase inhibitors, IL-1 antagonists, IL-10 agonists, IL-11 agonists, IL-12 antagonists, IL-15 antagonists, IL-17 antagonists, IL-17 receptor modulators, IL-8 ligand inhibitors, IL-2 agonists, IL-2 antagonists, IL-21 antagonists, IL-23 antagonists, IL-3 antagonists, IL-4 agonists, IL-6 antagonists, IL-6 receptor modulators, IL-6 neutralizing human antibodies, anti-IL6 antibody, immunoglobulin antagonists, immunoglobulin G1 agonists, immunoglobulin G1 antagonists, Immunoglobulin G1 modulators, Immunoglobulin G2 antagonists, immunoglobulin G2 modulators, immunoglobulin gamma Fc receptor II modulators, immunoglobulin gamma Fc receptor IIB antagonists, immunoglobulin kappa modulators, immunoglobulin M antagonists, inducible nitric oxide synthase inhibitors, Inosine monophosphate dehydrogenase inhibitors, insulin sensitizers, integrin alpha-1/beta-1 antagonists, integrin alpha-4/beta-1 antagonists, integrin alpha-9 antagonist, integrin antagonists, interferon beta ligands, interferon gamma ligands, interleukin 17A ligand inhibitors, Interleukin 17F ligand inhibitors, Interleukin 23A inhibitors, Interleukin ligands, Interleukin receptor 17A antagonists, Interleukin-1 beta ligand inhibitors, Interleukin-10 ligands, Interleukin-2 ligands, Interleukin-4 ligands, Interleukin-6 ligand inhibitors, Itk tyrosine kinase inhibitors, JAK tyrosine kinase inhibitors, Jak1 tyrosine kinase inhibitors, Jak2 tyrosine kinase inhibitors, JAK3 gene inhibitors, Jak3 tyrosine kinase inhibitors, Jun N terminal kinase inhibitors, KCNA voltage-gated potassium channel-3 modulators, Kelch like ECH associated protein 1 modulators, Kit tyrosine kinase inhibitors, LanC like protein 2 modulators, Leukotriene BLT receptor antagonist, LITAF gene inhibitors, Lymphocyte function antigen-3 receptor antagonists, Lyn tyrosine kinase inhibitors, Macrophage mannose receptor 1 modulators, MAdCAM inhibitors, MAP kinase modulators, MAP3K2 gene inhibitors, MAPKAPK5 inhibitors, Matrix metalloprotease inhibitors, MCL1 gene inhibitors, MEK protein kinase inhibitors, MEK-1 protein kinase inhibitors, MEK-2 protein kinase inhibitors, Membrane copper amine oxidase inhibitors, Metalloprotease-2 inhibitors, Metalloprotease-9 inhibitors, methylprednisolone, Midkine ligand inhibitors, Mitochondrial 10 kDa heat shock protein stimulators, mTOR complex 1 inhibitors, mTOR inhibitors, NAD ADP ribosyltransferase stimulators, NAMPT inhibitors, NF kappa B inhibitor stimulators, NFAT gene inhibitors, NFE2L2 gene stimulators, Nicotinic acetylcholine receptor antagonists, NK cell receptor modulators, NKG2 A B activating NK receptor antagonists, NKG2 D activating NK receptor antagonists, Nuclear erythroid 2-related factor 2 stimulators, Nuclear factor kappa B inhibitors, Nuclear factor kappa B modulators, Nuclear factor kappa B p105 inhibitors, Opioid growth factor receptor agonists, Opioid receptor delta antagonists, Osteoclast differentiation factor antagonists, Osteoclast differentiation factor ligand inhibitors, Oxidoreductase inhibitors, P2X7 purinoceptor agonists, p38 MAP kinase alpha inhibitors, p38 MAP kinase inhibitors, PDE 4 inhibitors, PDE 5 inhibitors, PDGF receptor agonists, PDGF receptor antagonists, PDGF-B ligand inhibitors, PERK gene inhibitors, Phosphoinositide-3 kinase delta inhibitors, Phosphoinositide-3 kinase gamma inhibitors, Phospholipase A2 inhibitors, Platelet activating factor receptor antagonists, PPAR gamma agonists, Programmed cell death protein 1 modulators, Prostaglandin D synthase stimulators, peptidylarginine deiminase inhibitors, Protein tyrosine kinase inhibitors, PurH purine biosynthesis protein inhibitors, Rho associated protein kinase 2 inhibitors, Seprase inhibitors, Signal transducer CD24 modulators, Signal transduction inhibitors, Sodium glucose transporter-2 inhibitors, Sphingosine 1 phosphate phosphatase modulators, STAT3 gene inhibitors, Superoxide dismutase stimulators, SYK family tyrosine kinase inhibitors, Syk tyrosine kinase inhibitors, Syndecan-1 inhibitors, T cell receptor antagonists, T cell receptor modulators, T cell surface glycoprotein CD28 inhibitors, T cell surface glycoprotein CD28 stimulators, TAK1 binding protein modulators, Talin modulators, T-cell differentiation antigen CD6 inhibitors, T-cell surface glycoprotein CD8 inhibitors, Tenascin modulators, TGF beta agonists, Thymulin agonists, TLR-2 antagonists, TLR-4 antagonists, TLR-9 antagonists, TNF alpha ligand inhibitors, TNF alpha ligand modulators, TNF antagonists, TNF gene inhibitors, TNF receptor modulators, TNFSF11 gene inhibitors, Transcription factor p65 inhibitors, Transcription factor RelB inhibitors, Transferrin modulators, Tumor necrosis factor 13C receptor antagonists, Tumor necrosis factor 15 ligand inhibitors, Tumor necrosis factor ligand 13 inhibitors, Tumor necrosis factor ligand inhibitors, Type I IL-1 receptor antagonists, Type I TNF receptor antagonists, Type II TNF receptor modulators, Unspecified GPCR agonists, VEGF receptor antagonists, VEGF-2 receptor antagonists, VEGF-2 receptor modulators, VEGF-B ligand inhibitors, X-linked inhibitor of apoptosis protein inhibitors, or Zap70 tyrosine kinase inhibitors.

Examples of active agents that may be combined with the compounds described herein include 99mTc labelled annexin V-128, abatacept, abatacept biosimilar, ABBV-257, ABT-122, ABT-494, acalabrutinib, aceclofenac, actarit, AdMSCs, MS-392, adalimumab, adalimumab biosimilar, adalimumab follow-on biologic, AK-106, ALX-0061, aminopterin, anakinra, anakinra biosimilar, anakinra follow-on biologic, ARG-301, ASLAN-003, ASP-5094, AT-132, AZD-9567, baricitinib, BI-655064, bimekizumab, BiP (rheumatoid arthritis), BLHP-006, blisibimod, BMS-986104, BMS-986142, ABBV-105, BTT-1023, canakinumab, Cartistem, CCX-354, CD24-IgFc, celecoxib, cerdulatinib, certolizumab pegol, CF-101, CFZ-533, CHR-5154, cibinetide, ciclosporin, clazakizumab, CNTO-6785, corticotropin, CR-6086, CreaVax-RA, CWG-92, CWG-940, Cx-611, DE-098, DEN-181, deflazacort, Rheumavax, denosumab, diacerein, diclofenac, E-6011, eicosapentaenoic acid monoglycerides, etanercept, etanercept biosimilar, etanercept follow-on biologic, etodolac, etoricoxib, filgotinib, fosdagrocorat, gerilimzumab, ginsenoside C-K, givinostat, goat polyclonal antibodies, golimumab, GS-5745, GS-9876, GSK-3196165, HM-71224, HMPL-523, hyaluronate sodium, IB-RA (injectable, rheumatoid arthritis), IB-RA (oral, rheumatoid arthritis), ICP-022, iguratimod, IMD-2560, imidazole salicylate, infliximab, infliximab biobetter, infliximab biosimilar, CT-P13, INSIX RA, interferon gamma follow-on biologic, interleukin-2 (injectable), interleukin-2 follow-on biologic, INV-103, IR-501, itolizumab, JNJ-40346527, Ka Shu Ning, KD-025, ketoprofen+omeprazole, leflunomide, lenzilumab, LLDT-8, LNP-1955, lumiracoxib, LY-3090106, masitinib, mavrilimumab, MBS-2320, MEDI-5117, meloxicam, methotrexate, MGD-010, misoprostol+diclofenac, MM-A01-01, monalizumab, MORAb-022, MPC-300-IV, MRC-375, nabumetone, namilumab, naproxen+esomeprazole, naproxen+esomeprazole strontium, ocaratuzumab, ofatumumab, OHR-118, olokizumab, OM-89, once-daily naproxen (oral controlled release, pain), ONO-4059, Oralgam, ozoralizumab, peficitinib, pelubiprofen, PF-06687234, piperidone hydrochloridum, piroxicam, prednisolone, prednisone, Procell, Prosorba, PRT-2607, PRTX-100, PRX-167700, QBSAU, rabeximod, RCT-18, recombinant human CD22 monoclonal antibody (iv infusion), Lonn Ryonn Pharma/SinoMab Bioscience (Shenzhen), RA-Curcusome, recombinant human interleukin-1 receptor antagonist (rheumatoid arthritis), recombinant human interleukin-2 recombinant TNF receptor 2-Fc fusion protein mutant, RG-6125, RhuDex, rifabutin+clarithromycin+clofazimine, rituximab, rituximab biosimilar, Toritz, rituximab follow-on biologic, RPI-78, SAN-300, sarilumab, SBI-087, seliciclib, SHR-0302, sirukumab, spebrutinib, SSS-07, KDDF-201110-06, Syn-1002, T-5224, TAB-08, tacrolimus, TAK-020, TAK-079, tarenflurbil (transdermal spraygel, skin disease/rheumatoid arthritis), technetium Tc 99m tilmanocept, technetium[99Tc]methylenediphosphonate, tenoxicam, Debio-0512, tocilizumab, tofacitinib, tofacitinib citrate, *Trichuris suis* ova, umbilical cord-derived mesenchymal stem cells (iv, RA/liver disease), ustekinumab, VAY-736, VB-201, WF-10, XmAb-5871, YHB-1411-2, or YRA-1909.

In certain embodiments, a compound described herein may be combined with a 14-3-3 protein eta inhibitor, such as anti-AGX-020 mAbs (rheumatoid arthritis) or Augurex; a 5-Lipoxygenase inhibitor, such as darbufelone, tebufelone, ZD-2138, etalocib, PGV-20229, L-708780, T-0757, T-0799, ZM-216800, L-699333, BU-4601A, or SKF-104351; a 5-Lipoxygenase/Cyclooxygenase inhibitor, such as tenoxicam, licofelone, tenidap, tepoxalin, flobufen, SKF-86002, WY-28342, or CI-986; or a 5-Lipoxygenase/PPAR gamma agonist, such as etalocib; a Abl tyrosine kinase inhibitor/Bcr protein inhibitor/Kit tyrosine kinase inhibitor/PDGF receptor antagonist/or Signal transduction inhibitors, such as imatinib; a ACTH receptor agonist/Adrenocorticotrophic hormone ligand/Opioid growth factor receptor agonist, such as FAR-404, or metenkefalin acetate+tridecactide acetate; an adenosine A3 receptor agonist, such as CF-101 (piclidenoson); an adenosine deaminase inhibitor, such as cladribine, pentostatin, or FR-221647; a ADP ribosyl cyclase-1 inhibitor, such as daratumumab; a ADP ribosyl cyclase-1 modulator/Syndecan-1 inhibitor, such as indatuximab ravtansine; a ADP ribosylation factor 6 inhibitor, such as NAV-2729; a adrenocorticotrophic hormone ligand, such as corticotropin or Mallinckrodt; aggrecanase-2/TNF gene inhibitors, such as GIBH-R-001-2; albumin modulators, such as ONS-1210; albumin modulators/IL-6 antagonists, such as ALX-0061 (vobarilizumab); albumin modulators/ TNF alpha ligand inhibitors, such as HOT-3010; a AP1 transcription factor/Nuclear factor kappa B inhibitor, such astarenflurbil or SP-100030; anti-TNF steroid antibody-drug conjugates (anti-TNF-GRM), such as ABBV-3373; Basigin inhibitors/Branched amino acid aminotransferase 1/Metalloprotease-9 inhibitors/Metalloprotease-2 inhibitors, such as ERG-240; BET inhibitors such as GSK-3358699; Bispecic anti-CD86/IL-10, such as APVO-210; bispecific humanized monoclonal antibody targeted against BAFF and IL-17A, such as tibulizumab; bispecific antibody-peptide conjugate (BAFF/ICOSL), such as AMG-570; B-lymphocyte antigen CD19 inhibitors, such as MDX-1342; B-lymphocyte antigen CD19 inhibitors/Immunoglobulin gamma Fc receptor IIB antagonists, such as XmAb-5871; B-lymphocyte antigen CD20 inhibitors, such as ocrelizumab, ofatumumab, rituximab, ABP-798, Maball, Mabtas, Reditux, Zytux, veltuzumab, ocaratuzumab, BLX-301, IDEC-102, ABP-798, GP-2013, MK-8808, HLX-01, CT-P10, TL-011, PF-05280586, IBPM-001RX, IBI-301, AME-133v, BCD-020, BT-D004, SAIT-101, or JHL-1101; B-lymphocyte antigen CD20 modulators, such as SBI-087, TRU-015, DXL-625, or MabionCD20; B-lymphocyte stimulator ligand inhibitors, such as belimumab, RCT-18, blisibimod, tabalumab, or briobacept; B-lymphocyte stimulator ligand/Tumor necrosis factor ligand 13 inhibitors, such as atacicept; bradykinin receptor modulators/Histone deacetylase inhibitors/P2X7 purinoceptor agonists, such asgivinostat; BRAF gene/MEK protein kinase/PERK gene inhibitors, such as binimetinib; Bromodomain containing protein inhibitors, such as RVX-297 or ZEN-003694; Btk tyrosine kinase inhibitors, such as AC-0058, acalabrutinib, HM-71224, spebrutinib, BMS-986142, TAK-020, tirabrutinib (ONO-4059), TAS-5315, ABBV-105, GDC-0834, EBI-1459, BMS-986195, evobrutinib, or fenebrutinib; Btk tyrosine kinase inhibitors/Syk tyrosine kinase inhibitors/VEGF-2 receptor antagonists, such as CG-026806; Btk tyrosine kinase inhibitors/IL-6 antagonists, such as RN-486; Btk tyrosine kinase/Jak1 tyrosine kinase inhibitors, such as upadacitinib+ABBV-105; Btk tyrosine kinase/Jak3 tyrosine kinase inhibitors, such as AC-0025; cadherin-11 antagonists, such as RG-6125; calcineurin inhibitors, such as ciclosporin; calcineurin inhibitors/opioid receptor delta antagonists, such as HS-378; calcium channel inhibitors, such as RP-3128; carbonic anhydrase/Cyclooxygenase 2 inhibitors, such as polmacoxib; cathepsin K inhibitors, such as CRA-013783 or VEL-0230; cathepsin K/cathepsin S inhibitors, such as AM-3876 or NPI-2019; cathepsin S inhibitors, such as MIV-247 or RWJ-445380; CCR1 chemokine antagonists, such as BX-471, BMS-817399, BI-638683, CCX-354, MLN-3701, MLN-3897, CP-481715 or PS-375179; CCR2 chemokine antagonists, such as MK-0812 or AZD-6942; CCR3 gene modulators/Eotaxin 2 ligand inhibitors, such as CM-102; CCR5 chemokine antagonists, such as OHR-118, NIBR-6465, AZD-5672, or AZD-8566; CD29 modulators/Interleukin-10 ligands, such as PF-06687234; CD3 modulators, such as otelixizumab; CD39/CD73 agonists, such as AAV5-CD39/CD73 (rheumatoid arthritis), or Arthrogen; CCR5 chemokine antagonists/CD4 agonists/HIV-1 gp120 protein inhibitors, such as maraviroc; CD4 antagonists, such as zanolimumab, MTRX-1011A, BW-4162W94, EP-1645, or clenoliximab; CD40 ligand inhibitors, such as dapirolizumab pegol; CD40 ligand receptor antagonists, such as BI-655064, anti-CD40-XTEN, teneliximab, VIB-4920, or iscalimab; CD40 ligand receptor modulators/Immunoglobulin G1 modulators, such as CFZ-533; CD52 antagonists/Clusterin stimulators, such as alemtuzumab; bispecific CD32B/CD79B antibody, such as PRV-3279 (MGD-010); CD80 antagonists, such as abatacept biobetter; CD80 antagonists/T cell surface glycoprotein CD28 inhibitors, such as RhuDex; CD80 antagonists/CD86 antagonists, such as XENP-9523 or ASP-2408; CD86 antagonists, such as abatacept or biosuperior; CD86 antagonists/Cytotoxic T-lymphocyte protein-4 modulators, such as ES-210; CD95 antagonists, such as DE-098 or CS-9507; cell adhesion molecule inhibitors, such as alicaforsen, NPC-17923, TK-280 and PD-144795; chemokine receptor antagonists, such as PF-06835375; complement $C_5$ factor inhibitors, such as eculizumab; complement $C_5$ factor inhibitors/IL-1 antagonists, such as antisense oligonucleotides (rheumatoid arthritis); Leiden University Medical CenterComplement Factor stimulators, such as CM-101; C-reactive protein inhibitors, such as ISIS-353512; C-reactive protein inhibitors/Cyclooxygenase 2 inhibitors/Nuclear factor kappa B inhibitors/Immunoglobulin M antagonists/IL-2 receptor antagonists/PGE2 antagonists, such as IB-RACSF-1 antagonists: masitinib, FPA-008, JNJ-27301937, JNJ-40346527, PLX-5622, CT-1578, PD-360324, or JNJ-28312141; CSF-1 antagonists/Fyn tyrosine kinase inhibitors/Kit tyrosine kinase inhibitors/Lyn tyrosine kinase inhibitors/NK cell receptor modulators/PDGF receptor antagonists, such as masitinib; CXC10 chemokine ligand inhibitors, such as 946414-98-8 or BMS-936557; CXCR4 chemokine antagonists, such as plerixafor; CDK-2/7/9 inhibitors/MCL1 gene inhibitors, such as seliciclib; CDK-1/2/5/7/9 inhibitors, such as BP-14; cyclooxygenase 2 inhibitors, such as celecoxib, etoricoxib, meloxicam, or lumiracoxib; cyclooxygenase 2/Oxidoreductase inhibitors, such as etodolac; cyclooxygenase 2 modulators, such as DRGT-46; cyclooxygenase inhibitors, such as aceclofenac, diclofenac, naproxcinod, naproxen etemesil, nabumetone, Aleve, pelubiprofen, LY-210073, NS-398, bromfenac, L-746483, LY-255283, ibuprofen, flurbiprofen, SC-57666, or bermoprofen; cyclooxygenase inhibitors/H+K+ATPase inhibitors, such as naproxen+esomeprazole strontium; cyclooxygenase inhibitors/PGE1 agonists, such as misoprostol+diclofenac; cyclooxygenase inhibitors/Oxidoreductase inhibitors, such as imidazole salicylate; cytosolic phospholipase A2 inhibitors/Phospholipase A2 inhibitors, such as AVX-002; cytotoxic T-lymphocyte protein-4 stimulators/T cell surface glycoprotein CD28 inhibitors, such as abatacept, (BMS-188667) or belatacept; DHFR inhibitors, such as MPI-2505, Jylamvo, or ZeNEO-Methotrexate; DHFR inhibitors/Folate antagonists/Transferrin modulators, such as methotrexate; Diamine acetyltransferase inhibitors, such as diminazene aceturate; dihydroorotate dehydrogenase inhibitors, such as ASLAN-003, HWA-486, or ABR-224050; dihydroorotate dehydrogenase/Protein tyrosine kinase inhibitors, such as leflunomide; elongation factor 2 inhibitors/interleukin-2 ligands/NAD ADP ribosyltransferase stimulators, such as denileukin diftitox; EP4 prostanoid receptor antagonists, such as CR-6086; Erythropoietin receptor agonists, such as cibinetide; Fas ligands, such as AP-300; FGF-2 ligand inhibitors, such as RBM-007; FK506 binding protein-12 modulators/mTOR inhibitors, such as temsirolimus; folate antagonists/Transferrin modulators/DHFR inhibitors, such as MBP-Y003; folate receptor modulators, such as technetium (99mTc) etarfolatide; fractalkine ligand inhibitors, such as E-6011; Fyn tyrosine kinase inhibitors/GABA A receptor modulators/Cyclooxygenase 2 inhibitors/Dihydroorotate dehydrogenase inhibitors, such as laflunimus; Glucocorticoid agonists, such as prednisone, prednisolone, or fosdagrocorat; Glucocorticoid antagonists, such as REC-200; Glucocorticoid induced leucine zipper stimulators, such as ART-G01; GM-CSF ligand inhibitors, such as namilumab, gimsilumab (MORAb-022), or TJM-2; GM-CSF receptor antagonists, such as mavrilimumab; GM-CSF receptor modulators, such as GSK-3196165 or otilimab; growth regulated protein alpha ligand inhibitors/AP1 transcription factor; inhibitors/IL-6 antagonists/Interleukin-1 beta ligand inhibitors/Cathepsin K inhibitors/NFAT gene inhibitors, such as T-5224; H+K+ATPase inhibitors, such as naproxen+esomeprazole, ketoprofen+omeprazole, KEO-25001, HC-1004, or PN-40020; histamine H4 receptor antagonists, such as toreforant or GD-48; histone deacetylase inhibitors, such as CHR-5154 (GSK-3117391); histone deacetylase-6 inhibitors, such as CKD-506; HLA class II antigen DQ-2 alpha modulators, such as NexVax2; HLA class II antigen inhibitors, such as HLA-DR1/DR4 inhibitors (rheumatoid arthritis) or Provid; HLA class II antigen modulators, such as recombinant T-cell receptor ligand (rheumatoid arthritis) or Artielle; Hsp 70 family inhibitors, such as gusperimus trihydrochloride; hypoxia inducible factor-1 inhibitors/VEGF receptor antagonists, such as 2-methoxyestradiol; IFNB gene stimulators, such as ART-102; I-kappa B kinase beta inhibitors, such as IMD-2560; I-kappa B kinase beta inhibitors/Nuclear factor kappa B inhibitors, such as IMD-0560; I-kappa B kinase inhibitors/NFE2L2 gene stimulators/Nuclear factor kappa B inhibitors/STAT3 gene inhibitors, such as bardoxolone methyl; IL-1 antagonists, such as recombinant human interleukin-1 receptor antagonist (rheumatoid arthritis), Shanghai Fudan-Zhangjiang Bio-Pharmaceutical; IL-1 antagonists/Interleukin-1 beta ligand inhibitors, such as rilonacept; IL-10 agonists, such as peg-ilodecakin; IL-11 agonists/PDGF receptor agonists, such as oprelvekin; IL-12 antagonists/IL-23 antagonists, such as ustekinumab or briakinumab; IL-15 antagonists, such as AMG-714; IL-17 antagonists, such as ixekizumab or secukinumab; IL-17 receptor modulators, such as CNTO-6785; IL-2 receptor agonists, such as interleukin-2 follow-on biologic (IL-2), Anteluke or Interking; IL-2/1L-21/IL-15 antagonists, such as BNZ-132-2; IL-21 antagonists, such as NN-8828; IL-4 agonists, such as SER-130-AMI; IL-6 antagonists, such as BCD-089, olokizumab, clazakizumab, sirukumab, SA-237, FB-704A, OP-R$^{003}$, peptide IL-6 antagonist, MEDI-5117, AMG-220, FM-101, BLX-1025, esonarimod, TA-383, or sarilumab; IL-6 antagonists/Interleukin-1 beta ligand inhibitors/TNF alpha ligand inhibitors, such as K-832; IL-6 antagonists/Insulin sensitizers/Interleukin-1 beta ligand inhibitors, such as BLX-1002; IL-6 receptor antagonists/modulators, such as tocilizumab, HS-628, or LusiNEX; IL-6 receptor modulators, such as BAT-1806 or RO-4877533; immunoglobulin antagonists, such as iguratimod; immunoglobulin G1 agonists, such as BX-2922 and HF-1020; immunoglobulin G1 agonists/Interleukin-1 beta ligand inhibitors, such as canakinumab; immunoglobulin G1 agonists/TNF alpha ligand inhibitors, such as STI-002; immunoglobulin G1 antagonists/TNF alpha ligand inhibitors, such as YHB-1411-2; immunoglobulin G1 modulators/GM-CSF ligand inhibitors/immunoglobulin kappa modulators, such as lenzilumab; immunoglobulin G2 antagonists/NF kappa B inhibitor stimulators/Osteoclast differentiation factor antagonists/Osteoclast differentiation factor ligand inhibitors/TNFSF11 gene inhibitors, such as denosumab; immunoglobulin gamma Fc receptor II modulators, such as MGD-010; inducible nitric oxide synthase inhibitors/Cyclooxygenase 2 inhibitors/MAP kinase modulators/Nuclear factor kappa B inhibitors, such as SKLB-023; inosine monophosphate dehydrogenase inhibitors, such as mizoribine; insulin sensitizers/Nuclear factor kappa B inhibitors/interleukin ligand inhibitors, such as HE-3286; integrin alpha-1/beta-1 antagonists, such as SAN-300; integrin alpha-4/beta-1 antagonists/cell adhesion molecule inhibitors, such as natalizumab; integrin alpha-9 antagonist, such as ASP-5094; integrin antagonists, such as PEG-HM-3 or CY-9652; interferon beta ligands, such as recombinant interferon beta-1a; interferon beta ligands/IL-6 antagonists, such as TA-383; interferon gamma ligands, such as Li Zhu Yin De Fu or Clongamma; interleukin 17A ligand inhibitors/Tumor necrosis factor ligand inhibitors, such as ABT-122 or ABBV-257; interleukin 17F ligand inhibitors, such as bimekizumab; interleukin 18 ligand inhibitors, such as tadekinig alfa; interleukin 23A inhibitors, such as guselkumab; interleukin ligands/IL-1 antagonists, such as IBPB-007-IL; interleukin receptor 17A antagonists, such as brodalumab; interleukin-1 beta ligand inhibitors, such as gevokizumab, LY-2189102 or CDP-484; interleukin-1 beta ligand inhibitors/TNF alpha ligand inhibitors, such as PMI-001; interleukin-1 beta ligands/TNF alpha ligand modulators, such as PUR-0110; interleukin-2 ligands, such as recombinant interleukin-2; IL-2 modulators, such as AMG-592; interleukin-4 ligands/Tenascin modulators, such as Tetravil; interleukin-6 ligand inhibitors, such as gerilimzumab or PF-4236921; IRAK-4 protein kinase inhibitor, such as BAY-1830839, BAY-1834845, or PF-06650833; Itk tyrosine kinase inhibitors, such as JTE-051; Itk tyrosine kinase inhibitors/Jak3 tyrosine kinase inhibitors, such as ARN-4079; JAK tyrosine kinase inhibitors, such as deuterated tofacitinib analog or SD-900; JAK tyrosine kinase inhibitors/Syk tyrosine kinase inhibitors, such as cerdulatinib or CVXL-0074; Jak1 tyrosine kinase inhibitors, such as ABT-494 (upadacitinib), ruxolitinib, filgotinib, itacitinib, NIP-585, YJC-50018, GLPG-0555, MRK-12, or SHR-0302; Jak⅓ tyrosine kinase inhibitors, such as tofacitinib, tofacitinib citrate, peficitinib, CKD-374, or CS-944X; Jak½ tyrosine kinase inhibitors, such as baricitinib or ruxolitinib; Jak2 tyrosine kinase inhibitors/CSF-1 antagonists, such as CT-1578; JAK3 gene inhibitors, such as PF-06651600; Jak3 tyrosine kinase inhibitors, such as decernotinib, DNX-04042, MTF-003, or PS-020613; Jun N terminal kinase inhibitors, such as IQ-1S; KCNA voltage-gated potassium channel-3 modulators, such as MRAD-P1; Kelch like ECH associated protein 1 modulators/Nuclear erythroid 2-related factor 2 stimulators, such as dimethyl fumarate; LanC like protein 2 modulators, such as BT-11; LDL receptor related protein-1 stimulator, such as SP-16; Leukotriene BLT receptor antagonists/complement $C_5$ factor inhibitors, such as nomacopan; LITAF gene inhibitors/JAK3 gene inhibitors/MAP3K2 gene inhibitors/TNF antagonists, such as GBL-5b; Lymphocyte function antigen-3 receptor antagonists, such as alefacept; Macrophage mannose receptor 1 modulators, such as technetium Tc 99m tilmanocept; MAdCAM inhibitors/Immunoglobulin G2 modulators, such as PF-547659; MAPKAPK5 inhibitors/matrix metalloprotease inhibitors, such as GLPG-0259; MEK protein kinase inhibitors, such as AD-GL0001; Membrane copper amine oxidase inhibitors, such as BTT-1023, PRX-167700, or vepalimomab; Metalloprotease-9 inhibitors, such as GS-5745; Microbiome modulator, such as EDP-1815; Midkine ligand inhibitors, such as CAB-102; Mitochondrial 10 kDa heat shock protein stimulators, such as INV-103; mTOR inhibitors, such as everolimus; NAMPT gene inhibitors, such as ART-DO1; Nicotinic acetylcholine receptor antagonists, such as RPI-78 or RPI-MN; NKG2 A B activating NK receptor antagonists, such as monalizumab; NKG2 D activating NK receptor antagonists, such as NNC-0142-002; Nuclear factor kappa B inhibitors, such as dehydroxymethylepoxyquinomicin, MP-42, VGX-1027, SP-650003, MG-132, SIM-916, VGX-350, VGX-300, GIT-027, MLN-1145, or NVP-IKK-005; Nuclear factor kappa B modulators/Nuclear factor kappa B p105 inhibitors/Transcription factor RelB inhibitors/Transcription factor p65 inhibitors, such as REM-1086; Osteoclast differentiation factor antagonists, such as cyclic peptidomimetics (rheumatoid arthritis/osteoporosis), University of Michigan; p38 MAP kinase alpha inhibitors, such as VX-745, BMS-582949, or BMS-751324; p38 MAP kinase inhibitors, such as BCT-197, losmapimod, or ARRY-797; PDE 4 inhibitors, such as apremilast; PDE 5 inhibitors, such as PDE5 inhibitors (rheumatoid arthritis), University of Rochester; PDGF-B ligand inhibitors/VEGF receptor antagonists, such as SL-1026; Phosphoinositide-3 kinase delta inhibitors, such as CT-732, INK-007 or GNE-293; Phosphoinositide-3 kinase delta/gamma inhibitors, such as duvelisib or RP-6503; Phospholipase A2 inhibitors, such as AK-106, varespladib methyl, Ro-31-4493, BM-162353, Ro-23-9358, or YM-26734; Platelet activating factor receptor antagonists, such as piperidone hydrochloridum; PPAR gamma agonists, such as rosiglitazone XR; PPAR gamma agonists/Insulin sensitizers, such as rosiglitazone; Programmed cell death protein 1 modulators, such as INSIX RA; Prostaglandin D synthase stimulators, such as HF-0220; Protein tyrosine kinase inhibitors, such as tairuimide; PurH purine biosynthesis protein inhibitors/Inosine monophosphate dehydrogenase inhibitors, such as mycophenolate mofetil; Rev protein modulators, such as ABX-464; RIP-1 kinase inhibitors, such as GSK-2982772; IL-17 antagonist/Rho associated protein kinase 2 inhibitor, such as KD-025; Signal transducer CD24 modulators, such as CD24-IgFc; Sodium glucose transporter-2 inhibitors/PPAR gamma agonists/Insulin sensitizers, such as THR-0921; STAT3 gene inhibitors, such as vidofludimus; STAT-3 inhibitors, such as HL-237; Superoxide dismutase stimulators, such as imisopasem manganese; SYK family tyrosine kinase inhibitors/Zap70 tyrosine kinase inhibitors, such as MK-8457; Syk tyrosine kinase inhibitors, such as fostamatinib, entospletinib, KDDF-201110-06, HMPL-523, AB-8779, GS-9876, PRT-2607, CG-103065, or SKI-O-703; T cell receptor antagonists, such as TCR inhibiting SCHOOL peptides (systemic/topical, rheumatoid arthritis/dermatitis/scleroderma), SignaBlok, CII modified peptide (rheumatoid arthritis), or Peking University; T cell receptor modulators/HLA class II antigen modulators, such as ARG-301; T cell surface glycoprotein CD28 stimulators, such as TAB-08 or theralizumab; TAK1 binding protein modulators, such as epigallocatechin 3-gallate; Talin modulators, such as short-form talin regulators (rheumatoid arthritis) or KayteeBio; T-cell differentiation antigen CD6 inhibitors, such as itolizumab; T-cell surface glycoprotein CD8 inhibitors/TGF beta agonists/CD4 antagonists, such as tregalizumab; Thymulin agonists, such as Syn-1002; TLR-2/TLR-4 antagonists, such as VB-201; TLR-4 antagonists, such as NI-0101; TLR-2/4/9 antagonists, such as P-13; TNF agonists/TNF antagonists/Type II TNF receptor modulators, such as Liftnior; TNF alpha ligand inhibitors, such as Adfrar, FKB-327, Exemptia, Cinnora Mabura, adalimumab, infliximab, Flixabi, PF-06438179, hadlima, recombinant humanized anti-TNF-alpha monoclonal antibody, CMAB-008, CT-P13, GB-242, golimumab (CNTO-148), ozoralizumab, AT-132, ISIS-104838, ISU-202, CT-P17, MB-612, Debio-0512, anti-TNF alpha human monoclonal antibody, UB-721, KN-002, DA-3113, BX-2922, R-TPR-015, BOW-050, PF-06410293, CKD-760, CHS-1420, GS-071, ABP-710, BOW-015, HLX-03, BI-695501, MYL-1401A, ABP-501, BAX-2923, SCH-215596, ABT-D2E7, BAT-1406, XPro-1595, Atsttrin, SSS-07, golimumab biosimilar, TA-101 BLX-1002, ABX-0401, TAQ-588, TeHL-1, placulumab, CYT-007-TNFQb, SSR-150106, PassTNF, Verigen, DOM-0200, DOM-0215, AME-527, anti-TNF-alpha mAb, GENZ-38167, BLX-1028, CYT-020-TNFQb, CC-1080, CC-1069, LBAL, GP-2017, Idacio, IBI-303, or HS-016; TNF alpha ligand inhibitors/TNF antagonists/Type II TNF receptor modulators, such as BAX-2200; TNF alpha ligand inhibitors/Type II TNF receptor modulators, such as Eucept, TNF alpha ligand modulators, such as MM-A01-01, CDP-571, camobucol, or JNJ-63823539; TNF antagonists, such as DNX-114, TNF antagonist+IL-12 antagonist (rheumatoid arthritis), University of Oxford, BN-006, pegsunercept, ACE-772, onercept, DE-096, PN-0615, lenercept, ITF-1779, MDL-201112, HD-203, Qiangke, or TNF a Fc; TNF antagonists/Type II TNF receptor modulators, such as Altebrel, Intacept, QL-0902, etanercept, Erelzi, opinercept, YISAIPU, Anbainuo, Benepali, YLB-113, SCB-808, DA-3853, or SCB-131; TNF antagonists/TNF alpha ligand inhibitors, such as certolizumab pegol; TNF receptor modulators, such as recombinant TNF receptor 2-Fc fusion protein mutant or T-0001; TNF receptor modulators/TNF alpha ligand inhibitors, such as tgAAV-TNFR: Fc; tumor necrosis factor 13C receptor antagonists, such as VAY-736; tumor necrosis factor 15 ligand inhibitors, such as anti-TL1A antibodies (rheumatoid arthritis/inflammatory bowel disease), or NIAMS; Tumor necrosis factor ligand inhibitors, such as etanercept biosimilar; Type I IL-1 receptor antagonists, such as anakinra, IL-1 Ra, anakinra follow-on biologic or AXXO; Type I TNF receptor antagonists, such as NM-9405; Type II TNF receptor modulators, such as LBEC-0101, DMB-3853, DWP-422, or BT-D001; Unspecified GPCR agonists, such as NCP-70X; VEGF receptor antagonists, such as NSC-650853; VEGF-2 receptor modulators, such as VEGFR2 neutralizing antibody (rheumatoid arthritis), University of Rochester; VEGF-B ligand inhibitors, such as CSL-346; X-linked inhibitor of apoptosis protein inhibitors, such as IAP inhibitors (oral) or Pharmascience; or Zap70 tyrosine kinase inhibitors, such as CT-5332.

In one embodiment, the compound of Formula I, or any formula described herein, or a pharmaceutically acceptable salt thereof, is useful for the treatment of cancer in combination with a JAK-1 inhibitor. An example of such JAK-1 inhibitor is a compound disclosed in WO2008/109943. Examples of other JAK inhibitors include, but are not limited to, AT9283, AZD1480, baricitinib, BMS-911543, fedratinib, filgotinib (GLPG0634), gandotinib (LY2784544), INCB039110 (itacitinib), lestaurtinib, momelotinib (CYT0387), NS-018, pacritinib (SB1518), peficitinib (ASP015K), ruxolitinib, tofacitinib (formerly tasocitinib), INCB052793, and XL019. In one embodiment, a compound as disclosed herein, such as a compound of Formula I or any formula described herein, or a pharmaceutically acceptable salt thereof, may be combined with filgotinib (GLPG0634).

Synthesis

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of typical compounds of Formula I, e.g., compounds having structures described by one or more of Formula I, or other formulas or compounds disclosed herein, or a pharmaceutically acceptable salt thereof, may be accomplished as described in the following examples.

General Syntheses

Typical embodiments of compounds in accordance with the present disclosure may be synthesized using the general reaction schemes and/or examples described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Starting materials are typically obtained from commercial sources or synthesized using published methods for synthesizing compounds which are embodiments of the present disclosure, inspection of the structure of the compound to be synthesized will provide the identity of each substituent group. The identity of the final product will generally render apparent the identity of the necessary starting materials by a simple process of inspection, given the examples herein.

Synthetic Reaction Parameters

The compounds of this disclosure can be prepared from readily available starting materials using, for example, the following general methods and procedures. It will be appreciated that where typical or preferred process conditions (e.g., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) *Protecting Groups in Organic Synthesis,* 3rd Edition, Wiley, New York, and references cited therein. Protective groups can be added or removed at any appropriate stage in order to enable the syntheses described herein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wisconsin, USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, $5^{th}$ Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

The following is a list of abbreviations and acronyms used throughout the application:

| Abbreviation | Meaning |
|---|---|
| ° C. | Degree Celsius |
| ATP | Adenosine-5'-triphosphate |
| AcOH | Acetic acid |
| Boc | Tert-butyloxycarbonyl |
| Bn | Benzyl |
| Bs | Benzenesulfonyl |
| CDI | 1,1'-Carbonyldiimidazole |
| d | Doublet |
| Dba | Dibenzylideneacetone |
| DBU | 1,8-Diazabicyclo[5.4.0]undec-7-ene |
| dd | Doublet of doublets |
| DCE | 1,2-dichloroethane |
| DCM | Dichloromethane |
| DEAD | Diethyl azodicarboxylate |
| Dess-Martin periodinane | 1,1,1-Tris(acetyloxy)-1,1-dihydro-1,2-benziodoxol-3-(1H)-one |
| DIAD | Diisopropyl azodicarboxylate |
| DIPEA, DIEA | N,N-diisopropylethylamine |
| DMAP | 4-Dimethylaminopyridine |
| DME | 1,2-dimethoxyethane |
| DMF | Dimethylformamide |
| DMSO | Dimethylsulfoxide |
| DMPU | 1,3-dimethyl-3,4,5,6-tetrahydro-2(1H)-pyrimidinone |
| Dppf | 1,1'-Bis(diphenylphosphino)ferrocene |
| DPPA | Diphenylphosphoryl azide |
| EDC | 1-Ethyl-3-(3-dimethylaminopropyl)carbodiimide |
| EDTA | Ethylenediaminetetraacetic acid |
| EGTA | Ethylene glycol tetraacetic acid |
| EtOAc | Ethyl acetate |
| equiv/eq | Equivalents |
| ESI | Electrospray ionization |
| Ac | Acetate |
| Et | Ethyl |
| g | Grams |
| HATU | 2-(7-Aza-1H-Benzotriazole-1-yl)-1,1,3,3-tetramethyluronium hexafluorophosphate |
| HCl | Hydrochloric acid |
| hERG | human Ether-a-go-go Related Gene |
| HPLC | High-performance liquid chromatography |
| h/hr | Hours |
| Hunig's Base | N,N-diisopropylethylamine |
| Hz | Hertz |
| $IC_{50}$ | The half maximal inhibitory concentration |
| IPTG | Isopropyl β-d-1-thiogalactopyranoside |

| Abbreviation | Meaning |
| --- | --- |
| Ir[dF(CF$_3$)ppy]$_2$(dtbbpy)PF$_6$ | [4,4'-Bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate |
| J | Coupling constant |
| Jackiephos | 2-{Bis[3,5-bis(trifluoromethyl)phenyl]phosphino}-3,6-dimethoxy-2',4',6'-triisopropyl-1,1'-biphenyl |
| Pd-Jackiephos G3 | [(2-{Bis[3,5-bis(trifluoromethyl)phenyl]phosphine}-3,6-dimethoxy-2',4',6'-triisopropyl-1,1'-biphenyl )-2-(2'-amino-1,1'-biphenyl)]palladium(II) methanesulfonate |
| kg | Kilogram |
| LC/MS, LCMS, LC-MS | Liquid chromatography mass spectrometry |
| LDA | Lithium diisopropylamide |
| LiHMDS | Lithium bis(trimethylsilyl)amide |
| L-selectride | Lithium tri-sec-butylborohydride solution |
| M | Molar |
| m | Multiplet |
| m/z | mass-to-charge ratio |
| M+ | Mass peak |
| M + H | Mass peak plus hydrogen |
| Me | Methyl |
| MeOH | Methyl alcohol/methanol |
| Mg | Milligram |
| MHz | Megahertz |
| min/m | Minute |
| ml/mL | Milliliter |
| mM | Millimolar |
| mmol | Millimole |
| MS | Mass spectroscopy |
| MTBE | Methyl tert-butyl ether |
| Mw | Microwave |
| N | Normal |
| Mol | Mole |
| NaHMDS | Sodium bis(trimethylsilyl)amide |
| NCS | N-chlorosuccinimide |
| NIS | N-iodosuccinimide |
| NMP | N-methylpyrrolidinone |
| NMR | Nuclear magnetic resonance |
| p | Pentuplet |
| PCR | Polymerase chain reaction |
| Pd-tBuXPhos G1 | [2-(Di-tert-butylphosphino)-2',4',6'-triisopropyl-1,1'-biphenyl][2-(2-aminoethyl)phenyl)]palladium(II) chloride |
| Pd-tBuXPhos G3 | [(2-Di-tert-butylphosphino-2',4',6'-triisopropyl-1,1'-biphenyl)-2-(2'-amino-1,1'-biphenyl)]palladium(II) methanesulfonate |
| Ph | Phenyl |
| ppm | Parts per million |
| PPTS | Pyridinium para-toluenesulfonate |
| Prep | Preparative |
| Rf | Retention factor |
| RP | Reverse phase |
| RT/rt | Room temperature |
| s | Second |
| s | Singlet |
| SEM | Trimethylsilylethoxymethyl |
| SPhos | 2-Dicyclohexylphosphino-2',6'-dimethoxybiphenyl |
| SUMO | Small ubiquitin-like modifier |
| t | Triplet |
| TBAF | Tetrabutylammonium fluoride |
| TBAI | Tetrabutylammonium iodide |
| TBS | Tert-butyldimethylsilyl |
| TBDPS | Tert-butyldiphenylsilyl |
| TCEP | Tris(2-carboxyethyl)phosphine |
| TEA | Triethylamine |
| Tf | Trifluoromethylsulfonyl |
| TFA | Trifluoroacetic acid |
| THP | Tetrahydropyranyl |
| TLC | Thin layer chromatography |
| Trt/Trityl | Triphenylmethyl |
| TMS | Trimethylsilyl |
| Ts | Toluenesulfonyl |
| WT | Wild type |
| Xantphos | 4,5-Bis(diphenylphosphino)-9,9-dimethylxanthene |
| XPhos | 2-Dicyclohexylphosphino-2',4',6'-triisopropylbiphenyl |
| Pd-XPho G3 | (2-Dicyclohexylphosphino-2',4',6'-triisopropyl-1,1'-biphenyl)[2-(2'-amino-1,1'-biphenyl)]palladium(II) methanesulfonate |

| Abbreviation | Meaning |
| --- | --- |
| Zhan 1b | 1,3-Bis(2,4,6-trimethylphenyl)-4,5-dihydroimidazol-2-ylidene[2-(i-propoxy)-5-(N,N-dimethylaminosulfonyl)phenyl]methyleneruthenium (II) dichloride |
| δ | Chemical shift |
| μg | Microgram |
| μL/μl | Microliter |
| μM | Micromolar |
| μm | Micrometer |
| μmol | Micromole |

1. General Synthesis Schemes

Compounds as provided herein may be synthesized according to the general schemes and/or synthetic procedures described below. In the Schemes below, it should be appreciated that each of the compounds shown therein may have protecting groups as required present at any step. Standard protecting groups are well within the purview of one skilled in the art. Further, unless otherwise defined, the various substituents depicted in the following Schemes (e.g., $X^5$, $X^7$, $R^1$, $R^2$, $R^3$, $R^4$, $R^6$, $R^{10}$, $R^{11}$, etc.) are as defined in the embodiments and compounds disclosed herein.

Scheme A shows an exemplary synthetic route for the synthesis of compounds provided herein (e.g., compounds of Formula I). In Scheme A, $X^5$, $X^7$, $R^1$, $R^2$, $R^3$, $R^4$, $R^6$, $R^{10}$, and $R^{11}$, are as defined herein, $P^1$ is hydrogen or a suitable protecting group, Z may be the moiety —$NR^{10}R^{11}$ or a suitable precurser thereto (e.g., a protected amino moiety, —OH or —O-alkyl, and the like), LG is a leaving group, and X and Y are each, respectively, suitable complimentary functional groups capable of forming a covalent bond therebetween.

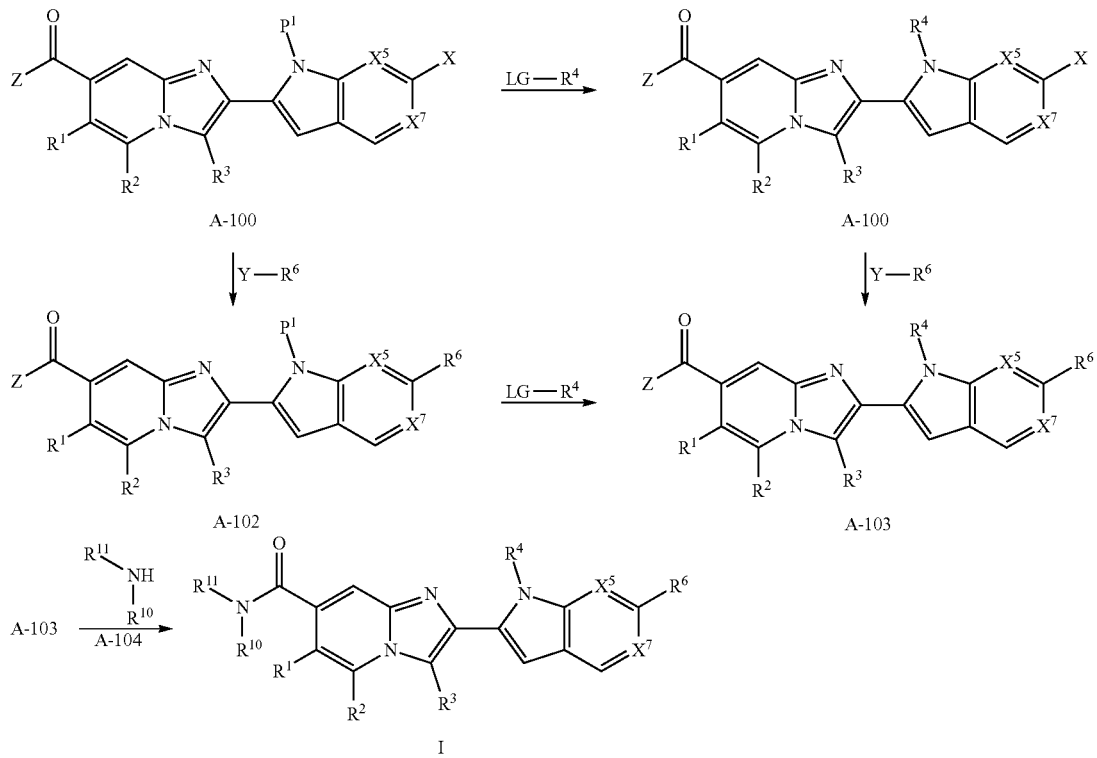

In Scheme A, a compound A-100 can first be deprotected as needed and then reacted with a compound of formula LG-$R^4$, where LG is a leaving group (e.g., halo), under suitable conditions to provide compound A-101. Compound A-101 can then be converted to compound A-103 upon contact with a compound of formula Y—$R^6$ under suitable coupling conditions. Alternatively, compound A-100 can be reacted with a compound of formula Y—$R^6$ under suitable coupling conditions to provide compound A-102. Exemplary functional groups, and well as other functional group modifications, are detailed in the Schemes and Procedures below.

In Scheme A, compound A-103 can be further modified to install the —$NR^{10}R^{11}$ moiety and thus provide compounds of Formula I. In certain embodiments of compound A-100, A-102 or A-103, Z is —NR$^{10}$R$^{11}$. Thus, it can be understood that at any point in the synthesis prior to the formation of the macrocyclic ring, an intermediate can be modified to convert a Z group, where Z is suitable precurser (e.g., —OH or —O-alkyl, and the like), to Z is —NR$^{10}$R$^{11}$.

In certain embodiments, R$^{10}$ or R$^{11}$ may contain a protected amine substituent (e.g., —NHP$^1$, —NP$^1$P$^2$, or —NR$^{12}$P$^1$, where examples of P$^1$ and P$^2$ include -Boc, —Cbz, -trityl, or any other group known to be useful as an amine protective group). Additionally, R$^{11}$ may be a nitrogen-containing heterocycle wherein the ring nitrogen is protected with P$^1$, as defined above. In these cases, removal of P$^1$ and P$^2$ can be carried out using standard conditions, including TFA or HCl for -Boc or -trityl, and hydrogenolysis over a suitable catalyst (e.g., Pd/C) for -Cbz to afford amine products.

Where the individual steps do not provide a desired isomer (e.g., stereoisomer), resolution of the isomers of Formula I, or any intermediate used in the preparation thereof, can be performed as needed using standard chiral separation/resolution conditions (e.g., chromatography, crystallization, etc.).

Suitably substituted compounds A-100, A-101, A-102, and A-103 for use in the methods provided herein can be purchased from commercial sources or synthesized by known methods, or according to methods described in the Schemes and Procedures detailed herein.

Scheme A-1

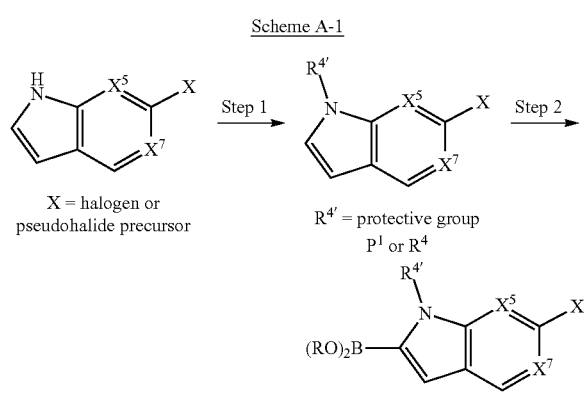

Scheme A-1 depicts the preparation of an indole or azaindole boronic acid or ester intermediate that contains a halogen functional handle.

Step 1 describes the protection of a halogenated indole or aza-indole with P$^1$. Such protective groups can be installed using standard procedures, including treatment with SEM-Cl, Boc$_2$O, or benzenesulfonyl chloride in the presence of a suitable base (e.g., Hunig's base, Et$_3$N, NaH, NaHMDS, etc.) to provide P$^1$=SEM, P$^1$=Boc, and P$^1$=benzenesulfonyl, respectively.

Alternatively, treatment with Y—R$^4$ in the presence of suitable base (e.g., Cs$_2$CO$_3$, NaH, NaHMDS) installs R$^4$, where R$^4$ is as described herein and Y=halogen (preferably Br or I) or pseudohalide (e.g., triflate). Installation of R$^4$ may be accomplished using a Mitsunobu protocol whenY=OH (for example, using DIAD and PPh$_3$).

In certain cases, X=a pseudohalide (e.g., triflate) precursor; for example, X=OBn. Conversion of this group to a pseudohalide in a subsequent step provides a handle for incorporation of R$^6$ groups or precursors thereof as described in Schemes below.

Step 2 describes installation of a boronic acid or ester group by deprotonation with a suitable base (e.g., BuLi, LDA) followed by treatment with a suitable borate ester, including 2-isopropoxy-4,4,5,5-tetramethyl-1,3,2-dioxaborolane to provide B(OR)$_2$=pinacolboronate or triisopropylborate to provide B(OR)$_2$=B(OH)$_2$ following appropriate workup. Additives such as TMEDA or HMPA facilitate the deprotonation in certain cases. An example intermediate prepared by this sequence is I-1.

Scheme A-2

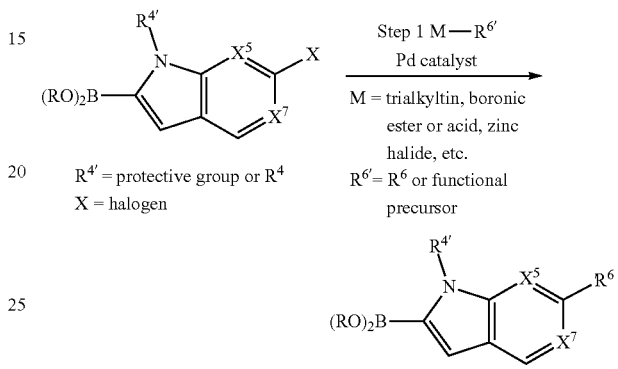

Scheme A-2 presents a generalized synthesis of a functionalized indole or azaindole intermediates. This may be accomplished by palladium-catalyzed cross coupling with M-R', where M=trialkyltin, boronic acid or ester, or other suitable metal species. A preferred substrate B(OR)$_2$ group is the cyclic methyiminodiacetic acid (MIDA) derivative. An example of M-R' is tributyl(vinyl)tin. An example intermediate prepared by this approach is I-3.

Scheme A-3

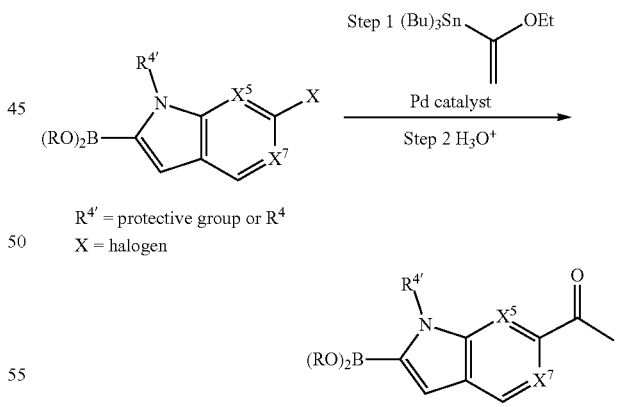

Scheme A-3 describes the synthesis of an acetyl containing indole or azaindole boronic ester. This can be accomplished by a Stille cross coupling using tributyl(1-ethoxyvinyl)stannane along with a suitable palladium catalyst (e.g., PdCl$_2$(dppf), bis(tri-tert-butylphosphine)palladium(O), etc.) followed by acidic hydrolysis. A preferred substrate boronic ester moiety is the cyclic methyiminodiacetic acid (MIDA) derivative. An example intermediate prepared using this sequence is I-4.

Scheme B-1

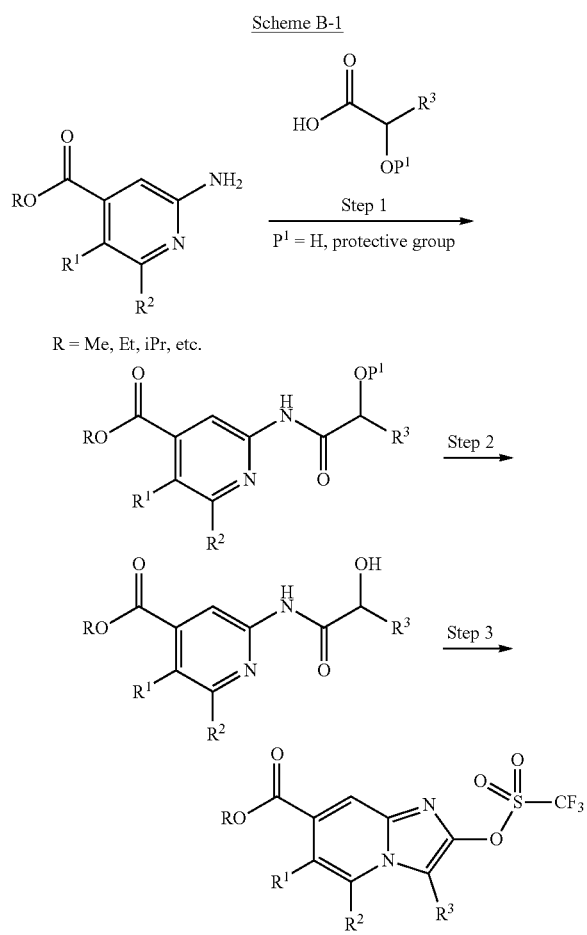

R = Me, Et, iPr, etc.

Scheme B-1 describes the synthesis of imidazopyridine triflate derivatives that can be used as coupling partners in subsequent transformations. This method is particularly useful when $R^2$ is H or is other than H.

Step 1 describes the acylation of an aminopyridine with either a free ($P^1$=H) or protected ($P^1$=Bn, SiMe$_3$, SiMe$_2$tBu, SiPh$_2$tBu, etc.) hydroxyacid. Free ($P^1$=H) hydroxyacids can be protected in situ and converted to corresponding acid chlorides by initial treatment with TMS-Cl and pyridine followed by oxalyl chloride, and exposure to the aminopyridine in the presence of a suitable base (e.g., Et$_3$N, pyridine, Hunig's base) provides the amide product. Alternatively, protected hydroxyacids ($P^1$=Bn, SiMe$_3$, SiMe$_2$tBu, SiPh$_2$tBu, etc.) can be directly coupled using standard peptide coupling reagents (e.g., HATU, EDC, etc.) in the presence of a suitable base or can also be converted to a corresponding acid chloride and coupled as described above.

Step 2 describes the removal of the $P^1$ protective group, which can be accomplished in situ when $P^1$=TMS under acidic conditions (e.g. -citric acid in MeOH). Alternatively, standard deprotection conditions can be used according protective group $P^1$; for instance, removal of the $P^1$=benzyl can be accomplished with H$_2$ over Pd/C in a suitable solvent.

Step 3 describes the direct cyclization of the hydroxyamides described in Step 2 to imidazopyridine triflate intermediates. This may be accomplished by treatment with Tf$_2$O in the presence of a suitable base (especially 2-methoxypyridine). An example intermediate prepared by this sequence is I-13.

Scheme B-2

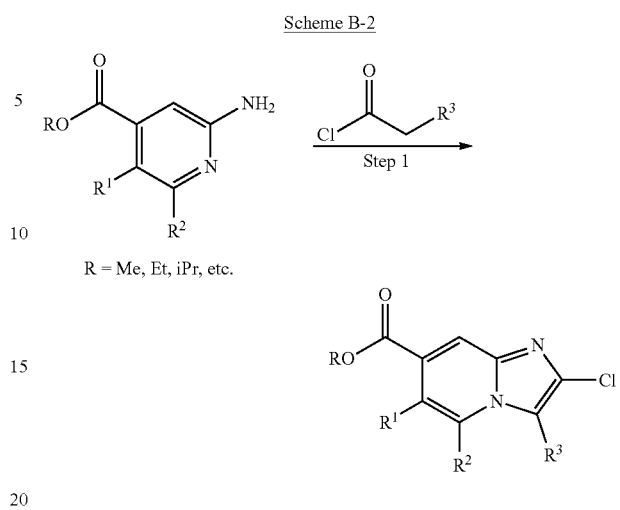

R = Me, Et, iPr, etc.

Scheme B-2 describes the synthesis of chloroimidazopyridine intermediates by treatment of an aminopyridine intermediate with an acid chloride and base (e.g., triethylamine) followed by thionyl chloride, generally at elevated temperature (e.g., −50° C.-100° C.). Chloroform is a preferred solvent for this transformation. This method is particularly useful when $R^2$ is other than H, for example when $R^2$=OMe. This transformation may be accomplished in stepwise fashion, where the intermediate amide formed can be isolated using standard approaches and subsequently treated with thionyl chloride and triethylamine to effect cyclization. An example intermediate prepared by this approach is I-15.

Scheme B-3

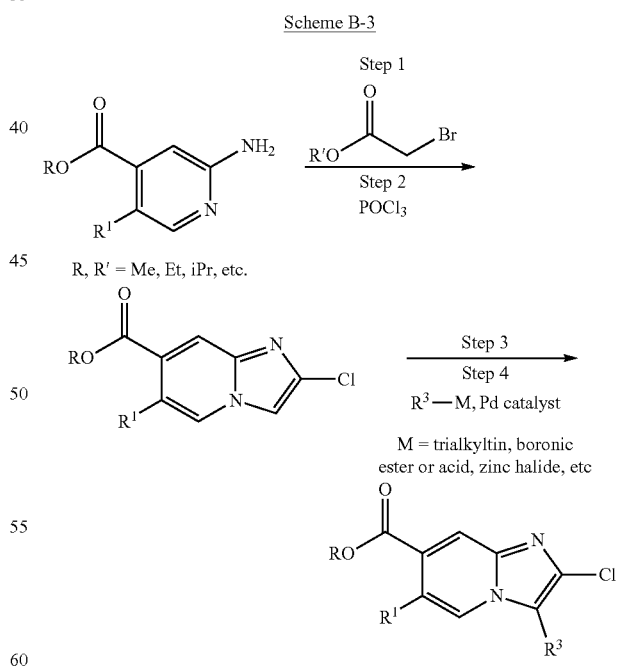

R, R' = Me, Et, iPr, etc.

M = trialkyltin, boronic ester or acid, zinc halide, etc

Scheme B-3 describes an alternate preparation of chloroimidazopyridine intermediates.

Step 1 describes the initial alkylation of 2-aminopyridines on the ring nitrogen with a suitable bromoacetate derivative (e.g., ethyl bromoacetate) to provide a pyridinium bromide salt.

Step 2 describes the conversion of the pyrdinium bromide salt from Step 1 to the corresponding 2-chloroimidazopyridine using phosphorous oxychloride.

Step 3 describes halogenation of the 2-chloroimidazopyridine heterocycle with an electrophilic halogenation reagent (e.g., N-iodosuccinimide) to provide the corresponding 3-halo 2-chloroimidazopyridine intermediate.

Step 4 describes the selective functionalization of the 3-position of prepared 3-halo 2-chloroimidazopyridine intermediates (especially when 3-iodo or 3-bromo intermediates are used). This can be accomplished using a variety of conditions known to those versed in the art and include palladium-mediated cross coupling reactions (e.g., by treatment with $R^3$-M, where M is a boronic ester, acid, or trifluoroborate group, or when M is a zinc or magnesium halide species, or when M is a trialkylstannane in the presence of a palladium catalyst). An example intermediate prepared by this approach is I-14.

Scheme C-1

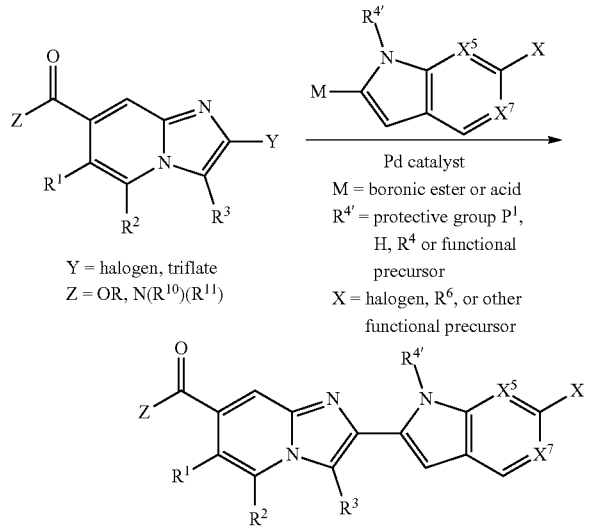

Scheme C-1 describes the cross coupling of an imidazopyridine halide or triflate (described in Schemes B-1, B-2, B-3) with a functionalized indole or azaindole partner (described in Schemes A-1, A-2, A-3), where M=boronic acid or ester, in the presence of a suitable palladium catalyst. It is understood that M=magnesium halide or zinc halide could be accessed by transmetalation from M=Li (prepared according to Step 2 in Scheme A-1). Example intermediates prepared using this sequence are I-22 and I-25.

Scheme D-1

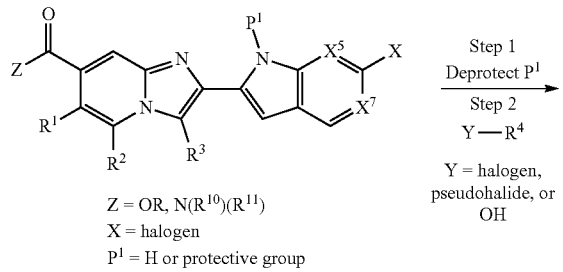

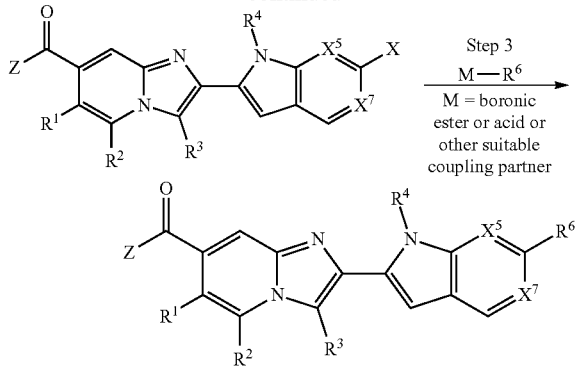

Scheme D-1 describes a general approach for the installation of various $R^4$ and $R^6$ groups from a coupling partner described in Scheme 7.

Step 1 describes the removal of $P^1$ (where $P^1$=protective group) to provide the corresponding NH indole or azaindole. This can be accomplished using standard methods (for example, by treatment with TFA or HCl when $P^1$=Boc or SEM, or by treatment with TBAF when $P^1$=benzenesulfonyl). This step is omitted when $P^1$=H.

Step 2 describes the installation of $R^4$. This may be accomplished by alkylation with Y—$R^4$, where $R^4$ is as described herein and Y=halogen (preferably Br or I) or pseudohalide (e.g., triflate) in the presence of a suitable base (e.g., $Cs_2CO_3$, NaH, NaHMDS). Alternatively, this may be accomplished using a Mitsunobu protocol when Y=OH (for example, using DIAD and $PPh_3$). It is understood that a functional precursor to the ultimately desired $R^4$ group may be used in this step, and that subsequent elaboration may be accomplished using known methods to provide the desired $R^4$ group.

Step 3 describes the installation or $R^6$. This may be accomplished by treatment with M-$R^6$, where $R^6$ is as defined herein and M=boronic ester, acid, or trifluoroborate group, or when M is a zinc or magnesium halide species, or when M is a trialkylstannane in the presence of a suitable palladium catalyst. It is understood that a functional precursor to the ultimately desired $R^6$ group may be used in this coupling step and that subsequent elaboration may be accomplished using known methods to furnish the desired $R^6$ group. Several examples of such elaboration are described generally below.

It is also understood that the order of steps depicted in Scheme 8 could be changed, for instance Step 3 may precede Steps 1 and 2. Where functional precursors to ultimately desired $R^4$ or $R^6$ are used in Steps 2 or 3, it is understood that other ordering of steps may be suitable to provide the desired groups.

Scheme D-2

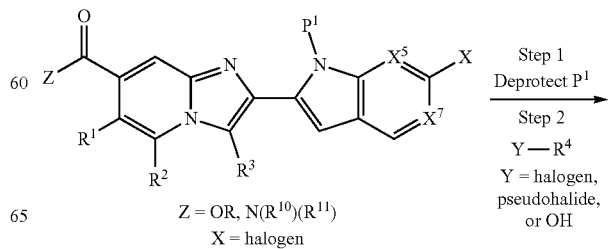

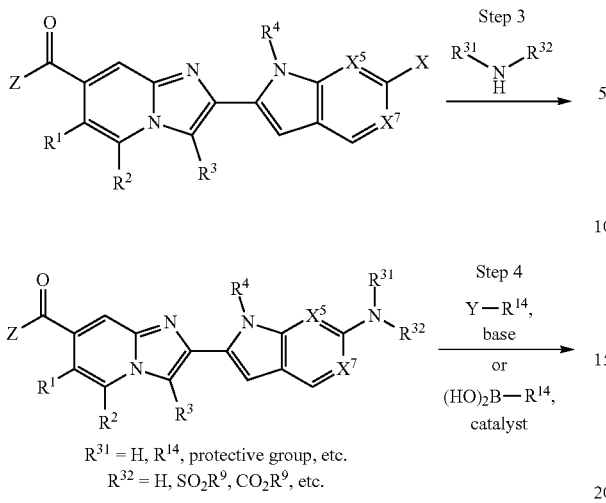

Scheme D-2 depicts synthesis of various N-linked $R^6$ groups.

Step 1 and 2 are as described in Scheme C—X above.

Step 3 describes the C—N coupling with $HN(R^{31})(R^{32})$ utilizing a suitable transition metal catalyst system (e.g. allyl palladium dimer+Jackiephos, Pd-tBuXPhos G3, copper iodide). This method is useful for synthesis of N-linked sulfonamide or carbamate $R^6$ groups (e.g., $HN(R^{31})(R^{32})=$ MeNHSO₂Me or EtNHCO₂Me, respectively) described herein.

Step 4 describes optional further derivatization of $NR^{31}R^{32}$. For instance, when $R^{31}$=H, alkylation with Y—$R^{14}$ where Y=halogen (preferably Br or I) in the presence of a suitable base (e.g., $Cs_2CO_3$, NaH, NaHMDS) installs $R^{14}$. Alternatively, $R^{14}$ may be installed using a cross coupling approach, for example a Chan-Lam type coupling in the presence of a suitable copper catalyst where Y—$R^{14}$=$R^{14}$—$B(OH)_2$. Examples of intermediates prepared by this approach include I-21c, I-36, and I-37.

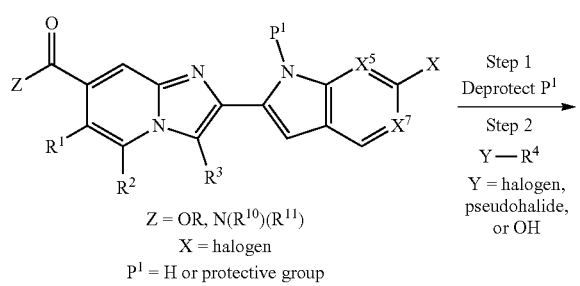

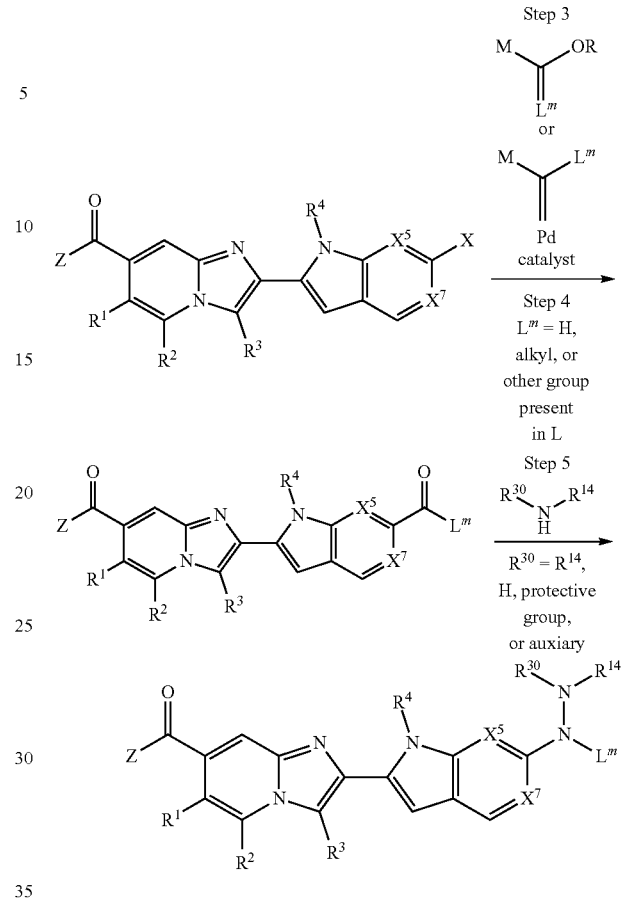

Scheme D-3 depicts installation of variable $R^4$ groups along with installation of an amine-containing $R^6$ group or functional precursor thereof.

Steps 1 and 2 are as described in Scheme D-1 and C-1 above.

Step 3 and 4 describe installation of a carbonyl-containing $R^6$ functional precursor. This may be accomplished either by cross coupling of an alkene ether coupling partner (e.g., 1-ethoxyvinyltributylstannane) mediated by a suitable palladium catalyst (e.g., $PdCl_2(dppf)$) followed by acidic hydrolysis. Similarly, a Heck coupling (where M=H) followed by hydrolysis provide the carbonyl-containing product. This may also be accomplished by cross coupling of an alkenyl partner (e.g., vinyltributylstannae, isopropenyl-BF₃K) in the presence of a suitable palladium catalyst followed by oxidative cleavage of the resulting olefin product using, for example, $OsO_4/NaIO_4$.

Step 5 describes the installation of a protected or unprotected amino moiety condensation of a suitable amine derivative followed by reduction of the formed imine intermediate. This transformation may be accomplished in several ways, including in situ reductive amination, where the acetyl intermediate is treated with amine and a suitable reducing agent (e.g., $NaBH(OAc)_3$, $NaBH_3CN$) concurrently. Alternatively, this can be accomplished stepwise, where a suitable amine derivative is condensed in the presence of a Lewis acid dehydrating reagent (e.g., Ti(OiPr)₄, Ti(OEt)₄, CuSO₄) to provide an imine followed by reduction in a second step with a suitable reducing agent (e.g., NaBH₄, L-selectride). tert-butyl sulfinamide ($HNR^{14}R^{30}$=$NH_2S(O)tBu$) is an especially useful amine derivative, due to the availability of enantiomeric forms and the known ability of these to exert control over stereoconfiguration in the reduction step. It is understood that protective group/auxiliary removal or manipulation can take after this step (e.g., $R^{30}$=S(O)tBu can be removed and/or converted to Boc).

It is understood that the order of events depicted in Scheme D-3 could be rearranged; for example, steps 3 and 4 could precede steps 1 and 2 or steps 3-5 might precede steps 1 and 2.

Scheme D-4

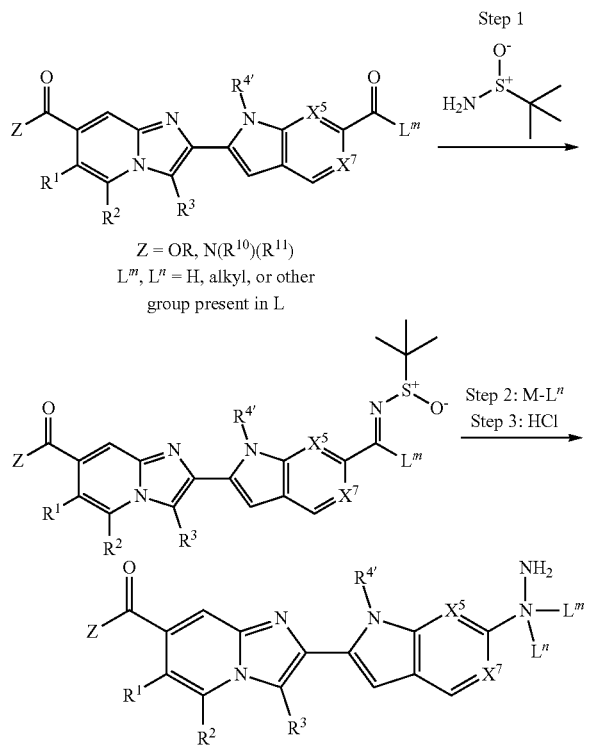

Scheme D-4 depicts the installation of amine-containing $R^6$ groups or functional precursor thereof.

Step 1 describes the initial condensation of a tert-butyl sulfinamide with an aldehyde ($L^m$=H) or ketone ($L^m$=Me, alkyl, or other group) in the presence of a Lewis acid dehydrating reagent (e.g., Ti(OiPr)$_4$, Ti(OEt)$_4$, CuSO$_4$) to provide a sulfinimine product.

Step 2 describes the reaction of the sulfinimine above with a suitable nucleophile (e.g., M=Li, magnesium halide or zinc halide, $L^n$=alkyl, aryl, alkenyl, etc.). This reaction can be facilitated by Lewis acid promoters (e.g., BF$_3$.OEt$_2$, AlMe$_3$, etc.). In certain cases, M-$L^n$ refers to a fluoroalkylsilane (e.g., TMS-CF$_3$, TMS-CHF$_2$, where M=trialkylsilane), and in these cases a suitable promoter is used to facilitate the reaction (e.g., tetrabutylammonium difluorotriphenylsilicate, tetraalkylammonium fluoride, etc.)

Steps 3 describes the removal of the tert-butanesulfinyl group with HCl

It is understood that the sulfinamide described in Step 1 could be racemic or enriched to good enantiomeric excess as either enantiomer, and that enantioenriched forms may allow for control over the stereocenter formed on addition of $L^n$.

Additionally, it is understood that $R^{4'}$ group in Scheme 11 may represent $R^4$ groups as defined herein, a functional precursor to said $R^4$ group, a protective group, or H.

Scheme D-5

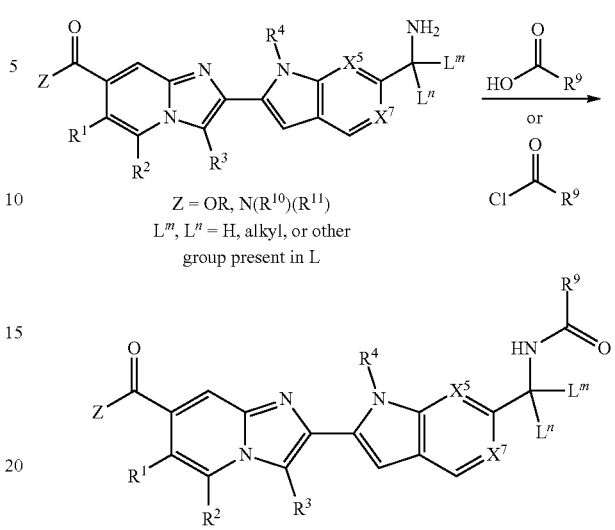

Scheme D-5 describes the synthesis of amide-containing $R^6$ groups. This may be accomplished using well known conditions, for example by treatment with a carboxylic acid in the presence of a suitable coupling reagent (e.g., HATU) and base (e.g., Hunig's base) or by treatment with an acid chloride and suitable base (e.g., TEA).

It is understood that similar well known chemistries could be used to afford related amine derivatives. For example, treatment with an isocyanate or chloroformate in the presence of base would yield a urea or carbamate derivate, respectively (e.g., providing —C(O)N(R$^{14}$)$_2$ or —C(O)OR$^9$ in place of —C(O)R$^9$ as depicted above). Several of these variations are depicted in Scheme 13 and 14 below.

Scheme D-6

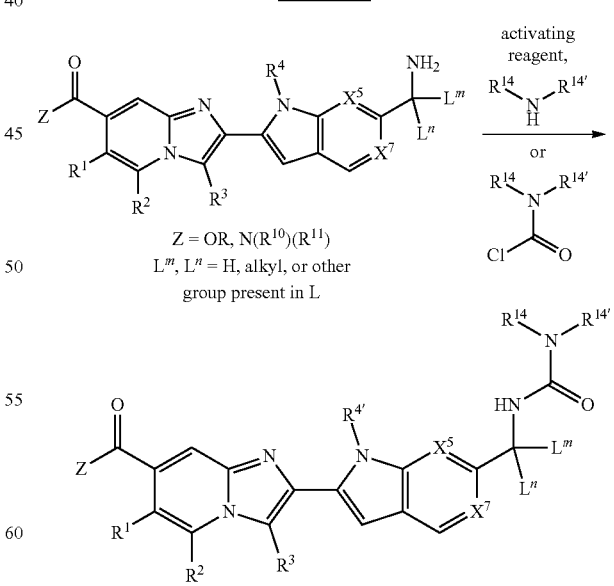

Scheme D-6 describes the synthesis of urea-containing $R^6$ groups. this may be accomplished by treatment of an amino $R^6$ group with an activating reagent (e.g. CDI, 4-nitrophenyl chloroformate), followed by a suitable amine HN(R$^{14}$)(R$^{14'}$)

and base (e.g., triethylamine). Alternatively, this may be accomplished by treatment with an amino carbonyl chloride and base.

Scheme D-7

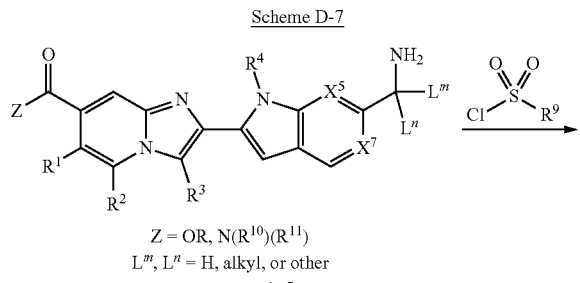

Scheme D-7 describes the synthesis of sulfonamide-containing $R^6$ groups. This may be accomplished amino group with a sulfonyl chloride (e.g., methanesulfonyl chloride) and a suitable base (e.g. triethylamine).

Scheme D-8

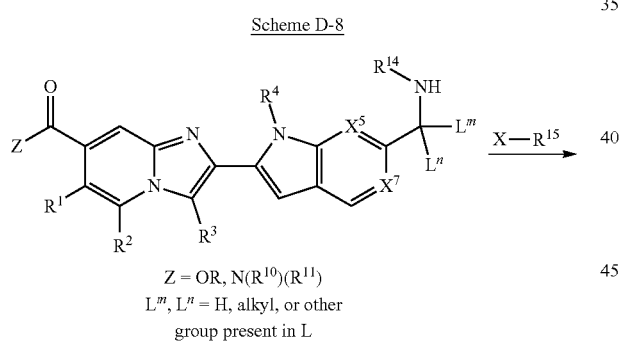

Scheme D-8 describes the derivatization of an amine-containing $R^6$ group to install substituent $R^{15}$. This may be accomplished by treatment with a suitable alkyl, aryl, or heteroaryl halide or pseudohalide (e.g., triflate) in the presence of base to provide the product by direct nucleophilic substitution. Alternatively, a palladium or copper-catalyzed coupling reaction with an aryl or heteroaryl halide or pseudohalide could install the desired $R^{15}$ group.

Scheme D-9

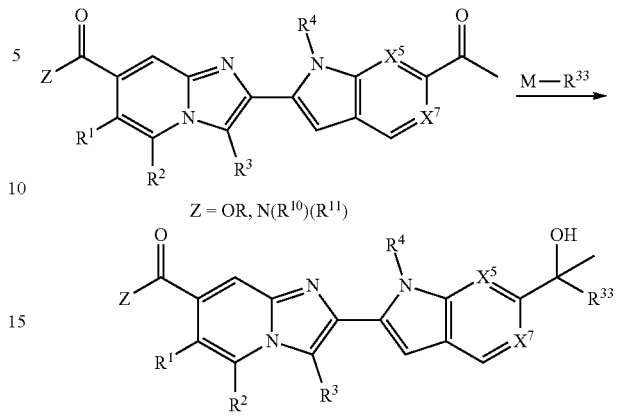

Scheme D-9 describes the installation of tertiary alcohol $R^6$ groups. This may be accomplished by treatment of an $R^6$ ketone with a suitable nucleophile (e.g., M=Li, magnesium halide or zinc halide, $R^{33}$=alkyl, aryl, alkenyl, etc.). This reaction can be facilitated by Lewis acid promoters (e.g., $BF_3 \cdot OEt_2$, $AlMe_3$, etc.). In certain cases, M-$R^{33}$ refers to a fluoroalkylsilane, where M=trialkylsilane (e.g., TMS-$CF_3$, TMS-$CHF_2$), and in these cases a suitable promoter is used to facilitate the reaction (e.g., tetrabutylammonium difluorotriphenylsilicate, tetraalkylammonium fluoride, etc.)

Scheme E-1

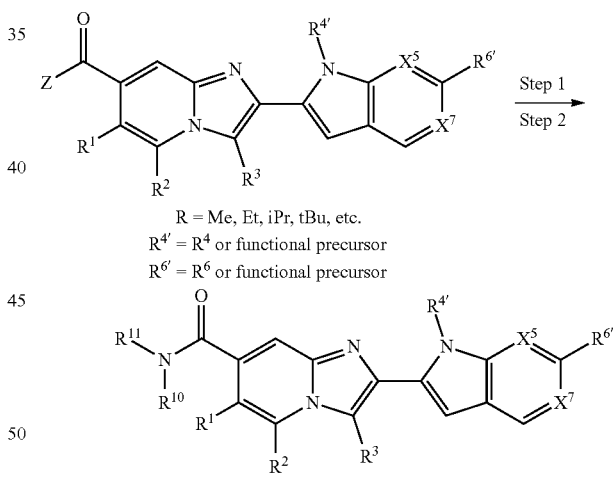

Scheme E-1 describes the installation of —N($R^{10}$)($R^{11}$) groups via amide bond formation.

Step 1 describes the hydrolysis of an ester motif to afford the corresponding carboxylic acid. This can be accomplished using a variety of conditions well known to those versed in the art, including treatment with hydroxide (e.g., LiOH, NaOH, KOH, etc.) in a suitable solvent mixture and temperature. This can also be accomplished under acidic conditions (e.g., TFA, HCl), especially when R=tert-butyl. This may also be accomplished with $Me_3SnOH$, especially when R=Me. Other known R groups that are compatible with the chemistry outlined herein can also be used, and these can be removed using standard conditions known to those versed in the art.

Step 2 shows the preparation of compounds of Formula I or precursors thereof via amide bond forming chemistry. Suitable coupling conditions, reagents and/or catalysts are well known in the art.

It is understood that the sequence described above can be carried out at any appropriate stage prior to full elaboration of compounds of Formula I.

PREPARATION EXAMPLES

Methods for preparing the novel compounds described herein will be apparent to those of skill in the art with suitable procedures being described, for example, in the reaction schemes and examples below.

The chemical names of the Examples in Table 1 were generated using OpenEye, implemented in Dassault Systemes' Biovia Pipeline Pilot (version 19.1.0.1963). ChemBioDraw Ultra 14.0 or the naming function residing within Biovia Notebook 2019 (version 19.1.0.23) was used to generate names for intermediates reported herein. It should be understood that other names may be used to identify Examples or intermediates of the same structure. Other compounds, such as reactants, reagents and solvents, may be named with common names, or systematic or non-systematic names. The compounds may also be named using other nomenclature systems and symbols that are commonly recognized in the art of chemistry including, for example, Chemical Abstract Service (CAS) and International Union of Pure and Applied Chemistry (IUPAC). The naming and numbering of the compounds of the present disclosure is illustrated with representative compounds of Formula I, (IA), (IB), or (IC) shown in Table 1 below. The compounds provided in Table 1 may be a single enantiomer (e.g., (S)-enantiomer, (R)-enantiomer), or the compounds may be present in a racemic or scalemic composition having one or more diastereomers or enantiomers as mixture.

2. Synthesis of Intermediates A1.01 to A13

The following intermediates were purchased from various vendors:

A1.01

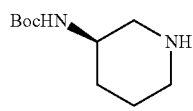

tert-butyl (R)-piperidin-3-ylcarbamate

A1.02

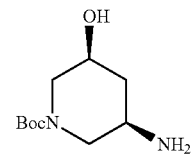

tert-butyl (3R,5S)-3-amino-5-hydroxypiperidine-1-carboxylate

A1.03

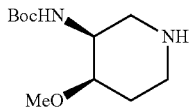

tert-butyl ((3S,4R)-4-methoxypiperidin-3-yl)carbamate

A1.04

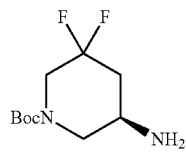

tert-butyl (R)-5-amino-3,3-difluoropiperidine-1-carboxylate

A1.05

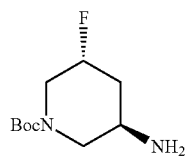

tert-butyl (3R,5R)-3-amino-5-fluoropiperidine-1-carboxylate

A1.06

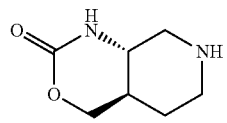

rac-(4aR,8aS)-octahydro-2H-pyrido[3,4-d][1,3]oxazin-2-one

A1.07

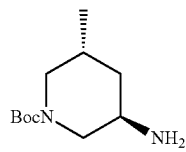

tert-butyl (3R,5R)-3-amino-5-methylpiperidine-1-carboxylate

A1.08

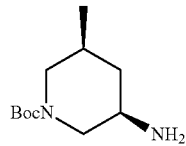

tert-butyl (3R,5S)-3-amino-5-methylpiperidine-1-carboxylate

A1.09

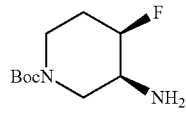

tert-butyl (3S,4R)-3-amino-4-fluoropiperidine-1-carboxylate

A1.10

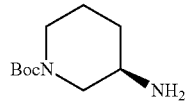

tert-butyl (R)-3-aminopiperidine-1-carboxylate

A1.11

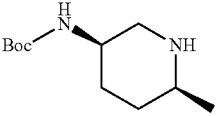

tert-butyl ((3R,6S)-6-methylpiperidin-3-yl)carbamate

| | | |
|---|---|---|
| 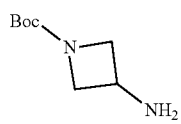<br>tert-butyl 3-aminoazetidine-1-carboxylate | A1.12 | 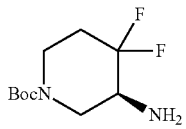<br>tert-butyl (S)-3-amino-4,4-difluoropiperidine-1-carboxylate | A1.20 |
| <br>1-benzyl 2-methyl (+/-)-(2R,5R)-5-aminopiperidine-1,2-dicarboxylate | A1.13 | 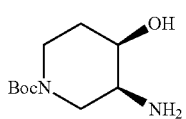<br>tert-butyl (3S,4R)-3-amino-4-hydroxypiperidine-1-carboxylate | A1.21 |
| <br>benzyl (2S,5R)-5-amino-2-methylpiperidine-1-carboxylate | A1.14 | tert-butyl (R)-3-aminoazepane-1-carboxylate | A1.22 |
| <br>tert-butyl (3S,4S)-3-amino-4-fluoropiperidine-1-carboxylate | A1.15 | 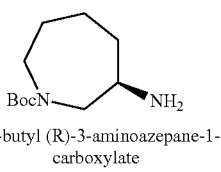<br>tert-butyl (R)-3-amino-4,4-difluoropiperidine-1-carboxylate | A1.23 |
| 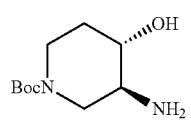<br>tert-butyl (3S,4S)-3-amino-4-hydroxypiperidine-1-carboxylate | A1.16 | tert-butyl (+/-)((3R,4R)-4-(trifluoromethyl)piperidin-3-yl)carbamate | A1.24 |
| 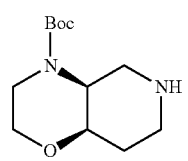<br>tert-butyl (+/-)-(4aS,8aR)-octahydro-4H-pyrido[4,3-b][1,4]oxazine-4-carboxylate | A1.17 | 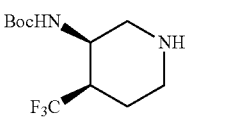<br>tert-butyl ((3R,5R)-5-fluoropiperidin-3-yl)carbamate | A1.25 |
| 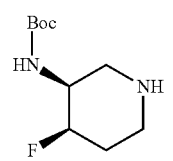<br>tert-butyl ((3S,4R)-4-fluoropiperidin-3-yl)carbamate | A1.18 | tert-butyl ((3S,4R)-4-hydroxypiperidin-3-yl)carbamate | A1.26 |
| 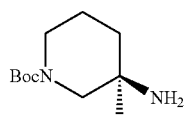<br>tert-butyl (R)-3-amino-3-methylpiperidine-1-carboxylate | A1.19 | tert-butyl ((3R,4R)-4-methylpiperidin-3-yl)carbamate | A1.27 |

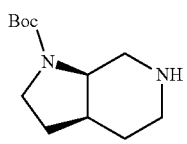

tert-butyl (+/-)-(3aS,7aR)-octahydro-1H-pyrrolo[2,3-c]pyridine-1-carboxylate

A1.28

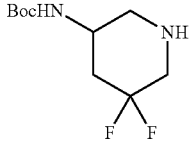

tert-butyl (5,5-difluoropiperidin-3-yl)carbamate

A1.36

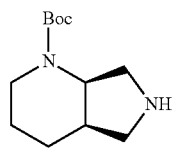

tert-butyl (4aR,7aR)-octahydro-1H-pyrrolo[3,4-b]pyridine-1-carboxylate

A1.29

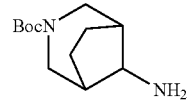

tert-butyl 8-amino-3-azabicyclo[3.2.1]octane-3-carboxylate (mixture of exo/endo)

A1.37

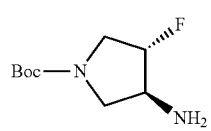

tert-butyl (3S,4S)-3-amino-4-fluoropyrrolidine-1-carboxylate

A1.30

Preparation of tert-butyl ((1R,2R,4S)-7-azabicyclo[2.2.1]heptan-2-yl)carbamate (A2)

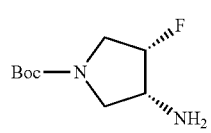

tert-butyl (3R,4S)-3-amino-4-fluoropyrrolidine-1-carboxylate

A1.31

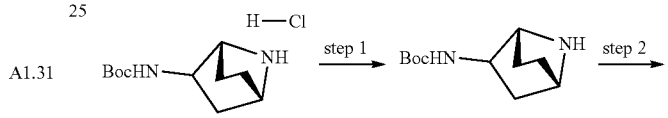

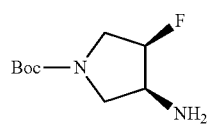

tert-butyl (3S,4R)-3-amino-4-fluoropyrrolidine-1-carboxylate

A1.32

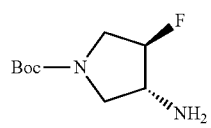

tert-butyl (3R,4R)-3-amino-4-fluoropyrrolidine-1-carboxylate

A1.33

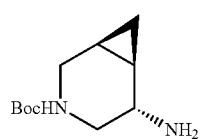

tert-butyl (+/-)-(1S,5S,6R)-5-amino-3-azabicyclo[4.1.0]heptane-3-carboxylate

A1.34

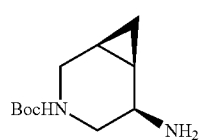

tert-butyl (+/-)-(1S,5R,6R)-5-amino-3-azabicyclo[4.1.0]heptane-3-carboxylate

A1.35

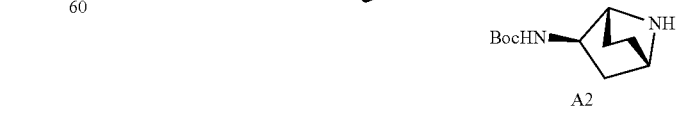

Step 1. The HCl salt of tert-butyl ((1R,4S)-7-azabicyclo[2.2.1]heptan-2-yl)carbamate (60.2 g, 242 mmol, commercially available as [2098589-07-O]) was dissolved in 100 mL water. To this was added a solution of sodium carbonate (38.5 g, 363 mmol) in 200 mL water, producing a voluminous white precipitate. The reaction was extracted into EtOAc (4×200 mL), dried over Na$_2$SO$_4$, filtered, and concentrated to give the free base. This material is commercially available as [2098589-06-9].

Step 2. tert-Butyl ((1R,4S)-7-azabicyclo[2.2.1]heptan-2-yl)carbamate (49.7 g, 234 mmol) was added to 900 mL MeCN. (−)-Dibenzoyl-L-tartaric acid [2743-38-6](83.9 g, 234 mmol) was added as a solid to give a suspension, which was stirred at ambient temperature. The solids were collected by filtration and washed with cold MeCN, then were re-suspended in MeCN and allowed to stir at ambient temperature. The solids were collected and treated 4 additional times with MeCN to provide. tert-Butyl ((1R,2R,4S)-7-azabicyclo[2.2.1]heptan-2-yl)carbamate (2R,3R)-2,3-bis(benzoyloxy)succinate. $^1$H NMR (400 MHz, DMSO-d6) δ 9.28 (br. s, 2H), 7.97-7.90 (m, 4H), 7.68-7.58 (m, 2H), 7.50 (t, J=7.8 Hz, 4H), 7.35 (d, J=5.9 Hz, 1H), 5.64 (s, 2H), 4.04-3.92 (m, 3H), 2.14-2.02 (m, 1H), 1.89-1.68 (m, 2H), 1.67-1.49 (m, 2H), 1.38 (s, 9H), 1.28 (dd, J=13.2, 4.1 Hz, 1H).

Step 3. tert-Butyl ((1R,2R,4S)-7-azabicyclo[2.2.1]heptan-2-yl)carbamate (2R,3R)-2,3-bis(benzoyloxy)succinate (64.3 g, 113 mmol) was added to a solution of sodium carbonate (17.9 g, 169 mmol) in water (500 mL). EtOAc (1000 mL) was added and the mixture stirred until all solids had dissolved. The phases were separated and the aqueous phase was extracted repeatedly with EtOAc, followed by DCM. The combined extracts were dried over Na$_2$SO$_4$, filtered, and concentrated to provide the product as a white foam. $^1$H NMR (400 MHz, DMSO-d6) δ 6.93 (d, J=6.8 Hz, 1H), 3.65-3.54 (m, 1H), 3.39 (t, J=4.6 Hz, 1H), 3.33 (t, J=4.7 Hz, 1H), 2.18 (s, 1H), 1.74 (tdd, J=11.8, 5.2, 2.6 Hz, 1H), 1.69-1.58 (m, 1H), 1.38 (s, 9H), 1.44-1.26 (m, 2H), 1.28-1.16 (m, 1H), 0.95 (dd, J=12.0, 4.7 Hz, 1H). Chiral purity 94.5-95.5% ee (see procedure below for determination). Note-chiral purity can be improved to >99% ee by repeating steps 2 (single treatment with MeCN rather than 5 treatments) and 3.

Determination of Chiral Purity of A2:

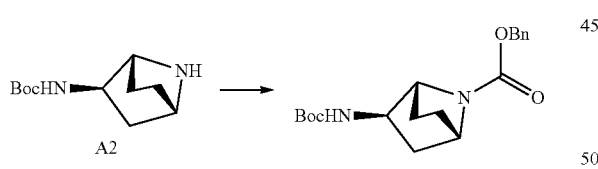

A2

To a solution of tert-butyl ((1R,2R,4S)-7-azabicyclo[2.2.1]heptan-2-yl)carbamate (100 mg, 0.175 mmol) in dioxane and water (1 mL each) was added sodium carbonate (0.84 mL of a 2 M aqueous solution, 1.7 mmol) and carbobenzoxysuccinimide (82 mg, 0.33 mmol). The mixture was allowed to stir at ambient temperature for 5 hours, at which point the thick suspension was diluted further with water. The mixture was extracted into EtOAc, then concentrated and adsorbed to isolute. Purification by silica gel chromatography (eluent: EtOAc in hexane) provided the benzyl (1R,2R,4S)-2-((tert-butoxycarbonyl)amino)-7-azabicyclo[2.2.1]heptane-7-carboxylate. ES/MS: m/z 369.1 [M+Na]$^+$. $^1$H NMR (400 MHz, DMSO-d6) δ 7.42-7.27 (m, 5H), 7.22 (d, J=6.4 Hz, 1H), 5.09-5.00 (m, 2H), 4.17 (t, J=4.4 Hz, 1H), 4.09 (t, J=4.9 Hz, 1H), 3.81-3.70 (m, 1H), 2.08-1.95 (m, 1H), 1.83-1.72 (m, 1H), 1.66-1.54 (m, 1H), 1.53-1.42 (m, 2H), 1.39 (s, 9H), 1.18 (dd, J=12.4, 4.8 Hz, 1H). Chiral purity determined by SFC using AZ-H column (5mic, 4.6×100 mm) with 10% EtOH as cosolvent, or with IF column (5mic, 4.6×100 mm) using 10% EtOH-TFA as cosolvent.

Preparation of tert-butyl ((1R,4R,7R)-2-azabicyclo[2.2.1]heptan-7-yl)carbamate (A3)

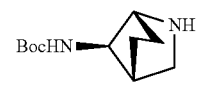

A3 tert-Butyl ((1R,4R,7R)-2-azabicyclo[2.2.1]heptan-7-yl)carbamate was prepared according to a literature procedure (Advanced Synthesis and Catalysis, 2005, vol. 347, #9, p. 1242-1246).

Preparation of benzyl ((1R,2R,4S)-7-azabicyclo[2.2.1]heptan-2-yl)carbamate (A4)

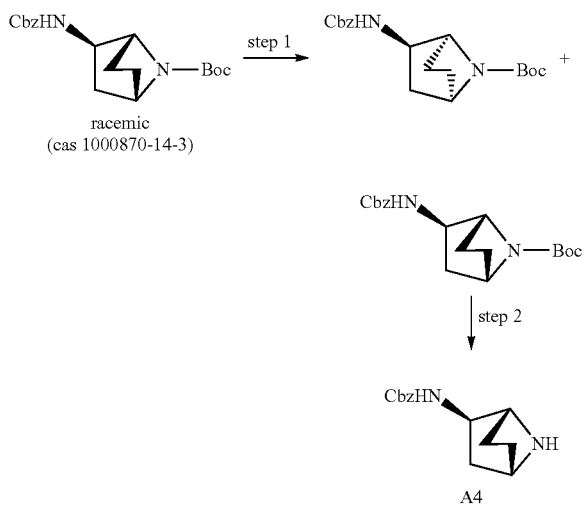

A4

Step 1. A racemic mixture (cas 1000870-14-3) of tert-butyl (1S,2S,4R)-2-(((benzyloxy)carbonyl)amino)-7-azabicyclo[2.2.1]heptane-7-carboxylate and tert-butyl (1R,2R,4S)-2-(((benzyloxy)carbonyl)amino)-7-azabicyclo[2.2.1]heptane-7-carboxylate was separated by chiral SFC (Chiralpak AD-H, 10% MeOH cosolvent). The second eluting isomer was determined to be tert-butyl (1R,2R,4S)-2-(((benzyloxy)carbonyl)amino)-7-azabicyclo[2.2.1]heptane-7-carboxylate.

Step 2. tert-butyl (1R,2R,4S)-2-(((benzyloxy)carbonyl)amino)-7-azabicyclo[2.2.1]heptane-7-carboxylate (46 mg, 0.13 mmol) was dissolved in dioxane. 4 M hydrochloric acid in dioxane (2 mL) was added, and the resulting mixture was stirred at ambient temperature for 1 h. The reaction mixture was concentrated to provide benzyl ((1R,2R,4S)-7-azabicyclo[2.2.1]heptan-2-yl)carbamate as the HCl salt. ES/MS: m/z 247.0 [1\4+1-1]$^+$.

Preparation of benzyl ((1R,2R,5S)-8-azabicyclo[3.2.1]octan-2-yl)carbamate (A5)

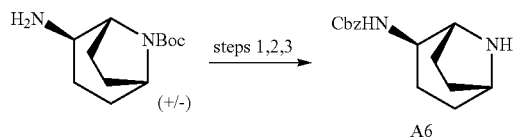

Step 1. tert-butyl rac-(1R,2R,5R)-2-amino-8-azabicyclo[3.2.1]octane-8-carboxylate (from Synthonix) (5.08 g, 22.4 mmol) was dissolved in DCM (125 mL). Aqueous NaOH (1 M, 224 mL, 224 mmol) was added followed by benzyl chloroformate (11.1 mL, 79 mmol). The mixture was stirred for 18 h, and the phases were separated and extracted with DCM. The combined organic phase was dried over $Na_2SO_4$, filtered, and concentrated. Purification by silica gel chromatography (0-40% EtOAc in hexanes) provided tert-butyl rac-(1R,2R,5R)-2-(((benzyloxy)carbonyl)amino)-8-azabicyclo[3.2.1]octane-8-carboxylate that was used directly in step 2.

Step 2. tert-butyl rac-(1R,2R,5R)-2-(((benzyloxy)carbonyl)amino)-8-azabicyclo[3.2.1]octane-8-carboxylate (7.80 g, 21.6 mmol) was dissolved in dioxane (50 mL). A solution of hydrochloric acid in dioxane (4M, 54 mL, 216 mmol) was added and the resulting mixture was stirred 18 h. The mixture was concentrated to afford a crude product that was used in Step 3.

Step 3. The product from Step 2 was subjected to preparative SFC chromatography using a Chiral Technologies Chiralpak IC SFC column (5 μM, 4.6×100 mm) with a 30% MeOH eluent, using multiple injections. The slower-eluting peak was confirmed to be benzyl ((1R,2R,5S)-8-azabicyclo[3.2.1]octan-2-yl)carbamate. $^1$H NMR (for HCl salt) (400 MHz, DMSO-d6) δ 9.28 (s, 2H), 7.59 (d, J=7.6 Hz, 1H), 7.42-7.28 (m, 5H), 5.06 (d, J=12.3 Hz, 1H), 5.01 (d, J=12.4 Hz, 1H), 3.96-3.83 (m, 2H), 3.74 (dd, J=6.9, 2.9 Hz, 1H), 2.05-1.89 (m, 2H), 1.89-1.73 (m, 2H), 1.74-1.63 (m, 2H), 1.63-1.54 (m, 1H), 1.47 (qd, J=12.9, 5.6 Hz, 1H).

Preparation of (3S,4R)-4-(2,2-difluoroethoxy)-N-tritylpiperidin-3-amine (A5a)

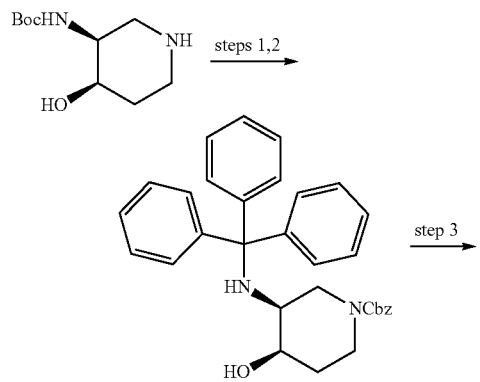

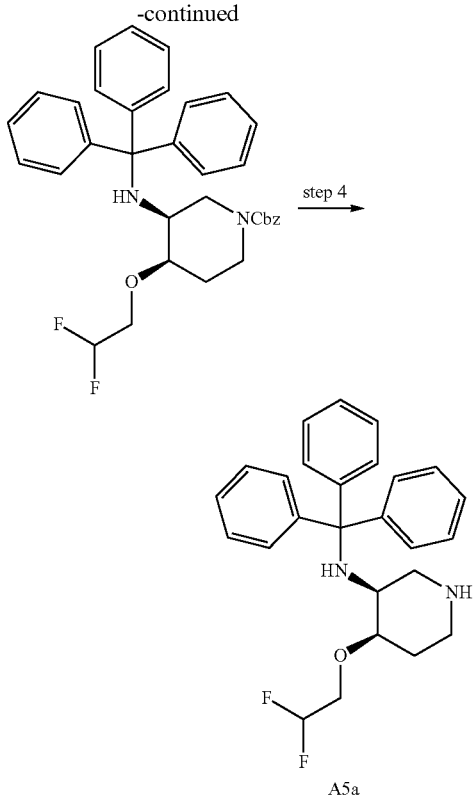

Step 1. tert-Butyl ((3S,4R)-4-hydroxypiperidin-3-yl)carbamate (Pharmablock) (4.98 g, 23 mmol) was dissolved in DCM (100 mL). Triethylamine (10 mL, 71 mmol) and benzyl (2,5-dioxopyrrolidin-1-yl) carbonate (6.05 g, 24.3 mmol) were added. After stirring 24 h, the reaction mixture was diluted with water and the aqueous phase was acidified with hydrochloric acid. The phases were separated, and the aqueous phase was extracted with DCM. The organic phase was concentrated directly onto silica gel. Purification by silica gel chromatography (0-60% acetone in hexanes) provided benzyl (3S,4R)-3-(tert-butoxycarbonylamino)-4-hydroxy-piperidine-1-carboxylate. ES/MS: m/z 350.7 $[M+H]^+$.

Step 2. (3S,4R)-3-(tert-butoxycarbonylamino)-4-hydroxy-piperidine-1-carboxylate (7.86 g, 22.4 mmol) was dissolved in dioxane. 4 M hydrochloric acid in dioxane (56 mL, 224 mmol) was added, and the resulting mixture was stirred at ambient temperature for 48 h. The reaction mixture was concentrated, and the crude product was dissolved in DCM (150 mL). N,N-diisopropylethylamine (19.5 mL, 112 mmol) was added followed by [chloro(diphenyl)methyl]benzene (7.19 g, 25.8 mmol). The reaction mixture was stirred until LCMS indicated complete conversion and was then diluted with EtOAc and water. The phases were separated, and the organic phase was dried over $Na_2SO_4$, filtered, and concentrated. Purification by silica gel (20-70% EtOAc in hexanes) provided benzyl (3S,4R)-4-hydroxy-3-(tritylamino)piperidine-1-carboxylate. ES/MS: m/z 515.3 $[M+Na]^+$.

Step 3. Benzyl (3S,4R)-4-hydroxy-3-(tritylamino)piperidine-1-carboxylate (200 mg, 0.41 mmol) was dissolved in DMF (2 mL) under $N_2$. 60% NaH dispersion in mineral oil (19.5 mg, 0.487 mmol) was added and the mixture was stirred several minutes. 2,2-difluoroethyl trifluoromethanesulfonate (0.11 mL, 0.832 mmol) was added. After 3.5 h, an additional portion of 60% NaH dispersion in mineral oil (11 mg, 0.28 mmol) and 2,2-difluoroethyl trifluoromethanesulfonate (0.05 mL, 0.4 mmol) were added. After stirring an additional 1 h, the mixture was partitioned between EtOAc and sat. aq. NH₄Cl. The organic phase was washed with water, dried over Na₂SO₄, filtered and concentrated to afford a crude residue that was purified by silica gel chromatography (0-50% EtOAc in hexanes) to afford benzyl (3S,4R)-4-(2,2-difluoroethoxy)-3-(tritylamino)piperidine-1-carboxylate. NMR (400 MHz, DMSO-d₆) δ 7.60-7.10 (m, 21H), 6.07 (tt, J=55.0, 3.7 Hz, 1H), 5.00 (s, 2H), 4.14-3.86 (m, 1H), 3.67-3.56 (m, 1H), 3.58-3.40 (m, 1H), 3.20-2.97 (m, 1H), 2.97-2.64 (m, 2H), 2.48-2.43 (m, 1H), 1.95-1.71 (m, 1H), 1.69-1.53 (m, 1H), 1.08-0.91 (m, 1H).

Step 4. Benzyl (3S,4R)-4-(2,2-difluoroethoxy)-3-(tritylamino)piperidine-1-carboxylate (130 mg, 0.234 mmol) was dissolved in EtOAc. Pd/C (10%) (50 mg, 0.047 mmol) was added and the vessel was purged with H₂. The reaction mixture was stirred under 1 atm H2 until full consumption of starting material was observed, at which time the reaction mixture was filtered. Filtrate was concentrated to afford (3S,4R)-4-(2,2-difluoroethoxy)-N-tritylpiperidin-3-amine. ES/MS: m/z 422.7 [M+H]⁺.

Preparation of tert-butyl ((2R,3R)-2-methylpiperidin-3-yl)carbamate (A6)

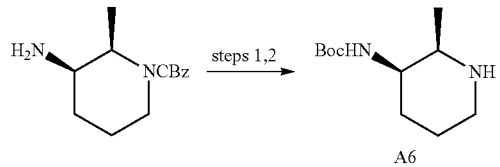

A6

Step 1. Benzyl (2R,3R)-3-amino-2-methyl-piperidine-1-carboxylate (from Synthonix) (7.4 g, 21 mmol) was dissolved in DCM (100 mL). Hunig's base (6.5 mL, 42 mmol) was added followed by tert-butoxycarbonyl tert-butyl carbonate (4.5 g, 21 mmol). The reaction mixture was stirred 24 h and was then partitioned between DCM and aq. HCl. The phases were separated, and the aqueous phase was extracted with DCM. The combined organic phase was dried over Na₂SO₄, filtered, and concentrated to afford crude benzyl (2R,3R)-3-((tert-butoxycarbonyl)amino)-2-methylpiperidine-1-carboxylate material that was used directly in step 2.

Step 2. Benzyl (2R,3R)-3-((tert-butoxycarbonyl)amino)-2-methylpiperidine-1-carboxylate (ca. 21 mmol) was dissolved in THF (200 mL). Palladium on carbon (10% dry basis, 50% total water content) (7.4 g, 3.5 mmol) was added and the vessel was purged with 1 atm H2. After stirring 18 h, the reaction mixture was filtered through a pad of Celite, and the filtrate was concentrated to afford tert-butyl N-[(2R,3R)-2-methyl-3-piperidyl]carbamate. ¹H NMR (400 MHz, DMSO-d₆) δ 6.30 (d, J=9.1 Hz, 1H), 3.49-3.39 (m, 1H), 2.87-2.77 (m, 1H), 2.76-2.65 (m, 1H), 2.49-2.42 (m, 1H), 1.73-1.58 (m, 1H), 1.56-1.43 (m, 2H), 1.39 (s, 9H), 1.33-1.20 (m, 1H), 0.87 (d, J=6.5 Hz, 3H).

Preparation of tert-butyl rac-(4aR,8aR)-octahydro-1,7-naphthyridine-1(2H)-carboxylate (A7)

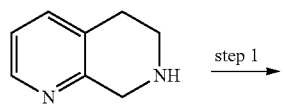

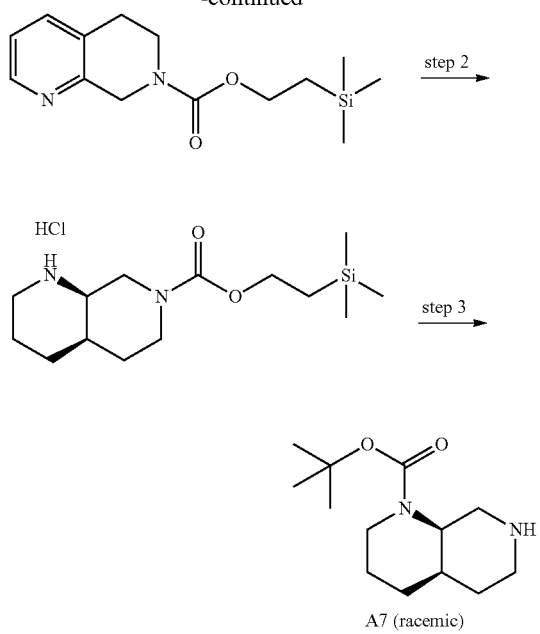

A7 (racemic)

Step 1. To a mixture of 5,6,7,8-tetrahydro-1,7-naphthyridine dihydrochloride (500 mg, 2.41 mmol) and 1-[2-(Trimethylsilyl)ethoxycarbonyloxy]pyrrolidin-2,5-dione (1.22 g, 4.70 mmol) in DCM (20 mL) was added DIPEA (1.26 mL, 7.23 mmol) at rt. After stirring overnight, the reaction mixture was concentrated under reduced pressure and the residue purified via silica gel column chromatography (15-60% ethyl acetate/hexanes) to yield 2-(trimethylsilyl)ethyl 5,8-dihydro-1,7-naphthyridine-7(6H)-carboxylate. ES/MS: m/z 278.8 [M+H]⁺.

Step 2. PtO₂ (236 mg, 1.04 mmol) was added to a mixture of 2-(trimethylsilyl)ethyl 5,8-dihydro-1,7-naphthyridine-7(6H)-carboxylate (672 mg, 2.41 mmol) in ethanol (25 mL) and aqueous HCl solution (6 N, 0.5 mL, 3 mmol) and the reaction mixture was hydrogenated under an atmosphere of hydrogen for 15 h. The reaction mixture was filtered over celite and the filtrate was concentrated and dried in vacuo to yield rac-2-(trimethylsilyl)ethyl (4aR,8aR)-octahydro-1,7-naphthyridine-7(1H)-carboxylate hydrochloride. ES/MS: m/z 285.0 [M+H]⁺.

Step 3. To a solution of rac-2-(trimethylsilyl)ethyl (4aR, 8aR)-octahydro-1,7-naphthyridine-7(1H)-carboxylate hydrochloride (350 mg, 1.09 mmol) and triethylamine (0.38 mL, 2.73 mmol) in DCM (8 mL) was added di-tert-butyl dicarbonate (358 mg, 1.64 mmol) and DMAP (21 mg, 0.174 mmol). After 5 h, the reaction mixture was diluted with water and the layers were separated. The aqueous was extracted with DCM and the combined organics washed with 1 N HCl, dried (MgSO₄), filtered and concentrated. The resulting residue was dissolved in THF (6 mL) and a solution of TBAF in THF (1M, 1.95 mL, 1.95 mmol) was added. After 10 minutes, the reaction mixture was heated at 55° C. overnight. After cooling to rt, the reaction mixture was diluted with DCM, ethyl acetate, and water. The layers were separated and the organics were dried (MgSO₄), filtered, and concentrated under reduced pressure to yield tert-butyl rac-(4aR,8aR)-octahydro-1,7-naphthyridine-1(2H)-carboxylate. ES/MS: m/z 240.9 [M+H]⁺.

Preparation of tert-butyl (R)-(1-methylhexahydropyridazin-4-yl)carbamate (A8)

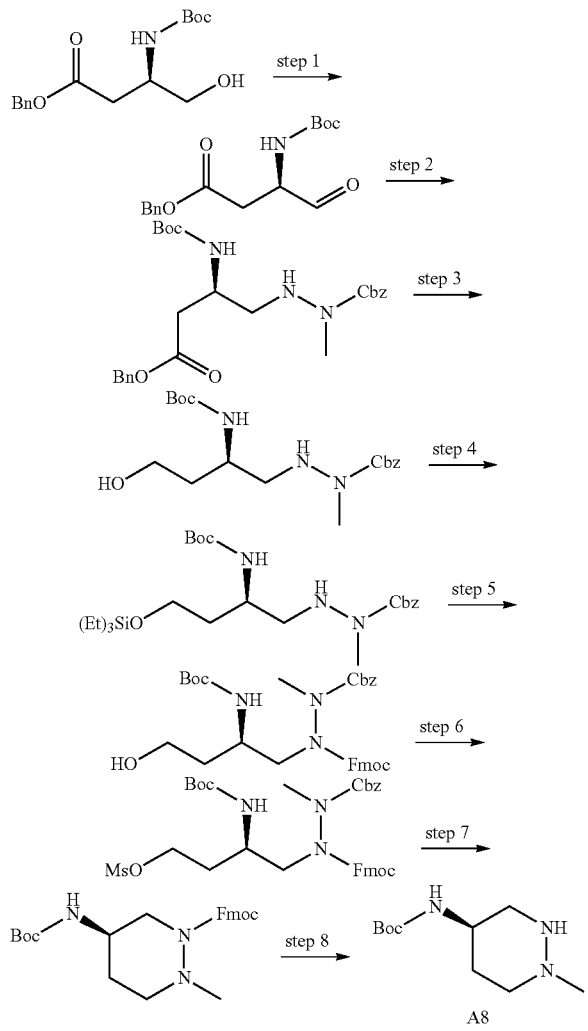

Step 1. To a solution of benzyl (3R)-3-(tert-butoxycarbonylamino)-4-hydroxy-butanoate (3.4 g, 10.99 mmol) in dichloromethane (34 mL) was added Dess-Martin periodinane (5.13 g, 12.09 mmol) in several portions over 15 minutes. After stirring for 4 h, the mixture was concentrated, diluted with ethyl acetate (50 mL), and washed with 1 M aqueous $NaS_2O_3$ (50 mL), followed by 1 M $NaHCO_3$ (aq, 50 mL). The organic layer was dried with $Na_2SO_4$, filtered, and concentrated under vacuum. The crude product was purified by silica chromatography using ethyl acetate in hexanes to afford benzyl (R)-3-((tert-butoxycarbonyl)amino)-4-hydroxybutanoate. $^1$H NMR (400 MHz, Methanol-d4) δ 9.55 (s, 1H), 7.37 (td, J=4.7, 1.7 Hz, 5H), 5.16 (d, J=1.0 Hz, 2H), 4.30 (ddd, J=7.8, 5.2, 2.4 Hz, 1H), 2.95 (dd, J=16.5, 5.4 Hz, 1H), 2.76 (dd, J=16.4, 7.2 Hz, 1H), 1.46 (s, 9H).

Step 2. A solution of benzyl (R)-3-((tert-butoxycarbonyl)amino)-4-hydroxybutanoate (3.4 g, 11.06 mmol), benzyl 1-methylhydrazine-1-carboxylate (1.99 g, 11.06 mmol), and acetic acid (1.99 g, 33.19 mmol) was stirred at ambient temperature for 30 minutes. To the mixture was added sodium cyanoborohydride (2.78 g, 44.25 mmol) over 5 minutes and the mixture was stirred at ambient temperature for 1 hour followed by heating at 40° C. for 30 minutes. The mixture was concentrated, diluted with EtOAc (50 ml), and washed with 1 M aqueous $K_2HPO_4$ (50 ml). The organic layer was dried with $Na_2SO_4$, filtered, and concentrated. Crude benzyl (R)-3-((tert-butoxycarbonyl)amino)-4-oxobutanoate was taken to next step without further purification. $^1$H NMR (400 MHz, Methanol-d4) δ 7.44-7.27 (m, 10H), 5.18-5.03 (m, 4H), 4.05-3.92 (m, 1H), 3.06 (s, 3H), 3.00-2.92 (m, 1H), 2.92-2.81 (m, 1H), 2.79-2.66 (m, 1H), 2.61-2.43 (m, 1H), 1.43 (s, 9H). ES/MS: m/z 472.2 [M+H]$^+$.

Step 3. To a solution of benzyl (R)-3-((tert-butoxycarbonyl)amino)-4-oxobutanoate (5.2 g, 11.03 mmol) in MeTHF (11 mL) was added 2 M LiBH$_4$ in THF (11 mL). After stirring for 1 h, the mixture was carefully quenched with 4N NH$_4$C$_1$ (aq, 20 ml) and stirred for 1 h. The organic layer was dried with Na$_2$SO$_4$, filtered, and concentrated under vacuum. The crude product was purified by silica chromatography using EtOAc in hexane to afford benzyl (R)-2-(2-((tert-butoxycarbonyl)amino)-4-hydroxybutyl)-1-methylhydrazine-1-carboxylate. ES/MS: m/z 368.2 [M+H]$^+$.

Step 4. To a solution of benzyl (R)-2-(2-((tert-butoxycarbonyl)amino)-4-hydroxybutyl)-1-methylhydrazine-1-carboxylate (2.5 g, 6.8 mmol) and EtN(i-Pr)$_2$ (1.77 ml, 10.21 mmol) in dichloromethane (30 mL) was added triethylsilyl trifluoromethanesulfonate (2.15 ml, 9.53 mmol) at −78° C. The mixture was warmed to ambient over 1 h. The mixture was washed with water (30 mL) and the organic layer was dried with Na$_2$SO$_4$, filtered, and concentrated under vacuum. The product was purified by silica chromatography using ethyl acetate in hexane. The partially purified product was refluxed in methanol for 1 h. The mixture was concentrated under vacuum and repurified by silica chromatography using ethyl acetate in hexane to afford benzyl (R)-2-(2-((tert-butoxycarbonyl)amino)-4-((triethylsilyl)oxy)butyl)-1-methylhydrazine-1-carboxylate. $^1$H NMR (400 MHz, Chloroform-d) δ 7.43-7.28 (m, 6H), 5.23-5.05 (m, 3H), 4.70 (s, 1H), 3.79-3.53 (m, 2H), 3.09 (s, 3H), 3.02-2.84 (m, 2H), 1.86-1.52 (m, 2H), 1.43 (s, 9H), 0.95 (t, J=7.9 Hz, 9H), 0.59 (q, J=8.0 Hz, 6H). ES/MS: m/z 482.3 [M+H]$^+$.

Step 5. To a solution of benzyl (R)-2-(2-((tert-butoxycarbonyl)amino)-4-((triethylsilyl)oxy)butyl)-1-methylhydrazine-1-carboxylate (2.7 g, 5.61 mmol) and EtN(i-Pr)$_2$ (1.46 ml, 8.41 mmol) in dichloromethane (10 mL) was added FmocCl (1.89 g, 7.29 mmol) at 0° C. The mixture was warmed to ambient temperature and stirred for 2 h. To the reaction was added triehthylamine trihydrofluoride (1.8 g, 11.21 mmol). After the stirring for 1 h, the crude product was purified by silica chromatography using EtOAc in hexane to afford 1-((9H-fluoren-9-yl)methyl) 2-benzyl (R)-1-(2-((tert-butoxycarbonyl)amino)-4-hydroxybutyl)-2-methylhydrazine-1,2-dicarboxylate. ES/MS: m/z 590.0 [M+H]$^+$.

Step 6. To a solution of 1-((9H-fluoren-9-yl)methyl) 2-benzyl (R)-1-(2-((tert-butoxycarbonyl)amino)-4-hydroxybutyl)-2-methylhydrazine-1,2-dicarboxylate (2.4 g, 4.07 mmol) and EtN(i-Pr)$_2$ (0.85 ml, 4.88 mmol) in dichloromethane (10 ml) was added methanesulfonyl chloride (0.35 ml, 4.48 mmol) at 0° C. After stirring for 30 minutes, the product was purified by silica chromatography using ethyl acetate in hexane to afford 1-((9H-fluoren-9-yl)methyl) 2-benzyl (R)-1-(2-((tert-butoxycarbonyl)amino)-4-((methylsulfonyl)oxy)butyl)-2-methylhydrazine-1,2-dicarboxylate. ES/MS: m/z 568.2 [M+H]$^+$.

Step 7. A mixture of 1-((9H-fluoren-9-yl)methyl) 2-benzyl (R)-1-(2-((tert-butoxycarbonyl)amino)-4-((methylsulfonyl)oxy)butyl)-2-methylhydrazine-1,2-dicarboxylate (2.3 g, 3.44 mmol) and 10% palladium on carbon (0.18 g, 0.17 mmol) in methanol (20 mL) was stirred for 2 h under 1 atm hydrogen. The mixture was filtered through celite and washed with methanol (10 ml). The filtrate was treated with pyridine (0.28 mL, 3.44 mmol) and stirred for 18 h. The mixture was concentrated under vacuum. The crude product was taken to next step without further purification. ES/MS: m/z 438.0 [M+H]$^+$.

Step 8. Crude (9H-fluoren-9-yl)methyl (R)-5-((tert-butoxycarbonyl)amino)-2-methyltetrahydropyridazine-1(2H)-carboxylate (0.91 g, 2.1 mmol) in 1:1 dichloromethane:diethylamine (5 mL) was stirred at ambient temperature for 2 h. The mixture was concentrated under vacuum and purified by silica chromatography using methanol in dichloromethane to afford tert-butyl (R)-(1-methylhexahydropyridazin-4-yl)carbamate. $^1$H NMR (400 MHz, Methanol-d4) δ 3.48-3.34 (m, 1H), 3.16-3.08 (m, 1H), 3.03-2.89 (m, 1H), 2.79-2.68 (m, 1H), 2.49 (s, 3H), 2.48-2.41 (m, 1H), 2.01-1.90 (m, 1H), 1.75-1.64 (m, 1H), 1.46 (s, 9H). ES/MS: m/z 216.2 [M+H]$^+$.

Preparation of tert-butyl ((3S,4R)-4-methoxypiperidin-3-yl)(methyl)carbamate (A9)

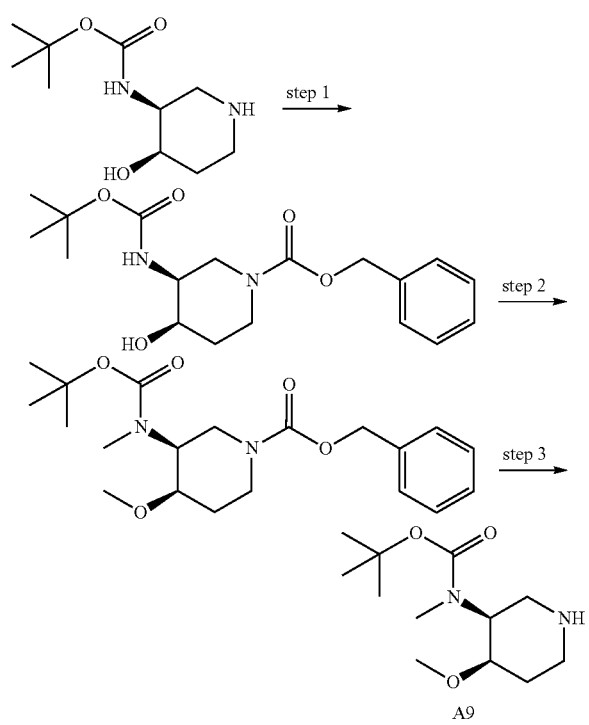

Step 1. To a solution of tert-butyl N-[(3S,4R)-4-hydroxy-3-piperidyl]carbamate A1.25 (5.0 g, 23 mmol) in DCM (100 mL) was added triethylamine (10 mL, 71 mmol) and benzyl (2,5-dioxopyrrolidin-1-yl) carbonate (6.1 g, 24 mmol). The mixture was allowed to stir at ambient temperature for 24 h. Water and HCl (3 M, 15 mL, 45 mmol) were added, and the product was extracted into DCM, concentrated, and purified by silica chromatography (eluent: 0-60% acetone in hexanes) to give benzyl (3S,4R)-3-(tert-butoxycarbonylamino)-4-hydroxy-piperidine-1-carboxylate. ES/MS: m/z 350.7 [M+H]$^+$.

Step 2. To a solution of benzyl (3S,4R)-3-(tert-butoxycarbonylamino)-4-hydroxy-piperidine-1-carboxylate (500 mg, 1.4 mmol) in DMF (4 mL) at 0° C. under N$_2$ was added sodium hydride (60% dispersion in mineral oil, 69 mg, 1.7 mmol). The reaction was removed from ice bath and allowed to stir for 5 minutes, then returned to ice bath. Methyl iodide (0.14 mL, 2.3 mmol) was added. The reaction was allowed to stir for 1 h, then was quenched with water. The mixture was poured into EtOAc and washed with water, then brine. The organic phase was adsorbed to isolute and purified by silica gel chromatography (0-100% EA in hexane) to afford benzyl (3S,4R)-3-(tert-butoxycarbonylamino)-4-methoxy-piperidine-1-carboxylate (also commercially available, see A1.03) and benzyl (3S,4R)-3{tert-butoxycarbonyl(methyl) amino-4-methoxy-piperidine-1-carboxylate (used in the next steps). ES/MS: m/z 401.2 [M+Na]$^+$.

Step 3. Benzyl (3S,4R)-3-[tert-butoxycarbonyl(methyl) amino]-4-methoxy-piperidine-1-carboxylate (105 mg, 0.28 mmol) was combined with 10% Pd/C in a mixture of EtOH (2 mL) and EtOAc (2 mL) and treated with H2 gas. After 18 h, the reaction was filtered through celite and the filtrate concentrated to give tert-butyl N-[(3S,4R)-4-methoxy-3-piperidyl]-N-methyl-carbamate, which was used directly in subsequent steps.

Preparation of benzyl (3S,4R)-3-amino-4-methoxypiperidine-1-carboxylate (A10)

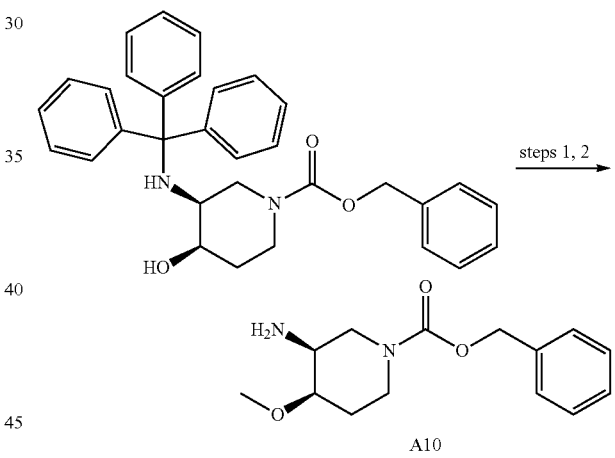

Step 1. To a solution of benzyl (3S,4R)-4-hydroxy-3-(tritylamino)piperidine-1-carboxylate (150 mg, 0.31 mmol, intermediate described in the synthesis of A5a) in DMF (1 mL) was added sodium hydride (60% dispersion in mineral oil, 23 mg, 0.61 mmol). After stirring for 35 minutes, methyl iodide (28 µL, 0.46 mmol) was added. The reaction was allowed to stir for 2 h, then was quenched with water. The mixture was poured into EtOAc and washed with aq. NaHCO$_3$, then brine. The organic phase was adsorbed to isolute and purified by silica gel chromatography (0-100% EA in hexane) to afford benzyl (3S,4R)-4-methoxy-3-(tritylamino)piperidine-1-carboxylate. ES/MS: m/z 529.2 [M+Na]$^+$.

Step 2. Benzyl (3S,4R)-4-methoxy-3-(tritylamino)piperidine-1-carboxylate (26 mg, 0.052 mmol) was dissolved in DCM and treated with TFA at ambient temperature. The resulting mixture was concentrated to give benzyl (3S,4R)-3-amino-4-methoxypiperidine-1-carboxylate, which was used directly in subsequent steps.

Preparation of tert-butyl ((1S,4R,5R)-2-azabicyclo[3.2.1]octan-4-yl)carbamate (A11)

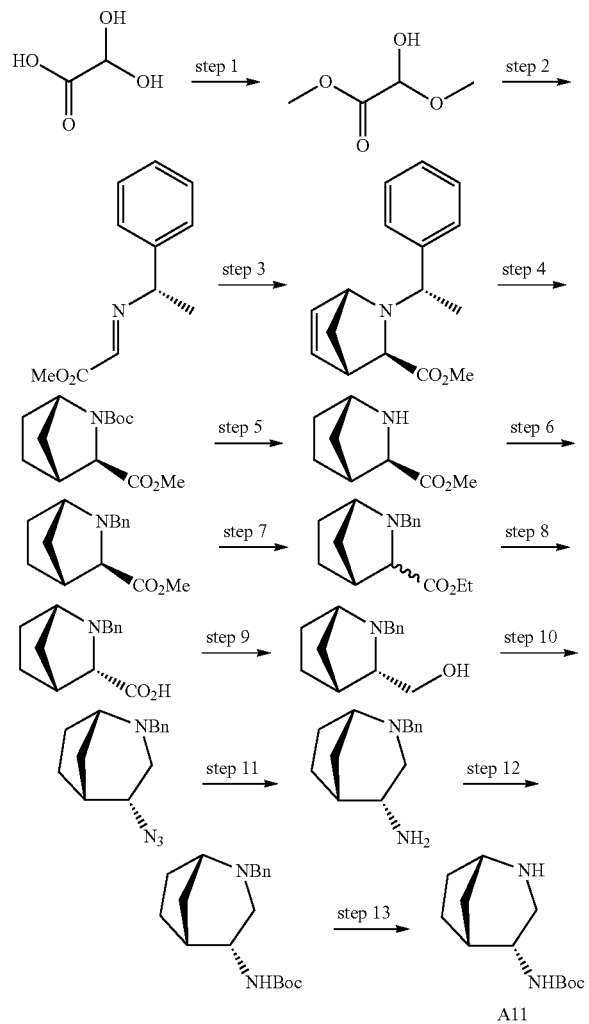

A11

Step 1. A mixture of 2,2-dihydroxyacetic acid (320 g, 3.48 mol) and MeOH (2.24 L) was refluxed for 20 h. The mixture was cooled to rt, concentrated to 1.4 L, and diluted with toluene (1.4 L). The mixture was concentrated to 500 mL, diluted with toluene (1.4 L), and concentrated to 800 mL. The mixture was diluted with toluene to 1.2 L total volume to produce methyl 2-hydroxy-2-methoxyacetate as a 2.3 M solution in toluene (concentration determined by $^1$H NMR). $^1$H NMR (400 MHz, CDCl$_3$) δ 4.79 (s, 1H), 3.74 (s, 3H), 3.41 (s, 3H).

Step 2. The solution of methyl 2-hydroxy-2-methoxyacetate (2.40 L of a 2.3 M soln in toluene, 5.54 mol) was sparged with N$_2$ and then cooled to −10° C. (S)-1-phenylethan-1-amine (714 mL, 5.54 mol) was added while maintaining reaction temperature below 5° C. The mixture was then allowed to warm to rt and was stirred for 2 h. The reaction mixture was diluted with toluene (150 mL) and water (750 mL) and stirred vigorously for 10 min. The mixture was extracted with toluene. The organic layer was washed with brine, dried (Na$_2$SO$_4$), filtered, and concentrated to yield methyl (S,E)-2-((1-phenylethyl)imino)acetate.

Step 3. A mixture of methyl (S,E)-2-((1-phenylethyl)imino)acetate (1.04 kg, 5.46 mol) in DMA (728 mL) was sparged with N$_2$ and cooled to −10° C. TFA (403 mL, 5.46 mol) was added, maintaining reaction temperature below −5° C. Cyclopentadiene (360 g, 5.46 mol) was added, maintaining reaction temperature below −5° C. Water (10 mL) was added, dropwise. The reaction mixture was stirred at −10° C. for 2 h. The mixture was diluted with heptane (400 mL), quenched with K2CO$_3$ (360 g in 2 L water), and stirred vigorously for 20 min. The mixture was extracted with heptane. The organic layer was washed with brine, dried (Na$_2$SO$_4$), filtered, and concentrated. The resulting residue was purified via flash column chromatography on silica gel to afford methyl (1R,3R,4S)-2-((S)-1-phenylethyl)-2-azabicyclo[2.2.1]hept-5-ene-3-carboxylate. $^1$H NMR (400 MHz, CDCl$_3$): δ 7.29-7.21 (m, 5H), 6.43-6.42 (m, 1H), 6.29-6.27 (m, 1H), 4.31 (s, 1H), 3.36 (s, 3H), 3.04 (q, J=6.8 Hz, 1H), 2.92-2.91 (m, 1H), 2.22 (s, 1H), 2.11 (d, J=8.4 Hz, 1H), 1.44-1.41 (m, 4H).

Step 4. To a mixture of Pd(OH)$_2$ (12.0 g, 85.4 mol) in MeOH (1.1 L) was added methyl (1R,3R,4S)-2-((S)-1-phenylethyl)-2-azabicyclo[2.2.1]hept-5-ene-3-carboxylate (110 g, 427 mol) and DIEA (111 mL, 641 mol). The mixture was stirred under 50 psi H2 at 50° C. for 16 h. The mixture was cooled to rt and Boc$_2$O (139 g, 641 mol) was added. The mixture was stirred under 15 psi H2 at rt for 16 h. The mixture was filtered to remove Pd(OH)$_2$. The filtrate was concentrated and the resulting residue was purified via flash column chromatography on silica gel. The crude product was slurried with EtOAc at 0° C. The resulting solid was collected via filtration to yield 2-(tert-butyl) 3-methyl (1S,3R,4R)-2-azabicyclo[2.2.1]heptane-2,3-dicarboxylate. $^1$H NMR (400 MHz, CDCl$_3$): δ 4.34-4.21 (m, 1H), 3.83-3.71 (m, 1H), 3.70 (s, 3H), 2.65 (s, 1H), 1.92-1.85 (m, 1H), 1.81-1.59 (m, 3H), 1.55-1.31 (m, 10H), 1.24-1.15 (m, 1H).

Step 5. A mixture of 2-(tert-butyl) 3-methyl (1S,3R,4R)-2-azabicyclo[2.2.1]heptane-2,3-dicarboxylate (150 g, 0.58 mol) in HCl solution (734 mL of a 4 M soln in MeOH) was stirred at rt for 3 h. The mixture was concentrated to afford methyl (1S,3R,4R)-2-azabicyclo[2.2.1]heptane-3-carboxylate.

Step 6. To a mixture of K2CO$_3$ (240 g, 1.74 mol) in MeCN (1.4 L) was added methyl (1S,3R,4R)-2-azabicyclo[2.2.1]heptane-3-carboxylate (90 g, 0.58 mol). The mixture was sparged with N$_2$ and cooled to 0° C. (Bromomethyl)benzene (69 mL, 0.58 mol) was added, dropwise. The reaction mixture was allowed to warm to rt and was stirred for 16 h. The mixture was filtered to remove solids, and the filtrate was concentrated. The residue was purified via flash column chromatography on silica gel to yield methyl (1S,3R,4R)-2-benzyl-2-azabicyclo[2.2.1]heptane-3-carboxylate.

Step 7. To a solution of diisopropylamine (19 mL, 0.13 mol) in THF (1.38 L) at −78° C. was added n-BuLi (56.2 mL of a 2.5 M soln, 0.14 mol). The reaction mixture was stirred at −78° C. for 30 min and was then warmed to −20° C. A solution of methyl (1S,3R,4R)-2-benzyl-2-azabicyclo[2.2.1]heptane-3-carboxylate (30 g, 0.12 mol) in THF (300 mL) was added and the resulting mixture was stirred at −20° C. for 40 min. The mixture was warmed to −5° C. and sat NH$_4$C$_1$ soln (1.5 mL) was added. The mixture was stirred at −5° C. for 15 min before it was allowed to warm to rt and stirred for 16 h. Brine was added, and the mixture was extracted with MTBE. The organic layer was concentrated and the resulting residue was purified via flash column chromatography on silica gel to give a mixture of ethyl (1S,3R,4R)-2-benzyl-2-azabicyclo[2.2.1]heptane-3-carboxylate and ethyl (1S,3S,4R)-2-benzyl-2-azabicyclo[2.2.1]heptane-3-carboxylate Step 8. The epimeric mixture of ethyl (1S,3R,4R)-2-benzyl-2-azabicyclo[2.2.1]heptane-3-carboxylate and ethyl (1S,3S,4R)-2-benzyl-2-azabicyclo[2.2.1]heptane-3-carboxylate (20 g, 0.81 mol) in HCl (204 mL of a 4 M aq, soln) was refluxed for 16 h. The mixture was cooled to rt and concentrated. The resulting residue was purified via preparative reverse phase HPLC (Phenomenex Luna C-18, water (0.05% HCl)/MeCN) to isolate (1S,3S,4R)-2-benzyl-2-azabicyclo[2.2.1]heptane-3-carboxylic acid. $^1$H NMR (400 MHz, Methanol-d$_4$) δ 7.58-7.55 (m, 2H), 7.44-7.43 (m, 3H), 4.56 (d, J=12.8 Hz, 1H), 4.10-3.97 (m, 2H), 3.96 (t, J=2.0 Hz, 1H), 2.95 (s, 1H), 2.39-2.36 (m, 1H), 1.97-1.87 (m, 3H), 1.73 (m, 1H), 1.51 (m, 1H).

Step 9. To a slurry of (1S,3S,4R)-2-benzyl-2-azabicyclo[2.2.1]heptane-3-carboxylic acid hydrochloride (7.00 g, 26.1 mmol) in THF (130 mL) at 0° C. was added BH$_3$.DMS (12.4 mL, 131 mmol). The mixture was allowed to warm to rt over 16 h. Reaction progress was monitored by LC-MS. The mixture was cooled to 0° C. and BH$_3$.DMS (3.1 mL, 33 mmol) was added. The mixture was allowed to warm to rt overnight and was then cooled to 0° C. and quenched via slow addition of MeOH. The mixture was partially concentrated and then diluted with EtOAc and washed successively with sat NaHCO$_3$soln and brine. The organic layer was dried (Na$_2$SO$_4$), filtered, and concentrated. The residue was purified via flash column chromatography to afford ((1S,3S,4R)-2-benzyl-2-azabicyclo[2.2.1]heptan-3-yl)methanol. $^1$H NMR (400 MHz, CDCl$_3$) δ 7.37-7.28 (m, 4H), 7.25-7.21 (m, 1H), 3.68 (d, J=13.4 Hz, 1H), 3.58 (d, J=13.4 Hz, 1H), 3.48 (dd, J=10.6, 3.9 Hz, 1H), 3.40 (dd, J=10.6, 6.3 Hz, 1H), 3.16-3.08 (m, 1H), 2.84-2.74 (m, 1H), 2.45-2.35 (m, 1H), 1.84-1.69 (m, 2H), 1.60-1.40 (m, 2H), 1.40-1.25 (m, 2H).

Step 10. To a solution of ((1S,3S,4R)-2-benzyl-2-azabicyclo[2.2.1]heptan-3-yl)methanol (0.496 g, 2.28 mmol) and TEA (0.56 mL, 3.99 mmol) in DMF (11 mL) at −40° C. was added Ms$_2$O (0.497 g, 2.85 mmol). The reaction mixture was stirred at −40° C. and reaction progress was monitored via LC-MS. After 30 min, Ms$_2$O (0.099 g, 0.568 mmol) was added. The mixture was stirred at −40° C. for 25 min. NaN$_3$ (0.163 g, 2.51 mmol) was added and the mixture was allowed to warm to rt overnight. The mixture was diluted with EtOAc and water. The aq, layer was extracted with EtOAc and the combined organic layers were washed successively with water and brine, dried (Na$_2$SO$_4$), filtered, and concentrated. The residue was purified via flash column chromatography to afford (1S,4R,5R)-4-azido-2-benzyl-2-azabicyclo[3.2.1]octane. $^1$H NMR (400 MHz, CDCl$_3$) δ 7.32-7.21 (m, 5H), 3.67 (ddd, J=10.7, 5.8, 2.9 Hz, 1H), 3.50 (d, J=13.3 Hz, 1H), 3.43 (d, J=13.3 Hz, 1H), 3.14-3.07 (m, 1H), 2.82 (dd, J=11.2, 5.8 Hz, 1H), 2.42-2.35 (m, 1H), 2.00 (t, J=10.9 Hz, 1H), 1.79-1.32 (m, 6H).

Step 11. To LAH (16.8 mL of a 2 M soln in THF, 33.5 mmol) in THF (100 mL) at 0° C. was added a soln of (1S,4R,5R)-4-azido-2-benzyl-2-azabicyclo[3.2.1]octane (4.64 g, 19.1 mmol) in THF (25 mL), slowly. The ice bath was removed and the mixture was stirred at rt for 2 h. The mixture was cooled to 0° C. and quenched via slow addition of water (1.3 mL) followed by NaOH (1.3 mL of a 15 w/v % aq, soln) and another portion of water (3.8 mL). The mixture was warmed to rt and was stirred for 15 min before it was dried (Mg$_2$SO$_4$), filtered, and concentrated to afford (1S,4R,5R)-2-benzyl-2-azabicyclo[3.2.1]octan-4-amine. ES/MS: m/z 217.2 [M+H]$^+$.

Step 12. To a solution of (1S,4R,5R)-2-benzyl-2-azabicyclo[3.2.1]octan-4-amine (3.75 g, 17.3 mmol) in DCM (115 mL) was added TEA (3.0 mL, 22 mmol), followed by Boc$_2$O (4.16 g, 19.1 mmol). The mixture was stirred at rt for 16 h. The mixture was diluted with DCM and water. The aq, layer was extracted with DCM and the combined organic layers were washed with brine, dried (Na$_2$SO$_4$), filtered, and concentrated. The resulting residue was purified via flash column chromatography to afford tert-butyl ((1S,4R,5R)-2-benzyl-2-azabicyclo[3.2.1]octan-4-yl)carbamate. ES/MS: m/z 317.2 [M+H]$^+$.

Step 13. A solution of tert-butyl ((1S,4R,5R)-2-benzyl-2-azabicyclo[3.2.1]octan-4-yl)carbamate (0.578 g, 1.83 mmol) in MeOH (12 mL) was sparged with N$_2$. Pd/C (0.116 g of 10% Pd/C) was added and the mixture was stirred under H$_2$ (1 atm) overnight. The mixture was filtered to remove Pd/C and the filtrate was concentrated to afford tert-butyl ((1S,4R,5R)-2-azabicyclo[3.2.1]octan-4-yl)carbamate. $^1$H NMR (400 MHz, CDCl$_3$) δ 4.46-4.33 (m, 1H), 3.66-3.52 (m, 1H), 3.43-3.35 (m, 1H), 3.06 (dd, J=12.8, 5.7 Hz, 1H), 2.44 (dd, J=12.8, 11.0 Hz, 1H), 2.39-2.31 (m, 1H), 1.85-1.70 (m, 1H), 1.67-1.51 (m, 5H), 1.44 (s, 9H).

Preparation of benzyl rac-((1S,5R,6R)-3-azabicyclo[4.1.0]heptan-5-yl)carbamate (A11a)

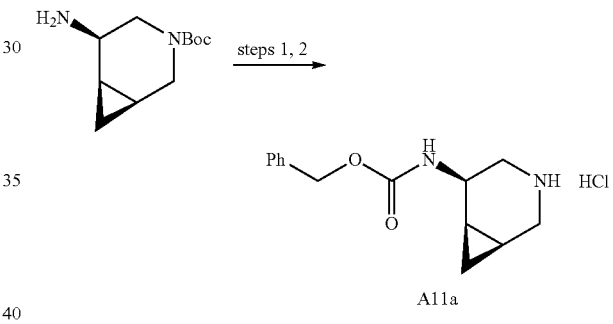

A11a

Step 1. Triethylamine (430 mg, 4.2 mmol) was added to a solution of tert-butyl rac-(1S,5R,6R)-5-amino-3-azabicyclo[4.1.0]heptane-3-carboxylate (300 mg, 1.41 mmol) and N-(benzyloxycarbonyloxy)succinimide (481 mg, 1.70 mmol). The mixture was stirred overnight then evaporated to dryness and purified by column chromatography (Hexane, EtOAc 0-15%) to afford tert-butyl rac-(1S,5R,6R)-5-(((benzyloxy)carbonyl)amino)-3-azabicyclo[4.1.0]heptane-3-carboxylate Step 2. tert-butyl rac-(1S,5R,6R)-5-(((benzyloxy)carbonyl)amino)-3-azabicyclo[4.1.0]heptane-3-carboxylate was dissolved in DCM (4 mL) and HCl in dioxane (4 N, 1 mL) was added. The resulting mixture was stirred at 35° C. until full conversion of the starting material. The solvents were then evaporated to afford benzyl rac-((1S,5R,6R)-3-azabicyclo[4.1.0]heptan-5-yl)carbamate hydrochloride. $^1$H NMR (400 MHz, DMSO-d6) δ 8.96 (brs, 2H), 7.49 (d, J=8.2 Hz, 1H), 7.42-7.35 (m, 4H), 7.35-7.31 (m, 1H), 5.05 (s, 2H), 4.40-4.29 (m, 1H), 3.52-3.42 (m, 1H), 3.07 (dd, J=12.6, 6.1 Hz, 1H), 2.88-2.79 (m, 1H), 2.27 (t, J=11.9 Hz, 1H), 1.43-1.22 (m, 2H), 0.77-0.72 (m, 1H), 0.67-0.58 (m, 1H).

benzyl rac-01R,5R,6S)-3-azabicyclo[4.1.0]heptan-5-yl)carbamate (A11b). Prepared following a similar procedure to A11a starting with tert-butyl rac-(1R,5R,6S)-5-amino-3-azabicyclo[4.1.0]heptane-3-carboxylate. $^1$H NMR (400 MHz, DMSO-d6) δ 8.89 (brs, 2H), 7.80 (d, J=7.8 Hz, 1H), 7.44-7.21 (m, 5H), 5.14-4.98 (m, 2H), 4.00-3.91 (m, 1H), 3.41 (dd, J=13.0, 7.1 Hz, 1H), 3.12-2.87 (m, 2H), 2.78 (dd, J=13.0, 5.7 Hz, 1H), 1.28-1.03 (m, 2H), 0.80 (dt, J=9.0, 4.5 Hz, 1H), 0.62-0.56 (m, 1H).

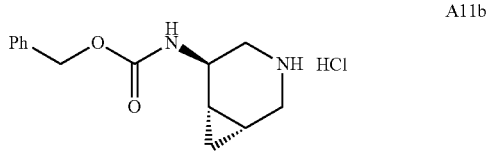 [SMILES: O=C(N[C@H]1CNC[C@@H]2C[C@@H]21)OCc1ccccc1 ; Cl]

A11b

Preparation of benzyl ((1R,2S,3R,5S)-3-hydroxy-8-azabicyclo[3.2.1]octan-2-yl)carbamate (A12)

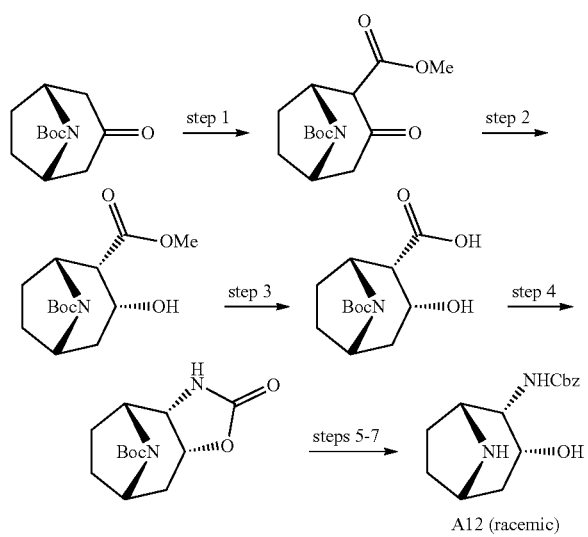

A12 (racemic)

Step 1. A solution of dimethyl carbonate (4.0 g, 44 mmol) in toluene (20 mL) was added dropwise (using an addition funnel) to a suspension of NaH (60% in mineral oil, 1.06 g, 44 mmol) in toluene (60 mL) at room temperature under argon. The mixture was heated to 80° C. upon completion of the addition and MeOH (0.5 mL) followed by a solution of Boc-tropinone (5 g, 22 mmol) in toluene (20 mL) were added dropwise via the addition funnel. The resulting mixture was stirred at 80° C. overnight. Water (4 mL) was added and the mixture was evaporated to dryness. The thick mixture was suspended in DCM and silica was added. After evaporation to dryness the solid was purified by column over silica gel (hexanes/EtOAc, 20% to 40%) to afford 8-(tert-butyl) rac-2-methyl (1R,5R)-3-oxo-8azabicyclo[3.2.1]octane-2,8-dicarboxylate. $^1$H NMR (400 MHz, Chloroform-d) δ 11.81 (s, 0.78H enol), 4.85 (brs, 1H), 4.56 (brs, 1H), 4.38 (brs, 1H), 3.80 (s, 2.34H enol), 3.73 (s, 0.66H ketone), 3.27 (s, 0.22H ketone), 3.10-3.03 (m, 0.22H ketone), 2.94 (brs, 1H), 2.41 (dd, J=15.1, 1.9 Hz, 0.44H, ketone), 2.36-1.96 (m, 2.66H), 1.92-1.82 (m, 0.78H, enol), 1.50 (s, 2H ketone), 1.46 (s, 7H enol).

Step 2. A solution of 8-(tert-butyl) rac-2-methyl (1R,5R)-3-oxo-8-azabicyclo[3.2.1]octane-2,8-dicarboxylate (2.5 g, 9 mmol) in methanol (27 mmol) was cooled to −20° C. and sodium borohydride (367 mg, 10 mmol) was added in small portions over 15 minutes. The mixture was warmed up to 0° C. over 2 h. LC/MS analysis showed full conversion and a solution of saturated ammonium chloride (30 mL) was added followed by DCM (60 mL). After usual work-up the organic layer was evaporated to dryness and the residue was purified by column chromatography over silica gel (Hexanes/EtOAc 5 to 70%). The top spot was found to be 8-(tert-butyl) 2-methyl rac-(1R,2S,3R,5R)-3-hydroxy-8-azabicyclo[3.2.1]octane-2,8-dicarboxylate. $^1$H NMR (400 MHz, Chloroform-d) δ 4.51 (brs, 1H), 4.40 (t, J=4.4 Hz, 1H), 4.20 (brs, 1H), 3.78 (s, 3H), 3.32 (s, 1H), 2.92 (brs, 1H), 2.24-2.12 (m, 2H), 2.09-1.82 (m, 3H), 1.48 (s, 9H).

Step 3. A solution of lithium hydroxide (2N in water, 5 mL) was added to a solution of 8-(tert-butyl) 2-methyl rac-(1R,2S,3R,5R)-3-hydroxy-8-azabicyclo[3.2.1]octane-2,8-dicarboxylate (1.43 g, 5 mmol) in THF (40 mL). The resulting biphasic mixture was stirred vigorously at room temperature until the starting ester was fully consumed as judged by TLC analysis. The reaction was then quenched with HCl (2 N, 5.5 mL) and DCM was added (100 mL) followed by distilled water (30 mL). After work-up, the organic layer was dried over anhydrous sodium sulfate and evaporated to dryness to afford rac-(1R,2S,3R,5R)-8-(tert-butoxycarbonyl)-3-hydroxy-8-azabicyclo[3.2.1]octane-2-carboxylic acid which was used without further purification.

Step 4. Crude rac-(1R,2S,3R,5R)-8-(tert-butoxycarbonyl)-3-hydroxy-8-azabicyclo[3.2.1]octane-2-carboxylic acid from above (ca. 1 mmol) was suspended in toluene (4 mL) and DPPA (1 mmol) was added. Triethylamine (1 mmol) was added and the mixture was stirred 80° C. overnight. LCMS shows the desired product mass and TLC analysis (Hex:EtOAc 1:1) using ninhydrin stain reveals the desired product. The crude was directly purified by silica gel (Hex:EtOAc 5% to 60%) to provide tert-butyl rac-(3aS,4R,7R,8aR)-2-oxooctahydro-2H-4,7-epiminocyclohepta[d]oxazole-9-carboxylate. $^1$H NMR (400 MHz, Chloroform-d) δ 6.00 (brs, 1H), 4.69 (t, J=6.2 Hz, 1H), 4.29 (brs, 1H), 4.21 (brs, 1H), 3.93 (brs, 1H), 2.21 (brs, 1H), 2.16-1.95 (m, 2H), 1.98-1.95 (m, 3H), 1.47 (s, 9H).

Step 5. LiOH (840 mg, 20 mmol) was added to a solution of (tert-butyl rac-(3aS,4R,7R,8aR)-2-oxooctahydro-2H-4,7-epiminocyclohepta[d]oxazole-9-carboxylate (1.07 g, 4 mmol) in THF/MeOH (1:2, 20 mL) and the reaction vessel was capped. The reaction was then heated at 90° C. for 48 h. After cooling the reaction to room temperature, excess acetic acid was added and the mixture was stirred for 15 minutes before silica (8 g) was added. After evaporation to dryness the residue was purified by column chromatography over silica gel (DCM/MeOH 0-10%) to afford tert-butyl rac-(1R,2S,3R,5S)-2-amino-3-hydroxy-8-azabicyclo[3.2.1]octane-8-carboxylate.

Step 6. Triethylamine (1.11 g, 10.8 mmol) was added to a solution of tert-butyl rac-(1R,2S,3R,5S)-2-amino-3-hydroxy-8-azabicyclo[3.2.1]octane-8-carboxylate (872 mg, 3.6 mmol) and N-(Benzyloxycarbonyloxy)succinimide (1.22 g, 4.3 mmol). The mixture was stirred overnight then evaporated to dryness and purified by column chromatography (Hexane, EtOAc 0-30%) to afford tert-butyl rac-(1R,2S,3R,5S)-2-(((benzyloxy)carbonyl)amino)-3-hydroxy-8-azabicyclo[3.2.1]octane-8-carboxylate.

Step 7. tert-Butyl rac-(1R,2S,3R,5S)-2-(((benzyloxy)carbonyl)amino)-3-hydroxy-8-azabicyclo[3.2.1]octane-8-carboxylate (1.19 g, 3.17 mmol) was dissolved in DCM (12 mL) and TFA (1 mL) was added. The mixture was stirred until full conversion of the starting material and then evaporated to dryness to afford benzyl ((1R,2S,3R,5S)-3-hydroxy-8-azabicyclo[3.2.1]octan-2-yl)carbamate. $^1$H NMR (400 MHz, DMSO-d6) δ 8.87 (s, 1H), 8.81 (s, 1H), 7.44-7.36 (m, 4H), 7.37-7.32 (m, 1H), 7.18 (d, J=8.3 Hz, 1H), 5.40 (brs, 1H), 5.07 (s, 2H), 4.02-3.86 (m, 3H), 3.80-3.75 (m, 1H), 2.48-2.41 (m, 1H), 2.24-2.16 (m, 1H), 2.12-1.98 (m, 1H), 1.94-1.80 (m, 2H), 1.77-1.62 (m, 1H).

Preparation of tert-butyl (4aS,8aR)-octahydro-4H-pyrido[4,3-b][1,4]oxazine-4-carboxylate (A13)

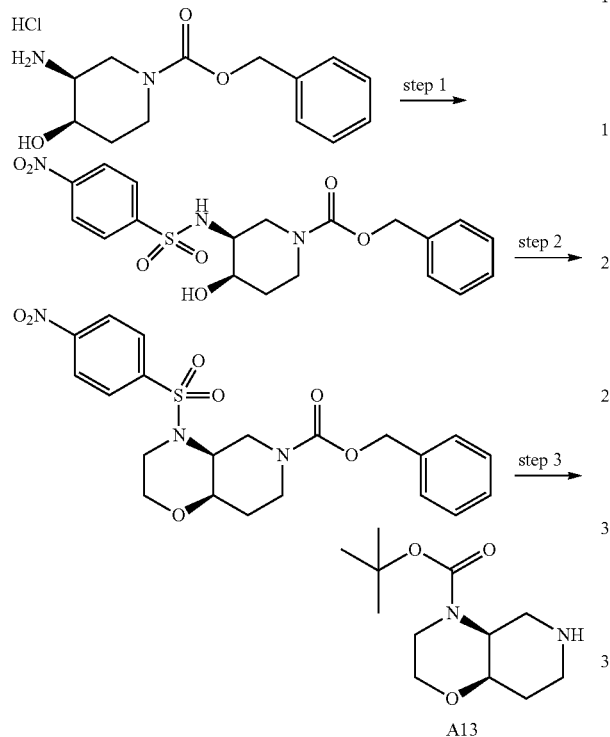

A13

Step 1. To a cooled solution of benzyl (3S,4R)-3-amino-4-hydroxypiperidine-1-carboxylate hydrochloride (350 mg, 1.22 mmol) and triethylamine (0.46 mL, 3.30 mmol) in DCM (7 mL) at 0° C. was added 4-nitrobenzenesulfonyl chloride (300 mg, 1.35 mmol). After 5 minutes, the reaction mixture was warmed to rt. After 30 minutes, the reaction mixture was diluted with DCM and water, and layers separated. The aqueous layer was extracted with DCM. The combined organic layers were dried (MgSO$_4$), filtered, and concentrated under reduced pressure to yield benzyl (3S,4R)-4-hydroxy-3-((4-nitrophenyl)sulfonamido)piperidine-1-carboxylate, that was used in the next step without purification. ES/MS: m/z 240.9 [M+H]$^+$.

Step 2. To a cooled solution of benzyl (3S,4R)-4-hydroxy-3-((4-nitrophenyl)sulfonamido)piperidine-1-carboxylate (345 mg, 0.742 mmol) in DCM (40 mL) at 0° C., was added sodium hydride (60.0% dispersion, 160 mg, 4.00 mmol). After 5 minutes, (2-bromoethyl)diphenylsulfonium trifluoromethanesulfonate (880 mg, 1.99 mmol) was added. The reaction mixture was stirred at 0° C., slowly warming as ice melts. After stirring overnight, triethylamine (0.270 mL, 1.94 mmol) was added. After 8 h, the reaction mixture was diluted with DCM and quenched with sat NH$_4$Cl. The layers were separated and the aqueous layer was extracted with DCM. The combined organic layers were dried (MgSO$_4$), filtered, and concentrated under reduced pressure. The resulting residue was purified via silica gel column chromatography (0-65% ethyl acetate/hexanes) to yield the desired benzyl (4aS,8aR)-4-((4-nitrophenyl)sulfonyl)hexahydro-2H-pyrido[4,3-b][1,4]oxazine-6(5H)-carboxylate. ES/MS: m/z 461.7 [M+H]$^+$.

Step 3. To a solution of benzyl (4aS,8aR)-4-((4-nitrophenyl)sulfonyl)hexahydro-2H-pyrido[4,3-b][1,4]oxazine-6(5H)-carboxylate (166 mg, 0.360 mmol) in DMF (3 mL) at rt was added thioglycolic acid (0.060 mL, 0.864 mmol) followed by lithium hydroxide, monohydrate (84.5 mg, 2.01 mmol). After stirring overnight, the reaction mixture was diluted with ethyl acetate and water. The layers were separated and aqueous extracted with ethyl acetate. The combined organics were dried (MgSO$_4$), filtered, and concentrated under reduced pressure. The resulting residue was dissolved in DCM (4 mL) and triethylamine (0.0800 mL, 0.574 mmol), di-tert-butyl dicarbonate (118 mg, 0.541 mmol), and 4-(dimethylamino)pyridine (7.00 mg, 0.0573 mmol) were added. After 2 h, the aqueous workup above was repeated, extracting with DCM. The combined organics washed with 1 N HCl, dried (MgSO$_4$), filtered, and concentrated under reduced pressure. The resulting residue was dissolved in EtOAc. Pd/C, (10.0%, 77.0 mg, 0.0724 mmol) was added and the mixture hydrogenated under atmosphere of hydrogen. After 1 h, the reaction mixture was diluted with ethyl acetate and filtered over celite. The filtrate was concentrated under reduced pressure to yield tert-butyl (4aS, 8aR)-octahydro-4H-pyrido[4,3-b][1,4]oxazine-4-carboxylate. ES/MS: m/z 242.9 [M+H]$^+$.

3. Synthesis of Intermediates I-1 to I-33A

Preparation of 6-chloro-1-(cyclopropylmethyl)-2-(4,4,5,5-tetramethyl-1,3,2-dioxaborolan-2-yl)-1H-pyrrolo[2,3-b]pyridine (I-1)

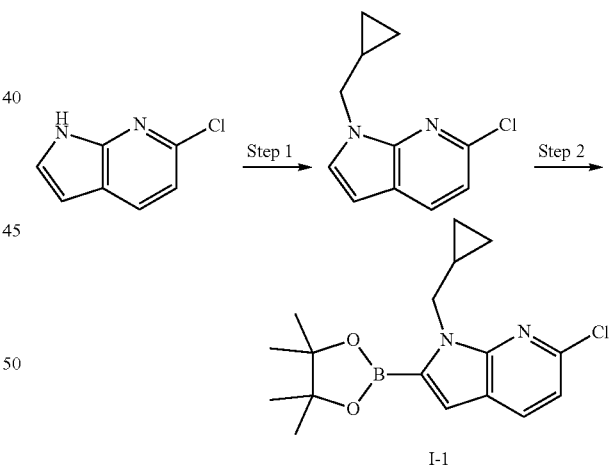

I-1

Step 1. Sodium hydride (60%, 1390 mg, 34.75 mmol) was added to a solution of 6-chloro-1H-pyrrolo[2,3-b]pyridine (4820 mg, 31.59 mmol) in DMF (150 mL) cooled to 0° C., followed by addition of bromomethylcyclopropane (4.3 mL, 50 mmol). The reaction mixture was warmed to room temperature.

After 21 hours, the reaction mixture was quenched with water and extracted with ethyl acetate. The combined organics were washed with water, dried (MgSO$_4$), filtered, and concentrated under reduced pressure to yield a crude product that was purified via silica gel column chromatography (0-15% ethyl acetate in hexanes) to yield 6-chloro-1-(cyclopropylmethyl)-1H-pyrrolo[2,3-b]pyridine. 1H NMR (400 MHz, DMSO-d) δ 8.02 (d, J=8.2 Hz, 1H), 7.65 (d, J=3.5 Hz, 1H), 7.13 (d, J=8.1 Hz, 1H), 6.52 (d, J=3.5 Hz, 1H), 4.06 (d, J=7.1 Hz, 2H), 1.32-1.20 (m, 1H), 0.54-0.47 (m, 2H), 0.44-0.36 (m, 2H).

Step 2. A solution of 6-chloro-1-(cyclopropylmethyl)-1H-pyrrolo[2,3-b]pyridine (3.22 g, 15.58 mmol) in THF (36 mL) was cooled to −78° C. A solution of 2.5M N-Butyllithium in hexanes (3.70 mL, 18.75 mmol) was added slowly. After complete addition, the mixture warmed to −40° C. After one hour, 2-isopropoxy-4,4,5,5-tetramethyl-1,3,2-dioxaborolane (4.6 mL, 22.55 mmol)) was added and the mixture warmed to room temperature and stirred overnight. The reaction mixture was quenched with 1N HCl (60 mL) and extracted with ethyl acetate (2×). The combined organics were dried (MgSO$_4$), filtered, concentrated under reduced pressure to yield the 6-chloro-1-(cyclopropylmethyl)-2-(4,4,5,5-tetramethyl-1,3,2-dioxaborolan-2-yl)-1H-pyrrolo[2,3-b]pyridine I-1. 1H NMR (400 MHz, DMSO-d6) δ 8.05 (d, J=8.2 Hz, 1H), 7.14 (d, J=8.2 Hz, 1H), 7.00 (s, 1H), 4.28 (d, J=7.1 Hz, 2H), 1.31 (s, 12H), 1.29-1.19 (m, 1H), 0.43-0.32 (m, 4H).

Preparation of 2-(6-chloro-1-(cyclopropylmethyl)-1H-pyrrolo[2,3-b]pyridin-2-yl)-6-methyl-1,3,6,2-dioxazaborocane-4,8-dione (I-2)

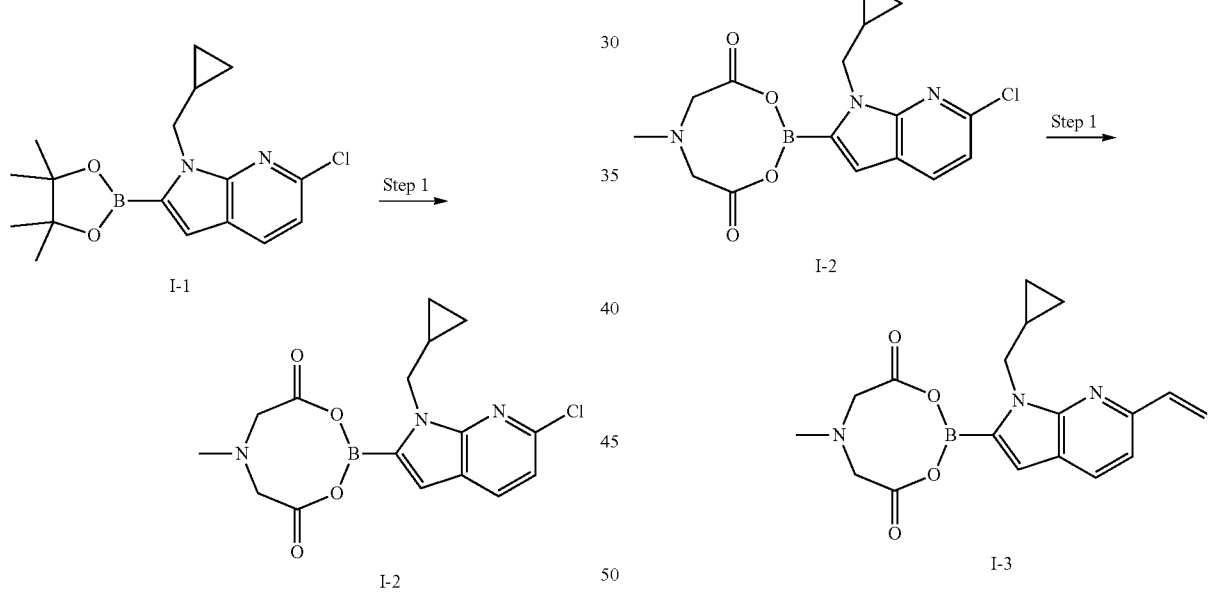

Step 1. To a solution of 6-chloro-1-(cyclopropylmethyl)-2-(4,4,5,5-tetramethyl-1,3,2-dioxaborolan-2-yl)-1H-pyrrolo[2,3-b]pyridine I-1 (15.1 g, 45.4 mmol) in THF (200 mL) and water (50 mL) was added sodium periodate (30 g, 140 mmol). After stirring 20 min at rt, an aqueous solution of hydrochloric acid (1 M, 36 mL, 36 mmol) was added. After an additional 2 h, the reaction mixture was partitioned between EtOAc and water. The organic phase was washed with brine, dried over Na$_2$SO$_4$, and filtered to afford a residue that was used directly. This crude product (ca. 45.4 mmol), methyliminodiacetic acid (20 g, 136 mmol) and 4 Å MS (28 g, heated to 120° C. under high vacuum for 4 h prior to use.) were taken up in DMF (100 mL) under N$_2$. The resulting mixture was heated to 120° C. and stirred for 2 h. The mixture was cooled to rt and filtered to remove sieves, washing with DMF. The filtrate was concentrated in vacuo and the resulting residue was partitioned between EtOAc and water. The phases were separated, and the organic phase was washed with water, brine, dried over Na$_2$SO$_4$, filtered and concentrated under reduced pressure to yield a crude residue. Crystallization was effected by addition of DCM and the resulting slurry was stirred overnight. Solids were collected by filtration, and the filter cakes was washed with DCM until red color elutes affording 2-(6-chloro-1(cyclopropylmethyl)-1H-pyrrolo[2,3-b]pyridin-2-yl)-6-methyl-1,3,6,2-dioxazaborocane-4,8-dione I-2. 1H NMR (400 MHz, DMSO-d6) δ 8.01 (d, J=8.1 Hz, 1H), 7.12 (d, J=8.1 Hz, 1H), 6.62 (s, 1H), 4.41 (d, J=17.3 Hz, 2H), 4.20 (d, J=17.4 Hz, 2H), 4.14 (d, J=7.1 Hz, 2H), 2.58 (s, 3H), 1.46-1.27 (m, 1H), 0.54-0.33 (m, 4H).

Preparation of 2-(1-(cyclopropylmethyl)-6-vinyl-1H-pyrrolo[2,3-b]pyridin-2-yl)-6-methyl-1,3,6,2-dioxazaborocane-4,8-dione (I-3)

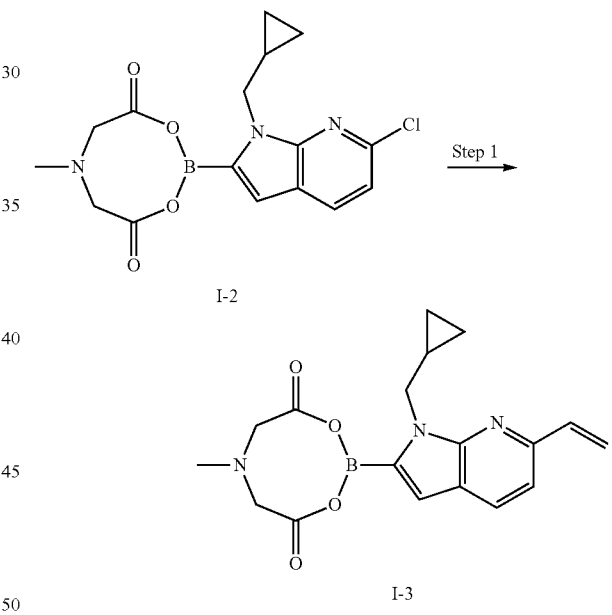

Step 1. A mixture of 2-(6-chloro-1-(cyclopropylmethyl)-1H-pyrrolo[2,3-b]pyridin-2-yl)-6-methyl-1,3,6,2-dioxazaborocane-4,8-dione I-2 (3 g, 8.3 mmol) and bis(tri-t-butylphosphine)palladium (0.42 g, 0.83 mmol) were taken up in dioxane (90 mL) under nitrogen. Vinyltributylstannane (4.81 ml, 16.46 mmol) was added and the resulting mixture was heated to 100° C. After 3 h, the reaction was cooled to rt and diluted with EtOAc and water. The biphasic mixture was filtered through Celite and the phases were separated. The aqueous phase was extracted with EtOAc, and the combined organic phase was dried over Na$_2$SO$_4$, filtered, and concentrated. The resulting residue was purified by silica gel chromatography to afford 2-(1-(cyclopropylmethyl)-6-vinyl-1H-pyrrolo[2,3-b]pyridin-2-yl)-6-methyl-1,3,6,2-dioxazaborocane-4,8-dione I-3. ES/MS: m/z 354.12 [M+H]$^+$

Preparation of 2-(6-acetyl-1-(cyclopropylmethyl)-1H-pyrrolo[2,3-b]pyridin-2-yl)-6-methyl-1,3,6,2-dioxazaborocane-4,8-dione (I-4)

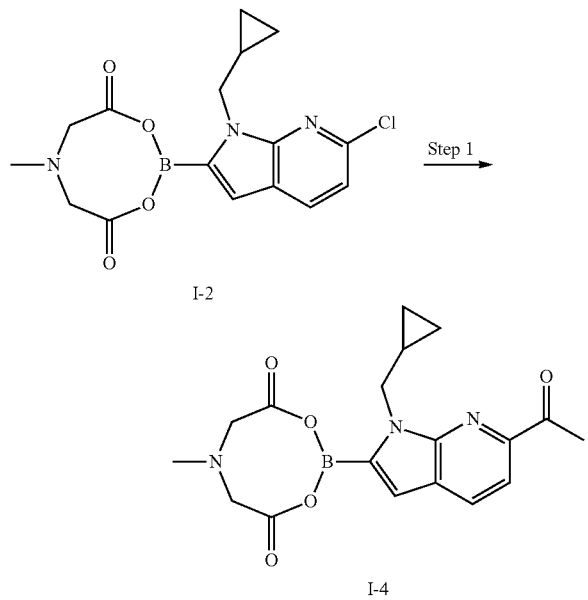

Step 1. A mixture of 2-(6-chloro-1-(cyclopropylmethyl)-1H-pyrrolo[2,3-b]pyridin-2-yl)-6-methyl-1,3,6,2-dioxazaborocane-4,8-dione I-2 (2 g, 5.5 mmol) and Bis(tri-t-butylphosphine)palladium (0.29 g, 0.57 mmol) were taken up in dioxane (60 mL) under nitrogen. 1-ethoxyvinyltributylstannane (3.7 mL, 11 mmol) was added and the resulting mixture was heated to 100° C. After 17 h, the reaction was cooled to rt, diluted with EtOAc and washed with water and brine. The aqueous phase was extracted with EtOAc, and the combined organic phase was washed with brine, dried over $Na_2SO_4$, filtered, and concentrated. The resulting residue was dissolved in THF (200 mL) and aqueous 1 M HCl (28 mL, 28 mmol) was added. After 10 min, the mixture was quenched with saturated $NaHCO_3$ $_{(aq)}$ and was diluted with EtOAc, water, and brine. The phases were separated, and the organic phase was dried over $Na_2SO_4$, filtered, and concentrated. The resulting residue was purified by silica gel chromatography to afford 2-(6-acetyl-1-(cyclopropylmethyl)-1H-pyrrolo[2,3-b]pyridin-2-yl)-6-methyl-1,3,6,2-dioxazaborocane-4,8-dione I-4. ES/MS: m/z 370.15 $[M+H]^+$

Preparation of N-(1-(cyclopropylmethyl)-2-(6-methyl-4,8-dioxo-1,3,6,2-dioxazaborocan-2-yl)-1H-pyrrolo[2,3-b]pyridin-6-yl)-N-(difluoromethyl)methanesulfonamide (I-5)

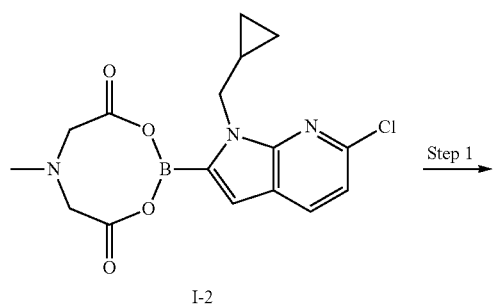

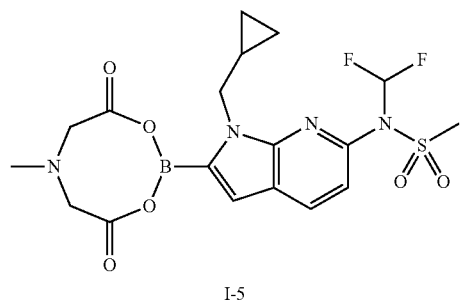

Step 1. A mixture of 2-(6-chloro-1-(cyclopropylmethyl)-1H-pyrrolo[2,3-b]pyridin-2-yl)-6-methyl-1,3,6,2-dioxazaborocane-4,8-dione I-2 (1.65 g, 4.56 mmol), methanesulfonamide (870 mg, 9.1 mmol), cesium carbonate (4.46 g, 13.69 mmol), and Pd-tBuXPhos G3 (0.27 g, 0.34 mmol) was taken up in dioxane (60 mL) under nitrogen. The resulting mixture was heated to 60° C. After stirring 90 min, the reaction mixture was cooled to rt, diluted with EtOAc and washed with water and brine. The layers were separated and aqueous was extracted with ethyl acetate. The combined organics were washed with brine, dried ($Na_2SO_4$), filtered, and concentrated under reduced pressure. The resulting crude residue (ca. 4.56 mmol) was dissolved in DMF (50 mL). Potassium carbonate (6.3 g, 46 mmol) was added, and chlorodifluoromethane was bubbled through the reaction mixture. The mixture was heated to 90° C. and stirred 7 min. The mixture was cooled, additional potassium carbonate (2 g, 14 mmol) was added, and chlorodifluoromethane was bubbled through the reaction mixture with heating at 90° C. for an additional 5 min. The reaction mixture was cooled to rt and filtered. The filtrate was concentrated to ~⅓ volume, and was then partitioned between EtOAc and water. The phases were separated, and the organic phase was washed with brine, dried over $Na_2SO_4$, filtered, and concentrated. The resulting residue was purified via silica gel column chromatography (20-100% acetone in hexanes) to yield N-(1-(cyclopropylmethyl)-2-(6-methyl-4,8-dioxo-1,3,6,2-dioxazaborocan-2-yl)-1H-pyrrolo[2,3-b]pyridin-6-yl)-N-(difluoromethyl)methanesulfonamide I-5. 1H NMR (400 MHz, DMSO-d6) δ 8.11 (d, J=8.1 Hz, 1H), 7.43 (t, J=59.5 Hz, 1H), 7.09 (d, J=8.1 Hz, 1H), 6.69 (s, 1H), 4.43 (d, J=17.4 Hz, 2H), 4.28-4.17 (m, 4H), 3.60 (s, 3H), 2.62 (s, 3H), 1.46-1.34 (m, 1H), 0.52-0.42 (m, 2H), 0.42-0.34 (m, 2H).

Preparation of 6-chloro-2-(4,4,5,5-tetramethyl-1,3,2-dioxaborolan-2-yl)-1-(2-(trimethylsilyl)ethoxy)methyl)-1H-pyrrolo[2,3-b]pyridine (I-6)

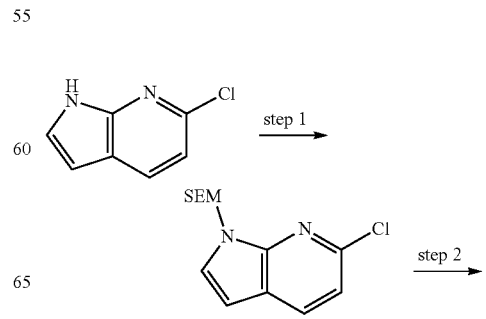

-continued

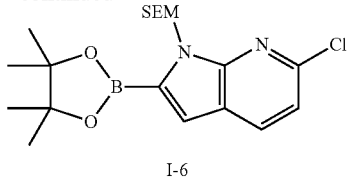

I-6

Step 1. Under an argon atmosphere, 6-chloro-1H-pyrrolo[2,3-b]pyridine (37.9 g, 248.1 mmol) and dry DMF (800 mL) were added to a round bottom flask. The mixture was cooled to 0° C. and sodium hydride (60% dispersion in mineral oil, 10.9 g, 273 mmol, 1.1 equiv) was added in portion over 10 minutes. The resulting mixture was stirred for 1 hour and 2-(trimethylsilyl) ethoxymethyl chloride (45.5 g, 273 mmol, 1.1 equiv) was added. The resulting mixture was warmed to rt and stirred overnight, diluted with dichloromethane (1.5 L), and then quenched with water (100 mL). Additional water (500 mL) was added. The organic layer was washed with water, and brine, and dried over magnesium sulfate, filtered and evaporated to dryness. The residue was purified by chromatography over silica gel (EtOAc in Hexane, 0 to 5%) to afford 6-chloro-1-((2-(trimethylsilyl)ethoxy)methyl)-1H-pyrrolo[2,3-b]pyridine. ES/MS: m/z 283.2 [M+H]$^+$. $^1$H NMR (300 MHz, Chloroform-d) δ 7.84 (d, J=8.1 Hz, 1H), 7.32 (d, J=3.6 Hz, 1H), 7.10 (d, J=8.1 Hz, 1H), 6.52 (d, J=3.6 Hz, 1H), 5.64 (s, 2H), 3.53 (t, J=7.2 Hz, 1H), 2H), 0.91 (t, J=7.2 Hz, 2H), −0.06 (s, 9H).

Step 2. A solution of 6-chloro-1-((2-(trimethylsilyl)ethoxy)methyl)-1H-pyrrolo[2,3-b]pyridine (8.8 g, 31.1 mmol) in THF (100 mL) was cooled to −78° C. and n-BuLi (2.5M in hexanes, 37.3 mmol, 1.2 equiv.) was added dropwise over 10 minutes. The resulting solution was stirred for an additional 2 h at this temperature. 2-Isopropoxy-4,4,5,5-tetramethyl-1,3,2-dioxaborolane (6.94 g, 37.3 mmol, 1.2 equiv.) was then added and the mixture was warmed to −20° C. over one hour. Then mixture was then stirred for 5 additional minutes at −20° C. before being quenched with HCl (1M, 60 mL). The mixture was diluted with EtOAc and water. The organic phase was dried and concentrated, and the residual orange oil was purified by chromatography over silica gel (Hexanes:EtOAc 0 to 10%). 6-Chloro-2-(4,4,5,5-tetramethyl-1,3,2-dioxaborolan-2-yl)-1-((2-(trimethylsilyl)ethoxy)methyl)-1H-pyrrolo[2,3-b]pyridine I-6 was obtained. ES/MS: m/z 409.3 [M+H]$^+$. $^1$H NMR (400 MHz, CDCl$_3$) δ 7.87 (d, J=8.2 Hz, 1H), 7.13-7.06 (m, 2H), 5.91 (s, 2H), 3.59-3.50 (m, 2H), 1.39 (s, 12H), 0.96-0.85 (m, 2H), −0.07 (s, 9H).

Preparation of (6-(benzyloxy)-1-(tert-butoxycarbonyl)-1H-pyrrolo[2,3-b]pyridin-2-yl)boronic acid (I-7)

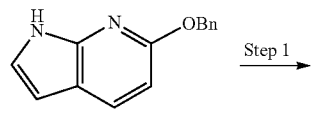

Step 1

-continued

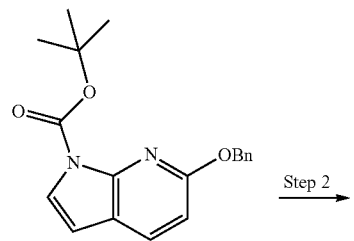

Step 2

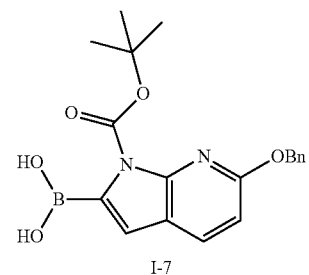

I-7

Step 1. Di-tert-butyl dicarbonate (749 mg, 3.43 mmol) was added to a mixture of 6-(benzyloxy)-1H-pyrrolo[2,3-b]pyridine (700 mg, 3.12 mmol), triethylamine (0.435 mL, 3.12 mmol) and 4-(Dimethylamino)pyridine (19.1 mg, 0.156 mmol) in DCM (20 mL). After 90 minutes, the reaction mixture was concentrated onto silica gel and purified via column chromatography (0-50% ethyl acetate in hexanes) to yield tert-butyl 6-(benzyloxy)-1H-pyrrolo[2,3-b]pyridine-1-carboxylate. ES/MS: m/z 324.94 [M+H]$^+$.

Step 2. Note: LDA was prepared by adding a solution of Butyllithium (2.50 M, 4.32 mL, 10.8 mmol) in hexanes to a solution of diisopropylamine (1.55 mL, 11.1 mmol) in THF (4.95 mL) under N$_2$ at 0° C. Stir 15 min prior to use.

The above LDA solution (3.8 mL) was added dropwise over 45 minutes to a solution of tert-butyl 6-(benzyloxy)-1H-pyrrolo[2,3-b]pyridine-1-carboxylate (1 g, 3.08 mmol) in THF (10 mL) under N$_2$ at 0° C. After 1 h, the reaction mixture was quenched with 40 mL 1M pH 7 phosphate buffer and diluted with EtOAc. The layers were separated and the aqueous was extracted with EtOAc. The combined organics were dried (Na$_2$SO$_4$), filtered, and concentrated under reduced pressure. The resulting solid was suspended in 2 mL EtOAc and hexanes (~15 mL) was added. Solids were filtered, washed with hexanes, and dried in vacuo to yield (6-(benzyloxy)-1-(tert-butoxycarbonyl)-1H-pyrrolo[2,3-b]pyridin-2-yl)boronic acid I-7. ES/MS: m/z 368.88 [M+H]$^+$.

Preparation of 2-(6-acetyl-14(2-(trimethylsilyl)ethoxy)methyl)-1H-pyrrolo[2,3-b]pyridin-2-yl)-6-methyl-1,3,6,2-dioxazaborocane-4,8-dione (I-9)

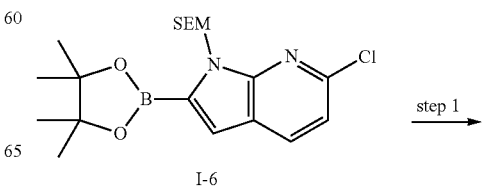

I-6 step 1

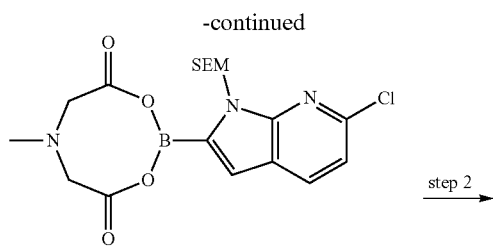

I-8

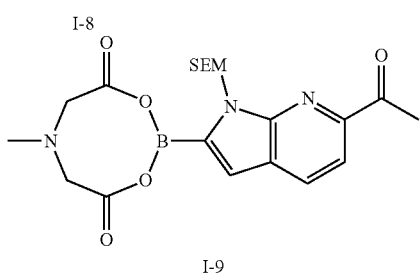

I-9

Step 1. To a solution of 6-chloro-2-(4,4,5,5-tetramethyl-1,3,2-dioxaborolan-2-yl)-1-((2-(trimethylsilyl)ethoxy)methyl)-1H-pyrrolo[2,3-b]pyridine (I-6, 9.6 g, 23.5 mmol) in THF (120 mL) and water (30 mL) was added sodium periodate (14 g, 70.5 mmol). After stirring 20 min at rt, hydrochloric acid (1 M, 18 mL) was added. After an additional 2.5 h, the reaction mixture was partitioned between EtOAc and water. The organic phase was washed with brine, dried over Na₂SO₄, filtered, and concentrated under reduced pressure. The resulting residue along with methyliminodiacetic acid (10.4 g, 70 mmol), and 4 Å MS (15 g) were taken up in DMF (52 mL), and that mixture was heated to 120° C. under N₂ for 2 h. The mixture was cooled and filtered to remove sieves, washing with DMF. The filtrate was concentrated in vacuo and the resulting residue was partitioned between EtOAc and water (~100 mL each). The phases were separated, and the organic phase was washed with water and brine, dried over Na₂SO₄, filtered and concentrated under reduced pressure. The resulting crude residue was purified on silica gel (5-25% acetone in hexanes) to yield 2-(6-chloro-1-((2-(trimethylsilyl)ethoxy)methyl)-1H-pyrrolo[2,3-b]pyridin-2-yl)-6-methyl-1,3,6,2-dioxazaborocane-4,8-dione I-8. $^1$H NMR (400 MHz, Chloroform-d) δ 7.82 (d, J=8.1 Hz, 1H), 7.09 (d, J=8.1 Hz, 1H), 6.84 (s, 1H), 5.76 (s, 2H), 4.09 (d, J=16.5 Hz, 2H), 3.94 (d, J=16.5 Hz, 2H), 3.68-3.59 (m, 2H), 2.75 (s, 3H), 1.00-0.81 (m, 2H), 0.00 (s, 9H).

Step 2. 2-(6-chloro-1-((2-(trimethylsilyl)ethoxy)methyl)-1H-pyrrolo[2,3-b]pyridin-2-yl)-6-methyl-1,3,6,2-dioxazaborocane-4,8-dione I-8 (4.51 g, 10.3 mmol) was taken up in dioxane (100 mL) under N₂. The reaction mixture was degassed by Ar bubbling for 10 min. 1-ethoxyvinyltributylstannane and (7.4 mL, 20.6 mmol) and PdCl₂(dppf) (750 mg, 1.23 mmol) were added and the resulting mixture was heated to 100° C. After 20 h, LCMS showed complete conversion, and the reaction was cooled to room temperature, filtered over a plug of celite and the plug was rinsed with EtOAc three times. The resulting solution was evaporated to dryness. The resulting residue was dissolved in THF (100 mL) and aqueous 1 M HCl (50 mL, 50 mmol) was added. The resulting mixture was stirred vigorously for 45 minutes and was then diluted with DCM (200 mL) and water (150 mL). The phases were separated, the aqueous layer was extracted with DCM (150 mL) and the organic phase was dried over Na₂SO₄, filtered, and concentrated. Purification by silica gel chromatography (5-70% acetone in hexanes) afforded 2-(6-acetyl-1-((2-(trimethylsilyl)ethoxy)methyl)-1H-pyrrolo[2,3-b]pyridin-2-yl)-6-methyl-1,3,6,2-dioxazaborocane-4,8-dione I-9. $^1$H NMR (400 MHz, DMSO-d6) δ 8.15 (d, J=8.1 Hz, 1H), 7.80 (d, J=8.1 Hz, 1H), 6.85 (s, 1H), 5.82 (s, 2H), 4.46 (d, J=17.3 Hz, 2H), 4.17 (d, J=17.2 Hz, 2H), 3.59-3.50 (m, 2H), 3.32 (s, 3H), 2.72 (s, 2H), 2.64 (s, 3H), 1.01-0.92 (m, 2H), −0.03-0.11 (m, 1H), -0.08 (s, 9H).

Preparation of tert-butyl (R)-(1-(2-(6-methyl-4,8-dioxo-1,3,6,2-dioxazaborocan-2-yl)-1H-pyrrolo[2,3-b]pyridin-6-yl)ethyl)carbamate (I-10)

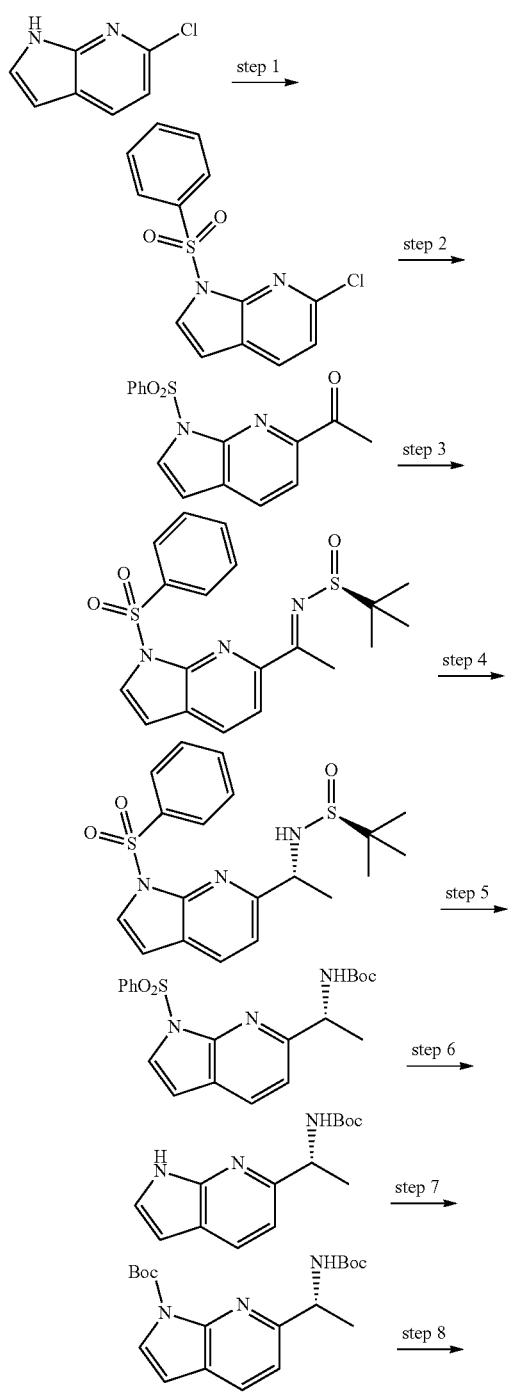

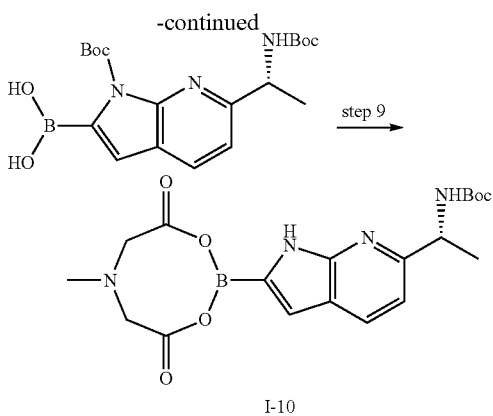

I-10

Step 1. Under an argon atmosphere, to a solution of 6-chloro-1H-pyrrolo[2,3-b]pyridine (950.0 g, 6.22 mol, 1.0 eq) in THF (9.5 L) at 0° C. was added sodium hydride (60% in oil, 373.5 g, 9.34 mol, 1.5 eq) by portion wise. The resulting mixture was vigorously stirred at rt for 1 h and PhSO$_2$C$_1$ (1209.5 g, 6.85 mol, 1.1 eq) in THF (1900 mL) was added drop wise at 0° C. After the addition, the reaction mixture was warmed to 25° C. and stirred for 1 h. Quenched with sat. aq. NaHCO$_3$(3800 mL) below 5° C. The mixture was extracted with EA (2000 mL×3). The combined organic layers were washed with brine (3000 mL×3) and dried over anhydrous sodium sulfate and then concentrated under reduced pressure to give a crude residue, which was slurry in MTBE (2000 mL) for 30 mins. The solid was collected by filtration to give 6-chloro-1-(phenylsulfonyl)-1H-pyrrolo[2,3-b]pyridine.

$^1$H NMR (400 MHz, CDCl$_3$): δ 8.25 (t, J=7.6 Hz, 2H), 7.77 (d, J=8.4 Hz, 1H), 7.71 (d, J=4.0 Hz, 1H), 7.61 (d, J=7.2 Hz, 1H), 7.52 (t, J=8.0 Hz, 2H), 7.18 (d, J=8.0 Hz, 1H), 6.57 (d, J=4.0 Hz, 1H). Step 2. Under N$_2$, 6-chloro-1-(phenylsulfonyl)-1H-pyrrolo[2,3-b]pyridine (900.0 g, 3.07 mol, 1.0 eq) was taken up in dioxane (18 L). The reaction mixture was degassed by N$_2$ bubbling for 10 minutes before 1-ethoxyvinyltributylstannane (2220.6 g, 6.15 mol, 2.0 eq) and PdCl$_2$(dppf) (269.9 g, 369 mmol, 12 mol %) were added and the resulting mixture was heated to 100° C. After stirring for 12 h, the reaction mixture was cooled to room temperature, filtered over a plug of celite and the filter cake was washed with EtOAc (1000 mL) three times. The filtrate was evaporated to dryness and the resulting residual was dissolved in THF (9 L) and aqueous HCl (1 M, 12.6 L, 12.6 mol) was added. The resulting mixture was stirred vigorously for 30 minutes. TLC indicated complete conversion. The resulting mixture was diluted with DCM (24 L) and water (24 L). The phases were separated, the aqueous layer was extracted with DCM (5 L). The organic phase was dried over Na$_2$SO$_4$, filtered and concentrated to give a crude residue, which was purified by silica gel chromatography (EA/PE 50% to 100%) to afford 1-(1-(phenylsulfonyl)-1H-pyrrolo[2,3-b]pyridin-6-yl)ethan-1-one. $^1$H NMR (400 MHz, CDCl$_3$): δ 8.25 (d, J=7.6 Hz, 2H), 8.00-7.93 (m, 3H), 7.65-7.61 (m, 1H), 7.55-7.51 (m, 2H), 6.68 (d, J=4.0 Hz, 1H), 2.80 (s, 3H).

Step 3. Under N$_2$, 1-(1-(phenylsulfonyl)-1H-pyrrolo[2,3-b]pyridin-6-yl)ethan-1-one (730.0 g, 2.43 mol, 1.0 eq) and (S)-2-methylpropane-2-sulfinamide (736.5 g, 6.08 mol, 2.5 eq) were dissolved in THF (14.6 L). Then Ti(OiPr)$_4$ (5526.7 g, 19.45 mol, 8.0 eq) were added and the resulting mixture was heated to 70° C. The mixture was stirred for 48 h. TLC showed completion. Cooled to room temperature.

Diluted with EA (15 L) and brine (15 L) was added. Filtered and washed with EA (10 L×3). The filtrate was washed with brine (10 L) and dried over anhydrous sodium sulfate and then concentrated under reduced pressure to give (S,E)-2-methyl-N-(1-(1-(phenylsulfonyl)-1H-pyrrolo[2,3-b]pyridin-6-yl)ethylidene)propane-2-sulfinamide, which was directly used for the next step without purification. $^1$H NMR (400 MHz, CDCl$_3$): δ 8.19 (d, J=7.6 Hz, 2H), 8.08 (d, J=8.4 Hz, 1H), 7.86 (t, J=4.0 Hz, 2H), 7.59 (d, J=7.6 Hz, 1H), 7.49 (t, J=8.0 Hz, 2H), 6.64 (d, J=4.0 Hz, 1H), 2.93 (s, 3H), 1.21 (s, 9H).

Step 4. Under N$_2$, a solution of (S,E)-2-methyl-N-(1-(1-(phenylsulfonyl)-1H-pyrrolo[2,3-b]pyridin-6-yl)ethylidene)propane-2-sulfinamide (1569.5 g, 3.89 mol, 1.0 eq) in THF (16 L) was cooled to −30° C. and L-selectride (1 M in THF, 3890 mL, 3.89 mol, 1.0 eq) was added by dropwise. The mixture was stirred at −30° C. for 3 h. Then quenched with NH$_4$C$_1$ (aq) (16 L) at −30° C., extracted with EtOAc (10 L). The organic layers were washed with brine (5 L×3) and dried over anhydrous sodium sulfate and then concentrated under reduced pressure to give a crude residue, which was purified by silica gel chromatography (EA/PE 10% to 30%) to afforded (S)-2-methyl-N—((R)-1-(1-(phenylsulfonyl)-1H-pyrrolo[2,3-b]pyridin-6-yl)ethyl)propane-2-sulfinamide. $^1$H NMR (400 MHz, CDCl$_3$): δ 8.21 (t, J=7.6 Hz, 2H), 7.80 (d, J=8.0 Hz, 1H), 7.71 (d, J=3.6 Hz, 1H), 7.58-7.55 (m, 1H), 7.51-7.47 (m, 2H), 7.16 (d, J=8.0 Hz, 1H), 6.56 (d, J=4.0 Hz, 1H), 4.71 (t, J=6.8 Hz, 1H), 4.06 (d, J=7.2 Hz, 1H), 1.61 (d, J=6.4 Hz, 3H), 1.19 (s, 9H).

Step 5. (S)-2-methyl-N—((R)-1-(1-(phenylsulfonyl)-1H-pyrrolo[2,3-b]pyridin-6-yl)ethyl)propane-2-sulfinamide (438.0 g, 1.08 mol, 1.0 eq) was dissolved in HCl/dioxane (4 mol/L, 2190 mL). The resulting mixture was stirred vigorously for 1 h. The resulting mixture was concentrated in vacuo to give crude (R)-1-(1-(phenylsulfonyl)-1H-pyrrolo[2,3-b]pyridin-6-yl)ethan-1-amine dihydrochloride, which was slurry in MTBE (3500 mL) for 30 mins. The solid was collected by filtration to give (R)-1-(1-(phenylsulfonyl)-1H-pyrrolo[2,3-b]pyridin-6-yl)ethan-1-amine dihydrochloride. $^1$HNMR (400 MHz, DMSO-d$_6$): δ 8.58 (s, 3H), 8.31 (t, J=7.6 Hz, 2H), 8.14 (d, J=8.0 Hz, 1H), 7.96 (d, J=4.0 Hz, 1H), 7.76 (t, J=7.2 Hz, 1H), 7.64 (t, J=8.0 Hz, 2H), 7.50 (d, J=8.4 Hz, 1H), 6.86 (d, J=4.0 Hz, 1H), 4.61 (d, J=5.6 Hz, 1H), 1.53 (d, J=6.8 Hz, 3H).

A solution of (R)-1-(1-(phenylsulfonyl)-1H-pyrrolo[2,3-b]pyridin-6-yl)ethan-1-amine dihydrochloride (338.2 g, 903.6 mmol, 1.0 eq) and Et$_3$N (274.3 g, 2.71 mol, 3.0 eq) in THF (3380 mL) was cooled to 0° C., (Boc)$_{20}$ (236.7 g, 1.08 mmol, 1.2 eq) was added dropwise. The resulting mixture was stirred vigorously for 2 h at room temperature. The resulting mixture was diluted with water (3300 mL). Phases were separated and the aqueous layer was extracted with EA (3000 mL×2). The organic layers were washed with saturated citric acid (6000 mL×2) and brine (6000 mL×2), dried over anhydrous sodium sulfate and then concentrated under reduced pressure to give a crude residue, which was purified by silica gel chromatography (EA/PE 10% to 30%) to afforded tert-butyl (R)-(1-(1-(phenylsulfonyl)-1H-pyrrolo[2,3-b]pyridin-6-yl)ethyl)carbamate. $^1$H NMR (400 MHz, CDCl$_3$): δ 8.21 (d, J=7.6 Hz, 2H), 7.79 (d, J=8.0 Hz, 1H), 7.73 (d, J=4.0 Hz, 1H), 7.60-7.50 (m, 3H), 7.12 (d, J=8.0 Hz, 1H), 6.57 (d, J=4.0 Hz, 1H), 5.61 (s, 1H), 4.90 (s, 1H), 1.49-1.45 (m, 12H).

Step 6. A mixture tert-butyl (R)-(1-(1-(phenylsulfonyl)-1H-pyrrolo[2,3-b]pyridin-6-yl)ethyl)carbamate (2.5 g, 6.23 mmol), 10M NaOH (3 mL), and MeOH (10 mL) was heated in a microwave reactor at 100° C. for 20 min. The methanol was removed and the product was extracted with MeTFIF and water. The organic layer was dried with Na$_2$SO$_4$, filtered, and concentrated. The crude product was taken to next step without further purification. ES/MS: m/z 262.1 [M+H]$^+$.

Step 7. A procedure analogous to Step 5, part 2 of this synthesis was utilized to produce tert-butyl (R)-6-(1-((tert-butoxycarbonyl)amino)ethyl)-1H-pyrrolo[2,3-b]pyridine-1-carboxylate from tert-butyl (R)-(1-(1H-pyrrolo[2,3-b]pyridin-6-yl)ethyl)carbamate. ES/MS: m/z 362.2 [M+H]$^+$.

Step 8. To a solution of tert-butyl 6-[(1R)-1-(tert-butoxycarbonylamino)ethyl]pyrrolo[2,3-b]pyridine-1-carboxylate (1 g, 2.77 mmol) in THF (20 mL) was added triisopropyl borate (1.28 mL, 5.53 mmol). The mixture was cooled to −40° C. and a solution of 0.5 M LDA in THF (16.6 mL, 8.4 mmol) was added dropwise maintaining an internal temperature below −10° C. The mixture was stirred for 5 mins after addition of LDA and the mixture was warmed to 0° C. and quenched with NH$_4$C$_1$ (aq). The mixture was diluted with ethyl acetate and the layers were separated. The organic layer was dried with Na$_2$SO$_4$, filtered, and concentrated. The resulting residue was purified by silica chromatography (0-5% MeOH in DCM) to yield (R)-(1-(tert-butoxycarbonyl)-6-(1-((tert-butoxycarbonyl)amino)ethyl)-1H-pyrrolo[2,3-b]pyridin-2-yl)boronic acid. ES/MS: m/z 406.2 [M+H]$^+$.

Step 9. A mixture of (R)-(1-(tert-butoxycarbonyl)-6-(1-((tert-butoxycarbonyl)amino)ethyl)-1H-pyrrolo[2,3-b]pyridin-2-yl)boronic acid (490 mg, 1.21 mmol) and 24carboxymethyl(methypaminolacetic acid (0.178 g, 1.21 mmol) in acetonitrile (2 mL) was heated at 130° C. in a microwave reactor. After 6 minutes, the reaction mixture was concentrated under reduced pressure and the resulting residue was purified by silica chromatography (50-100% ethyl acetate in hexanes) to yield tert-butyl (R)-(1-(2-(6-methyl-4,8-dioxo-1,3,6,2-dioxazaborocan-2-yl)-1H-pyrrolo[2,3-b]pyridin-6-yl)ethyl)carbamate I-10. ES/MS: m/z 417.1 [M+H]$^+$.

Preparation of (S)-3-methyl-1,2-thiazinane 1,1-dioxide (I-11)

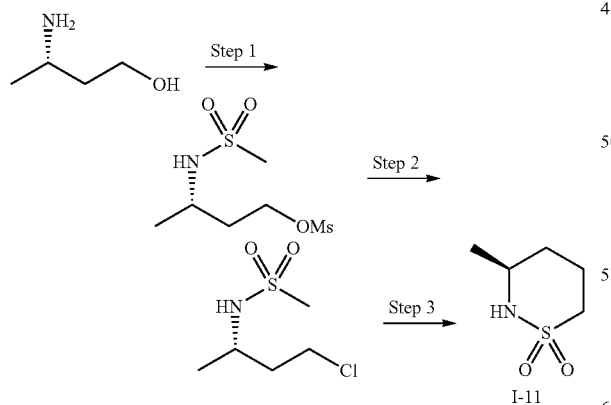

Step 1. Methanesulfonyl chloride (54.3 mL, 701 mmol) was added to a stirred solution of (S)-3-aminobutan-1-ol (25 g, 280 mmol) and triethylamine (97.5 mL, 701 mmol) in THF (500 mL) at roughly −5 to 0° C. and the reaction was allowed to room temperature and stirred for 2 h. The mixture was filtered and the solid was washed with THF. The filtrate was concentrated under reduced pressure to yield (S)-3-(methylsulfonamido)butyl methanesulfonate, which was used without purification. ES/MS: m/z 246.1 [M+H]$^+$.

Step 2. To a stirred solution of (S)-3-(methylsulfonamido) butyl methanesulfonate (48 g, 196 mmol) in DMF (833 mL), NaCl (48 g, 822 mmol) was added at room temperature and the mixture was heated at 80° C. for 16 h. The reaction mixture was cooled to room temperature and diluted with ethyl acetate and water. The layers were separated and the aqueous was extracted with EtOAc. The combined the organic layers were washed with brine solution, dried (Na$_2$SO$_4$), and concentrated under reduced pressure. The resulting residue was purified by silica gel column chromatography using 40%-50% EtOAc in pet ether to yield (S)—N-(4-chlorobutan-2-yl)methanesulfonamide. ES/MS: m/z 186.1 [M+H]$^+$.

Step 3. To a stirred solution of (S)—N-(4-chlorobutan-2-yl)methanesulfonamide (22 g, 119 mmol) in THF (393 mL), 1,10-Phenanthroline (55 mg, 0.5 mmol), diisopropylamine (4.2 mL, 29.7 mmol) were added and cooled to −78° C. n-BuLi (2.5 M in THF, 167 mL, 417 mmol) was added dropwise at −78° C. and the reaction mixture was warmed to rt and stirred 16 hours. The reaction mixture was quenched with aqueous ammonium chloride solution and the mixture was extracted with EtOAc.

Combined organics were dried (Na$_2$SO$_4$), filtered, and concentrated under reduced pressure. The resulting residue was purified by silica gel column chromatography using 40%-50% EtOAc in pet ether to yield (S)-3-methyl-1,2-thiazinane 1,1-dioxide I-11. ES/MS: m/z 150.2 [M+H]$^+$.

(R)-3-methyl-1,2-thiazinane 1,1-dioxide (I-12)

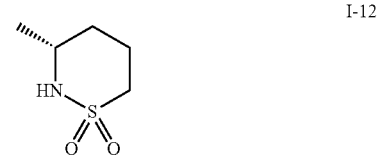

Following the procedure of I-11, beginning with (R)-3-aminobutan-1-ol, (R)-3-methyl-1,2-thiazinane 1,1-dioxide I-12 was synthesized. ES/MS: m/z 150.2 [M+H]$^+$.

Preparation of methyl 5-methoxy-3-methyl-2-(((trifluoromethyl)sulfonyl)oxy)imidazo[1,2-a]pyridine-7-carboxylate (I-13)

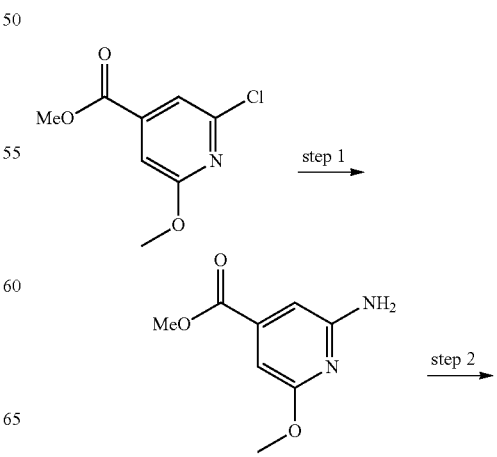

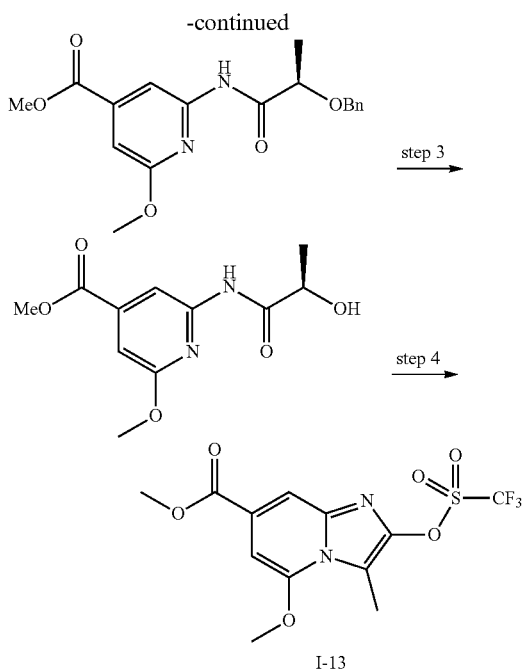

I-13

Step 1. Methyl 2-chloro-6-methoxyisonicotinate (10 g, 50 mmol), Pd$_2$(dba)$_3$ (900 mg, 1.0 mmol), Xantphos (1150 mg, 1.99 mmol), and cesium carbonate (33 g, 100 mmol) were taken up in 1,4-dioxane (300 mL) under N$_2$. Benzophenone imine (9.6 mL, 57 mmol) was added, and the resulting mixture was stirred at 90° C. for 16 h. The mixture was then cooled and partitioned between EtOAc and water. The phases were separated, and the organic phase was washed with brine, dried over Na$_2$SO$_4$, filtered, and concentrated. The crude residue was dissolved in THF (300 mL) and water (150 mL). Hydrochloric acid (12 M, 21 mL, 250 mmol) was added, and the resulting mixture was stirred until LC/MS indicated completion (~1 h). Solid NaHCO$_3$ (25 g, 300 mmol) was added, and the resulting mixture was diluted with EtOAc and water. The phases were separated, and the aqueous phase was extracted with EtOAc. The combined organic phase was dried over Na$_2$SO$_4$, filtered, and concentrated. The resulting residue was purified by silica gel chromatography (0-60% EtOAc in hexanes) to afford methyl 2-amino-6-methoxyisonicotinate. ES/MS: m/z 183.1 [M+H]$^+$.

Step 2. (R)-2-(benzyloxy)propanoic acid (3.84 g, 21.3 mmol) was dissolved in DCM (64 mL) under N$_2$. DMF (100 μL) was added followed by dropwise addition of oxalyl chloride (1.80 mL, 21.3 mmol). The resulting mixture was stirred for 2 h at rt and was then added to a solution of methyl 2-amino-6-methoxyisonicotinate (3 g, 16.5 mmol) and trimethylamine (6.9 mL, 50 mmol) in DCM (40 mL) cooled in an ice water bath. The stirred mixture was let warm to rt. After 90 min, the mixture was diluted with DCM and water. The phases were separated, and the aqueous phase was extracted with DCM. The combined organic phase was dried over Na$_2$SO$_4$, filtered, and concentrated. The crude residue was purified by silica gel chromatography (10-50% EtOAc in hexanes) to afford methyl (R)-2-(2-(benzyloxy)propanamido)-6-methoxyisonicotinate. ES/MS: m/z 345.1 [M+H]$^+$.

Step 3. Methyl (R)-2-(2-(benzyloxy)propanamido)-6-methoxyisonicotinate (5.19 g, 15 mmol) was dissolved in THF (100 mL) and EtOH (50 mL). Palladium on carbon (Degussa, 10% dry wt., 50% overall water wt.) (2 g, 0.94 mmol) was added and the reaction vessel was purged with H2. The resulting mixture was stirred under 1 atm H2 for 90 min and was then filtered through a pad of celite with THF. The filtrate was concentrated to afford methyl (R)-2-(2-hydroxypropanamido)-6-methoxyisonicotinate which was used without further purification. ES/MS: m/z 255.1 [M+H]$^+$.

Step 4. Methyl (R)-2-(2-hydroxypropanamido)-6-methoxyisonicotinate (3.78 g, 14.9 mmol) was dissolved in DCM (150 mL) under N$_2$ and was cooled in a CO$_2$/acetone bath. 2-Methoxypyridine (4.7 mL, 44.7 mmol) was added followed by dropwise trifluoromethanesulfonic anhydride (7.53 mL, 44.6 mmol). The resulting mixture was stirred for 5 min and was then allowed to warm to rt. After 5 h, the reaction mixture was partitioned between DCM and water, and the aqueous phase was acidified with HCl. The phases were separated, and the aqueous phase was extracted with DCM. The combined organic phase was dried over Na$_2$SO$_4$, filtered, and concentrated to afford a crude residue. Purification by silica gel chromatography (20-100% EtOAc in hexanes) provided methyl 5-methoxy-3-methyl-2-(((trifluoromethyl)sulfonyl)oxy)imidazo[1,2-a]pyridine-7-carboxylate I-13. ES/MS: m/z 368.9 [M+H]$^+$. 1H NMR (400 MHz, Chloroform-d) δ 7.89 (d, J=1.4 Hz, 1H), 6.64 (d, J=1.4 Hz, 1H), 4.07 (s, 3H), 3.94 (s, 3H), 2.71 (s, 3H).

Preparation of methyl 2-chloro-3-cyclopropylimidazo[1,2-a]pyridine-7-carboxylate (I-14)

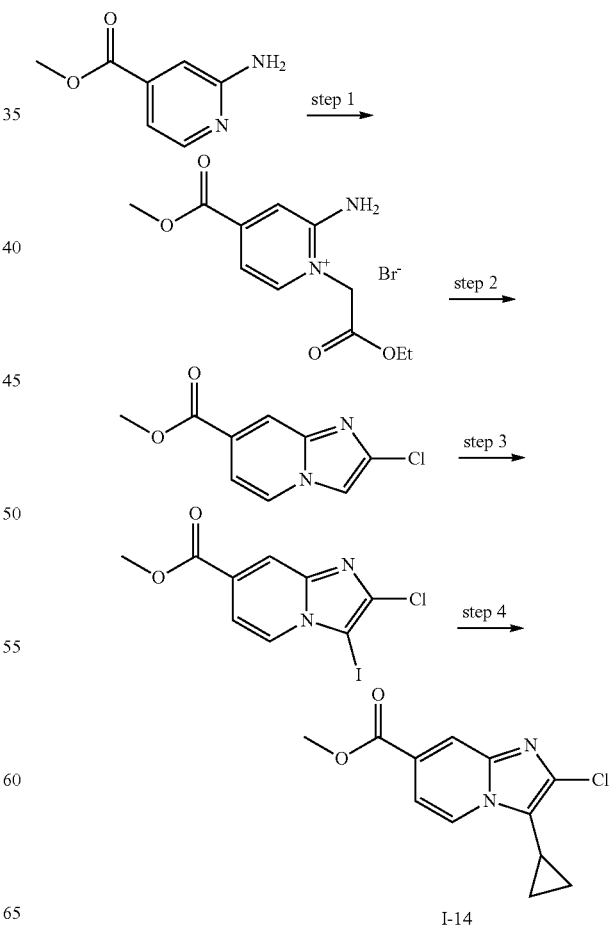

I-14

Step 1. Methyl 2-aminoisonicotinate (7 g, 46 mmol) was suspended in ethyl bromoacetate (22 mL) and the reaction mixture was stirred at rt for 96 h. The reaction mixture was diluted with ether, stirred for 1 h, and filtered. The solids were washed with diethyl ether, and then dried in vacuo to provide 2-amino-1-(2-ethoxy-2-oxoethyl)-4-(methoxycarbonyl)pyridin-1-ium bromide. $^1$H NMR (400 MHz, DMSO-d6) δ 9.02 (s, 2H), 8.15 (d, J=7.0 Hz, 1H), 7.62 (d, J=1.8 Hz, 1H), 7.25 (dd, J=7.0, 1.8 Hz, 1H), 5.21 (s, 2H), 4.21 (q, J=7.1 Hz, 2H), 3.92 (s, 3H), 1.25 (t, J=7.1 Hz, 3H).

Step 2. A mixture of 2-amino-1-(2-ethoxy-2-oxoethyl)-4-(methoxycarbonyl)pyridin-1-ium bromide (580 mg, 1.82 mmol) and phosphorus oxychloride (3.4 mL, 36.6 mmol) was heated at 110° C. for 2 h. The reaction mixture was cooled to rt and quenched in portions into room temperature water. The mixture was then diluted with EtOAc and quenched with saturated NaHCO$_3$(aq). The layers were separated and the aqueous phase was extracted with EtOAc. The combined organics were dried (MgSO$_4$), filtered, and concentrated under reduced pressure. The resulting residue was purified via silica gel column chromatography (0-50% acetone in hexanes) to yield methyl 2-chloroimidazo[1,2-a]pyridine-7-carboxylate. ES/MS: m/z 211.1 [M+H]$^+$.

Step 3. To a solution of methyl 2-chloroimidazo[1,2-a]pyridine-7-carboxylate (1.04 g, 4.94 mmol) in acetonitrile (50 mL) was added N-iodosuccinimide (1.35 g, 6 mmol). After 90 min, the reaction mixture was quenched with 10% aqueous sodium thiosulfate and diluted with water. The heterogeneous mixture was filtered, and the solids were washed with water and dried in vacuo to yield methyl 2-chloro-3-iodoimidazo[1,2-a]pyridine-7-carboxylate. ES/MS: m/z 337.2 [M+H]$^+$.

Step 4. A mixture of methyl 2-chloro-3-iodoimidazo[1,2-a]pyridine-7-carboxylate (2.09 g, 6.21 mmol), potassium cyclopropyltrifluoroborate (2315 mg, 15.64 mmol), palladium(II) acetate (167 mg, 0.74 mmol), butyldi-1-adamantylphosphine (539 mg, 1.5 mmol) and cesium carbonate (8150 mg, 25.01 mmol) in dioxane (15 mL) and water (1.5 mL) was heated at reflux for 15 h. After cooling to rt, the mixture was partitioned between ethyl acetate and water. The layers were separated and the aqueous was extracted with ethyl acetate. The combined organics were washed with brine, dried (MgSO$_4$), filtered, and concentrated under reduced pressure. The resulting residue was purified via silica gel column chromatography (0-40% ethyl acetate in hexanes) to yield methyl 2-chloro-3-cyclopropylimidazo[1,2-a]pyridine-7-carboxylate I-14. ES/MS: m/z 251.1 [M+H]$^+$.

Preparation of methyl 2-chloro-3-cyclopropyl-5-methoxyimidazo[1,2-a]pyridine-7-carboxylate (I-15)

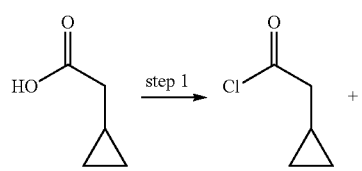

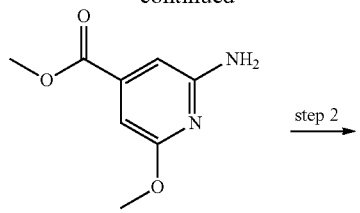

intermediate described in the synthesis of I-13

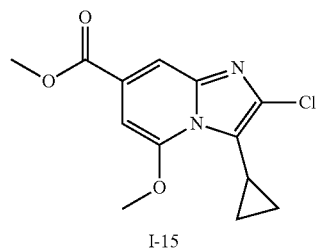

I-15

Step 1. A solution of oxalyl chloride (2 M, 10.3 mL, 20.6 mmol) in dichloromethane was added to a solution of 2-cyclopropylacetic acid (1.0 mL, 10.3 mmol) in dichloromethane (17 mL) at room temperature. DMF (4 drops) was added and the reaction mixture was stirred at room temperature. After 4 h, the reaction mixture was concentrated under reduced pressure to yield 2-cyclopropylacetyl chloride (1.22 g, quant.), which was used directly in the next step without purification.

Step 2. To a mixture of 2-cyclopropylacetyl chloride (1.22 g, 10.3 mmol, above) and methyl 2-amino-6-methoxyisonicotinate (intermediate described in the synthesis of I-13, 1.50 g, 8.23 mmol) in chloroform (50 mL) was added triethylamine (2.3 mL, 16.5 mmol) at room temperature. After stirring overnight, the reaction mixture was transferred into 5×10 mL sealed reaction vessels. Triethylamine (0.24 mL, 1.72 mmol) and thionyl chloride (0.26 mL, 3.6 mmol) was added to each vessel. Each vessel was sealed and the reaction mixtures were heated at 70° C. for 90 minutes. After cooling to room temperature, the reaction mixtures were combined, diluted with dichloromethane, and quenched with sat. NaHCO$_3$(aq). The organic and aqueous layers were separated and the aqueous layer was extracted with dichloromethane. The combined organic layers were dried (MgSO$_4$), filtered, and concentrated under reduced pressure. The resulting residue was purified via silica gel column chromatography (0-40% ethyl acetate/hexanes) to yield methyl 2-chloro-3-cyclopropyl-5-methoxyimidazo[1,2-a]pyridine-7-carboxylate I-15. ES/MS: m/z 281.0 [M+H]$^+$.

Preparation of methyl 3-methyl-2-(((trifluoromethyl)sulfonyl)oxy)imidazo[1,2-a]pyridine-7-carboxylate (I-16)

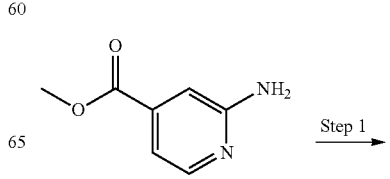

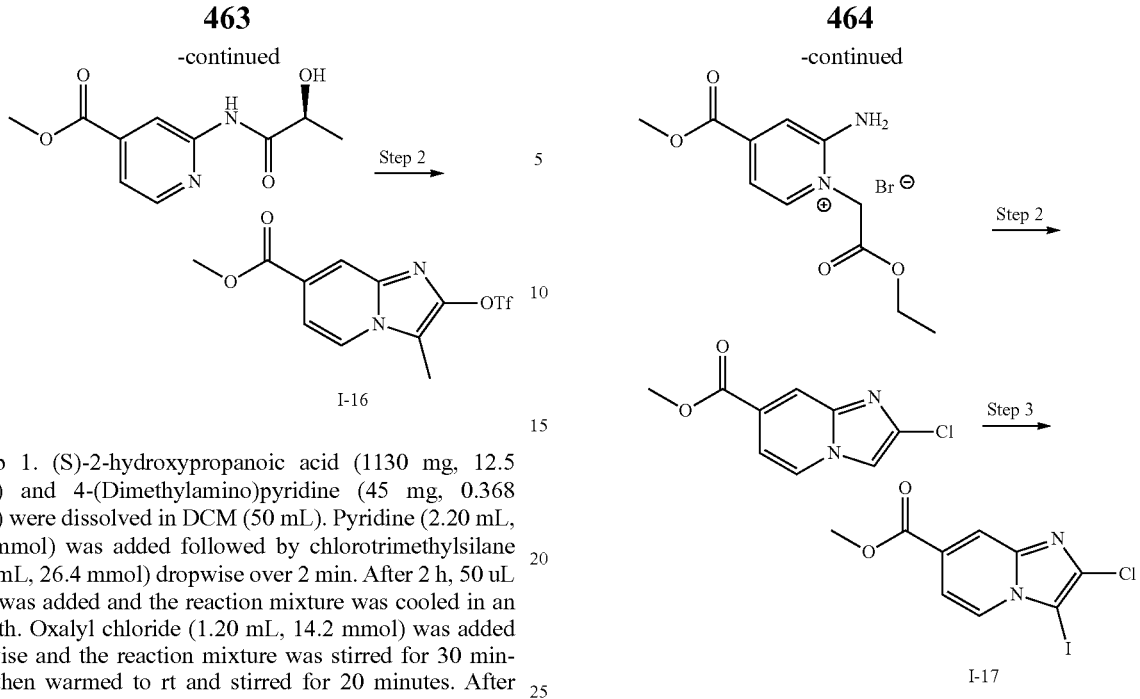

Step 1. (S)-2-hydroxypropanoic acid (1130 mg, 12.5 mmol) and 4-(Dimethylamino)pyridine (45 mg, 0.368 mmol) were dissolved in DCM (50 mL). Pyridine (2.20 mL, 27.3 mmol) was added followed by chlorotrimethylsilane (3.35 mL, 26.4 mmol) dropwise over 2 min. After 2 h, 50 uL DMF was added and the reaction mixture was cooled in an ice bath. Oxalyl chloride (1.20 mL, 14.2 mmol) was added dropwise and the reaction mixture was stirred for 30 minutes, then warmed to rt and stirred for 20 minutes. After cooling in an ice bath, methyl 2-aminoisonicotinate (1530 mg, 10.1 mmol), pyridine (2.46 mL, 30.5 mmol), and 4-(Dimethylamino)pyridine (120 mg, 0.982 mmol) were added as a suspension in DCM and the reaction mixture was warmed to rt. After 40 minutes, the reaction mixture was diluted with MeOH and citric acid. After 90 minutes, the reaction mixture was partitioned between DCM and water. The layers were separated and the aqueous extracted with DCM. The combined organics were dried, filtered, and concentrated under reduced pressure. The resulting residue was purified via silica gel column chromatography (0-45% ethyl acetate in hexanes) to yield methyl (S)-2-(2-hydroxypropanamido)isonicotinate. ES/MS: m/z 225.06 [M+H]$^+$ Step 2. methyl (S)-2-(2-hydroxypropanamido)isonicotinate (1.9 g, 8.47 mmol) was taken up in DCM (60 mL) and the mixture was cooled to 0° C. under nitrogen. 2-Methoxypyridine (2.67 mL, 25.4 mmol) was added followed by dropwise addition of trifluoromethanesulfonic anhydride (4.30 mL, 25.5 mmol). After 3 hours, the reaction mixture was partitioned between DCM and water. The mixture was acidified with aqueous HCl. The layers were separated and the aqueous extracted with DCM. The combined organics were dried, filtered, and concentrated under reduced pressure. The resulting residue was purified via silica gel column chromatography (0-60% ethyl acetate in hexanes) to yield methyl 3-methyl-2-(((trifluoromethyl)sulfonyl)oxy)imidazo[1,2-a]pyridine-7-carboxylate I-16. 1H NMR (400 MHz, DMSO-d6) δ 8.51 (dd, J=7.2, 1.0 Hz, 1H), 8.16 (dd, J=1.7, 0.9 Hz, 1H), 7.50 (dd, J=7.2, 1.7 Hz, 1H), 3.89 (s, 3H), 2.51 (s, 3H).

Preparation of methyl 2-chloro-3-iodoimidazo[1,2-a]pyridine-7-carboxylate (I-17)

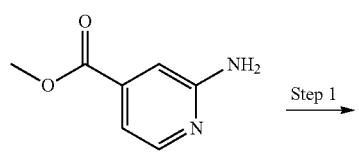

Step 1. A suspension of methyl 2-aminopyridine-4-carboxylate (3.5 g, 23.01 mmol) in ethyl bromoacetate (11 mL, 99.22 mmol) was stirred at rt. After 24 h, additional ethyl bromoacetate (~5.5 mL, 49.5 mmol) was added and the mixture was stirred at rt 4.5 d. The reaction mixture was diluted with ether, stirred at rt for 1 h, and filtered. The solids collected were washed with ether and dried in vacuum to yield 2-amino-1-(2-ethoxy-2-oxoethyl)-4-(methoxycarbonyl)pyridin-1-ium. 1H NMR (400 MHz, DMSO-d6) δ 9.02 (s, 2H), 8.15 (d, J=7.0 Hz, 1H), 7.62 (d, J=1.8 Hz, 1H), 7.25 (dd, J=7.0, 1.8 Hz, 1H), 5.21 (s, 2H), 4.21 (q, J=7.1 Hz, 2H), 3.92 (s, 3H), 1.25 (t, J=7.1 Hz, 3H).

Step 2. A suspension of 2-amino-1-(2-ethoxy-2-oxoethyl)-4-(methoxycarbonyl)pyridin-1-ium (7.3 g, 22.76 mmol) in phosphorus oxychloride (53.5 mL, 0.666 mol) was refluxed at 110° C. After 2 h, the reaction mixture was cooled to rt. The reaction mixture was concentrated to remove excess phosphorus oxychloride. The resulting residue was dissolved in ethyl acetate and carefully treated with saturated NaHCO$_3$(aq). The layers were separated, and the aqueous was extracted with ethyl acetate.

The combined organics were washed with saturated NaHCO$_3$(aq), dried, filtered, and concentrated under reduced pressure. The resulting residue was purified via silica gel column chromatography (0-45% ethyl acetate in hexanes) to yield methyl 2-chloroimidazo[1,2-a]pyridine-7-carboxylate. 1H NMR (400 MHz, Chloroform-d) δ 8.25 (s, 1H), 8.09 (d, J=7.0 Hz, 1H), 7.67 (s, 0.14H), 7.61 (s, 0.89H), 7.46 (d, J=6.7 Hz, 1H), 3.97 (s, 3H).

Step 3. N-iodosuccinimide (1.35 g, 6.00 mmol) was added to a solution of methyl 2-chloroimidazo[1,2-a]pyridine-7-carboxylate (1.04 g, 4.94 mmol) in acetonitrile (50 mL). The reaction mixture was stirred at rt. After 90 minutes, the reaction mixture was diluted with 10% Na$_2$S$_2$O$_3$ (aq) solution (45 mL) and water (45 mL), precipitating a solid. The resulting mixture was filtered and the was washed with water and dried in vacuo to yield methyl 2-chloro-3-iodoimidazo[1,2-a]pyridine-7-carboxylate I-17. 1H NMR (400 MHz, Chloroform-d) δ 8.28-8.19 (m, 1H), 8.15-8.05 (m, 1H), 7.57 (dd, J=7.2, 1.6 Hz, 1H), 3.98 (s, 3H).

Preparation of methyl 2-(6-chloro-1-((2-(trimethyl-silyl)ethoxy)methyl)-1H-pyrrolo[2,3-b]pyridin-2-yl)-5-methoxy-3-methylimidazo[1,2-a]pyridine-7-carboxylate (I-18)

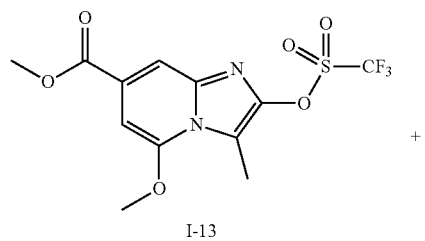

I-13

+

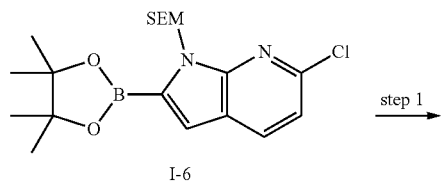

I-6 step 1

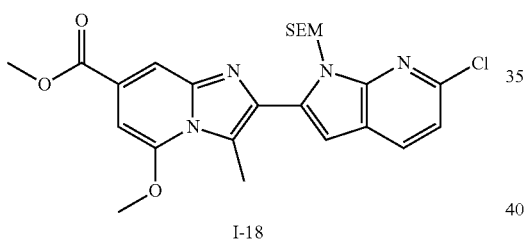

I-18

Step 1. A round bottom flask was loaded with 6-chloro-2-(4,4,5,5-tetramethyl-1,3,2-dioxaborolan-2-yl)-1-((2-(trimethylsilyl)ethoxy)methyl)-1H-pyrrolo[2,3-b]pyridine (I-6, 11.5 g, 1.1 equiv.), methyl 5-methoxy-3-methyl-2-(((trifluoromethyl)sulfonyl)oxy)imidazo[1,2-a]pyridine-7-carboxylate (I-13, 9.4 g, 1 equiv.) and potassium phosphate tribasic (16.2 g, 3 equiv.). Dioxane (120 mL) and water (14 mL) were added, and the mixture was degassed with argon for 15 minutes. PdCl$_2$(dppf) (1.56 g, 7.5 mol %) was added in one portion and the mixture was heated to 45° C. for 6 hours. The reaction was worked up using EtOAc and water, and the combined organics were dried over sodium sulfate then evaporated to dryness. Purification via silica gel column chromatography using a solid loading over silica (0-45% ether/(hexanes:DCM 1:1)) delivered methyl 2-(6-chloro-1-((2-(trimethylsilyl)ethoxy)methyl)-1H-pyrrolo[2,3-b]pyridin-2-yl)-5-methoxy-3-methylimidazo[1,2-a]pyridine-7-carboxylate I-18. ES/MS: m/z 501.2 [M+H]$^+$. $^1$H NMR (400 MHz, CDCl$_3$) δ 8.08 (brs, 1H), 7.88 (d, J=8.1 Hz, 1H), 7.16 (d, J=8.1 Hz, 1H), 6.68 (brs, 1H), 6.66 (brs, 1H), 6.08 (s, 2H), 4.13 (s, 3H), 3.99 (s, 3H), 3.48-3.37 (m, 2H), 2.89 (s, 3H), 0.82-0.71 (m, 2H), -0.18 (s, 9H).

Preparation of methyl 2-(6-(benzyloxy)-1-(tert-butoxycarbonyl)-1H-pyrrolo[2,3-b]pyridin-2-yl)-5-methoxy-3-methylimidazo[1,2-a]pyridine-7-carboxylate (I-19)

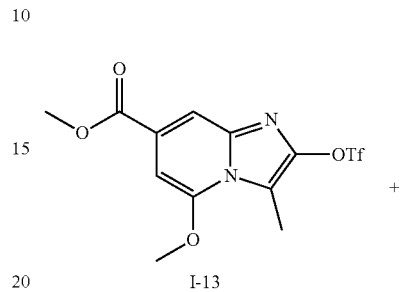

I-13

+

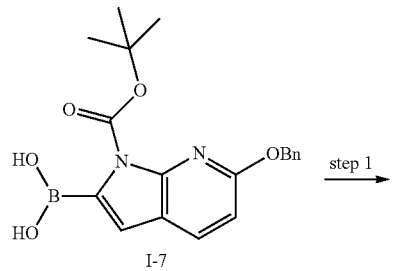

I-7 step 1

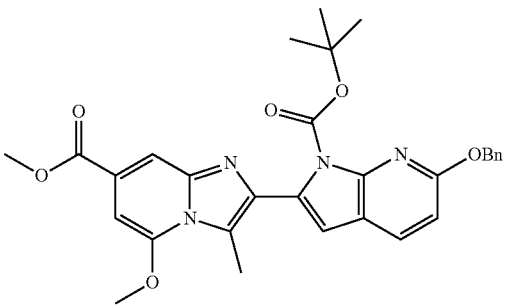

I-19

Step 1. A mixture of methyl 5-methoxy-3-methyl-2-(((trifluoromethyl)sulfonyl)oxy)imidazo[1,2-a]pyridine-7-carboxylate I-13 (1.92 g, 5.21 mmol), I-7 (2.88 g, 7.82 mmol), Pd(OAc)$_2$ (0.0585 g, 0.261 mmol), XPhos (0.249 g, 0.521 mmol), and tribasic potassium phosphate (3.32 g, 15.6 mmol) were taken up in dioxane (45 mL) and water (4.5 mL). The reaction mixture was heated at 95° C. for two hours. After cooling to rt, the reaction mixture was diluted with ethyl acetate and water. The layers were separated, and the aqueous was extracted with ethyl acetate.

The combined organics were washed with brine dried, filtered, and concentrated under reduced pressure. The resulting residue was purified via silica gel column chromatography (15-70% ethyl acetate in hexanes) to yield methyl 2-(6-(benzyloxy)-1-(tert-butoxycarbonyl)-1H-pyrrolo[2,3-b]pyridin-2-yl)-5-methoxy-3-methylimidazo[1,2-a]pyridine-7-carboxylate I-19. ES/MS: m/z 542.88 [M+H]$^+$.

Preparation of tert-butyl (R)-(1-(2-(1-(cyclopropylmethyl)-6-hydroxy-1H-pyrrolo[2,3-b]pyridin-2-yl)-5-methoxy-3-methylimidazo[1,2-a]pyridine-7-carbonyl)piperidin-3-yl)carbamate (I-19a)

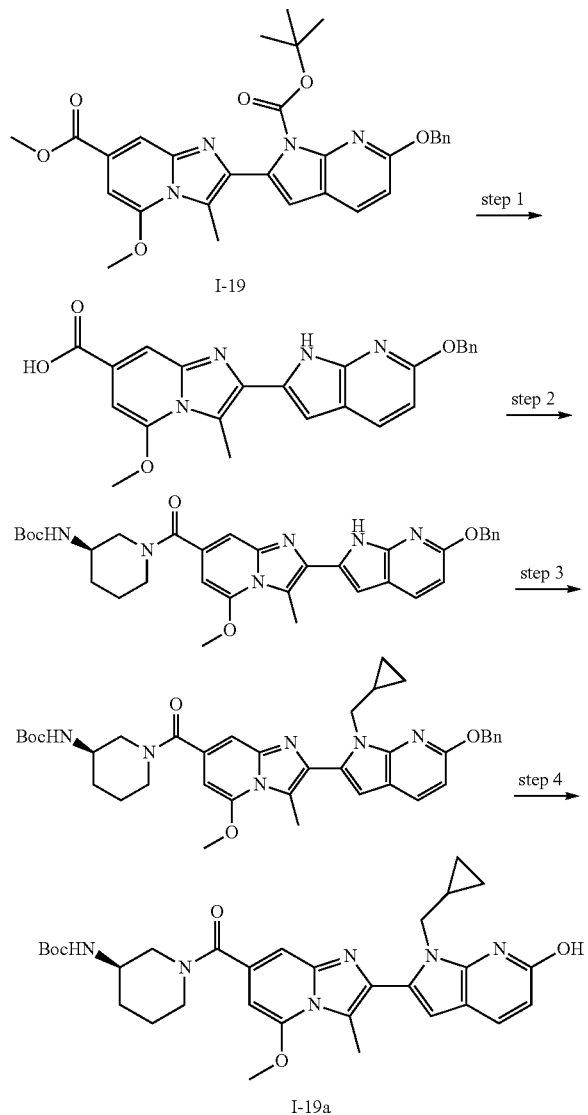

Step 1. A solution of methyl 2-(6-(benzyloxy)-1-(tert-butoxycarbonyl)-1H-pyrrolo[2,3-b]pyridin-2-yl)-5-methoxy-3-methylimidazo[1,2-a]pyridine-7-carboxylate I-19 (0.7 g, 1.29 mmol) in MeOH (10 mL) and 10 M NaOH (0.5 mL) was heated in a microwave reactor for 20 min. The mixture was concentrated, diluted with water and acidified to pH=3. The solids were filtered and the filtrate was extracted with MeTHF The organic layer was dried, filtered, and concentrated under reduced pressure. To yield 2-(6-benzyloxy-1H-pyrrolo[2,3-b]pyridin-2-yl)-5-methoxy-3-methyl-imidazo[1,2-a]pyridine-7-carboxylic acid, which was used in the next step without purification ES/MS: m/z 429.1 [M+H]$^+$.

Step 2. To a solution of 2-(6-benzyloxy-1H-pyrrolo[2,3-b]pyridin-2-yl)-5-methoxy-3-methyl-imidazo[1,2-a]pyridine-7-carboxylic acid (400 mg, 0.93 mmol), tert-butyl N-[(3R)-3-piperidyl]carbamate (224 mg, 1.12 mmol) A1.01, and DIPEA (0.24 mL, 1.4 mmol) in DMF (2 ml) was added HATU (390 mg, 1.03 mmol). After 15 min, the mixture was diluted with EtOAc and washed with 5% LiCl (aq). The organic layer was dried, filtered, and concentrated under reduced pressure to yield tert-butyl N-[(3R)-1 [2-(6-benzyloxy-1H-pyrrolo[2,3-b]pyridin-2-yl)-5-methoxy-3-methyl-imidazo[1,2-a]pyridine-7-carbonyl]-3-piperidyl]carbamate, which was used in the next step without further purification. ES/MS: m/z 611.3 [M+H]$^+$.

Step 3. A solution of tert-butyl N-[(3R)-1-[2-(6-benzyloxy-1H-pyrrolo[2,3-b]pyridin-2-yl)-5-methoxy-3-methyl-imidazo[1,2-a]pyridine-7-carbonyl]-3-piperidyl]carbamate (0.4 g, 0.65 mmol), bromomethylcyclopropane (0.18 g, 1.31 mmol), and Cs$_2$CO$_3$ (0.64 g, 1.96 mmol) in DMF (2 ml) was stirred at 40 C for 18 h. The mixture was diluted with EtOAc and washed with 5% LiCl (aq). The organic layer was dried, filtered, and concentrated under reduced pressure. The resulting residue was purified via silica gel column chromatography (0-100% ethyl acetate in hexanes) to yield tert-butyl N-[(3R)-1-[2-[6-benzyloxy-1-(cyclopropylmethyl)pyrrolo[2,3-b]pyridin-2-yl]-5-methoxy-3-methyl-imidazo[1,2-a]pyridine-7-carbonyl]-3-piperidyl]carbamate. ES/MS: m/z 665.3 [M+H]$^+$.

Step 4. A solution of tert-butyl N-[(3R)-1-[2-[6-benzyloxy-1-(cyclopropylmethyl)pyrrolo[2,3-b]pyridin-2-yl]-5-methoxy-3-methyl-imidazo[1,2-a]pyridine-7-carbonyl]-3-piperidyl]carbamate (234 mg, 0.35 mmol), 10% palladium on carbon (37.31 mg, 0.04 mmol), and methanol (10 ml) was stirred under an atmosphere of hydrogen for 2 h. The reaction mixture was filtered, and the filtrate concentrated was concentrated under reduced pressure to yield tert-butyl N-[(3R)-1-[2-[1-(cyclopropylmethyl)-6-hydroxy-pyrrolo[2,3-b]pyridin-2-yl]-5-methoxy-3-methyl-imidazo[1,2-a]pyridine-7-carbonyl]-3-piperidyl]carbamate I-19a, which was used without further purification. ES/MS: m/z 575.2 [M+H]$^+$.

((1R,2R,4S)-2-amino-7-azabicyclo[2.2.1]heptan-7-yl)(2-(1-(cyclopropylmethyl)-6-hydroxy-1H-pyrrolo[2,3-b]pyridin-2-yl)-5-methoxy-3-methylimidazo[1,2-a]pyridin-7-yl)methanone (I-19b)

Following the procedure for the synthesis of I-19a, I-19b was synthesized, using A2 instead of A1.01 in step 2. ES/MS: m/z 587.3 [M+H]$^+$.

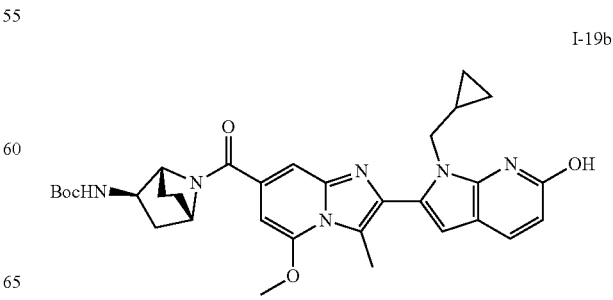

Preparation of methyl 2-(6-chloro-1-(cyclopropylmethyl)-1H-pyrrolo[2,3-b]pyridin-2-yl)-5-methoxy-3-methylimidazo[1,2-a]pyridine-7-carboxylate (I-20)

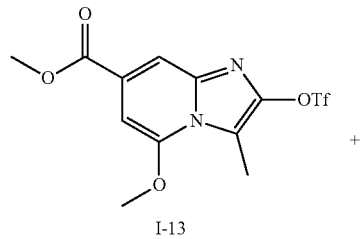

I-13

+

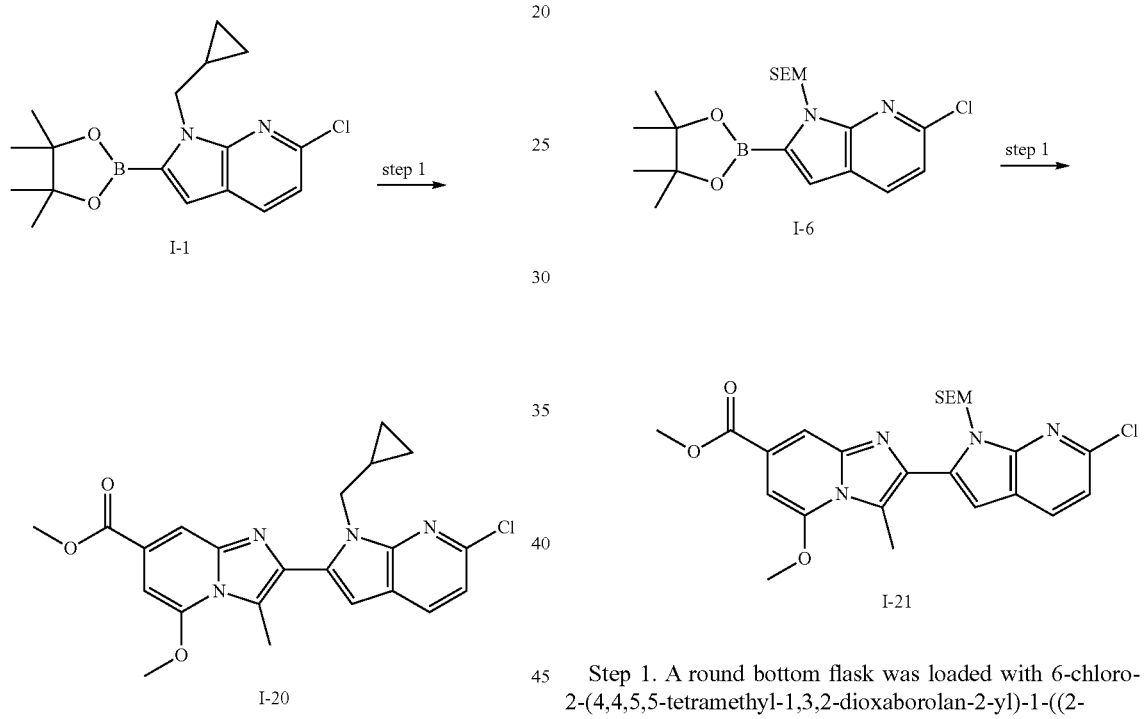

Step 1. A flask was charged with the I-13 (10 g, 27 mmol), I-1 (10 g, 30 mmol) and K₃PO₄ (17.3 g, 81 mmol), Dioxane (160 mL) and water (18 mL) were added and the mixture was stirred and degassed with argon for 10 minutes. PdCl₂(dppf) (1.66 g, 2 mmol) was added and the resulting solution was stirred at 45° C. for 6 hours. The hot solution was filtered over celite and the celite was rinsed with the minimum of ethyl acetate (50 mL). The resulting solution was kept at 4° C. for 24 hours and then filtered. The solid collected was rinsed with cold MTBE to afford methyl 2-(6-chloro-1-(cyclopropylmethyl)-1H-pyrrolo[2,3-b]pyridin-2-yl)-5-methoxy-3-methyl imidazo[1,2-a]pyridine-7-carboxylate I-20. The rest of the solution was concentrated down to remove the MTBE and ethyl acetate. Diethyl ether (150 mL) was added to the resulting dioxane solution and the mixture was kept at 4° C. overnight. A second crop I-20 was obtained. ES/MS: m/z 425.16 [M+H]⁺.

Preparation of methyl 2-(6-chloro-1-((2-(trimethylsilyl)ethoxy)methyl)-1H-pyrrolo[2,3-b]pyridin-2-yl)-5-methoxy-3-methylimidazo[1,2-a]pyridine-7-carboxylate (I-21)

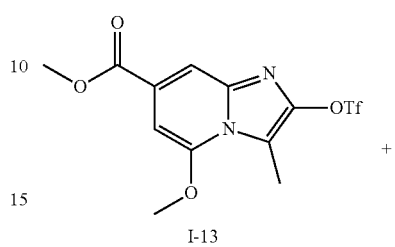

I-13

+

Step 1. A round bottom flask was loaded with 6-chloro-2-(4,4,5,5-tetramethyl-1,3,2-dioxaborolan-2-yl)-1-((2-(trimethylsilyl)ethoxy)methyl)-1H-pyrrolo[2,3-b]pyridine I-6 (11.5 g, 1.1 equiv.), methyl 5-methoxy-3-methyl-2-((((trifluoromethyl)sulfonyl)oxy)imidazo[1,2-a]pyridine-7-carboxylate I-13 (9.4 g, 1 equiv.) and potassium phosphate tribasic (16.2 g, 3 equiv.). Dioxane (120 mL) and water (14 mL) were added, and the mixture was degassed with argon for 15 minutes. PdCl₂(dppf) (1.56 g, 7.5 mol %) was added in one portion and the mixture was heated to 45° C. for 6 hours. The reaction was worked up using EtOAc and water, and the combined organics were dried over sodium sulfate then evaporated to dryness. Purification via silica gel column chromatography using a solid loading over silica (0-45% ether/(hexanes:DCM 1:1)) delivered methyl 2-(6-chloro-1-((2-(trimethylsilyl)ethoxy)methyl)-1H-pyrrolo[2,3-b]pyridin-2-yl)-5-methoxy-3-methylimidazo[1,2-a]pyridine-7-carboxylate I-21. ES/MS: m/z 501.2 [M+H]⁺. ¹H NMR (400 MHz, CDCl₃) δ 8.08 (brs, 1H), 7.88 (d, J=8.1 Hz, 1H), 7.16 (d, J=8.1 Hz, 1H), 6.68 (brs, 1H), 6.66 (brs, 1H), 6.08 (s, 2H), 4.13 (s, 3H), 3.99 (s, 3H), 3.48-3.37 (m, 2H), 2.89 (s, 3H), 0.82-0.71 (m, 2H), -0.18 (s, 9H).

Preparation of 2-[1-(cyclopropylmethyl)-6-[difluoromethyl(methylsulfonyl)amino]pyrrolo[2,3-b]pyridin-2-yl]-5-methoxy-3-methyl-imidazo[1,2-a]pyridine-7-carboxylic acid (I-22)

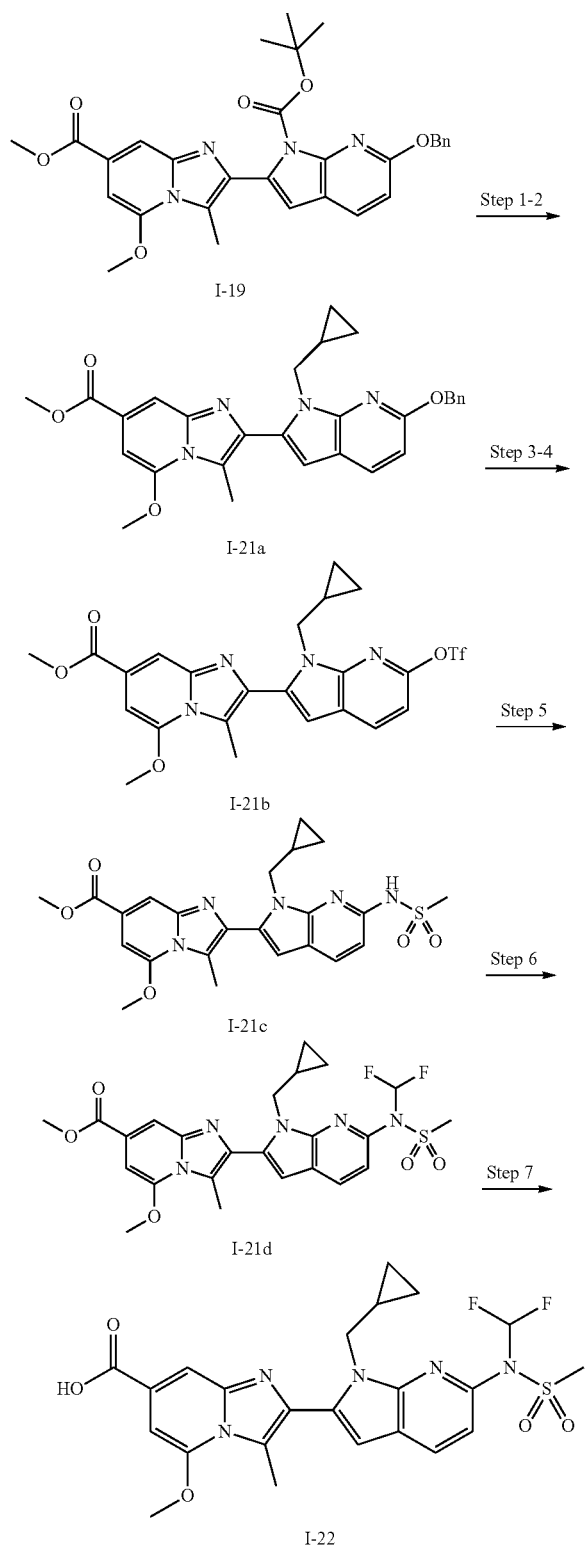

Steps 1-2. To a solution of methyl 2-(6-(benzyloxy)-1-(tert-butoxycarbonyl)-1H-pyrrolo[2,3-b]pyridin-2-yl)-5-methoxy-3-methylimidazo[1,2-a]pyridine-7-carboxylate I-19 (2.22 g, 4.09 mmol) in DCM (25 mL) was added TFA (10 mL). After stirring for 30 minutes, the reaction mixture was concentrated under reduced pressure and dissolved in DCM. This mixture was washed with saturated NaHCO$_3$ $_{(aq)}$, dried, filtered, and concentrated under reduced pressure. The resulting residue was dissolved in DMF (50 mL). Bromomethyl cyclopropane (1.85 mL, 20.6 mmol) was added at rt, followed by a solution of sodium bis(trimethylsilyl) amide (1.00 M, 5.35 mL, 5.35 mmol) in THF. After 4.5 hours, the reaction mixture was quenched with saturated NH$_4$C$_1$ (aq), dried, filtered, and concentrated under reduced pressure. The resulting residue was purified via silica gel column chromatography (15-100% ethyl acetate in hexanes) to yield methyl 2-(6-(benzyloxy)-1-(cyclopropylmethyl)-1H-pyrrolo[2,3-b]pyridin-2-yl)-5-methoxy-3-methylimidazo[1,2-a]pyridine-7-carboxylate I-21a. ES/MS: m/z 497.30 [M+H]$^+$.

Steps 3-4. A mixture of methyl 2-(6-(benzyloxy)-1-(cyclopropylmethyl)-1H-pyrrolo[2,3-b]pyridin-2-yl)-5-methoxy-3-methylimidazo[1,2-a]pyridine-7-carboxylate I-21a (1.59 g, 3.20 mmol) in ethanol (15 mL) and ethyl acetate (20 mL) was hydrogenated over Pd/C (10% dry weight, 50% water weight, 600 mg) under an atmosphere of hydrogen for 3.5 hours. The reaction mixture was diluted with THF and filtered over celite, washing with THF. The filtrate was concentrated under reduced pressure. The resulting residue was taken up in pyridine (20 mL) and trifluoromethanesulfonic anhydride (0.810 mL, 4.82 mmol) dropwise at rt. After 20 minutes, the reaction mixture was diluted with DCM and water.

A solution of HCl (aq) (6 N, 42 mL) was added. The resulting layers were separated and the aqueous extracted with DCM. The combined organics were washed with 0.5 M HCl (aq), dried, filtered, and concentrated under reduced pressure. The resulting residue was purified via silica gel column chromatography (10-60% ethyl acetate in hexanes) to yield methyl 2-(1-(cyclopropylmethyl)-6-(((trifluoromethyl)sulfonyl)oxy)-1H-pyrrolo[2,3-b]pyridin-2-yl)-5-methoxy-3-methylimidazo[1,2-a]pyridine-7-carboxylate I-21b. ES/MS: m/z 539.08 [M+H]$^+$.

Step 5. A mixture of methyl 2-(1-(cyclopropylmethyl)-6-(((trifluoromethyl)sulfonyl)oxy)-1H-pyrrolo[2,3-b]pyridin-2-yl)-5-methoxy-3-methylimidazo[1,2-a]pyridine-7-carboxylate I-21b (500 mg, 0.929 mmol), methanesulfonamide (0.181 g, 1.90 mmol), potassium carbonate (0.449 g, 3.25 mmol) and Pd-tBuXPhos G1 (64 mg, 0.0929 mmol) in MeTHF (20 mL) was heated at 80° C. under nitrogen for 6 hours. After cooling to rt, the reaction mixture was diluted with ethyl acetate and water. The resulting layers were separated and the aqueous was extracted with ethyl acetate. The combined organics were dried, filtered, and concentrated under reduced pressure to yield methyl 2-(1-(cyclopropylmethyl)-6-(methylsulfonamido)-1H-pyrrolo[2,3-b]pyridin-2-yl)-5-methoxy-3-methylimidazo[1,2-a]pyridine-7-carboxylate I-21c, which was used without purification. ES/MS: m/z 484.26 [M+H]$^+$.

Step 6. Crude methyl 2-(1-(cyclopropylmethyl)-6-(methylsulfonamido)-1H-pyrrolo[2,3-b]pyridin-2-yl)-5-methoxy-3-methylimidazo[1,2-a]pyridine-7-carboxylate I-21c (ca. 449 mg) above was dissolved in DMF (20 mL) and potassium carbonate (1.28 g, 9.29 mmol) was added. Chlorodifluoromethane was bubbled through the reaction mixture while heating at 90° C. After 20 minutes, the reaction mixture was cooled to rt and diluted with ethyl acetate and water. The resulting layers were separated and the aqueous was extracted with ethyl acetate. The combined organics were washed with water, dried, filtered, and concentrated under reduced pressure. The resulting residue was purified via silica gel column chromatography (10-100% ethyl acetate in hexanes) to yield methyl 2-(1-(cyclopropylmethyl)-6-(N-(difluoromethyl)methylsulfonamido)-1H-pyrrolo[2,3-b]pyridin-2-yl)-5-methoxy-3-methylimidazo[1,2-a]pyridine-7-carboxylate I-21d. ES/MS: m/z 534.12 [M+H]⁺.

Step 7. Lithium hydroxide monohydrate (96 mg, 2.29 mmol) was added to a mixture of methyl 2-(1-(cyclopropylmethyl)-6-(N-(difluoromethyl)methylsulfonamido)-1H-pyrrolo[2,3-b]pyridin-2-yl)-5-methoxy-3-methylimidazo[1,2-a]pyridine-7-carboxylate I-21d (365 mg, 0.684 mmol) in THF (10 mL), MeOH (5 mL), and water (5 mL) at rt. The reaction mixture was heated at 45° C. for 2.5 hours. After cooling to rt, a solution of HCl (aq) (3N, 0.800 mL, 2.40 mmol) was added and the reaction mixture was concentrated under reduced pressure to yield 2-(1-(cyclopropylmethyl)-6-(N-(difluoromethyl)methylsulfonamido)-1H-pyrrolo[2,3-b]pyridin-2-yl)-5-methoxy-3-methylimidazo[1,2-a]pyridine-7-carboxylic acid I-22, as the lithium chloride salt. ES/MS: m/z 520.22 [M+H]⁺.

Preparation of 2-(1-(cyclopropylmethyl)-6-ethyl-1H-pyrrolo[2,3-b]pyridin-2-yl)-5-methoxy-3-methylimidazo[1,2-a]pyridine-7-carboxylic acid (I-23)

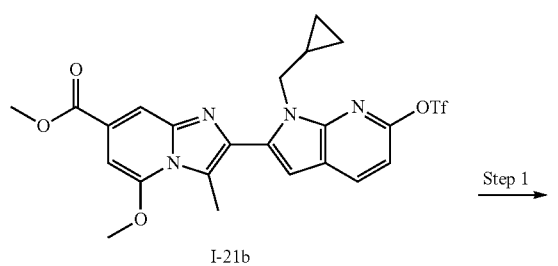

I-21b

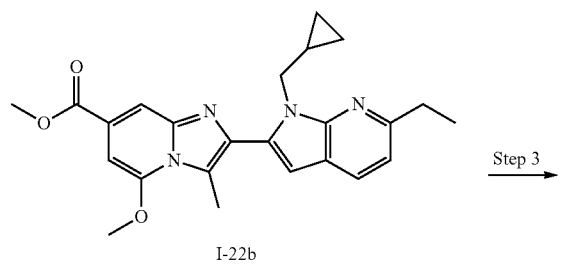

I-22a

I-22b

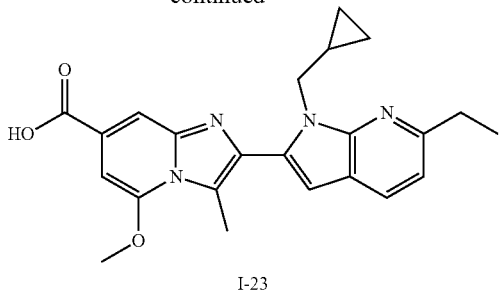

I-23

Step 1. A mixture of methyl 2-(1-(cyclopropylmethyl)-6-(((trifluoromethyl)sulfonyl)oxy)-1H-pyrrolo[2,3-b]pyridin-2-yl)-5-methoxy-3-methylimidazo[1,2-a]pyridine-7-carboxylate I-21b (640 mg, 1.19 mmol), potassium vinyltrifluoroborate (398 mg, 2.97 mmol), Triethylamine (0.160 mL, 1.15 mmol), and Dichloro 1,1'-bis(diphenylphosphino)ferrocene palladium (II) dichloromethane (0.0485 g, 0.0594 mmol) in iPrOH (10 mL) was flushed with nitrogen and heated at 100° C. in a sealed tube for 3 hours. After cooling to rt, the reaction mixture was diluted with ethyl acetate and water. The resulting layers were separated and the aqueous was extracted with ethyl acetate. The combined organics were dried, filtered, and concentrated under reduced pressure. The resulting residue was purified via silica gel column chromatography (20-100% ethyl acetate in hexanes) to yield methyl 2-(1-(cyclopropylmethyl)-6-vinyl-1H-pyrrolo[2,3-b]pyridin-2-yl)-5-methoxy-3-methylimidazo[1,2-a]pyridine-7-carboxylate I-22a. ES/MS: m/z 417.19 [M+H]⁺.

Step 2. methyl 2-(1-(cyclopropylmethyl)-6-vinyl-1H-pyrrolo[2,3-b]pyridin-2-yl)-5-methoxy-3-methylimidazo[1,2-a]pyridine-7-carboxylate I-22a (510 mg, 1.22 mmol) was dissolved in EtOAc (15 mL). Palladium on carbon (10%, 261 mg, 0.245 mmol) was added and the reaction mixture was hydrogenated under an atmosphere of hydrogen for 3 hours. The reaction mixture was filtered over celite and the filtrate was concentrated under reduced pressure to yield methyl 2-[1-(cyclopropylmethyl)-6-ethyl-pyrrolo[2,3-b]pyridin-2-yl]-5-methoxy-3-methyl-imidazo[1,2-a]pyridine-7-carboxylate I-22b, which was used without purification. ES/MS: m/z 419.19 [M+H]⁺.

Step 3. methyl 2-[1-(cyclopropylmethyl)-6-ethyl-pyrrolo[2,3-b]pyridin-2-yl]-5-methoxy-3-methyl-imidazo[1,2-a]pyridine-7-carboxylate I-22b (509 mg, 1.21 mmol) was taken up in a mixture of THF (10 mL), MeOH (3 mL), and water (3 mL). Lithium hydroxide monohydrate (0.257 g, 6.13 mmol) was added and the reaction mixture was stirred at rt for 3 hours. The mixture was acidified with an aqueous solution of HCl (6 N, 1.04 mL, 6.25 mmol) and diluted with water. The resulting solids were filtered and dried in vacuo to yield 2-(1-(cyclopropylmethyl)-6-ethyl-1H-pyrrolo[2,3-b]pyridin-2-yl)-5-methoxy-3-methylimidazo[1,2-a]pyridine-7-carboxylic acid I-23. ES/MS: m/z 405.21 [M+H]⁺.

Preparation of 2-[1-(cyclopropylmethyl)-6-vinyl-pyrrolo[2,3-b]pyridin-2-yl]-5-methoxy-3-methyl-imidazo[1,2-a]pyridine-7-carboxylic acid (I-23a)

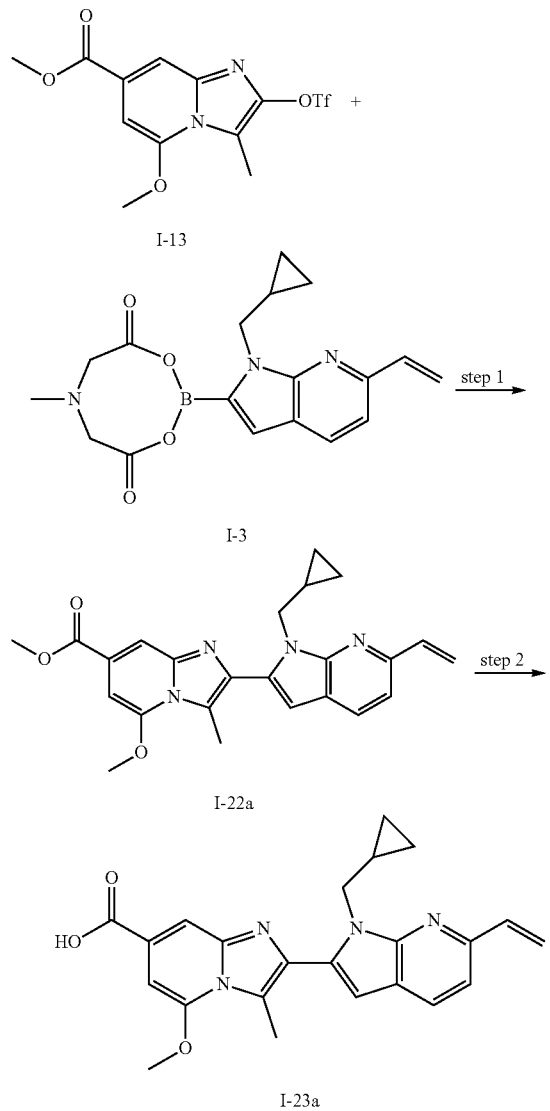

Step 1. A mixture of 2-[1-(cyclopropylmethyl)-6-vinyl-pyrrolo[2,3-b]pyridin-2-yl]-6-methyl-1,3,6,2-dioxazaborocane-4,8-dione I-3 (3.74 g, 10.6 mmol), methyl 5-methoxy-3-methyl-2-(trifluoromethylsulfonyloxy)imidazo[1,2-a]pyridine-7-carboxylate I-13 (3.00 g, 8.15 mmol), $K_3PO_4$ (10300 mg, 0.0485 mol), and Pd-XPhos Pd G3 (345 mg, 0.41 mmol) were taken up in dioxane (120 mL) and water (12 mL). The reaction mixture was heated at 100° C. for 1 hour. After cooling to rt, it was diluted with EtOAc and water and the resulting layers were separated. The aqueous was extracted with EtOAc. The combined organics were dried ($Na_2SO_4$), filtered, and concentrated under reduced pressure.

The resulting residue was purified via silica gel column chromatography (20-80% ethyl acetate in hexanes) to yield methyl 2-[1-(cyclopropylmethyl)-6-vinyl-pyrrolo[2,3-b]pyridin-2-yl]-5-methoxy-3-methyl-imidazo[1,2-a]pyridine-7-carboxylate I-22a. ES/MS: m/z 417.10 $[M+H]^+$.

Step 2. Lithium hydroxide, monohydrate (0.258 g, 6.15 mmol) was added to a mixture of methyl 2-[1-(cyclopropylmethyl)-6-vinyl-pyrrolo[2,3-b]pyridin-2-yl]-5-methoxy-3-methyl-imidazo[1,2-a]pyridine-7-carboxylate I-22a (500 mg, 1.20 mmol) in THF (10 mL), MeOH (3 mL), and water (3 mL) at rt. After stirring 3 hours, the reaction mixture was acidified with aqueous hydrochloric acid (6 N, 1.06 mL, 6.36 mmol) and diluted with water. The resulting solid was filtered, washing with water, and dried in vacuo to yield 2-[1-(cyclopropylmethyl)-6-vinyl-pyrrolo[2,3-b]pyridin-2-yl]-5-methoxy-3-methyl-imidazo[1,2-a]pyridine-7-carboxylic acid I-23a. ES/MS: m/z 403.16 $[M+H]^+$.

Preparation of ethyl (R)-2-(6-(1-aminoethyl)-1-(cyclopropylmethyl)-1H-pyrrolo[2,3-b]pyridin-2-yl)-5-methoxy-3-methylimidazo[1,2-a]pyridine-7-carboxylate (I-24)

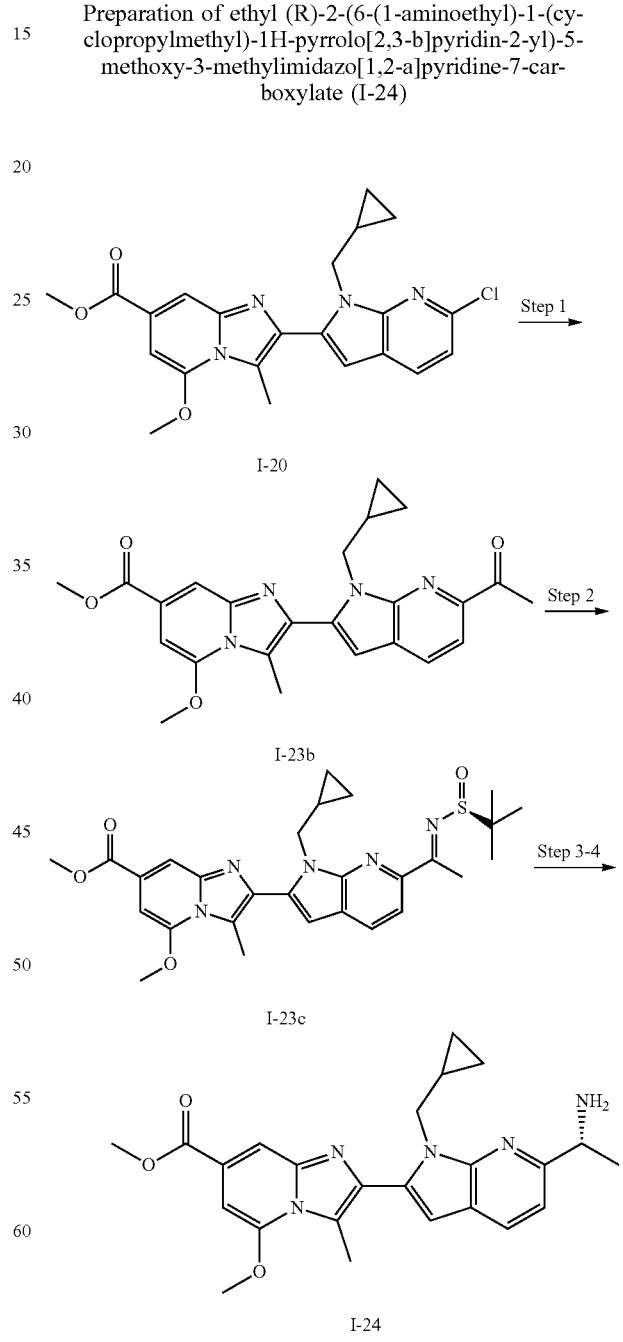

Step 1. Methyl 2-(6-chloro-1-(cyclopropylmethyl)-1H-pyrrolo[2,3-b]pyridin-2-yl)-5-methoxy-3-methylimidazo[1, 2-a]pyridine-7-carboxylate I-20 (3 g, 7.06 mmol) and Dichloro 1,1'-bis(diphenylphosphino)ferrocene palladium (II) dichloromethane (0.7 g, 0.86 mmol) were taken up in dioxane (75 mL) under $N_2$. 1-ethoxyvinyltributyltin (6 mL, 18 mmol) was added and the resulting mixture was heated to 100° C. After 3 h, the mixture was filtered with EtOAc through Celite and the filtrate was concentrated. The resulting residue was dissolved in THF (100 mL), and 3 M HCl (2.3 mL, 6.9 mmol) was added. The mixture was stirred 30 min, at which time it was diluted with EtOAc and water. Phases were separated, and the aqueous phase was extracted with EtOAc. The organic phase was dried over $Na_2SO_4$, filtered, and concentrated to crude solid. The solid was slurried in 50 mL 1:1 hexanes:EtOAc. The mixture was filtered to collect solids, and the filter cake was washed with additional 1:1 hexanes:EtOAc followed by hexanes to yield methyl 2-(6-acetyl-1-(cyclopropylmethyl)-1H-pyrrolo[2,3-b]pyridin-2-yl)-5-methoxy-3-methylimidazo[1,2-a]pyridine-7-carboxylate I-23b. ES/MS: m/z 433.12 [M+H]$^+$.

Step 2. methyl 2-(6-acetyl-1-(cyclopropylmethyl)-1H-pyrrolo[2,3-b]pyridin-2-yl)-5-methoxy-3-methylimidazo[1,2-a]pyridine-7-carboxylate I-23b (2.58 g, 5.96 mmol) and (S)-2-methylpropane-2-sulfinamide (2.9 g, 24 mmol) were suspended in THF (60 mL) under $N_2$. Titanium (IV) ethoxide (10.0 mL, 47.8 mmol) was added, and the resulting stirred mixture was heated at 60° C. overnight. After 18 h, the reaction mixture was poured into a vigorously stirred mixture of brine (150 mL) and EtOAc (100 mL). The heterogeneous mixture was diluted further with EtOAc and the phases were separated. The aqueous phase was diluted with EtOAc, and Celite (~50 g) was added and stirred with the resulting emulsion. The mixture was filtered through a pad of Celite with EtOAc, and the resulting clear biphasic mixture was separated. The combined organic phase was dried over $Na_2SO_4$, filtered and concentrated. Purification by silica gel (10-60% EtOAc in hexanes) provided ethyl (S,E)-2-(6-(1-((tert-butylsulfinyl)imino)ethyl)-1-(cyclopropylmethyl)-1H-pyrrolo[2,3-b]pyridin-2-yl)-5-methoxy-3-methylimidazo[1,2-a]pyridine-7-carboxylate I-23c. ES/MS: m/z 549.92 [M+H]$^+$.

Steps 3-4. ethyl (S,E)-2-(6-(1-((tert-butylsulfinyl)imino)ethyl)-1-(cyclopropylmethyl)-1H-pyrrolo[2,3-b]pyridin-2-yl)-5-methoxy-3-methylimidazo[1,2-a]pyridine-7-carboxylate I-23c (1.49 g, 2.71 mmol) was dissolved in THF (30 mL) under $N_2$. The resulting mixture was cooled in a $CO_2$/MeCN bath to approximately −50° C. A solution of L-Selectride (1M, 3 mL, 3 mmol) was then added dropwise over 2 min, and the resulting mixture was stirred for 20 min. The reaction was then placed in an ice water bath and was allowed to stir for an additional 10 min. The reaction was quenched with sat. aq. $NH_4Cl$ and diluted with EtOAc and water. The phases were separated, and the organic phase was dried over $Na_2SO_4$, filtered, and concentrated. The obtained residue was purified by silica gel chromatography (30-100% acetone in hexanes) to afford ethyl 2-(6-((R)-1-4(S)-tert-butylsulfinyl)amino)ethyl)-1-(cyclopropylmethyl)-1H-pyrrolo[2,3-b]pyridin-2-yl)-5-methoxy-3-methylimidazo[1,2-a]pyridine-7-carboxylate. ES/MS: m/z 552.07[M+H]$^+$. This product was dissolved in dioxane (30 mL). A solution of HCl in dioxane (4M, 2.08 mL, 8.32 mmol) was added. After 30 minutes, the reaction mixture was concentrated in vacuo to provide ethyl (R)-2-(6-(1-aminoethyl)-1-(cyclopropylmethyl)-1H-pyrrolo[2,3-b]pyridin-2-yl)-5-methoxy-3-methylimidazo[1,2-a]pyridine-7-carboxylate I-24 (putative bis-HCl salt) that was used without further purification. ES/MS: m/z 447.87 [M+H]$^+$.

Preparation of methyl 2-(6-acetyl-1-((2-(trimethylsilyl)ethoxy)methyl)-1H-pyrrolo[2,3-b]pyridin-2-yl)-3-cyclopropylimidazo[1,2-a]pyridine-7-carboxylate (I-25)

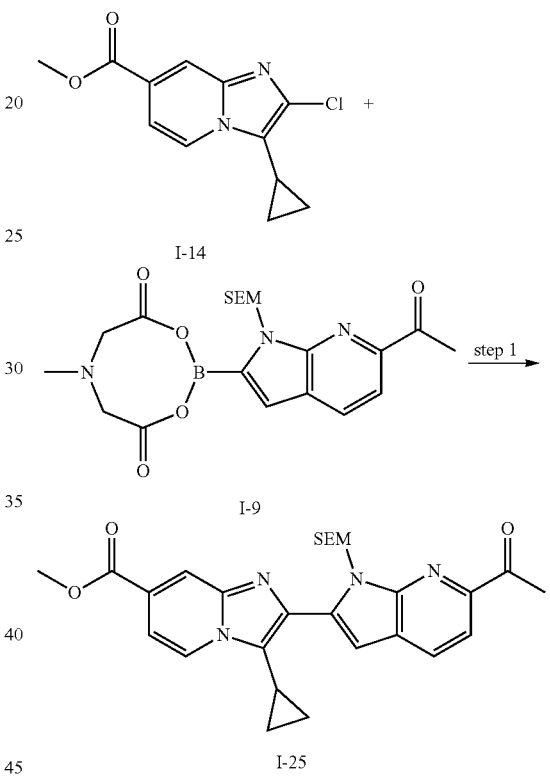

Step 1. A mixture of methyl 2-chloro-3-cyclopropylimidazo[1,2-a]pyridine-7-carboxylate (I-14, 800 mg, 3.19 mmol), $K_3PO_4$ (5.08 g, 23.9 mmol), 2-(6-acetyl-1-((2-(trimethylsilyl)ethoxy)methyl)-1H-pyrrolo[2,3-b]pyridin-2-yl)-6-methyl-1,3,6,2-dioxazaborocane-4,8-dione I-9 (1.84 g, 4.13 mmol), and Pd-XPhos G3 (271 mg, 0.32 mmol) in dioxane (25 mL) and water (5 mL) was heated at 100° C. After 3 h, additional I-9 (923 mg, 2.07 mmol), and Pd-XPhos G3 (270 mg, 0.32 mmol) were added and the reaction mixture was heated at 100° C. After 1 h, the reaction mixture was cooled to rt and partitioned between ethyl acetate and water. The layers were separated and the aqueous was extracted with ethyl acetate. The combined organics were washed with brine, dried ($MgSO_4$), filtered, and concentrated under reduced pressure. The resulting residue was purified via silica gel column chromatography (0-50% ethyl acetate in hexanes) to yield methyl 2-(6-acetyl-1-((2-(trimethylsilyl)ethoxy)methyl)-1H-pyrrolo[2,3-b]pyridin-2-yl)-3-cyclopropylimidazo[1,2-a]pyridine-7-carboxylate I-25. ES/MS: m/z 505.0 [M+H]$^+$.

methyl 2-(6-acetyl-1-((2-(trimethylsilyl)ethoxy)methyl)-1H-pyrrolo[2,3-b]pyridin-2-yl)-3-cyclopropyl-5-methoxyimidazo[1,2-a]pyridine-7-carboxylate (I-25b). Prepared following a similar procedure to I-25 starting with I-15 instead of I-14. ES/MS: m/z 535.0 [M+H]⁺

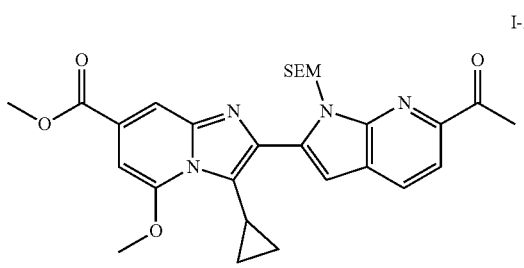

Preparation of (R)-2-(1-(cyclopropylmethyl)-6-(1-(3-fluorobicyclo[1.1.1]pentane-1-carboxamido)ethyl)-1H-pyrrolo[2,3-b]pyridin-2-yl)-5-methoxy-3-methylimidazo[1,2-a]pyridine-7-carboxylic acid (I-26)

Step 1. Ethyl (R)-2-(6-(1-aminoethyl)-1-(cyclopropylmethyl)-1H-pyrrolo[2,3-b]pyridin-2-yl)-5-methoxy-3-methylimidazo[1,2-a]pyridine-7-carboxylate I-24, hydrochloride salt (50 mg, 0.096 mmol) and 3-fluorobicyclo[1.1.1]pentane-1-carboxylic acid (18.8 mg, 0.144 mmol) were taken up in DMF (2 mL). DIPEA (0.0837 mL, 0.480 mmol) and HATU (0.0438 g, 0.115 mmol) were then added and the reaction mixture stirred for 30 minutes. Water was added, precipitating a solid that was filtered and washed with water. The solid was dried in vacuo to yield ethyl (R)-2-(1-(cyclopropylmethyl)-6-(1-(3-fluorobicyclo[1.1.1]pentane-1-carboxamido)ethyl)-1H-pyrrolo[2,3-b]pyridin-2-yl)-5-methoxy-3-methylimidazo[1,2-a]pyridine-7-carboxylate. ES/MS: m/z 560.22 [M+H]⁺.

Step 2. To a solution of ethyl (R)-2-(1-(cyclopropylmethyl)-6-(1-(3-fluorobicyclo[1.1.1]pentane-1-carboxamido)ethyl)-1H-pyrrolo[2,3-b]pyridin-2-yl)-5-methoxy-3-methylimidazo[1,2-a]pyridine-7-carboxylate (48 mg, 0.086 mmol) in THF (2 mL), MeOH (1 mL), and water (1 mL) was added lithium hydroxide, monohydrate (0.0201 g, 0.480 mmol). After stirring at rt overnight, a solution of HCl (aq) (6 N, 0.1 mL, 0.60 mmol) was added and the reaction mixture was concentrated under reduced pressure. The resulting solid was dried in vacuo to yield (R)-2-(1-(cyclopropylmethyl)-6-(1-(3-fluorobicyclo[1.1.1]pentane-1-carboxamido)ethyl)-1H-pyrrolo[2,3b]pyridin-2-yl)-5-methoxy-3-methylimidazo[1,2-a]pyridine-7-carboxylic acid I-26 as the lithium chloride salt, which was used without purification. ES/MS: m/z 532.20 [M+H]⁺.

(R)-2-(6-(1-benzamidoethyl)-1-(cyclopropylmethyl)-1H-pyrrolo[2,3-b]pyridin-2-yl)-5-methoxy-3-methylimidazo[1,2-a]pyridine-7-carboxylic acid (I-26a). Prepared following a similar procedure to I-26 starting with utilizing with benzoic acid in place of 3-fluorobicyclo[1.1.1]pentane-1-carboxylic acid in Step 1. ES/MS: m/z 524.2 [M+H]⁺.

Preparation of (R)-2-(1-(cyclopropylmethyl)-6-(1-(pyrrolidine-1-carboxamido)ethyl)-1H-pyrrolo[2,3-b]pyridin-2-yl)-5-methoxy-3-methylimidazo[1,2-a]pyridine-7-carboxylic acid (I-27)

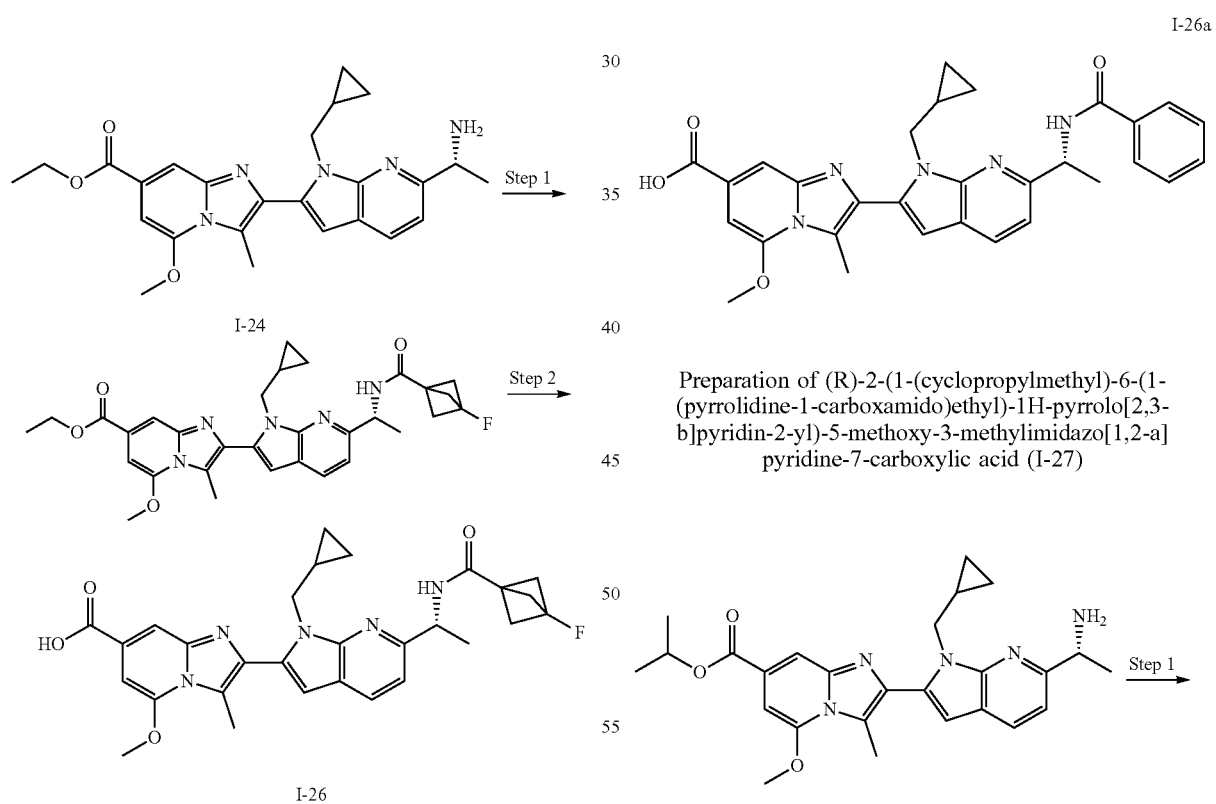

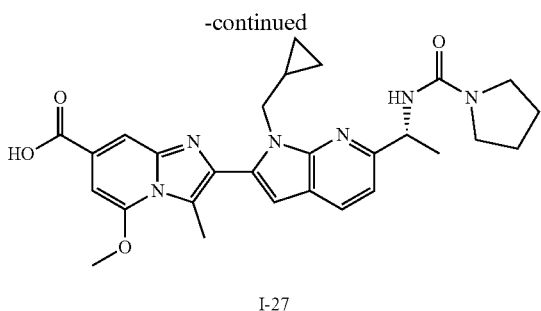

I-27

Step 1. Ethyl (R)-2-(6-(1-aminoethyl)-1-(cyclopropylmethyl)-1H-pyrrolo[2,3-b]pyridin-2-yl)-5-methoxy-3-methylimidazo[1,2-a]pyridine-7-carboxylate I-24 (200 mg, 0.372 mmol) was taken up in DCM (7 mL) and triethylamine (0.261 mL, 1.86 mmol) was added. To the resulting solution was added pyrrolidine carbonyl chloride (0.0821 mL, 0.744 mmol). After 30 minutes at rt, additional pyrrolidine carbonyl chloride (0.0821 mL, 0.744 mmol) was added the reaction mixture was heated to 35° C. After 5 hours, the reaction mixture was partitioned between ethyl acetate and sat. NaHCO₃(aq). The layers were separated, and organics were dried, filtered, and concentrated under reduced pressure. The resulting residue was purified via silica gel column chromatography (10-100% acetone in hexanes) to yield ethyl (R)-2-(1-(cyclopropylmethyl)-6-(1-(pyrrolidine-1-carboxamido)ethyl)-1H-pyrrolo[2,3-b]pyridin-2-yl)-5-methoxy-3-methylimidazo[1,2-a]pyridine-7-carboxylate. ES/MS: m/z 545.05 [M+H]⁺.

Step 2. To a solution of ethyl (R)-2-(1-(cyclopropylmethyl)-6-(1-(pyrrolidine-1-carboxamido)ethyl)-1H-pyrrolo[2,3-b]pyridin-2-yl)-5-methoxy-3-methylimidazo[1,2-a]pyridine-7carboxylate (200 mg, 0.367 mmol) in THF (5 mL), MeOH (2 mL), and water (2 mL) was added lithium hydroxide monohydrate (0.108 g, 2.57 mmol). After stirring at rt overnight, a solution of HCl (aq) (6 N, 0.46 mL, 2.75 mmol) was added and the reaction mixture was concentrated under reduced pressure. The resulting solid was dried in vacuo to yield (R)-2-(1-(cyclopropylmethyl)-6-(1-(pyrrolidine-1-carboxamido)ethyl)-1H-pyrrolo[2,3-b]pyridin-2-yl)-5-methoxy-3-methylimidazo[1,2-a]pyridine-7-carboxylic acid I-27 as the lithium chloride salt, which was used without purification. ES/MS: m/z 517.20 [M+H]⁺.

Preparation of benzyl ((1R,2R,4S)-7-(2-(6-((R)-1-aminoethyl)-1-(cyclopropylmethyl)-1H-pyrrolo[2,3-b]pyridin-2-yl)-5-methoxy-3-methylimidazo[1,2-a]pyridine-7-carbonyl)-7-azabicyclo[2.2.1]heptan-2-yl)carbamate (I-28)

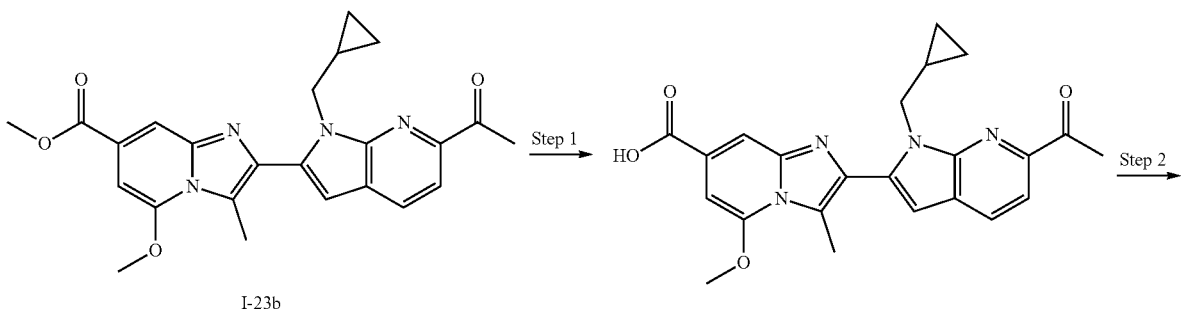

I-23b

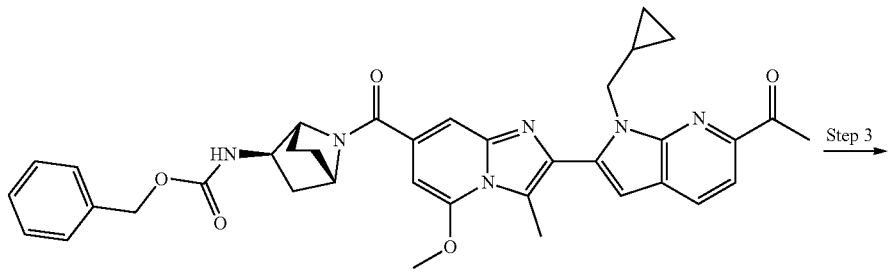

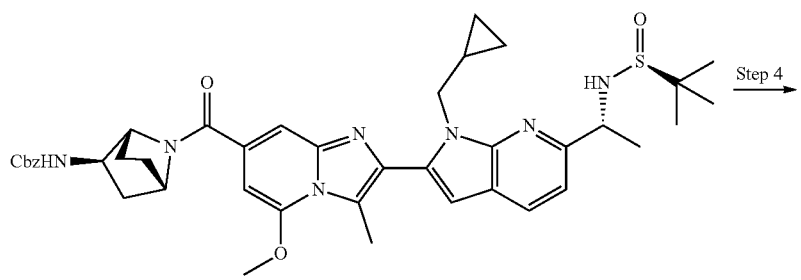

-continued

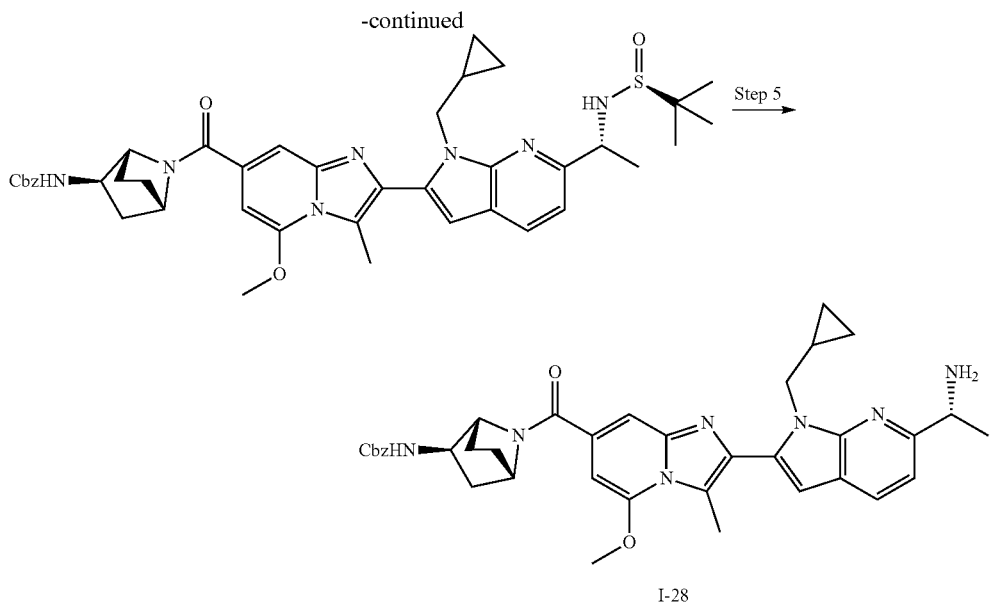

I-28

Step 1. To a solution of methyl 2-[6-acetyl-1-(cyclopropylmethyl)pyrrolo[2,3-b]pyridin-2-yl]-5-methoxy-3-methyl-imidazo[1,2-a]pyridine-7-carboxylate I-23b (250 mg, 0.578 mmol) in THF (10 mL), MeOH (3 mL), and water (3 mL) was added lithium hydroxide monohydrate (121 mg, 2.88 mmol). After stirring at rt for 4 hours, a solution of HCl (aq) (6N, 0.53 mL, 3.18 mmol) was added and the reaction mixture was concentrated under reduced pressure. The resulting solid was dried in vacuo to yield 2-(6-acetyl-1-(cyclopropylmethyl)-1H-pyrrolo[2,3-b]pyridin-2-yl)-5-methoxy-3-methylimidazo[1,2-a]pyridine-7-carboxylic acid as the lithium chloride salt, which was used without purification. ES/MS: m/z 419.17 [M+H]+.

Step 2. 2-(6-acetyl-1-(cyclopropylmethyl)-1H-pyrrolo[2,3-b]pyridin-2-yl)-5-methoxy-3-methylimidazo[1,2-a]pyridine-7-carboxylic acid (240 mg, 0.578 mmol) and tert-butyl ((1R,2R,4S)-7-azabicyclo[2.2.1]heptan-2-yl)carbamate A4 (135 mg, 0.636 mmol were taken up in DMF (5 mL). DIPEA (0.312 mL, 1.78 mmol) and HATU (264 mg, 0.694 mmol) were then added and the reaction mixture stirred for 90 minutes. The reaction mixture was partitioned between ethyl acetate and sat. NaHCO3(aq). The layers were separated, and organics were extracted with ethyl acetate. The combined organics were washed with water, brine, dried, filtered, and concentrated under reduced pressure. The resulting residue was purified via silica gel column chromatography (0-70% acetone in hexanes) to yield benzyl ((1R,2R,4S)-7-(2-(6-acetyl-1-(cyclopropylmethyl)-1H-pyrrolo[2,3-b]pyridin-2-yl)-5-methoxy-3-methylimidazo[1,2-a]pyridine-7-carbonyl)-7-azabicyclo[2.2.1]heptan-2-yl)carbamate. ES/MS: m/z 647.31 [M+H]+.

Step 3. To a mixture of benzyl ((1R,2R,4S)-7-(2-(6-acetyl-1-(cyclopropylmethyl)-1H-pyrrolo[2,3-b]pyridin-2-yl)-5-methoxy-3-methylimidazo[1,2-a]pyridine-7-carbonyl)-7-azabicyclo[2.2.1]heptan-2-yl)carbamate (600 mg, 0.928 mmol) and (S)-2-methylpropane-2-sulfinamide (622 mg, 5.13 mmol) in THF (12 mL) was added titanium (IV) ethoxide (2.15 mL, 10.2 mmol). The reaction mixture was heated at reflux for 21 hours. After cooling to rt, the reaction mixture was diluted with THF and poured into brine. The mixture was filtered over celite, washing with ethyl acetate.

The filtrate layers were separated and the aqueous was extracted with ethyl acetate. The combined organics were dried, filtered, and concentrated under reduced pressure. The resulting residue was purified via silica gel column chromatography (20-60% acetone in hexanes) to yield benzyl ((1R,2R,4S)-7-(2-(6-((E)-1-4(S)-tert-butylsulfinyl)imino)ethyl)-1-(cyclopropylmethyl)-1H-pyrrolo[2,3-b]pyridin-2-yl)-5-methoxy-3-methylimidazo[1,2-a]pyridine-7-carbonyl)-7-azabicyclo[2.2.1]heptan-2-yl)carbamate. ES/MS: m/z 750.04 [M+H]+.

Step 4. A solution of benzyl ((1R,2R,4S)-7-(2-(6-((E)-1-4(S)-tert-butylsulfinyl)imino)ethyl)-1-(cyclopropylmethyl)-1H-pyrrolo[2,3-b]pyridin-2-yl)-5-methoxy-3-methylimidazo[1,2-a]pyridine-7-carbonyl)-7-azabicyclo[2.2.1]heptan-2-yl)carbamate (696 mg, 0.930 mmol) in THF (20 mL) was cooled to −50° C. A solution of L-Selectride (1.00 M, 1.21 mL, 1.21 mmol) was added dropwise. After twenty minutes, the reaction mixture was warmed to 0° C. and stirred for 20 minutes. The reaction mixture was quenched via the addition of water and diluted with ethyl acetate and NH4Cl (aq). The layers were separated, and organics were extracted with ethyl acetate. The combined organics were dried, filtered, and concentrated under reduced pressure. The resulting residue was purified via silica gel column chromatography (20-100% acetone in hexanes) to yield benzyl ((1R,2R,4S)-7-(2-(6-((R)-1-4(S)-tert-butylsulfinyl)amino)ethyl)-1-(cyclopropylmethyl)-1H-pyrrolo[2,3-b]pyridin-2-yl)-5-methoxy-3-methylimidazo[1,2-a]pyridine-7-carbonyl)-7-azabicyclo[2.2-0.1]heptan-2-yl)carbamate. ES/MS: m/z 752.23 [M+H]+.

Step 5. A solution of HCl in dioxane (4 M, 0.470 mL, 1.88 mmol) was added to a solution of benzyl ((1R,2R,4S)-7-(2-(6-((R)-1-4(S)-tert-butylsulfinyl)amino)ethyl)-1-(cyclopropylmethyl)-1H-pyrrolo[2,3-b]pyridin-2-yl)-5-methoxy-3-methylimidazo[1,2-a]pyridine-7-carbonyl)-7-azabicyclo[2.2.1]heptan-2-yl)carbamate (470 mg, 0.625 mmol) in dioxane (15 mL) at rt. After 15 minutes, the reaction mixture was concentrated under reduced pressure and dried in vacuo to yield benzyl ((1R,2R,4S)-7-(2-(6-((R)-1-aminoethyl)-1-(cyclopropylmethyl)-1H-pyrrolo[2,3-b]pyridin-2-yl)-5methoxy-3-methylimidazo[1,2-a]pyridine-7-carbonyl)-7- azabicyclo[2.2.1]heptan-2-yl)carbamate I-28, hydrochloride salt. ES/MS: m/z 648.18 [M+H]+.

Preparation of benzyl ((R)-1-(2-(6-((E)-(((R)-tert-butylsulfinyl)imino)methyl)-1-(cyclopropylmethyl)-1H-pyrrolo[2,3-b]pyridin-2-yl)-5-methoxy-3-methylimidazo[1,2-a]pyridine-7-carbonyl)piperidin-3-yl)carbamate (I-29)

solid. The solid was filtered, washed with water, and dried in vacuo, to yield benzyl N-[(3R)-1-[2-[1-(cyclopropylmethyl)-6-vinyl-pyrrolo[2,3-b]pyridin-2-yl]-5-methoxy-3-methyl-imidazo[1,2-a]pyridine-7-carbonyl]-3-piperidyl]carbamate I-28a. ES/MS: m/z 619.37 [M+H]+.

Step 2. To a mixture of benzyl N-[(3R)-1-[2-[1-(cyclopropylmethyl)-6-vinyl-pyrrolo[2,3-b]pyridin-2-yl]-5-methoxy-3-methyl-imidazo[1,2-a]pyridine-7-carbonyl]-3-

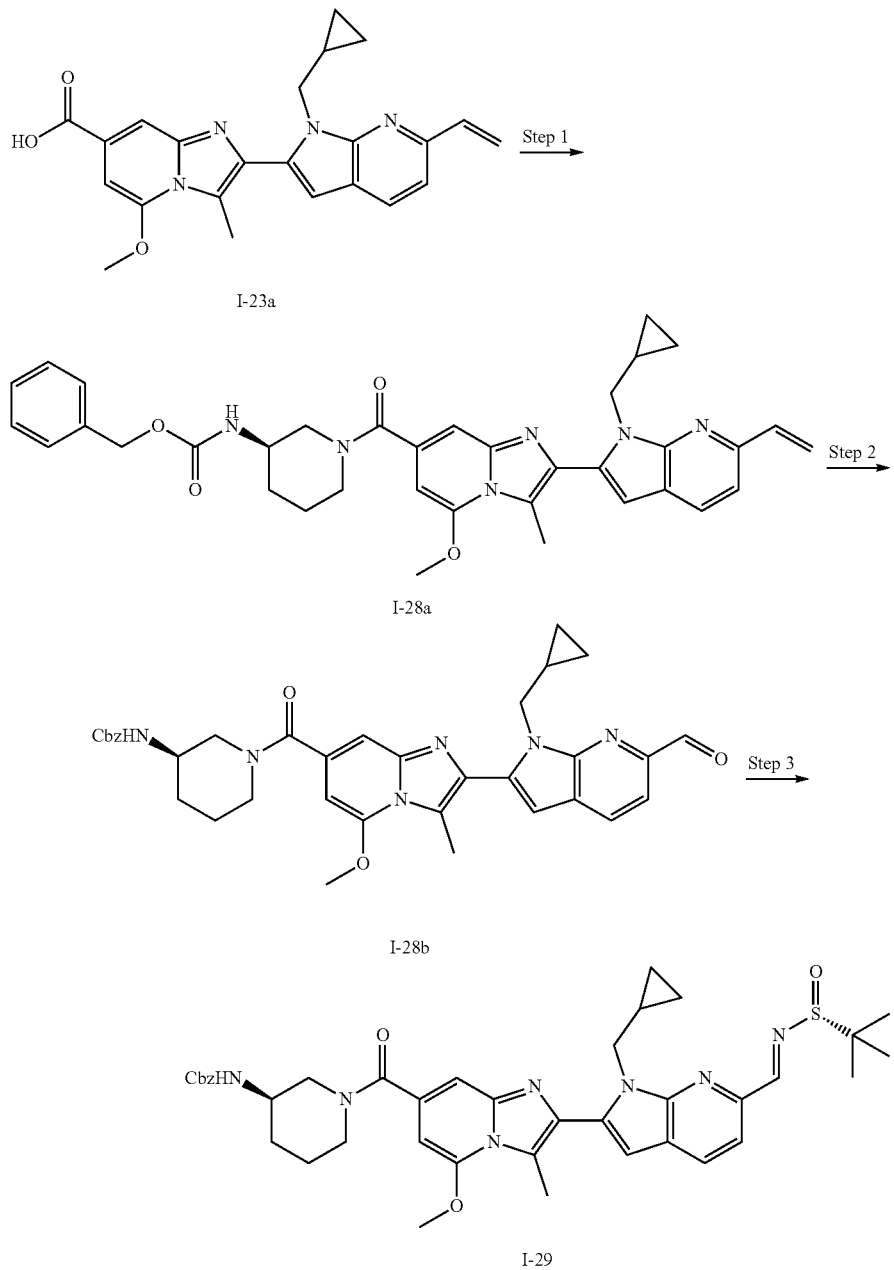

Step 1. DIPEA (1.50 mL, 8.61 mmol) and HATU (1351 mg, 3.55 mmol) were added to a mixture of 2-(1-(cyclopropylmethyl)-6-vinyl-1H-pyrrolo[2,3-b]pyridin-2-yl)-5-methoxy-3-methylimidazo[1,2-a]pyridine-7-carboxylic acid (953 mg, 2.37 mmol) I-23a (953 mg, 2.37 mmol) and benzyl (R)-piperidin-3-ylcarbamate (1110 mg, 4.74 mmol) in DMF (20 mL). After four hours, water was added, precipitating a piperidyl]carbamate I-28a (1540 mg, 2.49 mmol) in THF (40 mL) and water (40 mL) was added potassium osmate dihydrate (20 mg, 0.055 mmol) and sodium periodate (1636 mg, 7.65 mmol). After 4 hours, the reaction mixture was diluted with water and ethyl acetate. The layers were separated and the aqueous extracted with ethyl acetate. The combined organics were washed with brine, dried (MgSO4), filtered, and concentrated under reduced pressure. The resulting residue was purified via silica gel column chromatography (5-100% ethyl acetate in hexanes) to yield benzyl N-[(3R)-1-[2-[1-(cyclopropylmethyl)-6-formyl-pyrrolo[2,3-b]pyridin-2-yl]-5-methoxy-3-methyl-imidazo[1,2-a]pyridine-7-carbonyl]-3-piperidyl]carbamate I-28b. ES/MS: m/z 621.31.

Step 3. A mixture of benzyl N-[(3R)-1-[2-[1-(cyclopropylmethyl)-6-formyl-pyrrolo[2,3-b]pyridin-2-yl]-5-methoxy-3-methyl-imidazo[1,2-a]pyridine-7-carbonyl]-3-piperidyl]carbamate I-28b (704 mg, 1.13 mmol), (R)-2-methylpropane-2-sulfinamide (412 mg, 3.40 mmol), and cupric sulfate pentahydrate (1.70 g, 6.81 mmol) in DCM (15 mL) was heated at reflux overnight. After cooling to rt, the reaction mixture was filtered over celite, washing with DCM. The filtrate was concentrated and the resulting residue was purified via silica gel column chromatography (15-100% ethyl acetate in hexanes) to yield benzyl ((R)-1-(2-(6(E)-(((R)-tert-butylsulfinyl)imino)methyl)-1-(cyclopropylmethyl)-1H-pyrrolo[2,3-b]pyridin-2-yl)-5-methoxy-3-methylimidazo[1,2-a]pyridine-7-carbonyl)piperidin-3-yl)carbamate I-29. ES/MS: m/z 724.14 [M+H]$^+$.

Preparation of benzyl ((1R,2R,4S)-7-(2-(6-chloro-1-(cyclopropylmethyl)-1H-pyrrolo[2,3-b]pyridin-2-yl)-5-methoxy-3-methylimidazo[1,2-a]pyridine-7-carbonyl)-7-azabicyclo[2.2.1]heptan-2-yl)carbamate (I-28c). Prepared according to Step 1 and 2 of the synthesis of I-28, starting with I-20 rather than I-23b. ES/MS: m/z 639.3 [M+H]$^+$.

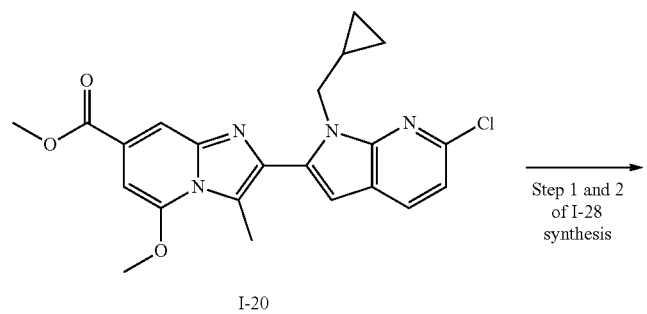

I-20

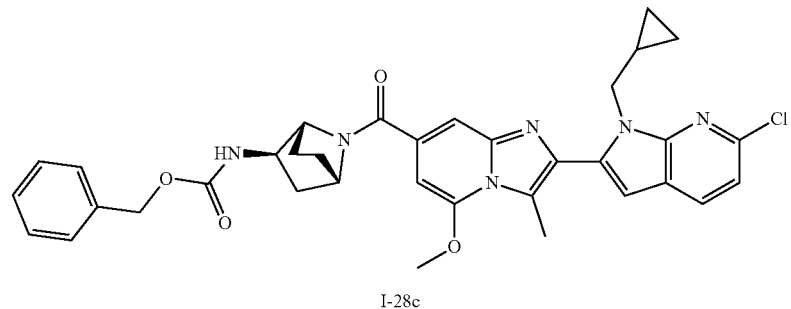

I-28c

Preparation of tert-butyl ((1R,2R,4S)-7-(2-(6-((R)-1-aminoethyl)-1-(cyclopropylmethyl)-1H-pyrrolo[2,3-b]pyridin-2-yl)-5-methoxy-3-methylimidazo[1,2-a]pyridine-7-carbonyl)-7-azabicyclo[2.2.1]heptan-2-yl)carbamate (I-30)

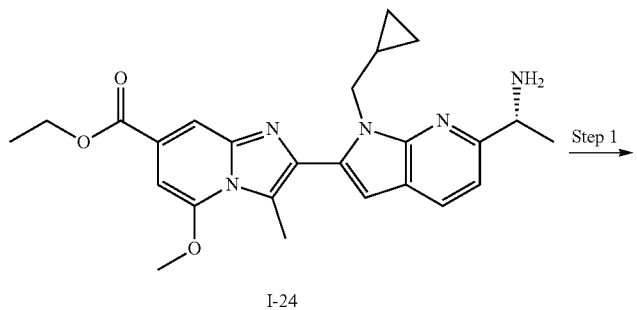

I-24

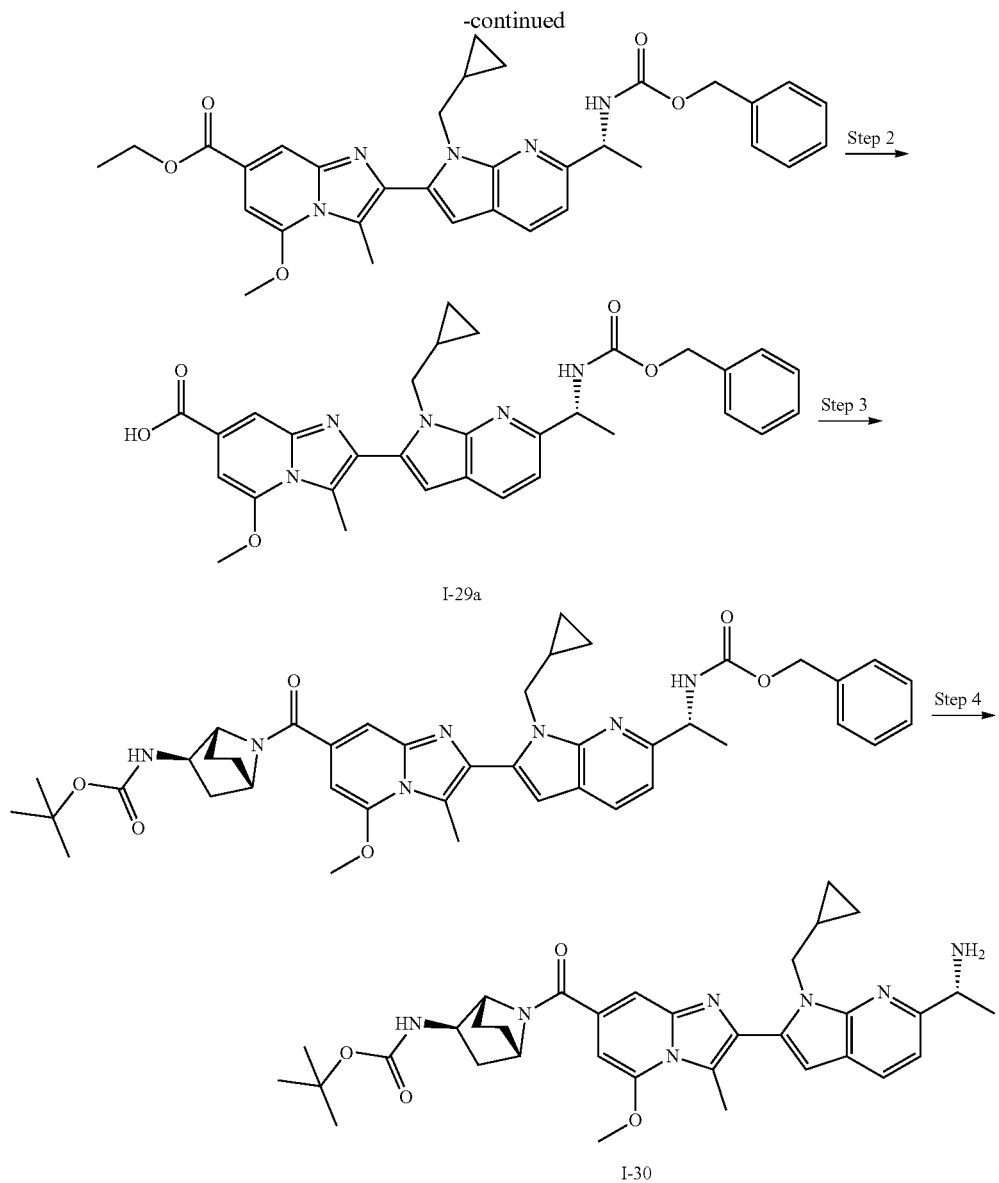

Step 1. Ethyl (R)-2-(6-(1-aminoethyl)-1-(cyclopropylmethyl)-1H-pyrrolo[2,3-b]pyridin-2-yl)-5-methoxy-3-methylimidazo[1,2-a]pyridine-7-carboxylate I-24 (2420 mg, 5.41 mmol) was taken up in DCM (25 mL) and triethylamine (2.28 mL, 16.2 mmol) was added, followed by benzyl (2,5-dioxopyrrolidin-1-yl) carbonate (1482 mg, 5.95 mmol). After stirring overnight, the reaction mixture was partioned between ethyl acetate and water. The layers were separated, and the aqueous was extracted with ethyl acetate. The combined organics were dried, filtered, and concentrated under reduced pressure. The resulting residue was purified via silica gel column chromatography (30-100% ethyl acetate in hexanes) to yield ethyl (R)-2-(6-(1-(((benzyloxy) carbonyl)amino)ethyl)-1-(cyclopropylmethyl)-1H-pyrrolo [2,3-b]pyridin-2-yl)-5-methoxy-3-methylimidazo[1,2-a] pyridine-7-carboxylate. ES/MS: m/z 582.10 [M+H]+.

Step 2. To a solution of ethyl (R)-2-(6-(1-(((benzyloxy) carbonyl)amino)ethyl)-1-(cyclopropylmethyl)-1H-pyrrolo [2,3-b]pyridin-2-yl)-5-methoxy-3-methylimidazo[1,2-a] pyridine-7-carboxylate (2.80 g, 4.81 mmol) in THF (50 mL), MeOH (25 mL), and water (25 mL) was added lithium hydroxide, monohydrate (1.01 g, 24 mmol). After stirring at rt for 5 hours, a solution of HCl (aq) (6 N, 4.1 mL, 24.5 mmol) was added and the reaction mixture was concentrated under reduced pressure. The resulting solid was dried in vacuo to yield (R)-2-(6-(1-(((benzyloxy)carbonyl)amino) ethyl)-1-(cyclopropylmethyl)-1H-pyrrolo[2,3-b]pyridin-2-yl)-5-methoxy-3-methylimidazo[1,2-a]pyridine-7-carboxylic acid I-29a as the lithium chloride salt, which was used without purification. ES/MS: m/z 554.17 [M+H]+.

Step 3. (R)-2-(6-(1-(((benzyloxy)carbonyl)amino)ethyl)-1-(cyclopropylmethyl)-1H-pyrrolo[2,3-b]pyridin-2-yl)-5-methoxy-3-methylimidazo[1,2-a]pyridine-7-carboxylic acid I-29a (2.66 g, 4.81 mmol) and tert-butyl ((1R,2R,4S)-7-azabicyclo[2.2.1]heptan-2-yl)carbamate A2 (1.07 g, 5.05 mmol) were taken up in DMF (30 mL). DIPEA (3.35 mL, 19.2 mmol) and HATU (2.19 g, 5.77 mmol) were then added and the reaction mixture stirred for 30 minutes. The reaction mixture was partioned between ethyl acetate and sat. NaHCO$_3$(aq). The layers were separated, and organics were extracted with ethyl acetate. The combined organics were washed with water, brine, dried, filtered, and concentrated under reduced pressure. The resulting residue was purified via silica gel column chromatography (30-100% acetone in hexanes) to yield tert-butyl ((1R,2R,4S)-7-(2-(6-((R)-1-(((benzyloxy)carbonyl)amino)ethyl)-1-(cyclopropylmethyl)-1H-pyrrolo[2,3-b]pyridin-2-yl)-5-methoxy-3-methylimidazo[1,2-a]pyridine-7-carbonyl)-7-azabicyclo[2.2.1]heptan-2-yl)carbamate. ES/MS: m/z 748.31 [M+H]⁺.

Step 4. A mixture of tert-butyl ((1R,2R,4S)-7-(2-(6-((R)-1-(((benzyloxy)carbonyl)amino)ethyl)-1-(cyclopropylmethyl)-1H-pyrrolo[2,3-b]pyridin-2-yl)-5-methoxy-3-methylimidazo[1,2-a]pyridine-7-carbonyl)-7-azabicyclo[2.2.1]heptan-2-yl)carbamate (3.60 g, 4.81 mmol) and palladium on carbon (10%, 1.28 g, 12 mmol) in ethyl acetate (50 mL) was hydrogenated under an atmosphere of hydrogen. After 16 hours, the reaction mixture was filtered over celite, washing with ethyl acetate. The filtrate was concentrated under reduced pressure to yield tert-butyl ((1R,2R,4S)-7-(2-(6-((R)-1-aminoethyl)-1-(cyclopropylmethyl)-1H-pyrrolo[2,3-b]pyridin-2-yl)-5-methoxy-3-methylimidazo[1,2-a]pyridine-7-carbonyl)-7-azabicyclo[2.2.1]heptan-2-yl)carbamate I-30. ES/MS: m/z 614.15 [M+H]⁺.

Preparation of ethyl (R)-2-(6-(1-((tert-butoxycarbonyl)amino)ethyl)-1H-pyrrolo[2,3-b]pyridin-2-yl)-5-methoxy-3-methylimidazo[1,2-a]pyridine-7-carboxylate (I-31)

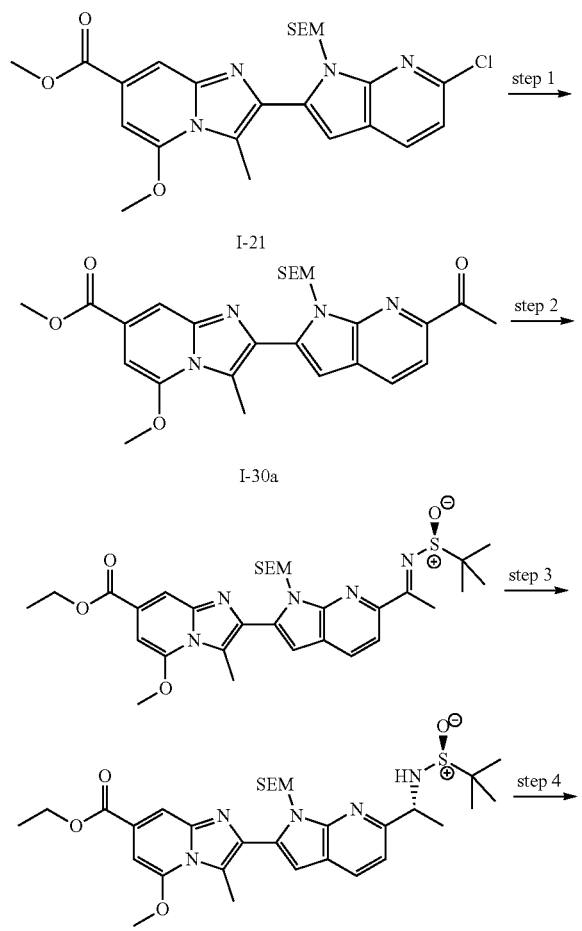

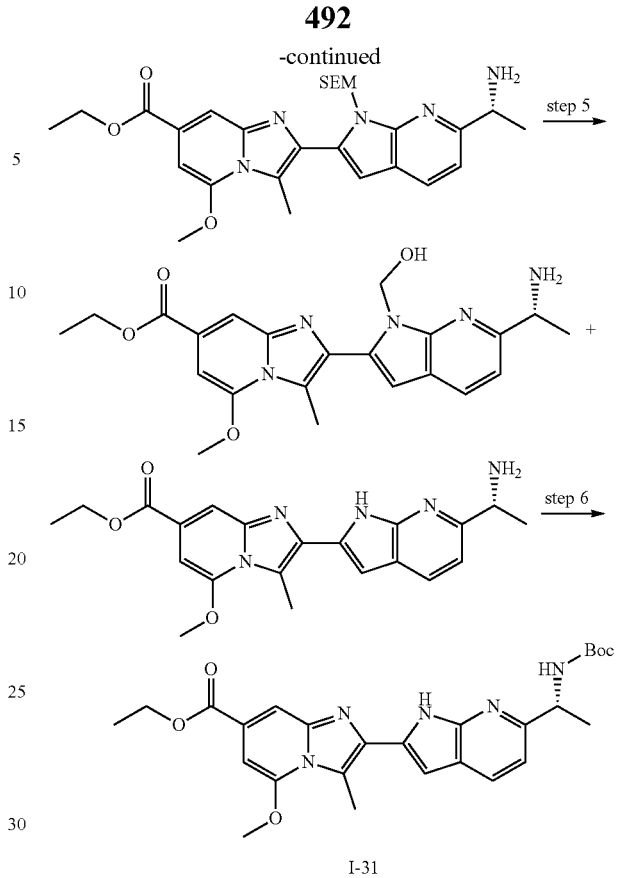

Step 1. Methyl 2-(6-chloro-1-((2-(trimethylsilyl)ethoxy)methyl)-1H-pyrrolo[2,3-b]pyridin-2-yl)-5-methoxy-3-methylimidazo[1,2-a]pyridine-7-carboxylate I-21 (2.1 g, 4.17 mmol) and PdCl₂(dppf).CH₂Cl₂ (341 mg, 0.42 mmol, 10 mol %) were taken up in dioxane (20 mL) in a pressure flask. The mixture was stirred and degassed with nitrogen for 10 minutes. 1-Ethoxyvinyltributyltin (2.8 ml, 8.34 mmol, 2 equiv.) was added and the resulting mixture was stirred at 100° C. for 3 hours. Upon cooling, the mixture was filtered with EtOAc through Celite and the filtrate was concentrated. The resulting residue was dissolved in THF (30 mL), and 1 N HCl (4.0 mL, 4.0 mmol, 0.95 equiv.) was added. The mixture was stirred 30 min, at which time it was diluted with EtOAc and water. Phases were separated, and the aqueous phase was extracted with EtOAc. The organic phase was dried over MgSO₄, filtered, and concentrated to crude solid. The solid was slurried in 30 mL hexanes for 30 min, and the mixture was filtered to collect solids. The filter cake was slurried in 30 mL hexanes for 30 minutes and the mixture was filtered to collect methyl 2-(6-acetyl-14(24trimethylsilypethoxy)methyl)-1H-pyrrolo[2,3-b]pyridin-2-yl)-5-methoxy-3-methylimidazo[1,2-a]pyridine-7-carboxylate I-30a, which was used without further purification for the next step. ES/MS: m/z 509.3 [M+H]⁺.

Step 2. Methyl 2-(6-acetyl-1-((2-(trimethylsilyl)ethoxy)methyl)-1H-pyrrolo[2,3-b]pyridin-2-yl)-5-methoxy-3-methylimidazo[1,2-a]pyridine-7-carboxylate (4.17 mmol) and (S)-2-methylpropane-2-sulfinamide (2.02 g, 16.7 mmol. 4 equiv.) were suspended in THF (30 mL) under nitrogen. Titanium (IV) ethoxide* (5.2 mL, 25 mmol, 6 equiv.) was added, and the resulting stirred mixture was heated at 60° C. After 18 h, the reaction mixture was poured into a vigorously stirred mixture of brine (150 mL) and EtOAc (100 mL). The heterogeneous mixture was diluted further with EtOAc and the phases were separated. The aqueous phase was diluted with EtOAc, Celite (~50 g) was added and stirred with the resulting emulsion. The mixture was filtered through a pad of Celite with EtOAc, and the resulting clear biphasic mixture was separated. The combined organic phase was dried over $Na_2SO_4$, filtered and concentrated. Purification by silica gel (10-60% EtOAc in hexanes) provided ethyl (S)-2-(6-(1-((tert-butylsulfinyl)imino)ethyl)-1-((2-(trimethylsilyl)ethoxy)methyl)-1H-pyrrolo[2,3-b]pyridin-2-yl)-5-methoxy-3-methylimidazo[1,2-a]pyridine-7-carboxylate. ES/MS: m/z 626.4 $[M+H]^+$. *Titanium (IV) isopropoxide can also be used; in that case, the resulting product of this step would be an isopropyl ester.

Step 3. Ethyl (S)-2-(6-(1-((tert-butylsulfinyl)imino) ethyl)-1-((2-(trimethylsilyl)ethoxy)methyl)-1H-pyrrolo[2,3-b]pyridin-2-yl)-5-methoxy-3-methylimidazo[1,2-a]pyridine-7-carboxylate (2.6 g, 4.2 mmol) was dissolved in THF (40 mL) under nitrogen. The resulting mixture was cooled in a $CO_2$/acetone bath to approximately −78° C. L-Selectride (1 M in THF, 4.6 mL, 4.6 mmol, 1.1 equiv.) was then added dropwise over 30 min, and the resulting mixture was stirred for 20 min at −78° C. The reaction was quenched with sat. aq. $NH_4C_1$ and diluted with EtOAc and water. The phases were separated, and the organic phase was dried over $MgSO_4$, filtered, and concentrated. The obtained residue was purified by silica gel chromatography (5-100% 3:1 EA/EtOH in hexane) to afford ethyl 2-(6-((R)-1-4(S)-tert-butylsulfinyl)amino)ethyl)-1-((2-(trimethylsilyl)ethoxy) methyl)-1H-pyrrolo[2,3-b]pyridin-2-yl)-5-methoxy-3-methylimidazo[1,2-a]pyridine-7-carboxylate. ES/MS: m/z 628.4 $[M+H]^+$.

Step 4. Ethyl 2-(6-((R)-1-4(S)-tert-butylsulfinyl)amino) ethyl)-1-((2-(trimethylsilyl)ethoxy)methyl)-1H-pyrrolo[2,3-b]pyridin-2-yl)-5-methoxy-3-methylimidazo[1,2-a]pyridine-7-carboxylate (675 mg, 1.08 mmol) was dissolved in dioxane (10 mL) at 0° C. HCl in dioxane (4 M, 1.34 mL, 5.4 mmol, 5 equiv.) was added, resulting in the immediate precipitation of solids. After stirring 15 min, the reaction mixture was concentrated in vacuo to provide crude ethyl (R)-2-(6-(1-aminoethyl)-1-((2-(trimethylsilyl)ethoxy) methyl)-1H-pyrrolo[2,3-b]pyridin-2-yl)-5-methoxy-3-methylimidazo[1,2-a]pyridine-7-carboxylate (putative bis-HCl salt) which was used without further purification. ES/MS: m/z 524.3 $[M+H]^+$.

Step 5. Ethyl (R)-2-(6-(1-aminoethyl)-1-((2-(trimethylsilyl)ethoxy)methyl)-1H-pyrrolo[2,3-b]pyridin-2-yl)-5-methoxy-3-methylimidazo[1,2-a]pyridine-7-carboxylate, hydrochloride salt (1.08 mmol) was dissolved in DCM (10 mL) at room temperature. TFA (1.6 mL, 20 equiv.) was added. After stirring 60 min, the reaction mixture was concentrated in vacuo and dried under vacuum to provide crude mixture of ethyl (R)-2-(6-(1-aminoethyl)-1-(hydroxymethyl)-1H-pyrrolo[2,3-b]pyridin-2-yl)-5-methoxy-3-methylimidazo[1,2-a]pyridine-7-carboxylate and ethyl (R)-2-(6-(1-aminoethyl)-1H-pyrrolo[2,3-b]pyridin-2-yl)-5-methoxy-3-methylimidazo[1,2-a]pyridine-7-carboxylate which was used without further purification. ES/MS: m/z 424.2 $[M+H]^+$, 394.2 $[M+H]^+$.

Step 6. Part A: The above crude mixture (ca. 1.08 mmol) was dissolved in DCM (5 mL). Di-tert-butyl dicarbonate (235 mg, 1.08 mmol, 1.0 equiv) and diisopropylethylamine (0.94 mL, 5.4 mmol, 5.0 equiv.) were added. The mixture was stirred at room temperature for 2 h. Water and EtOAc were added, phases were separated, and the aqueous phase was extracted with EtOAc. The organic phase was dried over $MgSO_4$, filtered, and concentrated. Part B: The resulting residue was dissolved in methanol (5 mL) and ethylenediamine (0.72 mL, 10.8 mmol, 10 equiv.) was added. The mixture was stirred at room temperature for 3.5 h. The mixture was concentrated and purified by silica gel chromatography (5-80% 3:1 EA/EtOH in hexane) to afford ethyl (R)-2-(6-(1-((tert-butoxycarbonyl)amino)ethyl)-1H-pyrrolo [2,3-b]pyridin-2-yl)-5-methoxy-3-methylimidazo[1,2-a] pyridine-7-carboxylate I-31. ES/MS: m/z 494.3 $[M+H]^+$.

Preparation of isopropyl (R)-2-(6-(1-(((benzyloxy) carbonyl)amino)ethyl)-1H-pyrrolo[2,3-b]pyridin-2-yl)-3-cyclopropylimidazo[1,2-a]pyridine-7-carboxylate (I-32)

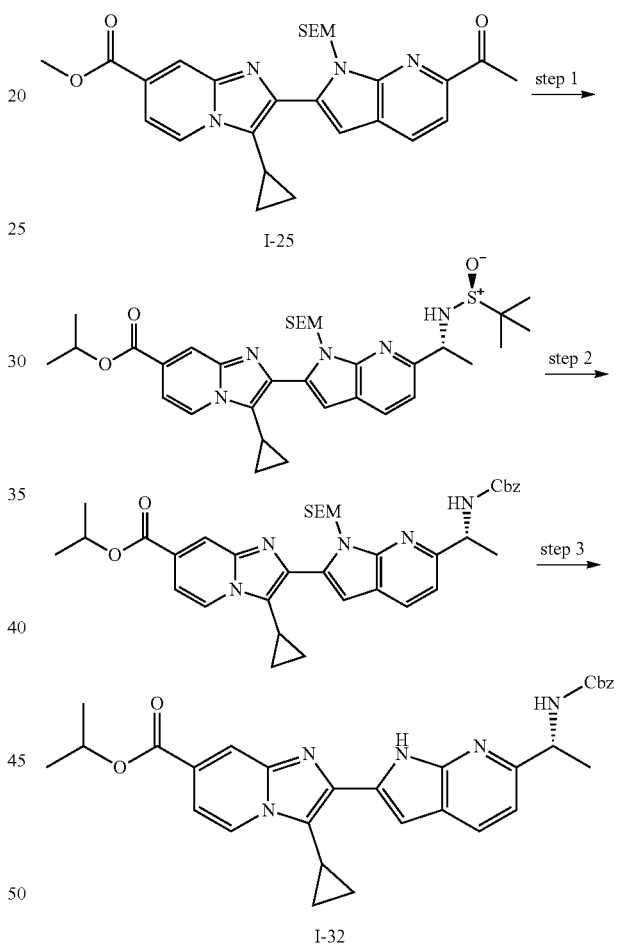

Step 1. Isopropyl 2-(6-((R)-1-(((S)-tert-butylsulfinyl) amino)ethyl)-1-((2-(trimethylsilyl)ethoxy)methyl)-1H-pyrrolo[2,3-b]pyridin-2-yl)-3-cyclopropylimidazo[1,2-a]pyridine-7-carboxylate was prepared following steps 2 and 3 of I-31 starting with I-25 in place of I-30a. ES/MS: m/z 637.9 $[M+H]^+$.

Step 2. Part A-A solution of 4 M HCl in Dioxane, (1.1 mL, 4.4 mmol) was added to a solution of isopropyl 2-(6-((R)-1-4(S)-tert-butylsulfinyl)amino)ethyl)-1-((2-(trimethylsilypethoxy)methyl)-1H-pyrrolo[2,3-b]pyridin-2-yl)-3-cyclopropylimidazo[1,2-a]pyridine-7-carboxylate (562 mg, 0.881 mmol) in dioxane (12 mL). After 4 hours, the reaction mixture was concentrated under reduced pressure. Part B-To the resulting residue in DCM (12 mL) was added triethylamine (0.7 mL, 5.0 mmol) and N-carbobenzoxyoxysuccinimide (0.26 g, 1.06 mmol). After stirring 3 days, sat. NaHCO₃(aq) was added and the reaction mixture was diluted with DCM. The layers were separated and the aqueous was extracted with DCM. The combined organics were washed with brine, dried (MgSO₄), filtered, and concentrated under reduced pressure. The resulting residue was purified via silica gel column chromatography (0-85% ethyl acetate in hexanes) to yield isopropyl (R)-2-(6-(1-(((benzyloxy)carbonyl)amino)ethyl)-1-((2-(trimethylsilyl)ethoxy)methyl)-1H-pyrrolo[2,3-b]pyridin-2-yl)-3-cyclopropylimidazo[1,2-a]pyridine-7-carboxylate. ES/MS: m/z 666.9 [M+H]⁺.

Step 3. Isopropyl (R)-2-(6-(1-(((benzyloxy)carbonyl)amino)ethyl)-1H-pyrrolo[2,3-b]pyridin-2-yl)-3-cyclopropylimidazo[1,2-a]pyridine-7-carboxylate I-32 was prepared following step 5 and Part B of step 6 of I-31. ES/MS: m/z 537.9 [M+H]⁺.

isopropyl (R)-2-(6-(1-(((benzyloxy)carbonyl)amino)ethyl)-1H-pyrrolo[2,3-b]pyridin-2-yl)-3-cyclopropyl-5-methoxyimidazo[1,2-a]pyridine-7-carboxylate (I-33). Prepared following a similar procedure to I-32 starting with I-25b. ¹H NMR (400 MHz, Chloroform-d) δ 11.99 (brs, 1H), 8.11 (d, J=8.0 Hz, 1H), 7.99 (s, 1H), 7.46-7.31 (m, 4H), 7.20 (d, J=8.0 Hz, 1H), 7.04 (s, 1H), 6.67 (s, 1H), 6.40 (d, J=7.8 Hz, 1H), 5.36-5.24 (m, 1H), 5.16 (d, J=12.4 Hz, 1H), 5.12 (d, J=7.6 Hs, 1H), 5.08 (d, J=12.3 Hz, 1H), 4.15 (s, 3H), 2.51-2.41 (m, 1H), 1.64 (d, J=7.0 Hz, 3H), 1.62-1.50 (m, 1H), 1.43 (d, J=6.2 Hz, 6H), 1.25-1.19 (m, 2H), 0.76-0.66 (m, 2H).

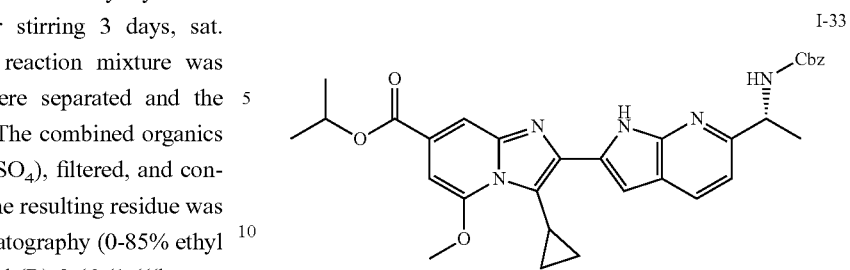

ethyl (R)-3-cyclopropyl-5-methoxy-2-(6-(1-pivalamidoethyl)-1H-pyrrolo[2,3-b]pyridin-2-yl)imidazo[1,2-a]pyridine-7-carboxylate (I-33a). Prepared following a similar procedure to I-32 starting with I-25b using titanium (IV) ethoxide in place of titanium (IV) isopropoxide in Step 1 and using pivaloyl chloride instead of carbobenzoxyoxysuccinimide in Step 2. ES/MS: m/z 504.2 [M+H]⁺.

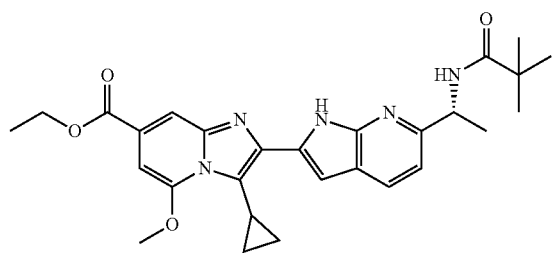

4. Representative Procedures and Example Tables

Representative Procedure 1—Preparation of N—((R)-1-(2-(7-(((1R,2R,4S)-2-amino-7-azabicyclo[2.2.1]heptane-7-carbonyl)-5-methoxy-3-methylimidazo[1,2-a]pyridin-2-yl)-1-(cyclopropylmethyl)-1H-pyrrolo[2,3-b]pyridin-6-yl)ethyl)-3-fluorobicyclo[1.1.1]pentane-1-carboxamide (Example 169)

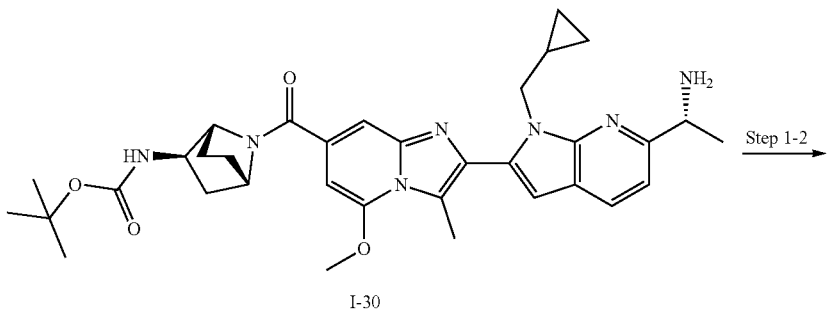

I-30

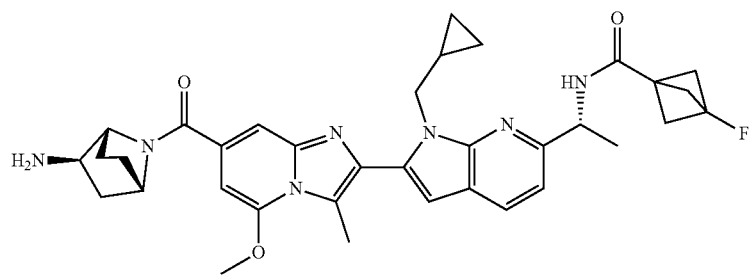

Example 169

To a mixture of tert-butyl N-[(2R)-7-[2-[6-[(1R)-1-aminoethyl]-1-(cyclopropylmethyl)pyrrolo[2,3-b]pyridin-2-yl]-5-methoxy-3-methyl-imidazo[1,2-a]pyridine-7-carbonyl]-7-azabicyclo[2.2.1]heptan-2-yl]carbamate I-30 (241 mg, 0.393 mmol) and 3-fluorobicyclo[1.1.1]pentane-1-carboxylic acid (0.0766 g, 0.589 mmol) in DMF (6 mL) was added DIPEA (0.327 mL, 1.88 mmol) and HATU (0.194 g, 0.510 mmol). After one hour, the reaction mixture was diluted with water, and the precipitated solid was filtered, washed with water, and dried in vacuo. Alternatively, an aqueous workup, extracting with ethyl acetate, could also be utilized. The filtered solid was dissolved in DCM (15 mL) and trifluoroacetic acid (3.03 mL, 39.6 mmol) was added. Alternatively, a 2:1 v:v mixture (or other relative mixture) of TFA could be utilized using TFA in excess. After one hour or once complete as judged by LCMS, the reaction mixture was concentrated under reduced pressure and the resulting residue was purified via prep HPLC to yield N—((R)-1-(2-(7-((1R,2R,4S)-2-amino-7-azabicyclo[2.2.1]heptane-7-carbonyl)-5-methoxy-3-methylimidazo[1,2-a]pyridin-2-yl)-1-(cyclopropylmethyl)-1H-pyrrolo[2,3-b]pyridin-6-yl)ethyl)-3-fluorobicyclo[1.1.1]pentane-1-carboxamide Example 169

Representative Procedure 2—Preparation of N—((R)-1-(2-(7-((1R,2R,4S)-2-amino-7-azabicyclo[2.2.1]heptane-7-carbonyl)-5-methoxy-3-methylimidazo[1,2-a]pyridin-2-yl)-1-(cyclopropylmethyl)-1H-pyrrolo[2,3-b]pyridin-6-yl)ethyl)pivalamide (Example 177)

Step 1. To a mixture of ethyl 2-[6-[(1R)-1-aminoethyl]-1-(cyclopropylmethyl)pyrrolo[2,3-b]pyridin-2-yl]-5-methoxy-3-methyl-imidazo[1,2-a]pyridine-7-carboxylate; dihydrochloride I-24 (187 mg, 0.359 mmol) in DCM (10 mL) was added triethylamine (0.305 mL, 2.17 mmol) and 2,2-dimethylpropanoyl chloride (0.060 mL, 0.49 mmol). After 30 minutes, the reaction mixture was concentrated and purified via silica gel column chromatography (0-75% ethyl acetate in hexanes) to yield ethyl (R)-2-(1-(cyclopropylmethyl)-6-(1-pivalamidoethyl)-1H-pyrrolo[2,3-b]pyridin-2-yl)-5-methoxy-3-methylimidazo[1,2-a]pyridine-7-carboxylate. ES/MS: m/z 532.1 [M+H]$^+$.

Step 2. ethyl (R)-2-(1-(cyclopropylmethyl)-6-(1-pivalamidoethyl)-1H-pyrrolo[2,3-b]pyridin-2-yl)-5-methoxy-3-methylimidazo[1,2-a]pyridine-7-carboxylate (126 mg, 0.237 mmol) was taken up in THF (2 mL), MeOH (1 mL), and water (1 mL). Lithium hydroxide monohydrate (0.0497 g, 1.18 mmol) was added and the reaction mixture stirred at rt for 5 hours (or until judged complete by LCMS). The reaction mixture was then acidified with an aqueous solution of hydrochloric acid (6 N, 0.237 mL, 1.42 mmol), concentrated under reduced pressure, and dried in vacuo to yield (R)-2-(1-(cyclopropylmethyl)-6-(1-pivalamidoethyl)-1H-pyrrolo[2,3-b]366yridine-2-yl)-5-methoxy-3-methylimidazo[1,2-a]pyridine-7-carboxylic acid I-34. ES/MS: m/z 504.1 [M+H]$^+$.

Steps 3-4. (R)-2-(1-(cyclopropylmethyl)-6-(1-pivalamidoethyl)-1H-pyrrolo[2,3-b]366yridine-2-yl)-5-methoxy-3-methylimidazo[1,2-a]pyridine-7-carboxylic acid I-34 (239 mg, 0.474 mmol) and tert-butyl N-[(2R)-7-azabicyclo[2.2.1]heptan-2-yl]carbamate (111 mg, 0.523 mmol) were taken up in DMF (6 mL). DIPEA (0.400 mL, 2.30 mmol) and HATU (234 mg, 0.616 mmol) were added. After one hour, the reaction mixture was diluted with water, and the precipitated solid was filtered, washed with water, and dried in vacuo. Alternatively, an aqueous workup followed by optional purification by silica gel chromatography could be used to provide the amide product. This resulting product was dissolved in acetonitrile (15 mL) and a solution of hydrogen chloride in dioxane (4 M, 2.40 mL, 9.60 mmol) was added. After 30 minutes or once complete as determined by LCMS, the reaction mixture was concentrated under reduced pressure and the resulting residue was purified via prep HPLC to yield N—((R)-1-(2-(7-((1R,2R,4S)-2-amino-7-azabicyclo[2.2.1]heptane-7-carbonyl)-5-methoxy-3-methylimidazo[1,2-a]pyridin-2-yl)-1-(cyclopropylmethyl)-1H-pyrrolo[2,3-b]pyridin-6-yl)ethyl)pivalamide Example 177. Alternatively, a TFA-mediated deprotection described in the preparation of Example 169 could be used to provide the fully deprotected crude product, which could then be purified by preparative HPLC as described above.

Representative Procedure 2b—Preparation of N—((R)-1-(2-(7-((1S,4R,5R)-4-amino-2-azabicyclo[3.2.1]octane-2-carbonyl)-5-methoxy-3-methylimidazo[1,2-a]pyridin-2-yl)-1-(cyclopropylmethyl)-1H-pyrrolo[2,3-b]pyridin-6-yl)ethyl)-3-fluorobicyclo[1.1.1]pentane-1-carboxamide (Example 189)

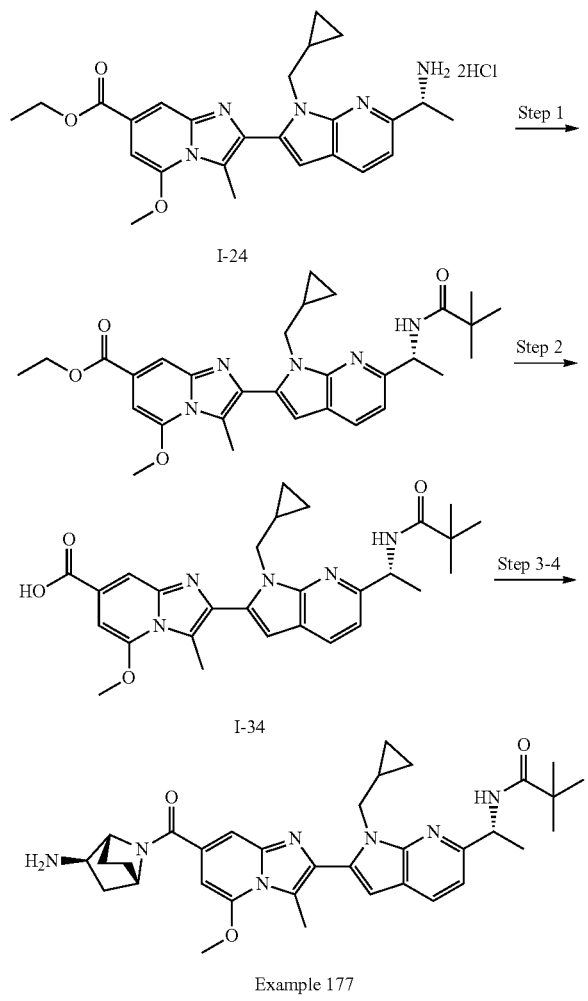

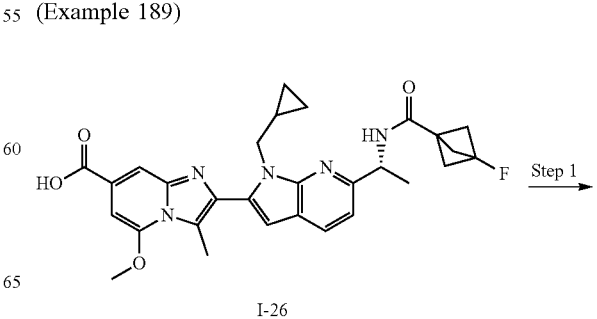

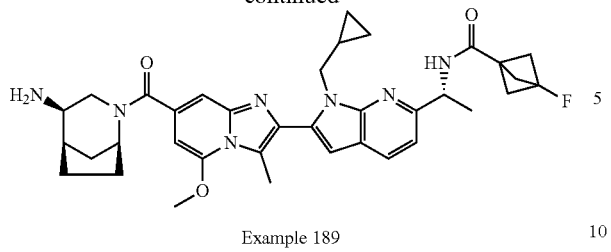

Example 189

Step 1. To a mixture of (R)-2-(1-(cyclopropylmethyl)-6-(1-(3-fluorobicyclo[1.1.1]pentane-1-carboxamido)ethyl)-1H-pyrrolo[2,3-b]pyridin-2-yl)-5-methoxy-3-methylimidazo[1,2-a]pyridine-7-carboxylic acid I-26 (45 mg, 0.085 mmol) and tert-butyl N-[(1S,4R,5R)-2-azabicyclo[3.2.1]octan-4-yl]carbamate (19.2 mg, 0.085 mmol) A11 in DCM (2 mL) was added DIPEA (0.0590 mL, 0.339 mmol) and HATU (0.0483 g, 0. 127 mmol). After 10 minutes, trifluoroacetic acid (0.648 mL, 8.47 mmol) was added, and the reaction mixture was stirred for one hour. The reaction mixture was concentrated under reduced pressure and purified via prep HPLC to yield N—((R)-1-(2-(7-(((1S,4R,5R)-4-amino-2-azabicyclo[3.2.1]octane-2-carbonyl)-5-methoxy-3-methylimidazo[1,2-a]pyridin-2-yl)-1-(cyclopropylmethyl)-1H-pyrrolo[2,3-b]pyridin-6-yl)ethyl)-3-fluorobicyclo[1.1.1]pentane-1-carboxamide Example 189.

The following examples as shown in Table 1 were synthesized using representative Procedure 1, 2, or 2b, variants thereof, or were prepared according to the general schemes shown in Part I.

| Ex | ES/MS m/z [M + H]+. |
|---|---|
| 1 | 623.3 |
| 2 | 626.3 |
| 3 | 626.3 |
| 4 | 654.50 |
| 5 | 654.46 |
| 6 | 628.46 |
| 7 | 638.34 |
| 8 | 658.37 |
| 9 | 646.34 |
| 10 | 686.3 |
| 11 | 668.32 |
| 12 | 682.39 |
| 13 | 682.35 |
| 14 | 712.44 |
| 15 | 636.32 |
| 16 | 654.34 |
| 17 | 648.35 |
| 18 | 720.75 |
| 19 | 612.20 |
| 20 | 626.3 |
| 21 | 626.3 |
| 22 | 670.37 |
| 23 | 666.35 |
| 24 | 612.3 |
| 25 | 612.3 |
| 26 | 652.34 |
| 27 | 682.31 |
| 28 | 712.2 |
| 29 | 640.37 |
| 30 | 649.3 |
| 31 | 654.44 |
| 32 | 640.34 |
| 33 | 626.37 |
| 34 | 600.36 |
| 35 | 643.21 |
| 36 | 632.38 |
| 37 | 628.4 |
| 38 | 628.4 |
| 39 | 628.44 |
| 40 | 600.41 |
| 41 | 626.38 |
| 42 | 612.38 |
| 43 | 636.41 |
| 44 | 664.34 |
| 45 | 680.35 |
| 46 | 667.3 |
| 47 | 633.3 |
| 48 | 653.2 |
| 49 | 633.3 |
| 50 | 669.3 |
| 51 | 653.3 |
| 52 | 637.3 |
| 53 | 644.32 |
| 54 | 626.32 |
| 55 | 622.34 |
| 56 | 654.32 |
| 57 | 606.30 |
| 58 | 623.23 |
| 59 | 632.34 |
| 60 | 628.42 |
| 61 | 632.30 |
| 62 | 663.28 |
| 63 | 668.36 |
| 64 | 582.32 |
| 65 | 638.26 |
| 66 | 660.34 |
| 67 | 694.28 |
| 68 | 626.31 |
| 69 | 608.31 |
| 70 | 624.29 |
| 71 | 610.31 |
| 72 | 625.3 |
| 73 | 609.3 |
| 74 | 648.4 |
| 75 | 656.3 |
| 76 | 656.3 |
| 77 | 636.4 |
| 78 | 582.26 |
| 79 | 649.3 |
| 80 | 623.3 |
| 81 | 658.3 |
| 82 | 664.4 |
| 83 | 620.3 |
| 84 | 646.36 |
| 85 | 632.34 |
| 86 | 640.3 |
| 87 | 612.4 |
| 88 | 626.3 |
| 89 | 584.25 |
| 90 | 584.31 |
| 91 | 586.3 |
| 92 | 626.4 |
| 93 | 628.4 |
| 94 |  |
| 95 | 612.4 |
| 96 | 647.19 |
| 97 | 598.3 |
| 98 | 652.33 |
| 99 | 606.33 |
| 100 | 618.31 |
| 101 | 596.28 |
| 102 | 632.34 |
| 103 | 646.26 |
| 104 | 710.24 |
| 105 | 609.3 |
| 106 | 648.3 |
| 107 | 658.3 |
| 108 | 622.3 |
| 109 | 638.36 |
| 110 | 654.2 |
| 111 | 664.33 |
| 112 | 650.33 |
| 113 | 523.30 |

501
-continued
| Ex | ES/MS m/z [M + H]+. |
|---|---|
| 114 | 636.30 |
| 115 | 622.30 |
| 116 | 622.3 |
| 117 | 609.3 |
| 118 | 620.3 |
| 119 | 619.3 |
| 120 | 619.3 |
| 121 | 632.3 |
| 122 | 643.3 |
| 123 | 643.3 |
| 124 | 654.39 |
| 125 | 614.35 |
| 126 | 600.3 |
| 127 | 588.3 |
| 128 | 612.3 |
| 129 | 600.4 |
| 130 | 618.31 |
| 131 | 618.33 |
| 132 | 624.32 |
| 133 | 642.36 |
| 134 | 614.4 |
| 135 | 640.39 |
| 136 | 600.3 |
| 137 | 632.35 |
| 138 | 680.29 |
| 139 | 647.34 |
| 140 | 659.39 |
| 141 | 632.32 |
| 142 | 644.33 |
| 143 | 612.44 |
| 144 | 652.35 |
| 145 | 640.33 |
| 146 | 627.25 |
| 147 | 684.3 |
| 148 | 696.25 |
| 149 | 639.3 |
| 150 | 626.42 |
| 151 | 596.29 |
| 152 | 642.35 |
| 153 | 648.28 |
| 154 | 634.31 |
| 155 | 628.17 |
502
-continued
| Ex | ES/MS m/z [M + H]+. |
|---|---|
| 156 | 753.27 |
| 157 | 676.31 |
| 158 | 633.3 |
| 159 | 666.31 |
| 160 | 608.27 |
| 161 | 642.24 |
| 162 | 610.25 |
| 163 | 614.19 |
| 164 | 575.28 |
| 165 | 607.31 |
| 166 | 612.32 |
| 167 | 612.31 |
| 168 | 612.20 |
| 169 | 626.26 |
| 170 | 612.32 |
| 171 | 652.34 |
| 172 | 614.27 |
| 173 | 614.29 |
| 174 | 598.34 |
| 175 | 619.22 |
| 176 | 618.26 |
| 177 | 598.32 |
| 178 | 582.25 |
| 179 | 556.22 |
| 180 | 654.37 |
| 181 | 654.39 |
| 182 | 670.37 |
| 183 | 670.37 |
| 184 | 565.30 |
| 185 | 632.30 |
| 186 | 620.39 |
| 187 | 558.21 |
| 188 | 715.40 |
| 189 | 640.23 |
| 190 | 666.19 |
| 632 | 673.20 |
Representative Procedure 3—Preparation of N-((2-(7-((R)-3-aminopiperidine-1-carbonyl)-5-methoxy-3-methyl-imidazo[1,2-a]pyridin-2-yl)-1-(cyclopropylmethyl)-1H-pyrrolo[2,3-b]pyridin-6-yl)(cyclopropyl)methyl)acetamide (Example 194)
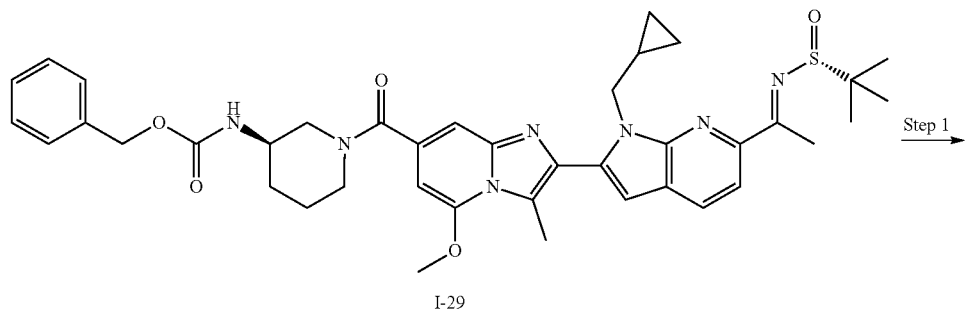
I-29
Step 1
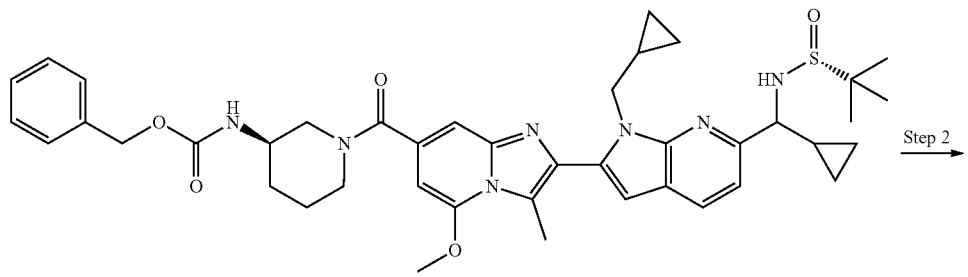
Step 2

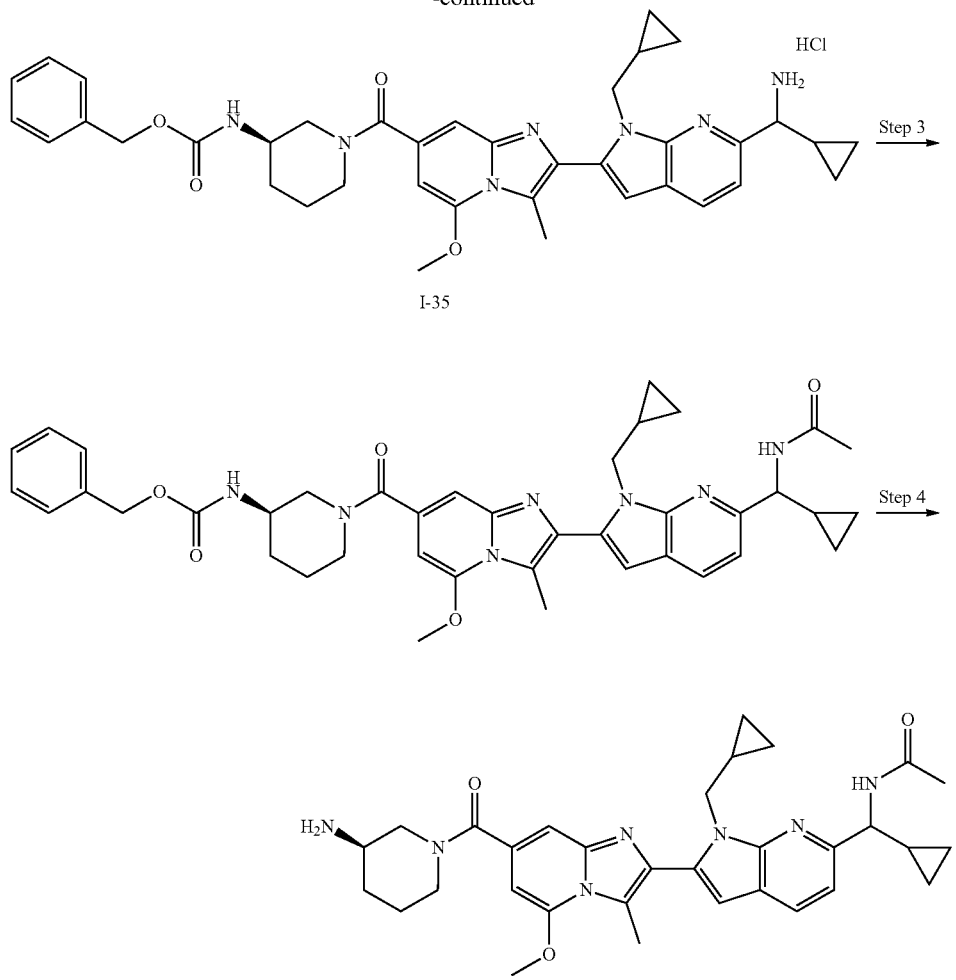

Example 194

Step 1. To a cooled mixture of benzyl ((R)-1-(2-(64(E)-(((R)-tert-butylsulfinyl)imino)methyl)-1-(cyclopropylmethyl)-1H-pyrrolo[2,3-b]pyridin-2-yl)-5-methoxy-3-methylimidazo[1,2-a]pyridine-7-carbonyl)piperidin-3-yl)carbamate I-29 (156 mg, 0.216 mmol) in THF (4 mL) at −40° C. was added a solution of cyclopropylmagnesium bromide (1.00 mol/L, 0.860 mL, 0.860 mmol) in 2-MeTHF. After 3 hours, additional cyclopropylmagnesium bromide (1.00 mol/L, 0.860 mL, 0.860 mmol) in 2-MeTHF was added. After one hour, the reaction mixture was quenched with sat. NH₄Cl(aq) and diluted with ethyl acetate. The layers were separated and the aqueous was extracted with ethyl acetate. The combined organics were washed with brine, dried (MgSO₄), filtered, and concentrated under reduced pressure to yield benzyl ((3R)-1-(2-(6-(4(R)-tert-butylsulfinyl)amino)(cyclopropyl)methyl)-1-(cyclopropylmethyl)-1H-pyrrolo[2,3-b]pyridin-2-yl)-5-methoxy-3-methylimidazo[1,2-a]pyridine-7-carbonyl)piperidin-3-yl)carbamate as a mixture of diastereomers, which was used without purification. ES/MS: m/z 766.16 [M+H]⁺.

Step 2. To a solution of benzyl ((3R)-1-(2-(6-4((R)-tert-butylsulfinyl)amino)(cyclopropyl)methyl)-1-(cyclopropylmethyl)-1H-pyrrolo[2,3-b]pyridin-2-yl)-5-methoxy-3-methylimidazo[1,2-a]pyridine-7-carbonyl)piperidin-3-yl)carbamate (159 mg, 0.208 mmol) in DCM (5 mL) was added a solution of hydrogen chloride (4.00 mol/L, 0.526 mL, 2.10 mmol) in dioxane. After 15 minutes, the reaction mixture was concentrated under reduced pressure to yield benzyl ((3R)-1-(2-(6-(amino(cyclopropyl)methyl)-1-(cyclopropylmethyl)-1H-pyrrolo[2,3-b]pyridin-2-yl)-5-methoxy-3-methylimidazo[1,2-a]pyridine-7-carbonyl)piperidin-3-yl)carbamate I-35, hydrochloride, as a mixture of diastereomers, which was used without purification. ES/MS: m/z 662.27.

Steps 3-4. To a mixture of benzyl ((3R)-1-(2-(6-(amino(cyclopropyl)methyl)-1-(cyclopropylmethyl)-1H-pyrrolo[2,3-b]pyridin-2-yl)-5-methoxy-3-methylimidazo[1,2-a]pyridine-7-carbonyl)piperidin-3-yl)carbamate hydrochloride I-35 (145 mg, 0.208 mmol) in DCM (15 mL) was added triethylamine (0.540 mL, 3.85 mmol) and acetic anhydride (0.100 mL, 1.06 mmol). After one hour, methylamine solution (40% in MeOH) (0.300 mL, 2.98 mmol) was added and the reaction mixture was diluted with ethyl acetate and water. The layers were separated and the aqueous was extracted with ethyl acetate. The combined organics were washed with brine, dried (MgSO₄), filtered, and concentrated under reduced pressure. The resulting residue was dissolved in THF (4 mL) and MeOH (4 mL). Pd/C, (10.0%, 110 mg, 0.104 mmol) was added and the reaction mixture was hydrogenated under an atmosphere of hydrogen for 6.5 hours. The reaction mixture was diluted with THF and filtered over celite, washing with THF. The filtrate was concentrated under reduced pressure and the resulting residue was purified via prep HPLC to yield N-((2-(7-((R)-3-aminopiperidine-1-carbonyl)-5-methoxy-3-methylimidazo[1,2-a]pyridin-2-yl)-1-(cyclopropylmethyl)-1H-pyrrolo[2,3-b]pyridin-6-yl)(cyclopropyl)methyl)acetamide Example 194.

The following examples as shown in Table 1 were synthesized utilizing a variation of procedure 3 with the appropriate intermediates:

| Ex | ES/MS m/z [M + H]+. |
|---|---|
| 191 | 661.29 |
| 192 | 652.35 |
| 193 | 558.22 |
| 194 | 570.23 |
| 195 | 572.27 |

Representative Procedure 4—Preparation of N—((R)-1-(2-(7-((1R,2R,4S)-2-amino-7-azabicyclo[2.2.1]heptane-7-carbonyl)-5-methoxy-3-methylimidazo[1,2-a]pyridin-2-yl)-1-(cyclopropylmethyl)-1H-pyrrolo[2,3-b]pyridin-6-yl)ethyl)pyrrolidine-1-carboxamide (Example 251)

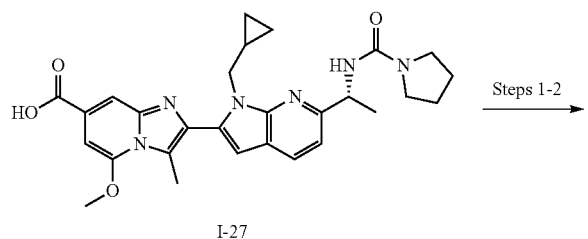

I-27

Steps 1-2 →

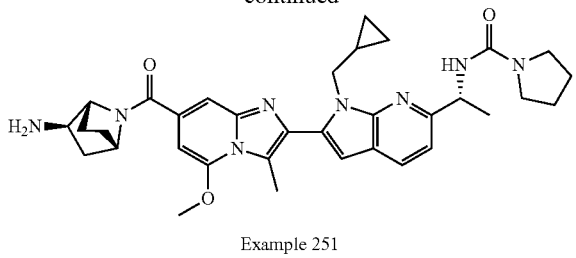

Example 251

To a mixture of 2-[1-(cyclopropylmethyl)-6-[(1R)-1-(pyrrolidine-1-carbonylamino)ethyl]pyrrolo[2,3-b]pyridin-2-yl]-5-methoxy-3-methyl-imidazo[1,2-a]pyridine-7-carboxylic acid I-27 (75 mg, 0.146 mmol) and tert-butyl N-[(2R)-7-azabicyclo[2.2.1]heptan-2-yl]carbamate A2 (40 mg, 0.188 mmol) in DMF (4 mL) was added DIPEA (0.102 mL, 0.584 mmol) and HATU (67 mg, 0.175 mmol). Once complete, the reaction mixture was diluted with sat. NaHCO3(aq), and the precipitated solid was filtered, washed with water, and dried in vacuo. The filtered solid was dissolved in DCM (4 mL) and Trifluoroacetic acid (2 mL, 26.4 mmol) was added. After one hour, the reaction mixture was concentrated under reduced pressure and the resulting residue was purified via prep HPLC to yield N—((R)-1-(2-(7-((1R,2R,4S)-2-amino-7-azabicyclo[2.2.1]heptane-7-carbonyl)-5-methoxy-3-methylimidazo[1,2-a]pyridin-2-yl)-1-(cyclopropylmethyl)-1H-pyrrolo[2,3-b]pyridin-6-yl)ethyl)pyrrolidine-1-carboxamide Example 251.

Representative Procedure 5—Preparation of N—((R)-1-(2-(7-((1R,2R,4S)-2-amino-7-azabicyclo[2.2.1]heptane-7-carbonyl)-5-methoxy-3-methylimidazo[1,2-a]pyridin-2-yl)-1-(cyclopropylmethyl)-1H-pyrrolo[2,3-b]pyridin-6-yl)ethyl)-3,3-difluoroazetidine-1-carboxamide Example 232

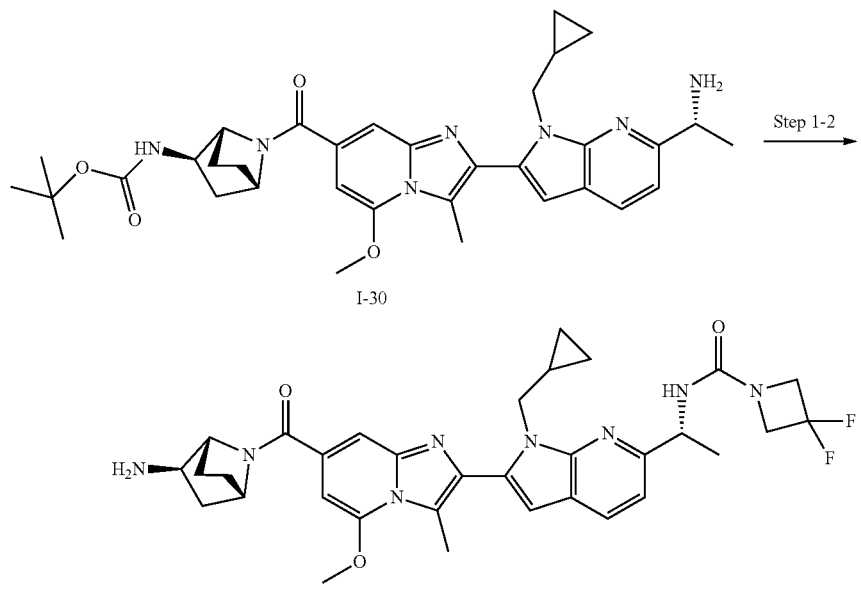

I-30

Step 1-2 →

Example 232

To a mixture of tert-butyl N-[(2R)-7-[2-[6-[(1R)-1-aminoethyl]-1-(cyclopropylmethyl)pyrrolo[2,3-b]pyridin-2-yl]-5-methoxy-3-methyl-imidazo[1,2-a]pyridine-7-carbonyl]-7-azabicyclo[2.2.1]heptan-2-yl]carbamate I-30 (33 mg, 0.045 mmol) in DMF (2 mL) was added CDI (11 mg, 0.068 mmol) and triethylamine (0.064 mL, 0.453 mmol). The mixture stirred at rt for one hour. To this mixture was added 3,3-difluoroazetidine hydrochloride (23.5 mg, 0.181 mmol) and the reaction mixture was heated at 70° C. for 2 hours. The reaction mixture was diluted with water, and the precipitated solid was filtered, washed with water, and dried in vacuo. Alternatively, an aqueous workup, extracting with ethyl acetate could also be utilized. The filtered solid was dissolved in DCM (3.5 mL) and trifluoroacetic acid (0.350 mL, 4.57 mmol) was added. After one hour, the reaction mixture was concentrated under reduced pressure and the resulting residue was purified via prep HPLC to yield N—((R)-1-(2-(7-(((1R,2R,4S)-2-amino-7-azabicyclo[2.2.1]heptane-7-carbonyl)-5-methoxy-3-methylimidazo[1,2-a]pyridin-2-yl)-1-(cyclopropylmethyl)-1H-pyrrolo[2,3-b]pyridin-6-yl)ethyl)-3,3-difluoroazetidine-1-carboxamide Example 232.

The following examples as shown in Table 1 were synthesized utilizing a variation of procedures 4 or 5; for carbamates the appropriate chloroformate reagents were used.

| Ex | ES/MS m/z [M + H]+. |
|---|---|
| 196 | 639.27 |
| 197 | 681.27 |
| 198 | 669.31 |
| 199 | 695.34 |
| 200 | 695.31 |
| 201 | 641.29 |
| 202 | 681.3 |
| 203 | 669.23 |
| 204 | 637.18 |
| 205 | 663.28 |
| 206 | 647.32 |
| 207 | 661.12 |
| 208 | 683.33 |
| 209 | 659.34 |
| 210 | 641.28 |
| 211 | 639.36 |
| 212 | 661.27 |
| 213 | 683.33 |
| 214 | 641.36 |
| 215 | 655.23 |
| 216 | 655.28 |
| 217 | 688.18 |
| 218 | 688.22 |
| 219 | 692.25 |
| 220 | 678.22 |
| 221 | 676.23 |
| 222 | 662.22 |
| 223 | 648.34 |
| 224 | 649.13 |
| 225 | 640.24 |
| 226 | 648.2 |
| 227 | 613.24 |
| 228 | 655.45 |
| 229 | 613.13 |
| 230 | 655.16 |
| 231 | 627.26 |
| 232 | 633.21 |
| 233 | 647.24 |
| 234 | 622.32 |
| 235 | 640.12 |
| 236 | 641.22 |
| 237 | 641.1 |
| 238 | 661.25 |
| 239 | 633.26 |
| 240 | 661.2 |
| 241 | 627.12 |
| 242 | 674.23 |
| 243 | 647.22 |
| 244 | 613.18 |
| 245 | 647.23 |
| 246 | 623.21 |
| 247 | 597.16 |
| 248 | 629.19 |
| 249 | 637.23 |
| 250 | 611.24 |
| 251 | 611.22 |
| 252 | 599.2 |
| 253 | 573.18 |
| 254 | 600.34 |
| 255 | 614.24 |
| 256 | 616.2 |
| 257 | 602.21 |
| 258 | 560.24 |

Representative Procedure 6—Preparation of ((1R,2R,4S)-2-amino-7-azabicyclo[2.2.1]heptan-7-yl)(2-(1-(cyclopropylmethyl)-6-((R)-1-(pyrimidin-2-ylamino)ethyl)-1H-pyrrolo[2,3-b]pyridin-2-yl)-5-methoxy-3-methylimidazo[1,2-a]pyridin-7-yl)methanone (Example 265)

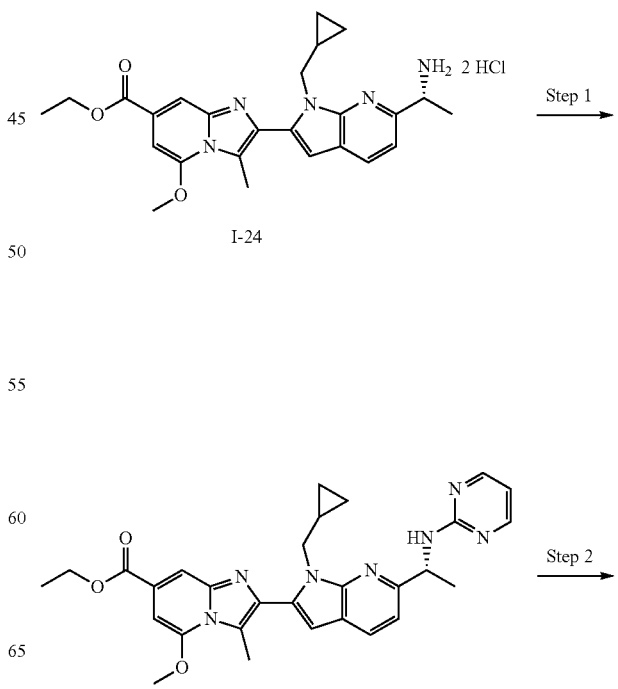

-continued

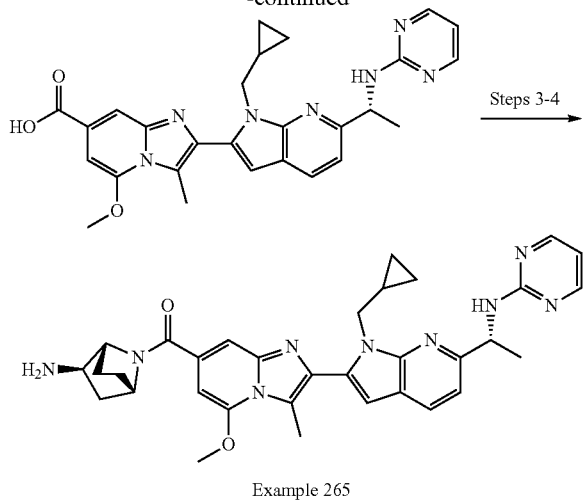

Example 265

Step 1. To a mixture of ethyl 2-[6-[(1R)-1-aminoethyl]-1-(cyclopropylmethyl)pyrrolo[2,3-b]pyridin-2-yl]-5-methoxy-3-methyl-imidazo[1,2-a]pyridine-7-carboxylate; dihydrochloride I-24 (75 mg, 0.144 mmol) and 2-chloropyrimidine (25.0 mg, 0.216 mmol) in NMP was added DIPEA (0.128 mL, 0.721 mmol). The reaction mixture was heated at 75° C. After 26 hours, the reaction mixture was diluted with water and ethyl acetate. The layers were separated and the aqueous was extracted with ethyl acetate. The combined organics were washed with brine, dried (Na$_2$SO$_4$), filtered, and concentrated under reduced pressure to yield ethyl 2-[1-(cyclopropylmethyl)-6-[(1R)-1-(pyrimidin-2-ylamino)ethyl]pyrrolo[2,3-b]pyridin-2-yl]-5-methoxy-3-methyl-imidazo[1,2-a]pyridine-7-carboxylate, which was used without further purification. ES/MS: m/z 498.0 [M+H]$^+$.

Step 2. Following step 2 of Representative Procedure 2, 2-[1-(cyclopropylmethyl)-6-[(1R)-1-(pyrimidin-2-ylamino)ethyl]pyrrolo[2,3-b]pyridin-2-yl]-5-methoxy-3-methyl-imidazo[1,2-a]pyridine-7-carboxylic acid was synthesized ES/MS: m/z 513.2 [M+H]$^+$.

Steps 3-4. Following steps 3-4 of Representative Procedure 2, 41R,2R,4S)-2-amino-7-azabicyclo[2.2.1]heptan-7-yl)(2-(1-(cyclopropylmethyl)-6-((R)-1-(pyrimidin-2-ylamino)ethyl)-1H-pyrrolo[2,3-b]pyridin-2-yl)-5-methoxy-3-methylimidazo[1,2-a]pyridin-7-yl)methanone Example 265 was synthesized.

Representative Procedure 7—Preparation of ((1R, 2R,4S)-2-amino-7-azabicyclo[2.2.1]heptan-7-yl)(2-(1-(cyclopropylmethyl)-6-((R)-1-((5-fluoropyridin-2-yl)amino)ethyl)-1H-pyrrolo[2,3-b]pyridin-2-yl)-5-methoxy-3-methylimidazo[1,2-a]pyridin-7-yl)methanone (Example 259)

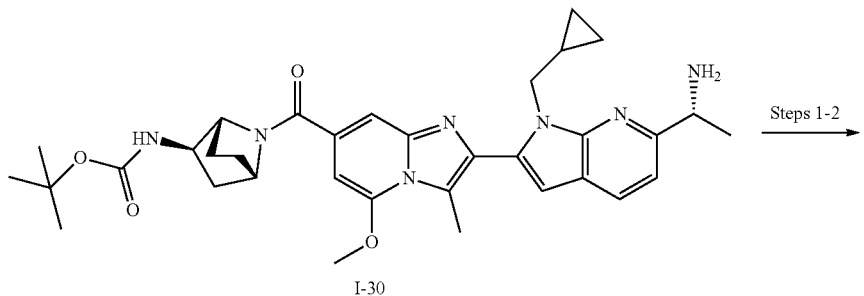

I-30

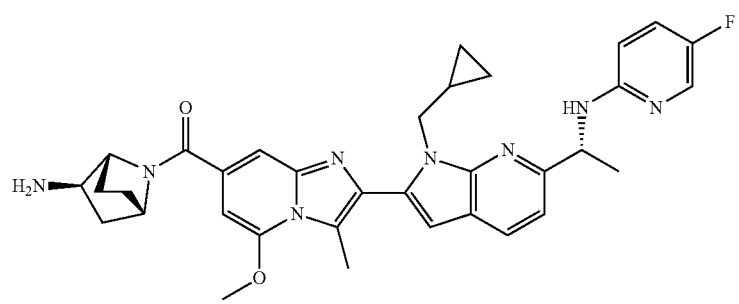

Example 259

Steps 1-2. A mixture of tert-butyl N-[(2R)-7-[2-[6-[(1R)-1-aminoethyl]-1-(cyclopropylmethyl)pyrrolo[2,3-b]pyridin-2-yl]-5-methoxy-3-methyl-imidazo[1,2-a]pyridine-7-carbonyl]-7-azabicyclo[2.2.1]heptan-2-yl]carbamate I-30 (30 mg, 0.049 mmol), 2-bromo-5-fluoro-pyridine (0.0215 g, 0.122 mmol), Pd-Xphos G3 (3.88 mg, 0.00489 mmol), and KOtBu (0.0165 g, 0.147 mmol) were taken up in dioxane (1 mL). The reaction mixture was heated to 100° C. and was stirred for 3 hours and was then diluted with water and ethyl acetate. The layers were separated and the aqueous was extracted with ethyl acetate. The combined organics were washed with brine, dried (Na$_2$SO$_4$), filtered, and concentrated under reduced pressure. The resulting residue was dissolved in DCM (2 mL) and TFA (1.00 mL, 0.0131 mol) was added. After stirring for twenty minutes, the reaction was concentrated under reduced pressure and the resulting residue was purified via prep HPLC to yield ((1R,2R,4S)-2-amino-7-azabicyclo[2.2.1]heptan-7-yl)(2-(1-(cyclopropylmethyl)-6-4R)-1-((5-fluoropyridin-2-yl)amino)ethyl)-1H-pyrrolo[2,3-b]pyridin-2-yl)-5-methoxy-3-methylimidazo[1,2-a]pyridin-7-yl)methanone Example 259.

The following examples as shown in Table 1 were synthesized utilizing a variation of procedure 6 and 7 with the appropriate intermediates:

| Ex | ES/MS m/z [M + H]$^+$ |
|---|---|
| 259 | 609.08 |
| 260 | 636.93 |
| 261 | 591.00 |
| 262 | 626.18 |
| 263 | 592.23 |
| 264 | 610.3 |
| 265 | 592.22 |
| 266 | 592.28 |
| 267 | 584.22 |
| 268 | 580.18 |

Representative Procedure 8—3-((R)-1-(2-(7-01R, 2R,4S)-2-amino-7-azabicyclo[2.2.1]heptane-7-carbonyl)-5-methoxy-3-methylimidazo[1,2-a]pyridin-2-yl)-1-(cyclopropylmethyl)-1H-pyrrolo[2,3-b]pyridin-6-yl)ethyl)oxazolidin-2-one (Example 275)

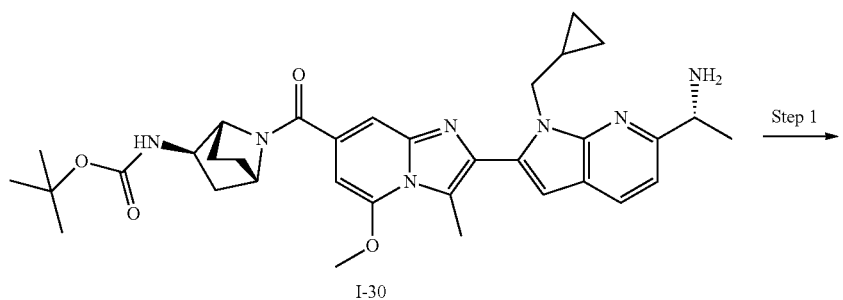

I-30

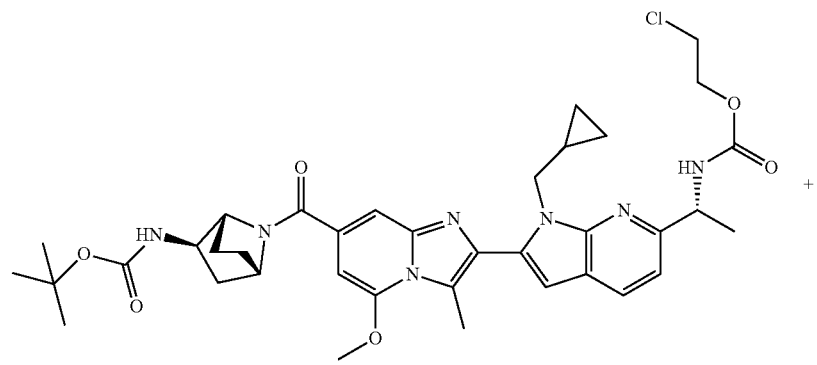

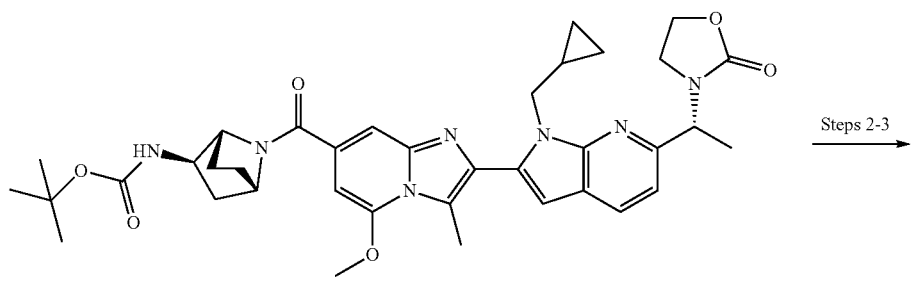

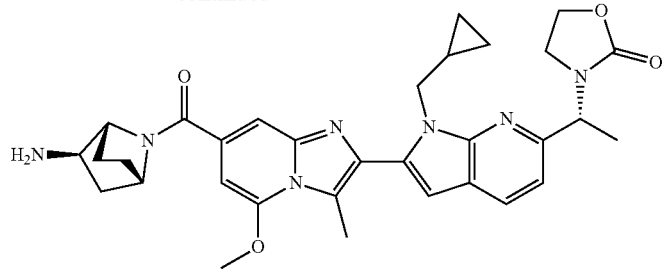

Example 275

Step 1. To a mixture of 3-((R)-1-(2-(7-((1R,2R,4S)-2-amino-7-azabicyclo[2.2.1]heptane-7-carbonyl)-5-methoxy-3-methylimidazo[1,2-a]pyridin-2-yl)-1-(cyclopropylmethyl)-1H-pyrrolo[2,3-b]pyridin-6-yl)ethyl)oxazolidin-2-one I-30 (30 mg, 0.049 mmol) and 2-chloroethyl chloroformate (6.1 μL, 0.059 mmol) in THF at rt was added DIPEA (0.043 mL, 0.244 mmol). After 30 minutes, the reaction mixture was diluted with water and ethyl acetate. The layers were separated and the aqueous was extracted with ethyl acetate. The combined organics were washed with brine, dried ($Na_2SO_4$), filtered, and concentrated under reduced pressure to yield a mixture of tert-butyl ((1R,2R,4S)-7-(2-(6-((R)-1-(((2-chloroethoxy)carbonyl)amino)ethyl)-1-(cyclopropylmethyl)-1H-pyrrolo[2,3-b]pyridin-2-yl)-5-methoxy-3-methylimidazo[1,2-a]pyridine-7-carbonyl)-7-azabicyclo[2.2.1]heptan-2-yl)carbamate and tert-butyl ((1R,2R,4S)-7-(2-(1-(cyclopropylmethyl)-6-4R)-1-(2-oxooxazolidin-3-yl)ethyl)-1H-pyrrolo[2,3-b]pyridin-2-yl)-5-methoxy-3-methylimidazo[1,2-a]pyridine-7-carbonyl)-7-azabicyclo[2.2.1]heptan-2-yl)carbamate, which was used without purification below, assuming complete recovery ES/MS: m/z 682.39 $[M+H]^+$.

Steps 2-3. To a mixture of the crude products above in THF (2 mL) at 0° C. was added sodium hydride (60.0% in mineral oil, 3.7 mg, 0.092 mmol). After 30 minutes, the reaction mixture was quenched with cold sat. $NH_4Cl$ (aq) and diluted with ethyl acetate. The layers were separated, and the organics dried, filtered, and concentrated under reduced pressure. The resulting residue was dissolved in 20% TFA in DCM and after one hour, concentrated under reduced pressure. The resulting residue was purified via prep HPLC to yield 34(R)-1-(2-(7-((1R,2R,4S)-2-amino-7-azabicyclo[2.2.1]heptane-7-carbonyl)-5-methoxy-3-methylimidazo[1,2-a]pyridin-2-yl)-1-(cyclopropylmethyl)-1H-pyrrolo[2,3-b]pyridin-6-yl)ethyl)oxazolidin-2-one Example 275.

The following examples as shown in Table 1 were synthesized utilizing a variation of procedure 8 with the appropriate intermediates, or were prepared according to General Schemes depicted in Part I.

| Ex | ES/MS m/z $[M + H]^+$ |
|---|---|
| 269 | 596.28 |
| 270 | 597.28 |
| 271 | 596.24 |
| 272 | 568.09 |
| 273 | 683.2 |
| 274 | 598.32 |
| 275 | 584.34 |
| 276 | 582.26 |
| 277 | 583.95 |

-continued

| Ex | ES/MS m/z $[M + H]^+$ |
|---|---|
| 278 | 572.22 |
| 279 | 570.24 |

Representative Procedure 9—Preparation of N-(2-(7-((1R,2R,4S)-2-amino-7-azabicyclo[2.2.1]heptane-7-carbonyl)-5-methoxy-3-methylimidazo[1,2-a]pyridin-2-yl)-1-(cyclopropylmethyl)-1H-pyrrolo[2,3-b]pyridin-6-yl)-N-(difluoromethyl)methanesulfonamide Example 389

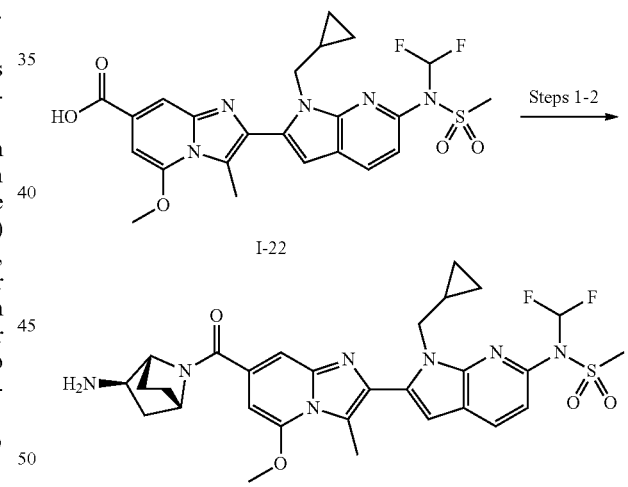

I-22

Example 389

Steps 1-2. 2-[1-(cyclopropylmethyl)-6-[difluoromethyl(methylsulfonyl)amino]pyrrolo[2,3-b]pyridin-2-yl]-5-methoxy-3-methyl-imidazo[1,2-a]pyridine-7-carboxylic acid I-22 (31.5 mg, 0.061 mmol) and tert-butyl N-[(2R)-7-azabicyclo[2.2.1]heptan-2-yl]carbamate A2 (15 mg, 0.068 mmol) was taken up in DMF (6 mL). DIPEA (0.05 mL, 0.287 mmol) and HATU (40.3 mg, 0.106 mmol) were added. After one hour, the reaction mixture was diluted with ethyl acetate and $NH_4Cl$ (aq). The layers were separated and the aqueous extracted with ethyl acetate. The combined organics were washed with sat. $NaHCO_3$(aq), brine, dried, filtered, and concentrated under reduced pressure. The resulting residue was dissolved in acetonitrile (3 mL) and a solution of hydrogen chloride in dioxanes (4N, 1.5 mL, 6.0 mmol) was added. After 30 minutes, the reaction mixture was concentrated under reduced pressure and the resulting residue was purified via prep HPLC to yield, N-(2-(7-(((1R,2R,4S)-2-amino-7-azabicyclo[2.2.1]heptane-7-carbonyl)-5-methoxy-3-methylimidazo[1,2-a]pyridin-2-yl)-1-(cyclopropylmethyl)-1H-pyrrolo[2,3-b]pyridin-6-yl)-N-(difluoromethyl)methanesulfonamide Example 389 was synthesized.

The following examples as shown in Table 1 were synthesized utilizing a variation of procedure 9 with the appropriate intermediates:

| Ex | ES/MS m/z [M + H]+ |
|---|---|
| 280 | 606.2 |
| 281 | 616.24 |
| 282 | 616.22 |
| 283 | 614.3 |
| 284 | 614.3 |
| 285 | 632.20 |
| 286 | 614.3 |
| 287 | 614.2 |
| 288 | 616.30 |
| 289 | 606.2 |
| 290 | 606.2 |
| 291 | 606.2 |
| 292 | 618.20 |
| 293 | 618.20 |
| 294 | 616.29 |
| 295 | 616.30 |
| 296 | 616.28 |
| 297 | 736.29 |
| 298 | 628.21 |
| 299 | 628.25 |
| 300 | 602.25 |
| 301 | 602.20 |
| 302 | 616.30 |
| 303 | 602.21 |
| 304 | 602.23 |
| 305 | 616.29 |
| 306 | 620.20 |
| 307 | 620.20 |
| 308 | 620.20 |
| 309 | 620.20 |
| 310 | 668.41 |
| 311 | 644.3 |
| 312 | 614.21 |
| 313 | 616.30 |
| 314 | 616.30 |
| 315 | 616.30 |
| 316 | 616.29 |
| 317 | 616.30 |
| 318 | 600.20 |
| 319 | 600.20 |
| 320 | 630.20 |
| 321 | 628.28 |
| 322 | 628.27 |
| 323 | 602.27 |
| 324 | 602.20 |
| 325 | 628.21 |
| 326 | 628.27 |
| 327 | 628.24 |
| 328 | 616.26 |
| 329 | 628.27 |
| 330 | 628.27 |
| 331 | 628.23 |
| 332 | 628.24 |
| 333 | 642.30 |
| 334 | 642.30 |
| 335 | 632.29 |
| 336 | 628.20 |
| 337 | 628.29 |
| 338 | 630.21 |
| 339 | 614.29 |
| 340 | 646.30 |
| 341 | 602.20 |
| 342 | 642.30 |
| 343 | 628.30 |
| 344 | 590.20 |
| 345 | 590.21 |
| 346 | 642.3 |
| 347 | 642.3 |
| 348 | 618.20 |
| 349 | 628.27 |
| 350 | 614.2 |
| 351 | 628.3 |
| 352 | 628.2 |
| 353 | 620.23 |
| 354 | 602.2 |
| 355 | 617.02 |
| 356 | 602.2 |
| 357 | 602.2 |
| 358 | 628.23 |
| 359 | 658.35 |
| 360 | 659.31 |
| 361 | 632.21 |
| 362 | 614.23 |
| 363 | 614.23 |
| 364 | 656.22 |
| 365 | 614.23 |
| 366 | 555.28 |
| 367 | 600.22 |
| 368 | 628.25 |
| 369 | 628.25 |
| 370 | 642.21 |
| 371 | 658.26 |
| 372 | 644.26 |
| 373 | 628.1 |
| 374 | 614.3 |
| 375 | 628.24 |
| 376 | 628.25 |
| 377 | 628.25 |
| 378 | 630.22 |
| 379 | 614.21 |
| 380 | 614.1 |
| 381 | 628.25 |
| 382 | 654.25 |
| 383 | 644.21 |
| 384 | 670.27 |
| 385 | 640.24 |
| 386 | 610.22 |
| 387 | 618.21 |
| 388 | 602.27 |
| 389 | 614.24 |
| 390 | 668.24 |
| 391 | 628.20 |
| 392 | 616.21 |
| 393 | 584.18 |
| 394 | 616.19 |
| 395 | 614.21 |
| 396 | 610.24 |
| 397 | 624.24 |
| 398 | 598.2 |
| 399 | 616.19 |
| 400 | 616.19 |
| 401 | 598.28 |
| 402 | 586.3 |
| 403 | 668.27 |
| 404 | 632.21 |
| 405 | 656.31 |
| 406 | 600.32 |
| 407 | 628.31 |
| 408 | 628.36 |
| 409 | 622.36 |
| 410 | 628.39 |
| 411 | 616.3 |
| 412 | 616.32 |
| 413 | 628.32 |
| 414 | 644.24 |
| 415 | 628.21 |
| 416 | 644.30 |
| 417 | 628.26 |

517

-continued

| Ex | ES/MS m/z [M + H]+ |
|---|---|
| 418 | 628.21 |
| 419 | 628.29 |
| 420 | 628.29 |
| 421 | 601.25 |
| 422 | 615.27 |
| 423 | 622.22 |
| 424 | 634.21 |
| 425 | 634.21 |
| 426 | 586.25 |
| 427 | 600.26 |
| 428 | 612.26 |
| 429 | 656.25 |
| 430 | 644.23 |
| 431 | 655.11 |
| 432 | 670.17 |
| 433 | 600.2 |
| 434 | 626.22 |
| 435 | 612.21 |
| 436 | 638.3 |
| 437 | 629.25 |
| 438 | 612.28 |

Representative Procedure 10—Preparation of ((1R,2R,4S)-2-amino-7-azabicyclo[2.2.1]heptan-7-yl)(2-(1-(cyclopropylmethyl)-64(S)-3-methyl-1,1-dioxido-1,2-thiazinan-2-yl)-1H-pyrrolo[2,3-b]pyridin-2-yl)-5-methoxy-3-methylimidazo[1,2-a]pyridin-7-yl) methanone Example 462

518

Step 1. A mixture of benzyl N-[(2R)-7-[2-[6-chloro-1-(cyclopropylmethyl)pyrrolo[2,3-b]pyridin-2-yl]-5-methoxy-3-methyl-imidazo[1,2-a]pyridine-7-carbonyl]-7-azabicyclo[2.2.1]heptan-2-yl]carbamate I-28c (100 mg, 0.156 mmol), (3S)-3-methylthiazinane 1,1-dioxide I-11 (117 mg, 0.782 mmol), Pd-JackiePhos G3 (36.5 mg, 0.0313 mmol), and cesium carbonate (102 mg, 0.313 mmol) in toluene (2 mL) was heated at 90° C. in a sealed tube. After 3 hours, the reaction mixture was cooled to rt and concentrated under reduced pressure. The resulting residue was purified via silica gel column chromatography (0-15% methanol in DCM) to yield benzyl ((1R,2R,4S)-7-(2-(1-(cyclopropylmethyl)-6-((S)-3-methyl-1,1-dioxido-1,2-thiazinan-2-yl)-1H-pyrrolo[2,3-b]pyridin-2-yl)-5-methoxy-3-methylimidazo[1,2-a]pyridine-7-carbonyl)-7-azabicyclo[2.2.1]heptan-2-yl)carbamate I-36. ES/MS: m/z 752.4 [M+H]+.

Step 2. A mixture of benzyl ((1R,2R,4S)-7-(2-(1-(cyclopropylmethyl)-6-((S)-3-methyl-1,1-dioxido-1,2-thiazinan-2-yl)-1H-pyrrolo[2,3-b]pyridin-2-yl)-5-methoxy-3-methyl-imidazo[1,2-a]pyridine-7-carbonyl)-7-azabicyclo[2.2.1]heptan-2-yl)carbamate I-36 (90 mg, 0.120 mmol), palladium on carbon (10%, 21 mg, 0.02 mmol), and one drop of TFA in methanol (5 mL) was hydrogenated under an atmosphere of hydrogen. After one hour, the reaction mixture was filtered over celite, and the filtrate was concentrated under reduced pressure. The resulting residue was purified via prep HPLC to yield ((1R,2R,4S)-2-amino-7-azabicyclo[2.2.1]heptan-7-yl)(2-(1-(cyclopropylmethyl)-6-((S)-3-methyl-1,

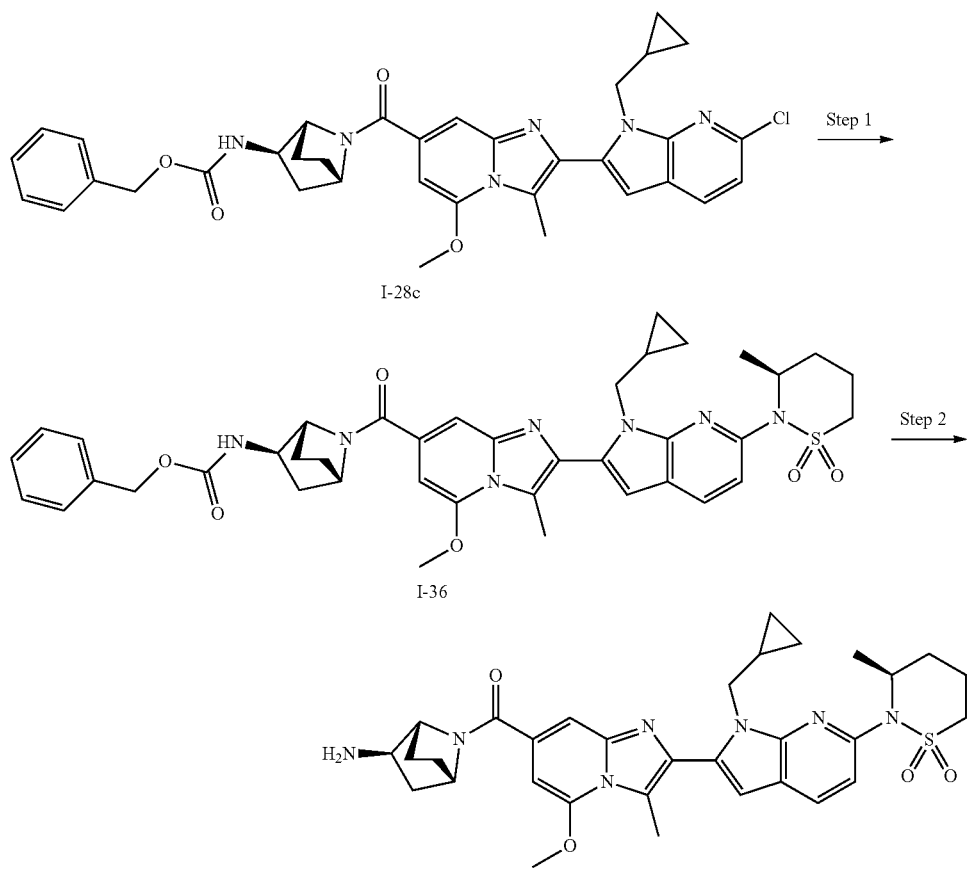

1-dioxido-1,2-thiazinan-2-yl)-1H-pyrrolo[2,3-b]pyridin-2-yl)-5-methoxy-3-methylimidazo[1,2-a]pyridin-7-yl)methanone Example 462.

Representative Procedure 11—Preparation of N-(2-(7-((2S,5R)-5-amino-2-methylpiperidine-1-carbonyl)-5-methoxy-3-methylimidazo[1,2-a]pyridin-2-yl)-1-(cyclopropylmethyl)-1H-pyrrolo[2,3-b]pyridin-6-yl)-N-methylmethanesulfonamide (Example 481)

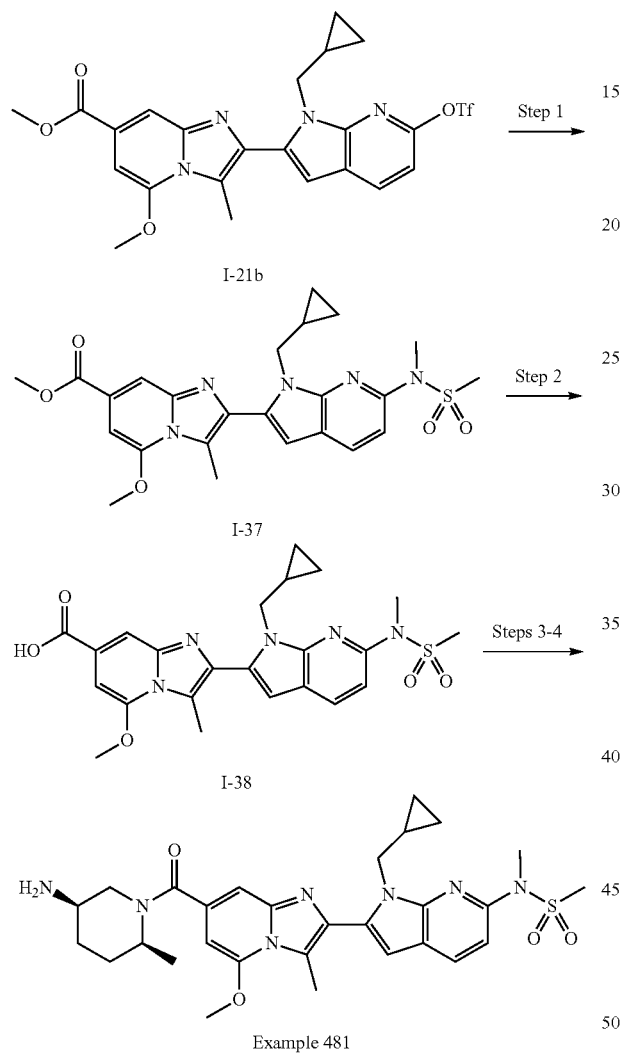

I-21b

I-37

I-38

Example 481

Step 1. A mixture of methyl 2-[1-(cyclopropylmethyl)-6-(trifluoromethylsulfonyloxy)pyrrolo[2,3-b]pyridin-2-yl]-5-methoxy-3-methyl-imidazo[1,2-a]pyridine-7-carboxylate I-21b (150 mg, 0.279 mmol), N-methylmethanesulfonamide (107 mg, 0.982 mmol), JackiePhos (45 mg, 0.0565 mmol), allylpalladium chloride dimer (5.00 mg, 1.37e-5 mol) and cesium carbonate (185 mg, 0.568 mmol) in toluene (3 mL) was heated at 130° C. in a sealed tube. After 75 minutes, the reaction mixture was cooled to rt and concentrated under reduced pressure. The resulting residue was purified via silica gel column chromatography (10-100% ethyl acetate in hexanes) to yield methyl 2-[1-(cyclopropylmethyl)-6-[methyl(methylsulfonyl)amino]pyrrolo[2,3-b]pyridin-2-yl]-5-methoxy-3-methyl-imidazo[1,2-a]pyridine-7-carboxylate I-37. ES/MS: m/z 496.3 [M+H]⁺.

Steps 2-4. Following steps 2-4 of Representative Procedure 2, using I-37 and A1.11, N-(2-(7-((2S,5R)-5-amino-2-methylpiperidine-1-carbonyl)-5-methoxy-3-methylimidazo[1,2-a]pyridin-2-yl)-1-(cyclopropylmethyl)-1H-pyrrolo[2,3-b]pyridin-6-yl)-N-methylmethanesulfonamide Example 481 was synthesized.

The following examples as shown in Table 1 were synthesized utilizing a variation of procedure 10 or 11 with the appropriate intermediates:

| Ex | ES/MS m/z [M + H]⁺. |
|---|---|
| 439 | 620.37 |
| 440 | 620.35 |
| 441 | 620.34 |
| 442 | 710.24 |
| 443 | 633.21 |
| 444 | 695.39 |
| 445 | 632.37 |
| 446 | 632.34 |
| 447 | 672.29 |
| 448 | 582.30 |
| 449 | 582.30 |
| 450 | 619.17 |
| 451 | 620.33 |
| 452 | 646.40 |
| 453 | 680.39 |
| 454 | 618.38 |
| 455 | 619.33 |
| 456 | 582.3 |
| 457 | 630.37 |
| 458 | 606.25 |
| 459 | 618.33 |
| 460 | 668.32 |
| 461 | 652.32 |
| 462 | 618.34 |
| 463 | 618.27 |
| 464 | 570.4 |
| 465 | 558.35 |
| 466 | 572.37 |
| 467 | 638.09 |
| 468 | 652.26 |
| 469 | 680.25 |
| 470 | 572.38 |
| 471 | 657.28 |
| 472 | 564.2 |
| 473 | 630.30 |
| 474 | 604.27 |
| 475 | 592.27 |
| 476 | 578.25 |
| 477 | 618.25 |
| 478 | 644.18 |
| 479 | 606.31 |
| 480 | 580.35 |
| 481 | 580.32 |
| 482 | 566.31 |
| 483 | 594.27 |
| 484 | 580.28 |
| 485 | 572.39 |

Representative Procedure 12—Preparation of N—((R)-1-(2-(7-((1R,2R,4S)-2-amino-7-azabicyclo[2.2.1]heptane-7-carbonyl)-3-cyclopropyl-5-methoxyimidazo[1,2-a]pyridin-2-yl)-1-(bicyclo[1.1.1]pentan-1-ylmethyl)-1H-pyrrolo[2,3-b]pyridin-6-yl)ethyl)pivalamide (Example 486)

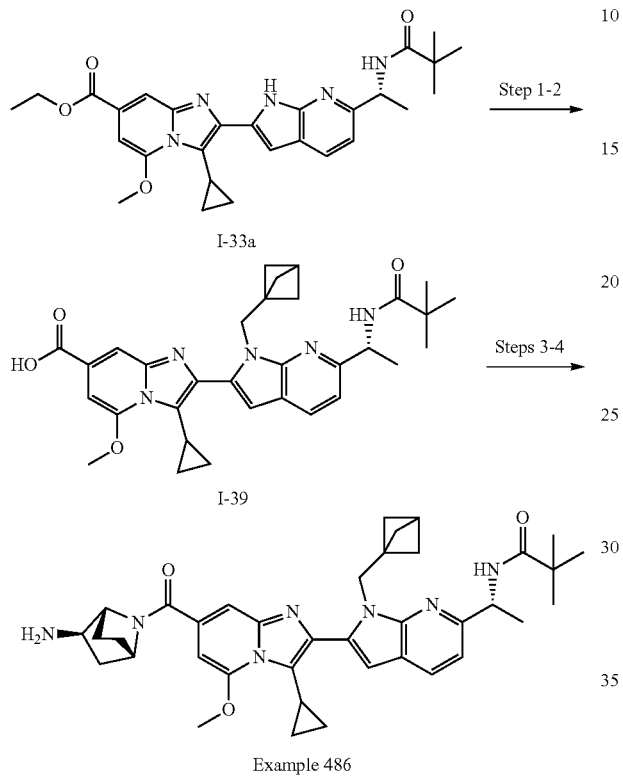

Steps 1-2. To a mixture of ethyl 3-cyclopropyl-2-[6-[(1R)-1-(2,2-dimethylpropanoylamino)ethyl]-1H-pyrrolo[2,3-b]pyridin-2-yl]-5-methoxy-imidazo[1,2-a]pyridine-7-carboxylate I-33a (71 mg, 0.141 mmol) in DMF (2.5 mL) was added 1-(bromomethyl)bicyclo[1.1.1]pentane (0.058 mL, 0.542 mmol) and a solution of NaHMDS in THF (1 M, 0.16 mL, 0.16 mmol). After 3 days, the reaction mixture was diluted with water and ethyl acetate. The layers were separated, and the organics dried, filtered, and concentrated under reduced pressure. The resulting residue was dissolved in a 1:1:1 mixture of THF/MeOH/water and LiOH monohydrate (22 mg, 0.51 mmol) was added. After stirring overnight, a solution of HCl in water (3 N, 0.19 mL, 0.563 mmol) was added. The reaction mixture was diluted with ethyl acetate and water. The layers were separated and separated, and the organics dried, filtered, and conc. under reduced pressure to yield (R)-2-(1-(bicyclo[1.1.1]pentan-1-ylmethyl)-6-(1-pivalamidoethyl)-1H-pyrrolo[2,3-b]pyridin-2-yl)-3-cyclopropyl-5-methoxyimidazo[1,2-a]pyridine-7-carboxylic acid I-39.

Steps 3-4. Following steps 3-4 of Representative Procedure 2, utilizing (R)-2-(1-(bicyclo[1.1.1]pentan-1-ylmethyl)-1H-pyrrolo[2,3-b]pyridin-2-yl)-3-cyclopropyl-5-methoxyimidazo[1,2-a]pyridine-7-carboxylic acid I-39 and A2, N—((R)-1-(2-(7-((1R,2R,4S)-2-amino-7-azabicyclo[2.2.1]heptane-7-carbonyl)-3-cyclopropyl-5-methoxyimidazo[1,2-a]pyridin-2-yl)-1-(bicyclo[1.1.1]pentan-1-ylmethyl)-1H-pyrrolo[2,3-b]pyridin-6-yl)ethyl) Example 486 was synthesized.

The following examples as shown in Table 1 were synthesized utilizing a variation of procedure 12 with the appropriate intermediates:

| Ex | ES/MS m/z [M + H]+. |
|---|---|
| 486 | 678.35 |
| 487 | 596.3 |
| 488 | 623.27 |
| 489 | 644.34 |
| 490 | 592.3 |
| 491 | 586.2 |
| 492 | 577.43 |
| 493 | 538.2 |
| 494 | 630.16 |
| 495 | 656.17 |
| 496 | 642.38 |
| 497 | 489.35 |
| 498 | 551.29 |
| 499 | 503.38 |
| 500 | 523.34 |
| 501 | 567.3 |
| 502 | 509.32 |
| 503 | 513.34 |
| 504 | 527.33 |
| 505 | 513.31 |
| 506 | 445.28 |
| 507 | 536.32 |
| 508 | 540.3 |
| 509 | 527.3 |
| 510 | 528.29 |
| 511 | 542.36 |
| 512 | 521.37 |
| 513 | 536.36 |

Representative Procedure 13—Preparation of 1-(2-(2-(7-((1R,2R,4S)-2-amino-7-azabicyclo[2.2.1]heptane-7-carbonyl)-5-methoxy-3-methylimidazo[1,2-a]pyridin-2-yl)-1-(cyclopropylmethyl)-1H-pyrrolo[2,3-b]pyridin-6-yl)piperidin-1-yl)-2,2-dimethylpropan-1-one Example 514

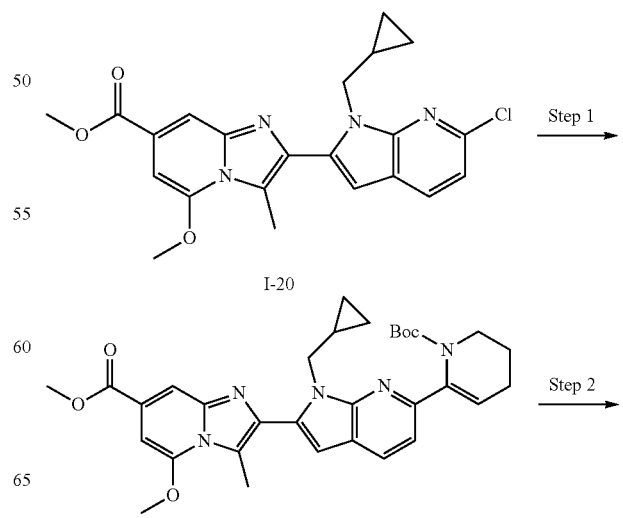

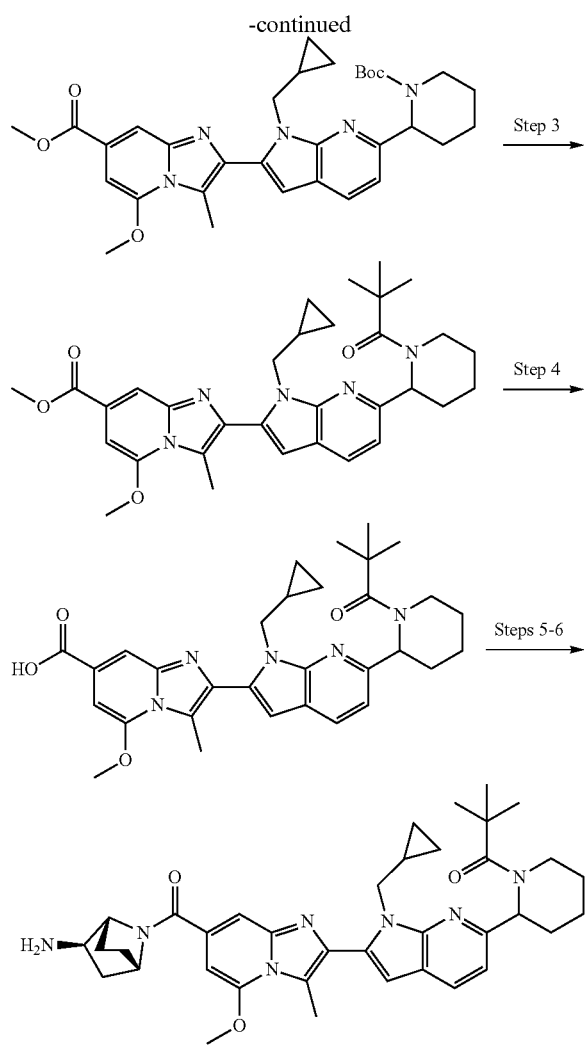

Example 514

Step 1. A mixture methyl 2-[6-chloro-1-(cyclopropylmethyl)pyrrolo[2,3-b]pyridin-2-yl]-5-methoxy-3-methyl-imidazo[1,2-a]pyridine-7-carboxylate I-20 (107 mg, 0.252 mmol), tert-butyl 6-(4,4,5,5-tetramethyl-1,3,2-dioxaborolan-2-yl)-3,4-dihydro-2H-pyridine-1-carboxylate (156 mg, 0.504 mmol), Pd(dppf)C$_{12}$DCM (18.4 mg, 0.0252 mmol), and potassium phosphate tribasic (160 mg, 0.755 mmol) in dioxane (2 mL) and water (0.25 mL) was heated at 100° C. in a sealed tube. After 2 hours, the reaction mixture was cooled to rt and diluted with ethyl acetate. The mixture was filtered over celite and the filtrate concentrated. The resulting residue was purified via silica gel column chromatography (50-100% ethyl acetate in hexanes) to yield methyl 2-[6-(1-tert-butoxycarbonyl-3,4-dihydro-2H-pyridin-6-yl)-1-(cyclopropylmethyl)pyrrolo[2,3-b]pyridin-2-yl]-5-methoxy-3-methyl-imidazo[1,2-a]pyridine-7-carboxylate. ES/MS: m/z 572.31 [M+H]$^+$.

Step 2. A mixture of methyl 2-[6-(1-tert-butoxycarbonyl-3,4-dihydro-2H-pyridin-6-yl)-1-(cyclopropylmethyl)pyrrolo[2,3-b]pyridin-2-yl]-5-methoxy-3-methyl-imidazo[1,2-a]pyridine-7-carboxylate (72.0 mg, 0.126 mmol) and palladium on carbon (10% loading, 13.4 mg, 0.0126 mmol) in MeOH (1 mL) was hydrogenated under an atmosphere of hydrogen for 3 days. TFA (19 µL, 0.25 mmol) was added and the mixture was hydrogenated overnight. The mixture was filtered over a silicycle carbonate plug, and the filtrate concentrated to yield methyl 2-(6-(1-(tert-butoxycarbonyl)piperidin-2-yl)-1-(cyclopropylmethyl)-1H-pyrrolo[2,3-b]pyridin-2-yl)-5-methoxy-3-methylimidazo[1,2-a]pyridine-7-carboxylate ES/MS: m/z 592.13.

Step 3. To a mixture of methyl 2-(6-(1-(tert-butoxycarbonyl)piperidin-2-yl)-1-(cyclopropylmethyl)-1H-pyrrolo[2,3-b]pyridin-2-yl)-5-methoxy-3-methylimidazo[1,2-a]pyridine-7-carboxylate (72 mg, 0.126 mmol) in DCM (0.6 mL) was added a solution of hydrogen chloride in dioxane (4 M, 0.628 mL, 2.51 mmol). After 1 hour, the reaction mixture was concentrated. The resulting residue was dissolved in DCM (1 mL) and triethylamine (0.0297 mL, 0.211 mmol) and pivaloyl chloride (0.0208 mL, 0.169 mmol) were added. After one hour, the reaction mixture was diluted with sat. NaHCO$_3$(aq) and DCM. The layers were separated and aqueous extracted with DCM. The combined organics were dried, filtered, and concentrated under reduced pressure to yield methyl 241-(cyclopropylmethyl)-6-(1-pivaloylpiperidin-2-yl)-1H-pyrrolo[2,3-b]pyridin-2-yl)-5-methoxy-3-methylimidazo[1,2-a]pyridine-7-carboxylate. ES/MS: m/z 558.38 [M+H]$^+$.

Step 4. To a solution of methyl 2-(1-(cyclopropylmethyl)-6-(1-pivaloylpiperidin-2-yl)-1H-pyrrolo[2,3-b]pyridin-2-yl)-5-methoxy-3-methylimidazo[1,2-a]pyridine-7-carboxylate (24 mg, 0.043 mmol) in THF (0.5 mL) and MeOH (0.5 mL) was added a solution of lithium hydroxide (1.00 M, 0.129 mL, 0.129 mmol) in water. After 11 hours, lithium hydroxide (1.00 M, 0.129 mL, 0.129 mmol) in water was added. After one hour, the reaction mixture was concentrated to yield 2-(1-(cyclopropylmethyl)-6-(1-pivaloylpiperidin-2-yl)-1H-pyrrolo[2,3-b]pyridin-2-yl)-5-methoxy-3-methylimidazo[1,2-a]pyridine-7-carboxylic acid. ES/MS: m/z 544.37 [M+H]$^+$.

Steps 5-6. To a mixture of 2-(1-(cyclopropylmethyl)-6-(1-pivaloylpiperidin-2-yl)-1H-pyrrolo[2,3-b]pyridin-2-yl)-5-methoxy-3-methylimidazo[1,2-a]pyridine-7-carboxylic acid (23 mg, 0.042 mmol) and tert-butyl N-[(2R)-7-azabicyclo[2.2.1]heptan-2-yl]carbamate (11 mg, 0.051 mmol) in DMF (0.5 mL) was added DIPEA (0.044 mL, 0.254 mmol) and HATU (32 mg, 0.085 mmol). After 2 hours, the reaction was diluted with water and DCM. The layers were separated and aqueous extracted with DCM. The combined organics were dried, filtered, and concentrated under reduced pressure. The resulting residue was dissolved in DCM (1 mL) and TFA (1 mL) was added. After one hour, the reaction mixture was concentrated under reduce pressure and the resulting residue purified via prep HPLC to yield 1-(2-(2-(7-((1R,2R,4S)-2-amino-7-azabicyclo[2.2.1]heptane-7-carbonyl)-5-methoxy-3-methylimidazo[1,2-a]pyridin-2-yl)-1-(cyclopropylmethyl)-1H-pyrrolo[2,3-b]pyridin-6-yl)piperidin-1-yl)-2,2-dimethylpropan-1-one Example 514.

Representative Procedure 13a—Preparation of ((1R,2R,4S)-2-amino-7-azabicyclo[2.2.1]heptan-7-yl)(2-(1-(cyclopropylmethyl)-6-(2-methylpyridin-3-yl)-1H-pyrrolo[2,3-b]pyridin-2-yl)-5-methoxy-3-methylimidazo[1,2-a]pyridin-7-yl)methanone (Example 575)

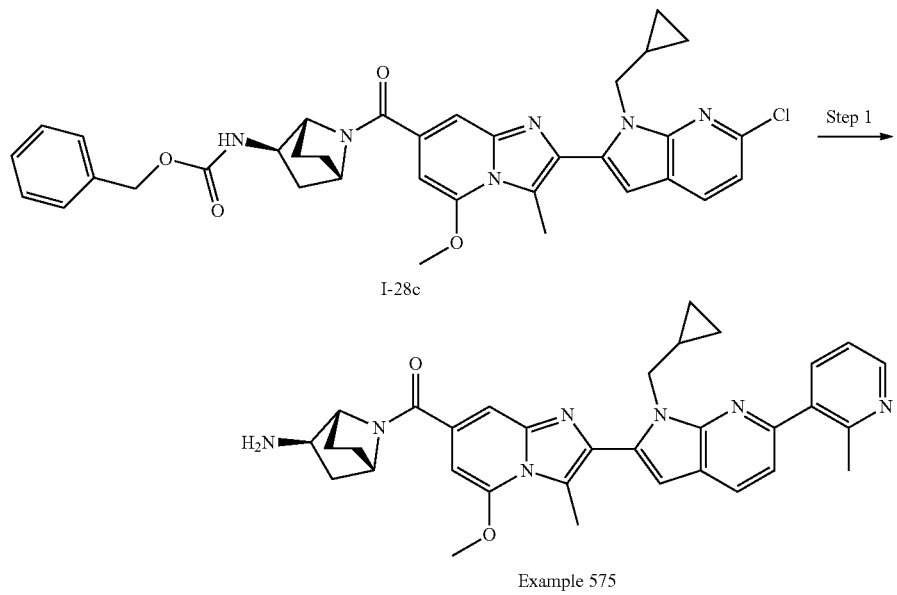

Example 575

A mixture of benzyl N-[(2R)-7-[2-[6-chloro-1-(cyclopropylmethyl)pyrrolo[2,3-b]pyridin-2-yl]-5-methoxy-3-methyl-imidazo[1,2-a]pyridine-7-carbonyl]-7-azabicyclo[2.2.1]heptan-2-yl]carbamate I-28c (60 mg, 0.097 mmol), 2-Methylpyridine-3-boronic acid (13 mg, 0.097 mmol), Dichloro 1,1'-bis(diphenylphosphino)ferrocene palladium (II) dichloromethane (8.0 mg, 0.0097 mmol), and potassium carbonate (40 mg, 0.29 mmol) in dioxane (2 mL) and water (0.4 mL) was heated at 110° C. in a sealed tube. After stirring overnight, the reaction mixture was cooled to rt, and diluted with ethyl acetate. MgSO₄ was added and the reaction mixture was filtered. The filtrate was concentrated under reduced pressure. The resulting residue was dissolved in ethanol (4 mL), and palladium on carbon (10%, 10 mg, 0.01 mmol) and one drop of TFA was added. The reaction mixture was hydrogenated under an atmosphere of hydrogen. After 24 h, the reaction mixture was filtered over celite, and the filtrate was concentrated under reduced pressure. The resulting residue was purified via prep HPLC to yield ((1R,2R,4S)-2-amino-7-azabicyclo[2.2.1]heptan-7-yl)(2-(1-(cyclopropylmethyl)-6-(2-methylpyridin-3-yl)-1H-pyrrolo[2,3-b]pyridin-2-yl)-5-methoxy-3-methylimidazo[1,2-a]pyridin-7-yl)methanone Example 575.

The following examples as shown in Table 1 were synthesized utilizing a variation of procedure 13 or 13a with the appropriate intermediates, or were prepared according to General Procedures.

| Ex | ES/MS m/z [M + H]⁺ |
|---|---|
| 514 | 638.4 |
| 515 | 596.3 |
| 516 | 595.32 |
| 517 | 638.4 |
| 518 | 651.4 |
| 519 | 632.39 |
| 520 | 556.33 |
| 521 | 612.35 |
| 522 | 610.4 |
| 523 | 610.4 |
| 524 | 570.32 |
| 525 | 651.4 |
| 526 | 638.4 |
| 527 | 596.3 |
| 528 | 610.40 |
| 529 | 637.40 |
| 530 | 624.30 |
| 531 | 582.30 |
| 532 | 558.26 |
| 533 | 570.27 |
| 534 | 572.22 |
| 535 | 572.24 |
| 536 | 572.29 |
| 537 | 554.18 |
| 538 | 646.30 |
| 539 | 584.62 |
| 540 | 624.36 |
| 541 | 638.39 |
| 542 | 636.40 |
| 543 | 598.40 |
| 544 | 651.40 |
| 545 | 542.30 |
| 546 | 566.29 |
| 547 | 568.21 |
| 548 | 578.25 |
| 549 | 615.35 |
| 550 | 561.41 |
| 551 | 616.36 |
| 552 | 500.3 |

| Ex | ES/MS m/z [M + H]+ |
|---|---|
| 553 | 488.3 |
| 554 | 568.34 |
| 555 | 568.35 |
| 556 | 592.36 |
| 557 | 538.35 |
| 558 | 580.35 |
| 559 | 585.32 |
| 560 | 582.32 |
| 561 | 566.34 |
| 562 | 568.36 |
| 563 | 562.73 |
| 564 | 580.37 |
| 565 | 543.29 |
| 566 | 543.32 |
| 567 | 631.27 |
| 568 | 524.28 |
| 569 | 569.25 |
| 570 | 527.91 |
| 571 | 557.29 |
| 572 | 543.29 |
| 573 | 591.29 |
| 574 | 529.28 |
| 575 | 562.25 |
| 576 | 527.31 |
| 577 | 539.31 |
| 578 | 525.31 |
| 579 | 517.25 |
| 580 | 499.28 |
| 581 | 531.28 |
| 582 | 513.25 |
| 583 | 513.31 |
| 584 | 499.28 |
| 585 | 513.31 |
| 586 | 504.25 |
| 587 | 499.28 |
| 588 | 499.29 |
| 589 | 504.29 |
| 590 | 510.25 |
| 591 | 529.31 |
| 592 | 513.35 |
| 593 | 513.36 |
| 594 | 513.33 |
| 595 | 515.3 |
| 596 | 523.26 |
| 597 | 483.29 |
| 598 | 573.29 |
| 599 | 493.26 |
| 600 | 591.24 |
| 601 | 604.32 |
| 602 | 590.29 |
| 603 | 590.29 |
| 604 | 550.26 |
| 605 | 565.29 |
| 606 | 621.32 |
| 607 | 612.30 |
| 608 | 501.27 |
| 609 | 624.39 |
| 610 | 496.37 |
| 611 | 567.37 |
| 612 | 513.34 |
| 613 | 487.34 |

Preparation of N—((R)-1-(2-(7-((R)-5-amino-2-methylhexahydropyridazine-1-carbonyl)-5-methoxy-3-methylimidazo[1,2-a]pyridin-2-yl)-1-(cyclopropylmethyl)-1H-pyrrolo[2,3-b]pyridin-6-yl)ethyl)benzamide (Example 614)

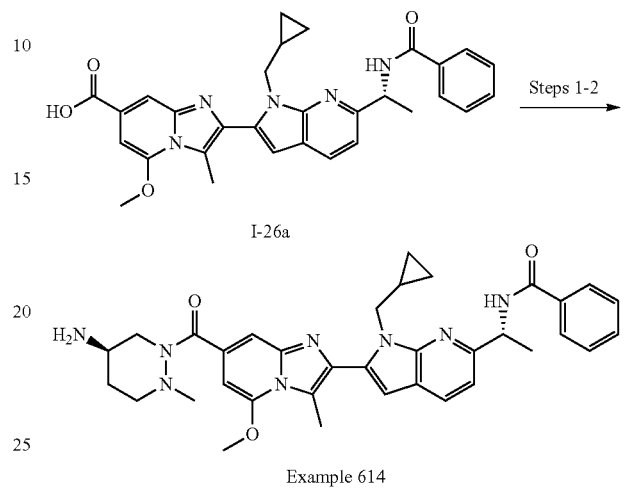

Example 614

To a mixture of 2-[6-[(1R)-1-benzamidoethyl]-1-(cyclopropylmethyl)pyrrolo[2,3-b]pyridin-2-yl]-5-methoxy-3-methyl-imidazo[1,2-a]pyridine-7-carboxylic acid (150 mg, 0.286 mmol) I-26a and tert-butyl N-[(4R)-1-methylhexahydropyridazin-4-yl]carbamate A8 (67.8 mg, 0.315 mmol) in NMP (0.4 mL) was added DIPEA (64.7 μL, 0.372 mmol) and HATU (131 mg, 0.344 mmol). After stirring overnight, the reaction mixture was diluted with DCM (5 mL) and TFA (10 mL). After stirring for one hour, the reaction mixture was concentrated under reduced pressure and the resulting residue was purified via prep HPLC to yield N-[(1R)-1-[2-[7-[(5R)-5-amino-2-methyl-hexahydropyridazine-1-carbonyl]-5-methoxy-3-methyl-imidazo[1,2-a]pyridin-2-yl]-1-(cyclopropylmethyl)pyrrolo[2,3-b]pyridin-6-yl]ethyl]benzamide Example 614. ES/MS: m/z 621.5 [M+1]+.

Preparation of N—((R)-1-(2-(74(R)-5-amino-2-methylhexahydropyridazine-1-carbonyl)-5-methoxy-3-methylimidazo[1,2-a]pyridin-2-yl)-1-(cyclopropylmethyl)-1H-pyrrolo[2,3-b]pyridin-6-yl)ethyl)-3-fluorobicyclo[1.1.1]pentane-1-carboxamide (Example 615)

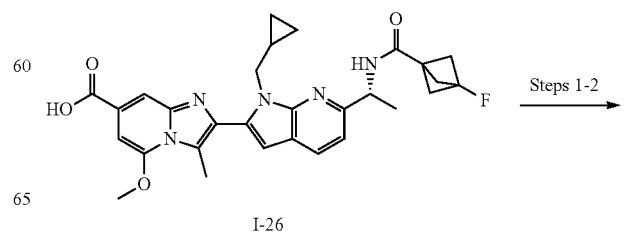

I-26

529

-continued

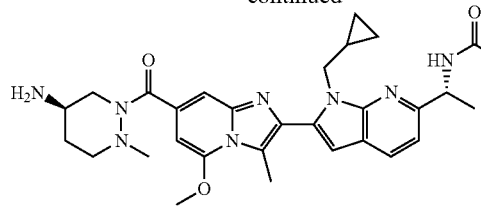

Example 615

Following the procedure of Example 614, beginning with I-26 and A8, N—((R)-1-(2-(7-((R)-5-amino-2-methylhexa-hydropyridazine-1-carbonyl)-5-methoxy-3-methylimidazo[1,2-a]pyridin-2-yl)-1-(cyclopropylmethyl)-1H-pyrrolo[2,3-b]pyridin-6-yl)ethyl)-3-fluorobicyclo[1.1.1]pentane-1-carboxamide Example 615 was synthesized. ES/MS: m/z 629.2 [M+H]$^+$.

Preparation of tert-butyl N-[(4R)-2-[2-[6-[(1R)-1-benzamidoethyl]-1-(cyclopropylmethyl)pyrrolo[2,3-b]pyridin-2-yl]-5-methoxy-3-methyl-imidazo[1,2-a]pyridine-7-carbonyl]hexahydropyridazin-4-yl]carbamate (Example 616)

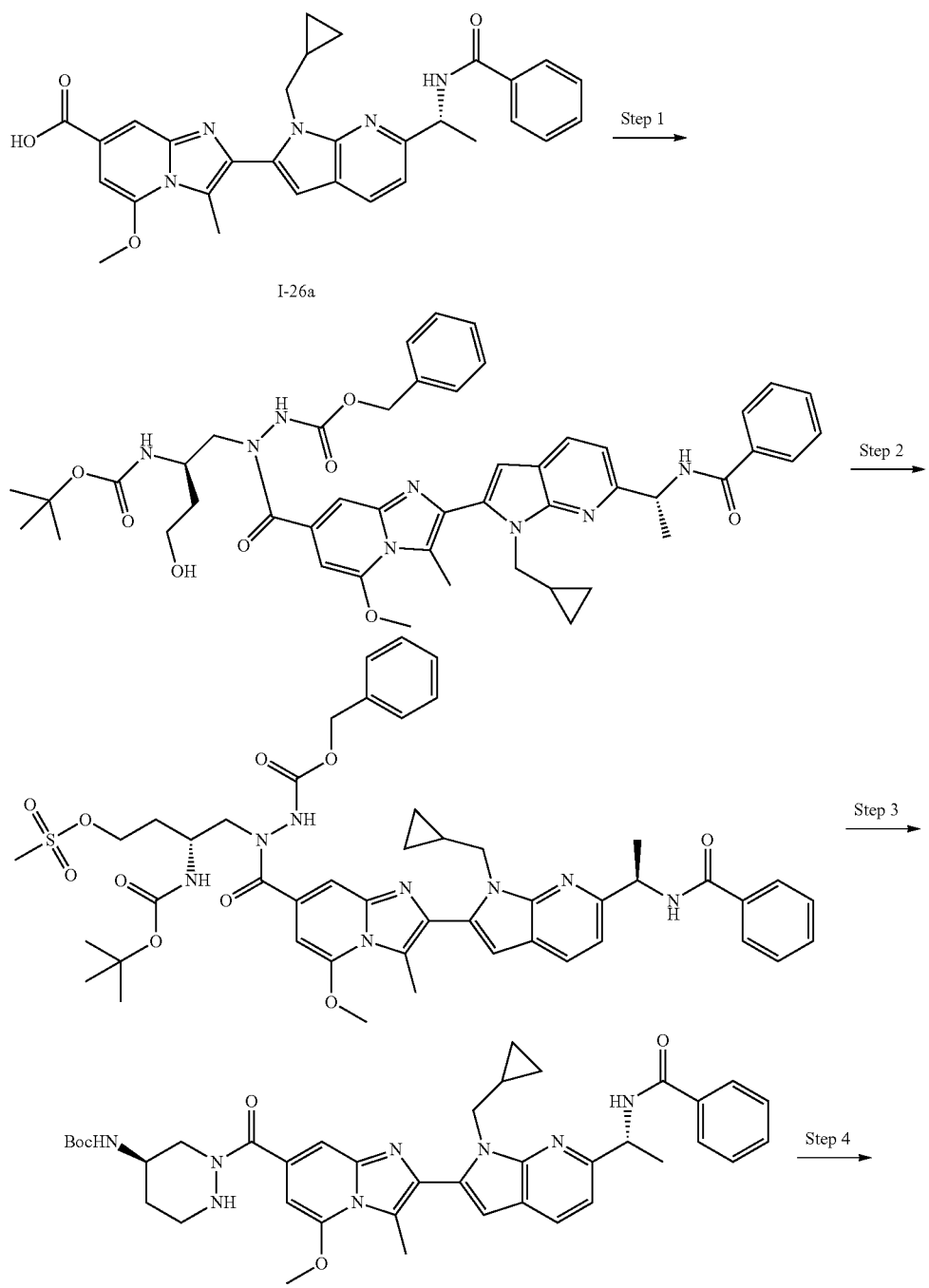

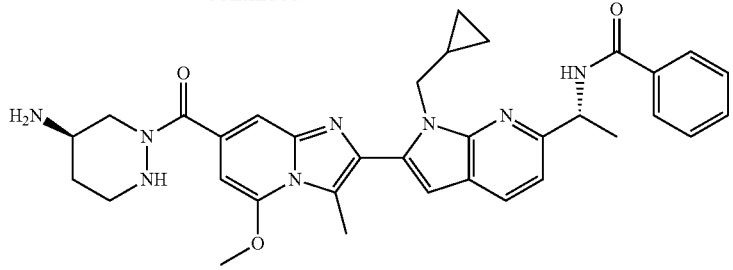

Example 616

Step 1: To a solution of 2-[1-(cyclopropylmethyl)-6-[(1R)-1-benzamidoethyl]pyrrolo[2,3-b]pyridin-2-yl]-5-methoxy-3-methyl-imidazo[1,2-a]pyridine-7-carboxylic acid I-26a (100 mg, 190 μmol) in DCM (1 mL) was added 2 M oxalyl chloride in DCM (0.5 mL) and the mixture was stirred for 30 min. The mixture was concentrated under vacuum and diluted with DCM (1 mL). To the reaction was added DIPEA (66 μL, 380 μmol) followed by tert-butyl N-[rac-(1R)-1-[(2-benzyloxycarbonylhydrazino)methyl]-3-triethylsilyloxy-propyl]carbamate (107 mg, 229 μmol). After stirring for 1 h, the product was purified by silica chromatography using EtOAc in hexane (0-15%) to yield benzyl 2-(2-(6-((R)-1-benzamidoethyl)-1-(cyclopropylmethyl)-1H-pyrrolo[2,3-b]pyridin-2-yl)-5-methoxy-3-methylimidazo[1,2-a]pyridine-7-carbonyl)-2-4R)-2-((tert-butoxycarbonyl)amino)-4-hydroxybutyphydrazine-1-carboxylate. ES/MS: m/z 859.3 [M+H]⁺

Step 2: To a solution of benzyl 2-(2-(6-((R)-1-benzamidoethyl)-1-(cyclopropylmethyl)-1H-pyrrolo[2,3-b]pyridin-2-yl)-5-methoxy-3-methylimidazo[1,2-a]pyridine-7-carbonyl)-2-4R)-2-((tert-butoxycarbonyl)amino)-4-hydroxybutyphydrazine-1-carboxylate (116 mg, 135 μmol) and DIPEA (59 μL, 340 μmol) in DCM (2 mL) was added methanesulfonyl chloride (12.1 μl, 148 μmol) at 0° C. After stirring for 15 min, the mixture was concentrated and residue was purified by silica chromatography using EtOAc in hexane (0-100%) to give benzyl 2-(2-(6-((R)-1-benzamidoethyl)-1-(cyclopropylmethyl)-1H-pyrrolo[2,3-b]pyridin-2-yl)-5-methoxy-3-methylimidazo[1,2-a]pyridine-7-carbonyl)-2-4R)-2-((tert-butoxycarbonyl)amino)-4-((methylsulfonyl)oxy)butyl)hydrazine-1-carboxylate ES/MS: m/z 937.2 [M+H]±

Step 3: A mixture of benzyl 2-(2-(6-((R)-1-benzamidoethyl)-1-(cyclopropylmethyl)-1H-pyrrolo[2,3-b]pyridin-2-yl)-5-methoxy-3-methylimidazo[1,2-a]pyridine-7-carbonyl)-24(R)-2-((tert-butoxycarbonyl)amino)-4-((methylsulfonyl)oxy)butyl)hydrazine-1-carboxylate (120 mg, 0.13 mmol), 10% Pd/C (10%, 13.6 mg, 0.01 mmol), and methanol (5 mL) was stirred under an atmosphere of hydrogen gas for 4 h. The catalyst was filtered and the filtrate was treated with DIPEA (33 mg, 0.26 mmol). The mixture was stirred overnight at 50° C. and then concentrated under reduced pressure to yield tert-butyl ((R)-2-(2-(6-((R)-1-benzamidoethyl)-1-(cyclopropylmethyl)-1H-pyrrolo[2,3-b]pyridin-2-yl)-5-methoxy-3-methylimidazo[1,2-a]pyridine-7-carbonyl)hexahydropyridazin-4-yl)carbamate, which was used in the next step without purification. ES/MS: m/z 707.3 [M+H]+

Step 4: A solution of tert-butyl ((R)-2-(2-(6-((R)-1-benzamidoethyl)-1-(cyclopropylmethyl)-1H-pyrrolo[2,3-b]pyridin-2-yl)-5-methoxy-3-methylimidazo[1,2-a]pyridine-7-carbonyl)hexahydropyridazin-4-yl)carbamate (90 mg, 127 μmol) in 1:1 TFA DCM (0.5 mL) was stirred for 1 h. The mixture was concentrated under reduced pressure and the resulting residue purified via prep HPLC (MeCN/water gradient, 0.1% TFA) to yield Example 616. ES/MS: m/z 560.2 [M+H]⁺

Representative Procedure 14—Preparation of ((1R, 2R,4S)-2-amino-7-azabicyclo[2.2.1]heptan-7-yl)(2-(1-(cyclopropylmethyl)-6-(oxetan-3-ylmethoxy)-1H-pyrrolo[2,3-b]pyridin-2-yl)-5-methoxy-3-methylimidazo[1,2-a]pyridin-7-yl)methanone (Example 626)

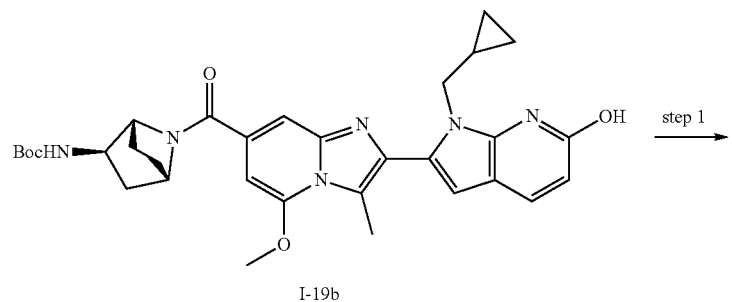

I-19b

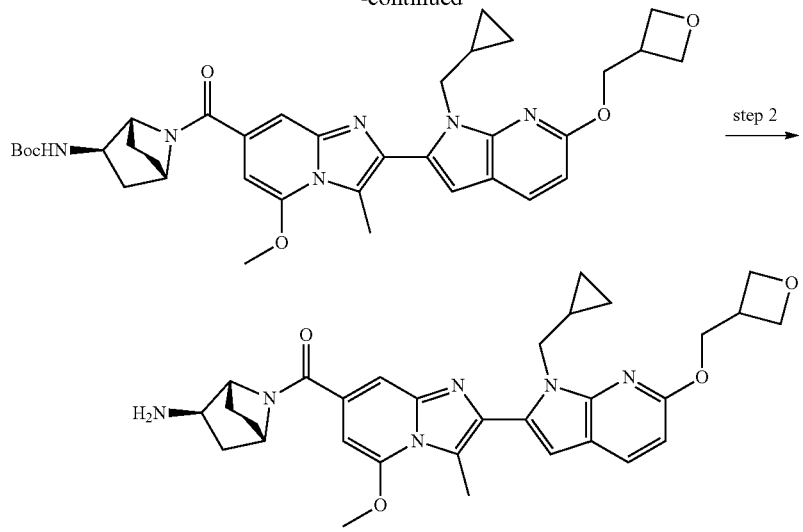

Example 626

Step 1. A mixture of tert-butyl N-[7-[2[1-(cyclopropylmethyl)-6-hydroxy-pyrrolo[2,3-b]pyridin-2-yl]-5-methoxy-3-methyl-imidazo[1,2-a]pyridine-7-carbonyl]-7-azabicyclo[2.2.1]heptan-2-yl]carbamate I-19b (20 mg, 0.03 mmol) and the 3-(iodomethyl)oxetane (20.2 mg, 0.102 mmol) was stirred at rt for 2 h. The mixture was diluted with EtOAc and washed with 5% LiCl (aq). The organic layer was dried, filtered, and concentrated under reduced pressure to yield tert-butyl ((1R,2R,4S)-7-(2-(1-(cyclopropylmethyl)-6-(oxetan-3-ylmethoxy)-1H-pyrrolo[2,3-b]pyridin-2-yl)-5-methoxy-3-methylimidazo[1,2-a]pyridine-7-carbonyl)-7-azabicyclo[2.2.1]heptan-2-yl)carbamate ES/MS: m/z 657.3 [M+H]⁺.

Step 2. A solution of tert-butyl ((1R,2R,4S)-7-(2-(1-(cyclopropylmethyl)-6-(oxetan-3-ylmethoxy)-1H-pyrrolo[2,3-b]pyridin-2-yl)-5-methoxy-3-methylimidazo[1,2-a]pyridine-7-carbonyl)-7-azabicyclo[2.2.1]heptan-2-yl)carbamate was stirred in 1:1 TFA:DCM for 20 min. The mixture was concentrated under reduced pressure and the resulting residue was purified via preparative HPLC to yield ((1R,2R,4S)-2-amino-7-azabicyclo[2.2.1]heptan-7-yl)(2-(1-(cyclopropylmethyl)-6-(oxetan-3-ylmethoxy)-1H-pyrrolo[2,3-b]pyridin-2-yl)-5-methoxy-3-methylimidazo[1,2-a]pyridin-7-yl)methanone Example 626

The following examples as shown in Table 1 were synthesized utilizing a variation of procedure 14 with the appropriate intermediates, or were prepared according to General Procedures described in Part I.

| Ex | ES/MS m/z [M + H]⁺ |
|---|---|
| 617 | 560.20 |
| 618 | 560.20 |
| 619 | 574.20 |
| 620 | 560.29 |
| 621 | 532.10 |
| 622 | 546.23 |
| 623 | 572.29 |
| 624 | 572.28 |
| 625 | 543.23 |
| 626 | 557.21 |
| 627 | 577.34 |
| 628 | 563.30 |
| 629 | 489.33 |
| 630 | 574.2 |
| 631 | 630.2 |

¹H NMR data for select compounds disclosed herein is listed in Table 2. It is understood that ¹H NMR signals and integrations are as observed, and that, due to factors including exchange, line broadening, rotation, or obscurement by residual solvent/moisture, integrations may differ from theoretical values.

TABLE 2

| Ex | NMR |
|---|---|
| 1 | 1H NMR (400 MHz, DMSO-d6) δ 8.82 (d, J = 7.9 Hz, 1H), 8.54 (s, 1H), 8.08 (s, 3H), 7.99 (d, J = 8.1 Hz, 1H), 7.47 (s, 1H), 7.23 (d, J = 8.1 Hz, 1H), 6.63 (s, 1H), 6.37 (s, 1H), 5.35-5.23 (m, 1H), 4.63-4.37 (m, 4H), 4.10 (s, 6H), 3.81-3.71 (m, 1H), 2.83 (s, 3H), 1.94-1.76 (m, 4H), 1.71-1.59 (m, 1H), 1.57 (d, J = 6.9 Hz, 3H), 1.35 (dd, J = 12.8, 4.4 Hz, 1H), 1.15 (p, J = 6.6 Hz, 1H), 0.38-0.20 (m, 4H). |
| 2 | 1H NMR (400 MHz, Methanol-d4) d 8.05 (d, J = 8.2 Hz, 1H), 7.69-7.44 (m, 1H), 7.21 (d, J = 8.1 Hz, 1H), 6.93-6.76 (m, 2H), 5.24 (q, J = 7.0 Hz, 1H), 4.88-4.74 (m, 1H), 4.41-4.21 (m, 5H), 4.18-3.95 (m, 2H), 3.95-3.65 (m, 2H), 3.62-3.40 (m, 1H), 2.99-2.66 (m, 4H), 2.46-1.85 (m, 10H), 1.59 (d, J = 7.0 Hz, 3H), 1.15-0.88 (m, 1H), 0.42-0.31 (m, 2H), 0.31-0.16 (m, 2H). |

TABLE 2-continued

| Ex | NMR |
|---|---|
| 3 | 1H NMR (400 MHz, Methanol-d4) d 8.06 (d, J = 8.1 Hz, 1H), 7.66-7.50 (m, 1H), 7.21 (d, J = 8.2 Hz, 1H), 6.98-6.78 (m, 2H), 5.24 (q, J = 6.9 Hz, 1H), 4.90-4.78 (m, 1H), 4.39-4.20 (m, 5H), 4.17-3.96 (m, 2H), 3.93-3.66 (m, 2H), 3.61-3.39 (m, 1H), 2.84 (d, J = 2.3 Hz, 4H), 2.43-1.82 (m, 10H), 1.59 (d, J = 7.1 Hz, 3H), 1.14-0.95 (m, 1H), 0.48-0.32 (m, 2H), 0.32-0.14 (m, 2H). |
| 7 | 1H NMR (400 MHz, Chloroform-d) δ 8.01 (dd, J = 8.1, 2.4 Hz, 1H), 7.81 (s, 1H), 7.68 (s, 0H), 7.14 (dd, J = 8.1, 3.2 Hz, 1H), 6.75 (s, 1H), 5.29 (dt, J = 6.9, 3.8 Hz, 1H), 4.69 (s, 2H), 4.21 (s, 4H), 3.85 (s, 3H), 3.30-3.12 (m, 1H), 2.84 (s, 3H), 2.38 (s, 1H), 2.23-2.05 (m, 1H), 1.95-1.71 (m, 3H), 1.58 (dd, J = 7.0, 2.2 Hz, 4H), 1.50-1.38 (m, 4H), 0.93 (s, 1H), 0.35 (d, J = 8.2 Hz, 2H), 0.13 (dt, J = 11.5, 6.1 Hz, 2H). |
| 8 | 1H NMR (400 MHz, Methanol-d) d 8.00 (d, J = 8.1 Hz, 1H), 7.50 (d, J = 1.3 Hz, 1H), 7.16 (s, 1H), 6.76-6.61 (m, 2H), 5.18 (q, J = 6.9 Hz, 1H), 4.41-4.29 (m, 2H), 4.23 (s, 3H), 3.95-3.81 (m, 1H), 2.85 (s, 3H), 2.65-2.35 (m, 3H), 2.35-2.13 (m, 2H), 2.13-1.98 (m, 2H), 1.98-1.66 (m, 5H), 1.59-1.43 (m, 5H), 1.06-0.89 (m, 1H), 0.41-0.27 (m, 2H), 0.20 (d, J = 5.8 Hz, 2H). |
| 9 | 1H NMR (400 MHz, Methanol-d) d 8.03 (d, J = 8.1 Hz, 1H), 7.45 (s, 1H), 7.20 (d, J = 8.1 Hz, 1H), 6.89-6.64 (m, 2H), 5.19 (q, J = 6.8 Hz, 1H), 4.59-4.29 (m, 3H), 4.26 (s, 3H), 3.55-3.37 (m, 2H), 2.84 (s, 3H), 2.62-2.36 (m, 2H), 2.36-2.13 (m, 3H), 2.01-1.65 (m, 7H), 1.57 (d, J = 7.0 Hz, 3H), 1.12-0.91 (m, 1H), 0.43-0.29 (m, 2H), 0.29-0.08 (m, 2H). |
| 10 | 1H NMR (400 MHz, Chloroform-d) δ 7.98 (d, J = 8.1 Hz, 1H), 7.72 (d, J = 8.1 Hz, 2H), 7.59 (dt, J = 20.6, 7.6 Hz, 3H), 7.47 (d, J = 7.5 Hz, 1H), 7.17 (d, J = 8.1 Hz, 1H), 6.71 (s, 1H), 5.48 (p, J = 6.8 Hz, 1H), 4.73-4.55 (m, 2H), 4.19 (d, J = 18.1 Hz, 5H), 3.79 (s, 1H), 2.81 (s, 3H), 2.33 (s, 1H), 2.16-1.99 (m, 0H), 1.78 (d, J = 42.0 Hz, 3H), 1.66 (d, J = 6.7 Hz, 3H), 1.55 (d, J = 12.7 Hz, 1H), 0.90 (d, J = 7.9 Hz, 1H), 0.28 (d, J = 8.3 Hz, 2H), 0.06 (t, J = 6.1 Hz, 3H). |
| 11 | 1H NMR (400 MHz, Chloroform-d) δ 8.01 (d, J = 8.1 Hz, 1H), 7.74 (dd, J = 14.7, 6.9 Hz, 3H), 7.66 (d, J = 7.4 Hz, 1H), 7.59-7.48 (m, 2H), 7.33 (s, 0H), 7.20 (d, J = 8.2 Hz, 1H), 6.75 (s, 1H), 6.72 (s, 0H), 5.46 (p, J = 6.7 Hz, 1H), 4.63 (d, J = 7.1 Hz, 2H), 4.23 (d, J = 11.4 Hz, 2H), 4.15 (d, J = 11.2 Hz, 3H), 3.82 (s, 1H), 2.82 (s, 3H), 2.36 (s, 1H), 2.18-2.02 (m, 0H), 1.94-1.71 (m, 3H), 1.67 (d, J = 6.7 Hz, 3H), 1.57 (d, J = 13.6 Hz, 1H), 0.91 (d, J = 6.3 Hz, 0H), 0.32 (dd, J = 8.3, 2.7 Hz, 2H), 0.13-0.03 (m, 3H). |
| 13 | 1H NMR (400 MHz, DMSO-d6) δ 9.38 (s, 1H), 9.02 (s, 1H), 8.25 (d, J = 7.9 Hz, 1H), 7.94 (d, J = 8.0 Hz, 1H), 7.34 (d, J = 1.2 Hz, 1H), 7.07 (d, J = 3.5 Hz, 1H), 6.58 (s, 1H), 6.34 (s, 1H), 5.12-4.95 (m, 1H), 4.95-4.74 (m, 1H), 4.58-4.29 (m, 2H), 4.28-4.11 (m, 1H), 4.07 (s, 3H), 4.06-3.82 (m, 6H), 3.16-2.92 (m, 3H), 2.81 (s, 3H), 2.05-1.90 (m, 1H), 1.91-1.63 (m, 1H), 1.46 (d, J = 6.9 Hz, 6H), 1.26-1.20 (m, 1H), 1.19-1.10 (m, 2H), 0.49-0.32 (m, 1H), 0.32-0.20 (m, 5H). |
| 15 | 1H NMR (400 MHz, Chloroform-d) δ 8.15 (td, J = 8.0, 1.9 Hz, 1H), 7.96 (d, J = 8.1 Hz, 1H), 7.78 (s, 1H), 7.51-7.43 (m, 1H), 7.27-7.21 (m, 1H), 7.15 (dt, J = 7.5, 6.0 Hz, 2H), 6.72 (d, J = 3.5 Hz, 2H), 5.53-5.41 (m, 1H), 4.65 (d, J = 29.4 Hz, 1H), 4.39-4.21 (m, 1H), 4.17 (s, 4H), 3.82 (s, 1H), 2.79 (s, 3H), 2.35 (s, 1H), 2.07 (dd, J = 18.8, 9.5 Hz, 1H), 1.79 (d, J = 44.4 Hz, 2H), 1.66 (d, J = 6.6 Hz, 3H), 1.57 (d, J = 13.2 Hz, 1H), 1.00-0.85 (m, 1H), 0.31 (d, J = 8.0 Hz, 2H), 0.22-0.11 (m, 2H). |
| 16 | 1H NMR (400 MHz, Chloroform-d) δ 7.99 (d, J = 8.1 Hz, 1H), 7.80-7.67 (m, 2H), 7.38 (ddd, J = 14.7, 8.4, 6.3 Hz, 1H), 7.19 (d, J = 8.1 Hz, 1H), 6.96 (t, J = 8.2 Hz, 2H), 6.73 (s, 1H), 5.50 (p, J = 6.9 Hz, 1H), 4.65 (s, 2H), 4.18 (s, 3H), 3.80 (s, 1H), 2.82 (s, 3H), 2.34 (s, 1H), 1.93-1.71 (m, 2H), 1.68 (d, J = 6.7 Hz, 3H), 1.55 (d, J = 13.3 Hz, 1H), 0.92 (s, 0H), 0.31 (d, J = 8.0 Hz, 2H), 0.12-0.03 (m, 3H). |
| 17 | 1H NMR (400 MHz, Chloroform-d) δ 8.18 (d, J = 7.6 Hz, 1H), 7.96 (d, J = 8.1 Hz, 1H), 7.80 (s, 1H), 7.46 (ddd, J = 8.9, 7.3, 1.9 Hz, 1H), 7.18 (d, J = 8.2 Hz, 1H), 7.11-6.98 (m, 2H), 6.74 (d, J = 5.7 Hz, 2H), 5.51 (q, J = 6.9 Hz, 1H), 4.69 (d, J = 23.4 Hz, 2H), 4.32 (d, J = 6.9 Hz, 2H), 4.19 (s, 4H), 4.02 (s, 3H), 3.83 (s, 2H), 2.83 (s, 3H), 2.36 (s, 1H), 2.15-2.02 (m, 0H), 1.78 (d, J = 36.1 Hz, 4H), 1.65 (d, J = 6.7 Hz, 3H), 1.57 (d, J = 13.3 Hz, 1H), 0.94 (s, 0H), 0.30 (d, J = 8.0 Hz, 3H), 0.18-0.01 (m, 2H). |
| 18 | 1H NMR (400 MHz, Acetonitrile-d3) δ 8.05 (d, J = 8.2 Hz, 1H), 7.93 (brs, 1H), 7.87 (s, 1H), 7.30-7.15 (m, 2H), 6.78 (s, 1H), 6.09 (t, J = 60 Hz, 0.5H), 6.08 (t, J = 60 Hz, 0.5H), 5.28-5.14 (m, 1H), 4.90 (brs, 1H), 4.58 (brs, 1H), 4.45-4.13 (m, 3H), 4.18 (s, 3H), 4.07 (m, 1H), 4.02-3.63 (m, 4H), 3.03 (brs, 2H), 2.78 (s, 3H), 2.38-2.21 (m, 1H), 2.35 (d, J = 2.6 Hz, 6H), 2.11-2.02 (m, 2H), 1.53 (d, J = 6.9 Hz, 3H), 1.19-1.03 (m, 1H), 0.41-0.17 (m, 4H). |
| 19 | 1H NMR (400 MHz, Methanol-d4) δ 8.03 (s, 1H), 7.19 (d, J = 8.1 Hz, 1H), 6.79 (s, 1H), 6.47 (s, 1H), 5.96 (d, J = 1.4 Hz, 1H), 5.23 (q, J = 6.9 Hz, 1H), 4.80-4.39 (m, 2H), 4.33-4.15 (m, 2H), 3.87-3.75 (m, 1H), 2.84 (s, 3H), 2.54-2.42 (m, 1H), 2.37 (d, J = 2.5 Hz, 6H), 2.10-1.86 (m, 3H), 1.76 (t, J = 7.8 Hz, 1H), 1.59 (d, J = 7.0 Hz, 3H), 1.46 (dd, J = 13.2, 4.5 Hz, 1H), 1.11-0.96 (m, 1H), 0.47-0.34 (m, 2H), 0.24-0.16 (m, 2H). |
| 20 | 1H NMR (400 MHz, Methanol-d4) δ 8.02 (d, J = 8.1 Hz, 1H), 7.47 (d, J = 1.2 Hz, 1H), 7.18 (d, J = 8.1 Hz, 1H), 6.75 (s, 1H), 6.69 (d, J = 1.4 Hz, 1H), 5.23 (q, J = 7.0 Hz, 1H), 4.47-4.40 (m, 1H), 4.33 (h, J = 7.1 Hz, 1H), 4.17-4.03 (m, 2H), 3.96 (dd, J = 12.2, 8.6 Hz, 1H), 3.78-3.54 (m, 1H), 3.55-3.37 (m, 2H), 2.85 (s, 3H), 2.44-2.28 (m, 7H), 2.13-1.92 (m, 1H), 1.59 (d, J = 7.0 Hz, 3H), 1.10-0.99 (m, 1H), 0.41-0.26 (m, 2H), 0.24-0.14 (m, 2H). |
| 21 | 1H NMR (400 MHz, Methanol-d4) d 8.02 (d, J = 8.1 Hz, 1H), 7.47 (d, J = 1.3 Hz, 1H), 7.18 (d, J = 8.1 Hz, 1H), 6.74 (s, 1H), 6.68 (d, J = 1.3 Hz, 1H), 5.23 (q, J = 7.0 Hz, 1H), 4.49-4.39 (m, 1H), 4.33 (h, J = 7.1 Hz, 2H), 4.23 (s, 3H), 4.09 (s, 2H), 3.96 (dd, J = 12.3, 8.6 Hz, 1H), 3.67 (s, 1H), 3.56-3.39 (m, 2H), 2.85 (s, 3H), 2.37 (d, J = 2.5 Hz, 7H), 2.13-1.86 (m, 1H), 1.59 (d, J = 7.0 Hz, 3H), 1.13-0.95 (m, 1H), 0.40-0.29 (m, 2H), 0.22-0.15 (m, 2H). |
| 23 | 1H NMR (400 MHz, Chloroform-d) δ 7.97 (d, J = 8.0 Hz, 1H), 7.79 (d, J = 19.4 Hz, 2H), 7.17 (d, J = 8.1 Hz, 1H), 6.70 (d, J = 13.5 Hz, 2H), 5.47-5.38 (m, 1H), 4.86 (s, 2H), 4.30 (s, 2H), 4.18 (s, 4H), 3.93 (s, 3H), 3.79 (s, 1H), 3.40 (s, 3H), 2.82 (s, 3H), 2.35 (s, 1H), 2.10 (d, J = 13.5 Hz, 1H), 1.79 (d, J = 47.4 Hz, 4H), 1.56 (d, J = 14.6 Hz, 2H), 0.95 (s, 0H), 0.33 (d, J = 8.0 Hz, 2H), 0.17-0.06 (m, 2H). |

TABLE 2-continued

| Ex | NMR |
|---|---|
| 24 | 1H NMR (400 MHz, Methanol-d4) δ 8.04 (d, J = 8.1 Hz, 1H), 7.48 (s, 1H), 7.20 (d, J = 8.1 Hz, 1H), 6.81 (s, 2H), 5.23 (q, J = 7.0, 6.1 Hz, 1H), 4.51-4.19 (m, 5H), 4.15-3.91 (m, 1H), 3.81-3.58 (m, 1H), 2.83 (s, 3H), 2.37 (d, J = 2.5 Hz, 6H), 2.19-2.06 (m, 1H), 1.59 (d, J = 7.0 Hz, 3H), 1.46-1.34 (m, 1H), 1.11-0.98 (m, 2H), 0.42-0.31 (m, 2H), 0.26-0.10 (m, 2H). |
| 25 | 1H NMR (400 MHz, Methanol-d4) δ 8.04 (d, J = 8.1 Hz, 1H), 7.48 (s, 1H), 7.20 (d, J = 8.1 Hz, 1H), 6.81 (s, 2H), 5.23 (q, J = 7.0, 6.1 Hz, 1H), 4.51-4.19 (m, 5H), 4.15-3.91 (m, 1H), 3.81-3.58 (m, 1H), 2.83 (s, 3H), 2.37 (d, J = 2.5 Hz, 6H), 2.19-2.06 (m, 1H), 1.59 (d, J = 7.0 Hz, 3H), 1.46-1.34 (m, 1H), 1.11-0.98 (m, 2H), 0.42-0.31 (m, 2H), 0.26-0.10 (m, 2H). |
| 26 | 1H NMR (400 MHz, Chloroform-d) δ 7.96 (d, J = 8.0 Hz, 1H), 7.82 (s, 1H), 7.78 (s, 1H), 7.14 (d, J = 8.1 Hz, 1H), 6.74 (d, J = 10.1 Hz, 2H), 5.49-5.38 (m, 1H), 4.69 (s, 2H), 4.35 (dt, J = 20.9, 10.5 Hz, 2H), 4.21 (s, 4H), 4.08 (s, 3H), 3.76 (s, 3H), 3.50 (s, 17H), 2.83 (s, 3H), 2.36 (s, 1H), 2.09 (d, J = 14.5 Hz, 0H), 1.79 (d, J = 42.2 Hz, 4H), 1.61 (d, J = 6.7 Hz, 4H), 0.99 (s, 0H), 0.33 (d, J = 7.9 Hz, 2H), 0.12 (d, J = 4.3 Hz, 3H). |
| 27 | 1H NMR (400 MHz, DMSO-d6) δ 8.58 (d, J = 5.7 Hz, 1H), 8.30 (d, J = 7.9 Hz, 1H), 7.98 (d, J = 8.0 Hz, 1H), 7.98 (d, J =1.2 Hz, 1H), 7.11 (d, J = 8.0 Hz, 1H), 6.65 (s, 1 H), 6.63 (d, J = 1.2 Hz, 1H), 5.13-5.01 (m, 1H), 4.54-4.39 (m, 2H), 4.34 (brs, 1H), 4.25 (brs, 1H), 4.12 (s, 3H), 3.54 (d, J = 12.4 Hz, 1H), 3.34 (d, J = 12.4 Hz, 1H), 2.86 (s, 3H), 2.32 (s, 3H), 2.32 (s, 3H), 2.18-1.87 (m, 4H), 1.48 (d, J = 6.2 Hz, 3H), 1.21-1.12 (m, 1H), 0.34-0.24 (m, 4H). |
| 29 | 1H NMR (400 MHz, DMSO-d6) δ 8.14 (brs, 3H), 7.97 (d, J = 8.1 Hz, 1H), 7.89 (d, J = 7.8 Hz, 1H), 7.48 (s, 1H), 7.16 (d, J = 8.1 Hz, 1H), 6.63 (s, 1H), 6.41 (s, 1H), 5.15-5.04 (m, 1H), 4.50-4.39 (m, 2H), 4.11 (s, 3H), 3.62 (s, 2H), 3.33 (s, 3H), 2.83 (s, 3H), 2.40-2.24 (m, 4H), 1.97-1.79 (m, 7H), 1.79-1.58 (m, 2H), 1.45 (d, J = 6.9 Hz, 3H), 1.36 (dd, J = 12.9, 4.4 Hz, 1H), 1.19-1.07 (m, 1H), 0.34-0.19 (m, 4H). |
| 30 | 1H NMR (400 MHz, DMSO-d6) δ 10.80 (d, J = 7.5 Hz, 1H), 8.34 (dd, J = 7.1, 2.1 Hz, 1H), 8.23-8.02 (m, 4H), 7.99 (d, J = 8.0 Hz, 1H), 7.47 (s, 1H), 7.17 (d, J = 8.0 Hz, 1H), 6.64 (s, 1H), 6.50 (t, J = 6.9 Hz, 1H), 6.39 (s, 1H), 5.29 (q, J = 6.9 Hz, 1H), 4.64-4.36 (m, 4H), 4.11 (s, 3H), 3.76 (s, 1H), 3.58 (s, 3H), 2.84 (s, 3H), 1.84 (s, 4H), 1.65 (d, J = 9.8 Hz, 1H), 1.53 (d, J = 6.7 Hz, 3H), 1.35 (dd, J = 13.0, 4.5 Hz, 1H), 1.16 (d, J = 6.7 Hz, 1H), 0.43-0.17 (m, 4H). |
| 32 | 1H NMR (400 MHz, DMSO-d6) δ 8.27 (d, J = 7.8 Hz, 1H), 8.14 (brs, 3H), 7.97 (d, J = 8.0 Hz, 1H), 7.48 (s, 1H), 7.16 (d, J = 8.1 Hz, 1H), 6.63 (s, 1H), 6.42 (s, 1H), 5.14-5.03 (m, 1H), 4.53 (brs, 2H), 4.50-4.37 (m, 2H), 4.11 (s, 3H), 3.77 (brs, 1H), 3.15 (s, 3H), 2.83 (s, 3H), 2.54 (d, J = 1.8 Hz, 2H), 2.39-2.27 (m, 1H), 2.13-1.99 (m, 4H), 1.95-1.73 (m, 3H), 1.72-1.51 (m, 3H), 1.44 (d, J = 6.9 Hz, 3H), 1.36 (dd, J = 12.8, 4.4 Hz, 1H), 1.17-1.05 (m, 1H), 0.37-0.17 (m, 4H). |
| 33 | 1H NMR (400 MHz, DMSO-d6) δ 8.30 (d, J = 7.7 Hz, 1H), 8.14 (brs, 3H), 7.97 (d, J = 8.1 Hz, 1H), 7.48 (s, 1H), 7.16 (d, J = 8.1 Hz, 1H), 6.63 (s, 1H), 6.40 (s, 1H), 5.13-5.04 (m, 1H), 4.52 (brs, 2H), 4.50-4.41 (m, 2H), 4.11 (s, 3H), 3.76 (brs, 1H), 3.22 (s, 3H), 2.83 (s, 3H), 2.35-2.30 (m, 1H), 1.93-1.73 (m, 3H), 1.71-1.58 (m, 1H), 1.45 (d, J = 6.9 Hz, 3H), 1.36 (dd, J = 12.8, 4.3 Hz, 1H), 1.20-1.06 (m, 1H), 0.72-0.67 (m, 2H), 0.65-0.58 (m, 2H), 0.33-0.18 (m, 4H). |
| 34 | 1H NMR (400 MHz, DMSO-d6) δ 8.27 (d, J = 7.8 Hz, 1H), 8.14 (brs, 3H), 7.97 (d, J = 8.0 Hz, 1H), 7.48 (s, 1H), 7.16 (d, J = 8.1 Hz, 1H), 6.63 (s, 1H), 6.42 (s, 1H), 5.14-5.03 (m, 1H), 4.53 (brs, 2H), 4.50-4.37 (m, 2H), 4.11 (s, 3H), 3.77 (brs, 1H), 3.15 (s, 3H), 2.83 (s, 3H), 2.54 (d, J = 1.8 Hz, 2H), 2.39-2.27 (m, 1H), 2.13-1.99 (m, 4H), 1.95-1.73 (m, 3H), 1.72-1.51 (m, 3H), 1.44 (d, J = 6.9 Hz, 3H), 1.36 (dd, J = 12.8, 4.4 Hz, 1H), 1.17-1.05 (m, 1H), 0.37-0.17 (m, 4H). |
| 35 | 1H NMR (400 MHz, DMSO-d6) δ 8.30 (d, J = 7.7 Hz, 1H), 8.14 (brs, 3H), 7.97 (d, J = 8.1 Hz, 1H), 7.48 (s, 1H), 7.16 (d, J = 8.1 Hz, 1H), 6.63 (s, 1H), 6.40 (s, 1H), 5.13-5.04 (m, 1H), 4.52 (brs, 2H), 4.50-4.41 (m, 2H), 4.11 (s, 3H), 3.76 (brs, 1H), 3.22 (s, 3H), 2.83 (s, 3H), 2.35-2.30 (m, 1H), 1.93-1.73 (m, 3H), 1.71-1.58 (m, 1H), 1.45 (d, J = 6.9 Hz, 3H), 1.36 (dd, J = 12.8, 4.3 Hz, 1H), 1.20-1.06 (m, 1H), 0.72-0.67 (m, 2H), 0.65-0.58 (m, 2H), 0.33-0.18 (m, 4H). |
| 36 | 1H NMR (400 MHz, DMSO-d6) δ 8.27 (d, J = 7.8 Hz, 1H), 8.14 (brs, 3H), 7.97 (d, J = 8.0 Hz, 1H), 7.48 (s, 1H), 7.16 (d, J = 8.1 Hz, 1H), 6.63 (s, 1H), 6.42 (s, 1H), 5.14-5.03 (m, 1H), 4.53 (brs, 2H), 4.50-4.37 (m, 2H), 4.11 (s, 3H), 3.77 (brs, 1H), 3.15 (s, 3H), 2.83 (s, 3H), 2.54 (d, J = 1.8 Hz, 2H), 2.39-2.27 (m, 1H), 2.13-1.99 (m, 4H), 1.95-1.73 (m, 3H), 1.72-1.51 (m, 3H), 1.44 (d, J = 6.9 Hz, 3H), 1.36 (dd, J = 12.8, 4.4 Hz, 1H), 1.17-1.05 (m, 1H), 0.37-0.17 (m, 4H). |
| 37 | 1H NMR (400 MHz, DMSO-d6) δ 8.30 (d, J = 7.7 Hz, 1H), 8.14 (brs, 3H), 7.97 (d, J = 8.1 Hz, 1H), 7.48 (s, 1H), 7.16 (d, J = 8.1 Hz, 1H), 6.63 (s, 1H), 6.40 (s, 1H), 5.13-5.04 (m, 1H), 4.52 (brs, 2H), 4.50-4.41 (m, 2H), 4.11 (s, 3H), 3.76 (brs, 1H), 3.22 (s, 3H), 2.83 (s, 3H), 2.35-2.30 (m, 1H), 1.93-1.73 (m, 3H), 1.71-1.58 (m, 1H), 1.45 (d, J = 6.9 Hz, 3H), 1.36 (dd, J = 12.8, 4.3 Hz, 1H), 1.20-1.06 (m, 1H), 0.72-0.67 (m, 2H), 0.65-0.58 (m, 2H), 0.33-0.18 (m, 4H). |
| 38 | 1H NMR (400 MHz, DMSO-d6) δ 8.27 (d, J = 7.8 Hz, 1H), 8.14 (brs, 3H), 7.97 (d, J = 8.0 Hz, 1H), 7.48 (s, 1H), 7.16 (d, J = 8.1 Hz, 1H), 6.63 (s, 1H), 6.42 (s, 1H), 5.14-5.03 (m, 1H), 4.53 (brs, 2H), 4.50-4.37 (m, 2H), 4.11 (s, 3H), 3.77 (brs, 1H), 3.15 (s, 3H), 2.83 (s, 3H), 2.54 (d, J = 1.8 Hz, 2H), 2.39-2.27 (m, 1H), 2.13-1.99 (m, 4H), 1.95-1.73 (m, 3H), 1.72-1.51 (m, 3H), 1.44 (d, J = 6.9 Hz, 3H), 1.36 (dd, J = 12.8, 4.4 Hz, 1H), 1.17-1.05 (m, 1H), 0.37-0.17 (m, 4H). |
| 39 | 1H NMR (400 MHz, DMSO-d6) δ 8.30 (d, J = 7.7 Hz, 1H), 8.14 (brs, 3H), 7.97 (d, J = 8.1 Hz, 1H), 7.48 (s, 1H), 7.16 (d, J = 8.1 Hz, 1H), 6.63 (s, 1H), 6.40 (s, 1H), 5.13-5.04 (m, 1H), 4.52 (brs, 2H), 4.50-4.41 (m, 2H), 4.11 (s, 3H), 3.76 (brs, 1H), 3.22 (s, 3H), 2.83 (s, 3H), 2.35-2.30 (m, 1H), 1.93-1.73 (m, 3H), 1.71-1.58 (m, 1H), 1.45 (d, J = 6.9 Hz, 3H), 1.36 (dd, J = 12.8, 4.3 Hz, 1H), 1.20-1.06 (m, 1H), 0.72-0.67 (m, 2H), 0.65-0.58 (m, 2H), 0.33-0.18 (m, 4H). |

TABLE 2-continued

| Ex | NMR |
|---|---|
| 40 | 1H NMR (400 MHz, DMSO-d6) δ 8.27 (d, J = 7.8 Hz, 1H), 8.14 (brs, 3H), 7.97 (d, J = 8.0 Hz, 1H), 7.48 (s, 1H), 7.16 (d, J = 8.1 Hz, 1H), 6.63 (s, 1H), 6.42 (s, 1H), 5.14-5.03 (m, 1H), 4.53 (brs, 2H), 4.50-4.37 (m, 2H), 4.11 (s, 3H), 3.77 (brs, 1H), 3.15 (s, 3H), 2.83 (s, 3H), 2.54 (d, J = 1.8 Hz, 2H), 2.39-2.27 (m, 1H), 2.13-1.99 (m, 4H), 1.95-1.73 (m, 3H), 1.72-1.51 (m, 3H), 1.44 (d, J = 6.9 Hz, 3H), 1.36 (dd, J = 12.8, 4.4 Hz, 1H), 1.17-1.05 (m, 1H), 0.37-0.17 (m, 4H). |
| 41 | 1H NMR (400 MHz, DMSO-d6) δ 8.30 (d, J = 7.7 Hz, 1H), 8.14 (brs, 3H), 7.97 (d, J = 8.1 Hz, 1H), 7.48 (s, 1H), 7.16 (d, J = 8.1 Hz, 1H), 6.63 (s, 1H), 6.40 (s, 1H), 5.13-5.04 (m, 1H), 4.52 (brs, 2H), 4.50-4.41 (m, 2H), 4.11 (s, 3H), 3.76 (brs, 1H), 3.22 (s, 3H), 2.83 (s, 3H), 2.35-2.30 (m, 1H), 1.93-1.73 (m, 3H), 1.71-1.58 (m, 1H), 1.45 (d, J = 6.9 Hz, 3H), 1.36 (dd, J = 12.8, 4.3 Hz, 1H), 1.20-1.06 (m, 1H), 0.72-0.67 (m, 2H), 0.65-0.58 (m, 2H), 0.33-0.18 (m, 4H). |
| 42 | 1H NMR (400 MHz, DMSO-d6) δ 8.27 (d, J = 7.8 Hz, 1H), 8.14 (brs, 3H), 7.97 (d, J = 8.0 Hz, 1H), 7.48 (s, 1H), 7.16 (d, J = 8.1 Hz, 1H), 6.63 (s, 1H), 6.42 (s, 1H), 5.14-5.03 (m, 1H), 4.53 (brs, 2H), 4.50-4.37 (m, 2H), 4.11 (s, 3H), 3.77 (brs, 1H), 3.15 (s, 3H), 2.83 (s, 3H), 2.54 (d, J = 1.8 Hz, 2H), 2.39-2.27 (m, 1H), 2.13-1.99 (m, 4H), 1.95-1.73 (m, 3H), 1.72-1.51 (m, 3H), 1.44 (d, J = 6.9 Hz, 3H), 1.36 (dd, J = 12.8, 4.4 Hz, 1H), 1.17-1.05 (m, 1H), 0.37-0.17 (m, 4H). |
| 46 | 1H NMR (400 MHz, DMSO-d6) δ 8.27 (d, J = 7.8 Hz, 1H), 8.14 (brs, 3H), 7.97 (d, J = 8.0 Hz, 1H), 7.48 (s, 1H), 7.16 (d, J = 8.1 Hz, 1H), 6.63 (s, 1H), 6.42 (s, 1H), 5.14-5.03 (m, 1H), 4.53 (brs, 2H), 4.50-4.37 (m, 2H), 4.11 (s, 3H), 3.77 (brs, 1H), 3.15 (s, 3H), 2.83 (s, 3H), 2.54 (d, J = 1.8 Hz, 2H), 2.39-2.27 (m, 1H), 2.13-1.99 (m, 4H), 1.95-1.73 (m, 3H), 1.72-1.51 (m, 3H), 1.44 (d, J = 6.9 Hz, 3H), 1.36 (dd, J = 12.8, 4.4 Hz, 1H), 1.17-1.05 (m, 1H), 0.37-0.17 (m, 4H). |
| 47 | 1H NMR (400 MHz, DMSO-d6) δ 8.30 (d, J = 7.7 Hz, 1H), 8.14 (brs, 3H), 7.97 (d, J = 8.1 Hz, 1H), 7.48 (s, 1H), 7.16 (d, J = 8.1 Hz, 1H), 6.63 (s, 1H), 6.40 (s, 1H), 5.13-5.04 (m, 1H), 4.52 (brs, 2H), 4.50-4.41 (m, 2H), 4.11 (s, 3H), 3.76 (brs, 1H), 3.22 (s, 3H), 2.83 (s, 3H), 2.35-2.30 (m, 1H), 1.93-1.73 (m, 3H), 1.71-1.58 (m, 1H), 1.45 (d, J = 6.9 Hz, 3H), 1.36 (dd, J = 12.8, 4.3 Hz, 1H), 1.20-1.06 (m, 1H), 0.72-0.67 (m, 2H), 0.65-0.58 (m, 2H), 0.33-0.18 (m, 4H). |
| 48 | 1H NMR (400 MHz, DMSO-d6) δ 8.27 (d, J = 7.8 Hz, 1H), 8.14 (brs, 3H), 7.97 (d, J = 8.0 Hz, 1H), 7.48 (s, 1H), 7.16 (d, J = 8.1 Hz, 1H), 6.63 (s, 1H), 6.42 (s, 1H), 5.14-5.03 (m, 1H), 4.53 (brs, 2H), 4.50-4.37 (m, 2H), 4.11 (s, 3H), 3.77 (brs, 1H), 3.15 (s, 3H), 2.83 (s, 3H), 2.54 (d, J = 1.8 Hz, 2H), 2.39-2.27 (m, 1H), 2.13-1.99 (m, 4H), 1.95-1.73 (m, 3H), 1.72-1.51 (m, 3H), 1.44 (d, J = 6.9 Hz, 3H), 1.36 (dd, J = 12.8, 4.4 Hz, 1H), 1.17-1.05 (m, 1H), 0.37-0.17 (m, 4H). |
| 49 | 1H NMR (400 MHz, DMSO-d6) δ 8.30 (d, J = 7.7 Hz, 1H), 8.14 (brs, 3H), 7.97 (d, J = 8.1 Hz, 1H), 7.48 (s, 1H), 7.16 (d, J = 8.1 Hz, 1H), 6.63 (s, 1H), 6.40 (s, 1H), 5.13-5.04 (m, 1H), 4.52 (brs, 2H), 4.50-4.41 (m, 2H), 4.11 (s, 3H), 3.76 (brs, 1H), 3.22 (s, 3H), 2.83 (s, 3H), 2.35-2.30 (m, 1H), 1.93-1.73 (m, 3H), 1.71-1.58 (m, 1H), 1.45 (d, J = 6.9 Hz, 3H), 1.36 (dd, J = 12.8, 4.3 Hz, 1H), 1.20-1.06 (m, 1H), 0.72-0.67 (m, 2H), 0.65-0.58 (m, 2H), 0.33-0.18 (m, 4H). |
| 50 | 1H NMR (400 MHz, DMSO-d6) δ 8.27 (d, J = 7.8 Hz, 1H), 8.14 (brs, 3H), 7.97 (d, J = 8.0 Hz, 1H), 7.48 (s, 1H), 7.16 (d, J = 8.1 Hz, 1H), 6.63 (s, 1H), 6.42 (s, 1H), 5.14-5.03 (m, 1H), 4.53 (brs, 2H), 4.50-4.37 (m, 2H), 4.11 (s, 3H), 3.77 (brs, 1H), 3.15 (s, 3H), 2.83 (s, 3H), 2.54 (d, J = 1.8 Hz, 2H), 2.39-2.27 (m, 1H), 2.13-1.99 (m, 4H), 1.95-1.73 (m, 3H), 1.72-1.51 (m, 3H), 1.44 (d, J = 6.9 Hz, 3H), 1.36 (dd, J = 12.8, 4.4 Hz, 1H), 1.17-1.05 (m, 1H), 0.37-0.17 (m, 4H). |
| 51 | 1H NMR (400 MHz, DMSO-d6) δ 8.30 (d, J = 7.7 Hz, 1H), 8.14 (brs, 3H), 7.97 (d, J = 8.1 Hz, 1H), 7.48 (s, 1H), 7.16 (d, J = 8.1 Hz, 1H), 6.63 (s, 1H), 6.40 (s, 1H), 5.13-5.04 (m, 1H), 4.52 (brs, 2H), 4.50-4.41 (m, 2H), 4.11 (s, 3H), 3.76 (brs, 1H), 3.22 (s, 3H), 2.83 (s, 3H), 2.35-2.30 (m, 1H), 1.93-1.73 (m, 3H), 1.71-1.58 (m, 1H), 1.45 (d, J = 6.9 Hz, 3H), 1.36 (dd, J = 12.8, 4.3 Hz, 1H), 1.20-1.06 (m, 1H), 0.72-0.67 (m, 2H), 0.65-0.58 (m, 2H), 0.33-0.18 (m, 4H). |
| 52 | 1H NMR (400 MHz, DMSO-d6) δ 8.27 (d, J = 7.8 Hz, 1H), 8.14 (brs, 3H), 7.97 (d, J = 8.0 Hz, 1H), 7.48 (s, 1H), 7.16 (d, J = 8.1 Hz, 1H), 6.63 (s, 1H), 6.42 (s, 1H), 5.14-5.03 (m, 1H), 4.53 (brs, 2H), 4.50-4.37 (m, 2H), 4.11 (s, 3H), 3.77 (brs, 1H), 3.15 (s, 3H), 2.83 (s, 3H), 2.54 (d, J = 1.8 Hz, 2H), 2.39-2.27 (m, 1H), 2.13-1.99 (m, 4H), 1.95-1.73 (m, 3H), 1.72-1.51 (m, 3H), 1.44 (d, J = 6.9 Hz, 3H), 1.36 (dd, J = 12.8, 4.4 Hz, 1H), 1.17-1.05 (m, 1H), 0.37-0.17 (m, 4H). |
| 53 | 1H NMR (400 MHz, DMSO-d6) δ 8.30 (d, J = 7.7 Hz, 1H), 8.14 (brs, 3H), 7.97 (d, J = 8.1 Hz, 1H), 7.48 (s, 1H), 7.16 (d, J = 8.1 Hz, 1H), 6.63 (s, 1H), 6.40 (s, 1H), 5.13-5.04 (m, 1H), 4.52 (brs, 2H), 4.50-4.41 (m, 2H), 4.11 (s, 3H), 3.76 (brs, 1H), 3.22 (s, 3H), 2.83 (s, 3H), 2.35-2.30 (m, 1H), 1.93-1.73 (m, 3H), 1.71-1.58 (m, 1H), 1.45 (d, J = 6.9 Hz, 3H), 1.36 (dd, J = 12.8, 4.3 Hz, 1H), 1.20-1.06 (m, 1H), 0.72-0.67 (m, 2H), 0.65-0.58 (m, 2H), 0.33-0.18 (m, 4H). |
| 57 | 1H NMR (400 MHz, DMSO-d6) δ 8.83 (d, J = 7.8 Hz, 1H), 8.77-8.65 (m, 3H), 8.02-7.90 (m, 3H), 7.87 (s, 1H), 7.60-7.44 (m, 3H), 7.33-7.02 (m, 1H), 6.66 (d, J = 4.7 Hz, 2H), 5.32 (p, J = 7.5 Hz, 1H), 4.52-4.35 (m, 2H), 4.23-4.15 (m, 1H), 4.12 (s, 3H), 3.37 (d, J = 12.1 Hz, 1H), 3.23 (d, J = 12.3 Hz, 1H), 2.94-2.79 (m, 2H), 2.84 (s, 3H), 1.99-1.90 (m, 2H), 1.76-1.54 (m, 2H), 1.60 (d, J = 7.1 Hz, 3H), 1.19 (p, J = 6.8 Hz, 1H), 0.32-0.21 (m, 4H). |
| 58 | 1H NMR (400 MHz, DMSO-d6) δ 9.15-8.89 (m, 1H), 8.84 (d, J = 7.7 Hz, 1H), 8.61-8.51 (m, 1H), 8.02-7.90 (m, 3H), 7.59-7.40 (m, 4H), 7.22 (d, J = 7.9 Hz, 1H), 6.64 (s, 1H), 6.47-6.40 (m, 1H), 5.32 (p, J = 7.4 Hz, 1H), 4.43-4.37 (m, 2H), 4.11 (s, 3H), 4.03-3.76 (m, 1H), 3.77-3.44 (m, 3H), 3.34-3.19 (m, 1H), 2.99-2.89 (m, 1H), 2.81 (s, 3H), 2.70-2.65 (m, 1H), 1.85-1.51 (m, 5H), 1.60 (d, J = 7.1 Hz, 3H), 1.21-1.12 (m, 1H), 0.44-0.14 (m, 4H). |

TABLE 2-continued

| Ex | NMR |
|---|---|
| 59 | 1H NMR (400 MHz, DMSO-d6) δ 9.29 (s, 1H), 8.84 (d, J = 7.7 Hz, 1H), 8.65 (s, 1H), 7.99 (d, J = 8.1 Hz, 1H), 7.92 (d, J = 7.6 Hz, 2H), 7.58-7.51 (m, 1H), 7.50-7.43 (m, 2H), 7.38 (s, 1H), 7.23 (d, J = 8.1 Hz, 1H), 6.66 (s, 1H), 6.52 (s, 1H), 5.31 (p, J = 7.2 Hz, 1H), 4.41-4.26 (m, 2H), 4.10 (s, 3H), 3.75-3.46 (m, 3H), 3.43-3.08 (m, 4H), 2.78 (s, 3H), 2.52-2.40 (m, 1H), 2.15-2.05 (m, 1H), 1.84-1.74 (m, 2H), 1.58 (d, J = 7.1 Hz, 3H), 1.56-1.42 (m, 1H), 1.11 (p, J = 6.9 Hz, 1H), 0.42-0.08 (m, 4H). |
| 60 | 1H NMR (400 MHz, DMSO-d6) δ 8.09 (brs, 2H), 7.97 (d, J = 8.0 Hz, 1H), 7.89 (brs, 1H), 7.81 (d, J = 7.7 Hz, 1H), 7.35 (s, 1H), 7.13 (d, J = 8.1 Hz, 1H), 6.62 (s, 1H), 6.39 (s, 1H), 5.72 (brs, 1H), 5.13-5.01 (m, 1H), 4.78-4.58 (m, 1H), 4.52-4.35 (m , 2H), 4.20 (brs, 1H), 4.10 (s, 3H), 4.06 (brs, 2H), 3.50 (brs, 1H), 2.83 (s, 3H), 2.25-1.71 (m, 5H), 1.47 (d, J = 7.0 Hz, 3H), 1.18 (s, 9H), 0.38-0.24 (m, 4H). |
| 65 | 1H NMR (400 MHz, DMSO-d6) δ 8.12 (s, 4H), 8.00-7.87 (m, 2H), 7.46 (s, 1H), 7.10 (dd, J = 8.1, 3.6 Hz, 1H), 6.62 (s, 1H), 6.43 (d, J = 1.3 Hz, 1H), 5.14-4.97 (m, 1H), 4.64-4.21 (m, 3H), 4.10 (s, 3H), 3.73 (s, 1H), 3.37 (s, 2H), 2.79 (s, 3H), 2.39-2.18 (m, 1H), 1.95 (s, 2H), 1.80 (s, 8H), 1.70-1.55 (m, 1H), 1.44 (d, J = 7.0 Hz, 3H), 1.34 (dd, J = 12.8, 4.4 Hz, 1H), 1.16-1.04 (m, 1H), 0.31-0.25 (m, 2H), 0.25-0.15 (m, 2H). |
| 68 | 1H NMR (400 MHz, DMSO-d6) d 8.18 (s, 3H), 8.10 (d, J = 7.6 Hz, 1H), 7.97 (d, J = 8.0 Hz, 1H), 7.46 (s, 1H), 7.13 (d, J = 8.1 Hz, 1H), 6.63 (s, 1H), 6.41 (d, J = 1.3 Hz, 1H), 5.11 (p, J = 6.8 Hz, 1H), 4.72-4.51 (m, 2H), 4.54-4.33 (m, 2H), 4.10 (s, 3H), 3.79 (d, J = 37.4 Hz, 3H), 3.57-3.47 (m, 2H), 3.36 (s, 3H), 2.81 (s, 3H), 2.38-2.21 (m, 1H), 1.94-1.74 (m, 3H), 1.70-1.57 (m, 1H), 1.41 (d, J = 6.8 Hz, 3H), 1.35 (dd, J = 12.9, 4.4 Hz, 1H), 1.19-1.06 (m, 1H), 1.06-0.94 (m, 2H), 0.73-0.58 (m, 2H), 0.31-0.25 (m, 2H), 0.25-0.13 (m, 2H). |
| 69 | 1H NMR (400 MHz, DMSO-d6) δ 8.27 (dd, J = 7.9, 4.3 Hz, 1H), 8.18 (s, 3H), 7.95 (dd, J = 8.0, 5.7 Hz, 1H), 7.47 (s, 1H), 7.09 (dd, J = 20.1, 8.1 Hz, 1H), 6.61 (d, J = 3.3 Hz, 1H), 6.43 (s, 1H), 5.13-5.00 (m, 1H), 4.65-4.28 (m, 2H), 4.10 (s, 3H), 3.95-3.49 (m, 1H), 2.79 (d, J = 0.9 Hz, 3H), 2.38-2.17 (m, 1H), 2.10-1.98 (m, 1H), 1.92-1.73 (m, 3H), 1.69-1.56 (m, 1H), 1.42 (dd, J = 7.0, 5.8 Hz, 3H), 1.35 (dd, J = 12.8, 4.4 Hz, 1H), 1.28 (t, J = 3.9 Hz, 1H), 1.23-1.03 (m, 3H), 0.87-0.69 (m, 4H), 0.65-0.54 (m, 1H), 0.33-0.13 (m, 4H). |
| 72 | 1H NMR (400 MHz, DMSO-d6) δ 9.23 (s, 1H), 9.08 (d, J = 7.8 Hz, 1H), 8.64 (s, 1H), 8.11 (s, 3H), 7.98 (d, J = 8.1 Hz, 1H), 7.47 (s, 1H), 7.20 (d, J = 8.0 Hz, 1H), 6.62 (d, J = 1.1 Hz, 1H), 6.39 (s, 1H), 5.27 (p, J = 7.1 Hz, 1H), 4.62-4.33 (m, 4H), 4.10 (s, 3H), 3.89-3.64 (m, 1H), 2.82 (s, 3H), 2.39-2.22 (m, 1H), 1.96-1.77 (m, 3H), 1.74-1.51 (m, 4H), 1.35 (dd, J = 12.7, 4.3 Hz, 1H), 1.20-1.00 (m, 1H), 0.37-0.13 (m, 4H). |
| 73 | 1H NMR (400 MHz, DMSO-d6) δ 9.22 (d, J = 7.8 Hz, 1H), 8.35 (s, 1H), 8.09 (s, 3H), 7.99 (d, J = 8.1 Hz, 1H), 7.49 (s, 1H), 7.47 (s, 1H), 7.23 (d, J = 8.1 Hz, 1H), 6.63 (s, 1H), 6.38 (s, 1H), 5.26 (p, J = 7.2 Hz, 1H), 4.71-4.35 (m, 4H), 4.10 (s, 3H), 3.82-3.71 (m, 1H), 2.83 (s, 3H), 2.41-2.22 (m, 1H), 1.94-1.76 (m, 3H), 1.72-1.49 (m, 4H), 1.46-1.29 (m, 1H), 1.22-1.06 (m, 1H), 0.36-0.17 (m, 4H). |
| 74 | 1H NMR (400 MHz, DMSO-d6) δ 8.18 (d, J = 7.9 Hz, 1H), 8.10 (s, 3H), 8.04 (s, 1H), 7.96 (d, J = 8.0 Hz, 1H), 7.46 (s, 1H), 7.18 (d, J = 8.1 Hz, 1H), 6.61 (s, 1H), 6.39 (s, 1H), 5.24 (p, J = 7.1 Hz, 1H), 4.66-4.35 (m, 4H), 4.10 (s, 3H), 4.07 (t, J = 7.3 Hz, 2H), 3.83-3.73 (m, 1H), 2.98 (t, J = 7.4 Hz, 2H), 2.82 (s, 3H), 2.63-2.53 (m, 2H), 2.41-2.26 (m, 1H), 1.94-1.75 (m, 3H), 1.72-1.59 (m, 1H), 1.54 (d, J = 6.9 Hz, 3H), 1.35 (dd, J = 12.8, 4.4 Hz, 1H), 1.19-1.03 (m, 1H), 0.35-0.16 (m, 4H). |
| 75 | 1H NMR (400 MHz, DMSO-d6) δ 8.44 (d, J = 7.8 Hz, 1H), 8.14 (s, 1H), 8.10 (s, 3H), 7.98 (d, J = 8.1 Hz, 1H), 7.46 (s, 1H), 7.19 (d, J = 8.1 Hz, 1H), 6.62 (s, 1H), 6.39 (s, 1H), 5.25 (p, J = 7.1 Hz, 1H), 4.69-4.36 (m, 4H), 4.10 (s, 3H), 3.82 (s, 3H), 3.78-3.67 (m, 1H), 2.83 (s, 3H), 2.41-2.23 (m, 1H), 1.84 (s, 3H), 1.71-1.59 (m, 1H), 1.55 (d, J = 6.9 Hz, 3H), 1.35 (dd, J = 13.0, 4.4 Hz, 1H), 1.19-1.04 (m, 1H), 0.37-0.13 (m, 4H). |
| 76 | 1H NMR (400 MHz, DMSO-d6) δ 8.36 (d, J = 7.3 Hz, 1H), 8.35 (s, 1H), 8.09 (s, 3H), 7.99 (d, J = 8.0 Hz, 1H), 7.46 (s, 1H), 7.21 (d, J = 8.0 Hz, 1H), 6.63 (s, 1H), 6.38 (s, 1H), 5.25 (p, J = 7.0 Hz, 1H), 4.65-4.39 (m, 4H), 4.10 (s, 3H), 3.85 (s, 3H), 3.80-3.68 (m, 1H), 2.83 (s, 3H), 2.40-2.23 (m, 1H), 1.94-1.73 (m, 3H), 1.73-1.56 (m, 1H), 1.52 (d, J = 6.9 Hz, 3H), 1.35 (dd, J = 13.0, 4.3 Hz, 1H), 1.20-1.01 (m, 1H), 0.38-0.11 (m, 4H). |
| 77 | 1H NMR (400 MHz, DMSO-d6) δ 8.38 (d, J = 8.0 Hz, 1H), 8.25 (s, 1H), 8.09 (s, 3H), 7.95 (d, J = 8.1 Hz, 1H), 7.93 (s, 1H), 7.46 (s, 1H), 7.17 (d, J = 8.1 Hz, 1H), 6.60 (s, 1H), 6.38 (s, 1H), 5.25 (p, J = 7.3 Hz, 1H), 4.68-4.33 (m, 4H), 4.15 (q, J = 7.3 Hz, 2H), 4.10 (s, 3H), 3.82-3.74 (m, 1H), 2.82 (s, 3H), 2.41-2.24 (m, 1H), 1.93-1.74 (m, 3H), 1.72-1.59 (m, 1H), 1.55 (d, J = 7.0 Hz, 3H), 1.38 (t, J = 7.3 Hz, 3H), 1.40-1.28 (m, 1H), 1.21-1.02 (m, 1H), 0.37-0.17 (m, 4H). |
| 79 | 1H NMR (400 MHz, DMSO-d6) δ 8.75 (d, J = 7.8 Hz, 1H), 8.11 (s, 3H), 7.98 (d, J = 8.0 Hz, 1H), 7.68 (s, 1H), 7.47 (s, 1H), 7.18 (d, J = 8.0 Hz, 1H), 6.62 (s, 1H), 6.39 (s, 1H), 5.25 (p, J = 7.2 Hz, 1H), 4.62-4.22 (m, 4H), 4.10 (s, 3H), 3.76 (s, 1H), 2.82 (s, 3H), 2.41-2.24 (m, 1H), 2.25-2.09 (m, 1H), 2.00-1.75 (m, 3H), 1.72-1.47 (m, 4H), 1.35 (dd, J = 12.8, 4.3 Hz, 1H), 1.22-0.93 (m, 5H), 0.40-0.10 (m, 4H). |
| 80 | 1H NMR (400 MHz, DMSO-d6) δ 8.81 (d, J = 7.8 Hz, 1H), 8.10 (s, 3H), 7.98 (d, J = 8.1 Hz, 1H), 7.72 (s, 1H), 7.47 (s, 1H), 7.19 (d, J = 8.1 Hz, 1H), 6.62 (s, 1H), 6.39 (s, 1H), 5.25 (p, J = 6.9 Hz, 1H), 4.59-4.21 (m, 4H), 4.10 (s, 3H), 3.88-3.60 (m, 1H), 2.82 (s, 3H), 2.50 (s, 3H), 2.41-2.20 (m, 1H), 1.98-1.73 (m, 3H), 1.71-1.50 (m, 4H), 1.35 (dd, J = 12.9, 4.4 Hz, 1H), 1.23-0.98 (m, 1H), 0.39-0.10 (m, 4H). |
| 81 | 1H NMR (400 MHz, DMSO-d6) δ 8.75 (d, J = 7.8 Hz, 1H), 8.36 (d, J = 2.7 Hz, 1H), 8.11 (s, 3H), 8.00 (d, J = 8.0 Hz, 1H), 7.88 (t, J = 58.8 Hz, 1H), 7.47 (s, 1H), 7.23 (d, J = 8.0 Hz, 1H), 6.92 (d, J = 2.6 Hz, 1H), 6.64 (s, 1H), 6.39 (s, 1H), 5.29 (p, J = 6.9 Hz, 1H), 4.66-4.31 (m, 4H), 4.11 (s, 3H), 3.92-3.61 (m, 1H), 2.83 (s, 3H), 2.41-2.23 (m, 1H), 2.00-1.72 (m, 3H), 1.72-1.50 (m, 4H), 1.35 (dd, J = 12.8, 4.3 Hz, 1H), 1.14 (p, J = 6.6 Hz, 1H), 0.40-0.12 (m, 4H). |

TABLE 2-continued

| Ex | NMR |
|---|---|
| 82 | 1H NMR (400 MHz, DMSO-d6) δ 8.38 (s, 1H), 8.35 (d, J = 8.0 Hz, 1H), 8.11 (s, 3H), 7.96 (d, J = 8.0 Hz, 1H), 7.91 (s, 1H), 7.47 (s, 1H), 7.17 (d, J = 8.1 Hz, 1H), 6.61 (s, 1H), 6.39 (s, 1H), 5.26 (p, J = 7.2 Hz, 1H), 4.55-4.28 (m, 4H), 4.10 (s, 3H), 3.87-3.63 (m, 1H), 2.82 (s, 3H), 2.39-2.17 (m, 1H), 1.97-1.72 (m, 3H), 1.74-1.44 (m, 13H), 1.35 (dd, J = 12.8, 4.4 Hz, 1H), 1.21-1.02 (m, 1H), 0.37-0.13 (m, 4H). |
| 83 | 1H NMR (400 MHz, DMSO-d6) δ 9.39 (d, J = 7.8 Hz, 1H), 9.23 (d, J = 1.4 Hz, 1H), 8.92 (d, J = 2.4 Hz, 1H), 8.76 (dd, J = 2.5, 1.4 Hz, 1H), 8.11 (s, 3H), 8.01 (d, J = 8.0 Hz, 1H), 7.47 (s, 1H), 7.26 (d, J = 8.1 Hz, 1H), 6.65 (s, 1H), 6.39 (s, 1H), 5.34 (p, J = 6.9 Hz, 1H), 4.61-4.31 (m, 4H), 4.11 (s, 3H), 3.88-3.59 (m, 1H), 2.83 (s, 3H), 2.43-2.21 (m, 1H), 1.97-1.72 (m, 3H), 1.72-1.50 (m, 4H), 1.36 (dd, J = 12.9, 4.3 Hz, 1H), 1.28-1.12 (m, 1H), 0.44-0.16 (m, 4H). |
| 86 | 1H NMR (400 MHz, DMSO-d6) δ 8.13 (s, 3H), 8.04 (d, J = 7.5 Hz, 1H), 7.95 (d, J = 8.1 Hz, 1H), 7.43 (s, 1H), 7.12 (d, J = 8.1 Hz, 1H), 6.64 (s, 1H), 6.42 (d, J = 1.3 Hz, 1H), 5.06 (p, J = 7.0 Hz, 1H), 4.43 (d, J = 7.1 Hz, 2H), 4.12 (s, 3H), 3.48-3.35 (m, 2H), 2.39 (tt, J = 8.3, 5.4 Hz, 1H), 2.34-2.23 (m, 0H), 1.92-1.74 (m, 4H), 1.72-1.53 (m, 2H), 1.43 (d, J = 6.9 Hz, 3H), 1.34 (dd, J = 12.8, 4.4 Hz, 1H), 1.07 (s, 3H), 1.07 (s, 3H), 1.03-0.92 (m, 1H), 0.88 (dd, J = 8.0, 1.9 Hz, 2H), 0.44-0.30 (m, 2H), 0.28-0.18 (m, 4H), 0.18-0.07 (m, 2H). |
| 87 | 1H NMR (400 MHz, DMSO-d6) δ 8.16-8.05 (m, 3H), 8.00 (d, J = 7.9 Hz, 1H), 7.96 (d, J = 8.1 Hz, 1H), 7.47 (s, 1H), 7.10 (d, J = 8.0 Hz, 1H), 6.61 (s, 1H), 6.41-6.36 (m, 1H), 5.05 (p, J = 7.0 Hz, 1H), 4.45 (ddp, J = 21.3, 14.0, 7.0 Hz, 4H), 4.10 (s, 3H), 3.87-3.65 (m, 1H), 2.82 (s, 3H), 2.39-2.27 (m, 1H), 2.01 (s, 6H), 1.92-1.77 (m, 2H), 1.71-1.55 (m, 1H), 1.45 (d, J = 7.0 Hz, 3H), 1.35 (dd, J = 12.8, 4.3 Hz, 1H), 1.19-1.06 (m, 1H), 0.32-0.21 (m, 4H). |
| 88 | 1H NMR (400 MHz, DMSO-d6) δ 8.25 (d, J = 7.9 Hz, 1H), 8.15-8.06 (m, 3H), 7.98 (d, J = 8.0 Hz, 1H), 7.47 (s, 1H), 7.17 (d, J = 8.0 Hz, 1H), 6.63 (s, 1H), 6.39 (d, J = 1.2 Hz, 1H), 5.07 (p, J = 6.9 Hz, 1H), 4.59-4.33 (m, 4H), 4.10 (s, 3H), 3.83-3.69 (m, 1H), 2.83 (s, 3H), 2.41-2.26 (m, 1H), 2.07-1.53 (m, 12H), 1.46 (d, J = 6.8 Hz, 3H), 1.35 (dd, J = 12.9, 4.4 Hz, 1H), 1.21-1.08 (m, 1H), 0.34-0.21 (m, 4H). |
| 91 | 1H NMR (400 MHz, DMSO-d6) δ 8.21-8.06 (m, 4H), 7.98 (d, J = 7.9 Hz, 1H), 7.47 (s, 1H), 7.17 (d, J = 8.0 Hz, 1H), 6.63 (s, 1H), 6.39 (d, J = 1.4 Hz, 1H), 5.08 (p, J = 6.9 Hz, 1H), 4.59-4.34 (m, 4H), 4.10 (s, 3H), 4.01 (q, J = 6.8 Hz, 1H), 3.85-3.65 (m, 1H), 2.83 (s, 3H), 2.40-2.26 (m, 1H), 1.86 (d, J = 18.8 Hz, 2H), 1.71-1.56 (m, 1H), 1.45 (d, J = 6.8 Hz, 3H), 1.35 (dd, J = 12.8, 4.3 Hz, 1H), 1.27 (d, J = 6.8 Hz, 3H), 1.20-1.04 (m, 1H), 0.34-0.19 (m, 4H). |
| 92 | 1H NMR (400 MHz, DMSO-d6) δ 8.17-8.03 (m, 4H), 7.98 (d, J = 8.0 Hz, 1H), 7.47 (s, 1H), 7.17 (dd, J = 8.1, 1.1 Hz, 1H), 6.63 (s, 1H), 6.39 (d, J = 1.3 Hz, 1H), 5.05 (p, J = 6.9 Hz, 1H), 4.56-4.34 (m, 4H), 4.11 (s, 3H), 3.85-3.66 (m, 1H), 2.83 (d, J = 1.4 Hz, 3H), 2.33 (s, 1H), 1.94-1.77 (m, 2H), 1.72-1.58 (m, 1H), 1.48-1.40 (m, 3H), 1.40-1.27 (m, 4H), 1.27-1.05 (m, 2H), 0.46-0.18 (m, 8H). |
| 93 | 1H NMR (400 MHz, DMSO-d6) δ 8.21-8.08 (m, 4H), 7.99 (d, J = 5.0 Hz, 0.5H), 7.97 (d, J = 5.1 Hz, 0.5H), 7.47 (s, 1H), 7.18 (d, J = 3.6 Hz, 0.5H), 7.16 (d, J = 3.6 Hz, 0.5H), 6.64 (s, 0H), 6.63 (s, 0H), 6.40 (s, 1H), 5.07 (p, J = 6.9 Hz, 1H), 4.64-4.36 (m, 4H), 4.11 (s, 3H), 3.84-3.69 (m, 1H), 2.83 (s, 3H), 2.40-2.24 (m, 1H), 2.06-1.76 (m, 3H), 1.74-1.58 (m, 1H), 1.50-1.42 (m, 3H), 1.42-1.32 (m, 2H), 1.26 (s, 1.5H), 1.21 (s, 1.5H), 1.19-1.10 (m, 1H), 0.97-0.67 (m, 6H), 0.34-0.22 (m, 4H). |
| 94 | 1H NMR (400 MHz, DMSO-d6) δ 8.20-8.09 (m, 4H), 7.99 (d, J = 8.0 Hz, 1H), 7.47 (s, 1H), 7.16 (d, J = 8.1 Hz, 1H), 6.64 (s, 1H), 6.40 (d, J = 1.3 Hz, 1H), 5.07 (p, J = 6.9 Hz, 1H), 4.61-4.36 (m, 4H), 4.11 (s, 3H), 4.05 (q, J = 6.7 Hz, 1H), 3.86-3.66 (m, 1H), 2.83 (s, 3H), 2.42-2.23 (m, 1H), 1.95-1.76 (m, 3H), 1.71-1.57 (m, 1H), 1.46 (d, J = 6.9 Hz, 3H), 1.36 (dd, J = 12.8, 4.3 Hz, 1H), 1.22 (d, J = 6.8 Hz, 3H), 1.20-1.08 (m, 1H), 0.35-0.20 (m, 4H). |
| 95 | 1H NMR (400 MHz, DMSO-d6) δ 8.15-8.07 (m, 3H), 8.02 (d, J = 7.9 Hz, 1H), 7.98 (d, J = 8.0 Hz, 1H), 7.47 (s, 1H), 7.16 (d, J = 8.0 Hz, 1H), 6.63 (s, 1H), 6.39 (s, 1H), 5.07 (p, J = 6.9 Hz, 1H), 4.56-4.36 (m, 4H), 4.10 (s, 3H), 3.87-3.69 (m, 1H), 2.92-2.75 (m, 4H), 2.47-2.28 (m, 2H), 2.05 (dq, J = 20.3, 9.6 Hz, 2H), 1.92-1.72 (m, 5H), 1.70-1.56 (m, 1H), 1.45 (d, J = 6.8 Hz, 3H), 1.35 (dd, J = 12.8, 4.4 Hz, 1H), 1.21-1.08 (m, 1H), 0.36-0.20 (m, 4H). |
| 96 | 1H NMR (400 MHz, DMSO-d6) δ 8.41 (d, J = 7.9 Hz, 1H), 8.19 (s, 3H), 7.97 (d, J = 8.0 Hz, 1H), 7.45 (s, 1H), 7.14 (d, J = 8.1 Hz, 1H), 6.63 (s, 1H), 6.41 (d, J = 1.3 Hz, 1H), 5.93-5.16 (m, 2H), 5.19-5.04 (m, 1H), 4.62-4.29 (m, 2H), 4.10 (s, 3H), 3.78 (s, 2H), 3.76-3.66 (m, 1H), 3.39 (s, 6H), 2.80 (s, 3H), 2.41-2.21 (m, 1H), 1.93-1.76 (m, 3H), 1.69-1.58 (m, 1H), 1.46 (d, J = 6.8 Hz, 3H), 1.35 (dd, J = 12.8, 4.4 Hz, 1H), 1.20-1.05 (m, 1H), 0.31-0.23 (m, 2H), 0.23-0.15 (m, 2H). |
| 97 | 1H NMR (400 MHz, DMSO-d6) δ 8.31 (d, J = 7.9 Hz, 1H), 8.18-8.05 (m, 3H), 8.00 (d, J = 8.0 Hz, 1H), 7.47 (s, 1H), 7.20 (d, J = 8.0 Hz, 1H), 6.64 (s, 1H), 6.38 (s, 1H), 5.11 (p, J = 6.9 Hz, 1H), 4.53-4.37 (m, 4H), 4.10 (s, 3H), 3.86-3.66 (m, 1H), 2.83 (s, 3H), 2.40-2.25 (m, 1H), 1.94-1.78 (m, 2H), 1.70-1.58 (m, 1H), 1.55-1.41 (m, 4H), 1.41-1.33 (m, 1H), 1.22-1.13 (m, 1H), 1.13-0.98 (m, 2H), 0.94-0.80 (m, 2H), 0.35-0.23 (m, 4H). |
| 98 | 1H NMR (400 MHz, DMSO-d6) δ 8.25 (d, J = 7.9 Hz, 1H), 8.20 (s, 3H), 7.96 (d, J = 8.1 Hz, 1H), 7.46 (s, 1H), 7.10 (d, J = 8.1 Hz, 1H), 6.67 (s, 1H), 6.52 (d, J = 1.3 Hz, 1H), 5.64-5.28 (m, 3H), 5.04 (p, J = 7.1 Hz, 1H), 4.39 (d, J = 7.2 Hz, 2H), 4.14 (s, 3H), 3.93-3.81 (m, 2H), 3.81-3.58 (m, 1H), 3.39-3.22 (m, 2H), 2.44-2.35 (m, 1H), 2.35-2.10 (m, 1H), 1.91-1.76 (m, 3H), 1.69-1.50 (m, 5H), 1.43 (d, J = 7.0 Hz, 3H), 1.35 (dd, J = 12.9, 4.3 Hz, 1H), 1.03-0.92 (m, 1H), 0.92-0.81 (m, 2H), 0.47-0.32 (m, 2H), 0.28-0.16 (m, 2H), 0.15-0.01 (m, 2H). |
| 104 | 1H NMR (400 MHz, DMSO-d6) δ 9.13 (d, J = 7.8 Hz, 1H), 9.11 (d, J = 1.7 Hz, 1H), 8.07 (d, J = 5.9 Hz, 3H), 7.99 (d, J = 8.1 Hz, 1H), 7.47 (s, 1H), 7.22 (d, J = 8.1 Hz, 1H), 6.93 (d, J = 1.7 Hz, 1H), 6.63 (s, 1H), 6.37 (s, 1H), 5.29 (p, J = 7.2 Hz, 1H), 4.75-4.32 (m, 4H), 4.10 (s, 3H), 3.81-3.74 (m, 1H), 2.83 (s, 3H), 1.98-1.72 (m, 4H), 1.72-1.49 (m, 4H), 1.41-1.26 (m, 1H), 1.21-1.03 (m, 1H), 0.37-0.17 (m, 4H). |

TABLE 2-continued

| Ex | NMR |
|---|---|
| 105 | 1H NMR (400 MHz, DMSO-d6) δ 8.68 (d, J = 1.0 Hz, 1H), 8.64 (d, J = 7.9 Hz, 1H), 8.56 (d, J = 0.9 Hz, 1H), 8.09 (s, 3H), 8.00 (d, J = 8.0 Hz, 1H), 7.47 (s, 1H), 7.22 (d, J = 8.1 Hz, 1H), 6.64 (s, 1H), 6.38 (s, 1H), 5.28 (p, J = 6.9 Hz, 1H), 4.75-4.25 (m, 4H), 4.10 (s, 3H), 3.85-3.67 (m, 1H), 2.83 (s, 3H), 1.98-1.74 (m, 4H), 1.73-1.45 (m, 4H), 1.42-1.29 (m, 1H), 1.26-1.08 (m, 1H), 0.48-0.20 (m, 4H). |
| 106 | 1H NMR (400 MHz, DMSO-d6) δ 8.36 (d, J = 7.9 Hz, 1H), 8.31 (s, 1H), 8.09 (s, 3H), 7.95 (d, J = 8.1 Hz, 1H), 7.89 (s, 1H), 7.46 (s, 1H), 7.16 (d, J = 8.0 Hz, 1H), 6.60 (s, 1H), 6.38 (s, 1H), 5.24 (p, J = 7.0 Hz, 1H), 4.63-4.34 (m, 4H), 4.10 (s, 3H), 3.87-3.69 (m, 2H), 2.82 (s, 3H), 2.41-2.26 (m, 1H), 1.96-1.74 (m, 3H), 1.72-1.59 (m, 1H), 1.55 (d, J = 7.1 Hz, 3H), 1.35 (dd, J = 12.9, 4.4 Hz, 1H), 1.20-0.92 (m, 5H), 0.34-0.17 (m, 4H). |
| 107 | 1H NMR (400 MHz, DMSO-d6) δ 8.77 (s, 1H), 8.70 (d, J = 7.8 Hz, 1H), 8.23 (s, 1H), 8.09 (s, 3H), 7.96 (d, J = 8.0 Hz, 1H), 7.87 (t, J = 58.9 Hz, 1H), 7.46 (s, 1H), 7.18 (d, J = 8.1 Hz, 1H), 6.61 (s, 1H), 6.38 (s, 1H), 5.26 (p, J = 7.1 Hz, 1H), 4.63-4.25 (m, 4H), 4.10 (s, 3H), 3.76 (s, 1H), 2.82 (s, 3H), 1.95-1.71 (m, 4H), 1.71-1.48 (m, 4H), 1.35 (dd, J = 12.9, 4.4 Hz, 1H), 1.20-1.01 (m, 1H), 0.36-0.15 (m, 4H). |
| 108 | 1H NMR (400 MHz, DMSO-d6) δ 8.47 (d, J = 7.8 Hz, 1H), 8.06 (d, J = 19.3 Hz, 3H), 7.99 (d, J = 8.0 Hz, 1H), 7.80 (d, J = 2.2 Hz, 1H), 7.47 (s, 1H), 7.22 (d, J = 8.1 Hz, 1H), 6.74-6.58 (m, 2H), 6.38 (s, 1H), 5.25 (p, J = 6.9 Hz, 1H), 4.74-4.27 (m, 4H), 4.10 (s, 3H), 3.92 (s, 3H), 3.83-3.71 (m, 1H), 2.83 (s, 3H), 1.98-1.73 (m, 4H), 1.72-1.46 (m, 4H), 1.45-1.30 (m, 1H), 1.30-1.08 (m, 1H), 0.53-0.21 (m, 4H). |
| 109 | 1H NMR (400 MHz, DMSO-d6) δ 8.26 (d, J = 7.8 Hz, 1H), 8.08 (s, 3H), 7.95 (d, J = 8.0 Hz, 1H), 7.42 (s, 1H), 7.10 (d, J = 8.1 Hz, 1H), 6.63 (s, 1H), 6.40 (s, 1H), 5.08 (p, J = 7.1 Hz, 1H), 4.75 (dd, J = 18.5, 5.9 Hz, 2H), 4.61-4.49 (m, 1H), 4.43 (s, 2H), 4.28 (d, J = 6.0 Hz, 2H), 4.11 (s, 3H), 2.45-2.35 (m, 1H), 2.35-2.24 (m, 1H), 2.05 (s, 1H), 1.88-1.76 (m, 4H), 1.69-1.56 (m, 1H), 1.54 (s, 3H), 1.47 (d, J = 7.1 Hz, 3H), 1.33 (dd, J = 12.8, 4.4 Hz, 1H), 1.01-0.91 (m, 1H), 0.92-0.82 (m, 2H), 0.43-0.29 (m, 2H), 0.28-0.16 (m, 2H), 0.17-0.02 (m, 2H). |
| 111 | 1H NMR (400 MHz, DMSO-d6) δ 8.83 (d, J = 7.8 Hz, 1H), 8.07-7.85 (m, 3H), 7.97 (d, J = 8.1 Hz, 1H), 7.95-7.91 (m, 2H), 7.59-7.51 (m, 1H), 7.53-7.44 (m, 2H), 7.34 (s, 1H), 7.22 (d, J = 8.1 Hz, 1H), 6.62 (s, 1H), 6.39 (s, 1H), 5.31 (p, J = 7.3 Hz, 1H), 4.41 (qd, J = 14.1, 7.0 Hz, 2H), 4.09 (s, 3H), 3.96-3.59 (m, 4H), 3.56-3.36 (m, 4H), 2.82 (s, 3H), 1.93-1.88 (m, 1H), 1.82-1.71 (m, 1H), 1.65-1.52 (m, 5H), 1.16 (p, J = 6.6 Hz, 1H), 0.91 (t, J = 7.4 Hz, 3H), 0.31-0.20 (m, 4H). |
| 112 | 1H NMR (400 MHz, DMSO-d6) δ 8.85 (d, J = 7.8 Hz, 1H), 8.13-7.94 (m, 3H), 7.99 (d, J = 8.1 Hz, 1H), 7.95-7.90 (m, 2H), 7.59-7.52 (m, 1H), 7.49 (dd, J = 8.1, 6.5 Hz, 2H), 7.37 (s, 1H), 7.23 (d, J = 8.1 Hz, 1H), 6.65 (s, 1H), 6.48 (s, 1H), 5.32 (p, J = 7.1 Hz, 1H), 4.37 (hept, J = 7.3 Hz, 2H), 4.10 (s, 3H), 3.99-3.69 (m, 3H), 3.68-3.30 (m, 5H), 2.80 (s, 3H), 1.91-1.86 (m, 1H), 1.82-1.72 (m, 1H), 1.60 (d, J = 7.0 Hz, 3H), 1.19 (t, J = 7.0 Hz, 3H), 1.19-1.06 (m, 1H), 0.34-0.21 (m, 4H). |
| 113 | 1H NMR (400 MHz, DMSO-d6) δ 8.84 (d, J = 7.8 Hz, 1H), 8.24 (s, 1H), 7.99 (d, J = 8.1 Hz, 1H), 7.96-7.90 (m, 2H), 7.83 (d, J = 1.3 Hz, 1H), 7.66 (s, 1H), 7.59-7.52 (m, 1H), 7.52-7.44 (m, 2H), 7.23 (d, J = 8.1 Hz, 1H), 6.80 (s, 1H), 6.67 (s, 1H), 5.32 (p, J = 7.1 Hz, 1H), 4.37 (hept, J = 7.2 Hz, 2H), 4.12 (s, 3H), 2.81 (s, 3H), 1.60 (d, J = 7.0 Hz, 3H), 1.15 (p, J = 6.4 Hz, 1H), 0.33-0.19 (m, 4H). |
| 114 | 1H NMR (400 MHz, DMSO-d6) δ 8.85 (d, J = 7.7 Hz, 1H), 8.05 (s, 3H), 8.00 (d, J = 8.1 Hz, 1H), 7.96-7.90 (m, 2H), 7.60-7.52 (m, 1H), 7.52-7.44 (m, 2H), 7.38 (s, 1H), 7.24 (d, J = 8.1 Hz, 1H), 6.67 (s, 1H), 6.51 (s, 1H), 5.32 (p, J = 7.1 Hz, 1H), 4.36 (hept, J = 7.3 Hz, 2H), 4.11 (s, 3H), 3.98-3.69 (m, 2H), 3.59-3.54 (m, 2H), 3.45-3.40 (m, 2H), 3.38 (s, 3H), 2.80 (s, 3H), 2.01-1.90 (m, 1H), 1.84-1.73 (m, 1H), 1.60 (d, J = 7.0 Hz, 3H), 1.19-1.08 (m, 1H), 0.34-0.20 (m, 4H). |
| 115 | 1H NMR (400 MHz, DMSO-d6) δ 8.84 (d, J = 7.8 Hz, 1H), 7.98 (d, J = 8.1 Hz, 1H), 8.08-7.83 (m, 5H), 7.59-7.52 (m, 1H), 7.49 (dd, J = 8.2, 6.4 Hz, 2H), 7.35 (s, 1H), 7.22 (d, J = 8.1 Hz, 1H), 6.63 (s, 1H), 6.44 (s, 1H), 5.73 (br. s, 1H), 5.31 (p, J = 7.1 Hz, 1H), 4.47-4.31 (m, 2H), 4.09 (s, 3H), 4.08-4.00 (m, 1H), 3.55-3.42 (m, 2H), 3.41-3.33 (m, 3H), 2.81 (s, 3H), 1.87-1.66 (m, 2H), 1.59 (d, J = 7.0 Hz, 3H), 1.14 (p, J = 6.5 Hz, 1H), 0.31-0.20 (m, 4H). |
| 116 | 1H NMR (400 MHz, DMSO-d6) δ 8.38 (d, J = 8.0 Hz, 1H), 8.19 (s, 1H), 8.08 (s, 3H), 7.95 (d, J = 8.1 Hz, 1H), 7.92 (s, 1H), 7.46 (s, 1H), 7.16 (d, J = 8.1 Hz, 1H), 6.60 (s, 1H), 6.38 (s, 1H), 5.24 (p, J = 7.2 Hz, 1H), 4.66-4.30 (m, 4H), 4.10 (s, 3H), 3.86 (s, 3H), 3.82-3.70 (m, 1H), 2.82 (s, 3H), 2.38-2.20 (m, 1H), 1.95-1.71 (m, 3H), 1.72-1.60 (m, 1H), 1.55 (d, J = 7.1 Hz, 3H), 1.35 (dd, J = 12.8, 4.4 Hz, 1H), 1.22-1.01 (m, 1H), 0.34-0.16 (m, 4H). |
| 117 | 1H NMR (400 MHz, DMSO-d6) δ 8.98 (d, J = 7.9 Hz, 1H), 8.58 (d, J = 8.10 (s, 3H), 7.98 (d, J = 8.1 Hz, 1H), 7.88 (s, 1H), 7.46 (s, 1H), 7.19 (d, J = 8.1 Hz, 1H), 6.62 (s, 1H), 6.39 (d, J = 1.4 Hz, 1H), 5.27 (p, J = 7.0 Hz, 1H), 4.60-4.34 (m, 4H), 4.10 (s, 3H), 3.85-3.66 (m, 1H), 2.82 (s, 3H), 1.98-1.73 (m, 4H), 1.72-1.48 (m, 4H), 1.35 (dd, J = 12.9, 4.4 Hz, 1H), 1.19-1.03 (m, 1H), 0.36-0.16 (m, 4H). |
| 118 | 1H NMR (400 MHz, DMSO-d6) δ 9.43 (d, J = 7.8 Hz, 1H), 8.99 (d, J = 4.9 Hz, 2H), 8.08 (s, 3H), 8.01 (d, J = 8.0 Hz, 1H), 7.72 (t, J = 4.9 Hz, 1H), 7.47 (s, 1H), 7.26 (d, J = 8.0 Hz, 1H), 6.64 (s, 1H), 6.38 (s, 1H), 5.38-5.23 (m, 1H), 4.73-4.24 (m, 4H), 4.10 (s, 3H), 3.84-3.74 (m, 1H), 2.84 (s, 3H), 2.02-1.72 (m, 4H), 1.71-1.44 (m, 4H), 1.35 (dd, J = 12.8, 4.5 Hz, 1H), 1.28-1.06 (m, 1H), 0.52-0.19 (m, 4H). |
| 119 | 1H NMR (400 MHz, DMSO-d6) δ 9.18 (d, J = 7.7 Hz, 1H), 8.78 (d, J = 6.2 Hz, 2H), 8.12 (s, 3H), 7.98 (d, J = 8.1 Hz, 1H), 7.89 (d, J = 6.2 Hz, 2H), 7.47 (s, 1H), 7.22 (d, J = 8.1 Hz, 1H), 6.63 (s, 1H), 6.41 (s, 1H), 5.31 (p, J = 7.1 Hz, 1H), 4.79-4.29 (m, 4H), 4.11 (s, 3H), 3.91-3.61 (m, 1H), 2.82 (s, 3H), 1.98-1.74 (m, 3H), 1.74-1.51 (m, 4H), 1.35 (dd, J = 12.8, 4.4 Hz, 1H), 1.23 (dd, J = 6.7, 3.2 Hz, 1H), 1.18-1.02 (m, 1H), 0.37-0.15 (m, 4H). |
| 120 | 1H NMR (400 MHz, DMSO-d6) δ 9.11 (dd, J = 2.2, 0.8 Hz, 1H), 9.08 (d, J = 7.7 Hz, 1H), 8.74 (dd, J = 4.9, 1.7 Hz, 1H), 8.31 (dt, J = 8.0, 2.0 Hz, 1H), 8.11 (s, 3H), 7.98 (d, J = 8.1 Hz, 1H), 7.57 (ddd, J = 8.0, 4.9, 0.9 Hz, 1H), 7.47 (s, 1H), 7.23 (d, J = 8.1 Hz, 1H), 6.63 (s, 1H), |

TABLE 2-continued

| Ex | NMR |
|---|---|
| | 6.41 (d, J = 1.3 Hz, 1H), 5.32 (p, J = 7.0 Hz, 1H), 4.62-4.33 (m, 4H), 4.11 (s, 3H), 3.88-3.67 (m, 1H), 2.82 (s, 3H), 1.95-1.73 (m, 4H), 1.71-1.51 (m, 4H), 1.35 (dd, J = 12.9, 4.4 Hz, 1H), 1.19-1.02 (m, 1H), 0.35-0.15 (m, 4H). |
| 121 | 1H NMR (400 MHz, DMSO-d6) δ 8.84 (d, J = 7.8 Hz, 1H), 7.98 (d, J = 8.1 Hz, 1H), 8.08-7.83 (m, 5H), 7.59-7.52 (m, 1H), 7.49 (dd, J = 8.2, 6.4 Hz, 2H), 7.35 (s, 1H), 7.22 (d, J = 8.1 Hz, 1H), 6.63 (s, 1H), 6.44 (s, 1H), 5.73 (br. s, 1H), 5.31 (p, J = 7.1 Hz, 1H), 4.47-4.31 (m, 2H), 4.09 (s, 3H), 4.08-4.00 (m, 1H), 3.55-3.42 (m, 2H), 3.41-3.33 (m, 3H), 2.81 (s, 3H), 1.87-1.66 (m, 2H), 1.59 (d, J = 7.0 Hz, 3H), 1.14 (p, J = 6.5 Hz, 1H), 0.31-0.20 (m, 4H). |
| 122 | 1H NMR (400 MHz, DMSO-d6) δ 8.38 (d, J = 8.0 Hz, 1H), 8.19 (s, 1H), 8.08 (s, 3H), 7.95 (d, J = 8.1 Hz, 1H), 7.92 (s, 1H), 7.46 (s, 1H), 7.16 (d, J = 8.1 Hz, 1H), 6.60 (s, 1H), 6.38 (s, 1H), 5.24 (p, J = 7.2 Hz, 1H), 4.66-4.30 (m, 4H), 4.10 (s, 3H), 3.86 (s, 3H), 3.82-3.70 (m, 1H), 2.82 (s, 3H), 2.38-2.20 (m, 1H), 1.95-1.71 (m, 3H), 1.72-1.60 (m, 1H), 1.55 (d, J = 7.1 Hz, 3H), 1.35 (dd, J = 12.8, 4.4 Hz, 1H), 1.22-1.01 (m, 1H), 0.34-0.16 (m, 4H). |
| 123 | 1H NMR (400 MHz, DMSO-d6) δ 8.98 (d, J = 7.9 Hz, 1H), 8.58 (s, 1H), 8.10 (s, 3H), 7.98 (d, J = 8.1 Hz, 1H), 7.88 (s, 1H), 7.46 (s, 1H), 7.19 (d, J = 8.1 Hz, 1H), 6.62 (s, 1H), 6.39 (d, J = 1.4 Hz, 1H), 5.27 (p, J = 7.0 Hz, 1H), 4.60-4.34 (m, 4H), 4.10 (s, 3H), 3.85-3.66 (m, 1H), 2.82 (s, 3H), 1.98-1.73 (m, 4H), 1.72-1.48 (m, 4H), 1.35 (dd, J = 12.9, 4.4 Hz, 1H), 1.19-1.03 (m, 1H), 0.36-0.16 (m, 4H). |
| 125 | 1H NMR (400 MHz, DMSO-d6) δ 8.30 (d, J = 7.9 Hz, 1H), 8.05 (s, 3H), 7.98 (d, J = 8.0 Hz, 1H), 7.33 (s, 1H), 7.12 (d, J = 8.1 Hz, 1H), 6.63 (s, 1H), 6.42 (s, 1H), 5.09 (p, J = 7.0 Hz, 1H), 4.52-4.27 (m, 2H), 4.10 (s, 3H), 3.44-3.01 (m, 5H), 2.81 (s, 3H), 2.32 (d, J = 2.6 Hz, 6H), 2.13-1.93 (m, 1H), 1.86-1.71 (m, 1H), 1.71-1.53 (m, 2H), 1.48 (d, J = 7.0 Hz, 3H), 1.20-1.08 (m, 1H), 0.48--0.05 (m, 4H). |
| 126 | 1H NMR (400 MHz, DMSO-d6) δ 8.22-8.09 (m, 4H), 7.99 (d, J = 8.0 Hz, 1H), 7.47 (s, 1H), 7.17 (d, J = 8.0 Hz, 1H), 6.64 (s, 1H), 6.41 (d, J = 1.4 Hz, 1H), 5.04 (p, J = 6.9 Hz, 1H), 4.60-4.33 (m, 4H), 4.11 (s, 3H), 3.84-3.69 (m, 1H), 2.82 (s, 3H), 2.38-2.27 (m, 1H), 1.93-1.75 (m, 3H), 1.72-1.59 (m, 1H), 1.45 (d, J = 6.8 Hz, 3H), 1.36 (dd, J = 12.9, 4.4 Hz, 1H), 1.31 (s, 3H), 1.25 (s, 3H), 1.21-1.08 (m, 1H), 0.34-0.17 (m, 4H). |
| 127 | 1H NMR (400 MHz, DMSO-d6) δ 8.16 (d, J = 7.9 Hz, 1H), 8.08-7.90 (m, 4H), 7.34 (s, 1H), 7.17 (d, J = 8.1 Hz, 1H), 6.65 (s, 1H), 6.44 (s, 1H), 5.04 (p, J = 6.9 Hz, 1H), 4.47-4.32 (m, 2H), 4.10 (s, 3H), 3.35-3.07 (m, 5H), 2.81 (s, 3H), 2.06-1.97 (m, 1H), 1.83-1.71 (m, 1H), 1.69-1.53 (m, 2H), 1.45 (d, J = 6.8 Hz, 3H), 1.31 (s, 3H), 1.25 (s, 3H), 1.22-1.10 (m, 1H), 0.34-0.21 (m, 4H). |
| 128 | 1H NMR (400 MHz, DMSO-d6) δ 8.43 (d, J = 7.5 Hz, 1H), 8.17-8.09 (m, 3H), 7.98 (d, J = 8.0 Hz, 1H), 7.47 (s, 1H), 7.15 (d, J = 8.1 Hz, 1H), 6.64 (s, 1H), 6.41 (d, J = 1.3 Hz, 1H), 5.12 (p, J = 6.9 Hz, 1H), 4.55-4.40 (m, 3H), 4.11 (s, 3H), 3.83-3.69 (m, 2H), 3.56 (d, J = 2.3 Hz, 2H), 2.83 (s, 3H), 1.93-1.77 (m, 4H), 1.71-1.56 (m, 1H), 1.45 (d, J = 6.8 Hz, 3H), 1.36 (dd, J = 12.8, 4.3 Hz, 1H), 1.15 (p, J = 6.3 Hz, 1H), 1.01-0.85 (m, 2H), 0.68-0.54 (m, 2H), 0.32-0.19 (m, 4H). |
| 129 | 1H NMR (400 MHz, DMSO-d6) δ 8.44 (d, J = 7.5 Hz, 1H), 8.05-7.89 (m, 4H), 7.32 (s, 1H), 7.15 (d, J = 8.1 Hz, 1H), 6.64 (s, 1H), 6.41 (s, 1H), 5.12 (p, J = 6.7 Hz, 1H), 4.42 (dd, J = 7.1, 4.3 Hz, 2H), 4.09 (s, 3H), 3.56 (s, 2H), 3.25 (s, 5H), 2.82 (s, 3H), 2.08-1.97 (m, 1H), 1.82-1.69 (m, 1H), 1.68-1.54 (m, 2H), 1.45 (d, J = 6.8 Hz, 3H), 1.21-1.09 (m, 1H), 1.00-0.89 (m, 2H), 0.69-0.55 (m, 2H), 0.36-0.19 (m, 4H). |
| 132 | 1H NMR (400 MHz, DMSO-d6) δ 8.11 (d, J = 8.0 Hz, 1H), 8.10 (s, 3H), 7.97 (d, J = 8.0 Hz, 1H), 7.45 (s, 1H), 7.14 (d, J = 8.1 Hz, 1H), 6.61 (s, 1H), 6.37 (d, J = 1.3 Hz, 1H), 5.18-5.02 (m, 1H), 4.47 (dd, J = 14.1, 6.6 Hz, 1H), 4.35 (dd, J = 14.1, 7.5 Hz, 1H), 4.09 (s, 3H), 3.88-3.75 (m, 2H), 3.74-3.57 (m, 3H), 2.92 (t, J = 3.2 Hz, 1H), 2.81 (s, 3H), 2.38-2.22 (m, 1H), 2.13-2.01 (m, 2H), 1.89-1.75 (m, 3H), 1.68-1.48 (m, 3H), 1.45 (d, J = 6.9 Hz, 3H), 1.34 (dd, J = 12.8, 4.3 Hz, 1H), 1.21-1.07 (m, 1H), 0.37-0.13 (m, 4H). |
| 133 | 1H NMR (400 MHz, DMSO-d6) δ 8.29 (d, J = 7.9 Hz, 1H), 8.16 (s, 3H), 7.97 (d, J = 8.0 Hz, 1H), 7.48 (s, 1H), 7.11 (d, J = 8.1 Hz, 1H), 6.63 (s, 1H), 6.42 (s, 1H), 5.06 (p, J = 7.1 Hz, 1H), 4.69-4.28 (m, 4H), 4.12 (s, 3H), 3.90-3.65 (m, 1H), 2.82 (s, 3H), 2.41 (s, 6H), 2.36-2.19 (m, 1H), 1.94-1.78 (m, 3H), 1.73-1.58 (m, 1H), 1.48 (d, J = 7.0 Hz, 3H), 1.37 (dd, J = 12.9, 4.3 Hz, 1H), 1.20-1.06 (m, 1H), 0.37-0.14 (m, 4H). |
| 134 | 1H NMR (400 MHz, DMSO-d6) δ 8.11 (s, 3H), 8.05 (d, J = 7.5 Hz, 1H), 7.96 (d, J = 8.0 Hz, 1H), 7.47 (s, 1H), 7.14 (d, J = 8.1 Hz, 1H), 6.62 (s, 1H), 6.40 (d, J = 1.3 Hz, 1H), 5.07 (p, J = 7.0 Hz, 1H), 4.56-4.40 (m, 4H), 4.11 (s, 3H), 3.84-3.69 (m, 1H), 3.43 (d, J = 1.2 Hz, 2H), 2.83 (s, 3H), 2.39-2.26 (m, 1H), 1.86 (d, J = 18.9 Hz, 3H), 1.70-1.58 (m, 1H), 1.44 (d, J = 6.9 Hz, 3H), 1.39-1.30 (m, 1H), 1.27-1.11 (m, 1H), 1.08 (d, J = 4.0 Hz, 6H), 0.33-0.19 (m, 4H). |
| 136 | 1H NMR (400 MHz, DMSO-d6) δ 8.66 (d, J = 7.8 Hz, 1H), 8.10 (s, 4H), 7.97 (d, J = 8.0 Hz, 1H), 7.45 (s, 1H), 7.17 (d, J = 8.1 Hz, 1H), 6.60 (s, 1H), 6.35 (s, 1H), 5.24-5.07 (m, 1H), 4.65-4.29 (m, 4H), 4.08 (s, 3H), 3.99-3.40 (m, 2H), 2.81 (s, 3H), 1.86-1.71 (m, 4H), 1.68-1.54 (m, 1H), 1.51 (d, J = 7.0 Hz, 3H), 1.41-1.26 (m, 3H), 1.26-1.03 (m, 2H), 0.38-0.11 (m, 4H). |
| 137 | 1H NMR (400 MHz, DMSO-d6) δ 8.05 (s, 3H), 7.97 (d, 1H), 7.44 (s, 1H), 7.11 (d, J = 8.1 Hz, 1H), 6.61 (s, 1H), 6.35 (s, 1H), 6.26 (t, J = 56.3 Hz, 1H), 5.19-4.98 (m, 1H), 4.43 (d, J = 7.3 Hz, 2H), 4.08 (s, 3H), 3.90-3.33 (m, 3H), 2.81 (s, 3H), 1.89-1.73 (m, 4H), 1.71-1.54 (m, 1H), 1.44 (d, J = 6.9 Hz, 3H), 1.33 (dd, J = 12.8, 4.2 Hz, 1H), 1.27-1.18 (m, 3H), 1.16-1.07 (m, 1H), 1.03 (t, J = 3.7 Hz, 2H), 0.36-0.12 (m, 4H). |
| 138 | 1H NMR (400 MHz, DMSO-d6) δ 8.11 (s, 4H), 7.92 (d, 2H), 7.53 (s, 0H), 7.44 (s, 1H), 7.08 (t, J = 7.9 Hz, 1H), 6.58 (s, 1H), 6.34 (s, 1H), 5.20-4.86 (m, 1H), 4.48-4.18 (m, 4H), 4.08 (s, 3H), 3.68-3.37 (m, 5H), 2.81 (s, 3H), 1.88-1.73 (m, 4H), 1.44 (d, J = 7.0, 4.0 Hz, 3H), 1.26-1.13 (m, 3H), 0.97-0.82 (m, 3H), 0.31-0.12 (m, 4H). |
| 139 | 1H NMR (400 MHz, DMSO-d6) δ 8.35 (d, J = 7.9 Hz, 1H), 7.99 (s, 3H), 7.96 (d, J = 8.1 Hz, 1H), 7.31 (s, 1H), 7.09 (d, J = 8.1 Hz, 1H), 6.66 (s, 1H), 6.50 (s, 1H), 5.04 (p, J = 7.2 Hz, 1H), 4.41-4.33 (m, 2H), 4.12 (s, 3H), 3.38-2.98 (m, 5H), 2.45 (s, 6H), 2.43-2.35 (m, 1H), 2.07- |

TABLE 2-continued

| Ex | NMR |
|---|---|
| | 1.94 (m, 1H), 1.81-1.68 (m, 1H), 1.68-1.52 (m, 2H), 1.46 (d, J = 7.0 Hz, 3H), 1.06-0.93 (m, 1H), 0.93-0.78 (m, 2H), 0.43-0.32 (m, 2H), 0.28-0.19 (m, 2H), 0.18-0.08 (m, 2H). |
| 140 | ~{N}-[(1~{R})-1-[2-[7-[(1~{R},2~{R},4~{S})-2-amino-7-azabicyclo[2.2.1]heptane-7-carbonyl]-3-cyclopropyl-5-methoxyimidazo[1,2-a]pyridin-2-yl]-1-(cyclopropylmethyl)pyrrolo[2,3-b]pyridin-6-yl]ethyl]-3-cyanobicyclo[1.1.1]pentane-1-carboxamide |
| 141 | 1H NMR (400 MHz, DMSO-d6) δ 8.35 (d, J = 7.9 Hz, 1H), 8.13 (s, 3H), 7.95 (d, J = 8.1 Hz, 1H), 7.43 (s, 1H), 7.08 (d, J = 8.1 Hz, 1H), 6.65 (s, 1H), 6.45 (d, J = 1.3 Hz, 1H), 5.03 (p, J = 7.2 Hz, 1H), 4.54-4.27 (m, 4H), 4.12 (s, 3H), 3.86-3.65 (m, 1H), 2.45 (s, 6H), 2.43-2.35 (m, 1H), 2.35-2.24 (m, 1H), 1.92-1.76 (m, 3H), 1.70-1.55 (m, 1H), 1.46 (d, J = 7.0 Hz, 3H), 1.34 (dd, J = 12.8, 4.4 Hz, 1H), 1.02-0.91 (m, 1H), 0.91-0.84 (m, 2H), 0.44-0.30 (m, 2H), 0.29-0.18 (m, 2H), 0.15-0.08 (m, 2H). |
| 142 | 1H NMR (400 MHz, DMSO-d6) δ 8.82 (d, J = 7.8 Hz, 1H), 8.10-7.78 (m, 3H), 7.56-7.41 (m, 3H), 7.27 (s, 1H), 7.20 (d, J = 8.1 Hz, 1H), 6.63 (s, 1H), 6.39 (s, 1H), 5.38-5.08 (m, 1H), 4.43 (dt, J = 14.3, 7.2 Hz, 2H), 4.09 (s, 3H), 3.95-3.40 (m, 7H), 3.33-3.04 (m, 2H), 2.44-2.32 (m, 1H), 2.08-1.91 (m, 1H), 1.86-1.67 (m, 1H), 1.58 (d, J = 7.0 Hz, 3H), 1.63-1.56 (m, 1H, 0.99 (t, J = 7.2 Hz, 1H), 0.93-0.81 (m, 2H), 0.42-0.29 (m, 2H), 0.25-0.05 (m, 4H). |
| 143 | 1H NMR (400 MHz, DMSO-d6) δ 8.83 (d, J = 7.8 Hz, 1H), 8.10 (s, 3H), 7.95 (d, J = 8.1 Hz, 1H), 7.94-7.87 (m, 2H), 7.57-7.38 (m, 4H), 7.20 (d, J = 8.1 Hz, 1H), 6.64 (s, 1H), 6.41 (d, J = 1.4 Hz, 1H), 5.30 (p, J = 7.1 Hz, 1H), 4.43 (hept, J = 7.1 Hz, 2H), 4.11 (s, 3H), 3.99-2.91 (m, 4H), 2.43-2.35 (m, 1H), 1.92-1.72 (m, 3H), 1.67-1.60 (m, 1H), 1.58 (d, J = 7.0 Hz, 3H), 1.34 (d, J = 12.8, 4.4 Hz, 1H), 1.03-0.91 (m, 1H), 0.92-0.80 (m, 2H), 0.44-0.29 (m, 2H), 0.26-0.14 (m, 2H), 0.14-0.02 (m, 2H). |
| 144 | 1H NMR (400 MHz, DMSO-d6) δ 8.04 (brs, 3H), 7.98 (d, J = 8.1 Hz, 1H), 7.82 (d, J = 7.7 Hz, 1H), 7.32 (s, 1H), 7.14 (d, J = 8.1 Hz, 1H), 6.67 (s, 1H), 6.46 (s, 1H), 5.15-5.02 (m 1H), 4.42 (d, J = 7.2 Hz, 2H), 4.13 (s, 3H), 3.27 (brs, 4H), 2.47-2.35 (m, 1H), 2.09-1.96 (m, 1H), 1.87-1.69 (m, 1H), 1.71-1.63 (m, 2H), 1.48 (d, J = 7.0 Hz, 3H), 1.18 (s, 9H), 1.09-0.96 (m, 1H), 0.91 (dd, J = 8.0, 2.1 Hz, 2H), 0.44-0.33 (m, 2H), 0.32-0.19 (m, 2H), 0.20-0.10 (m, 2H). |
| 145 | 1H NMR (400 MHz, DMSO-d6) δ 8.33 (d, J = 7.9 Hz, 1H), 8.18 (s, 3H), 7.99 (d, J = 8.0 Hz, 1H), 7.47 (s, 1H), 7.12 (d, J = 8.1 Hz, 1H), 6.68 (s, 1H), 6.50 (s, 1H), 6.03-5.52 (m, 4H), 5.09 (p, J = 7.1 Hz, 1H), 4.77-4.22 (m, 2H), 4.15 (s, 3H), 3.93-3.54 (m, 1H), 2.32 (s, 6H), 1.97-1.77 (m, 3H), 1.71-1.58 (m, 1H), 1.49 (d, J = 7.0 Hz, 3H), 1.37 (dd, J = 12.8, 4.4 Hz, 1H), 1.05-0.95 (m, 1H), 0.94-0.85 (m, 2H), 0.47-0.33 (m, 2H), 0.32-0.18 (m, 2H), 0.18-0.05 (m, 2H). |
| 146 | 1H NMR (400 MHz, DMSO-d6) δ 8.33 (d, J = 7.9 Hz, 1H), 8.04 (s, 3H), 7.99 (d, J = 8.1 Hz, 1H), 7.33 (s, 1H), 7.13 (d, J = 8.1 Hz, 1H), 6.68 (s, 1H), 6.51 (s, 1H), 5.80-5.37 (m, 2H), 5.09 (p, J = 7.1 Hz, 1H), 4.50-4.30 (m, 2H), 4.14 (s, 3H), 3.43-2.95 (m, 1H), 2.47-2.37 (m, 1H), 2.32 (s, 6H), 2.10-1.96 (m, 1H), 1.87-1.71 (m, 2H), 1.69-1.54 (m, 1H), 1.49 (d, J = 7.0 Hz, 3H), 1.08-0.95 (m, 1H), 0.95-0.79 (m, 2H), 0.47-0.31 (m, 2H), 0.31-0.20 (m, 2H), 0.21-0.02 (m, 2H). |
| 147 | 1H NMR (400 MHz, DMSO-d6) δ 8.13 (d, J = 8.0 Hz, 1H), 8.08 (s, 3H), 7.95 (d, J = 8.1 Hz, 1H), 7.44 (s, 1H), 7.35-7.17 (m, 5H), 7.12 (d, J = 8.1 Hz, 1H), 7.07 (s, 1H), 6.94 (s, 1H), 6.59 (s, 1H), 6.35 (s, 1H), 5.08 (t, J = 7.5 Hz, 1H), 4.71-4.30 (m, 2H), 4.08 (s, 3H), 2.81 (s, 3H), 2.21 (s, 6H), 1.88-1.52 (m, 3H), 1.48 (d, J = 7.0 Hz, 3H), 1.45-1.38 (m, 2H), 1.38-1.28 (m, 1H), 1.27-1.06 (m, 1H), 0.51-0.33 (m, 2H), 0.33-0.18 (m, 2H). |
| 148 | 1H NMR (400 MHz, DMSO-d6) δ 8.38 (d, J = 7.9 Hz, 1H), 8.21 (s, 2H), 8.06 (s, 5H), 7.92 (d, J = 8.0 Hz, 1H), 7.44 (s, 1H), 7.20 (s, 0H), 7.09 (d, J = 8.3 Hz, 1H), 6.58 (s, 1H), 6.36 (s, 1H), 5.02 (q, J = 7.0 Hz, 1H), 4.64-4.29 (m, 2H), 4.08 (s, 3H), 3.60-3.49 (m, 2H), 2.81 (s, 3H), 2.46-2.41 (m, 2H), 2.35-2.21 (m, 1H), 1.86-1.73 (m, 3H), 1.70-1.52 (m, 1H), 1.41 (d, J = 7.1 Hz, 4H), 1.37-1.28 (m, 2H), 1.24 (s, 6H), 1.15-1.02 (m, 1H), 0.55-0.31 (m, 2H), 0.31-0.15 (m, 2H). |
| 149 | 1H NMR (400 MHz, DMSO-d6) δ 8.53-8.40 (m, 1H), 8.11 (s, 3H), 7.94 (dd, J = 8.1, 0.8 Hz, 1H), 7.45 (s, 1H), 7.10 (dd, J = 8.0, 2.0 Hz, 1H), 6.60 (s, 1H), 6.38 (d, J = 1.3 Hz, 1H), 5.07 (td, J = 7.3, 2.2 Hz, 1H), 4.52-4.30 (m, 2H), 4.23-4.10 (m, 2H), 4.09 (s, 3H), 4.05 (dd, J = 8.2, 5.8 Hz, 0H), 4.02-3.61 (m, 5H), 3.44-3.30 (m, 1H), 2.80 (s, 3H), 1.92-1.75 (m, 4H), 1.71 (d, J = 4.7 Hz, 3H), 1.68-1.56 (m, 1H), 1.44 (d, J = 7.0 Hz, 3H), 1.34 (dd, J = 12.8, 4.4 Hz, 1H), 1.28-1.16 (m, 1H), 1.16-0.99 (m, 1H), 0.32-0.13 (m, 4H). |
| 151 | 1H NMR (400 MHz, DMSO-d6) δ 8.11 (s, 3H), 7.96 (d, J = 8.1 Hz, 1H), 7.45 (s, 1H), 7.13 (d, J = 8.1 Hz, 1H), 6.61 (s, 1H), 6.38 (s, 1H), 5.08 (p, J = 7.0 Hz, 1H), 4.52-4.34 (m, 2H), 4.34-3.76 (m, 5H), 2.80 (s, 3H), 2.40-2.18 (m, 1H), 1.92-1.74 (m, 4H), 1.69-1.55 (m, 1H), 1.45 (d, J = 6.9 Hz, 3H), 1.35 (s, 3H), 1.32 (d, J = 4.2 Hz, 1H), 1.19-1.08 (m, 1H), 1.04-0.90 (m, 3H), 0.59-0.46 (m, 3H), 0.34-0.14 (m, 4H). |
| 158 | 1H NMR (400 MHz, DMSO-d6) δ 8.32 (d, J = 7.9 Hz, 1H), 8.25-8.03 (m, 4H), 7.94 (d, J = 8.1 Hz, 1H), 7.45 (s, 1H), 7.07 (d, J = 8.1 Hz, 1H), 6.60 (s, 1H), 6.40 (d, J = 1.3 Hz, 1H), 5.03 (p, J = 7.2 Hz, 1H), 4.47-4.27 (m, 2H), 4.09 (s, 3H), 2.80 (s, 3H), 2.45 (s, 8H), 1.92-1.75 (m, 4H), 1.69-1.55 (m, 1H), 1.45 (dd, J = 7.0, 2.5 Hz, 4H), 1.34 (dd, J = 12.8, 4.4 Hz, 1H), 1.26-1.17 (m, 1H), 1.16-0.97 (m, 1H), 0.34-0.13 (m, 4H). |
| 159 | 1H NMR (400 MHz, DMSO-d6) δ 8.23 (d, J = 7.9 Hz, 1H), 8.17 (s, 3H), 7.98 (d, J = 8.1 Hz, 1H), 7.49 (s, 1H), 7.12 (d, J = 8.1 Hz, 1H), 6.64 (s, 1H), 6.45 (s, 1H), 5.07 (p, J = 7.0 Hz, 1H), 4.64-4.31 (m, 6H), 4.12 (s, 3H), 3.92-3.67 (m, 1H), 3.63 (m, 1H), 2.82 (s, 3H), 2.44-2.26 (m, 1H), 2.20 (s, 6H), 1.94-1.78 (m, 1H), 1.72-1.57 (m, 1H), 1.48 (d, J = 7.0 Hz, 3H), 1.37 (dd, J = 12.9, 4.3 Hz, 1H), 1.19-1.04 (m, 1H), 0.39-0.07 (m, 4H). |
| 160 | 1H NMR (400 MHz, DMSO-d6) δ 8.13 (d, J = 24.2 Hz, 3H), 7.99 (d, J = 8.0 Hz, 1H), 7.94 (d, J = 8.0 Hz, 1H), 7.44 (s, 1H), 7.09 (d, J = 8.1 Hz, 1H), 6.59 (s, 1H), 6.36 (d, J = 1.4 Hz, 1H), 5.03 (p, J = 7.1 Hz, 1H), 4.69-4.25 (m, 3H), 4.08 (s, 3H), 2.87 (s, 1H), 2.81 (s, 3H), |

TABLE 2-continued

| Ex | NMR |
|---|---|
| | 2.41 (d, J = 1.0 Hz, 1H), 1.98 (d, J = 1.5 Hz, 6H), 1.88-1.74 (m, 4H), 1.70-1.52 (m, 1H), 1.43 (dd, J = 7.0, 6.0 Hz, 4H), 1.34 (dd, J = 12.8, 4.3 Hz, 1H), 1.18-1.01 (m, 1H), 0.50-0.32 (m, 1H), 0.32-0.17 (m, 4H). |
| 165 | 1H NMR (400 MHz, DMSO-d6) δ 8.52 (d, J = 7.1 Hz, 1H), 8.10 (s, 3H), 7.99 (d, J = 8.0 Hz, 1H), 7.44 (s, 1H), 7.16 (d, J = 8.1 Hz, 1H), 6.63 (s, 1H), 6.37 (s, 1H), 5.08 (p, J = 6.8 Hz, 1H), 4.45 (d, J = 7.2 Hz, 2H), 4.09 (s, 3H), 3.93-3.35 (m, 4H), 2.81 (s, 3H), 1.94-1.74 (m, 4H), 1.50 (s, 5H), 1.48 (d, J = 6.9 Hz, 3H), 1.34 (dd, J = 12.8, 4.4 Hz, 1H), 1.18-1.04 (m, 1H), 0.32-0.18 (m, 4H). |
| 166 | 1H NMR (400 MHz, DMSO-d6) δ 8.24 (d, J = 7.8 Hz, 1H), 8.07 (s, 3H), 7.94 (dd, J = 8.1, 4.7 Hz, 1H), 7.44 (s, 1H), 7.10 (d, J = 8.1 Hz, 1H), 6.59 (s, 1H), 6.35 (s, 1H), 5.12-5.00 (m, 1H), 4.75 (dd, J = 18.7, 5.9 Hz, 2H), 4.48-4.37 (m, 2H), 4.27 (d, J = 6.0 Hz, 2H), 4.08 (s, 3H), 3.84-3.27 (m, 3H), 2.81 (s, 3H), 1.89-1.76 (m, 4H), 1.68-1.58 (m, 1H), 1.54 (s, 3H), 1.46 (d, J = 7.0 Hz, 3H), 1.42-1.27 (m, 1H), 1.18-1.07 (m, 1H), 0.32-0.14 (m, 4H). |
| 167 | 1H NMR (400 MHz, DMSO-d6) δ 8.09 (s, 3H), 7.96 (s, 0.5H), 7.94 (s, 0.5H), 7.77 (s, 0.5H), 7.75 (s, 0.5H), 7.42 (s, 0.5H), 7.26 (s, 0.5H), 7.11 (d, J = 1.2 Hz, 1H), 7.09 (s, 1H), 6.59 (d, J = 3.8 Hz, 1H), 6.34 (d, J = 10.3 Hz, 1H), 5.05 m, 1H), 4.42 (m, 2H), 4.34 (s, 0.5H), 4.07 (d, J = 6.0 Hz, 4H), 3.54 (m, 3H), 3.18 (d, J = 10.2 Hz, 0.5H), 3.16 (d, J = 10.2 Hz, 0.5H), 2.81 (d, J = 6.1 Hz, 3H), 2.70 (m, 0.5H), 2.62 (m, 0.5H), 1.99 (m, 1H), 1.84-1.65 (m, 1H), 1.44 (d, J = 7.0 Hz, 3H), 1.15 (s, 9H), 1.07 (d, J = 7.6 Hz, 1.5H), 0.96 (d, J = 7.7 Hz, 1.5H), 0.24 (m, 4H). |
| 169 | 1H NMR (400 MHz, DMSO-d6) δ 8.26 (d, J = 7.9 Hz, 1H), 8.07 (s, 3H), 7.94 (d, J = 8.1 Hz, 1H), 7.44 (s, 1H), 7.08 (d, J = 8.0 Hz, 1H), 6.59 (s, 1H), 6.36 (d, J = 1.3 Hz, 1H), 5.14-4.95 (m, 1H), 4.59-4.30 (m, 2H), 4.08 (s, 3H), 4.01-3.40 (m, 5H), 2.81 (s, 3H), 2.29 (d, J = 2.6 Hz, 6H), 1.92-1.74 (m, 3H), 1.71-1.56 (m, 1H), 1.46 (d, J = 7.0 Hz, 3H), 1.33 (dd, J = 12.8, 4.4 Hz, 1H), 1.16-1.03 (m, 1H), 0.36-0.14 (m, 4H). |
| 177 | 1H NMR (400 MHz, DMSO-d6) δ 8.08 (s, 3H), 7.95 (d, J = 8.1 Hz, 1H), 7.78 (d, J = 7.7 Hz, 1H), 7.45 (s, 1H), 7.10 (d, J = 8.1 Hz, 1H), 6.59 (s, 1H), 6.37 (s, 1H), 5.04 (p, J = 7.0 Hz, 1H), 4.48-4.35 (m, 2H), 4.08 (s, 3H), 3.85-3.64 (m, 1H), 2.80 (s, 3H), 1.94-1.73 (m, 3H), 1.67-1.55 (m, 1H), 1.44 (d, J = 6.9 Hz, 3H), 1.39-1.27 (m, 1H), 1.22-1.06 (m, 10H), 0.36-0.17 (m, 4H). (Expect 44, Observe 41) |
| 178 | 1H NMR (400 MHz, DMSO-d6) δ 8.28 (d, J = 7.9 Hz, 1H), 8.07 (s, 3H), 7.93 (d, J = 8.0 Hz, 1H), 7.42 (s, 1H), 7.09 (d, J = 8.1 Hz, 1H), 6.62 (s, 1H), 6.37 (s, 1H), 5.04 (q, J = 7.2 Hz, 1H), 4.67-4.36 (m, 2H), 4.11 (s, 3H), 3.15-3.03 (m, 3H), 2.43-2.33 (m, 1H), 1.87 (s, 3H), 1.84 (d, J = 11.9 Hz, 2H), 1.69-1.53 (m, 1H), 1.43 (d, J = 7.0 Hz, 3H), 1.42-1.36 (m, 1H), 1.37-1.28 (m, 1H), 1.26-1.20 (m, 1H), 1.03-0.92 (m, 1H), 0.88 (d, J = 8.0 Hz, 2H), 0.39-0.30 (m, 2H), 0.27-0.18 (m, 2H), 0.15-0.06 (m, 2H). |
| 182 | 1H NMR (400 MHz, DMSO-d6) δ 8.31 (d, J = 7.9 Hz, 1H), 8.15 (brs, 3H), 7.97 (d, J = 8.1 Hz, 1H), 7.37 (s, 1H), 7.11 (d, J = 8.1 Hz, 1H), 6.62 (s, 1H), 6.39 (s, 1H), 5.15-5.03 (m, 1H), 4.76-4.53 (m, 1H), 4.52-4.34 (m, 2H), 4.19 (brs, 1H), 4.10 (s, 3H), 3.65 (s, 2H), 2.83 (s, 3H), 2.32 (s, 3H), 2.32 (s, 3H), 1.99-1.86 (m, 4H), 1.48 (d, J = 7.0 Hz, 3H), 1.21-1.10 (m, 1H), 0.34-0.20 (m, 4H). |
| 183 | 1H NMR (400 MHz, DMSO-d6) δ 8.31 (d, J = 7.9 Hz, 1H), 8.15 (brs, 3H), 7.97 (d, J = 8.1 Hz, 1H), 7.36 (s, 1H), 7.11 (d, J = 8.1 Hz, 1H), 6.62 (s, 1H), 6.39 (s, 1H), 5.14-5.03 (m, 1H), 4.75-4.58 (m, 1H), 4.51-4.34 (m, 2H), 4.19 (brs, 1H), 4.10 (s, 3H), 3.64 (s, 2H), 2.83 (s, 3H), 2.33 (s, 3H), 2.32 (s, 3H), 2.02-1.84 (m, 4H), 1.48 (d, J = 7.0 Hz, 3H), 1.20-1.12 (m, 1H), 0.33-0.25 (m, 4H). |
| 184 | 1H NMR (400 MHz, DMSO-d6) δ 8.02 (d, J = 7.9 Hz, 1H), 7.52 (s, 1H), 7.46 (s, 5H), 7.25 (d, J = 1.3 Hz, 1H), 7.32-7.02 (m, 0.8H), 6.66 (s, 1H), 6.39 (s, 1H), 6.07-5.93 (m, 0.2H), 5.10-5.05 (m, 1H), 4.40 (d, J = 7.0 Hz, 2H), 4.09 (s, 3H), 3.02 (s, 6H), 2.81 (s, 3H), 2.75 (s, 3H), 1.69-1.63 (m, 3H), 1.17-1.12 (m, 1H), 0.32-0.22 (m, 4H). |
| 185 | 1H NMR (400 MHz, DMSO-d6) δ 8.13 (s, 3H), 8.02 (d, J = 8.0 Hz, 1H), 7.55-7.50 (m, 1H), 7.49-7.43 (m, 5H), 7.28-6.95 (m, 0.6H), 6.65 (s, 1H), 6.40 (d, J = 1.4 Hz, 1H), 6.04-5.99 (m, 0.4H), 5.10-5.05 (m, 1H), 4.44 (d, J = 7.1 Hz, 2H), 4.11 (s, 3H), 3.82-3.71 (m, 3H), 2.83 (s, 3H), 2.76 (s, 3H), 1.92-1.78 (m, 4H), 1.70-1.61 (m, 4H), 1.36 (dd, J = 12.8, 4.4 Hz, 1H), 1.20-1.09 (m, 1H), 0.33-0.22 (m, 4H). |
| 186 | 1H NMR (400 MHz, DMSO-d6) δ 8.03 (d, J = 8.0 Hz, 1H), 8.16-7.82 (m, 3H), 7.55-7.50 (m, 2H), 7.50-7.43 (m, 4H), 7.34 (s, 1H), 7.27-7.03 (m, 0.5H), 6.67 (s, 1H), 6.45 (s, 1H), 6.04-5.99 (m, 0.5H), 5.11-5.04 (m, 1H), 4.39 (d, J = 7.1 Hz, 2H), 4.10 (s, 3H), 3.33-3.21 (m, 5H), 2.81 (s, 3H), 2.75 (s, 3H), 2.06-1.99 (m, 1H), 1.80-1.72 (m, 1H), 1.66 (d, J = 6.9 Hz, 3H), 1.64-1.55 (m, 2H), 1.21-1.10 (m, 1H), 0.33-0.23 (m, 4H). |
| 188 | 1H NMR (400 MHz, Methanol-d4) δ 9.12-8.97 (m, 2H), 8.04 (d, J = 8.1 Hz, 1H), 7.20 (d, J = 8.1 Hz, 1H), 6.81 (s, 1H), 6.57-6.39 (m, 2H), 5.31-5.10 (m, 1H), 4.81-4.58 (m, 1H), 4.35-4.16 (m, 2H), 4.16-4.03 (m, 1H), 2.85 (s, 3H), 2.40-2.33 (m, 8H), 1.90-1.64 (m, 2H), 1.65-1.52 (m, 4H), 1.38-1.26 (m, 1H), 1.14-0.95 (m, 1H), 0.47-0.35 (m, 2H), 0.31-0.18 (m, 2H). |
| 189 | 1H NMR (400 MHz, DMSO-d6) δ 8.31 (d, J = 7.9 Hz, 1H), 8.17-8.02 (m, 2H), 7.98 (d, J = 8.1 Hz, 1H), 7.94-7.79 (m, 1H), 7.41-7.21 (m, 1H), 7.12 (d, J = 8.1 Hz, 1H), 6.64 (s, 1H), 6.45 (s, 1H), 5.09 (p, J = 7.1 Hz, 1H), 5.03-4.81 (m, 0.5H), 4.62-4.48 (m, 1H), 4.46-4.31 (m, 2H), 4.27-4.17 (m, 0.5H), 4.11 (s, 3H), 3.90-3.76 (m, 0.5H), 3.46-3.25 (m, 1H), 3.22-3.04 (m, 0.5H), 2.80 (s, 3H), 2.32 (d, J = 2.6 Hz, 7H), 2.05-1.93 (m, 1H), 1.91-1.76 (m, 1H), 1.74-1.53 (m, 3H), 1.48 (d, J = 7.0 Hz, 3H), 1.20-1.02 (m, 1H), 0.37-0.19 (m, 4H)., rotamers present |
| 190 | 1H NMR (400 MHz, DMSO-d6) δ 8.32 (d, J = 7.9 Hz, 1H), 8.02 (s, 1H), 7.98 (d, J = 8.1 Hz, 1H), 7.81 (s, 1H), 7.32 (s, 0.35H minor rotamer), 7.26 (s, 0.65H major rotamer), 7.12 (d, J = 8.1 Hz, 1H), 6.67 (s, 1H), 6.45 (s, 1H), 5.15-5.04 (m, 1H), 4.99 (brs, 0.35H minor rotamer), 4.54 (s, 1H), 4.48-4.36 (m, 2H), 4.23 (brs, 0.65H major rotamer), 4.13 (s, 3H), 3.45-3.09 (m, 3H), 2.77 (brs, 1H), 2.45-2.35 (m, 1H), 2.32 (d, J = 2.6 Hz, 6H), 2.05-1.44 (m, 5H), 1.49 (d, J = 7.0 Hz, 3H), 1.07-0.95 (m, 1H), 0.90 (d, J = 8.0 Hz, 2H), 0.37 (d, J = 6.3 Hz, 2H), 0.29-0.21 (m, 2H), 0.21-0.10 (m, 2H). |

TABLE 2-continued

| Ex | NMR |
|---|---|
| 191 | 1H NMR (400 MHz, DMSO-d6) δ 8.78 (d, J = 8.2 Hz, 1H), 8.13 (dd, J = 8.1, 1.4 Hz, 1H), 7.99 (s, 3H), 7.59-7.31 (m, 2H), 6.73 (d, J = 1.4 Hz, 1H), 6.37 (s, 1H), 6.15-5.75 (m, 1H), 4.56 (dd, J = 14.2, 6.6 Hz, 1H), 4.40 (dd, J = 14.3, 7.6 Hz, 1H), 4.09 (d, J = 1.4 Hz, 3H), 4.44-3.35 (m, 4H), 2.82 (d, J = 1.4 Hz, 3H), 2.31 (s, 1H), 1.92-1.46 (m, 8H), 1.39-1.25 (m, 1H), 1.15 (s, 1H), 0.40-0.11 (m, 4H). |
| 192 | 1H NMR (400 MHz, DMSO-d6) δ 8.16 (d, J = 9.1 Hz, 1H), 8.08 (d, 1H), 8.07 (s, 3H), 7.93 (s, 0H), 7.45 (s, 1H), 7.42 (s, 1H), 6.68 (s, 1H), 6.35 (s, 1H), 6.11-5.83 (m, 1H), 4.54 (d, J = 8.1 Hz, 0H), 4.47 (d, J = 7.2 Hz, 2H), 4.08 (s, 3H), 3.64-3.54 (m, 1H), 2.87 (s, 1H), 2.82 (s, 3H), 2.71 (d, J = 0.6 Hz, 2H), 1.88-1.78 (m, 4H), 1.77-1.71 (m, 1H), 1.69-1.55 (m, 1H), 1.39-1.28 (m, 1H), 1.19 (s, 12H), 1.18 (s, 4H), 1.17-1.12 (m, 1H), 0.32-0.18 (m, 4H). |
| 195 | 1H NMR (400 MHz, DMSO-d6) δ 8.16 (d, J = 8.2 Hz, 0H), 8.11 (d, J = 9.0 Hz, 1H), 8.03 (d, J = 8.1 Hz, 0H), 7.95 (s, 6H), 7.92 (d, J = 8.0 Hz, 1H), 7.29 (s, 1H), 7.21 (s, 0H), 7.10-7.02 (m, 1H), 6.95 (s, 0H), 6.58 (s, 1H), 6.36 (s, 1H), 4.75 (dd, J = 9.0, 7.7 Hz, 1H), 4.58-4.29 (m, 1H), 4.07 (s, 2H), 3.36-2.88 (m, 2H), 2.81 (s, 2H), 2.19 (q, J = 9.8, 8.4 Hz, 1H), 2.02 (d, J = 24.7 Hz, 1H), 1.87 (d, J = 4.4 Hz, 3H), 1.74 (s, 0H), 1.68-1.46 (m, 2H), 1.25 (s, 1H), 1.09 (s, 0H), 0.90 (t, J = 6.6 Hz, 3H), 0.76 (t, J = 7.3 Hz, 3H), 0.49-0.31 (m, 1H), 0.31-0.11 (m, 3H). |
| 196 | 1H NMR (400 MHz, DMSO-d6) δ 8.16 (s, 3H), 7.97 (dd, J = 8.0, 0.9 Hz, 1H), 7.48 (s, 1H), 7.17 (dd, J = 8.1, 3.2 Hz, 1H), 6.67-6.56 (m, 1H), 6.62 (s, 1H), 6.43 (s, 1H), 5.02-4.86 (m, 1H), 4.84-4.77 (m, 1H), 4.75-4.68 (m, 1H), 4.65-4.31 (m, 2H), 4.63-4.26 (m, 3H), 4.16-4.08 (m, 1H), 4.12 (s, 3H), 4.02-3.94 (m, 1H), 3.95-3.84 (m, 1H), 3.63-3.52 (m, 1H), 2.82 (s, 3H), 2.42-2.18 (m, 1H), 2.08 (td, J = 12.6, 4.9 Hz, 1H), 1.93-1.73 (m, 3H), 1.73-1.55 (m, 2H), 1.45 (d, J = 7.0 Hz, 3H), 1.37 (dd, J = 12.8, 4.4 Hz, 1H), 1.19-1.04 (m, 1H), 0.26 (dtd, J = 18.3, 8.2, 5.4 Hz, 4H). |
| 197 | 1H NMR (400 MHz, DMSO-d6) δ 8.12 (brs, 3H), 7.97 (d, J = 8.1 Hz, 1H), 7.48 (s, 1H), 7.29 (s, 1H), 7.15 (d, J = 8.0 Hz, 1H), 6.99 (d, J = 8.0 Hz, 1H), 6.61 (s, 1H), 6.39 (s, 1H), 4.99-4.88 (m, 1H), 4.47 (dd, J = 14.2, 6.9 Hz, 1H), 4.41 (dd, J = 14.2, 7.3 Hz, 1H), 4.11 (s, 3H), 4.07 (dd, J = 9.6, 2.8 Hz, 2H), 3.88 (d, J = 9.7 Hz, 2H), 3.74 (brs, 2H), 2.83 (s, 3H), 2.43-2.28 (m, 1H), 1.93-1.76 (m, 3H), 1.72-1.60 (m, 1H), 1.46 (d, J = 7.0 Hz, 3H), 1.36 (dd, J = 12.9, 4.4 Hz, 1H), 1.18-1.06 (m, 1H), 0.32-0.22 (m, 4H). |
| 202 | 1H NMR (400 MHz, DMSO-d6) δ 8.17 (brs, 3H), 7.97 (d, J = 8.1 Hz, 1H), 7.49 (s, 1H), 7.17 (d, J = 8.1 Hz, 1H), 6.96 (d, J = 8.0 Hz, 1H), 6.63 (s, 1H), 6.45 (s, 1H), 5.24-5.14 (m, 1H), 4.97-4.86 (m, 1H), 4.59 (brs, 2H), 4.50-4.34 (m, 2H), 4.31-4.20 (m, 2H), 4.12 (s, 3H), 3.92 (td, J = 9.3, 3.9 Hz, 2H), 3.77 (brs, 1H), 2.82 (s, 3H), 2.39-2.25 (m, 1H), 2.00-1.59 (m, 4H), 1.46 (d, J = 7.0 Hz, 3H), 1.37 (dd, J = 12.8, 4.4 Hz, 1H), 1.28-0.85 (m, 1H), 0.36-0.17 (m, 4H). |
| 203 | 1H NMR (400 MHz, DMSO-d6) δ 8.17 (d, J = 5.4 Hz, 3H), 7.94 (d, J = 8.1 Hz, 1H), 7.46 (s, 1H), 7.16 (d, J = 8.1 Hz, 1H), 6.60 (s, 1H), 6.40 (d, J = 1.3 Hz, 1H), 6.31 (d, J = 7.8 Hz, 1H), 5.52-4.98 (m, 4H), 5.04-4.89 (m, 1H), 4.48-4.31 (m, 2H), 4.09 (s, 3H), 3.74 (s, 1H), 3.52-3.41 (m, 1H), 3.41-3.30 (m, 1H), 3.25-3.02 (m, 2H), 2.80 (s, 3H), 2.39-2.21 (m, 1H), 2.24-2.08 (m, 1H), 1.94-1.58 (m, 6H), 1.44 (d, J = 7.0 Hz, 3H), 1.35 (dd, J = 12.8, 4.4 Hz, 1H), 1.09 (s, 6H), 0.31-0.24 (m, 2H), 0.23-0.14 (m, 2H). |
| 204 | 1H NMR (400 MHz, DMSO-d6) δ 8.12 (s, 4H), 8.00-7.87 (m, 2H), 7.46 (s, 1H), 7.10 (dd, J = 8.1, 3.6 Hz, 1H), 6.62 (s, 1H), 6.43 (d, J = 1.3 Hz, 1H), 5.14-4.97 (m, 3H), 4.64-4.21 (m, 3H), 4.10 (s, 3H), 3.73 (s, 1H), 3.37 (s, 2H), 2.79 (s, 3H), 2.39-2.18 (m, 1H), 1.95 (s, 2H), 1.80 (s, 8H), 1.70-1.55 (m, 1H), 1.44 (d, J = 7.0 Hz, 3H), 1.34 (dd, J = 12.8, 4.4 Hz, 1H), 1.16-1.04 (m, 1H), 0.31-0.25 (m, 2H), 0.25-0.15 (m, 2H). |
| 205 | ¹H NMR (400 MHz, DMSO-d₆) δ 8.13 (brs, 3H), 7.96 (d, J = 8.1 Hz, 1H), 7.48 (s, 1H), 7.16 (d, J = 8.1 Hz, 1H), 6.86 (d, J = 8.0 Hz, 1H), 6.76 (t, J = 74.8 Hz, 1H), 6.61 (s, 1H), 6.40 (d, J = 1.3 Hz, 1H), 4.98-4.86 (m, 2H), 4.56 (brs, 2H), 4.53-4.35 (m, 2H), 4.22-4.13 (m, 2H), 4.11 (s, 3H), 3.82 (td, J = 8.6, 4.1 Hz, 2H), 2.83 (s, 3H), 2.46-2.29 (m, 1H), 1.95-1.77 (m, 3H), 1.71-1.59 (m, 1H), 1.46 (d, J = 7.0 Hz, 3H), 1.36 (dd, J = 12.9, 4.4 Hz, 1H), 1.24-0.98 (m, 1H), 0.38-0.20 (m, 4H). |
| 215 | 1H NMR (400 MHz, DMSO-d6) δ 8.15 (s, 3H), 7.97 (d, J = 8.1 Hz, 1H), 7.49 (s, 1H), 7.18 (d, J = 8.0 Hz, 1H), 6.64 (s, 1H), 6.45 (d, J = 1.3 Hz, 1H), 6.34 (d, J = 7.7 Hz, 1H), 5.04-4.89 (m, 1H), 4.84-4.26 (m, 6H), 4.12 (s, 3H), 4.00-3.66 (m, 1H), 3.65-3.50 (m, 1H), 3.50-3.36 (m, 2H), 3.29-3.12 (m, 1H), 2.96-2.83 (m, 1H), 2.82 (s, 3H), 2.41-2.27 (m, 1H), 2.28-2.11 (m, 1H), 2.08-1.94 (m, 0H), 1.93-1.77 (m, 3H), 1.72-1.59 (m, 1H), 1.58-1.49 (m, 2H), 1.46 (d, J = 7.0 Hz, 3H), 1.37 (dd, J = 13.0, 4.4 Hz, 1H), 1.23-1.01 (m, 1H), 0.48--0.20 (m, 4H). |
| 217 | ¹H NMR (400 MHz, DMSO-d₆) δ 8.70 (d, J =2.1 Hz, 1H), 8.62 (dd, J = 5.3, 1.5 Hz, 1H), 8.15 (brs, 3H), 7.94 (d, J = 8.0 Hz, 1H), 7.71 (dd, J = 8.0, 5.2 Hz, 1H), 7.45 (s, 1H), 7.08 (d, J = 8.1 Hz, 1H), 6.81 (d, J = 7.2 Hz, 1H), 6.65 (s, 1H), 6.55 (d, J =8.1 Hz, 1H), 6.44 (s, 1H), 4.94-4.80 (m, 2H), 4.59 (brs, 2H), 4.54-4.45 (m, 2H), 4.14 (s, 3H), 3.77 (brs, 1H), 2.46-2.30 (m, 1H), 1.94-1.76 (m, 3H), 1.69-1.57 (m, 1H), 1.42 (d, J = 6.9 Hz, 6H), 1.36 (dd, J = 13.4, 5.0 Hz, 1H), 1.04-0.83 (m, 3H), 0.43-0.30 (m, 2H), 0.29 0.17 (m, 2H), 0.17-0.05 (m, 2H). |
| 218 | 1H NMR (400 MHz, DMSO-d6) δ 8.72 (d, J = 2.1 Hz, 1H), 8.71-8.65 (m, 1H), 8.15 (brs, 3H), 7.97 (d, J = 8.1 Hz, 1H), 7.76 (dd, J = 8.0, 5.3 Hz, 1H), 7.45 (s, 1H), 7.10 (d, J = 8.0 Hz, 1H), 6.77 (d, J = 7.2 Hz, 1H), 6.67 (s, 1H), 6.53 (d, J = 8.2 Hz, 1H), 6.44 (s, 1H), 4.95-4.78 (m, 2H), 4.59-4.40 (m, 3H), 4.31 (brs, 2H), 4.14 (s, 3H), 3.79 (brs, 2H), 2.47-2.28 (m, 1H), 1.94-1.76 (m, 3H), 1.70-1.58 (m, 1H), 1.45-1.29 (m, 7H), 1.03-0.85 (m, 3H), 0.42-0.35 (m, 2H), 0.29-0.19 (m, 2H), 0.16-0.05 (m, 2H). |
| 219 | 1H NMR (400 MHz, DMSO-d6) δ 8.29 (d, J = 7.9 Hz, 1H), 8.12 (brs, 3H), 7.97 (d, J = 8.0 Hz, 1H), 7.45 (s, 1H), 7.10 (d, J = 8.1 Hz, 1H), 6.69 (s, 1H), 6.43 (s, 1H), 5.15-5.03 (m, 1H), 4.85 (s, 2H), 4.48 (brs, 2H), 4.14 (s, 3H), 3.77 (brs, 1H), 2.47-2.40 (m, 2H), 2.33 (s, 3H), 2.32 (s, 3H), 1.91-1.79 (m, 4H), 1.70-1.59 (m, 1H), 1.48 (d, J = 7.0 Hz, 3H), 1.36 (dd, J = 13.4, 5.0 Hz, 1H), 1.33-1.27 (m, 6H), 1.04-0.94 (m, 2H), 0.48-0.37 (m, 2H). |

TABLE 2-continued

| Ex | NMR |
|---|---|
| 220 | ¹H NMR (400 MHz, DMSO-d$_6$) δ 11.48 (brs, 1H), 8.13 (brs, 3H), 7.96 (d, J = 8.1 Hz, 1H), 7.48 (s, 1H), 7.38 (dd, J = 9.1, 6.8 Hz, 1H), 7.17 (d, J = 8.1 Hz, 1H), 6.85 (d, J = 7.6 Hz, 1H), 6.62 (s, 1H), 6.42 (s, 1H), 6.20 (d, J =9.1 Hz, 1H), 5.95 (d, J = 6.8 Hz, 1H), 5.07-4.95 (m, 1H), 4.53 (brs, 2H), 4.49-4.35 (m, 2H), 4.34-4.21 (m, 2H), 4.12 (s, 3H), 3.77 (brs, 1H), 2.97 (s, 3H), 2.83 (s, 3H), 2.44-2.27 (m, 1H), 1.91-1.74 (m, 3H), 1.72-1.59 (m 1H), 1.49 (d, J = 7.0 Hz, 3H), 1.36 (dd, J = 12.8, 4.4 Hz, 1H), 1.19-1.05 (m, 1H), 0.34-0.19 (m, 4H). |
| 221 | ¹H NMR (400 MHz, DMSO-d$_6$) δ 8.70-8.57 (m, 2H), 8.15 (brs, 3H), 8.08 (d, J = 8.1 Hz, 0.5H), 8.02 (d, J = 8.1 Hz, 0.5H), 7.97 (d, J = 8.1 Hz, 1H), 7.73 (dd, J = 8.0, 5.2 Hz, 0.5H), 7.68 (dd, J = 8.0, 5.2 Hz, 0.5H), 7.47 (s, 1H), 7.19 (d, J = 8.1 Hz, 0.5H), 7.17 (d, J = 8.1 Hz, 0.5H), 6.78 (d, J = 7.6 Hz, 0.5H), 6.76 (d, J = 7.6 Hz, 0.5H), 6.63 (s, 0.5H), 6.62 (s, 0.5H), 6.41 (s, 1H), 5.69-5.58 (m, 1H), 5.10-4.97 (m, 1H), 4.55 (brs, 2H), 4.51-4.37 (m, 2H), 4.12 (s, 3H), 3.77 (s, 1H), 2.83 (s, 3H), 2.75 (s, 3H), 2.41-2.28 (m, 1H), 1.93-1.74 (m, 3H), 1.71-1.59 (m, 1H), 1.57-1.43 (m, 2H), 1.53 (d, J = 7.1 Hz, 1.5H), 1.50 (d, J = 7.1 Hz, 1.5H), 1.37 (dd, J = 12.8, 4.4 Hz, 1H), 1.16-1.08 (m, 2H), 0.37-0.12 (m, 4H). |
| 222 | ¹H NMR (400 MHz, DMSO-d$_6$) δ 8.68-8.64 (m, 2H), 8.62 (s, 1H), 8.14 (brs, 3H), 7.99 (d, J = 8.5 Hz, 1H), 7.95 (d, J = 8.0 Hz, 1H), 7.68 (dd, J = 7.9, 5.2 Hz, 1H), 7.47 (s, 1H), 7.17 (d, J = 8.1 Hz, 1H), 6.83 (d, J = 7.6 Hz, 1H), 6.62 (s, 1H), 6.41 (s, 1H), 5.09-4.95 (m, 1H), 4.63-4.52 (m, 2H), 4.50-4.36 (m, 2H), 4.12 (s, 3H), 3.76 (brs, 1H), 2.96 (s, 3H), 2.83 (s, 3H), 2.42-2.20 (m, 1H), 1.95-1.75 (m, 3H), 1.73-1.59 (m, 1H), 1.49 (d, J = 7.0 Hz, 3H), 1.37 (dd, J = 12.9, 4.4 Hz, 1H), 1.20-1.08 (m, 1H), 0.30-0.20 (m, 4H). |
| 223 | ¹H NMR (400 MHz, DMSO-d$_6$) δ 8.73 (d, J = 6.5 Hz, 1H), 8.13 (brs, 3H), 7.98 (d, J = 8.0 Hz, 1H), 7.70 (d, J = 5.7 Hz, 2H), 7.46 (s, 1H), 7.15 (d, J = 8.0 Hz, 1H), 6.86 (t, J = 6.0 Hz, 1H), 6.80 (d, J = 8.1 Hz, 1H), 6.62 (s, 1H), 6.39 (s, 1H), 5.00-4.88 (m, 1H), 4.51 (brs, 2H), 4.49-4.39 (m, 2H), 4.46 (d, J = 4.8 Hz, 2H), 4.11 (s, 3H), 3.76 (brs, 1H), 2.83 (s, 3H), 1.94-1.79 (m, 3H), 1.73-1.59 (m, 1H), 1.45 (d, J = 6.9 Hz, 3H), 1.36 (dd, J = 12.9, 4.3 Hz, 1H), 1.18-1.07 (m, 1H), 0.37-0.17 (m, 4H). |
| 224 | 1H NMR (400 MHz, DMSO-d6) δ 8.78 (d, J = 4.9 Hz, 2H), 8.15 (brs, 3H), 7.97 (d, J = 8.0 Hz, 1H), 7.48 (brs, 1H), 7.40 (t, J = 4.9 Hz, 1H), 7.16 (d, J = 8.0 Hz, 1H), 6.81 (d, J = 8.1 Hz, 1H), 6.66 (brs, 1H), 6.63 (s, 1H), 6.42 (s, 1H), 4.98-4.87 (m, 1H), 4.52 (brs, 2H), 4.45 (d, J = 4.7 Hz, 2H), 4.12 (s, 3H), 3.77 (s, 1H), 2.83 (s, 3H), 2.45-2.21 (m, 1H), 1.95-1.73 (m, 3H), 1.73-1.63 (m, 1H), 1.43 (d, J = 6.9 Hz, 3H), 1.37 (dd, J = 12.8, 4.4 Hz, 1H), 1.20-1.04 (m, 1H), 0.33-0.16 (m, 4H). |
| 225 | ¹H NMR (400 MHz, DMSO-d$_6$) δ 8.12 (brs, 3H), 7.96 (d, J = 8.1 Hz, 1H), 7.48 (s, 1H), 7.42 (s, 1H), 7.16 (d, J = 8.1 Hz, 1H), 6.98 (s, 1H), 6.68 (d, J = 8.1 Hz, 1H), 6.62 (s, 1H), 6.41 (d, J = 1.3 Hz, 1H), 4.97-4.85 (m, 1H), 4.54 (brs, 2H), 4.43 (ddt, J = 21.3, 14.0, 7.1 Hz, 2H), 4.12 (s, 3H), 4.03-3.83 (m, 4H), 3.78 (brs, 1H), 3.25 (tt, J = 8.7, 6.1 Hz, 1H), 2.83 (s, 3H), 2.38-2.29 (m, 1H), 1.93-1.78 (m, 3H), 1.70-1.59 (m, 1H), 1.45 (d, J =7.0 Hz, 3H), 1.36 (dd, J = 12.8, 4.4 Hz, 1H), 1.21-1.06 (m, 1H), 0.41-0.16 (m, 4H). |
| 226 | ¹H NMR (400 MHz, DMSO-d$_6$) δ 8.62 (s, 1H), 8.61 (s, 1H), 8.12 (brs, 3H), 8.05-7.99 (m, 1H), 7.96 (d, J = 8.0 Hz, 1H), 7.66 (dd, J = 7.7, 5.2 Hz, 1H), 7.46 (s, 1H), 7.13 (d, J = 8.0 Hz, 1H), 6.73 (t, J = 6.0 Hz, 1H), 6.66 (d, J = 8.0 Hz, 1H), 6.62 (s, 1H), 6.39 (s, 1H), 5.00-4.86 (m, 1H), 4.52 (brs, 2H), 4.46 (d, J = 7.3 Hz, 2H), 4.33 (d, J = 5.7 Hz, 2H), 4.11 (s, 3H), 3.76 (brs, 1H), 2.84 (s, 3H), 2.42-2.22 (m, 1H), 1.95-1.76 (m, 3H), 1.70-1.56 (m, 1H), 1.43 (d, J = 6.9 Hz, 3H), 1.36 (dd, J = 12.9, 4.4 Hz, 1H), 1.19-1.06 (m, 1H), 0.33-0.15 (m, 4H). |
| 227 | 1H NMR (400 MHz, DMSO-d6) δ 8.12 (brs, 3H), 7.96 (d, J = 8.1 Hz, 1H), 7.48 (s, 1H), 7.16 (d, J = 8.1 Hz, 1H), 6.62 (d, J = 8.0 Hz, 1H), 6.62 (s, 1H), 6.41 (d, J = 1.3 Hz, 1H), 4.99-4.85 (m, 1H), 4.55 (brs, 1H), 4.54-4.34 (m, 3H), 4.12 (s, 3H), 4.03 (t, J = 6.8 Hz, 2H), 3.76 (brs, 1H), 3.62 (dt, J = 8.7, 4.4 Hz, 2H), 2.83 (s, 3H), 2.38-2.25 (m, 2H), 1.95-1.75 (m, 3H), 1.70-1.59 (m, 1H), 1.45 (d, J = 7.0 Hz, 3H), 1.36 (dd, J = 12.9, 4.4 Hz, 1H), 1.19-1.06 (m, 1H), 0.34-0.20 (m, 4H). |
| 228 | 1H NMR (400 MHz, DMSO-d6) δ 12.49 (brs, 1H), 8.11 (brs, 3H), 7.96 (d, J = 8.1 Hz, 1H), 7.48 (s, 1H), 7.18 (d, J = 8.1 Hz, 1H), 6.61 (s, 1H), 6.46 (d, J = 7.8 Hz, 1H), 6.40 (s, 1H), 5.10-4.88 (m, 1H), 4.54 (brs, 2H), 4.43 (ddt, J = 21.4, 14.1, 7.0 Hz, 2H), 4.11 (s, 3H), 3.77 (brs, 1H), 3.66-3.24 (m, 3H), 3.13-3.02 (m, 1H), 2.83 (s, 3H), 2.39-2.27 (m, 1H), 2.18-1.96 (m, 2H), 1.96-1.76 (m, 3H), 1.71-1.60 (m, 1H), 1.47 (d, J = 7.0 Hz, 3H), 1.36 (dd, J = 12.8, 4.4 Hz, 1H), 1.20-1.05 (m, 1H), 0.36-0.15 (m, 4H). |
| 229 | 1H NMR (400 MHz, DMSO-d6) δ 8.16 (brs, 3H), 8.06 (dd, J = 8.0, 2.2 Hz, 1H), 7.44 (s, 1H), 7.26-7.15 (m, 1H), 6.66 (s, 1H), 6.38 (s, 1H), 5.25 (brs, 1H), 5.11-4.87 (m, 1H), 4.90-4.69 (m, 2H), 4.68-4.51 (m, 2H), 4.42-4.14 (m, 2H), 4.11 (s, 3H), 4.09-3.68 (m, 3H), 3.65-3.43 (m, 2H), 2.84 (s, 3H), 2.45-2.26 (m, 1H), 1.97-1.75 (m, 3H), 1.69-1.55 (m, 1H), 1.63 (d, J = 6.8 Hz, 3H), 1.37 (dd, J = 12.9, 4.3 Hz, 1H), 1.20-1.06 (m, 1H), 0.37-0.18 (m, 4H). |
| 230 | ¹H NMR (400 MHz, DMSO-d$_6$) δ 12.71 (brs, 1H), 8.13 (brs, 3H), 7.96 (d, J = 8.1 Hz, 1H), 7.48 (s, 1H), 7.16 (d, J = 8.1 Hz, 1H), 6.74 (d, J = 8.1 Hz, 1H), 6.61 (s, 1H), 6.41 (s, 1H), 4.98-4.85 (m, 1H), 4.53 (brs, 2H), 4.43 (ddt, J = 21.4, 14.1, 7.0 Hz, 2H), 4.11 (s, 3H), 4.08 (dd, J = 8.0, 4.6 Hz, 2H), 3.77 (brs, 1H), 3.62 (dd, J = 8.0, 1.4 Hz, 2H), 2.83 (s, 3H), 2.41-2.23 (m, 1H), 1.90-1.74 (m, 3H), 1.71-1.60 (m, 1H), 1.46 (s, 3H), 1.45 (d, J =6.9 Hz, 3H), 1.36 (dd, J = 12.8, 4.4 Hz, 1H), 1.18-1.06 (m, 1H), 0.33-0.21 (m, 4H). |
| 231 | 1H NMR (400 MHz, DMSO-d6) δ 8.13 (brs, 3H), 7.96 (d, J = 8.0 Hz, 1H), 7.48 (s, 1H), 7.11 (dd, J = 8.1, 1.3 Hz, 1H), 6.62 (s, 1H), 6.41 (s, 1H), 6.38-6.27 (m, 2H), 4.99-4.85 (m, 1H), 4.53 (brs, 2H), 4.46 (d, J = 7.1 Hz, 2H), 4.12 (s, 3H), 3.82-3.62 (m, 3H), 3.40 (ddd, J = 24.9, 8.8, 3.7 Hz, 1H), 2.83 (s, 3H), 2.41-2.24 (m, 1H), 2.13-1.99 (m, 1H), 1.94-1.75 (m, 3H), 1.70-1.56 (m, 2H), 1.40 (d, J = 7.0 Hz, 3H), 1.36 (dd, J = 12.8, 4.3 Hz, 1H), 1.17-1.05 (m, 1H), 0.36-0.16 (m, 4H). |

TABLE 2-continued

| Ex | NMR |
|---|---|
| 232 | 1H NMR (400 MHz, DMSO-d6) δ 8.14 (d, J = 32.1 Hz, 3H), 7.94 (d, J = 8.0 Hz, 1H), 7.44 (s, 1H), 7.15 (dd, J = 8.1, 5.0 Hz, 2H), 6.59 (s, 1H), 6.37 (d, J = 1.3 Hz, 1H), 4.91 (p, J = 7.1 Hz, 1H), 4.41 (ddt, J = 21.3, 14.1, 7.1 Hz, 2H), 4.24 (t, J = 12.8 Hz, 5H), 4.08 (s, 3H), 3.95-3.30 (m, 2H), 2.81 (s, 3H), 1.93-1.72 (m, 4H), 1.68-1.56 (m, 1H), 1.45 (d, J = 7.1 Hz, 3H), 1.34 (dd, J = 12.8, 4.4 Hz, 1H), 1.26-1.14 (m, 1H), 1.16-1.00 (m, 1H), 0.32-0.14 (m, 4H). |
| 233 | $^1$H NMR (400 MHz, DMSO-d$_6$) δ 8.13 (brs, 3H), 7.97 (d, J = 8.0 Hz, 1H), 7.47 (s, 1H), 7.33-7.16 (m, 6H), 7.13 (d, J = 8.1 Hz, 1H), 6.62 (s, 1H), 6.55 (dd, J = 6.0, 6.0 Hz, 1H), 6.49 (d, J = 8.1 Hz, 1H), 6.40 (s, 1H), 5.03-4.90 (m, 1H), 4.54 (brs, 2H), 4.46 (d, J = 7.2 Hz, 2H), 4.28-4.15 (m, 2H), 4.11 (s, 3H), 3.75 (brs, 1H), 2.83 (s, 3H), 1.93-1.76 (m, 3H), 1.71-1.57 (m, 1H), 1.43 (d, J = 6.9 Hz, 3H), 1.36 (dd, J = 12.8, 4.4 Hz, 1H), 1.20-1.05 (m, 1H), 0.34-0.12 (m, 4H). |
| 234 | $^1$H NMR (400 MHz, DMSO-d$_6$) δ 8.14 (brs, 3H), 7.96 (d, J = 8.1 Hz, 1H), 7.48 (s, 1H), 7.16 (d, J = 8.1 Hz, 1H), 6.95 (d, J = 8.0 Hz, 1H), 6.62 (s, 1H), 6.41 (d, J = 1.4 Hz, 1H), 4.99-4.83 (m, 1H), 4.54 (brs, 2H), 4.43 (ddt, J = 21.3, 14.1, 7.0 Hz, 2H), 4.15 (td, J = 8.6, 2.6 Hz, 2H), 4.12 (s, 3H), 4.03-3.94 (m, 2H), 2.83 (s, 3H), 2.44-2.22 (m, 1H), 1.93-1.57 (m, 4H), 1.46 (d, J = 7.0 Hz, 3H), 1.36 (dd, J = 12.8, 4.4 Hz, 1H), 1.17-1.07 (m, 1H), 0.32-0.21 (m, 4H). |
| 237 | $^1$H NMR (400 MHz, DMSO-d$_6$) δ 8.12 (brs, 3H), 7.96 (d, J = 8.0 Hz, 1H), 7.47 (s, 1H), 7.12 (d, J = 8.1 Hz, 1H), 6.61 (s, 1H), 6.57 (d, J = 8.1 Hz, 1H), 6.39 (s, 1H), 6.31 (t, J = 6.1 Hz, 1H), 6.06 (d, J = 1.5 Hz, 1H), 5.62 (d, J = 1.8 Hz, 1H), 4.98-4.87 (m, 1H), 4.47 (d, J = 7.2 Hz, 2H), 4.11 (s, 3 H), 3.82 (d, J = 5.7 Hz, 2H), 2.84 (s, 3H), 2.02-1.57 (m, 5H), 1.52-1.33 (m, 2H), 1.41 (d, J = 6.9 Hz, 3H), 1.19-1.05 (m, 2H), 0.34-0.17 (m, 5H). |
| 240 | $^1$H NMR (400 MHz, DMSO-d$_6$) δ 8.14 (brs, 3H), 7.97 (d, J = 8.1 Hz, 1H), 7.48 (s, 1H), 7.37-7.31 (m, 2H), 7.29-7.21 (m, 4H), 7.18 (d, J = 8.1 Hz, 1H), 6.71 (d, J = 7.6 Hz, 1H), 6.63 (s, 1H), 6.43 (s, 1H), 5.76 (s, 3H), 5.11-4.94 (m, 1H), 4.49 (d, J = 3.4 Hz, 2H), 4.47-4.35 (m, 2H), 4.12 (s, 3H), 2.87 (s, 3H), 2.83 (s, 3H), 1.93-1.75 (m, 3H), 1.78-1.55 (m, 1H), 1.49 (d, J = 7.0 Hz, 3H), 1.37 (dd, J = 12.8, 4.4 Hz, 1H), 1.19-1.07 (m, 1H), 0.33-0.18 (m, 4H). |
| 243 | 1H NMR (400 MHz, DMSO-d6) δ 8.14 (s, 3H), 7.94 (d, J = 8.1 Hz, 1H), 7.45 (s, 1H), 7.16 (d, J = 8.1 Hz, 1H), 6.66 (d, J = 7.9 Hz, 1H), 6.59 (s, 1H), 6.39 (s, 1H), 4.96 (p, J = 6.9 Hz, 1H), 4.81-4.13 (m, 7H), 4.09 (s, 3H), 3.82-3.62 (m, 3H), 3.52 (t, J = 7.4 Hz, 2H), 2.80 (s, 3H), 2.45-2.22 (m, 3H), 1.92-1.72 (m, 4H), 1.70-1.53 (m, 1H), 1.34 (dd, J = 12.8, 4.4 Hz, 1H), 1.15-0.96 (m, 1H), 0.25 (ddd, J = 11.2, 7.8, 5.4 Hz, 4H). |
| 245 | 1H NMR (400 MHz, DMSO-d6) δ 8.11 (s, 3H), 7.96 (d, J = 8.1 Hz, 1H), 7.47 (s, 1H), 7.18 (d, J = 8.1 Hz, 1H), 6.68 (d, J = 7.9 Hz, 1H), 6.61 (s, 1H), 6.40 (s, 1H), 5.44-5.33 (m, 1H), 5.30-5.21 (m, 1H), 4.98 (p, J = 7.0 Hz, 1H), 4.51-4.35 (m, 2H), 4.11 (s, 3H), 3.81-3.66 (m, 2H), 3.58-3.42 (m, 2H), 2.83 (s, 3H), 1.96-1.78 (m, 3H), 1.71-1.60 (m, 1H), 1.48 (d, J = 7.0 Hz, 3H), 1.36 (dd, J = 12.8, 4.4 Hz, 1H), 1.20-1.08 (m, 1H), 0.33-0.21 (m, 4H). (Expect 41, See 37) |
| 246 | 1H NMR (400 MHz, DMSO-d6) δ 8.16 (dd, J = 8.0, 2.1 Hz, 1H), 7.92 (d, J = 46.6 Hz, 3H), 7.49-7.38 (m, 1H), 7.16 (d, J = 8.0 Hz, 1H), 6.77 (d, J = 7.3 Hz, 1H), 6.37 (s, 1H), 4.46-4.38 (m, 2H), 4.08 (d, J = 6.8 Hz, 3H), 3.98-3.92 (m, 5H), 3.90-3.69 (m, 1H), 3.66-3.61 (m, 1H), 3.59 (s, 3H), 3.57-3.27 (m, 3H), 3.07 (t, J = 9.8 Hz, 1H), 2.84 (d, J = 8.5 Hz, 3H), 2.79-2.59 (m, 1H), 2.13 (dd, J = 14.3, 7.3 Hz, 1H), 2.07-1.86 (m, 2H), 1.28-1.00 (m, 4H), 0.33-0.15 (m, 4H). |
| 248 | 1H NMR (400 MHz, DMSO-d6) δ 8.10 (s, 3H), 7.96 (d, J = 8.1 Hz, 1H), 7.47 (s, 1H), 7.19 (d, J = 8.1 Hz, 1H), 6.61 (s, 1H), 6.52 (d, J = 7.9 Hz, 1H), 6.40 (s, 1H), 5.44-5.21 (m, 1H), 5.04-4.93 (m, 1H), 4.52-4.35 (m, 2H), 4.11 (s, 3H), 3.85-3.70 (m, 1H), 3.68-3.29 (m, 4H), 2.83 (s, 3H), 2.20-2.09 (m, 1H), 1.92-1.78 (m, 3H), 1.72-1.59 (m, 1H), 1.48 (d, J = 7.0 Hz, 3H), 1.36 (dd, J = 12.9, 4.3 Hz, 1H), 1.18-1.08 (m, 1H), 0.32-0.19 (m, 4H). (Expect 42, Observe 38) |
| 249 | 1H NMR (400 MHz, DMSO-d6) δ 8.19 (s, 3H), 7.96 (d, J = 8.1 Hz, 1H), 7.46 (s, 1H), 7.18 (d, J = 8.1 Hz, 1H), 6.67 (s, 1H), 6.53 (d, J = 1.3 Hz, 1H), 6.35 (d, J = 7.9 Hz, 1H), 5.04-4.90 (m, 1H), 4.83-4.49 (m, 2H), 4.47-4.31 (m, 2H), 4.14 (s, 3H), 3.74 (s, 1H), 3.34-3.21 (m, 4H), 2.45-2.35 (m, 1H), 2.35-2.22 (m, 1H), 1.93-1.75 (m, 7H), 1.71-1.58 (m, 1H), 1.45 (d, J = 7.0 Hz, 3H), 1.35 (dd, J = 12.8, 4.4 Hz, 1H), 1.05-0.92 (m, 1H), 0.90-0.72 (m, 2H), 0.48-0.30 (m, 2H), 0.29-0.18 (m, 2H), 0.17-0.07 (m, 2H). |
| 251 | 1H NMR (400 MHz, DMSO-d6) δ 8.84 (d, J = 7.8 Hz, 1H), 8.13 (s, 3H), 7.98 (d, J = 8.1 Hz, 1H), 7.96-7.91 (m, 2H), 7.59-7.52 (m, 1H), 7.52-7.45 (m, 3H), 7.23 (d, J = 8.1 Hz, 1H), 6.63 (s, 1H), 6.41 (d, J = 1.4 Hz, 1H), 5.32 (p, J = 7.1 Hz, 1H), 4.44 (qd, J = 14.1, 7.0 Hz, 2H), 4.11 (s, 3H), 3.83-3.68 (m, 1H), 2.83 (s, 3H), 2.39-2.27 (m, 1H), 1.93-1.78 (m, 3H), 1.70-1.54 (m, 4H), 1.36 (dd, J = 12.9, 4.4 Hz, 1H), 1.19-1.06 (m, 1H), 0.33-0.18 (m, 4H). (Expect 40, observe 38) |
| 253 | 1H NMR (400 MHz, DMSO-d6) δ 8.09-7.77 (m, 4H), 7.30 (s, 1H), 7.14 (d, J = 8.1 Hz, 1H), 6.59 (s, 1H), 6.52 (d, J = 7.6 Hz, 1H), 6.38 (s, 1H), 4.94 (p, J = 7.2 Hz, 1H), 4.41 (dd, J = 14.2, 6.7 Hz, 1H), 4.33 (dd, J = 14.1, 7.3 Hz, 1H), 4.07 (s, 3H), 3.34-3.04 (m, 2H), 2.83 (s, 6H), 2.79 (s, 3H), 2.04-1.96 (m, 1H), 1.80-1.69 (m, 1H), 1.66-1.50 (m, 2H), 1.43 (d, J = 7.0 Hz, 3H), 1.18-1.08 (m, 1H), 0.31-0.20 (m, 4H). (Expect 41H, see 38H) |
| 255 | 1H NMR (400 MHz, DMSO-d6) δ 8.12-7.81 (m, 4H), 7.57 (d, J = 8.1 Hz, 1H), 7.32 (s, 1H), 7.14 (d, J = 8.0 Hz, 1H), 6.61 (s, 1H), 6.39 (s, 1H), 4.99-4.89 (m, 1H), 4.85-4.75 (m, 1H), 4.48-4.32 (m, 2H), 4.10 (s, 3H), 3.36-3.13 (m, 5H), 2.82 (s, 3H), 2.08-1.98 (m, 1H), 1.87-1.72 (m, 2H), 1.72-1.49 (m, 7H), 1.42 (d, J = 7.1 Hz, 3H), 1.20-1.08 (m, 1H), 0.33-0.20 (m, 4H). (Expect 44, see 42) |
| 256 | 1H NMR (400 MHz, DMSO-d6) δ 7.97 (d, J = 8.1 Hz, 4H), 7.63 (d, J = 8.0 Hz, 1H), 7.32 (s, 1H), 7.16 (d, J = 8.1 Hz, 1H), 6.61 (s, 1H), 6.39 (s, 1H), 4.87-4.76 (m, 1H), 4.48-4.33 (m, 2H), 4.09 (s, 3H), 3.67 (s, 2H), 3.37-3.07 (m, 3H), 2.82 (s, 3H), 2.08-1.96 (m, 1H), 1.85-1.71 (m, 1H), 1.69-1.54 (m, 2H), 1.45 (d, J = 7.2 Hz, 3H), 1.21-1.07 (m, 1H), 0.91 (s, 9H), 0.75-0.64 (m, 2H), 0.34-0.18 (m, 4H). (Expect 46, see 46) |

TABLE 2-continued

| Ex | NMR |
|---|---|
| 257 | 1H NMR (400 MHz, DMSO-d6) δ 8.12-7.82 (m, 4H), 7.40-7.29 (m, 2H), 7.14 (d, J = 8.1 Hz, 1H), 6.60 (s, 1H), 6.37 (s, 1H), 4.83-4.72 (m, 1H), 4.50-4.33 (m, 2H), 4.09 (s, 3H), 3.34-3.16 (m, 3H), 2.83 (s, 3H), 2.11-1.96 (m, 1H), 1.84-1.70 (m, 1H), 1.69-1.52 (m, 2H), 1.46-1.34 (m, 12H), 1.31-1.21 (m, 1H), 1.20-1.09 (m, 1H), 0.35-0.21 (m, 4H). (Expect 44, see 43) |
| 258 | 1H NMR (400 MHz, DMSO-d6) δ 8.09-7.77 (m, 4H), 7.30 (s, 1H), 7.14 (d, J = 8.1 Hz, 1H), 6.59 (s, 1H), 6.52 (d, J = 7.6 Hz, 1H), 6.38 (s, 1H), 4.94 (p, J = 7.2 Hz, 1H), 4.41 (dd, J = 14.2, 6.7 Hz, 1H), 4.33 (dd, J = 14.1, 7.3 Hz, 1H), 4.07 (s, 3H), 3.34-3.04 (m, 2H), 2.83 (s, 6H), 2.79 (s, 3H), 2.04-1.96 (m, 1H), 1.80-1.69 (m, 1H), 1.66-1.50 (m, 2H), 1.43 (d, J = 7.0 Hz, 3H), 1.18-1.08 (m, 1H), 0.31-0.20 (m, 4H). (Expect 38, see 35) |
| 280 | 1H NMR (400 MHz, DMSO-d6) δ 8.36 (br s, 3H), 8.19 (dd, J = 8.0, 2.0 Hz, 1H), 7.63-7.28 (m, 2H), 7.18 (dd, J = 8.2, 2.0 Hz, 1H), 6.79 (d, J = 2.0 Hz, 1H), 6.40 (s, 1H), 5.37 (dm, J = 49.6 Hz, 1H), 4.45 (d, J = 7.0 Hz, 2H), 4.11 (s, 3H), 3.97-3.69 (m, 4H), 3.61 (s, 3H), 2.86 (d, J = 1.9 Hz, 3H), 1.15 (br s, 1H), 0.36-0.18 (m, 4H). Expected 32, observed 30 |
| 281 | 1H NMR (400 MHz, DMSO-d6) δ 8.74-8.59 (m, 2H), 8.26 (d, J = 8.5 Hz, 1H), 8.19 (d, J = 8.0 Hz, 1H), 7.99-7.85 (m, 1H), 7.45 (t, J = 59.5 Hz, 1H), 7.18 (d, J = 8.1 Hz, 1H), 6.84-6.78 (m, 1H), 6.66-6.58 (m, 1H), 4.49 (d, J = 7.3 Hz, 2H), 4.47-4.37 (m, 1H), 4.12 (s, 3H), 3.61 (s, 3H), 3.38-3.11 (m, 3H), 3.03-2.94 (m, 1H), 2.88 (s, 3H), 2.17-2.04 (m, 1H), 1.98-1.62 (m, 2H), 1.22-1.09 (m, 1H), 0.96 (d, J = 6.7 Hz, 3H), 0.34-0.21 (m, 4H). |
| 282 | 1H NMR (400 MHz, DMSO-d6) δ 8.18 (d, J = 8.0 Hz, 1H), 8.10 (d, J = 9.8 Hz, 1H), 7.93 (s, 1H), 7.45 (t, J = 59.5 Hz, 1H), 7.17 (d, J = 8.3 Hz, 1H), 6.80 (s, 1H), 6.62 (s, 1H), 4.49 (d, J = 7.2 Hz, 2H), 4.27-4.08 (m, 1H), 4.11 (s, 3H), 3.61 (s, 3H), 3.00-2.93 (m, 2H), 2.88 (s, 3H), 2.86-2.78 (m, 1H), 2.67-2.59 (m, 1H), 1.99-1.86 (m, 1H), 1.63-1.38 (m, 1H), 1.35-1.11 (m, 1H), 0.97-0.79 (m, 1H), 0.88 (d, J = 6.8 Hz, 3H), 0.33-0.21 (m, 4H). |
| 283 | 1H NMR (400 MHz, DMSO-d6) δ 8.74-8.55 (m, 2H), 8.18 (d, J = 8.1 Hz, 1H), 7.60 (s, 1H), 7.60 (s, 1H), 7.45 (t, J = 59.6 Hz, 1H), 7.18 (d, J = 8.1 Hz, 1H), 6.79 (s, 1H), 6.44-6.40 (m, 1H), 4.81-4.62 (m, 1H), 4.47 (d, J = 7.2 Hz, 2H), 4.42-4.27 (m, 2H), 4.10 (s, 3H), 3.61 (s, 3H), 3.45-3.07 (m, 4H), 2.98-2.87 (m, 1H), 2.86 (s, 3H), 2.21-1.95 (m, 2H), 1.17-1.04 (m, 1H), 0.36-0.13 (m, 4H). |
| 284 | 1H NMR (400 MHz, DMSO-d6) δ 8.74-8.55 (m, 2H), 8.18 (d, J = 8.1 Hz, 1H), 7.60 (s, 1H), 7.60 (s, 1H), 7.45 (t, J = 59.6 Hz, 1H), 7.18 (d, J = 8.1 Hz, 1H), 6.79 (s, 1H), 6.44-6.40 (m, 1H), 4.81-4.62 (m, 1H), 4.47 (d, J = 7.2 Hz, 2H), 4.42-4.27 (m, 2H), 4.10 (s, 3H), 3.61 (s, 3H), 3.45-3.07 (m, 4H), 2.98-2.87 (m, 1H), 2.86 (s, 3H), 2.21-1.95 (m, 2H), 1.17-1.04 (m, 1H), 0.36-0.13 (m, 4H). |
| 285 | 1H NMR (400 MHz, DMSO-d6) δ 8.76-8.58 (m, 2H), 8.68 (d, J = 7.7 Hz, 1H), 8.19 (d, J = 8.1 Hz, 1H), 7.88 (s, 1H), 7.45 (t, J = 59.6 Hz, 1H), 7.18 (d, J = 8.1 Hz, 1H), 6.81 (s, 1H), 6.63 (s, 1H), 4.48 (d, J = 7.0 Hz, 2H), 4.25-4.17 (m, 1H), 4.12 (s, 3H), 3.61 (s, 3H), 3.58-3.48 (m, 1H), 3.34 (s, 3H), 3.39-3.26 (m, 2H), 3.07-2.90 (m, 2H), 2.88 (s, 3H), 2.35-2.25 (m, 1H), 1.69-1.56 (m, 1H), 1.22-1.11 (m, 1H), 0.36-0.21 (m, 4H). |
| 286 | 1H NMR (400 MHz, DMSO-d6) δ 8.82-8.67 (m, 2H), 8.18 (d, J = 8.2 Hz, 1H), 7.59 (s, 1H), 7.45 (t, J = 59.6 Hz, 1H), 7.18 (d, J = 7.8 Hz, 1H), 6.79 (s, 1H), 6.43 (s, 1H), 4.77-4.64 (m, 1H), 4.52-4.40 (m, 2H), 4.39-4.25 (m, 2H), 4.11 (s, 3H), 3.68-3.25 (m, 6H), 3.21-3.09 (m, 1H), 2.96-2.78 (m, 4H), 2.15-2.01 (m, 1H), 1.94-1.77 (m, 1H), 1.21-1.08 (m, 1H), 0.35-0.17 (m, 4H). |
| 287 | 1H NMR (400 MHz, DMSO-d6) δ 8.82-8.67 (m, 2H), 8.18 (d, J = 8.2 Hz, 1H), 7.59 (s, 1H), 7.45 (t, J = 59.6 Hz, 1H), 7.18 (d, J = 7.8 Hz, 1H), 6.79 (s, 1H), 6.43 (s, 1H), 4.77-4.64 (m, 1H), 4.52-4.40 (m, 2H), 4.39-4.25 (m, 2H), 4.11 (s, 3H), 3.68-3.25 (m, 6H), 3.21-3.09 (m, 1H), 2.96-2.78 (m, 4H), 2.15-2.01 (m, 1H), 1.94-1.77 (m, 1H), 1.21-1.08 (m, 1H), 0.35-0.17 (m, 4H). |
| 288 | 1H NMR (400 MHz, DMSO-d6) δ 8.73 (br. d, J = 10.2 Hz, 1H), 8.64 (d, J = 8.7 Hz, 0H), 8.34 (br. q, J = 10.0 Hz, 1H), 8.26 (s, 0H), 8.19 (d, J = 8.1 Hz, 1H), 7.96 (s, 1H), 7.87 (s, 0H), 7.45 (t, J = 59.6 Hz, 1H), 7.18 (d, J = 8.1 Hz, 1H), 6.82 (s, 1H), 6.65 (s, 0H), 6.61 (s, 1H), 4.49 (d, J = 7.1 Hz, 2H), 4.40 (br. dd, J = 8.5, 4.3 Hz, 1H), 4.12 (s, 3H), 3.61 (s, 3H), 3.36-3.13 (m, 3H), 2.99 (br. dd, J = 21.7, 10.0 Hz, 1H), 2.88 (s, 3H), 2.17-2.05 (m, 1H), 1.87-1.62 (m, 2H), 1.21-1.09 (m, 1H), 0.96 (d, J = 6.8 Hz, 3H), 0.34-0.20 (m, 4H). |
| 289 | 1H NMR (400 MHz, DMSO-d6) δ 8.48 (br s, 2H), 8.42 (br s, 2H), 8.18 (d, J = 8.1 Hz, 1H), 7.63-7.28 (m, 2H), 7.18 (d, J = 8.1 Hz, 1H), 6.79 (s, 1H), 6.43-6.34 (m, 1H), 5.51-5.25 (m, 1H), 4.45 (d, J = 7.0 Hz, 2H), 4.10 (s, 3H), 4.04-3.81 (m, 4H), 3.61 (s, 3H), 2.86 (s, 3H), 1.15 (br s, 1H), 0.33-0.21 (m, 4H). Expected 32, observed 31 |
| 290 | 1H NMR (400 MHz, DMSO-d6) δ 8.31 (br s, 3H), 8.18 (d, J = 8.1 Hz, 1H), 7.62-7.28 (m, 2H), 7.18 (d, J = 8.1 Hz, 1H), 6.79 (s, 1H), 6.39 (s, 1H), 5.37 (dm, J = 49.5 Hz, 1H), 4.45 (d, J = 7.1 Hz, 2H), 4.10 (s, 3H), 3.93-3.72 (m, 3H), 3.61 (s, 3H), 2.86 (s, 3H), 1.15 (brs, 1H), 0.36-0.19 (m, 4H). Expected 32, observed 29 |
| 291 | 1H NMR (400 MHz, DMSO-d6) δ 8.47 (br s, 2H), 8.41 (br s, 2H), 8.18 (d, J = 8.1 Hz, 1H), 7.63-7.28 (m, 2H), 7.18 (d, J = 8.1 Hz, 1H), 6.78 (s, 1H), 6.43-6.35 (m, 1H), 5.51-5.26 (m, 1H), 4.45 (d, J = 7.1 Hz, 2H), 4.10 (s, 3H), 4.02-3.82 (m, 3H) 3.61 (s, 3H), 2.86 (s, 3H), 1.15 (br s, 1H), 0.33-0.22 (m, 4H). Expected 32, observed 30 |
| 292 | 1H NMR (400 MHz, DMSO-d6) δ 9.21 (br. d, J = 10.5 Hz, 1H), 8.98-8.90 (m, 2H), 8.19 (d, J = 8.1 Hz, 1H), 7.88 (s, 1H), 7.45 (t, J = 59.6 Hz, 1H), 7.19 (d, J = 8.1 Hz, 1H), 6.83 (s, 1H), 6.68 (s, 1H), 4.46 (d, J = 7.0 Hz, 2H), 4.13 (s, 3H), 4.00 (d, J = 12.0 Hz, 1H), 3.90 (d, J = 12.5 Hz, 1H), 3.70 (t, J = 11.4 Hz, 1H), 3.61 (s, 3H), 3.64-3.42 (m, 4H), 3.31 (d, J = 13.0 Hz, 1H), 3.19-3.09 (m, 1H), 2.88 (s, 3H), 1.22-1.11 (m, 1H), 0.35-0.20 (m, 4H). |
| 293 | 1H NMR (400 MHz, DMSO-d6) δ 9.14 (br. d, J = 10.6 Hz, 1H), 8.95-8.81 (m, 2H), 8.19 (d, J = 8.0 Hz, 1H), 7.87 (s, 1H), 7.45 (t, J = 59.6 Hz, 1H), 7.18 (d, J = 8.2 Hz, 1H), 6.82 (s, 1H), 6.66 (s, 1H), 4.47 (d, J = 7.0 Hz, 2H), 4.12 (s, 3H), 4.00 (d, J = 11.9 Hz, 1H), 3.90 (d, J = 12.6 Hz, 1H), 3.70 (t, J = 11.4 Hz, 1H), 3.61 (s, 3H), 3.63-3.45 (m, 4H), 3.31 (d, J = 13.1 Hz, 1H), 3.19-3.06 (m, 1H), 2.88 (s, 3H), 1.22-1.11 (m, 1H), 0.35-0.20 (m, 4H). |

TABLE 2-continued

| Ex | NMR |
|---|---|
| 294 | 1H NMR (400 MHz, DMSO-d6) δ 8.93 (br. t, J = 5.9 Hz, 1H), 8.64 br. (d, J = 10.8 Hz, 1H), 8.37 (br. dd, J = 20.6, 9.5 Hz, 1H), 8.19 (d, J = 8.0 Hz, 1H), 7.89 (s, 1H), 7.46 (t, J = 59.6 Hz, 1H), 7.19 (d, J = 8.1 Hz, 1H), 6.83 (s, 1H), 6.68 (s, 1H), 4.47 (d, J = 7.0 Hz, 2H), 4.13 (s, 3H), 3.62 (s, 3H), 3.59-3.41 (m, 2H), 3.35-3.19 (m, 2H), 2.88 (s, 3H), 2.96-2.82 (m, 1H), 1.93-1.69 (m, 3H), 1.67-1.39 (m, 3H), 1.22-1.11 (m, 1H), 0.36-0.20 (m, 4H). |
| 295 | 1H NMR (400 MHz, DMSO-d6) δ 8.92 (br. t, J = 5.8 Hz, 1H), 8.61 (br. d, J = 10.7 Hz, 1H), 8.33 (br. dd, J = 20.8, 9.8 Hz, 1H), 8.19 (d, J = 8.0 Hz, 1H), 7.89 (s, 1H), 7.45 (t, J = 59.6 Hz, 1H), 7.18 (d, J = 8.1 Hz, 1H), 6.82 (s, 1H), 6.67 (s, 1H), 4.47 (d, J = 7.0 Hz, 2H), 4.12 (s, 3H), 3.61 (s, 3H), 3.60-3.41 (m, 2H), 3.35-3.16 (m, 2H), 2.88 (s, 3H), 2.96-2.81 (m, 1H), 1.92-1.70 (m, 3H), 1.65-1.38 (m, 3H), 1.21-1.11 (m, 1H), 0.36-0.20 (m, 4H). |
| 296 | 1H NMR (400 MHz, DMSO-d6) δ 8.82-8.76 (m, 2H), 8.70 (d, J = 7.3 Hz, 1H), 8.19 (d, J = 8.1 Hz, 1H), 7.86 (s, 1H), 7.45 (t, J = 59.6 Hz, 1H), 7.18 (d, J = 8.0 Hz, 1H), 6.81 (s, 1H), 6.64 (s, 1H), 4.47 (d, J = 7.1 Hz, 2H), 4.36-4.22 (m, 1H), 4.12 (s, 3H), 3.61 (s, 3H), 3.41-3.31 (m, 1H), 3.21-3.11 (m, 3H), 2.87 (s, 3H), 2.10-1.95 (m, 1H), 1.93-1.71 (m, 4H), 1.63-1.55 (m, 1H), 1.23-1.12 (m, 1H), 0.35-0.21 (m, 4H). |
| 297 | 1H NMR (400 MHz, DMSO-d6) δ 8.74 (s, 3H), 8.19 (d, J = 8.1 Hz, 1H), 7.63-7.28 (m, 6H), 7.26 (s, 1H), 7.18 (d, J = 8.1 Hz, 1H), 6.79 (s, 1H), 6.36 (s, 1H), 5.31 (s, 2H), 4.41 (d, J = 7.1 Hz, 2H), 4.10 (s, 3H), 4.07-3.87 (m, 2H), 3.61 (s, 3H), 3.66-3.50 (m, 2H), 2.84 (s, 3H), 2.23-2.18 (m, 2H), 1.94-1.89 (m, 2H), 1.14 (h, J = 6.0 Hz, 1H), 0.35-0.20 (m, 4H). |
| 298 | 1H NMR (400 MHz, DMSO-d6) δ 8.69 (br. d, J = 10.4 Hz, 1H), 8.53 (d, J = 5.0 Hz, 1H), 8.43 (br. d, J = 11.3 Hz, 1H), 8.19 (d, J = 8.0 Hz, 1H), 8.10 (s, 1H), 7.45 (t, J = 59.6 Hz, 1H), 7.18 (d, J = 8.1 Hz, 1H), 6.82 (s, 1H), 6.62 (s, 1H), 4.50 (d, J = 7.1 Hz, 2H), 4.16-4.08 (m, 1H), 4.12 (s, 3H), 4.04-3.95 (m, 2H), 3.61 (s, 3H), 2.89 (s, 3H), 2.21 (br. t, J = 13.9 Hz, 1H), 2.09-1.86 (m, 5H), 1.74-1.65 (m, 1H), 1.57 (br. d, J = 14.6 Hz, 1H), 1.20-1.12 (m, 1H), 0.36-0.21 (m, 4H). |
| 299 | 1H NMR (400 MHz, DMSO-d6) δ 8.89 (br. d, J = 10.5 Hz, 1H), 8.79 (br. d, J = 10.0 Hz, 1H), 8.60 (d, J = 7.3 Hz, 1H), 8.19 (d, J = 8.0 Hz, 1H), 7.91 (s, 1H), 7.45 (t, J = 59.6 Hz, 1H), 7.18 (d, J = 8.1 Hz, 1H), 6.81 (s, 1H), 6.63 (s, 1H), 4.48 (d, J = 7.1 Hz, 2H), 4.40-4.30 (m, 1H), 4.12 (s, 3H), 4.04-3.97 (m, 1H), 3.95-3.88 (m, 1H), 3.61 (s, 3H), 2.88 (s, 3H), 2.28-2.15 (m, 1H), 2.04-1.93 (m, 1H), 1.87-1.67 (m, 6H), 1.23-1.12 (m, 1H), 0.36-0.21 (m, 4H). |
| 300 | 1H NMR (400 MHz, DMSO-d6) δ 8.18 (d, J = 8.1 Hz, 1H), 7.87 (br. s, 3H), 7.49 (s, 1H), 7.45 (t, J = 59.6 Hz, 1H), 7.18 (d, J = 8.1 Hz, 1H), 6.79 (s, 1H), 6.42 (s, 1H), 4.52-4.33 (m, 3H), 4.10 (s, 3H), 3.61 (s, 3H), 3.69-3.49 (m, 2H), 3.20-3.06 (m, 2H), 2.86 (s, 3H), 2.15-2.01 (m, 1H), 1.97-1.77 (m, 3H), 1.23-1.13 (m, 1H), 0.35-0.22 (m, 4H). |
| 301 | 1H NMR (400 MHz, DMSO-d6) δ 8.19 (d, J = 8.1 Hz, 1H), 7.90 (br. s, 3H), 7.50 (s, 1H), 7.45 (t, J = 59.6 Hz, 1H), 7.18 (d, J = 8.1 Hz, 1H), 6.80 (s, 1H), 6.45 (s, 1H), 4.50-4.33 (m, 3H), 4.10 (s, 3H), 3.67-3.57 (m, 1H), 3.61 (s, 3H), 3.57-3.48 (m, 1H), 3.24-3.02 (m, 2H), 2.85 (s, 3H), 2.14-2.04 (m, 1H), 1.95-1.74 (m, 3H), 1.22-1.10 (m, 1H), 0.35-0.20 (m, 4H). |
| 302 | 1H NMR (400 MHz, DMSO-d6) δ 8.88 (d, J = 11.1 Hz, 1H), 8.69 (d, J = 8.7 Hz, 1H), 8.55 (q, J = 11.1 Hz, 1H), 8.19 (d, J = 8.1 Hz, 1H), 7.85 (s, 1H), 7.45 (t, J = 59.6 Hz, 1H), 7.18 (d, J = 8.1 Hz, 1H), 6.81 (s, 1H), 6.65 (s, 1H), 4.47 (d, J = 7.1 Hz, 2H), 4.12 (s, 3H), 4.11-3.97 (m, 1H), 3.61 (s, 3H), 3.31 (d, J = 12.2 Hz, 1H), 3.21-3.09 (m, 1H), 3.00-2.83 (m, 1H), 2.87 (s, 3H), 1.92 (t, J = 12.6 Hz, 2H), 1.82-1.55 (m, 2H), 1.24 (d, J = 6.3 Hz, 3H), 1.22-1.12 (m, 1H), 0.36-0.21 (m, 4H). |
| 303 | 1H NMR (400 MHz, DMSO-d6) δ 9.04 (br. s, 1H), 8.97 (t, J = 5.7 Hz, 1H), 8.39 (br. s, 1H), 8.19 (d, J = 8.1 Hz, 1H), 7.85 (s, 1H), 7.45 (t, J = 59.6 Hz, 1H), 7.18 (d, J = 8.1 Hz, 1H), 6.81 (s, 1H), 6.65 (s, 1H), 4.47 (d, J = 7.1 Hz, 2H), 4.12 (s, 3H), 3.76-3.51 (m, 3H), 3.61 (s, 3H), 3.35-3.11 (m, 2H), 2.88 (s, 3H), 2.14-2.03 (m, 1H), 2.01-1.83 (m, 2H), 1.78-1.63 (m, 1H), 1.23-1.12 (m, 1H), 0.35-0.20 (m, 4H). |
| 304 | 1H NMR (400 MHz, DMSO-d6) δ 9.08 (br. s, 1H), 8.99 (t, J = 5.7 Hz, 1H), 8.42 (br. s, 1H), 8.19 (d, J = 8.1 Hz, 1H), 7.85 (s, 1H), 7.45 (t, J = 59.6 Hz, 1H), 7.18 (d, J = 8.0 Hz, 1H), 6.82 (s, 1H), 6.67 (s, 1H), 4.46 (d, J = 7.1 Hz, 2H), 4.12 (s, 3H), 3.76-3.50 (m, 3H), 3.61 (s, 3H), 3.34-3.11 (m, 2H), 2.88 (s, 3H), 2.14-2.04 (m, 1H), 2.03-1.83 (m, 2H), 1.71 (dq, J = 12.6, 8.5 Hz, 1H), 1.23-1.12 (m, 1H), 0.35-0.20 (m, 4H). |
| 305 | 1H NMR (400 MHz, DMSO-d6) δ 8.81-8.74 (m, 1H), 8.39 (d, J = 8.3 Hz, 1H), 8.44-8.29 (m, 1H), 8.19 (d, J = 8.0 Hz, 1H), 7.91 (s, 1H), 7.45 (t, J = 59.6 Hz, 1H), 7.18 (d, J = 8.1 Hz, 1H), 6.81 (s, 1H), 6.62 (s, 1H), 4.48 (d, J = 7.0 Hz, 2H), 4.43-4.36 (m, 2H), 4.12 (s, 3H), 3.68-3.61 (m, 1H), 3.61 (s, 3H), 3.30-3.23 (m, 1H), 3.06-2.96 (m, 1H), 2.88 (s, 3H), 1.99-1.63 (m, 3H), 1.21 (d, J = 6.7 Hz, 3H), 1.29-1.06 (m, 2H), 0.35-0.20 (m, 4H). |
| 306 | 1H NMR (400 MHz, DMSO-d6) δ 9.33-9.06 (m, 2H), 8.78 (d, J = 7.6 Hz, 1H), 8.19 (d, J = 8.1 Hz, 1H), 7.86 (s, 1H), 7.45 (t, J = 59.6 Hz, 1H), 7.18 (d, J = 8.1 Hz, 1H), 6.81 (s, 1H), 6.64 (s, 1H), 5.25 (d, J = 44.7 Hz, 1H), 4.47 (d, J = 7.1 Hz, 2H), 4.54-4.38 (m, 1H), 4.12 (s, 3H), 3.61 (s, 3H), 3.54 (t, J = 13.0 Hz, 1H), 3.42-3.15 (m, 3H), 2.97-2.83 (m, 1H), 2.88 (s, 3H), 2.32-2.27 (m, 1H), 1.96 (dt, J = 43.7, 13.2 Hz, 1H), 1.24-1.14 (m, 1H), 0.36-0.21 (m, 4H). |
| 307 | 1H NMR (400 MHz, DMSO-d6) δ 8.19 (d, J = 8.1 Hz, 1H), 8.03 (s, 3H), 7.45 (t, J = 59.6 Hz, 1H), 7.39 (s, 1H), 7.19 (d, J = 8.1 Hz, 1H), 6.79 (s, 1H), 6.46 (s, 1H), 4.95 (d, J = 46.6 Hz, 1H), 4.43 (d, J = 7.2 Hz, 2H), 4.09 (s, 3H), 3.86 (s, 1H), 3.76-3.40 (m, 4H), 3.61 (s, 3H), 2.85 (s, 3H), 2.38-2.22 (m, 1H), 2.11-2.06 (m, 1H), 1.21-1.11 (m, 1H), 0.35-0.21 (m, 4H). |
| 308 | 1H NMR (400 MHz, DMSO-d6) δ 8.89 (d, J = 7.9 Hz, 1H), 8.87-8.76 (m, 2H), 8.19 (d, J = 8.1 Hz, 1H), 7.88 (s, 1H), 7.45 (t, J = 59.6 Hz, 1H), 7.18 (d, J = 8.0 Hz, 1H), 6.82 (s, 1H), 6.65 (s, 1H), 4.84 (dtd, J = 49.0, 9.6, 4.6 Hz, 1H), 4.47 (d, J = 7.2 Hz, 2H), 4.45-4.35 (m, 1H), 4.13 (s, 3H), 3.61 (s, 3H), 3.52-3.33 (m, 2H), 3.16-2.91 (m, 2H), 2.88 (s, 3H), 2.42-2.31 (m, 1H), 2.00-1.83 (m, 1H), 1.26-1.11 (m, 1H), 0.36-0.21 (m, 4H). |

TABLE 2-continued

| Ex | NMR |
|---|---|
| 309 | 1H NMR (400 MHz, DMSO-d6) δ 8.91-8.73 (m, 3H), 8.19 (d, J = 8.0 Hz, 1H), 7.93 (s, 1H), 7.45 (t, J = 59.6 Hz, 1H), 7.18 (d, J = 8.1 Hz, 1H), 6.81 (s, 1H), 6.67 (s, 1H), 5.02 (d, J = 50.1 Hz, 1H), 4.57-4.40 (m, 3H), 4.12 (s, 3H), 3.61 (s, 3H), 3.40-2.98 (m, 4H), 2.88 (s, 3H), 2.35-1.95 (m, 2H), 1.23-1.13 (m, 1H), 0.36-0.21 (m, 4H). |
| 310 | 1H NMR (400 MHz, DMSO-d6) δ 8.97 (s, 1H), 8.19 (d, J = 8.1 Hz, 1H), 8.15 (s, 1H), 7.46 (t, J = 59.6 Hz, 1H), 7.41 (s, 1H), 7.18 (d, J = 8.1 Hz, 1H), 6.83 (s, 1H), 6.39 (d, J = 1.2 Hz, 1H), 4.48 (d, J = 7.2 Hz, 2H), 4.12 (s, 3H), 4.33-3.76 (m, 3H), 3.62 (s, 3H), 3.56-3.39 (m, 1H), 3.37-3.19 (m, 1H), 3.20-2.74 (m, 2H), 2.46-2.39 (m, 1H), 2.25-2.08 (m, 1H), 2.04-1.82 (m, 1H), 1.81-1.57 (m, 4H), 1.58-1.39 (m, 1H), 1.08-0.87 (m, 3H), 0.47-0.34 (m, 2H), 0.26 (d, J = 7.8 Hz, 2H), 0.20--0.05 (m, 2H). |
| 311 | ¹H NMR (400 MHz, DMSO-d₆) δ 8.53 (brs, 3H), 8.19 (d, J = 8.1 Hz, 1H), 8.09 (s, 1H), 7.89 (brs, 1H), 7.54 (s, 0.5H), 7.46 (t, J = 59.6 Hz, 1H), 7.36 (s, 0.5H), 7.19 (d, J = 8.1 Hz, 1H), 6.80 (s, 0.5H), 6.79 (s, 0.5H), 6.49 (s, 0.5H), 6.38 (s, 0.5H), 5.72 (s, 0.5H), 4.61 (brs, 1 H), 4.45 (d, J = 6.9 Hz, 2H), 4.36 (brs, 0.5 H), 4.11 (d, J = 6.1 Hz, 3H), 3.62 (s, 3H), 3.50 (s, 1H), 3.16-3.03 (m, 1H), 2.87 (s, 1.5H), 2.86 (s, 1.5H), 2.21-1.50 (m, 4H), 1.22-1.10 (m, 1H), 0.35-0.21 (m, 4H). |
| 312 | 1H NMR (400 MHz, DMSO-d6) δ 8.88 (d, J = 6.1 Hz, 1H), 8.84-8.76 (m, 2H), 8.19 (d, J = 8.1 Hz, 1H), 7.94 (d, J = 1.5 Hz, 1H), 7.45 (t, J = 59.6 Hz, 1H), 7.18 (d, J = 8.1 Hz, 1H), 6.81 (s, 1H), 6.62 (d, J = 1.4 Hz, 1H), 4.51-4.45 (m, 3H), 4.31 (d, J = 4.6 Hz, 1H), 4.19 (t, J = 4.9 Hz, 1H), 4.11 (s, 3H), 3.61 (s, 3H), 2.88 (s, 3H), 2.32-2.21 (m, 1H), 2.07-1.95 (m, 1H), 1.90-1.70 (m, 4H), 1.22-1.09 (m, 1H), 0.36-0.21 (m, 4H). |
| 313 | 1H NMR (400 MHz, DMSO-d6) δ 8.81 (br d, J = 10.8 Hz, 1H), 8.38 (br d, J = 9.6 Hz, 1H), 8.30 (d, J = 8.3 Hz, 1H), 8.19 (d, J = 8.1 Hz, 1H), 7.96 (d, J = 1.4 Hz, 1H), 7.45 (t, J = 59.6 Hz, 1H), 7.18 (d, J = 8.1 Hz, 1H), 6.82 (s, 1H), 6.63 (d, J = 1.4 Hz, 1H), 4.49 (d, J = 7.1 Hz, 2H), 4.44-4.36 (m, 1H), 4.12 (s, 3H), 3.61 (s, 3H), 3.39-3.15 (m, 3H), 3.06-2.96 (m, 1H), 2.88 (s, 3H), 2.17-2.05 (m, 1H), 1.87-1.65 (m, 2H), 1.21-1.09 (m, 1H), 0.96 (d, J = 6.9 Hz, 3H), 0.35-0.20 (m, 4H). |
| 314 | 1H NMR (400 MHz, DMSO-d6) δ 8.91 (d, J = 10.9 Hz, 1H), 8.70 (d, J = 7.6 Hz, 1H), 8.60 (q, J = 10.6 Hz, 1H), 8.19 (d, J = 8.1 Hz, 1H), 7.86 (d, J = 1.4 Hz, 1H), 7.45 (t, J = 59.6 Hz, 1H), 7.18 (d, J = 8.1 Hz, 1H), 6.82 (s, 1H), 6.66 (d, J = 1.4 Hz, 1H), 4.46 (d, J = 7.1 Hz, 2H), 4.24-4.13 (m, 1H), 4.12 (s, 3H), 3.61 (s, 3H), 3.41 (d, J = 10.8 Hz, 1H), 3.20-3.13 (m, 1H), 2.87 (s, 3H), 2.86-2.74 (m, 1H), 2.02-1.91 (m, 2H), 1.74-1.46 (m, 2H), 1.23 (d, J = 6.4 Hz, 3H), 1.22-1.12 (m, 1H), 0.36-0.21 (m, 4H). |
| 315 | 1H NMR (400 MHz, DMSO-d6) δ 8.93 (d, J = 11.3 Hz, 1H), 8.51 (d, J = 6.3 Hz, 1H), 8.35-8.25 (m, 2H), 8.19 (d, J = 8.4 Hz, 1H), 7.95 (s, 1H), 7.45 (t, J = 59.6 Hz, 1H), 7.18 (d, J = 8.0 Hz, 1H), 6.82 (s, 1H), 6.63 (s, 1H), 4.49 (d, J = 7.1 Hz, 2H), 4.25-4.18 (m, 1H), 4.12 (s, 3H), 3.61 (s, 3H), 3.50-3.16 (m, 3H), 2.88 (s, 3H), 1.91-1.76 (m, 4H), 1.28 (d, J = 6.4 Hz, 3H), 1.20-1.09 (m, 1H), 0.34-0.20 (m, 4H). |
| 316 | 1H NMR (400 MHz, DMSO-d6) δ 8.83 (s, 2H), 8.72 (d, J = 7.3 Hz, 1H), 8.19 (d, J = 8.0 Hz, 1H), 7.86 (s, 1H), 7.45 (t, J = 59.6 Hz, 1H), 7.18 (d, J = 8.0 Hz, 1H), 6.82 (s, 1H), 6.65 (s, 1H), 4.46 (d, J = 7.0 Hz, 2H), 4.37-4.24 (m, 1H), 4.12 (s, 3H), 3.61 (s, 3H), 3.44-3.31 (m, 1H), 3.23-3.11 (m, 3H), 2.87 (s, 3H), 2.05-1.96 (m, 1H), 1.92-1.71 (m, 4H), 1.65-1.55 (m, 1H), 1.21-1.11 (m, 1H), 0.35-0.20 (m, 4H). |
| 317 | 1H NMR (400 MHz, DMSO-d6) δ 8.97 (d, J = 11.0 Hz, 1H), 8.81-8.68 (m, 2H), 8.19 (d, J = 8.1 Hz, 1H), 7.86 (s, 1H), 7.45 (t, J = 59.4 Hz, 1H), 7.18 (d, J = 8.1 Hz, 1H), 6.82 (s, 1H), 6.66 (s, 1H), 4.46 (d, J = 7.1 Hz, 2H), 4.26-4.15 (m, 1H), 4.12 (s, 3H), 3.61 (s, 3H), 3.46-3.37 (m, 1H), 3.28-3.19 (m, 1H), 2.87 (s, 3H), 2.70 (q, J = 11.4 Hz, 1H), 2.58-2.40 (m, 1H), 2.00 (d, J = 12.9 Hz, 1H), 1.93 (s, 1H), 1.32 (q, J = 12.1 Hz, 1H), 1.22-1.12 (m, 1H), 0.97 (d, J = 6.4 Hz, 3H), 0.36-0.21 (m, 4H). |
| 318 | 1H NMR (400 MHz, DMSO-d6) δ 8.23-8.15 (m, 4H), 7.45 (t, J = 59.6 Hz, 1H), 7.36 (s, 1H), 7.18 (d, J = 8.1 Hz, 1H), 6.78 (s, 1H), 6.38 (s, 1H), 4.44 (d, J = 7.2 Hz, 2H), 4.08 (s, 3H), 4.02-3.86 (m, 2H), 3.61 (s, 3H), 3.60-3.48 (m, 2H), 2.84 (s, 3H), 2.54 (s, 1H), 2.04-1.97 (m, 2H), 1.19-1.06 (m, 1H), 0.34-0.18 (m, 4H). |
| 319 | 1H NMR (400 MHz, DMSO-d6) δ 8.23-8.15 (m, 4H), 7.45 (t, J = 59.6 Hz, 1H), 7.36 (s, 1H), 7.18 (d, J = 8.1 Hz, 1H), 6.78 (s, 1H), 6.39 (s, 1H), 4.44 (d, J = 7.1 Hz, 2H), 4.08 (s, 3H), 4.02-3.75 (m, 2H), 3.61 (s, 3H), 3.61-3.47 (m, 2H), 2.84 (s, 3H), 2.57-2.51 (m, 1H), 2.01 (d, J = 6.5 Hz, 2H), 1.20-1.05 (m, 1H), 0.34-0.18 (m, 4H). |
| 320 | 1H NMR (400 MHz, DMSO-d6) δ 9.56-9.10 (m, 2H), 8.18 (d, J = 8.1 Hz, 1H), 7.58-7.33 (m, 1H), 7.45 (t, J = 59.6 Hz, 1H), 7.18 (d, J = 8.1 Hz, 1H), 6.79 (s, 1H), 6.48-6.34 (m, 1H), 4.50-4.40 (m, 2H), 4.36-4.18 (m, 2H), 4.14-4.07 (m, 3H), 4.04-3.48 (m, 6H), 3.61 (s, 3H), 3.48-3.25 (m, 1H), 3.18-3.08 (m, 1H), 2.89-2.82 (m, 3H), 1.17-1.09 (m, 1H), 0.33-0.19 (m, 4H). |
| 321 | 1H NMR (400 MHz, DMSO-d6) δ 8.75-8.52 (m, 2H), 8.19 (d, J = 8.1 Hz, 1H), 7.58 (s, 1H), 7.45 (t, J = 59.6 Hz, 1H), 7.18 (d, J = 8.1 Hz, 1H), 6.80 (s, 1H), 6.43 (s, 1H), 4.50-4.37 (m, 2H), 4.25-4.16 (m, 1H), 4.11 (s, 3H), 3.81-3.70 (m, 1H), 3.61 (s, 3H), 3.58-3.45 (m, 2H), 3.38-3.29 (m, 1H), 3.23-3.18 (m, 1H), 3.04-2.96 (m, 1H), 2.86 (s, 3H), 2.00-1.67 (m, 5H), 1.21-1.11 (m, 1H), 0.34-0.20 (m, 4H). |
| 322 | 1H NMR (400 MHz, DMSO-d6) δ 9.23-8.40 (m, 2H), 8.19 (d, J = 8.1 Hz, 1H), 7.67-7.26 (m, 2H), 7.18 (d, J = 8.1 Hz, 1H), 6.82-6.76 (m, 1H), 6.44-6.38 (m, 1H), 4.48-4.37 (m, 2H), 4.32-3.87 (m, 4H), 4.12-4.08 (m, 3H), 3.84-3.46 (m, 2H), 3.61 (s, 3H), 3.46-3.10 (m, 2H), 2.88-2.80 (m, 3H), 2.19-1.39 (m, 4H), 1.22-1.08 (m, 1H), 0.35-0.20 (m, 4H). |
| 323 | 1H NMR (400 MHz, DMSO-d6) δ 8.73-8.62 (m, 4H), 8.19 (d, J = 8.1 Hz, 1H), 7.88 (d, J = 1.4 Hz, 1H), 7.45 (t, J = 59.6 Hz, 1H), 7.18 (d, J = 8.1 Hz, 1H), 6.81 (s, 1H), 6.64 (d, J = 1.4 Hz, 1H), 4.47 (d, J = 7.1 Hz, 2H), 4.25-4.13 (m, 1H), 4.12 (s, 3H), 3.61 (s, 3H), 3.41-3.33 (m, 1H), 3.23 (d, J = 12.6 Hz, 1H), 2.88 (s, 3H), 2.95-2.80 (m, 2H), 1.99-1.90 (m, 2H), 1.76-1.59 (m, 2H), 1.23-1.10 (m, 1H), 0.36-0.21 (m, 4H). |

TABLE 2-continued

| Ex | NMR |
|---|---|
| 324 | 1H NMR (400 MHz, DMSO-d6) δ 8.79-8.62 (m, 3H), 8.19 (d, J = 8.1 Hz, 1H), 7.88 (d, J = 1.3 Hz, 1H), 7.45 (t, J = 59.6 Hz, 1H), 7.18 (d, J = 8.0 Hz, 1H), 6.82 (s, 1H), 6.66 (s, 1H), 4.47 (d, J = 7.1 Hz, 2H), 4.26-4.13 (m, 1H), 4.12 (s, 3H), 3.61 (s, 3H), 3.37 (d, J = 11.4 Hz, 1H), 3.23 (d, J = 12.4 Hz, 1H), 2.88 (s, 3H), 2.96-2.81 (m, 2H), 1.99-1.90 (m, 2H), 1.79-1.58 (m, 2H), 1.24-1.12 (m, 1H), 0.36-0.21 (m, 4H). |
| 325 | 1H NMR (400 MHz, DMSO-d6) δ 9.21 (s, 1H), 8.59 (s, 1H), 8.19 (d, J = 8.1 Hz, 1H), 7.45 (t, J = 59.6 Hz, 1H), 7.36 (s, 1H), 7.19 (d, J = 8.1 Hz, 1H), 6.80 (s, 1H), 6.43 (s, 1H), 4.47-4.36 (m, 2H), 4.10 (s, 3H), 3.68 (s, 3H), 3.61 (s, 3H), 3.45-3.09 (m, 3H), 2.84 (s, 3H), 2.58-2.40 (m, 1H), 2.16-2.06 (m, 1H), 1.89-1.69 (m, 3H), 1.55-1.42 (m, 1H), 1.20-1.08 (m, 1H), 0.35-0.20 (m, 4H). |
| 326 | 1H NMR (400 MHz, DMSO-d6) δ 8.19 (d, J = 8.1 Hz, 1H), 7.85 (d, J = 6.0 Hz, 3H), 7.45 (t, J = 59.6 Hz, 1H), 7.33 (s, 1H), 7.18 (d, J = 8.1 Hz, 1H), 6.79 (s, 1H), 6.38 (s, 1H), 4.69-4.64 (m, 1H), 4.43 (d, J = 7.2 Hz, 2H), 4.11 (s, 3H), 3.61 (s, 3H), 3.49-3.39 (m, 1H), 2.84 (s, 3H), 2.44-2.39 (m, 2H), 2.16-1.94 (m, 3H), 1.87-1.54 (m, 4H), 1.19-1.07 (m, 1H), 0.34-0.19 (m, 4H). |
| 327 | 1H NMR (400 MHz, DMSO-d6) δ 8.19 (d, J = 8.1 Hz, 1H), 7.89-7.82 (m, 3H), 7.62-7.27 (m, 2H), 7.18 (d, J = 8.1 Hz, 1H), 6.80 (s, 1H), 6.35 (s, 1H), 4.68-4.63 (m, 1H), 4.42 (d, J = 7.1 Hz, 2H), 4.31-4.26 (m, 1H), 4.11 (s, 3H), 3.70-3.55 (m, 1H), 3.61 (s, 3H), 2.85 (s, 3H), 2.21-1.59 (m, 8H), 1.20-1.09 (m, 1H), 0.35-0.20 (m, 4H). |
| 328 | 1H NMR (400 MHz, DMSO-d6) δ 9.02-8.33 (m, 3H), 8.18 (d, J = 8.1 Hz, 1H), 7.63-7.21 (m, 2H), 7.18 (d, J = 8.1 Hz, 1H), 6.78 (s, 1H), 6.37 (s, 1H), 4.43 (d, J = 7.2 Hz, 2H), 4.10 (s, 3H), 4.05-3.74 (m, 1H), 3.61 (s, 3H), 3.38-3.03 (m, 3H), 2.92 (s, 3H), 2.85 (s, 3H), 2.83-2.68 (m, 1H), 2.05-1.35 (m, 4H), 1.19-1.10 (m, 1H), 0.33-0.21 (m, 4H). |
| 333 | 1H NMR (400 MHz, DMSO-d6) δ 8.87-8.78 (m, 1H), 8.64-8.57 (m, 1H), 8.19 (d, J = 8.1 Hz, 1H), 7.45 (t, J = 59.6 Hz, 1H), 7.40-7.20 (m, 1H), 7.18 (d, J = 8.1 Hz, 1H), 6.79 (s, 1H), 6.33 (d, J = 1.3 Hz, 1H), 4.42 (d, J = 7.1 Hz, 2H), 4.10 (s, 3H), 3.70-3.65 (m, 1H), 3.61 (s, 3H), 3.29-3.24 (m, 1H), 3.18-2.98 (m, 2H), 2.84 (s, 3H), 2.21-1.99 (m, 3H), 1.84-1.32 (m, 7H), 1.19-1.06 (m, 1H), 0.34-0.19 (m, 4H). |
| 334 | 1H NMR (400 MHz, DMSO-d6) δ 8.84 (d, J = 10.9 Hz, 1H), 8.52-8.39 (m, 1H), 8.19 (d, J = 8.1 Hz, 1H), 7.45 (t, J = 59.6 Hz, 1H), 7.23 (d, J = 1.2 Hz, 1H), 7.18 (d, J = 8.1 Hz, 1H), 6.79 (s, 1H), 6.33 (d, J = 1.3 Hz, 1H), 4.42 (d, J = 7.1 Hz, 2H), 4.10 (s, 3H), 4.04-3.56 (m, 2H), 3.61 (s, 3H), 3.34 (d, J = 12.3 Hz, 1H), 3.06 (dd, J = 21.1, 9.8 Hz, 2H), 2.98-2.78 (m, 2H), 2.84 (s, 3H), 2.23-1.73 (m, 3H), 1.72-1.44 (m, 5H), 1.20-1.07 (m, 1H), 0.35-0.20 (m, 4H). |
| 335 | 1H NMR (400 MHz, DMSO-d6) δ 8.19 (d, J = 8.1 Hz, 1H), 8.04 (s, 3H), 7.45 (t, J = 59.6 Hz, 1H), 7.36 (s, 1H), 7.18 (d, J = 8.1 Hz, 1H), 6.79 (s, 1H), 6.42 (d, J = 1.3 Hz, 1H), 4.42 (d, J = 7.1 Hz, 2H), 4.10 (s, 3H), 3.96-3.75 (m, 1H), 3.76-3.68 (m, 1H), 3.61 (s, 3H), 3.58-3.54 (m, 2H), 3.49-3.39 (m, 2H), 3.37 (s, 3H), 2.84 (s, 3H), 1.96-1.91 (m, 1H), 1.83-1.73 (m, 1H), 1.21-1.07 (m, 1H), 0.35-0.18 (m, 4H). |
| 336 | 1H NMR (400 MHz, DMSO-d6) δ 9.16-8.88 (m, 1H), 8.59-8.51 (m, 1H), 8.19 (d, J = 8.1 Hz, 1H), 7.49-7.41 (m, 1H), 7.45 (t, J = 59.6 Hz, 1H), 7.18 (d, J = 8.1 Hz, 1H), 6.79 (s, 1H), 6.44-6.36 (m, 1H), 4.51-4.35 (m, 2H), 4.10 (s, 3H), 4.05-3.78 (m, 1H), 3.77-3.40 (m, 3H), 3.61 (s, 3H), 3.34-3.19 (m, 1H), 2.97-2.92 (m, 1H), 2.85 (s, 3H), 2.72-2.62 (m, 1H), 1.87-1.58 (m, 5H), 1.21-1.09 (m, 1H), 0.33-0.20 (m, 4H). |
| 337 | 1H NMR (400 MHz, DMSO-d6) δ 9.09-8.79 (m, 1H), 8.57-8.46 (m, 1H), 8.18 (d, J = 8.1 Hz, 1H), 7.45 (t, J = 59.6 Hz, 1H), 7.48-7.42 (m, 1H), 7.18 (d, J = 8.1 Hz, 1H), 6.79 (s, 1H), 6.43-6.35 (m, 1H), 4.51-4.36 (m, 2H), 4.10 (s, 3H), 3.81-3.62 (m, 4H), 3.61 (s, 3H), 3.53-3.19 (m, 1H), 3.00-2.89 (m, 1H), 2.85 (s, 3H), 2.72-2.62 (m, 1H), 1.85-1.59 (m, 5H), 1.24-1.06 (m, 1H), 0.33-0.22 (m, 4H). |
| 338 | 1H NMR (400 MHz, DMSO-d6) δ 8.21 (d, J = 8.1 Hz, 1H), 7.45 (t, J = 59.5 Hz, 1H), 7.43-7.25 (m, 2H), 7.19 (d, J = 8.1 Hz, 1H), 6.90 (s, 1H), 6.83 (s, 1H), 6.46 (s, 1H), 4.36 (d, J = 7.1 Hz, 2H), 4.30-3.80 (m, 3H), 4.11 (s, 3H), 3.61 (s, 3H), 3.47-2.84 (m, 1H), 2.80 (s, 3H), 2.42-2.30 (m, 2H), 1.95 (d, J = 12.1 Hz, 1H), 1.78-1.33 (m, 2H), 1.17-1.06 (m, 1H), 0.34-0.18 (m, 4H). |
| 339 | 1H NMR (400 MHz, DMSO-d6) δ 9.62-9.50 (m, 2H), 9.13-9.04 (m, 2H), 8.86 (d, J = 3.9 Hz, 1H), 8.19 (d, J = 8.1 Hz, 1H), 7.79 (d, J = 1.4 Hz, 1H), 7.45 (t, J = 59.6 Hz, 1H), 7.18 (d, J = 8.1 Hz, 1H), 6.81 (s, 1H), 6.67 (d, J = 1.4 Hz, 1H), 4.44 (d, J = 7.0 Hz, 2H), 4.12 (s, 3H), 3.61 (s, 3H), 3.30-3.22 (m, 1H), 3.01-2.92 (m, 2H), 2.86 (s, 3H), 2.78-2.65 (m, 1H), 2.00-1.85 (m, 2H), 1.69-1.55 (m, 2H), 1.48-1.32 (m, 1H), 1.24-1.10 (m, 1H), 0.35-0.20 (m, 4H). |
| 340 | 1H NMR (400 MHz, DMSO-d6) δ 8.19 (d, J = 8.1 Hz, 1H), 7.98 (s, 3H), 7.45 (t, J = 59.6 Hz, 1H), 7.35 (s, 1H), 7.18 (d, J = 8.1 Hz, 1H), 6.79 (s, 1H), 6.40 (d, J = 1.3 Hz, 1H), 4.42 (d, J = 7.1 Hz, 2H), 4.09 (s, 3H), 3.85-3.77 (m, 1H), 3.61 (s, 3H), 3.68-3.39 (m, 8H), 2.84 (s, 3H), 1.93-1.84 (m, 1H), 1.82-1.70 (m, 1H), 1.19 (t, J = 7.0 Hz, 3H), 1.23-1.09 (m, 1H), 0.35-0.16 (m, 4H). |
| 341 | 1H NMR (400 MHz, DMSO-d6) δ 8.80-8.61 (m, 4H), 8.19 (d, J = 8.1 Hz, 1H), 7.88 (d, J = 1.4 Hz, 1H), 7.45 (t, J = 59.6 Hz, 1H), 7.18 (d, J = 8.1 Hz, 1H), 6.81 (s, 1H), 6.65 (d, J = 1.4 Hz, 1H), 4.47 (d, J = 7.1 Hz, 2H), 4.12 (s, 3H), 3.61 (s, 3H), 3.41-3.32 (m, 1H), 3.23 (d, J = 12.6 Hz, 1H), 2.96-2.80 (m, 3H), 2.87 (s, 3H), 1.98-1.89 (m, 2H), 1.76-1.59 (m, 2H), 1.23-1.11 (m, 1H), 0.36-0.21 (m, 4H). |
| 342 | 1H NMR (400 MHz, DMSO-d6) δ 8.78 (t, J = 5.7 Hz, 3H), 8.19 (d, J = 8.1 Hz, 1H), 7.45 (t, J = 59.6 Hz, 1H), 7.27 (d, J = 1.3 Hz, 1H), 7.18 (d, J = 8.1 Hz, 1H), 6.79 (s, 1H), 6.36 (d, J = 1.4 Hz, 1H), 4.42 (d, J = 7.1 Hz, 2H), 4.09 (s, 3H), 3.61 (s, 3H), 3.42-3.32 (m, 2H), 3.31-3.23 (m, 2H), 2.84 (s, 3H), 2.05-1.92 (m, 6H), 1.92-1.79 (m, 4H), 1.20-1.08 (m, 1H), 0.36-0.12 (m, 4H). |
| 343 | 1H NMR (400 MHz, DMSO-d6) δ 8.83 (dd, J = 10.7, 7.4 Hz, 1H), 8.19 (d, J = 8.1 Hz, 1H), 8.13 (s, 3H), 7.95 (dd, J = 7.6, 1.4 Hz, 1H), 7.45 (t, J = 59.6 Hz, 1H), 7.18 (d, J = 8.1 Hz, 1H), 6.81 (s, 1H), 6.69 (dd, J = 5.3, 1.4 Hz, 1H), 4.64 (q, J = 7.9 Hz, 0.4H), 4.47 (d, J = 7.1 Hz, 2H), 4.19 (dt, J = 9.9, 7.5 Hz, 0.6H), 4.13 (s, 3H), 3.61 (s, 3H), 3.35-3.25 (m, 1H), 2.88 (s, 3H), 2.48-2.35 (m, 1H), 2.31-1.91 (m, 5H), 1.91-1.60 (m, 2H), 1.18 (p, J = 6.0, 5.5 Hz, 1H), 0.36-0.21 (m, 4H). |

TABLE 2-continued

| Ex | NMR |
|---|---|
| 344 | 1H NMR (400 MHz, DMSO-d6) δ 8.90 (t, J = 6.3 Hz, 1H), 8.19 (d, J = 8.1 Hz, 1H), 7.93 (d, J = 1.4 Hz, 1H), 7.83 (s, 3H), 7.45 (t, J = 59.6 Hz, 1H), 7.18 (d, J = 8.1 Hz, 1H), 6.82 (s, 1H), 6.66 (d, J = 1.4 Hz, 1H), 4.48 (d, J = 7.1 Hz, 2H), 4.12 (s, 3H), 3.61 (s, 3H), 3.46 (d, J = 6.3 Hz, 2H), 2.88 (s, 3H), 1.29 (s, 6H), 1.21-1.11 (m, 1H), 0.35-0.18 (m, 4H). |
| 345 | 1H NMR (400 MHz, DMSO-d6) δ 8.22-8.15 (m, 2H), 7.95 (s, 1H), 7.94-7.85 (m, 3H), 7.45 (t, J = 59.5 Hz, 1H), 7.18 (d, J = 8.1 Hz, 1H), 6.82 (s, 1H), 6.62 (s, 1H), 4.48 (d, J = 7.1 Hz, 2H), 4.11 (s, 3H), 3.61 (s, 3H), 3.28 (q, J = 5.9 Hz, 2H), 2.87 (s, 3H), 1.43 (s, 6H), 1.21-1.10 (m, 1H), 0.35-0.17 (m, 4H). |
| 346 | 1H NMR (400 MHz, DMSO-d6) δ 8.17 (dd, J = 13.3, 6.2 Hz, 5H), 7.62-7.27 (m, 2H), 7.23-7.10 (m, 3H), 6.79 (s, 1H), 6.35 (s, 1H), 4.49-4.41 (m, 2H), 4.10 (s, 3H), 3.61 (s, 3H), 2.85 (s, 3H), 1.85 (d, J = 34.8 Hz, 3H), 1.66-1.31 (m, 4H), 1.14 (s, 4H), 0.91 (s, 4H), 0.35-0.16 (m, 4H). |
| 347 | 1H NMR (400 MHz, DMSO-d6) δ 8.19 (d, J = 8.1 Hz, 1H), 8.12 (s, 4H), 7.63-7.28 (m, 2H), 7.18 (d, J = 8.1 Hz, 1H), 6.79 (s, 1H), 6.44 (s, 1H), 4.45 (d, J = 7.2 Hz, 2H), 4.11 (s, 3H), 3.61 (s, 3H), 2.96 (s, 1H), 2.86 (s, 3H), 2.18-1.40 (m, 5H), 1.31 (s, 1H), 1.14 (d, J = 10.1 Hz, 1H), 0.99-0.82 (m, 3H), 0.35-0.19 (m, 4H). |
| 348 | 1H NMR (400 MHz, DMSO-d6) δ 8.19 (d, J = 8.1 Hz, 1H), 7.94 (s, 4H), 7.45 (t, J = 59.6 Hz, 1H), 7.35 (s, 1H), 7.18 (d, J = 8.1 Hz, 1H), 6.79 (s, 1H), 6.41 (s, 1H), 5.91-5.47 (m, 1H), 4.42 (d, J = 7.1 Hz, 2H), 4.09 (s, 3H), 4.09-4.01 (m, 2H), 3.61 (s, 3H), 3.52-3.41 (m, 2H), 3.42-3.33 (m, 2H), 2.84 (s, 3H), 1.88-1.64 (m, 2H), 1.20-1.09 (m, 1H), 0.35-0.17 (m, 4H). |
| 350 | 1H NMR (400 MHz, DMSO-d6) δ 9.07 (s, 1H), 8.91 (s, 1H), 8.18 (d, J = 8.1 Hz, 1H), 7.62-7.29 (m, 2H), 7.18 (d, J = 8.1 Hz, 1H), 6.79 (s, 1H), 6.40 (d, J = 1.3 Hz, 1H), 4.78 (d, J = 5.5 Hz, 1H), 4.44 (h, J = 7.1 Hz, 2H), 4.29 (s, 1H), 4.10 (s, 3H), 3.85-3.65 (m, 2H), 3.61 (s, 3H), 3.36 (d, J = 9.1 Hz, 2H), 2.85 (s, 3H), 2.19 (s, 4H), 1.22-1.08 (m, 1H), 0.33-0.21 (m, 4H). |
| 351 | 1H NMR (400 MHz, DMSO-d6) δ 8.18 (d, J = 8.1 Hz, 1H), 8.15 (s, 3H), 7.62-7.29 (m, 2H), 7.20-7.09 (m, 2H), 6.78 (s, 1H), 6.39 (d, J = 1.3 Hz, 1H), 4.45 (d, J = 7.1 Hz, 2H), 4.11 (s, 3H), 3.61 (s, 3H), 2.85 (d, J = 1.2 Hz, 3H), 2.36-1.97 (m, 3H), 1.60 (dd, J = 13.5, 5.1 Hz, 1H), 1.35 (dd, J = 13.5, 6.0 Hz, 1H), 1.10 (d, J = 18.4 Hz, 4H), 0.34-0.19 (m, 4H).; 1H NMR (400 MHz, DMSO-d6) δ 8.18 (d, J = 8.1 Hz, 1H), 8.05 (d, J = 55.3 Hz, 4H), 7.67-7.28 (m, 2H), 7.18 (d, J = 8.1 Hz, 1H), 6.78 (d, J = 2.2 Hz, 1H), 6.42 (d, J = 1.3 Hz, 1H), 4.45 (d, J = 7.0 Hz, 2H), 4.10 (s, 3H), 3.61 (s, 3H), 2.86 (s, 3H), 2.30-1.78 (m, 3H), 1.21-0.86 (m, 6H), 0.34-0.21 (m, 4H). |
| 352 | 1H NMR (400 MHz, DMSO-d6) δ 8.18 (d, J = 8.1 Hz, 1H), 8.15 (s, 3H), 7.62-7.29 (m, 2H), 7.20-7.09 (m, 2H), 6.78 (s, 1H), 6.39 (d, J = 1.3 Hz, 1H), 4.45 (d, J = 7.1 Hz, 2H), 4.11 (s, 3H), 3.61 (s, 3H), 2.85 (d, J = 1.2 Hz, 3H), 2.36-1.97 (m, 3H), 1.60 (dd, J = 13.5, 5.1 Hz, 1H), 1.35 (dd, J = 13.5, 6.0 Hz, 1H), 1.10 (d, J = 18.4 Hz, 4H), 0.34-0.19 (m, 4H).; 1H NMR (400 MHz, DMSO-d6) δ 8.18 (d, J = 8.1 Hz, 1H), 8.05 (d, J = 55.3 Hz, 4H), 7.67-7.28 (m, 2H), 7.18 (d, J = 8.1 Hz, 1H), 6.78 (d, J = 2.2 Hz, 1H), 6.42 (d, J = 1.3 Hz, 1H), 4.45 (d, J = 7.0 Hz, 2H), 4.10 (s, 3H), 3.61 (s, 3H), 2.86 (s, 3H), 2.30-1.78 (m, 3H), 1.21-0.86 (m, 6H), 0.34-0.21 (m, 4H). |
| 356 | 1H NMR (400 MHz, DMSO-d6) δ 8.20 (d, J = 8.1 Hz, 1H), 7.52 (s, 1H), 7.46 (d, J = 1.3 Hz, 1H), 7.45 (t, J = 59.5 Hz, 1H), 7.18 (d, J = 8.1 Hz, 1H), 7.10 (s, 1H), 6.81 (s, 1H), 6.50 (d, J = 1.3 Hz, 1H), 4.58 (t, J = 8.7 Hz, 1H), 4.45-4.35 (m, 3H), 4.18 (t, J = 9.5 Hz, 1H), 4.12 (s, 3H), 4.11-4.04 (m, 1H), 3.61 (s, 3H), 3.39 (tt, J = 9.0, 6.0 Hz, 1H), 2.83 (s, 3H), 1.20-1.05 (m, 1H), 0.34-0.17 (m, 4H). |
| 357 | Appears as a ~3:7 ratio of rotamers: 1H NMR (400 MHz, DMSO-d6) δ 8.18 (d, J = 8.1 Hz, 1H), 7.63-7.52 (m, 2H), 7.44 (t, J = 59.8, 59.2 Hz, 1H), 7.34-7.23 (m, 1H), 7.17 (d, J = 8.1 Hz, 1H), 6.79 (s, 1H), 6.53-6.31 (m, 1H), 5.16-5.06 (m, 0.3H), 4.74-4.62 (m, 0.7H), 4.58-4.46 (m, 1H), 4.46-4.36 (m, 2H), 4.30-4.16 (m, 0.7H), 4.14-4.04 (m, 3.3H), 3.61 (s, 3H), 2.84 (s, 3H), 2.24-1.97 (m, 1H), 1.18-1.08 (m, 1H), 0.36-0.18 (m, 4H). |
| 358 | 1H NMR (400 MHz, DMSO-d6) δ 9.03 (s, 1H), 8.49 (s, 1H), 8.28-8.13 (m, 1H), 7.64-7.27 (m, 2H), 7.18 (d, J = 8.1 Hz, 1H), 6.79 (d, J = 1.4 Hz, 1H), 6.36 (s, 1H), 4.46 (d, J = 7.0 Hz, 2H), 4.18 (d, J = 5.8 Hz, 1H), 4.10 (s, 3H), br 3.92 (s, 2H), 3.61 (s, 3H), 3.20-2.80 (m, 2H), 2.86 (s, 3H), 2.15 (s, 2H), 1.99-1.51 (m, 3H), 1.16 (d, J = 9.2 Hz, 1H), 0.27 (dd, J = 19.7, 6.6 Hz, 4H). |
| 359 | 1H NMR (400 MHz, Methanol-d4) δ 8.20 (d, J = 8.2 Hz, 1H), 7.48-7.42 (m, 1H), 7.36-7.21 (m, 2H), 6.89 (s, 1H), 6.69 (s, 1H), 4.32 (d, J = 7.1 Hz, 2H), 4.24 (s, 4H), 4.09 (dt, J = 12.3, 5.3 Hz, 1H), 3.83-3.70 (m, 3H), 3.56 (s, 3H), 3.46 (d, J = 11.7 Hz, 2H), 2.85 (s, 3H), 2.24-2.04 (m, 2H), 1.97 (s, 2H), 1.10-0.98 (m, 1H), 0.40-0.29 (m, 2H), 0.19 (dt, J = 6.3, 4.6 Hz, 2H). |
| 360 | 1H NMR (400 MHz, Methanol-d4) δ 8.17 (d, J = 8.2 Hz, 1H), 7.41 (d, J = 19.6 Hz, 1H), 7.31-7.21 (m, 1H), 7.14 (d, J = 0H), 6.81 (s, 1H), 6.57-6.51 (m, 1H), 4.37 (d, J = 7.1 Hz, 3H), 4.21 (s, 3H), 3.98 (s, 4H), 3.90 (d, J = 17.8 Hz, 2H), 3.64 (s, 2H), 3.55 (s, 3H), 2.87 (s, 3H), 2.07 (s, 3H), 1.97 (s, 1H), 1.84 (s, 1H), 0.39-0.29 (m, 2H), 0.21-0.09 (m, 2H). |
| 361 | 1H NMR (400 MHz, DMSO-d6) δ 8.20 (s, 2H), 8.16 (d, J = 8.0 Hz, 1H), 8.09 (s, 1H), 7.61-7.25 (m, 2H), 7.15 (d, J = 8.1 Hz, 1H), 6.76 (s, 1H), 6.43-6.31 (m, 1H), 4.72 (s, 1H), 4.43 (d, J = 7.2 Hz, 3H), 4.07 (d, J = 2H), 3.76-3.68 (m, 2H), 3.58 (s, 3H), 3.57-3.29 (m, 3H), 3.09 (d, J = 8.4 Hz, 1H), 2.83 (s, 3H), 2.80-2.74 (m, 0H), 2.34-2.29 (m, 1H), 2.29-2.18 (m, 1H), 1.22 (s, 1H), 1.17-1.01 (m, 1H), 0.35-0.16 (m, 4H). |
| 362 | 1H NMR (400 MHz, Methanol-d4) δ 8.12 (d, J = 8.1 Hz, 1H), 7.42 (s, 0H), 7.30-7.16 (m, 2H), 7.12 (s, 0H), 6.73 (s, 1H), 6.33 (s, 1H), 5.51 (s, 1H), 4.53 (s, 0H), 4.40 (d, J = 7.0 Hz, 2H), 4.16 (s, 3H), 4.00 (s, 1H), 3.55 (s, 3H), 3.00 (d, J = 7.2 Hz, 0H), 2.86 (s, 3H), 2.17 (s, 1H), 1.78 (s, 1H), 1.30 (d, J = 7.1 Hz, 1H), 1.03 (qd, J = 8.8, 8.4, 3.5 Hz, 1H), 0.85 (s, 1H), 0.52 (s, 1H), 0.31 (dt, J = 8.0, 3.0 Hz, 2H), 0.14 (d, J = 5.2 Hz, 2H) |
| 363 | 1H NMR (400 MHz, Methanol-d4) δ 8.12 (d, J = 8.1 Hz, 1H), 7.71-7.61 (m, 0H), 7.61-7.53 (m, 0H), 7.40 (d, J = 19.1 Hz, 0H), 7.30-7.17 (m, 3H), 7.12 (s, 0H), 6.73 (s, 1H), 6.33 (s, 1H), 5.51 (s, 1H), 5.12 (d, J = 6.8 Hz, 0H), 4.53 (s, 0H), 4.40 (d, J = 7.0 Hz, 2H), 4.15 (s, 3H), 4.21-4.11 (m, 0H), 3.99 (s, 1H), 3.67 (s, 0H), 3.55 (s, 3H), 3.00 (q, J = 7.1 Hz, 1H), 2.86 (s, 3H), 2.16 (s, 1H), 1.78 (s, 1H), 1.34-1.19 (m, 2H), 1.03 (tt, J = 8.9, 5.3 Hz, 1H), 0.84 (s, 1H), 0.51 (s, 1H), 0.31 (dt, J = 8.2, 3.1 Hz, 2H), 0.14 (d, J = 5.2 Hz, 2H). |

TABLE 2-continued

| Ex | NMR |
|---|---|
| 365 | 1H NMR (400 MHz, Methanol-d4) δ 8.20 (d, J = 8.2 Hz, 1H), 7.47-7.37 (m, 1H), 7.32-7.21 (m, 2H), 7.14 (s, 0H), 6.89 (s, 1H), 6.65 (s, 1H), 4.49 (s, 1H), 4.32 (d, J = 7.1 Hz, 2H), 4.24 (s, 3H), 3.89 (d, J = 13.5 Hz, 1H), 3.56 (s, 3H), 2.85 (s, 3H), 2.24 (s, 1H), 1.81 (s, 1H), 1.63 (t, J = 8.1 Hz, 1H), 1.45 (s, 0H), 1.29 (s, 1H), 1.13-0.99 (m, 1H), 0.41-0.29 (m, 2H), 0.23-0.14 (m, 2H). |
| 368 | 1H NMR (400 MHz, Methanol-d4) δ 8.23 (d, J = 8.2 Hz, 1H), 7.68 (d, J = 1.3 Hz, 0H), 7.48-7.42 (m, 1H), 7.33-7.25 (m, 1H), 7.15 (s, 0H), 6.98-6.92 (m, 1H), 6.79 (d, J = 1.2 Hz, 0H), 4.74 (q, J = 2.6 Hz, 0H), 4.28 (dd, J = 8.4, 5.8 Hz, 5H), 4.01 (dt, J = 4.1, 2.0 Hz, 0H), 3.78-3.52 (m, 3H), 3.57 (s, 3H), 2.84 (d, J = 8.1 Hz, 3H), 2.41-2.29 (m, 0H), 2.27 (s, 1H), 2.27 (s, 0H), 2.12 (s, 0H), 2.05-1.93 (m, 0H), 1.92-1.81 (m, 1H), 1.77-1.56 (m, 1H), 1.07 (dq, J = 11.8, 3.7 Hz, 1H), 0.43-0.31 (m, 2H), 0.30-0.16 (m, 2H). |
| 369 | 1H NMR (400 MHz, Methanol-d4) δ 8.23 (d, J = 8.2 Hz, 1H), 7.68 (d, J = 1.3 Hz, 0H), 7.48-7.42 (m, 1H), 7.33-7.25 (m, 1H), 7.15 (s, 0H), 6.98-6.92 (m, 1H), 6.79 (d, J = 1.2 Hz, 0H), 4.74 (q, J = 2.6 Hz, 0H), 4.28 (dd, J = 8.4, 5.8 Hz, 5H), 4.01 (dt, J = 4.1, 2.0 Hz, 0H), 3.78-3.52 (m, 3H), 3.57 (s, 3H), 2.84 (d, J = 8.1 Hz, 3H), 2.41-2.29 (m, 0H), 2.27 (s, 1H), 2.27 (s, 0H), 2.12 (s, 0H), 2.05-1.93 (m, 0H), 1.92-1.81 (m, 1H), 1.77-1.56 (m, 1H), 1.07 (dq, J = 11.8, 3.7 Hz, 1H), 0.43-0.31 (m, 2H), 0.30-0.16 (m, 2H). |
| 371 | 1H NMR (400 MHz, DMSO-d6) δ 8.23-7.96 (m, 3H), 7.92 (d, J = 8.1 Hz, 1H), 7.45 (s, 1H), 7.12 (d, J = 8.1 Hz, 1H), 6.58 (s, 1H), 6.37 (s, 1H), 6.35 (d, J = 8.0 Hz, 1H), 4.93 (t, J = 7.1 Hz, 1H), 4.40 (ddd, J = 31.5, 14.1, 7.1 Hz, 2H), 4.09 (s, 3H), 3.51 (d, J = 10.0 Hz, 2H), 3.34-3.16 (m, 3H), 2.80 (s, 3H), 1.86 (d, J = 26.6 Hz, 4H), 1.70-1.57 (m, 1H), 1.58-1.47 (m, 3H), 1.47-1.38 (m, 3H), 1.38-1.27 (m, 1H), 1.18-1.02 (m, 1H), 0.64 (td, J = 7.7, 4.4 Hz, 1H), 0.33-0.16 (m, 4H), 0.06 (q, J = 4.1 Hz, 1H). |
| 372 | 1H NMR (400 MHz, DMSO-d6) δ 8.16 (d, J = 8.2 Hz, 1H), 8.04-7.96 (m, 2H), 7.88 (s, 2H), 7.46 (s, 1H), 7.43 (t, J = 56 Hz, 1H), 7.16 (d, J = 8.1 Hz, 1H), 6.77 (d, J = 5.6 Hz, 1H), 6.38 (s, 1H), 4.42 (d, J = 7.1 Hz, 2H), 4.09 (s, 3H), 4.07 (s, 3H), 3.59 (s, 3H), 3.08 (t, J = 10.1 Hz, 1H), 2.83 (d, J = 6.7 Hz, 3H), 2.78-2.62 (m, 2H), 2.18-2.08 (m, 1H), 2.04-1.82 (m, 1H), 1.19-1.02 (m, 2H), 0.34--0.01 (m, 6H). |
| 376 | 1H NMR (400 MHz, Methanol-d4) δ 8.20 (d, J = 8.2 Hz, 1H), 7.51 (d, J = 1.3 Hz, 0H), 7.47-7.39 (m, 1H), 7.32-7.23 (m, 2H), 7.15 (s, 0H), 6.89 (d, J = 3.8 Hz, 1H), 6.73 (dd, J = 19.1, 1.3 Hz, 1H), 4.73 (d, J = 2.9 Hz, 0H), 4.32 (dd, J = 7.1, 2.9 Hz, 2H), 4.24 (d, J = 5.9 Hz, 3H), 4.06-4.00 (m, 1H), 3.82 (s, 1H), 3.56 (s, 5H), 2.85 (d, J = 4.2 Hz, 3H), 2.38 (q, J = 11.9 Hz, 1H), 2.27 (s, 1H), 2.11 (s, 1H), 2.08-1.88 (m, 1H), 1.85 (dd, J = 15.1, 7.6 Hz, 2H), 1.61 (d, J = 14.4 Hz, 1H), 1.06 (s, 1H), 1.09-0.98 (m, 0H), 0.41-0.29 (m, 2H), 0.20 (qd, J = 6.9, 6.1, 4.6 Hz, 2H). |
| 377 | 1H NMR (400 MHz, Methanol-d4) δ 8.23 (d, J = 8.2 Hz, 1H), 7.68 (d, J = 1.3 Hz, 0H), 7.48-7.42 (m, 1H), 7.33-7.25 (m, 1H), 7.15 (s, 0H), 6.98-6.92 (m, 1H), 6.79 (d, J = 1.2 Hz, 0H), 4.74 (q, J = 2.6 Hz, 0H), 4.28 (dd, J = 8.4, 5.8 Hz, 5H), 4.01 (dt, J = 4.1, 2.0 Hz, 0H), 3.78-3.52 (m, 3H), 3.57 (s, 3H), 2.84 (d, J = 8.1 Hz, 3H), 2.41-2.29 (m, 0H), 2.27 (s, 1H), 2.27 (s, 0H), 2.12 (s, 0H), 2.05-1.93 (m, 0H), 1.92-1.81 (m, 1H), 1.77-1.56 (m, 1H), 1.07 (dq, J = 11.8, 3.7 Hz, 1H), 0.43-0.31 (m, 2H), 0.30-0.16 (m, 2H). |
| 378 | 1H NMR (400 MHz, DMSO-d6) δ 8.16 (d, J = 8.1 Hz, 1H), 7.99 (s, 4H), 7.44 (t, 1H), 7.43 (s, 1H), 7.16 (dd, J = 8.1, 2.1 Hz, 1H), 6.76 (s, 1H), 6.36 (d, J = 3.7 Hz, 1H), 4.43 (d, J = 7.5 Hz, 2H), 4.16 (dd, J = 25.4, 7.4 Hz, 1H), 4.10-4.03 (m, 3H), 3.59 (s, 4H), 3.45-3.29 (m, 1H), 3.06 (d, J = 9.4 Hz, 1H), 2.83 (d, J = 5.8 Hz, 3H), 2.78-2.66 (m, 1H), 2.24-2.04 (m, 1H), 1.93-1.70 (m, 2H), 1.18-0.98 (m, 1H), 0.34-0.14 (m, 5H). |
| 379 | 1H NMR (400 MHz, DMSO-d6) δ 8.16 (d, J = 8.1 Hz, 1H), 8.14 (s, 2H), 8.01 (s, 2H), 7.44 (t, J = 60 Hz, 1H), 7.43 (s, 1H), 7.28 (s, 1H), 7.16 (d, J = 8.1 Hz, 1H), 6.76 (s, 1H), 6.36 (d, J = 5.5 Hz, 1H), 4.42 (d, J = 7.1 Hz, 2H), 4.08 (s, 3H), 3.59 (s, 3H), 3.21 (dd, J = 17.6, 10.1 Hz, 1H), 2.83 (s, 3H), 2.01-1.79 (m, 4H), 1.71-1.50 (m, 1H), 1.18-1.04 (m, 1H), 0.32-0.24 (m, 4H), 0.24-0.16 (m, 2H). |
| 381 | 1H NMR (400 MHz, Methanol-d4) δ 8.20 (d, J = 8.2 Hz, 1H), 7.51 (d, J = 1.3 Hz, 0H), 7.47-7.39 (m, 1H), 7.32-7.23 (m, 2H), 7.15 (s, 0H), 6.89 (d, J = 3.8 Hz, 1H), 6.73 (dd, J = 19.1, 1.3 Hz, 1H), 4.73 (d, J = 2.9 Hz, 0H), 4.32 (dd, J = 7.1, 2.9 Hz, 2H), 4.24 (d, J = 5.9 Hz, 3H), 4.06-4.00 (m, 1H), 3.82 (s, 1H), 3.56 (s, 5H), 2.85 (d, J = 4.2 Hz, 3H), 2.38 (q, J = 11.9 Hz, 1H), 2.27 (s, 1H), 2.11 (s, 1H), 2.08-1.88 (m, 1H), 1.85 (dd, J = 15.1, 7.6 Hz, 2H), 1.61 (d, J = 14.4 Hz, 1H), 1.06 (s, 1H), 1.09-0.98 (m, 0H), 0.41-0.29 (m, 2H), 0.20 (qd, J = 6.9, 6.1, 4.6 Hz, 2H). |
| 382 | 1H NMR (400 MHz, DMSO-d6) δ 8.20 (d, J = 8.1 Hz, 1H), 7.97 (s, 3H), 7.46 (t, J = 59.6 Hz, 1H), 7.36 (s, 1H), 7.18 (d, J = 8.1 Hz, 1H), 6.84 (s, 1H), 6.45 (s, 1H), 4.85-4.57 (m, 1H), 4.46 (d, J = 7.2 Hz, 2H), 4.36-4.18 (m, 1H), 4.14 (s, 3H), 3.63 (s, 3H), 3.51-3.30 (m, 1H), 2.48-2.38 (m, 1H), 2.17-1.96 (m, 3H), 1.96-1.78 (m, 2H), 1.75-1.51 (m, 3H), 1.07-0.85 (m, 3H), 0.51-0.33 (m, 2H), 0.26 (d, J = 7.8 Hz, 2H), 0.19-0.07 (m, 2H). |
| 384 | 1H NMR (400 MHz, DMSO-d6) δ 9.48 (s, 1H), 8.97 (s, 1H), 8.20 (d, J = 8.1 Hz, 1H), 7.46 (t, J = 59.6 Hz, 1H), 7.34 (s, 1H), 7.19 (d, J = 8.1 Hz, 1H), 6.84 (s, 1H), 6.44 (s, 1H), 5.69-4.80 (m, 4H), 4.46 (d, J = 7.1 Hz, 2H), 4.13 (s, 3H), 4.11-3.97 (m, 2H), 3.75 (t, J = 11.6 Hz, 1H), 3.63 (s, 3H), 3.45-2.94 (m, 3H), 2.48-2.38 (m, 1H), 2.00-1.80 (m, 2H), 1.07-0.85 (m, 3H), 0.41 (d, J = 5.4 Hz, 2H), 0.25 (dd, J = 7.0, 5.1 Hz, 2H), 0.21-0.06 (m, 2H). |
| 385 | 1H NMR (400 MHz, DMSO-d6) δ 8.19 (d, J = 8.1 Hz, 1H), 8.12 (s, 3H), 7.54 (t, J = 58.9 Hz, 1H), 7.46 (s, 1H), 7.18 (d, J = 8.1 Hz, 1H), 6.84 (s, 1H), 6.43 (s, 1H), 4.48 (d, J = 7.2 Hz, 2H), 4.14 (s, 3H), 3.89-3.68 (m, 1H), 3.62 (s, 3H), 2.47-2.39 (m, 1H), 2.40-2.14 (m, 1H), 1.95-1.77 (m, 3H), 1.71-1.52 (m, 1H), 1.36 (dd, J = 12.8, 4.4 Hz, 1H), 1.23 (s, 2H), 1.06-0.81 (m, 3H), 0.46-0.35 (m, 2H), 0.31-0.19 (m, 2H), 0.20-0.07 (m, 2H). |
| 386 | 1H NMR (400 MHz, DMSO-d6) δ 8.62 (d, J = 7.1 Hz, 1H), 8.18 (d, J = 8.1 Hz, 1H), 8.16-8.03 (m, 3H), 7.91 (s, 1H), 7.44 (t, 1H), 7.24-7.19 (m, 1H), 7.16 (d, J = 8.1 Hz, 1H), 6.95 (s, 1H), 4.58 (d, J = 7.1 Hz, 2H), 4.55-4.35 (m, 1H), 3.60 (s, 3H), 2.25-2.09 (m, 1H), 1.94-1.73 (m, 5H), 1.70-1.46 (m, 1H), 1.34 (dd, J = 12.8, 4.5 Hz, 2H), 1.17-0.98 (m, 4H), 0.50-0.31 (m, 3H), 0.28-0.18 (m, 2H), 0.20-0.07 (m, 2H). |

TABLE 2-continued

| Ex | NMR |
|---|---|
| 387 | 1H NMR (400 MHz, Methanol-d4) δ 8.16 (d, J = 8.2 Hz, 1H), 7.57 (d, J = 1.4 Hz, 1H), 7.27 (t, J = 60.0 Hz, 1H), 7.22 (d, J = 8.1 Hz, 1H), 7.04-6.93 (m, 1H), 6.82 (s, 1H), 4.33 (d, J = 7.1 Hz, 2H), 3.77-3.59 (m, 2H), 3.53 (s, 3H), 3.43 (br, 3H), 3.06 (s, 3H), 2.75 (s, 3H), 2.18 (s, 1H), 1.85 (s, 1H), 1.73 (d, J = 8.1 Hz, 2H), 1.02 (tt, J = 7.9, 4.9 Hz, 1H), 0.41-0.23 (m, 2H), 0.23-0.05 (m, 2H).; 1H NMR (400 MHz, Chloroform-d) δ 8.02 (d, J = 8.1 Hz, 1H), 7.53 (s, 1H), 7.21 (d, J = 8.1 Hz, 1H), 7.11 (t, J = 60.8 Hz, 1H), 6.72 (s, 1H), 6.62 (s, 1H), 4.62 (s, 1H), 4.43 (d, J = 7.1 Hz, 2H), 4.50-3.20 (m, 4H), 3.07 (s, 3H), 2.66 (s, 3H), 2.01 (s, 1H), 1.80 (s, 1H), 1.7-1.2 (br, 2H), 1.41 (s, 9H), 1.11 (td, J = 7.6, 4.0 Hz, 1H), 0.32 (dd, J = 8.2, 1.8 Hz, 2H), 0.17 (q, J = 4.4 Hz, 2H). |
| 388 | 1H NMR (400 MHz, Methanol-d4) δ 8.18 (d, J = 8.2 Hz, 1H), 7.44 (s, 0H), 7.36 (d, J = 1.1 Hz, 1H), 7.32-7.21 (m, 2H), 7.14 (s, 0H), 6.83 (s, 1H), 6.55 (s, 1H), 4.36 (d, J = 7.1 Hz, 2H), 4.21 (s, 3H), 3.56 (s, 3H), 3.44 (s, 3H), 3.01 (s, 0H), 2.86 (s, 3H), 2.21 (s, 1H), 1.95 (s, 0H), 1.89 (s, 1H), 1.76 (s, 3H), 1.07-1.00 (m, 0H), 0.39-0.30 (m, 2H), 0.17 (q, J = 5.0 Hz, 2H). |
| 389 | 1H NMR (400 MHz, Chloroform-d) δ 8.02 (d, J = 8.1 Hz, 1H), 7.52 (s, 1H), 7.21 (d, J = 8.1 Hz, 1H), 7.11 (t, J = 60.8 Hz, 1H), 6.63 (s, 1H), 6.35 (s, 1H), 4.65 (br, 2H), 4.46 (d, J = 7.1 Hz, 2H), 4.11 (s, 3H), 4.05 (br, 1H), 3.46 (s, 3H), 2.86 (s, 3H), 2.50 (d, J = 14.0 Hz, 1H), 2.03-1.50 (m, 4H), 1.42 (s, 9H), 1.10 (m, 1H), 1.04 (dd, J = 12.8, 4.5 Hz, 1H), 0.32 (dd, J = 7.8, 1.9 Hz, 2H), 0.18 (t, J = 3.4 Hz, 2H).; 1H NMR (400 MHz, Methanol-d4) δ 8.17 (d, J = 8.2 Hz, 1H), 7.51 (d, J = 1.3 Hz, 1H), 7.27 (t, J = 60.1 Hz, 1H), 7.24 (d, J = 8.2 Hz, 1H), 6.86 (s, 1H), 6.70 (d, J = 1.3 Hz, 1H), 4.48 (br, 2H), 4.31 (d, J = 7.1 Hz, 2H), 4.22 (s, 3H), 3.92-3.75 (m, 1H), 3.53 (s, 3H), 2.84 (s, 3H), 2.59-2.41 (m, 1H), 2.03 (d, J = 6.3 Hz, 2H), 1.97-1.86 (m, 1H), 1.76 (t, J = 8.2 Hz, 1H), 1.47 (dd, J = 13.2, 4.5 Hz, 1H), 1.01 (td, J = 7.8, 4.1 Hz, 1H), 0.41-0.25 (m, 2H), 0.16 (dt, J = 6.2, 4.6 Hz, 2H). |
| 390 | 1H NMR (400 MHz, Methanol-d4) δ 8.21 (d, J = 8.2 Hz, 1H), 7.50 (d, J = 1.3 Hz, 1H), 7.32-7.24 (m, 1H), 6.90 (s, 1H), 6.75 (d, J = 1.3 Hz, 1H), 6.01 (s, 1H), 5.63 (dd, J = 32.8, 13.3 Hz, 1H), 5.02 (s, 1H), 4.32 (d, J = 7.1 Hz, 2H), 4.25 (s, 3H), 3.77 (d, J = 31.9 Hz, 2H), 3.64 (d, J = 8.6 Hz, 1H), 3.56 (s, 3H), 2.86 (s, 3H), 2.18 (d, J = 32.1 Hz, 4H), 1.83 (d, J = 31.0 Hz, 3H), 1.05 (pd, J = 7.1, 3.5 Hz, 1H), 0.36 (dt, J = 8.2, 3.0 Hz, 2H), 0.24-0.15 (m, 2H). |
| 391 | 1H NMR (400 MHz, DMSO-d6) δ 8.19 (d, J = 8.1 Hz, 1H), 7.99 (s, 3H), 7.54 (t, J = 59.6 Hz, 1H), 7.32 (s, 1H), 7.18 (d, J = 8.1 Hz, 1H), 6.83 (s, 1H), 6.42 (d, J = 1.3 Hz, 1H), 4.46 (d, J = 7.2 Hz, 2H), 4.13 (s, 3H), 3.62 (s, 3H), 3.40-2.97 (m, 3H), 2.47-2.35 (m, 1H), 2.11-1.97 (m, 1H), 1.86-1.69 (m, 1H), 1.70-1.49 (m, 2H), 1.23 (s, 2H), 1.11-0.75 (m, 3H), 0.46-0.36 (m, 2H), 0.30-0.20 (m, 2H), 0.20-0.05 (m, 2H). |
| 392 | 1H NMR (400 MHz, Methanol-d4) δ 8.85 (d, J = 4.7 Hz, 1H), 8.17 (d, J = 8.2 Hz, 1H), 7.84 (d, J = 5.9 Hz, 1H), 7.48-7.08 (m, 2H), 6.93 (s, 1H), 4.53 (d, J = 7.1 Hz, 2H), 3.82 (dd, J = 124.4, 10.2 Hz, 1H), 3.56 (s, 3H), 3.52-3.40 (m, 3H), 2.34-2.09 (m, 1H), 1.81 (d, J = 43.2 Hz, 3H), 1.19 (d, J = 7.7 Hz, 2H), 1.01 (m, J = 7.3 Hz, 1H), 0.60-0.47 (m, 2H), 0.29 (d, J = 7.8 Hz, 2H), 0.13 (d, J = 4.4 Hz, 2H). |
| 395 | 1H NMR (400 MHz, DMSO-d6) δ 8.64 (dd, J = 7.1, 1.0 Hz, 1H), 8.18 (d, J = 8.1 Hz, 1H), 7.94 (s, 3H), 7.81 (s, 1H), 7.44 (t, J = 59.6 Hz, 1H), 7.20-7.05 (m, 2H), 6.94 (s, 1H), 4.56 (d, J = 7.2 Hz, 2H), 4.36-4.14 (m, 1H), 4.06-3.99 (m, 2H), 3.60 (s, 3H), 3.53-3.44 (m, 2H), 3.41-3.28 (m, 2H), 2.23-2.10 (m, 1H), 1.88-1.56 (m, 2H), 1.28-1.01 (m, 2H), 0.44 (d, J = 5.2 Hz, 2H), 0.24 (dd, J = 7.9, 3.6 Hz, 2H), 0.18 (dt, J = 4.7, 2.5 Hz, 2H). |
| 396 | 1H NMR (400 MHz, DMSO-d6) δ 8.63 (dd, J = 18.5, 7.1 Hz, 1H), 8.18 (d, J = 8.1 Hz, 1H), 8.09 (s, 1H), 7.97 (s, 2H), 7.75 (s, 1H), 7.43 (t, J = 59.6 Hz, 1H), 7.16 (q, J = 7.1 Hz, 2H), 6.95 (d, J = 1.8 Hz, 1H), 5.26-4.61 (m, 3H), 4.57 (d, J = 7.1 Hz, 2H), 3.60 (s, 3H), 3.35-3.10 (m, 1H), 2.71-2.56 (m, 1H), 2.28-2.12 (m, 1H), 2.06-1.79 (m, 3H), 1.73-1.58 (m, 1H), 1.20-1.11 (m, 2H), 1.09-0.94 (m, 1H), 0.51-0.32 (m, 2H), 0.17-0.01 (m, 2H). |
| 397 | 1H NMR (400 MHz, DMSO-d6) δ 8.62 (d, J = 7.1 Hz, 1H), 8.17 (d, J = 8.1 Hz, 1H), 7.99 (s, 2H), 7.81 (s, 1H), 7.43 (t, J = 59.6 Hz, 1H), 7.21-7.11 (m, 2H), 6.94 (s, 1H), 4.56 (d, J = 7.1 Hz, 2H), 4.06-3.65 (m, 6H), 3.60 (s, 3H), 3.47-3.27 (m, 2H), 2.24-2.13 (m, 1H), 2.13-1.94 (m, 1H), 1.87 (d, J = 10.7 Hz, 1H), 1.62 (q, J = 11.1 Hz, 2H), 1.19-1.11 (m, 2H), 1.08 (t, J = 7.2 Hz, 1H), 0.44 (d, J = 5.3 Hz, 2H), 0.23 (d, J = 7.9 Hz, 2H), 0.18 (d, J = 4.6 Hz, 2H). |
| 398 | 1H NMR (400 MHz, DMSO-d6) δ 8.63 (d, J = 7.1 Hz, 1H), 8.17 (d, J = 8.1 Hz, 1H), 7.99 (s, 3H), 7.76 (d, J = 11.8 Hz, 1H), 7.20 (s, 1H), 7.16 (d, J = 8.2 Hz, 1H), 7.10 (d, J = 7.3 Hz, 1H), 6.94 (t, 1H), 4.57 (d, J = 6.9 Hz, 2H), 4.50-4.42 (m, 1H), 3.61 (s, 3H), 2.07-1.92 (m, 2H), 1.84-1.39 (m, 5H), 1.29-1.04 (m, 4H), 0.50-0.36 (m, 4H), 0.30-0.08 (m, 4H). |
| 399 | 1H NMR (400 MHz, DMSO-d6) δ 8.17 (d, J = 8.1 Hz, 1H), 7.95 (s, 3H), 7.50 (t, J = 59.5 Hz, 1H), 7.33 (s, 1H), 6.76 (s, 1H), 6.45-6.30 (m, 1H), 4.41 (d, J = 7.1 Hz, 2H), 4.11 (s, 3H), 4.37-3.68 (m, 5H), 3.59 (s, 3H), 3.20 (q, J = 7.4 Hz, 2H), 2.08-1.91 (m, 1H), 1.84-1.69 (m, 1H), 1.59 (d, J = 8.5 Hz, 2H), 1.30 (t, J = 7.2 Hz, 3H), 1.16-1.00 (m, 1H), 0.31-0.24 (m, 2H), 0.24-0.11 (m, 2H). |
| 400 | 1H NMR (400 MHz, DMSO-d6) δ 10.48 (s, 1H), 8.17 (d, J = 8.1 Hz, 1H), 7.94 (d, J = 8.3 Hz, 1H), 7.91 (s, 3H), 7.39-7.29 (m, 1H), 7.16 (d, J = 8.1 Hz, 1H), 6.75 (d, J = 6.9 Hz, 1H), 6.57 (t, 1H), 6.40 (d, 1H), 4.41 (d, J = 7.1 Hz, 1H), 4.31 (d, J = 7.1 Hz, 1H), 4.11 (s, 3H), 4.05-4.00 (m, 1H), 3.90-3.73 (m, 2H), 3.59 (s, 3H), 3.25-3.10 (m, 2H), 1.87-1.59 (m, 3H), 1.29 (q, J = 7.3 Hz, 3H), 1.17-1.01 (m, 2H), 0.53-0.30 (m, 1H), 0.29-0.13 (m, 4H). |
| 401 | H NMR (400 MHz, DMSO-d6) δ 8.51 (d, J = 7.1 Hz, 1H), 8.16 (d, J = 8.1 Hz, 1H), 8.11-7.85 (m, 3H), 7.83 (s, 1H), 7.43 (t, J = 59.6 Hz, 1H), 7.16 (d, J = 8.1 Hz, 1H), 7.13 (dd, J = 7.1, 1.6 Hz, 1H), 6.84 (s, 1H), 4.80-4.67 (m, 1H), 4.54 (d, J = 7.1 Hz, 2H), 4.29-4.08 (m, 1H), 3.59 (s, 3H), 3.42 (s, 1H), 2.68 (s, 3H), 2.14-1.95 (m, 2H), 1.95-1.74 (m, 3H), 1.72-1.50 (m, 1H), 1.26-1.13 (m, 1H), 0.35-0.24 (m, 4H). |
| 402 | 1H NMR (400 MHz, DMSO-d6) δ 8.51 (d, J = 7.0 Hz, 1H), 8.16 (d, J = 8.1 Hz, 1H), 7.89 (s, 3H), 7.74 (s, 1H), 7.43 (t, J = 59.6 Hz, 1H), 7.16 (d, J = 8.1 Hz, 1H), 7.05 (dd, J = 7.0, 1.6 Hz, 1H), 6.83 (s, 1H), 4.62-4.48 (m, 2H), 3.59 (s, 3H), 3.25-3.09 (m, 1H), 3.09-2.91 (m, 1H), 2.68 (s, 3H), 1.91-1.69 (m, 4H), 1.65-1.51 (m, 1H), 1.23-1.15 (m, 4H), 0.34-0.23 (m, 4H). (Expect 34, see 33) |

TABLE 2-continued

| Ex | NMR |
|---|---|
| 403 | 1H NMR (400 MHz, DMSO-d6) δ 8.16 (d, J = 8.1 Hz, 1H), 8.07-7.73 (m, 3H), 7.43 (t, J = 59.6 Hz, 1H), 7.37 (s, 1H), 7.15 (d, J = 8.1 Hz, 1H), 6.75 (s, 1H), 6.41 (s, 1H), 4.46-4.33 (m, 2H), 4.14 (s, 3H), 3.59 (s, 3H), 3.40 (s, 2H), 3.19 (d, J = 6.6 Hz, 2H), 2.13-1.96 (m, 2H), 1.93-1.76 (m, 2H), 1.72-1.53 (m, 3H), 1.16-0.99 (m, 2H), 0.38-0.30 (m, 2H), 0.31-0.20 (m, 3H), 0.09--0.02 (m, 2H). (Expect 40, see 37) |
| 404 | 1H NMR (400 MHz, DMSO-d6) δ 8.17 (d, J = 8.1 Hz, 1H), 7.90 (s, 3H), 7.43 (t, J = 59.5 Hz, 1H), 7.34 (s, 1H), 7.16 (d, J = 8.1 Hz, 1H), 6.76 (s, 1H), 6.40 (d, J = 1.4 Hz, 1H), 5.72 (s, 1H), 4.41 (d, J = 7.1 Hz, 2H), 4.11 (s, 3H), 4.07-3.99 (m, 1H), 3.88-3.64 (m, 3H), 3.59 (s, 3H), 3.54-3.43 (m, 1H), 3.42-3.29 (m, 1H), 3.19 (q, J = 7.3 Hz, 2H), 1.89-1.63 (m, 2H), 1.29 (t, J = 7.3 Hz, 3H), 1.17-1.01 (m, 1H), 0.34-0.24 (m, 2H), 0.24-0.16 (m, 2H). |
| 405 | 1H NMR (400 MHz, DMSO-d6) δ 8.16 (d, J = 8.1 Hz, 1H), 7.91 (s, 3H), 7.43 (t, J = 59.6 Hz, 1H), 7.30 (d, J = 1.3 Hz, 1H), 7.15 (d, J = 8.1 Hz, 1H), 6.76 (s, 1H), 6.39 (d, J = 1.3 Hz, 1H), 4.44-4.29 (m, 2H), 4.13 (s, 3H), 3.59 (s, 3H), 3.25-3.12 (m, 3H), 3.10-2.91 (m, 1H), 1.95-1.70 (m, 3H), 1.67-1.52 (m, 1H), 1.21 (d, J = 6.9 Hz, 3H), 1.15-1.00 (m, 2H), 0.40-0.19 (m, 6H), 0.10--0.03 (m, 2H). (Expect 40, see 38) |
| 406 | 1H NMR (400 MHz, DMSO-d6) δ 8.59 (d, J = 7.1 Hz, 1H), 8.17 (d, J = 8.1 Hz, 1H), 7.88 (s, 3H), 7.74 (s, 1H), 7.43 (t, J = 59.6 Hz, 1H), 7.16 (d, J = 8.1 Hz, 1H), 7.03 (dd, J = 7.0, 1.6 Hz, 1H), 6.81 (s, 1H), 4.60-4.45 (m, 2H), 3.59 (s, 3H), 3.28-3.09 (m, 3H), 3.08-2.93 (m, 1H), 1.91-1.68 (m, 4H), 1.59 (d, J = 10.3 Hz, 1H), 1.26 (t, J = 7.4 Hz, 3H), 1.20 (d, J = 6.9 Hz, 3H), 1.18-1.10 (m, 1H), 0.31-0.19 (m, 4H). (Epxect36, see 35) |
| 409 | 1H NMR (400 MHz, DMSO-d6) δ 8.75 (dd, J = 7.0, 1.0 Hz, 1H), 8.23 (d, J = 8.1 Hz, 1H), 8.04-7.76 (m, 4H), 7.56 (t, J = 51.1 Hz, 1H), 7.44 (t, J = 59.6 Hz, 1H), 7.23-7.17 (m, 2H), 6.84 (s, 1H), 4.47 (d, J = 7.1 Hz, 2H), 3.60 (s, 3H), 3.30-2.89 (m, 2H), 1.99-1.66 (m, 3H), 1.66-1.47 (m, 1H), 1.28-1.11 (m, 4H), 0.29 (t, J = 7.5 Hz, 4H). (Expect 32, see 30) |
| 411 | 1H NMR (400 MHz, DMSO-d6) δ 8.16 (d, J = 8.1 Hz, 1H), 7.94 (s, 3H), 7.42 (t, J = 59.6 Hz, 1H), 7.25 (s, 1H), 7.15 (d, J = 8.1 Hz, 1H), 6.75 (s, 1H), 6.33 (s, 1H), 4.41 (d, J = 7.1 Hz, 2H), 4.07 (s, 3H), 3.58 (s, 3H), 3.43-3.29 (m, 1H), 2.82 (s, 3H), 1.85-1.46 (m, 5H), 1.19 (d, J = 6.9 Hz, 3H), 1.16-1.06 (m, 1H), 0.34-0.14 (m, 4H). (Expect 36, see 34) |
| 412 | 1H NMR (400 MHz, DMSO-d6) δ 8.16 (d, J = 8.1 Hz, 1H), 7.89 (s, 3H), 7.42 (t, J = 59.6 Hz, 1H), 7.25 (d, J = 1.2 Hz, 1H), 7.16 (d, J = 8.1 Hz, 1H), 6.75 (s, 1H), 6.33 (d, J = 1.3 Hz, 1H), 4.46-4.33 (m, 2H), 4.07 (s, 3H), 3.59 (s, 3H), 3.26-3.11 (m, 1H), 3.08-2.90 (m, 1H), 2.82 (s, 3H), 1.93-1.66 (m, 3H), 1.65-1.50 (m, 1H), 1.20 (d, J = 6.9 Hz, 3H), 1.17-1.04 (m, 1H), 0.34-0.14 (m, 4H). (Expect 36, See 34) |
| 413 | 1H NMR (400 MHz, DMSO-d6) δ 8.16 (d, J = 8.1 Hz, 1H), 7.89 (s, 3H), 7.42 (t, J = 59.6 Hz, 1H), 7.25 (d, J = 1.2 Hz, 1H), 7.16 (d, J = 8.1 Hz, 1H), 6.75 (s, 1H), 6.33 (d, J = 1.3 Hz, 1H), 4.46-4.33 (m, 2H), 4.07 (s, 3H), 3.59 (s, 3H), 3.26-3.11 (m, 1H), 3.08-2.90 (m, 1H), 2.82 (s, 3H), 1.93-1.66 (m, 3H), 1.65-1.50 (m, 1H), 1.20 (d, J = 6.9 Hz, 3H), 1.17-1.04 (m, 1H), 0.34-0.14 (m, 4H). (Missing 3) |
| 414 | 1H NMR (400 MHz, DMSO-d6) δ 8.53 (brs, 2H), 8.19 (d, J = 8.1 Hz, 1H), 7.89 (s, 1H), 7.54 (s, 1H), 7.46 (t, J = 59.6 Hz, 1H), 7.19 (d, J = 8.1 Hz, 1H), 6.80 (s, 1H), 6.49 (s, 1H), 5.72 (s, 1H), 4.81-4.51 (m, 1H), 4.46-4.32 (m, 2H), 4.26-4.03 (m, 2H), 4.12 (s, 3H), 3.62 (s, 3H), 3.50 (brs, 1H), 3.13-3.05 (m, 1H), 2.87 (s, 3H), 2.26-1.53 (m, 4H), 1.26-1.09 (m, 1H), 0.35-0.20 (m, 4H). |
| 415 | "1H NMR (400 MHz, DMSO-d6) δ 8.78-8.48 (m, 2H), 8.18 (d, J = 8.1 Hz, 1H), 7.57 (s, 1H), 7.45 (t, J = 59.6 Hz, 1H), 7.17 (d, J = 8.0 Hz, 1H), 7.14 (t, J = 51.1 Hz, 6H-presumed ammonium peak), 6.81-6.74 (m, 1H), 6.42-6.32 (m, 1H), 4.53-4.42 (m, 2H), 4.23-4.17 (m, 1H), 4.12-4.06 (m, 3H), 3.96-3.70 (m, 1H), 3.61 (s, 3H), 3.70-3.45 (m, 2H), 3.41-3.13 (m, 2H), 3.08-2.91 (m, 1H), 2.89-2.83 (m, 3H), 2.18-1.67 (m, 5H), 1.28-1.07 (m, 1H), 0.35-0.22 (m, 4H). Expect 37 H for bis-TFA adduct; see 36 H." |
| 416 | ¹H NMR (400 MHz, DMSO-d₆) δ 8.53 (brs, 2H), 8.19 (dd, J = 8.1 Hz, 1H), 8.09 (s, 1H), 7.46 (t, J = 59.6 Hz, 1H), 7.36 (s, 1H), 7.19 (d, J = 8.1 Hz, 1H), 6.78 (d, J = 3.5 Hz, 1H), 6.38 (s, 1H), 5.72 (brs, 1H), 4.81-4.51 (m, 1H), 4.46-4.32 (m, 2H), 4.26-4.03 (m, 2H), 4.11 (s, 3H), 3.62 (s, 3H), 3.50 (brs, 1H), 3.13-3.05 (m, 1H), 2.86 (s, 3H), 2.26-1.53 (m, 4H), 1.26-1.09 (m, 1H), 0.35-0.20 (m, 4H). |
| 417 | "1H NMR (400 MHz, DMSO-d6) δ 9.14-9.09 (m, 1H), 8.55 (br. s, 1H), 8.19 (d, J = 8.1 Hz, 1H), 7.45 (t, J = 59.6 Hz, 1H), 7.35 (s, 1H), 7.18 (d, J = 8.1 Hz, 1H), 6.79 (s, 1H), 6.40 (s, 1H), 4.43 (d, J = 7.3 Hz, 2H), 4.34-4.21 (m, 1H), 4.10 (s, 3H), 3.81-3.64 (m, 3H), 3.61 (s, 3H), 3.43-3.11 (m, 3H), 2.84 (s, 3H), 2.19-2.03 (m, 1H), 1.99-1.70 (m, 2H), 1.48 (dd, J = 20.5, 9.6 Hz, 1H), 1.29-0.38 (m, 2H), 0.33-0.20 (m, 4H). Expect 37 H for bis-TFA adduct; see 36 H." |
| 418 | "1H NMR (400 MHz, DMSO-d6) δ 9.10 (br. s, 1H), 8.54 (br. s, 1H), 8.18 (d, J = 8.1 Hz, 1H), 7.45 (t, J = 59.6 Hz, 1H), 7.35 (s, 1H), 7.18 (d, J = 8.1 Hz, 1H), 6.78 (s, 1H), 6.39 (s, 1H), 4.43 (d, J = 7.2 Hz, 2H), 4.30-4.18 (m, 1H), 4.09 (s, 3H), 3.99-3.79 (m, 1H), 3.74-3.46 (m, 2H), 3.61 (s, 3H), 3.44-3.04 (m, 3H), 2.85 (s, 3H), 2.14-2.06 (m, 1H), 1.89-1.65 (m, 1H), 1.56-1.09 (m, 3H), 0.96-0.36 (m, 1H), 0.35-0.20 (m, 4H). Expect 37 H for bis-TFA adduct; see 36 H." |
| 419 | 1H NMR (400 MHz, DMSO-d6) δ 8.17 (d, J = 8.9 Hz, 1H), 7.44 (t, J = 59.6 Hz, 1H), 7.28 (s, 1H), 7.17 (d, J = 8.5 Hz, 1H), 6.76 (s, 1H), 6.35 (s, 1H), 4.45 (d, J = 7.1 Hz, 2H), 4.36-4.00 (m, 2H), 4.08 (s, 3H), 3.81-3.53 (m, 2H), 3.61 (s, 3H), 3.53-3.26 (m, 2H), 3.15 (t, J = 11.6 Hz, 1H), 2.85 (s, 3H), 2.30-1.76 (m, 1H), 1.77-1.21 (m, 3H), 1.20-0.81 (m, 2H), 0.33-0.21 (m, 4H). |
| 420 | 1H NMR (400 MHz, DMSO-d6) δ 8.17 (d, J = 8.5 Hz, 1H), 7.44 (t, J = 59.6 Hz, 1H), 7.28-7.19 (m, 1H), 7.17 (d, J = 8.1 Hz, 1H), 6.76 (s, 1H), 6.35 (s, 1H), 4.45 (d, J = 7.1 Hz, 2H), 4.08 (s, 3H), 4.29-3.99 (m, 3H), 3.61 (s, 3H), 3.74-3.43 (m, 3H), 3.19-3.08 (m, 1H), 2.84 (s, 3H), 2.31-2.14 (m, 1H), 1.97-1.77 (m, 1H), 1.75-1.35 (m, 2H), 1.26-0.76 (m, 2H), 0.32-0.21 (m, 4H). |
| 421 | 1H NMR (400 MHz, Methanol-d4) δ 8.20 (d, J = 8.2 Hz, 1H), 7.28 (t, J = 60.0 Hz, 1H), 7.26 (d, J = 8.2 Hz, 1H), 7.08 (s, 1H), 6.92 (s, 1H), 6.35 (s, 1H), 4.44 (s, 1H), 4.25 (d, J = 7.1 Hz, 2H), 3.77-3.57 (m, 1H), 3.54 (s, 3H), 3.5-3.2 (m, 3H), 3.03 (s, 3H), 2.94 (s, 3H), 2.20 (d, J = |

TABLE 2-continued

| Ex | NMR |
|---|---|
| | 13.3 Hz, 1H), 1.74 (s, 3H), 1.03 (td, J = 7.7, 4.0 Hz, 1H), 0.36 (dt, J = 10.8, 3.0 Hz, 2H), 0.23-0.12 (m, 2H). |
| 422 | 1H NMR (400 MHz, Methanol-d4) δ 8.21 (d, J = 8.2 Hz, 1H), 7.61 (s, 1H), 7.28 (t, J = 60.0 Hz, 1H), 7.27 (d, J = 8.2 Hz, 1H), 7.05 (s, 1H), 6.96 (s, 1H), 4.29 (d, J = 7.1 Hz, 2H), 3.77-3.56 (m, 2H), 3.54 (s, 3H), 3.50-3.20 (m, 4H), 2.93 (s, 6H), 2.87 (s, 3H), 2.18 (m, 1H), 1.80 (m, 3H), 1.03 (ddd, J = 12.5, 7.7, 4.8 Hz, 1H), 0.41-0.31 (m, 2H), 0.18 (dt, J = 6.2, 4.6 Hz, 2H). |
| 423 | 1H NMR (400 MHz, Methanol-d4) δ 8.14 (d, J = 8.1 Hz, 1H), 7.95-7.89 (m, 1H), 7.62 (d, J = 53.2 Hz, 1H), 7.53 (d, J = 1.6 Hz, 1H), 7.26 (d, J = 60.1 Hz, 1H), 7.21 (d, J = 8.1 Hz, 1H), 6.79 (s, 1H), 4.40 (d, J = 7.1 Hz, 2H), 4.30 (br, 1H), 3.94-3.60 (br, 1H), 3.53 (s, 3H), 3.46 (br, 3H), 2.84 (s, 3H), 2.19 (d, J = 12.7 Hz, 1H), 1.85 (s, 1H), 1.81-1.63 (m, 2H), 1.03 (td, J = 7.7, 4.2 Hz, 1H), 0.35-0.24 (m, 2H), 0.14 (dt, J = 6.2, 4.6 Hz, 2H). |
| 424 | 1H NMR (400 MHz, Methanol-d4) δ 8.14 (d, J = 8.1 Hz, 1H), 7.93-7.85 (m, 1H), 7.79 (dd, J = 4.4, 1.6 Hz, 1H), 7.26 (t, J = 60.1 Hz, 1H), 7.20 (d, J = 8.1 Hz, 1H), 6.81 (s, 1H), 4.54-4.39 (m, 2H), 4.40-3.58 (m, 4H), 3.53 (s, 3H), 3.47 (dt, J = 4.6, 2.3 Hz, 1H), 3.07 (s, 3H), 2.85 (s, 3H), 2.23-2.12 (m, 1H), 1.92-1.66 (m, 3H), 1.63 (m, 5H), 1.17-0.97 (m, 1H), 0.37-0.25 (m, 2H), 0.18 (dd, J = 8.5, 5.0 Hz, 2H). |
| 425 | 1H NMR (400 MHz, Methanol-d4) δ 8.14 (d, J = 8.1 Hz, 1H), 7.93-7.85 (m, 1H), 7.79 (dd, J = 4.4, 1.6 Hz, 1H), 7.26 (t, J = 60.1 Hz, 1H), 7.20 (d, J = 8.1 Hz, 1H), 6.81 (s, 1H), 4.54-4.39 (m, 2H), 4.40-3.58 (m, 4H), 3.53 (s, 3H), 3.47 (dt, J = 4.6, 2.3 Hz, 1H), 3.07 (s, 3H), 2.85 (s, 3H), 2.23-2.12 (m, 1H), 1.92-1.66 (m, 3H), 1.63 (m, 5H), 1.17-0.97 (m, 1H), 0.37-0.25 (m, 2H), 0.18 (dd, J = 8.5, 5.0 Hz, 2H). |
| 426 | 1H NMR (400 MHz, Methanol-d4) δ 8.20 (d, J = 8.2 Hz, 1H), 7.73-7.68 (m, 1H), 7.45 (s, 0H), 7.32-7.22 (m, 2H), 7.15 (s, 0H), 7.07 (s, 1H), 6.89 (s, 1H), 4.40 (s, 1H), 4.34 (d, J = 7.1 Hz, 2H), 4.12 (q, J = 7.2 Hz, 0H), 3.56 (s, 3H), 3.43 (s, 3H), 3.37 (s, 0H), 3.13 (s, 3H), 2.95 (s, 3H), 2.72 (s, 0H), 2.23 (d, J = 7.1 Hz, 0H), 2.20 (s, 1H), 2.04 (d, J = 8.7 Hz, 0H), 1.88 (s, 1H), 1.75 (d, J = 8.4 Hz, 3H), 1.34-1.22 (m, 0H), 1.06 (td, J = 8.1, 7.7, 3.8 Hz, 1H), 0.41-0.28 (m, 2H), 0.20 (dt, J = 6.1, 4.5 Hz, 2H). |
| 427 | 1H NMR (400 MHz, Methanol-d4) δ 8.19 (d, J = 8.1 Hz, 1H), 7.69 (s, 1H), 7.45 (s, 0H), 7.32-7.22 (m, 2H), 7.15 (s, 0H), 7.05 (s, 1H), 6.86 (s, 1H), 4.35 (d, J = 7.0 Hz, 2H), 3.74 (s, 1H), 3.55 (d, J = 12.5 Hz, 5H), 3.45 (s, 3H), 2.95 (s, 3H), 2.21 (s, 1H), 1.88 (s, 1H), 1.76 (s, 3H), 1.49 (t, J = 7.3 Hz, 3H), 1.37 (s, 2H), 1.31 (s, 1H), 1.05 (ddd, J = 12.5, 7.9, 5.0 Hz, 1H), 0.93 (dd, J = 13.4, 6.5 Hz, 1H), 0.40-0.30 (m, 2H), 0.22-0.09 (m, 2H). |
| 428 | 1H NMR (400 MHz, Methanol-d4) δ 8.21 (d, J = 8.2 Hz, 1H), 7.74-7.68 (m, 1H), 7.45 (s, 0H), 7.33-7.21 (m, 2H), 7.15 (s, 0H), 7.08 (t, J = 1.4 Hz, 1H), 6.91 (s, 1H), 4.41 (s, 1H), 4.34 (d, J = 7.1 Hz, 2H), 3.57 (s, 3H), 3.44 (s, 2H), 3.09 (s, 3H), 2.83 (q, J = 7.6, 6.7 Hz, 1H), 2.21 (d, J = 11.4 Hz, 1H), 1.86 (s, 1H), 1.75 (s, 3H), 1.34-1.17 (m, 4H), 1.08 (ddd, J = 12.5, 7.8, 4.9 Hz, 0H), 0.93 (dd, J = 13.0, 6.1 Hz, 0H), 0.42-0.31 (m, 2H), 0.21 (dt, J = 6.3, 4.6 Hz, 2H). |
| 429 | 1H NMR (400 MHz, DMSO-d6) δ 8.17 (d, J = 8.1 Hz, 1H), 8.08 (s, 3H), 7.47 (s, 1H), 7.43 (t, J = 35 Hz, 1H), 7.16 (d, J = 8.1 Hz, 1H), 6.82 (s, 1H), 6.39 (s, 1H), 4.66-4.44 (m, 4H), 4.40 (d, J = 7.1 Hz, 2H), 4.12 (d, J = 3.2 Hz, 3H), 3.59 (s, 3H), 3.16 (d, J = 6.9 Hz, 2H), 2.02-1.88 (m, 1H), 1.89-1.75 (m, 3H), 1.68-1.46 (m, 1H), 1.34 (dd, J = 12.8, 4.4 Hz, 1H), 1.18-1.01 (m, 1H), 0.78 (dd, J = 6.7, 2.4 Hz, 6H), 0.35-0.15 (m, 4H). |
| 430 | 1H NMR (400 MHz, DMSO-d6) δ 8.17 (d, J = 8.1 Hz, 1H), 7.93 (d, J = 7.9 Hz, 1H), 7.90 (s, 3H), 7.43 (t, J = 7.1 Hz, 1H), 7.33 (s, 1H), 7.15 (d, J = 8.1 Hz, 1H), 6.80 (s, 1H), 6.36 (s, 1H), 4.39 (d, J = 7.2 Hz, 2H), 4.10 (s, 3H), 3.59 (s, 3H), 3.57-3.40 (m, 3H), 3.32-3.20 (m, 1H), 3.15 (d, J = 7.0 Hz, 2H), 2.09-1.86 (m, 2H), 1.84-1.67 (m, 1H), 1.67-1.45 (m, 2H), 0.79 (dd, J = 6.6, 2.8 Hz, 6H), 0.50-0.30 (m, 1H), 0.28 (d, J = 6.5 Hz, 4H). |
| 433 | 1H NMR (400 MHz, DMSO-d6) δ 8.69 (dd, J = 7.2, 1.0 Hz, 1H), 8.18 (d, J = 8.1 Hz, 1H), 8.03 (s, 3H), 7.78 (t, J = 1.2 Hz, 1H), 7.43 (t, J = 59.6 Hz, 1H), 7.17 (d, J = 8.1 Hz, 1H), 7.03 (dd, J = 7.2, 1.7 Hz, 1H), 6.74 (s, 1H), 4.35 (d, J = 7.1 Hz, 2H), 3.76-3.65 (m, 1H), 3.59 (s, 3H), 3.38-3.08 (m, 4H), 2.11-1.90 (m, 1H), 1.86-1.69 (m, 2H), 1.67-1.47 (m, 2H), 1.41 (s, 3H), 1.39 (s, 3H), 1.22 (s, 0H), 1.19-0.98 (m, 1H), 0.52-0.34 (m, 0H), 0.27 (dt, J = 7.9, 2.5 Hz, 2H), 0.22-0.09 (m, 2H). |
| 434 | 1H NMR (400 MHz, DMSO-d6) δ 8.68 (d, J = 7.1 Hz, 1H), 8.18 (d, J = 8.1 Hz, 1H), 7.99 (s, 3H), 7.82 (s, 1H), 7.43 (t, J = 59.6 Hz, 1H), 7.17 (d, J = 8.1 Hz, 1H), 7.06 (dd, J = 7.2, 1.7 Hz, 1H), 6.74 (s, 1H), 4.36 (d, J = 7.1 Hz, 2H), 3.83-3.60 (m, 8H), 2.16-1.92 (m, 2H), 1.92-1.72 (m, 2H), 1.71-1.47 (m, 3H), 1.40 (d, J = 7.2 Hz, 6H), 1.15-0.98 (m, 1H), 0.33-0.22 (m, 2H), 0.22-0.08 (m, 2H). |
| 436 | 1H NMR (400 MHz, Methanol-d4) δ 8.74 (d, J = 7.0 Hz, 1H), 8.16 (d, J = 8.1 Hz, 1H), 7.94 (s, 1H), 7.36 (dd, J = 7.1, 1.5 Hz, 1H), 7.28-7.19 (m, 2H), 6.89 (s, 1H), 4.40 (d, J = 7.1 Hz, 2H), 3.71-3.56 (m, 0H), 3.53 (s, 3H), 3.14 (d, J = 6.6 Hz, 2H), 2.33-1.64 (m, 9H), 1.46-0.79 (m, 2H), 0.61-0.44 (m, 2H), 0.41-0.27 (m, 2H), 0.26-0.12 (m, 4H). |
| 438 | 1H NMR (400 MHz, Methanol-d4) δ 8.71 (dd, J = 7.2, 1.0 Hz, 1H), 8.15 (d, J = 8.1 Hz, 1H), 7.85 (t, J = 1.2 Hz, 1H), 7.30-7.18 (m, 3H), 6.87 (s, 1H), 4.50-4.35 (m, 2H), 3.53 (s, 3H), 3.42 (s, 2H), 3.14 (d, J = 6.5 Hz, 2H), 2.31-1.58 (m, 4H), 1.20-0.94 (m, 2H), 0.59-0.43 (m, 2H), 0.39-0.28 (m, 2H), 0.27-0.15 (m, 4H). |
| 448 | 1H NMR (400 MHz, DMSO-d6) δ 8.20 (s, 3H), 7.70 (d, J = 8.4 Hz, 1H), 7.48 (s, 1H), 7.02 (d, J = 8.8 Hz, 1H), 6.51 (s, 1H), 6.47 (d, J = 8.6 Hz, 1H), 6.47 (s, 1H), 5.13-5.00 (m, 1H), 4.63-4.35 (m, 2H), 4.32-4.14 (m, 2H), 4.13 (s, 3H), 3.75 (s, 1H), 2.78 (s, 3H), 2.33 (s, 1H), 1.93-1.77 (m, 3H), 1.70-1.60 (m, 1H), 1.42-1.30 (m, 1H), 1.35 (d, J = 6.8 Hz, 3H), 1.05 (p, J = 6.4 Hz, 1H), 0.32-0.11 (m, 4H). |
| 449 | 1H NMR (400 MHz, DMSO-d6) δ 8.27 (s, 3H), 7.70 (d, J = 8.4 Hz, 1H), 7.51 (s, 1H), 7.04 (d, J = 8.7 Hz, 1H), 6.58 (s, 1H), 6.51-6.44 (m, 2H), 5.12-5.01 (m, 1H), 4.93-4.28 (m, 2H, buried under water peak), 4.25-4.09 (m, 2H), 4.13 (s, 3H), 3.74 (s, 1H), 2.76 (s, 3H), 2.31 (s, 1H), 1.94-1.76 (m, 3H), 1.70-1.59 (m, 1H), 1.42-1.31 (m, 1H), 1.34 (d, J = 7.1 Hz, 3H), 1.08-0.98 (m, 1H), 0.32-0.09 (m, 4H). |
| 456 | 1H NMR (400 MHz, DMSO-d6) δ 8.11 (s, 3H), 8.00 (d, J = 8.2 Hz, 1H), 7.46 (s, 1H), 7.10 (d, J = 8.2 Hz, 1H), 6.66 (s, 1H), 6.38 (s, 1H), 4.57-4.41 (m, 5H), 4.32 (dd, J = 14.2, 7.5 Hz, |

TABLE 2-continued

| Ex | NMR |
|---|---|
| | 1H), 4.11 (s, 3H), 2.85 (s, 3H), 2.48-2.28 (m, 2H), 2.14-1.57 (m, 10H), 1.35 (dd, J = 12.7, 4.4 Hz, 1H), 1.05 (d, J = 6.4 Hz, 3H), 0.31-0.24 (m, 2H), 0.23-0.16 (m, 2H). |
| 464 | $^1$H NMR (400 MHz, DMSO-d$_6$) δ 8.13 (brs, 3H), 8.01 (d, J = 8.5 Hz, 1H), 7.48 (s, 1H), 7.45 (d, J = 8.5 Hz, 1H), 6.65 (s, 1H), 6.40 (d, J = 1.3 Hz, 1H), 4.44-4.34 (m, 4H), 4.11 (s, 3H), 3.98 (t, J = 6.2 Hz, 2H), 2.84 (s, 3H), 2.42-2.27 (m, 1H), 2.25-2.10 (m, 2H), 1.93-1.75 (m, 4H), 1.72-1.58 (m, 1H), 1.36 (dd, J = 12.9, 4.4 Hz, 1H), 1.21-1.06 (m, 1H), 0.35-0.25 (m, 2H), 0.25-0.14 (m, 2H). |
| 465 | $^1$H NMR (400 MHz, DMSO-d$_6$) δ 8.23 (brs, 3H), 8.04 (d, J = 8.4 Hz, 1H), 7.52 (s, 1H), 7.35 (d, J = 8.4 Hz, 1H), 6.72 (s, 1H), 6.46 (s, 1H), 4.42 (d, J = 7.0 Hz, 2H), 4.15 (s, 3H), 3.75 (s, 3H), 3.43 (s, 3H), 2.86 (s, 3H), 2.47-2.27 (m, 1H), 2.01-1.56 (m, 5H), 1.49-1.32 (m, 1H), 1.26-1.04 (m, 2H), 0.35-0.25 (m, 1H), 0.47-0.12 (m, 4H). |
| 466 | $^1$H NMR (400 MHz, DMSO-d$_6$) δ 8.13 (brs, 3H), 8.01 (d, J = 8.4 Hz, 1H), 7.47 (s, 1H), 7.34 (d, J = 8.4 Hz, 1H), 6.65 (s, 1H), 6.40 (s, 1H), 4.39 (d, J = 7.0 Hz, 2H), 4.17 (q, J = 7.1 Hz, 2H), 4.12 (s, 3H), 3.40 (s, 3H), 2.84 (s, 3H), 2.43-2.24 (m, 1H), 1.96-1.74 (m, 4H), 1.72-1.59 (m, 1H), 1.36 (dd, J = 12.9, 4.4 Hz, 1H), 1.23 (t, J = 7.1 Hz, 3H), 1.20-1.05 (m, 1H), 0.35-0.25 (m, 2H), 0.26-0.18 (m, 2H). |
| 470 | $^1$H NMR (400 MHz, DMSO-d$_6$) δ 8.14 (brs, 3H), 8.01 (d, J = 8.3 Hz, 1H), 7.47 (s, 1H), 7.25 (d, J = 8.3 Hz, 1H), 6.66 (s, 1H), 6.41 (d, J = 1.4 Hz, 1H), 4.39 (d, J = 7.0 Hz, 2H), 4.12 (s, 3H), 3.91 (q, J = 7.0 Hz, 2H), 3.68 (s, 3H), 2.84 (s, 3H), 2.37-2.19 (m, 2H), 1.92-1.74 (m 4H), 1.71-1.57 (m, 2H), 1.36 (dd, J = 12.9, 4.4 Hz, 1H), 1.20 (t, J = 7.0 Hz, 3H), 1.21-1.00 (m, 1H), 0.34-0.25 (m, 2H), 0.25-0.18 (m, 2H). |
| 475 | 1H NMR (400 MHz, Methanol-d4) δ 8.13 (d, J = 8.3 Hz, 1H), 7.63 (d, J = 1.3 Hz, 1H), 7.27 (d, J = 8.3 Hz, 1H), 6.94-6.89 (m, 2H), 4.27 (d, J = 22.5 Hz, 5H), 4.02 (q, J = 7.1 Hz, 2H), 3.89 (s, 1H), 3.37 (s, 0H), 3.19 (s, 3H), 2.85 (s, 3H), 2.60-2.48 (m, 1H), 2.07 (s, 2H), 2.05-1.93 (m, 1H), 1.80 (t, J = 8.1 Hz, 1H), 1.52 (dd, J = 13.2, 4.5 Hz, 1H), 1.37 (s, 0H), 1.22 (t, J = 7.1 Hz, 3H), 1.06 (dqd, J = 12.2, 7.5, 4.8 Hz, 1H), 0.44-0.33 (m, 2H), 0.20 (dt, J = 6.2, 4.5 Hz, 2H). |
| 476 | 1H NMR (400 MHz, Methanol-d4) δ 8.11 (d, J = 8.4 Hz, 1H), 7.64 (d, J = 1.3 Hz, 1H), 7.30 (d, J = 8.4 Hz, 1H), 6.97-6.88 (m, 2H), 4.30 (s, 3H), 4.23 (d, J = 7.1 Hz, 2H), 3.90 (s, 1H), 3.48 (s, 3H), 3.17 (s, 3H), 2.84 (s, 3H), 2.55 (d, J = 11.6 Hz, 1H), 2.01 (dd, J = 28.8, 12.2 Hz, 3H), 1.80 (t, J = 7.5 Hz, 1H), 1.52 (dd, J = 13.2, 4.5 Hz, 1H), 1.07 (dqd, J = 12.2, 7.5, 4.7 Hz, 1H), 0.44-0.32 (m, 2H), 0.22 (dt, J = 6.3, 4.5 Hz, 2H). |
| 477 | 1H NMR (400 MHz, Methanol-d4) δ 8.11 (d, J = 8.1 Hz, 1H), 7.48 (d, J = 1.3 Hz, 1H), 7.13 (d, J = 8.1 Hz, 1H), 6.79 (s, 1H), 6.60 (d, J = 1.4 Hz, 1H), 4.72-4.60 (m, 1H), 4.36 (d, J = 7.0 Hz, 2H), 4.22 (s, 3H), 3.92-3.84 (m, 1H), 3.20 (s, 3H), 2.87 (s, 3H), 2.53 (t, J = 12.1 Hz, 1H), 2.33-2.23 (m, 2H), 2.28-2.14 (m, 1H), 2.17-2.03 (m, 4H), 2.02-1.90 (m, 1H), 1.78 (t, J = 8.8 Hz, 1H), 1.77-1.63 (m, 1H), 1.61 (d, J = 10.0 Hz, 1H), 1.49 (dd, J = 13.2, 4.4 Hz, 1H), 1.39 (t, J = 7.1 Hz, 0H), 1.05 (ddd, J = 12.4, 7.6, 4.9 Hz, 0H), 0.40-0.31 (m, 2H), 0.14 (dt, J = 5.3, 4.2 Hz, 3H). |
| 480 | 1H NMR (400 MHz, DMSO-d6) δ 8.04 (d, J = 8.3 Hz, 1H), 8.01-7.73 (m, 3H), 7.24 (s, 1H), 7.15 (d, J = 8.3 Hz, 1H), 6.65 (s, 1H), 6.35 (s, 1H), 4.35 (d, J = 7.0 Hz, 2H), 4.07 (s, 3H), 3.43-3.28 (m, 4H), 3.16 (s, 3H), 2.80 (s, 3H), 1.86-1.48 (m, 4H), 1.19 (d, J = 6.9 Hz, 3H), 1.17-1.09 (m, 1H), 0.36-0.15 (m, 4H). (missing 3) |
| 481 | 1H NMR (400 MHz, DMSO-d6) δ 8.04 (d, J = 8.3 Hz, 1H), 7.90 (s, 3H), 7.24 (s, 1H), 7.15 (d, J = 8.3 Hz, 1H), 6.65 (s, 1H), 6.34 (s, 1H), 4.35 (d, J = 7.1 Hz, 2H), 4.07 (s, 3H), 3.33 (s, 3H), 3.16 (s, 3H), 2.99 (s, 1H), 2.80 (s, 3H), 1.91-1.68 (m, 3H), 1.58 (s, 1H), 1.20 (d, J = 6.9 Hz, 3H), 1.18-1.08 (m, 1H), 0.37-0.14 (m, 4H). (Missing 3) |
| 482 | 1H NMR (400 MHz, DMSO-d6) δ 8.03 (d, J = 8.3 Hz, 1H), 7.93 (s, 3H), 7.28 (s, 1H), 7.15 (d, J = 8.3 Hz, 1H), 6.65 (s, 1H), 6.34 (s, 1H), 4.36 (d, J = 7.0 Hz, 2H), 4.06 (s, 3H), 3.33 (s, 3H), 3.31-3.19 (m, 4H), 3.16 (s, 3H), 2.81 (s, 3H), 2.07-1.93 (m, 1H), 1.82-1.68 (m, 1H), 1.68-1.50 (m, 2H), 1.22-1.10 (m, 1H), 0.34-0.19 (m, 4H). (Missing 1) |
| 483 | 1H NMR (400 MHz, DMSO-d6) δ 8.04 (d, J = 8.2 Hz, 1H), 8.01-7.79 (m, 3H), 7.23 (s, 1H), 7.11 (d, J = 8.2 Hz, 1H), 6.66 (s, 1H), 6.33 (s, 1H), 4.37 (d, J = 7.0 Hz, 2H), 4.07 (s, 3H), 3.84 (q, J = 7.1 Hz, 2H), 3.42-3.29 (m, 1H), 3.17 (s, 3H), 2.81 (s, 3H), 1.84-1.64 (m, 3H), 1.64-1.49 (m, 2H), 1.19 (d, J = 6.9 Hz, 3H), 1.17-1.11 (m, 1H), 1.08 (t, J = 7.1 Hz, 3H), 0.33-0.25 (m, 2H), 0.25-0.17 (m, 2H). (Missing 2) |
| 484 | 1H NMR (400 MHz, DMSO-d6) δ 8.04 (d, J = 8.2 Hz, 1H), 8.02-7.81 (m, 3H), 7.28 (s, 1H), 7.11 (d, J = 8.2 Hz, 1H), 6.66 (s, 1H), 6.33 (s, 1H), 4.38 (d, J = 7.1 Hz, 2H), 4.06 (s, 3H), 3.84 (q, J = 7.1 Hz, 2H), 3.25 (s, 2H), 3.17 (s, 3H), 2.82 (s, 3H), 2.07-1.94 (m, 1H), 1.81-1.68 (m, 1H), 1.65-1.52 (m, 2H), 1.19-1.11 (m, 1H), 1.08 (t, J = 7.1 Hz, 3H), 0.32-0.26 (m, 2H), 0.25-0.19 (m, 2H). (Missing 3) |
| 497 | 1H NMR (400 MHz, DMSO-d6) δ 8.17 (brs, 3H), 7.95 (d, J = 7.9 Hz, 1H), 7.48 (s, 1H), 7.08 (d, J = 8.0 Hz, 1H), 6.62 (s, 1H), 6.46 (s, 1H), 4.54 (t, J = 6.3 Hz, 2H), 2.47 (brs, 1H), 4.13 (s, 3H), 3.77 (s, 1H), 3.62 (t, J = 6.3 Hz, 2H), 2.86 (q, J = 7.5 Hz, 2H), 2.81 (s, 3H), 2.38-2.24 (m, 1H), 1.92-1.74 (m, 4H), 1.70-1.59 (m, 1H), 1.37 (dd, J = 12.8, 4.4 Hz, 1H), 1.31 (t, J = 7.6 Hz, 3H). |
| 498 | $^1$H NMR (400 MHz, DMSO-d$_6$) δ 8.15 (brs, 3H), 7.96 (d, J = 8.0 Hz, 1H), 7.47 (s, 1H), 7.10 (d, J = 8.0 Hz, 1H), 6.68 (s, 1H), 6.39 (s, 1H), 4.99-4.87 (m, 1H), 4.48 (brs, 2H), 4.12 (s, 3H), 3.77 (brs, 1H), 3.64 (t, J = 7.5 Hz, 2H), 3.03 (s, 3H), 2.90 (q, J = 7.6 Hz, 1H), 2.87 (s, 3H), 2.41-2.24 (m, 1H), 1.95-1.77 (m, 3H), 1.74-1.63 (m, 1H), 1.37 (dd, J = 12.8, 4.4 Hz, 1H), 1.33 (t, J = 7.6 Hz, 3H). |
| 499 | $^1$H NMR (400 MHz, DMSO-d$_6$) δ 8.14 (brs, 3H), 7.94 (d, J = 7.9 Hz, 1H), 7.44 (s, 1H), 7.07 (d, J = 8.0 Hz, 1H), 6.62 (s, 1H), 6.43 (s, 1H), 4.54 (t, J = 6.9 Hz, 2H), 4.46 (brs, 1H), 4.12 (s, 3H), 3.76 (s, 1H), 3.23 (t, J = 6.4 Hz, 2H), 2.86 (q, J = 7.9 Hz, 3H), 2.82 (s, 3H), 2. 40-2.25 (m, 1H), 1.95-1.72 (m, 5H), 1.73-1.58 (m, 1H), 1.37 (dd, J = 12.9, 4.4 Hz, 1H), 1.31 (t, J = 7.6 Hz, 3H). |
| 500 | 1H NMR (400 MHz, DMSO-d6) δ 8.12 (brs, 3H), 7.96 (d, J = 7.9 Hz, 1H), 7.48 (s, 1H), 7.10 (d, J = 8.0 Hz, 1H), 6.69 (s, 1H), 6.38 (s, 1H), 5.26 (t, J = 13.5 Hz, 2H), 4.48 (brs, 2H), 4.11 (s, 3H), 4.07 (brs, 2H), 2.88 (q, J = 7.5 Hz, 1H), 2.85 (s, 3H), 1.93-1.78 (m, 3H), 1.72-1.56 (m, 1H), 1.37-1.28 (m, 7H). |

TABLE 2-continued

| Ex | NMR |
|---|---|
| 501 | ¹H NMR (400 MHz, DMSO-d$_6$) δ 8.17 (brs, 3H), 7.94 (d, J = 8.0 Hz, 1H), 7.45 (s, 1H), 7.07 (d, J = 8.0 Hz, 1H), 6.65 (s, 1H), 6.41 (d, J = 1.3 Hz, 1H), 4.85 (dt, J = 14.0, 4.2 Hz, 1H), 4.67-4.51 (m, 1H), 4.47 (brs, 2H), 4.12 (s, 3H), 3.76 (brs, 1H), 2.89 (q, J = 7.5 Hz, 1H), 2.84 (s, 3H), 2.43-2.25 (m, 1H), 1.94-1.75 (m, 4H), 1.72-1.55 (m, 2H), 1.37 (dd, J = 12.8, 4.4 Hz, 1H), 1.31 (t, J = 7.6 Hz, 3H), 0.93-0.76 (m, 2H). |
| 502 | ¹H NMR (400 MHz, DMSO-d$_6$) δ 8.16 (brs, 3H), 7.97 (d, J = 8.0 Hz, 1H), 7.48 (s, 1H), 7.11 (d, J = 8.0 Hz, 1H), 6.72 (s, 1H), 6.40 (s, 1H), 6.39 (tt, J = 56.0, 4.2 Hz, 1H), 5.05 (td, J = 14.7, 4.2 Hz, 2H), 4.49 (brs, 2H), 4.12 (s, 3H), 3.77 (brs, 1H), 2.89 (q, J = 7.5 Hz, 1H), 2.86 (s, 3H), 2.42-2.25 (m, 1H), 1.92-1.76 (m, 3H), 1.70-1.61 (m, 1H), 1.37 (dd, J = 12.9, 4.4 Hz, 1H), 1.31 (t, J = 7.6 Hz, 3H). |
| 503 | 1H NMR (400 MHz, DMSO-d6) δ 8.13 (brs, 3H), 7.92 (d, J = 7.9 Hz, 1H), 7.47 (s, 1H), 7.05 (d, J = 8.0 Hz, 1H), 6.59 (s, 1H), 6.42 (s, 1H), 4.68-4.33 (m, 2H), 4.12 (s, 3H), 3.76 (brs, 2H), 2.88 (q, J = 7.5 Hz, 2H), 2.83 (s, 3H), 2.38-2.23 (m, 1H), 1.94-1.80 (m, 4H), 1.71-1.61 (m, 1H), 1.37 (dd, J = 12.8, 4.3 Hz, 1H), 1.3l(t, J = 7.5 Hz, 3H), 0.77 (d, J = 5.9 Hz, 3H), 0.60-0.49 (m, 1H), 0.33 (dt, J = 8.7, 4.5 Hz, 1H), 0.02 (dt, J = 8.8, 4.6 Hz, 1H). |
| 504 | ¹H NMR (400 MHz, DMSO-d$_6$) δ 8.11 (brs, 3H), 7.99 (d, J = 8.0 Hz, 1H), 7.48 (s, 1H), 7.14 (d, J = 7.9 Hz, 1H), 6.77 (s, 1H), 6.38 (d, J = 1.3 Hz, 1H), 5.69 (q, J = 9.1 Hz, 2H), 4.11 (s, 3H), 3.76 (brs, 1H), 2.88 (s, 3H), 2.85 (q, J = 7.6 Hz, 2H), 2.39-2.28 (m, 1H), 1.91-1.75 (m, 4H), 1.71-1.59 (m, 1H), 1.36 (dd, J = 12.9, 4.4 Hz, 1H), 1.31 (t, J = 7.6 Hz, 3H). |
| 505 | ¹H NMR (400 MHz, DMSO-d$_6$) δ 8.15 (brs, 3H), 7.92 (d, J = 7.9 Hz, 1H), 7.45 (s, 1H), 7.03 (d, J = 8.0 Hz, 1H), 6.59 (s, 1H), 6.40 (d, J = 1.4 Hz, 1H), 4.71-4.41 (m, 4H), 4.11 (s, 3H), 3.72 (brs, 1H), 2.86 (q, J =7.6 Hz, 2H), 2.83 (s, 3H), 1.94-1.55 (m, 5H), 1.52-1.45 (m, 2H), 1.36 (dd, J = 12.9, 4.4 Hz, 1H), 1.31 (t, J = 7.6 Hz, 3H), 0.52-0.30 (m, 1H), 0.24-0.08 (m, 2H), −0.19--030 (m, 2H). |
| 507 | ¹H NMR (400 MHz, DMSO-d$_6$) δ 8.55 (d, J = 6.4 Hz, 1H), 8.13 (brs, 3H), 8.01 (d, J = 8.0 Hz, 1H), 7.36 (s, 1H), 7.27 (d, J = 5.5 Hz, 2H), 7.11 (d, J = 8.0 Hz, 1H), 6.79 (s, 1H), 6.35 (d, J = 1.3 Hz, 1H), 5.99 (s, 2H), 4.44 (brs, 4H), 4.08 (s, 3H), 3.72 (brs, 1H), 2.83 (s, 2H), 2.80 (q, J = 7.6 Hz, 2H), 2.40-2.22 (m, 1H), 1.94-1.68 (m, 2H), 1.70-1.58 (m, 1H), 1.35 (dd, J = 12.8, 4.4 Hz, 1H), 1.24 (t, J = 7.6 Hz, 2H). |
| 508 | ¹H NMR (400 MHz, DMSO-d$_6$) δ 8.14 (brs, 3H), 7.93 (d, J = 7.9 Hz, 1H), 7.42 (s, 1H), 7.06 (d, J = 8.0 Hz, 1H), 6.64 (s, 1H), 6.38 (d, J = 1.3 Hz, 1H), 4.78-4.67 (m, 2H), 4.45 (brs, 2H), 4.11 (s, 3H), 3.77 (brs, 1H), 2.89 (q, J = 7.5 Hz, 1H), 2.87 (s, 3H), 2.39-2.24 (m, 1H), 2.02-1.92 (m, 2H), 1.91-1.76 (m, 3H), 1.70-1.59 (m, 1H), 1.37 (dd, J = 12.8, 4.4 Hz, 1H), 1.34 (t, J = 7.6 Hz, 3H), 1.31 (s, 6H). |
| 510 | 1H NMR (400 MHz, DMSO-d6) δ 8.13 (brs, 3H), 8.10 (d, J = 8.0 Hz, 1H), 7.65 (d, J = 3.5 Hz, 1H), 7.50 (d, J = 3.5 Hz, 1H), 7.37 (s, 1H), 7.29 (d, J = 8.0 Hz, 1H), 6.94 (s, 1H), 6.42 (s, 1H), 4.43 (brs, 2H), 4.10 (s, 3H), 3.73 (brs, 1H), 2.92 (q, J = 7.5 Hz, 2H), 2.63 (s, 3H), 2.39-2.22 (m 1H), 1.94-1.72 (m, 3H), 1.70-1.57 (m, 1H), 1.35 (t, J = 7.6 Hz, 3H). |
| 511 | ¹H NMR (400 MHz, DMSO-d$_6$) δ 8.12 (brs, 3H), 8.05 (d, J = 8.0 Hz, 1H), 7.43 (s, 1H), 7.39 (s, 1H), 7.21 (d, J = 8.0 Hz, 1H), 6.85 (s, 1H), 6.38 (s, 1H), 4.47 (brs, 2H), 4.08 (s, 3H), 3.75 (brs, 1H), 2.84 (q, J = 7.5 Hz, 2H), 2.66 (s, 3H), 2.61 (s, 3H), .39-2.22 (m 1H), 1.94-1.72 (m, 3H), 1.67-1.59 (m, 1H), 1.35 (dd, J = 12.8, 4.4 Hz, 1H), 1.28 (t, J = 7.6 Hz, 3H). |
| 512 | ¹H NMR (400 MHz, DMSO-d$_6$) δ 8.14 (brs, 3H), 8.04 (d, J = 8.0 Hz, 1H), 7.45-7.36 (m, 2H), 7.36-7.26 (m, 4H), 7.17 (d, J = 8.0 Hz, 1H), 6.84 (s, 1H), 6.38 (d, J = 1.4 Hz, 1H), 4.45 (brs, 4H), 4.05 (s, 3H), 3.73 (brs, 1H), 2.79 (q, J = 7.6 Hz, 2H), 2.39-2.23 (m, 1H), 1.95-1.71 (m, 3H), 1.71-1.56 (m, 1H), 1.34 (dd, J = 13.0, 4.4 Hz, 1H), 1.24 (t, J = 7.6 Hz, 3H). |
| 513 | 1H NMR (400 MHz, DMSO-d6) δ 8.56-8.42 (m, 2H), 8.17 (brs, 3H), 7.97 (d, J = 7.9 Hz, 1H), 7.79 (d, J = 8.0 Hz, 1H), 7.49 (dd, J = 8.0, 5.2 Hz, 1H), 7.46 (s, 1H), 7.10 (d, J = 8.0 Hz, 1H), 6.72 (s, 1H), 6.39 (d, J = 1.3 Hz, 1H), 5.88 (s, 2H), 4.45 (brs, 2H), 4.10 (s, 3H), 3.75 (s, 1H), 2.86 (q, J = 7.6 Hz, 2H), 2.79 (s, 3H), 2.41-2.25 (m, 1H), 1.93-1.72 (m, 3H), 1.72-1.58 (m, 1H), 1.37 (dd, J = 12.9, 4.4 Hz, 1H), 1.29 (t, J = 7.6 Hz, 3H). |
| 514 | 1H NMR (400 MHz, DMSO-d6) δ 8.09 (s, 3H), 7.99 (d, J = 8.1 Hz, 1H), 7.46 (s, 1H), 6.96 (d, J = 8.2 Hz, 1H), 6.62 (s, 1H), 6.38 (s, 1H), 5.82 (s, 1H), 4.54-4.32 (m, 4H), 4.24-4.14 (m, 2H), 4.10 (s, 3H), 3.87-3.67 (m, 1H), 2.84 (s, 3H), 2.80-2.69 (m, 1H), 2.37-2.25 (m, 1H), 1.91-1.32 (m, 10H), 1.29 (s, 9H), 1.17-1.08 (m, 1H), 0.34-0.14 (m, 4H). |
| 515 | NMR shows roughly 1:1 mixture of rotamers; 1H NMR (400 MHz, DMSO-d6) δ 8.08 (s, 3H), 8.02 (d, J = 8.1 Hz, 0.5H), 7.97 (d, J = 8.1 Hz, 0.5H), 7.46 (s, 1H), 7.05 (d, J = 8.1 Hz, 0.5H), 6.99 (d, J = 8.2 Hz, 0.5H), 6.64 (s, 0.5H), 6.61 (s, 0.5H), 6.38 (s, 1H), 5.87-5.82 (m, 0.5H), 5.30-5.25 (m, 0.5H), 4.57-4.32 (m, 4H), 4.10 (s, 3H), 3.87-3.72 (m, 2H), 3.23 (t, J = 12.5 Hz, 1H), 2.84 (s, 3H), 2.70-2.60 (m, 2H), 2.38-2.26 (m, 1H), 2.15 (s, 1.5H), 2.05 (s, 1.5H), 1.95-1.05 (m, 10H), 0.34-0.17 (m, 4H). |
| 517 | 1H NMR (400 MHz, DMSO-d6) δ 8.07 (s, 3H), 7.96 (d, J = 8.0 Hz, 1H), 7.46 (s, 1H), 7.08 (d, J = 8.0 Hz, 1H), 6.60 (s, 1H), 6.37 (s, 1H), 4.61-4.32 (m, 5H), 4.10 (s, 3H), 3.74-3.40 (m, 3H), 3.06-2.94 (m, 1H), 2.92-2.77 (m, 4H), 2.15-2.06 (m, 1H), 1.94-1.77 (m, 5H), 1.69-1.44 (m, 1H), 1.41-1.30 (m, 1H), 1.24 (d, J = 4.9 Hz, 9H), 1.20-1.09 (m, 1H), 0.35-0.23 (m, 4H). |
| 518 | 1H NMR (400 MHz, DMSO-d6) δ 8.07 (s, 3H), 7.94 (d, J = 8.0 Hz, 1H), 7.46 (s, 1H), 7.08 (d, J = 8.1 Hz, 1H), 6.59 (s, 1H), 6.37 (s, 1H), 4.43 (d, J = 7.1 Hz, 2H), 4.10 (s, 3H), 3.82 (dd, J = 63.1, 11.8 Hz, 4H), 3.33-3.06 (m, 5H), 3.00-2.87 (m, 2H), 2.83 (s, 3H), 2.81-2.70 (m, 1H), 2.10-2.02 (m, 1H), 1.89-1.70 (m, 9H), 1.69-1.52 (m, 2H), 1.35 (d, J = 13.4 Hz, 1H), 1.18-1.07 (m, 1H), 1.04 (t, J = 7.1 Hz, 1H), 0.32-0.19 (m, 4H). |
| 525 | 1H NMR (400 MHz, DMSO-d6) δ 8.12 (s, 3H), 7.94 (d, J = 8.0 Hz, 1H), 7.47 (s, 1H), 7.07 (d, J = 8.0 Hz, 1H), 6.60 (s, 1H), 6.41 (s, 1H), 4.41 (d, J = 7.0 Hz, 2H), 4.11 (s, 3H), 3.86-3.77 (m, 2H), 3.33-3.18 (m, 8H), 3.02-2.76 (m, 5H), 1.95-1.56 (m, 13H), 1.36 (dd, J = 12.7, 4.3 Hz, 1H), 1.16-1.03 (m, 1H), 0.32-0.17 (m, 4H). |
| 526 | 1H NMR (400 MHz, DMSO-d6) δ 8.17-8.10 (m, 3H), 7.94 (d, J = 8.0 Hz, 1H), 7.48 (s, 1H), 7.08 (d, J = 8.0 Hz, 1H), 6.61 (s, 1H), 6.43 (s, 1H), 4.41 (dd, J = 21.6, 10.0 Hz, 5H), 4.11 (s, 3H), 3.13-3.01 (m, 1H), 3.01-2.89 (m, 2H), 2.82 (s, 3H), 2.00-1.59 (m, 9H), 1.36 (dd, J = 12.9, 4.3 Hz, 1H), 1.24 (s, 9H), 1.15-1.05 (m, 1H), 0.32-0.20 (m, 4H). |

TABLE 2-continued

| Ex | NMR |
|---|---|
| 527 | 1H NMR (400 MHz, DMSO-d6) δ 8.19-8.10 (m, 3H), 7.95 (d, J = 8.0 Hz, 1H), 7.48 (s, 1H), 7.08 (d, J = 8.1 Hz, 1H), 6.62 (s, 1H), 6.44 (s, 1H), 4.59-4.50 (m, 2H), 4.39 (d, J = 7.0 Hz, 2H), 4.01-3.92 (m, 2H), 3.26-3.13 (m, 2H), 3.09-2.97 (m, 2H), 2.81 (s, 3H), 2.74-2.63 (m, 2H), 2.33 (s, 1H), 2.05 (s, 3H), 2.00-1.57 (m, 6H), 1.36 (dd, J = 12.9, 4.4 Hz, 1H), 1.18-1.03 (m, 1H), 0.33-0.14 (m, 4H). |
| 529 | 1H NMR (400 MHz, DMSO-d6) δ 8.11 (s, 3H), 7.95 (d, J = 8.0 Hz, 1H), 7.47 (s, 1H), 7.12 (d, J = 8.0 Hz, 1H), 6.61 (s, 1H), 6.40 (d, J = 1.4 Hz, 1H), 4.41 (d, J = 7.0 Hz, 2H), 4.11 (s, 3H), 3.83-3.39 (m, 7H), 3.37-3.20 (m, 5H), 2.82 (s, 3H), 2.40-2.07 (m, 3H), 1.93-1.58 (m, 8H), 1.35 (dd, J = 12.8, 4.4 Hz, 1H), 1.18-1.05 (m, 1H), 0.34-0.19 (m, 4H). |
| 530 | 1H NMR (400 MHz, DMSO-d6) δ 8.12 (s, 3H), 7.96 (d, J = 8.0 Hz, 1H), 7.47 (s, 1H), 7.14 (d, J = 8.0 Hz, 1H), 6.62 (s, 1H), 6.40 (d, J = 1.3 Hz, 1H), 4.11 (s, 3H), 4.00-3.40 (m, 8H), 2.82 (s, 3H), 2.45-2.03 (m, 3H), 1.94-1.76 (m, 3H), 1.70-1.57 (m, 1H), 1.40-1.29 (m, 1H), 1.21 (s, 9H), 1.16-1.01 (m, 1H), 0.32-0.15 (m, 4H). |
| 531 | 1H NMR (400 MHz, DMSO-d6) δ 8.13 (s, 3H), 7.96 (dd, J = 8.0, 4.9 Hz, 1H), 7.47 (s, 1H), 7.13 (t, J = 8.2 Hz, 1H), 6.62 (d, J = 1.2 Hz, 1H), 6.40 (d, J = 1.4 Hz, 1H), 4.40 (d, J = 7.0 Hz, 2H), 4.11 (s, 3H), 3.94-3.30 (m, 8H), 2.82 (s, 3H), 2.40-2.09 (m, 3H), 1.92-1.76 (m, 3H), 1.70-1.58 (m, 1H), 1.41-1.31 (m, 1H), 1.19-1.06 (m, 2H), 0.32-0.16 (m, 4H). |
| 532 | 1H NMR (400 MHz, DMSO-d6) δ 8.01 (s, 3H), 7.92 (d, J = 7.9 Hz, 1H), 7.34 (s, 1H), 7.08 (d, J = 8.0 Hz, 1H), 6.63 (s, 1H), 6.47 (s, 1H), 4.34 (d, J = 7.1 Hz, 2H), 4.11 (s, 3H), 3.38-3.13 (m, 3H), 3.09 (t, J = 7.3 Hz, 2H), 3.02 (s, 3H), 2.85-2.77 (m, 8H), 2.09-1.96 (m, 1H), 1.84-1.68 (m, 1H), 1.68-1.51 (m, 2H), 1.16-1.03 (m, 1H), 0.36-0.14 (m, 4H). (Expect 40, See 38) |
| 538 | 1H NMR (400 MHz, DMSO-d6) δ 8.01 (s, 3H), 7.92 (d, J = 7.9 Hz, 1H), 7.34 (s, 1H), 7.08 (d, J = 8.0 Hz, 1H), 6.63 (s, 1H), 6.47 (s, 1H), 4.34 (d, J = 7.1 Hz, 2H), 4.11 (s, 3H), 3.38-3.13 (m, 3H), 3.09 (t, J = 7.3 Hz, 2H), 3.02 (s, 3H), 2.85-2.77 (m, 8H), 2.09-1.96 (m, 1H), 1.84-1.68 (m, 1H), 1.68-1.51 (m, 2H), 1.16-1.03 (m, 1H), 0.36-0.14 (m, 4H). (Expect 40, See 38) |
| 539 | $^1$H NMR (400 MHz, DMSO-d$_6$) δ 8.12 (brs, 3H), 7.92 (d, J = 8.2 Hz, 1H), 7.66 (q, J = 4.6 Hz, 1H), 7.48 (s, 1H), 7.20 (d, J = 8.2 Hz, 1H), 6.59 (brs, 1H), 6.40 (m, 1H), 4.41 (d, J = 7.0 Hz, 2H), 4.11 (s, 3H), 2.83 (s, 3H), 2.59 (s, 2H), 2.40-2.27 (m, 1H), 1.91-1.77 (m, 4H), 1.69-1.59 (m, 2H), 1.44 (s, 6H), 1.35 (dd, J = 12.8, 4.4 Hz, 2H), 1.18-1.09 (m, 2H), 0.34-0.24 (m, 4H). |
| 543 | 1H NMR (400 MHz, DMSO-d6) δ 9.44 (s, 1H), 8.22 (s, 3H), 8.03 (d, J = 7.9 Hz, 1H), 7.44 (s, 1H), 7.18 (d, J = 8.0 Hz, 1H), 6.65 (s, 1H), 6.39 (s, 1H), 4.53-4.36 (m, 6H), 4.11 (s, 3H), 4.01-3.87 (m, 1H), 3.78-3.52 (m, 2H), 3.49-3.41 (m, 1H), 3.36-3.29 (m, 1H), 3.24-3.00 (m, 3H), 2.83 (s, 3H), 2.33 (s, 2H), 1.93-1.80 (m, 4H), 1.71-1.59 (m, 1H), 1.42-1.35 (m, 1H), 1.35 (d, J = 6.7 Hz, 3H), 1.20-1.11 (m, 1H), 0.36-0.23 (m, 2H), 0.24-0.14 (m, 2H). |
| 544 | 1H NMR (400 MHz, DMSO-d6) δ 8.09 (s, 3H), 7.97 (d, J = 8.1 Hz, 1H), 7.46 (s, 1H), 7.14 (d, J = 8.2 Hz, 1H), 6.61 (s, 1H), 6.38 (s, 1H), 5.09 (t, J = 4.1 Hz, 1H), 4.49-4.33 (m, 4H), 4.10 (s, 3H), 3.83-3.68 (m, 1H), 3.63-3.54 (m, 1H), 3.37-3.28 (m, 4H), 3.13-3.01 (m, 1H), 2.84 (s, 3H), 2.38-2.27 (m, 1H), 1.90-1.39 (m, 14H), 1.35 (dd, J = 12.8, 4.4 Hz, 1H), 1.17-1.06 (m, 1H), 0.33-0.16 (m, 4H). |
| 545 | 1H NMR (400 MHz, DMSO-d6) δ 8.09 (s, 3H), 7.94 (d, J = 8.2 Hz, 1H), 7.46 (s, 1H), 7.34 (s, 1H), 7.16 (d, J = 8.0 Hz, 1H), 6.91 (s, 1H), 6.60 (s, 1H), 6.38 (s, 1H), 4.65-4.33 (m, 4H), 4.10 (s, 3H), 3.93-3.62 (m, 2H), 2.83 (s, 3H), 1.98-1.70 (m, 4H), 1.70-1.55 (m, 1H), 1.45 (d, J = 7.8 Hz, 3H), 1.35 (dd, J = 12.8, 4.3 Hz, 1H), 1.18-0.98 (m, 1H), 0.36-0.14 (m, 4H). |
| 548 | 1H NMR (400 MHz, DMSO-d6) δ 8.85 (s, 1H), 8.07 (s, 1H), 8.00 (d, J = 8.1 Hz, 1H), 8.15-7.79 (m, 3H), 7.32 (s, 1H), 7.07 (d, J = 8.0 Hz, 1H), 6.65 (s, 1H), 6.38 (s, 1H), 5.88 (q, J = 7.0 Hz, 1H), 4.46-4.27 (m, 2H), 4.09 (s, 3H), 3.37-3.06 (m, 3H), 2.81 (s, 3H), 2.08-1.94 (m, 1H), 1.92 (d, J = 7.0 Hz, 3H), 1.81-1.70 (m, 1H), 1.70-1.51 (m, 2H), 1.16-1.04 (m, 1H), 0.34-0.11 (m, 4H). (Expect 36, See 34) |
| 549 | 1H NMR (400 MHz, DMSO-d6) δ 8.11 (s, 0H), 7.92-7.85 (m, 1H), 7.79 (t, J = 7.6 Hz, 1H), 7.72-7.61 (m, 2H), 7.47 (s, 1H), 7.28 (d, J = 8.0 Hz, 1H), 6.74 (s, 1H), 6.38 (s, 1H), 4.48 (d, J = 7.2 Hz, 2H), 4.12 (s, 3H), 2.89 (s, 3H), 1.88 (d, J = 26.9 Hz, 3H), 1.66 (d, J = 9.1 Hz, 1H), 1.37 (dd, J = 12.8, 4.4 Hz, 1H), 1.24 (s, 1H), 1.17-1.01 (m, 0H), 0.29-0.09 (m, 4H). |
| 550 | 1H NMR (400 MHz, Chloroform-d) δ 8.05 (d, J = 17.3 Hz, 1H), 7.72 (s, 1H), 7.59 (s, 1H), 7.54 (s, 1H), 7.44 (s, 1H), 7.34 (d, J = 5.8 Hz, 1H) 7.02 (s, 1H), 6.78 (s, 2H), 4.68 (d, J = 7.4 Hz, 2H), 4.20 (d, J = 23.6 Hz, 4H), 3.82 (s, 2H), 2.74 (d, J = 34.3 Hz, 3H), 2.42 (s, 3H), 1.82 (s, 2H), 1.50 (s, 2H), 1.28 (s, 1H), 0.91 (s, 2H), 0.28 (s, 2H), 0.08 (d, J = 15.8 Hz, 2H). |
| 551 | 1H NMR (400 MHz, Chloroform-d) δ 8.79 (d, J = 4.7 Hz, 1H), 8.04 (dd, J = 23.0, 8.0 Hz, 2H), 7.75 (s, 1H), 7.62 (dd, J = 7.8, 4.7 Hz, 1H), 6.81 (s, 1H), 6.73 (s, 1H), 4.23 (d, J = 26.9 Hz, 5H), 3.82 (s, 1H), 2.85 (s, 3H), 2.36 (s, 1H), 2.09 (d, J = 18.2 Hz, 0H), 1.78 (d, J = 41.5 Hz, 2H), 1.56 (s, 1H), 0.92 (d, J = 10.6 Hz, 1H), 0.30 (d, J = 7.8 Hz, 2H), 0.10 (d, J = 0.8 Hz, 0H). |
| 552 | 1H NMR (400 MHz, DMSO-d6) δ 8.13 (d, J = 5.7 Hz, 3H), 7.88 (d, J = 7.9 Hz, 1H), 7.30 (s, 1H), 7.01 (d, J = 7.9 Hz, 1H), 6.71 (s, 1H), 6.25 (s, 1H), 4.57-4.41 (m, 4H), 4.09 (s, 3H), 3.81-3.67 (m, 1H), 2.84 (q, J = 7.5 Hz, 2H), 2.37-2.25 (m, 1H), 1.92-1.75 (m, 3H), 1.70-1.57 (m, 1H), 1.35 (dd, J = 12.8, 4.4 Hz, 1H), 1.29 (t, J = 7.5 Hz, 3H), 1.15 (p, J = 6.6 Hz, 1H), 0.35-0.24 (m, 4H). |
| 553 | 1H NMR (400 MHz, DMSO-d6) δ 8.02 (s, 3H), 7.91 (d, J = 7.9 Hz, 1H), 7.19 (s, 1H), 7.04 (d, J = 8.0 Hz, 1H), 6.72 (d, J = 1.0 Hz, 1H), 6.38 (s, 1H), 4.40 (d, J = 7.0 Hz, 2H), 4.10 (s, 3H), 3.35-3.10 (m, 5H), 2.85 (q, J = 7.5 Hz, 2H), 2.08-1.97 (m, 1H), 1.82-1.70 (m, 1H), 1.69-1.49 (m, 2H), 1.29 (td, J = 7.6, 1.1 Hz, 3H), 1.13 (p, J = 6.6 Hz, 1H), 0.34-0.23 (m, 4H). |
| 556 | $^1$H NMR (400 MHz, DMSO-d$_6$) δ 8.14 (brs, 3H), 8.10 (d, J = 8.1 Hz, 1H), 7.84 (d, J = 8.4 Hz, 1H), 7.48 (s, 1H), 7.33 (d, J = 8.1 Hz, 1H), 6.79 (d, J = 8.3 Hz, 1H), 6.71 (s, 1H), 6.41 (d, J = 1.4 Hz, 1H), 4.61 (brs, 2H), 4.48 (d, J = 7.0 Hz, 2H), 4.12 (s, 3H), 3.92 (s, 3H), 3.75 (brs, 1H), 2.87 (s, 3H), 2.58 (s, 3H), 2.43-2.24 (m, 1H), 1.96-1.78 (m, 3H), 1.72-1.53 (m, 1H), 1.37 (dd, J = 12.8, 4.4 Hz, 1H), 1.24-1.04 (m, 1H), 0.36-0.24 (m, 2H), 0.24-0.11 (m, 2H). |
| 563 | $^1$H NMR (400 MHz, DMSO-d$_6$) δ 11.78 (brs, 1H), 8.14 (brs, 3H), 8.05 (d, J = 8.1 Hz, 1H), 7.73 (d, J = 9.4 Hz, 1H), 7.48 (s, 1H), 7.27 (d, J = 8.1 Hz, 1H), 6.68 (s, 1H), 6.41 (s 1H), 6.32 (d, J = 9.4 Hz, 1H), 4.56 (brs, 2H), 4.47 (d, J = 7.0 Hz, 2H), 4.12 (s, 3H), 3.77 (s, 1H), 2.86 |

TABLE 2-continued

| Ex | NMR |
|---|---|
| | (s, 3H), 2.44 (s, 3H), 2.41-2.25 (m, 1H), 1.98-1.75 (m, 3H), 1.71-1.59 (m, 1H), 1.37 (dd, J = 12.9, 4.4 Hz, 1H), 1.29-1.04 (m, 1H), 0.38-0.25 (m, 2H), 0.24-0.12 (m, 2H). |
| 564 | $^1$H NMR (400 MHz, DMSO-d$_6$) δ 8.57 (s, 1H), 8.18 (d, J = 8.0 Hz, 1H), 8.16 (brs, 3H), 7.48 (brs, 1H), 7.44 (d, J = 8.0 Hz, 1H), 6.77 (s, 1H), 6.41 (s, 1H), 4.93 (brs, 2H), 4.50 (d, J = 7.1 Hz, 2H), 4.13 (s, 3H), 3.77 (brs, 1H), 2.88 (s, 3H), 2.42 (d, J = 2.1 Hz, 3H), 2.40-2.27 (m, 1H), 1.96-1.79 (m, 3H), 1.72-1.58 (m, 1H), 1.37 (dd, J = 12.8, 4.4 Hz, 1H), 1.24-1.09 (m, 1H), 0.37-0.27 (m, 2H), 0.23-0.12 (m, 2H). |
| 567 | 1H NMR (400 MHz, DMSO-d6) δ 8.96 (d, J = 0.6 Hz, 1H), 8.68 (dd, J = 4.7, 1.7 Hz, 1H), 8.14 (d, J = 7.9 Hz, 1H), 8.06 (s, 3H), 7.91 (dd, J = 7.7, 1.7 Hz, 1H), 7.53-7.48 (m, 1H), 7.43 (s, 1H), 7.25 (d, J = 8.0 Hz, 1H), 7.12 (s, 1H), 6.75 (s, 1H), 6.35 (s, 1H), 4.38 (d, J = 6.9 Hz, 2H), 4.09 (s, 3H), 3.73-3.18 (m, 4H), 2.87 (s, 3H), 1.88-1.67 (m, 4H), 1.35-1.21 (m, 3H), 0.18-0.07 (m, 2H), 0.05--0.06 (m, 2H). |
| 569 | 1H NMR (400 MHz, DMSO-d6) δ 8.09 (s, 3H), 8.07 (d, J = 8.1 Hz, 1H), 7.45 (d, J = 5.9 Hz, 1H), 7.36 (d, J = 8.1 Hz, 1H), 6.90 (s, 1H), 6.67 (s, 1H), 6.35 (d, J = 1.4 Hz, 1H), 5.31-5.00 (m, 2H), 4.77-4.26 (m, 2H), 4.08 (s, 3H), 2.83 (s, 3H), 1.93-1.74 (m, 5H), 1.68-1.50 (m, 1H), 1.34 (dd, J = 12.8, 4.4 Hz, 1H), 1.29-1.18 (m, 2H), 1.13-0.96 (m, 1H), 0.52-0.30 (m, 2H), 0.31-0.11 (m, 2H). |
| 575 | $^1$H NMR (400 MHz, DMF-d$_7$) δ 9.25-9.13 (m, 1H), 8.89 (d, J = 8.2 Hz, 1H), 8.64 (d, J = 8.2 Hz, 1H), 8.61 (brs, 3H), 8.32-8.20 (m, 1H), 7.99-7.84 (m, 2H), 7.20 (s, 1H), 6.82 (s, 1H), 4.94 (d, J = 7.0 Hz, 2H), 4.54 (s, 3H), 3.30 (s, 3H), 3.23 (s, 3H), 2.38-2.03 (m, 5H), 1.86-1.45 (m, 4H), 0.78-0.64 (m, 2H), 0.66-0.52 (m, 2H). |
| 579 | 1H NMR (400 MHz, DMSO-d6) δ 8.00 (s, 3H), 7.92 (d, J = 7.9 Hz, 1H), 7.35 (s, 1H), 7.04 (d, J = 8.0 Hz, 1H), 6.60 (s, 1H), 6.41 (s, 1H), 4.39 (d, J = 7.0 Hz, 2H), 4.09 (s, 3H), 3.76-3.68 (m, 1H), 3.62-3.52 (m, 1H), 3.50-3.39 (m, 1H), 3.37 (s, 3H), 2.86 (q, J = 7.6 Hz, 2H), 2.82 (s, 3H), 1.91 (s, 1H), 1.85-1.72 (m, 1H), 1.30 (t, J = 7.6 Hz, 3H), 1.19-1.05 (m, 1H), 0.33-0.17 (m, 4H). (Expect 37, See 34) |
| 584 | 1H NMR (400 MHz, Methanol-d4) δ 8.12 (d, J = 8.1 Hz, 1H), 7.53 (d, J = 1.2 Hz, 1H), 7.20 (d, J = 8.1 Hz, 1H), 6.85 (s, 1H), 6.78 (d, J = 1.2 Hz, 1H), 4.32 (d, J = 7.0 Hz, 2H), 4.24 (s, 3H), 3.95-3.76 (m, 1H), 2.98 (q, J = 7.6 Hz, 2H), 2.83 (s, 3H), 2.59-2.40 (m, 1H), 2.13-1.97 (m, 4H), 1.97-1.86 (m, 1H), 1.83-1.68 (m, 1H), 1.48 (dd, J = 13.2, 4.5 Hz, 1H), 1.39 (t, J = 7.6 Hz, 3H), 1.01 (ddd, J = 12.5, 7.7, 4.8 Hz, 1H), 0.43-0.26 (m, 2H), 0.12 (dt, J = 6.3, 4.6 Hz, 2H). |
| 585 | 1H NMR (400 MHz, DMSO-d6) δ 7.97 (s, 3H), 7.90 (d, J = 7.9 Hz, 1H), 7.28 (s, 1H), 7.02 (d, J = 8.0 Hz, 1H), 6.61 (s, 1H), 6.42 (s, 1H), 4.38 (d, J = 7.1 Hz, 2H), 4.10 (s, 3H), 3.34-3.02 (m, 2H), 2.83 (q, J = 7.5 Hz, 3H), 2.44-2.34 (m, 1H), 2.07-1.89 (m, 2H), 1.82-1.67 (m, 1H), 1.59 (d, J = 9.4 Hz, 2H), 1.29 (t, J = 7.5 Hz, 3H), 1.27-1.14 (m, 1H), 1.03-0.92 (m, 1H), 0.88 (d, J = 7.9 Hz, 2H), 0.47-0.40 (m, 1H), 0.40-0.30 (m, 2H), 0.26-0.18 (m, 2H), 0.13-0.06 (m, 2H). |
| 587 | 1H NMR (400 MHz, DMSO-d6) δ 8.71-8.47 (m, 3H), 7.97-7.89 (m, 1H), 7.48-7.29 (m, 1H), 7.10-7.00 (m, 1H), 6.64-6.57 (m, 1H), 6.50-6.41 (m, 1H), 4.64-4.23 (m, 3H), 4.11 (s, 3H), 3.76-3.52 (m, 1H), 3.53-3.36 (m, 1H), 2.94-2.73 (m, 5H), 2.04-1.73 (m, 6H), 1.30 (t, J = 7.6 Hz, 3H), 1.19-1.03 (m, 1H), 0.34-0.15 (m, 4H). (Expect 35, see 35, retainers) |
| 588 | 1H NMR (400 MHz, DMSO-d6) δ 8.79-8.46 (m, 3H), 7.98-7.90 (m, 1H), 7.49-7.30 (m, 1H), 7.05 (dd, J = 8.0, 3.0 Hz, 1H), 6.65-6.60 (m, 1H), 6.47 (s, 1H), 4.60-4.23 (m, 3H), 4.11 (s, 3H), 3.73-3.53 (m, 1H), 3.51-3.36 (m, 1H), 2.93-2.62 (m, 5H), 2.06-1.72 (m, 6H), 1.30 (t, J = 7.6 Hz, 3H), 1.17-1.00 (m, 1H), 0.35-0.15 (m, 4H). (Expect 35, see 35, retainers observed) |
| 591 | 1H NMR (400 MHz, Methanol-d4) δ 8.10 (d, J = 8.1 Hz, 1H), 7.48 (d, J = 1.4 Hz, 1H), 7.20 (d, J = 8.1 Hz, 1H), 6.89-6.77 (m, 2H), 4.32 (d, J = 7.0 Hz, 2H), 4.26 (s, 3H), 4.23-4.08 (m, 2H), 4.04-3.38 (m, 2H), 3.29-3.05 (m, 0H), 2.99 (q, J = 7.6 Hz, 2H), 2.85 (s, 3H), 2.02 (d, J = 27.3 Hz, 3H), 1.41 (t, J = 7.6 Hz, 3H), 1.04 (td, J = 7.6, 3.9 Hz, 0H), 0.46-0.24 (m, 2H), 0.18 (t, J = 5.1 Hz, 2H). |
| 592 | 1H NMR (400 MHz, DMSO-d6) δ 8.27 (s, 3H), 7.94 (d, J = 8.0 Hz, 1H), 7.30 (d, J = 1.3 Hz, 1H), 7.06 (d, J = 8.0 Hz, 1H), 6.62 (s, 1H), 6.48 (s, 1H), 4.46-4.32 (m, 2H), 4.10 (s, 3H), 3.83-3.75 (m, 1H), 3.54 (s, 2H), 2.91-2.81 (m, 2H), 2.79 (s, 3H), 2.12-1.97 (m, 2H), 1.91-1.79 (m, 4H), 1.80-1.68 (m, 2H), 1.30 (t, J = 7.6 Hz, 3H), 1.13-1.04 (m, 1H), 0.36-0.13 (m, 4H). (Expect 37 observe 32) |
| 593 | 1H NMR (400 MHz, DMSO-d6) δ 8.27 (s, 3H), 7.94 (d, J = 8.0 Hz, 1H), 7.30 (d, J = 1.3 Hz, 1H), 7.06 (d, J = 8.0 Hz, 1H), 6.62 (s, 1H), 6.48 (s, 1H), 4.46-4.32 (m, 2H), 4.10 (s, 3H), 3.83-3.75 (m, 1H), 3.54 (s, 2H), 2.91-2.81 (m, 2H), 2.79 (s, 3H), 2.12-1.97 (m, 2H), 1.91-1.79 (m, 4H), 1.80-1.68 (m, 2H), 1.30 (t, J = 7.6 Hz, 3H), 1.13-1.04 (m, 1H), 0.36-0.13 (m, 4H). (Epxect 37. See 37, retainers) |
| 594 | 1H NMR (400 MHz, DMSO-d6) δ 8.70-8.43 (m, 2H), 7.93 (d, J = 7.9 Hz, 1H), 7.49 (d, J = 1.3 Hz, 1H), 7.05 (d, J = 8.0 Hz, 1H), 6.62 (s, 1H), 6.49 (d, J = 1.4 Hz, 1H), 4.48-4.39 (m, 2H), 4.35 (d, J = 8.8 Hz, 1H), 4.23 (d, J = 8.8 Hz, 1H), 4.11 (s, 3H), 3.96 (d, J = 10.2 Hz, 1H), 3.79 (d, J = 10.2 Hz, 1H), 3.42-3.22 (m, 2H), 2.98 (s, 2H), 2.89-2.81 (m, 5H), 1.91-1.80 (m, 2H), 1.75-1.61 (m, 2H), 1.30 (t, J = 7.6 Hz, 3H), 1.15-1.04 (m, 1H), 0.32-0.16 (m, 4H). (Expect 37, see 37) |
| 596 | 1H NMR (400 MHz, DMSO-d6) δ 8.17 (d, J = 8.1 Hz, 1H), 7.95 (s, 3H), 7.47 (d, J = 8.2 Hz, 1H), 7.32 (s, 1H), 6.75 (s, 1H), 6.36 (s, 1H), 4.47 (d, J = 7.0 Hz, 2H), 4.09 (s, 3H), 3.33-3.13 (m, 3H), 2.85 (s, 3H), 2.10 (t, J = 18.8 Hz, 3H), 2.05-1.98 (m, 1H), 1.84-1.71 (m, 1H), 1.70-1.55 (m, 2H), 1.23-1.13 (m, 1H), 0.38-0.25 (m, 4H). (Expect 33, observe 31) |
| 598 | 1H NMR (400 MHz, DMSO-d6) δ 8.18-7.79 (m, 4H), 7.33 (s, 1H), 7.09 (d, J = 8.0 Hz, 1H), 6.61 (s, 1H), 6.42 (s, 1H), 4.44-4.30 (m, 2H), 4.10 (s, 3H), 4.06-3.95 (m, 2H), 3.51-3.38 (m, 1H), 3.28 (s, 3H), 2.90 (dd, J = 15.6, 8.1 Hz, 1H), 2.82 (s, 3H), 2.65 (dd, J = 15.7, 6.8 Hz, 1H), 2.08-1.97 (m, 1H), 1.85-1.70 (m, 1H), 1.68-1.52 (m, 2H), 1.30 (d, J = 6.9 Hz, 3H), 1.17-1.07 (m, 4H), 0.34-0.20 (m, 4H). (Expect 41, see 39) |

TABLE 2-continued

| Ex | NMR |
|---|---|
| 599 | 1H NMR (400 MHz, DMSO-d6) δ 8.08 (d, J = 8.2 Hz, 1H), 8.05-7.84 (m, 3H), 7.31 (s, 1H), 7.21 (d, J = 8.1 Hz, 1H), 6.71 (s, 1H), 6.36 (s, 1H), 4.41 (d, J = 7.0 Hz, 2H), 4.09 (s, 3H), 3.38-3.10 (m, 3H), 2.84 (s, 3H), 2.09-1.96 (m, 1H), 1.85-1.71 (m, 1H), 1.69-1.53 (m, 2H), 1.20-1.07 (m, 2H), 0.34-0.27 (m, 2H), 0.26-0.14 (m, 2H). (Expect 30, see 29) |
| 603 | 1H NMR (400 MHz, DMSO-d6) δ 10.47 (s, 1H), 8.09 (d, J = 8.2 Hz, 1H), 7.96 (s, 3H), 7.66 (d, J = 8.2 Hz, 1H), 7.53 (d, J = 8.0 Hz, 1H), 7.36-7.26 (m, 2H), 6.87 (d, J = 7.7 Hz, 1H), 6.68 (s, 1H), 6.37 (s, 1H), 4.51 (d, J = 7.0 Hz, 2H), 4.45-4.13 (m, 4H), 4.08 (s, 3H), 3.91 (s, 2H), 3.26 (s, 3H), 2.07-1.93 (m, 1H), 1.85-1.68 (m, 1H), 1.70-1.48 (m, 2H), 1.31-1.05 (m, 2H), 0.34-0.25 (m, 2H), 0.21-0.12 (m, 2H). |
| 604 | 1H NMR (400 MHz, DMSO-d6) δ 8.70 (d, J = 5.5 Hz, 1H), 8.34 (s, 1H), 8.18 (d, J = 8.1 Hz, 1H), 7.97 (s, 3H), 7.74 (s, 1H), 7.46 (d, J = 8.1 Hz, 1H), 7.28 (s, 1H), 6.74 (s, 1H), 6.36 (s, 1H), 4.47 (d, J = 7.1 Hz, 2H), 4.43-4.13 (m, 3H), 4.08 (s, 3H), 3.39-3.02 (m, 2H), 2.85 (s, 3H), 2.76 (s, 3H), 2.09-1.94 (m, 1H), 1.86-1.70 (m, 1H), 1.68-1.49 (m, 2H), 1.16 (s, 1H), 0.34-0.24 (m, 2H), 0.24-0.07 (m, 2H). |
| 607 | 1H NMR (400 MHz, DMSO-d6) δ 8.72 (dd, J = 4.8, 1.7 Hz, 1H), 8.10 (dd, J = 7.8, 1.7 Hz, 1H), 7.95 (s, 3H), 7.91 (d, J = 8.1 Hz, 1H), 7.57 (dd, J = 7.8, 4.8 Hz, 1H), 7.33-7.26 (m, 3H), 7.26-7.19 (m, 3H), 7.01 (d, J = 8.1 Hz, 1H), 6.62 (s, 1H), 6.36 (s, 1H), 4.72-3.55 (m, 5H), 4.25 (d, J = 7.1 Hz, 2H), 4.07 (s, 3H), 2.81 (s, 3H), 2.11-1.91 (m, 1H), 1.84-1.68 (m, 1H), 1.70-1.40 (m, 2H), 0.97-0.73 (m, 1H), 0.20-0.11 (m, 2H), 0.10-0.01 (m, 2H). |
| 609 | 1H NMR (400 MHz, DMSO-d6) δ 8.02 (d, J = 8.1 Hz, 1H), 7.96 (s, 4H), 7.55 (s, 1H), 7.28 (d, J = 1.2 Hz, 1H), 7.23 (d, J = 8.4 Hz, 1H), 7.19 (d, J = 8.1 Hz, 1H), 6.65 (s, 1H), 6.44 (s, 1H), 4.70 (s, 2H), 4.38 (d, J = 7.0 Hz, 2H), 4.09 (s, 3H), 3.27-3.09 (m, 2H), 3.10-2.89 (m, 1H), 2.80 (s, 3H), 2.38 (s, 3H), 2.31 (s, 3H), 1.93-1.82 (m, 1H), 1.83-1.68 (m, 1H), 1.68-1.46 (m, 1H), 1.20 (d, J = 6.9 Hz, 3H), 1.18-1.08 (m, 1H), 0.35-0.21 (m, 2H), 0.22-0.03 (m, 2H). |
| 610 | 1H NMR (400 MHz, DMSO-d6) δ 8.21 (d, J = 8.0 Hz, 1H), 7.90 (s, 3H), 7.69 (d, J = 8.0 Hz, 1H), 7.24 (d, J = 1.3 Hz, 1H), 6.84 (s, 1H), 6.32 (d, J = 1.3 Hz, 1H), 4.52-4.44 (m, 2H), 4.07 (s, 3H), 3.22-3.13 (m, 1H), 3.05-2.90 (m, 1H), 2.83 (s, 3H), 1.90-1.69 (m, 3H), 1.66-1.52 (m, 1H), 1.20 (d, J = 6.9 Hz, 3H), 1.18-1.08 (m, 1H), 0.34-0.25 (m, 2H), 0.25-0.16 (m, 2H). (Missing 2) |
| 611 | 1H NMR (400 MHz, DMSO-d6) δ 7.99 (d, J = 8.2 Hz, 1H), 7.88 (s, 5H), 7.27-7.10 (m, 2H), 6.60 (d, J = 4.4 Hz, 1H), 6.33 (s, 1H), 4.43 (d, J = 7.1 Hz, 2H), 4.08 (s, 3H), 3.82-3.54 (m, 2H), 3.25-3.13 (m, 1H), 3.06-2.89 (m, 2H), 2.83 (s, 3H), 2.41 (s, 6H), 1.92-1.69 (m, 3H), 1.68-1.50 (m, 1H), 1.21 (d, J = 6.9 Hz, 3H), 0.30-0.23 (m, 2H), 0.21-0.08 (m, 2H). |
| 612 | 1H NMR (400 MHz, DMSO-d6) δ 7.99 (s, 3H), 7.84 (d, J = 8.0 Hz, 1H), 7.26 (d, J = 1.3 Hz, 1H), 7.06 (d, J = 8.0 Hz, 1H), 6.56 (s, 1H), 6.41 (s, 1H), 5.14-4.37 (m, 2H), 4.26 (d, J = 7.0 Hz, 2H), 4.08 (s, 3H), 3.16 (d, J = 7.9 Hz, 1H), 3.09-2.85 (m, 1H), 2.77 (s, 3H), 2.21-2.07 (m, 1H), 1.96-1.84 (m, 1H), 1.80-1.71 (m, 2H), 1.58 (s, 1H), 1.20 (d, J = 6.9 Hz, 3H), 1.06 (dd, J = 7.2, 4.5 Hz, 1H), 1.01-0.91 (m, 4H), 0.31-0.22 (m, 2H), 0.22-0.13 (m, 2H). |
| 613 | 1H NMR (400 MHz, DMSO-d6) δ 8.11-7.77 (m, 4H), 7.30 (s, 1H), 7.02 (d, J = 8.0 Hz, 1H), 6.58 (s, 1H), 6.40 (s, 1H), 4.35 (d, J = 7.0 Hz, 2H), 4.07 (s, 3H), 3.38-3.02 (m, 3H), 2.87-2.73 (m, 5H), 2.07-1.92 (m, 1H), 1.82-1.66 (m, 1H), 1.67-1.49 (m, 2H), 1.27 (t, J = 7.5 Hz, 3H), 1.16-1.03 (m, 1H), 0.32-0.13 (m, 4H). (Missing 2) |
| 614 | 1H NMR (400 MHz, Methanol-d4) δ 8.06 (d, J = 8.1 Hz, 1H), 7.95-7.90 (m, 2H), 7.61-7.47 (m, 4H), 7.30 (d, J = 8.1 Hz, 1H), 6.88 (s, 1H), 6.83 (s, 1H), 5.44 (q, J = 6.9 Hz, 1H), 4.71-4.60 (m, 1H), 4.38-4.26 (m, 2H), 4.25 (s, 3H), 3.60-3.46 (m, 1H), 3.30-3.17 (m, 2H), 3.09-2.96 (m, 1H), 2.82 (s, 3H), 2.74 (s, 3H), 2.19-2.04 (m, 1H), 1.93-1.83 (m, 1H), 1.70 (d, J = 7.0 Hz, 3H), 1.12-0.99 (m, 1H), 0.39-0.25 (m, 2H), 0.22-0.13 (m, 2H). |
| 615 | 1H NMR (400 MHz, Methanol-d4) δ 8.06 (d, J = 8.1 Hz, 1H), 7.58 (d, J = 1.2 Hz, 1H), 7.21 (d, J = 8.2 Hz, 1H), 6.96 (d, J = 1.2 Hz, 1H), 6.86 (s, 1H), 5.24 (q, J = 7.0 Hz, 1H), 4.71-4.59 (m, 1H), 4.36-4.18 (m, 5H), 3.62-3.46 (m, 1H), 3.32-3.16 (m, 2H), 3.08-2.93 (m, 1H), 2.82 (s, 3H), 2.73 (s, 3H), 2.37 (d, J = 2.5 Hz, 6H), 2.22-2.07 (m, 1H), 1.95-1.83 (m, 1H), 1.59 (d, J = 7.0 Hz, 3H), 1.15-0.99 (m, 1H), 0.47-0.33 (m, 2H), 0.29-0.15 (m, 2H). |
| 616 | 1H NMR (400 MHz, Methanol-d4) δ 8.07 (d, J = 8.2 Hz, 1H), 7.98-7.84 (m, 2H), 7.64-7.54 (m, 2H), 7.54-7.45 (m, 2H), 7.31 (d, J = 8.1 Hz, 1H), 6.95 (s, 1H), 6.85 (s, 1H), 5.44 (q, J = 7.0 Hz, 1H), 4.71-4.44 (m, 1H), 4.39-4.17 (m, 5H), 3.68-3.50 (m, 1H), 3.22-3.08 (m, 1H), 3.04-2.90 (m, 1H), 2.82 (s, 3H), 2.24-2.08 (m, 1H), 1.83-1.73 (m, 1H), 1.70 (d, J = 7.1 Hz, 3H), 1.12-0.98 (m, 1H), 0.41-0.26 (m, 2H), 0.24-0.10 (m, 2H). |
| 617 | 1H NMR (400 MHz, Methanol-d4) δ 7.96 (d, J = 8.5 Hz, 1H), 7.43 (s, 1H), 6.81 (s, 1H), 6.78-6.70 (m, 2H), 5.74 (q, J = 6.7 Hz, 1H), 4.58-4.33 (m, 1H), 4.31-4.19 (m, 4H), 3.99 (dd, J = 14.5, 7.1 Hz, 1H), 3.75-3.56 (m, 1H), 3.54-3.35 (m, 6H), 3.00 (s, 3H), 2.80 (s, 3H), 2.26-2.16 (m, 1H), 1.98-1.67 (m, 3H), 1.60 (d, J = 6.8 Hz, 3H), 1.12-1.00 (m, 1H), 0.41-0.33 (m, 2H), 0.18-0.04 (m, 2H). |
| 618 | 1H NMR (400 MHz, Methanol-d4) δ 7.98 (d, J = 8.5 Hz, 1H), 7.46 (s, 1H), 6.83 (s, 1H), 6.81-6.74 (m, 2H), 5.36 (q, J = 6.8 Hz, 1H), 4.44 (s, 1H), 4.26 (s, 3H), 4.21 (dd, J = 14.6, 7.3 Hz, 1H), 4.09 (dd, J = 14.6, 6.9 Hz, 1H), 3.78-3.58 (m, 1H), 3.55-3.35 (m, 3H), 2.82 (s, 3H), 2.75 (s, 3H), 2.29-2.13 (m, 1H), 2.03-1.66 (m, 3H), 1.61 (d, J = 6.9 Hz, 3H), 1.07-0.92 (m, 1H), 0.42-0.27 (m, 2H), 0.23-0.11 (m, 2H). |
| 619 | 1H NMR (400 MHz, Methanol-d4) δ 7.97 (d, J = 8.5 Hz, 1H), 7.45 (s, 1H), 6.84 (s, 1H), 6.79-6.71 (m, 2H), 5.74 (q, J = 6.8 Hz, 1H), 4.55-4.39 (m, 1H), 4.29-4.19 (m, 4H), 3.97 (dd, J = 14.6, 7.1 Hz, 1H), 3.77-3.61 (m, 1H), 3.54-3.34 (m, 6H), 3.00 (s, 3H), 2.80 (s, 3H), 2.29-2.11 (m, 1H), 2.00-1.65 (m, 3H), 1.60 (d, J = 6.8 Hz, 3H), 1.12-0.98 (m, 1H), 0.43-0.31 (m, 2H), 0.19-0.03 (m, 2H). |
| 620 | 1H NMR (400 MHz, Methanol-d4) d 7.98 (d, J = 8.5 Hz, 1H), 7.48 (s, 1H), 6.86 (s, 1H), 6.81-6.73 (m, 2H), 5.14 (s, 2H), 4.54-4.34 (m, 1H), 4.26 (s, 3H), 4.12 (d, J = 7.1 Hz, 2H), 3.74-3.54 (m, 1H), 3.54-3.35 (m, 3H), 3.23 (s, 3H), 3.00 (s, 3H), 2.81 (s, 3H), 2.30-2.12 (m, 1H), 2.06-1.48 (m, 3H), 1.12-0.92 (m, 1H), 0.44-0.28 (m, 2H), 0.24-0.11 (m, 2H). |
| 621 | 1H NMR (400 MHz, Methanol-d4) d 8.01 (d, J = 8.5 Hz, 1H), 7.48 (s, 1H), 6.86 (s, 1H), 6.82 (d, J = 8.5 Hz, 1H), 6.79 (s, 1H), 4.88 (s, 2H), 4.52-4.31 (m, 1H), 4.27 (s, 3H), 4.17 (d, J = |

TABLE 2-continued

| Ex | NMR |
|---|---|
|  | 7.1 Hz, 2H), 3.73-3.53 (m, 1H), 3.53-3.35 (m, 3H), 2.82 (s, 3H), 2.29-2.13 (m, 1H), 2.03-1.51 (m, 3H), 1.12-0.99 (m, 1H), 0.42-0.31 (m, 2H), 0.26-0.16 (m, 2H). |
| 622 | 1H NMR (400 MHz, Methanol-d4) d 8.01 (d, J = 8.5 Hz, 1H), 7.48 (s, 1H), 6.87-6.80 (m, 2H), 6.78 (s, 1H), 4.88 (s, 2H), 4.51-4.33 (m, 1H), 4.26 (s, 3H), 4.16 (d, J = 7.1 Hz, 2H), 3.74-3.59 (m, 1H), 3.53-3.35 (m, 3H), 2.82 (s, 3H), 2.80 (s, 3H), 2.30-2.14 (m, 1H), 1.98-1.64 (m, 3H), 1.09-0.91 (m, 1H), 0.41-0.32 (m, 2H), 0.22-0.16 (m, 2H). |
| 623 | 1H NMR (400 MHz, Methanol-d4) d 7.99 (d, J = 8.5 Hz, 1H), 7.48 (s, 1H), 6.86 (s, 1H), 6.78 (s, 1H), 6.74 (d, J = 8.5 Hz, 1H), 5.74 (t, J = 8.0 Hz, 1H), 4.55-4.31 (m, 1H), 4.31-3.97 (m, 5H), 3.76-3.37 (m, 5H), 2.98 (s, 3H), 2.87-2.72 (m, 4H), 2.30-2.08 (m, 2H), 2.04-1.61 (m, 3H), 1.20-0.95 (m, 1H), 0.46-0.32 (m, 2H), 0.23-0.07 (m, 2H). |
| 624 | 1H NMR (400 MHz, Methanol-d4) d 7.97 (d, J = 8.5 Hz, 1H), 7.54 (d, J = 1.3 Hz, 1H), 6.84-6.75 (m, 2H), 6.73 (s, 1H), 5.14 (s, 2H), 4.82-4.39 (m, 2H), 4.26 (s, 3H), 4.15 (d, J = 7.1 Hz, 2H), 3.96-3.81 (m, 1H), 3.23 (s, 3H), 3.00 (s, 3H), 2.83 (s, 3H), 2.60-2.46 (m, 1H), 2.13-1.90 (m, 3H), 1.84-1.72 (m, 1H), 1.56-1.44 (m, 1H), 1.07-0.95 (m, 1H), 0.41-0.30 (m, 2H), 0.20-0.10 (m, 2H). |
| 625 | 1H NMR (400 MHz, Methanol-d4) d 8.63 (d, J = 8.8 Hz, 1H), 7.46 (d, J = 1.3 Hz, 1H), 7.19 (d, J = 8.7 Hz, 1H), 7.05 (s, 1H), 6.53 (d, J = 1.3 Hz, 1H), 5.67-5.57 (m, 1H), 5.47 (t, J = 10.1 Hz, 1H), 5.36 (dd, J = 10.7, 6.4 Hz, 1H), 4.66-4.51 (m, 2H), 3.99-3.81 (m, 2H), 2.87 (s, 3H), 2.59-2.45 (m, 1H), 2.14-1.89 (m, 3H), 1.85-1.72 (m, 1H), 1.50 (dd, J = 13.2, 4.5 Hz, 1H), 1.17-1.04 (m, 1H), 0.52-0.38 (m, 2H), 0.00--0.11 (m, 2H). |
| 626 | 1H NMR (400 MHz, Methanol-d4) d 8.54 (d, J = 8.8 Hz, 1H), 7.46 (d, J = 1.3 Hz, 1H), 7.15 (d, J = 8.7 Hz, 1H), 7.04 (s, 1H), 6.55 (d, J = 1.4 Hz, 1H), 5.20 (dd, J = 12.2, 5.1 Hz, 1H), 5.01-4.93 (m, 2H), 4.89-4.84 (m, 2H), 4.73-4.61 (m, 3H), 4.41 (ddd, J = 16.1, 7.5, 2.3 Hz, 1H), 4.21 (s, 3H), 3.87 (h, J = 5.7 Hz, 3H), 2.89 (s, 3H), 2.83-2.71 (m, 1H), 2.59-2.45 (m, 1H), 2.10-1.90 (m, 3H), 1.83-1.72 (m, 1H), 1.50 (dd, J = 13.2, 4.4 Hz, 1H), 1.20-1.06 (m, 1H), 0.53-0.32 (m, 2H), -0.07 (dd, J = 9.2, 4.4 Hz, 2H). |
| 627 | 1H NMR (400 MHz, Methanol-d4) d 7.94 (d, J = 8.5 Hz, 1H), 7.56-7.44 (m, 3H), 7.42-7.34 (m, 2H), 7.33-7.22 (m, 1H), 6.77 (d, J = 1.3 Hz, 1H), 6.74-6.69 (m, 2H), 5.49 (s, 2H), 4.25 (s, 3H), 4.20 (d, J = 7.0 Hz, 2H), 3.95-3.78 (m, 1H), 2.84 (s, 3H), 2.61-2.44 (m, 1H), 2.16-1.90 (m, 3H), 1.85-1.71 (m, 1H), 1.50 (dd, J = 13.2, 4.5 Hz, 1H), 1.04-0.86 (m, 1H), 0.36-0.23 (m, 2H), 0.14-0.03 (m, 2H). |
| 628 | 1H NMR (400 MHz, DMSO-d6) δ 8.17 (s, 3H), 8.08 (d, J = 8.3 Hz, 1H), 7.48-7.38 (m, 3H), 7.20 (t, J = 7.3 Hz, 1H), 7.15 (d, J = 8.0 Hz, 2H), 6.81 (d, J = 8.3 Hz, 1H), 6.65 (s, 1H), 6.40 (s, 1H), 4.94-4.24 (m, 2H, buried under water peak), 4.18 (d, J = 7.0 Hz, 2H), 4.10 (s, 3H), 3.75 (s, 3H), 2.82 (s, 3H), 2.32 (s, 1H), 1.92-1.76 (m, 3H), 1.69-1.58 (m, 1H), 1.36 (dd, J = 12.8, 4.3 Hz, 1H), 1.02 (p, J = 5.6 Hz, 1H), 0.22 (q, J = 4.9 Hz, 2H), 0.05 (q, J = 4.9 Hz, 2H). |
| 629 | 1H NMR (400 MHz, DMSO-d6) δ 8.10-7.79 (m, 3H), 7.89 (d, J = 8.4 Hz, 1H), 7.28 (s, 1H), 6.58 (d, J = 8.4 Hz, 1H), 6.54 (s, 1H), 6.37 (s, 1H), 4.30 (d, J = 7.0 Hz, 2H), 4.07 (s, 3H), 3.90 (s, 3H), 3.36-3.03 (m, 3H), 2.78 (s, 3H), 2.09-1.93 (m, 1H), 1.82-1.68 (m, 1H), 1.67-1.49 (m, 2H), 1.22-1.08 (m, 1H), 0.36-0.18 (m, 4H). (Missing 2) |
| 630 | 1H NMR (400 MHz, Methanol-d4) δ 7.99 (d, J = 8.5 Hz, 1H), 7.47 (s, 1H), 6.85 (s, 1H), 6.82-6.74 (m, 2H), 5.36 (q, J = 6.9 Hz, 1H), 4.55-4.33 (m, 1H), 4.26 (s, 3H), 4.21 (dd, J = 14.6, 7.3 Hz, 1H), 4.09 (dd, J = 14.5, 7.0 Hz, 1H), 3.73-3.59 (m, 1H), 3.56-3.36 (m, 3H), 2.82 (s, 3H), 2.75 (s, 3H), 2.29-2.15 (m, 1H), 2.04-1.65 (m, 3H), 1.61 (d, J = 6.9 Hz, 3H), 1.07-0.95 (m, 1H), 0.42-0.28 (m, 2H), 0.22-0.12 (m, 2H). |
| 631 | 1H NMR (400 MHz, Methanol-d4) δ 7.98 (d, J = 8.5 Hz, 1H), 7.45 (s, 1H), 6.82 (s, 1H), 6.80-6.73 (m, 2H), 5.28 (q, J = 6.9 Hz, 1H), 4.54-4.16 (m, 5H), 4.08 (dd, J = 14.5, 7.2 Hz, 1H), 3.77-3.55 (m, 1H), 3.54-3.35 (m, 3H), 2.82 (s, 3H), 2.43-2.30 (m, 6H), 2.27-2.13 (m, 1H), 1.94-1.65 (m, 3H), 1.59 (d, J = 6.9 Hz, 3H), 1.14-0.96 (m, 1H), 0.42-0.29 (m, 2H), 0.25-0.09 (m, 2H). |
| 632 | $^1$H NMR (400 MHz, DMSO-$d_6$) δ 8.37 (d, J = 7.9 Hz, 1H), 8.01 (brs, 2H), 7.97 (d, J = 8.1 Hz, 1H), 7.80 (brs, 2H), 7.31 (brs, 1H), 7.24 (brs, 1H), 7.10 (d, J = 8.0 Hz, 1H), 6.66 (s, 1H), 6.43 (s, 1H), 5.15-4.90 (m, 2H), 4.60-4.19 (m, 3H), 4.13 (s, 3H), 3.44-3.06 (m, 3H), 2.84-2.69 (m, 1H), 2.47 (s, 3H), 2.45-2.34 (m, 1H), 2.09-1.52 (m, 6H), 1.48 (d, J = 7.0 Hz, 3H), 1.08-0.84 (m, 3H), 0.46-0.32 (m, 2H), 0.30-0.20 (m, 2H), 0.20-0.11 (m, 2H). |

Biological Example

Protein Expression and Purification

The open reading frame of human PAD4 (NM_012387), A2P663, was PCR amplified from a DNA template purchased from OriGene (catalog number RC206501) using Taq polymerase with the following pair of 5' (GCCCAGGGGACATTGATCCGT) (SEQ ID NO: 1) and 3' (TCAGGGCACCATGTTCCACCA) (SEQ ID NO: 2) primer that contains a stop codon. The PCR product was ligated into linearized pET-SUMO vector (Invitrogen, Carlsbad, CA), which is part of the Champion™ pET SUMO Protein Expression System. After sequence verification for the correct orientation, the pET-SUMO-hPAD4 expression plasmid was transformed into BL21(DE3) cells.

*E. Coli* BL21(DE3) cells were inoculated in LB medium with kanamycin at 37° C. until A600 nm reached about 0.5. Protein expression was induced by addition of 0.5 mM IPTG (final) and continued overnight at 16° C. at 220 rpm.

Cells were harvested by centrifugation at 5000 rpm for 10 minutes at 4° C. The pellet was resuspended in 300 ml lysis buffer (20 mM Tris-HCl, pH 8.0, 1 mM EDTA, 500 mM NaCl, 1 mM (tris(2-carboxyethyl)phosphine) (TCEP), 10% glycerol, and 1% Triton X100 and EDTA free protease inhibitor) and lysed by 3× passage through a microfluidizer (Microfluidics, Newton, MA) at 18,000 psi. The cell lysate was clarified by centrifugation at 30,000 rpm for 60 minutes at 4° C. The supernatant was applied to a 5 ml Ni-HP (GE HealthCare Cat#17524701) column preequilibrated in Ni-A buffer (20 mM Tris-HCl, pH 8.0, 20 mM Imidazole, 1 mM TCEP, 10% glycerol, and 400 mM NaCl). Bound protein was eluted with a 0-100% linear gradient of 100 mL Ni-B buffer (Ni A buffer+0.5 M Imidazole).

The His-Sumo tag was cleaved using sumo protease (Thermo Fisher Cat#: 12588018) while dialyzing in buffer (20 mM Tris-HCl, pH 8.0, 1 mM EDTA, 500 mM NaCl, 1 mM TCEP, 10% glycerol). The protein was then reloaded onto a Ni—HP column for a reverse purification step and recovered in flow through fraction. The protein with His-Sumo tag removed was then polished using a 16/60 Superdex-200 gel filtration column with gel filtration buffer (20 mM Tris pH 8.0, NaCl 400 mM and 1 mM TCEP). The fractions containing the protein were pulled and frozen at −80° C.

In Vitro PAD4 BAEE Biochemical Assay

The enzymatic activity of human PAD4 was monitored in a biochemical assay in the presence or absence of compounds using the small peptidyl arginine mimic BAEE (Na-Benzoyl-L-arginine ethyl ester hydrochloride) as substrate. PAD4 activity led to deamination of BAEE and release of ammonia. Levels of ammonia were monitored by using an amine coupling reaction and were indicative of PAD4 enzymatic activity.

One hundred nanoliters of test compounds dissolved in DMSO at various concentrations were dispensed into a 384-well black OptiPlate using a Labcyte Echo instrument. Ten microliters of a solution of recombinant PAD4 and calcium chloride diluted in PAD4 assay buffer (50 mM MOPS [3-(N-morpholino) propanesulfonic acid], pH 7.6; 50 mM sodium chloride; 0.05% Tween-20; 2 mM dithiothreitol) was added to the compound-containing plate and was incubated for 30 minutes at 25° C. Ten microliters of a solution of BAEE (Sigma-Aldrich #B4500) diluted in PAD4 assay buffer was then added to start the reaction. Final concentrations were 5 nM PAD4, 2 mM calcium chloride, and 3 mM BAEE. The reaction mixture was incubated at 25° C. for 2 hours and was stopped with the addition of 10 microliters of a solution of 75 mM EDTA (Ethylenediaminetetraacetic acid) in PAD4 assay buffer. Thirty microliters of detection solution (5 mM o-phthalaldehyde, 50 mM MOPS [3-(N-morpholino) propanesulfonic acid], pH 7.6; 50 mM sodium chloride; 0.05% Tween-20; 5 mM dithiothreitol) was then added and the reaction was incubated for 1 hour at 25° C. The level of fluorescent thiol-substituted isoindole resulting from the reaction of ammonia, o-phthalaldehyde, and dithiothreitol was measured on an Envision plate reader (PerkinElmer) with 405 nm excitation and 535 nm emission.

Data were normalized based on maximum inhibition (50 micromolar of the covalent PAD inhibitor BB-Cl-Amidine (Bicker, K. L.; Anguish, L.; Chumanevich, A. A.; Cameron, M. D.; Cui, X.; Witalison, E.; Subramanian, V.; Zhang, X.; Chumanevich, A. P.; Hofseth, L. J.; Coonrod, S. A.; Thompson, P. R. ACS Med. Chem. Lett. 2012, 3, 1081-1085). and no inhibition (DMSO) controls. Least squares curve fittings were performed using a four-parameter variable slope non-linear regression model. $IC_{50}$ is defined as the concentration of compound required to inhibit 50% of maximum activity. $IC_{50}$ values from multiple experiments were averaged by geometric mean and the standard deviation was calculated. Data is shown in Table 3.

TABLE 3

| Ex | $IC_{50}$ (nM) |
|---|---|
| 1 | 85.7 |
| 2 | 50000 |
| 3 | 11000 |
| 4 | 23400 |
| 5 | 19000 |
| 6 | 50000 |
| 7 | 127 |
| 8 | 144 |
| 9 | 28 |
| 10 | 259 |
| 11 | 253 |
| 12 | 29100 |
| 13 | 1780 |
| 14 | 50000 |
| 15 | 297 |
| 16 | 114 |
| 17 | 348 |
| 18 | 578 |
| 19 | 50000 |
| 20 | 3860 |
| 21 | 2060 |
| 22 | 483 |
| 23 | 61.3 |
| 24 | 9010 |
| 25 | 4450 |
| 26 | 151 |
| 27 | 50000 |
| 29 | 108 |
| 30 | 82.4 |
| 31 | 487 |
| 32 | 83.0 |
| 33 | 69.8 |
| 34 | 57.9 |
| 35 | 50000 |
| 36 | 369 |
| 37 | 50000 |
| 38 | 30600 |
| 39 | 86.2 |
| 40 | 64.5 |
| 41 | 27.0 |
| 42 | 23.3 |
| 43 | 49.6 |
| 44 | 56.1 |
| 45 | 25.1 |
| 46 | 33.4 |
| 47 | 24.22 |
| 48 | 34.4 |
| 49 | 22.2 |
| 50 | 30.6 |
| 51 | 30.9 |
| 52 | 31.4 |
| 53 | 37.2 |
| 54 | 28.7 |
| 55 | 52.6 |
| 56 | 254 |
| 57 | 589 |
| 58 | 771 |
| 59 | 194 |
| 60 | 226 |
| 61 | 37.8 |
| 62 | 48.3 |
| 63 | 84.9 |
| 64 | 38.5 |
| 65 | 33.6 |
| 66 | 68.5 |
| 67 | 124 |
| 68 | 45.3 |
| 69 | 41.0 |
| 70 | 63.2 |
| 71 | 63.4 |
| 72 | 32.7 |
| 73 | 38.7 |
| 74 | 28.3 |
| 75 | 39.2 |
| 76 | 58.0 |
| 77 | 30.7 |
| 78 | 41.4 |
| 79 | 56.0 |
| 80 | 28.6 |
| 81 | 112 |
| 82 | 51.2 |
| 83 | 47.2 |
| 84 | 59.7 |
| 85 | 28.7 |
| 86 | 57.8 |

TABLE 3-continued

| Ex | IC$_{50}$ (nM) |
|---|---|
| 87 | 28.6 |
| 88 | 44.2 |
| 89 | 40.1 |
| 90 | 30.4 |
| 91 | 43.0 |
| 92 | 59.7 |
| 93 | 68.4 |
| 94 | 38.0 |
| 95 | 43.5 |
| 96 | 39.0 |
| 97 | 30.6 |
| 98 | 33.2 |
| 99 | 52.2 |
| 100 | 76.7 |
| 101 | 22.5 |
| 102 | 46.6 |
| 103 | 66.6 |
| 104 | 88.3 |
| 105 | 56.0 |
| 106 | 40.6 |
| 107 | 44.3 |
| 108 | 52.3 |
| 109 | 31.7 |
| 110 | 50000 |
| 111 | 305 |
| 112 | 307 |
| 113 | 50000 |
| 114 | 220 |
| 115 | 177 |
| 116 | 34.8 |
| 117 | 33.4 |
| 118 | 63.7 |
| 119 | 34.5 |
| 120 | 30.1 |
| 121 | 108 |
| 122 | 78.5 |
| 123 | 79.0 |
| 124 | 13000 |
| 125 | 78.7 |
| 126 | 45.9 |
| 127 | 76.24 |
| 128 | 35.8 |
| 129 | 56.3 |
| 130 | 47.2 |
| 131 | 30.4 |
| 132 | 698 |
| 133 | 56.1 |
| 134 | 66.5 |
| 135 | 106 |
| 136 | 143 |
| 137 | 107 |
| 138 | 328 |
| 139 | 208 |
| 140 | 118 |
| 141 | 187 |
| 142 | 121 |
| 143 | 139 |
| 144 | 130 |
| 145 | 215 |
| 146 | 160 |
| 147 | 403 |
| 148 | 56.2 |
| 149 | 77.0 |
| 150 | 41.0 |
| 151 | 59.8 |
| 152 | 63.5 |
| 153 | 68.7 |
| 154 | 53.4 |
| 155 | 45.5 |
| 156 | 20.3 |
| 157 | 133 |
| 158 | 73.8 |
| 159 | 58.3 |
| 160 | 53.2 |
| 161 | 79.8 |
| 162 | 99.1 |
| 163 | 19.1 |
| 164 | 79.0 |

TABLE 3-continued

| Ex | IC$_{50}$ (nM) |
|---|---|
| 165 | 60.5 |
| 166 | 56.0 |
| 167 | 2700 |
| 168 | 171 |
| 169 | 68.5 |
| 170 | 161 |
| 171 | 179 |
| 172 | 98.3 |
| 173 | 497 |
| 174 | 297 |
| 175 | 181 |
| 176 | 88.7 |
| 177 | 76.3 |
| 178 | 89.4 |
| 179 | 85.0 |
| 180 | 494 |
| 181 | 10500 |
| 182 | 1360 |
| 183 | 237 |
| 184 | 17700 |
| 185 | 139 |
| 186 | 274 |
| 187 | 300 |
| 188 | 50000 |
| 189 | 67.3 |
| 190 | |
| 191 | 708 |
| 192 | 689 |
| 193 | 400 |
| 194 | 1090 |
| 195 | 519 |
| 196 | 29.3 |
| 197 | 41.3 |
| 198 | 185 |
| 199 | 35.4 |
| 200 | 44.1 |
| 201 | 17.4 |
| 202 | 52.0 |
| 203 | 32.4 |
| 204 | 30.1 |
| 205 | 34.8 |
| 206 | 37.9 |
| 207 | 46.0 |
| 208 | 111 |
| 209 | 37.8 |
| 210 | 39.7 |
| 211 | 31.6 |
| 212 | 64.5 |
| 213 | 46.9 |
| 214 | 45.0 |
| 215 | 44.2 |
| 216 | 48.3 |
| 217 | 45.9 |
| 218 | 55.5 |
| 219 | 124 |
| 220 | 79.1 |
| 221 | 62.0 |
| 222 | 20.0 |
| 223 | 77.3 |
| 224 | 31.5 |
| 225 | 81.3 |
| 226 | 42.3 |
| 227 | 65.2 |
| 228 | 48.6 |
| 229 | 108 |
| 230 | 70.0 |
| 231 | 64.2 |
| 232 | 68.5 |
| 233 | 103 |
| 234 | 149 |
| 235 | 63.6 |
| 236 | 55.6 |
| 237 | 35.6 |
| 238 | 145 |
| 239 | 81.7 |
| 240 | 84.4 |
| 241 | 54.5 |
| 242 | 238 |

TABLE 3-continued

| Ex | IC$_{50}$ (nM) |
|---|---|
| 243 | 80.7 |
| 244 | 89.6 |
| 245 | 62.2 |
| 246 | 82.2 |
| 247 | 70.0 |
| 248 | 55.9 |
| 249 | 66.0 |
| 250 | 193 |
| 251 | 50.2 |
| 252 | 98.1 |
| 253 | 135 |
| 254 | 110 |
| 255 | 286 |
| 256 | 486 |
| 257 | 208 |
| 258 | 225 |
| 259 | 180 |
| 260 | 122 |
| 261 | 144 |
| 262 | 867 |
| 263 | 71.1 |
| 264 | 134 |
| 265 | 72.0 |
| 266 | 341 |
| 267 | 521 |
| 268 | 257 |
| 269 | 67.8 |
| 270 | 34.7 |
| 271 | 35.6 |
| 272 | 134 |
| 273 | 83.1 |
| 274 | 252 |
| 275 | 14.1 |
| 276 | 61.6 |
| 277 | 191 |
| 278 | 144 |
| 279 | 234 |
| 280 | 33800 |
| 281 | 16200 |
| 282 | 10400 |
| 283 | 11700 |
| 284 | 13400 |
| 285 | 14000 |
| 286 | 50000 |
| 287 | 46300 |
| 288 | 8360 |
| 289 | 50000 |
| 290 | 9870 |
| 291 | 6360 |
| 292 | 50000 |
| 293 | 50000 |
| 294 | 38400 |
| 295 | 27200 |
| 296 | 24600 |
| 297 | 50000 |
| 298 | 30000 |
| 299 | 8050 |
| 300 | 50000 |
| 301 | 50000 |
| 302 | 21700 |
| 303 | 23500 |
| 304 | 19200 |
| 305 | 36200 |
| 306 | 1610 |
| 307 | 25600 |
| 308 | 241 |
| 309 | 780 |
| 310 | 886 |
| 311 | 383 |
| 312 | 31200 |
| 313 | 24200 |
| 314 | 38700 |
| 315 | 350 |
| 316 | 306 |
| 317 | 813 |
| 318 | 50000 |
| 319 | 50000 |
| 320 | 19100 |
| 321 | 278 |
| 322 | 258 |
| 323 | 49900 |
| 324 | 611 |
| 325 | 154 |
| 326 | 3560 |
| 327 | 50000 |
| 328 | 4880 |
| 329 | 5660 |
| 330 | 233 |
| 331 | 1420 |
| 332 | 390 |
| 333 | 50000 |
| 334 | 50000 |
| 335 | 178 |
| 336 | 484 |
| 337 | 12100 |
| 338 | 50000 |
| 339 | 21500 |
| 340 | 230 |
| 341 | 643 |
| 342 | 14100 |
| 343 | 50000 |
| 344 | 50000 |
| 345 | 50000 |
| 346 | 2130 |
| 347 | 10100 |
| 348 | 144 |
| 349 | 485 |
| 350 | 50000 |
| 351 | 6510 |
| 352 | 711 |
| 353 | 26800 |
| 354 | 1890 |
| 355 | 50000 |
| 356 | 50000 |
| 357 | 50000 |
| 358 | 50000 |
| 359 | 420 |
| 360 | 725 |
| 361 | 258 |
| 362 | 248 |
| 363 | 1960 |
| 364 | 50000 |
| 365 | 403 |
| 366 | 499 |
| 367 | 5310 |
| 368 | 43600 |
| 369 | 13600 |
| 370 | 17100 |
| 371 | 10600 |
| 372 | 2000 |
| 373 | 50000 |
| 374 | 50000 |
| 375 | 2730 |
| 376 | 404 |
| 377 | 18200 |
| 378 | 341 |
| 379 | 163 |
| 380 | 24700 |
| 381 | 538 |
| 382 | 204 |
| 383 | 447 |
| 384 | 888 |
| 385 | 156 |
| 386 | 126 |
| 387 | 779 |
| 388 | 95.3 |
| 389 | 84.8 |
| 390 | 3790 |
| 391 | 104 |
| 392 | 148 |
| 393 | 2010 |
| 394 | 1070 |
| 395 | 259 |
| 396 | 194 |
| 397 | 74.8 |
| 398 | 60.7 |

TABLE 3-continued

| Ex | IC$_{50}$ (nM) |
|---|---|
| 399 | 285 |
| 400 | 847 |
| 401 | 136 |
| 402 | 203 |
| 403 | 754 |
| 404 | 10600 |
| 405 | 589 |
| 406 | 194 |
| 407 | 129 |
| 408 | 3020 |
| 409 | 1170 |
| 410 | 233 |
| 411 | 143 |
| 412 | 156 |
| 413 | 253 |
| 414 | 5250 |
| 415 | 27900 |
| 416 | 337 |
| 417 | 7180 |
| 418 | 151 |
| 419 | 1170 |
| 420 | 60.6 |
| 421 | 341 |
| 422 | 6370 |
| 423 | 1770 |
| 424 | 18000 |
| 426 | 125 |
| 427 | 94.7 |
| 428 | 1020 |
| 429 | 851 |
| 430 | 943 |
| 431 | 2030 |
| 432 | 2490 |
| 433 | 7040 |
| 434 | 3410 |
| 435 | 11300 |
| 436 | 202 |
| 437 | 550 |
| 438 | 194 |
| 439 | 24.3 |
| 440 | 207 |
| 441 | 73.1 |
| 442 | 40.9 |
| 443 | 34.4 |
| 444 | 130 |
| 445 | 80.6 |
| 446 | 73.3 |
| 447 | 187 |
| 448 | 6710 |
| 449 | 6670 |
| 450 | 21.6 |
| 451 | 21.8 |
| 452 | 246 |
| 453 | 9320 |
| 454 | 145 |
| 455 | 113 |
| 456 | 250 |
| 457 | 52.2 |
| 458 | 52.3 |
| 459 | 28.0 |
| 460 | 99.9 |
| 461 | 294 |
| 462 | 39.7 |
| 463 | 133 |
| 464 | 100 |
| 465 | 85.6 |
| 466 | 143 |
| 467 | 361 |
| 468 | 238 |
| 469 | 781 |
| 470 | 165 |
| 471 | 1360 |
| 472 | 50000 |
| 473 | 117 |
| 474 | 44.2 |
| 475 | 75.1 |
| 476 | 46.8 |
| 477 | 100 |
| 478 | 236 |
| 479 | 181 |
| 480 | 166 |
| 481 | 152 |
| 482 | 171 |
| 483 | 128 |
| 484 | 145 |
| 485 | 50000 |
| 486 | 666 |
| 487 | 331 |
| 488 | 86.8 |
| 489 | 177 |
| 490 | 75.4 |
| 491 | 32000 |
| 492 | 2086 |
| 493 | 2500 |
| 494 | 276 |
| 495 | 202 |
| 496 | 418 |
| 497 | 1230 |
| 498 | 673 |
| 499 | 481 |
| 500 | 160 |
| 501 | 827 |
| 502 | 258 |
| 503 | 115 |
| 504 | 132 |
| 505 | 170 |
| 506 | 42300 |
| 507 | 152 |
| 508 | 277 |
| 509 | 655 |
| 510 | 17100 |
| 511 | 4680 |
| 512 | 17700 |
| 513 | 179 |
| 514 | 741 |
| 515 | 125 |
| 516 | 65.6 |
| 517 | 618 |
| 518 | 344 |
| 519 | 101 |
| 520 | 73.8 |
| 521 | 122 |
| 522 | 135 |
| 523 | 59.1 |
| 524 | 78.9 |
| 525 | 228 |
| 526 | 458 |
| 527 | 220 |
| 528 | 64.3 |
| 529 | 151 |
| 530 | 274 |
| 531 | 134 |
| 532 | 1480 |
| 533 | 933 |
| 534 | 140 |
| 535 | 305 |
| 536 | 128 |
| 537 | 571 |
| 538 | 175 |
| 539 | 58.6 |
| 540 | 102 |
| 541 | 270 |
| 542 | 119 |
| 543 | 108 |
| 544 | 361 |
| 545 | 81.8 |
| 546 | 156 |
| 547 | 715 |
| 548 | 532 |
| 549 | 3670 |
| 550 | 1850 |
| 551 | 511 |
| 552 | 153 |
| 553 | 757 |
| 554 | 81.0 |
| 555 | 69.3 |

TABLE 3-continued

| Ex | IC$_{50}$ (nM) |
|---|---|
| 556 | 296 |
| 557 | 77.7 |
| 558 | 220 |
| 559 | 96.5 |
| 560 | 114 |
| 561 | 193 |
| 562 | 83.1 |
| 563 | 106 |
| 564 | 332 |
| 565 | 159 |
| 566 | 123 |
| 567 | 114 |
| 568 | 133 |
| 569 | 145 |
| 570 | 227 |
| 571 | 465 |
| 572 | 152 |
| 573 | 1000 |
| 574 | 110 |
| 575 | 130 |
| 576 | 2150 |
| 577 | 996 |
| 578 | 346 |
| 579 | 412 |
| 580 | 50000 |
| 581 | 23000 |
| 582 | 50000 |
| 583 | 535 |
| 584 | 84.5 |
| 585 | 174 |
| 586 | 3210 |
| 587 | 4460 |
| 588 | 10600 |
| 589 | 2680 |
| 590 | 9820 |
| 591 | 936 |
| 592 | 9000 |
| 593 | 1900 |
| 594 | 1700 |
| 595 | 31500 |
| 596 | 997 |
| 597 | 299 |
| 598 | 312 |
| 599 | 1910 |
| 600 | 666 |
| 601 | 6880 |
| 602 | 2150 |
| 603 | 1920 |
| 604 | 427 |
| 605 | 518 |
| 606 | 373 |
| 607 | 345 |
| 608 | 544 |
| 609 | 711 |
| 610 | 4630 |
| 611 | 726 |
| 612 | 743 |
| 613 | 302 |
| 614 | 90.2 |
| 615 | 69.6 |
| 616 | 294 |
| 617 | 6980 |
| 618 | 401 |
| 619 | 686 |
| 620 | 1190 |
| 621 | 1020 |
| 622 | 894 |
| 623 | 131 |
| 624 | 114 |
| 625 | 50000 |
| 626 | 50000 |
| 627 | 3360 |
| 628 | 553 |
| 629 | 2270 |
| 630 | 9400 |
| 631 | 10000 |
| 632 | 140 |

What is claimed is:
1. A compound of Formula I:

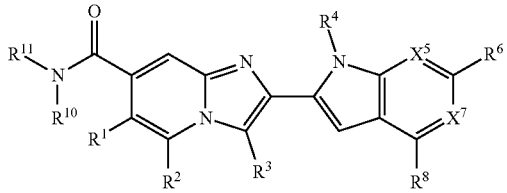

or a pharmaceutically acceptable salt thereof, wherein:
$X^5$ is N;
$X^7$ is CH or CF;
$R^1$ is hydrogen, or halo;
$R^2$ is hydrogen, halo, —CN, —$OR^{12}$, —$N(R^{12})_2$, —$SR^{12}$, —$S(O)R^{20}$, $C_{1-8}$ alkyl optionally substituted with 1 to 5 $Z^1$, $C_{3-6}$ cycloalkyl optionally substituted with 1 to 5 $Z^1$, or 4-6 membered heterocyclyl optionally substituted with 1 to 5 $Z^1$;
$R^3$ is hydrogen, —$N(R^{12})_2$, $C_{1-8}$ alkyl optionally substituted with 1 to 5 $Z^1$, $C_{2-8}$ alkenyl optionally substituted with 1 to 5 $Z^1$, $C_{2-8}$ alkynyl optionally substituted with 1 to 5 $Z^1$, $C_{3-10}$ cycloalkyl optionally substituted with 1 to 5 $Z^1$, or 4-10 membered heterocyclyl optionally substituted with 1 to 5 $Z^1$; or
$R^2$ and $R^3$ are taken together with the atoms to which they are attached to form an optionally substituted 6 to 8 membered heterocyclyl ring;
$R^4$ is hydrogen, $C_{1-8}$ alkyl optionally substituted with 1 to 5 $Z^1$, $C_{6-10}$ aryl optionally substituted with 1 to 5 $Z^1$, or 5-10 membered heteroaryl optionally substituted with 1 to 5 $Z^1$;
$R^6$ is —$N(R^{14})S(O)_2R^9$, —$N(R^{14})C(O)OR^9$, —$OC(O)R^9$, —$OC(O)OR^9$, -L-$R^{13}$, —$OR^{15}$, $C_{2-8}$ alkenyl optionally substituted with 1 to 5 $Z^1$, $C_{2-8}$ alkynyl optionally substituted with 1 to 5 $Z^1$, $C_{3-10}$ cycloalkyl substituted with 1 to 5 $Z^1$, $C_{6-10}$ aryl substituted with 1 to 5 $Z^1$, 4-10 membered heterocyclyl substituted with 1 to 5 $Z^1$,

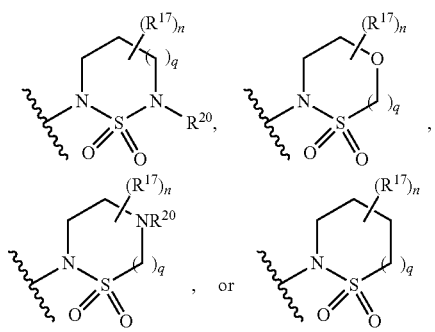

where q is 0, 1 or 2; and n is 0,1,2, 3, 4, 5, or 6;
$R^8$ is hydrogen;
each $R^9$ is independently $C_{1-8}$ alkyl optionally substituted with 1 to 5 $Z^1$, $C_{2-8}$ alkenyl optionally substituted with 1 to 5 $Z^1$, $C_{2-8}$ alkynyl optionally substituted with 1 to 5 $Z^1$, $C_{3-10}$ cycloalkyl optionally substituted with 1 to 5 $Z^1$, 4-10 membered heterocyclyl optionally substituted with 1 to 5 $Z^1$, $C_{6-10}$ aryl optionally substituted with 1 to 5 $Z^1$, or 5-10 membered heteroaryl optionally substituted with 1 to 5 $Z^1$;

the moiety

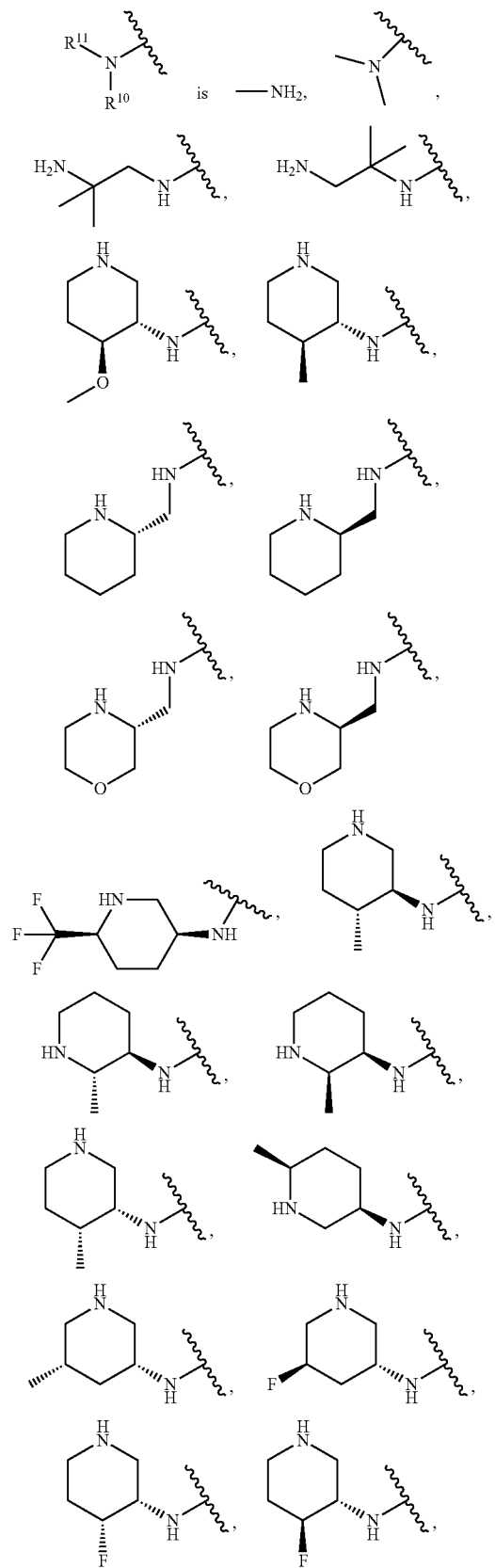

601
-continued
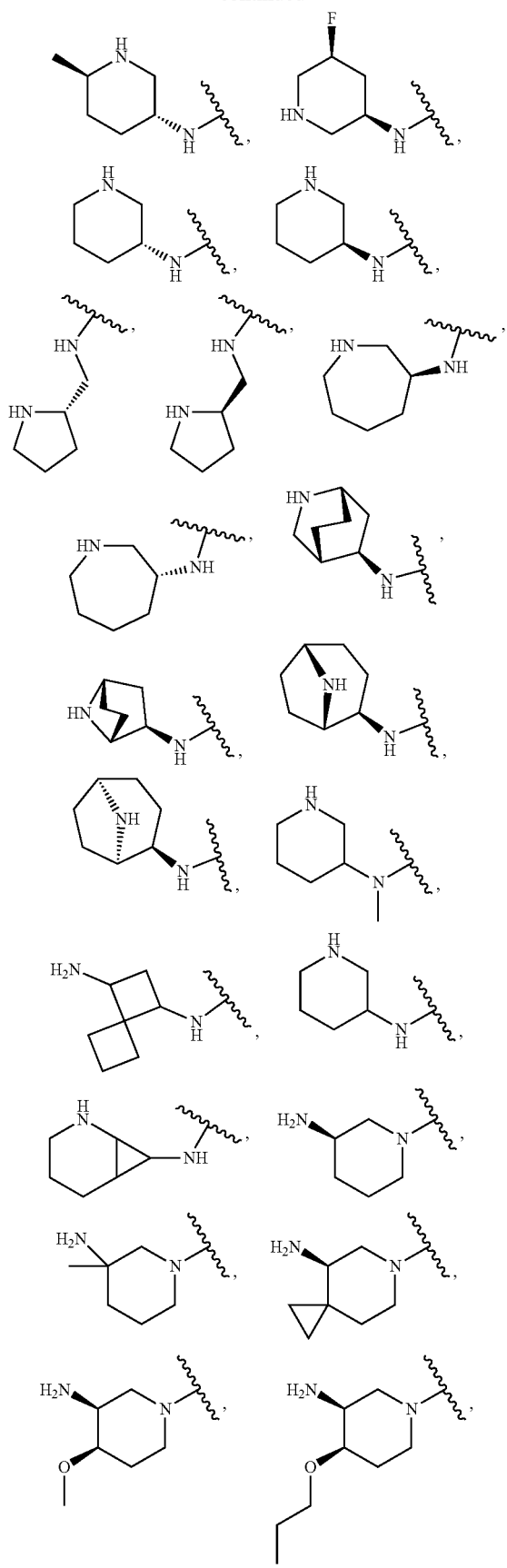
602
-continued
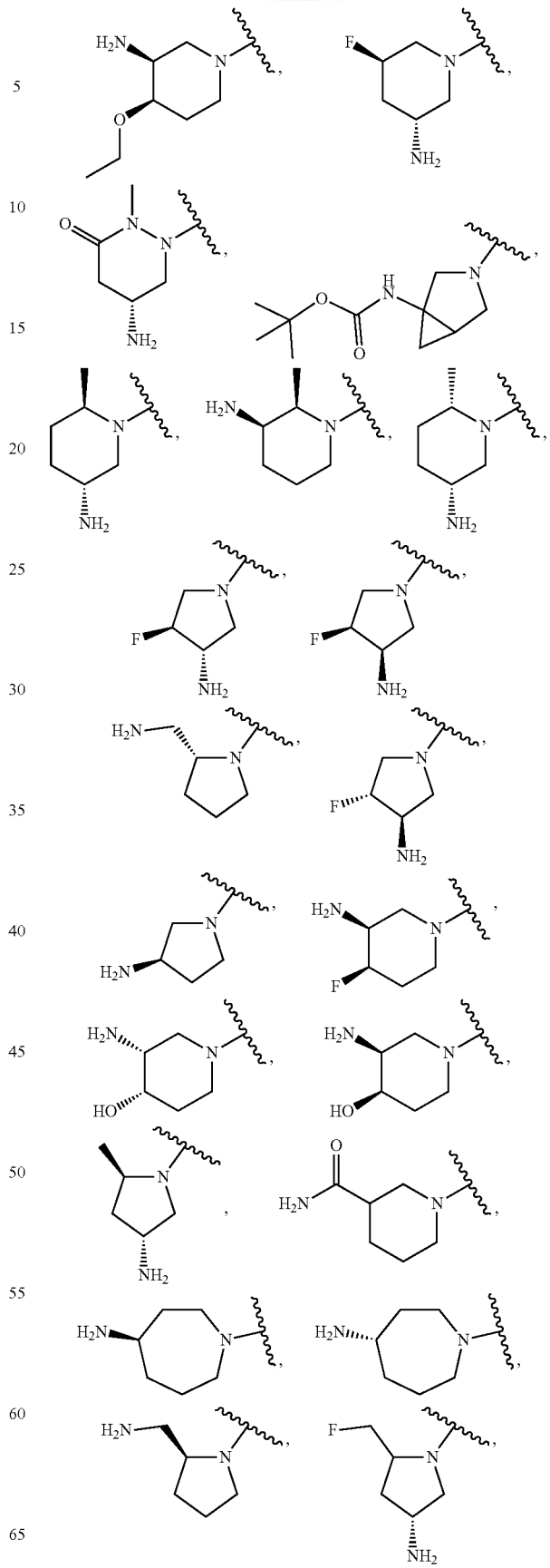

603
-continued
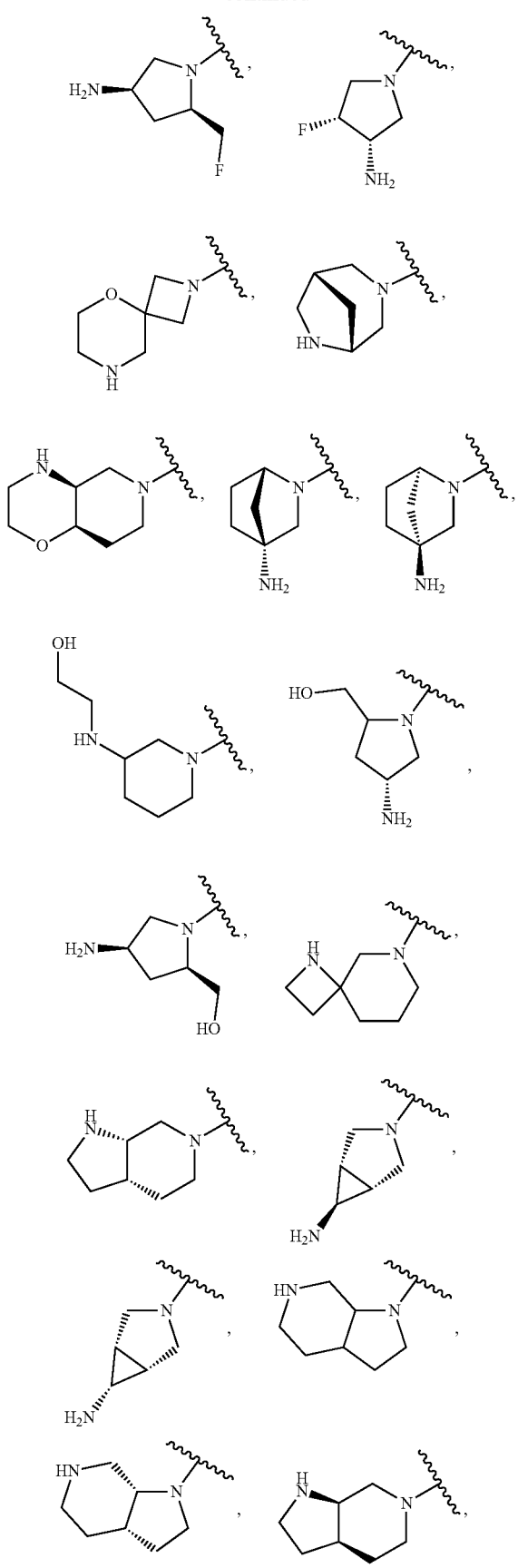
604
-continued
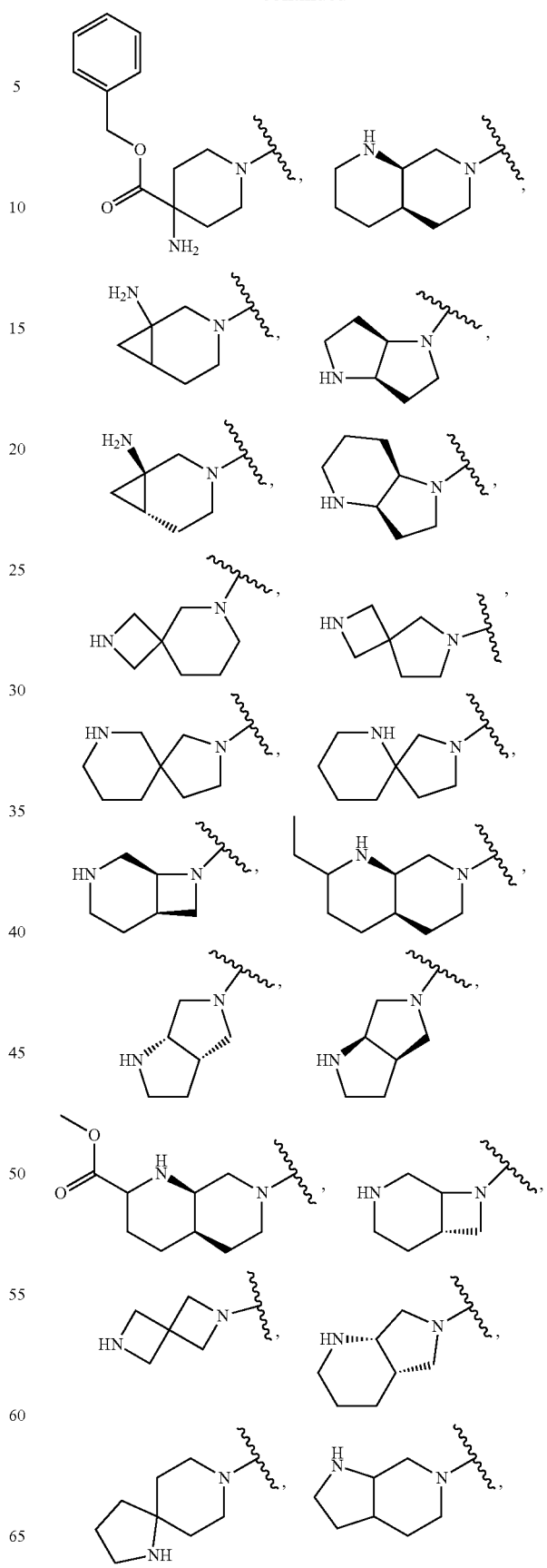

605
-continued
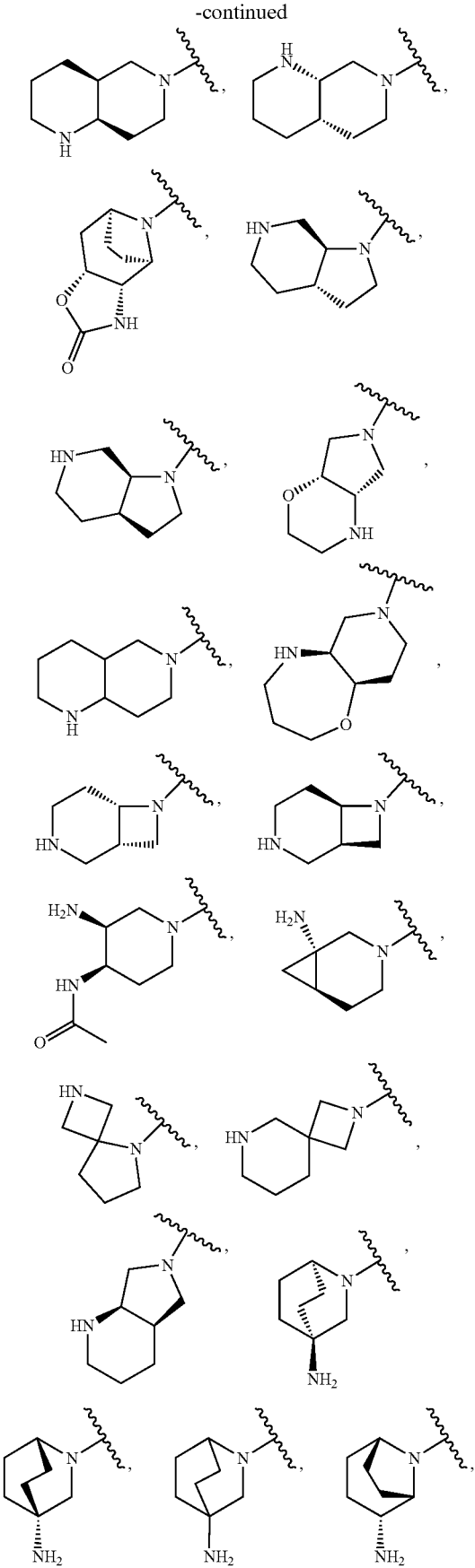
606
-continued
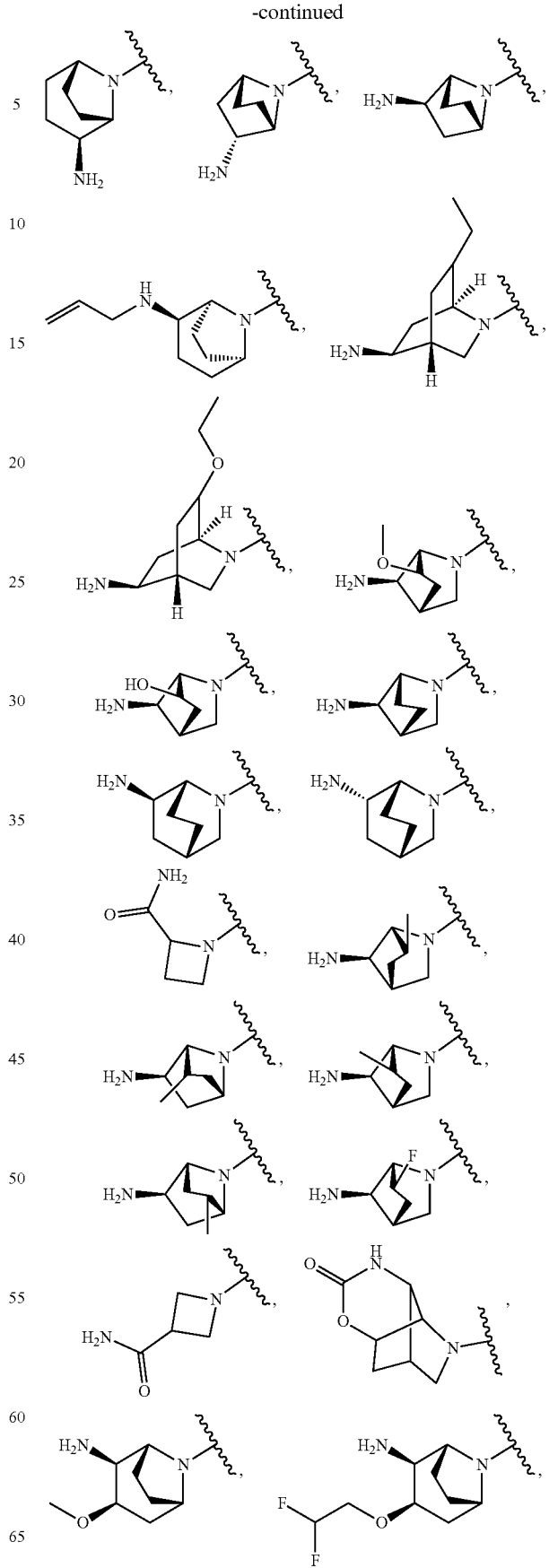

-continued

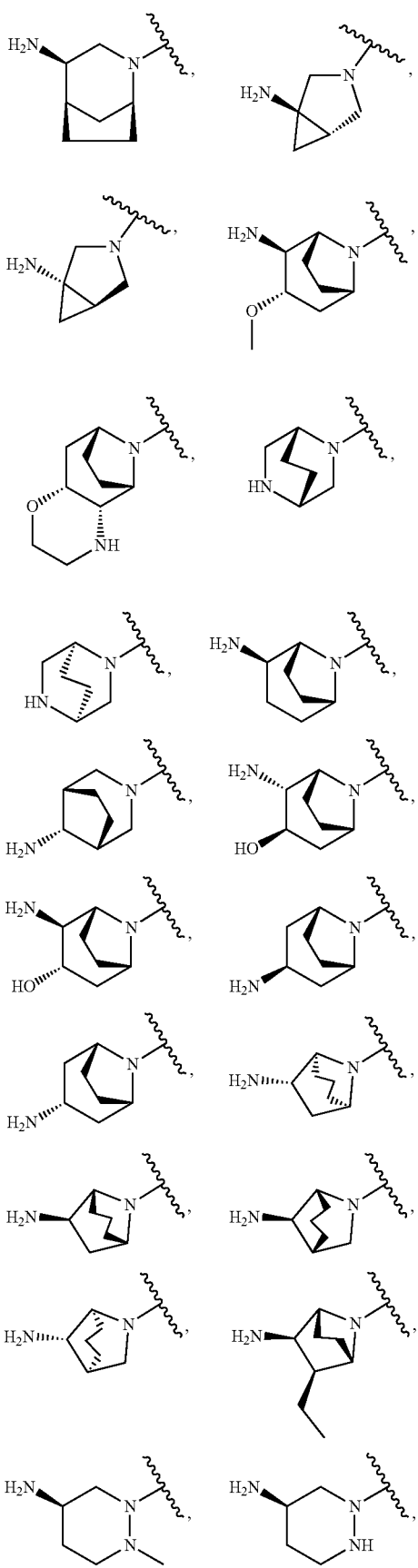
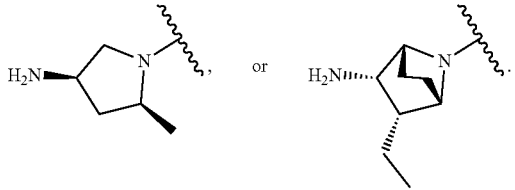

each $R^{12}$ is independently hydrogen, $C_{1-8}$ alkyl optionally substituted with 1 to 5 $Z^{1b}$, $C_{3-8}$ alkenyl optionally substituted with 1 to 5 $Z^{1b}$, $C_{3-8}$ alkynyl optionally substituted with 1 to 5 $Z^{1b}$, $C_{3-10}$ cycloalkyl optionally substituted with 1 to 5 $Z^{1b}$, 4-10 membered heterocyclyl optionally substituted with 1 to 5 $Z^{1b}$, $C_{6-10}$ aryl optionally substituted with 1 to 5 $Z^{1b}$, or 5-10 membered heteroaryl optionally substituted with 1 to 5 $Z^{1b}$;

L is $C_{1-8}$ alkylene, $C_{1-8}$ haloalkylene, or 5-10 membered heteroarylene; and each $C_{1-8}$ alkylene, $C_{1-8}$ haloalkylene, or 5-10 membered heteroarylene of L is optionally substituted with 1 to 5 $Z^1$;

$R^{13}$ is $-OR^{15}$, $-N(R^{15})(R^{14})$, $-C(O)N(R^{14})_2$, $-OC(O)N(R^{14})_2$, $-N(R^{14})C(O)R^9$, $-N(R^{14})C(O)OR^9$, $-N(R^{14})C(O)N(R^{14})_2$, $-N(R^{14})S(O)_2R^9$, $-NR^{14}S(O)_2N(R^{14})_2$, $-NR^{14}S(O)_2OR^9$, $-NS(O)(R^9)_2$, $-Si(R^{14})_2R^9$, $-SR^9$, $-S(O)R^9$, $-S(O)_2R^9$, $-SF_5$, $-S(O)(NR^{14})R^9$, $-S(NR^{14})(NR^{14})R^9$, $-S(O)(NR^{14})N(R^{14})_2$, $-S(O)(NCN)R^9$, $-S(O)_2N(R^{14})_2$, $-C(O)N(R^{14})S(O)_2R^9$, $-S(O)_2N(R^{14})C(O)R^9$, or $C_{3-10}$ cycloalkyl substituted with 1 to 5 $Z^1$;

each $R^{14}$ is independently hydrogen, $C_{1-8}$ alkyl optionally substituted with 1 to 5 $Z^1$, $C_{2-8}$ alkenyl optionally substituted with 1 to 5 $Z^1$, $C_{2-8}$ alkynyl optionally substituted with 1 to 5 $Z^1$, $C_{3-10}$ cycloalkyl optionally substituted with 1 to 5 $Z^1$, 4-10 membered heterocyclyl optionally substituted with 1 to 5 $Z^1$, $C_{6-10}$ aryl optionally substituted with 1 to 5 $Z^1$, or 5-10 membered heteroaryl optionally substituted with 1 to 5 $Z^1$;

$R^{15}$ is cycloalkyl optionally substituted with 1 to 5 $Z^1$, 4-10 membered heterocyclyl optionally substituted with 1 to 5 $Z^1$, $C_{6-10}$ aryl optionally substituted with 1 to 5 $Z^1$, 5-10 membered heteroaryl optionally substituted with 1 to 5 $Z^1$;

each $R^{17}$ is independently hydrogen, halo, $-NO_2$, $-N_3$, $-CN$, $C_{1-8}$ alkyl optionally substituted by 1 to 3 $Z^{1a}$, $C_{2-8}$ alkenyl optionally substituted by 1 to 3 $Z^{1a}$, $C_{2-8}$ alkynyl optionally substituted by 1 to 3 $Z^{1a}$, $C_{3-8}$ cycloalkyl optionally substituted by 1 to 3 $Z^{1a}$, 6-10 membered aryl optionally substituted by 1 to 3 $Z^{1a}$, 4-10 membered heterocyclyl optionally substituted by 1 to 3 $Z^{1a}$, 5-10 membered heteroaryl optionally substituted with 1 to 3 $Z^{1a}$, $-OR^{20}$, $-C(O)R^{20}$, $-C(O)OR^{20}$, $-C(O)N(R^{20})_2$, $-N(R^{20})_2$, $-N(R^{20})_3+$, $-N(R^{20})C(O)R^{20}$, $-N(R^{20})C(O)OR^{20}$, $-N(R^{20})C(O)N(R^{20})_2$, $-N(R^{20})S(O)_2(R^{20})$, $-NR^{20}S(O)_2N(R^{20})_2$, $-NR^{20}S(O)_2O(R^{20})$, $-NS(O)(R^{20})_2$, $-OC(O)R^{20}$, $-OC(O)OR^{20}$, $-OC(O)N(R^{20})_2$, $-Si(R^{20})_3$, $-SR^{20}$, $-S(O)R^{20}$, $-SF_5$, $-S(O)(NR^{20})R^{20}$, $-S(NR^{20})(NR^{20})R^{20}$, $-S(O)(NR^{20})N(R^{20})_2$, $-S(O)(NCN)R^{20}$, $-S(O)_2R^{20}$, $-S(O)_2N(R^{20})_2$, $-C(O)N(R^{20})S(O)_2R^{20}$, or $-S(O)_2N(R^{20})C(O)R^{20}$; or two $R^{17}$ on the same or different carbon atoms are taken together to form a 3-8-membered ring optionally substituted with 1 to $4Z^1$;

each $Z^1$ is independently halo, $-NO_2$, $-N_3$, $-CN$, $C_{1-8}$ alkyl optionally substituted by 1 to 5 Zia $C_{2-8}$ alkenyl optionally substituted by 1 to 5 $Z^{1a}$, $C_{2-8}$ alkynyl optionally substituted by 1 to 5 Zia $C_{3-10}$ cycloalkyl optionally substituted by 1 to 5 $Z^{1a}$, 6-10 membered $C_{6-10}$ aryl optionally substituted by 1 to 5 $Z^{1a}$, 4-10 membered heterocyclyl optionally substituted by 1 to 5 $Z^{1a}$, 5-10 membered heteroaryl optionally substituted with 1 to 5 $Z^{1a}$, —$OR^{20}$, —$C(O)R^{20}$, —$C(O)OR^{20}$, —$C(O)N(R^{20})_2$, —$N(R^{20})_2$, —$N(R^{20})_3+$, —$N(R^{20})C(O)R^{20}$, —$N(R^{20})C(O)OR^{20}$, —$N(R^{20})C(O)N(R^{20})_2$, —$N(R^{20})S(O)_2(R^{20})$, —$NR^{20}S(O)_2N(R^{20})_2$, —$NR^{20}S(O)_2O(R^{20})$, —$NS(O)(R^{20})_2$, —$OC(O)R^{20}$, —$OC(O)OR^{20}$, —$OC(O)N(R^{20})_2$, —$Si(R^{20})_3$, —$SR^{20}$, —$S(O)R^{20}$, —$SF_5$, —$S(O)(NR^{20})R^{20}$, —$S(NR^{20})(NR^{20})R^{20}$, —$S(O)(NR^{20})N(R^{20})_2$, —$S(O)(NCN)R^{20}$, —$S(O)_2R^{20}$, —$S(O)_2N(R^{20})_2$, —$C(O)N(R^{20})S(O)_2R^{20}$, or —$S(O)_2N(R^{20})C(O)R^{20}$;

each $Z^{1a}$ is independently oxo, halo, —$NO_2$, —$N_3$, —CN, $C_{1-8}$ alkyl optionally substituted by 1 to 5 $Z^{1}b$, $C_{2-8}$ alkenyl optionally substituted by 1 to 5 $Z^{1b}$, $C_{2-8}$ alkynyl optionally substituted by 1 to 5 $Z^{1b}$, $C_{3-10}$ cycloalkyl optionally substituted by 1 to 5 $Z^{1b}$, 6-10 membered aryl optionally substituted by 1 to 5 $Z^{1b}$, 4-10 membered heterocyclyl optionally substituted by 1 to 5 $Z^{1b}$, 5-10 membered heteroaryl optionally substituted with 1 to 5 $Z^{1b}$, —$OR^{21}$, —$C(O)R^{21}$, —$C(O)OR^{21}$, —$C(O)N(R^{21})_2$, —$N(R^{21})_2$, —$N(R^{21})_3+$, —$N(R^{21})C(O)R^{21}$, —$N(R^{21})C(O)OR^{21}$, —$N(R^{21})C(O)N(R^{21})_2$, —$N(R^21)S(O)_2(R^{21})$, —$NR^{21}S(O)_2N(R^{21})_2$, —$NR^{21}S(O)_2O(R^{21})$, —$NS(O)(R^{21})_2$, —$OC(O)R^{21}$, —$OC(O)OR^{21}$, —$OC(O)N(R^{21})_2$, —$Si(R^{21})_3$, —$SR^{21}$, —$S(O)R^{21}$, —$SF_5$, —$S(O)(NR^{21})R^{21}$, —$S(NR^{21})(NR^{21})R^{21}$, —$S(O)(NR^{21})N(R^{21})_2$, —$S(O)(NCN)R^{21}$, —$S(O)_2R^{21}$, —$S(O)_2N(R^21)_2$, —$C(O)N(R^21)S(O)_2R^{21}$, or —$S(O)_2N(R^{21})C(O)R^{21}$;

each $R^{20}$, $R^{21}$ and $R^{22}$ is independently hydrogen, $C_{1-8}$ alkyl optionally substituted with 1 to 5 $Z^{1b}$, $C_{2-8}$ alkenyl optionally substituted with 1 to 5 $Z^{1b}$, $C_{2-8}$ alkynyl optionally substituted with 1 to 5 $Z^{1b}$, $C_{3-10}$ cycloalkyl optionally substituted with 1 to 5 $Z^{1b}$, 4-10 membered heterocyclyl optionally substituted with 1 to 5 $Z^{1b}$, $C_{6-10}$ aryl optionally substituted with 1 to 5 $Z^{1b}$, or 5-10 membered heteroaryl optionally substituted with 1 to 5 $Z^{1b}$; and each $Z^{1b}$ is independently oxo, hydroxy, halo, —$NO_2$, —$N_3$, —CN, $C_{1-9}$ alkyl, $C_{2-6}$ alkenyl, $C_{2-6}$ alkynyl, $C_{3-10}$ cycloalkyl, $C_{1-8}$ haloalkyl, $C_60.1o$ aryl, 5-10 membered heteroaryl, 4-10 membered heterocyclyl, —$O(C_{1-9}$ alkyl), —$O(C_{2-6}$ alkenyl), —$O(C_{2-6}$ alkynyl), —$O(C_{3-10}$ cycloalkyl), —$O(C_{1-8}$ haloalkyl), —O(aryl), —O(heteroaryl), —O(heterocyclyl), —OC(O) ($C_{1-9}$ alkyl), —$OC(O)(C_{2-6}$ alkenyl), —$OC(O)(C_{2-6}$ alkenyl), —$OC(O)(C_{2-6}$ alkynyl), —$OC(O)(C_{3-10}$ cycloalkyl), —$OC(O)(C_{1-8}$ haloalkyl), —OC(O)(aryl), —OC(O)(heteroaryl), —OC(O)(heterocyclyl), —$NH_2$, —NH($C_{1-9}$ alkyl), —NH($C_{2-6}$ alkenyl), —NH($C_{2-6}$ alkynyl), —NH($C_{3-10}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-10}$ cycloalkyl)$_2$, —N($C_{2-6}$ alkenyl)$_2$, —N($C_{2-6}$ alkynyl)$_2$, —N($C_{3-10}$ cycloalkyl)$_2$, —N($C_{1-8}$ haloalkyl)$_2$, —N(aryl)$_2$, —N(heteroaryl)$_2$, —N(heterocyclyl)$_2$, —N($C_{1-9}$ alkyl)($C_{3-10}$ cycloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-10}$ cycloalkyl), —N($C_{1-9}$ alkyl)($C_{1-8}$ haloalkyl), —N($C_{1-9}$ alkyl)(aryl), —N($C_{1-9}$ alkyl)(heteroaryl), —N($C_{1-9}$ alkyl)(heterocyclyl), —C(O)($C_{1-9}$ alkyl), —C(O)($C_{2-6}$ alkenyl), —C(O)($C_{2-6}$ alkynyl), —C(O)($C_{3-10}$ cycloalkyl), —C(O)($C_{1-8}$ haloalkyl), —C(O)(aryl), —C(O)(heteroaryl), —C(O)(heterocyclyl), —C(O)O($C_{1-9}$ alkyl), —C(O)O($C_{2-6}$ alkenyl), —C(O)O($C_{2-6}$ alkynyl), —C(O)O($C_{3-10}$ cycloalkyl), —C(O)O($C_{1-8}$ haloalkyl), —C(O)O(aryl), —C(O)O(heteroaryl), —C(O)O(heterocyclyl), —C(O)$NH_2$, —C(O)NH($C_{1-9}$ alkyl), —C(O)NH($C_{2-6}$ alkenyl), —C(O)NH($C_{2-6}$ alkynyl), —C(O)NH($C_{3-10}$ cycloalkyl), —C(O)NH($C_{1-8}$ haloalkyl), —C(O)NH(aryl), —C(O)NH(heteroaryl), —C(O)NH(heterocyclyl), —C(O)N($C_{1-9}$ alkyl)$_2$, —C(O)N($C_{3-10}$ cycloalkyl)$_2$, —C(O)N($C_{2-6}$ alkenyl)$_2$, —C(O)N($C_{2-6}$ alkynyl)$_2$, —C(O)N($C_{1-8}$ haloalkyl)$_2$, —C(O)N(aryl)$_2$, —C(O)N(heteroaryl)$_2$, —C(O)N(heterocyclyl)$_2$, —NHC(O)($C_{1-9}$ alkyl), —NHC(O)($C_{2-6}$ alkenyl), —NHC(O)($C_{2-6}$ alkynyl), —NHC(O)($C_{3-10}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkenyl), —NHC(O)O($C_{2-6}$ alkynyl), —NHC(O)O($C_{3-10}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —NHC(O)NH($C_{2-6}$ alkenyl), —NHC(O)NH($C_{2-6}$ alkynyl), —NHC(O)NH($C_{3-10}$ cycloalkyl), —NHC(O)NH($C_{1-8}$ haloalkyl), —NHC(O)NH(aryl), —NHC(O)NH(heteroaryl), —NHC(O)NH(heterocyclyl), —SH, —S($C_{1-9}$ alkyl), —S($C_{2-6}$ alkenyl), —S($C_{2-6}$ alkynyl), —S($C_{3-10}$ cycloalkyl), —S($C_{1-8}$ haloalkyl), —S(aryl), —S(heteroaryl), —S(heterocyclyl), —NHS(O)($C_{1-9}$ alkyl), —N($C_{1-9}$ alkyl)(S(O)($C_{1-9}$ alkyl), —S(O)N($C_{1-9}$ alkyl)$_2$, —S(O)($C_{1-9}$ alkyl), —S(O)(NH)($C_{1-9}$ alkyl), —S(O)($C_{2-6}$ alkenyl), —S(O)($C_{2-6}$ alkynyl), —S(O)($C_{3-10}$ cycloalkyl), —S(O)($C_{1-8}$ haloalkyl), —S(O)(aryl), —S(O)(heteroaryl), —S(O)(heterocyclyl), —$S(O)_2$($C_{1-9}$ alkyl), —$S(O)_2$($C_{2-6}$ alkenyl), —$S(O)_2$($C_{2-6}$ alkynyl), —$S(O)_2$($C_{3-10}$ cycloalkyl), —$S(O)_2$($C_{1-8}$ haloalkyl), —$S(O)_2$(aryl), —$S(O)_2$(heteroaryl), —$S(O)_2$(heterocyclyl), —$S(O)_2$NH($C_{1-9}$ alkyl), or —$S(O)_2$N($C_{1-9}$ alkyl)$_2$;

wherein any alkyl, cycloalkyl, aryl, heteroaryl, or heterocyclyl of $Z^{1b}$ is optionally substituted with one or more halo, $C_{1-9}$ alkyl, $C_{1-8}$ haloalkyl, —OH, —$NH_2$, —NH($C_{1-9}$ alkyl), —NH($C_{3-10}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-10}$ cycloalkyl)$_2$, —NHC(O)($C_{3-10}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkynyl), —NHC(O)O($C_{3-10}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —S(O)(NH)($C_{1-9}$ alkyl), —$S(O)_2$($C_{1-9}$ alkyl), —$S(O)_2$($C_{3-10}$ cycloalkyl), —$S(O)_2$($C_{1-8}$ haloalkyl), —$S(O)_2$(aryl), —$S(O)_2$(heteroaryl), —$S(O)_2$(heterocyclyl), —$S(O)_2$NH($C_{1-9}$ alkyl), —$S(O)_2$N($C_{1-9}$ alkyl)$_2$, —O($C_{3-10}$ cycloalkyl), —O($C_{1-8}$ haloalkyl), —O(aryl), —O(heteroaryl), —O(heterocyclyl), or —O($C_{1-9}$ alkyl).

2. The compound of claim 1, or a pharmaceutically acceptable salt thereof, wherein $R^2$ is hydrogen, halo, —$OR^{12}$, —$N(R^{12})_2$, —$SR^{20}$, —$S(O)R^{20}$, $C_{1-8}$ alkyl optionally substituted with 1 to 5 $Z^1$, $C_{3-6}$ cycloalkyl optionally substituted with 1 to 5 $Z^1$.

3. The compound of claim 1, or a pharmaceutically acceptable salt thereof, wherein $R^3$ is hydrogen, $C_{1-8}$ alkyl optionally substituted with 1 to 5 $Z^1$, or $C_{3-10}$ cycloalkyl optionally substituted with 1 to 5 $Z^1$.

4. The compound of claim 1, or a pharmaceutically acceptable salt thereof, wherein $R^6$ is —$N(R^{14})S(O)_2R^9$, —$N(R^{14})C(O)OR^9$, —$OC(O)R^9$, or —$OC(O)OR^9$.

5. The compound of claim 1, or a pharmaceutically acceptable salt thereof, wherein $R^6$ is -L-$R^{13}$;

L is $C_{1-8}$ alkylene, $C_{1-8}$ haloalkylene, or 5-10 membered heteroarylene; and each $C_{1-8}$ alkylene, $C_{1-8}$ haloalkylene, or 5-10 membered heteroarylene of L is optionally substituted with 1 to 5 $Z^1$; and $R^{13}$ is —$OR^{15}$, —$N(R^{15})(R^{14})$, —$C(O)N(R^{14})_2$, —$OC(O)N(R^{14})_2$, —$N(R^{14})C(O)R^9$, —$N(R^{14})C(O)OR^9$, —$N(R^{14})C(O)N(R^{14})_2$, —$N(R^{14})S(O)_2R^9$, —$NR^{14}S(O)_2N(R^{14})_2$, —$NR^{14}S(O)_2OR^9$, —$NS(O)(R^9)_2$, —$Si(R^{14})_2R^9$, —$SR^9$, —$S(O)R^9$, —$S(O)_2R^9$, —$SF_5$, —$S(O)(NR^{14})R^9$, —$S(NR^{14})(NR^{14})R^9$, —$S(O)(NR^{14})N(R^{14})_2$, —$S(O)(NCN)R^9$, —$S(O)_2N(R^{14})_2$, —$C(O)N(R^{14})S(O)_2R^9$, —$S(O)_2N(R^{14})C(O)R^9$, or $C_{3-10}$ cycloalkyl substituted with 1 to 5 $Z^1$.

6. The compound of claim 1, or a pharmaceutically acceptable salt thereof, wherein $R^6$ is

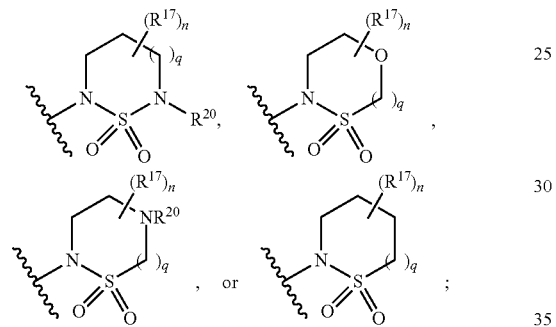

where q is 0, 1 or 2; and n is 0, 1, 2, 3, 4, 5, or 6.

7. The compound of claim 1, or a pharmaceutically acceptable salt thereof, wherein $R^6$ is

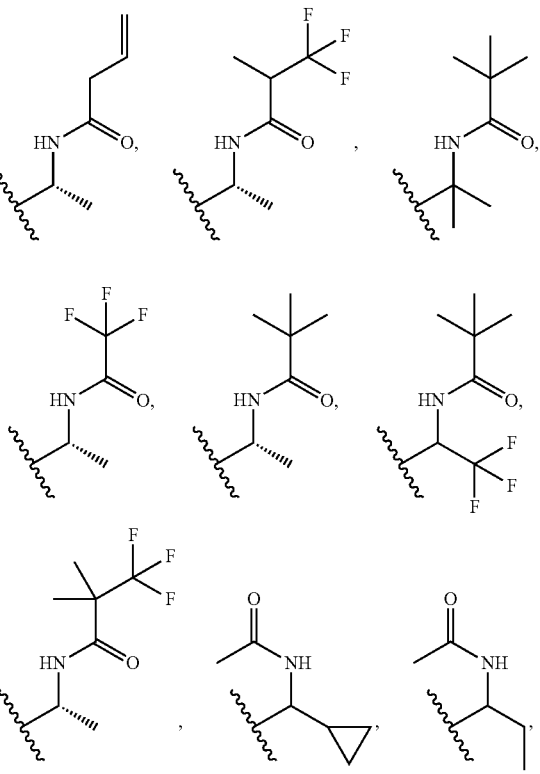

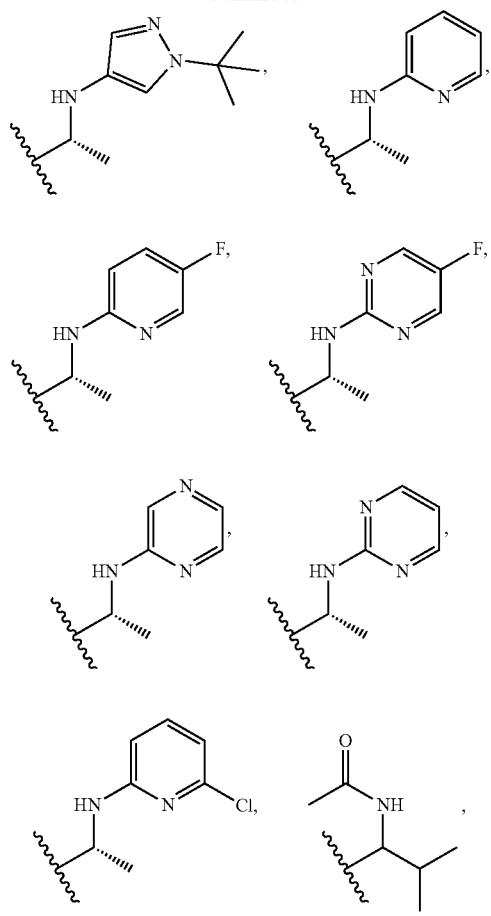

-continued

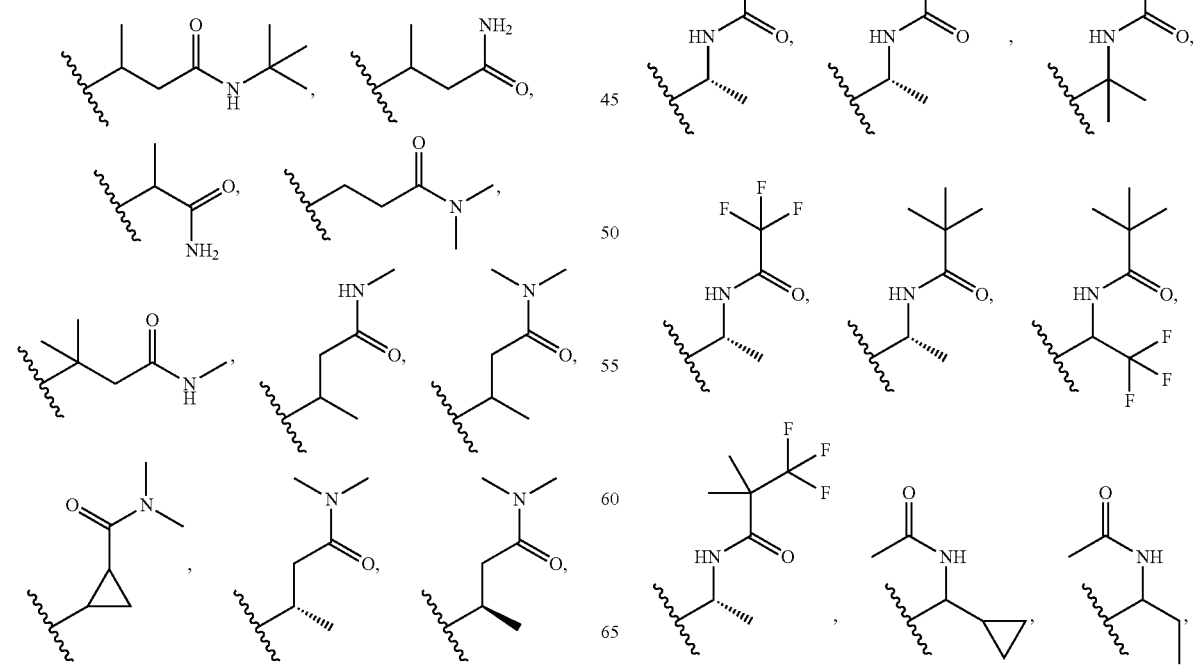

-continued
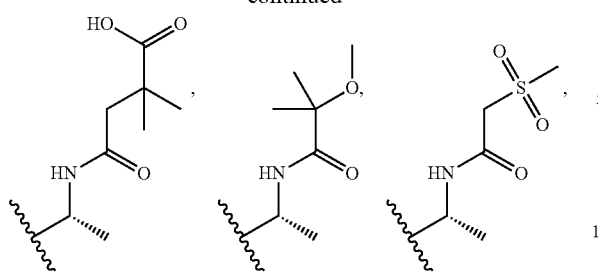
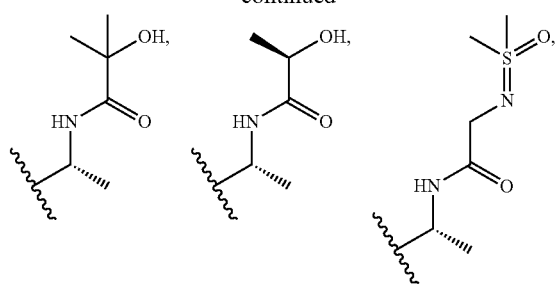
-continued
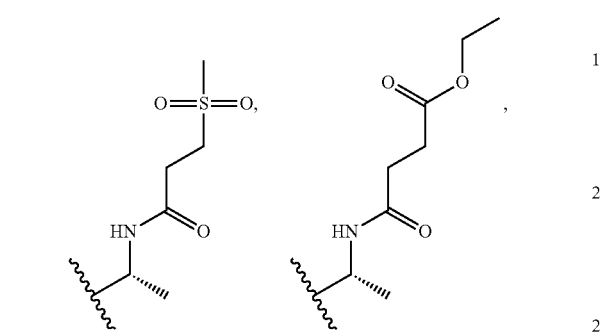
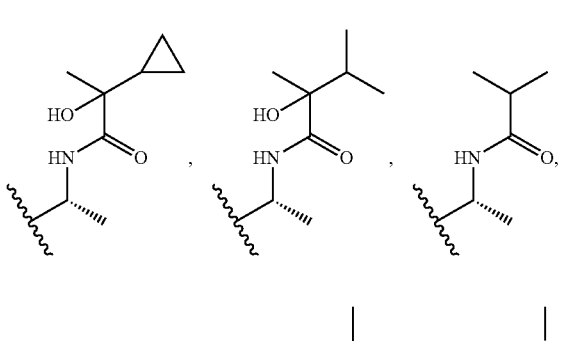
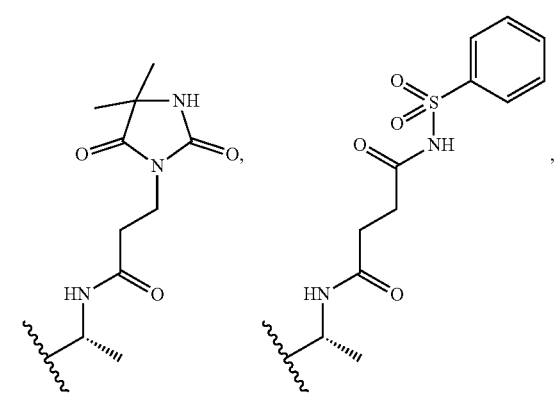
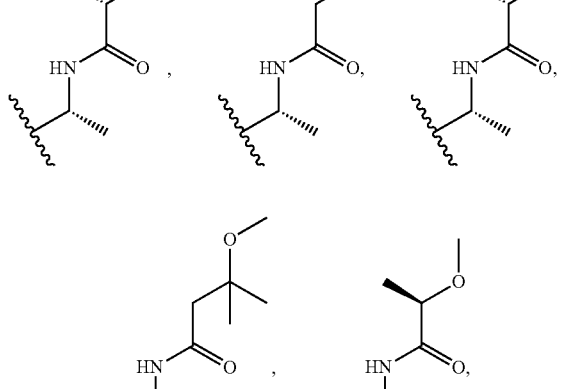
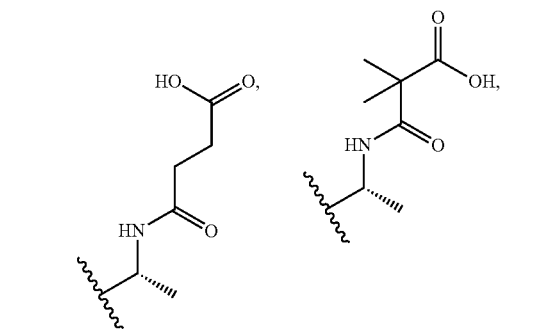
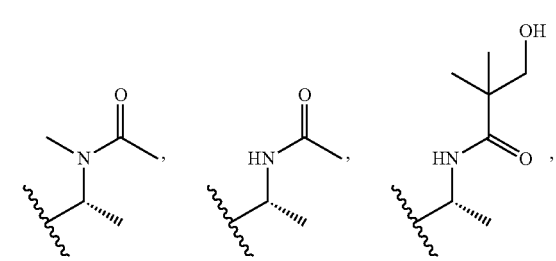
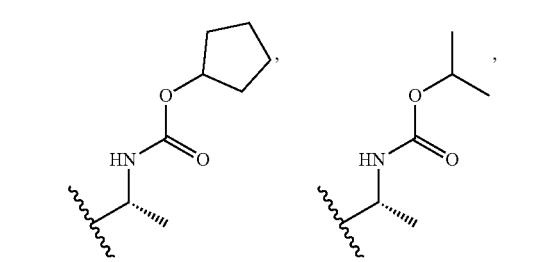

615
-continued
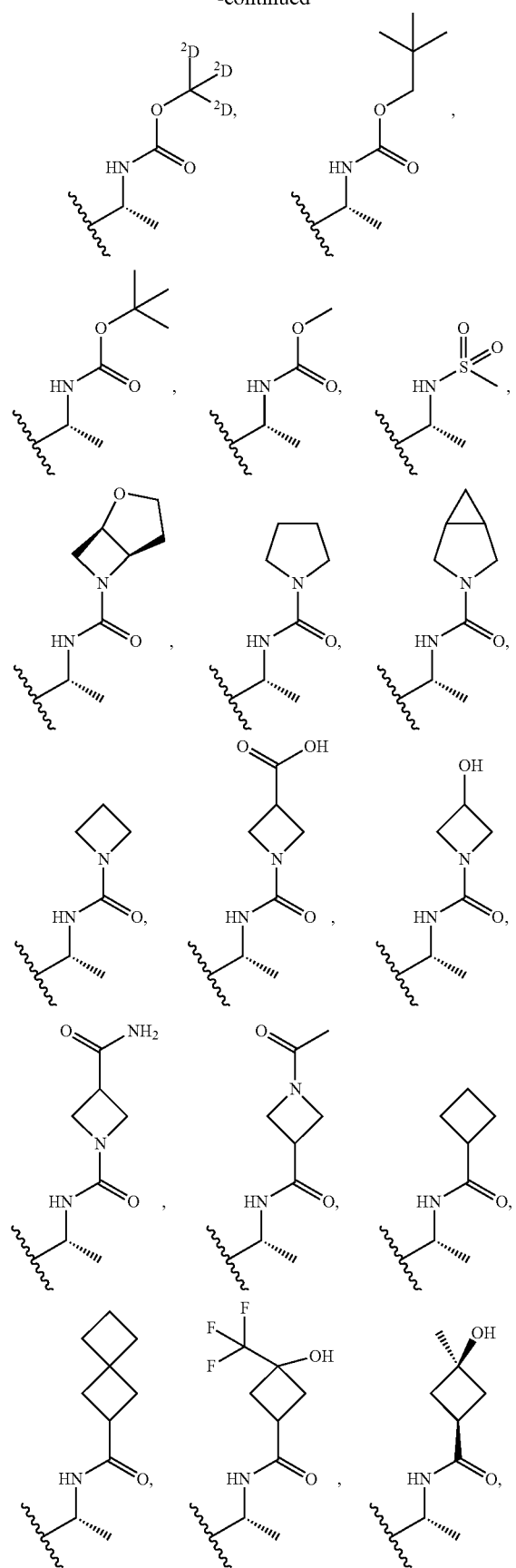
616
-continued
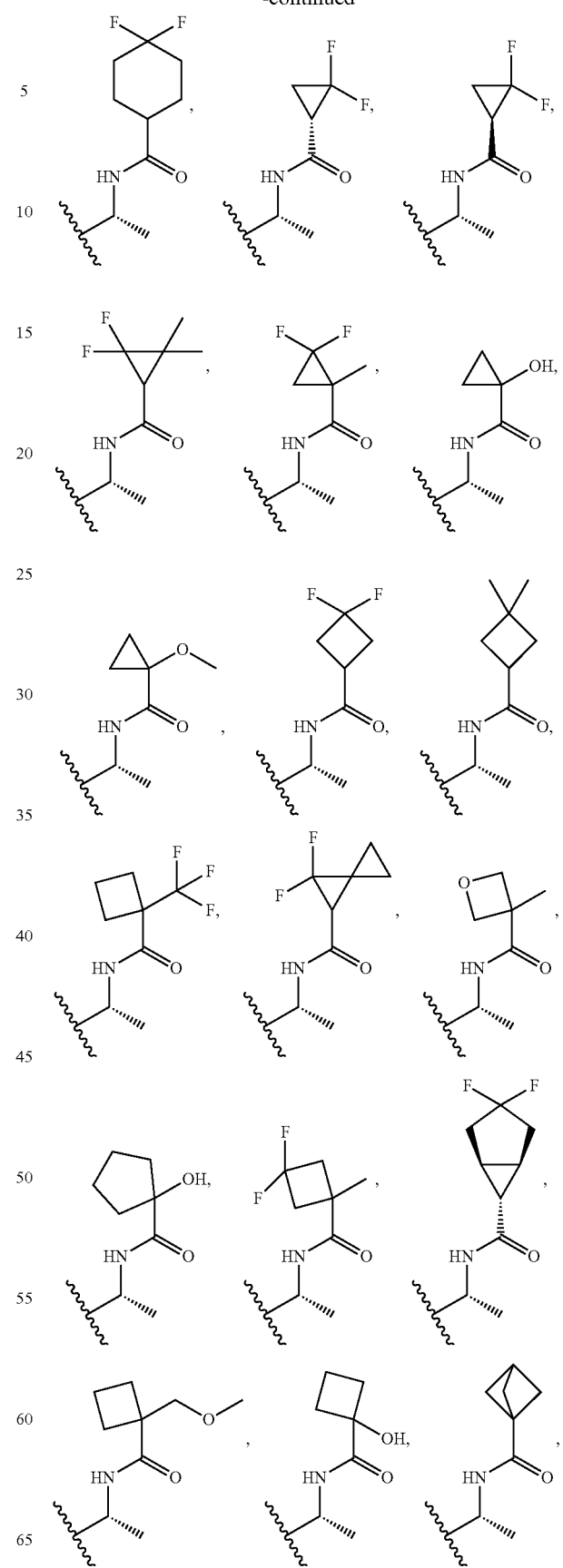

617
-continued
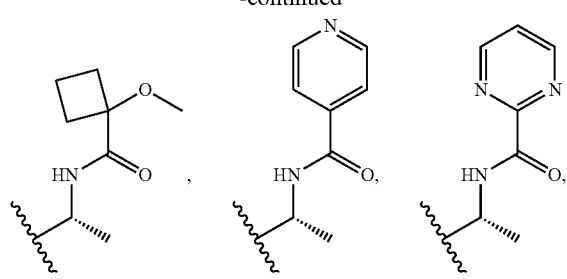
618
-continued
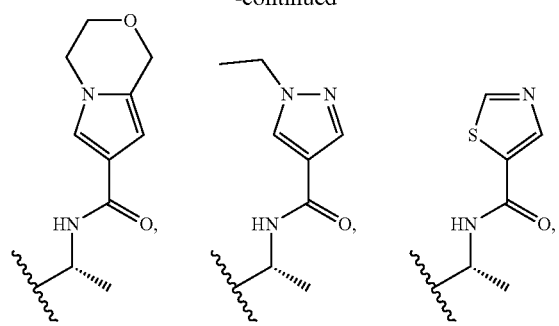
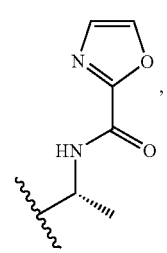
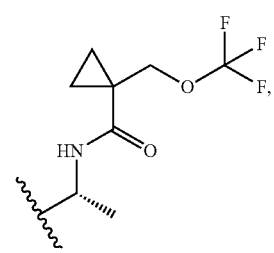
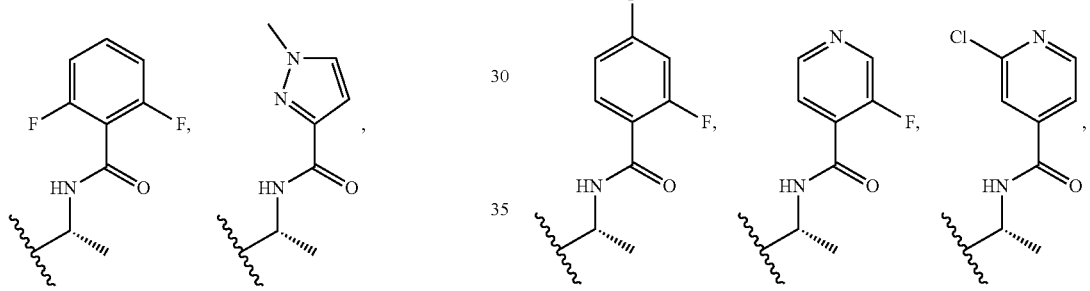
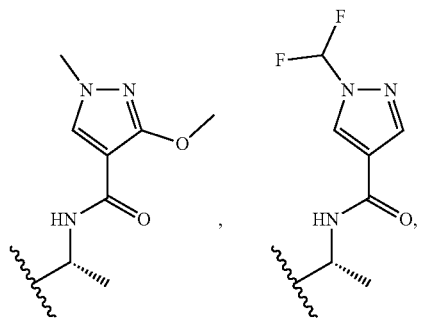
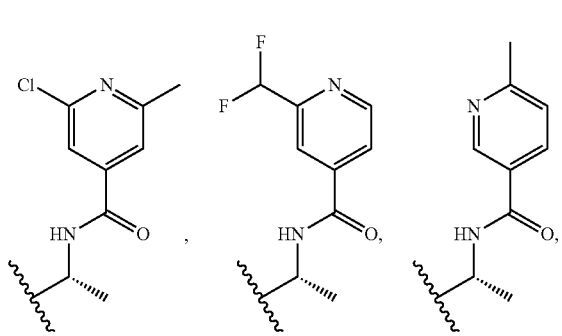
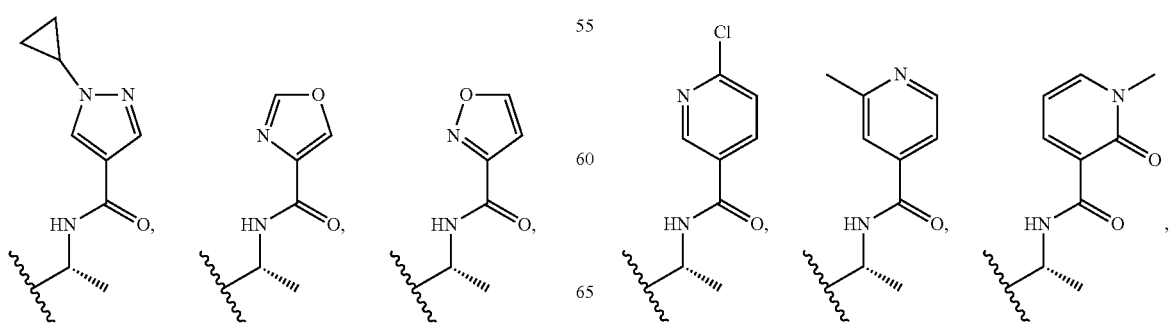

619
-continued
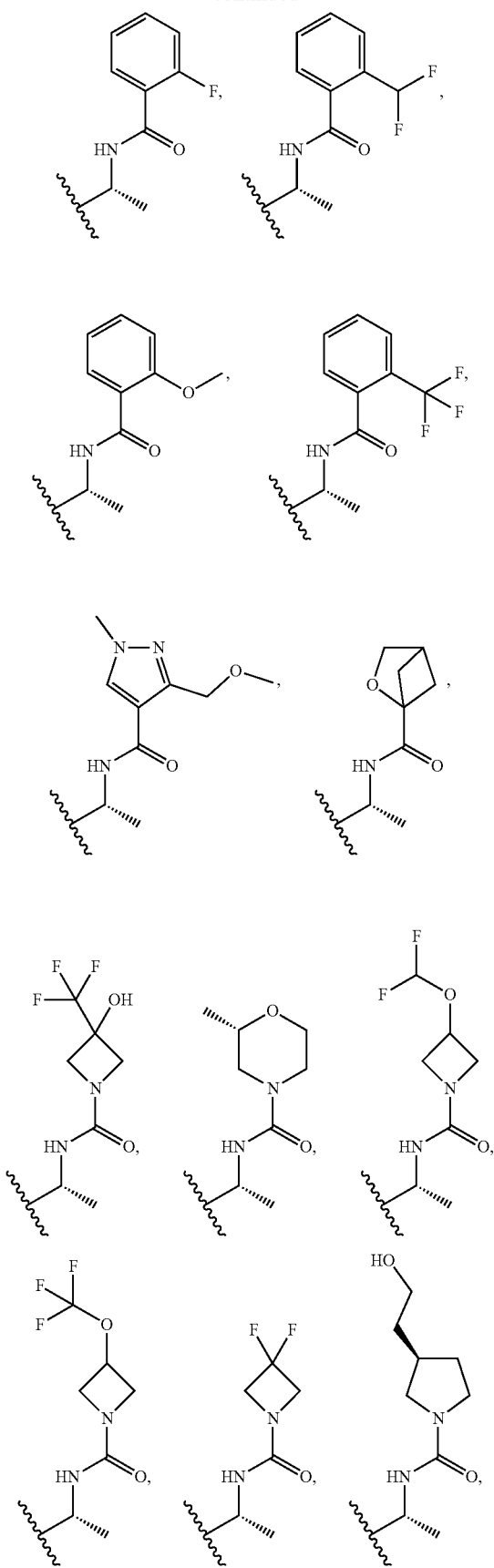
620
-continued
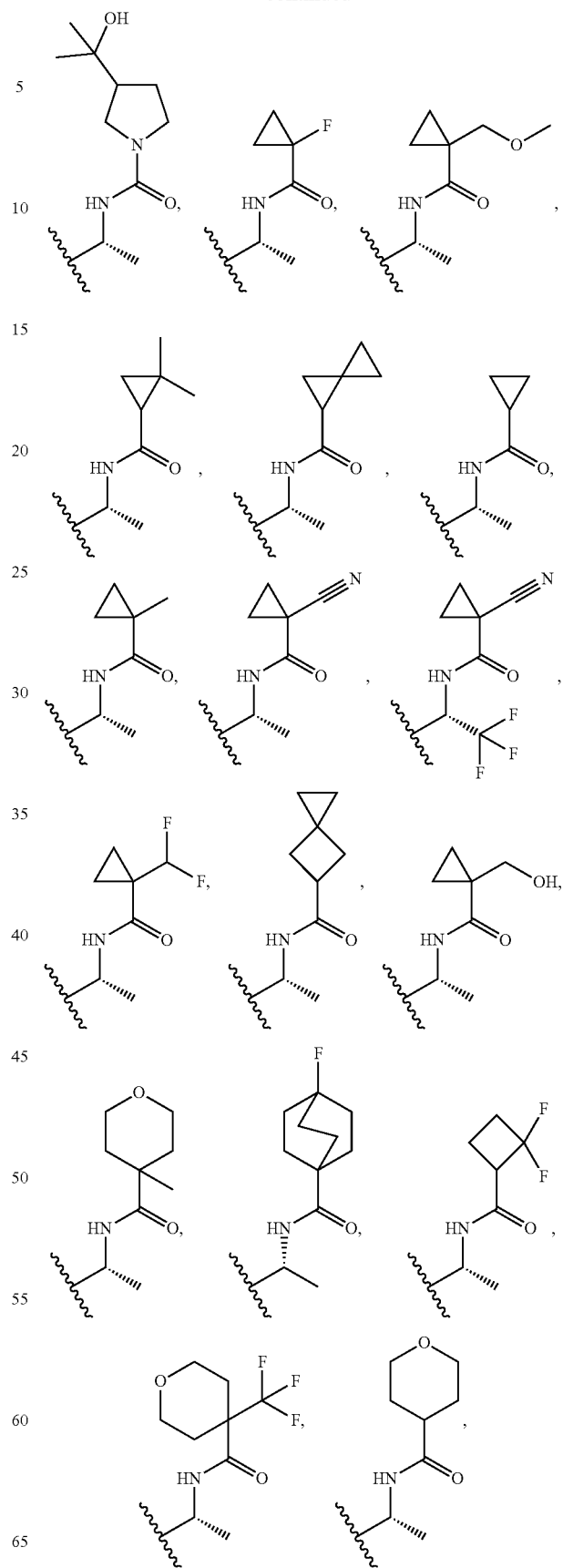

621
-continued
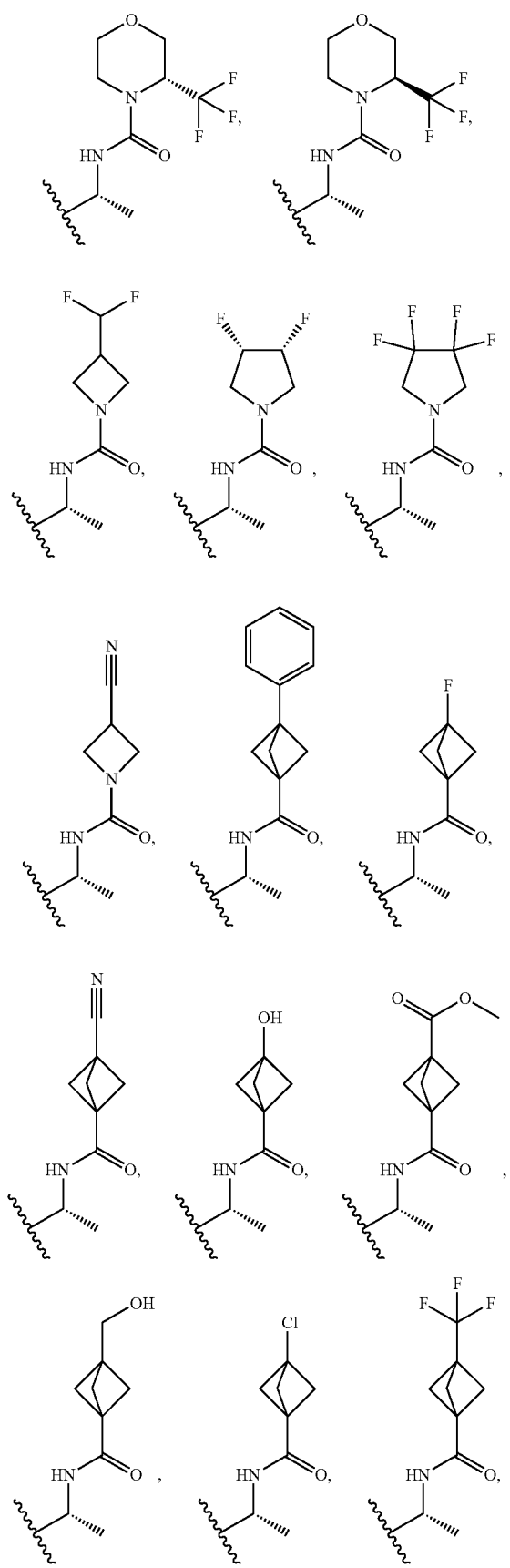
622
-continued
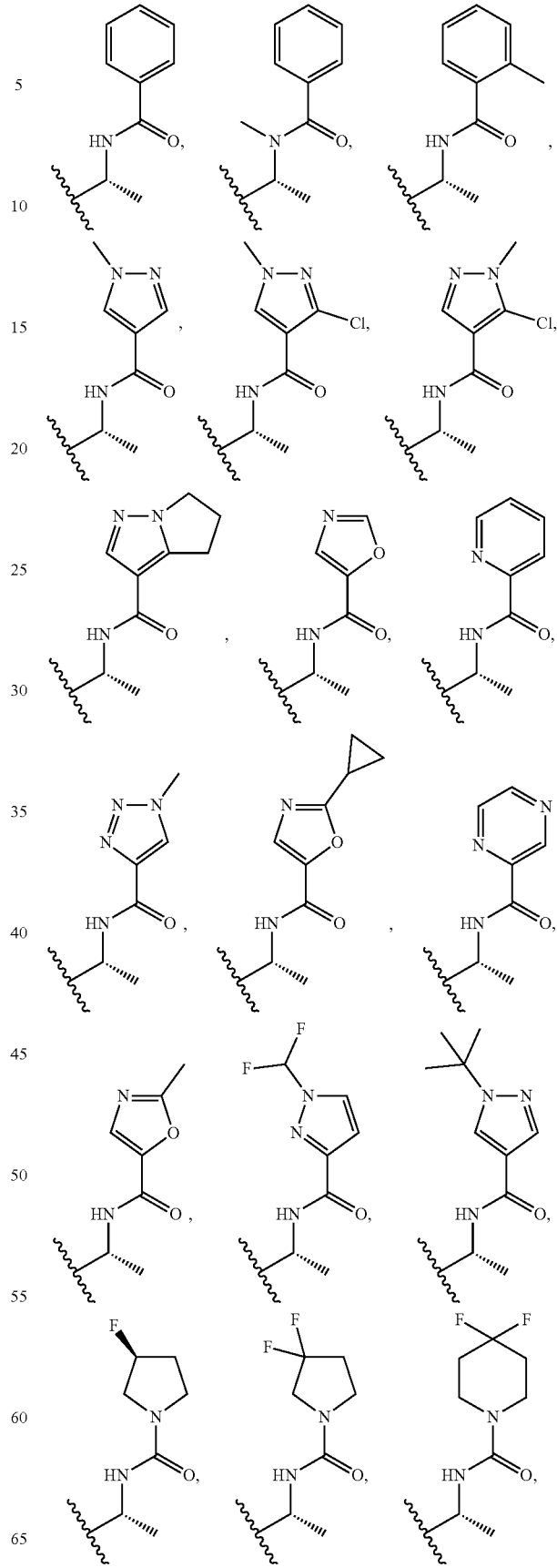

623
-continued
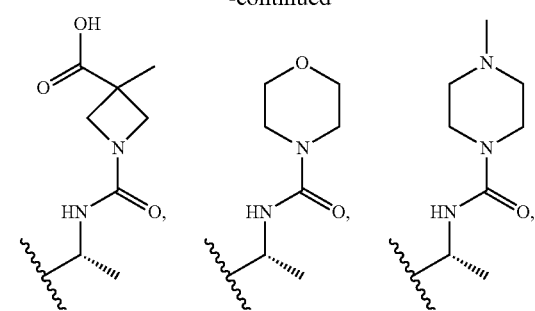
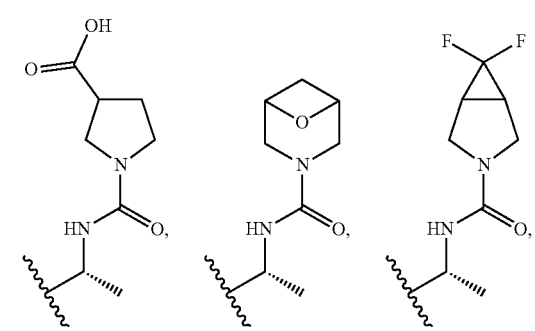
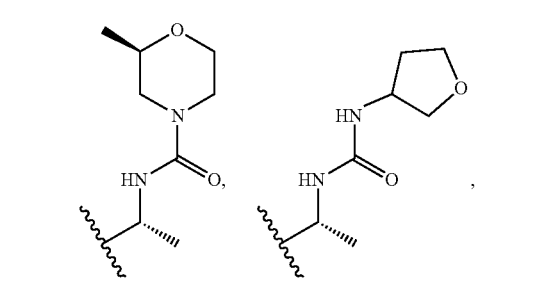
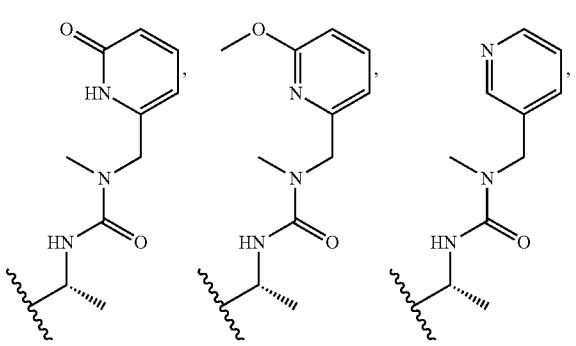
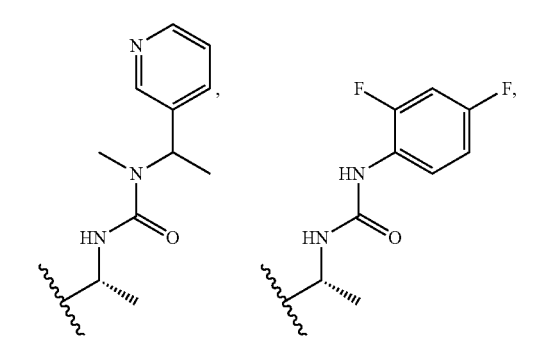
624
-continued
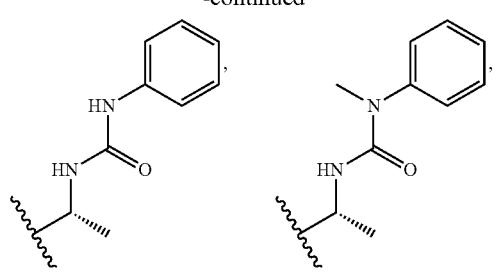
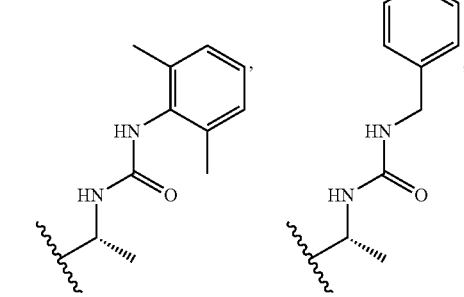
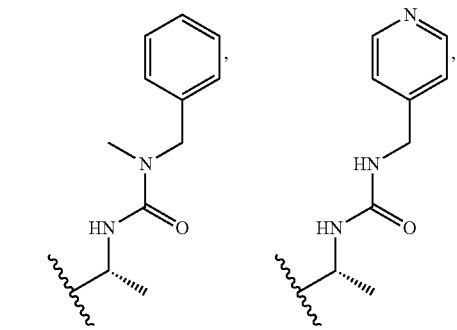
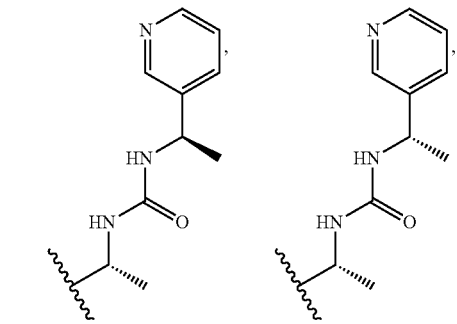
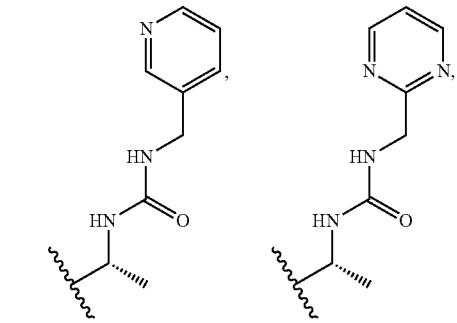

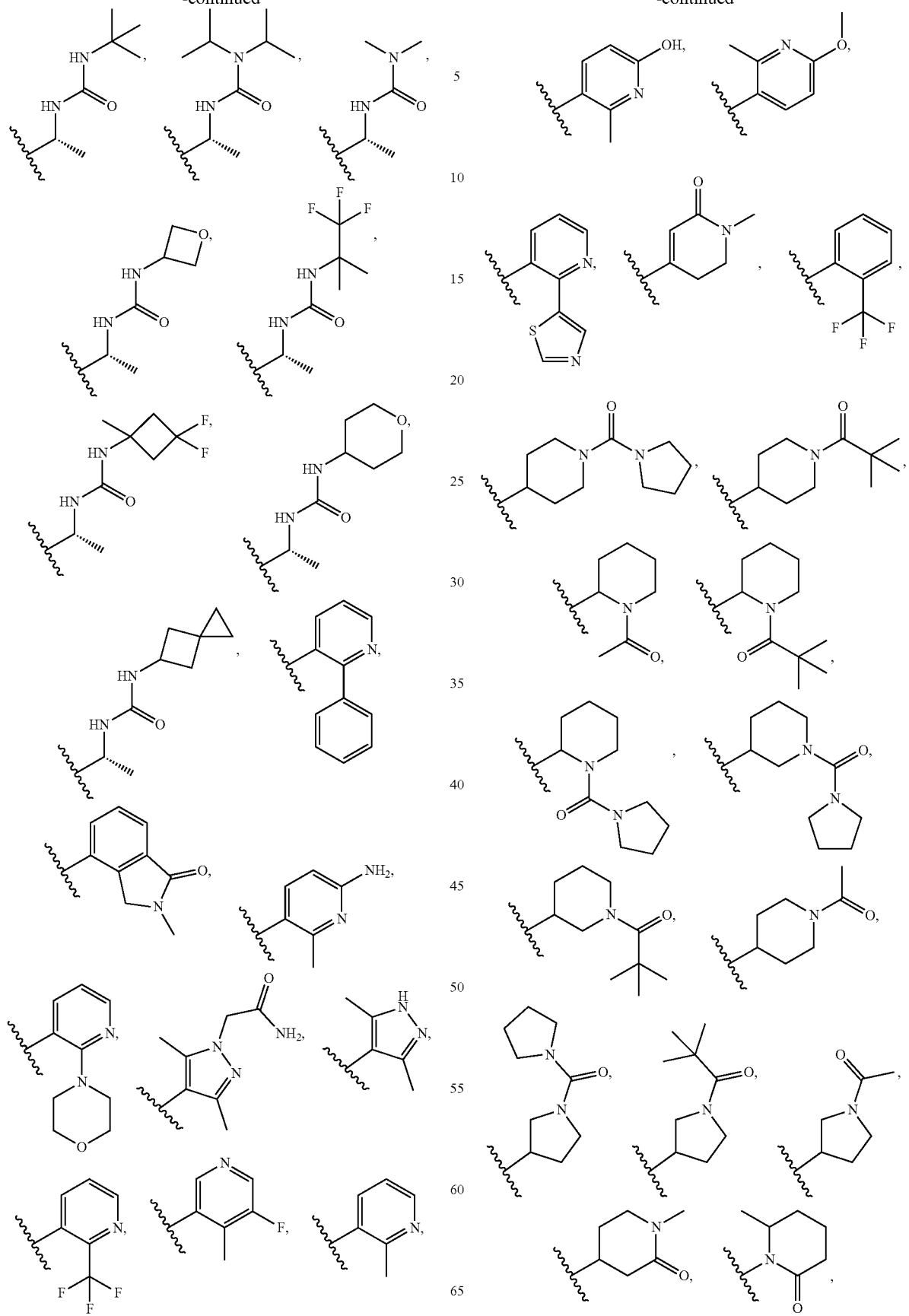

627
-continued
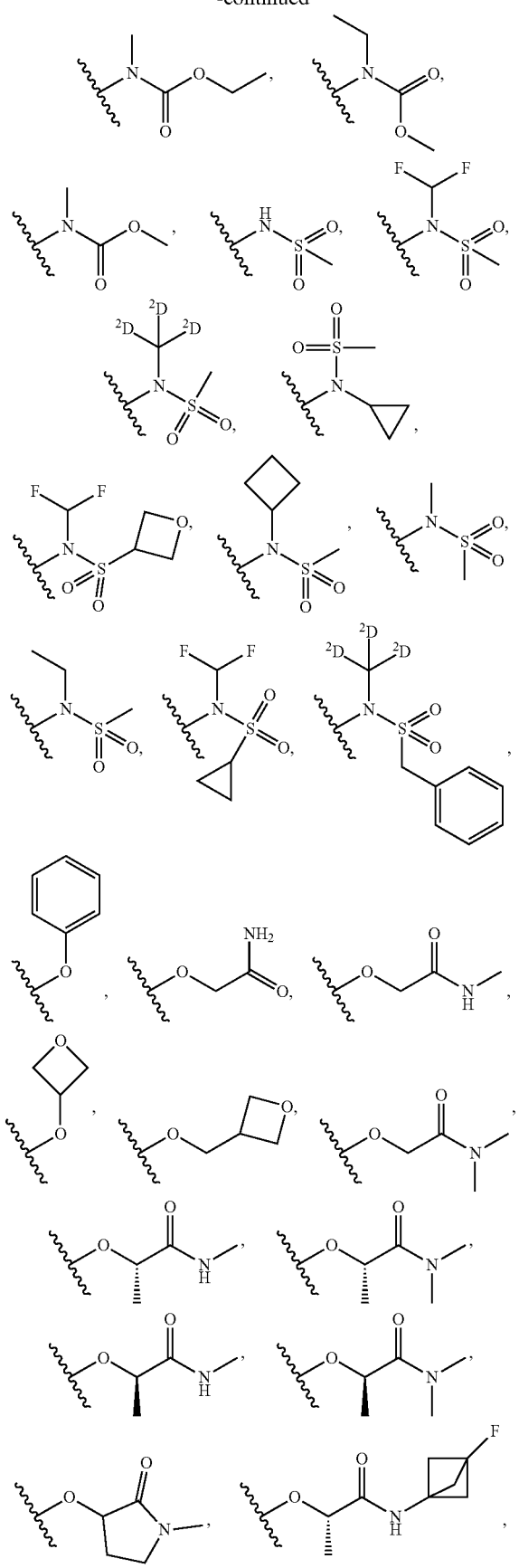
628
-continued
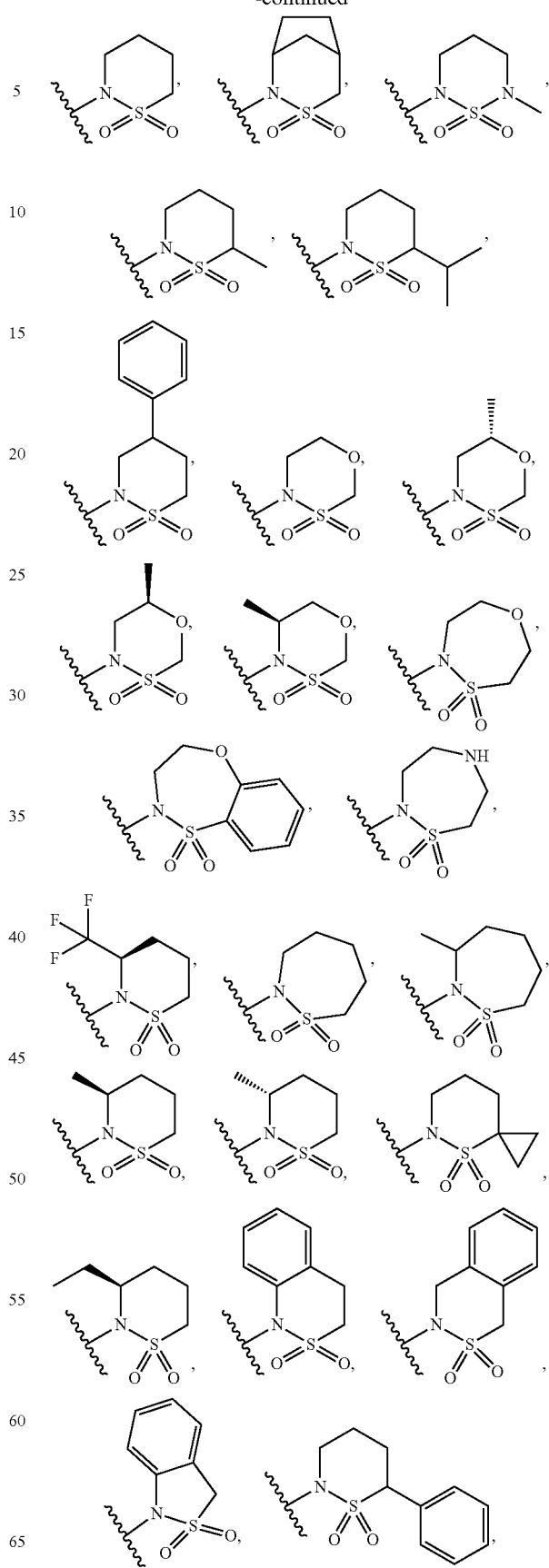

629

-continued

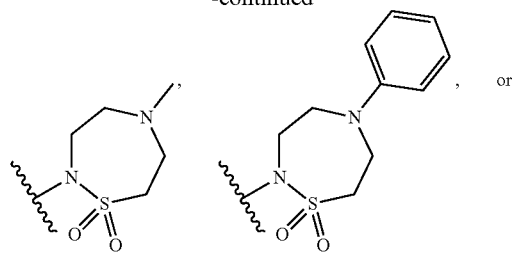, or

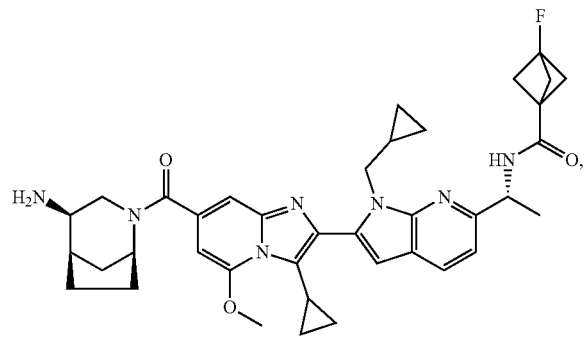

8. A compound selected from the group consisting of:

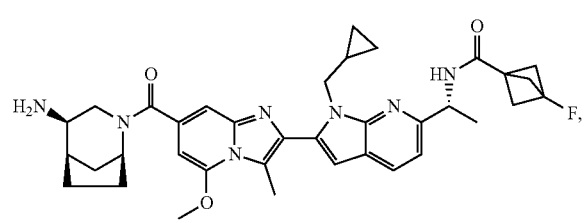

630

-continued

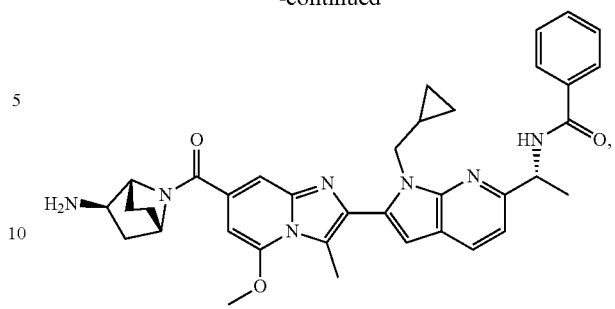

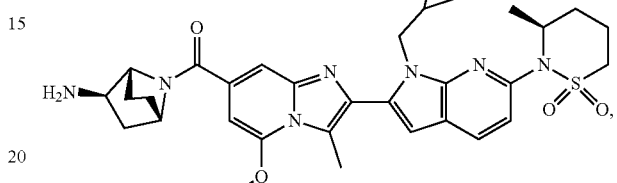

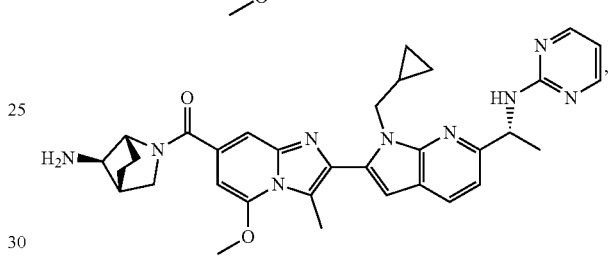

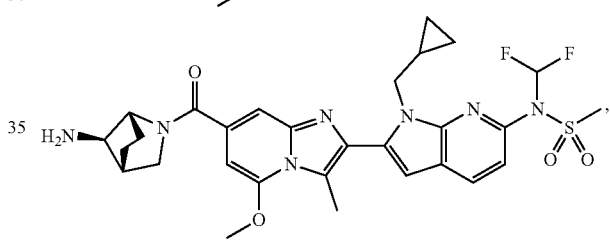

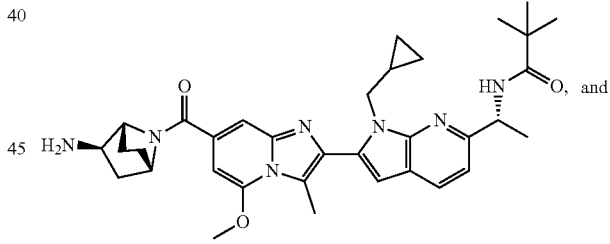

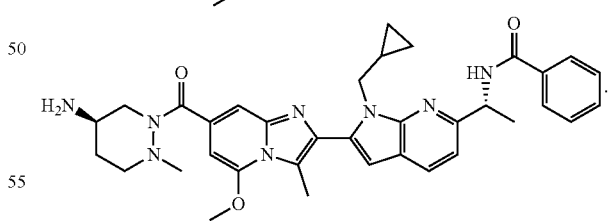

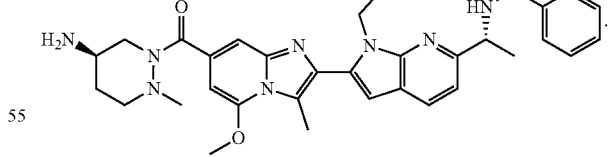

or a pharmaceutically acceptable salt thereof.

9. A pharmaceutical composition comprising a compound according to claim 1 or a pharmaceutically acceptable salt thereof, and at least one pharmaceutically acceptable excipient.

10. The pharmaceutical composition of claim 9, further comprising at least one additional therapeutic agent, wherein the additional therapeutic agent is a Janus kinase inhibitor.

11. A compound selected from
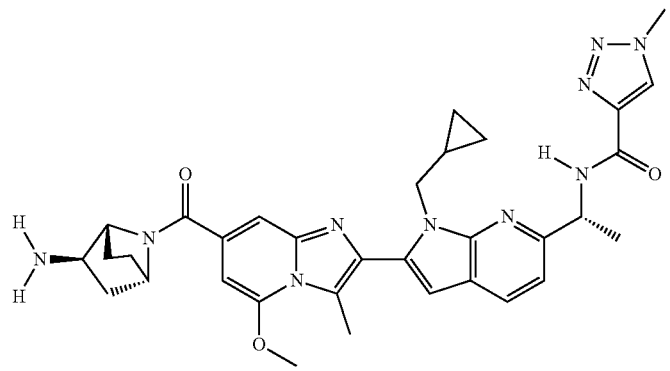
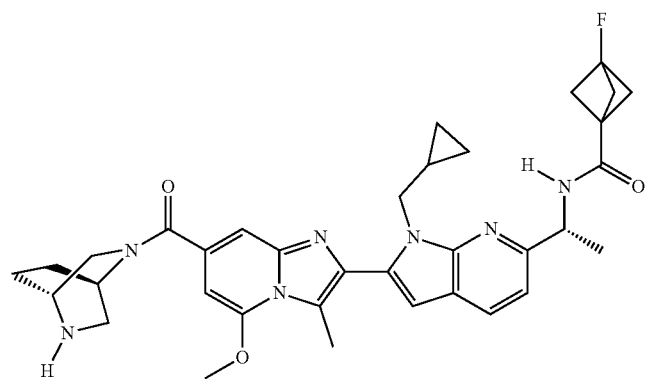
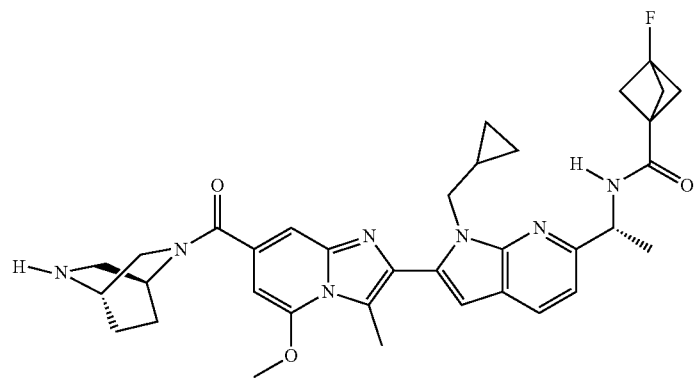
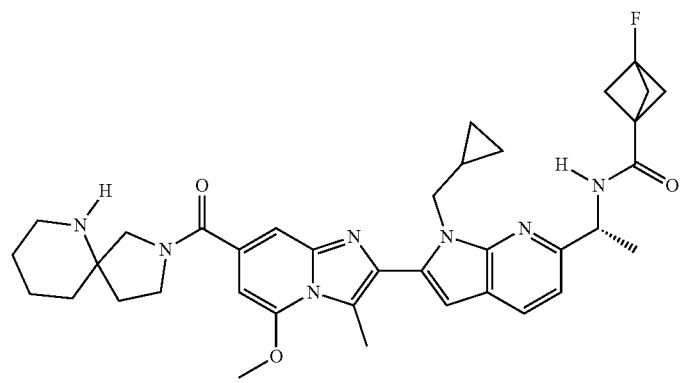

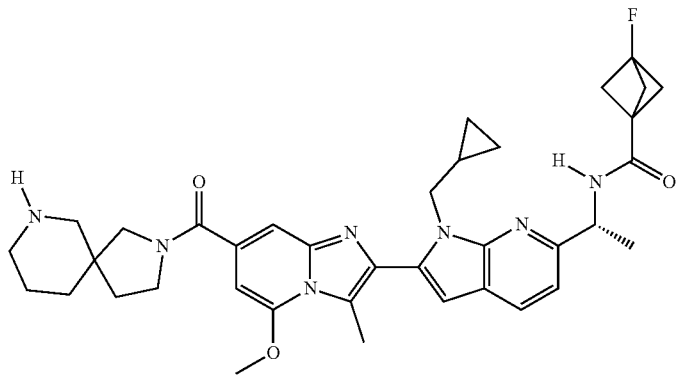
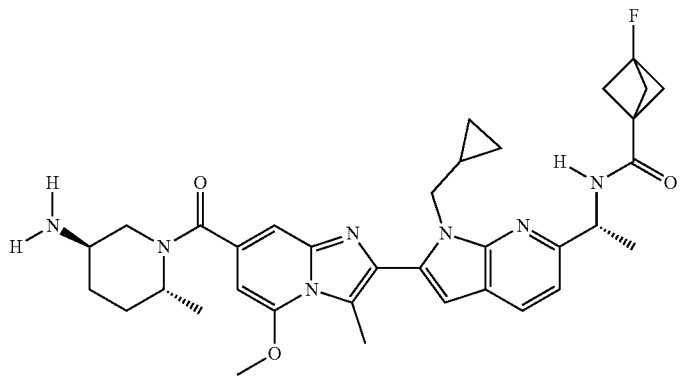
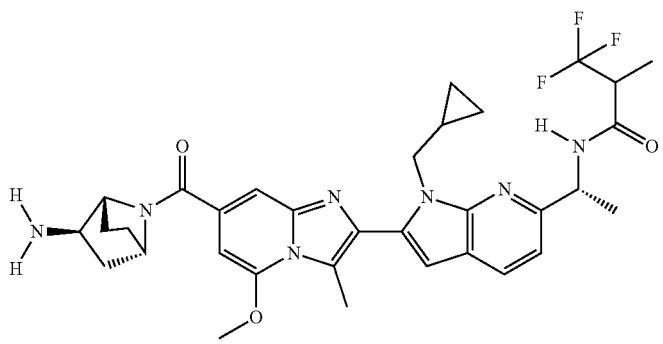
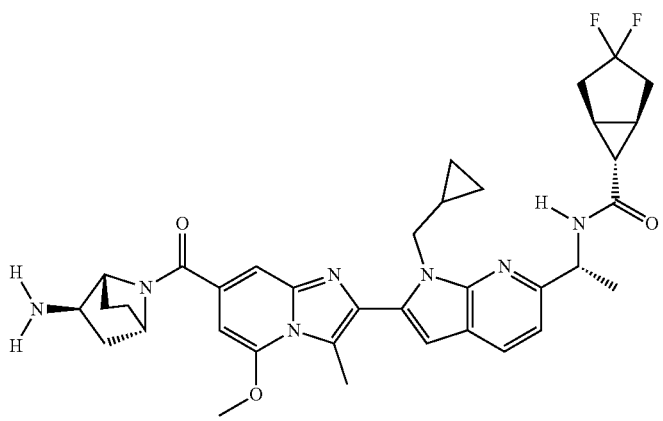

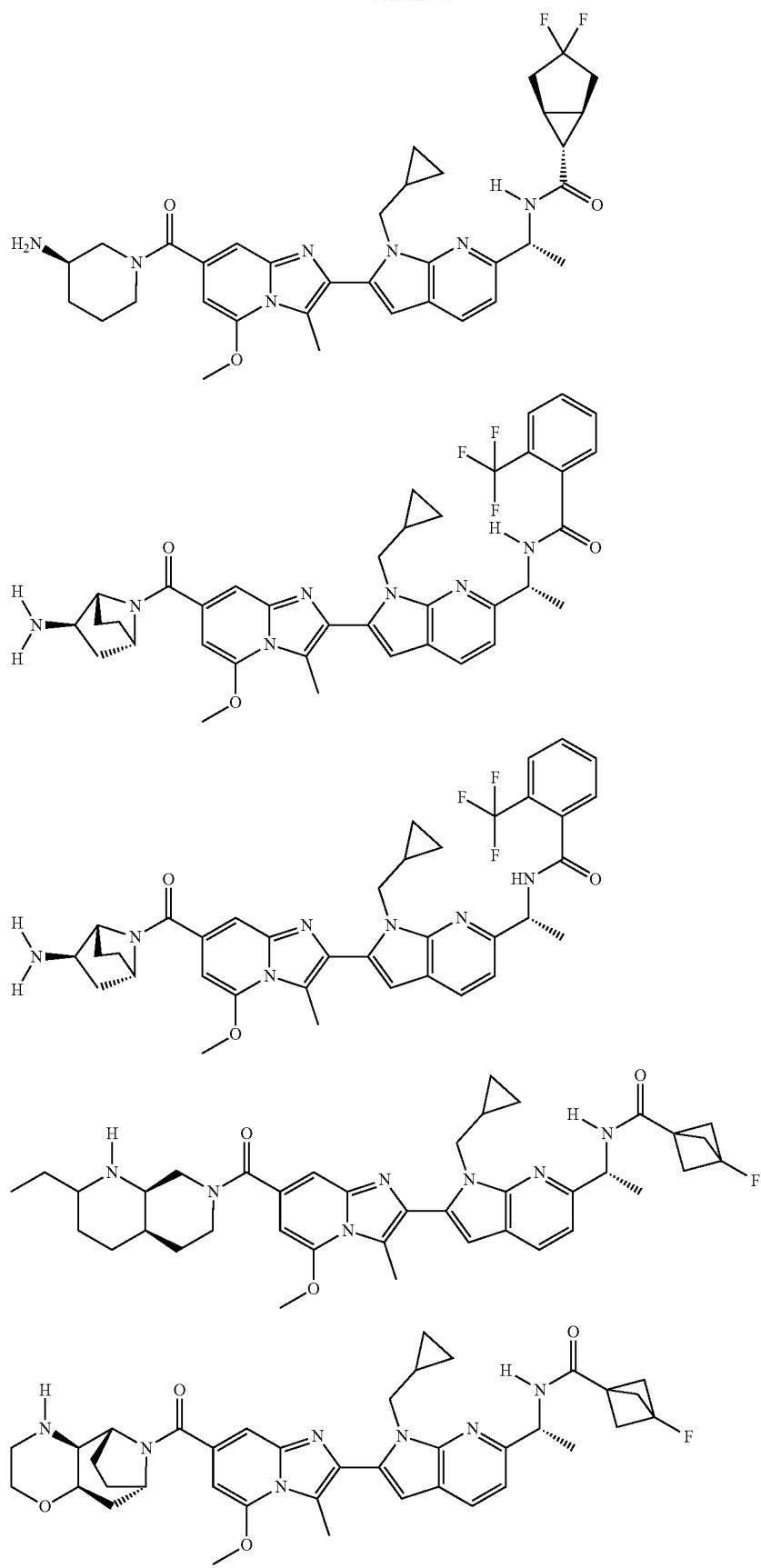

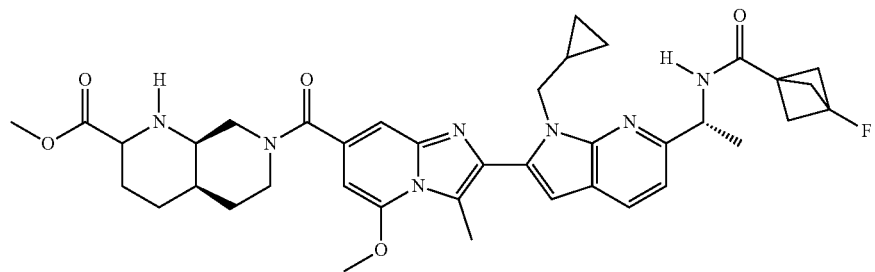
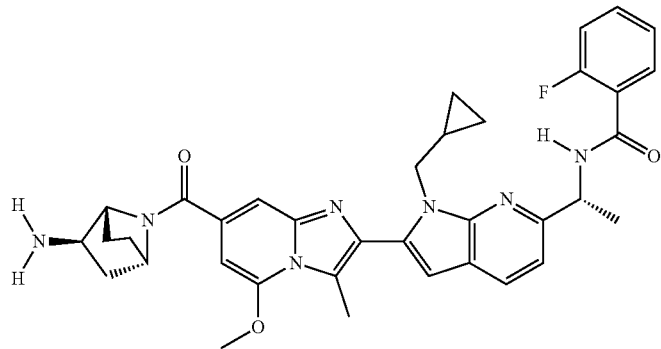
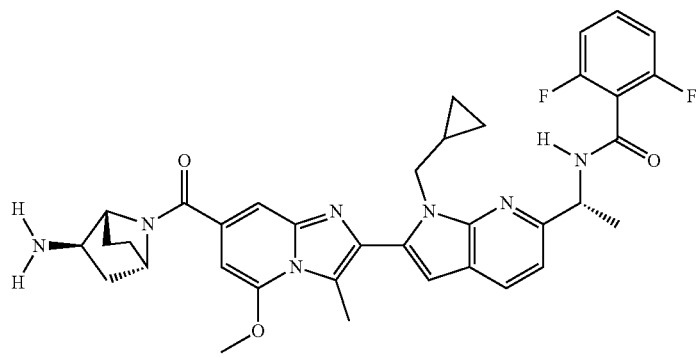
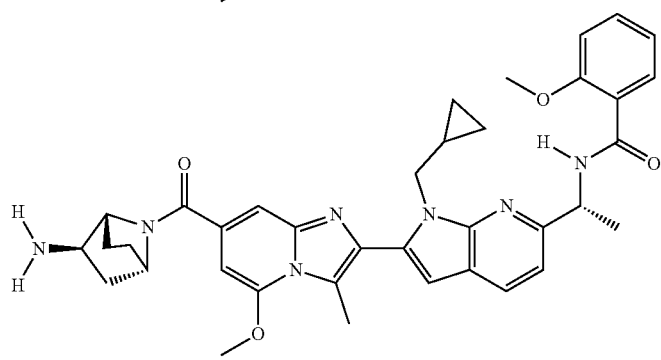
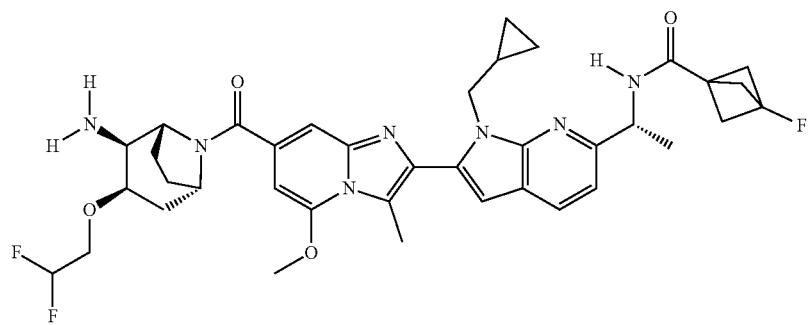

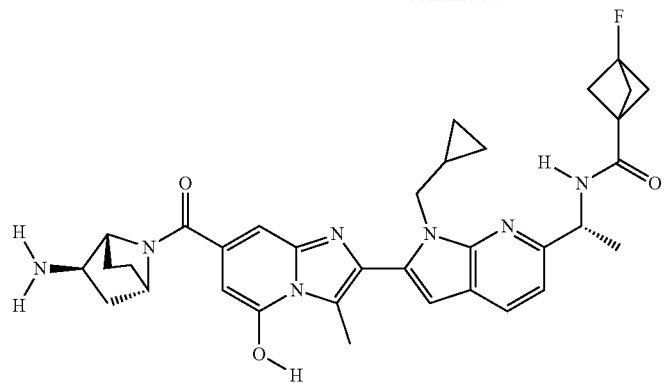
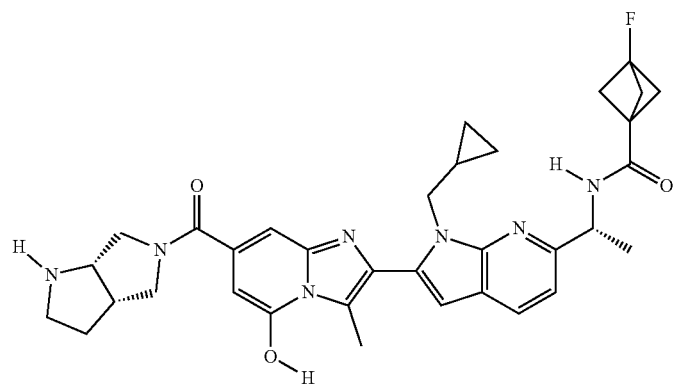
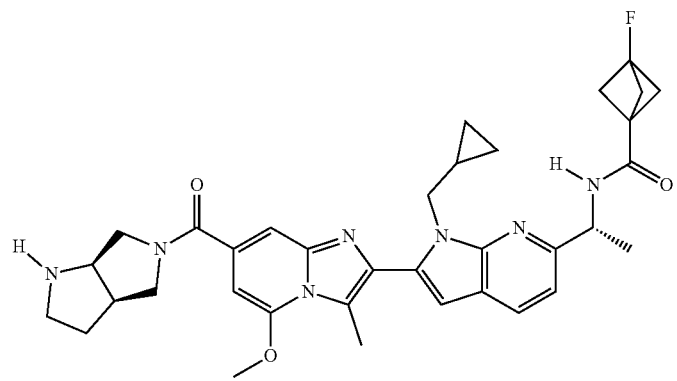
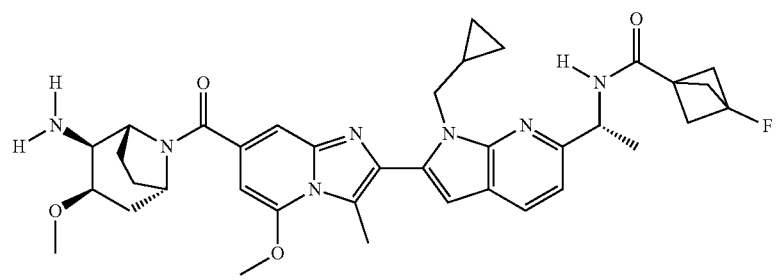

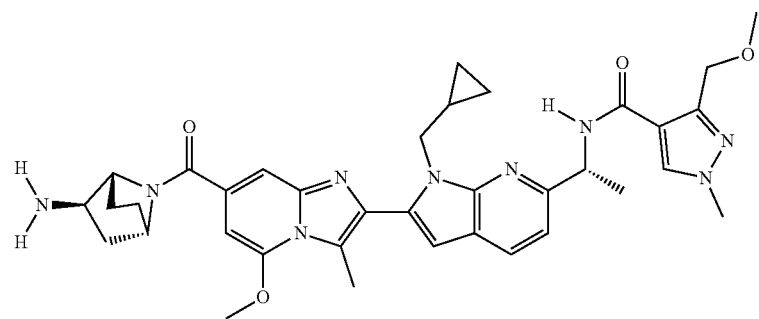
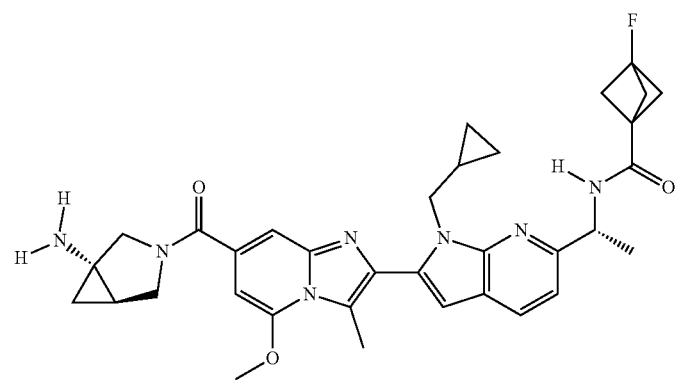
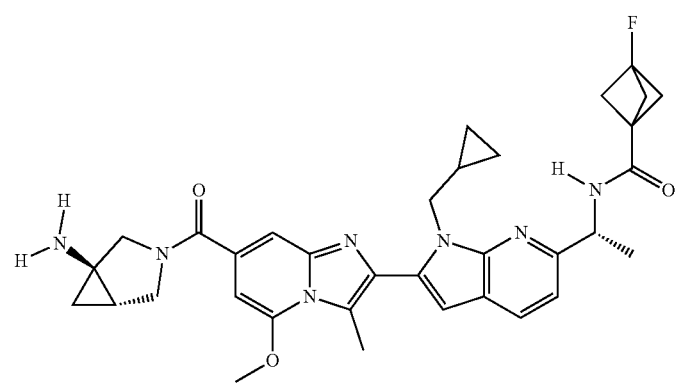
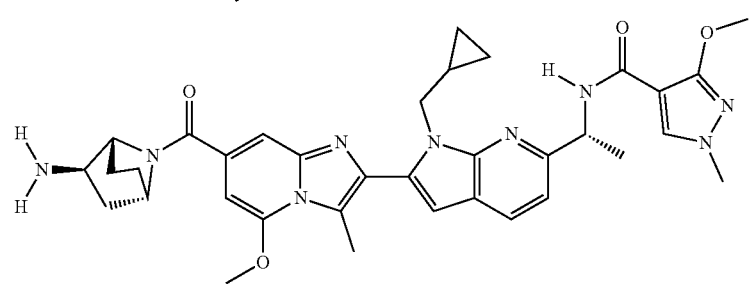
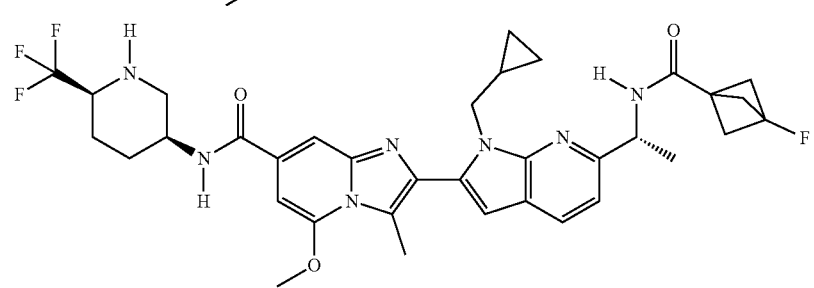

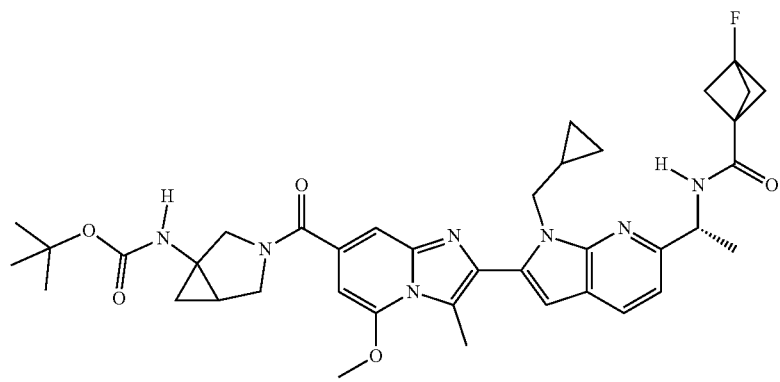
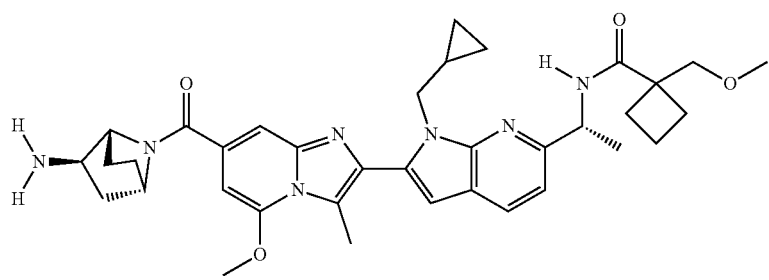
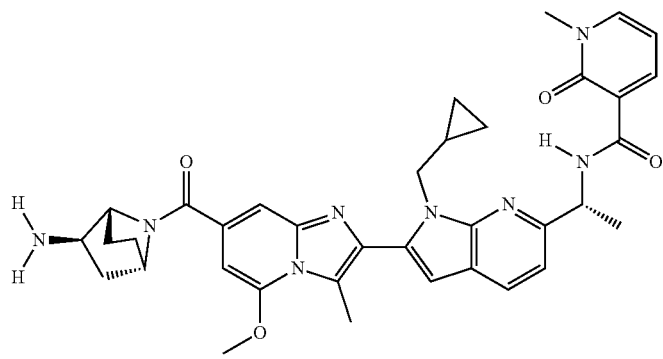
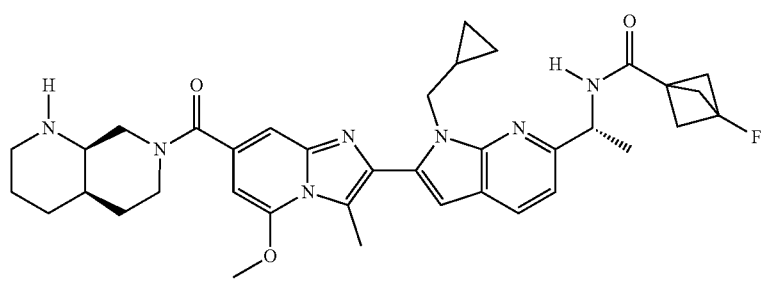
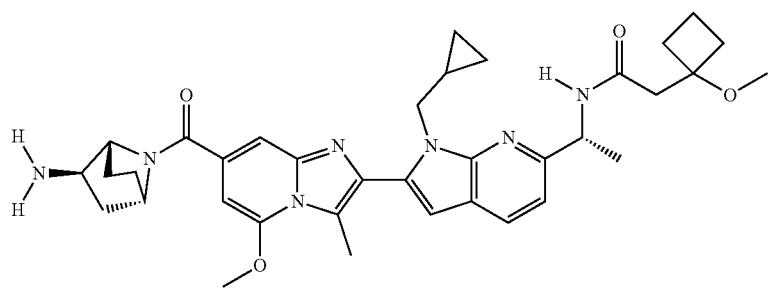

-continued
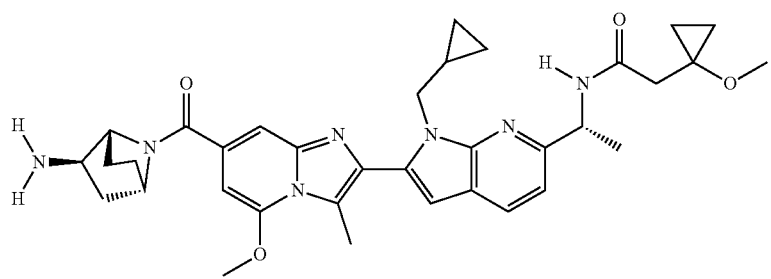
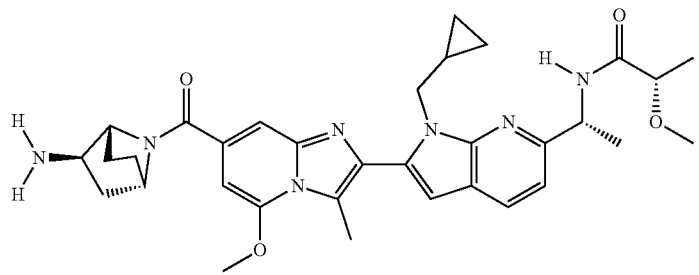
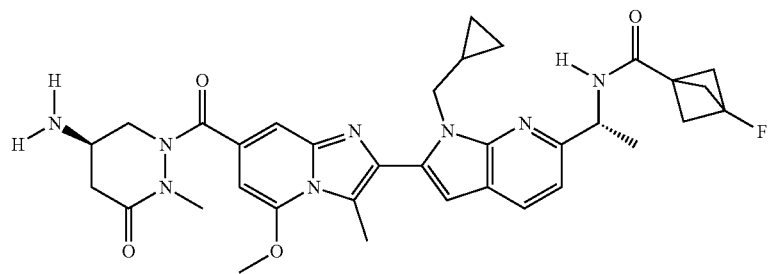
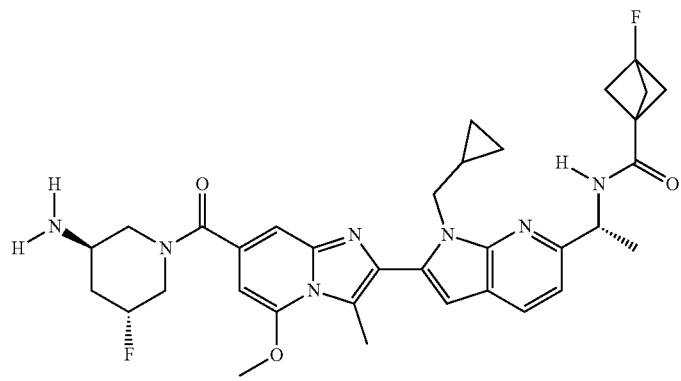
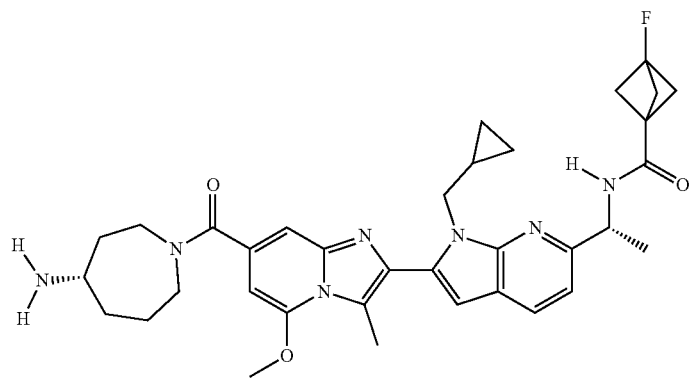

-continued
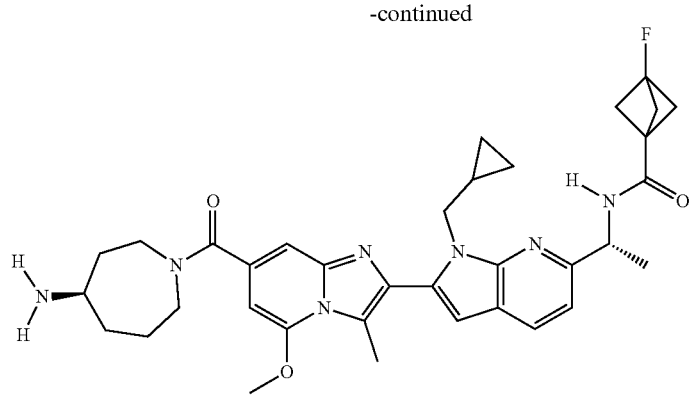
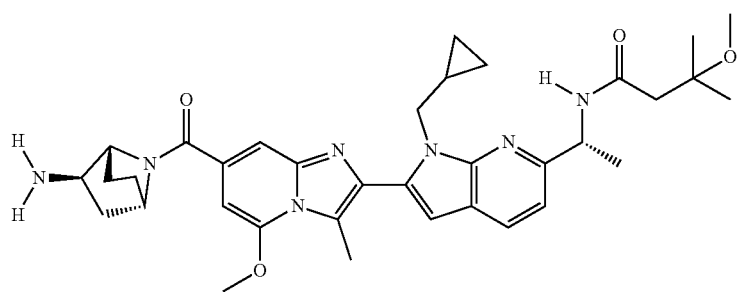
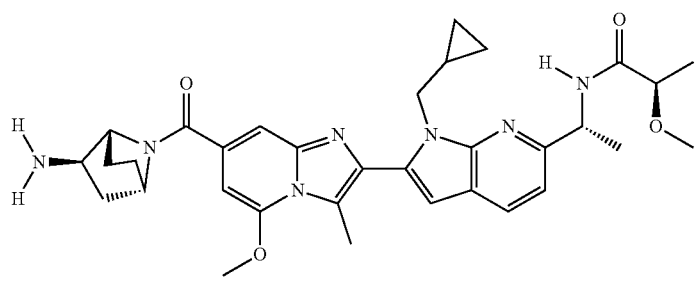
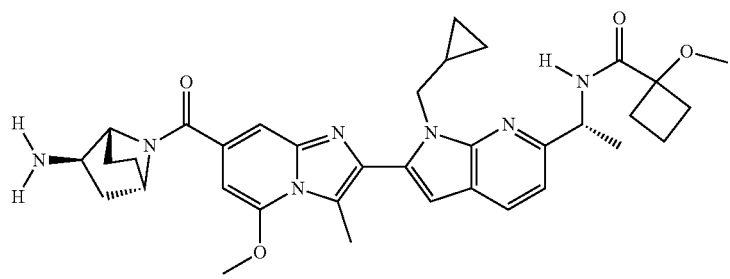
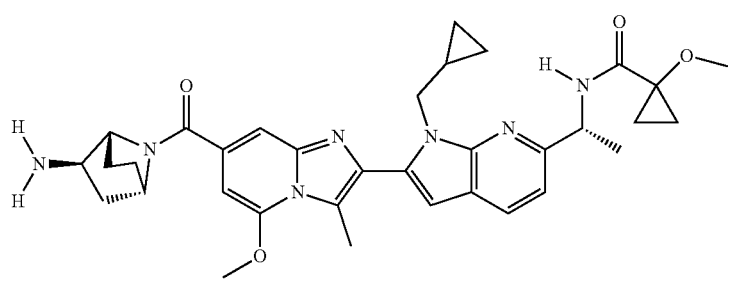

-continued
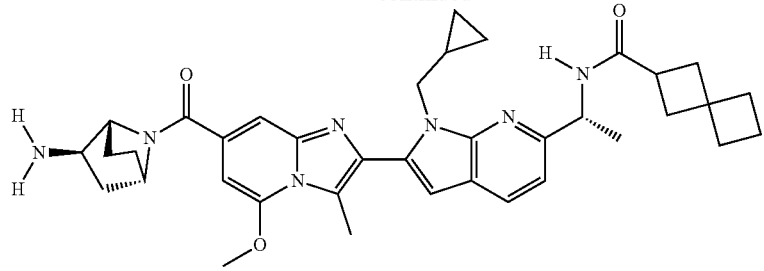
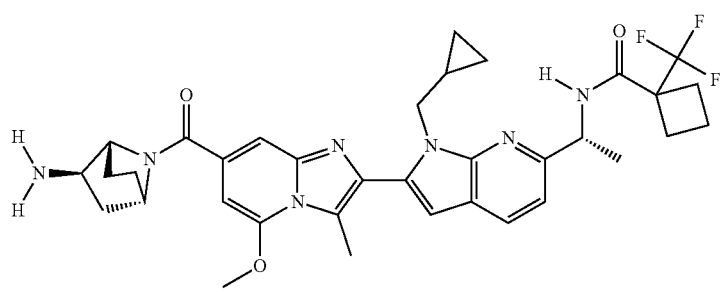
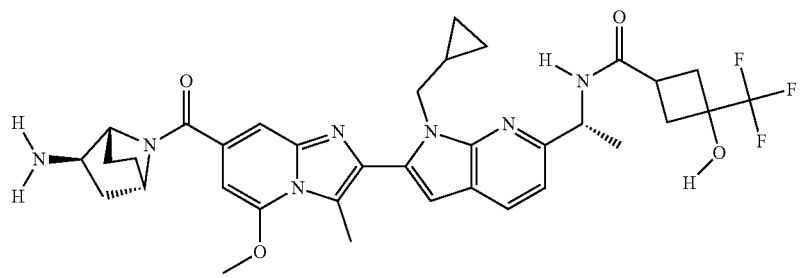
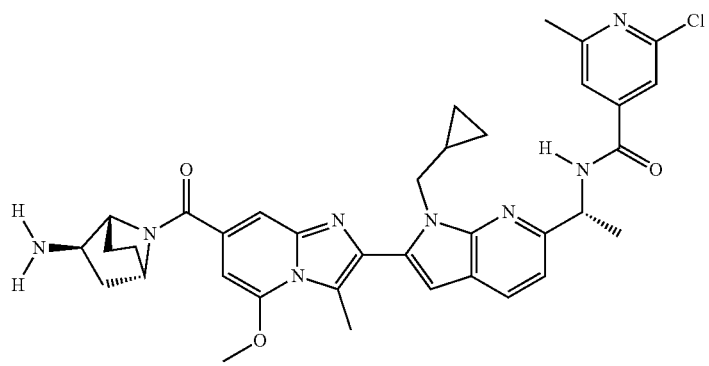
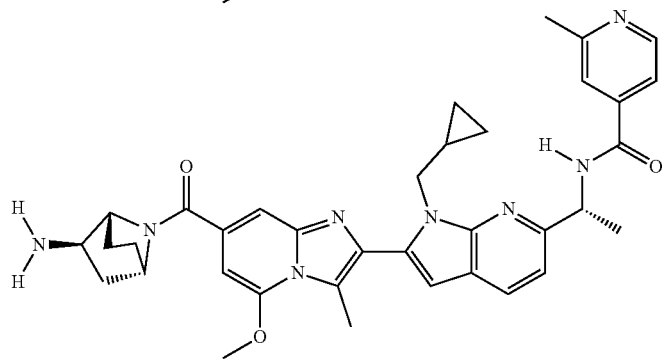

-continued
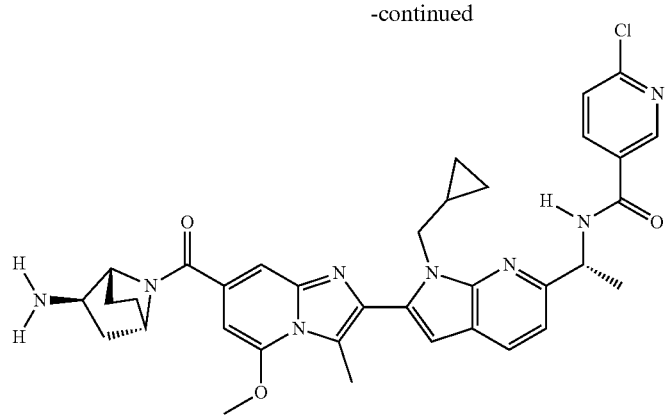
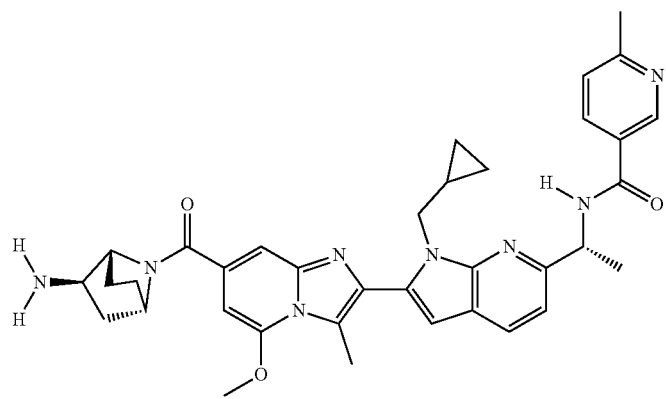
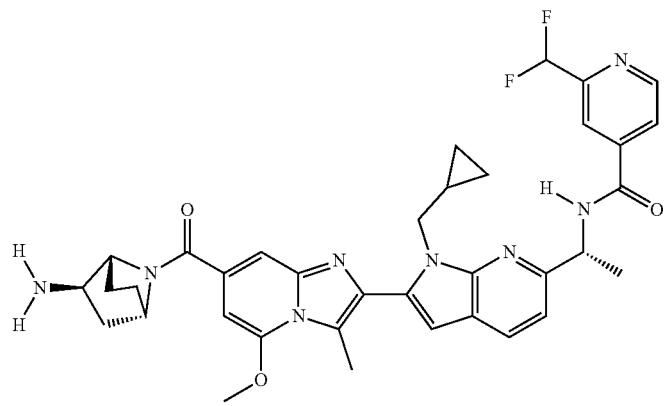
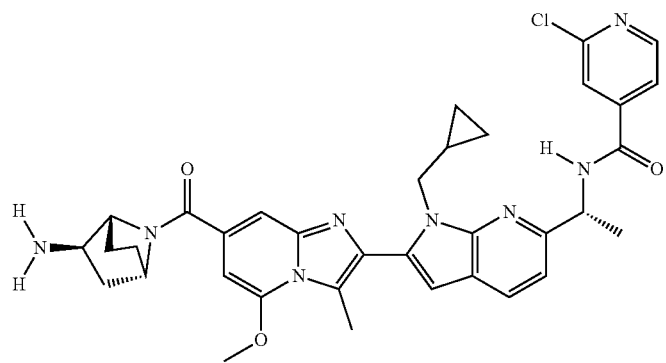

-continued
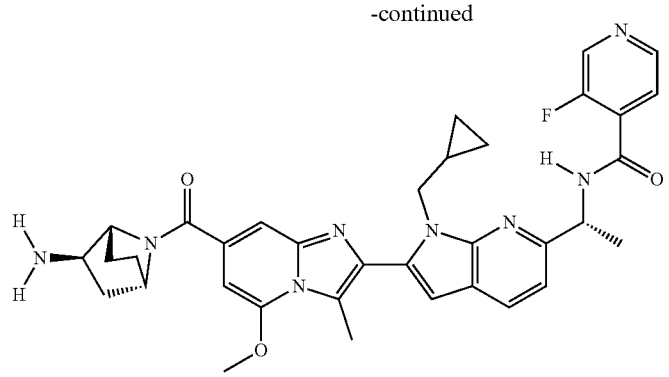
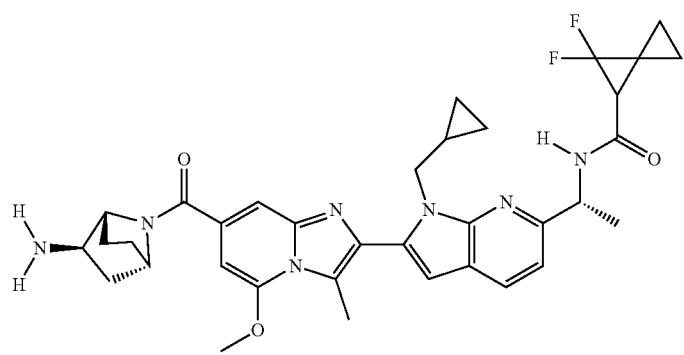
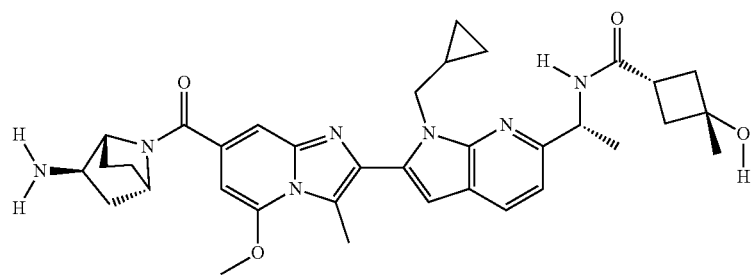
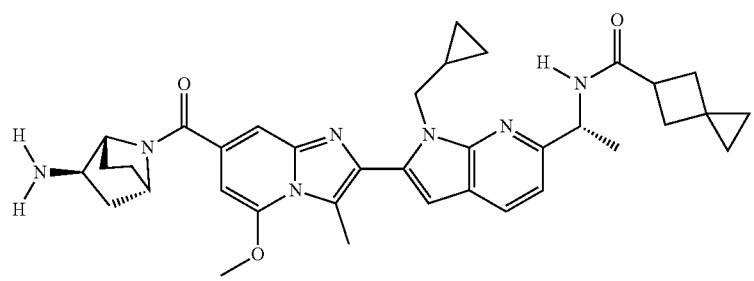
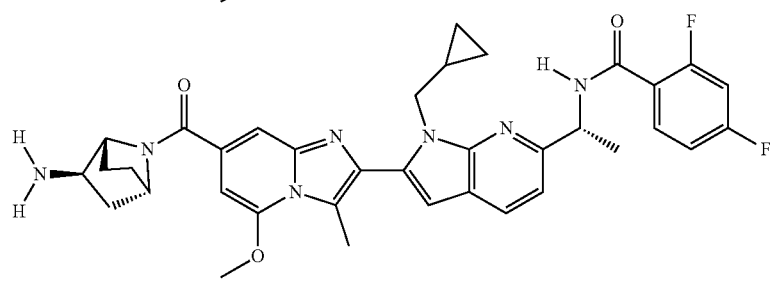

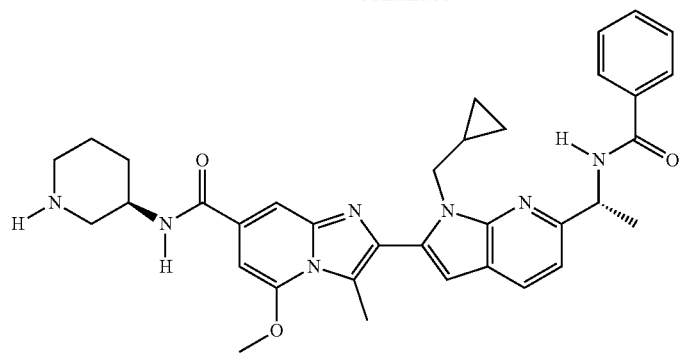
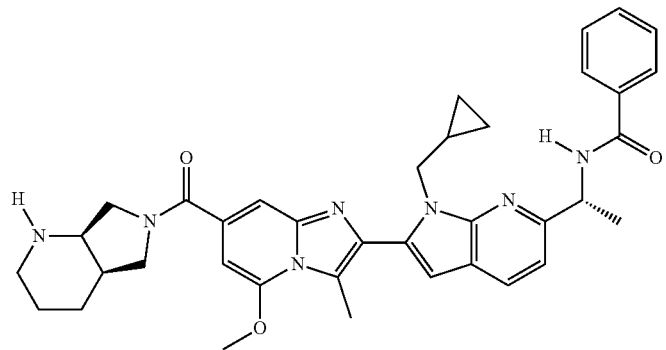
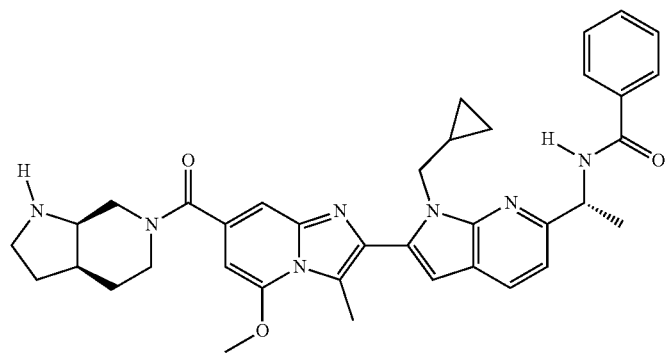
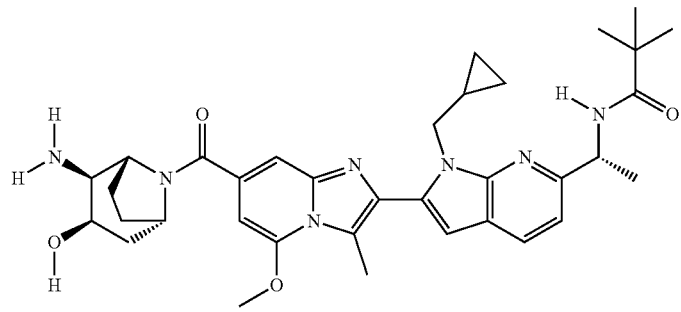
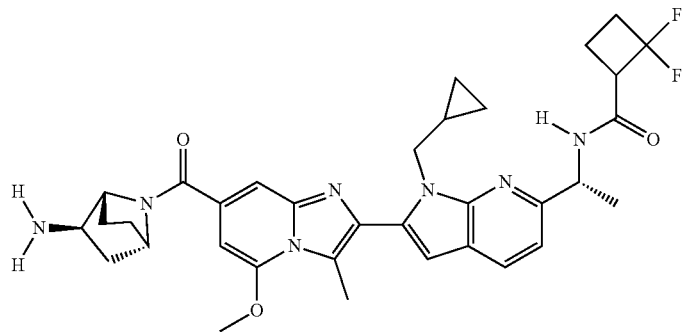

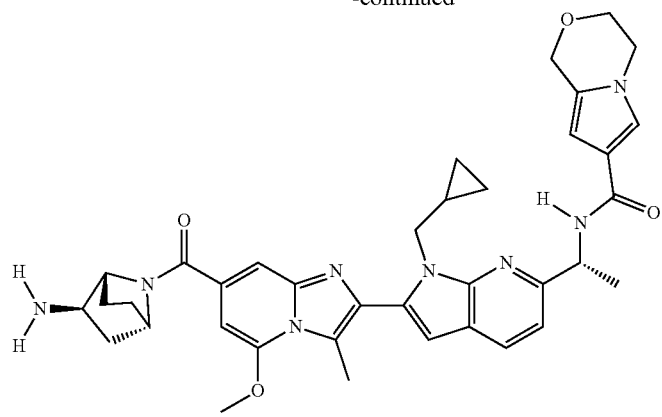
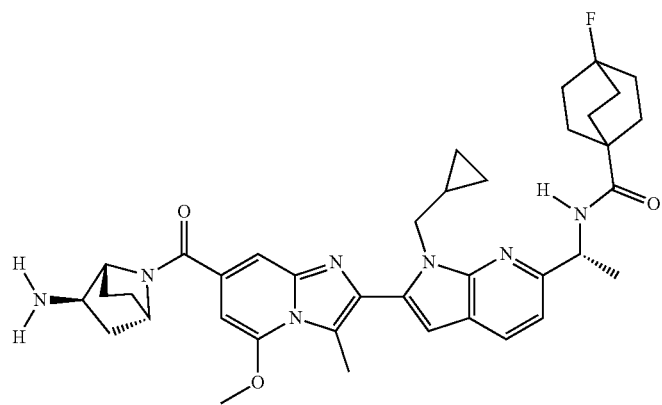
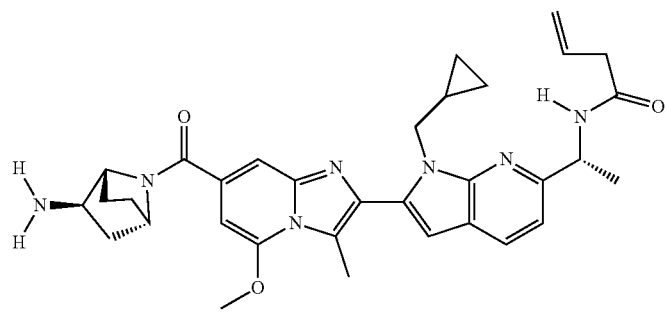
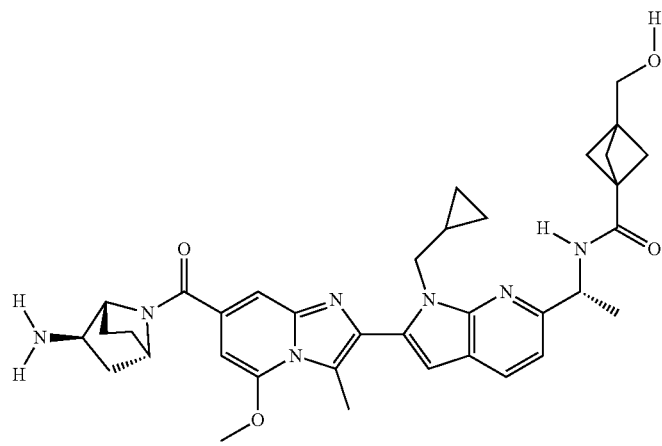

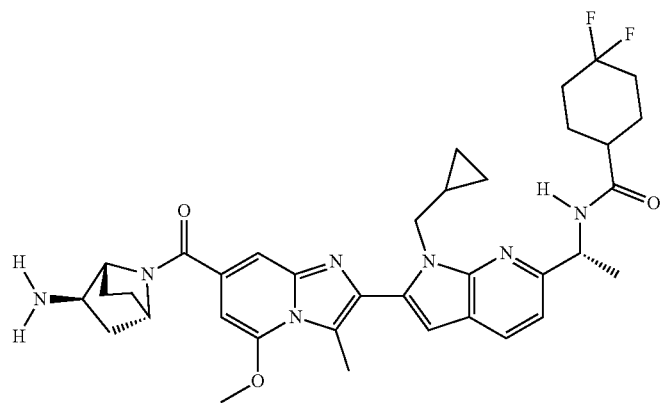
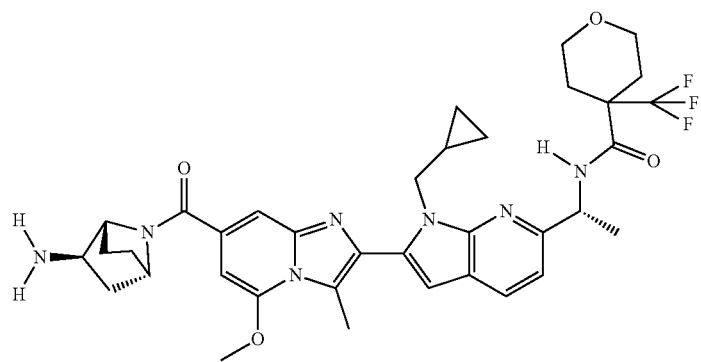
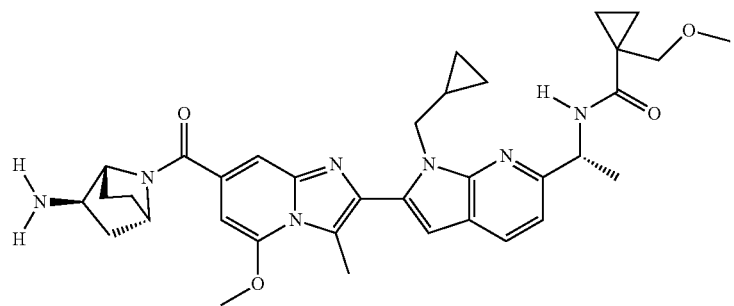
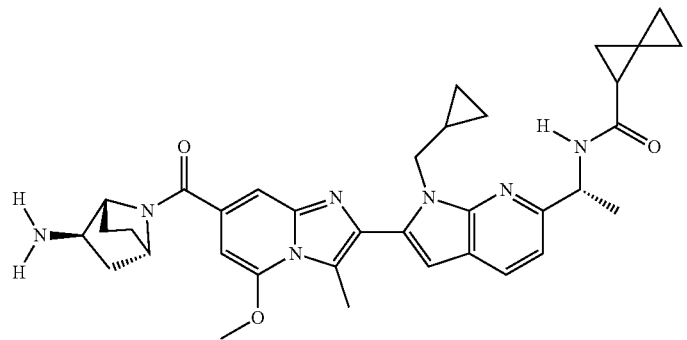

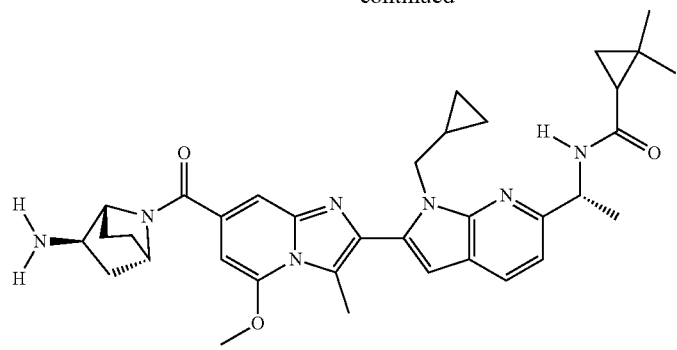
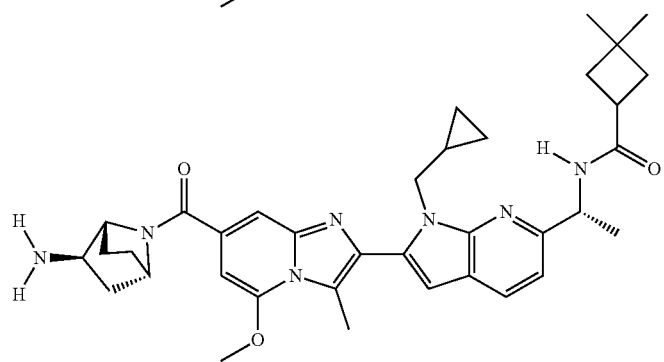
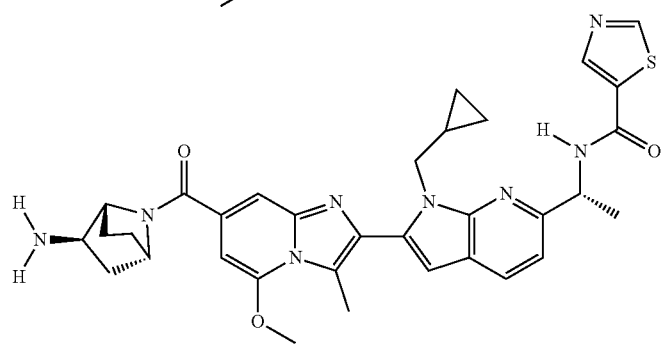
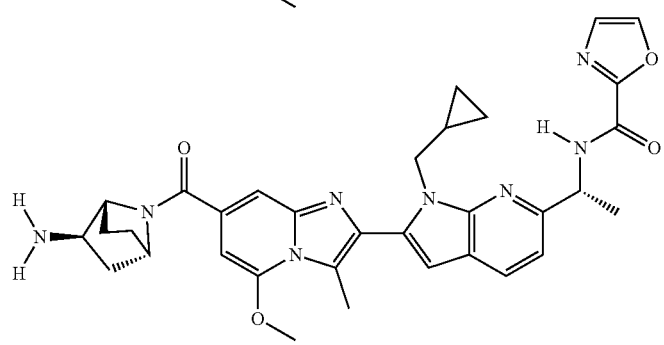
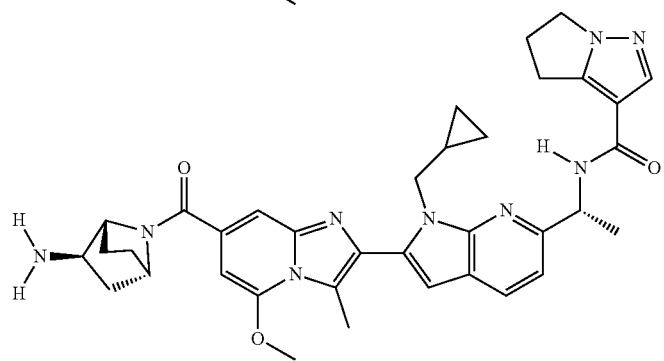

-continued
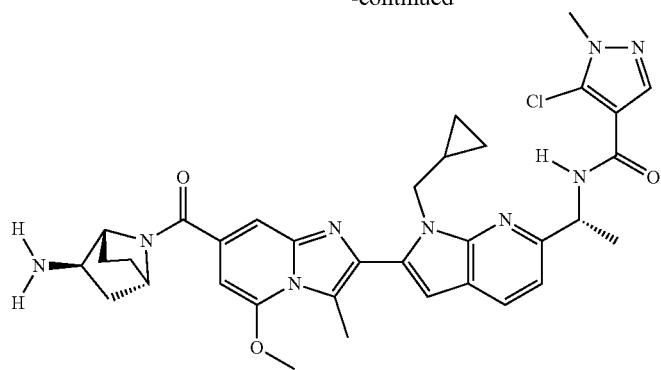
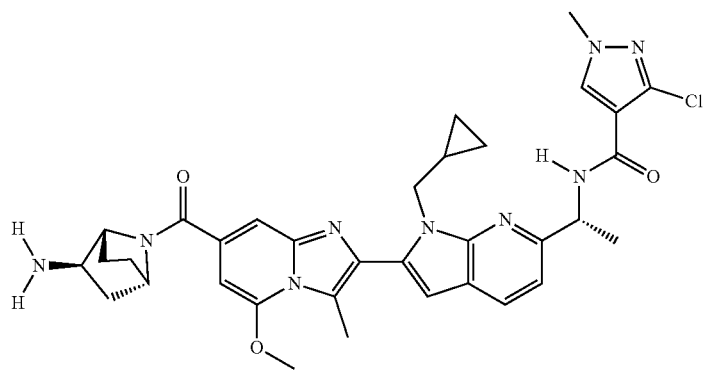
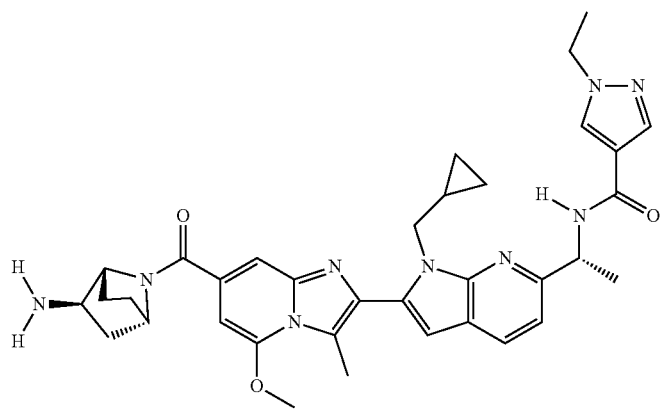
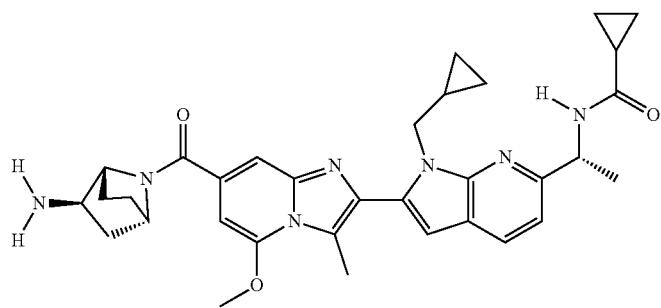

665
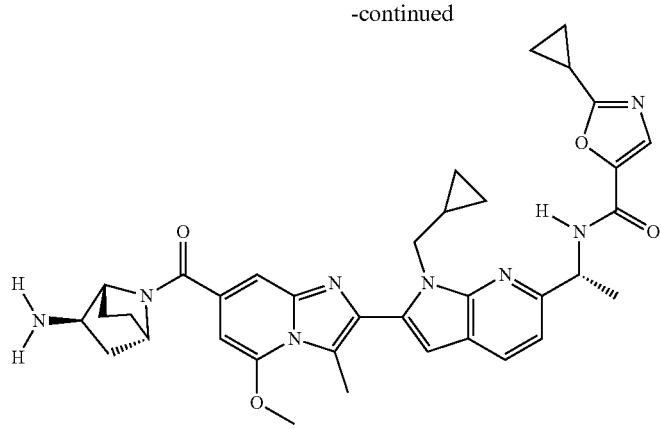
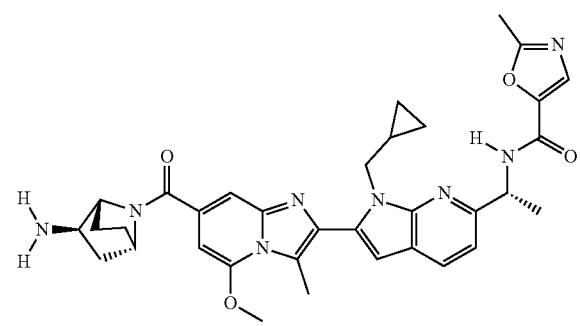
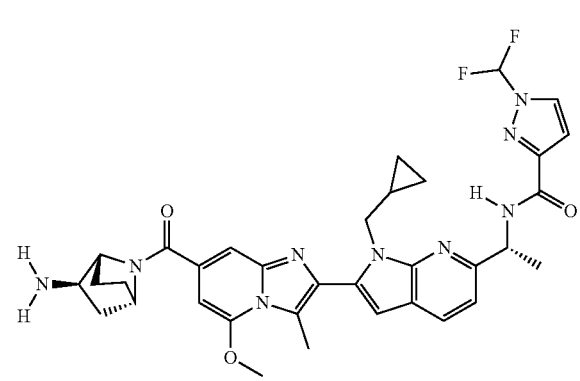
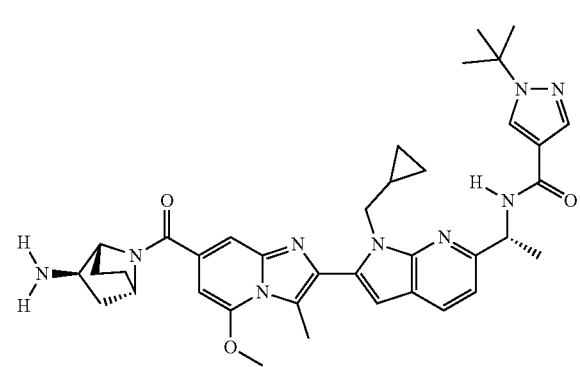
666
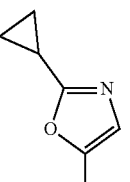
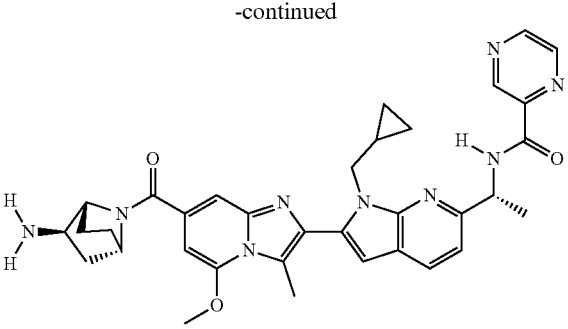
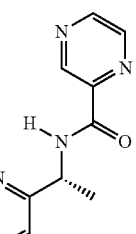
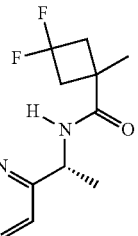
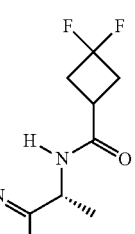
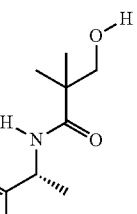

667
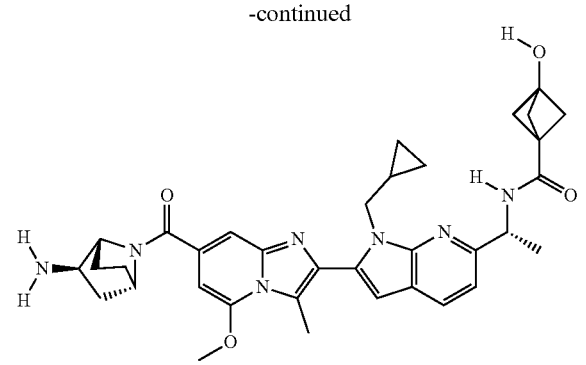
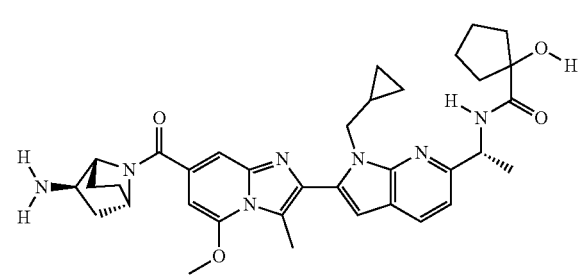
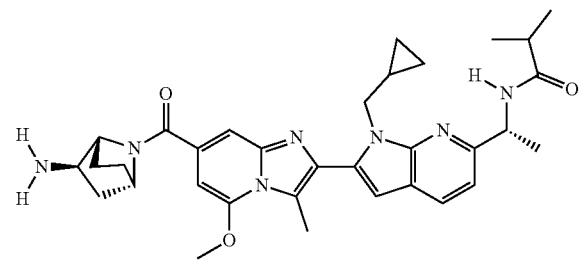
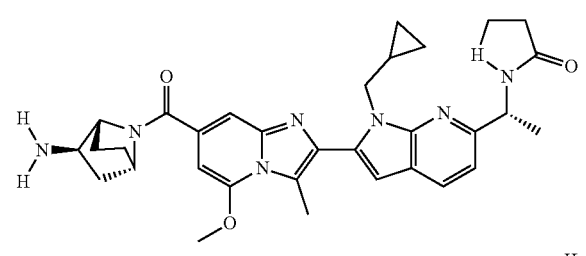
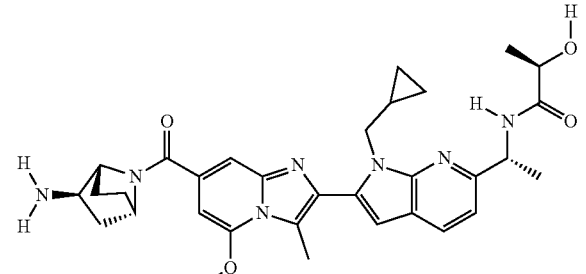
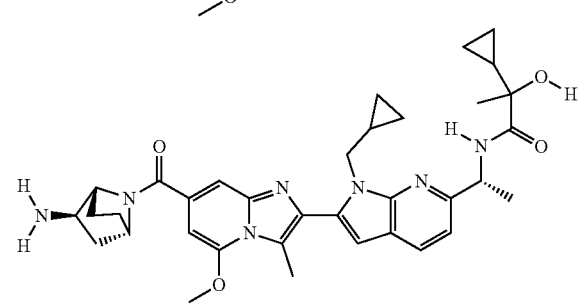
668
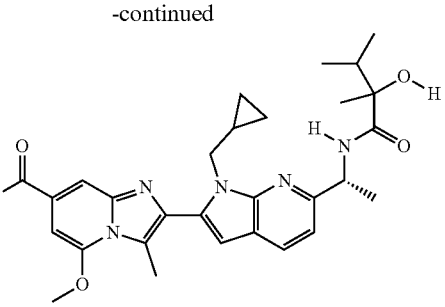
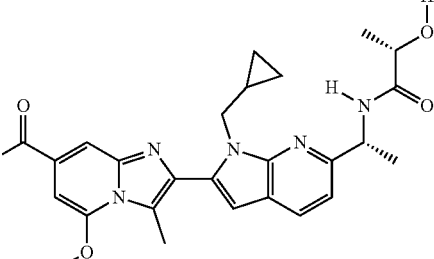
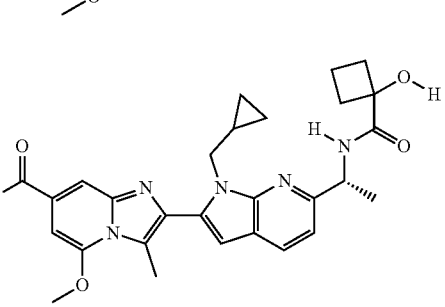
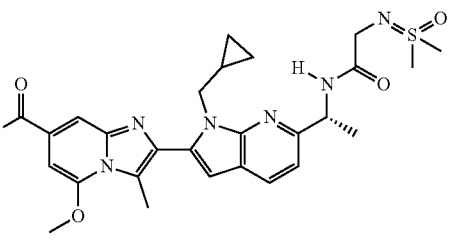
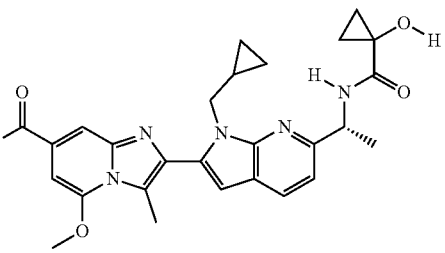
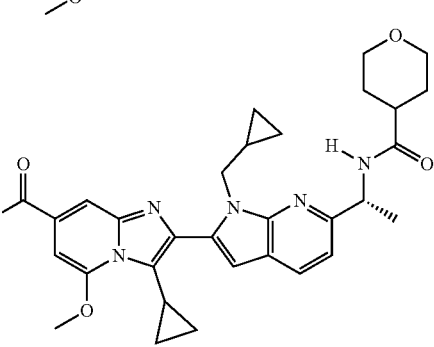

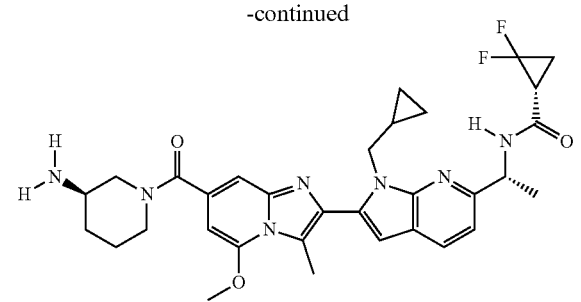
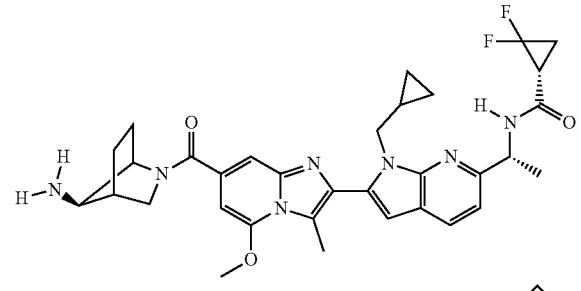
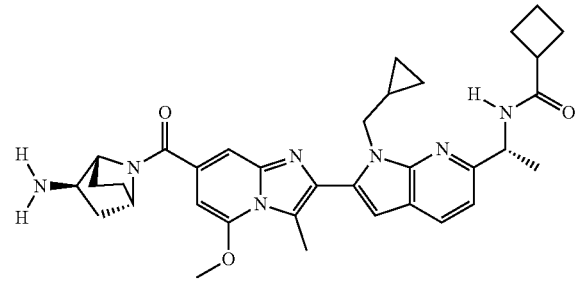
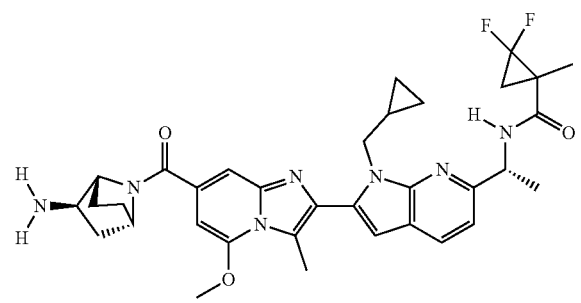
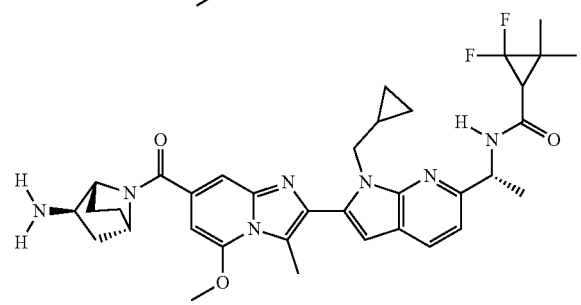
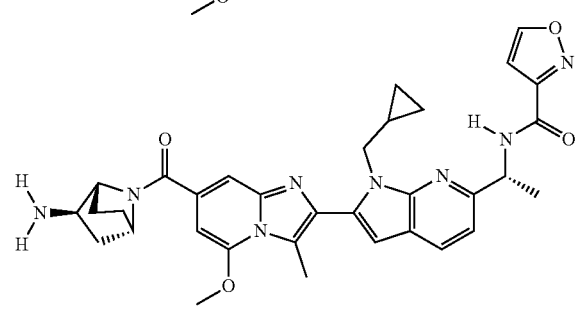
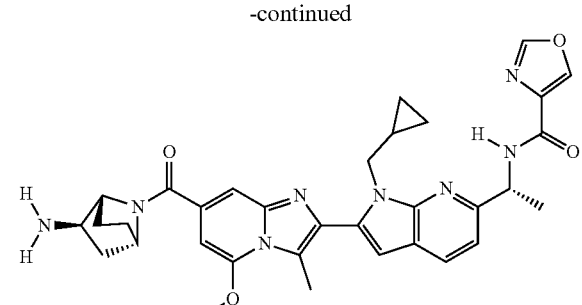
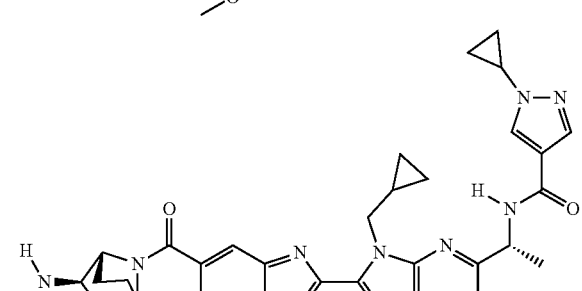
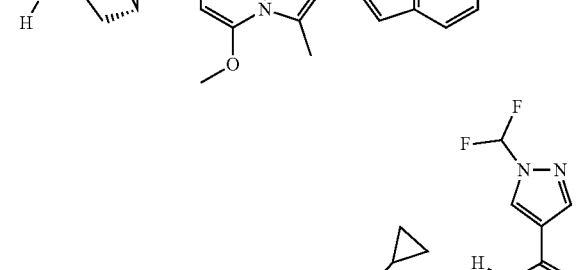
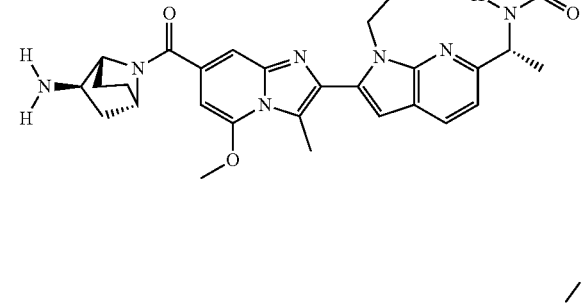
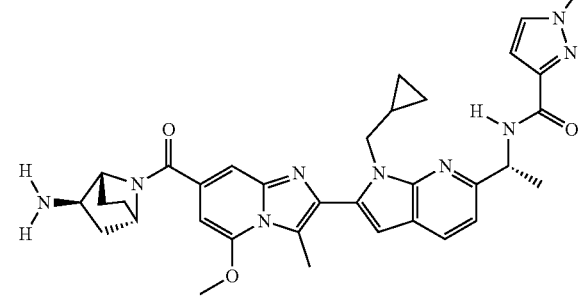
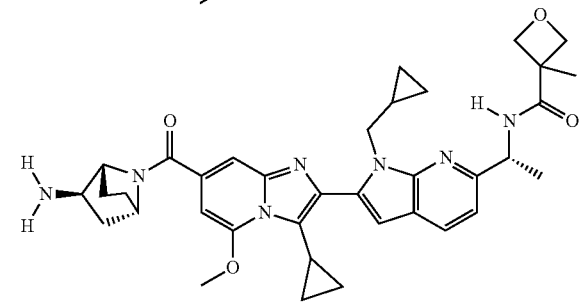

671
-continued
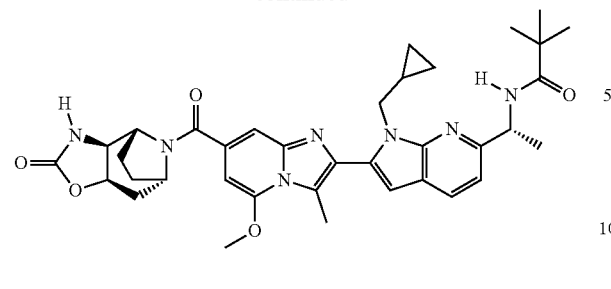
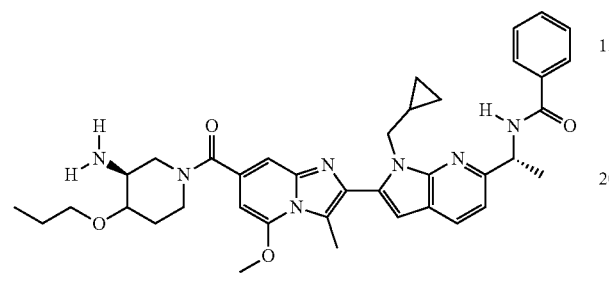
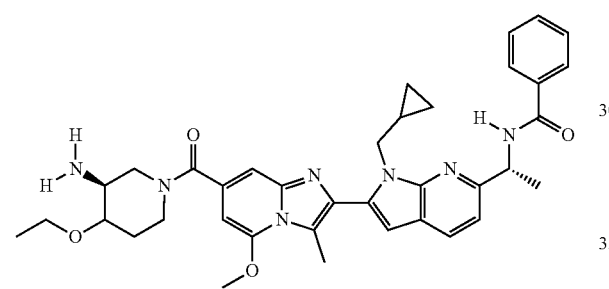
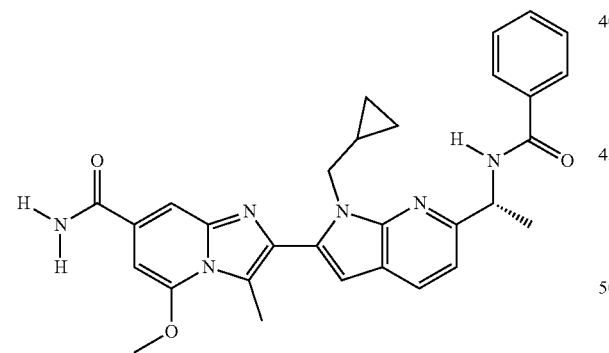
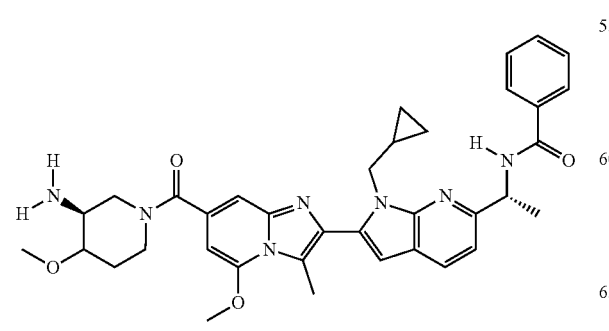
672
-continued
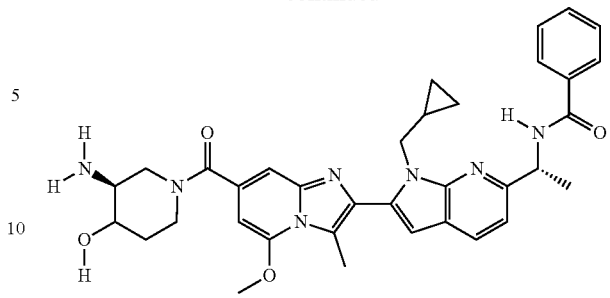
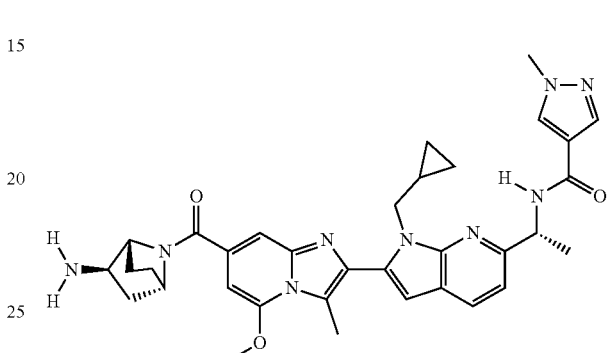
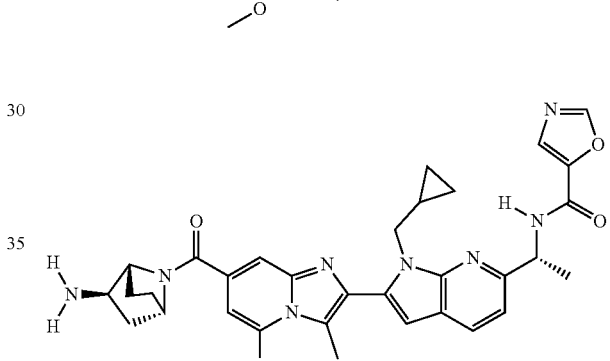
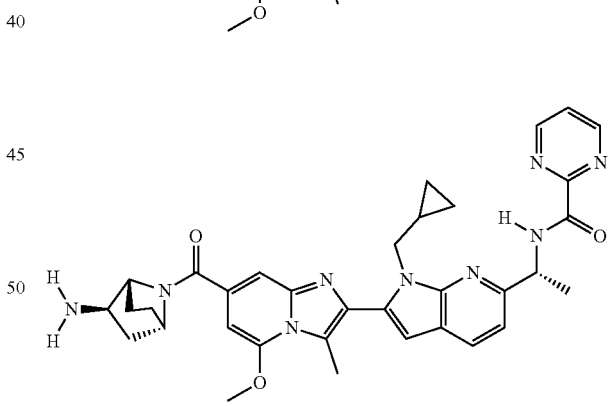
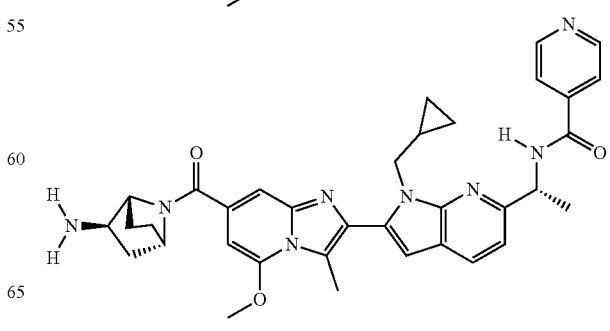

673
-continued
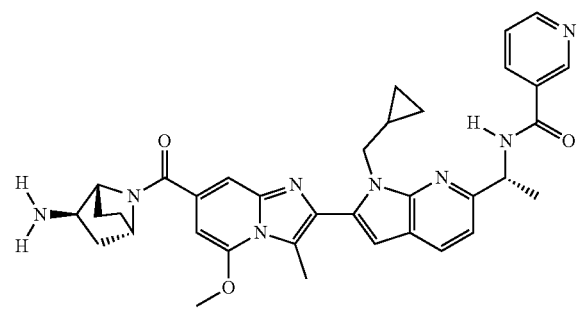
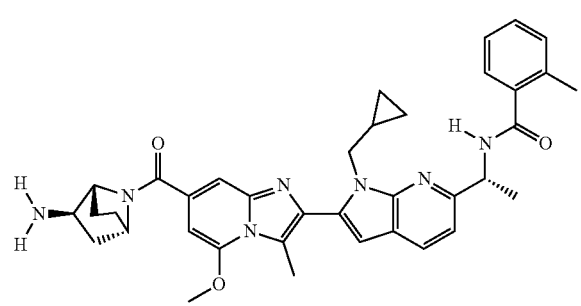
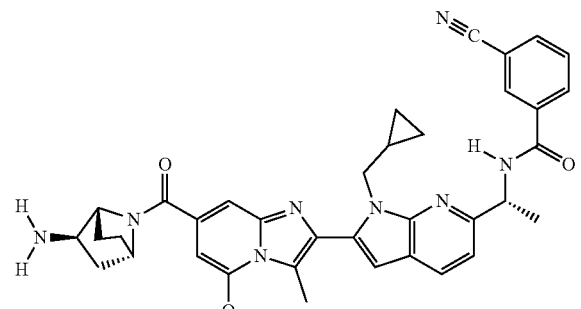
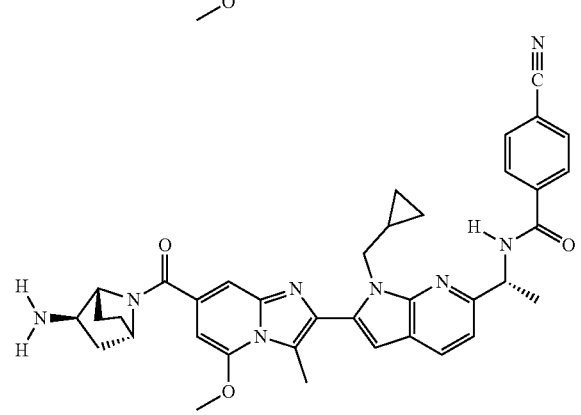
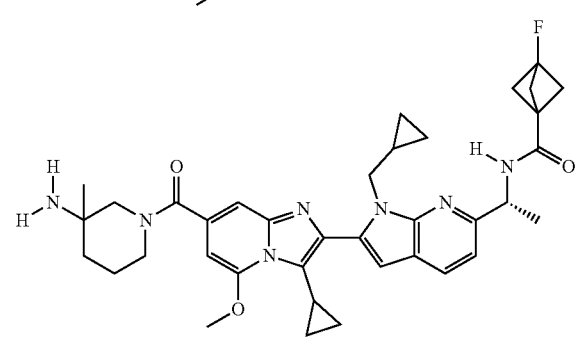
674
-continued
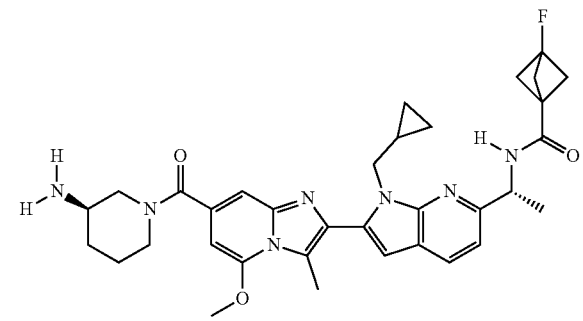
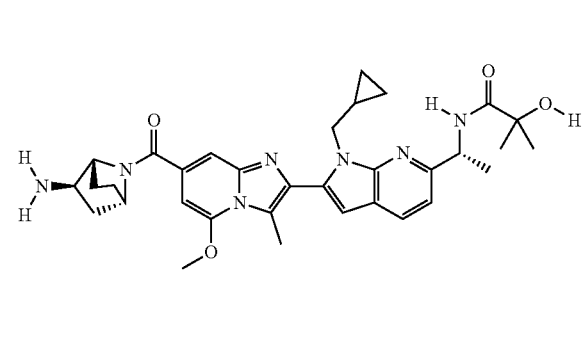
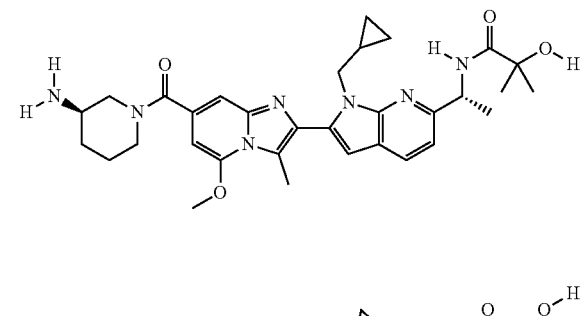
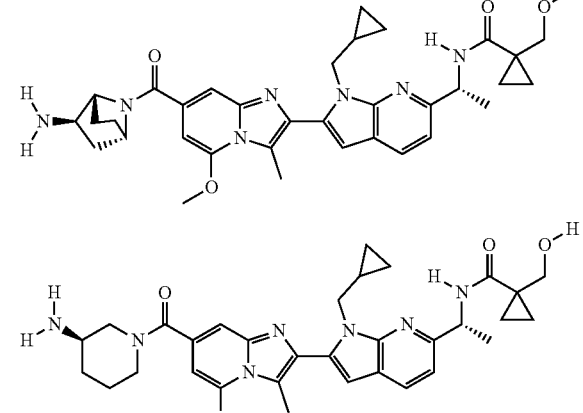
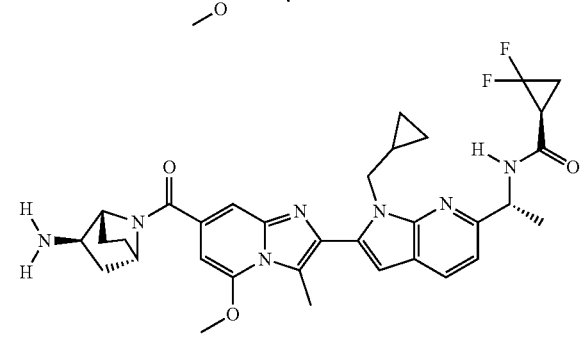

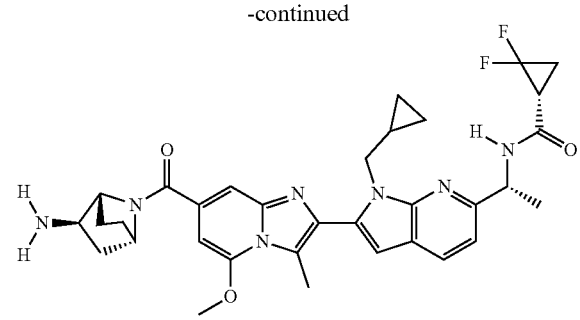
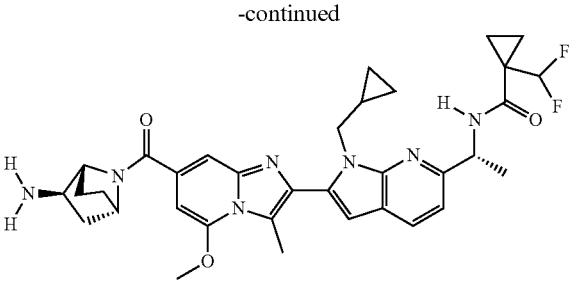
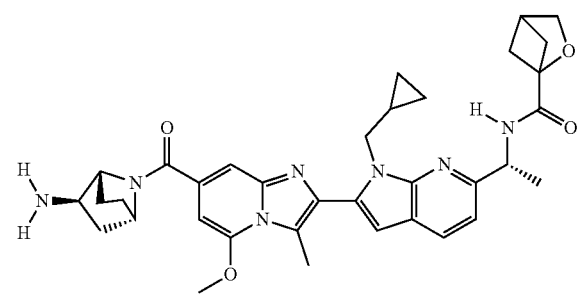
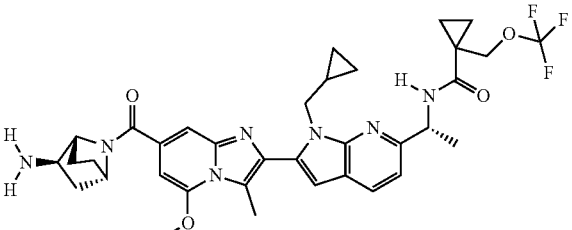
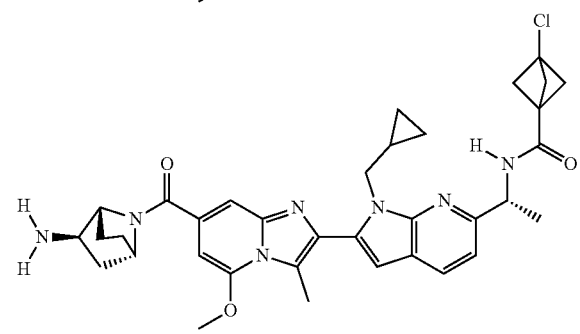
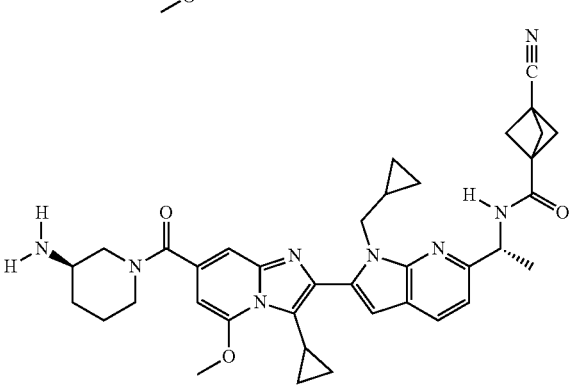
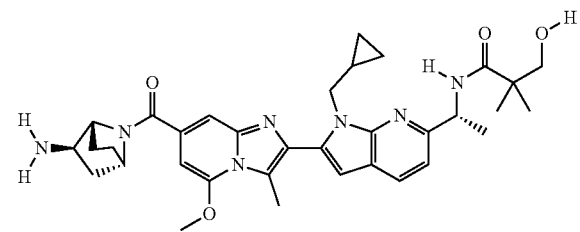
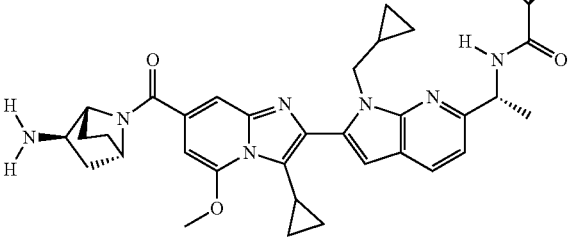
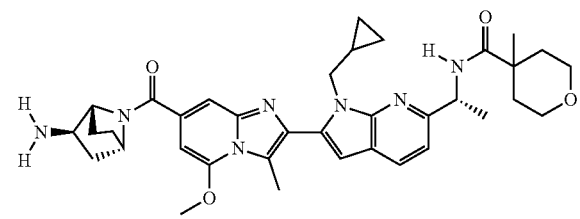
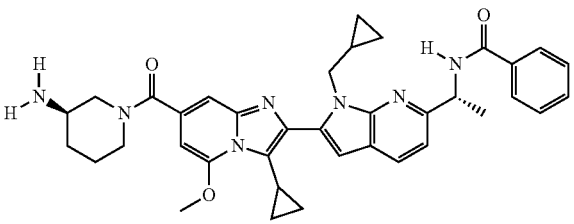
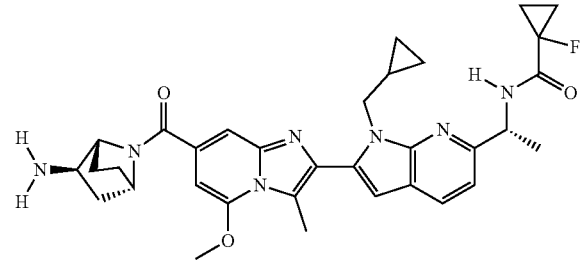
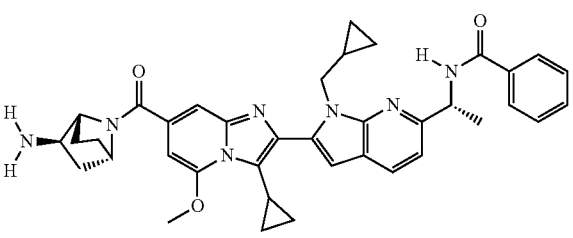

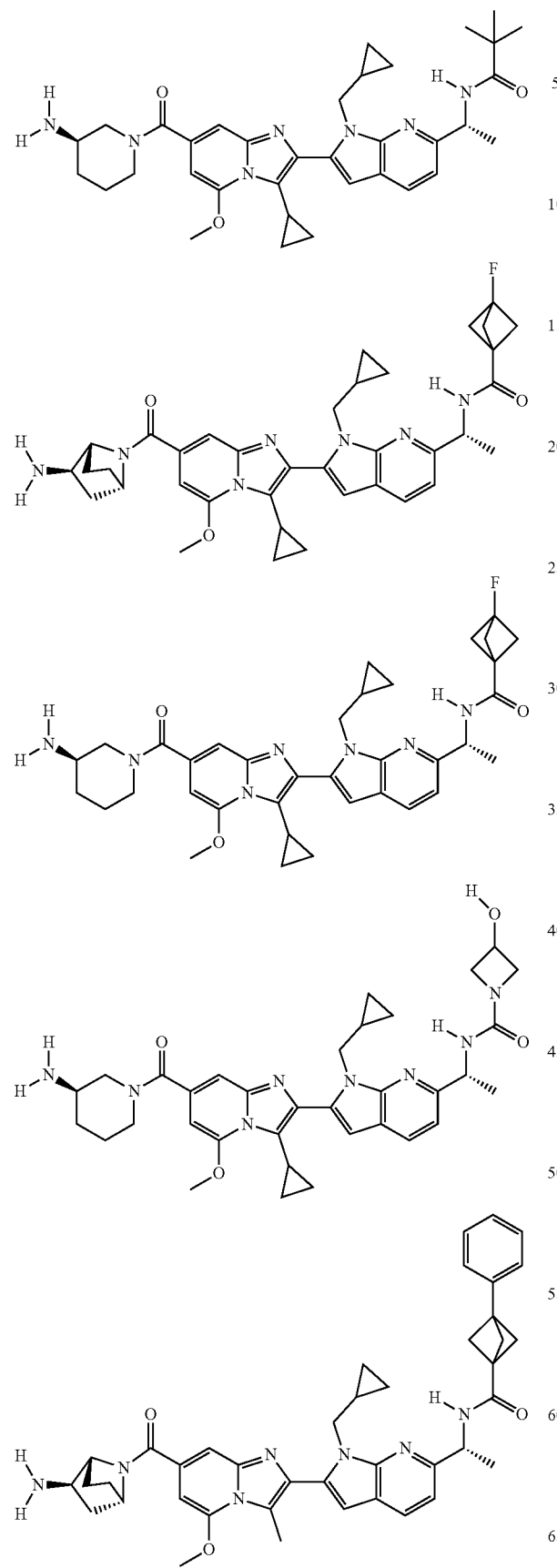
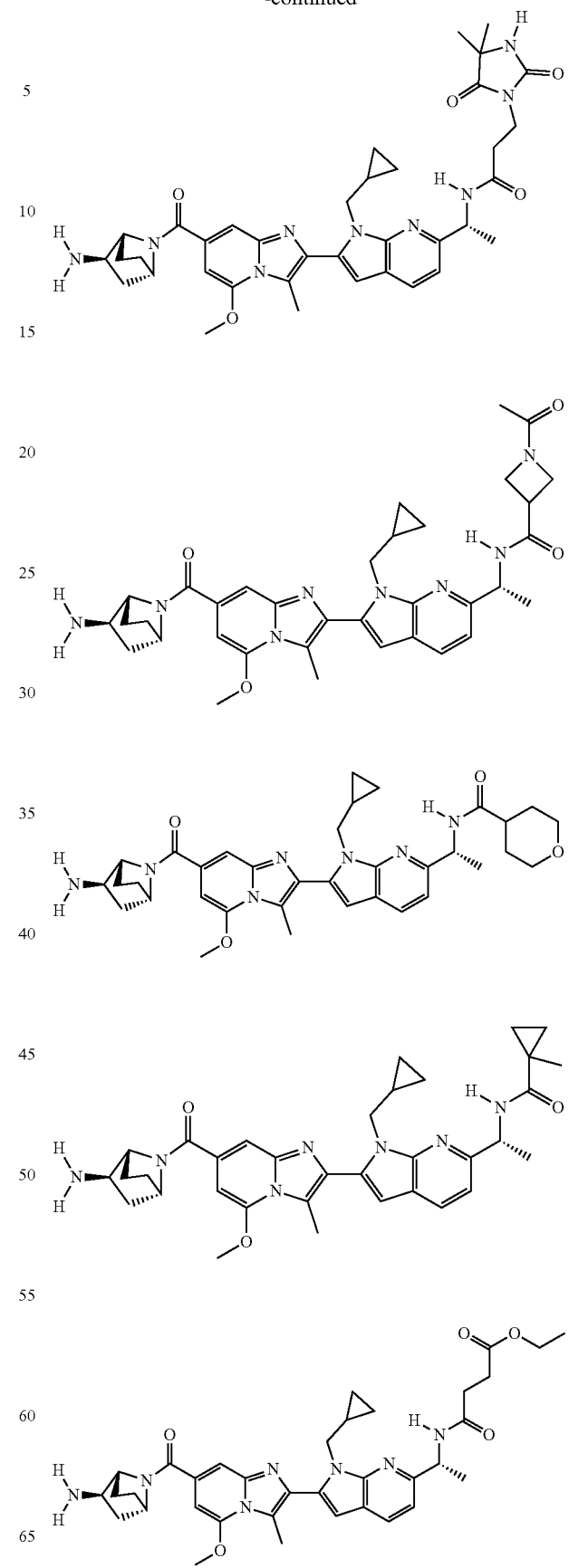

679
-continued
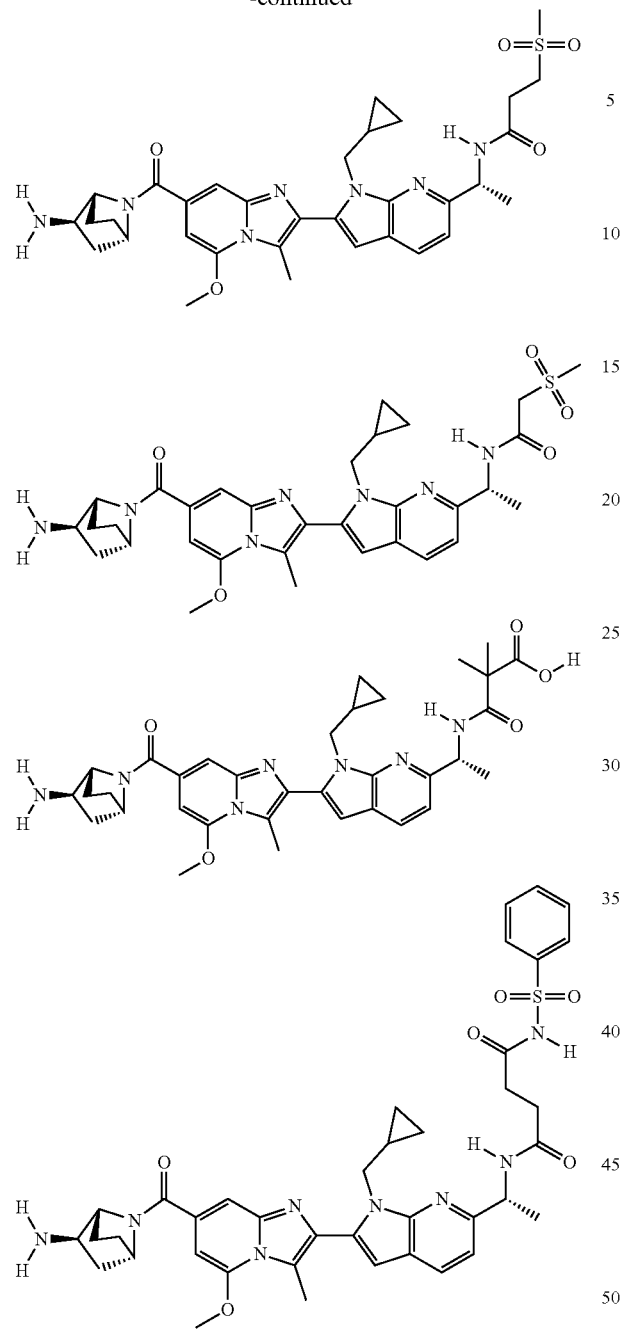
680
-continued
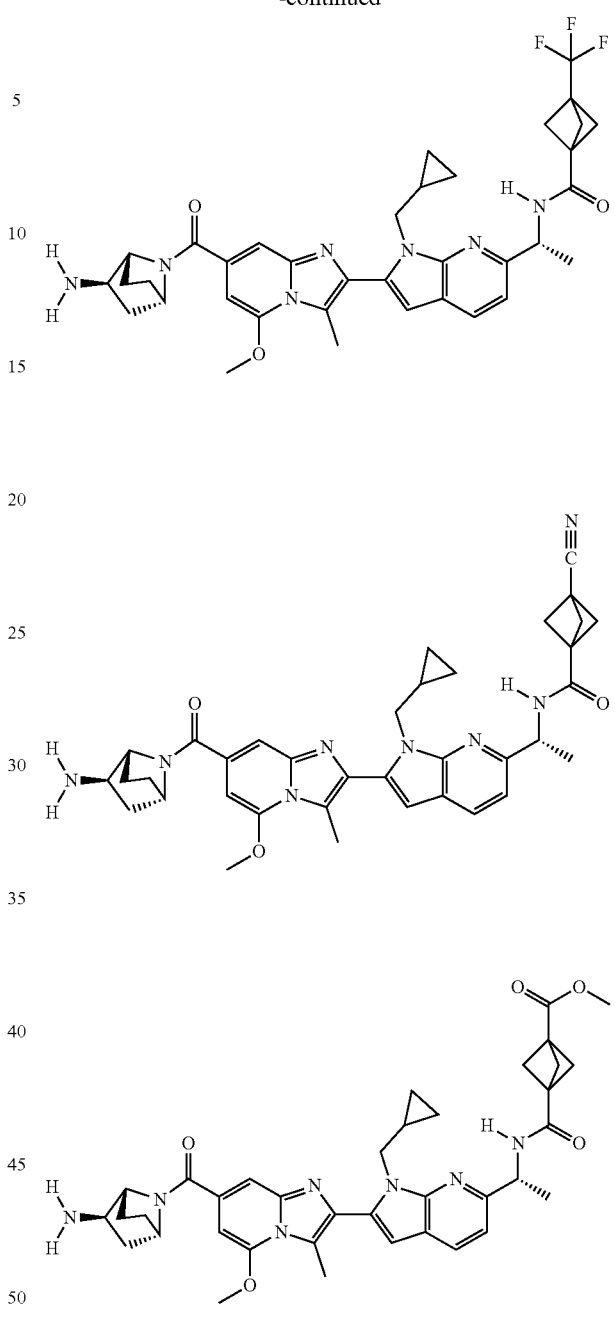
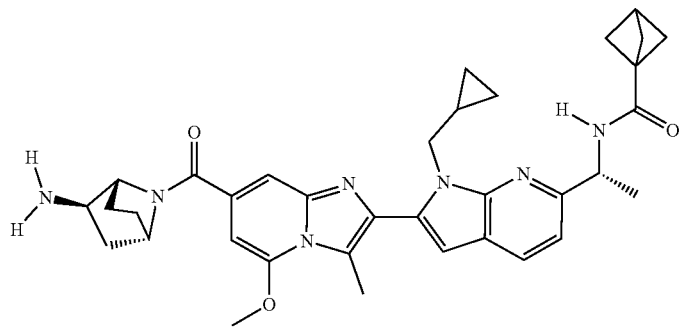

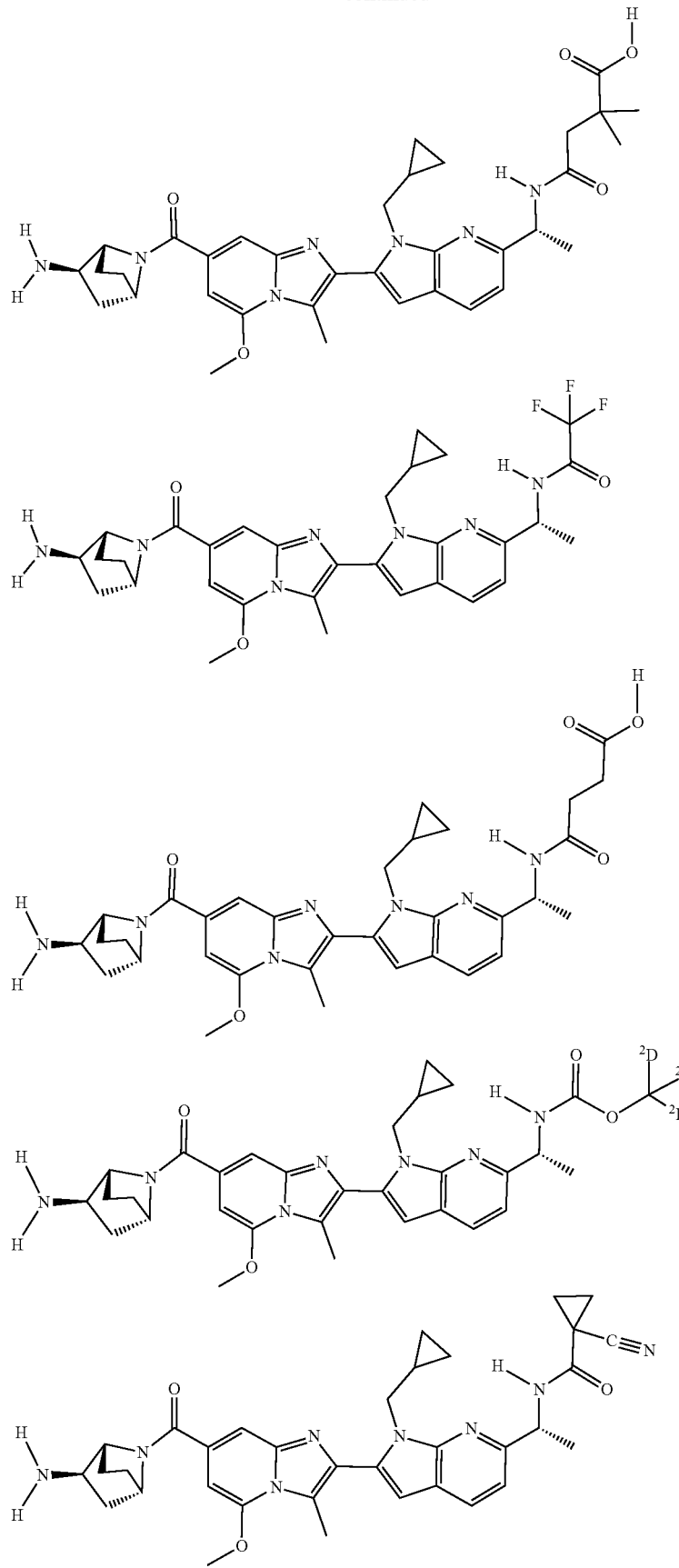

-continued
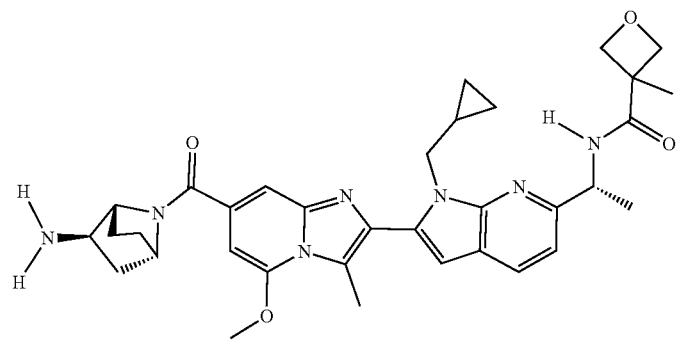
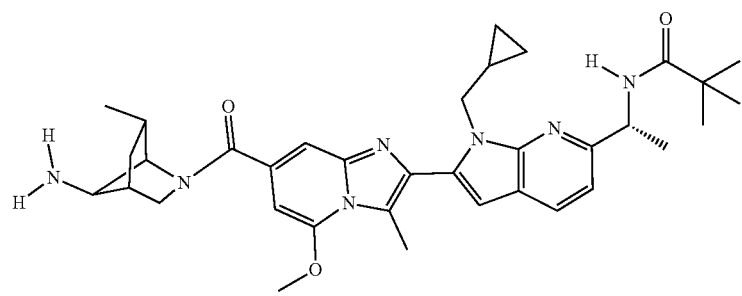
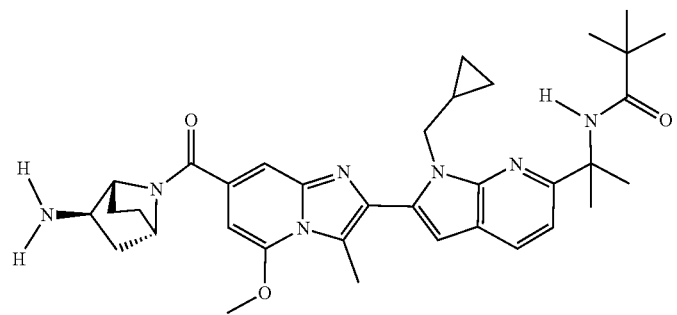
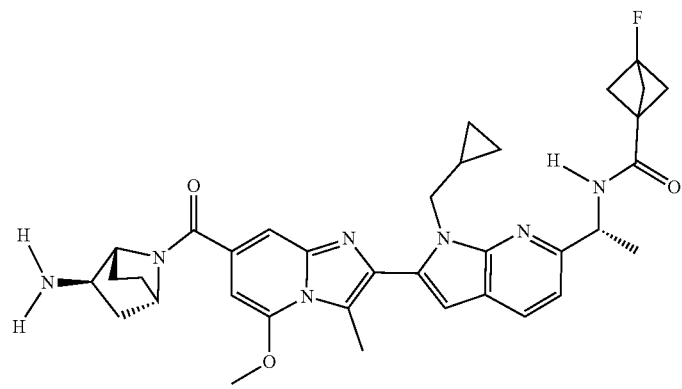
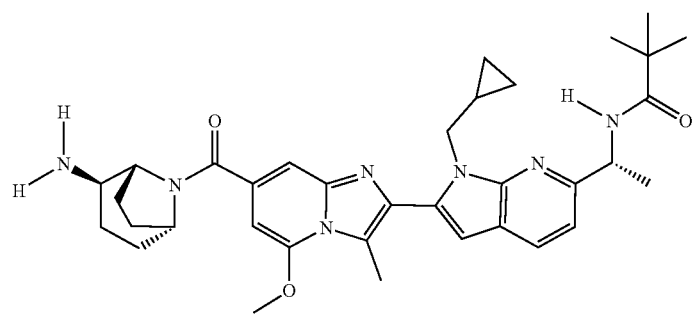

-continued
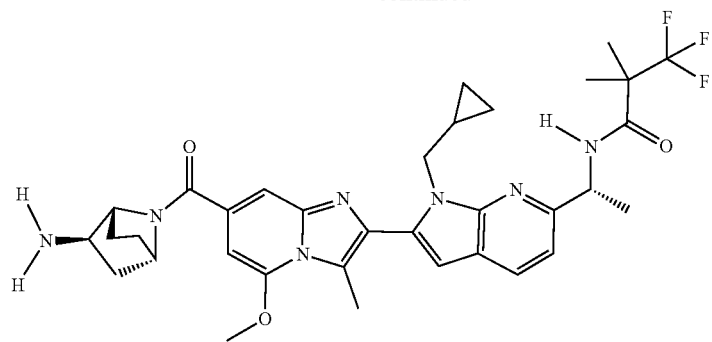
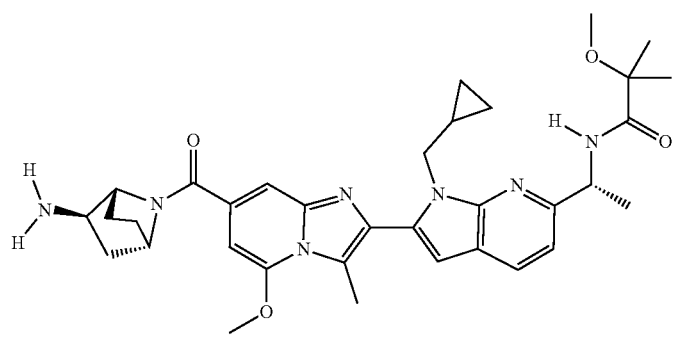
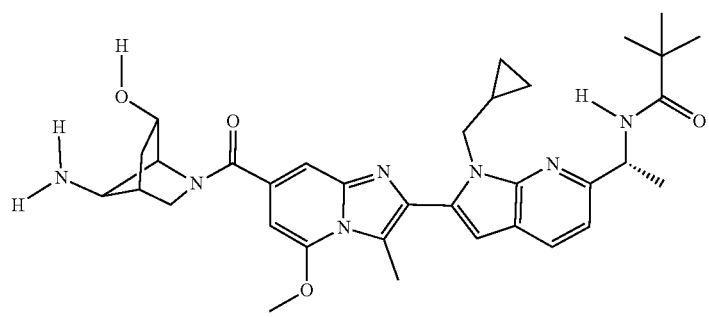
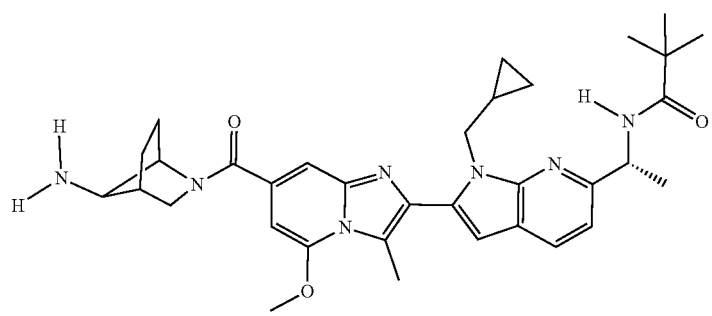
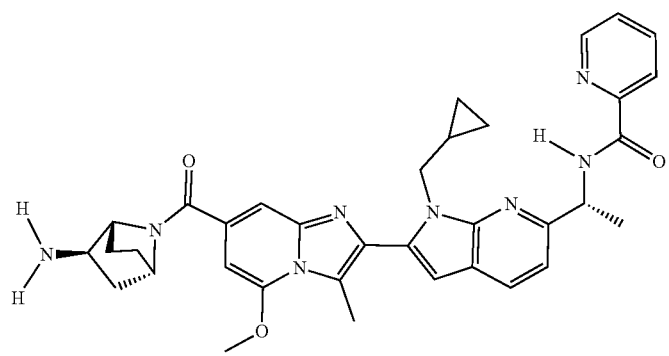

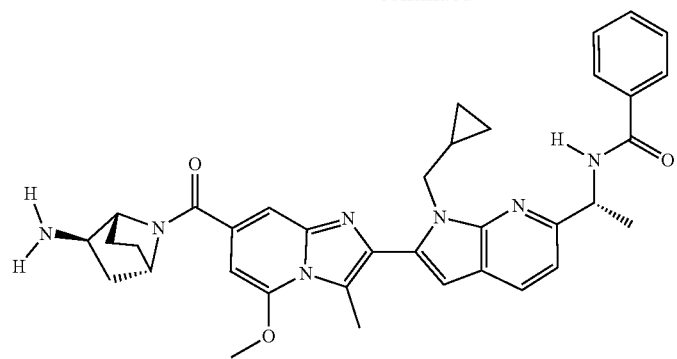
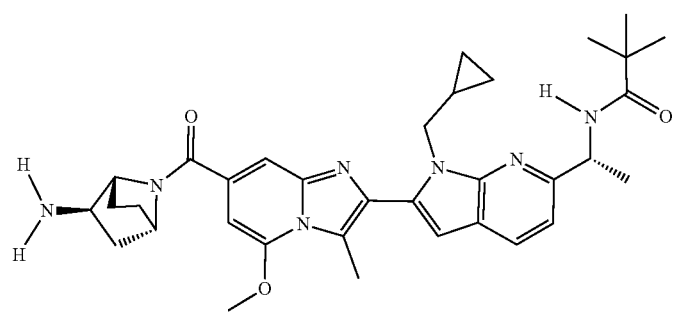
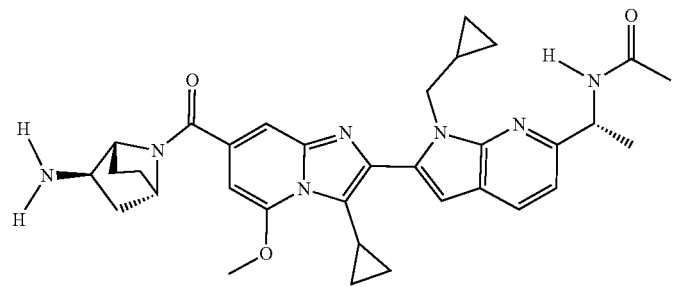
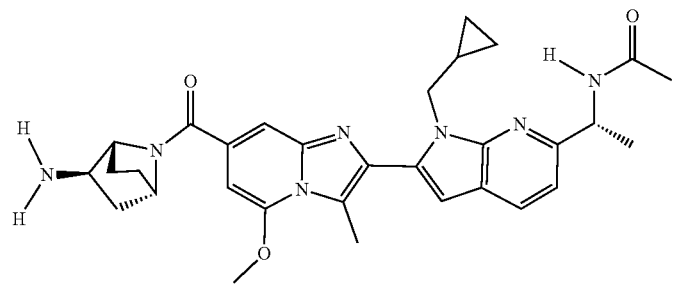
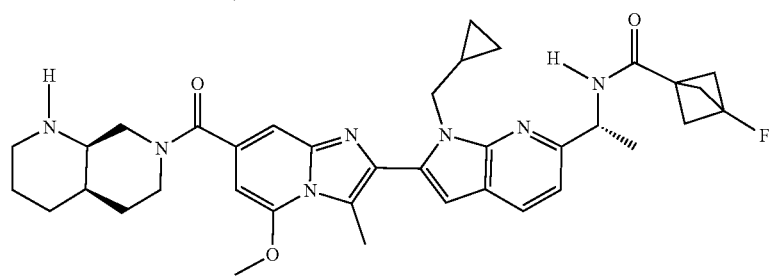

-continued
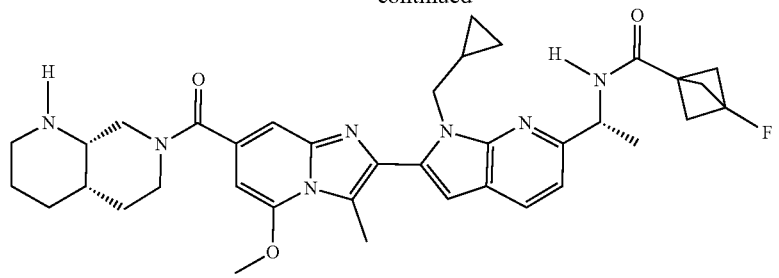
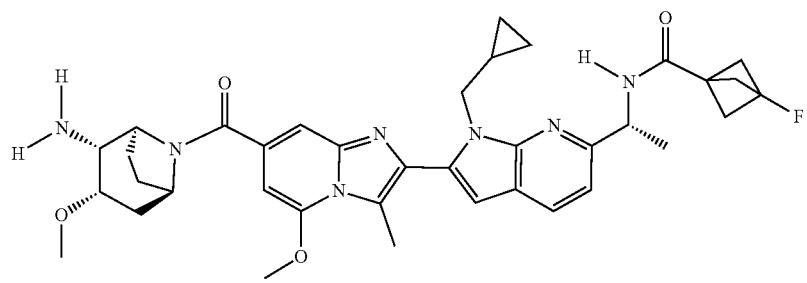
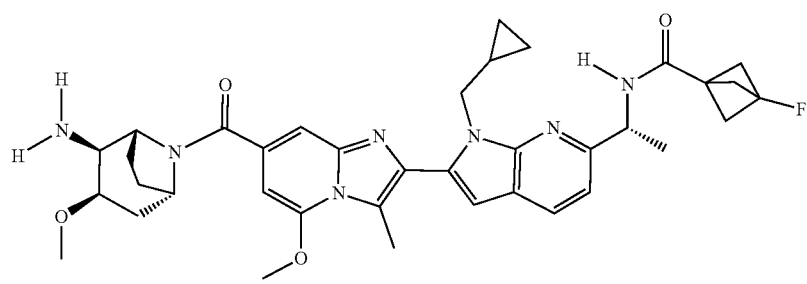
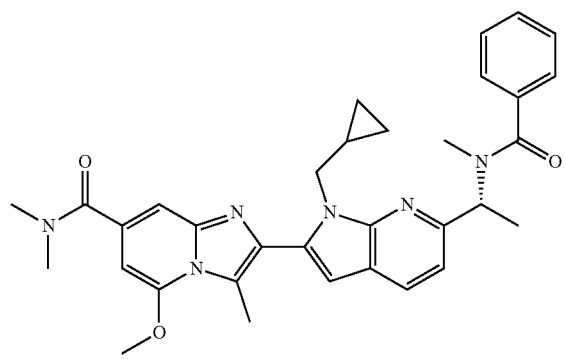
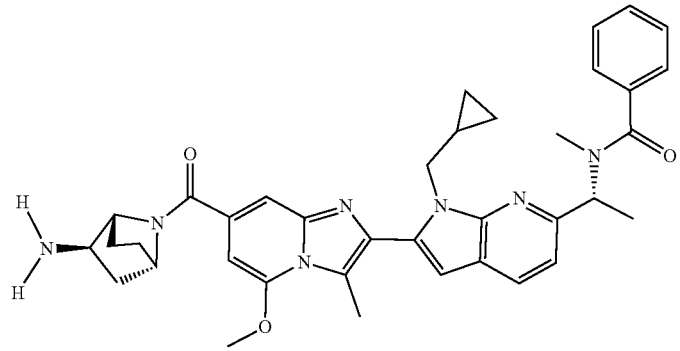

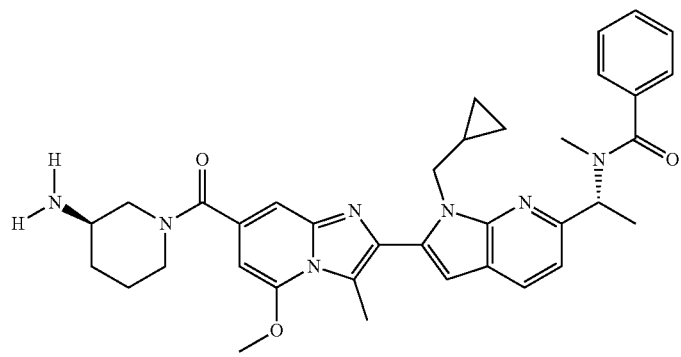
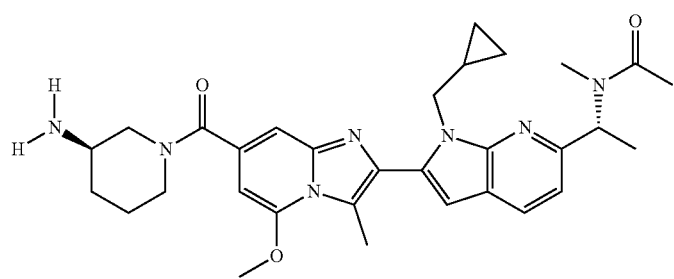
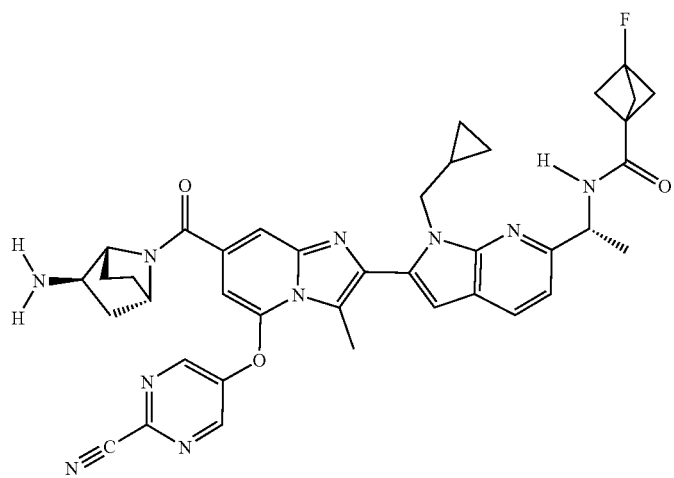
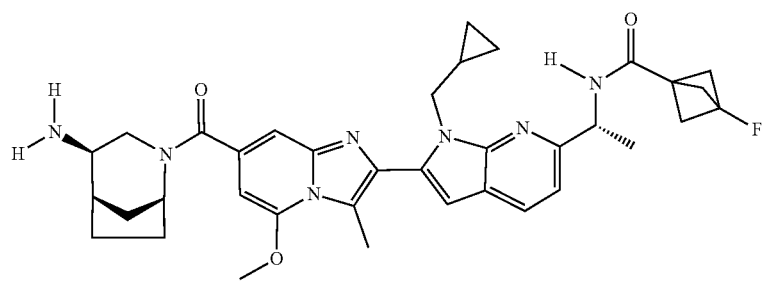

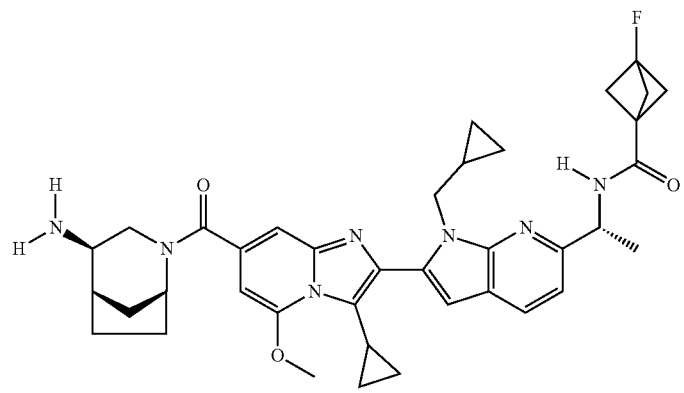 [SMILES: COc1cc(C(=O)N2C[C@H](N)[C@H]3CC[C@@H]2C3)cc2nc(-c3cc4ccc([C@@H](C)NC(=O)C56CC(F)(C5)C6)nc4n3CC3CC3)c(C3CC3)n12]
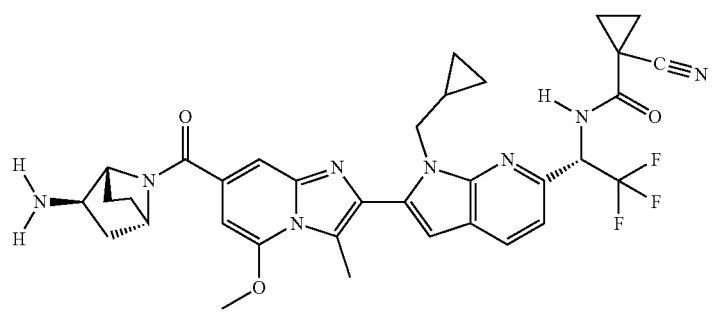
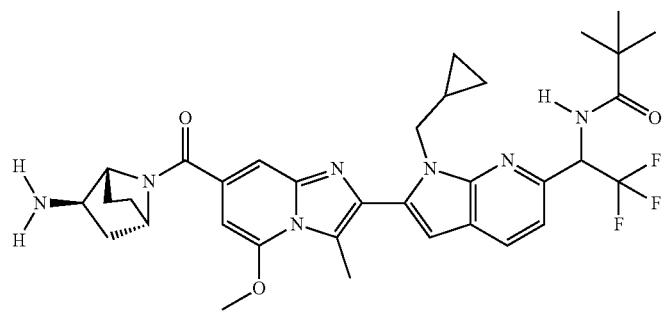
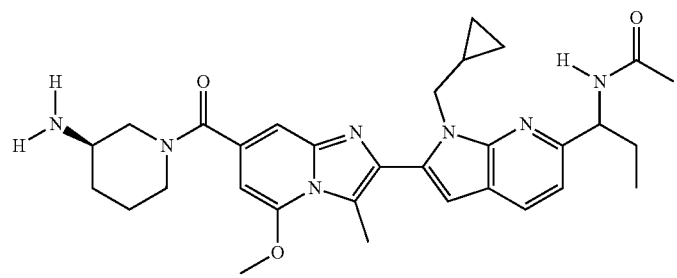
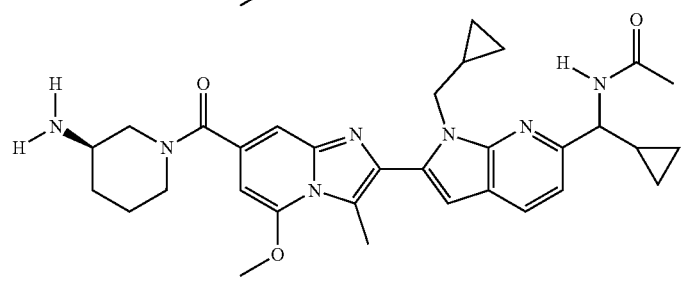

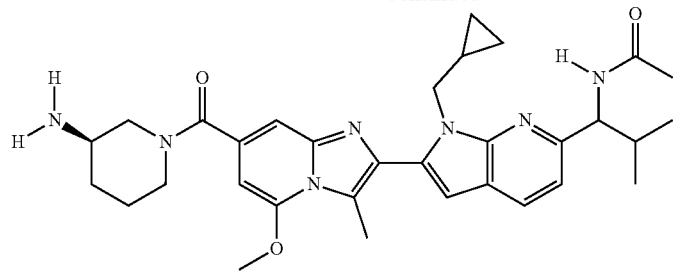
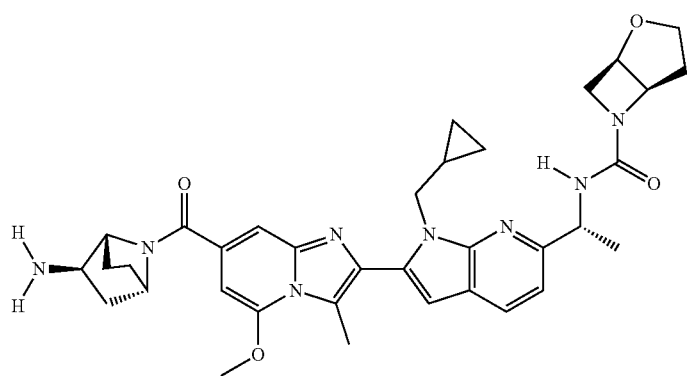
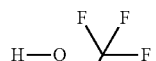
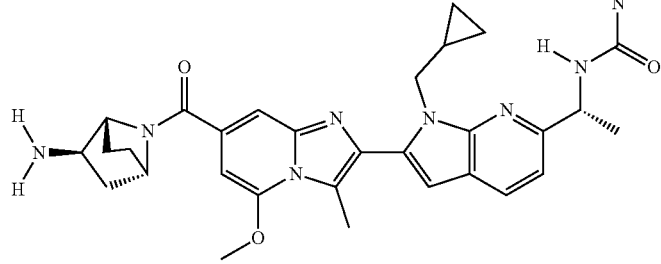
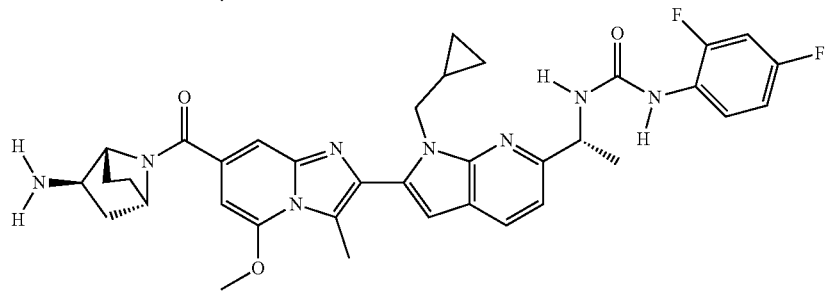
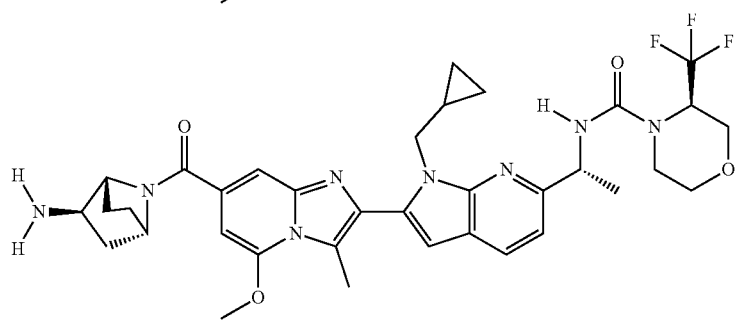

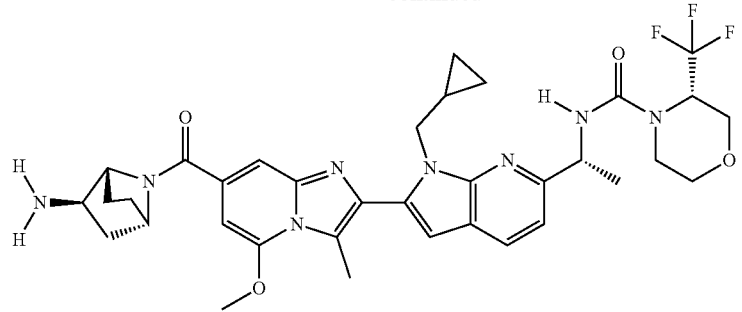
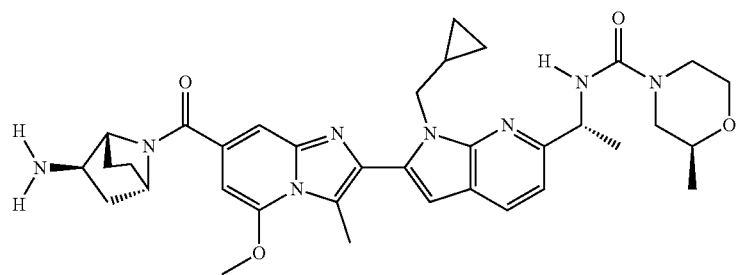
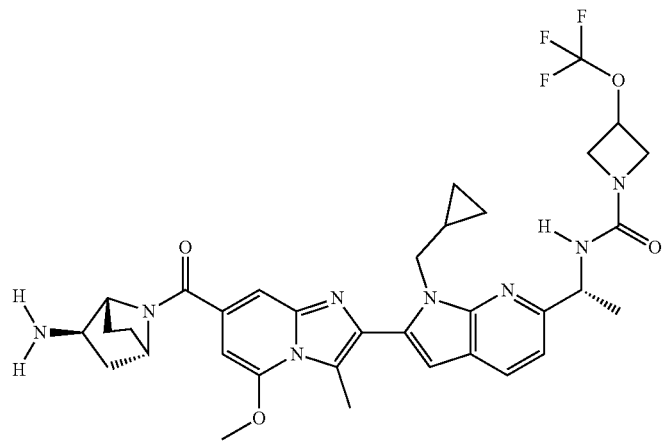
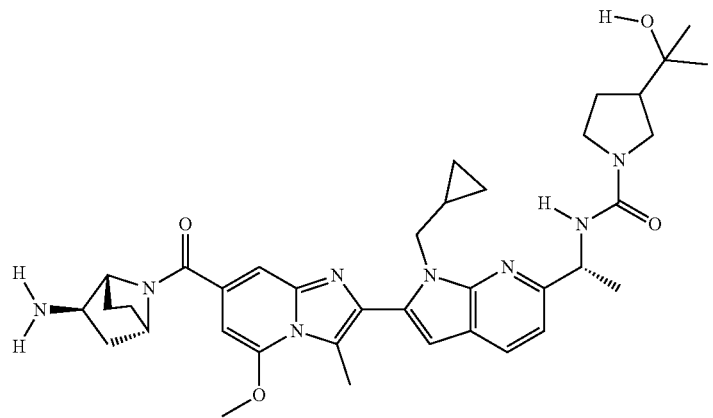

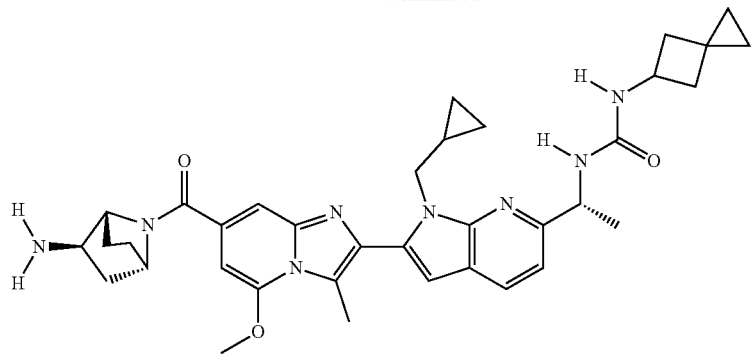
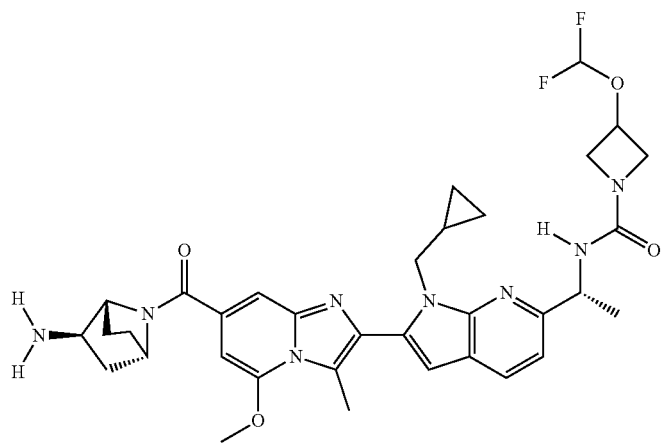
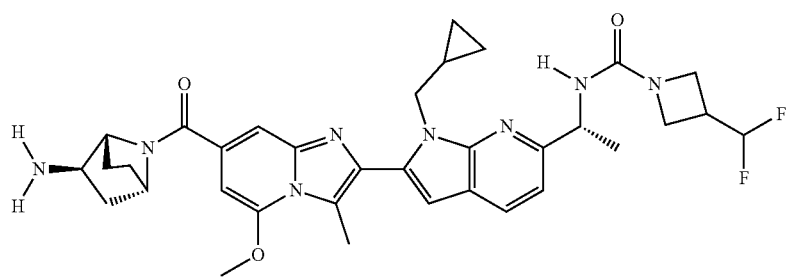
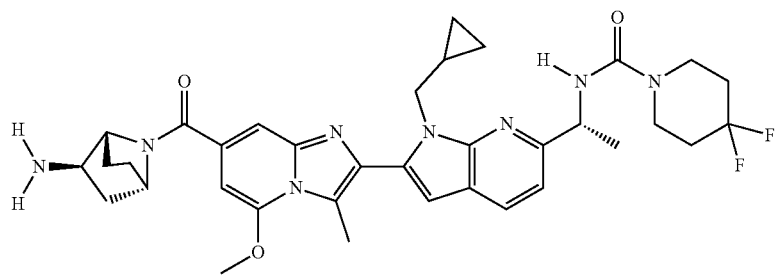
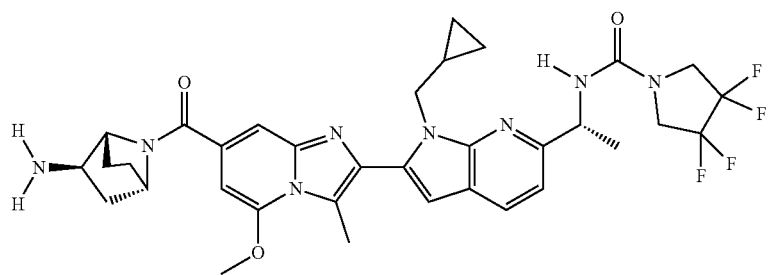

-continued
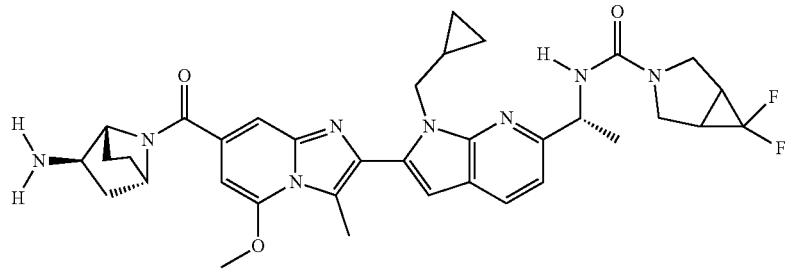
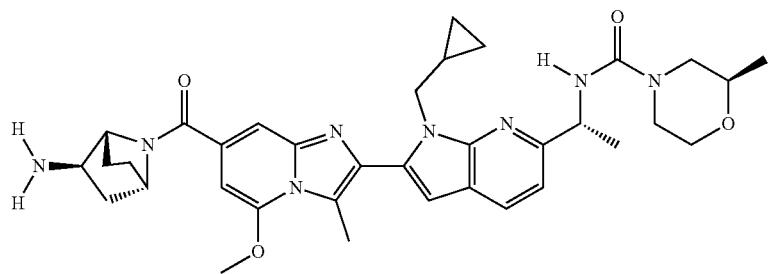
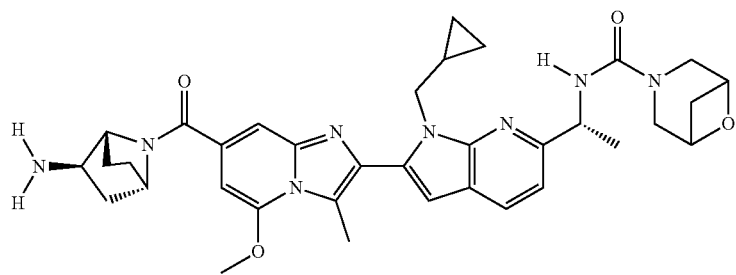
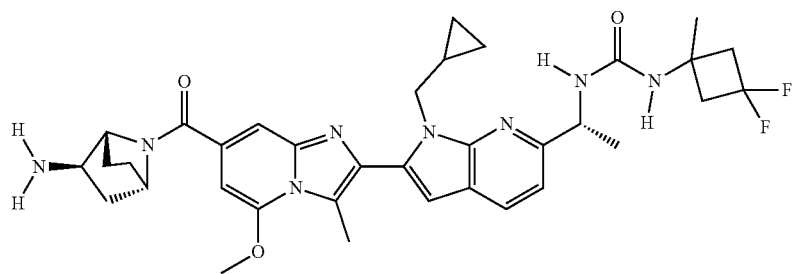
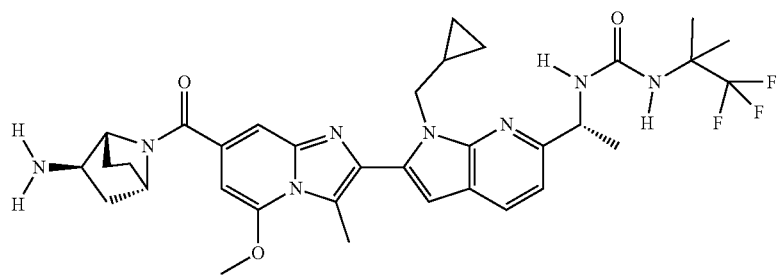
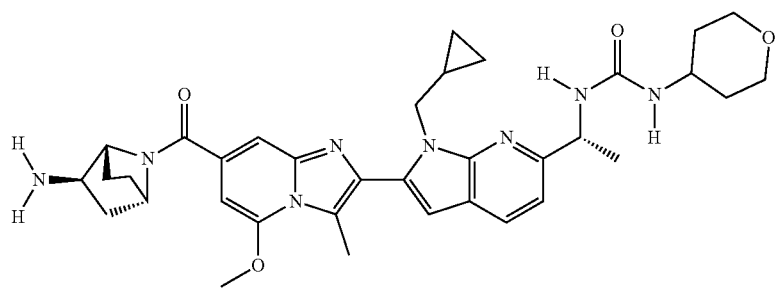

-continued
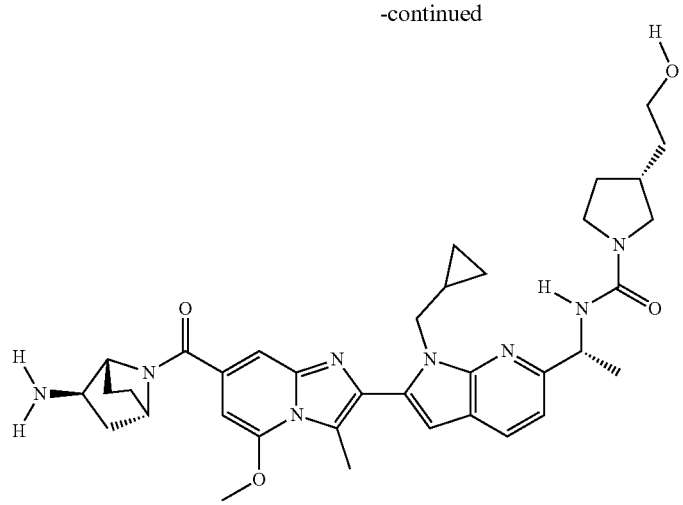
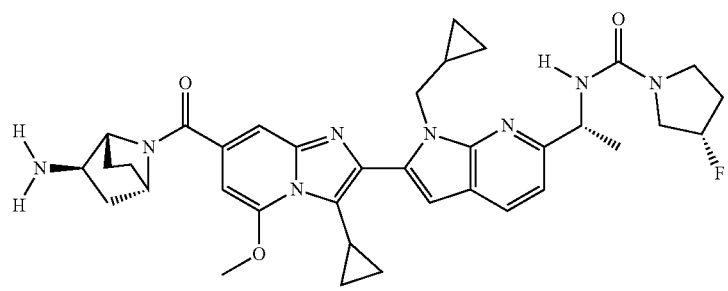
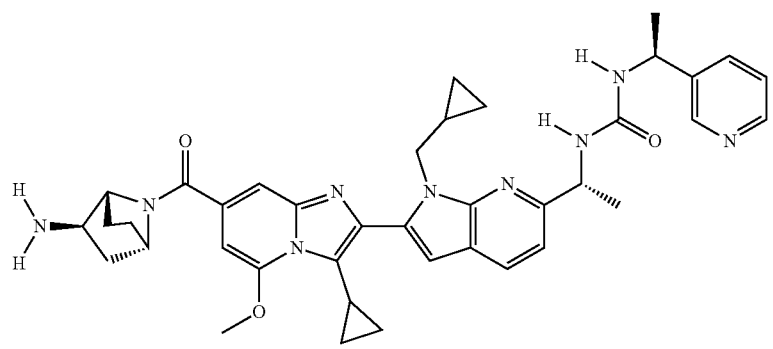
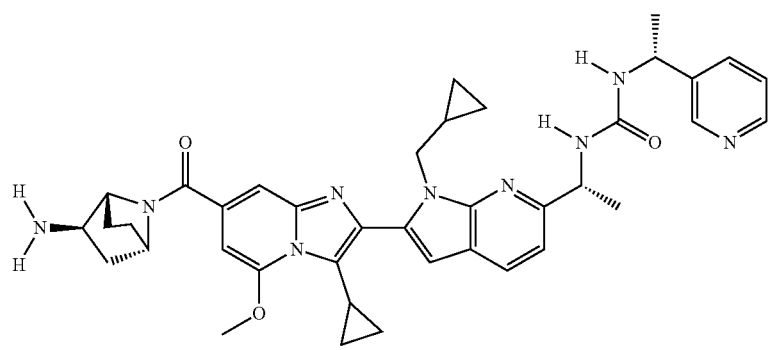

-continued
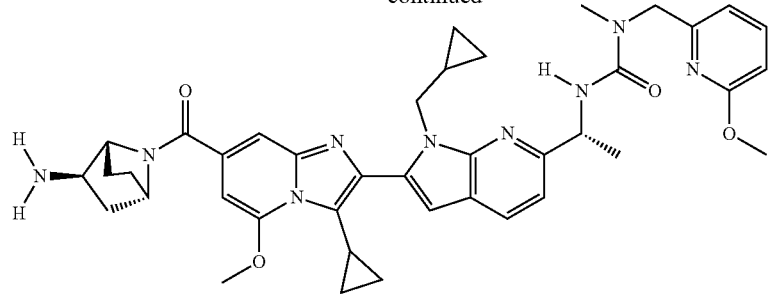
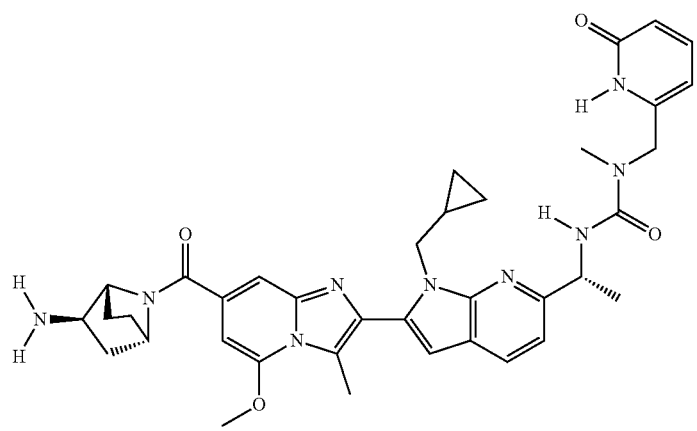
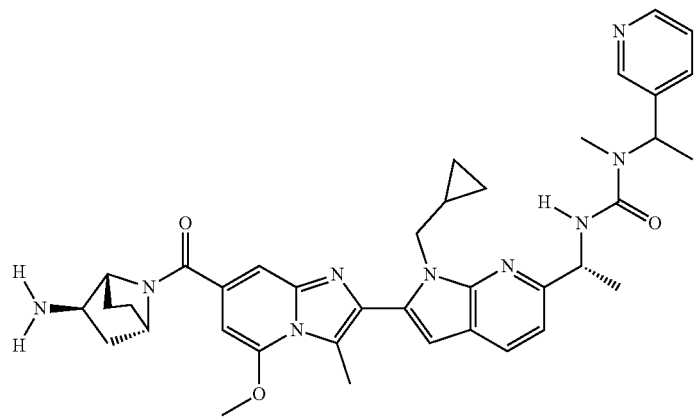
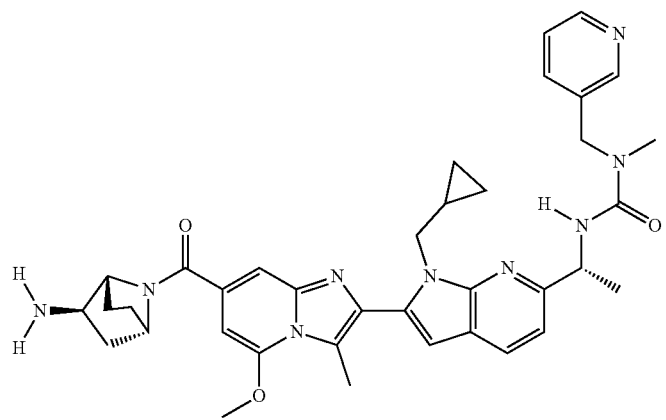

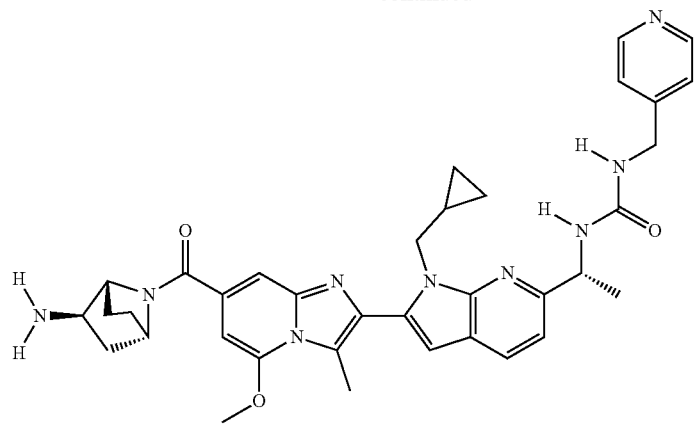
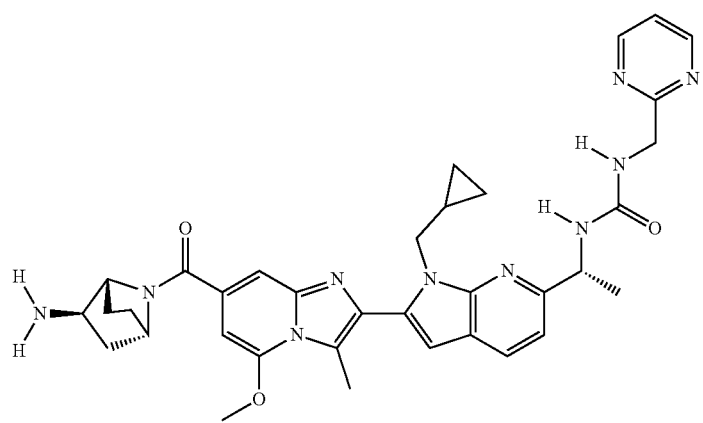
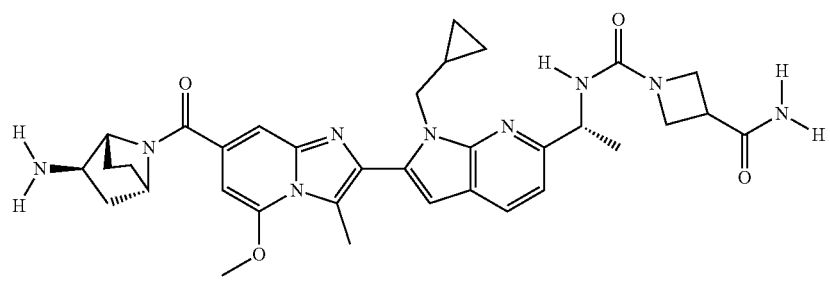
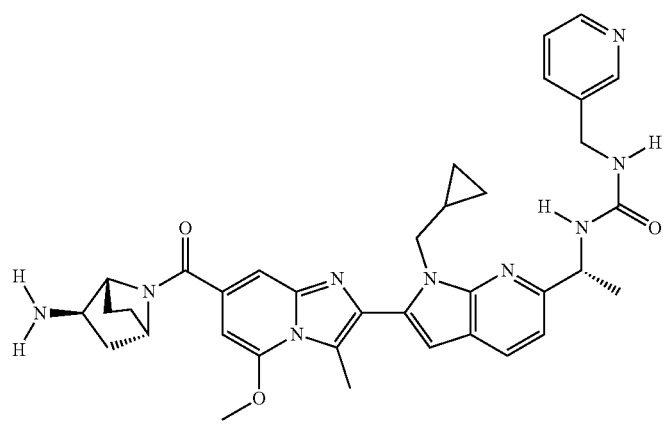

-continued
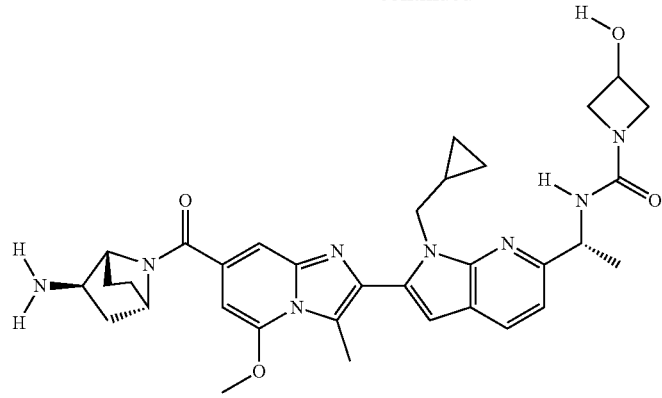
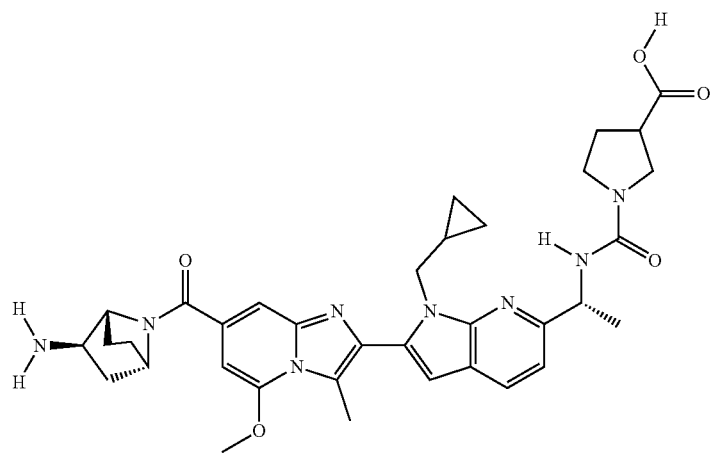
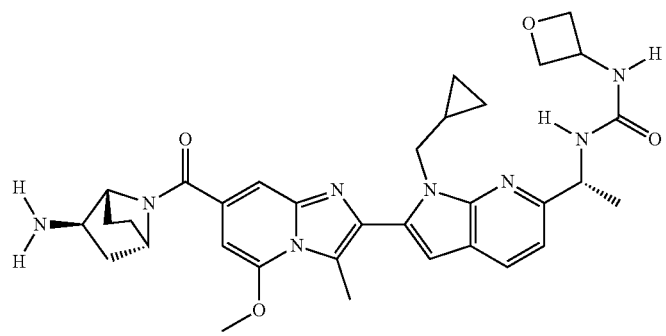
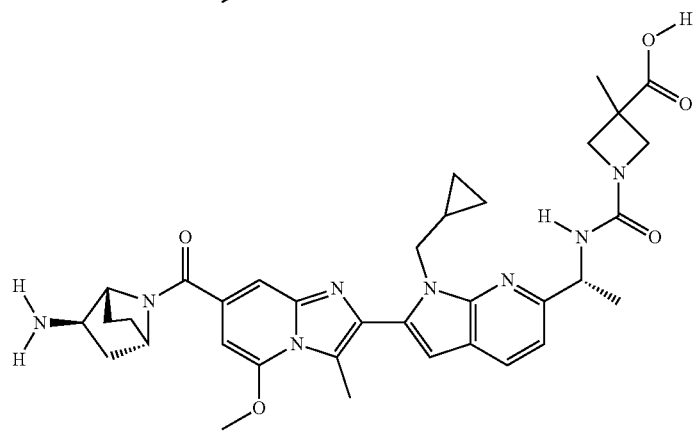

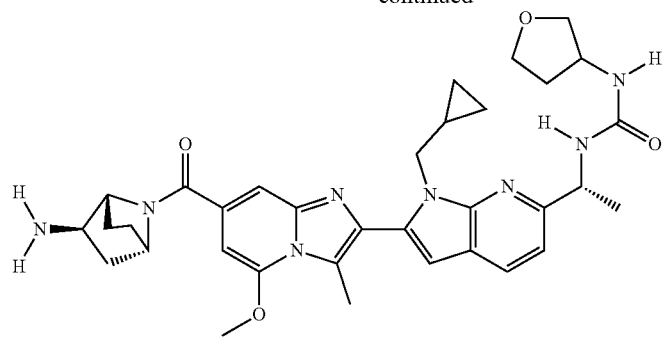
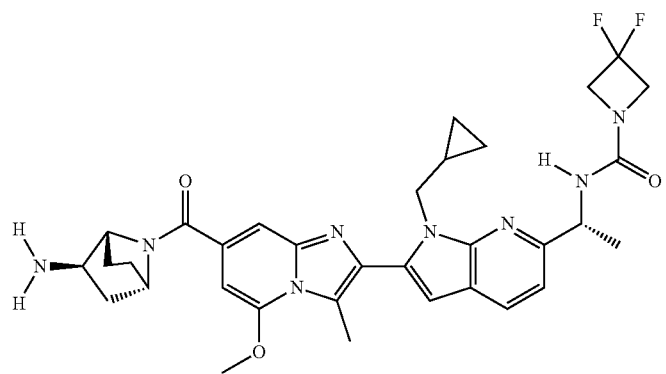
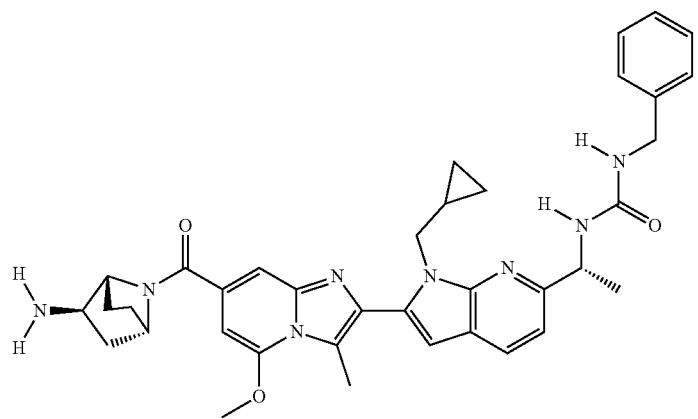
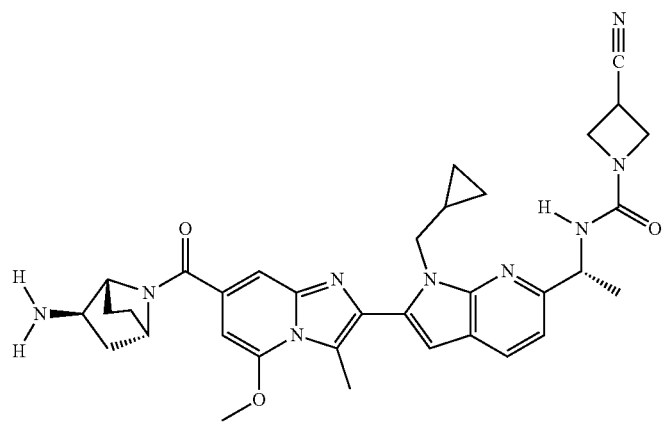

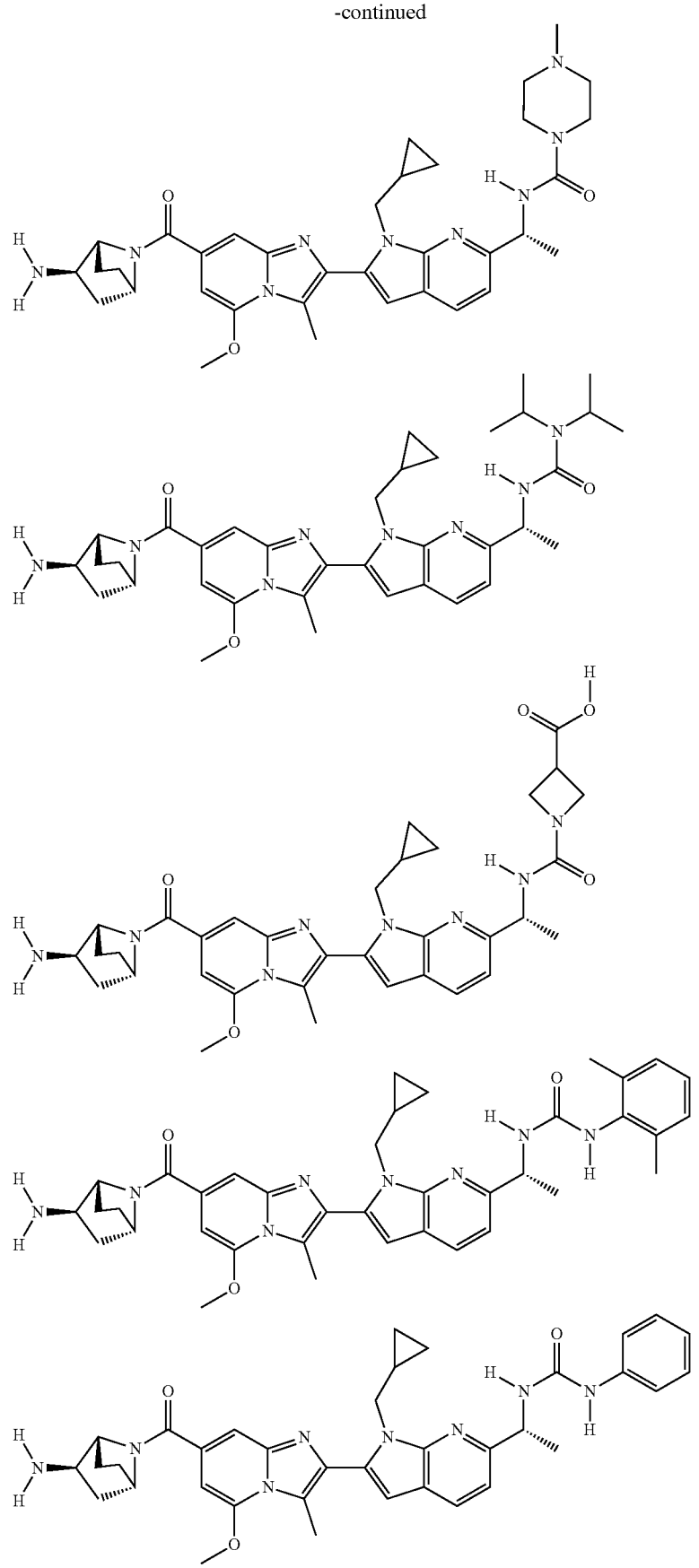

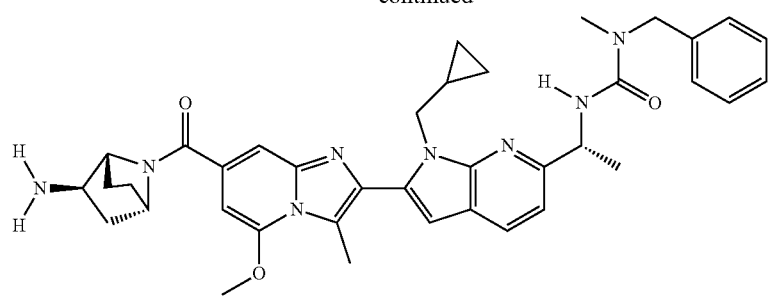
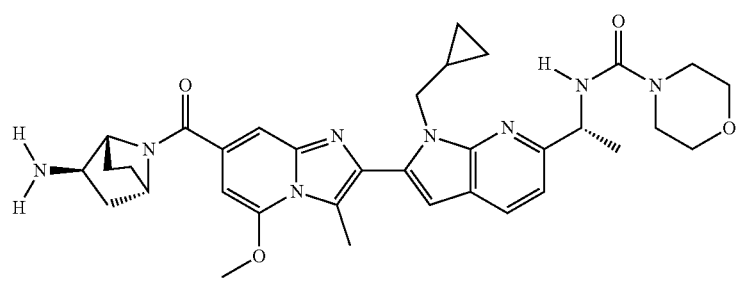
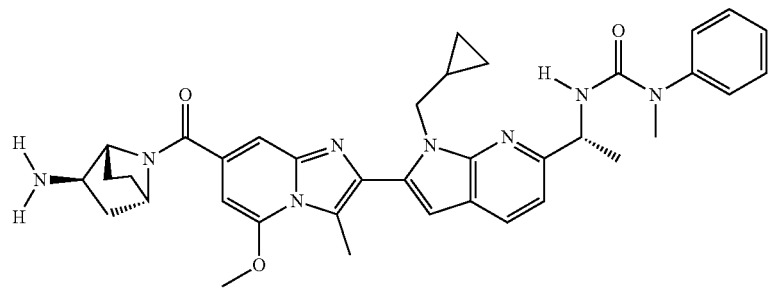
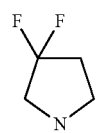
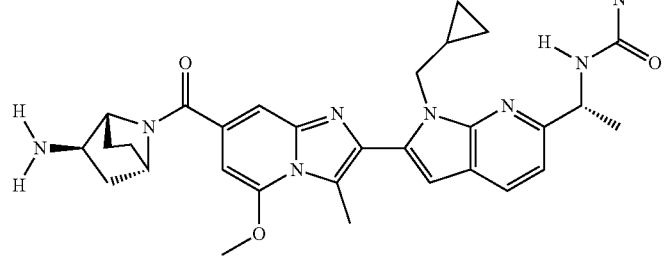
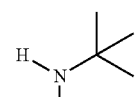
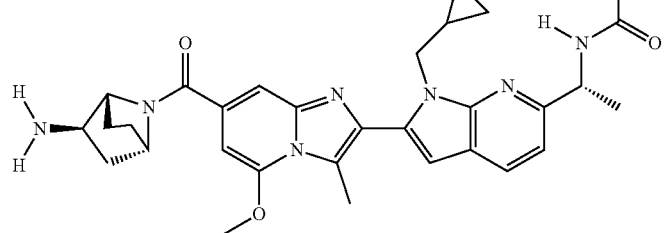

717 718
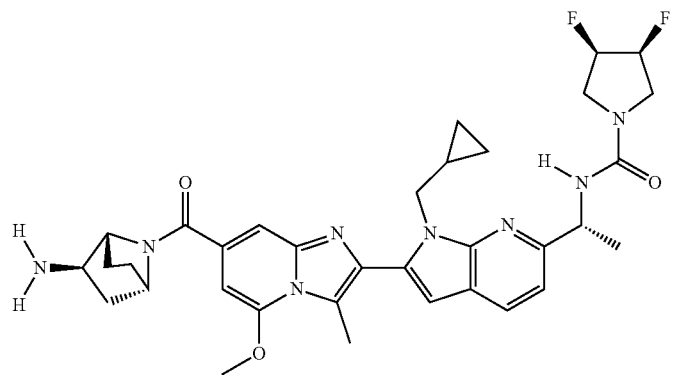
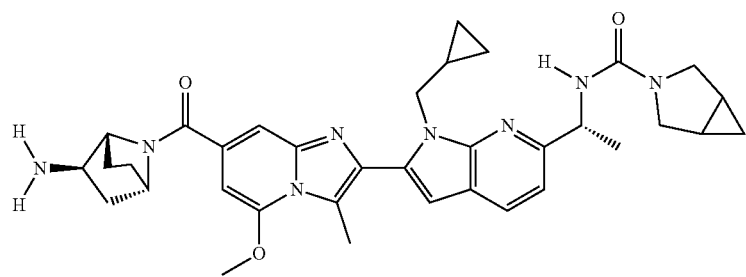
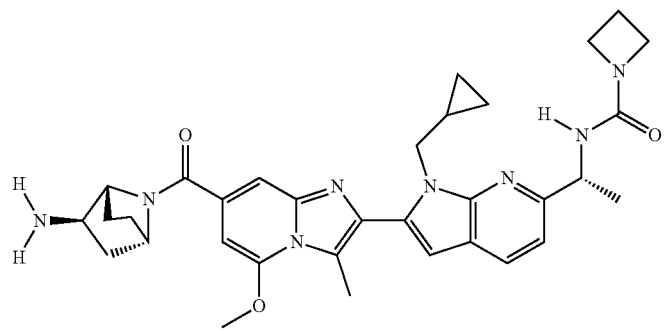
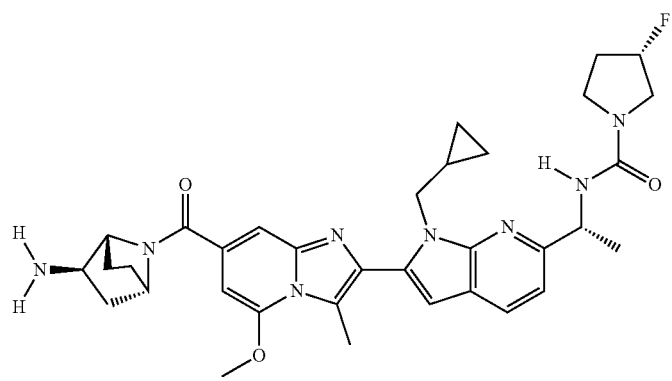
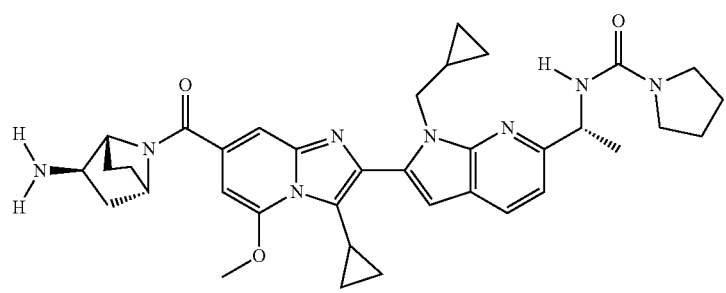

-continued
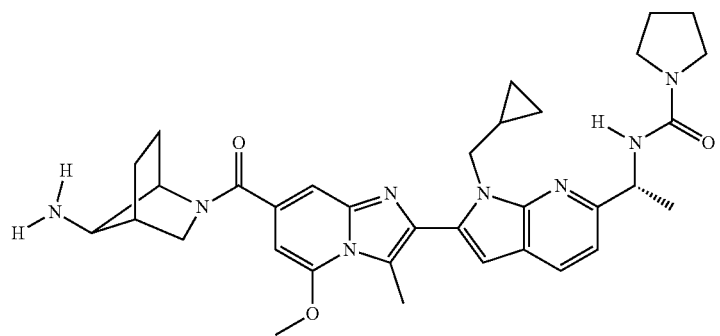
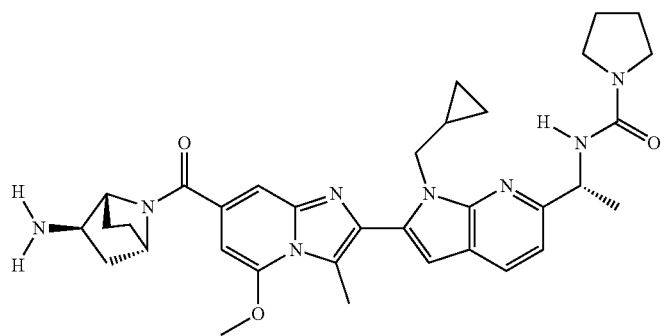
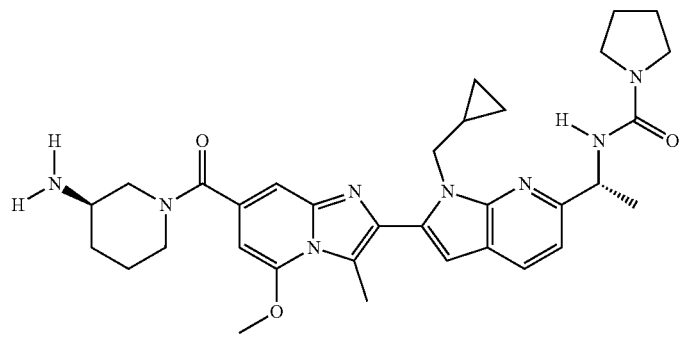
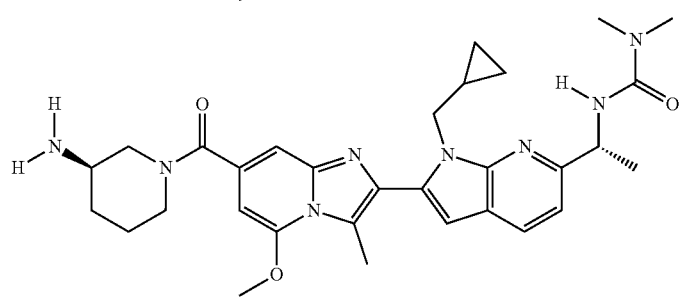
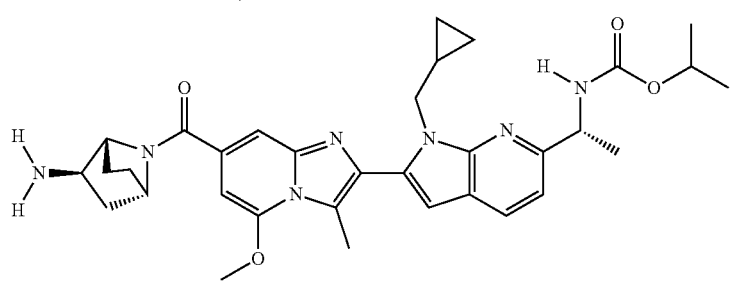

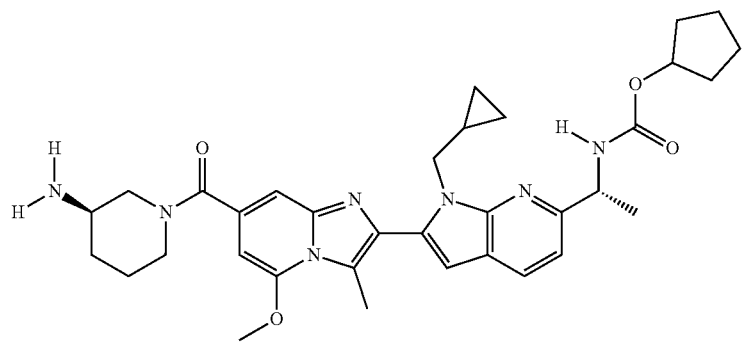
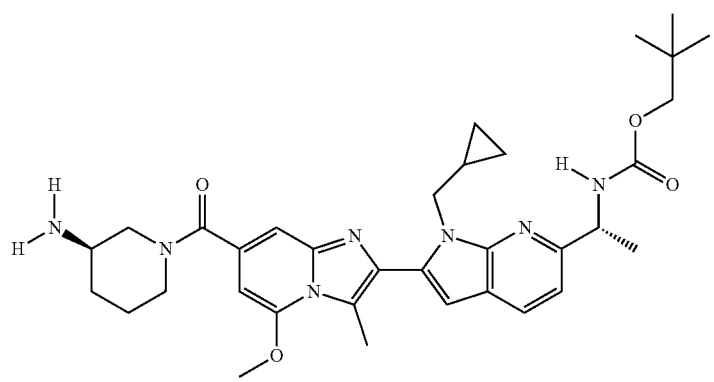
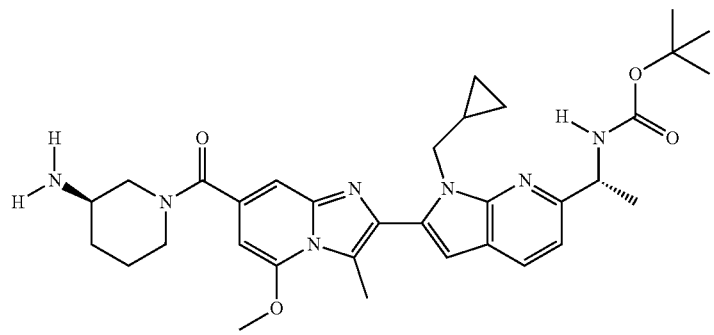
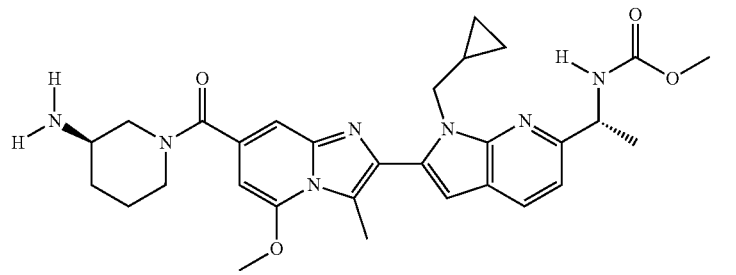
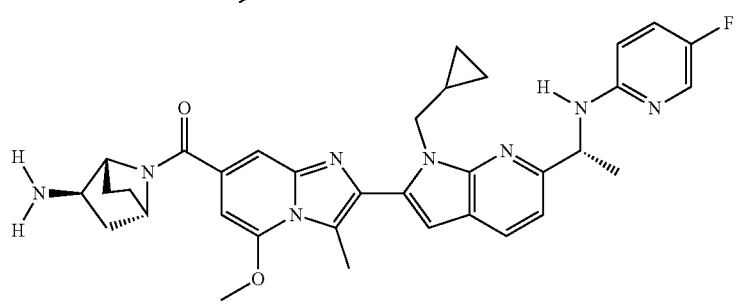

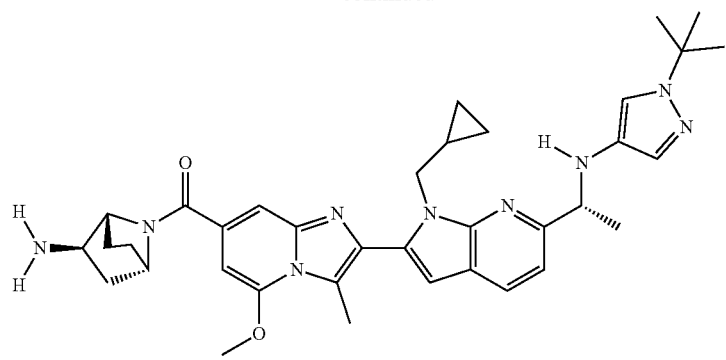
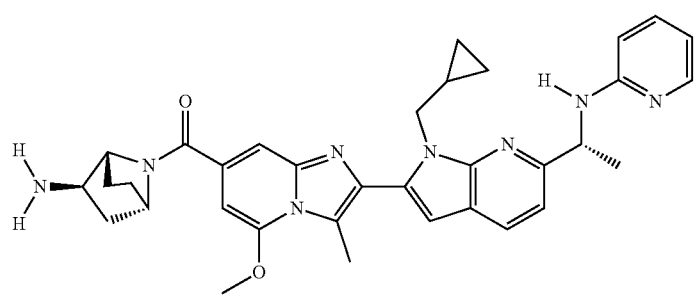
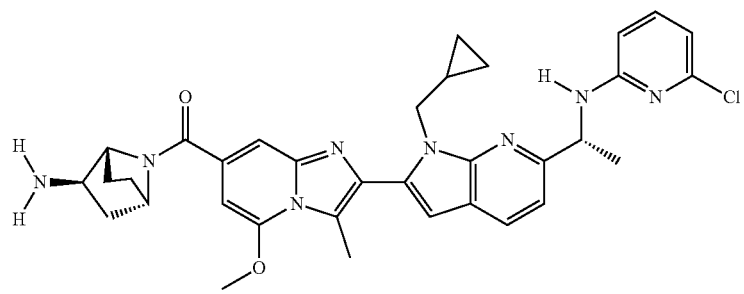
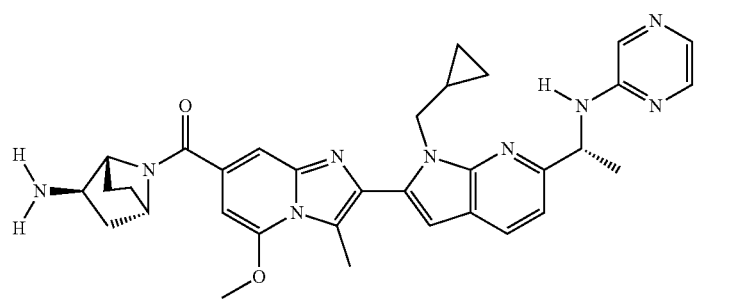
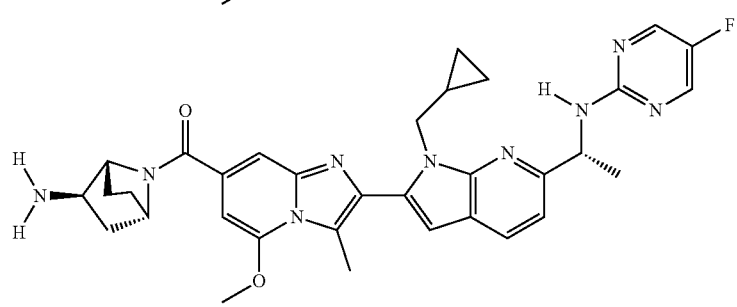

-continued
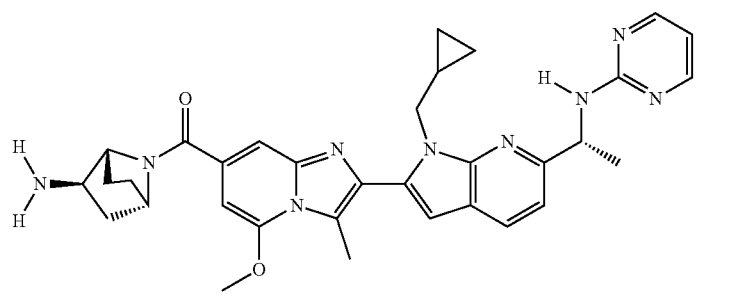
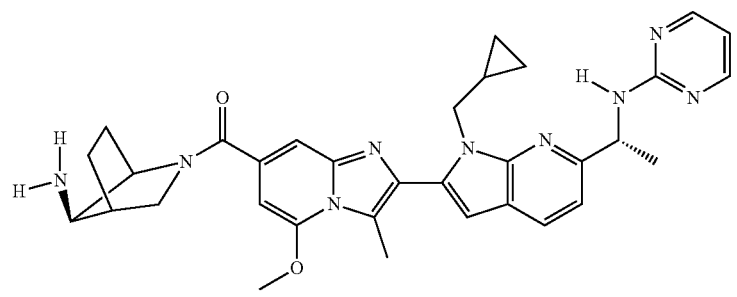
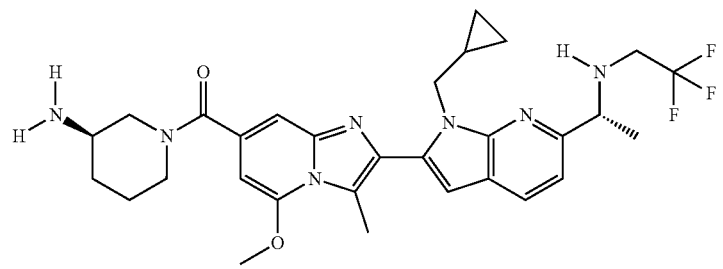
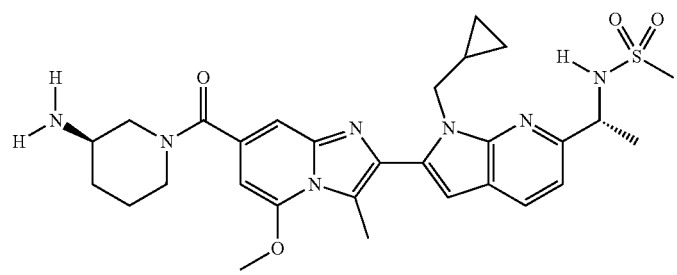
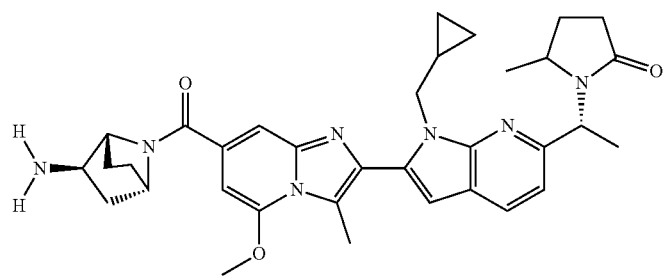
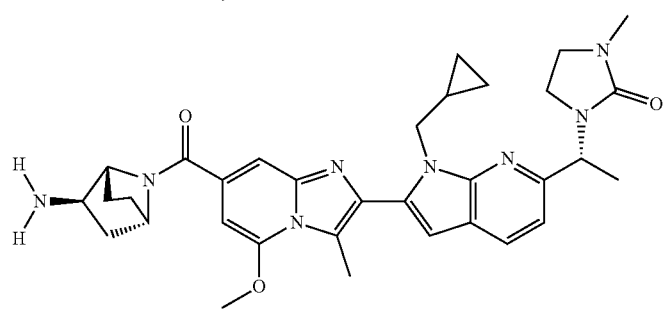

-continued
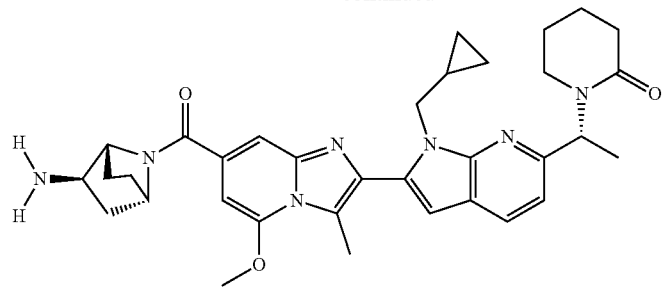
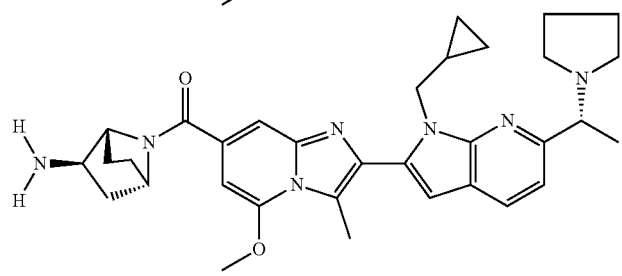
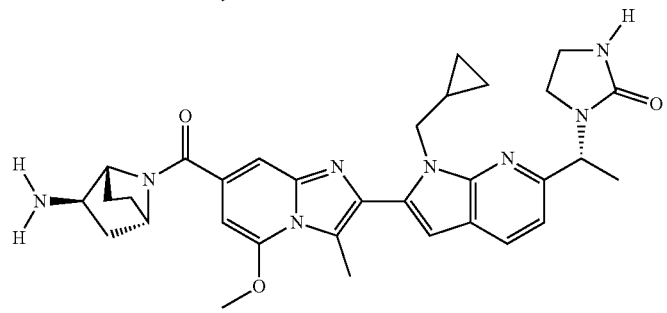
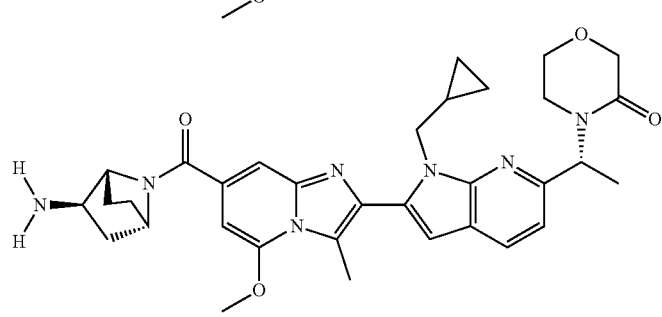
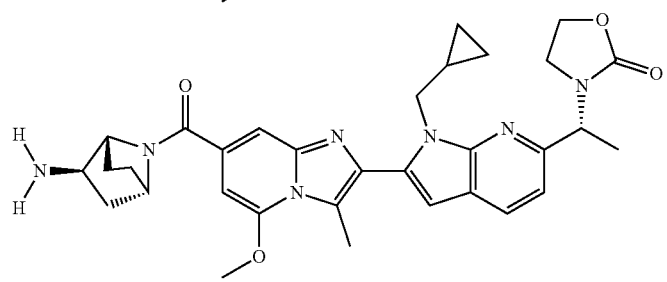
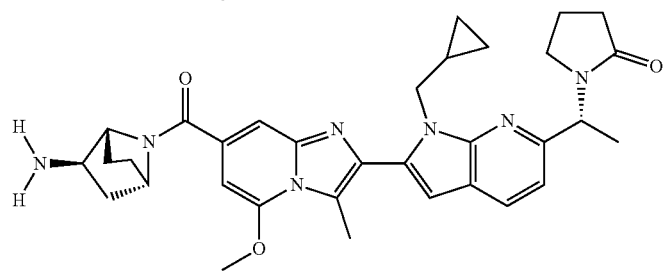

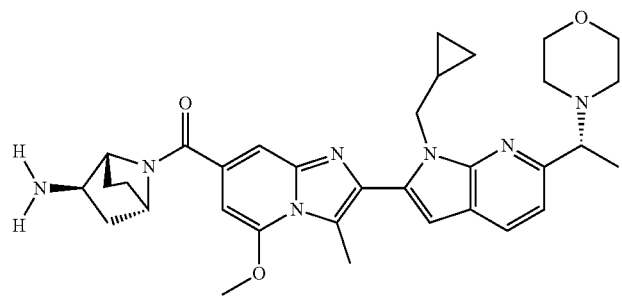
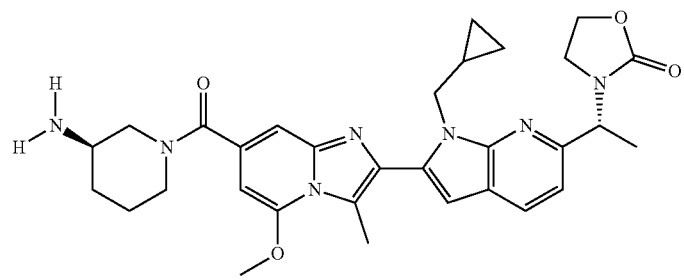
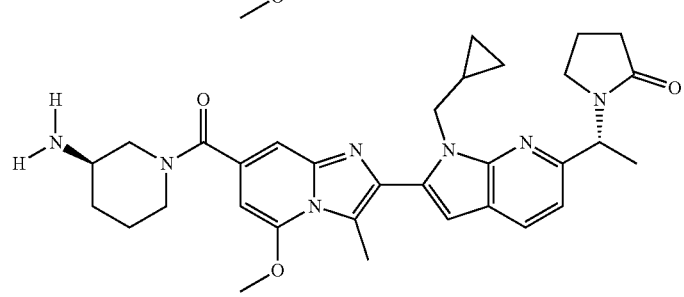
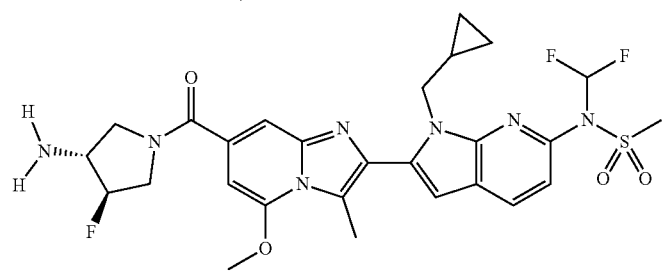
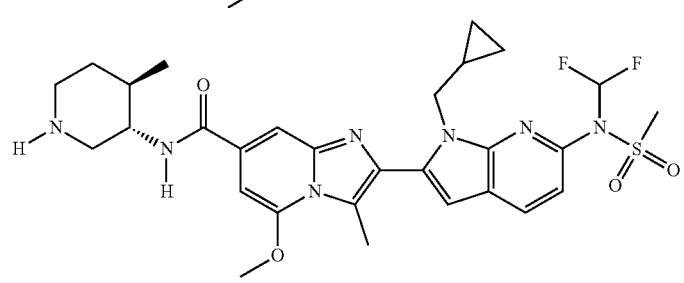
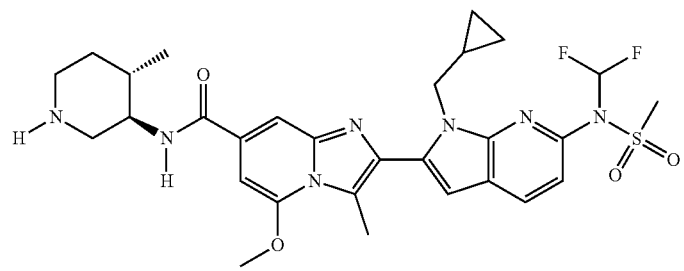

731
732
-continued
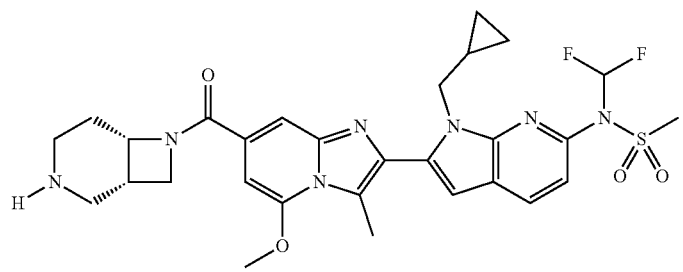
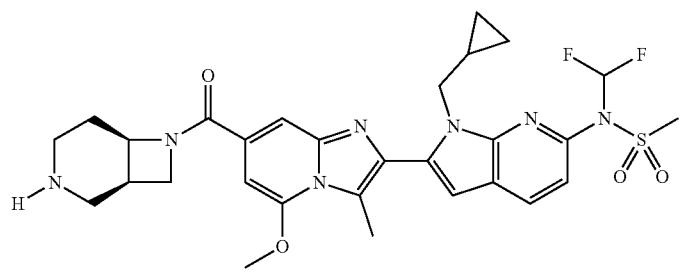
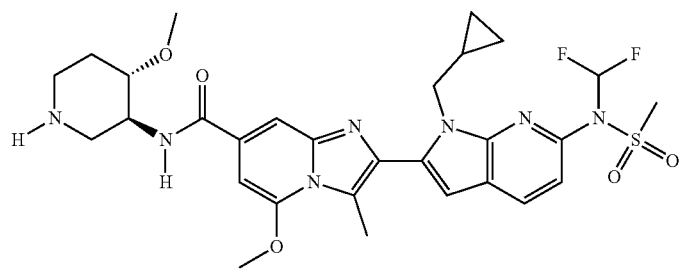
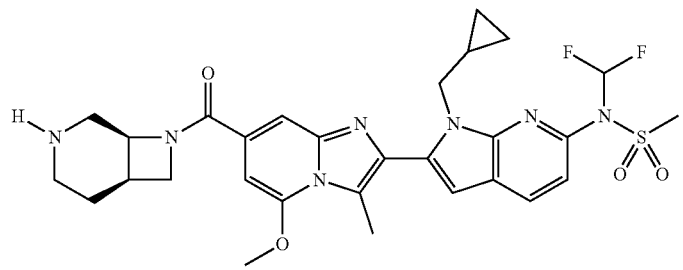
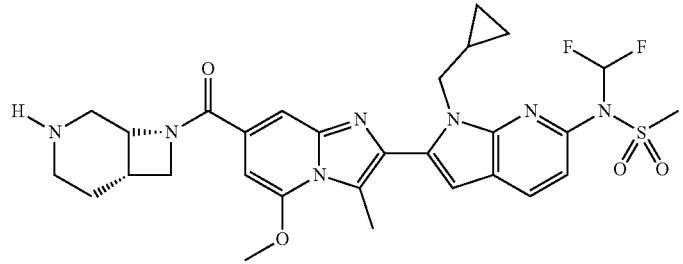
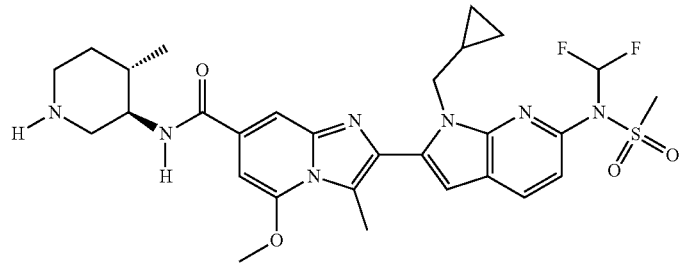

-continued
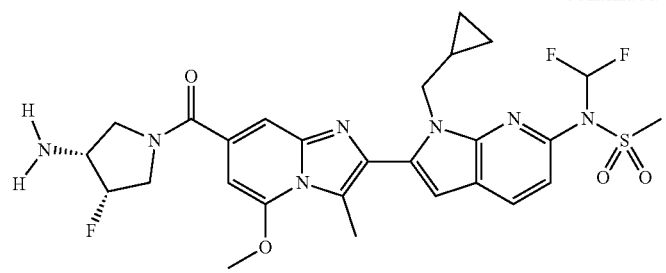
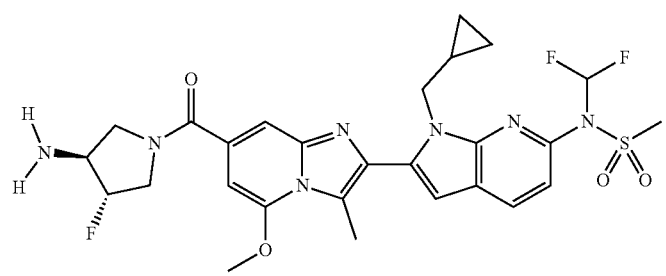
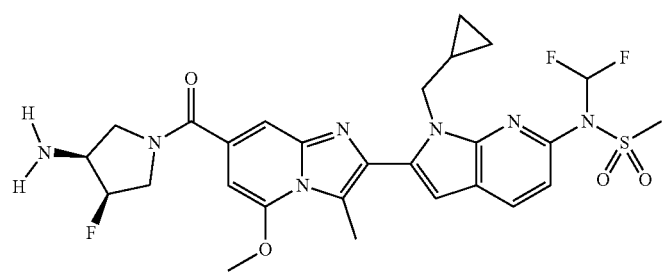
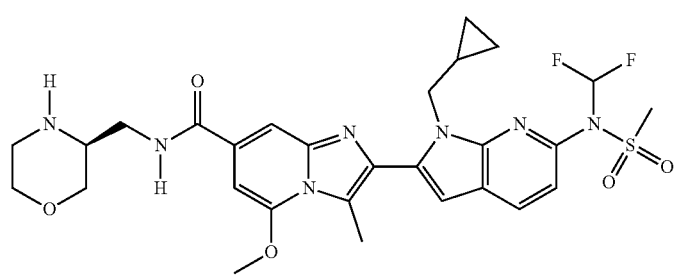
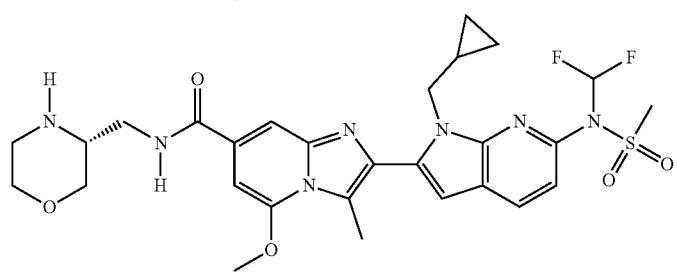
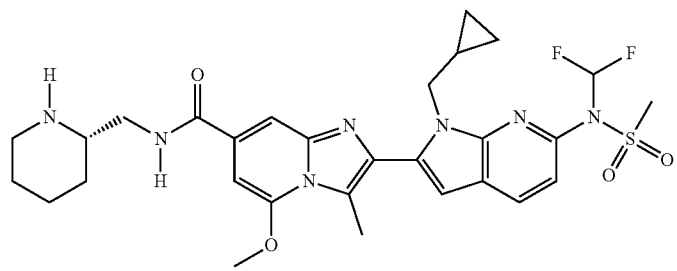

-continued
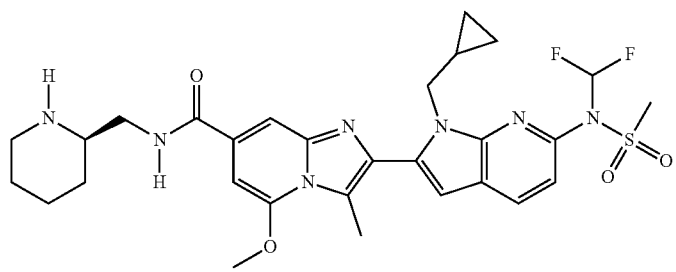
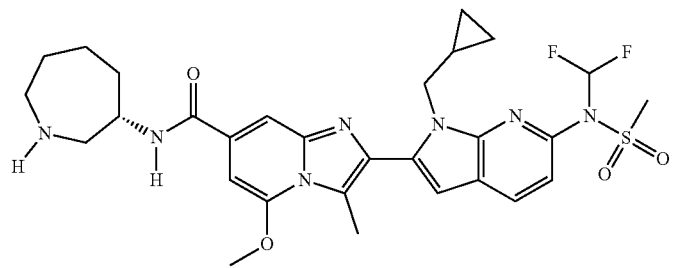
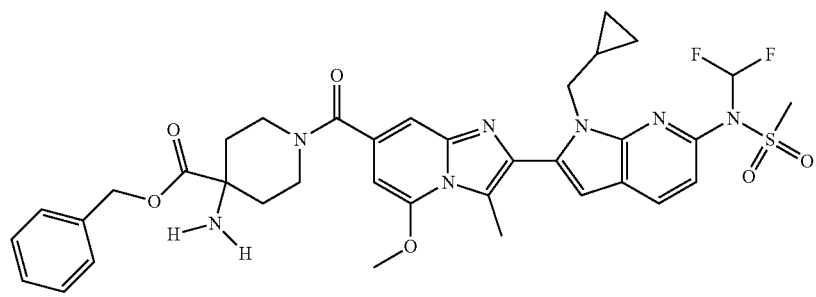
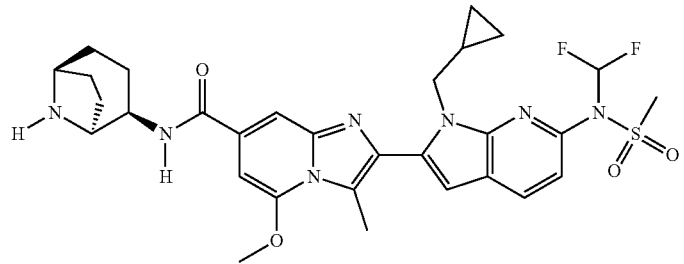
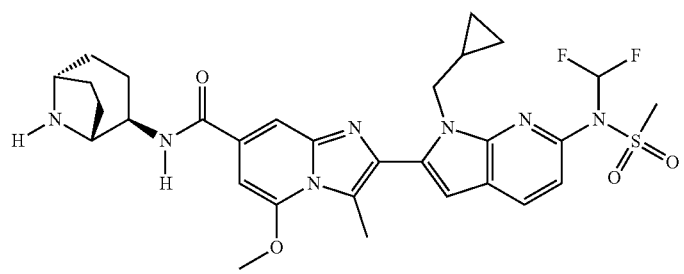
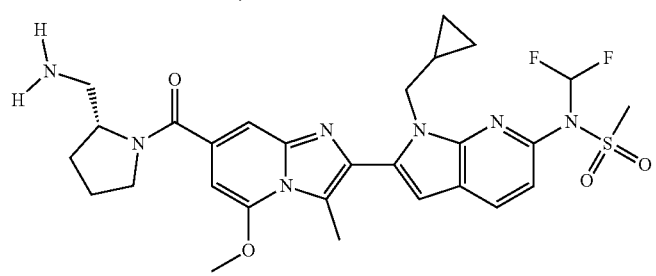

737
-continued
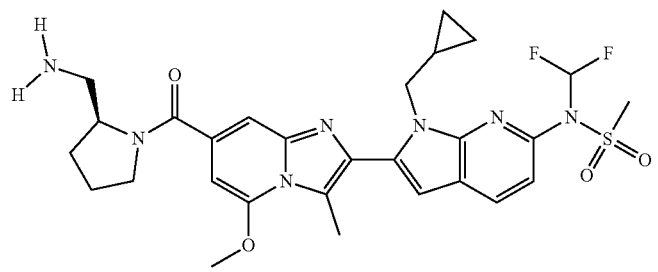
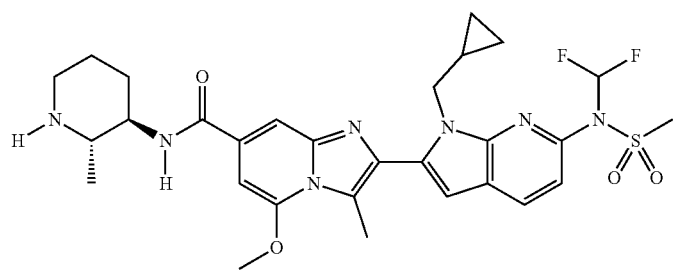
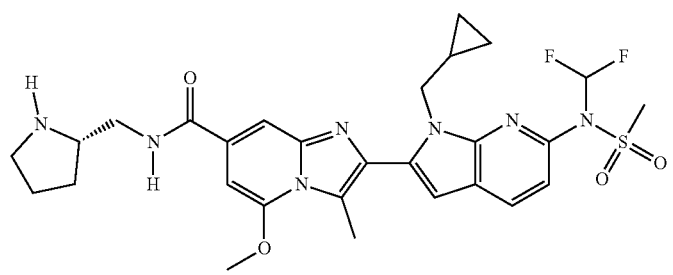
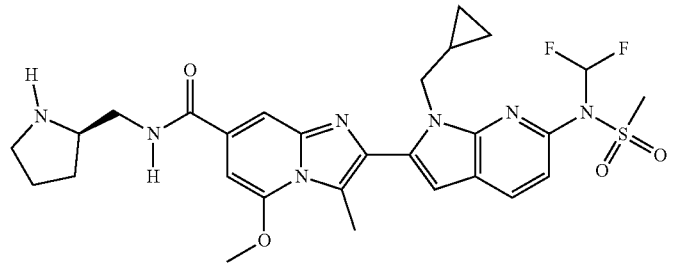
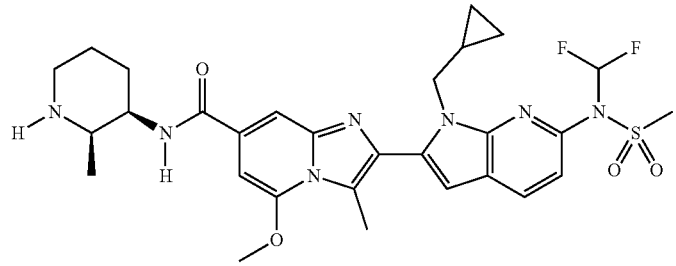
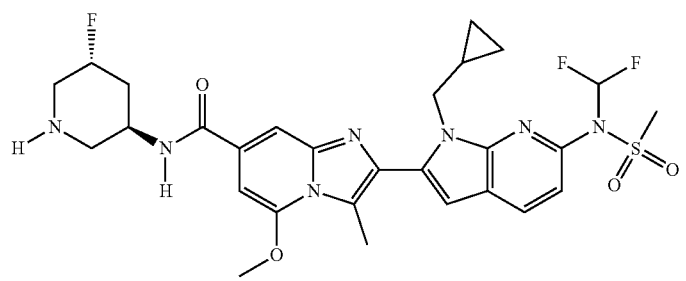
738

-continued
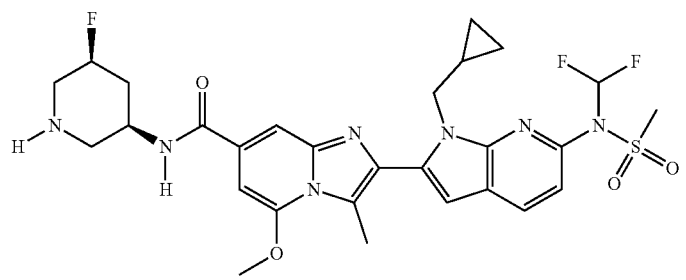
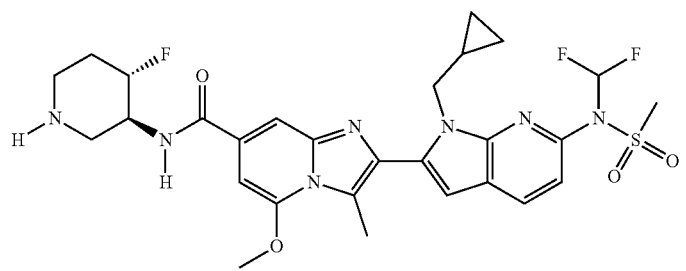
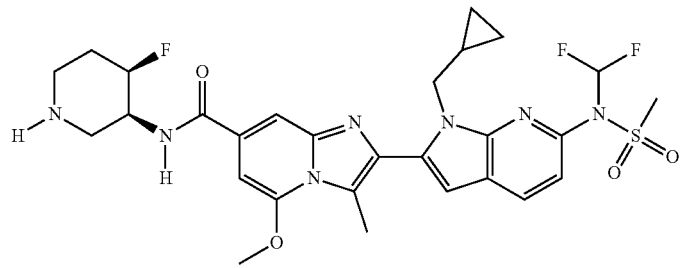
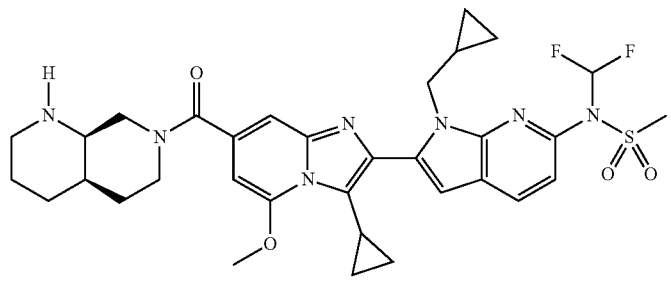
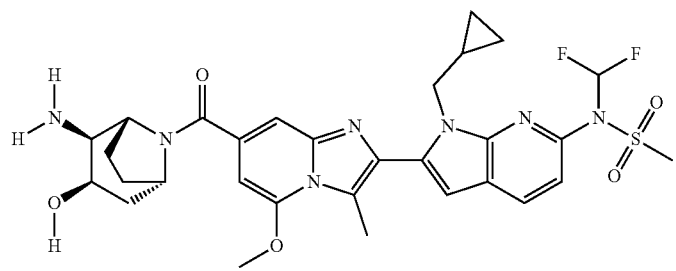
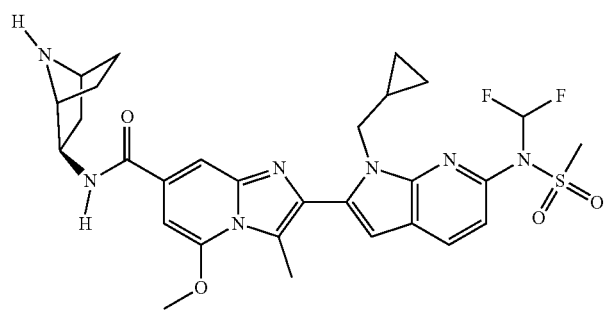

741
-continued
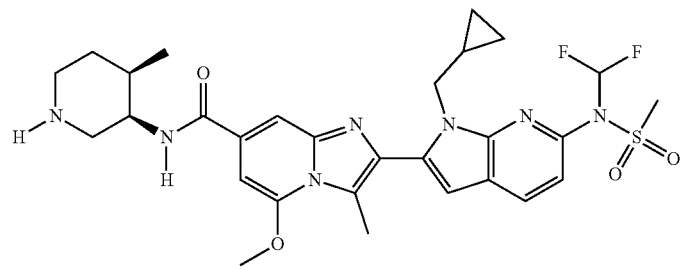
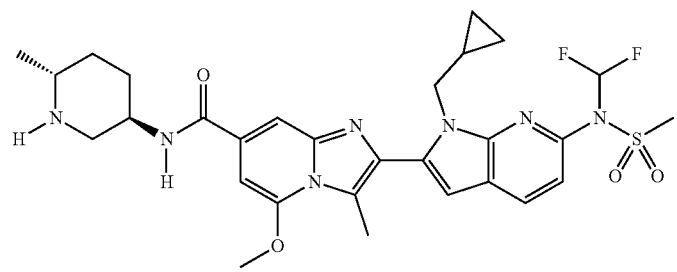
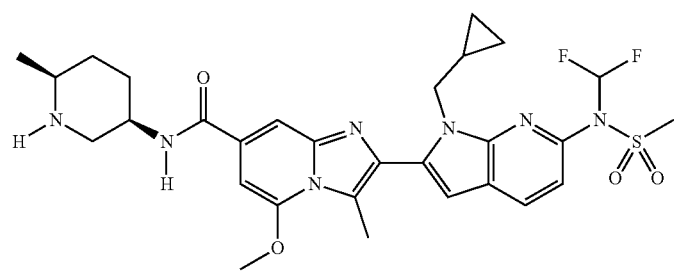
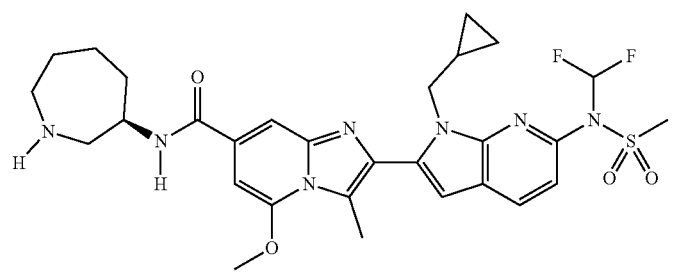
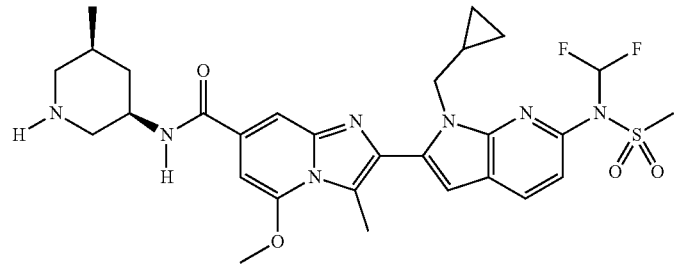
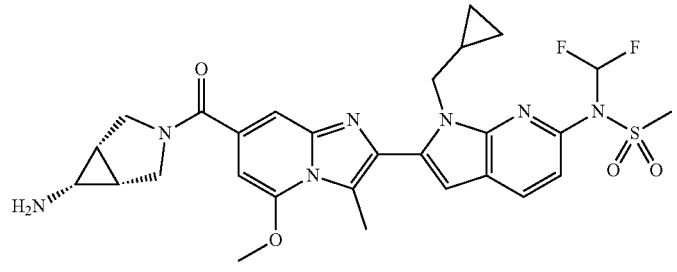
742

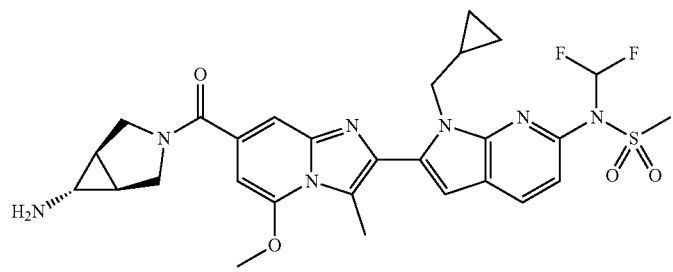
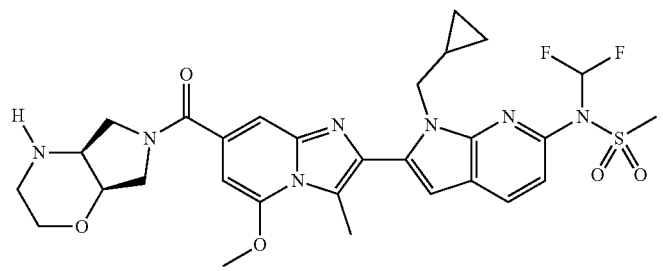
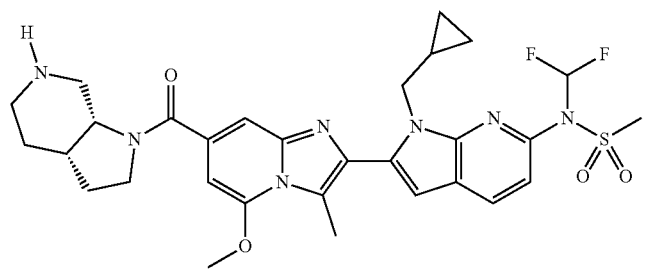
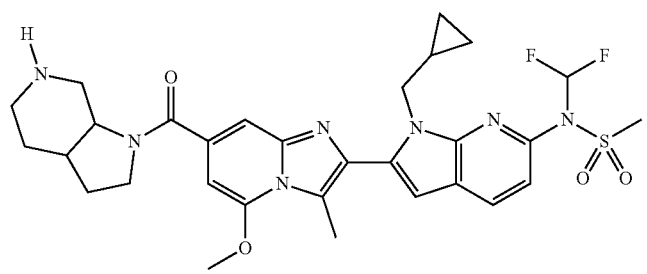
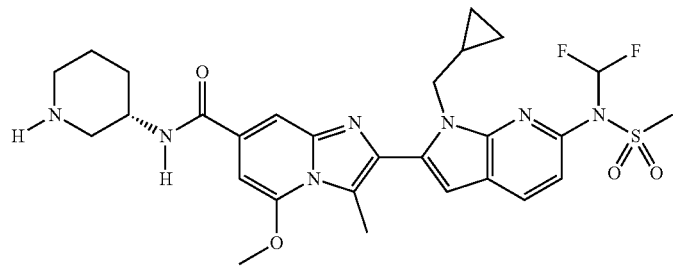
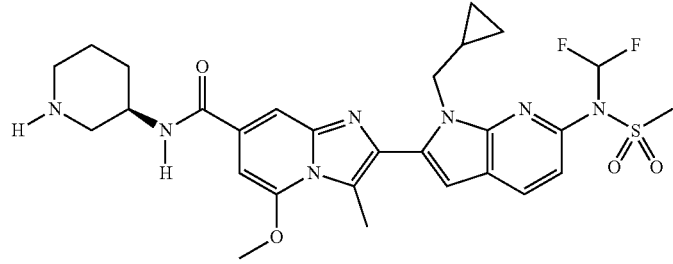

-continued
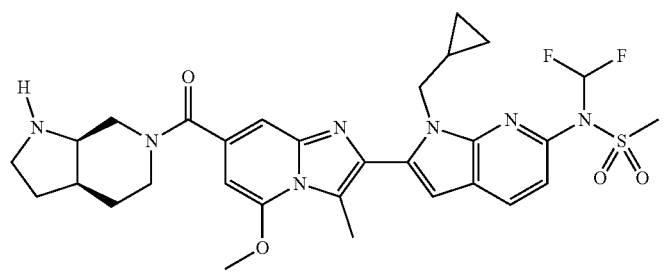
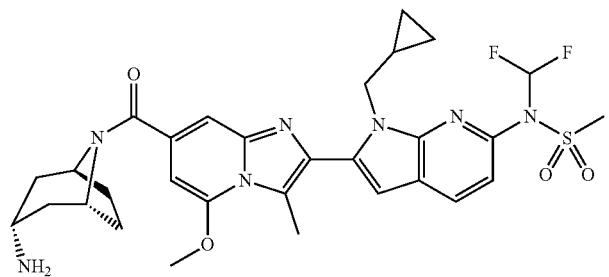
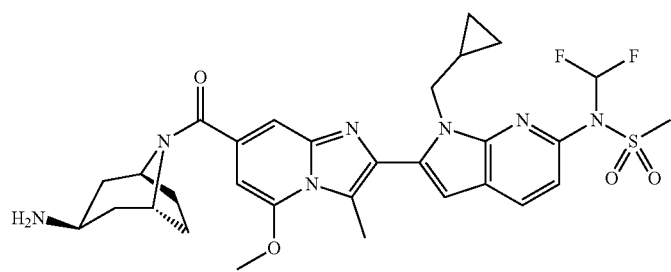
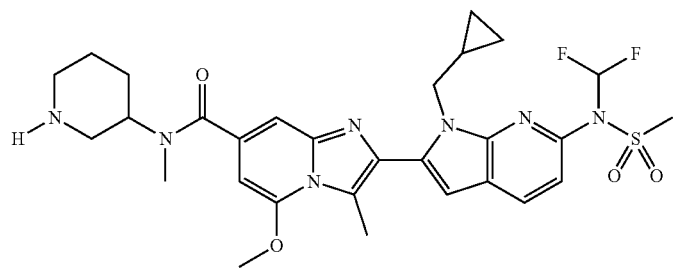
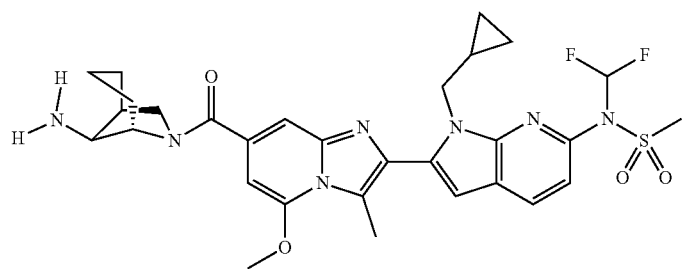
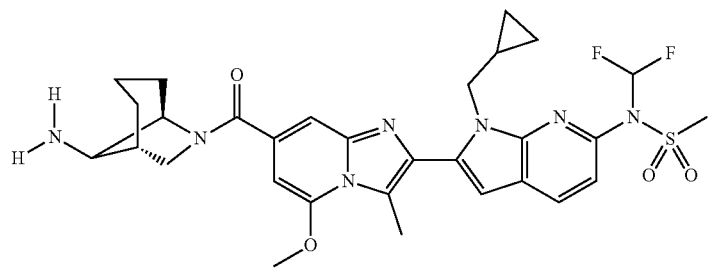

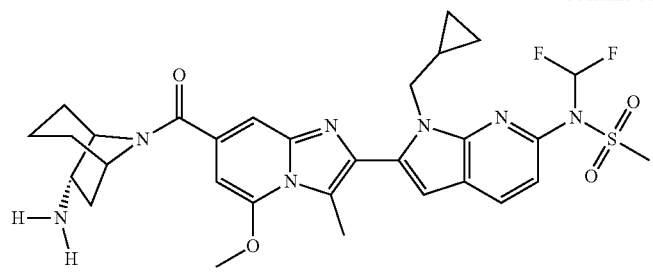
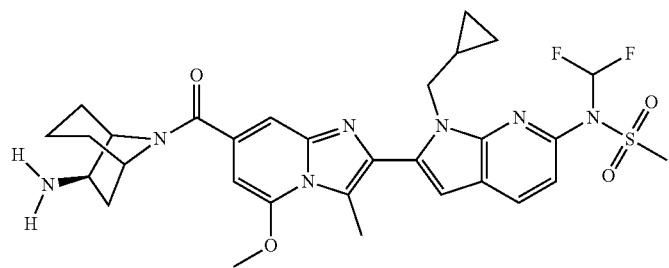
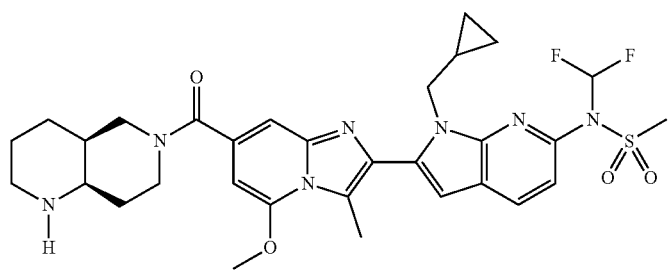
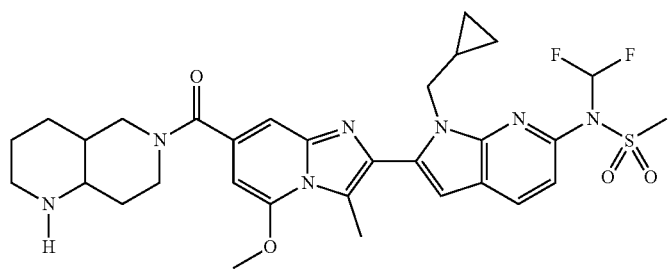
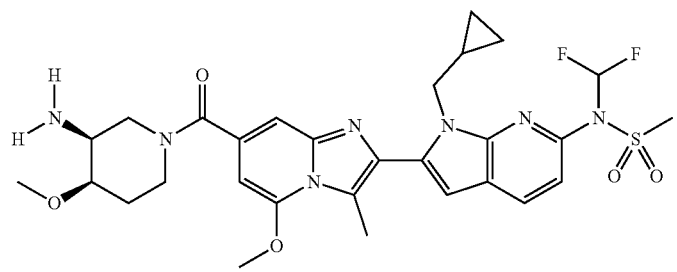
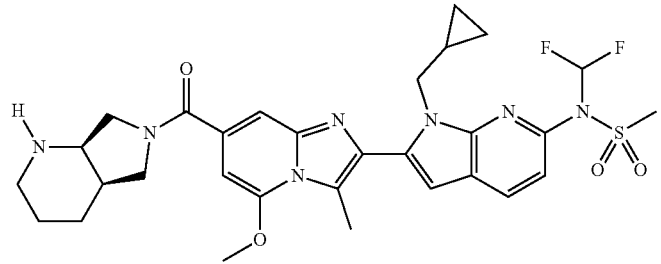

-continued
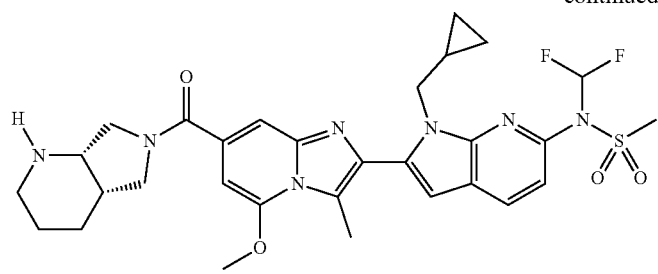
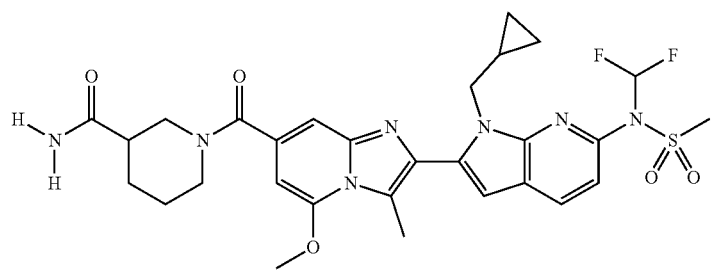
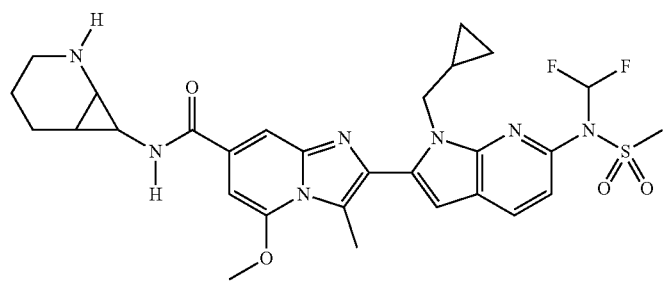
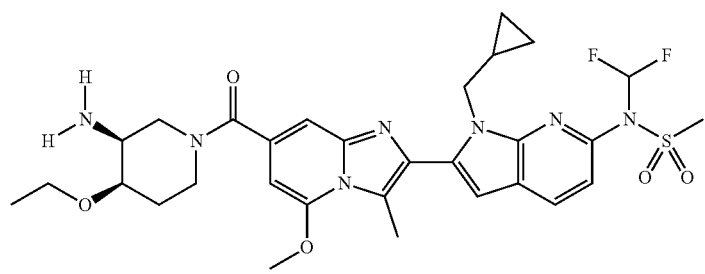
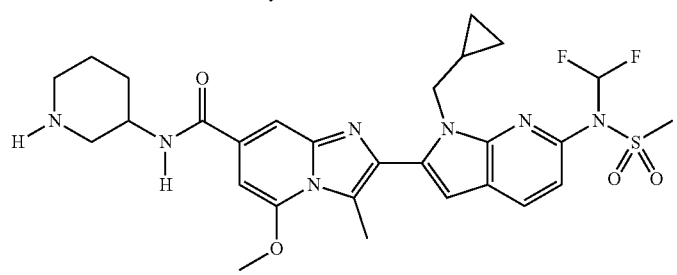
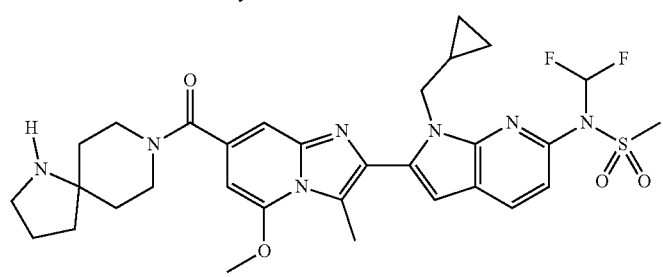

751
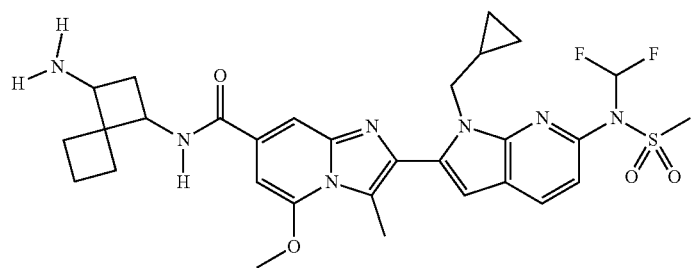
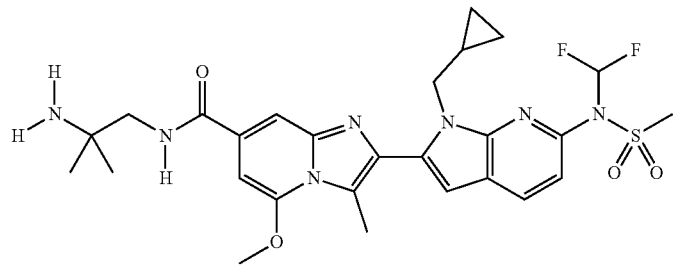
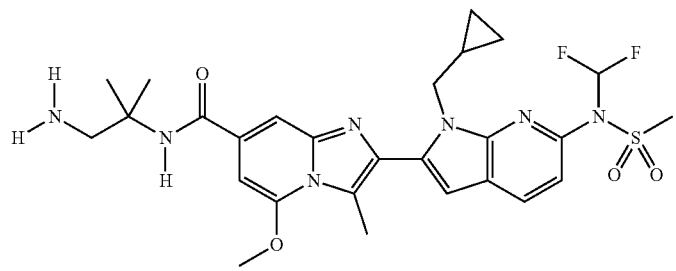
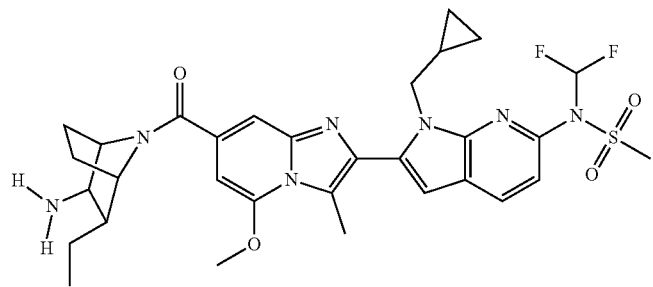
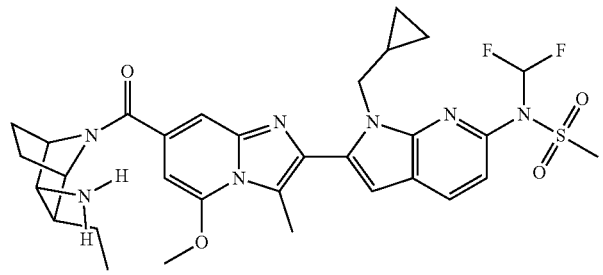
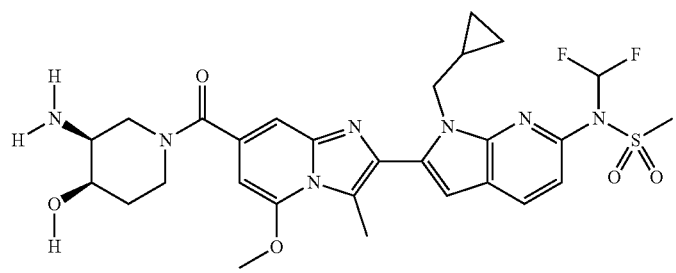

753
-continued
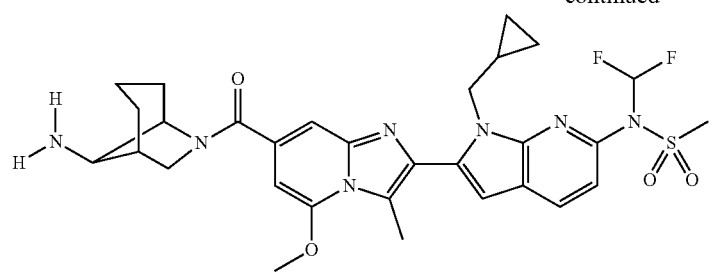
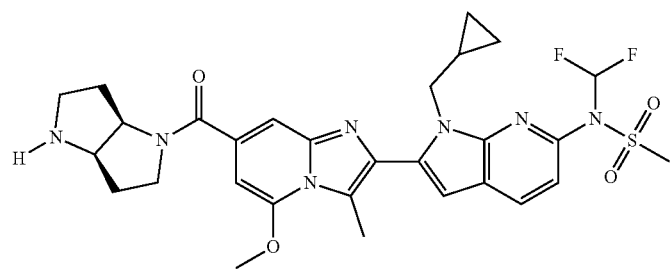
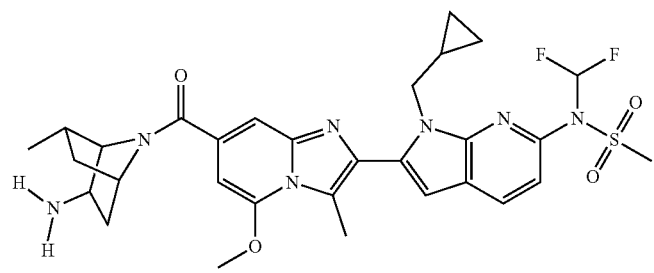
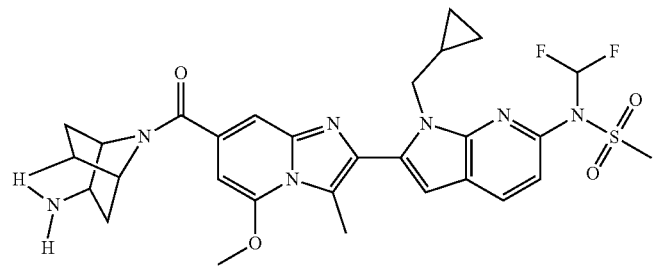
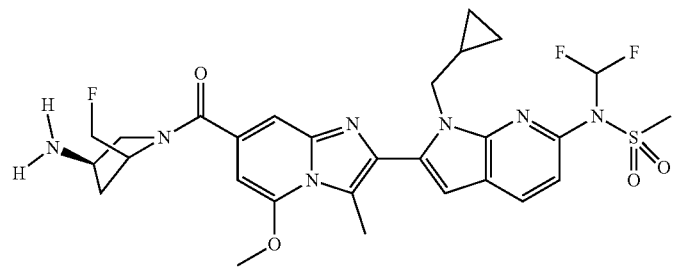
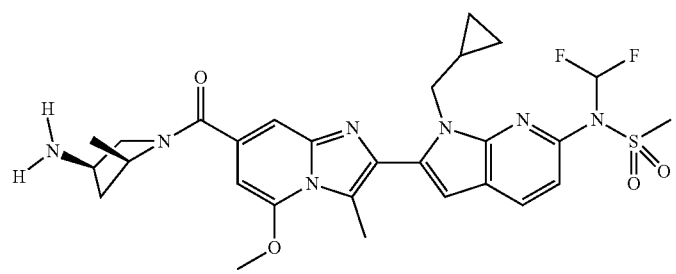
754

-continued
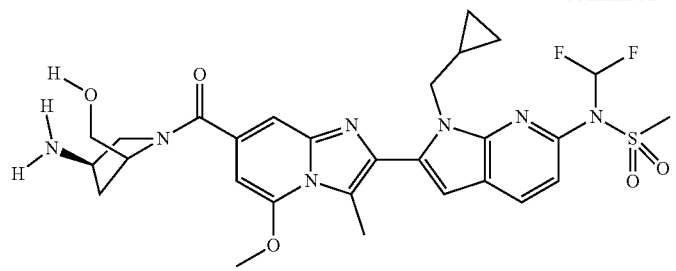
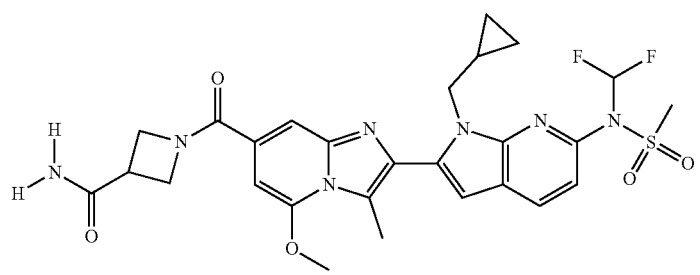
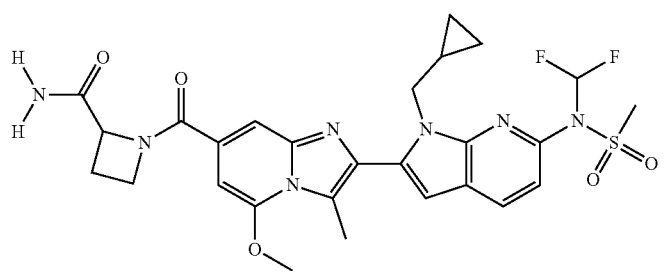
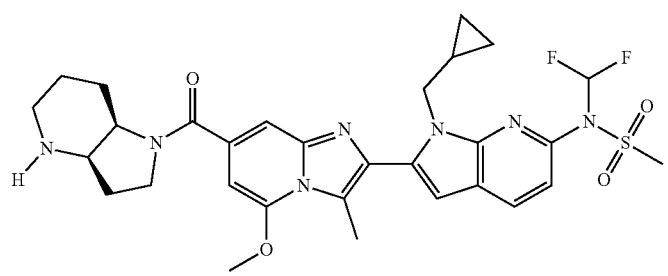
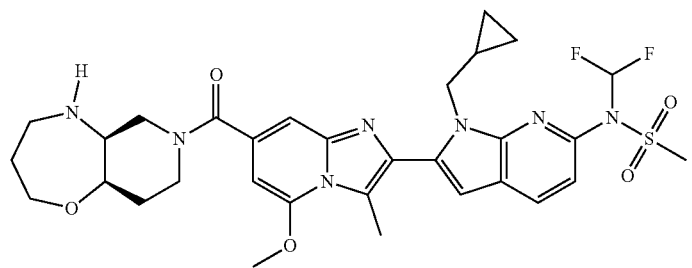
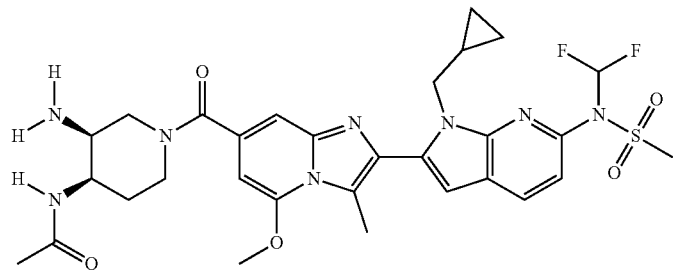

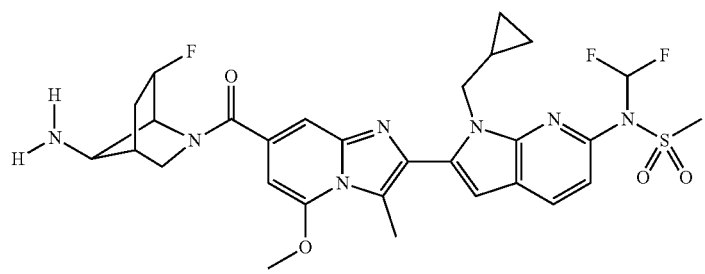
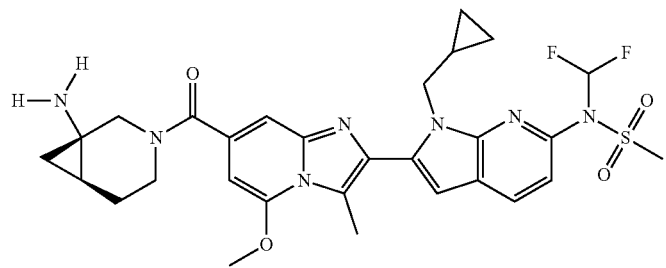
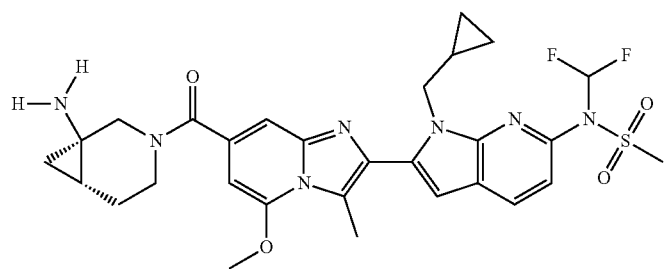
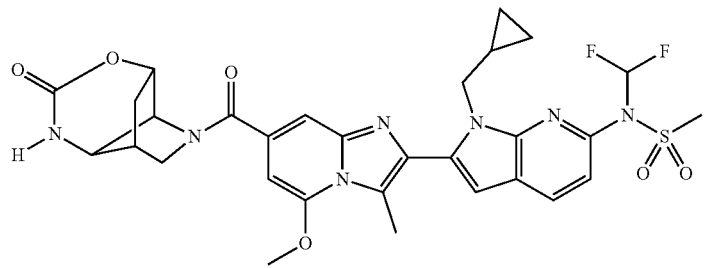
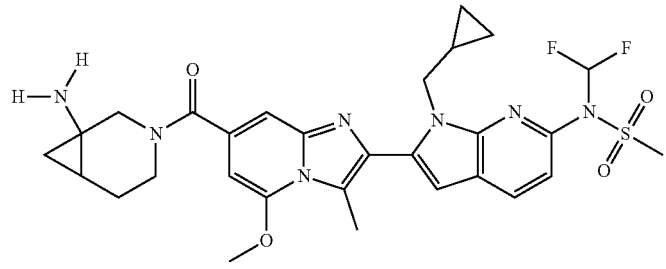
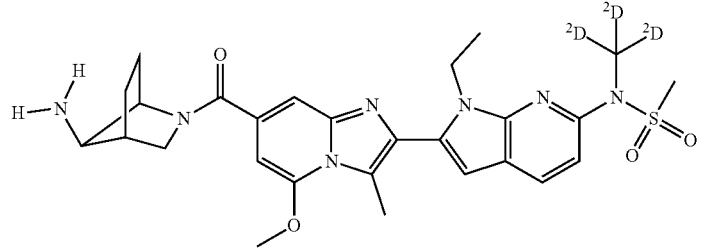

-continued
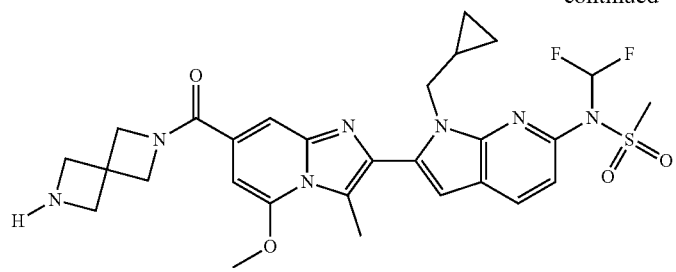
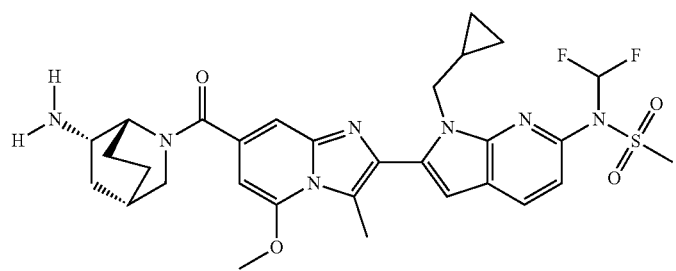
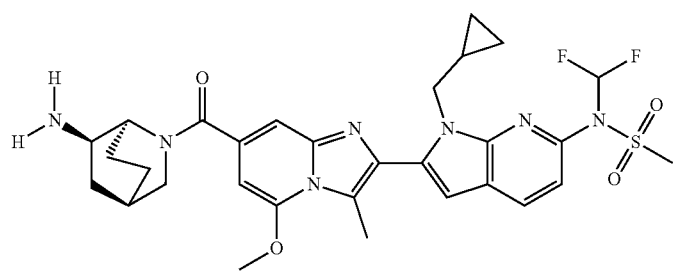
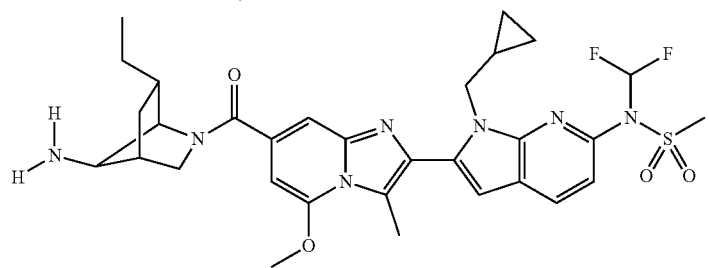
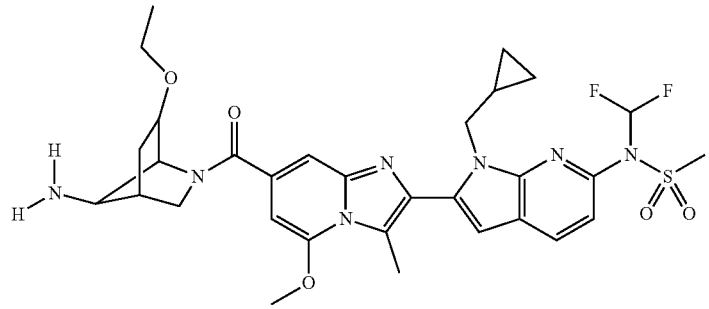
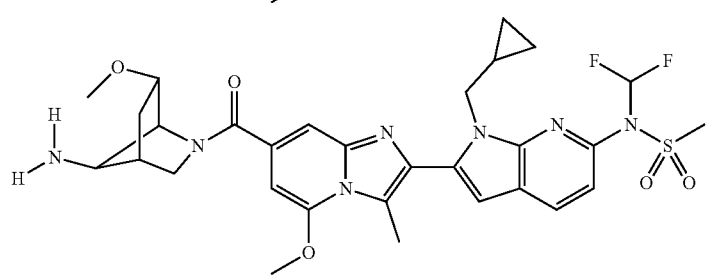

-continued
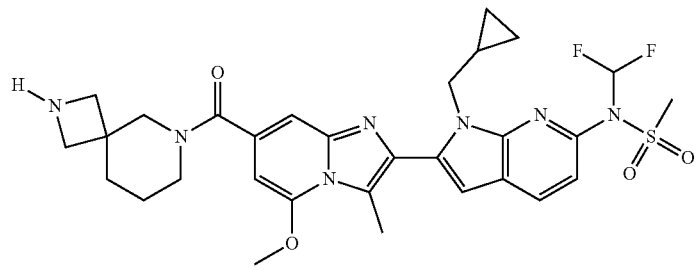
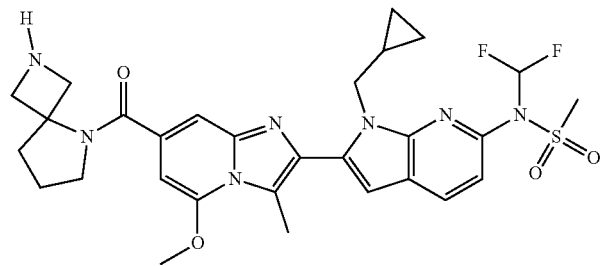
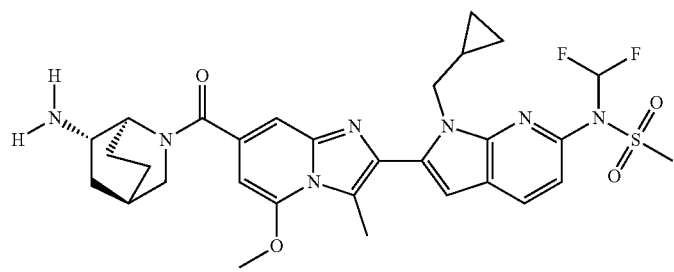
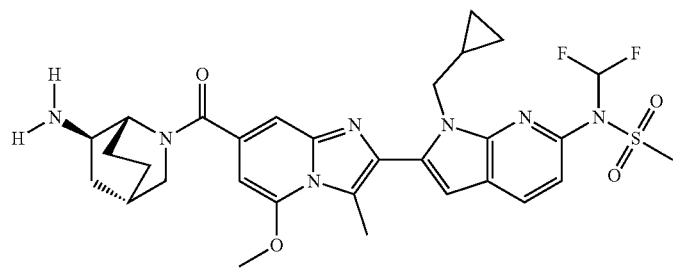
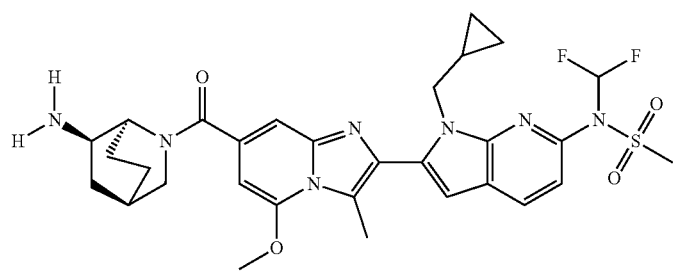
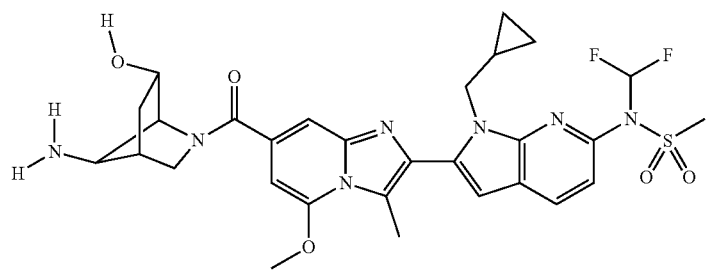

-continued
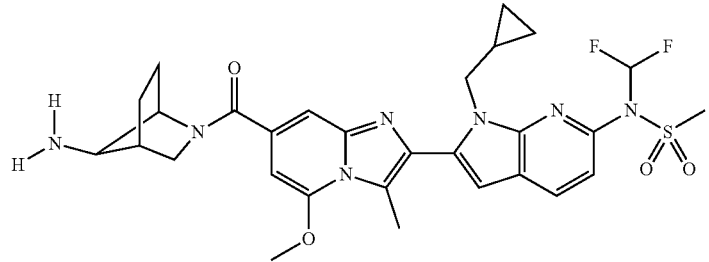
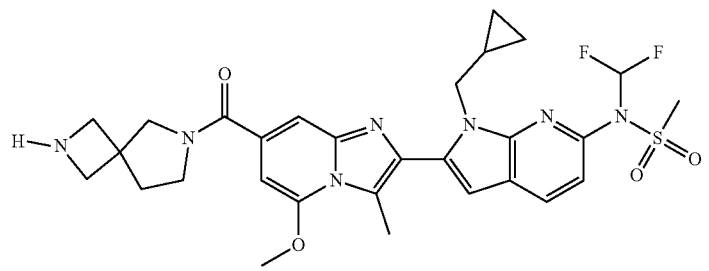
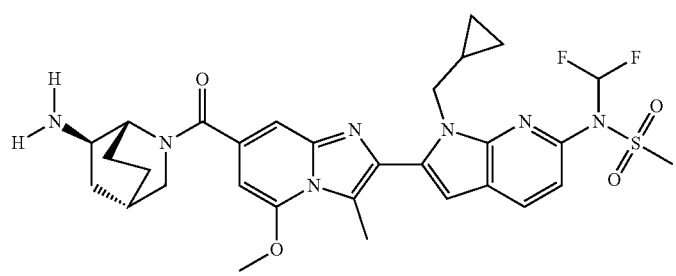
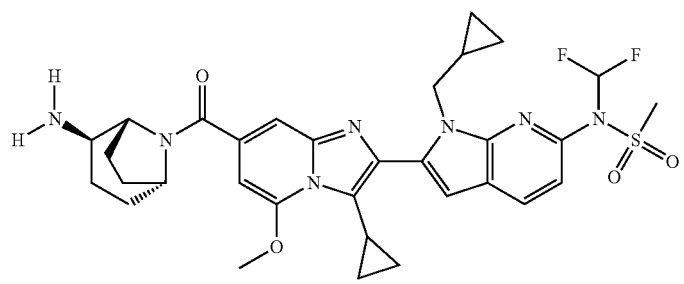
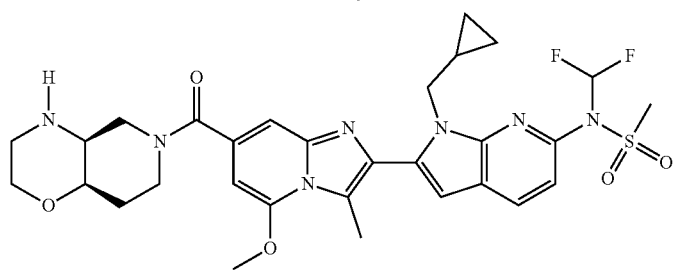
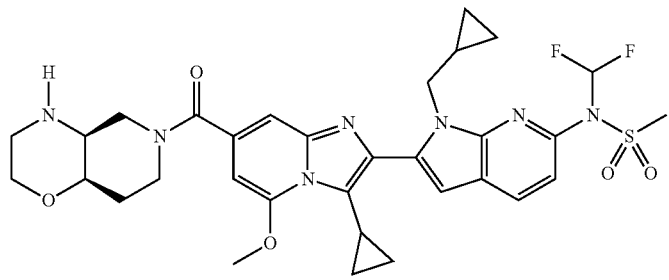

-continued
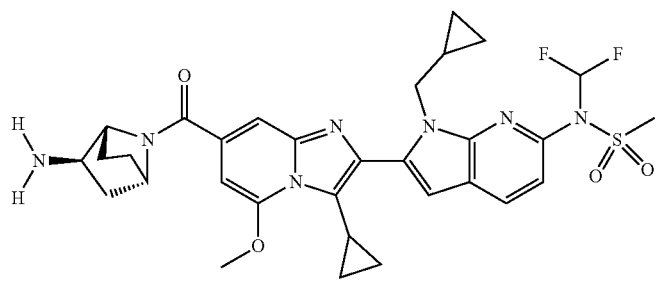
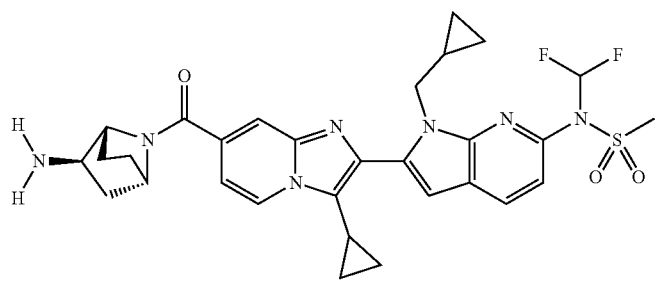
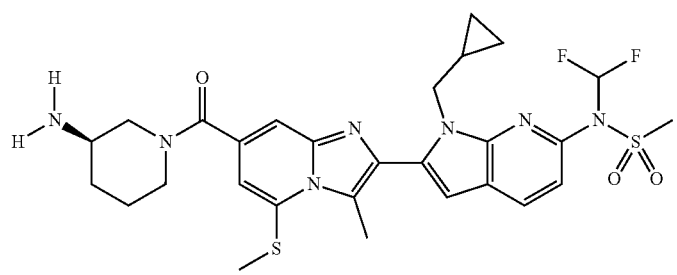
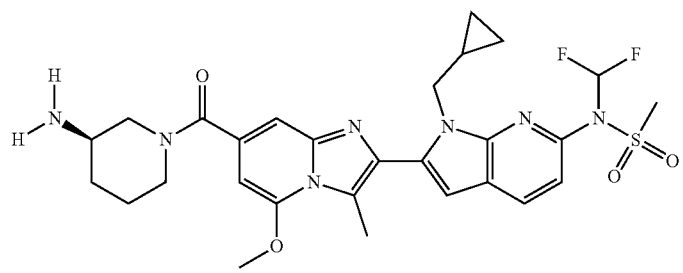
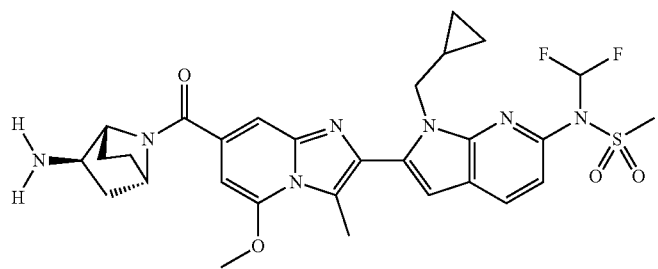
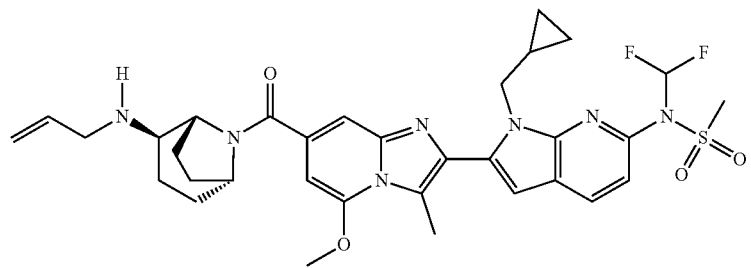

-continued
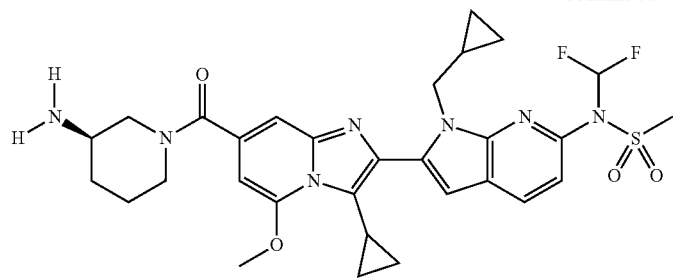
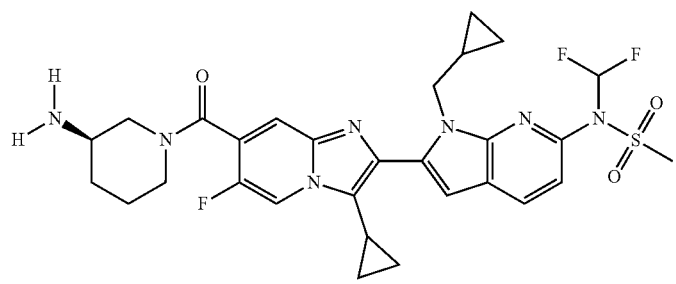
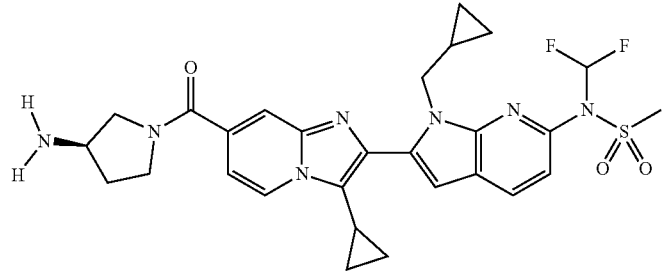
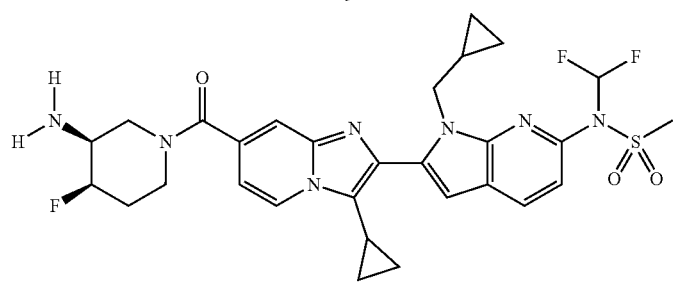
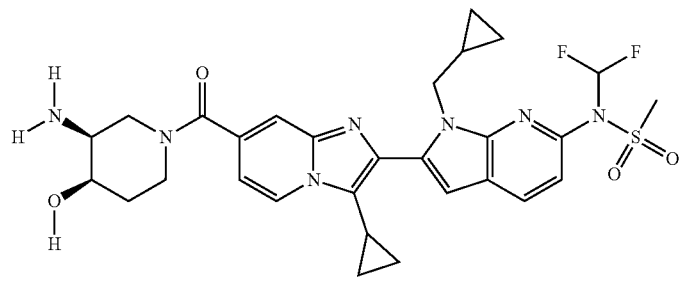
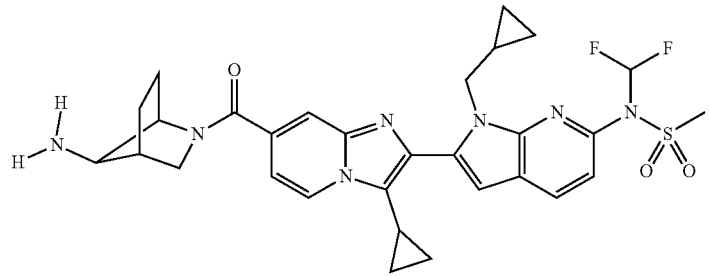

-continued
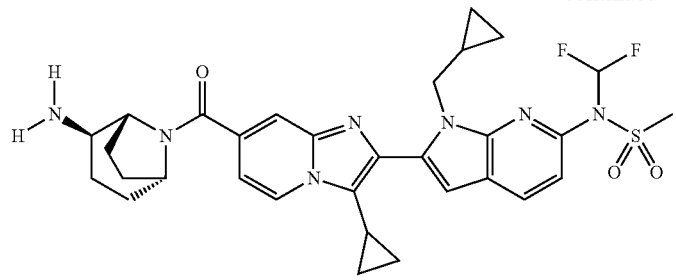
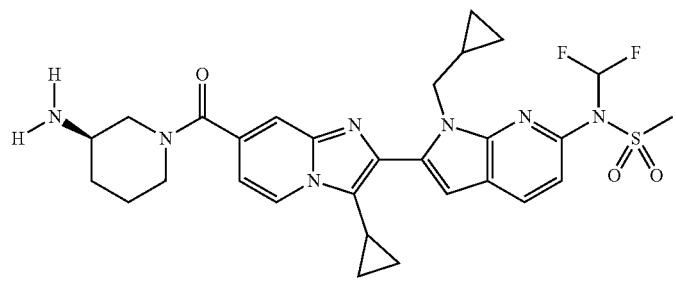
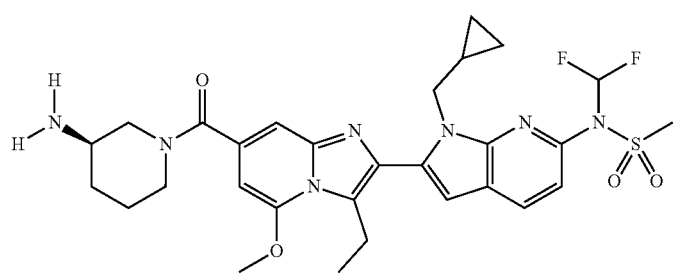
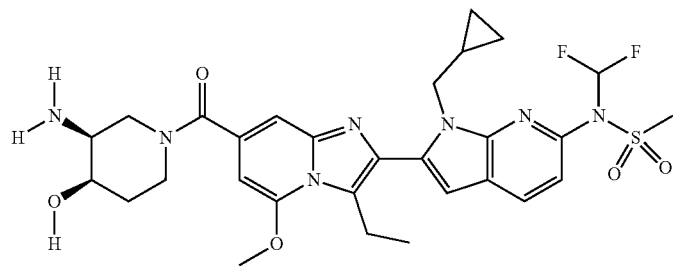
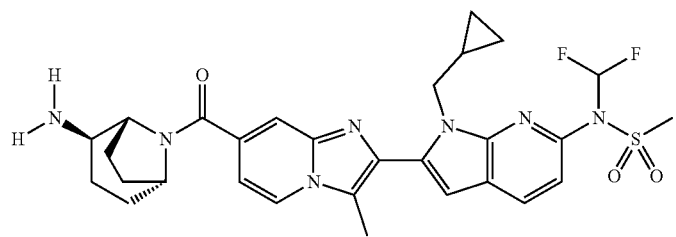
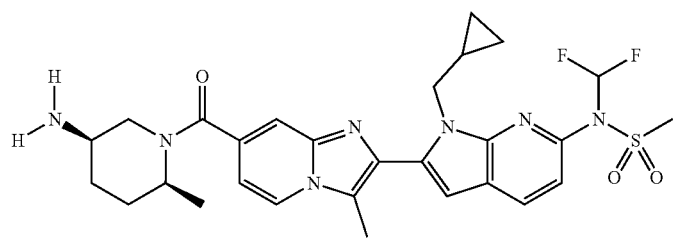

-continued
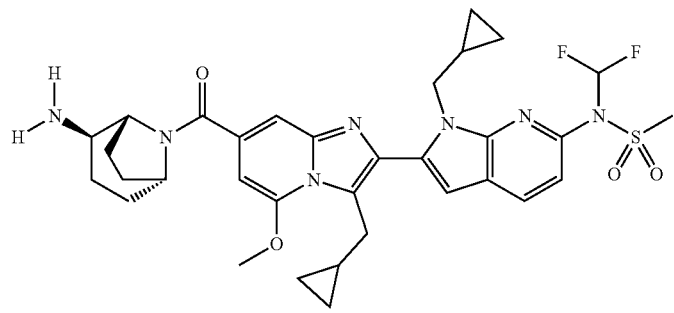
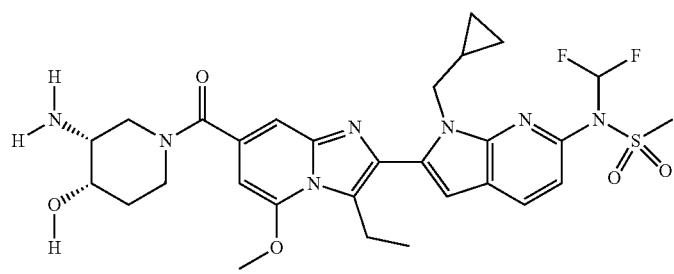
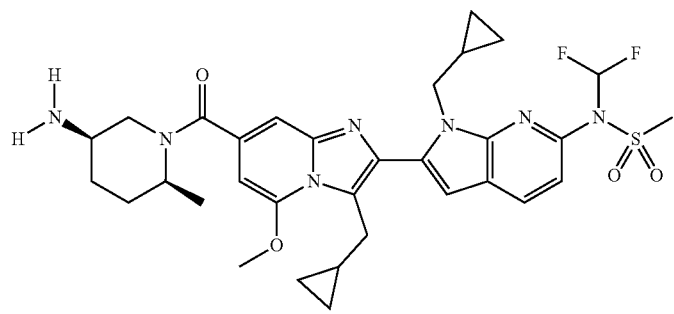
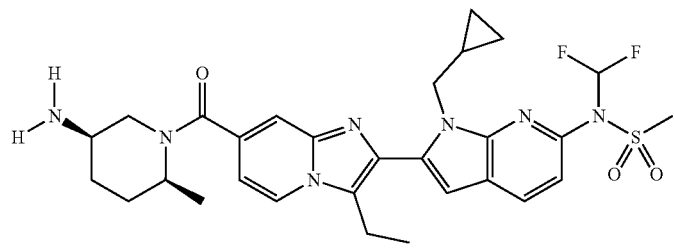
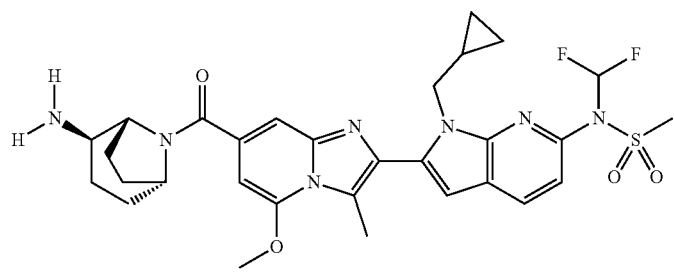
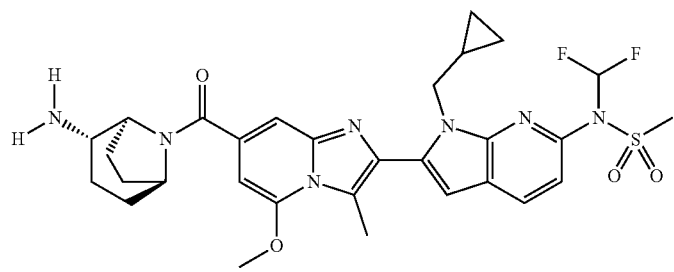

-continued
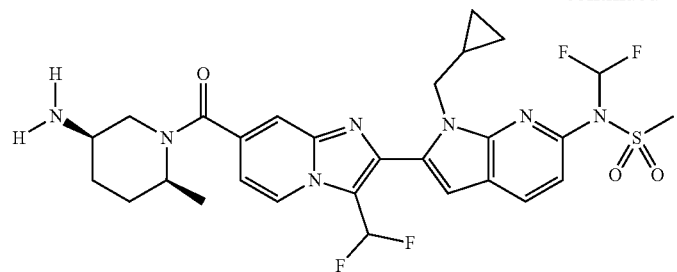
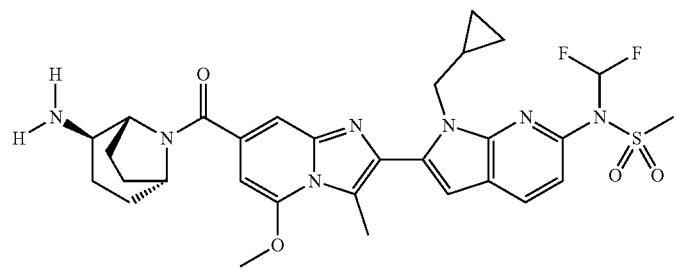
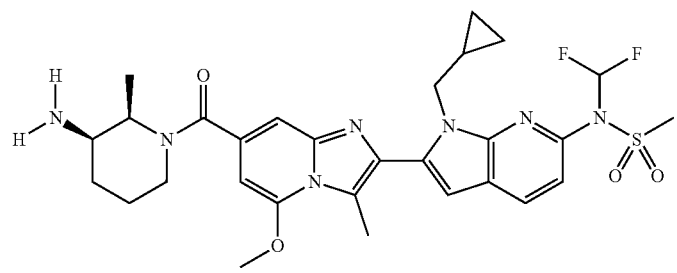
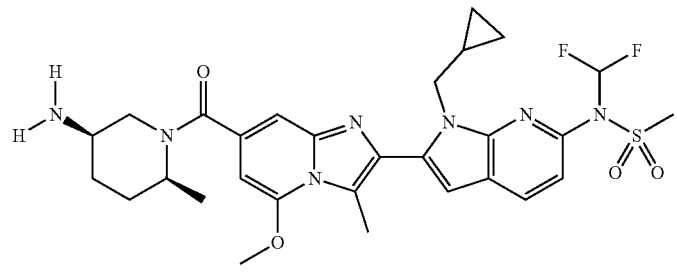
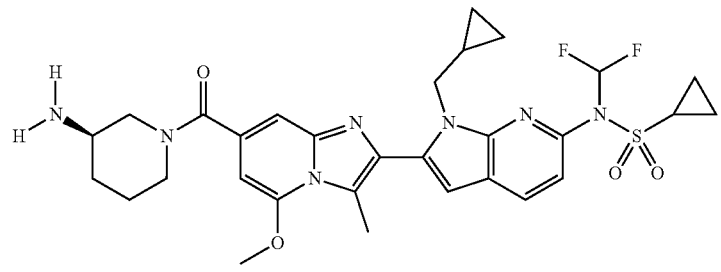
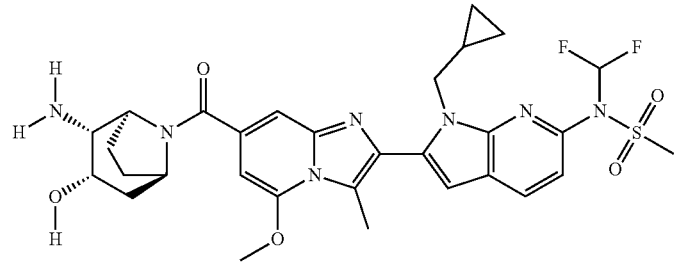

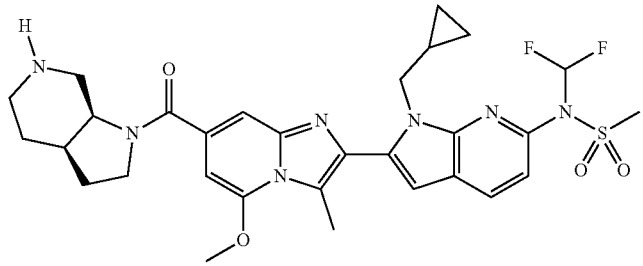
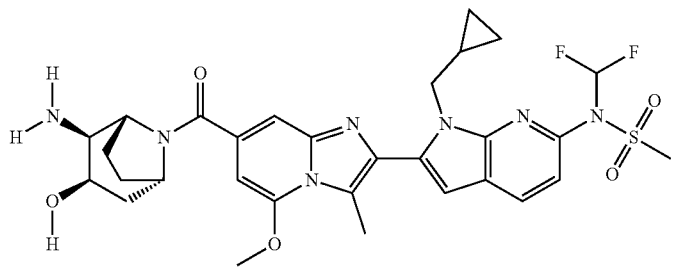
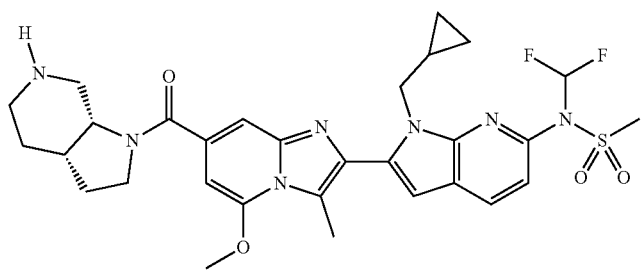
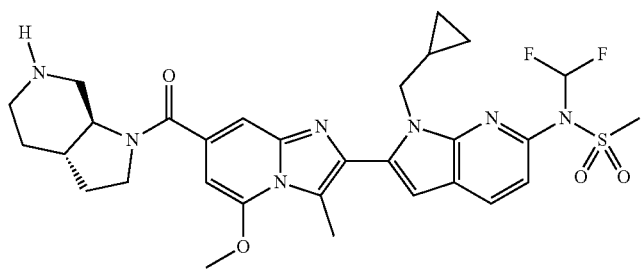
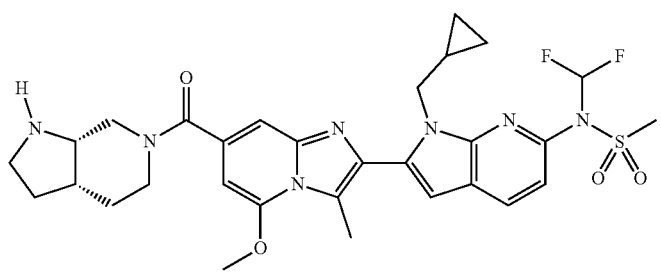
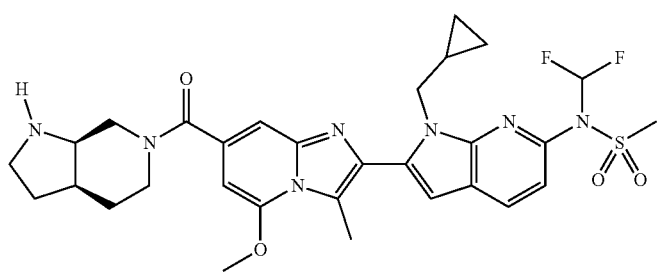

-continued
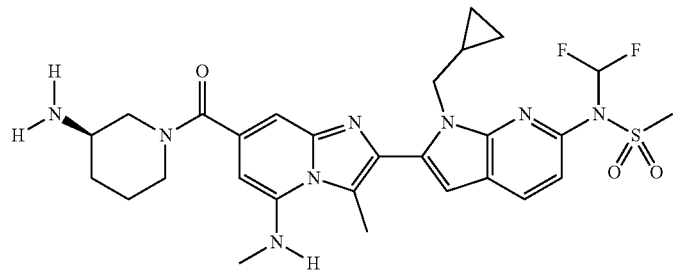
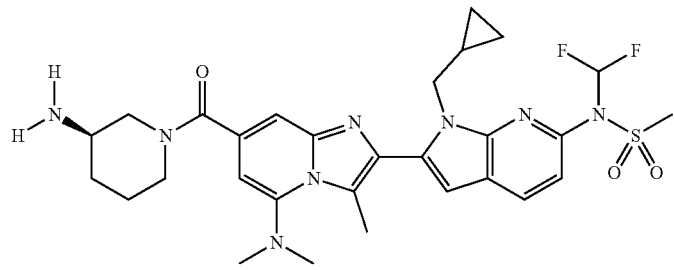
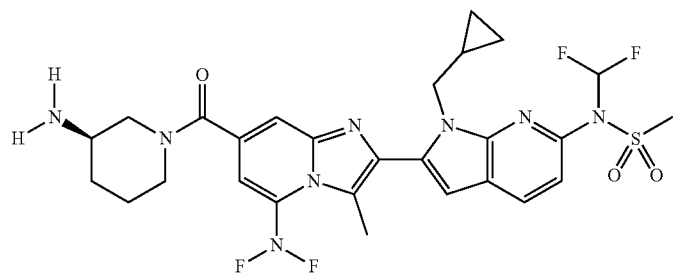
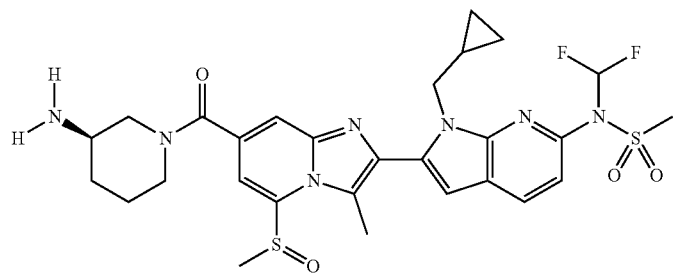
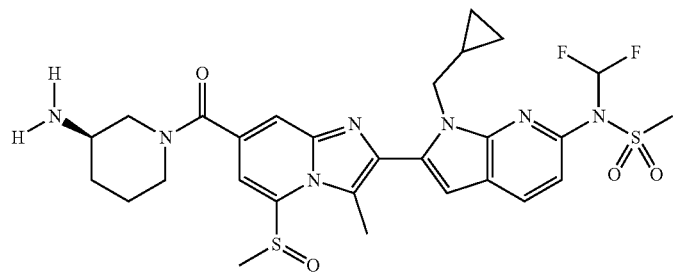
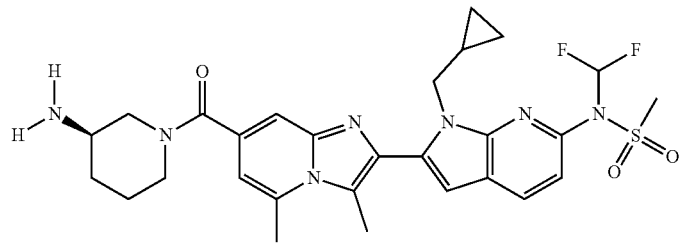

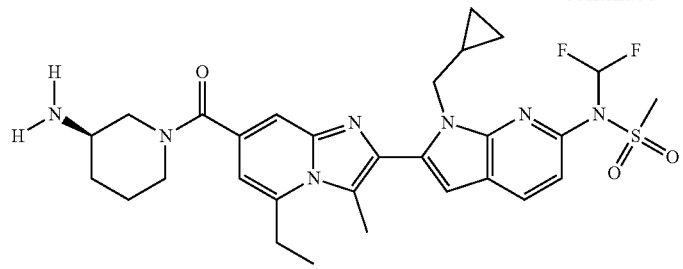
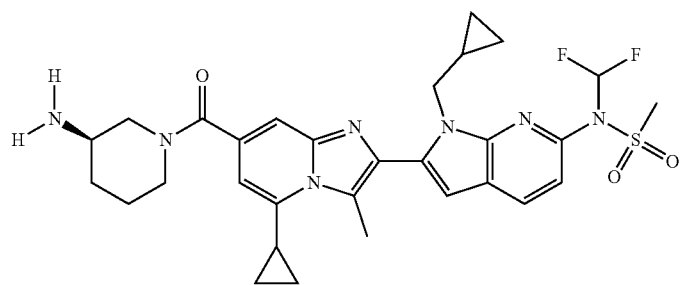
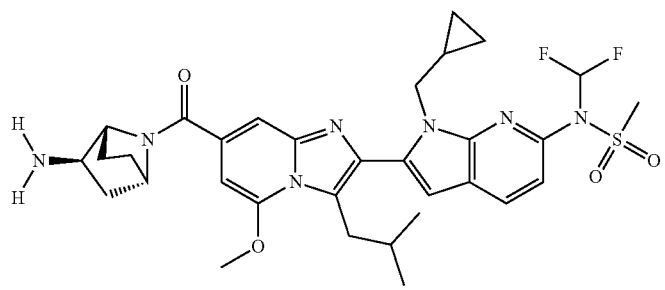
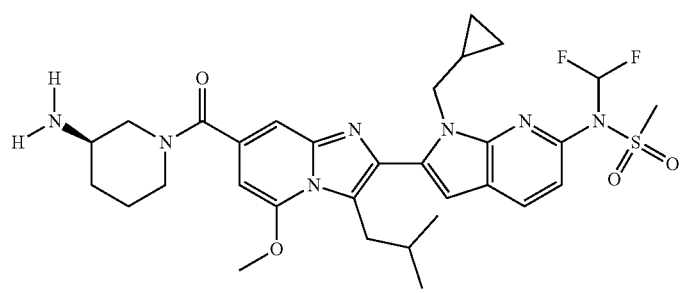
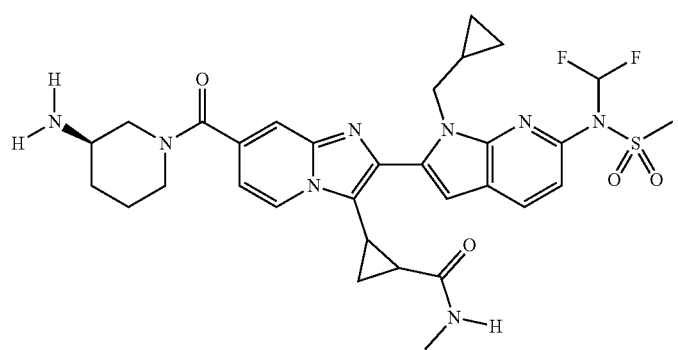

-continued
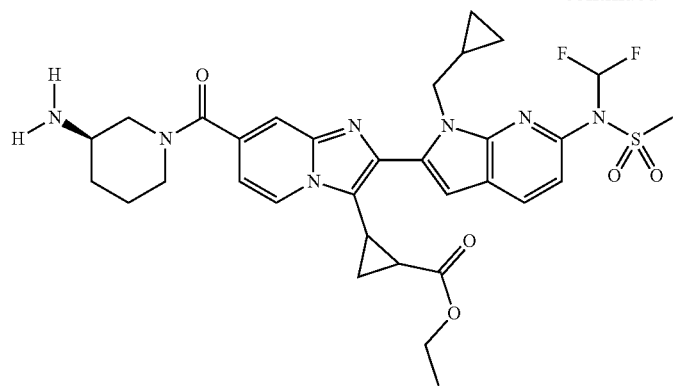
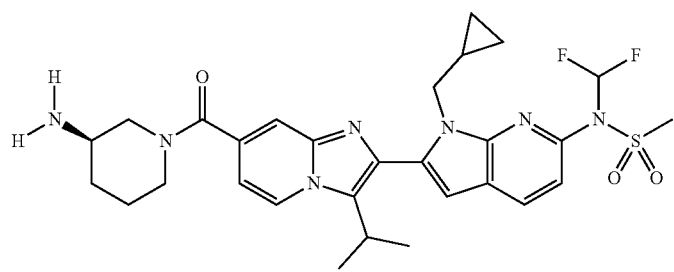
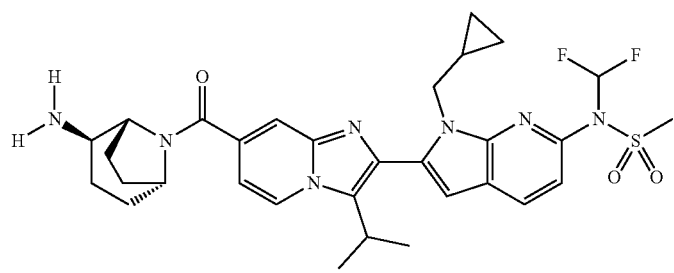
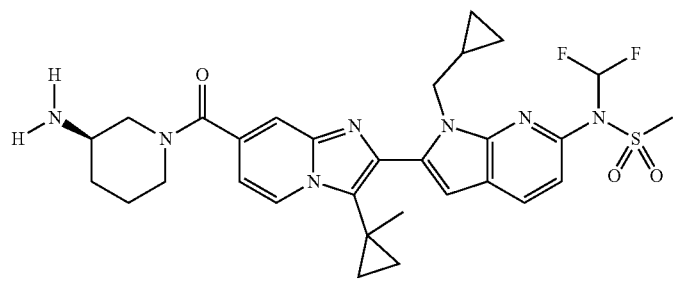
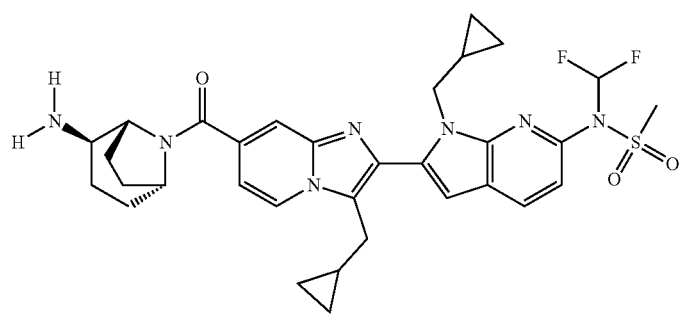

-continued
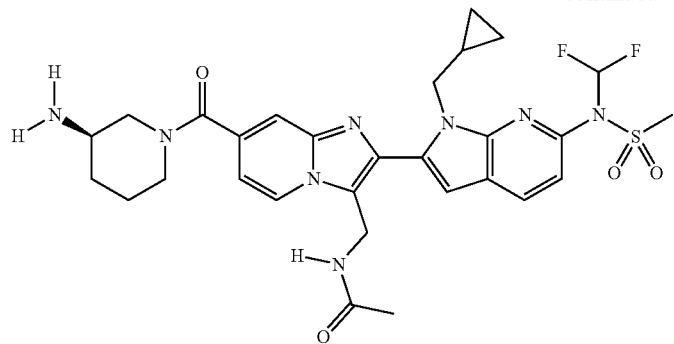
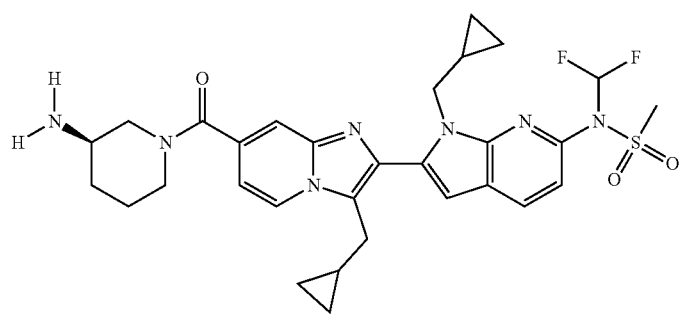
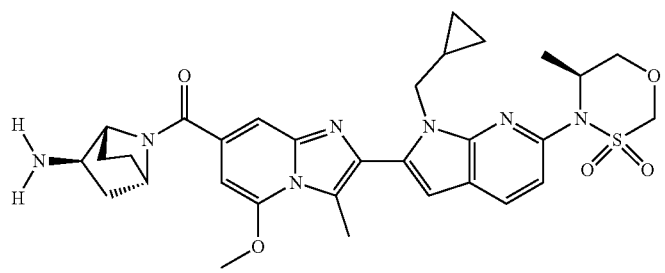
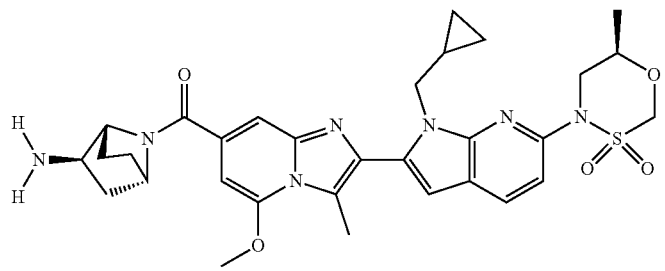
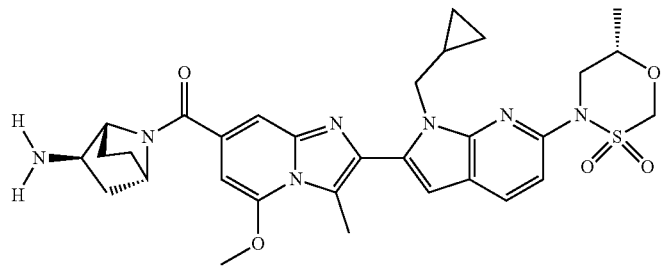

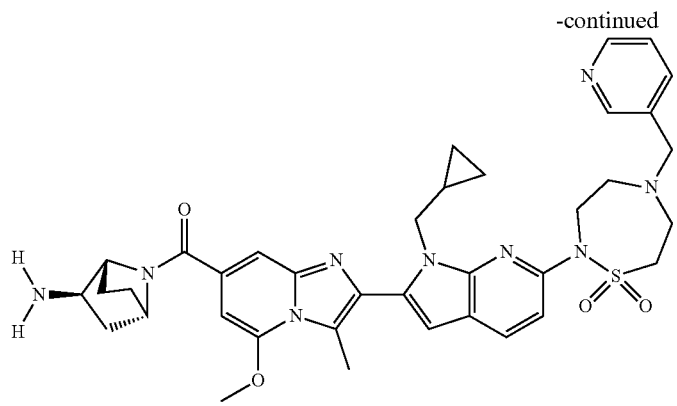
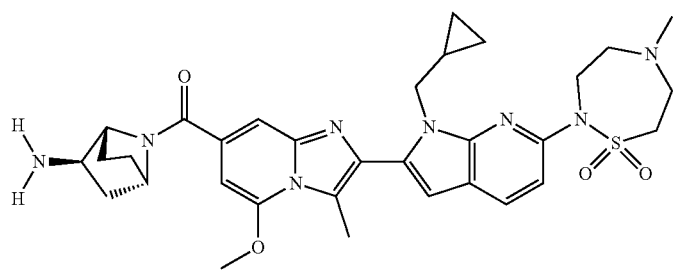
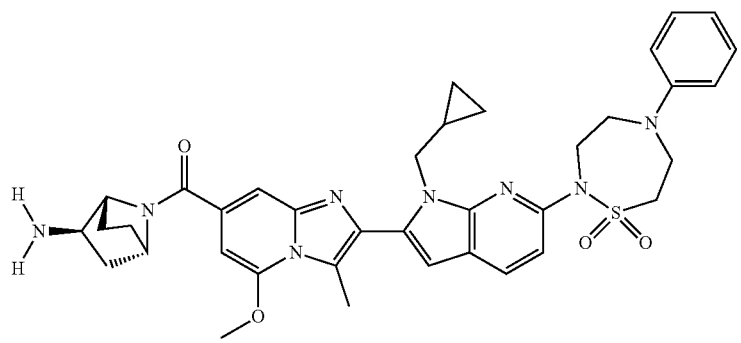
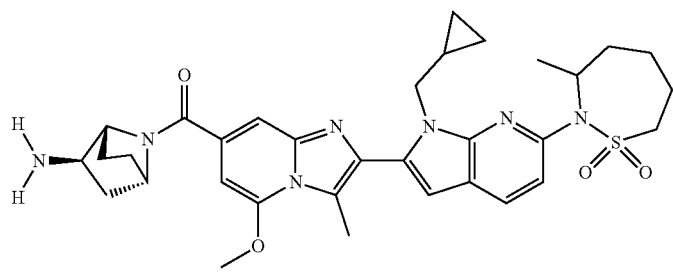
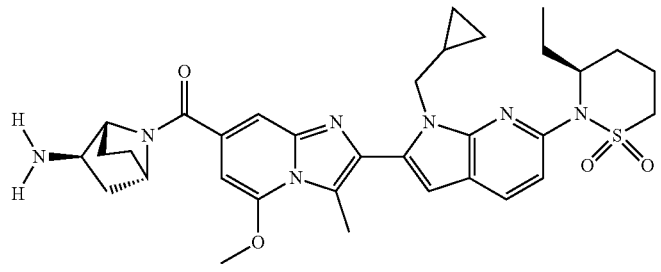

-continued
787
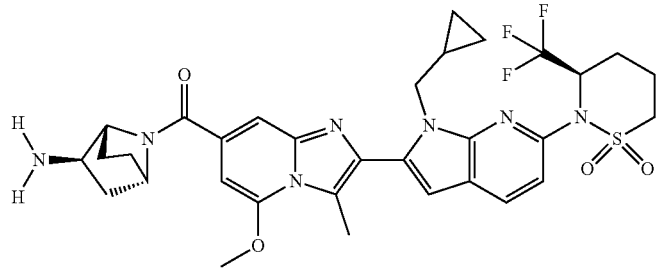
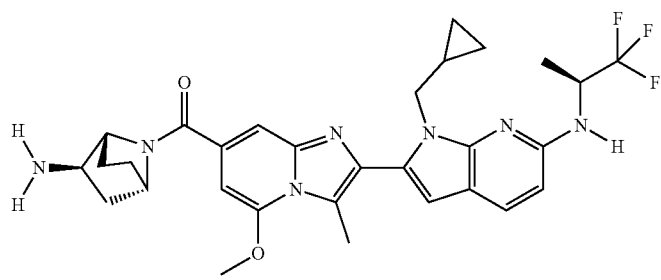
788
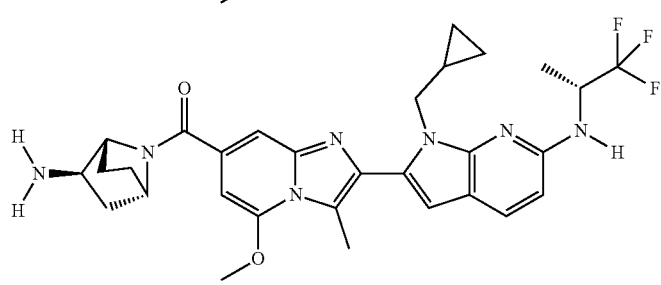
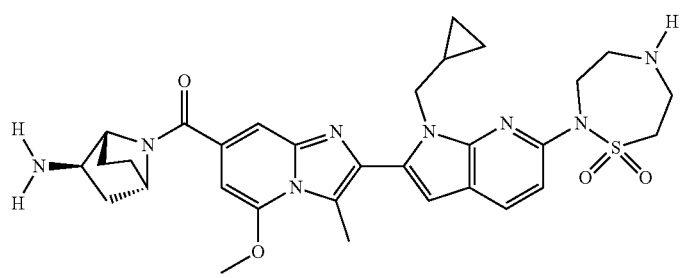
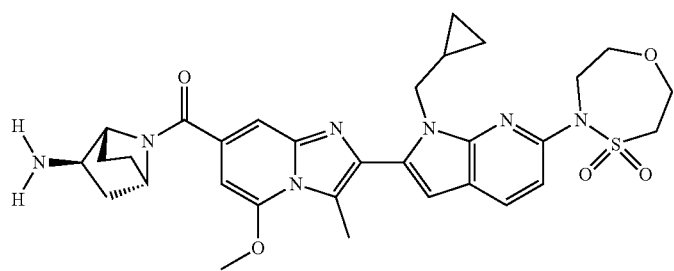
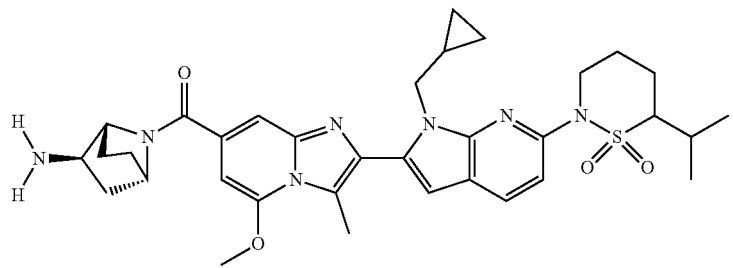

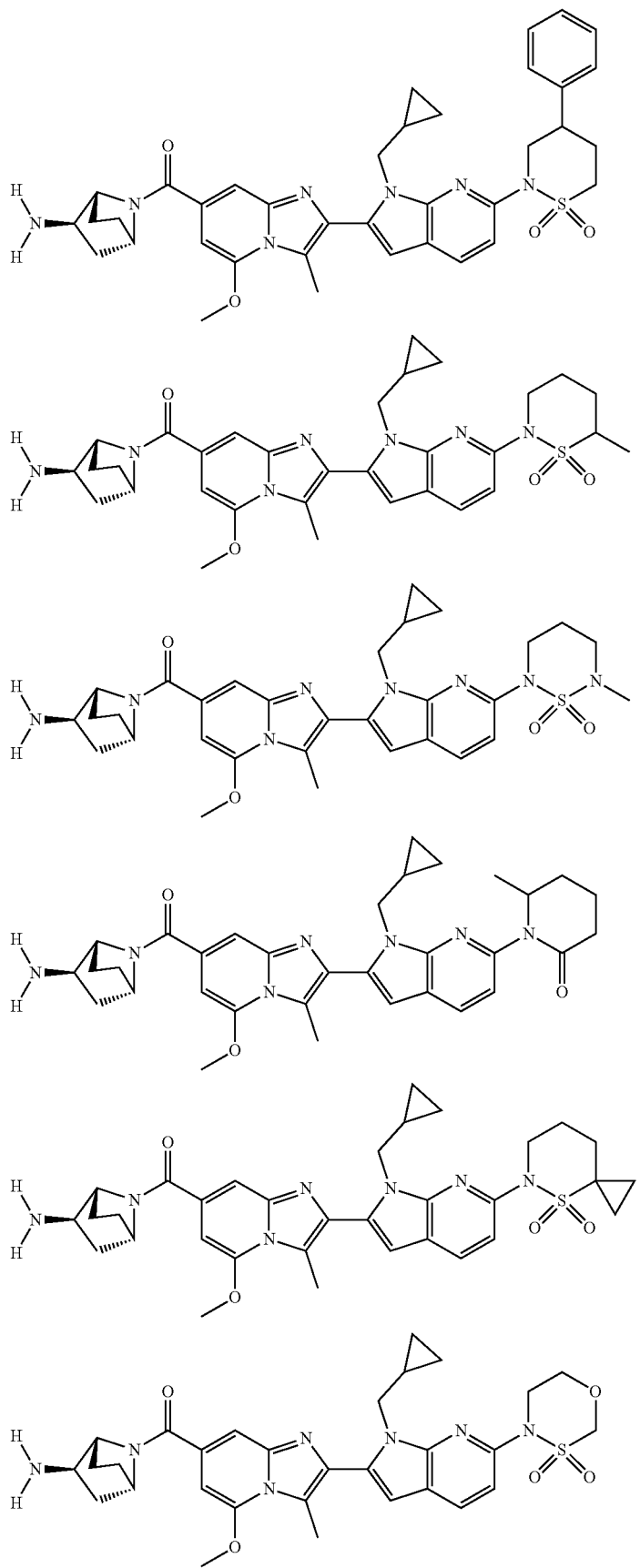

791
-continued
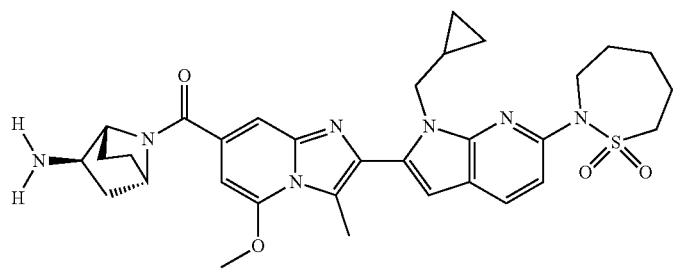
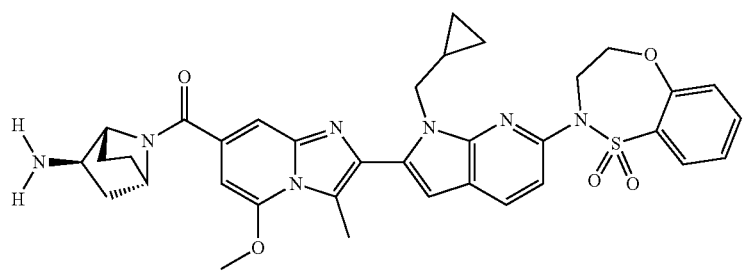
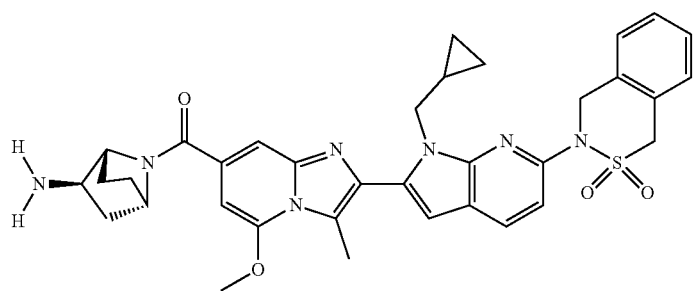
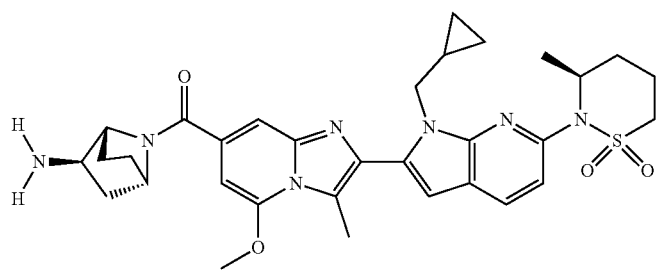
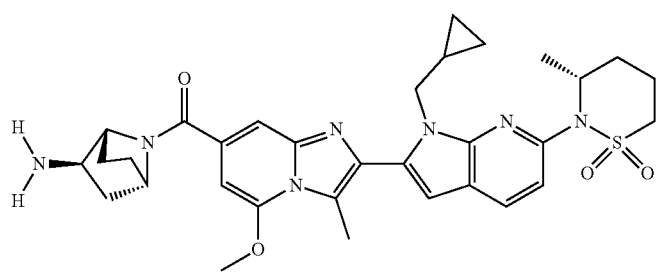
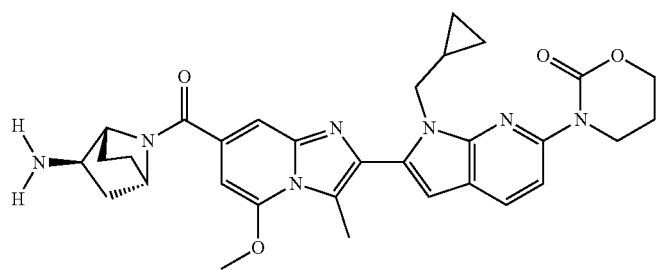
792

793
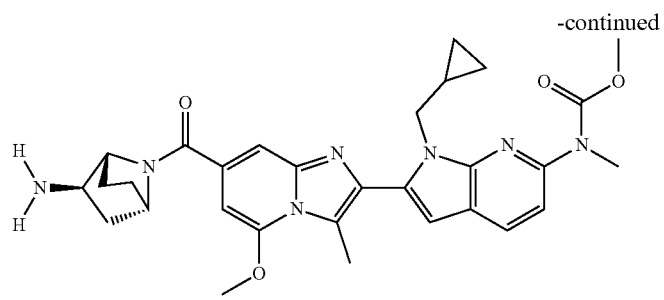
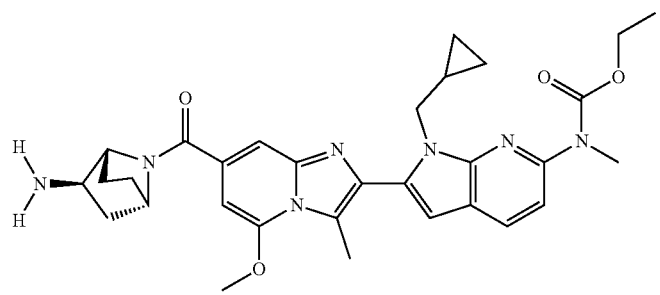
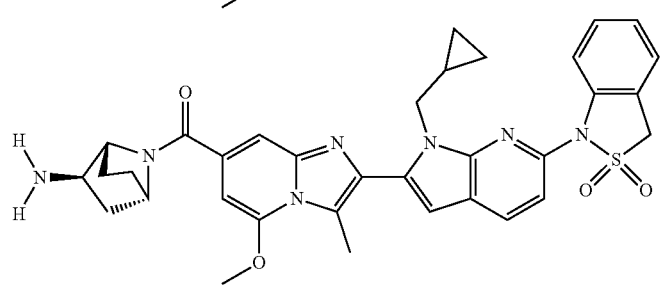
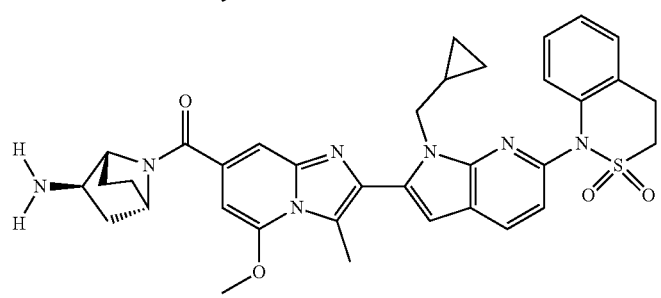
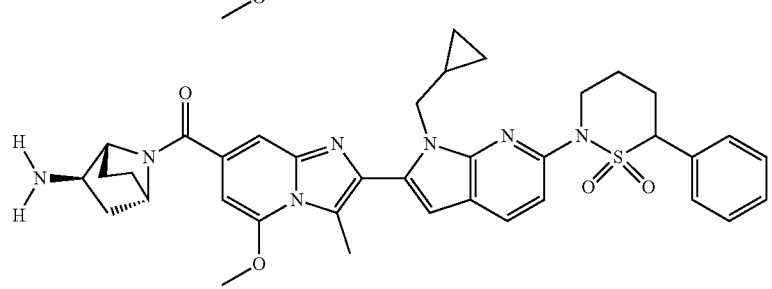
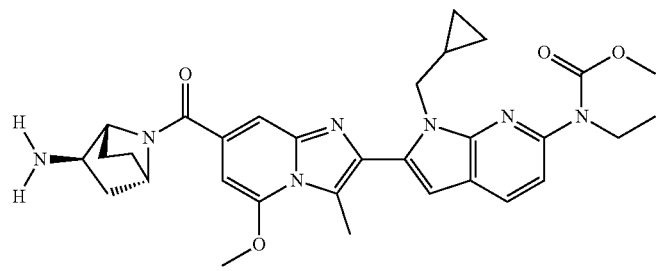
794
-continued -continued
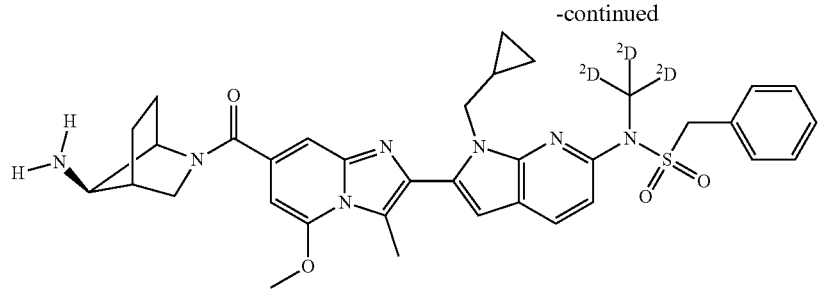
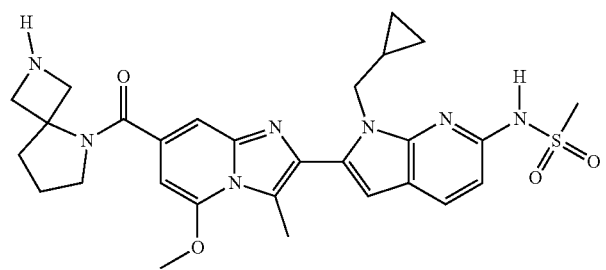
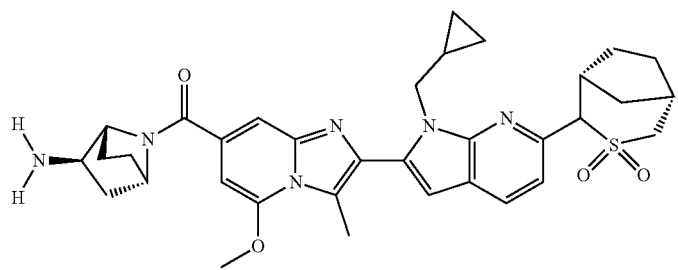
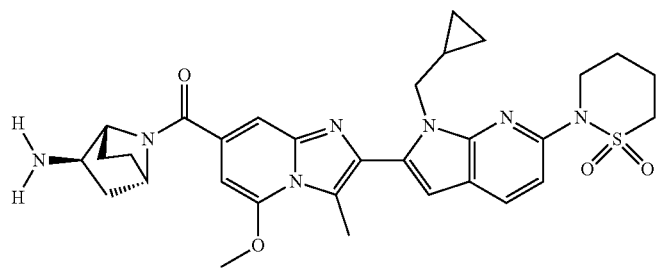
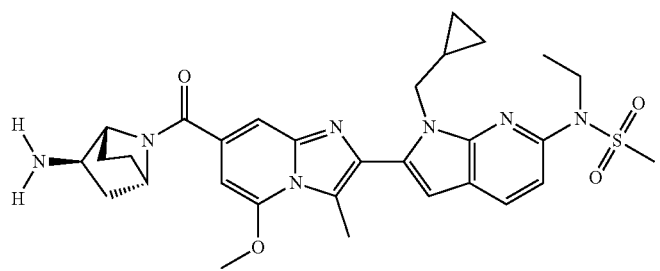
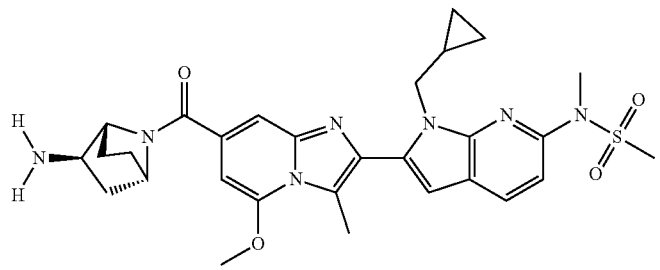

797
-continued
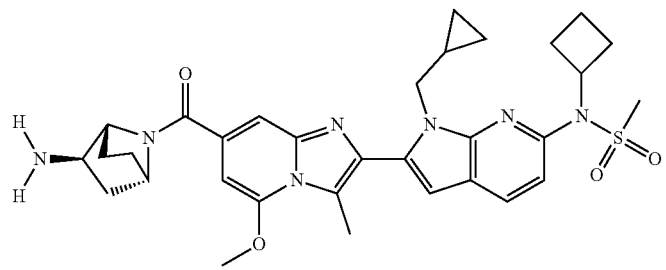
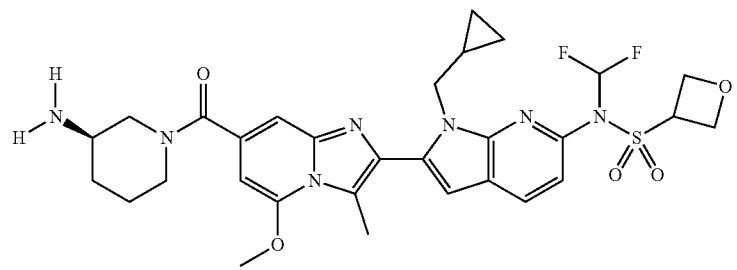
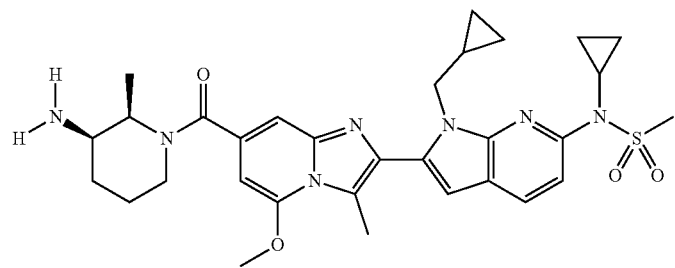
798
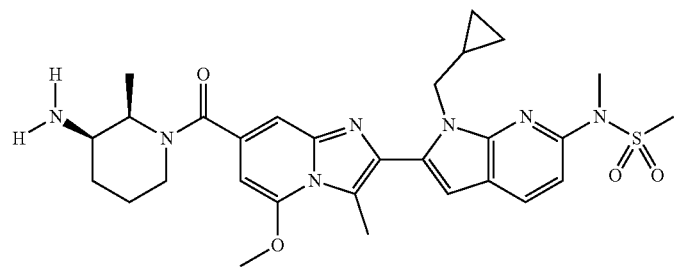
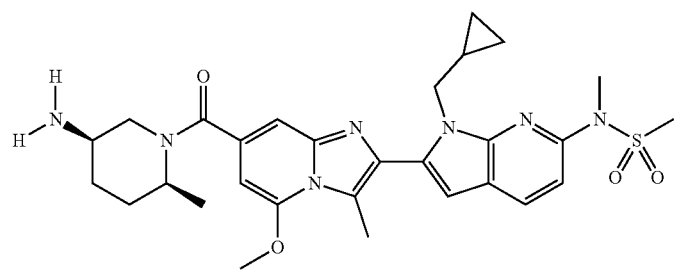
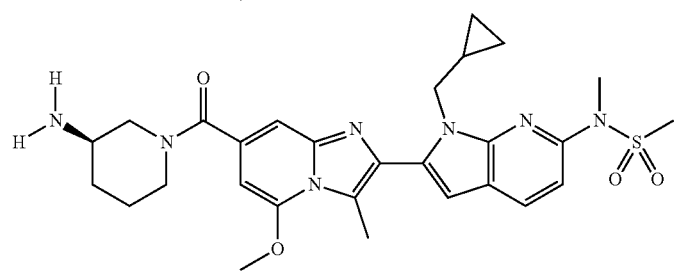

-continued
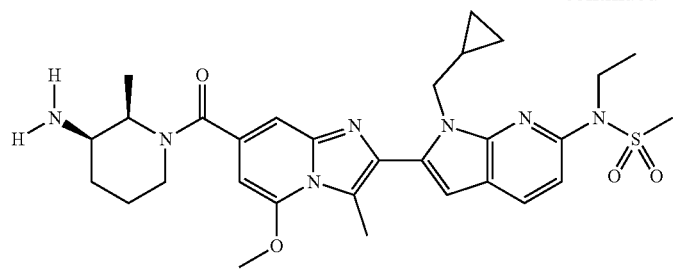
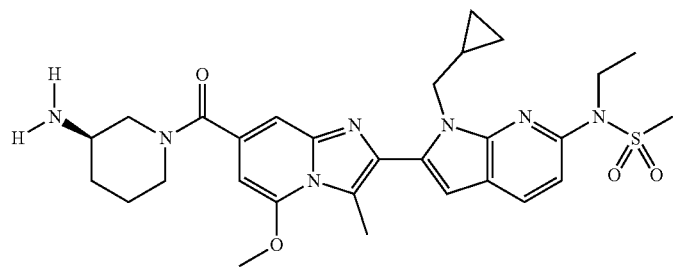
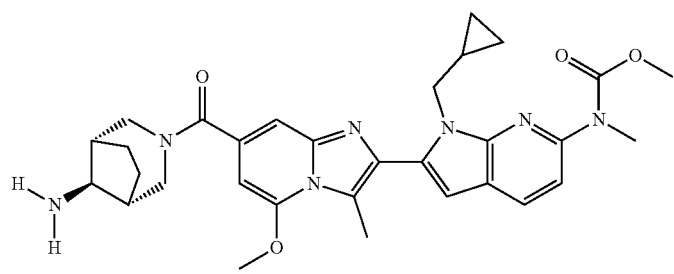
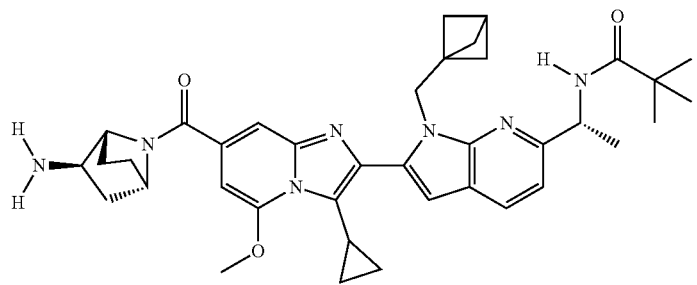
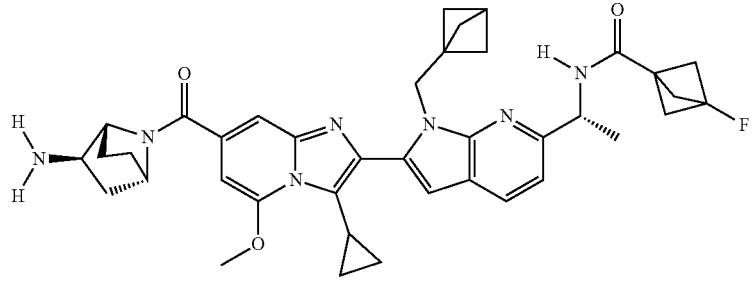
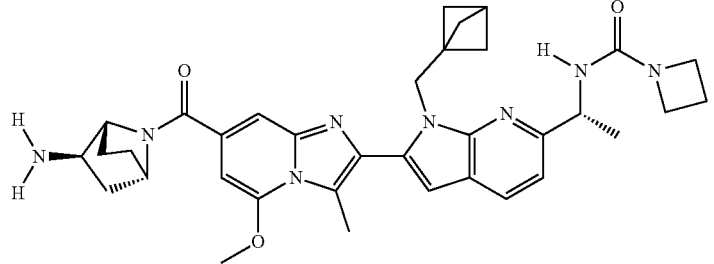

-continued
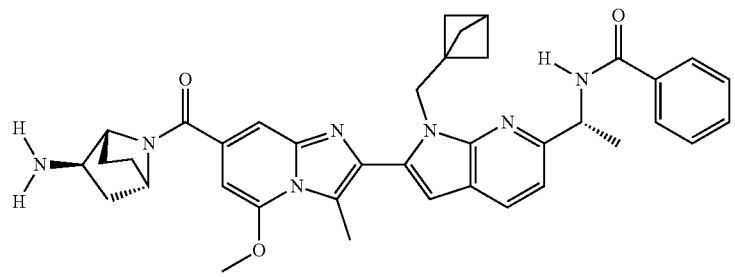
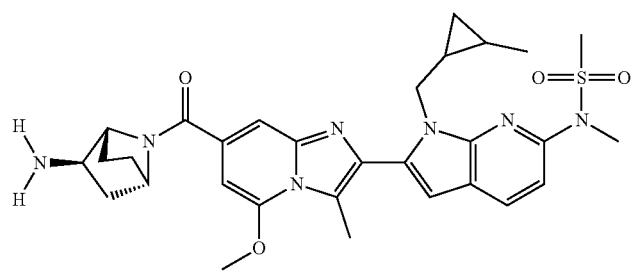
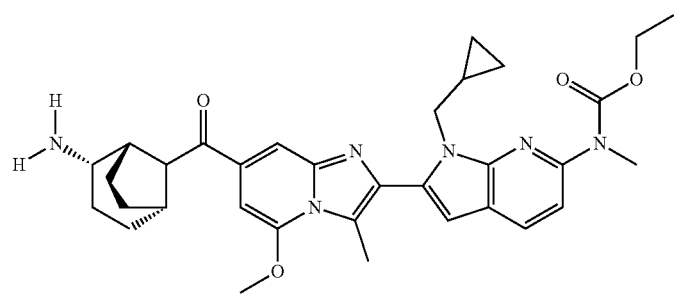
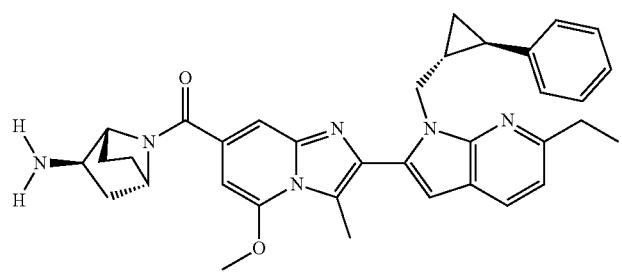
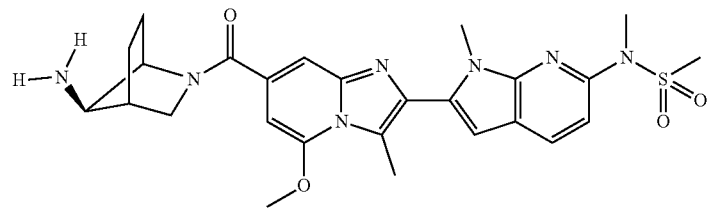
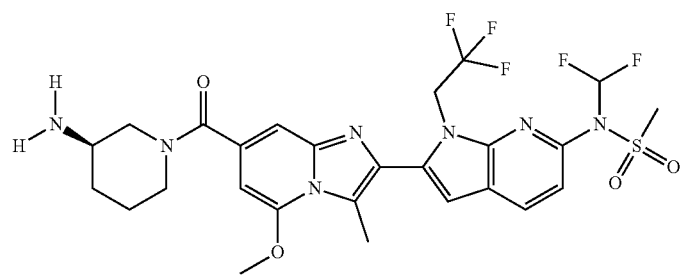

803
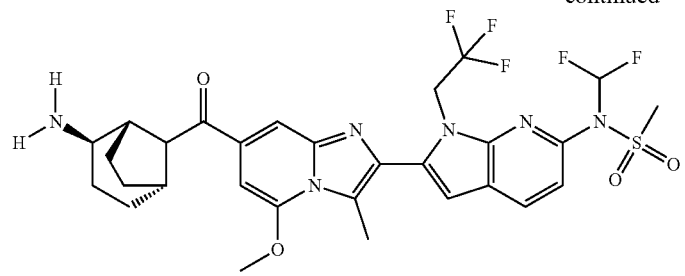
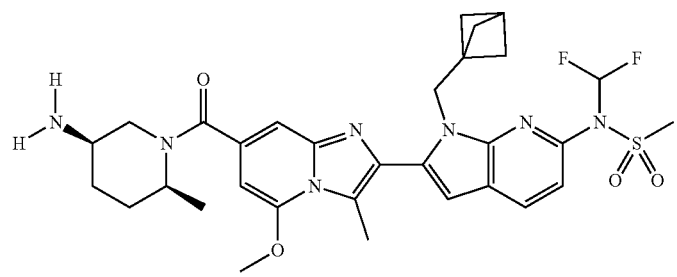
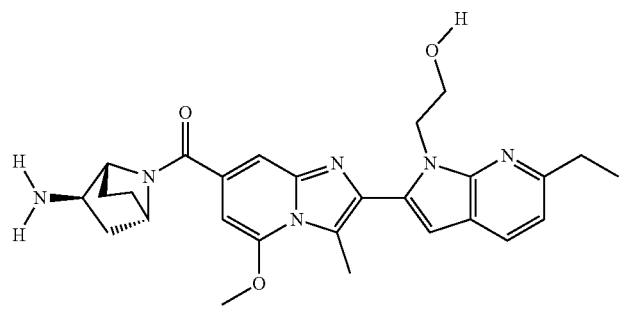
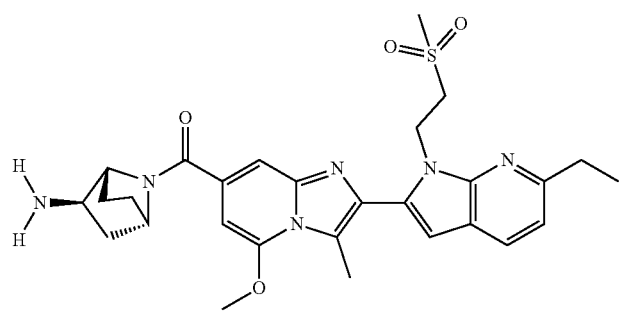
804
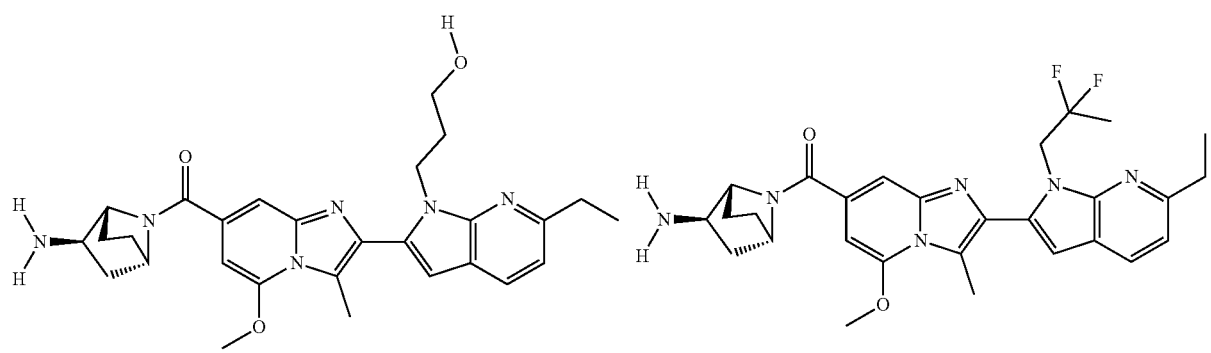

805 806
-continued
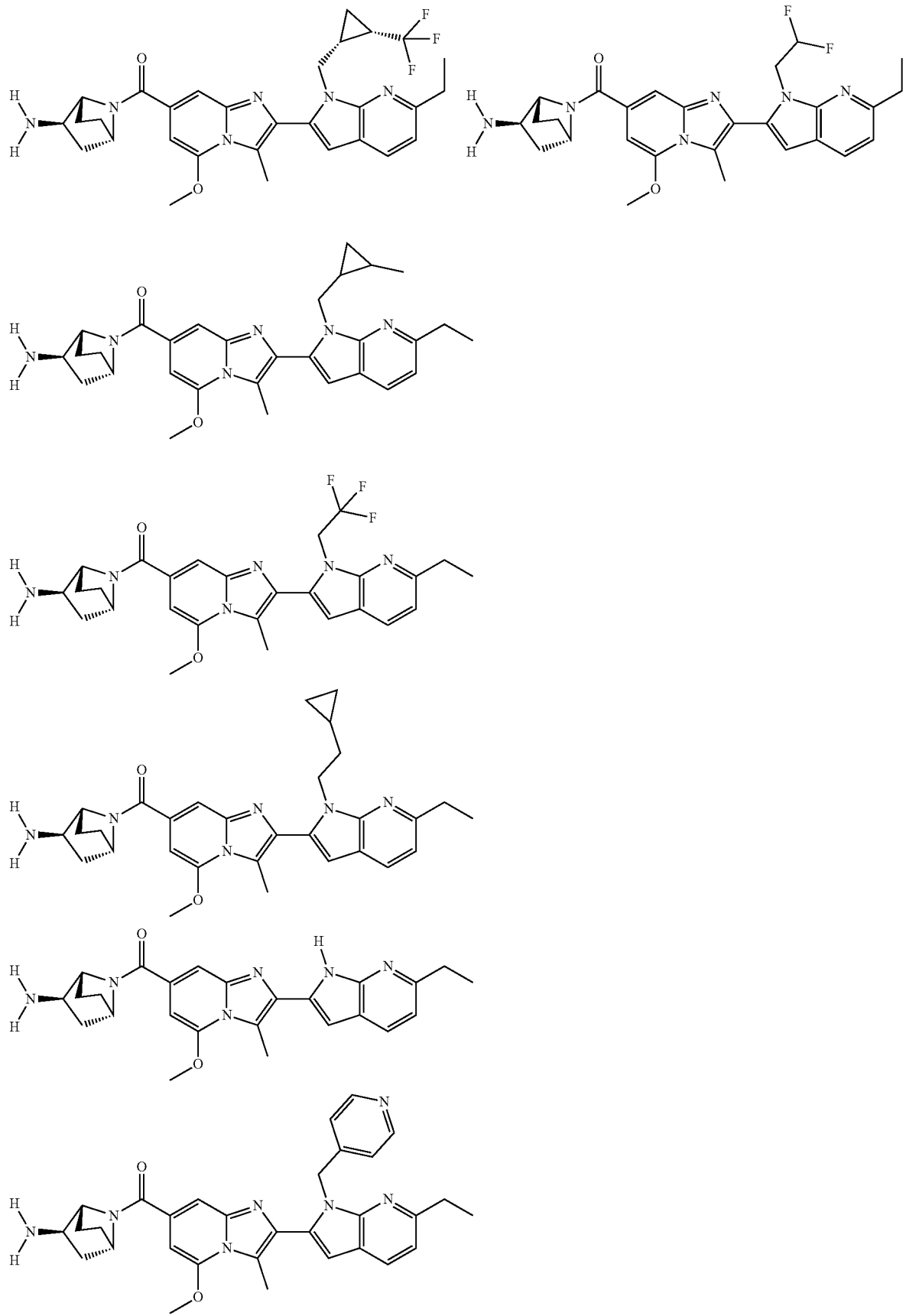

-continued
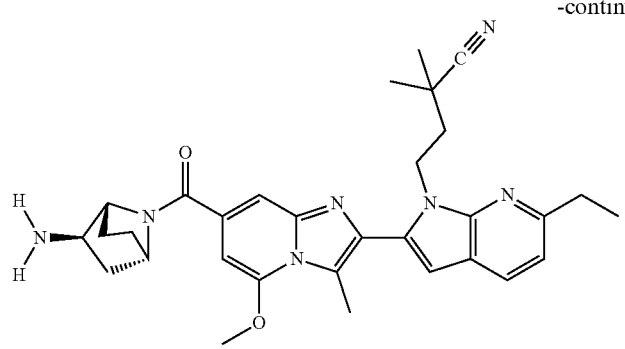
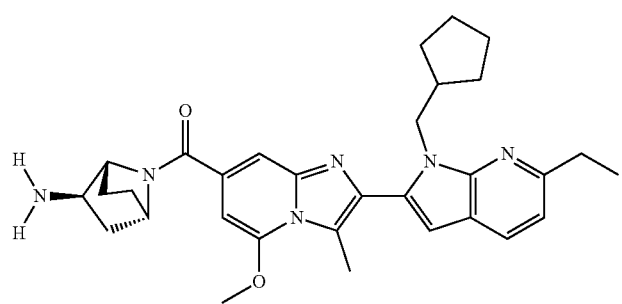
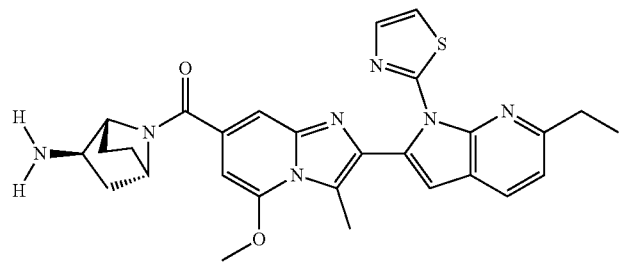
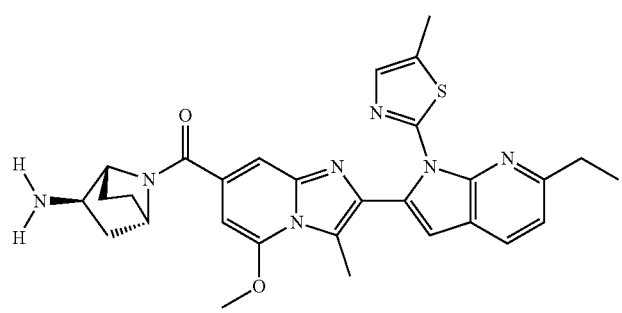
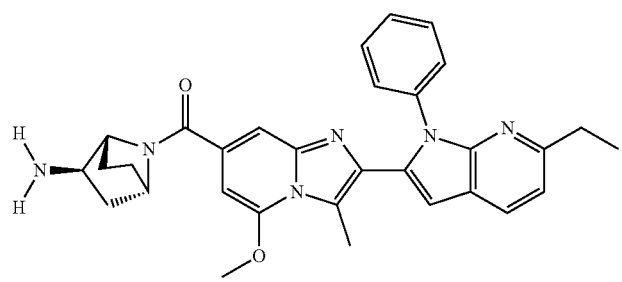

-continued
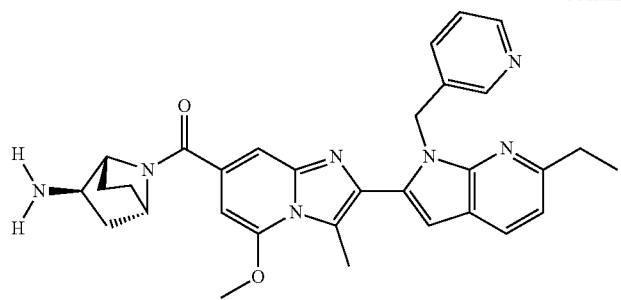
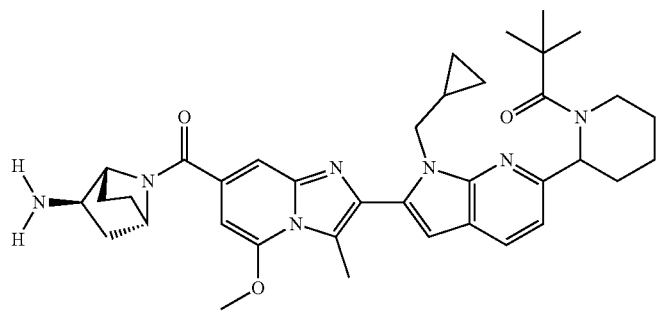
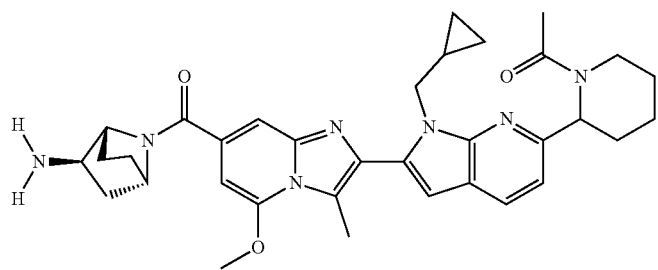
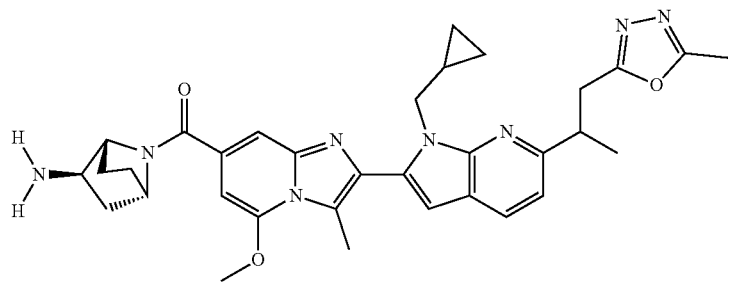
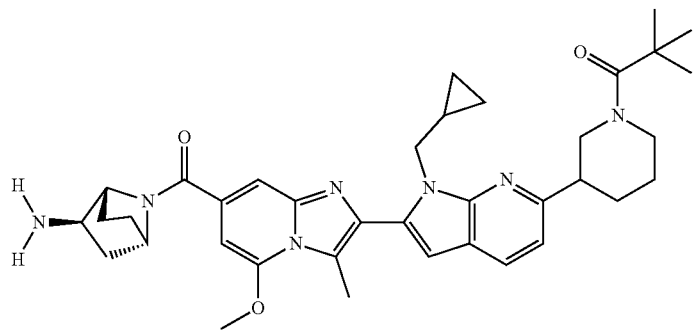

-continued
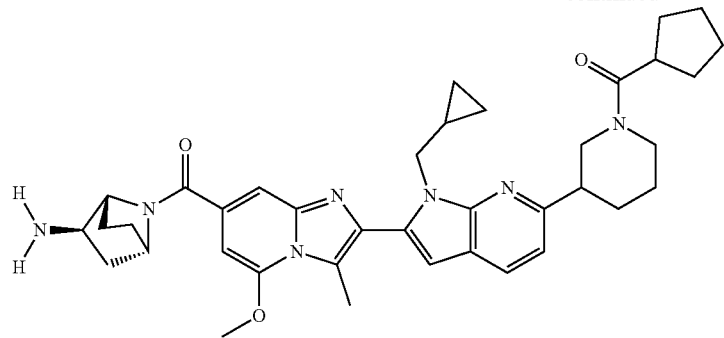
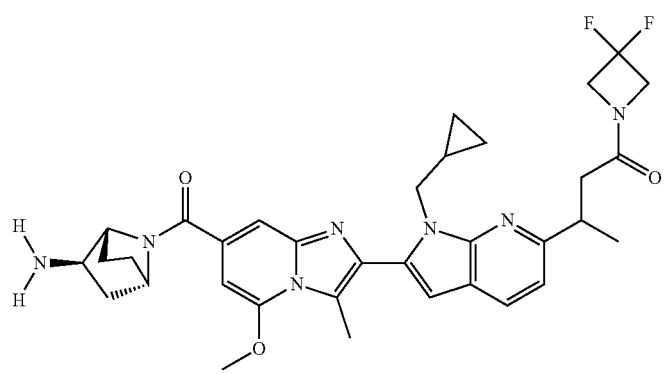
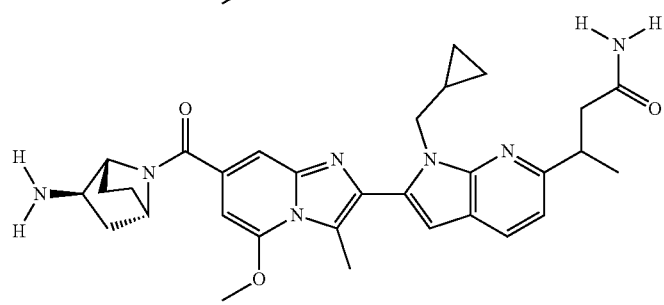
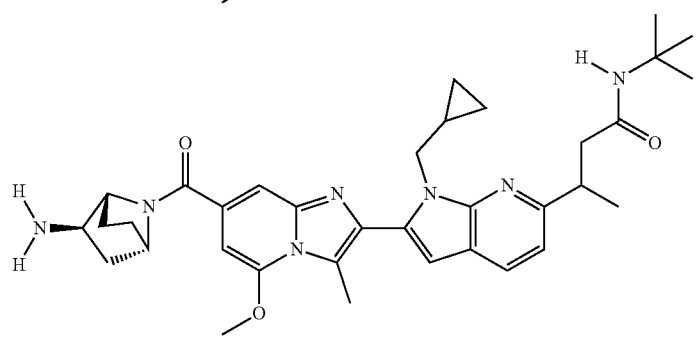
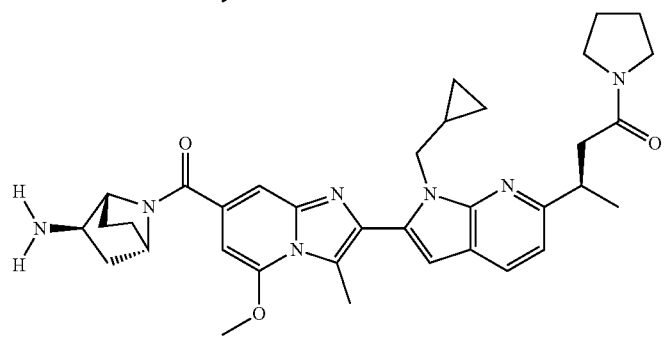

-continued
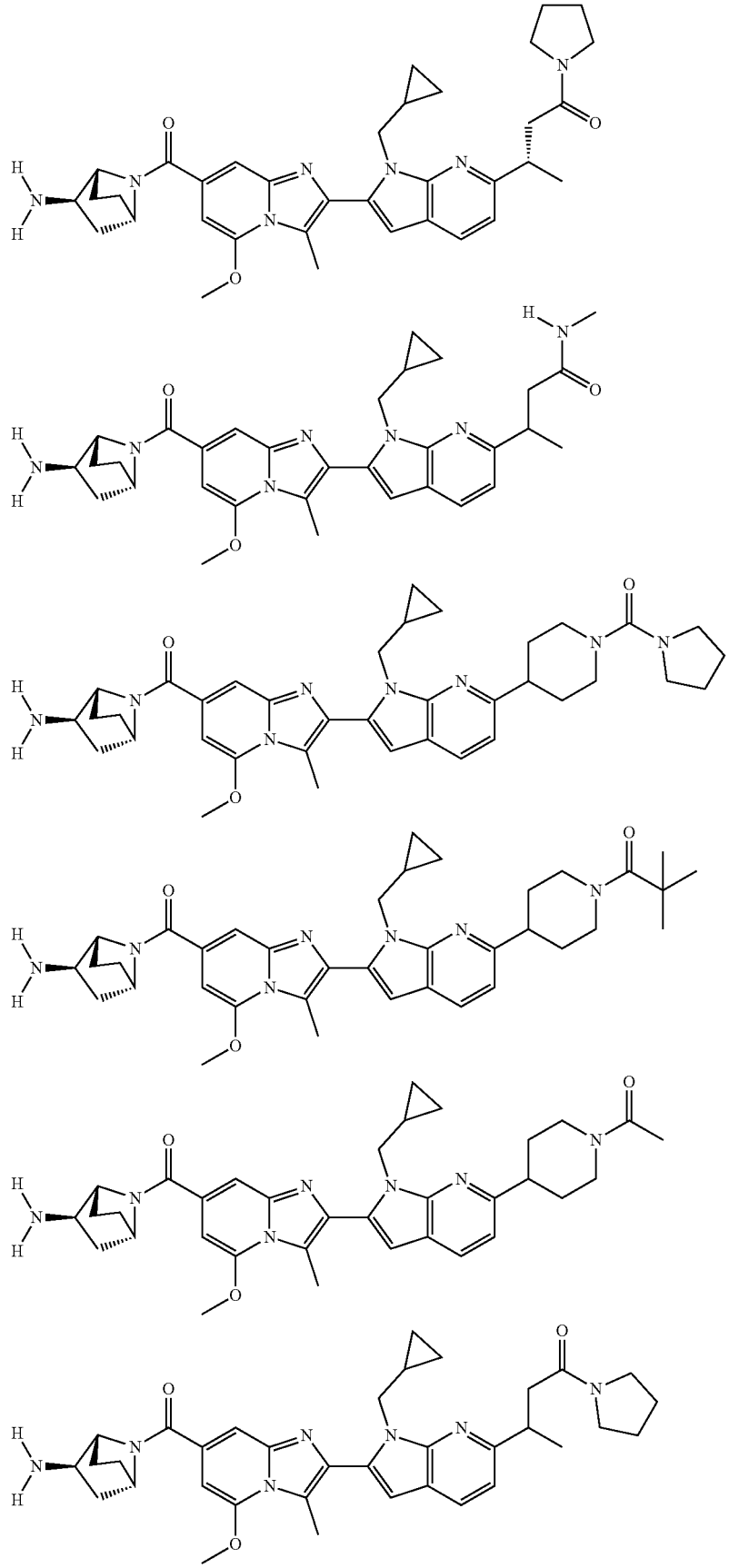

815
-continued
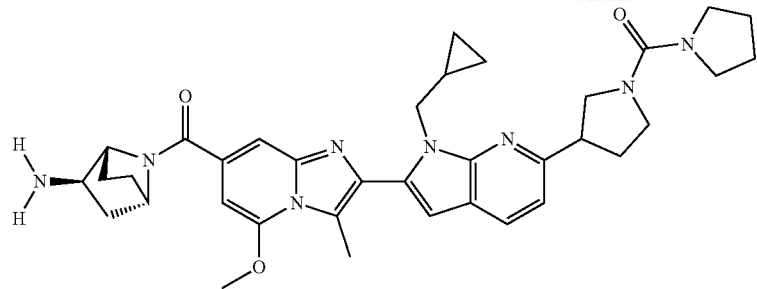
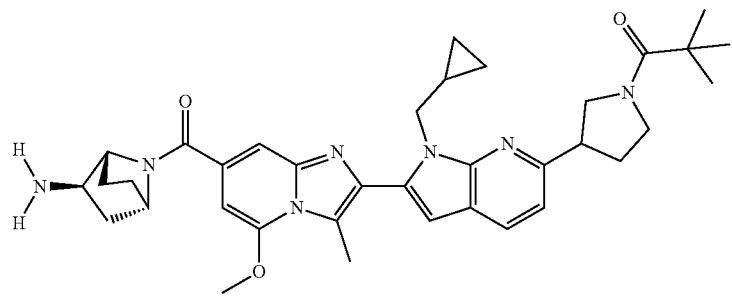
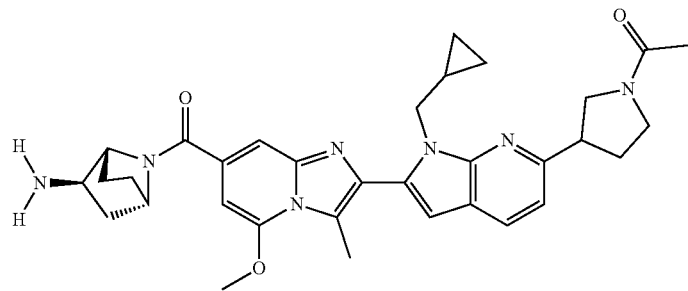
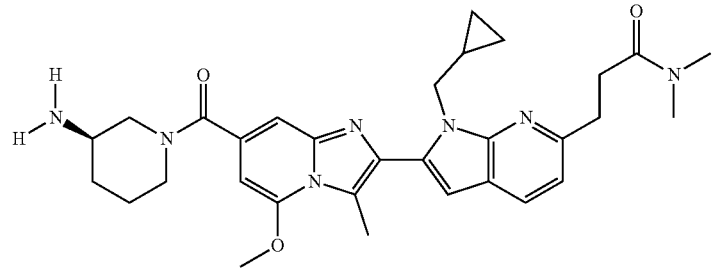
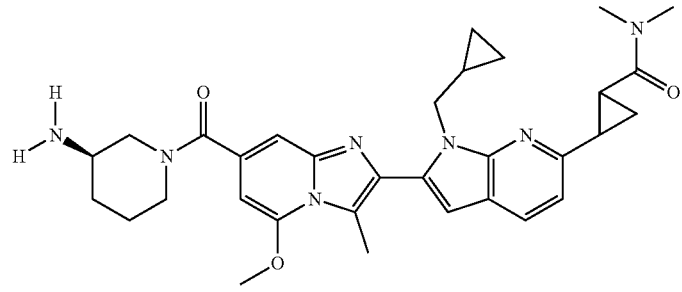
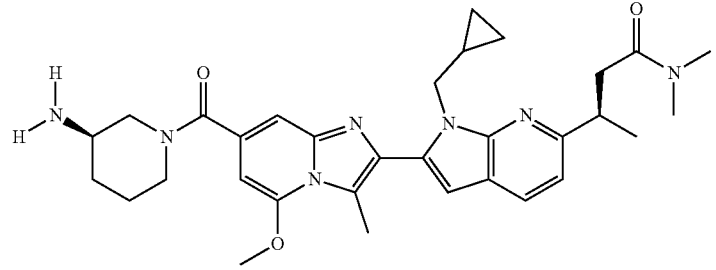

-continued
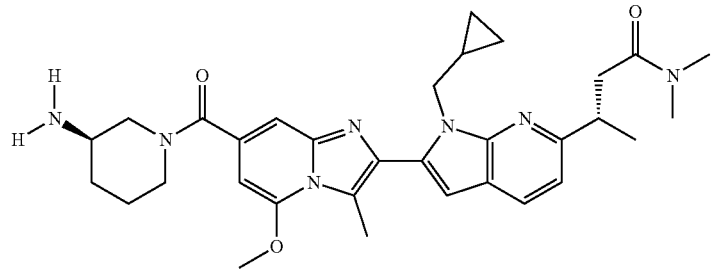
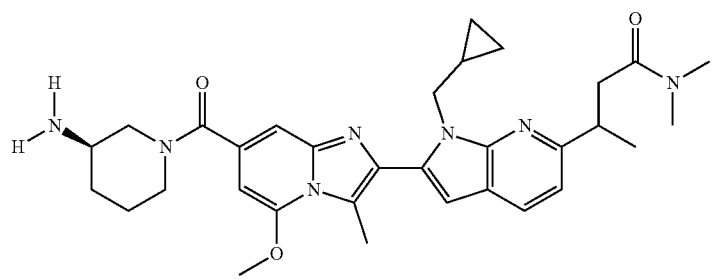
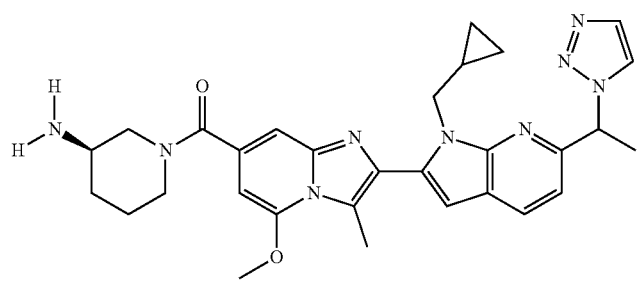
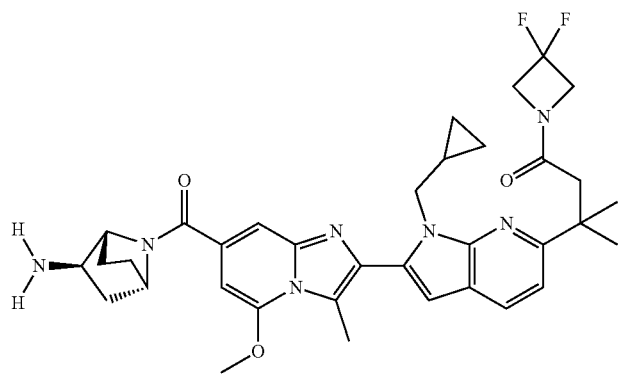
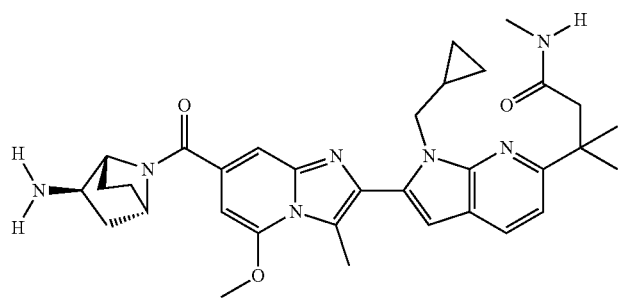

-continued
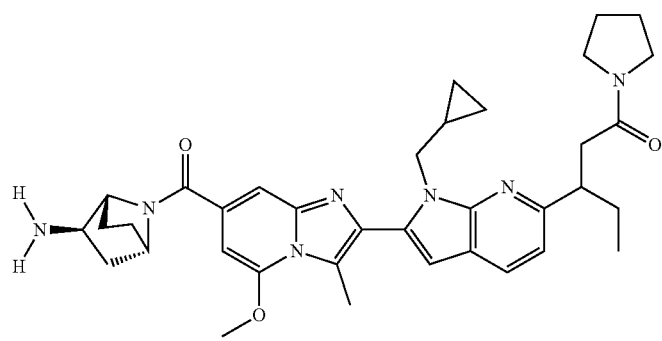
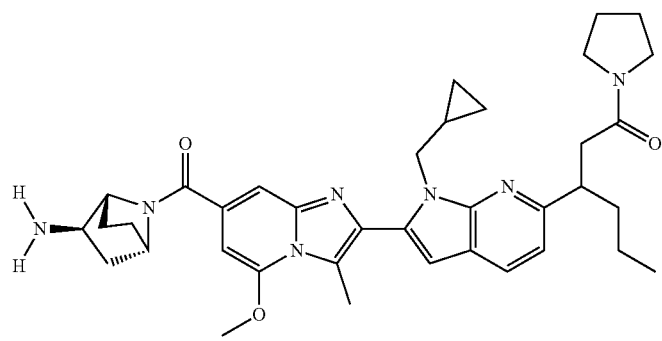
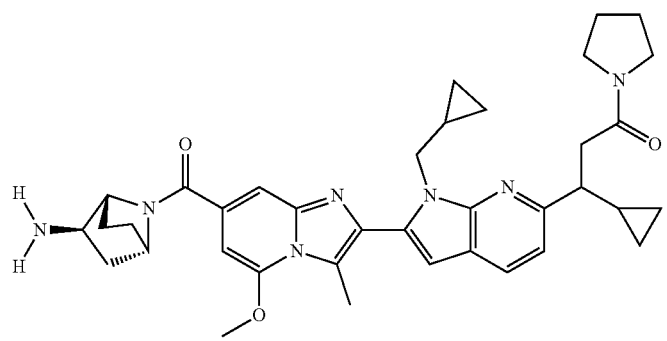
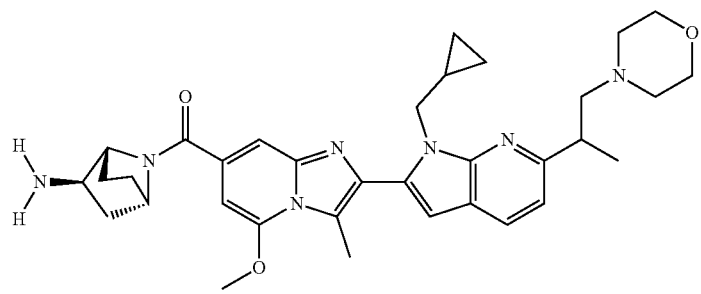
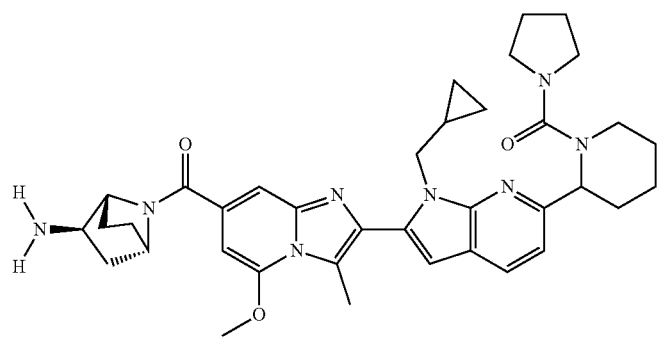

821
-continued
822
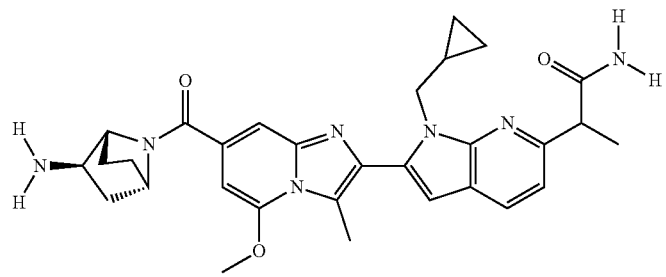
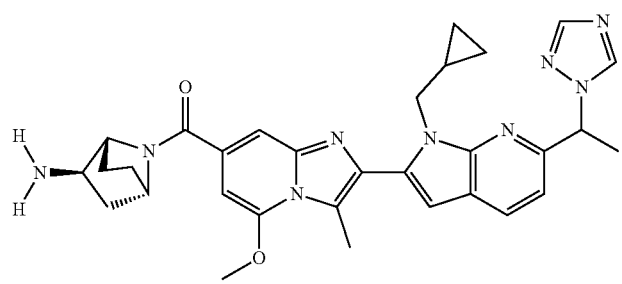
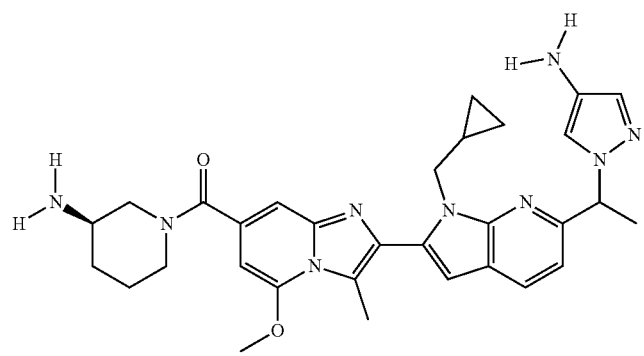
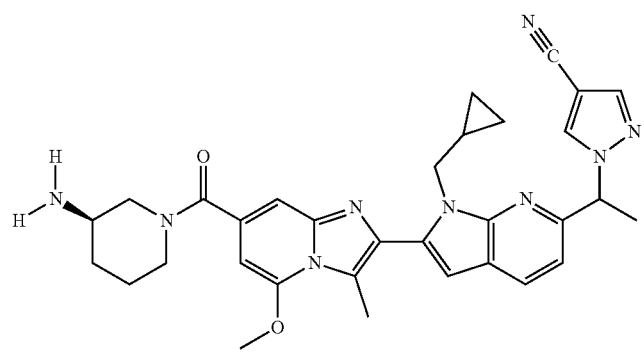
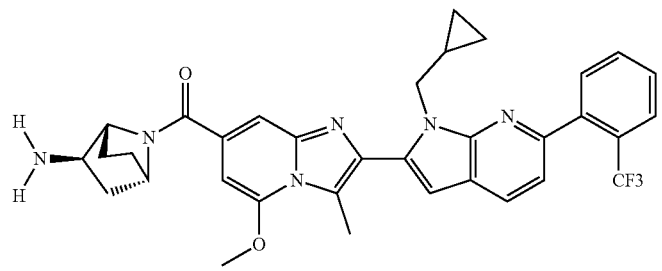

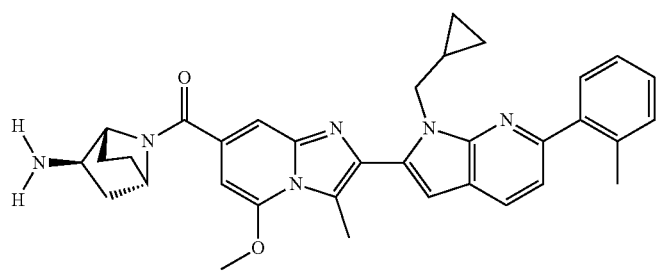
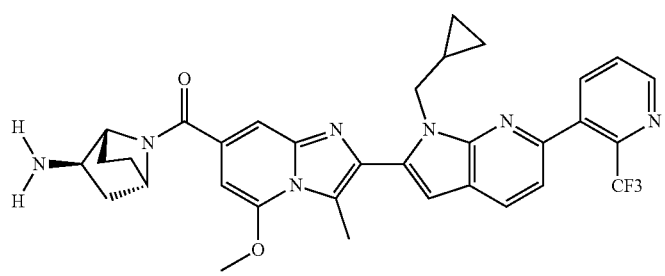
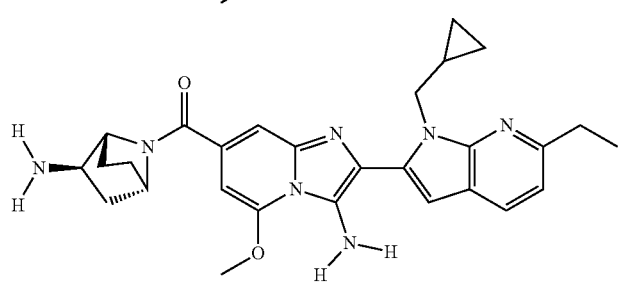
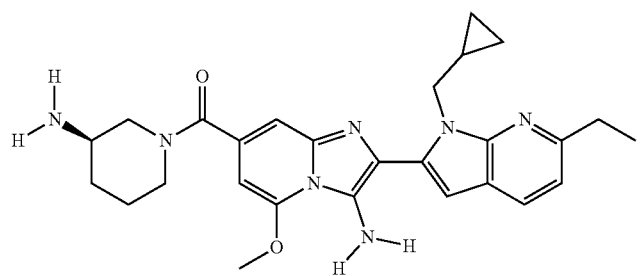
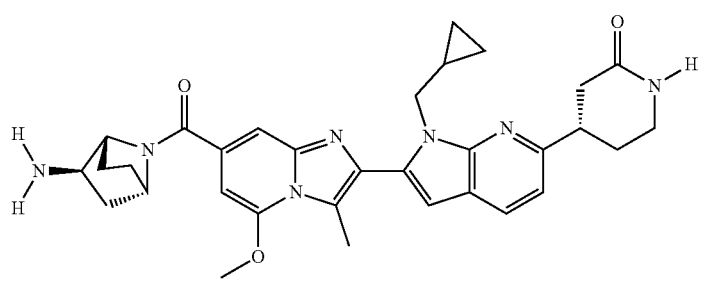
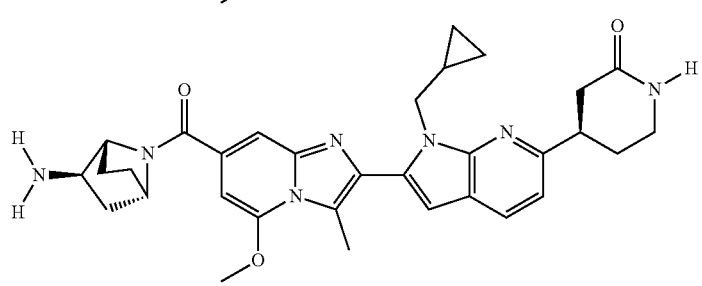

825
826
-continued
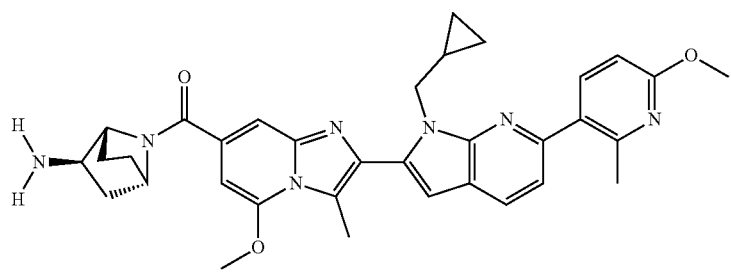
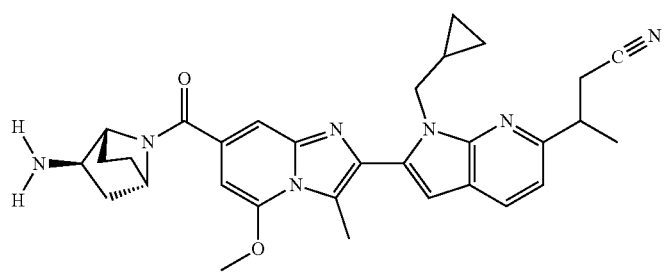
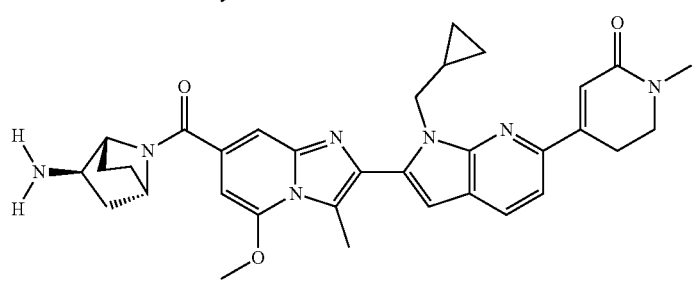
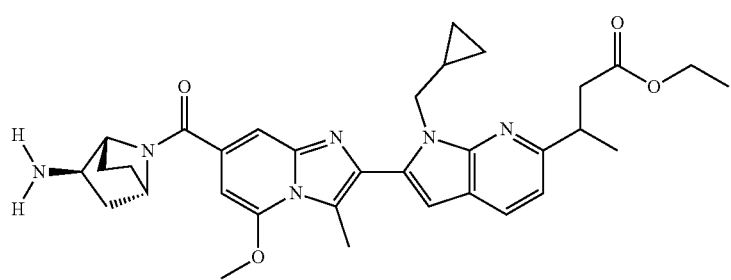
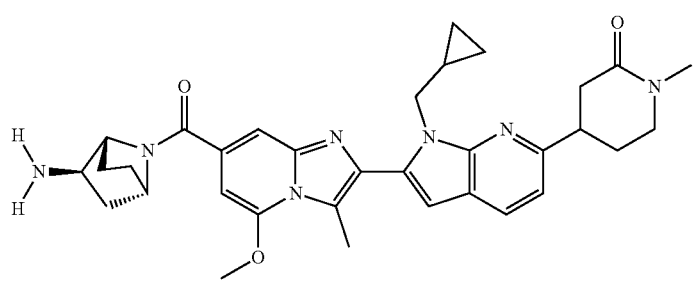
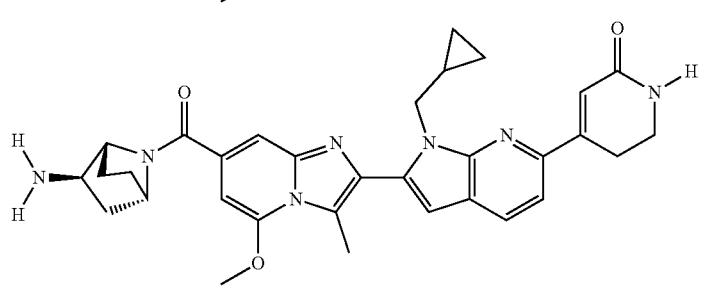

827
-continued
828
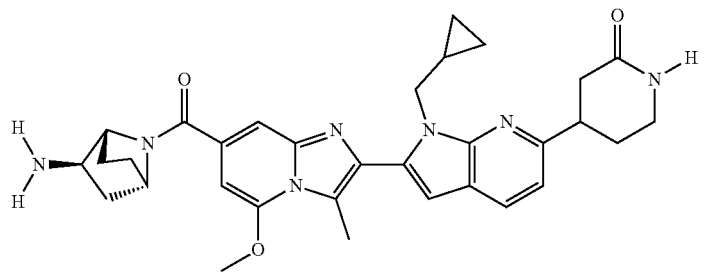
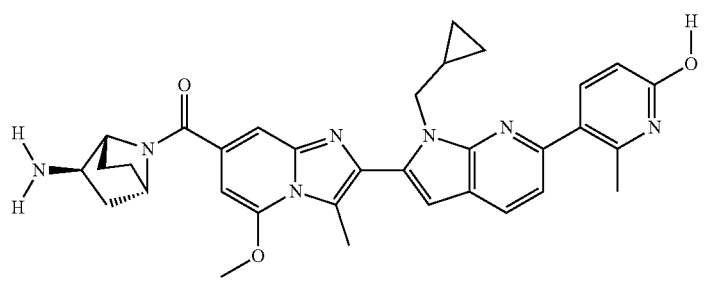
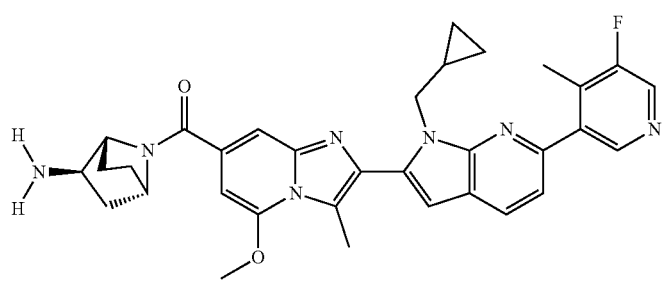
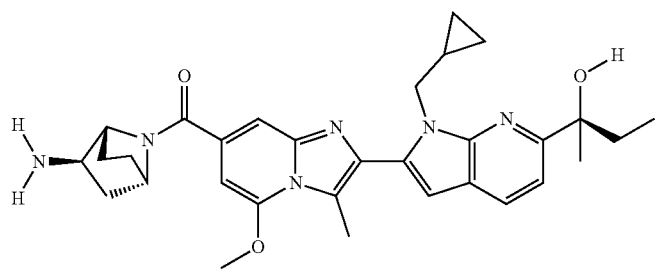
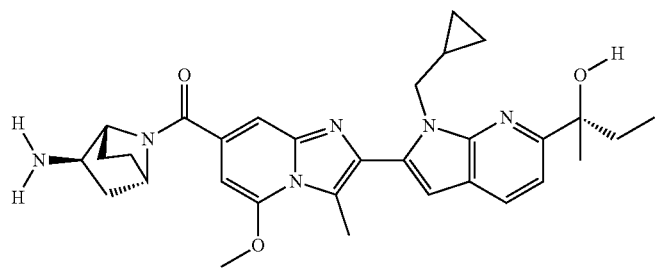
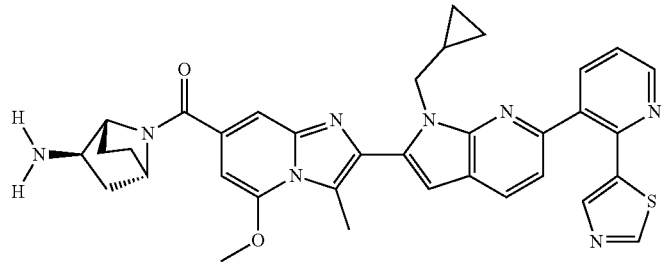

-continued
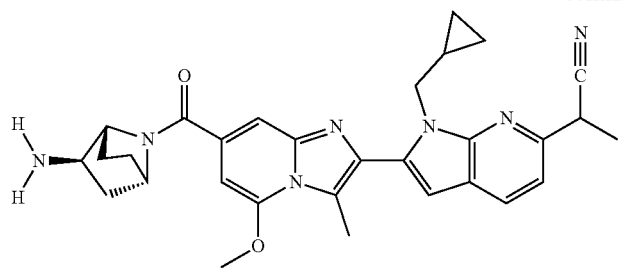
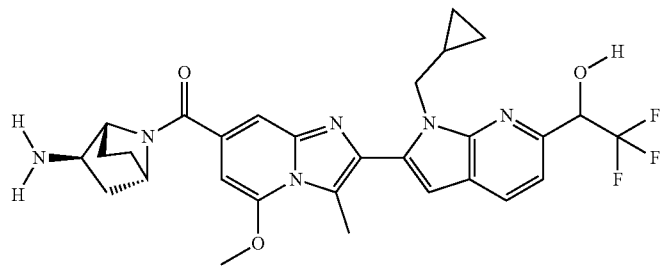
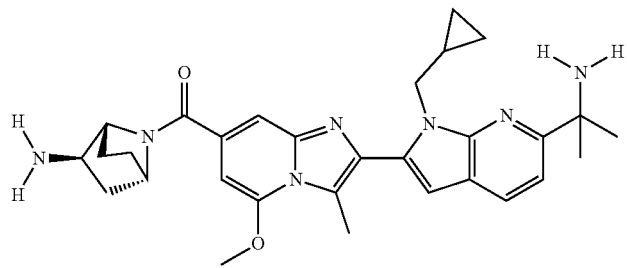
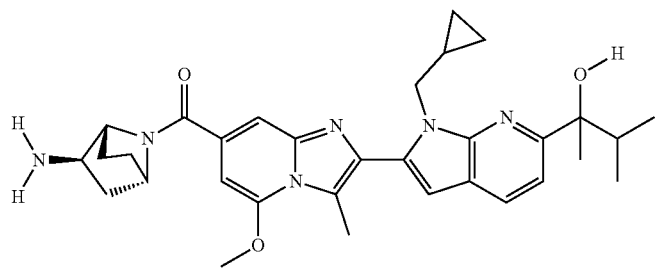
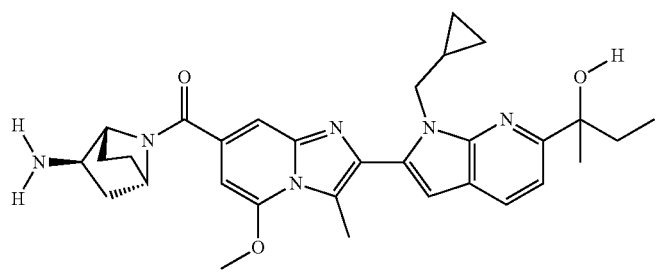
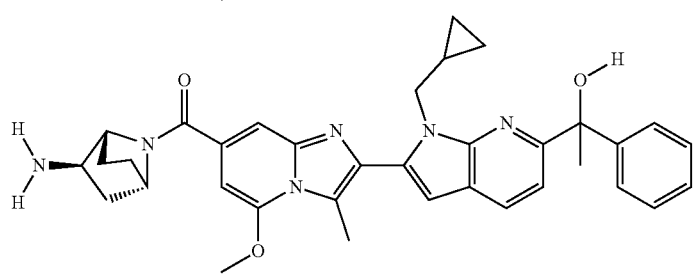

-continued
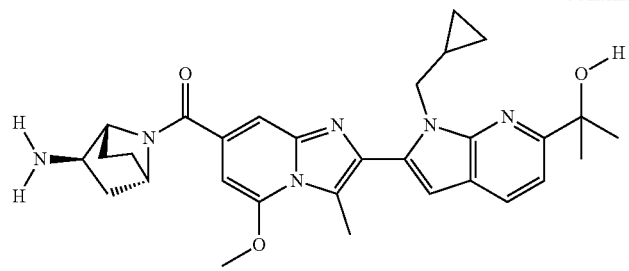
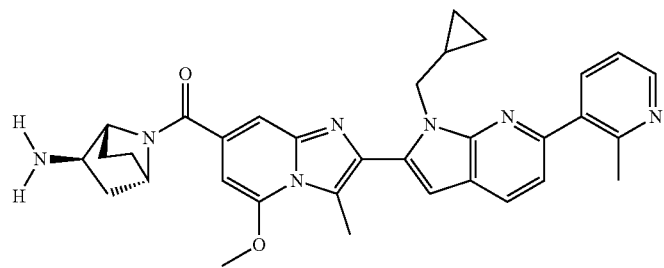
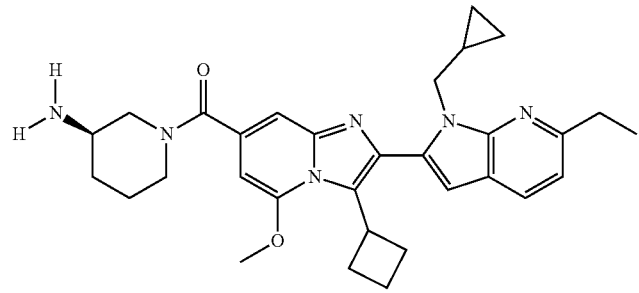
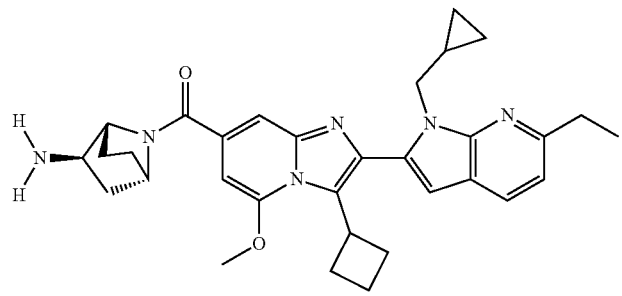
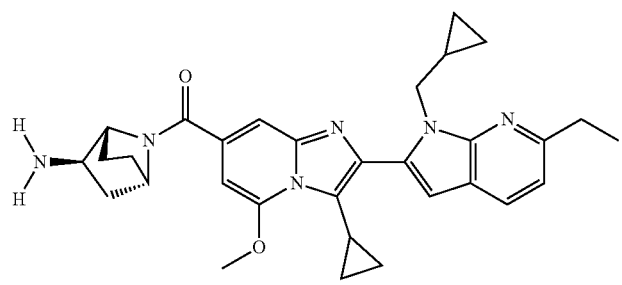
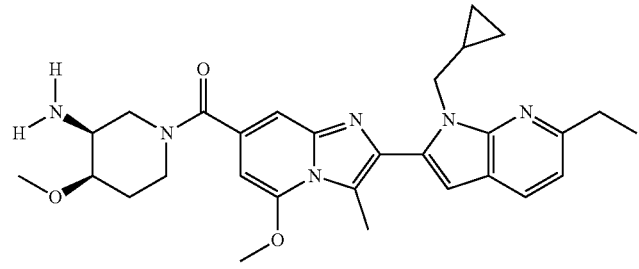

-continued
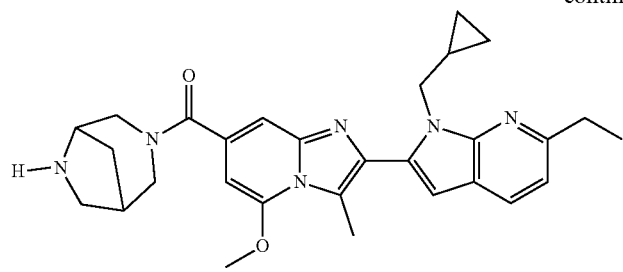
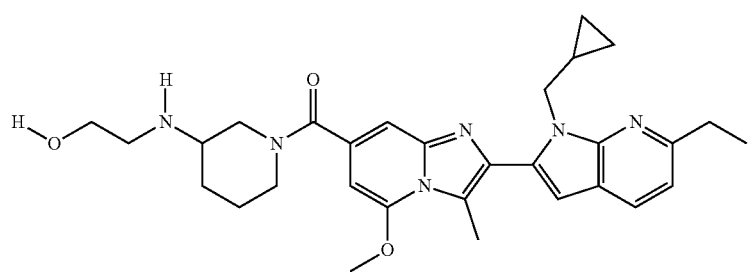
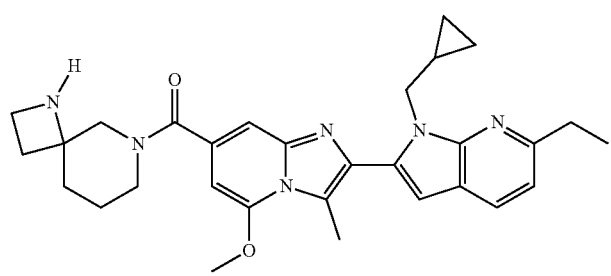
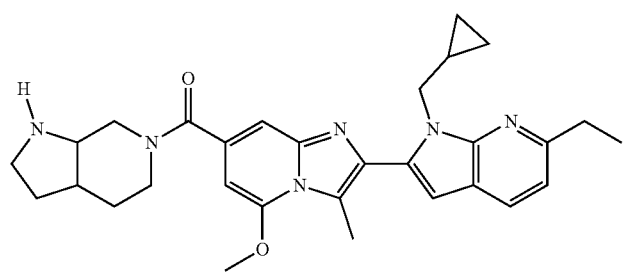
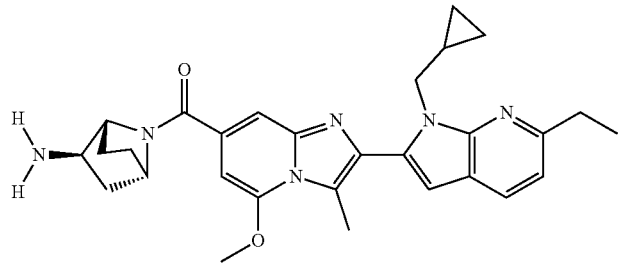
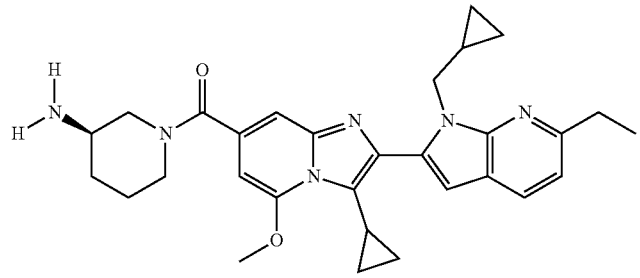

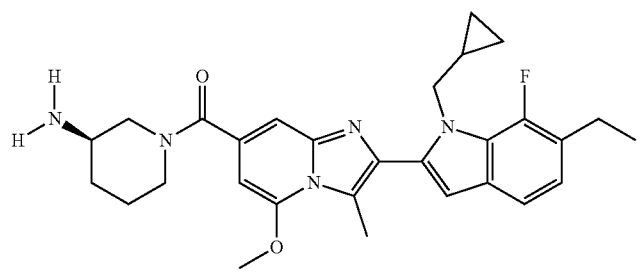
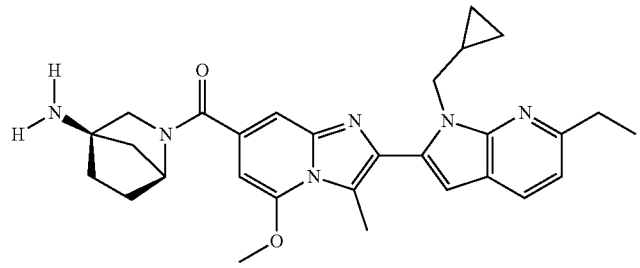
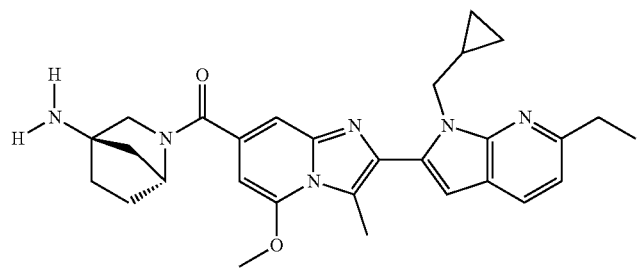
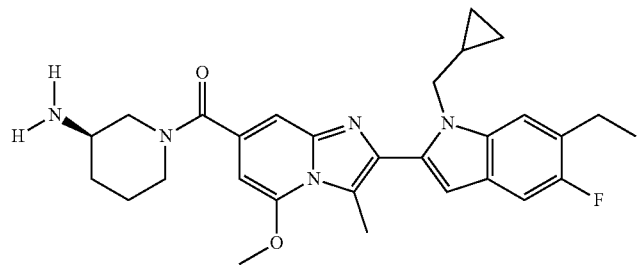
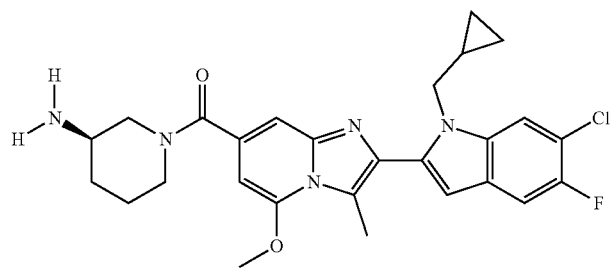
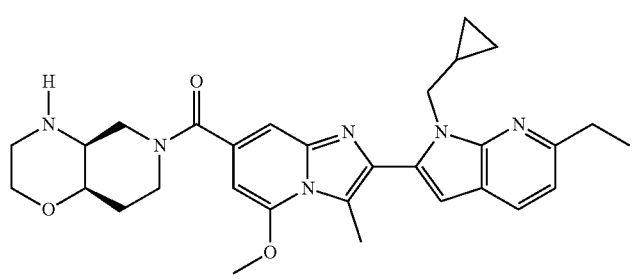

-continued
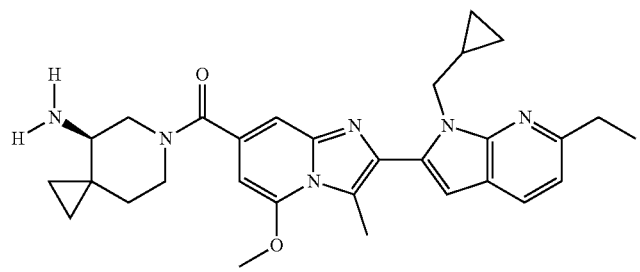
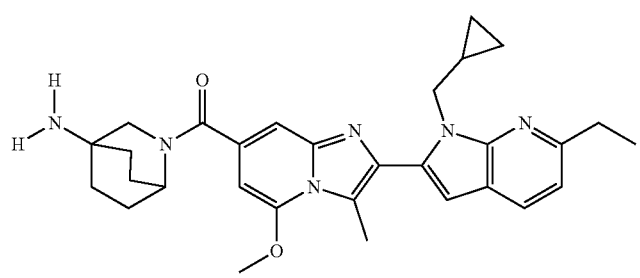
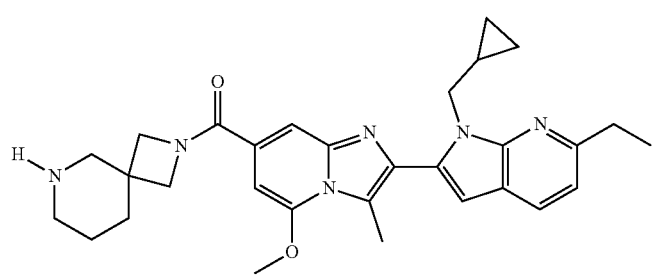
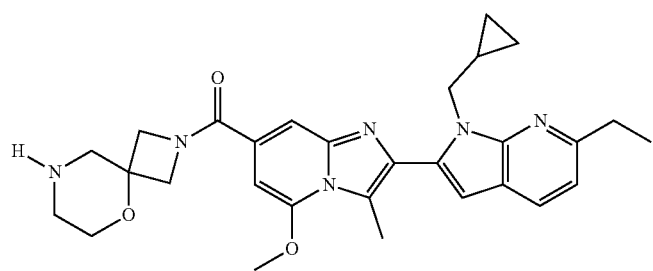
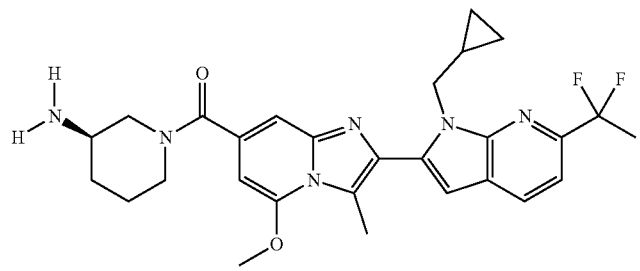
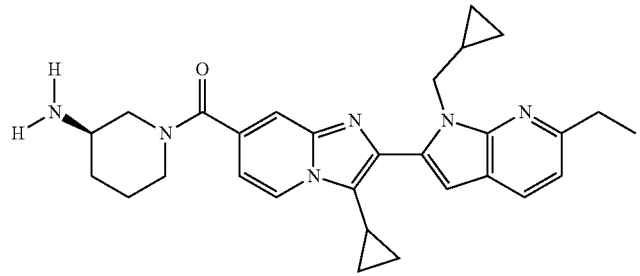

-continued
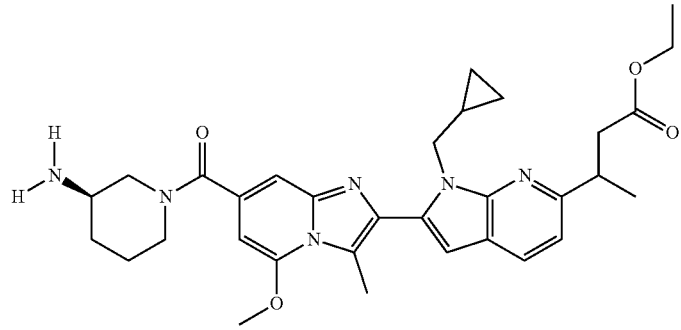
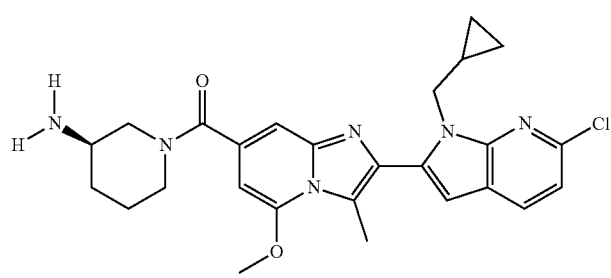
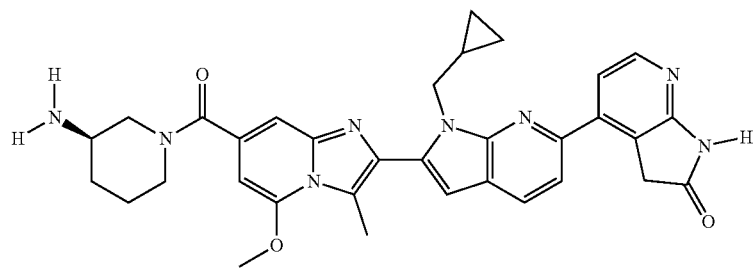
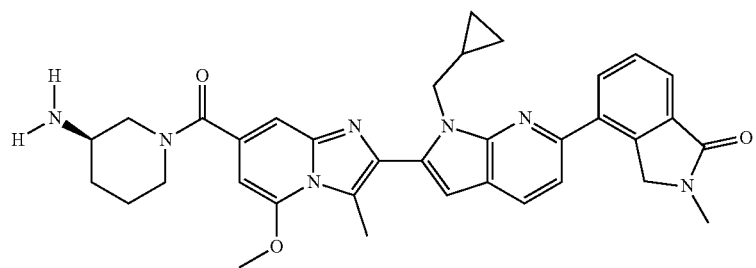
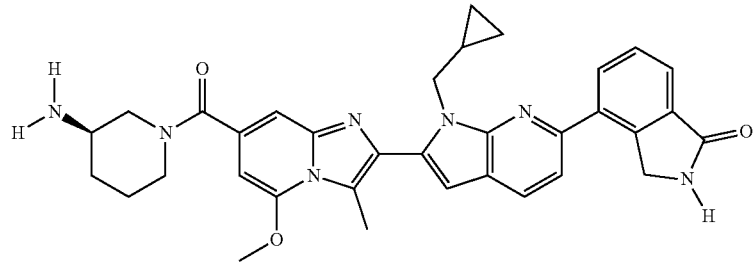
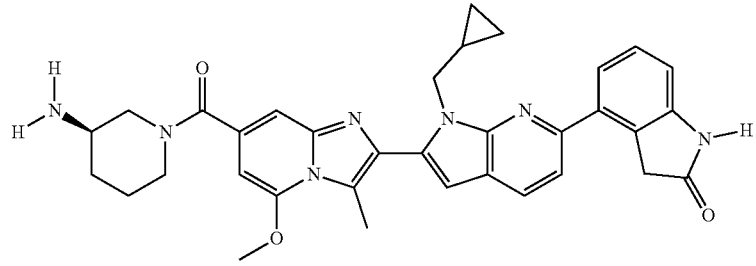

-continued
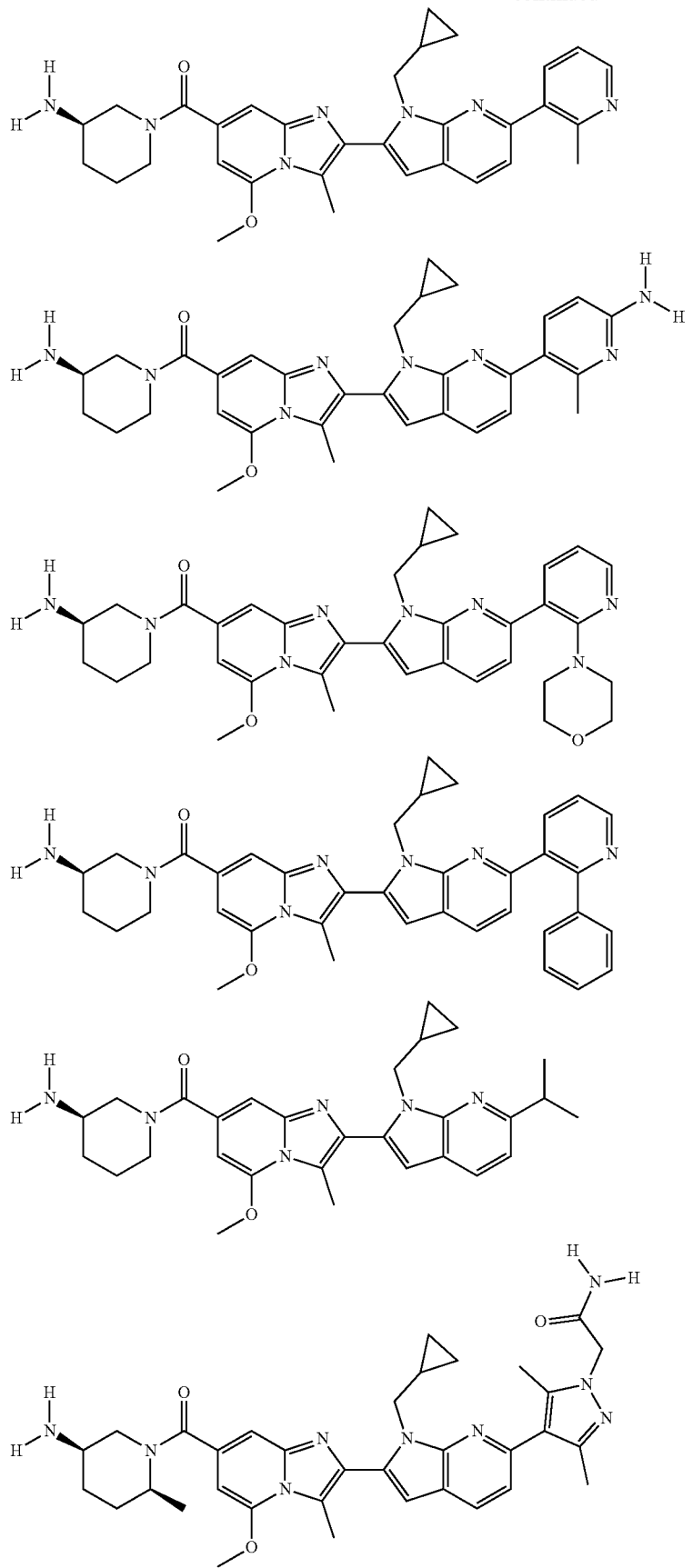

-continued
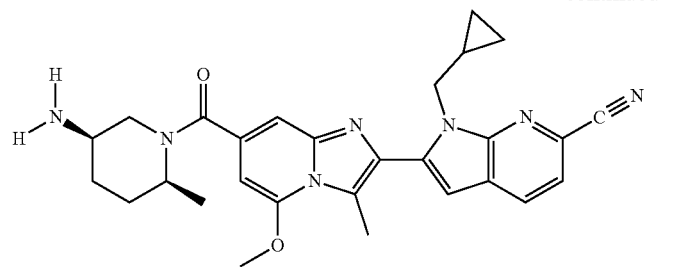
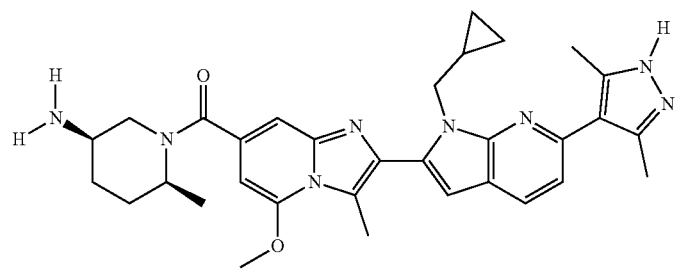
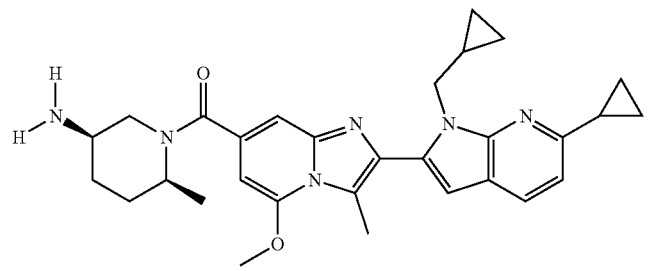
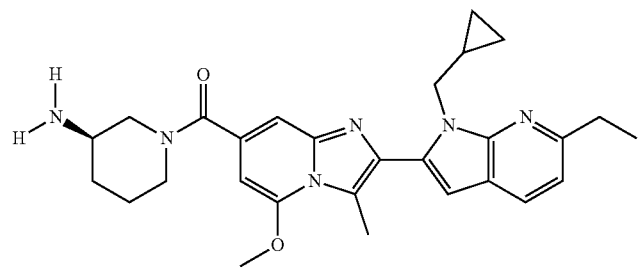
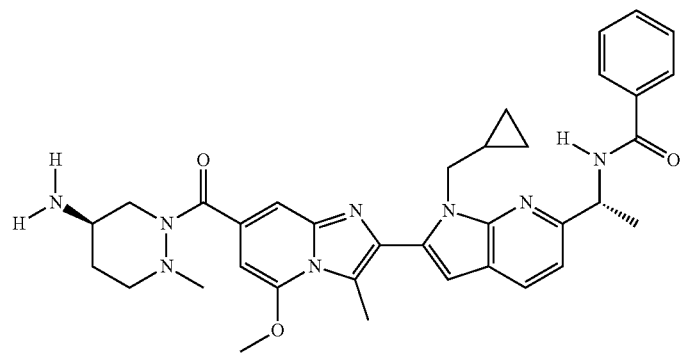
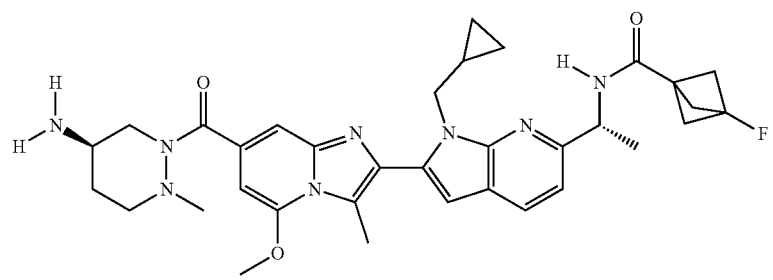

-continued
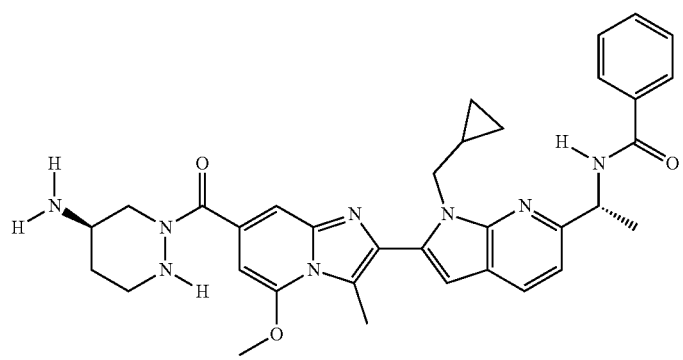
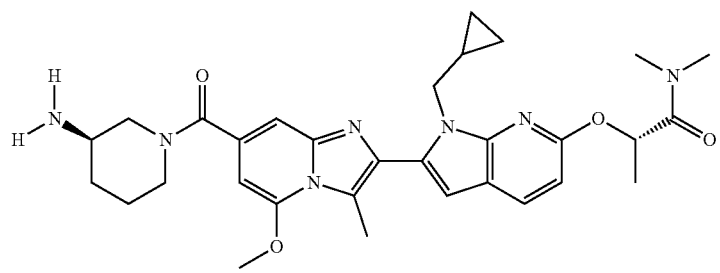
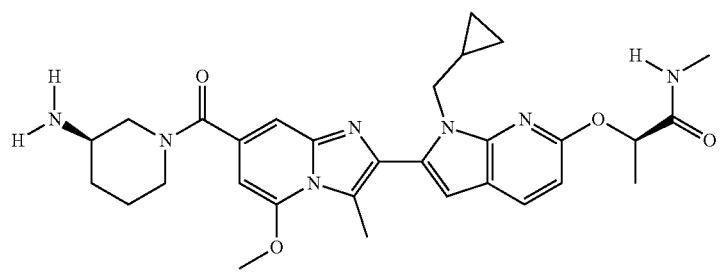
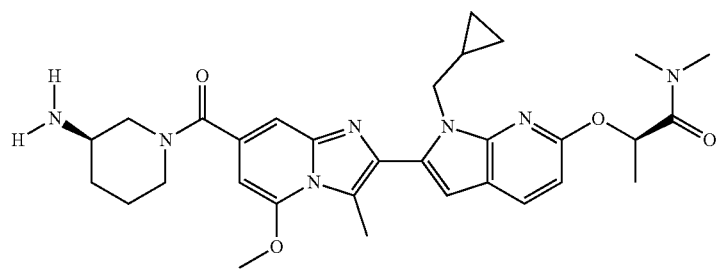
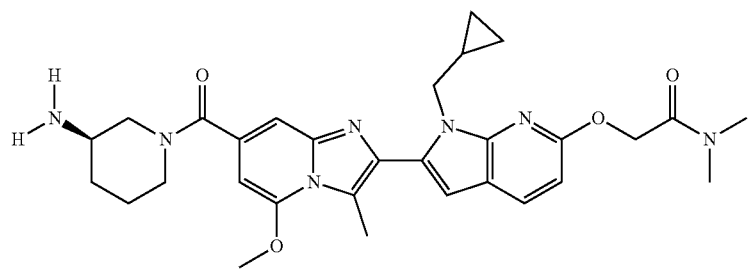
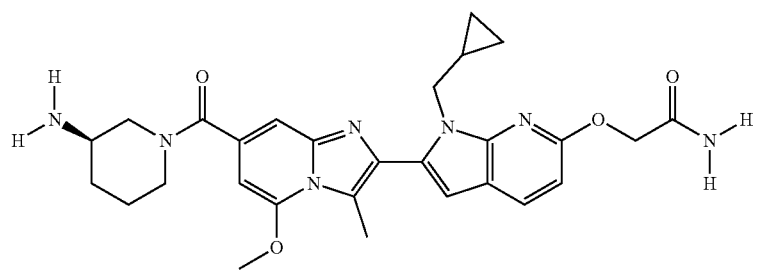

-continued
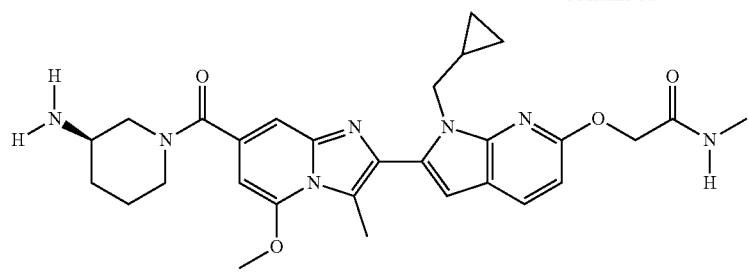
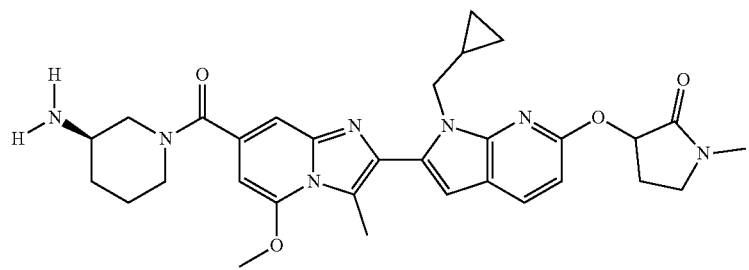
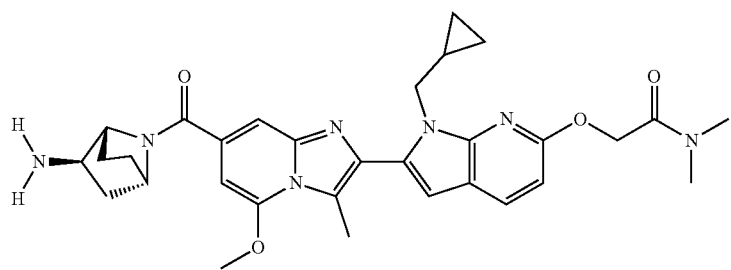
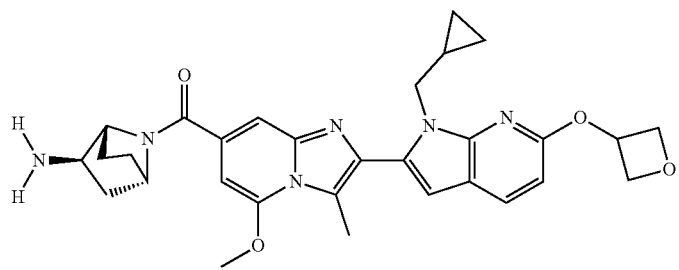
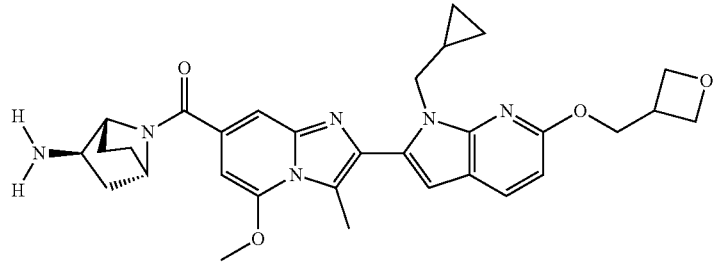
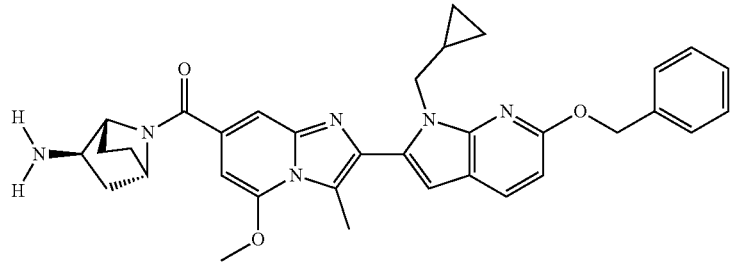

-continued
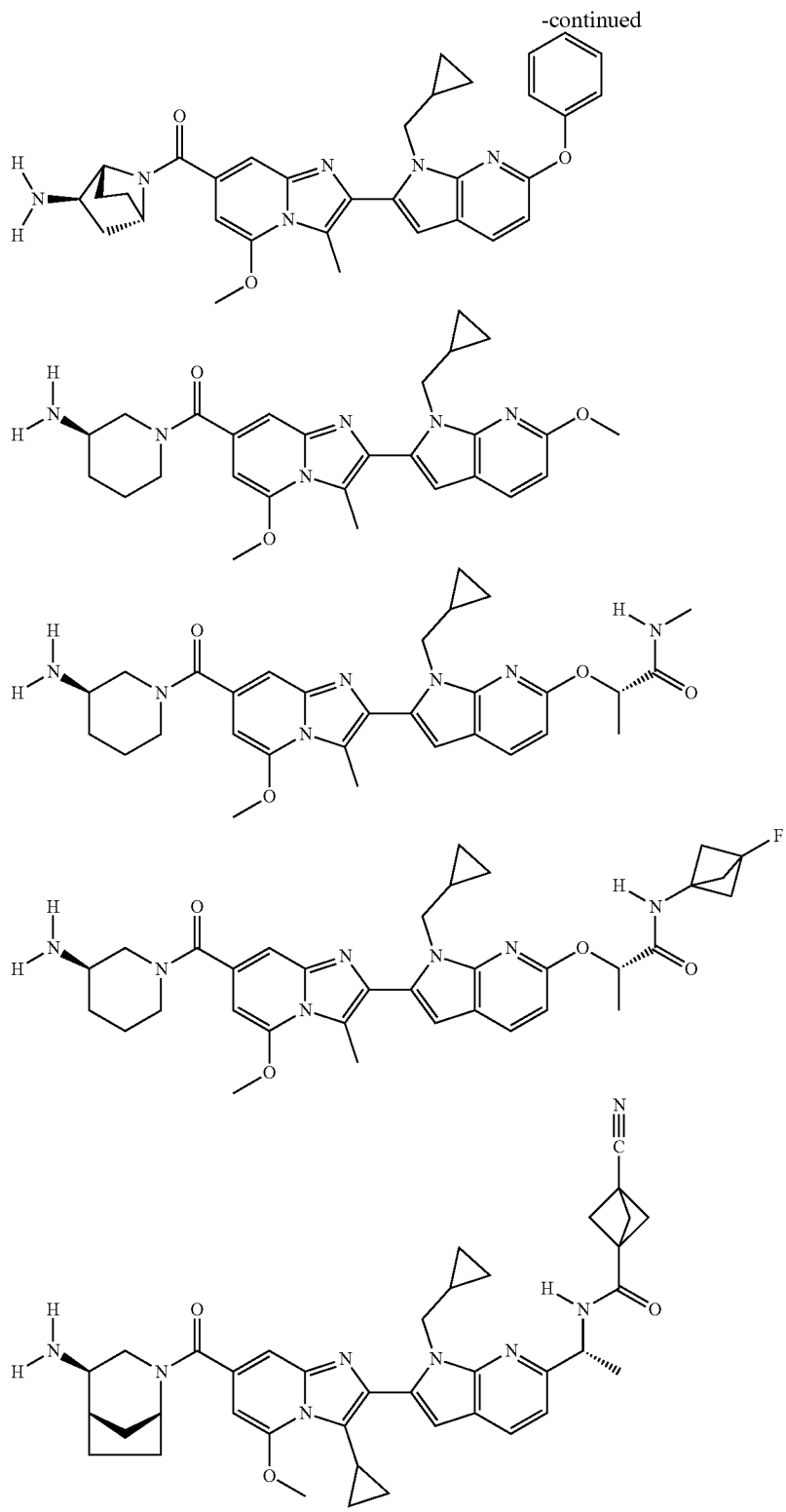
or a pharmaceutically acceptable salt thereof.
12. A pharmaceutical composition comprising a compound according to claim 11 or a pharmaceutically acceptable salt thereof, and at least one pharmaceutically acceptable excipient.
* * * * *